US010030016B2

(12) United States Patent
Arndt et al.

(10) Patent No.: US 10,030,016 B2
(45) Date of Patent: Jul. 24, 2018

(54) HETEROCYCLIC COMPOUNDS USEFUL AS PDK1 INHIBITORS

(71) Applicants: Sunesis Pharmaceuticals, Inc., South San Francisco, CA (US); Millennium Pharmaceuticals, Inc., Cambridge, MA (US)

(72) Inventors: Joseph Arndt, Peabody, MA (US); Timothy Chan, Newton, MA (US); Kevin Guckian, Northborough, MA (US); Gnanasambandam Kumaravel, Westford, MA (US); Wen-Cherng Lee, Lexington, MA (US); Edward Yin-Shiang Lin, Chestnut Hill, MA (US); Daniel Scott, Weston, MA (US); Lihong Sun, Lexington, MA (US); Jermaine Thomas, Chelsea, MA (US); Kurt van Vloten, Bellingham, MA (US); Deping Wang, Sharon, MA (US); Lei Zhang, Westford, MA (US); Daniel Erlanson, San Francisco, CA (US)

(73) Assignees: Sunesis Pharmaceuticals, Inc., South San Francisco, CA (US); Millenium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 14/966,821

(22) Filed: Dec. 11, 2015

(65) Prior Publication Data
US 2016/0331756 A1 Nov. 17, 2016

Related U.S. Application Data

(62) Division of application No. 13/499,835, filed as application No. PCT/US2010/051517 on Oct. 5, 2010.
(Continued)

(51) Int. Cl.
| | | |
|---|---|---|
| C07D 471/04 | (2006.01) |
| C07D 487/04 | (2006.01) |
| C07D 239/94 | (2006.01) |
| C07D 241/26 | (2006.01) |
| C07D 213/82 | (2006.01) |
| C07D 213/85 | (2006.01) |
| C07D 401/12 | (2006.01) |
| C07D 401/14 | (2006.01) |
| C07D 403/12 | (2006.01) |
| C07D 403/14 | (2006.01) |
| C07D 405/14 | (2006.01) |
| C07D 409/04 | (2006.01) |
| C07D 409/14 | (2006.01) |
| C07D 417/14 | (2006.01) |
| C07D 473/34 | (2006.01) |
| C07D 491/052 | (2006.01) |
| C07D 519/00 | (2006.01) |
| C07D 241/28 | (2006.01) |
| C07D 498/04 | (2006.01) |
| A61P 35/02 | (2006.01) |

(Continued)

(52) U.S. Cl.
CPC .......... *C07D 471/04* (2013.01); *A61K 31/437* (2013.01); *A61K 31/444* (2013.01); *A61K 31/4439* (2013.01); *A61K 31/452* (2013.01); *A61K 31/4725* (2013.01); *A61K 31/496* (2013.01); *A61K 31/497* (2013.01); *A61K 31/498* (2013.01); *A61K 31/4985* (2013.01); *A61K 31/517* (2013.01); *A61K 31/519* (2013.01); *A61K 31/53* (2013.01); *A61K 31/5377* (2013.01); *A61K 31/5383* (2013.01); *C07D 213/82* (2013.01); *C07D 213/85* (2013.01); *C07D 241/26* (2013.01); *C07D 241/28* (2013.01); *C07D 401/12* (2013.01); *C07D 401/14* (2013.01); *C07D 403/12* (2013.01); *C07D 403/14* (2013.01); *C07D 405/14* (2013.01); *C07D 409/04* (2013.01); *C07D 409/14* (2013.01); *C07D 417/14* (2013.01); *C07D 473/34* (2013.01); *C07D 487/04* (2013.01); *C07D 491/052* (2013.01); *C07D 498/04* (2013.01); *C07D 519/00* (2013.01)

(58) Field of Classification Search
CPC .. C07D 487/04; C07D 471/04; C07D 519/00; C07D 239/94; C07D 241/20
See application file for complete search history.

(56) References Cited

U.S. PATENT DOCUMENTS

| | | |
|---|---|---|
| 3,175,980 A | 3/1965 | Daglish et al. |
| 7,105,563 B2 | 9/2006 | Arnaiz et al. |

(Continued)

FOREIGN PATENT DOCUMENTS

| | | |
|---|---|---|
| CN | 1396912 A | 2/2003 |
| CN | 101056870 A | 10/2007 |

(Continued)

OTHER PUBLICATIONS

Cancer Drug Design and Discovery Neidle, Stephen, ed. (Elsevier/Academic Press, 2008) pp. 427-431.*
(Continued)

*Primary Examiner* — Susanna Moore
(74) *Attorney, Agent, or Firm* — Cooley LLP; Heidi A. Erlacher; Ashley M. Dreis

(57) ABSTRACT

The present invention provides compounds useful as inhibitors of PDK1. The present invention also provides compositions thereof, and methods of treating PDK1-mediated diseases.

16 Claims, No Drawings

Related U.S. Application Data

(60) Provisional application No. 61/249,095, filed on Oct. 6, 2009.

(51) Int. Cl.

| | | |
|---|---|---|
| *A61P 35/04* | (2006.01) | |
| *A61K 31/437* | (2006.01) | |
| *A61K 31/4439* | (2006.01) | |
| *A61K 31/444* | (2006.01) | |
| *A61K 31/452* | (2006.01) | |
| *A61K 31/4725* | (2006.01) | |
| *A61K 31/496* | (2006.01) | |
| *A61K 31/497* | (2006.01) | |
| *A61K 31/498* | (2006.01) | |
| *A61K 31/4985* | (2006.01) | |
| *A61K 31/517* | (2006.01) | |
| *A61K 31/519* | (2006.01) | |
| *A61K 31/53* | (2006.01) | |
| *A61K 31/5377* | (2006.01) | |
| *A61K 31/5383* | (2006.01) | |

(56) References Cited

U.S. PATENT DOCUMENTS

| 9,546,165 B2 | 1/2017 | Arndt et al. |
|---|---|---|
| 2005/0182061 A1 | 8/2005 | Green et al. |
| 2009/0023761 A1 | 1/2009 | Chen et al. |
| 2013/0023497 A1 | 1/2013 | Tao et al. |

FOREIGN PATENT DOCUMENTS

| JP | 2002-533453 A | 10/2002 |
|---|---|---|
| JP | 2003-520853 A | 7/2003 |
| JP | 2004-522689 A | 7/2004 |
| JP | 2005-530760 A | 10/2005 |
| JP | 2006-501195 A | 1/2006 |
| JP | 2007-503450 A | 2/2007 |
| JP | 2008-518893 A | 6/2008 |
| JP | 2008-545756 A | 12/2008 |
| JP | 2009-510113 A | 3/2009 |
| JP | 2009-513523 A | 4/2009 |
| JP | 2009-523812 A | 6/2009 |
| RU | 2296124 C2 | 3/2007 |
| WO | WO-2000/039111 A1 | 7/2000 |
| WO | WO-2000/039117 A1 | 7/2000 |
| WO | WO-2001/055114 A1 | 8/2001 |
| WO | WO-2003/093297 A2 | 11/2003 |
| WO | WO-2004/007458 A1 | 1/2004 |
| WO | WO-2005/005421 A1 | 1/2005 |
| WO | WO-2005/021532 A1 | 3/2005 |
| WO | WO-2006/048249 A1 | 5/2006 |
| WO | WO-2006/133006 A2 | 12/2006 |
| WO | WO-2007/041379 A1 | 4/2007 |
| WO | WO-2007/084667 A2 | 7/2007 |
| WO | WO-2008/001115 A2 | 1/2008 |
| WO | WO-2008/005457 A2 | 1/2008 |
| WO | WO-2008/016643 A2 | 2/2008 |
| WO | WO-2008/079294 A1 | 7/2008 |
| WO | WO-2008/156726 A1 | 12/2008 |
| WO | WO-2009/059162 A1 | 5/2009 |

OTHER PUBLICATIONS

CAS Registry No. 689214-64-0, STN International, 3-Pyridinecarboxamide,N-(4-methoxyphenyl)-2-[[[1-(4-pyridinyl)-4-piperidinyl]methyl]amino]-, File Registry [online], Entered STN: Jun. 3, 2004, Retrieved on Jun. 29, 2016.

CAS Registry No. 778563-70-5, STN International, 3-Pyridinecarboxamide, N-(5-methyl-2-pyridinyl)-2-[[[1-(4-pyridinyl)-4-piperidinyl]methyl]amino]-, File Registry [online], Entered STN: Nov. 11, 2004, Retrieved on Jun. 29, 2016.

CAS Registry No. 785036-41-1, STN International, 3-Pyridinecarboxamide,5-chloro-N-(5-chloro-2-pyridinyl)-2-[[[1-(4-pyridinyl)-4-piperidinyl]methyl]amino]-, File Registry [online], Entered STN: Nov. 21, 2004, Retrieved on Jun. 29, 2016.

CAS Registry No. 790196-17-7, STN International, 3-Pyridinecarboxamide, N-(6-chloro-3-pyridinyl)-2-[[[1-(4-pyridinyl)-4-piperidinyl]methyl]amino]-, File Registry [online], ED Entered STN: Nov. 29, 2004, Retrieved on Jun. 29, 2016.

International Search Report for PCT/US2010/51517, 2 pages. (dated Dec. 6, 2010).

Office Action for U.S. Appl. No. 13/499,835, 8 pages (dated Sep. 11, 2014).

Written Opinion for PCT/US2010/51517, 12 pages (dated Dec. 6, 2010).

\* cited by examiner

HETEROCYCLIC COMPOUNDS USEFUL AS PDK1 INHIBITORS

BACKGROUND OF THE INVENTION

The 3-phosphoinositide-dependent protein kinase-1 (PDK1) includes a 556 amino acid protein, an N-terminal catalytic domain, and a C-terminal pleckstrin homology (PH) domain that activates substrate kinases via activation loop phosphorylation (Belham, C. et al., Curr. Biol., 9, pp. R93-R96, 1999). PDK1 is involved in regulating the activity of AGC subfamily of protein kinases (Alessi, D. et al., *Biochem. Soc. Trans*, 29: 1 (2001)) such as isoforms of protein kinase B (PKB, also known as AKT), p70 ribosomal S6 kinase (S6K) (Avruch, J. et al., *Prog. Mol. Subcell. Biol.*, 26: 115, (2001)), p90 ribosomal S6 kinase (Frodin, M. et al., *EMBO J.*, 19: 2924-2934, (2000)), and protein kinase C (PKC) (an 80 kDa enzyme that is recruited to the plasma membrane by diacylglycerol and, in many cases, by calcium) (Le Good et al., *Science* 281: 2042-2045 (1998). PDK1 mediated signaling increases in response to insulin, growth factors, and extracellular matrix cell binding (integrin signaling) resulting in diverse cellular events such as cell survival, growth, proliferation and glucose regulation [(Lawlor, M. A. et al., J. Cell Sci., 114, pp. 2903-2910, 2001), (Lawlor, M. A. et al., EMBO J., 21, pp. 3728-3738, 2002)]. Elevated PDK1 signaling has been detected in several cancers resulting from distinct genetic events such as PTEN mutations or over-expression of certain key regulatory proteins [(Graff, J. R., Expert Opin. Ther. Targets, 6, pp. 103-113, 2002), (Brognard, J., et al., Cancer Res., 61, pp. 3986-3997, 2001)].

The tumor-suppressor phosphatase with tensin homology (PTEN) is an important negative regulator of the cell-survival signaling pathway initiated by phosphatidylinositol 3-kinase (PI3K). The PDK1/Akt pathway is activated in many cancer via mutations in Receptor Tyrosine Kinases (RTKs), Ras, PI-3 kinase or PTEN (Cully et al., *Nature Reviews Cancer* 6:184-192 (2006)). The potential of PDK1 inhibitors as anti-cancer compounds was demonstrated by transfection of a PTEN negative human cancer cell line (U87MG) with antisense oligonucleotides directed against PDK1. The resulting decrease in PDK1 protein levels led to a reduction in cellular proliferation and survival (Flynn, P., et al., *Curr. Biol.*, 10: 1439-1442 (2000)).

Moreover, currently known inhibitors of PDK1 typically affect both PDK1 mediated Akt phosphorylation and PDK1 mediated PKC phosphorylation thereby raising concerns regarding clinical side effects. Feldman et al., *J. Biol. Chem.* 280: 19867-19874 (2005).

Consequently, there is a great need for effective inhibitors of PDK1. The present invention fulfills these and other needs.

SUMMARY OF THE INVENTION

It has now been found that compounds of this invention, and pharmaceutically acceptable compositions thereof, are effective as inhibitors of one or more protein kinases. Such compounds are of formula I:

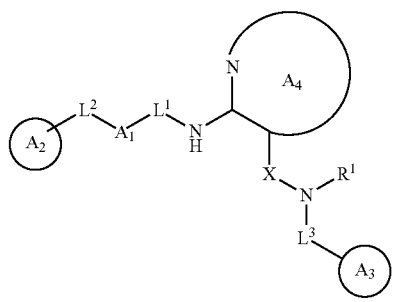

I or a pharmaceutically acceptable salt thereof, wherein each of $A_1$, Ring $A_2$, Ring $A_3$, Ring $A_4$, $L^1$, $L^2$, $L^3$, X, and $R^1$ are as defined and described in classes and subclasses herein. Provided compounds are useful as inhibitors of protein kinases (e.g., PDK1), and thus are useful, for example, for the treatment of PDK1-mediated diseases.

In certain other embodiments, the invention provides pharmaceutical compositions comprising a compound of the invention, wherein the compound is present in an amount effective to inhibit PDK1 activity. In certain other embodiments, the invention provides pharmaceutical compositions comprising a compound of the invention and optionally further comprising an additional therapeutic agent. In yet other embodiments, the additional therapeutic agent is an agent for the treatment of cancer.

In yet another aspect, the present invention provides methods for inhibiting kinase (e.g., PDK1) activity in a patient or a biological sample, comprising administering to said patient, or contacting said biological sample with, an effective inhibitory amount of a compound of the invention. In still another aspect, the present invention provides methods for treating any disorder involving PDK1 activity, comprising administering to a subject in need thereof a therapeutically effective amount of a compound of the invention. Such methods are described in detail herein.

DETAILED DESCRIPTION OF CERTAIN EMBODIMENTS OF THE INVENTION

1. General Description of Compounds of the Invention:

In certain embodiments, the present invention provides a compound of formula I:

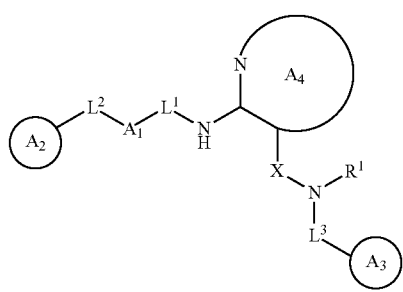

I or a pharmaceutically acceptable salt thereof, wherein:
$R^1$ is hydrogen or optionally substituted $C_{1-6}$ aliphatic, or:
  $R^1$ and a substituent on Ring $A_4$ are taken together with their intervening atoms to form an optionally substituted 5-7 membered partially unsaturated or aromatic fused ring having 1-3 heteroatoms independently selected from nitrogen, oxygen, or sulfur;

X is —C(O)— or —S(O)$_2$—, $L^1$ is a covalent bond or an optionally substituted bivalent group selected from $C_{1-4}$ alkylene, $C_{2-4}$ alkenylene, or $C_{2-4}$ alkynylene wherein one or more methylene units of $L^1$ are optionally and independently replaced by -Cy$^1$-, —O—, —S—, —N(R$^2$)—, —C(O)—, —C(O)N(R$^2$)—, —N(R$^2$)C(O)N(R$^2$)—, —N(R$^2$)C(O)—, —N(R$^2$)C(O)O—, —OC(O)N(R$^2$)—, —S(O)$_2$—, —S(O)$_2$N(R$^2$)—, —N(R$^2$)S(O)$_2$—, —OC(O)—, or —C(O)O;

Cy$^1$ is an optionally substituted bivalent ring selected from phenylene, 3-7 membered saturated or partially unsaturated carbocyclylene, 4-7 membered saturated or partially unsaturated heterocyclylene having 1-2 heteroatoms independently selected from nitrogen, oxygen, or sulfur, or 5-6 membered heteroarylene having 1-3 heteroatoms independently selected from nitrogen, oxygen, or sulfur;

each R$^2$ is hydrogen or optionally substituted $C_{1-6}$ aliphatic;

$A_1$ is a covalent bond or an optionally substituted bivalent ring selected from 3-7 membered saturated or partially unsaturated monocyclic carbocyclylene, 7-10 membered saturated or partially unsaturated bicyclic carbocyclylene, 4-7 membered saturated or partially unsaturated monocyclic heterocyclylene having 1-2 heteroatoms independently selected from nitrogen, oxygen, or sulfur, 7-10 membered saturated or partially unsaturated bicyclic heterocyclylene having 1-3 heteroatoms independently selected from nitrogen, oxygen, or sulfur, phenylene, 8-10 membered bicyclic arylene, 5-6 membered monocyclic heteroarylene having 1-3 heteroatoms independently selected from nitrogen, oxygen, or sulfur, or 8-10 membered bicyclic heteroarylene having 1-4 heteroatoms independently selected from nitrogen, oxygen, or sulfur;

$L^2$ is a covalent bond, alkylidenylene, or an optionally substituted alkylene chain wherein one or more methylene units of $L^2$ are optionally and independently replaced by —O—, —S—, —N(R$^2$)—, —C(O)—, —C(O)N(R$^2$)—, —N(R$^2$)C(O)N(R$^2$)—, —N(R$^2$)C(O)—, —N(R$^2$)C(O)O—, —OC(O)N(R$^2$)—, —S(O)$_2$—, —S(O)$_2$N(R$^2$)—, —N(R$^2$)S(O)$_2$—, —OC(O)—, or —C(O)O—;

Ring $A_2$ is a 3-7 membered saturated or partially unsaturated monocyclic carbocyclic ring, a 7-10 membered saturated or partially unsaturated bicyclic carbocyclic ring, a 4-7 membered saturated or partially unsaturated monocyclic heterocyclic ring having 1-2 heteroatoms independently selected from nitrogen, oxygen, or sulfur, a 7-10 membered saturated or partially unsaturated bicyclic heterocyclic ring having 1-3 heteroatoms independently selected from nitrogen, oxygen, or sulfur, a phenyl ring, an 8-10 membered bicyclic aryl ring, a 5-6 membered monocyclic heteroaryl ring having 1-3 heteroatoms independently selected from nitrogen, oxygen, or sulfur, an 8-10 membered bicyclic heteroaryl ring having 1-4 heteroatoms independently selected from nitrogen, oxygen, or sulfur, or a 10-16 membered saturated, partially unsaturated, or aromatic tricyclic ring having 0-4 heteroatoms independently selected from nitrogen, oxygen, or sulfur, wherein Ring $A_2$ is optionally substituted with 1-4 R$^x$ groups;

each R$^x$ is independently —R, optionally substituted alkylidenyl, oxo, -halo, —NO$_2$, —CN, —OR, —SR, —N(R')$_2$, —C(O)R, —CO$_2$R, —C(O)C(O)R, —C(O)CH$_2$C(O)R, —S(O)R, —S(O)$_2$R, —C(O)N(R')$_2$, —S(O)$_2$N(R')$_2$, —OC(O)R, —N(R')C(O)R, —N(R')N(R')$_2$, —N(R')OR, —N(R')C(=NR')N(R')$_2$, —C(=NR')N(R')$_2$, —C=NOR, —N(R')C(O)N(R')$_2$, —N(R')S(O)$_2$N(R')$_2$, —N(R')S(O)$_2$R, or —OC(O)N(R')$_2$;

each R is independently hydrogen or an optionally substituted group selected from $C_{1-6}$ aliphatic, a 3-7 membered saturated or partially unsaturated monocyclic carbocyclic ring, a 7-10 membered saturated or partially unsaturated bicyclic carbocyclic ring, a 4-7 membered saturated or partially unsaturated monocyclic heterocyclic ring having 1-2 heteroatoms independently selected from nitrogen, oxygen, or sulfur, a 7-10 membered saturated or partially unsaturated bicyclic heterocyclic ring having 1-3 heteroatoms independently selected from nitrogen, oxygen, or sulfur, a phenyl ring, an 8-10 membered bicyclic aryl ring, a 5-6 membered heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur;

each R' is independently —R, or two R' groups on the same nitrogen are taken together with their intervening atoms to form an optionally substituted 5-8 membered saturated, partially unsaturated, or aromatic ring having 1-4 heteroatoms independently selected from nitrogen, oxygen, or sulfur;

$L^3$ is a covalent bond or an optionally substituted $C_{1-4}$ alkylene chain wherein one or more methylene units of $L^3$ are optionally and independently replaced by —O—, —S—, —N(R$^2$)—, —C(O)—, —C(O)N(R$^2$)—, —N(R$^2$)C(O)N(R$^2$)—, —N(R$^2$)C(O)—, —N(R$^2$)C(O)O—, —OC(O)N(R$^2$)—, —S(O)$_2$—, —S(O)$_2$N(R$^2$)—, —N(R$^2$)S(O)$_2$—, —OC(O)—, or —C(O)O—;

Ring $A_3$ is an optionally substituted ring selected from a 3-7 membered saturated or partially unsaturated monocyclic carbocyclic ring, a 7-10 membered saturated or partially unsaturated bicyclic carbocyclic ring, a 4-7 membered saturated or partially unsaturated monocyclic heterocyclic ring having 1-2 heteroatoms independently selected from nitrogen, oxygen, or sulfur, a 7-10 membered saturated or partially unsaturated bicyclic heterocyclic ring having 1-3 heteroatoms independently selected from nitrogen, oxygen, or sulfur, a phenyl ring, an 8-10 membered bicyclic aryl ring, a 5-6 membered monocyclic heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur;

Ring $A_4$ is a 5-6 membered heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur; wherein any substitutable carbon on Ring $A_4$ is optionally substituted with R$^3$, R$^4$, or R$^5$, and any substitutable nitrogen on Ring $A_4$ is optionally substituted with R$^6$;

each of R$^3$, R$^4$, and R$^5$ is independently —R, -halo, —NO$_2$, —CN, —OR, —SR, —N(R')$_2$, —C(O)R, —CO$_2$R, —C(O)C(O)R, —C(O)CH$_2$C(O)R, —S(O)R, —S(O)$_2$R, —C(O)N(R')$_2$, —S(O)$_2$N(R')$_2$, —OC(O)R, —N(R')C(O)R, —N(R')N(R')$_2$, —N(R')OR, —N(R')C(=NR')N(R')$_2$, —C(=NR')N(R')$_2$, —C=NOR, —N(R')C(O)N(R')$_2$, —N(R')S(O)$_2$N(R')$_2$, —N(R')S(O)$_2$R, or —OC(O)N(R')$_2$; or:

R$^3$ and R$^4$ or R$^4$ and R$^5$ are taken together with their intervening atoms to form an optionally substituted fused ring selected from a 4-7 membered partially unsaturated carbocyclic ring, phenyl, a 5-6 membered partially unsaturated heterocyclic ring having 1-3 heteroatoms independently selected from nitrogen, oxygen, or sulfur, or a 5-6 membered heteroaryl ring having 1-3 heteroatoms independently selected from nitrogen, oxygen, or sulfur;

each $R^6$ is independently —R, —C(O)R, —CO$_2$R, —C(O)C(O)R, —C(O)CH$_2$C(O)R, —S(O)R, —S(O)$_2$R, —C(O)N(R')$_2$, or —S(O)$_2$N(R')$_2$; or:

$R^3$ and $R^6$ are taken together with their intervening atoms to form an optionally substituted fused ring selected from a 5-6 membered saturated or partially unsaturated heterocyclic ring having 1-3 heteroatoms independently selected from nitrogen, oxygen, or sulfur, or a 5-6 membered heteroaryl ring having 1-3 heteroatoms independently selected from nitrogen, oxygen, or sulfur.

In certain embodiments, when $A_1$ is bivalent monocyclic ring and $L^1$ is a covalent bond, $L^2$ is not —O—. In certain embodiments, when $A_1$ is a bivalent monocyclic or bicyclic ring, $L^1$ and $L^2$ do not occur simultaneously as a covalent bond.

It will be appreciated by one of ordinary skill in the art that when two adjacent variables are covalent bonds, those two variables exist as one covalent bond. For example, when $L^2$ and $A_1$ are each a covalent bond, $L^1$ and Ring $A_2$ are attached via one covalent bond. Likewise, when $L^1$ and $A_1$ are each a covalent bond, Ring $A_2$ and Ring $A_4$ are attached via one covalent bond. In certain embodiments, $L^1$, $A_1$, and $L^2$ do not occur simultaneously as a covalent bond.

2. Compounds and Definitions:

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

Where a particular enantiomer is preferred, it may, in some embodiments be provided substantially free of the corresponding enantiomer, and may also be referred to as "optically enriched." "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, N Y, 1962); Wilen, S. H. *Tables of Resolving Agents and Optical Resolutions* p. 268 (E. L. Eliel, Ed., Univ. of Notre Dame Press, Notre Dame, Ind. 1972).

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

As used herein a "direct bond" or "covalent bond" refers to a single, double or triple bond. In certain embodiments, a "direct bond" or "covalent bond" refers to a single bond.

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-6 carbon atoms. In some embodiments, aliphatic groups contain 1-4 carbon atoms, and in yet other embodiments aliphatic groups contain 1-3 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "unsaturated", as used herein, means that a moiety has one or more units of unsaturation.

The terms "cycloaliphatic", "carbocycle", "carbocyclyl", "carbocyclo", or "carbocyclic", used alone or as part of a larger moiety, refer to a saturated or partially unsaturated cyclic aliphatic monocyclic or bicyclic ring systems, as described herein, having from 3 to 10 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons. The terms "cycloaliphatic", "carbocycle", "carbocyclyl", "carbocyclo", or "carbocyclic" also include aliphatic rings that are fused to one or more aromatic or nonaromatic rings, such as decahydronaphthyl, tetrahydronaphthyl, decalin, or bicyclo[2.2.2]octane, where the radical or point of attachment is on an aliphatic ring.

As used herein, the term "cycloalkylene" refers to a bivalent cycloalkyl group. In certain embodiments, a cycloalkylene group is a 1,1-cycloalkylene group (i.e., a spiro-fused ring). Exemplary 1,1-cycloalkylene groups include

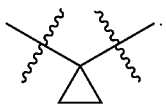 [SMILES: *C1(*)CC1]

In other embodiments, a cycloalkylene group is a 1,2-cycloalkylene group or a 1,3-cycloalkylene group. Exemplary 1,2-cycloalkylene groups include

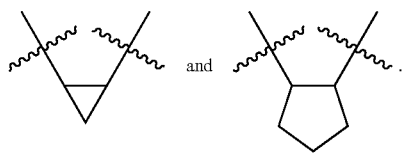 [SMILES: *C1CC1* ; *C1CCCC1*]

Similarly, the term "carbocyclylene" refers to a bivalent carbocyclic group.

The term "alkyl," as used herein, refers to saturated, straight- or branched-chain hydrocarbon radicals derived from an aliphatic moiety containing between one and six carbon atoms by removal of a single hydrogen atom. In some embodiments, the alkyl group employed in the invention contains 1-5 carbon atoms. In another embodiment, the alkyl group employed contains 1-4 carbon atoms. In still other embodiments, the alkyl group contains 1-3 carbon atoms. In yet another embodiment, the alkyl group contains 1-2 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes a monovalent group derived from a straight- or branched-chain aliphatic moiety having at least one carbon-carbon double bond by the removal of a single hydrogen atom. In certain embodiments, the alkenyl group employed in the invention contains 2-6 carbon atoms. In certain embodiments, the alkenyl group employed in the invention contains 2-5 carbon atoms. In some embodiments, the alkenyl group employed in the invention contains 2-4 carbon atoms. In another embodiment, the alkenyl group employed contains 2-3 carbon atoms. Alkenyl groups include, for example, ethenyl, propenyl, butenyl, 1-methyl-2-buten-1-yl, and the like.

The term "alkynyl," as used herein, refers to a monovalent group derived from a straight- or branched-chain aliphatic moiety having at least one carbon-carbon triple bond by the removal of a single hydrogen atom. In certain embodiments, the alkynyl group employed in the invention contains 2-6 carbon atoms. In certain embodiments, the alkynyl group employed in the invention contains 2-5 carbon atoms. In some embodiments, the alkynyl group employed in the invention contains 2-4 carbon atoms. In another embodiment, the alkynyl group employed contains 2-3 carbon atoms. Representative alkynyl groups include, but are not limited to, ethynyl, 2-propynyl (propargyl), 1-propynyl, and the like.

The term "aryl" used alone or as part of a larger moiety as in "aralkyl", "aralkoxy", or "aryloxyalkyl", refers to monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl", as it is used herein, is a group in which an aromatic ring is fused to one or more non-aromatic rings, such as indanyl, phthalimidyl, naphthimidyl, phenantriidinyl, or tetrahydronaphthyl, and the like. The term "arylene" refers to a bivalent aryl group.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted. The term "heteroarylene" refers to a bivalent heteroaryl group.

As used herein, the terms "heterocycle", "heterocyclyl", "heterocyclic radical", and "heterocyclic ring" are used interchangeably and refer to a stable 4- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, 2-azabicyclo[2.2.1]heptanyl, octahydroindolyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted. The term "heterocyclylene" refers to a bivalent heterocyclic group.

As used herein, the term "partially unsaturated" refers to a ring moiety that includes at least one double or triple bond between ring atoms. The term "partially unsaturated" is intended to encompass rings having multiple sites of unsaturation, but is not intended to include aryl or heteroaryl moieties, as herein defined.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

As defined herein, an alkylene chain also can be optionally replaced by a functional group. An alkylene chain is "replaced" by a functional group when an internal methylene unit is replaced with the functional group. Examples of suitable "interrupting functional groups" are described in the specification and claims herein.

Generally, the suffix "-ene" is used to describe a bivalent group. Thus, any of the terms above can be modified with the suffix "-ene" to describe a bivalent version of that moiety. For example, a bivalent carbocycle is "carbocyclylene", a bivalent aryl ring is "arylene", a bivalent benzene ring is "phenylene", a bivalent heterocycle is "heterocyclylene", a bivalent heteroaryl ring is "heteroarylene", a bivalent alkyl chain is "alkylene", a bivalent alkenyl chain is "alkenylene", a bivalent alkynyl chain is "alkynylene", and so forth.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned under this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH═CHPh, which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; —SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet_2$, —NO$_2$, —SiR$^\bullet_3$, —OSiR$^\bullet_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include ═O and ═S.

Suitable divalent substituents on a saturated carbon atom of an "optionally substituted" group include the following: ═O, ═S, ═NNR$^*_2$, ═NNHC(O)R$^*$, ═NNHC(O)OR$^*$, ═NNHS(O)$_2$R$^*$, ═NR$^*$, ═NOR$^*$, —O(C(R$^*_2$))$_{2-3}$O—, or —S(C(R$^*_2$))$_{2-3}$S—, wherein each independent occurrence of R$^*$ is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR$^*_2$)$_{2-3}$O—, wherein each independent occurrence of R$^*$ is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R$^*$ include halogen, —R$^\bullet$, -(haloR$^\bullet$), —OH, —OR$^\bullet$, —O(haloR$^\bullet$), —CN, —C(O)OH, —C(O)OR●, —NH₂, —NHR●, —NR●₂, or —NO₂, wherein each R● is unsubstituted or where preceded by "halo" is substituted only with one or more halogens, and is independently C₁₋₄ aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†₂, —C(O)R†, —C(O)OR†, —C(O)C(O)R†, —C(O)CH₂C(O) R†, —S(O)₂R†, —S(O)₂NR†₂, —C(S)NR†₂, —C(NH)NR†₂, or —N(R†)S(O)₂R†; wherein each R† is independently hydrogen, C₁₋₆ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur. Suitable substituents on the aliphatic group of R† are independently halogen, —R●, -(haloR●), —OH, —OR●, —O(haloR●), —CN, —C(O) OH, —C(O)OR●, —NH₂, —NHR●, —NR●₂, or —NO₂, wherein each R● is unsubstituted or where preceded by "halo" is substituted only with one or more halogens, and is independently C₁₋₄aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur.

3. Description of Exemplary Compounds:

As defined above, L¹ is a covalent bond or an optionally substituted bivalent group selected from C₁₋₄ alkylene, C₂₋₄ alkenylene, or C₂₋₄ alkynylene wherein one or more methylene units of L¹ are optionally and independently replaced by -Cy¹-, —O—, —S—, —N(R²)—, —C(O)—, —C(O)N (R²)—, —N(R²)C(O)N(R²)—, —N(R²)C(O)—, —N(R²)C (O)O—, —OC(O)N(R²)—, —S(O)₂—, —S(O)₂N(R²)—, —N(R²)S(O)₂—, —OC(O)—, or —C(O)O, wherein R² is as defined and described herein. In some embodiments, L¹ is a covalent bond. In certain embodiments, L¹ is a single bond. In some embodiments, L¹ is an optionally substituted C₁₋₄ alkylene group wherein one or more methylene units of L¹ are optionally and independently replaced by —O—, —S—, —N(R²)—, —C(O)—, —C(O)N(R²)—, —N(R²)C (O)N(R²)—, —N(R²)C(O)—, —N(R²)C(O)O—, —OC(O) N(R²)—, —S(O)₂—, —S(O)₂N(R²)—, —N(R²)S(O)₂—, —OC(O)—, or —C(O)O. In other embodiments, L¹ is an optionally substituted C₂₋₄ alkyenylene group. In yet other embodiments, L¹ is an optionally substituted C₂₋₄ alkynylene group. In certain embodiments, L¹ is optionally substituted C₁₋₃ alkylene, optionally substituted C₂₋₃ alkylene, or optionally substituted C₂₋₃ alkynylene. In certain other embodiments, L¹ is optionally substituted —O—C₁₋₃ alkylene. In some embodiments, L¹ is optionally substituted methylene. In certain embodiments, L¹ is unsubstituted methylene. In certain embodiments, L¹ is propenylene or propynylene. In certain embodiments, L¹ is optionally substituted —O—C₂ alkylene, C₃ alkylene, or C₃ alkynylene. In some embodiments, L¹ is substituted with an optionally substituted group selected from alkyl, cycloalkyl, aryl, or heteroaryl. In certain embodiments, L¹ is —O—C₂ alkylene, C₃ alkenylene, or C₃ alkynylene, wherein L¹ is substituted with an optionally substituted group selected from C₁₋₄ alkyl, a 3-7 membered carbocyclic ring, a 4-7 membered heterocyclic ring having 1-2 heteroatoms selected from nitrogen, oxygen, or sulfur, phenyl, or a 5-6 membered heteroaryl ring having 1-3 heteroatoms selected from nitrogen, oxygen, or sulfur. In certain embodiments, L¹ is —O—C₂ alkylene, C₃ alkenylene, or C₃ alkynylene, wherein L¹ is substituted with methyl, cyclopropyl, oxetanyl, azetidinyl, phenyl, or pyridyl. In certain embodiments, L¹ is substituted with —(CH₂)₀₋₄CO₂R° or —(CH₂)₀₋₄CON (R°)₂. In certain embodiments, a substituent on L¹ is of the R stereochemistry. In certain embodiments, a substituent on L¹ is of the S stereochemistry. In certain embodiments, L¹ is one of the following:

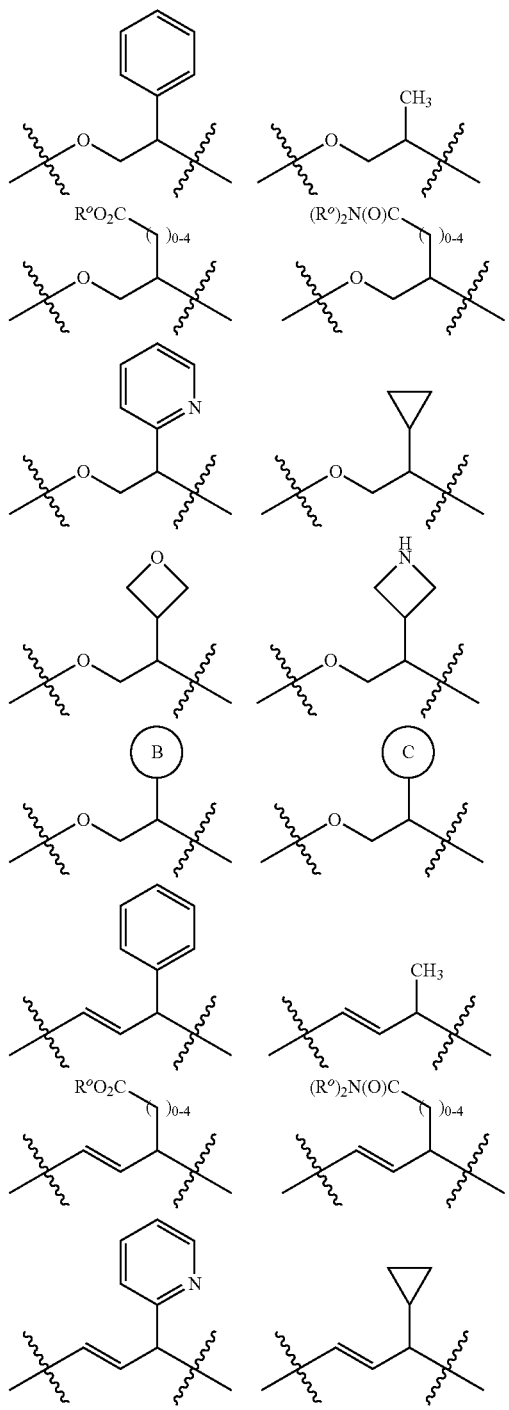

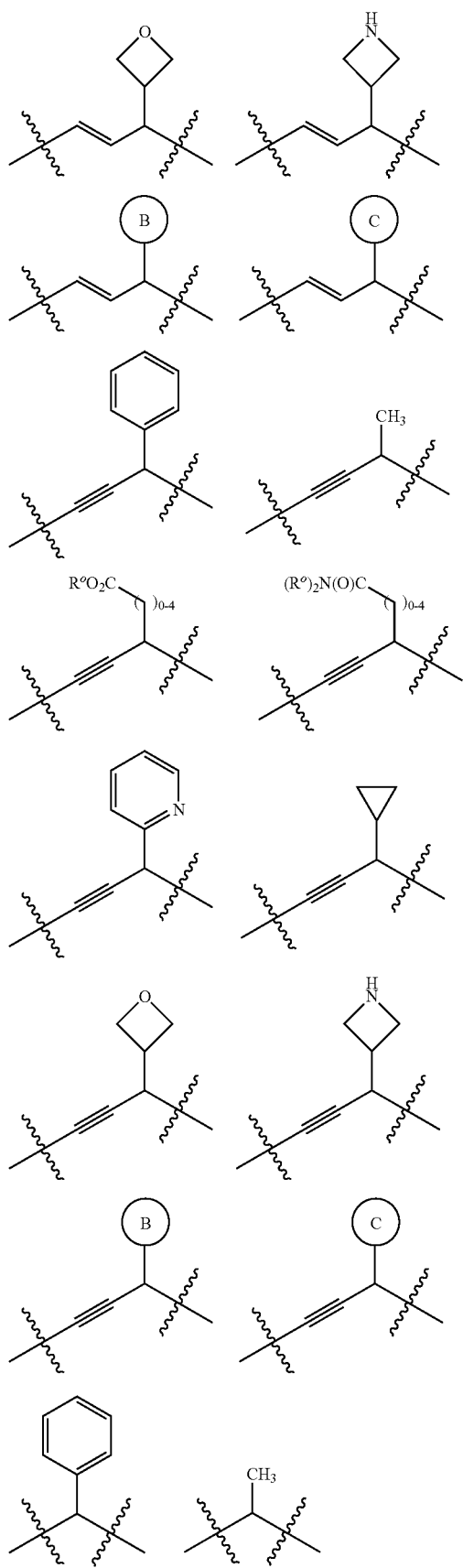
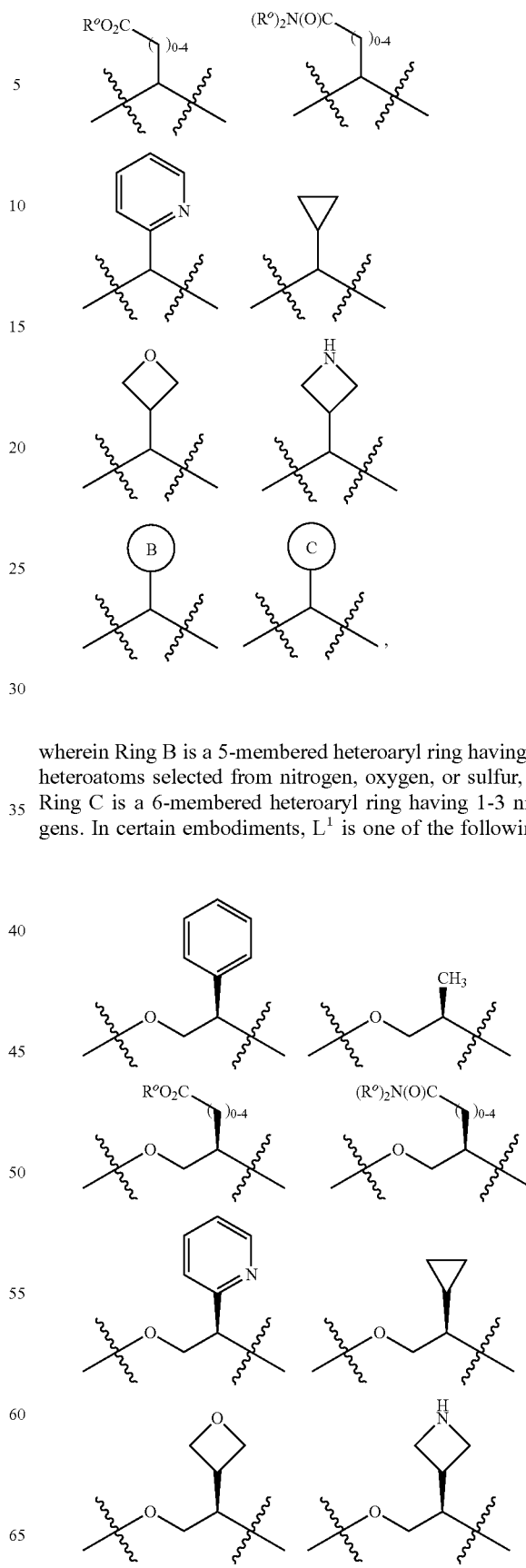
wherein Ring B is a 5-membered heteroaryl ring having 1-3 heteroatoms selected from nitrogen, oxygen, or sulfur, and Ring C is a 6-membered heteroaryl ring having 1-3 nitrogens. In certain embodiments, $L^1$ is one of the following:

-continued

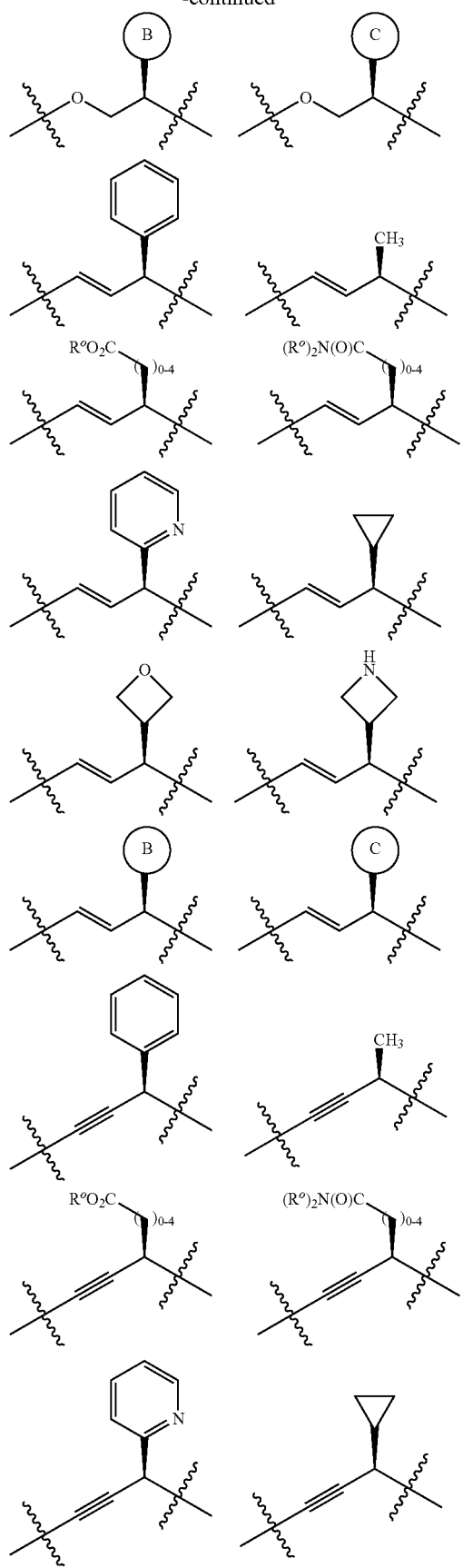

-continued

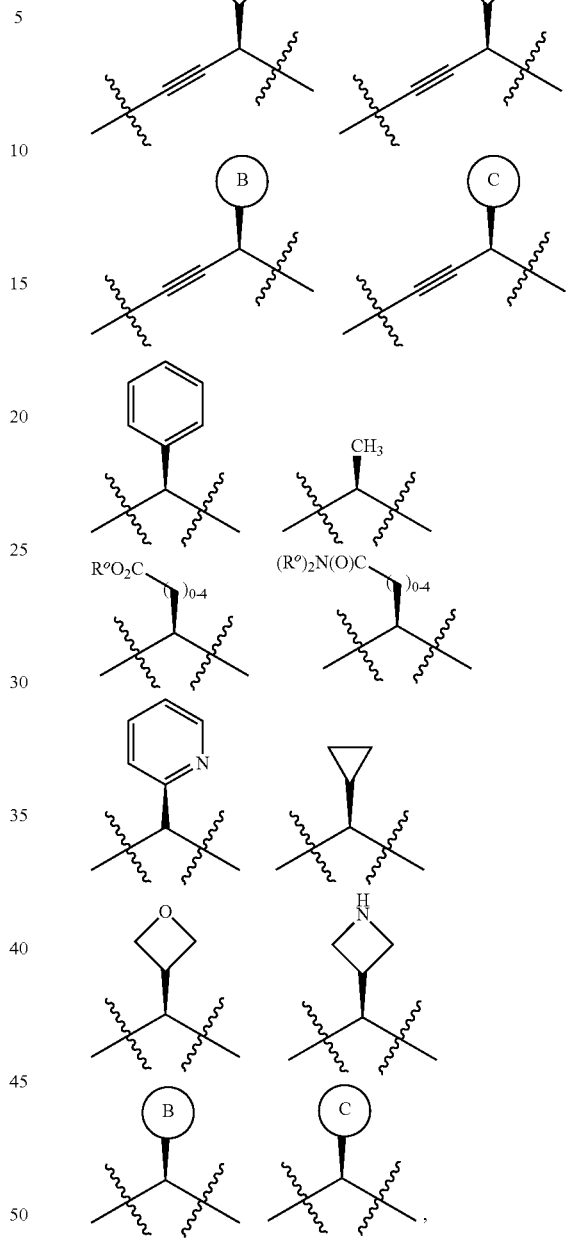

In some embodiments, $L^1$ comprises -Cy$^1$-. As defined above, -Cy$^1$- is an optionally substituted bivalent ring selected from phenylene, 3-7 membered saturated or partially unsaturated carbocyclylene, 4-7 membered saturated or partially unsaturated heterocyclylene having 1-2 heteroatoms independently selected from nitrogen, oxygen, or sulfur, or 5-6 membered heteroarylene having 1-3 heteroatoms independently selected from nitrogen, oxygen, or sulfur. In some embodiments, $L^1$ comprises phenylene. In some embodiments, $L^1$ is phenylene. In some embodiments, $L^1$ comprises 3-7 membered saturated or partially unsaturated carbocyclylene. In certain embodiments, $L^1$ is 3-7 membered saturated or partially unsaturated carbocyclylene. In some embodiments, $L^1$ comprises 4-7 membered saturated or partially unsaturated heterocyclylene having 1-2 heteroatoms independently selected from nitrogen, oxygen, or sulfur. In certain embodiments, L¹ is 4-7 membered saturated or partially unsaturated heterocyclylene having 1-2 heteroatoms independently selected from nitrogen, oxygen, or sulfur. In some embodiments, L¹ comprises a 5-6 membered heteroarylene having 1-3 heteroatoms independently selected from nitrogen, oxygen, or sulfur. In certain embodiments, L¹ comprises a 5-6 membered heteroarylene having 1-3 heteroatoms independently selected from nitrogen, oxygen, or sulfur.

As defined above, A₁ is a covalent bond or an optionally substituted bivalent ring selected from 3-7 membered saturated or partially unsaturated monocyclic carbocyclylene, 7-10 membered saturated or partially unsaturated bicyclic carbocyclylene, 4-7 membered saturated or partially unsaturated monocyclic heterocyclylene having 1-2 heteroatoms independently selected from nitrogen, oxygen, or sulfur, 7-10 membered saturated or partially unsaturated bicyclic heterocyclylene having 1-3 heteroatoms independently selected from nitrogen, oxygen, or sulfur, phenylene, 8-10 membered bicyclic arylene, 5-6 membered monocyclic heteroarylene having 1-3 heteroatoms independently selected from nitrogen, oxygen, or sulfur, or 8-10 membered bicyclic heteroarylene having 1-4 heteroatoms independently selected from nitrogen, oxygen, or sulfur. In some embodiments, A₁ is a covalent bond. In certain embodiments, A₁ is a single bond.

In some embodiments, A₁ is an optionally substituted bivalent ring selected from 3-7 membered saturated or partially unsaturated carbocyclylene, 7-10 membered saturated or partially unsaturated bicyclic carbocyclylene, 4-7 membered saturated or partially unsaturated heterocyclylene having 1-2 heteroatoms independently selected from nitrogen, oxygen, or sulfur, or 7-10 membered saturated or partially unsaturated bicyclic heterocyclylene having 1-3 heteroatoms independently selected from nitrogen, oxygen, or sulfur.

In some embodiments, A₁ is optionally substituted 5-10 membered carbocyclylene. In certain embodiments, A₁ is cyclopentylene or cyclohexylene. In other embodiments, A₁ is optionally substituted 5-10 membered heterocyclylene. In certain embodiments, A₁ is oxiranylene, oxetanylene, tetrahydrofuranylene, tetrahydropyranylene, oxepaneylene, aziridineylene, azetidineylene, pyrrolidinylene, piperidinylene, azepanylene, thiiranylene, thietanylene, tetrahydrothiophenylene, tetrahydrothiopyranylene, thiepanylene, dioxolanylene, oxathiolanylene, oxazolidinylene, imidazolidinylene, thiazolidinylene, dithiolanylene, dioxanylene, morpholinylene, oxathianylene, piperazinylene, thiomorpholinylene, dithianylene, dioxepanylene, oxazepanylene, oxathiepanylene, dithiepanylene, diazepanylene, dihydrofuranonylene, tetrahydropyranonylene, oxepanonylene, pyrolidinonylene, piperidinonylene, azepanonylene, dihydrothiophenonylene, tetrahydrothiopyranonylene, thiepanonylene, oxazolidinonylene, oxazinanonylene, oxazepanonylene, dioxolanonylene, dioxanonylene, dioxepanonylene, oxathiolinonylene, oxathianonylene, oxathiepanonylene, thiazolidinonylene, thiazinanonylene, thiazepanonylene, imidazolidinonylene, tetrahydropyrimidinonylene, diazepanonylene, imidazolidinedionylene, oxazolidinedionylene, thiazolidinedionylene, dioxolanedionylene, oxathiolanedionylene, piperazinedionylene, morpholinedionylene, thiomorpholinedionylene, tetrahydropyranylene, tetrahydrofuranylene, morpholinylene, thiomorpholinylene, piperidinylene, piperazinylene, pyrrolidinylene, tetrahydrothiophenylene, or tetrahydrothiopyranylene.

In some embodiments, A₁ is an optionally substituted bivalent ring selected from phenylene, 8-10 membered bicyclic arylene, 5-6 membered heteroarylene having 1-3 heteroatoms independently selected from nitrogen, oxygen, or sulfur, or 8-10 membered bicyclic heteroarylene having 1-4 heteroatoms independently selected from nitrogen, oxygen, or sulfur. In certain embodiments, A₁ is phenylene. In some embodiments, A₁ is 8-10 membered arylene. In other embodiments, A₁ is 5-10 membered heteroarylene. In certain embodiments, A₁ is 5-6 membered heteroarylene. In certain embodiments, A₁ is thienylene, furanylene, pyrrolylene, imidazolylene, pyrazolylene, triazolylene, tetrazolylene, oxazolylene, isoxazolylene, oxadiazolylene, thiazolylene, isothiazolylene, thiadiazolylene, pyridylene, pyridazinylene, pyrimidinylene, pyrazinylene, indolizinylene, purinylene, naphthyridinylene, pteridinylene, indolylene, isoindolylene, benzothienylene, benzofuranylene, dibenzofuranylene, indazolylene, benzimidazolylene, benzthiazolylene, quinolylene, isoquinolylene, cinnolinylene, phthalazinylene, quinazolinylene, quinoxalinylene, 4H-quinolizinylene, carbazolylene, acridinylene, phenazinylene, phenothiazinylene, phenoxazinylene, tetrahydroquinolinylene, tetrahydroisoquinolinylene, pyrido[2,3-b]-1,4-oxazin-3(4H)-onylene, or chromanylene.

In certain embodiments, A, is an optionally substituted bivalent ring selected from:

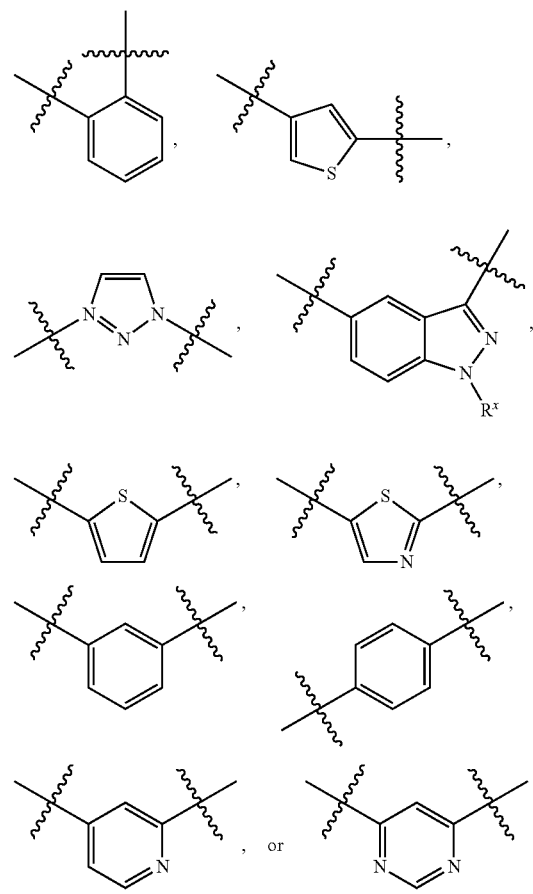

In certain other embodiments, A₁ is an optionally substituted bivalent ring selected from:

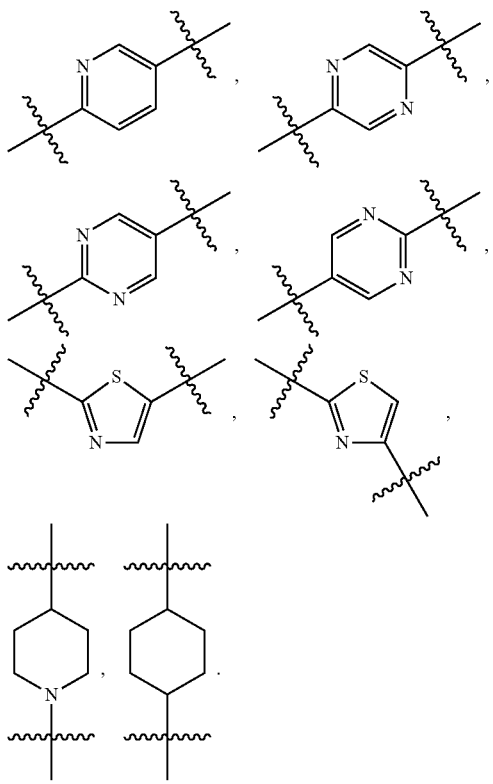

As defined above, L² is a covalent bond, alkylidenylene, or an optionally substituted alkylene chain wherein one or more methylene units of L² are optionally and independently replaced by —O—, —S—, —N(R²)—, —C(O)—, —C(O)N(R²)—, —N(R²)C(O)N(R²)—, —N(R²)C(O)—, —N(R²)C(O)O—, —OC(O)N(R²)—, —S(O)₂—, —S(O)₂N(R²)—, —N(R²)S(O)₂—, —OC(O)—, or —C(O)O—, wherein R² is as defined and described herein. In some embodiments, L² is a covalent bond. In certain embodiments, L² is a single bond, a double bond or a triple bond. In certain embodiments, L² is alkylidenylene. In certain other embodiments, L² is —O—. In other embodiments, L² is not a C₁ alkylene replaced by a bivalent oxygen. In some embodiments, L² is —N(R²)—, —S—, —S(O)—, or —S(O)₂—. In other embodiments, L² is an optionally substituted alkylene chain wherein one or more methylene units of L² are optionally and independently replaced by —O—, —S—, —N(R²)—, —C(O)—, —C(O)N(R²)—, —N(R²)C(O)N(R²)—, —N(R²)C(O)—, —N(R²)C(O)O—, —OC(O)N(R²)—, —SO₂—, —SO₂N(R²)—, —N(R²)SO₂—, —OC(O)—, or —C(O)O—. In some embodiments, L² is optionally substituted C₁₋₄ alkylene. In certain embodiments, L² is methylene.

As defined above, Ring A₂ is a 3-7 membered saturated or partially unsaturated monocyclic carbocyclic ring, a 7-10 membered saturated or partially unsaturated bicyclic carbocyclic ring, a 4-7 membered saturated or partially unsaturated monocyclic heterocyclic ring having 1-2 heteroatoms independently selected from nitrogen, oxygen, or sulfur, a 7-10 membered saturated or partially unsaturated bicyclic heterocyclic ring having 1-3 heteroatoms independently selected from nitrogen, oxygen, or sulfur, a phenyl ring, an 8-10 membered bicyclic aryl ring, a 5-6 membered monocyclic heteroaryl ring having 1-3 heteroatoms independently selected from nitrogen, oxygen, or sulfur, an 8-10 membered bicyclic heteroaryl ring having 1-4 heteroatoms independently selected from nitrogen, oxygen, or sulfur, or a 10-16 membered saturated, partially unsaturated, or aromatic tricyclic ring having 0-4 heteroatoms independently selected from nitrogen, oxygen, or sulfur, wherein Ring A₂ is optionally substituted with 1-4 R$^x$ groups, wherein R$^x$ is as defined and described herein.

In certain embodiments, Ring A₂ is optionally substituted with 1-4 R$^x$ groups and is selected from phenyl, an 8-10 membered bicyclic aryl ring, a 5-6 membered heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur.

In certain embodiments, Ring A₂ is an optionally substituted C₈₋₁₀ bicyclic aryl ring. In some embodiments, Ring A₂ is an optionally substituted phenyl ring. In certain embodiments, Ring A₂ is a 5-6 membered heteroaryl ring having 1-3 heteroatoms independently selected from nitrogen, oxygen, or sulfur. In certain embodiments, Ring A₂ is an 8-10 membered bicyclic heteroaryl ring having 1-4 heteroatoms independently selected from nitrogen, oxygen, or sulfur.

In some embodiments, Ring A₂ is an optionally substituted 4-7 membered saturated monocyclic heterocyclic ring having 1-2 heteroatoms independently selected from nitrogen, oxygen, or sulfur. In some embodiments, Ring A₂ is an optionally substituted 5-6 membered saturated monocyclic ring having 1-2 heteroatoms independently selected from nitrogen, oxygen, or sulfur. In some embodiments, Ring A₂ is an optionally substituted 7-10 membered saturated bicyclic ring having 1-3 heteroatoms selected from nitrogen, oxygen, or sulfur. In certain embodiments, Ring A₂ is an optionally substituted 5,6- or 6,6-fused saturated bicyclic ring having 1-3 heteroatoms independently selected from nitrogen, oxygen, or sulfur.

In certain embodiments, Ring A₂ is an optionally substituted 5-membered saturated monocyclic ring having 1-2 heteroatoms independently selected from nitrogen, oxygen, or sulfur. In some embodiments, Ring A₂ is an optionally substituted 5-membered saturated monocyclic ring having 2 heteroatoms independently selected from nitrogen, oxygen, or sulfur. In other embodiments, Ring A₂ is an optionally substituted 5-membered saturated monocyclic ring having 2 heteroatoms independently selected from nitrogen or oxygen. In certain embodiments, Ring A₂ is an optionally substituted 5-membered saturated monocyclic ring having 1 heteroatom selected from nitrogen, oxygen, or sulfur.

In certain embodiments, Ring A₂ is an optionally substituted 6-membered saturated monocyclic ring having 1-2 heteroatoms independently selected from nitrogen, oxygen, or sulfur. In some embodiments, Ring A₂ is an optionally substituted 6-membered saturated monocyclic ring having 2 heteroatoms independently selected from nitrogen, oxygen, or sulfur. In other embodiments, Ring A₂ is an optionally substituted 6-membered saturated monocyclic ring having 2 heteroatoms independently selected from nitrogen or oxygen. In certain embodiments, Ring A₂ is an optionally substituted 6-membered saturated monocyclic ring having 1 heteroatom selected from nitrogen, oxygen, or sulfur.

Exemplary Ring A₂ groups include optionally substituted octahydroazocinyl, thiocyclopentanyl, thiocyclohexanyl, pyrrolidinyl, piperidinyl, piperazinyl, tetrahydrothiopyranyl, tetrahydrothiophenyl, dithiolanyl, tetrahydrofuranyl, tetrahydropyranyl, dioxanyl, thioxanyl, morpholinyl, oxathiolanyl, imidazolidinyl, oxathiolanyl, oxazolidinyl, or thiazolidinyl groups.

In certain embodiments, Ring $A_2$ is an optionally substituted 5-membered heteroaryl ring having 1-3 heteroatoms selected from nitrogen, oxygen, or sulfur. In some embodiments, Ring $A_2$ is an optionally substituted 5-membered heteroaryl ring having 1-2 heteroatoms selected from nitrogen, oxygen, or sulfur. In other embodiments, Ring $A_2$ is an optionally substituted 5-membered heteroaryl ring having 2 heteroatoms selected from nitrogen, oxygen, or sulfur. In some embodiments, Ring $A_2$ is an optionally substituted 5-membered heteroaryl ring having 1 heteroatom selected from nitrogen, oxygen, or sulfur. In certain embodiments, Ring $A_2$ is an optionally substituted 5-membered heteroaryl ring having 1 nitrogen atom, and an additional heteroatom selected from sulfur or oxygen. Exemplary Ring $A_2$ groups include optionally substituted pyrrolyl, pyrazolyl, imidazolyl, triazolyl, tetrazolyl, thienyl, furanyl, thiazolyl, isothiazolyl, thiadiazolyl, oxazolyl, isoxazolyl, or oxadiazolyl.

In certain embodiments, Ring $A_2$ is an optionally substituted 6-membered heteroaryl ring having 1-3 nitrogens. In other embodiments, Ring $A_2$ is an optionally substituted 6-membered heteroaryl ring having 1-2 nitrogens. In some embodiments, Ring $A_2$ is an optionally substituted 6-membered heteroaryl ring having 2 nitrogens. In certain embodiments, Ring $A_2$ is an optionally substituted 6-membered heteroaryl ring having 1 nitrogen. Exemplary Ring $A_2$ groups include optionally substituted pyridinyl, pyrimidinyl, pyrazinyl, pyridazinyl, triazinyl, or tetrazinyl.

In certain embodiments, Ring $A_2$ is an optionally substituted 5-6 membered partially unsaturated monocyclic ring having 1-2 heteroatoms independently selected from nitrogen, oxygen, or sulfur. In certain embodiments, Ring $A_2$ is an optionally substituted tetrahydropyridinyl group. In some embodiments, Ring $A_2$ is an optionally substituted 7-10 membered partially unsaturated bicyclic ring having 1-3 heteroatoms independently selected from nitrogen, oxygen, or sulfur.

In certain embodiments, Ring $A_2$ is an optionally substituted 8-10 membered bicyclic heteroaryl ring having 1-4 heteroatoms independently selected from nitrogen, oxygen, or sulfur. In some embodiments, Ring $A_2$ is an optionally substituted 5,6-fused heteroaryl ring having 1-4 heteroatoms independently selected from nitrogen, oxygen, or sulfur. In other embodiments, Ring $A_2$ is an optionally substituted 5,6-fused heteroaryl ring having 1-2 heteroatoms independently selected from nitrogen, oxygen, or sulfur. In certain embodiments, Ring $A_2$ is an optionally substituted 5,6-fused heteroaryl ring having 1 heteroatom independently selected from nitrogen, oxygen, or sulfur. In some embodiments, Ring $A_2$ is an optionally substituted indole. In certain embodiments, Ring $A_2$ is an optionally substituted 5,6-fused heteroaryl ring having 2 heteroatoms independently selected from nitrogen, oxygen, or sulfur. In some embodiments, Ring $A_2$ is an optionally substituted azaindole. In some embodiments, Ring $A_2$ is an indazole. In certain embodiments, Ring $A_2$ is an optionally substituted 5,6-fused heteroaryl ring having 3 heteroatoms independently selected from nitrogen, oxygen, or sulfur.

In certain embodiments, Ring $A_2$ is an optionally substituted 6,6-fused heteroaryl ring having 1-4 heteroatoms independently selected from nitrogen, oxygen, or sulfur. In some embodiments, Ring $A_2$ is an optionally substituted 6,6-fused heteroaryl ring having 1-2 heteroatoms independently selected from nitrogen, oxygen, or sulfur. In other embodiments, Ring $A_2$ is an optionally substituted 6,6-fused heteroaryl ring having 1 heteroatom independently selected from nitrogen, oxygen, or sulfur. In some embodiments, Ring $A_2$ is a quinoline. According to one aspect, Ring $A_2$ is an optionally substituted 6,6-fused heteroaryl ring having 2 heteroatoms independently selected from nitrogen, oxygen, or sulfur. In some embodiments, Ring $A_2$ is a quinazoline or a quinoxaline.

In certain embodiments, Ring $A_2$ is an optionally substituted 10-16 membered saturated tricyclic ring having 0-4 heteroatoms selected from nitrogen, oxygen, or sulfur. In some embodiments, Ring $A_2$ is an optionally substituted 10-16 membered partially unsaturated tricyclic ring having 0-4 heteroatoms selected from nitrogen, oxygen, or sulfur. In other embodiments, Ring $A_2$ is an optionally substituted 10-16 membered aromatic tricyclic ring having 0-4 heteroatoms selected from nitrogen, oxygen, or sulfur.

In certain embodiments, Ring $A_2$ is optionally substituted with 1-4 $R^x$ groups and is selected from:

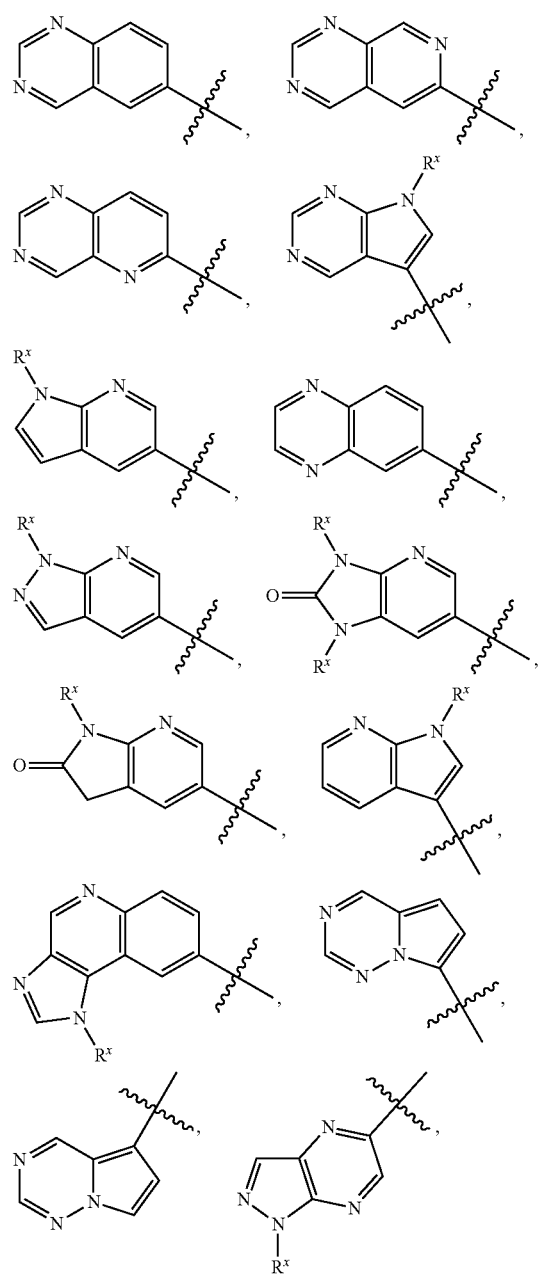

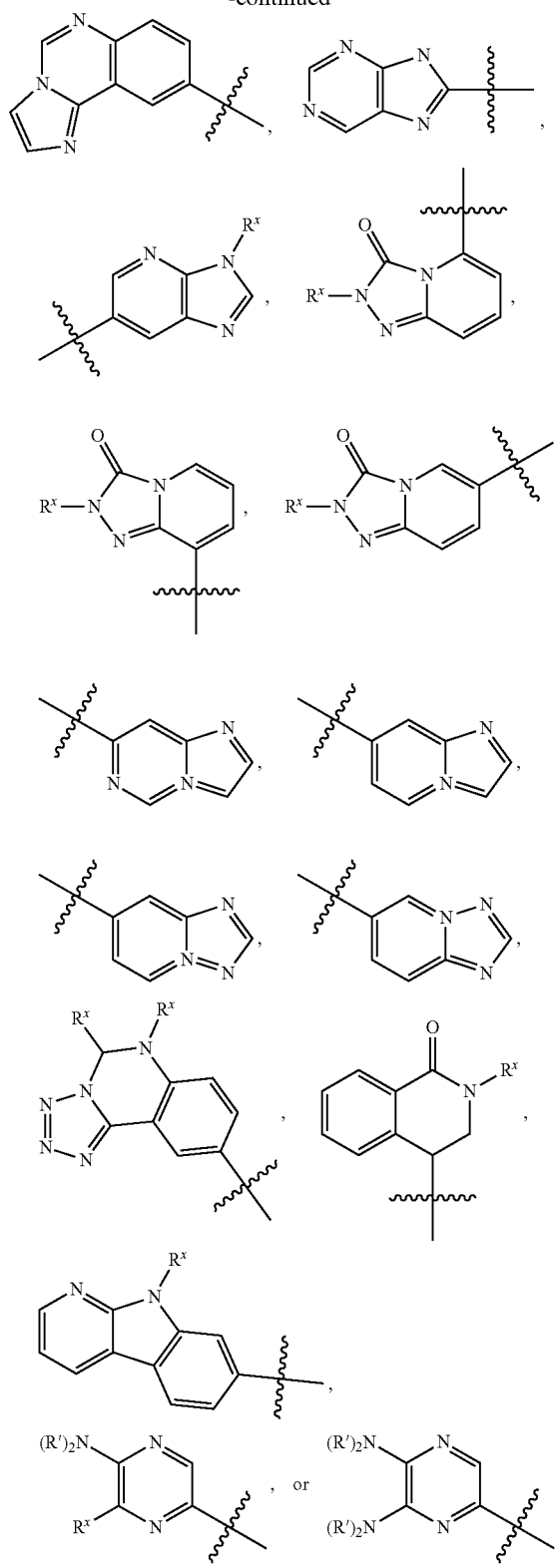

wherein each R^x on a nitrogen is independently hydrogen or C_{1-4} alkyl. In some embodiments, a carbon on one of the rings shown above is substituted with R^x. In certain other embodiments, A_2 is optionally substituted with 1-4 R^x groups and is selected from:

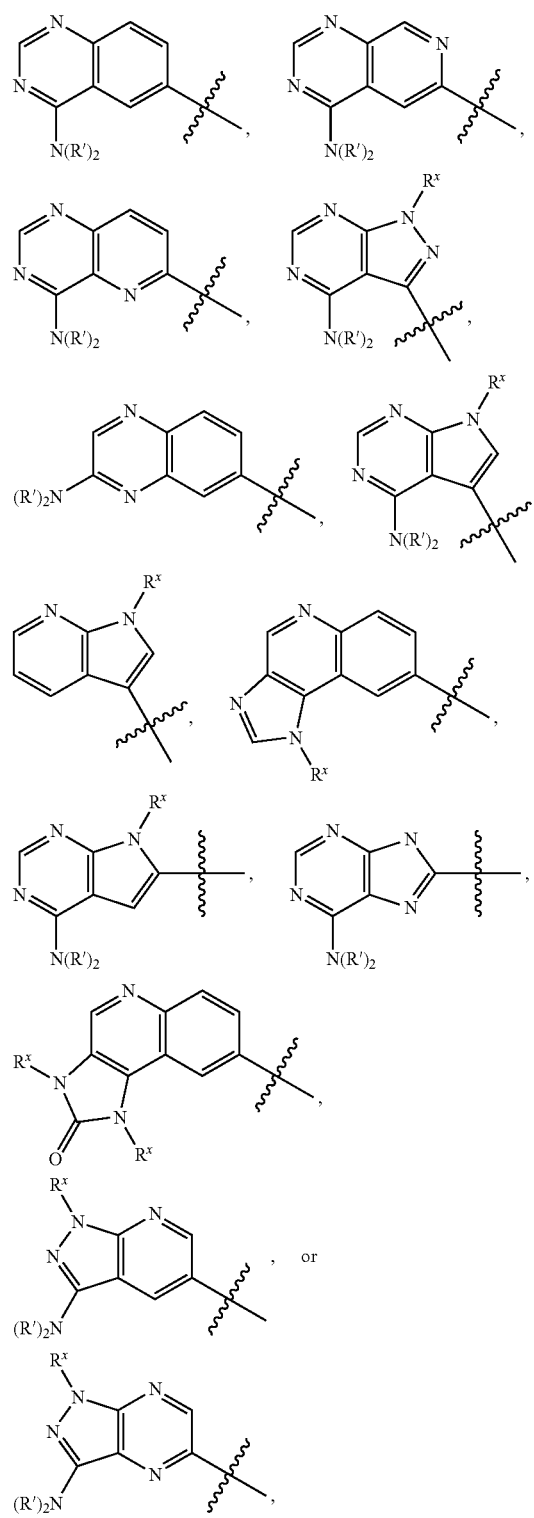

wherein each R^x on a nitrogen is independently hydrogen or C_{1-4} alkyl and each R' is independently hydrogen or C_{1-4} alkyl, or two R' on the same nitrogen are taken together with the intervening nitrogen to form a 4-7 membered heterocylic ring having 1-2 heteroatoms independently selected from nitrogen, oxygen, or sulfur. In some embodiments, a carbon on one of the rings shown above is substituted with R^x.

In certain embodiments, $A_2$ is

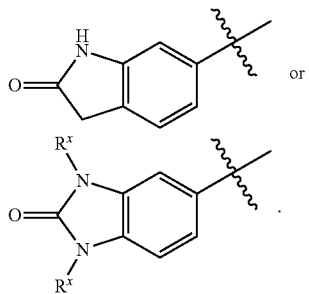

or

In certain embodiments, $A_2$ is optionally substituted with 1-4 $R^x$ groups and is selected from

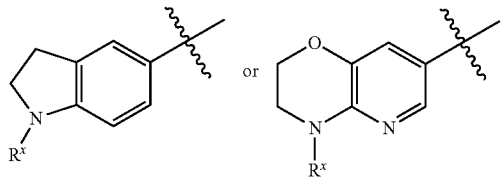

wherein each $R^x$ on a nitrogen is independently hydrogen or $C_{1-4}$ alkyl.

In certain embodiments, $A_2$ optionally substituted with 1-4 $R^x$ groups and is selected from

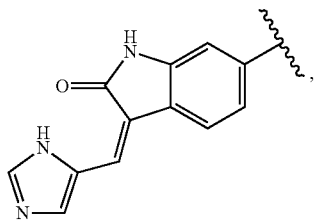

As defined above, each $R^x$ is independently —R, optionally substituted alkylidenyl, oxo, -halo, —NO$_2$, —CN, —OR, —SR, —N(R')$_2$, —C(O)R, —CO$_2$R, —C(O)C(O)R, —C(O)CH$_2$C(O)R, —S(O)R, —S(O)$_2$R, —C(O)N(R')$_2$, —S(O)$_2$N(R')$_2$, —OC(O)R, —N(R')C(O)R, —N(R')N(R')$_2$, —N(R')OR, —N(R')C(=NR')N(R')$_2$, —C(=NR')N(R')$_2$, —C=NOR, —N(R')C(O)N(R')$_2$, —N(R')S(O)$_2$N(R')$_2$, —N(R')S(O)$_2$R, or —OC(O)N(R')$_2$. In some embodiments, $R^x$ is —R. In certain embodiments, $R^x$ is hydrogen. In certain embodiments, $R^x$ is optionally substituted alkylidenyl. In certain embodiments, $R^x$ is alkylidenyl substituted with a heteroaryl group. In some embodiments, $R^x$ is $C_{1-4}$ alkyl. In certain embodiments, $R^x$ is methyl. In some embodiments, $R^x$ is —N(R')$_2$. In certain embodiments, $R^x$ is —NH$_2$. In certain embodiments, $R^x$ is —NH(R'). In some embodiments, $R^x$ is —C(O)N(R')$_2$. In certain embodiments, $R^x$ is —C(O)NH(R'). In certain embodiments, $R^x$ is —C(O)NH ($C_{1-4}$ alkyl). In certain embodiments, $R^x$ is —C(O)NH(cycloalkyl). In some embodiments, $R^x$ is a 4-7 membered heterocyclic group having 1-2 heteroatoms selected from nitrogen, oxygen, or sulfur. In certain embodiments, $R^x$ is a 4-7 membered heterocyclic group having 1 nitrogen. In certain embodiments, $R^x$ is azetidinyl. In certain embodiments, $R^x$ is oxo. In some embodiments, $R^x$ is —N(R')OR. In certain embodiments, $R^x$ is —NHOCH$_3$.

As defined above, $L^3$ is a covalent bond or an optionally substituted $C_{1-4}$ alkylene chain wherein one or more methylene units of $L^3$ are optionally and independently replaced by —O—, —S—, —N(R$^2$)—, —C(O)—, —C(O)N(R$^2$)—, —N(R$^2$)C(O)N(R$^2$)—, —N(R$^2$)C(O)—, —N(R$^2$)C(O)O—, —OC(O)N(R$^2$)—, —SO$_2$—, —SO$_2$N(R$^2$)—, —N(R$^2$)SO$_2$—, —OC(O)—, or —C(O)O—, wherein R$^2$ is as defined and described herein. In some embodiments, $L^3$ is a covalent bond. In certain embodiments, $L^3$ is a single bond. In some embodiments, $L^3$ is optionally substituted $C_{1-4}$ alkylene. In some embodiments, $L^3$ is unsubstituted. In some embodiments, $L^3$ is an optionally substituted methylene. In certain embodiments, $L^3$ is unsubstituted methylene. In certain other embodiments, $L^3$ is substituted methylene. In certain embodiments, $L^3$ is methylene substituted with methyl or ethyl. In certain embodiments, the substituent on $L^3$ is of the R stereochemistry. In certain embodiments, the substituent on $L^3$ is of the S stereochemistry. In certain embodiments, $L^3$ is

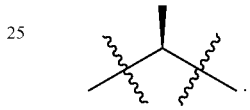

As defined above, Ring $A_3$ is an optionally substituted ring selected from a 3-7 membered saturated or partially unsaturated monocyclic carbocyclic ring, a 7-10 membered saturated or partially unsaturated bicyclic carbocyclic ring, a 4-7 membered saturated or partially unsaturated monocyclic heterocyclic ring having 1-2 heteroatoms independently selected from nitrogen, oxygen, or sulfur, a 7-10 membered saturated or partially unsaturated bicyclic heterocyclic ring having 1-3 heteroatoms independently selected from nitrogen, oxygen, or sulfur, a phenyl ring, an 8-10 membered bicyclic aryl ring, a 5-6 membered monocyclic heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur.

In certain embodiments, Ring $A_3$ is an optionally substituted 8-10 membered bicyclic aryl ring. In some embodiments, Ring $A_3$ is an optionally substituted phenyl ring. In some embodiments, Ring $A_3$ is a cyclopropyl ring. In some embodiments, Ring $A_3$ is an optionally substituted cyclopentyl ring. In some embodiments, Ring $A_3$ is an optionally substituted cyclohexyl ring. In some embodiments, Ring $A_3$ is an optionally substituted cycloheptyl ring.

In some embodiments, Ring $A_3$ is an optionally substituted 4-7 membered saturated heterocyclic ring having 1-2 heteroatoms independently selected from nitrogen, oxygen, or sulfur. In some embodiments, Ring $A_3$ is an optionally substituted 4-membered saturated heterocyclic ring having 1 heteroatom independently selected from nitrogen, oxygen or sulfur. In some embodiments, Ring $A_3$ is an oxetane. In some embodiments, Ring $A_3$ is an azetidine. In some embodiments, Ring $A_3$ is an optionally substituted 5-6 membered saturated monocyclic ring having 1-2 heteroatoms independently selected from nitrogen, oxygen, or sulfur. In some embodiments, Ring $A_3$ is an optionally substituted 7-10 membered saturated bicyclic ring having 1-3 heteroatoms selected from nitrogen, oxygen, or sulfur. In certain embodiments, Ring $A_3$ is an optionally substituted 5,6- or 6,6-fused saturated bicyclic ring having 1-3 heteroatoms independently selected from nitrogen, oxygen, or sulfur.

In certain embodiments, Ring $A_3$ is an optionally substituted 5-membered saturated monocyclic ring having 1-2 heteroatoms independently selected from nitrogen, oxygen, or sulfur. In some embodiments, Ring $A_3$ is an optionally substituted 5-membered saturated monocyclic ring having 2 heteroatoms independently selected from nitrogen, oxygen, or sulfur. In other embodiments, Ring $A_3$ is an optionally substituted 5-membered saturated monocyclic ring having 2 heteroatoms independently selected from nitrogen or oxygen. In certain embodiments, Ring $A_3$ is an optionally substituted 5-membered saturated monocyclic ring having 1 heteroatom selected from nitrogen, oxygen, or sulfur.

In certain embodiments, Ring $A_3$ is an optionally substituted 6-membered saturated monocyclic ring having 1-2 heteroatoms independently selected from nitrogen, oxygen, or sulfur. In some embodiments, Ring $A_3$ is an optionally substituted 6-membered saturated monocyclic ring having 2 heteroatoms independently selected from nitrogen, oxygen, or sulfur. In other embodiments, Ring $A_3$ is an optionally substituted 6-membered saturated monocyclic ring having 2 heteroatoms independently selected from nitrogen or oxygen. In certain embodiments, Ring $A_3$ is an optionally substituted 6-membered saturated monocyclic ring having 1 heteroatom selected from nitrogen, oxygen, or sulfur.

Exemplary Ring $A_3$ groups include optionally substituted octahydroazocinyl, thiocyclopentanyl, thiocyclohexanyl, pyrrolidinyl, piperidinyl, piperazinyl, tetrahydrothiopyranyl, tetrahydrothiophenyl, dithiolanyl, tetrahydrofuranyl, tetrahydropyranyl, dioxanyl, thioxanyl, morpholinyl, oxathiolanyl, imidazolidinyl, oxathiolanyl, oxazolidinyl, or thiazolidinyl.

In certain embodiments, Ring $A_3$ is an optionally substituted 5-membered heteroaryl ring having 1-3 heteroatoms selected from nitrogen, oxygen, or sulfur. In some embodiments, Ring $A_3$ is an optionally substituted 5-membered heteroaryl ring having 1-2 heteroatoms selected from nitrogen, oxygen, or sulfur. In other embodiments, Ring $A_3$ is an optionally substituted 5-membered heteroaryl ring having 2 heteroatoms selected from nitrogen, oxygen, or sulfur. In some embodiments, Ring $A_3$ is an optionally substituted 5-membered heteroaryl ring having 1 heteroatom selected from nitrogen, oxygen, or sulfur. In certain embodiments, Ring $A_3$ is an optionally substituted 5-membered heteroaryl ring having 1 nitrogen atom, and an additional heteroatom selected from sulfur or oxygen. Exemplary Ring $A_3$ groups include optionally substituted pyrrolyl, pyrazolyl, imidazolyl, triazolyl, tetrazolyl, thienyl, furanyl, thiazolyl, isothiazolyl, thiadiazolyl, oxazolyl, isoxazolyl, or oxadiaziolyl group.

In certain embodiments, Ring $A_3$ is an optionally substituted 6-membered heteroaryl ring having 1-3 nitrogens. In other embodiments, Ring $A_3$ is an optionally substituted 6-membered heteroaryl ring having 1-2 nitrogens. In some embodiments, Ring $A_3$ is an optionally substituted 6-membered heteroaryl ring having 2 nitrogens. In certain embodiments, Ring $A_3$ is an optionally substituted 6-membered heteroaryl ring having 1 nitrogen. Exemplary Ring $A_3$ groups include optionally substituted pyridinyl, pyrimidinyl, pyrazolyl, pyrazinyl, pyridazinyl, triazinyl, or tetrazinyl.

In certain embodiments, Ring $A_3$ is an optionally substituted 5-6 membered partially unsaturated monocyclic ring having 1-2 heteroatoms independently selected from nitrogen, oxygen, or sulfur. In certain embodiments, Ring $A_3$ is an optionally substituted tetrahydropyridinyl group. In some embodiments, Ring $A_3$ is an optionally substituted 7-10 membered partially unsaturated bicyclic ring having 1-3 heteroatoms independently selected from nitrogen, oxygen, or sulfur.

In certain embodiments, Ring $A_3$ is an optionally substituted 8-10 membered bicyclic heteroaryl ring having 1-4 heteroatoms independently selected from nitrogen, oxygen, or sulfur. In certain embodiments, Ring $A_3$ is an optionally substituted 7-10 membered saturated or partially unsaturated bicyclic heterocyclic ring having 1-3 heteroatoms independently selected from nitrogen, oxygen, or sulfur. In some embodiments, Ring $A_3$ is an indoline ring. In some embodiments, Ring $A_3$ is a tetrahydroisoquinoline ring. In some embodiments, Ring $A_3$ is an optionally substituted 5,6-fused heteroaryl ring having 1-4 heteroatoms independently selected from nitrogen, oxygen, or sulfur. In other embodiments, Ring $A_3$ is an optionally substituted 5,6-fused heteroaryl ring having 1-2 heteroatoms independently selected from nitrogen, oxygen, or sulfur. In some embodiments, Ring $A_3$ is a benzoxazole or a benzimidazole. In some embodiments, Ring $A_3$ is a quinoline ring. In certain embodiments, Ring $A_3$ is an optionally substituted 5,6-fused heteroaryl ring having 1 heteroatom independently selected from nitrogen, oxygen, or sulfur.

In certain embodiments, Ring $A_3$ is an optionally substituted 6,6-fused heteroaryl ring having 1-4 heteroatoms independently selected from nitrogen, oxygen, or sulfur. In some embodiments, Ring $A_3$ is an optionally substituted 6,6-fused heteroaryl ring having 1-2 heteroatoms independently selected from nitrogen, oxygen, or sulfur. In other embodiments, Ring $A_3$ is an optionally substituted 6,6-fused heteroaryl ring having 1 heteroatom independently selected from nitrogen, oxygen, or sulfur. According to one aspect, Ring $A_3$ is an optionally substituted 6,6-fused heteroaryl ring having 2 heteroatoms independently selected from nitrogen, oxygen, or sulfur.

In certain embodiments, Ring $A_3$ is phenyl, an 8-10 membered bicyclic aryl ring, a 5-6 membered heteroaryl ring having 1-3 heteroatoms independently selected from nitrogen, oxygen, or sulfur, or an 8-10 membered bicyclic heteroaryl ring having 1-4 heteroatoms selected from nitrogen, oxygen, or sulfur, wherein Ring $A_3$ is optionally substituted with one or more halo or alkyl groups.

In certain embodiments, Ring $A_3$ is optionally substituted phenyl. In certain embodiments, Ring $A_3$ is substituted with at least one halogen. In certain embodiments, Ring $A_3$ is substituted with at least one fluorine. In other embodiments, Ring $A_3$ is substituted with at least one chlorine. In other embodiments, Ring $A_3$ is substituted with at least one alkyl group. In some embodiments, Ring $A_3$ is substituted with at least one trifluoromethyl group. In other embodiments, Ring $A_3$ is substituted with at least one methoxy group. In some embodiments, Ring $A_3$ is substituted at the para position. In some embodiments, Ring $A_3$ is substituted at the meta position. In certain embodiments, Ring $A_3$ is one of the following:

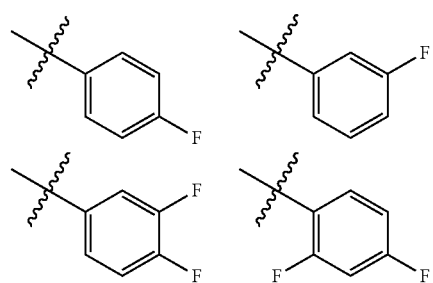

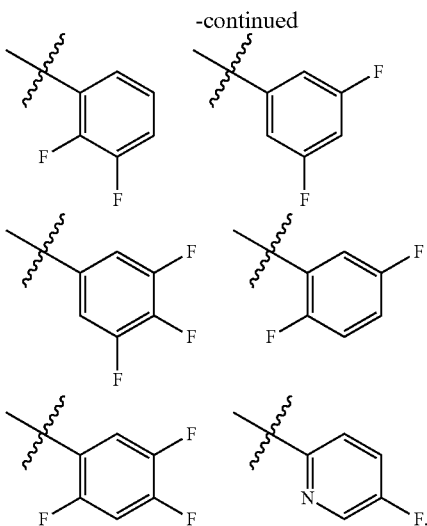

As defined above, X is —C(O)— or —S(O)$_2$—. In certain embodiments, X is —C(O)—. In other embodiments, X is —S(O)$_2$—.

As defined above, Ring $A_4$ is a 5-6 membered heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur; wherein any substitutable carbon on Ring $A_4$ is optionally substituted with $R^3$, $R^4$, or $R^5$, and any substitutable nitrogen on Ring $A^4$ is optionally substituted with $R^6$, wherein $R^3$, $R^4$, $R^5$, and $R^6$ are as defined and described herein. One of ordinary skill in the art will appreciate that the explicit nitrogen of Ring $A_4$ is alpha to the methine, i.e. the point of attachment of Ring $A_4$ to -L$^1$-NH—.

In certain embodiments, Ring $A_4$ is an optionally substituted 5-membered heteroaryl ring having 1-3 heteroatoms selected from nitrogen, oxygen, or sulfur. In some embodiments, Ring $A_4$ is an optionally substituted 5-membered heteroaryl ring having 1-2 heteroatoms selected from nitrogen, oxygen, or sulfur. In other embodiments, Ring $A_4$ is an optionally substituted 5-membered heteroaryl ring having 2 heteroatoms selected from nitrogen, oxygen, or sulfur. According to one aspect, Ring $A_4$ is an optionally substituted 5-membered heteroaryl ring having 1 heteroatom selected from nitrogen, oxygen, or sulfur. In certain embodiments, Ring $A_4$ is an optionally substituted 5-membered heteroaryl ring having 1 nitrogen, and an additional heteroatom selected from sulfur or oxygen. Exemplary Ring $A_4$ groups include optionally substituted pyrrolyl, pyrazolyl, imidazolyl, triazolyl, tetrazolyl, thiazolyl, isothiazolyl, thiadiazolyl, oxazolyl, isoxazolyl, or oxadiazolyl.

In certain embodiments, Ring $A_4$ is an optionally substituted 6-membered heteroaryl ring having 1-3 nitrogens. In other embodiments, Ring $A_4$ is an optionally substituted 6-membered heteroaryl ring having 1-2 nitrogen atoms. In some embodiments, Ring $A_4$ is an optionally substituted 6-membered heteroaryl ring having 2 nitrogens. Exemplary $A_4$ groups include an optionally substituted pyridinyl, pyrimidinyl, pyrazolyl, pyrazinyl, pyridazinyl, triazinyl, or tetrazinyl.

In certain embodiments, Ring $A_4$ is an optionally substituted 8-10 membered aromatic bicyclic heteroaryl ring having 1-4 heteroatoms independently selected from nitrogen, oxygen, or sulfur. In some embodiments, Ring $A_4$ is an optionally substituted 5,6-fused heteroaryl ring having 1-4 heteroatoms independently selected from nitrogen, oxygen, or sulfur. In other embodiments, Ring $A_4$ is an optionally substituted 5,6-fused heteroaryl ring having 1-2 heteroatoms independently selected from nitrogen, oxygen, or sulfur. In certain embodiments, Ring $A_4$ is an optionally substituted 5,6-fused heteroaryl ring having 1 nitrogen.

In certain embodiments, Ring $A_4$ is an optionally substituted 6,6-fused heteroaryl ring having 1-4 heteroatoms independently selected from nitrogen, oxygen, or sulfur. In some embodiments, Ring $A_4$ is an optionally substituted 6,6-fused heteroaryl ring having 1-2 nitrogens. In other embodiments, Ring $A_4$ is an optionally substituted 6,6-fused heteroaryl ring having 1 nitrogen. In some embodiments, Ring $A_4$ is a quinoline ring. In certain embodiments, Ring $A_4$ is an optionally substituted 6,6-fused heteroaryl ring having 2 nitrogens.

In certain embodiments, Ring $A_4$ is an optionally substituted 5,5-fused heteroaryl ring having 1-4 heteroatoms independently selected from nitrogen, oxygen, or sulfur. In some embodiments, Ring $A_4$ is an optionally substituted 5,5-fused heteroaryl ring having 1-2 heteroatoms selected from nitrogen, oxygen, or sulfur. In other embodiments, Ring $A_4$ is an optionally substituted 5,5-fused heteroaryl ring having 1 nitrogen. In certain embodiments, Ring $A_4$ is an optionally substituted 5,5-fused heteroaryl ring having 2 nitrogens. In certain embodiments, Ring $A_4$ is an optionally substituted 5,5-fused heteroaryl ring having 1 nitrogen and 1-2 other heteroatoms selected from nitrogen, oxygen, or sulfur.

In some embodiments, Ring $A_4$ is selected from:

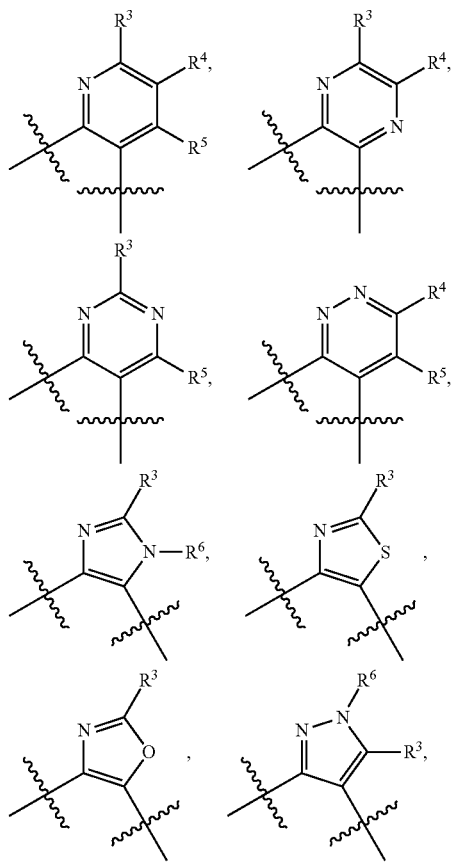

-continued

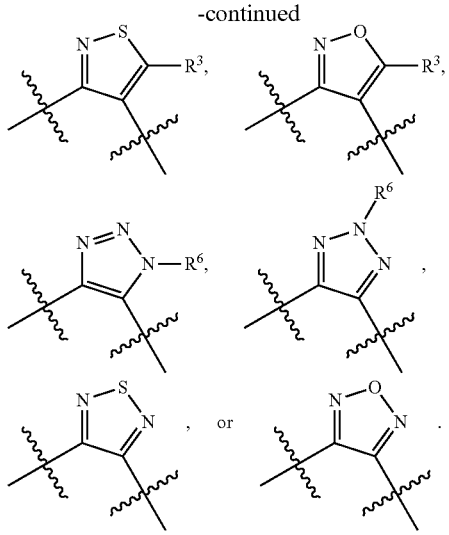

In certain embodiments, Ring $A_4$ is of formula:

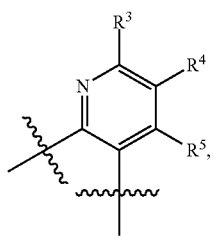

wherein $R^3$ and $R^4$ are taken together with their intervening atoms to form an optionally substituted fused ring selected from a 4-7 membered saturated or partially unsaturated carbocyclic ring, phenyl, a 5-6 membered saturated or partially unsaturated bicyclic heterocyclic ring having 1-3 heteroatoms independently selected from nitrogen, oxygen, or sulfur, or a 5-6 membered heteroaryl ring having 1-3 heteroatoms independently selected from nitrogen, oxygen, or sulfur.

In certain embodiments, Ring $A_4$ is of formula:

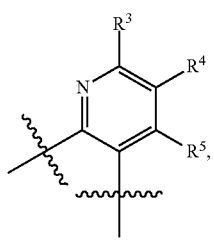

wherein $R^4$ and $R^5$ are taken together with their intervening atoms to form an optionally substituted fused ring selected from a 4-7 membered saturated or partially unsaturated carbocyclic ring, phenyl, a 5-6 membered saturated or partially unsaturated bicyclic heterocyclic ring having 1-3 heteroatoms independently selected from nitrogen, oxygen, or sulfur, or a 5-6 membered heteroaryl ring having 1-3 heteroatoms independently selected from nitrogen, oxygen, or sulfur.

In certain embodiments, Ring $A_4$ is of formula:

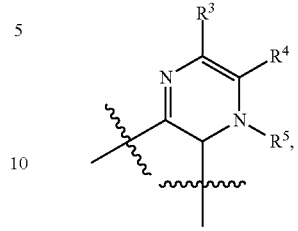

wherein $R^4$ and $R^5$ are taken together with their intervening atoms to form an optionally substituted 5-membered heteroaryl fused ring having 1-3 heteroatoms independently selected from nitrogen, oxygen, or sulfur.

In certain embodiments, Ring $A_4$ is of formula:

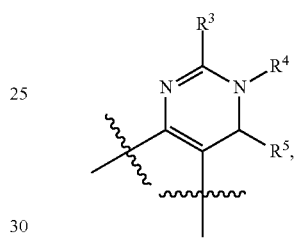

wherein $R^4$ and $R^5$ are taken together with their intervening atoms to form an optionally substituted 5-membered heteroaryl fused ring having 1-3 heteroatoms independently selected from nitrogen, oxygen, or sulfur.

In certain embodiments, Ring $A_4$ is of formula:

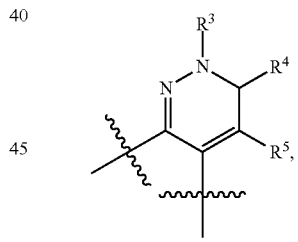

wherein $R^3$ and $R^4$ are taken together with their intervening atoms to form an optionally substituted 5-membered heteroaryl fused ring having 1-3 heteroatoms independently selected from nitrogen, oxygen, or sulfur.

In certain embodiments, Ring $A_4$ is selected from:

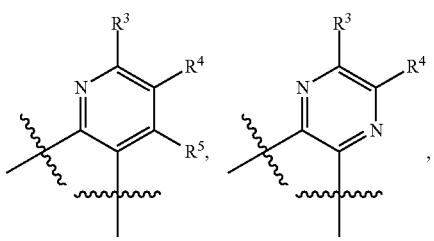

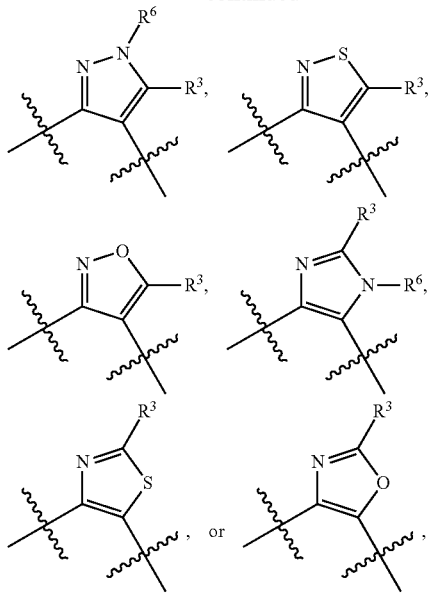

wherein:
R³ is hydrogen, —Cl, or —CF₃;
R⁴ is hydrogen, —F, —Cl, —Br, —I, C₁₋₆alkyl, C₁₋₆alkenyl, C₁₋₆alkynyl, —CN, —NO₂, —NH₂, —N(R')₂, —NHC(O)C₁₋₆alkyl, —CO₂H, —CO₂C₁₋₄alkyl, —C(O)N(R')₂, —NHS(O)C₁₋₆alkyl, —NHS(O)₂C₁₋₆alkyl, —SC₁₋₆alkyl, —S(O)C₁₋₆alkyl, —S(O)₂C₁₋₆alkyl, —S(O)N(R')₂, —S(O)₂N(R')₂, —CF₃, —OCH₃, —OCH₂CH₃, benzyloxy, phenyl; or an optionally substituted 3-5 membered saturated or partially unsaturated heterocyclic ring having 1-2 heteroatoms selected from nitrogen, oxygen or sulfur.
R⁵ is hydrogen, —OCH₃, —OCH₂CH₃, —CF₃ or —NH₂;
R⁶ is hydrogen or an optionally substituted group selected from C₁₋₄ alkyl, phenyl, or a 5-6 membered heteroaryl ring having 1-3 heteroatoms selected from nitrogen, oxygen, or sulfur; and
each R' is independently hydrogen or C₁₋₄ alkyl, or two R' on the same nitrogen are taken together with the intervening nitrogen to form an optionally substituted 5-6 membered saturated, partially unsaturated, or aromatic ring having 1-3 heteroatoms independently selected from nitrogen, oxygen, or sulfur.

As defined above, R¹ is hydrogen or optionally substituted C₁₋₆ aliphatic, or R¹ and a substituent on Ring A₄ are taken together with their intervening atoms to form an optionally substituted 5-7 membered partially unsaturated or aromatic fused ring having 0-3 ring heteroatoms independently selected from nitrogen, oxygen, or sulfur. In certain embodiments, R¹ is hydrogen. In some embodiments, R¹ is C₁₋₆ aliphatic. In some embodiments, R¹ is C₁₋₄ alkyl. In certain embodiments, R¹ is methyl.

In some embodiments, R¹ and a substituent on Ring A₄ are taken together with their intervening atoms to form an optionally substituted 5-7 membered partially unsaturated or aromatic fused ring having 0-3 ring heteroatoms independently selected from nitrogen, oxygen, or sulfur. In certain embodiments, R¹ and a substituent on Ring A₄ are taken together with their intervening atoms to form an optionally substituted fused ring selected from a 5-6 membered partially unsaturated heterocyclic ring having 1-3 heteroatoms independently selected from nitrogen, oxygen, or sulfur, or a 5-6 membered heteroaryl ring having 1-3 heteroatoms independently selected from nitrogen, oxygen, or sulfur. In certain embodiments, R¹ and a substituent on ring A₄ are taken together with their intervening atoms to form a fused pyrimidinone, dihydropyrimidinone, dihydropyridinone, or pyrrolone.

As defined above, R² is hydrogen or optionally substituted C₁₋₆ aliphatic. In certain embodiments, R² is hydrogen. In some embodiments, R² is optionally substituted C₁₋₆ aliphatic. In certain embodiments, R² is C₁₋₄ alkyl. In certain embodiments, R² is methyl, ethyl, or propyl.

As defined above, R³ is —R, -halo, —NO₂, —CN, —OR, —SR, —N(R')₂, —C(O)R, —CO₂R, —C(O)C(O)R, —C(O)CH₂C(O)R, —S(O)R, —S(O)₂R, —C(O)N(R')₂, —S(O)₂N(R')₂, —OC(O)R, —N(R')C(O)R, —N(R')N(R')₂, —N(R')OR, —N(R')C(=NR')N(R')₂, —C(=NR')N(R')₂, —C=NOR, —N(R')C(O)N(R')₂, —N(R')S(O)₂N(R')₂, —N(R')S(O)₂R, or —OC(O)N(R')₂, wherein R and R' are as defined and described herein, or R³ and R⁴ are taken together with their intervening atoms to form an optionally substituted fused ring selected from a 4-7 membered partially unsaturated carbocyclic ring, phenyl, a 5-6 membered partially unsaturated heterocyclic ring having 1-3 heteroatoms independently selected from nitrogen, oxygen, or sulfur, or a 5-6 membered heteroaryl ring having 1-3 heteroatoms independently selected from nitrogen, oxygen, or sulfur, or R³ and R⁶ are taken together with their intervening atoms to form an optionally substituted fused ring selected from a 5-6 membered saturated or partially unsaturated heterocyclic ring having 1-3 heteroatoms independently selected from nitrogen, oxygen, or sulfur, or a 5-6 membered heteroaryl ring having 1-3 heteroatoms independently selected from nitrogen, oxygen, or sulfur. In some embodiments, R³ is —R. In certain embodiments, R³ is hydrogen. In some embodiments, R³ is halo. In some embodiments, R³ is —OR, —SR, or —N(R')₂. In some embodiments, R³ is —C(O)R, —CO₂R, —C(O)C(O)R, or —C(O)CH₂C(O)R. In some embodiments, R³ is —S(O)R, —S(O)₂R, —C(O)N(R')₂, —S(O)₂N(R')₂, —OC(O)R, —N(R')C(O)R, —N(R')N(R')₂, —N(R')C(=NR')N(R')₂, —C(=NR')N(R')₂, —C=NOR, —N(R')C(O)N(R')₂, —N(R')S(O)₂N(R')₂, —N(R')S(O)₂R, or —OC(O)N(R')₂. In certain embodiments, R³ is —Cl. In certain embodiments, R³ is —CF₃. In certain embodiments, R³ is —CN.

As defined above, R⁴ is —R, -halo, —NO₂, —CN, —OR, —SR, —N(R')₂, —C(O)R, —CO₂R, —C(O)C(O)R, —C(O)CH₂C(O)R, —S(O)R, —S(O)₂R, —C(O)N(R')₂, —S(O)₂N(R')₂, —OC(O)R, —N(R')C(O)R, —N(R')N(R')₂, —N(R')OR, —N(R')C(=NR')N(R')₂, —C(=NR')N(R')₂, —C=NOR, —N(R')C(O)N(R')₂, —N(R')S(O)₂N(R')₂, —N(R')S(O)₂R, or —OC(O)N(R')₂, wherein R and R' are as defined and described herein, or R³ and R⁴ or R⁴ and R⁵ are taken together with their intervening atoms to form an optionally substituted fused ring selected from a 4-7 membered partially unsaturated carbocyclic ring, phenyl, a 5-6 membered partially unsaturated heterocyclic ring having 1-3 heteroatoms independently selected from nitrogen, oxygen, or sulfur, or a 5-6 membered heteroaryl ring having 1-3 heteroatoms independently selected from nitrogen, oxygen, or sulfur. In some embodiments, R⁴ is —R. In certain embodiments, R⁴ is hydrogen. In some embodiments, R⁴ is halo. In certain embodiments, R⁴ is fluorine. In some embodiments, R⁴ is C₁₋₆ aliphatic. In certain embodiments, R⁴ is C₁₋₄ alkyl. In certain embodiments, R⁴ is methyl or ethyl. In certain embodiments, R⁴ is optionally substituted alkynyl. In certain embodiments, R⁴ is optionally substituted alkenyl. In some embodiments, R⁴ is —CN, —NO₂, —NH₂, —NHC(O)C₁₋₆alkyl, —CO₂H, —CO₂C₁₋₄alkyl, —C(O)N (R')$_2$, —NHS(O)C$_{1-6}$alkyl, —NHS(O)$_2$C$_{1-6}$alkyl, —SC$_{1-6}$alkyl, —S(O)C$_{1-6}$alkyl, —S(O)$_2$C$_{1-6}$alkyl, —S(O)N(R')$_2$, —S(O)$_2$N(R')$_2$, —CF$_3$, —OCH$_3$, —OCH$_2$CH$_3$, or benzyloxy. In certain embodiments, R$^4$ is halo, —NH$_2$, —CN, —NO$_2$, —SC$_{1-4}$alkyl, —S(O)C$_{1-4}$ alkyl, —S(O)$_2$C$_{1-4}$ alkyl, —S(O)N(R')$_2$, —CF$_3$, —OCH$_3$, —OCH$_2$CH$_3$, benzyloxy, —C(O)N(R')$_2$, or —NHC(O)C$_{1-4}$alkyl. In certain embodiments, R$^4$ is —CN, —NO$_2$, —SC$_{1-4}$alkyl, —S(O)C$_{1-4}$ alkyl, —S(O)$_2$C$_{1-4}$ alkyl, —S(O)N(R')$_2$, —S(O)$_2$N(R')$_2$, —CF$_3$, —OCH$_3$, —OCH$_2$CH$_3$, or benzyloxy.

As defined above, R$^5$ is —R, -halo, —NO$_2$, —CN, —OR, —SR, —N(R')$_2$, —C(O)R, —CO$_2$R, —C(O)C(O)R, —C(O)CH$_2$C(O)R, —S(O)R, —S(O)$_2$R, —C(O)N(R')$_2$, —S(O)$_2$N(R')$_2$, —OC(O)R, —N(R')C(O)R, —N(R')N(R')$_2$, —N(R')OR, —N(R')C(=NR')N(R')$_2$, —C(=NR')N(R')$_2$, —C=NOR, —N(R')C(O)N(R')$_2$, —N(R')S(O)$_2$N(R')$_2$, —N(R')S(O)$_2$R, or —OC(O)N(R')$_2$, wherein R and R' are as defined and described herein, or R$^4$ and R$^5$ are taken together with their intervening atoms to form an optionally substituted fused ring selected from a 4-7 membered partially unsaturated carbocyclic ring, phenyl, a 5-6 membered partially unsaturated heterocyclic ring having 1-3 heteroatoms independently selected from nitrogen, oxygen, or sulfur, or a 5-6 membered heteroaryl ring having 1-3 heteroatoms independently selected from nitrogen, oxygen, or sulfur. In some embodiments, R$^5$ is —R. In certain embodiments, R$^5$ is hydrogen. In some embodiments, R$^5$ is halo. In some embodiments, R$^5$ is —OR, —SR, or —N(R')$_2$. In some embodiments, R$^5$ is —C(O)R, —CO$_2$R, —C(O)C(O)R, or —C(O)CH$_2$C(O)R. In some embodiments, R$^5$ is —S(O)R, —S(O)$_2$R, —C(O)N(R')$_2$, —S(O)$_2$N(R')$_2$, —OC(O)R, —N(R')C(O)R, —N(R')N(R')$_2$, —N(R')C(=NR')N(R')$_2$, —C(=NR')N(R')$_2$, —C=NOR, —N(R')C(O)N(R')$_2$, —N(R')S(O)$_2$N(R')$_2$, —N(R')S(O)$_2$R, or —OC(O)N(R')$_2$. In certain embodiments, R$^5$ is —OCH$_3$ or —NH$_2$. In certain embodiments, R$^5$ is —CF$_3$.

As defined above, each R$^6$ is independently —R, —C(O)R, —CO$_2$R, —C(O)C(O)R, —C(O)CH$_2$C(O)R, —S(O)R, —S(O)$_2$R, —C(O)N(R')$_2$, or —S(O)$_2$N(R')$_2$. In some embodiments, R$^6$ is —R. In certain embodiments, R$^6$ is hydrogen. In some embodiments, R$^6$ is C$_{1-6}$ aliphatic. In certain embodiments, R$^6$ is C$_{1-4}$ alkyl. In certain embodiments, R$^6$ is methyl. In some embodiments, R$^6$ is —C(O)R, —CO$_2$R, —C(O)C(O)R, —C(O)CH$_2$C(O)R, —S(O)R, —S(O)$_2$R, —C(O)N(R')$_2$, or —S(O)$_2$N(R')$_2$. In certain embodiments, R$^6$ is phenyl. In some embodiments, R$^6$ is a 5-6 membered heteroaryl ring having 1-3 heteroatoms selected from nitrogen, oxygen, or sulfur. In certain embodiments, R$^6$ is pyridyl.

In certain embodiments, R$^1$ and R$^5$ are taken together with their intervening atoms to form an optionally substituted fused ring selected from a 5-6 membered partially unsaturated heterocyclic ring having 1-3 heteroatoms independently selected from nitrogen, oxygen, or sulfur, or a 5-6 membered heteroaryl ring having 1-3 heteroatoms independently selected from nitrogen, oxygen, or sulfur. In certain embodiments, R$^1$ and R$^5$ are taken together with their intervening atoms to form a fused pyrimidinone, dihydropyrimidinone, dihydropyridinone, or pyrrolone.

In certain embodiments, R$^3$ and R$^4$ are taken together with their intervening atoms to form an optionally substituted fused ring selected from a 4-7 membered partially unsaturated carbocyclic ring, phenyl, a 5-6 membered partially unsaturated bicyclic heterocyclic ring having 1-3 heteroatoms independently selected from nitrogen, oxygen, or sulfur, or a 5-6 membered heteroaryl ring having 1-3 heteroatoms independently selected from nitrogen, oxygen, or sulfur. In certain embodiments, R$^3$ and R$^4$ are taken together with their intervening atoms to form a fused benzene ring. In other embodiments, R$^3$ and R$^4$ are taken together with their intervening atoms to form a fused 4-7 membered partially unsaturated carbocyclic ring. In certain embodiments, R$^3$ and R$^4$ are taken together with their intervening atoms to form a fused cyclopentene ring.

In certain embodiments, R$^4$ and R$^5$ are taken together with their intervening atoms to form an optionally substituted fused ring selected from a 4-7 membered partially unsaturated carbocyclic ring, phenyl, a 5-6 membered partially unsaturated bicyclic heterocyclic ring having 1-3 heteroatoms independently selected from nitrogen, oxygen, or sulfur, or a 5-6 membered heteroaryl ring having 1-3 heteroatoms independently selected from nitrogen, oxygen, or sulfur.

In certain embodiments, R$^3$ and R$^6$ are taken together with their intervening atoms to form an optionally substituted fused ring selected from a 5-6 membered partially unsaturated heterocyclic ring having 1-3 heteroatoms independently selected from nitrogen, oxygen, or sulfur, or a 5-6 membered heteroaryl ring having 1-3 heteroatoms independently selected from nitrogen, oxygen, or sulfur.

As defined above, each R is independently hydrogen or an optionally substituted group selected from C$_{1-6}$ aliphatic, a 3-7 membered saturated or partially unsaturated monocyclic carbocyclic ring, a 7-10 membered saturated or partially unsaturated bicyclic carbocyclic ring, a 4-7 membered saturated or partially unsaturated monocyclic heterocyclic ring having 1-2 heteroatoms independently selected from nitrogen, oxygen, or sulfur, a 7-10 membered saturated or partially unsaturated bicyclic heterocyclic ring having 1-3 heteroatoms independently selected from nitrogen, oxygen, or sulfur, a phenyl ring, an 8-10 membered bicyclic aryl ring, a 5-6 membered heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur. In certain embodiments, R is hydrogen. In some embodiments, R is an optionally substituted C$_{1-6}$ aliphatic group. In certain embodiments, R is a C$_{1-6}$ alkyl group. In certain embodiments, R is a C$_{1-4}$ alkyl group. In certain embodiments, R is methyl, ethyl, or propyl. In some embodiments, R is optionally substituted phenyl. In some embodiments, R is an optionally substituted group selected from an 8-10 membered bicyclic aryl ring, a 5-6 membered heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur.

As defined above, each R' is independently R, or two R' groups on the same nitrogen are taken together with the intervening nitrogen to form an optionally substituted 4-8 membered saturated, partially unsaturated, or aromatic ring having 1-4 heteroatoms independently selected from nitrogen, oxygen, or sulfur. In certain embodiments, R' is hydrogen. In some embodiments, R' is an optionally substituted C$_{1-6}$ aliphatic group. In certain embodiments, R' is a C$_{1-6}$ alkyl group. In certain embodiments, R' is a C$_{1-4}$ alkyl group. In certain embodiments, R' is methyl, ethyl, or propyl. In some embodiments, R' is optionally substituted phenyl. In some embodiments, R' is an optionally substituted group selected from an 8-10 membered bicyclic aryl ring, a 5-6 membered heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur. In certain embodiments, two R' groups on the same nitrogen are taken together with the intervening nitrogen to form an optionally substituted 4-8 membered saturated, partially unsaturated, or aromatic ring having 1-4 heteroatoms independently selected from nitrogen, oxygen, or sulfur.

In certain embodiments, -A$_1$-L$^1$- is one of the following:

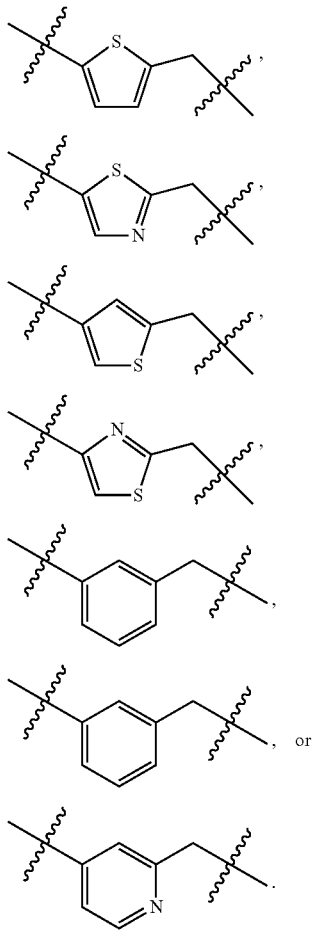

In certain embodiments, -L$^2$-A$_1$-L$^1$- is —OCH$_2$CH$_2$—, —CH═CHCH$_2$—, or —C≡C—CH$_2$—. In certain embodiments, -L$^2$-A$_1$-L$^1$- is optionally substituted —O—C$_2$ alkylene, C$_3$ alkenylene, or C$_3$ alkynylene. In certain embodiments, -L$^2$-A$_1$-L$^1$- is:

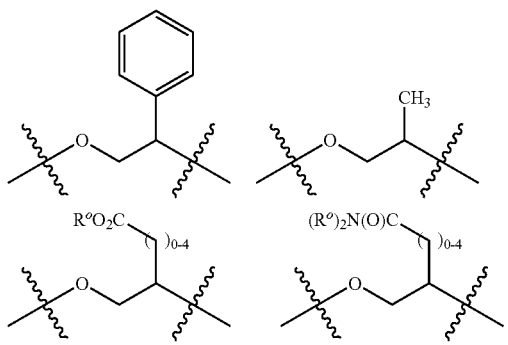

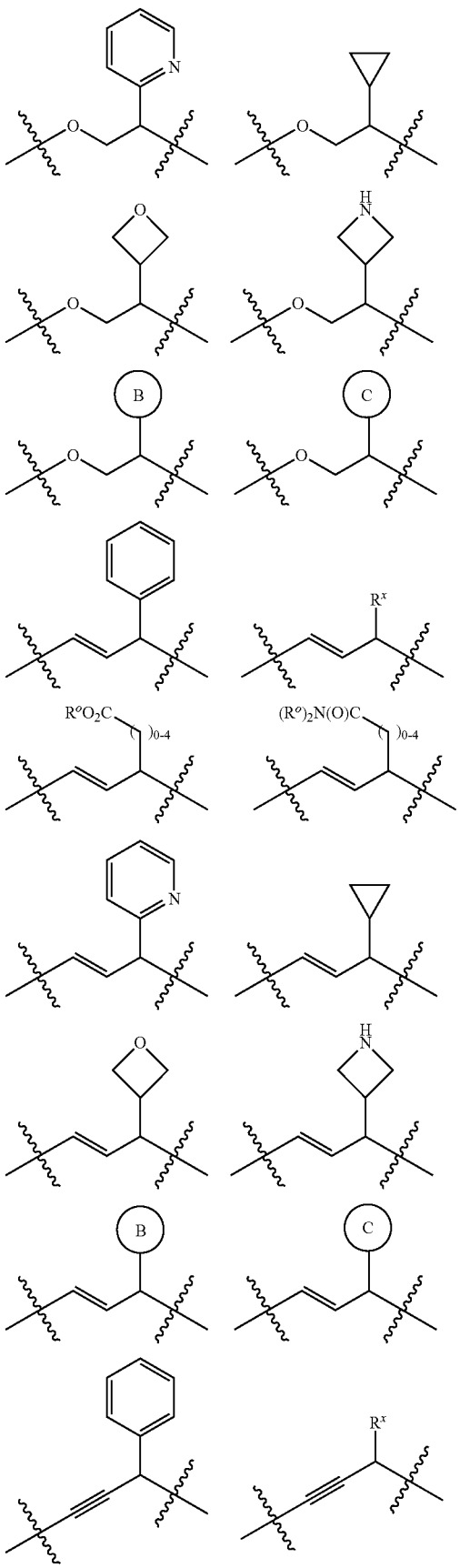

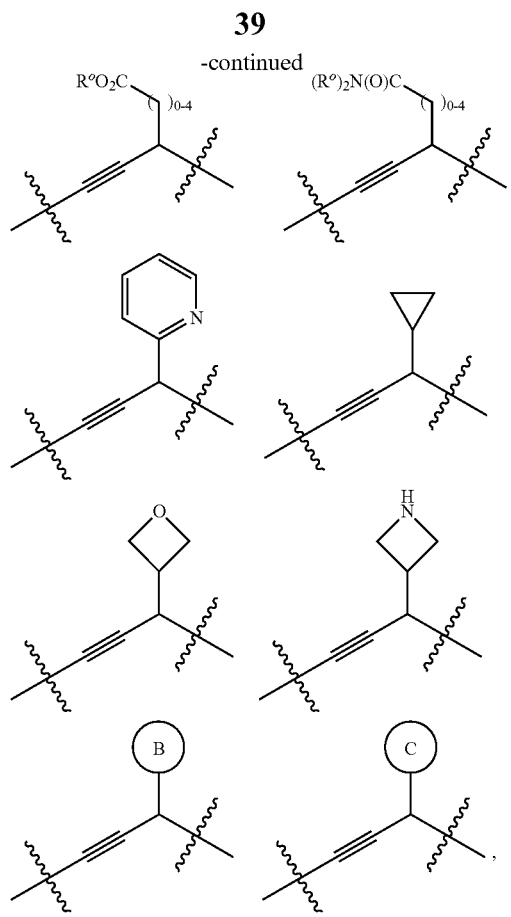
wherein Ring B is a 5-membered heteroaryl ring having 1-3 heteroatoms selected from nitrogen, oxygen, or sulfur, and Ring C is a 6-membered heteroaryl ring having 1-3 nitrogens. In certain embodiments, -L²-A₁-L¹- is one of the following:
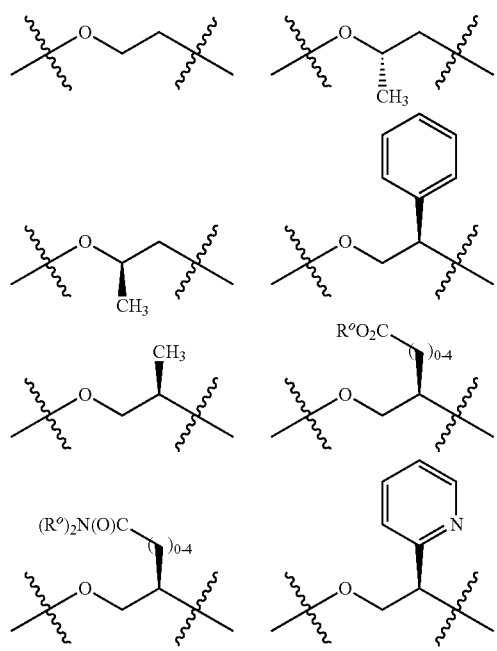
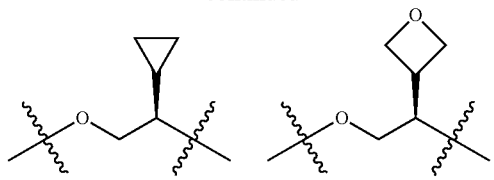
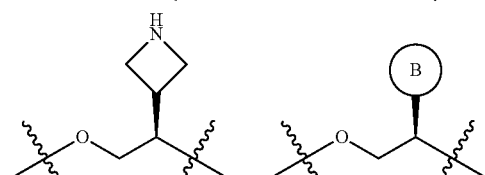
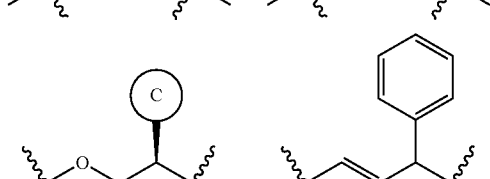
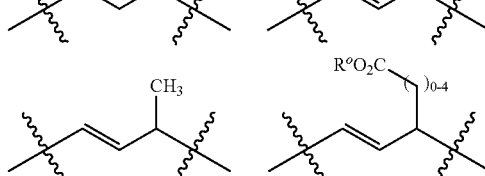
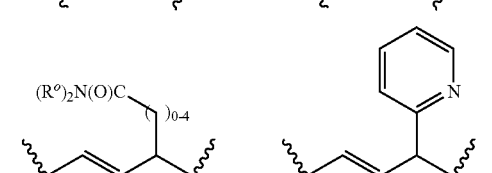
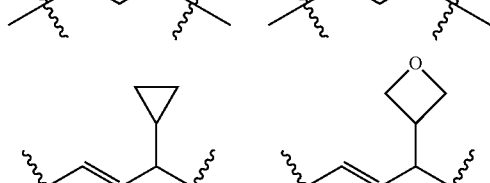
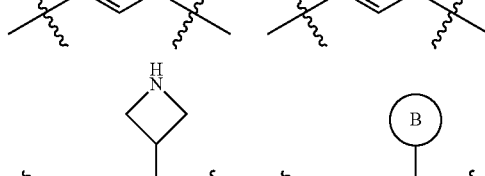
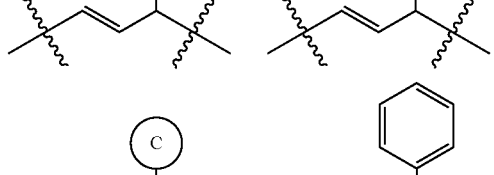
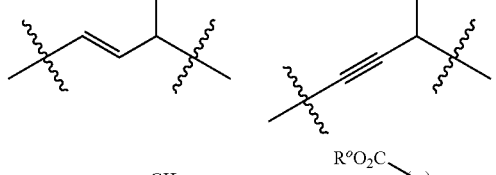
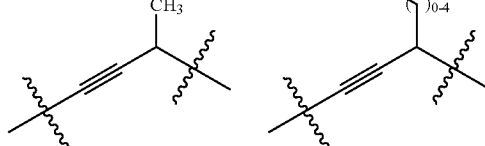

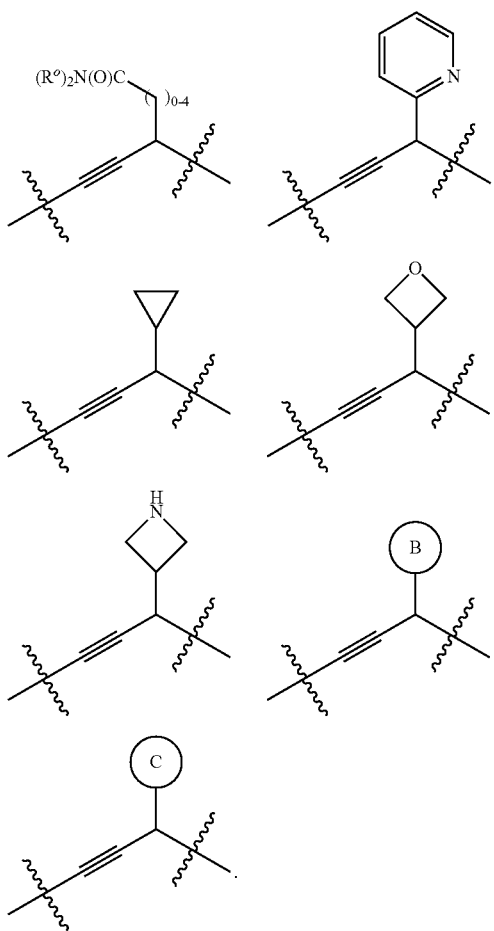
In certain embodiments, -L²-A₁-L¹- is optionally substituted with 1-4 Rˣ groups and is selected from:
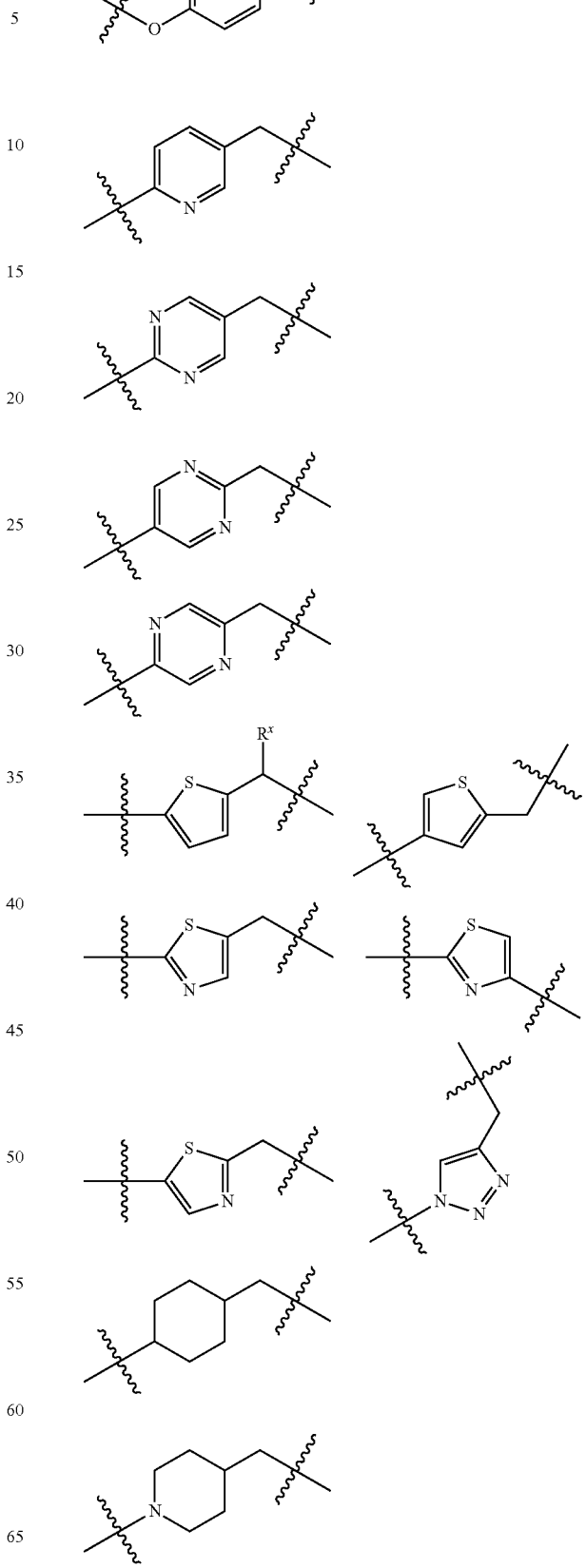

In certain embodiments, $A_2$-$L^2$-$A_1$- is

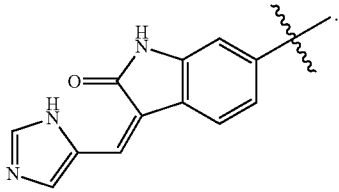 [SMILES: *c1ccc2c(c1)NC(=O)/C2=C\c1cnc[nH]1]

In certain other embodiments, Ring $A_2$ is

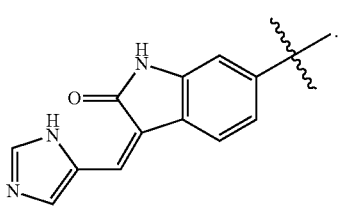 [SMILES: *c1ccc2c(c1)NC(=O)/C2=C\c1cnc[nH]1]

In some embodiments, -$L^3$-Ring $A_3$ is optionally substituted benzyl. In certain embodiments, -$L^3$-Ring $A_3$ is one of the following:

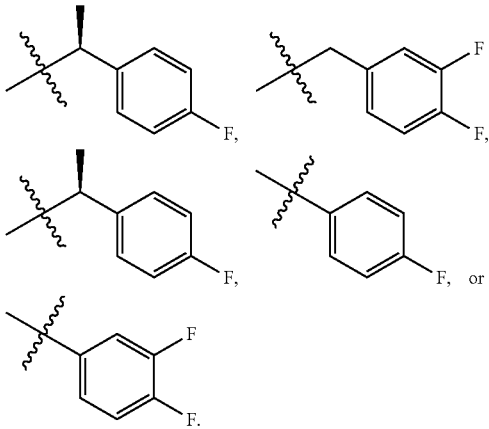

According to one aspect, the present invention provides a compound of formula II:

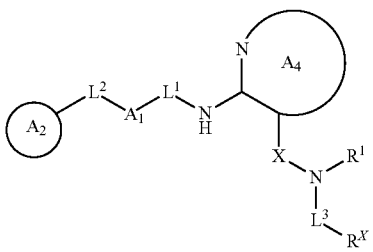

or a pharmaceutically acceptable salt thereof, wherein $L^1$, $L^2$, $L^3$, $A_1$, Ring $A_2$, Ring $A_4$, X, $R^x$ are as defined above for formula I and described herein.

According to one aspect, the present invention provides a compound of formulae II or II-a:

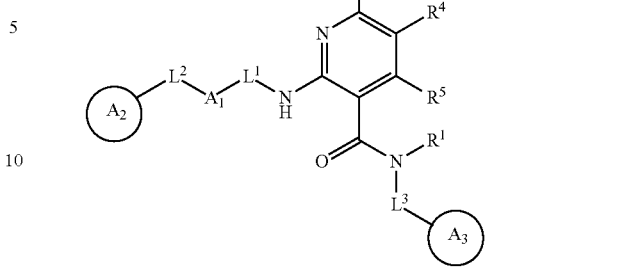

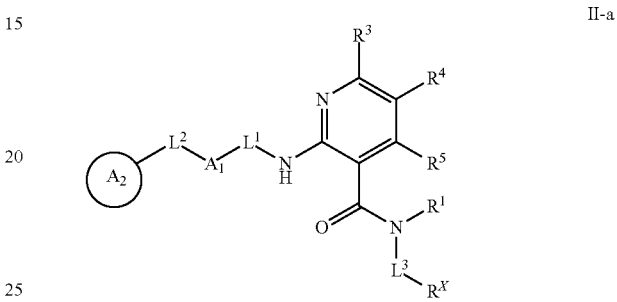

or a pharmaceutically acceptable salt thereof, wherein $L^1$, $L^2$, $L^3$, $A_1$, Ring $A_2$, Ring $A_3$, $R^x$, $R^1$, $R^3$, $R^4$, and $R^5$ are as defined above for formula I and described herein. In certain embodiments, $R^3$ of formula II is hydrogen, —Cl, or —CF$_3$. In certain embodiments, $R^4$ is —CN, —NO$_2$, —SC$_{1-4}$alkyl, —S(O)C$_{1-4}$ alkyl, —S(O)$_2$C$_{1-4}$ alkyl, —S(O)N(R')$_2$, —S(O)$_2$ N(R')$_2$, —CF$_3$, —OCH$_3$, —OCH$_2$CH$_3$, or benzyloxy, wherein each R' is independently hydrogen or C$_{1-4}$alkyl. In certain embodiments, $R^5$ is hydrogen, —OCH$_3$, or —NH$_2$. In some embodiments, $R^1$ and $R^5$ are taken together with their intervening atoms to form an optionally substituted ring selected from a 5-6 membered saturated or partially unsaturated heterocyclic ring having 1-3 heteroatoms independently selected from nitrogen, oxygen, or sulfur, or a 5-6 membered heteroaryl ring having 1-3 heteroatoms independently selected from nitrogen, oxygen, or sulfur. In some embodiments, $R^3$ and $R^4$ are taken together with their intervening atoms to form an optionally substituted ring selected from a 4-7 membered saturated or partially unsaturated carbocyclic ring, phenyl, a 5-6 membered saturated or partially unsaturated bicyclic heterocyclic ring having 1-3 heteroatoms independently selected from nitrogen, oxygen, or sulfur, or a 5-6 membered heteroaryl ring having 1-3 heteroatoms independently selected from nitrogen, oxygen, or sulfur. In other embodiments, $R^4$ and $R^5$ are taken together with their intervening atoms to form an optionally substituted ring selected from a 4-7 membered saturated or partially unsaturated carbocyclic ring, phenyl, a 5-6 membered saturated or partially unsaturated bicyclic heterocyclic ring having 1-3 heteroatoms independently selected from nitrogen, oxygen, or sulfur, or a 5-6 membered heteroaryl ring having 1-3 heteroatoms independently selected from nitrogen, oxygen, or sulfur.

In some embodiments, $L^3$ of formula II is optionally substituted methylene. In certain embodiments, $L^3$ is unsubstituted methylene. In certain other embodiments, $L^3$ is methylene substituted with methyl. In some embodiments, Ring $A_3$ is optionally substituted phenyl. In certain embodiments, Ring $A_3$ is phenyl substituted with at least one fluorine at the para position or meta position. In some embodiments, $L^1$ is optionally substituted methylene, propylene, propynylene, or —O—$C_{1-3}$ alkylene. In certain embodiments, $L^1$ is optionally substituted —O—$C_2$ alkylene. In certain embodiments, $L^1$ is optionally substituted methylene. In certain embodiments, $L^1$ is —$CH_2$—.

In some embodiments, $A_1$ of formula II is an optionally substituted group selected from:

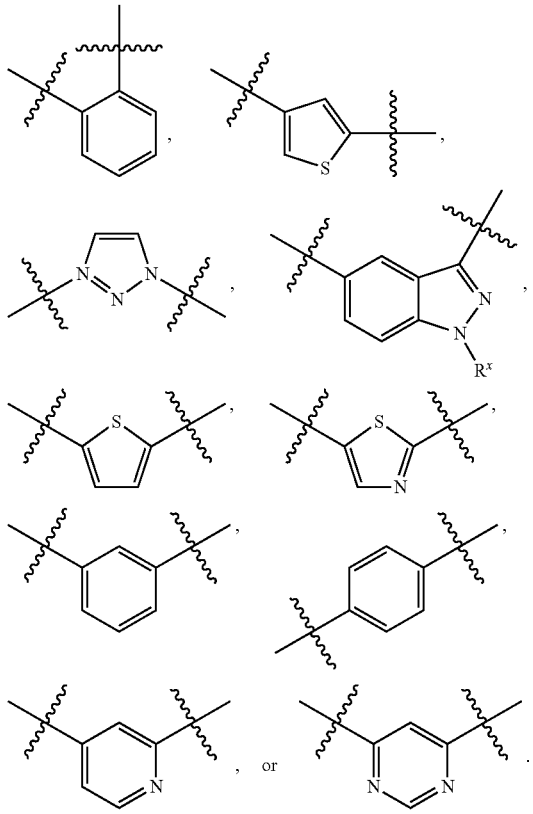

In some embodiments, $L^2$ of formula II is a covalent bond or methylene. In certain embodiments, Ring $A_2$ is optionally substituted with 1-4 $R^x$ groups and is selected from:

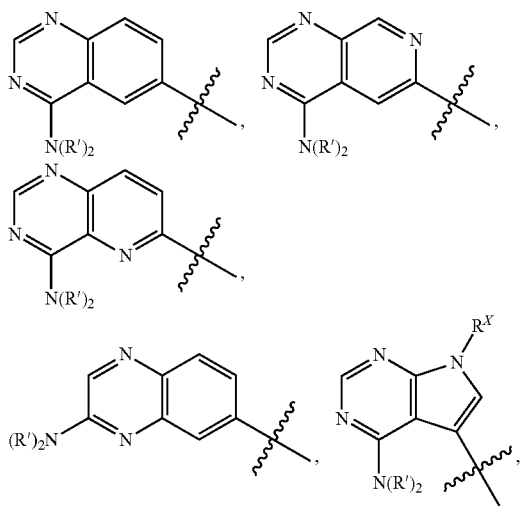

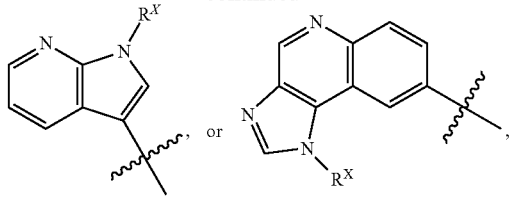

wherein each $R^x$ on a nitrogen is independently hydrogen or $C_{1-4}$ alkyl, and each R' is independently hydrogen or $C_{1-4}$ alkyl, or two R' on the same nitrogen are taken together with the intervening nitrogen to form a 4-7 membered heterocylic ring having 1-2 heteroatoms independently selected from nitrogen, oxygen, or sulfur.

In some embodiments, $L^3$ of formula II-a is a covalent bond. In certain embodiments, $R^x$ of formula II-a is $C_{1-4}$ alkyl, $C_{1-4}$ alkenyl, or $C_{1-4}$ alkynyl. In some embodiments, $R^x$ of formula II-a is a methyl group. In some embodiments, $R^x$ of formula II-a is a propargyl group.

Another aspect of the present invention provides a compound of formula III:

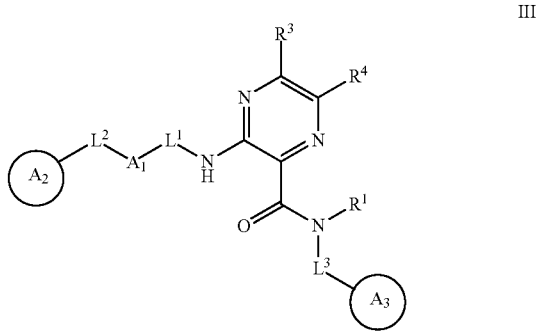

III or a pharmaceutically acceptable salt thereof, wherein $L^1$, $L^2$, $L^3$, $A_1$, Ring $A_2$, Ring $A_3$, $R^1$, $R^3$, and $R^4$ are as defined above for formula I and described herein.

According to another aspect, the present invention provides a compound of formula IV:

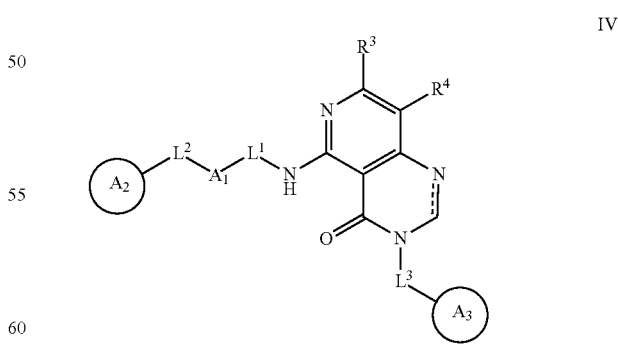

IV or a pharmaceutically acceptable salt thereof, wherein ---- is a single or double bond, and $L^1$, $L^2$, $L^3$, $A_1$, Ring $A_2$, Ring $A_3$, $R^3$, and $R^4$ are as defined above for formula I and described herein. In certain embodiments, the compound of formula IV is of formula IV-a or IV-b:

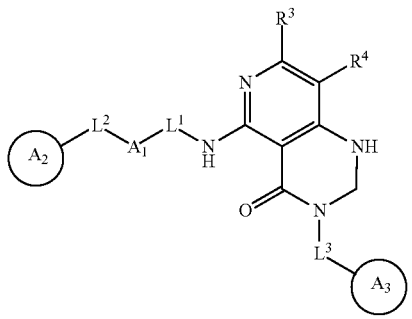

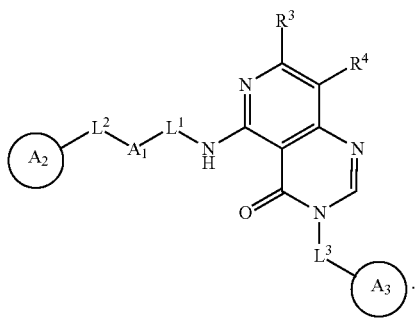

According to yet another aspect, the present invention provides a compound of formula V:

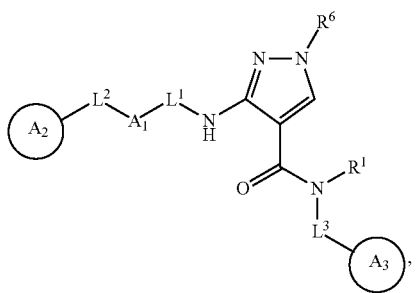

or a pharmaceutically acceptable salt thereof, wherein $L^1$, $L^2$, $L^3$, $A_1$, Ring $A_2$, Ring $A_3$, $R^1$, and $R^6$ are as defined above for formula I and described herein.

In certain embodiments, $R^6$ of formula V is $C_{1-4}$ alkyl or a 5-6 membered heteroaryl ring having 1-3 heteroatoms selected from nitrogen, oxygen, or sulfur. In certain embodiments, $R^6$ is methyl. In certain embodiments, $R^6$ is pyridyl.

In certain embodiments, each of $L^1$, $L^2$, $L^3$, $A_1$, Ring $A_2$, Ring $A_3$, Ring $A_4$, $R^1$, $R^2$, $R^3$, $R^4$, $R^5$, $R^6$, R, and R' is selected from those groups depicted in the Schemes and Examples found in the Examples section, infra.

According to yet another aspect, the present invention provides a compound of formula VI:

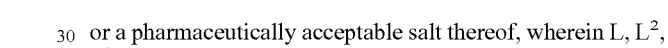

or a pharmaceutically acceptable salt thereof, wherein L, $L^2$, $A_1$, Ring $A_2$, X, $R^1$, $R^3$, $R^4$ and $R^6$ are as defined above for formula I and described herein.

According to yet another aspect, the present invention provides a compound of formula VII:

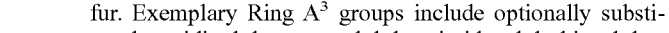

or a pharmaceutically acceptable salt thereof, wherein L, $L^2$, $L^3$, $A_1$, Ring $A_2$, Ring $A_3$, and Ring $A_4$ are as defined above for formula I and described herein.

In certain embodiments, $L^3$ of formula VII is a covalent bond. In some embodiments, Ring $A^3$ of formula VII is a 4-7 membered saturated heterocyclic ring having 1-2 heteroatoms independently selected from nitrogen, oxygen or sulfur. In some embodiments, Ring $A^3$ is a 5-6 membered monocyclic heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur. Exemplary Ring $A^3$ groups include optionally substituted azetidinyl, benzoxazolyl, benzimidazolyl, thiazolyl or oxazolyl.

According to yet another aspect, the present invention provides a compound of formula VIII:

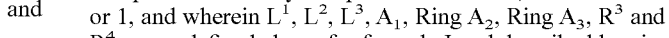

or a pharmaceutically acceptable salt thereof, wherein n is 0 or 1, and wherein $L^1$, $L^2$, $L^3$, $A_1$, Ring $A_2$, Ring $A_3$, $R^3$ and $R^4$ are as defined above for formula I and described herein. In some embodiments of formula VIII, n is 0. In some embodiments of formula VIII, n is 1.

According to yet another aspect, the present invention provides a compound of formula VIII:

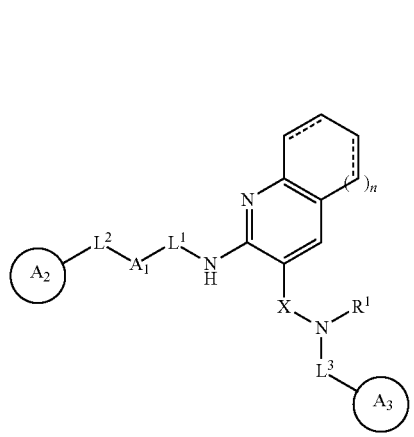

or a pharmaceutically acceptable salt thereof, wherein ═══ is a single or double bond, n is 0 or 1, and wherein X, $L^1, L^2, L^3, A_1$, Ring $A_2$, Ring $A_3$, and $R^1$ are as defined above for formula I and described herein. In some embodiments of formula IX, n is 0. In some embodiments of formula IX, n is 1.

In some embodiments, the present invention provides the following compounds:

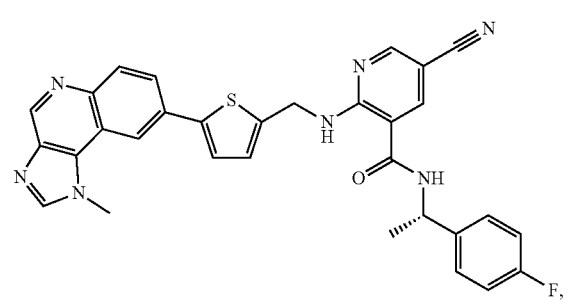

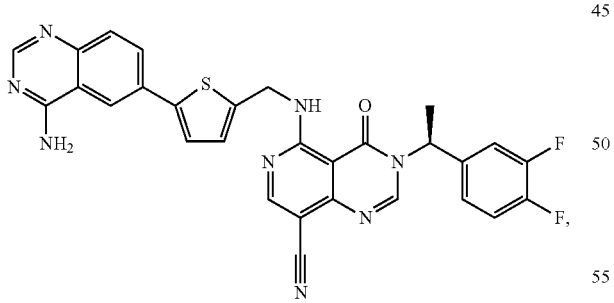

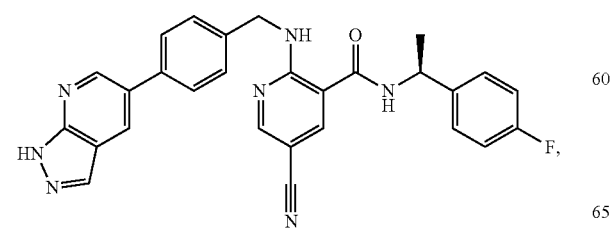

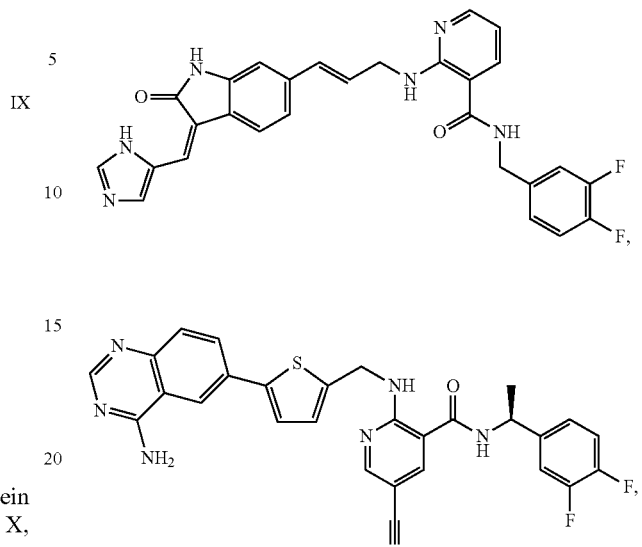

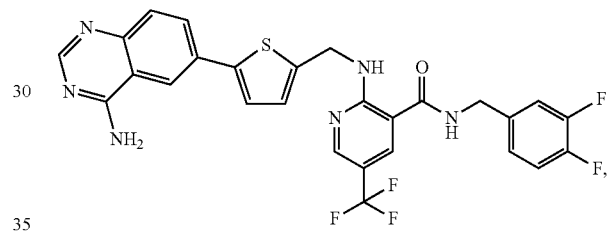

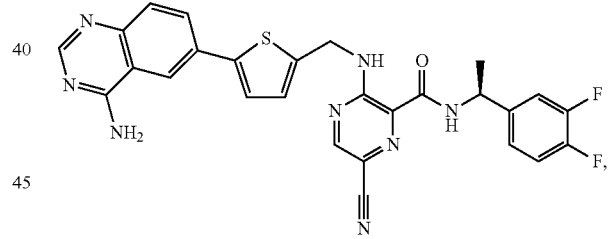

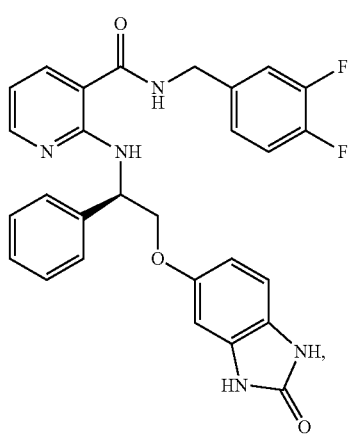

51
-continued
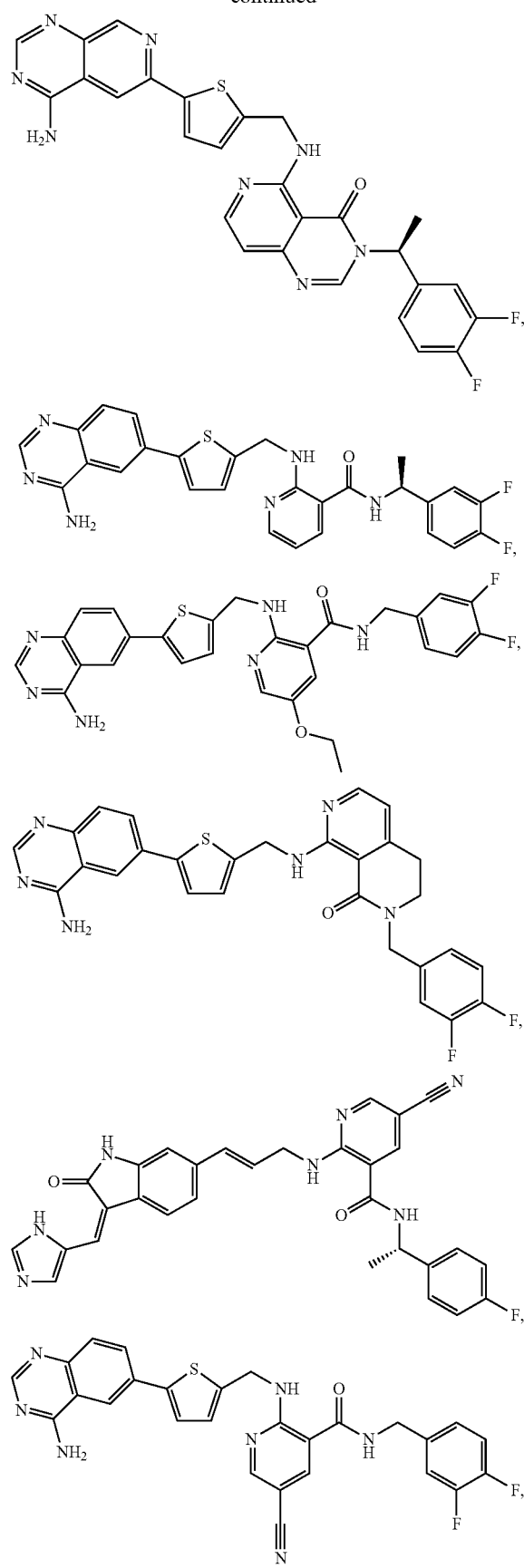
52
-continued
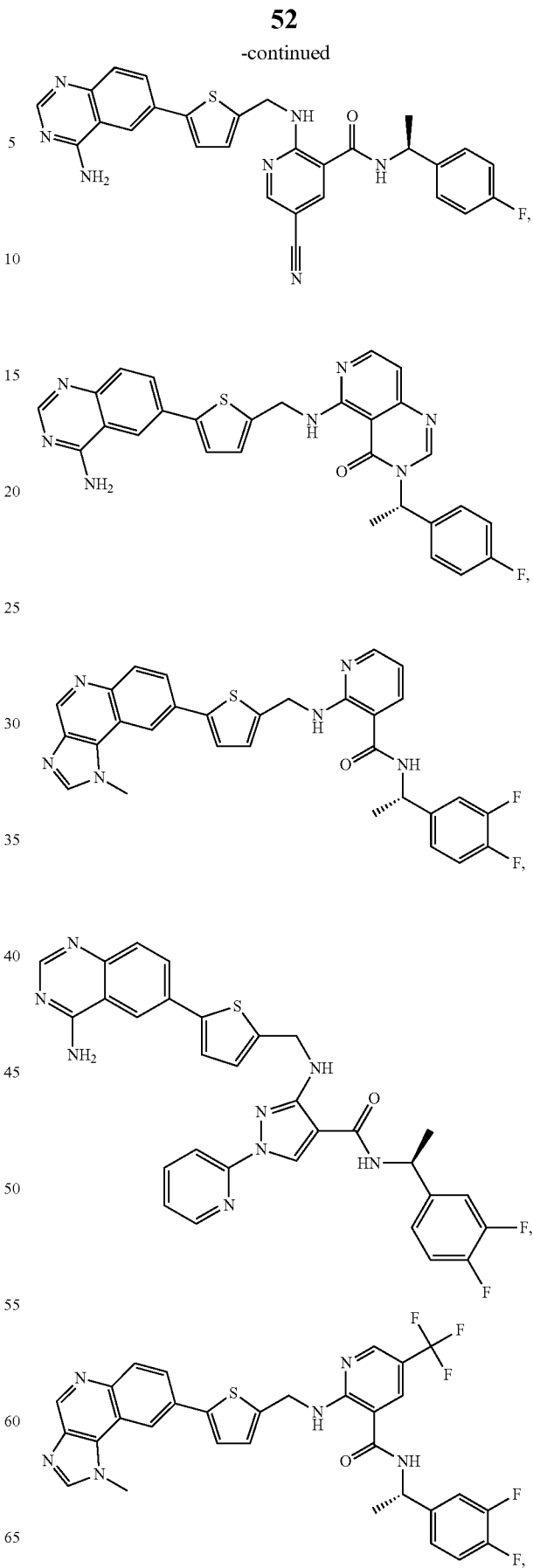

53
-continued
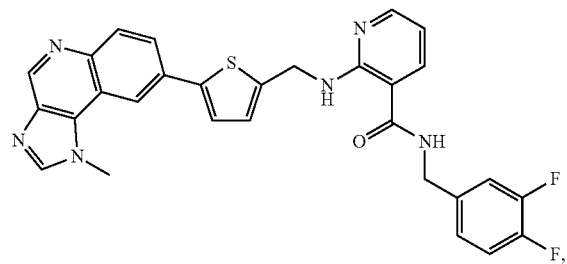
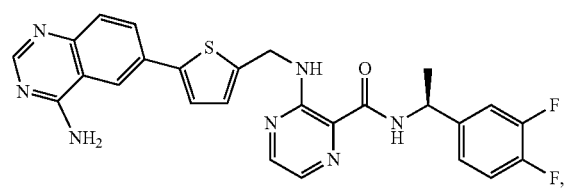
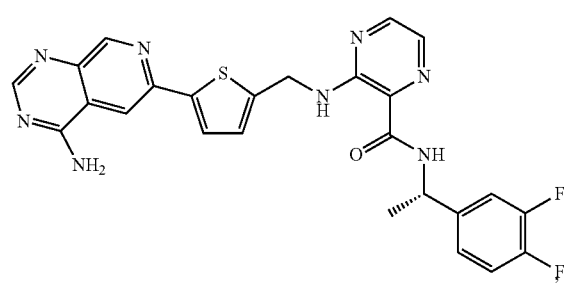
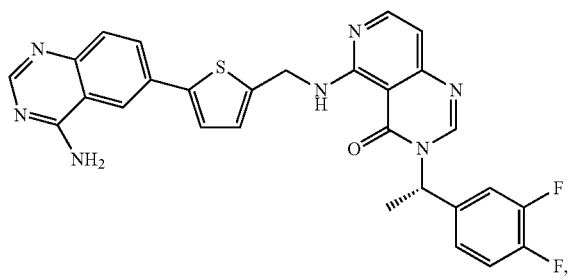
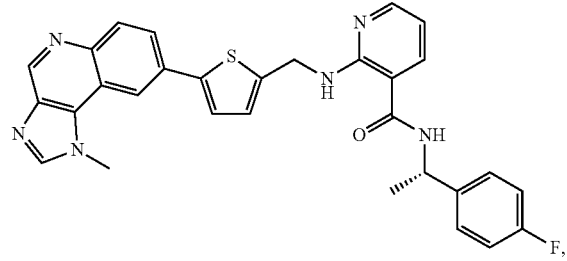
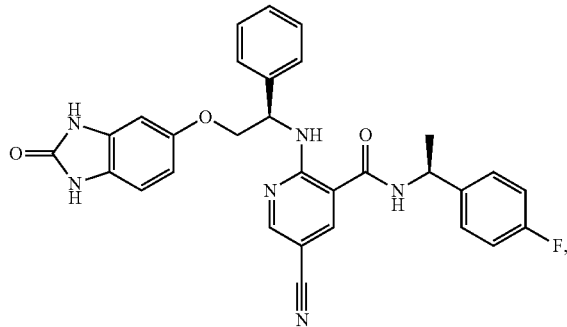
54
-continued
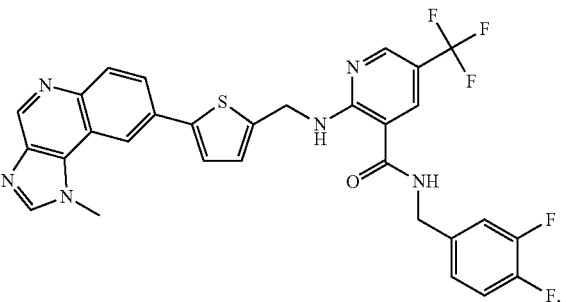
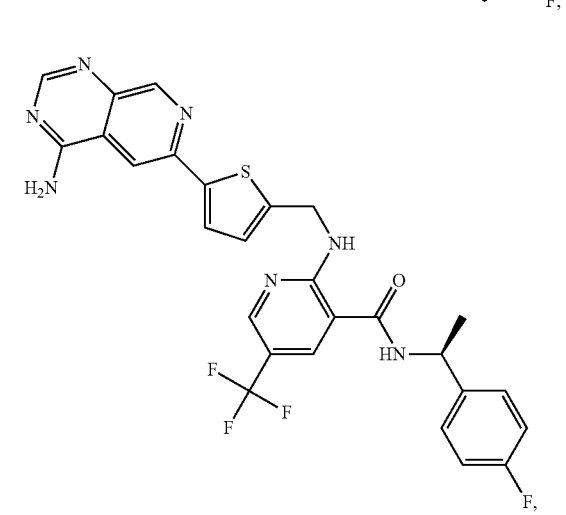
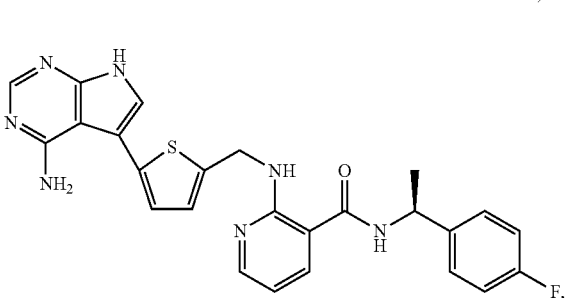
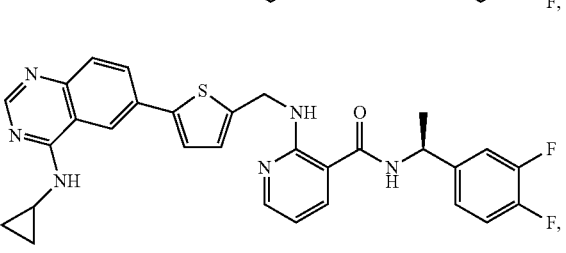
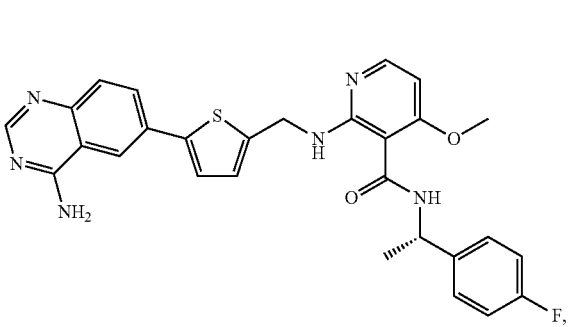

55
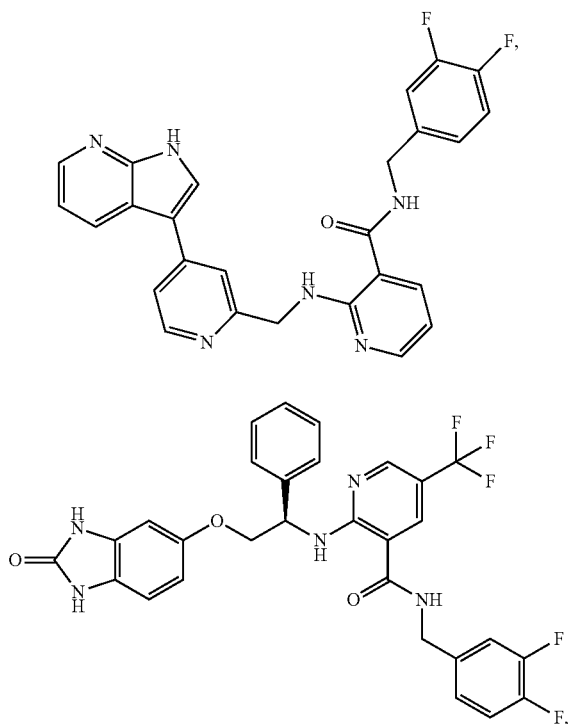
56
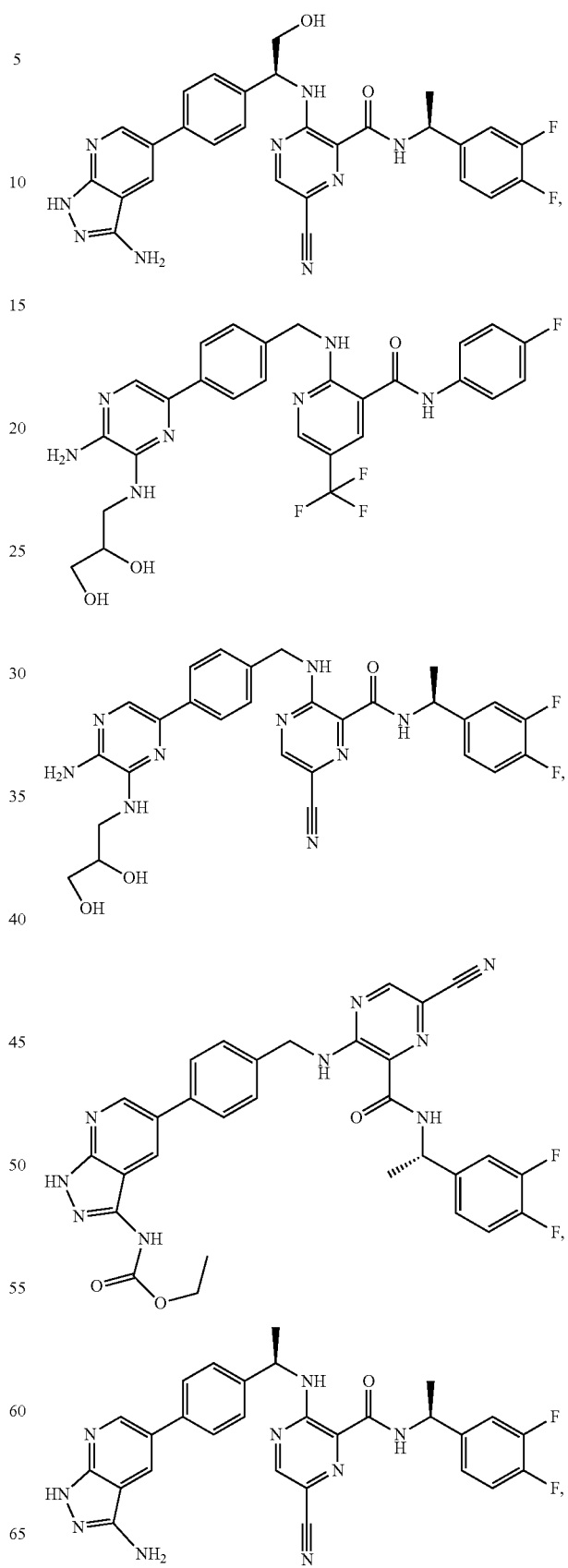

57
-continued
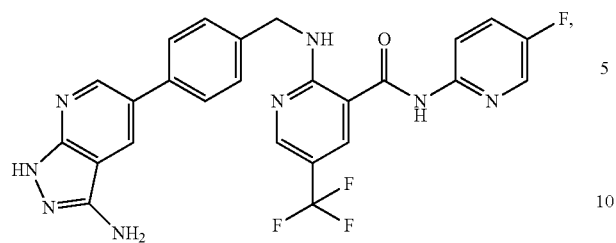
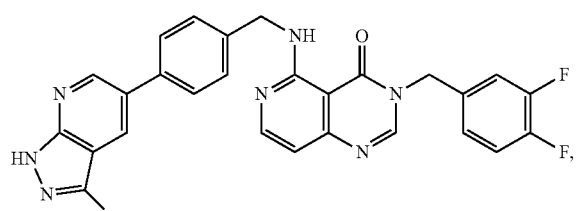
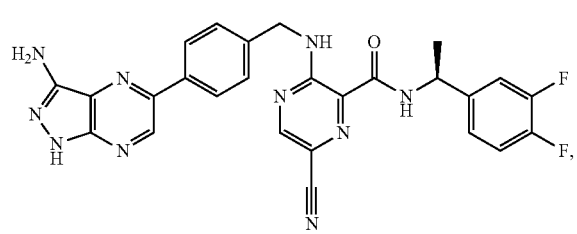
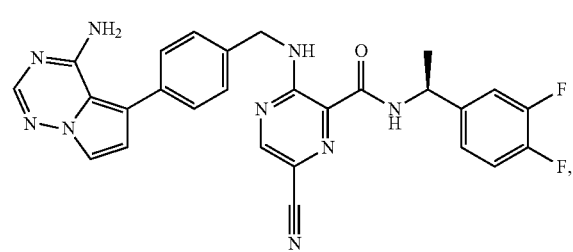
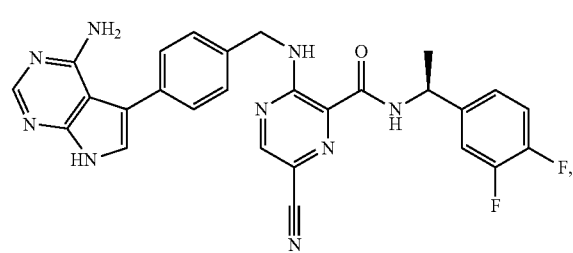
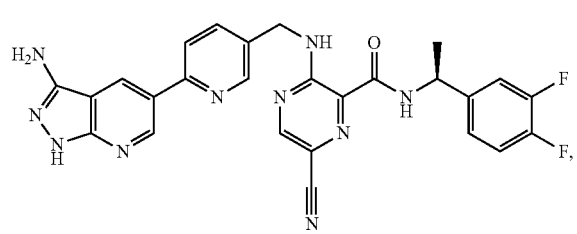
58
-continued
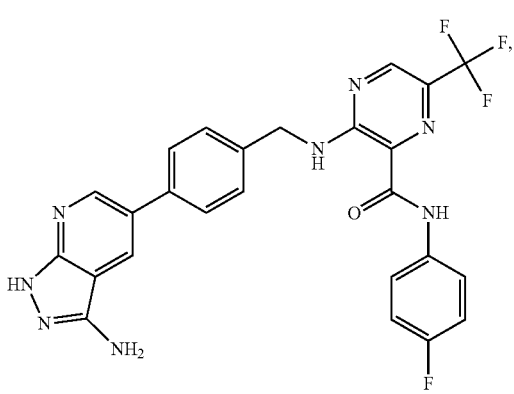
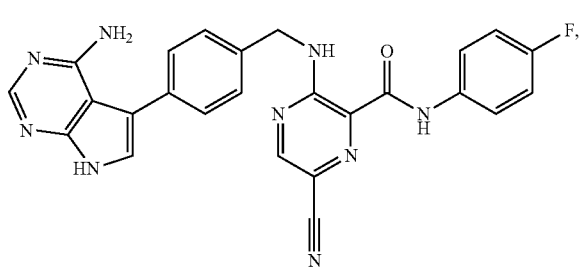
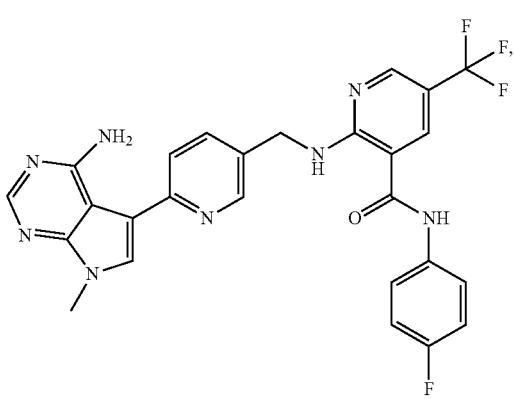
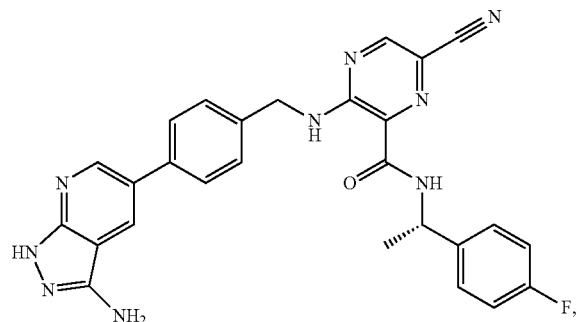
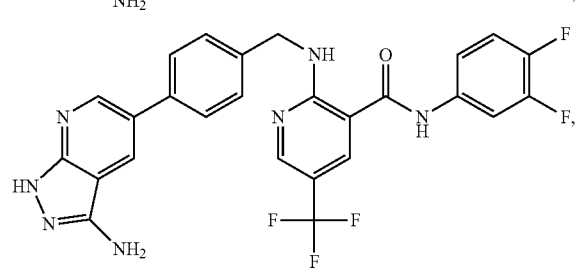

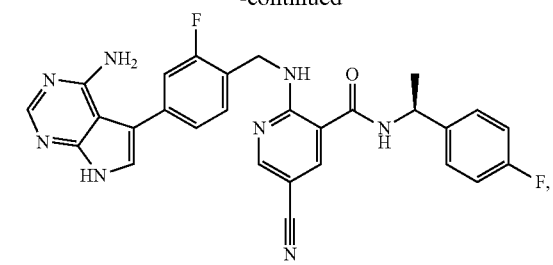
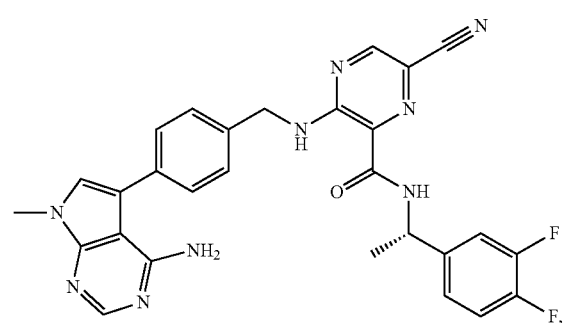
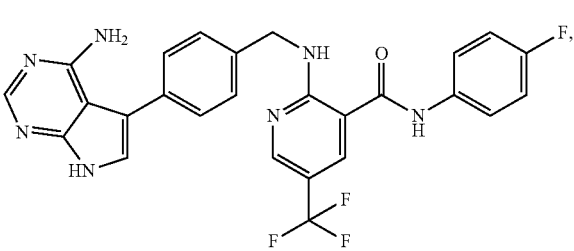
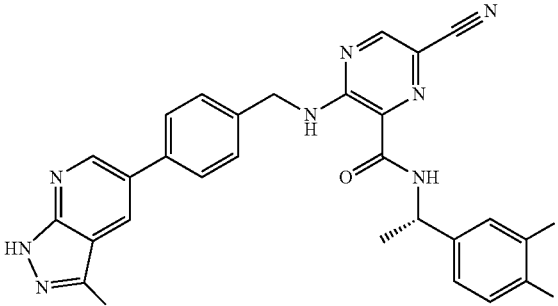
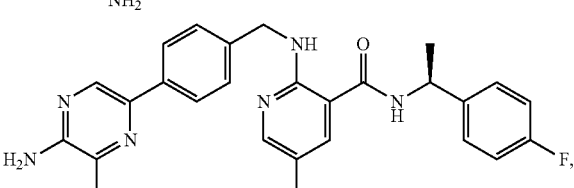
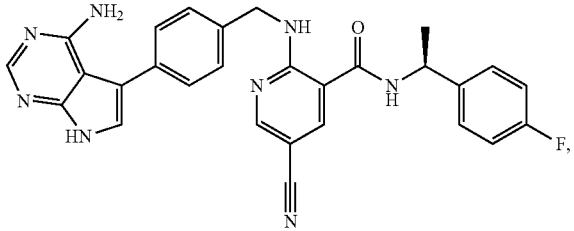
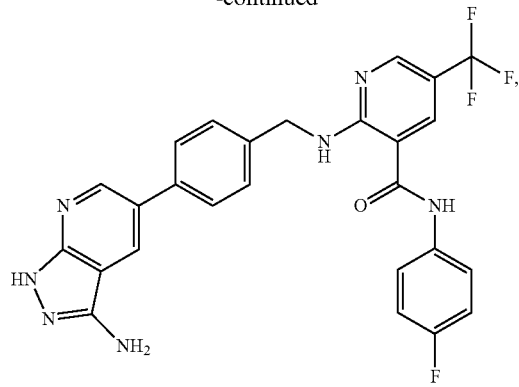
In certain embodiments, the present invention provides the following compounds:
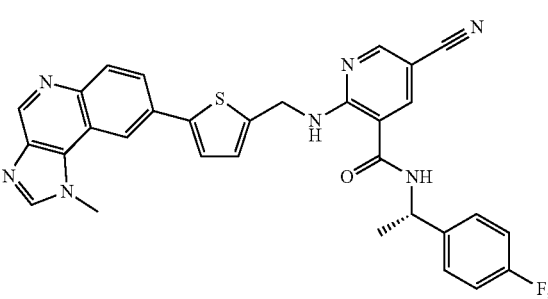
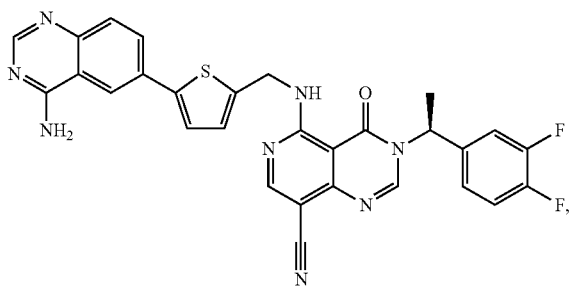

-continued

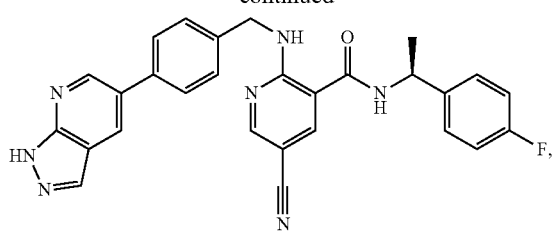

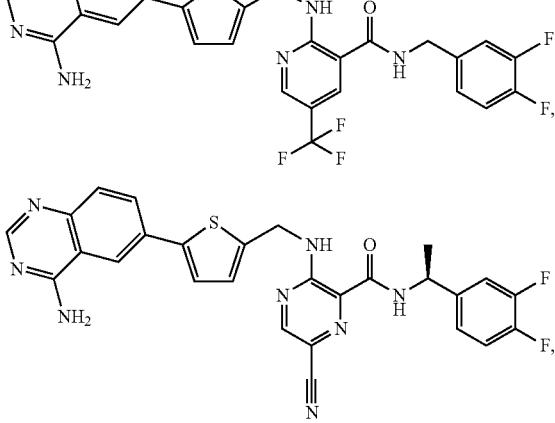

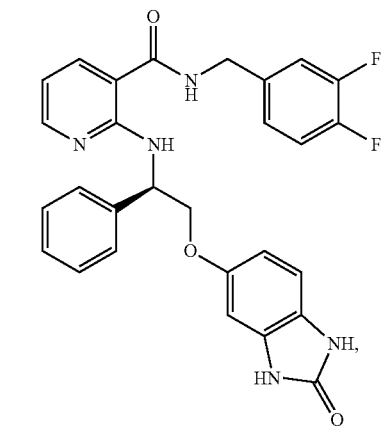

-continued

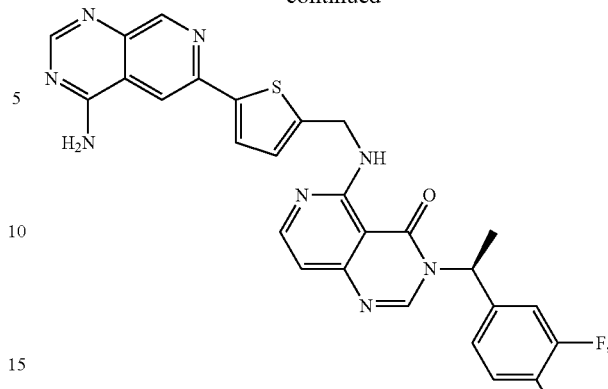

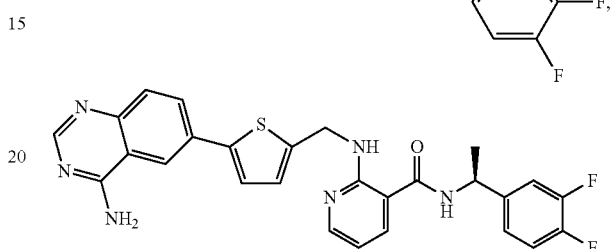

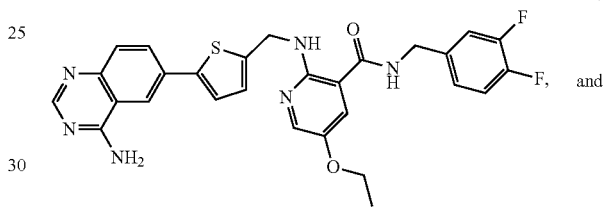

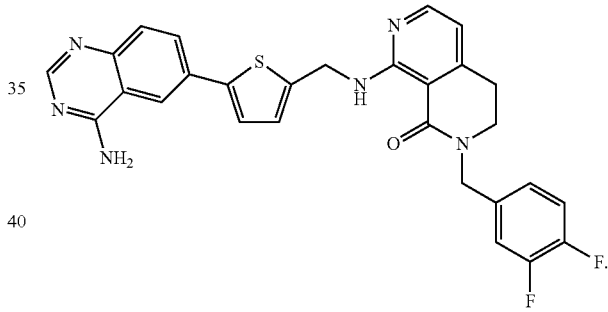

4. Methods

In another aspect, the present invention provides a method of decreasing PDK1 catalytic activity. The method includes contacting a PDK1 kinase with an effective amount of a compound of the present invention. Therefore, the present invention further provides a method of inhibiting PDK1 catalytic activity by contacting a PDK1 kinase with a provided compound.

PDK1 catalytic activity, as used herein, refers to PDK1 kinase catalytic activity. Thus, where PDK1 catalytic activity is decreased in the presence of a provided compound, the phosphorylation of a PDK1 substrate (e.g. Akt) is decreased relative to the phosphorylation rate in the absence of the provided compound. In some embodiments, the $IC_{50}$ of a provided compound against PDK1 is less than 1 µM. In other embodiments, the $IC_{50}$ of a provided compound against PDK1 is less than 500 nM. In other embodiments, the $IC_{50}$ of a provided compound against PDK1 is less than 100 nM. In other embodiments, the $IC_{50}$ of a provided compound against PDK1 is less than 10 nM. In other embodiments, the $IC_{50}$ of a provided compound against PDK1 is less than 1 nM. In other embodiments, the $IC_{50}$ of a provided compound against PDK1 is from 0.1 nM to 10 µM. In other embodiments, the $IC_{50}$ of a provided compound against PDK1 is from 0.1 nM to 1 µM. In other embodiments, the $IC_{50}$ of a provided compound against PDK1 is from 0.1 nM to 100 nM. In other embodiments, the $IC_{50}$ of a provided compound against PDK1 is from 0.1 nM to 10 nM.

In another aspect, provided compounds are useful for the treatment of one or more diseases, disorders, and/or conditions that may be alleviated by inhibiting (i.e. decreasing) PDK1 catalytic activity. As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

In some embodiments, the present invention provides a method of treating cancer in a subject in need thereof. In some embodiments, provided methods include administering to the subject a therapeutically effective amount of a provided compound. The term "cancer" includes diseases or disorders involving abnormal cell growth and/or proliferation, such as glioma, thyroid carcinoma, breast carcinoma, lung cancer (e.g. small-cell lung carcinoma, non-small-cell lung carcinoma), gastric carcinoma, gastrointestinal stromal tumors, pancreatic carcinoma, bile duct carcinoma, ovarian carcinoma, endometrial carcinoma, prostate carcinoma, renal cell carcinoma, anaplastic large-cell lymphoma, leukemia (e.g. acute myeloid leukemia, T-cell leukemia, chronic lymphocytic leukemia), multiple myeloma, malignant mesothelioma, malignant melanoma, colon cancer (e.g. microsatellite instability-high colorectal cancer).

In another aspect, the present invention provides methods for reducing PDK1-mediated phosphorylation of Akt. Provided methods include contacting PDK1 with a provided compound in the presence of Akt. In some embodiments, PDK1-mediated phosphorylation of Akt is reduced relative to PDK1-mediated phosphorylation of PKC (e.g. PKC isoforms zeta, delta, and/or theta). In some embodiments, the PDK1-mediated phosphorylation of Akt is inhibited at least 5-, 10-, 50-, 100-, or 1000-fold relative to the PDK1-mediated phosphorylation of PKC. Exemplary assays for determining the inhibition of PDK1-mediated phosphorylation of Akt are provided in the Examples below.

In some embodiments, the PDK1-mediated phosphorylation of Akt is reduced in a cell. In some embodiments, the present invention provides methods for reducing PDK1-mediated phsophorylation of Akt in a cell. In some embodiments, provided methods include contacting the cell with a compound of the present invention. In some embodiments, PDK1-mediated phsophorylation of Akt is reduced relative to PDK1-mediated phosphorylation of PKC (e.g. PKC isoforms zeta, delta, and/or theta). In some embodiments, the PDK1-mediated phosphorylation of Akt is inhibited at least 5-, 10-, 50-, 100-, or 1000-fold relative to the PDK1-mediated phosphorylation of PKC. Exemplary assays for determining the inhibition of PDK1-mediated phosphorylation of Akt are provided in the Examples below. In some embodiments, the cell in which PDK1-mediated phsophorylation of Akt is reduced is a mammalian cell, such as a domestic animal (e.g. cat, dog, hose, cow, etc.) or human.

5. Assays

To develop useful PDK1 inhibitors, candidate inhibitors capable of decreasing PDK1 catalytic activity may be identified in vitro. The activity of provided compounds can be assayed utilizing methods known in the art and/or those methods presented herein.

Compounds that decrease PDK1 catalytic activity may be identified and tested using biologically active PDK1, either recombinant or naturally occurring. PDK1 can be found in native cells, isolated in vitro, or co-expressed or expressed in a cell. Measuring the reduction in the PDK1 catalytic activity in the presence of an inhibitor relative to the activity in the absence of the inhibitor may be performed using a variety of methods known in the art, such as the assay described in Example 21. Other methods for assaying the activity of PDK1 are known in the art. The selection of appropriate assay methods is well within the capabilities of those of skill in the art.

Once compounds are identified that are capable of reducing PDK1 catalytic activity, the compounds may be further tested for their ability to selectively inhibit PDK1 relative to other enzymes. Inhibition by a compound of the invention is measured using standard in vitro or in vivo assays such as those well known in the art or as otherwise described herein.

Compounds may be further tested in cell models or animal models for their ability to cause a detectable changes in phenotype related to PDK1 activity. In addition to cell cultures, animal models may be used to test inhibitors of PDK1 for their ability to treat cancer in an animal model.

6. Pharmaceutical Compositions

In another aspect, the present invention provides pharmaceutical compositions comprising a provided compound optionally in combination with a pharmaceutically acceptable excipient (e.g. carrier).

Provided pharmaceutical compositions include optical isomers, diastereomers, or pharmaceutically acceptable salts of the compounds disclosed herein. For example, in some embodiments, pharmaceutical compositions include a pharmaceutically acceptable salt. A compound included in the pharmaceutical composition may be covalently attached to a pharmaceutically acceptable carrier. Alternatively, the inventive compound included in the pharmaceutical composition is not covalently linked to a pharmaceutically acceptable carrier.

A "pharmaceutically acceptable carrier," as used herein refers to pharmaceutical excipients, for example, pharmaceutically, physiologically, acceptable organic, or inorganic carrier substances suitable for enteral or parenteral application which do not deleteriously react with the extract. Suitable pharmaceutically acceptable carriers include water, salt solutions (such as Ringer's solution), alcohols, oils, gelatins and carbohydrates such as lactose, amylose or starch, fatty acid esters, hydroxymethycellulose, and polyvinyl pyrrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like which do not deleteriously react with the compounds of the invention.

Provided compounds can be administered alone or can be coadministered to a patient along with one or more other drugs. Coadministration is meant to include simultaneous or sequential administration of the compounds individually or in combination (more than one compound). In some embodiments, the preparations are combined with other active substances (e.g. to reduce metabolic degradation).

A. Formulations

Compounds of the present invention can be prepared and administered in a wide variety of oral, parenteral and topical dosage forms. In some embodiments, provided compounds are administered by injection (e.g. intravenously, intramuscularly, intracutaneously, subcutaneously, intraduodenally, or intraperitoneally). In some embodiments, compounds described herein are administered by inhalation, for example, intranasally. In some embodiments, provided compounds are administered transdermally. It is also envisioned that multiple routes of administration (e.g., intramuscular, oral, transdermal) can be used to administer the compounds of the invention. The present invention also provides pharmaceutical compositions comprising one or more provided compounds and one or more pharmaceutically acceptable carriers or excipients.

For preparing pharmaceutical compositions from provided compounds, pharmaceutically acceptable carriers can be either solid or liquid. Solid form preparations include powders, tablets, pills, capsules, cachets, suppositories, and dispersible granules. In some embodiments, a solid carrier is one or more substances, which may also act as diluents, flavoring agents, binders, preservatives, tablet disintegrating agents, or an encapsulating material.

In some embodiments, when the composition is a powder, the carrier is a finely divided solid in a mixture with the finely divided active component. In some embodiments, when the composition is formulated for a tablet, the active component is mixed with the carrier having the necessary binding properties in suitable proportions and compacted in the shape and size desired.

In some embodiments, provided powders and tablets contain from 5% to 70% of the active compound. Suitable carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. In some embodiments, the composition is formulated for a cachet or lozenge. In some embodiments, tablets, powders, capsules, pills, cachets, and/or lozenges are used as solid dosage forms suitable for oral administration.

In some embodiments, for preparing suppositories, a low melting wax, such as a mixture of fatty acid glycerides or cocoa butter, is first melted and the active component is dispersed homogeneously therein. The molten homogeneous mixture is then poured into convenient sized molds, allowed to cool and solidify.

Liquid form preparations include solutions, suspensions, and emulsions, for example, water or water/propylene glycol solutions. In some embodiments, for parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampules are convenient unit dosages. The compounds of the invention can also be incorporated into liposomes or administered via transdermal pumps or patches. Pharmaceutical admixtures suitable for use in the present invention include those described, for example, in Pharmaceutical Sciences (17th Ed., Mack Pub. Co., Easton, Pa.) and WO 96/05309, each of which is hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations intended for conversion shortly before use to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

In some embodiments, provided pharmaceutical compositions are in unit dosage form. In such form the composition is subdivided into unit doses containing appropriate quantities of the active component. The unit dosage form can be a packaged preparation, the package containing discrete quantities of a pharmaceutical composition, such as packeted tablets, capsules, and powders in vials or ampoules. In some embodiments, the unit dosage form is a capsule, tablet, cachet, or lozenge itself, or it is the appropriate number of any of these in packaged form.

The quantity of active component in a unit dosage form may be varied or adjusted from 0.1 mg to 10000 mg, more typically 1.0 mg to 1000 mg, most typically 10 mg to 500 mg, according to the particular application and the potency of the active component. In some embodiments, provided compositions contain other compatible therapeutic agents.

Some compounds may have limited solubility in water and may require a surfactant or other appropriate co-solvent in the composition. Such co-solvents include: Polysorbate 20, 60 and 80, Pluronic F-68, F-84 and P-103, cyclodextrin, and polyoxyl 35 castor oil. Such co-solvents are typically employed at a level between about 0.01% and about 2% by weight.

In some embodiments, viscosity greater than that of simple aqueous solutions may be desirable to decrease variability in dispensing the formulations, to decrease physical separation of components of a suspension or emulsion of formulation and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, combinations of the foregoing. Such agents are typically employed at a level between about 0.01% and about 2% by weight.

Provided compositions may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

B. Effective Dosages

Provided pharmaceutical compositions include compositions wherein the active ingredient is contained in a therapeutically effective amount, i.e., in an amount effective to achieve its intended purpose. The actual amount effective for

67 a particular application will depend, inter alia, on the condition being treated. In certain embodiments, when administered in methods to treat cancer, provided compositions will contain an amount of active ingredient effective to achieve the desired result (e.g. decreasing the number of cancer cells in a subject).

The dosage and frequency (single or multiple doses) of administered to a mammal can vary depending upon a variety of factors, including a disease that results in increased activity of PDK1, whether the mammal suffers from another disease, and its route of administration; size, age, sex, health, body weight, body mass index, and diet of the recipient; nature and extent of symptoms of the disease being treated (e.g., cancer), kind of concurrent treatment, complications from the disease being treated or other health-related problems. Other therapeutic regimens or agents can be used in conjunction with the methods and compounds of the invention.

For any compound described herein, a therapeutically effective amount may be initially determined from cell culture assays. Target concentrations will be those concentrations of active compound(s) that are capable of reducing the activity of PDK1 catalytic activity, as measured, for example, using the methods described herein.

Therapeutically effective amounts for use in humans may be determined from animal models. For example, a dose for humans can be formulated to achieve a concentration that has been found to be effective in animals. The dosage in humans can be adjusted by monitoring PDK1 inhibition and adjusting the dosage upwards or downwards, as described above.

Dosages may be varied depending upon the requirements of the patient and the compound being employed. In some embodiments, the dose administered to a patient is sufficient to effect a beneficial therapeutic response in the patient over time. The size of the dose also will be determined by the existence, nature, and extent of any adverse side-effects. In some embodiments, treatment is initiated with smaller dosages that are less than the optimum dose of the compound. Thereafter, the dosage is increased by small increments until the optimum effect under circumstances is reached. In one embodiment of the invention, the dosage range is 0.001% to 10% w/v. In another embodiment, the dosage range is 0.1% to 5% w/v.

EQUIVALENTS

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples that follow and the references to the scientific and patent literature cited herein. It should further be appreciated that the contents of those cited references are incorporated herein by reference to help illustrate the state of the art.

It will be appreciated that for compound preparations described herein, when reverse phase HPLC is used to purify a compound, a compound may exist as a mono-, di-, or tri-trifluoroacetic acid salt.

It will further be appreciated that the present invention contemplates individual compounds described herein. Where individual compounds exemplified are isolated and/or characterized as a salt, for example, as a trifluoroacetic

68 acid salt, the present invention contemplates a free base of the salt, as well as other pharmaceutically acceptable salts of the free base.

The following examples contain important additional information, exemplification and guidance that can be adapted to the practice of this invention in its various embodiments and the equivalents thereof.

EXAMPLES

As depicted in the Examples below, in certain exemplary embodiments, compounds are prepared according to the following general procedures. It will be appreciated that, although the synthetic methods and Schemes depict the synthesis of certain compounds of the present invention, the following methods and other methods known to one of ordinary skill in the art can be applied to all compounds and subclasses and species of each of these compounds, as described herein.

Example 1

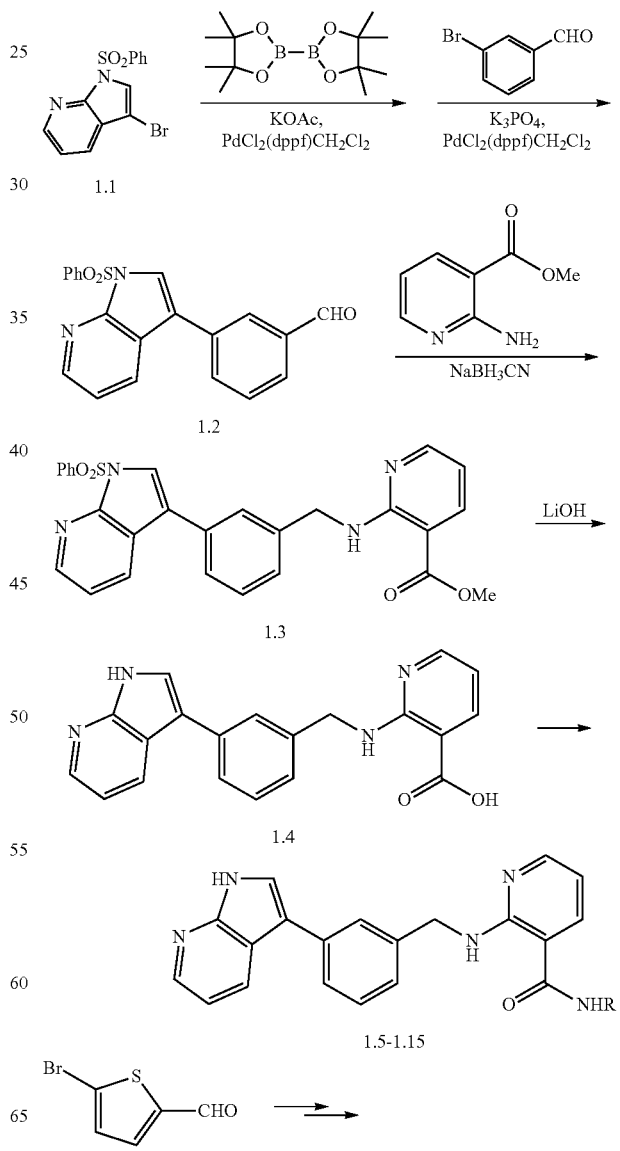

-continued

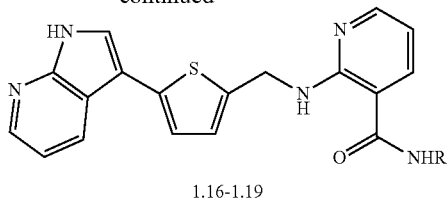

1.16-1.19

Step 1: Synthesis of 3-(1-(phenylsulfonyl)-1H-pyrrolo[2,3-b]pyridin-3-yl)benzaldehyde (Ex. 1.2)

A flask charged with 3-bromo-1-(phenylsulfonyl)-1H-pyrrolo[2,3-b]pyridine (1.1, prepared by the method reported in application WO2008005457) (3.0 g, 8.9 mmol), bis(pinacolato)diboron (9.0 g, 35.6 mmol), KOAc (1.8 g, 17.8 mmol), Pd(dppf)Cl$_2$CH$_2$Cl$_2$ (0.23 g, 0.28 mmol) and DMSO (1 ml) was flushed with nitrogen. 1,4-Dioxane (30 mL) was added and the reaction was heated to 90° C. for 2 h until it was cooled to room temperature. The compound 3-bromobenzaldehyde (5.5 g, 17.8 mmol), Pd(dppf)Cl$_2$CH$_2$Cl$_2$(0.23 g, 0.28 mmol), and K$_3$PO$_4$ (10 ml, 2M, 0.02 mmol) were added and heated to 90° C. under nitrogen for another 5 hrs. Cooled to room temperature and extracted with ethyl acetate (3×50 mL). The combined ester layer was dried over Na$_2$SO$_4$ and concentrated in vacuum. Purification on silica gel with 14% ethyl acetate in hexane gives 2.43 g of compound 1.2 (58%). ESI-MS (M+H$^+$): 363.1.

Synthesis of methyl-2-aminonicotinate

A suspension of 2-aminonicotinic acid (13.8 g, 0.1 mol) and K$_2$CO$_3$ (27.6 g, 0.2 mol, 2.0 equiv) in DMSO was heated to reflux, and then the solution was cooled to ambient temperature. Iodomethane (14.2 g, 0.1 mol, 1.0 equiv.) was then added to the mixture and the solution was stirred for 18 hrs. The mixture was filtered and concentrated. The residue was filtered through a pad of silica, eluting with 5/95 (EtOH/CH$_2$Cl$_2$) containing 0.1% NH$_4$OH. The resulting solution was concentrated and the residue was suspended in Et$_2$O, filtered, and dried to yield methyl 2-aminonicotinate (10.8 g, 71%). ESI-MS (M+H$^+$): 153.1.

Step 2: Synthesis of methyl 2-(3-(1-(phenylsulfonyl)-1H-pyrrolo[2,3-b]pyridin-3-yl)benzyl-amino)nicotinate (Ex. 1.3)

A solution of 3-(1-(phenylsulfonyl)-1H-pyrrolo[2,3-b]pyridin-3-yl)benzaldehyde (1.2) (4.85 g, 13.4 mmol), methyl-2-aminonicotinate (2.05 g, 13.4 mmol) and p-toluenesulfonic acid monohydrate catalyst (217 mg, 1.34 mmol) in refluxing toluene with the removal of water using a Dean-Stark apparatus fixed with anhydrous Na$_2$SO$_4$ and 4A molecular sieves. After 18 hr, the reaction mixture was cooled to ambient temperature, and the organic solvent was then removed to give a crude product (6.65 g, 13.4 mmol), which was dissolved in anhydrous methanol and slowly added NaBH$_3$CN (12.6 g, 20 mmol) at 0° C. The resulted mixture was stirred at room temperature for 5 hrs. TLC show the reaction was completed. The organic solvent was then removed to give a crude product, which was purified through silica column gel (eluted with 33% ethyl acetate in petroleum ether) to obtain 2-(3-(1-(phenylsulfonyl)-1H-pyrrolo[2,3-b]pyridin-3-yl)benzylamino)nicotinate (3.35 g), yield 51%. ESI-MS (M+H$^+$): 499.1.

Step 3: Synthesis of 2-(3-(1H-pyrrolo[2,3-b]pyridin-3-yl)benzylamino)nicotinic acid (Ex. 1.4)

A solution of 2-(3-(1-(phenylsulfonyl)-1H-pyrrolo[2,3-b]pyridin-3-yl)benzylamino)-nicotinate (3.347 g, 6.72 mmol) in a mixed solvent (THF:MeOH:H$_2$O=3:2:1) was slowly added LiOH (323 mg, 13.44 mmol) to the solution. The resulted mixture was stirred at room temperature for 15 hrs. TLC show the reaction was completed. The organic solvent was then removed to give a crude product which was purified through silica column gel (eluted with 33% ethyl acetate in petroleum ether) to obtain 2-(3-(1H-pyrrolo[2,3-b]pyridin-3-yl)benzylamino)nicotinic acid (1.2 g), yield 52%. ESI-MS (M+H$^+$): 345.1.

Ex. 1.5

Synthesis of 2-(3-(1H-pyrrolo[2,3-b]pyridin-3-yl)benzylamino)-N-(3,4-difluorobenzyl)nicotinamide To a solution of 2-(3-(1H-pyrrolo[2,3-b]pyridin-3-yl)benzylamino)nicotinic acid (344 mg, 1 mmol) in anhydrous DMF (20 ml) was added DIPEA (265 mg, 2 mmol) dropwise. The reaction mixture was stirred at room temperature for 30 min., and then 3, 4-difluorobenzylamine (286 mg, 2 mmol) and HATU (760 mg. 2 mmol) were added. The mixture was stirred at room temperature 18 hrs. After the reaction ended, the solvent was removed and the residue was purified by column chromatography to give the desired product (100 mg), Yield 22%. ESI-MS (M+H$^+$): 470.2. $^1$H NMR (400 MHz, DMSO-d$_6$) δ: 9.15-9.30 (m, 2H), 8.16-8.27 (m, 4H), 7.85 (d, 1H), 7.70 (s, 1H), 7.59 (d, 1H), 7.29-7.41 (m, 3H), 7.08-7.22 (m, 3H), 6.73-6.77 (m, 1H), 4.71 (s, 2H), 4.42 (d, 2H), 2.16 (s, 1H).

Examples 1.6-1.15 were prepared in a manner analogous to Ex. 1.5.

Synthesis of Cyclopentylmethanamine Hydrochloride, intermediate for Ex. 1.8 and 1.19

A solution of borane (1 M in tetrahydrofuran, 52.7 mL, 52.7 mmol, 1.1 equiv.) was added drop wise over 2 h to a stirred solution of cyclopentanecarbonitrile (4.56 g, 47.9 mmol) in dry tetrahydrofuran (20 mL). The resultant solution was refluxed with stirring for 18 h. The reaction was cooled to ambient temperature and cautiously diluted in small portions with methanol (67 mL). The solution was cooled on an ice bath, and hydrogen chloride gas was bubbled through the solution for 0.5 h. The reaction was refluxed for 1.5 h, and the volatiles were removed by spin evaporation in vacuo. Methanol (50 mL) was added to the residue, and the mixture was spin evaporated in vacuo. This methanol addition procedure was repeated twice to give a white solid, which was further purified by precipitation from ethanol: ethyl acetate to give 3.62 g (56%) of (cyclopentylmethyl) amine hydrochloride. ESI-MS (M+H$^+$): 136.0.

Examples 1.16-1.19 were prepared following the same synthetic scheme as Ex. 1.5-1.15 starting with 5-bromothiophene-2-carbaldehyde.

Ex. 1.20 was prepared in a manner analogous to Ex. 1.5.

Example 2

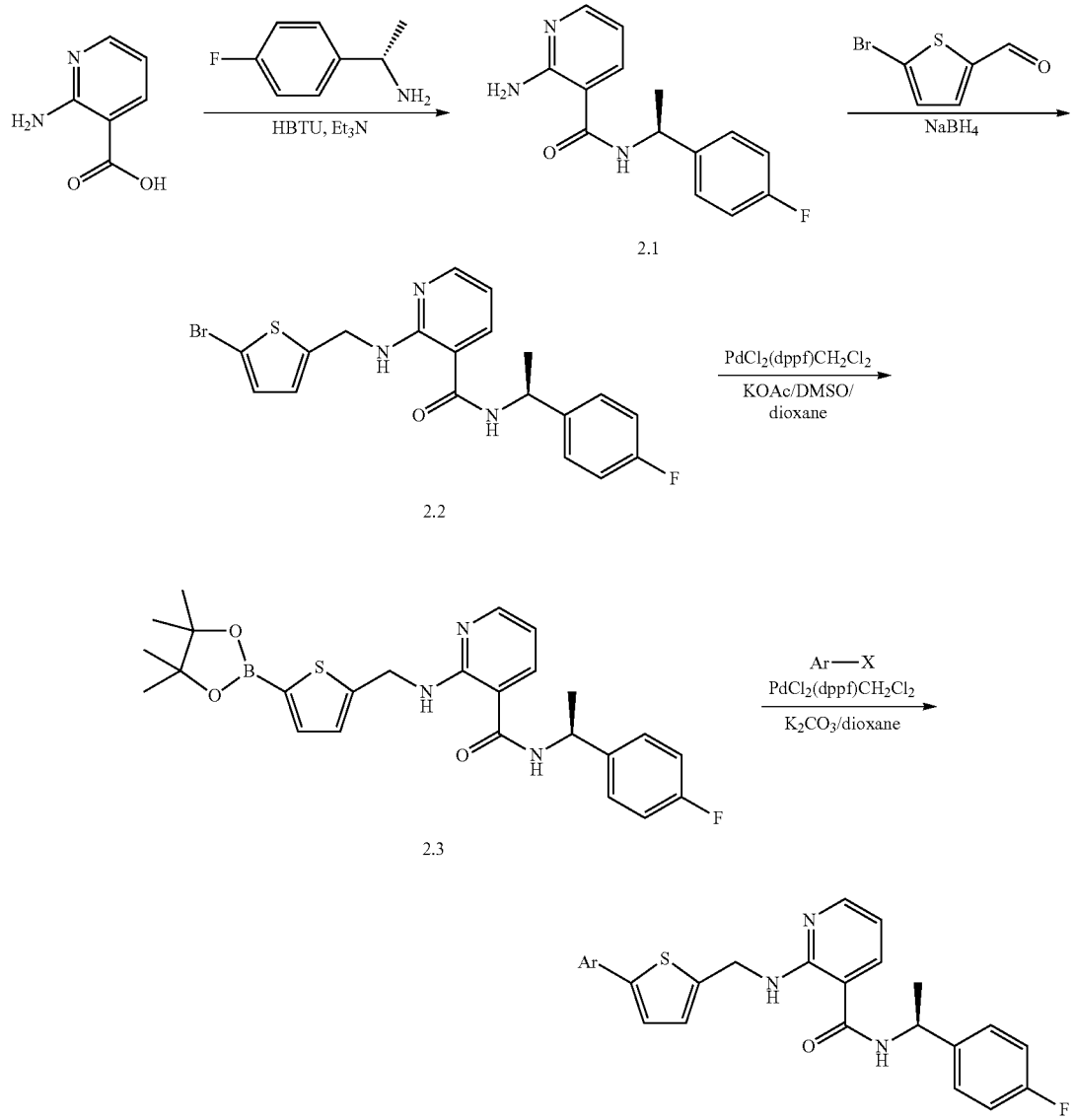

Step 1. Synthesis of (S)-2-amino-N-(1-(4-fluorophenyl)ethyl)nicotinamide (Ex. 2.1)

To a solution of 2-aminonicotinic acid (3 g, 21.7 mmol) in DCM (100 ml), was added HBTU (16.5 g, 43.4 mmol, 2.0 equiv), (S)-1-(4-fluorophenyla)ethanamine (3.02 g 21.7 mmol, 1.0 eq.) and TEA (10.97 g 0.11 mol, 5.0 eq). The reaction mixture was stirred at room temperature for 18 h. The solvent was filtrated, and removed and the residue was purified by column chromatography (PE/EA=2:1) to give the desired product, 4.2 g (yield: 74%). ESI-MS (M+H$^+$): 260.1; $^1$H NMR (400 MHz, CD$_3$OD) δ: 8.03 (q, 1H), 7.94 (dd, 1H), 7.38-7.42 (m, 2H), 7.02-7.08 (m, 2H), 6.66 (dd, 1H), 5.16-5.21 (q, 1H), 1.53 (d, 3H).

Step 2. Synthesis of (S)-2-(((5-bromothiophen-2-yl)methyl)amino)-N-(1-(4-fluorophenyl)ethyl)-nicotinamide To a solution of (S)-2-amino-N-(1-(4-fluorophenyl)ethyl) nicotinamide (2.6 g 10 mmol) in 5 mL of methanol was added 5-bromothiophene-2-carbaldehyde (2.29 g, 12 mmol 1.2 eq) at rt. The reaction mixture was heated to refluxing and stirred for 16 h. Then 10 mL of methanol and NaBH$_4$ (380 mg, 10 mmol, 1.0 equiv) was added to the reaction mixture at rt. The reaction mixture was stirred of 2 h at rt. The solvent was removed by rotation evaporation, and the residue was purified on silica gel chromatography (PE/EA=2:1) to give the desired product, 2.48 g, (yield: 58%). ESI-MS (M+H$^+$): 434.0; $^1$H NMR (400 MHz, CD$_3$OD) δ: 8.10 (dd, 1H), 7.85 (dd, 1H), 7.28-7.33 (m, 2H), 6.94-7.00 (m, 2H), 6.81 (d, 1H), 6.70 (d, 1H), 6.58 (dd, 1H), 5.06-5.12 (q, 1H), 4.64 (s, 2H), 1.45 (d, 3H).

Step 3. (S)-N-(1-(4-fluorophenyl)ethyl)-2-(((5-(4,4,5,5-tetramethyl-1,3,2-dioxaborolan-2-yl)-thiophen-2-yl)methyl)amino)nicotinamide A flask charged with (S)-2-(((5-bromothiophen-2-yl)methyl)amino)-N-(1-(4-fluorophenyl)ethyl)nicotinamide (0.58 g, 1.4 mmol), 4,4,4',4',5,5,5',5'-octamethyl-2,2'-bi(1,3,2-dioxaborolane) (690 mg, 2.8 mmol, 2.0 equiv), KOAc (248 mg, 2.8 mmol, 2.0 equiv) and [1,1-Bis(diphenylphosphino)ferrocene]dichloropalladium(II) complex with dichloromethane (1:1) (1.2 g, 1.5 mmol, 0.05 equiv) was flushed with nitrogen. 1,4-Dioxane (20 ml) and DMSO (3 ml) were added and the reaction was stirred at 90° C. for 2 h. The solution was cooled to rt. The solvent was removed and the residue was purified by silica gel chromatography (PE/EA=5:1) to give the desired product 540 mg (yield: 61%). ESI-MS (M+H$^+$): 482.2; $^1$H NMR (400 MHz, CDCl$_3$) δ: 8.47 (d, 1H), 8.23 (dd, 1H), 7.57 (dd, 1H), 7.47 (d, 1H), 7.31-7.34 (m, 2H), 7.02-7.06 (m, 3H), 6.51-6.54 (q, 1H), 6.22 (s, 1H), 5.20 (q, 1H), 4.89 (t, 2H), 1.55 (d, 3H), 1.30 (s, 12H).

Ex. 2.4

Synthesis of N-[(1S)-1-(4-fluorophenyl)ethyl]-2-({[5-([1,2,4]triazolo[1,5-a]pyridin-6-yl)thiophen-2-yl]methyl}amino)pyridine-3-carboxamide A flask charged with compound (S)-N-(1-(4-fluorophenyl)ethyl)-2-(((5-(4,4,5,5-tetramethyl-1,3,2-dioxaborolan-2-yl)thiophen-2-yl)methyl)amino)nicotinamide (58 mg, 1.2 mmol), 6-iodo-[1,2,4]triazolo[1,5-a]pyridine (29 mg, 1.2 mmol, prepared according to a procedure reported in WO 2004/072033), 2M K$_2$CO$_3$ (1.20 mL) and [1,1-Bis(diphenylphosphino)ferrocene]dichloropalladium(II) complex with dichloromethane (1:1) (9.8 mg, 0.012 mmol) was flushed with nitrogen. 1, 4-Dioxane (5 mL) was added and the reaction was heated to 90° C. for 2 h. The solution was cooled to room temperature. The solvent was removed and the residue was purified by prep HPLC to give (S)-2-(((5-([1,2,4]triazolo[1,5-a]pyridin-6-yl)thiophen-2-yl)methyl)amino)-N-(1-(4-fluorophenyl)ethyl)nicotinamide (Ex. 2.4, 11 mg, 19.4%). ESI-MS (M+H$^+$): 472.1; $^1$H NMR (400 MHz, CD$_3$OD) δ: 8.93 (br, 1H), 8.35 (br, 1H), 8.23 (d, 1H), 8.01-8.03 (dd, 1H), 7.84 (d, 1H), 7.69 (d, 1H), 7.28-7.31 (m, 3H), 7.03 (d, 1H), 6.91-6.96 (m, 2H), 6.81-6.85 (m, 1H), 5.06-5.11 (q, 1H), 4.77 (s, 2H), 1.44 (d, 3H).

Examples 2.5-2.14 were prepared in a manner analogous to Ex. 2.4.

Synthesis of 6-chloropyrido[3,4-d]pyrimidin-4-amine, intermediate for Ex. 2.13.1

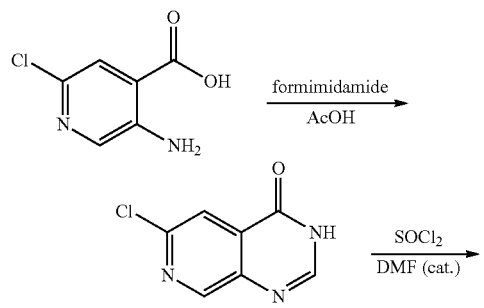

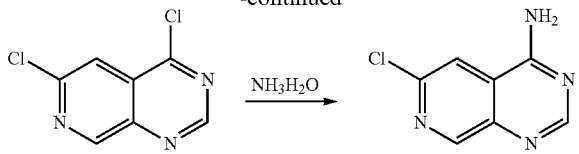

Step 1: A solution of 5-amino-2-chloroisonicotinic acid (1.3 g, 7.6 mmol), formimidamide (0.66 g, 15.1 mmol, 2.0 equiv) in AcOH was heated to 120° C. for 4 h. and then the solvent was removed, water was added and adjusted pH to 8 with NaHCO3, filtered to give 6-chloropyrido[3,4-d]pyrimidin-4(3H)-one (1.1 g, yield 81.5%). ESI-MS (M+H$^+$): 182.0; $^1$H NMR (400 MHz, DMSO) δ: 12.77 (s, 1H), 8.92 (s, 1H), 8.25 (s, 1H), 7.98 (s, 1H).

Step 2: A solution of SOCl$_2$ (20 ml), 6-chloropyrido[3,4-d]pyrimidin-4(3H)-one (1.81 g, 10 mmol), and DMF (cat amount) was heated to reflux for 2 h. Evaporated off the solvents and the crude product was used for the next step without further purifications. ESI-MS (M+H$^+$): 200.0.

Step 3: The above product (2 g, 10 mmol) was dissolved in ammonia (20 ml), the reaction was stirred at rt for 1 h, and filtered to give 6-chloropyrido[3,4-d]pyrimidin-4-amine (1.56 g, 87%). ESI-MS (M+H$^+$): 181.0; $^1$H NMR (400 MHz, DMSO) δ: 8.93 (s, 1H), 8.53 (s, 1H), 8.33 (s, 1H), 8.28 (s, 2H).

Synthesis of 2-(6-iodoquinazolin-4-ylamino)ethanol, the intermediate for Ex. 2.14

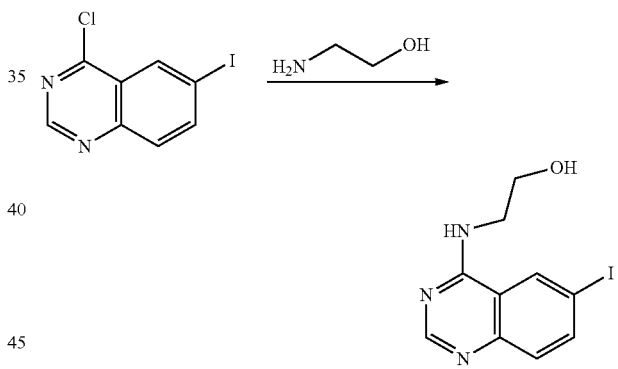

To a solution of 4-chloro-6-iodoquinazoline (500 mg 1.72 mmol) in isopropanol (15 mL), was added 2-aminoethanol (213 mg, 3.4 mmol). The reaction mixture was heated to 100° C. for 3 h. Cooled to room temperature, the precipitates from the reaction mixture was collected and washed with petroleum ether to give the desired product (326 mg, 60%). ESI-MS (M+H$^+$): 316.0; $^1$H NMR (400 MHz, CD$_3$OD) δ: 9.35 (br, 1H), 8.89 (s, 1H), 8.68 (s, 1H), 8.15 (d, 1H), 7.54 (d, 1H), 3.66 (s, 4H).

Synthesis of (S)-2-(((5-(4-chloroquinazolin-6-yl)thiophen-2-yl)methyl)amino)-N-(1-(4-fluorophenyl)ethyl)nicotinamide, the intermediate for Ex. 2.15, following the procedure for Ex. 2.4

ESI-MS (M+H$^+$): 517.0; $^1$H NMR (400 MHz, CD$_3$OD) δ:6.27 (s 1H), 8.97 (s, 1H), 8.64 (s, 1H), 8.29-8.31 (m, 2H), 8.15 (dd, 1H), 8.04 (d, 1H), 7.65 (d, 1H), 7.32-7.36 (m, 3H), 7.02-7.06 (m, 3H), 6.61 (dd, 1H), 5.24 (q, 1H), 4.9 (dd, 2H), 1.58 (d, 3H).

Ex. 2.15

(S)-2-(((5-(4-(2-aminoethylamino)quinazolin-6-yl)
thiophen-2-yl)methyl)amino)-N-(1-(4-fluorophenyl)
ethyl)nicotinamide

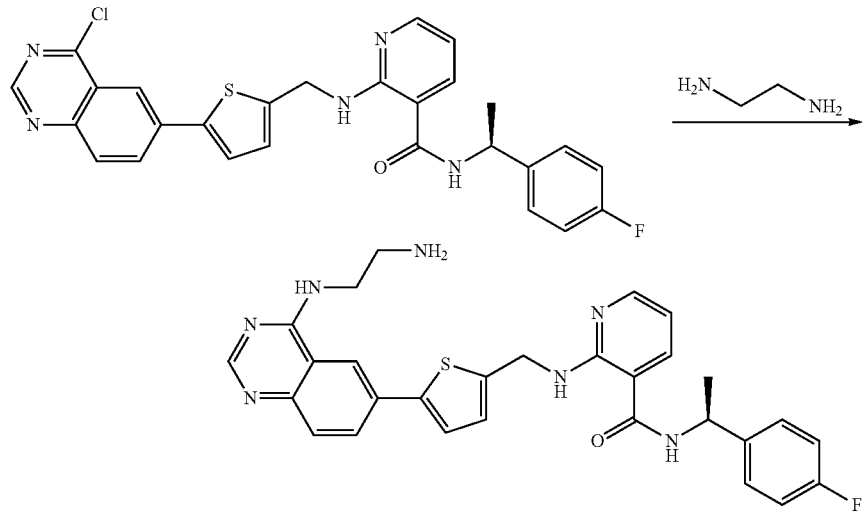

To a flask charged with 10 ml ethane-1,2-diamine, (S)-2-(((5-(4-chloroquinazolin-6-yl)thiophen-2-yl)methyl)amino)-N-(1-(4-fluorophenyl)ethyl)nicotinamide was added. The reaction mixture was heated to 80° C. for 2 h. Cooled to rt., evaporated off the excess ethane-1, 2-diamine and purified by prep HPLC to give the desired product (20 mg, 48%). ESI-MS (M+H$^+$): 542.0; $^1$H NMR (400 MHz, CD$_3$OD) δ:8.48 (s, 1H), 8.29 (d, 1H), 8.19 (dd, 1H), 8.05 (dd, 1H), 7.96 (dd, 1H), 7.72 (d, 1H), 7.41-7.37 (m, 3H), 7.06-7.02 (m, 3H), 6.66 (dd, 1H), 5.18 (q, 1H), 4.83 (s, 2H), 3.93 (t, 1H), 3.29 (t, 1H), 1.53 (d, 3H).

Examples 2.16-2.39 were prepared in a manner analogous to Ex. 2.4.

Synthesis of intermediates for Examples 2.16-2.19

Synthesis of 6-bromo-N-methyl-3-nitroquinolin-4-amine

To a solution of 6-bromo-4-chloro-3-nitroquinoline (4.5 g, 15.65 mmol, prepared according to the procedure reported in *Bioorganic & Medicinal Chemistry Letters,* 18(3), 1027-1030; 2008.) in Et$_2$O (20 ml), was added methanamine (0.58 g, 18.8 mmol, 1.2 equiv) slowly at rt. The resulted mixture was stirred at rt for 0.5 h, until TLC showed the starting material disappeared. The solution was concentrated in vacuo and purified by silica gel column to give the desired product (4. g, 93%). ESI-MS (M+H$^+$): 282.0; $^1$H NMR (400 MHz, CDCl$_3$) δ: 9.35 (s, 1H), 8.54 (d, 1H), 7.82-7.89 (m, 2H), 9.85 (br, 1H), 3.64 (d, 3H).

Synthesis of 6-bromo-N$^4$-methylquinoline-3,4-diamine

A mix of 6-bromo-N-methyl-3-nitroquinolin-4-amine (2 g, 7.1 mmol) and Raney-Ni (0.2 g) in MeOH-THF (1:1, 50 mL) was stirred under 1.1 bar of H₂ for 1 h at room temperature. Then the catalyst was filtered off and the filtrate was evaporated to dryness. The residue was purified by silica gel column chromatography (PE-EA 3:1) to give the desired product as a greenish solid (1.78 g, 100%). ESI-MS: 252.0 (M+H)⁺; ¹H NMR (400 MHz, CDCl₃) δ: 8.47 (s, 1H), 7.98 (d, 1H), 7.82 (d, 1H), 7.52 (dd, 1H), 3.82 (br, 1H), 3.66 (br, 1H), 2.98 (d, 3H).

Synthesis of 8-bromo-1-methyl-1H-imidazo[4,5-c] quinolin-2(3H)-one

To a solution of 6-bromo-N4-methylquinoline-3,4-diamine (1.78 g, 7.06 mmol) in THF, was added CDI (2.28 g 14.12 mmol) at 0° C. After the reaction mixture was stirred for 24 h at rt, the solvent was evaporated off and residue was purified by silica gel column to give the desired product (0.78 g, 39%). ESI-MS (M+H⁺): 278.0; ¹H NMR (400 MHz, DMSO-d₆) δ: 3.77 (d, 3H), 7.73 (dd, 1H), 7.93 (d, 1H), 8.43 (s, 1H), 8.68 (s, 1H), 11.65 (s, 1H).

Synthesis of 8-bromo-1,3-dimethyl-1H-imidazo[4,5-c]quinolin-2(3H)-one

To a solution of 8-bromo-1-methyl-1H-imidazo[4,5-c] quinolin-2(3H)-one (400 mg, 1.4 mmol), was added Cs₂CO₃ (420 mg, 2.2 mmol) and CH₃I (410 mg, 2.9 mmol). The reaction mixture was stirred at rt for 12 h, and was filtered. The filtrates were concentrated and purified by silica gel column to give the product (330 mg, 78%). ESI-MS (M+H⁺): 292.0; ¹H NMR (400 MHz, CDCl₃) δ: 8.73 (s, 1H), 8.38 (d, 1H), 8.06 (d, 1H), 7.71 (dd, 1H), 3.94 (s, 3H), 3.63 (s, 3H).

Synthesis of 8-bromo-1-methyl-1H-imidazo[4,5-c] quinoline

To a solution of 6-bromo-N4-methylquinoline-3,4-diamine (1.35 g, 5.35 mmol) in MeOH (30 ml) was added triethoxymethane (1.6 g, 10.7 mmol). The reaction mixture was stirred at rt for 3 h and then was concentrated and purified by silica gel column to give the desired product as a brown solid (510 mg, 36%). ESI-MS (M+H⁺): 262, 264; ¹H NMR (400 MHz, CDCl₃) δ: 9.33 (s, 1H), 8.42 (d, 1H), 8.17 (d, 1H), 7.97 (s, 1H), 7.78 (dd, 1H), 4.30 (s, 3H).

8-bromo-1,2-dimethyl-1H-imidazo[4,5-c]quinoline was prepared similarly from triethoxyethane ESI-MS (M+H⁺): 276.0; ¹H NMR (400 MHz, CDCl₃) δ: 9.23 (s, 1H), 8.37 (d, 1H), 8.12 (d, 1H), 7.73 (dd, 1H), 4.15 (s, 3H), 2.72 (s, 3H).

Synthesis of intermediates for Ex. 2.20

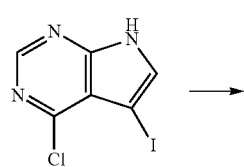

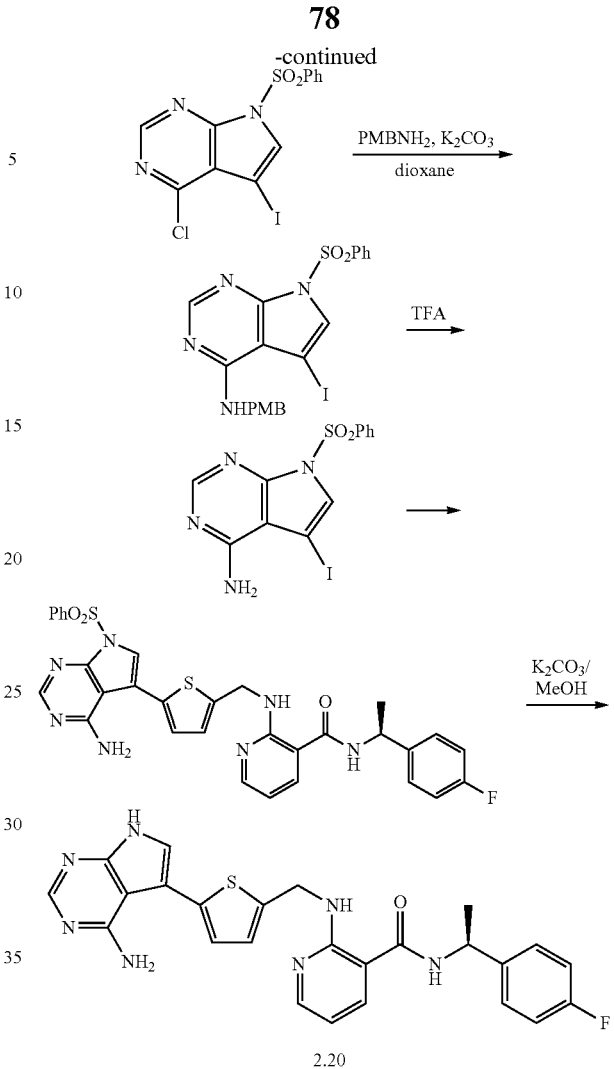

2.20

Step 1: Synthesis of 4-chloro-5-iodo-7-(phenylsulfonyl)-7H-pyrrolo[2,3-d]pyrimidine To a suspension of 4-chloro-5-iodo-7H-pyrrolo[2,3-d] pyrimidine (ref. Young, et al. JMC (2008), 51(13), 3934-3945.)(2.5 g, 0.0089 mol), and N,N-Diisopropylethylamine (3 mL, 0.02 mol), 4-Dimethylaminopyridine (0.01 g, 0.00009 mol) in Methylene chloride (50 mL, 0.8 mol) was added Benzenesulfonyl chloride (1.4 mL, 0.011 mol) and stirred at room temperature for 1 h and it became a clear solution. LC-MS showed completed reaction. Worked up with DCM and water. Dried over MgSO4 and conctd. The residue was then purified on a short silica gel column with DCM to give the desired product as a white solid (3.0 g, 80%). ES+/420.00.

Step 2: Synthesis of 5-iodo-N-(4-methoxybenzyl)-7-(phenylsulfonyl)-7H-pyrrolo[2,3-d]pyrimidin-4-amine A mixture of 4-chloro-5-iodo-7-(phenylsulfonyl)-7H-pyrrolo[2,3-d]pyrimidine (420 mg, 1 mmol), K₂CO₃ (280 mg, 2 mmol, 2 equiv), and p-methoxybenzylamine (280 mg, 2 mmol) in dioxane (200 ml) was heated to 90° C. for 1 h. The solvent was removed and the residue was purified on silica gel column to give the desired product (440 mg, 50%). ESI-MS (M+H+): 521.

Step 3: Synthesis of 5-iodo-7-(phenylsulfonyl)-7H-pyrrolo[2,3-d]pyrimidin-4-amine A solution of 5-iodo-N-(4-methoxybenzyl)-7-(phenylsulfonyl)-7H-pyrrolo[2,3-d]pyrimidin-4-amine (520 mg, 1 mmol) in trifluoroacetic acid (10 ml) was heated to reflux for 1 h. Evaporated off the solvent and the residue was neutralized with NaHCO$_3$ and purified by column chromatography to give the desired product (344 mg, 86%). ESI-MS (M+H+): 401; $^1$H NMR (400 MHz, CD$_3$OD) δ: 8.22 (s, 1H), 8.15-8.13 (d, 2H), 7.87 (s, 1H), 7.78 (t, 1H), 7.69-7.65 (t, 2H), 7.0 (s, 2H).

Step 4: Synthesis of (S)-2-(((5-(4-amino-7-(phenylsulfonyl)-7H-pyrrolo[2,3-d]pyrimidin-5-yl)thiophen-2-yl)methyl)amino)-N-(1-(4-fluorophenyl)ethyl) nicotinamide A mixture of (S)-N-(1-(4-fluorophenyl)ethyl)-2-(((5-(4,4,5,5-tetramethyl-1,3,2-dioxaborolan-2-yl)thiophen-2-yl)methyl)amino)nicotinamide (400 mg, 0.83 mmol), 5-iodo-7-(phenylsulfonyl)-7H-pyrrolo[2,3-d]pyrimidin-4-amine (332 mg, 0.83 mmol), 2M K$_2$CO$_3$ (230 mg, 1.66 mmol) and [1,1-Bis(diphenylphosphino)ferrocene]dichloropalladium (II) complex with dichloromethane (1:1) (34 mg, 0.02 mmol) in 1,4-Dioxane (200 mL) was heated 90° C. for 3 h under nitrogen. The reaction was cooled to room temperature. The solvent was removed and the residue was purified by column chromatography (PE/EA=1/2) to give the desired product (84 mg, 16%). ESI-MS (M+H+): 628.1.

Ex. 2.20

(S)-2-(((5-(4-amino-7H-pyrrolo[2,3-d]pyrimidin-5-yl)thiophen-2-yl)methyl)amino)-N-(1-(4-fluorophenyl)ethyl)nicotinamide A mixture of (S)-2-(((5-(4-amino-7-(phenylsulfonyl)-7H-pyrrolo[2,3-d]pyrimidin-5-yl)thiophen-2-yl)methyl)amino)-N-(1-(4-fluorophenyl)ethyl)nicotinamide (144 mg, 0.23 mmol) and K$_2$CO$_3$ (127 mg, 0.92 mmol) in MeOH (20 ml) was heated to reflux for 2 h. Cooled to room temperature and concentrated. Purified by prep HPLC to give the desired product as a light yellow solid (40 mg, 35.6%). ESI-MS (M+H+): 488.2; $^1$H NMR (400 MHz, CD$_3$OD) δ: 8.19-8.17 (dd, 2H), 8.13 (br, 1H), 7.89-7.75 (m, 2H), 7.34-7.31 (m, 2H), 7.09 (s, 1H), 6.99-6.97 (m, 3H), 6.89 (d, 1H), 6.62-6.58 (m, 1H), 5.20-5.15 (m, 1H), 4.79 (q, 2H), 1.52 (d, 3H).

Synthesis of intermediates for Ex. 2.23

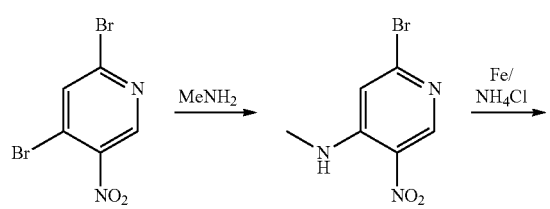

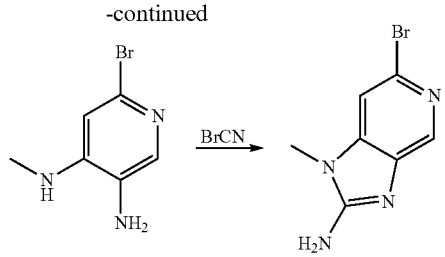

Step 1: A mixture 2,4-dibromo-5-nitropyridine (700 mg, 2.5 mmol), MeNH$_2$ (155 mg, 5 mmol), and K$_2$CO$_3$(690 mg, 5 mmol) in DCM/H$_2$O was stirred at rt for 6 h. Evaporated off the solvents to give the product, 2-bromo-N-methyl-5-nitropyridin-4-amine, which was used in the next step without further purifications. ESI-MS (M+H+): 232.0; $^1$H NMR (400 MHz, CDCl$_3$) δ: 8.97 (s, 1H), 6.93 (s, 1H), 3.06 (s, 3H).

Step 2: A mixture of 2-bromo-N-methyl-5-nitropyridin-4-amine (519 mg, 2.2 mmol), iron (440 mg, 7.9 mmol), and NH$_4$Cl (1.2 g, 22 mmol) in THF/H$_2$O was heated to reflux for 2 h. The reaction mixture was filtered, and THF was removed under vacuo to give the product, 6-bromo-N$^4$-methylpyridine-3,4-diamine, which was used in the next step without further purifications. ESI-MS (M+H+): 202.1; $^1$H NMR (400 MHz, CD$_3$OD) δ: 7.18 (s, 1H), 6.50 (s, 1H), 2.66 (s, 3H).

Step 3: A mixture of 6-bromo-N4-methylpyridine-3,4-diamine (390 mg, 1.94 mmol), H$_2$O, and CNBr (1 g, 9.7 mmol) in THF was stirred at reflux for 16 h. The solvent was removed and the residue was purified on silica gel column (DCM:MeOH=20:1) to give the desired product, 6-bromo-1-methyl-1H-imidazo[4,5-c]pyridin-2-amine. ESI-MS (M+H+): 227.0

Example 3

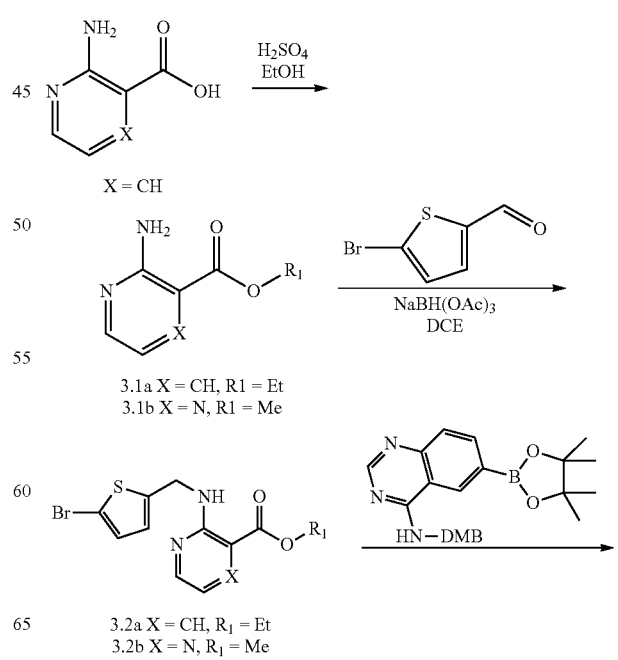

3.1a X = CH, R1 = Et
3.1b X = N, R1 = Me 3.2a X = CH, R$_1$ = Et
3.2b X = N, R$_1$ = Me

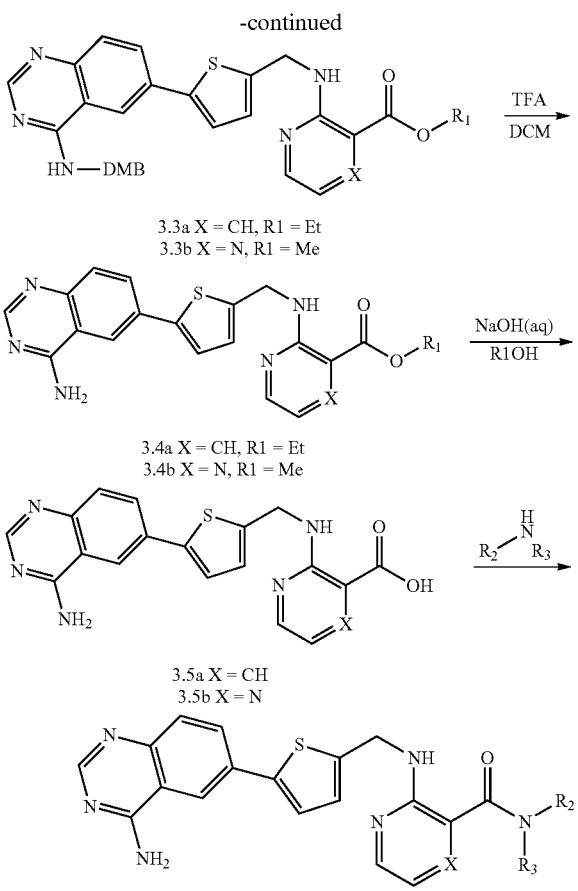

3.3a X = CH, R1 = Et
3.3b X = N, R1 = Me 3.4a X = CH, R1 = Et
3.4b X = N, R1 = Me 3.5a X = CH
3.5b X = N

Synthesis of ethyl 2-aminonicotinate

A mixture of 2-aminonicotinic acid (5.01 g, 0.0363 mol), ethanol (50 mL, 0.8 mol) and sulfuric acid (6.0 mL, 0.11 mol) were refluxed overnight. Water was added to dilute the reaction solution and then neutralized with aqueous sodium carbonate. The solution was then extracted with 3×100 mL of ethyl acetate. The combined organic extracts were dried over magnesium sulfate and evaporated. Collected 5.05 g of a white solid (84%). $^1$H NMR (300 MHz, CDCl$_3$): 8.21 (dd, J=4.8; 1.8 Hz, 1H), 8.14 (dd, J=8.1; 1.8 Hz, 1H), 6.62 (dd, J=7.9; 4.9 Hz, 1H), 6.47 (br s, 2H), 4.34 (q, J=7.0 Hz, 2H), 1.38 (t, J=7.2 Hz, 3H).

Synthesis of ethyl 2-(((5-bromothiophen-2-yl)methyl)amino)nicotinate

Ethyl 2-aminonicotinate (5.00 g, 30.1 mmol) and 5-bromo-thiophene-2-carbaldehyde (5.37 mL, 45.1 mmol) were dissolved in 1,2-dichloroethane (120 mL) and stirred at room temperature for 5 hours. Sodium triacetoxyborohydride (12.8 g, 60.2 mmol) was added portionwise as a finely ground powder. The reaction mixture was stirred at room temperature for 72 hours. Upon completion the reaction was quenched by adding hydrochloric acid and stirring vigorously for 1 hour. The mixture was neutralized with saturated aqueous sodium carbonate solution extracted with ethyl acetate (300 mL). The organic phase was washed with sodium bicarbonate, water, and then brine. Dried over magnesium sulfate and evaporated. The oil was purified by flash chromatography using a 10-30% ethyl acetate:hexanes gradient. Collected 6.68 g of a yellow oil (65%). ES (+) MS m/e=341.0 (M+1). $^1$H NMR (300 MHz, CDCl$_3$): 8.32 (dd, J=4.9; 1.9 Hz, 2H), 8.14 (dd, J=7.7; 1.9 Hz, 1H), 6.86 (d, J=3.9 Hz, 1H), 6.76 (d, J=3.6 Hz, 1H), 6.59 (dd, J=7.8; 4.8 Hz, 1H), 4.81 (dd, J=5.7; 0.9 Hz, 2H), 4.32 (q, J=7.1 Hz, 2H), 1.37 (t, J=7.0 Hz, 3H).

Synthesis of ethyl 2-(((5-(4-(2,4-dimethoxybenzylamino)quinazolin-6-yl)thiophen-2-yl)methyl)amino)nicotinate Ethyl 2-(((5-bromothiophen-2-yl)methyl)amino)nicotinate, 3.2a (4.078 g, 0.01195 mol), (2,4-dimethoxybenzyl)-[6-(4,4,5,5-tetramethyl-1,3,2-dioxaborolan-2-yl)-quinazolin-4-yl]-amine (6.057 g, 0.01438 mol) and [1,1'-bis(diphenylphosphino)ferrocene]dichloropalladium(II) complex with dichloromethane (1:1) (400 mg, 0.0005 mol) were stirred in 1,4-dioxane (70 mL, 0.9 mol) and 25.6 mL of saturated sodium carbonate in water. The reaction was heated at 90° C. for 1 hour, deemed complete by HPLC-MS and cooled to room temperature. The reaction was diluted with ethyl acetate, filtered through Celite, and evaporated. The crude material was purified by flash chromatography (70-100% EtOAc:hexanes gradient, 220 g silica). ES (+) MS m/e=556.3 (M+1).

Synthesis of 2-(((5-(4-aminoquinazolin-6-yl)thiophen-2-yl)methyl)amino)nicotinic acid Acetonitrile (30 mL, 500 mmol) was added to a flask containing ethyl 2-(((5-(4-(2,4-dimethoxybenzylamino)quinazolin-6-yl)thiophen-2-yl)methyl)amino)nicotinate, 3.3a (5.614 g, 10.10 mmol). Trifluoroacetic acid (44.4 mL, 576 mmol) was added and the reaction was stirred at 60° C. for 6 hours. The reaction was quenched with saturated aqueous sodium carbonate, and partitioned between 200 mL EtOAc and 200 mL water. The organic phase was separated and washed with aqueous sodium bicarbonate, water, then brine. Dried over magnesium sulfate and evaporated. Collected 3.93 g (96%) of ethyl 2-(((5-(4-aminoquinazolin-6-yl)thiophen-2-yl)methyl)amino)-nicotinate as a crude solid. ES (+) MS m/e=406.2 (M+1).

Ethyl 2-(((5-(4-aminoquinazolin-6-yl)thiophen-2-yl)methyl)amino)nicotinate (1.516 g, 3.739 mmol) was stirred in ethanol (24.5 mL, 4.20E2 mmol). Added 1.0 M of Sodium hydroxide in water (11.2 mL, 11.2 mmol) and stirred at 40° C. for 3 hours. The reaction was neutralized with 1N HCl (~11.2 mL), and reduced in volume by rotary evaporation. The resulting suspension was filtered, and a yellow brown solid (1.33 g, 94%) was isolated and dried overnight. ES (+) MS m/e=378.2 (M+1); $^1$H NMR (300 MHz, DMSO-d$_6$) δ 8.55 (t, J=5.67 Hz, 1H), 8.46 (d, J=1.89 Hz, 1H), 8.44 (s, 1H), 8.33 (dd, J=2.27, 4.91 Hz, 1H), 8.11 (dd, J=2.08, 7.74 Hz, 1H), 8.05 (dd, J=2.08, 8.88 Hz, 1H), 7.67 (d, J=8.69 Hz, 1H), 7.49 (d, J=3.78 Hz, 1H), 7.10 (d, J=3.78 Hz, 1H), 6.68 (dd, J=4.91, 7.55 Hz, 1H), 4.91 (d, J=6.04 Hz, 2H).

Synthesis of methyl 3-aminopyrazine-2-carboxylate

Methyl 3-aminopyrazine-2-carboxylate (3.690 g, 24.10 mmol), 5-bromo-thiophene-2-carbaldehyde (13.302 g, 69.627 mmol) were stirred in 1,2-dichloroethane (87.2 mL). Added Acetic acid (2.60 mL, 45.7 mmol) and prestirred for 15 minutes, then sodium triacetoxyborohydride (14.53 g, 68.56 mmol) was added and stirred overnight at room temperature. Some aldehyde was still present by HPLC-MS, and 1 equiv of sodium triacetoxyborohydride was added and the reaction was stirred for 24 hours. The reaction was quenched with 30 mL of 1M HCl, stirred vigorously for 30 minutes, and neutralized with sodium bicarbonate. The reaction was extracted with ethyl acetate and washed with aqueous sodium bicarbonate, water, then brine. Dried over magnesium sulfate and evaporated. The mixture was purified by flash chromatography (0-25% ethyl acetate:hexanes). Collected 1.612 g of methyl 3-aminopyrazine-2-carboxylate as a white solid. ES (+) MS m/e=328.0 (M+1).

Synthesis of methyl 3-((5-(4-(2,4-dimethoxybenzylamino)quinazolin-6-yl)thiophen-2-yl)methyl)amino)pyrazine-2-carboxylate, 3.3b Methyl 3-aminopyrazine-2-carboxylate, 3.2b (1.612 g, 4.912 mmol), (2,4-dimethoxy-benzyl)-[6-(4,4,5,5-tetramethyl-1,3,2-dioxaborolan-2-yl)-quinazolin-4-yl]-amine (2.681 g, 6.363 mmol), [1,1'-bis(diphenylphosphino)ferrocene]dichloropalladium(II), complex with dichloromethane (1:1) (320 mg, 0.39 mmol) were stirred in 1,4-Dioxane (48.9 mL, 626 mmol). Added saturated sodium carbonate in water (7.84 mL, 14.7 mmol) and heated at 100° C. The reaction was monitored by HPLC-MS and deemed complete after 1.5 hours. The reaction was cooled to room temperature, diluted with ethyl acetate, filtered through Celite and evaporated. The reaction was purified by flash chromatography (0-5% MeOH:DCM). Collected 2.002 g of a brown amorphous solid. ES (+) MS m/e=543.3 (M+1).

Synthesis of methyl 3-((5-(4-aminoquinazolin-6-yl)thiophen-2-yl)methyl)amino)pyrazine-2-carboxylate, 3.4b Trifluoroacetic acid (10.00 mL, 129.8 mmol) was added to a flask containing 3.3b (1.89 g, 3.49 mmol) and stirred at 60° C. for 40 minutes. The reaction was deemed complete by LCMS and Quenched with saturated aqueous sodium carbonate. The mixture was partitioned between 100 mL EtOAc and 100 mL water, and the organic phase was separated and washed with aqueous sodium bicarbonate, water, then brine. A solid crashed out of solution and was isolated by filtration of both phases. The remaining organic phase was dried over magnesium sulfate and evaporated. The products were identical by LCMS and combined to give 1.28 g of a solid (94%). ES (+) MS m/e=393.2 (M+1).

Synthesis of 3-((5-(4-aminoquinazolin-6-yl)thiophen-2-yl)methyl)amino)pyrazine-2-carboxylic acid, 3.5b 1.0 M of Sodium hydroxide in water (7.25 mL, 7.25 mmol) was added to 3.4b (949 mg, 2.42 mmol) in methanol (16.8 mL, 415 mmol). The reaction was heated at 40° C. for 2 hours then 60° C. for one hour. Neutralized with 1N HCl (~7.25 mL). The methanol was removed by rotary evaporation and the resulting suspension was filtered. A brown solid was isolated and placed on the high vacuum overnight. Collected 801 mg of a crude material. ES (+) MS m/e=379.2 (M+1).

General Procedure for Library 2-(((5-(4-Aminoquinazolin-6-yl)thiophen-2-yl)methyl)amino)nicotinic acid, 3.5a (80.0 mg, 0.175 mmol) and HATU (88.6 mg, 0.236 mmol) were dissolved in DMF (2.0 mL). The mixture was briefly stirred at room temperature before N,N-diisopropylethylamine (92.3 μL, 0.530 mmol) and amine (0.318 mmol) were added. The reaction was stirred at room temperature and monitored by HPLC-MS. Upon completion, 4 mL DCM, 2 mL water, and 2 mL brine were added and shaken well. The organic phase was collected while the aqueous phase was reextracted twice with 1 mL DCM. The organic extracts were combined and evaporated. Purification by preparatory HPLC followed by lyophilization produced the product as a TFA salt. TFA stoichiometry was determined by $^{19}$F-NMR when possible. In some cases, the compound was instead purified by silica gel chromatography and isolated as the parent.

Ex. 3.6

2-({[5-(4-aminoquinazolin-6-yl)thiophen-2-yl]methyl}amino)-N-(2,5-difluorobenzyl)pyridine-3-carboxamide (TFA salt)

Example 3.6 was synthesized from 3.5a using the library procedure above. ES (+) MS m/e=503.2 (M+1); $^1$H NMR (300 MHz, DMSO-$d_6$) δ 9.83 (br s, 1H), 9.75 (br s, 1H), 9.11 (t, J=6.0 Hz, 1H), 8.65-8.75 (m, 2H), 8.59 (s, 1H), 8.26 (d, J=12.0 Hz, 1H), 8.25 (s, 1H), 8.06 (d, J=6.0 Hz, 1H), 7.76 (d, J=9.0 Hz, 1H), 7.54 (s, 1H), 7.27-7.11 (m, 5H), 6.69 (dd, J=3.0; 3.0 Hz, 1H), 4.85 (d, J=6.0 Hz, 2H), 4.46 (d, J=6.0 Hz, 2H).

Examples 3.7-3.87 were synthesized in an analogous manner to Example 3.6.

Example 4

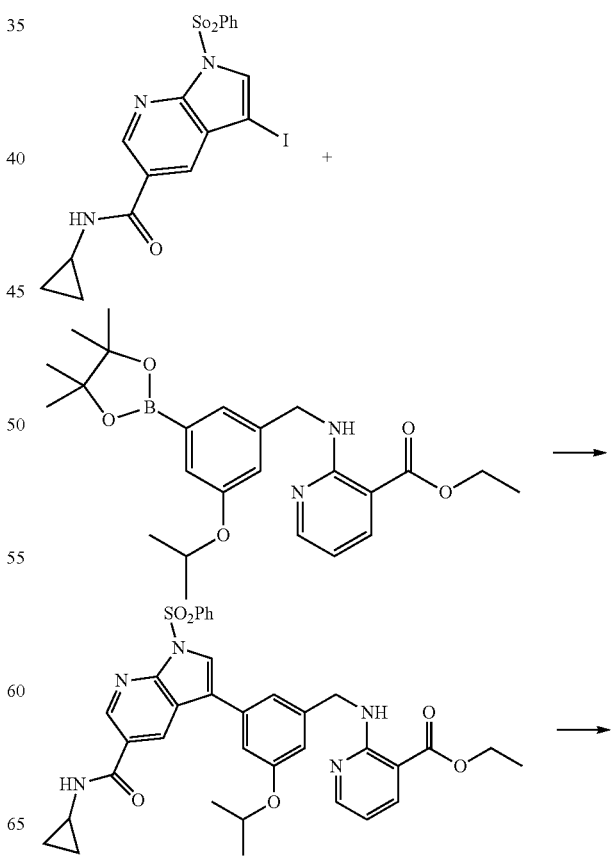

85

-continued

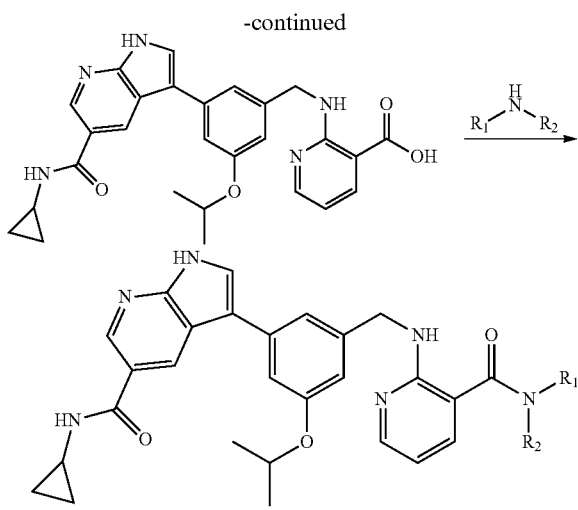

Synthesis of ethyl 2-(3-isopropoxy-5-(4,4,5,5-tetramethyl-1,3,2-dioxaborolan-2-yl)benzylamino)nicotinate Ethyl 2-aminonicotinate (0.498 g, 3.00 mmol), 3-formyl-5-isopropoxyphenylboronic acid (0.625 g, 3.00 mmol), and p-toluenesulfonic acid monohydrate (44 mg, 0.23 mmol) were dissolved in ethanol (10.0 mL) and heated at 100° C. overnight. The reaction was evaporated and redissolved in 1,2-dichloroethane (12.0 mL). Finely ground sodium triacetoxyborohydride (2.03 g, 9.58 mmol) was added portionwise, and the reaction was allowed to stir at room temperature overnight. The reaction was quenched by vigorously stirring with aqueous sodium bicarbonate (20 mL). Added ethyl acetate (125 mL) and washed twice with aqueous sodium bicarbonate, then with brine. The organic layer was dried over magnesium sulfate and evaporated. The crude boronic acid was isolated as a brown oil (1.18 g). The crude boronic acid (1.18 g, 3.29 mmol) was dissolved in tetrahydrofuran (8.0 mL) and stirred with pinacol (0.578 g, 4.89 mmol) overnight at room temperature. The reaction was monitored by TLC, evaporated, and purified by flash chromatography (0-25% ethyl acetate:hexanes, silica). Collected an oil (537.7 mg, 41% over two steps).

Synthesis of ethyl 2-(3-(5-(cyclopropylcarbamoyl)-1-(phenylsulfonyl)-1H-pyrrolo[2,3-b]pyridin-3-yl)-5-isopropoxybenzylamino)nicotinate N-cyclopropyl-3-iodo-1-(phenylsulfonyl)-1H-pyrrolo[2,3-b]pyridine-5-carboxamide (preparation see ref.: WO2008005457) (351.9 mg, 0.7531 mmol), ethyl 2-(3-isopropoxy-5-(4,4,5,5-tetramethyl-1,3,2-dioxaborolan-2-yl)benzylamino)nicotinate (365.1 mg, 0.8291 mmol), [1,1'-bis(diphenylphosphino)ferrocene]dichloropalladium(II), complex with dichloromethane (1:1) (53.8 mg, 0.0659 mmol) were stirred in N,N-dimethylformamide (5.00 mL, 64.6 mmol). Added 1.04 M of aqueous sodium bicarbonate (2.17 mL, 2.25 mmol) and microwaved at 100 degrees Celcius for 7.5 minutes. The reaction was cooled to room temperature, poured into 200 mL ethyl acetate and washed twice with 150 mL aqueous sodium bicarbonate, then with 150 mL brine. The organic phase was dried with magnesium sulfate, evaporated, purified by flash chromatography (15-50% ethyl acetate:hexanes, silica), and dried by high-vacuum. Collected 327.0 mg of a light orange foam (66%).

86

Synthesis of 2-(3-(5-(cyclopropylcarbamoyl)-1H-pyrrolo[2,3-b]pyridin-3-yl)-5-isopropoxybenzylamino)nicotinoyl chloride Ethyl 2-(3-(5-(cyclopropylcarbamoyl)-1-(phenylsulfonyl)-1H-pyrrolo[2,3-b]pyridin-3-yl)-5-isopropoxybenzylamino)nicotinate (327.0 mg, 0.5002 mmol) was dissolved in ethanol (9.4 mL) and 1.00 M of aqueous sodium hydroxide (2.35 mL, 2.35 mmol) was added. The reaction was heated at 100° C. and monitored by LCMS. The reaction was complete after 1.5 hours, but was heated for a total of 2.5 hours. The reaction was cooled to room temperature, concentrated, and diluted with water (10 mL). The reaction was acidified with 2.35 mL 1N hydrochloric acid and a white precipitate crashed out. The mixture was stirred overnight, filtered, washed with water, and dried under high-vacuum. Collected 222 mg of the carboxylic acid as a yellow solid (91%). The solid was carried onto the next step by stirring in DCM (9.1 mL), adding thionyl chloride (334 μL), followed by triethylamine (500 μL) and stirring at room temperature. The reaction was done instantly, and the reaction was evaporated to dryness and the acid chloride was carried on as crude.

Ex. 4.1.1

Synthesis of N-cyclopropyl-3-(3-((3-(3,4-difluorophenylcarbamoyl)pyridin-2-ylamino)methyl)-5-isopropoxyphenyl)-1H-pyrrolo[2,3-b]pyridine-5-carboxamide A solution of 2-(3-(5-(cyclopropylcarbamoyl)-1H-pyrrolo[2,3-b]pyridin-3-yl)-5-isopropoxybenzylamino)nicotinoyl chloride (23.0 mg, 0.0456 mmol) in methylene chloride (2.00 mL) was added to a vial containing 3,4-difluoroaniline (34.4 mg, 0.266 mmol) and stirred overnight. The reaction was evaporated to dryness, redissolved in 1 mL DMSO, and filtered through a course filter. The DMSO solution was purified by Gilson Prep HPLC and the fractions were lyophilized. Collected a yellow powder (8.1 mg, 30%). ES (+) MS m/e=593.3 (M+1); $^1$H NMR (300 MHz, DMSO-$d_6$) δ 12.13 (d, J=2.27 Hz, 1H), 10.45 (s, 1H), 8.71 (d, J=1.89 Hz, 1H), 8.60 (d, J=1.89 Hz, 1H), 8.55 (d, J=3.78 Hz, 1H), 8.44 (br. s., 1H), 8.26 (dd, J=1.89, 4.91 Hz, 1H), 8.11 (dd, J=1.51, 7.55 Hz, 1H), 7.90 (d, J=2.64 Hz, 1H), 7.84 (ddd, J=1.70, 7.65, 13.31 Hz, 1H), 7.37-7.47 (m, 2H), 7.28 (s, 1H), 7.06-7.11 (m, 1H), 6.80-6.87 (m, 1H), 6.72 (dd, J=4.91, 7.55 Hz, 1H), 4.61-4.75 (m, 3H), 2.80-2.93 (m, 1H), 1.28 (d, J=6.04 Hz, 6H), 0.66-0.76 (m, 2H), 0.53-0.62 (m, 2H).

Examples 4.1.2-4.1.18 were synthesized by methods analogous to Ex. 4.1.1.

Synthesis of 6-bromo-N-(2,4-dimethoxybenzyl)quinazolin-4-amine

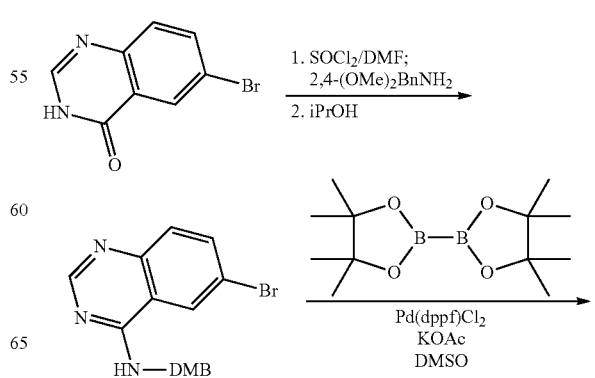

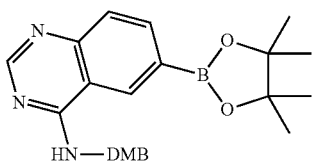

6-Bromoquinazolin-4-one (0.800 g, 3.56 mmol), thionyl chloride (10.0 mL, 137 mmol), and N,N-dimethylformamide (0.100 mL, 1.29 mmol) were combined and refluxed for 2 hours, then evaporated to dryness. Added isopropyl alcohol (10.0 mL, 131 mmol) and [B]2,4-dimethoxy-benzylamine (0.655 g, 3.92 mmol) and refluxed for 2.5 hours. Added 150 mL of ethyl acetate, and washed with 2×75 mL aqueous sodium bicarbonate, and 1×75 mL brine. The organic phase was dried over magnesium sulfate, evaporated, and purified by flash chromatography (0-5% methanol:dichloromethane). Collected 1.02 g of a yellow powder (77%). ES (+) MS m/e=374.1 (M+1).

Synthesis of N-(2,4-dimethoxybenzyl)-6-(4,4,5,5-tetramethyl-1,3,2-dioxaborolan-2-yl)quinazolin-4-amine 6-Bromo-N-(2,4-dimethoxybenzyl)quinazolin-4-amine (452.0 mg, 1.208 mmol), bis(pinacolato)diboron (338 mg, 1.33 mmol), potassium acetate (440. mg, 4.48 mmol), and [1,1'-bis(diphenylphosphino)ferrocene]dichloropalladium (II), complex with dichloromethane (1:1) (49.9 mg, 0.0611 mmol) were high-vac'd for 15 minutes, flushed with nitrogen and added dimethyl sulfoxide (5.5 mL, 78 mmol). The reaction was heated at 90° C. for 2 hours, diluted with ethyl acetate, and filtered through Celite. The organic phase was washed thrice with water, dried over magnesium sulfate, filtered, and evaporated. The crude material was purified by flash chromatography (30-100% ethyl acetate:hexanes, silica). Collected 438 mg of a yellow oil (86%). $^1$H NMR (300 MHz, CDCl$_3$): 8.70 (s, 1H), 8.11 (s, 1H), 8.09 (dd, J=8.2; 1.6 Hz, 1H), 7.78 (d, J=8.4 Hz, 1H), 7.31 (d, J=8.4 Hz, 1H), 6.52 (d, J=2.1 Hz, 1H), 6.47 (dd, J=8.3; 2.2 Hz, 1H), 6.24 (br t, J=5.3 Hz, 1H), 4.79 (d, J=5.4 Hz, 2H), 3.88 (s, 3H), 3.82 (s, 3H), 1.37 (s, 12H).

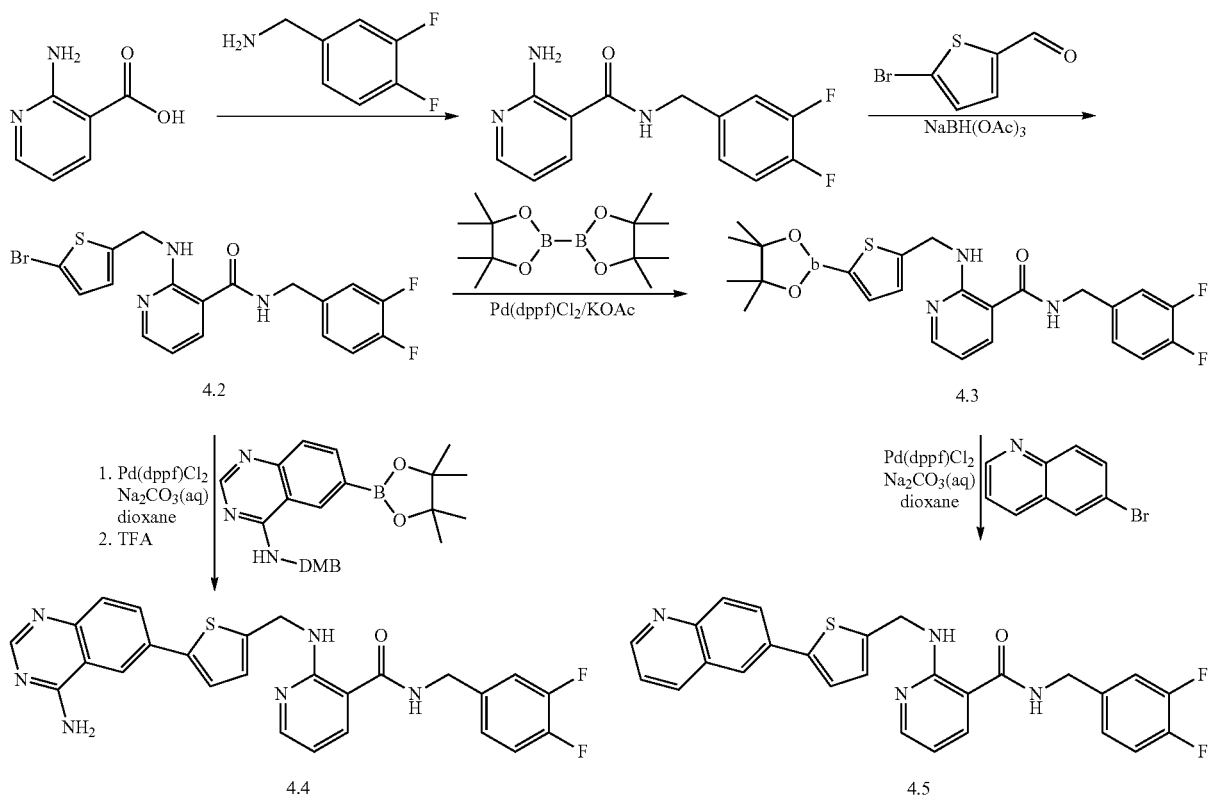

Synthesis of 2-(((5-bromothiophen-2-yl)methyl)amino)-N-(3,4-difluorobenzyl)nicotinamide (4.2)

2-amino-N-(3,4-difluorobenzyl)nicotinamide (5.00 g, 19.0 mmol) was dissolved in 1,2-dichloroethane (80.0 mL). Added 5-bromo-thiophene-2-carbaldehyde (5.489 g, 28.73 mmol), pre-stirred for 60 minutes, and then added sodium triacetoxyborohydride (8.04 g, 37.9 mmol) portionwise. The reaction was stirred at room temperature overnight. The reaction was quenched with 1M aqueous hydrochloric acid, stirred vigorously, then neutralized with aqueous sodium carbonate. Added 100 mL of ethyl acetate, washed with aqueous sodium bicarbonate, water, then brine. The organic phase was dried over magnesium sulfate, evaporated and purified by flash chromatography (20-50% ethyl acetate: hexanes, silica). After chromatography, the mixture was further purified by precipitation from methylene chloride and hexanes to yield 3.09 g of a white solid. Second crop: 0.30 g of a light yellow powder (3.39 g, 41%). ES (+) MS m/e=438.1 (M+1); $^1$H NMR (300 MHz, CDCl$_3$): 8.46 (br t, J=5.2 Hz, 1H), 8.27 (dd, J=4.7; 1.7 Hz, 1H), 7.61 (dd, J=7.5; 1.8 Hz, 1H), 6.87-6.65 (m, 5H), 6.55 (dd, J=7.5; 4.8 Hz, 1H), 4.76 (d, J=5.7 Hz, 2H), 4.52 (d, J=6.3 Hz, 2H).

Synthesis of N-(3,4-difluorobenzyl)-2-(((5-(4,4,5,5-tetramethyl-1,3,2-dioxaborolan-2-yl)thiophen-2-yl)methyl)amino)nicotinamide (4.3)

Into a microwave vial was added 2-[(5-Bromo-thiophen-2-ylmethyl)-amino]-N-(3,4-difluoro-benzyl)-nicotinamide (2.19 g, 5.00 mmol), bis(pinacolato)diboron (5.085 g, 20.02 mmol), Potassium acetate (2.72 g, 27.7 mmol), [1,1'-Bis(diphenylphosphino)ferrocene]-dichloropalladium(II), complex with dichloromethane (1:1) (438.0 mg, 0.5363 mmol) and N,N-Dimethylformamide (21.9 mL, 283 mmol). The reaction mixture was degassed under an atmosphere of Nitrogen. The reaction was microwaved on 300 watts, 70° C. for 5 minutes. The crude reaction mixture was washed H$_2$O (DI), was extracted EtOAc, dried over MgSO$_4$ and solvent removed in vacuo. A gradient elution (0->50%) EtOAc (B) in hexanes (A) was used to purify the crude product. Collected 2.42 g relatively pure compound 13.1 (75% yield). LC-MS (Agilent 460, acidic method): RT: 1.5 min.; ES (+) MS m/e 486.3 (M+1).

Ex. 4.4

Synthesis of 2-(((5-(4-aminoquinazolin-6-yl)thiophen-2-yl)methyl)amino)-N-(3,4-difluorobenzyl)nicotinamide 2-(((5-bromothiophen-2-yl)methyl)amino)-N-(3,4-difluorobenzyl)nicotinamide (4.2) (93.7 mg, 0.214 mmol), 10.3 (111.5 mg, 0.2646 mmol) were dissolved in 1,4-dioxane (2.00 mL, 25.6 mmol). Added saturated aqueous sodium carbonate (0.458 mL, 1.28 mmol) followed by [1,1'-bis(diphenylphosphino)ferrocene]dichloropalladium(II), complex with dichloromethane (1:1) (15.8 mg, 0.0193 mmol). The reaction was heated at 100° C. for 2.5 hours, and cooled to room temperature. Reaction was partitioned between 30 mL of ethyl acetate and 30 mL of water, stirred, and filtered. The organic phase was separated and washed with aqueous sodium bicarbonate and brine, then dried over magnesium sulfate, evaporated, and purified by flash chromatography (50-100% ethyl acetate:Hexanes, silica). The material was further purified by trituration with 10 mL ethyl acetate. Collected a beige powder (60.4 mg, 43%). $^1$H NMR (300 MHz, CD$_3$OD/DMSO-d$_6$): 8.45 (d, J=1.5 Hz, 1H), 8.39 (s, 1H), 8.24 (dd, J=3.4; 1.4 Hz, 1H), 8.02 (dd, J=6.6; 1.5 Hz, 1H), 7.96 (dd, J=5.8; 1.0 Hz, 1H), 7.68 (d, J=6.6 Hz, 1H), 7.43 (d, J=2.7 Hz, 1H), 7.18 (d, J=6.3 Hz, 1H), 7.06 (d, J=2.7 Hz, 1H), 6.96 (dd, J=6.6; 1.5 Hz, 2H), 6.87 (t, J=6.9 Hz, 1H), 6.67 (dd, J=5.7; 3.6 Hz, 1H), 6.57 (d, J=1.8 Hz, 1H), 6.46 (dd, J=6.2; 1.6 Hz, 1H), 4.87 (s, 2H), 4.74 (s, 2H), 4.50 (s, 2H), 3.85 (s, 3H), 3.77 (s, 3H).

The above product (293.3 mg, 0.4494 mmol) was dissolved in methylene chloride (5.00 mL) and trifluoroacetic acid (2.50 mL, 32.4 mmol). The reaction was stirred at room temperature for 48 hours, concentrated, and diluted with ethyl acetate. The organics were washed with aqueous sodium bicarbonate, water, then brine, dried over magnesium sulfate, evaporated and purified by preparatory reverse-phase HPLC. Collected 128.95 mg of a bright yellow powder (57%). ES (+) MS m/e=503.2 (M+1); $^1$H NMR (300 MHz, DMSO-d$_6$): 9.88 (br s, 1H), 9.78 (br s, 1H), 9.18 (t, J=6.0 Hz, 1H), 8.83 (t, J=6.2 Hz, 1H), 8.81 (s, 1H), 8.61 (d, J=1.8 Hz, 1H), 8.27 (dd, J=12.7; 1.7 Hz, 1H), 8.26 (s, 1H), 8.08 (dd, J=7.6; 1.6 Hz, 1H), 7.77 (d, J=8.7 Hz, 1H), 7.54 (d, J=3.9 Hz, 1H), 7.17-6.99 (m, 4H), 6.70 (dd, J=7.8; 4.8 Hz, 1H), 4.86 (d, J=5.4 Hz, 2H), 4.46 (d, J=5.4 Hz, 2H).

Ex. 4.5

Synthesis of N-(3,4-difluorobenzyl)-2-(((5-(quinolin-6-yl)thiophen-2-yl)methyl)amino)nicotinamide N-(3,4-difluorobenzyl)-2-(((5-(4,4,5,5-tetramethyl-1,3,2-dioxaborolan-2-yl)thiophen-2-yl)methyl)amino)nicotinamide (4.3) (100 mg, 0.206 mmol), 6-bromoquinoline (49.5 mg, 0.238 mmol), [1,1'-bis(diphenylphosphino)ferrocene]dichloropalladium(II), complex with dichloromethane (1:1) (20.2 mg, 0.0247 mmol), 1,4-dioxane (2.00 mL, 25.6 mmol), and 1.88 M of aqueous sodium carbonate (0.329 mL, 0.618 mmol) were combined and heated in a microwave reactor at 100° C. for 5 minutes. Ethyl acetate was added and the reaction was filtered through Celite, rinsed with additional ethyl acetate, and evaporated. The mixture was purified by preparatory reverse-phase HPLC. Collected 13.75 mg of a bright yellow powder (14%). ES (+) MS m/e=487.2 (M+1); $^1$H NMR (300 MHz, DMSO-d$_6$): 9.27 (t, J=5.8 Hz, 1H), 9.05 (dd, J=4.5; 1.5 Hz, 1H), 9.00 (br s, 1H), 8.77 (d, J=8.1 Hz, 1H), 8.33 (d, J=1.8 Hz, 1H), 8.26 (t, J=1.2 Hz, 1H), 8.24 (dd, J=5.2; 1.7 Hz, 1H), 8.17 (s, 1H), 8.15-8.13 (m, 1H), 7.81 (dd, J=8.3; 5.0 Hz, 1H), 7.60 (d, J=3.6 Hz, 1H), 7.17-7.00 (m, 4H), 6.76 (dd, J=7.7; 4.9 Hz, 1H), 4.89 (s, 2H), 4.47 (d, J=5.4 Hz, 2H).

Ex. 4.6 was prepared in a manner similar to Ex. 4.5 using 6-iodoquinazoline.

Ex. 4.7

2-(((5-(7H-pyrrolo[2,3-d]pyrimidin-5-yl)thiophen-2-yl)methyl)amino)-N-(3,4-difluorobenzyl)nicotinamide

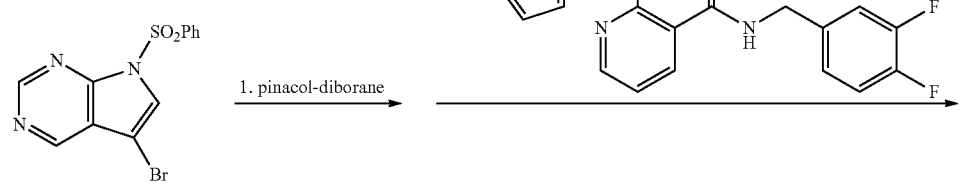

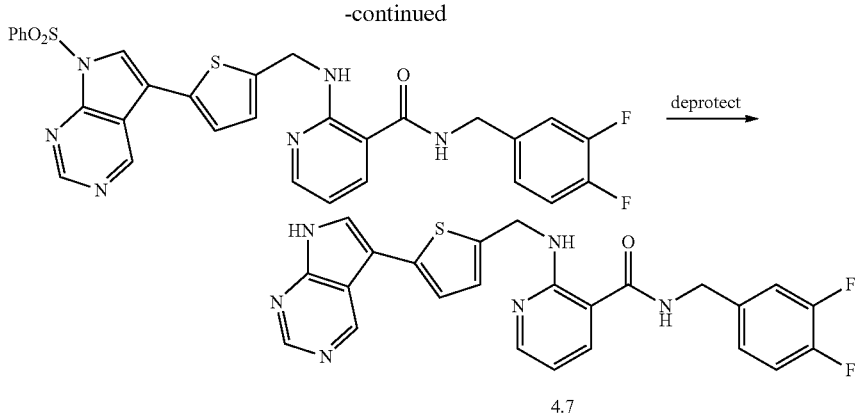

5-Bromo-7-(phenylsulfonyl)-7H-pyrrolo[2,3-d]pyrimidine (98.7 mg, 0.292 mmol), bis(pinacolato)diboron (73.2 mg, 0.288 mmol), [1,1'-bis(diphenylphosphino)ferrocene]-dichloropalladium(II), complex with dichloromethane (1:1) (23.5 mg, 0.0288 mmol), and potassium acetate (86.2 mg, 0.878 mmol) were stirred in 1,2-dimethoxyethane (2.00 mL, 19.2 mmol) and heated in a microwave reactor at 150 degrees for 10 minutes. Added [1,1'-bis(diphenylphosphino)ferrocene]dichloropalladium(II), complex with dichloromethane (1:1) (18 mg, 0.023 mmol), 1.88 M of sodium carbonate in water (0.362 mL, 0.680 mmol) and heated in a microwave reactor at 130 degrees for 10 minutes. The reaction was diluted with ethyl acetate, filtered through Celite, dried over magnesium sulfate and evaporated. The crude material was purified by flash chromatography (0-100% ethyl acetate:hexanes). Collected 80.0 mg of a brown oil (55%) and carried to the next step.

The above product (80.0 mg, 0.130 mmol), potassium carbonate (93.3 mg, 0.675 mmol), and methanol (2.00 mL, 49.4 mmol) were heated at 100° C. for 1 hour. 75 mL of ethyl acetate were added and washed twice with 75 mL aqueous sodium bicarbonate, then 75 mL of brine. The organic phase was dried over magnesium sulfate, evaporated, and purified by preparatory reverse-phase HPLC. Collected 10.3 mg of a yellow powder (17%). ES (+) MS m/e=477.3 (M+1); $^1$H NMR (300 MHz, DMSO-$d_6$): 13.19 (br s, 1H), 9.47 (s, 1H), 9.21 (t, J=6.0 Hz, 1H), 9.06 (s, 1H), 8.88 (br s, 1H), 8.26 (dd, J=4.8; 1.8 Hz, 1H), 8.14-8.08 (m, 2H), 7.40 (d, J=3.9 Hz, 1H), 7.14-6.99 (m, 4H), 6.72 (dd, J=7.5; 5.1 Hz, 1H), 4.84 (s, 2H), 4.45 (d, J=5.7 Hz, 2H).

Ex. 4.8

2-(((5-(4-amino-7H-pyrrolo[2,3-d]pyrimidin-5-yl)thiophen-2-yl)methyl)amino)-N-(3,4-difluorobenzyl)nicotinamide

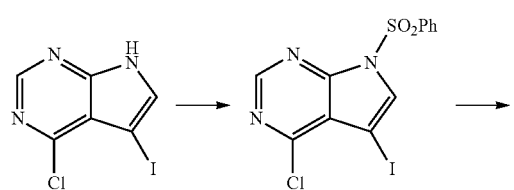

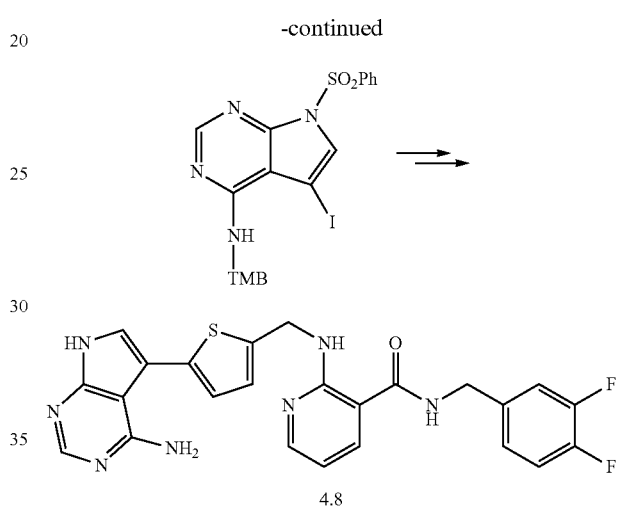

Step 1: Synthesis of 4-chloro-5-iodo-7-(phenylsulfonyl)-7H-pyrrolo[2,3-d]pyrimidine To a suspension of 4-chloro-5-iodo-7H-pyrrolo[2,3-d]pyrimidine (ref. Young, et al. *JMC* (2008), 51(13), 3934-3945.) (2.5 g, 0.0089 mol), and N,N-Diisopropylethylamine (3 mL, 0.02 mol), 4-Dimethylaminopyridine (0.01 g, 0.00009 mol) 4-Dimethylaminopyridine in Methylene chloride (50 mL, 0.8 mol) was added Benzenesulfonyl chloride (1.4 mL, 0.011 mol) and stirred at room temperature for 1 h and it became a clear solution. LC-MS showed completed reaction. Worked up with DCM and water. Dried over MgSO$_4$ and conctd. The residue was then purified on a short silica gel column with DCM to give the desired product as a white solid (3.0 g, 80%). LCMS: RT 1.72 min, ES+/ 420.00.

Step 2: Synthesis of 5-iodo-7-(phenylsulfonyl)-N-(2,4,6-trimethoxybenzyl)-7H-pyrrolo[2,3-d]pyrimidin-4-amine A suspension of 4-chloro-5-iodo-7-(phenylsulfonyl)-7H-pyrrolo[2,3-d]pyrimidine (0.5 g, 0.001 mol), 2,4,6-Trimethoxybenzylamine hydrochloride (0.31 g, 0.0013 mol), and Cesium Carbonate (0.78 g, 0.0024 mol) in trifluoromethylbenzene (100 mL, 1 mol) was heated to reflux for overnight. LC-MS showed complete reaction with only formation of the desired product (1.81 min, ES+/581.1). Evaporated off the solvent and the ppts were collected and washed with MeOH, water and then dried to give the desired product as an off white solid (0.5 g, 70%). $^1$H NMR (400 MHz, CDCl$_3$) δ 8.46 (s, 1H), 8.17 (d, J=7.59 Hz, 2H), 7.39-7.68 (m, 5H), 6.60-6.72 (m, 1H), 6.15 (s, 2H), 4.79 (d, J=5.27 Hz, 2H), 3.85 (s, 6H), 3.82 (s, 3H).

Step 3: Synthesis of N-(3,4-difluorobenzyl)-2-(((5-(7-(phenylsulfonyl)-4-(2,4,6-trimethoxybenzylamino)-7H-pyrrolo[2,3-d]pyrimidin-5-yl)thiophen-2-yl)methyl)amino)nicotinamide A mixture of 2-[(5-Bromo-thiophen-2-ylmethyl)-amino]-N-(3,4-difluoro-benzyl)-nicotinamide 2-[(5-Bromo-thiophen-2-ylmethyl)-amino]-N-(3,4-difluoro-benzyl)-nicotinamide (200 mg, 0.4 mmol), bis(pinacolato)diboron (100 mg, 0.4 mmol), Potassium acetate (170 mg, 1.8 mmol), and [1,1'-Bis(diphenylphosphino)ferrocene]dichloropalladium (II), complex with dichloromethane (1:1) (37 mg, 0.046 mmol) in N,N-Dimethylformamide (2.34 mL, 30.2 mmol) was degassed under an atmosphere of Nitrogen. The reaction was microwaved on 150 watts, 90° C. for 10 minutes and LC-MS showed no more starting materials. The above reaction mixture was then added 5-iodo-7-(phenylsulfonyl)-N-(2,4,6-trimethoxybenzyl)-7H-pyrrolo[2,3-d]pyrimidin-4-amine (300 mg, 0.4 mmol) and 1.2 M of Sodium bicarbonate in water (0.7 mL, 0.8 mmol) and was microwaved on 150 watts, 90° C. for 10 minutes and LC-MS showed the formation of the desired product (1.66 min, ES+/812.3). Worked up with water and DCM, dried over MgSO$_4$. Purified on silica gel column with 0-60% EtOAc in hexane to give the desired product (100 mg, 30%).

Synthesis of 2-(((5-(4-amino-7H-pyrrolo[2,3-d]pyrimidin-5-yl)thiophen-2-yl)methyl)amino)-N-(3,4-difluorobenzyl)nicotinamide (Ex. 4.8)

N-(3,4-difluorobenzyl)-2-(((5-(7-(phenylsulfonyl)-4-(2,4,6-trimethoxybenzylamino)-7H-pyrrolo[2,3-d]pyrimidin-5-yl)thiophen-2-yl)methyl)amino)nicotinamide (0.1 g, 0.0001 mol) and Potassium carbonate (0.08 g, 0.0006 mol) in Methanol (10 mL, 0.2 mol) was heated to reflux for 1 h and LC-MS showed the only formation of the desired product (1.23 min, ES+/672.4). Evaporated off the solvent. Worked up with EtOAc and water. Dried over MgSO$_4$ and concentrated. The above residue was dissolved in Methylene chloride (4 mL, 0.06 mol) and added Trifluoroacetic Acid (1 mL, 0.01 mol) and stirred at room temperature for overnight. LC-MS showed complete reaction (0.955 min, ES+/492.20). Evaporated off the solvents. Purified on Gilson HPLC with 10-60% B to give the desired product as a bis-TFA salt (10 mg, 20%). $^1$H NMR (400 MHz, CD$_3$OD) δ 8.30 (s, 1H), 8.26-8.30 (m, 1H), 8.16 (dd, J=1.66, 5.74 Hz, 1H), 7.47 (s, 1H), 7.19 (dt, J=0.91, 3.51 Hz, 1H), 7.08 (d, J=3.58 Hz, 1H), 6.88-6.99 (m, 3H), 6.79-6.86 (m, 1H), 4.92 (s, 2H), 4.55 (s, 2H). MH+: 492.20.

Ex. 4.9

Synthesis of 2-(((5-(4-(azetidin-1-yl)quinazolin-6-yl)thiophen-2-yl)methyl)amino)-N-(3,4-difluorobenzyl)nicotinamide

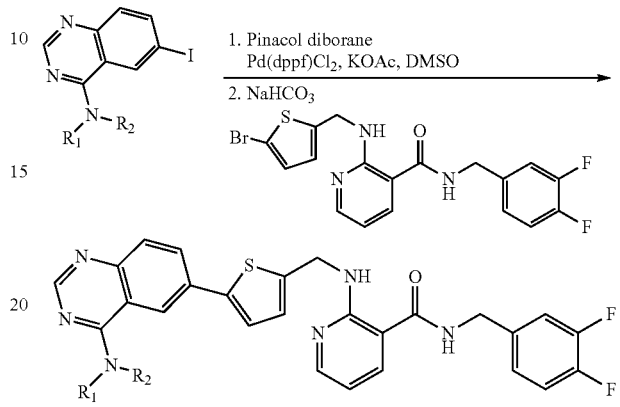

4-(Azetidin-1-yl)-6-iodoquinazoline (Prepared from 4-chloro-6-iodoquinazoline and azetidine following the same procedure as 2-(6-iodoquinazolin-4-ylamino)ethanol in the synthesis of Ex. 2.14.) (299.7 mg, 0.9633 mmol), bis(pinacolato)diboron (270.2 mg, 1.064 mmol), [1,1'-bis(diphenylphosphino)ferrocene]dichloropalladium(II), complex with dichloromethane (1:1) (39.3 mg, 0.0481 mmol), potassium acetate (285.9 mg, 2.913 mol) were combined in a vial, evacuated for 15 minutes, and flushed with nitrogen gas. Added dimethyl sulfoxide (4.38 mL, 0.0616 mol) and heated at 90° C. for 2 hours. Reaction progress was monitored by the disappearance of 4-(Azetidin-1-yl)-6-iodoquinazoline by HPLC-MS and TLC. Upon completion, added 2-(((5-bromothiophen-2-yl)methyl)amino)-N-(3,4-difluorobenzyl)nicotinamide (107.1 mg, 0.2444 mmol) and saturated aqueous Sodium bicarbonate (0.708 mL, 0.733 mmol). The reaction was heated at 110° C. for 1 hour, and cooled to room temperature. The reaction was diluted with ethyl acetate, and filtered through Celite. The organic phase was then washed twice with aqueous sodium bicarbonate and then brine. Finally, the organic phase was dried over magnesium sulfate, evaporated, and purified by flash chromatography (0-10% methanol:dichloromethane, silica). Collected 121.3 mg of a brown powder (91%). ES (+) MS m/e=543.3 (M+1); $^1$H NMR (300 MHz, CDCl$_3$): 8.55 (s, 2H), 8.31 (dd, J=4.9; 1.6 Hz, 1H), 7.94 (d, J=1.8 Hz, 1H), 7.89 (dd, J=8.9; 1.9 Hz, 1H), 7.76 (d, J=8.7 Hz, 1H), 7.65 (dd, J=7.8; 1.8 Hz, 1H), 7.16 (d, J=3.9 Hz, 1H), 7.02 (d, J=3.9 Hz, 1H), 6.88-6.80 (m, 2H), 6.72 (tt, J=8.9; 2.2 Hz, 1H), 6.57 (dd, J=7.5; 4.8 Hz, 1H), 6.54 (br s, 1H), 4.89 (d, J=5.7 Hz, 2H), 4.61 (t, J=7.6 Hz, 4H), 4.57 (d, J=6.0 Hz, 2H), 2.55 (quintet, J=7.7 Hz, 2H).

Ex. 4.10

Synthesis of 2-(((5-(4-(cyclopropylamino)quinazolin-6-yl)thiophen-2-yl)methyl)amino)-N-(3,4-difluorobenzyl)nicotinamide N-cyclopropyl-6-iodoquinazolin-4-amine (Prepared from 4-chloro-6-iodoquinazoline and cyclopropylamine following the same procedure as 2-(6-iodoquinazolin-4-ylamino)

ethanol in the synthesis of Ex. 2.14.) (252.1 mg, 0.8103 mmol), bis(pinacolato)diboron (258.0 mg, 1.016 mmol), potassium acetate (316.3 mg, 3.223 mmol), and [1,1'-bis(diphenylphosphino)ferrocene]dichloropalladium(II), complex with dichloromethane (1:1) (36.0 mg, 0.0441 mmol) were high-vac'd for 15 minutes and flushed with nitrogen. Added dimethyl sulfoxide (4.0 mL, 56 mmol) and heated at 90° C. for 1 hour. The reaction was diluted with 60 mL ethyl acetate, filtered through Celite, and washed with 60 mL ethyl acetate. The combined organic extracts were washed twice with water, then brine, dried over magnesium sulfate and evaporated. Collected 0.38 g of a crude heterogeneous material.

The crude material (252.2 mg, 0.8103 mmol) was combined with 2-(((5-bromothiophen-2-yl)methyl)amino)-N-(3,4-difluorobenzyl)nicotinamide (107.1 mg, 0.2444 mmol) and [1,1'-bis(diphenylphosphino)ferrocene]dichloropalladium(II), complex with dichloromethane (1:1) (10.2 mg, 0.0125 mmol) in a scintillation vial and dried under high-vacuum. Added 1,4-dioxane (2.00 mL) and saturated aqueous sodium carbonate (0.52 mL, 1.5 mmol) before heating at 110° C. for 1 hour. The reaction was cooled to room temperature, diluted with ethyl acetate and filtered through Celite. The organic extract was washed twice with aqueous sodium bicarbonate and once with brine. It was then dried over magnesium sulfate, filtered, evaporated, and purified by flash chromatography (0-10% methanol:dichloromethane, silica). The product was not pure and re-purified by flash chromatography (50-100% ethyl acetate; hexanes, silica). Collected 40.3 mg of an amorphous yellow solid (30%). ES (+) MS m/e=543.3 (M+1); $^1$H NMR (300 MHz, CDCl$_3$): 8.69 (s, 1H), 8.43 (t, J=5.4 Hz, 1H), 8.29 (dd, J=5.1; 1.5 Hz, 1H), 7.85 (dd, J=8.7; 1.5 Hz, 1H), 7.77-7.72 (m, 2H), 7.67 (dd, J=7.6; 1.7 Hz, 1H), 7.08 (d, J=3.9 Hz, 1H), 6.97-6.90 (m, 2H), 6.85-6.78 (m, 2H), 6.69 (tt, J=9.0; 2.3 Hz, 1H), 6.62 (br s, 1H), 6.53 (dd, J=7.9; 5.0 Hz, 1H), 4.81 (d, J=5.7 Hz, 2H), 4.54 (d, J=6.0 Hz, 2H), 3.06 (br s, 1H), 1.01-0.93 (m, 2H), 0.78-0.71 (m, 2H).

Ex. 4.11

N-(3,4-difluorobenzyl)-2-(((5-(4-morpholinoquinazolin-6-yl)thiophen-2-yl)methyl)amino)nicotinamide Ex. 4.11 was prepared in a similar manner as in Examples 4.9 and 4.10 from N-cyclopropyl-6-iodoquinazolin-4-amine (Prepared from 4-chloro-6-iodoquinazoline and morpholine following the same procedure as 2-(6-iodoquinazolin-4-ylamino)ethanol in the synthesis of Ex. 2.14.). ES (+) MS m/e 573.3 (M+1); $^1$H NMR (300 MHz, DMSO-d$_6$) δ 9.20 (t, J=5.67 Hz, 1H), 8.82 (s, 2H), 8.14-8.32 (m, 3H), 8.09 (d, J=6.80 Hz, 1H), 7.83 (d, J=8.31 Hz, 1H), 7.55 (d, J=3.40 Hz, 1H), 6.94-7.19 (m, 4H), 6.71 (dd, J=4.91, 7.55 Hz, 1H), 4.84 (br. s., 2H), 4.45 (d, J=5.67 Hz, 2H), 4.23 (br. s., 4H), 3.78 (br. s., 4H).

Ex. 4.12

N-(3,4-difluorobenzyl)-2-(((5-(4-(isopropylamino)quinazolin-6-yl)thiophen-2-yl)methyl)amino)nicotinamide

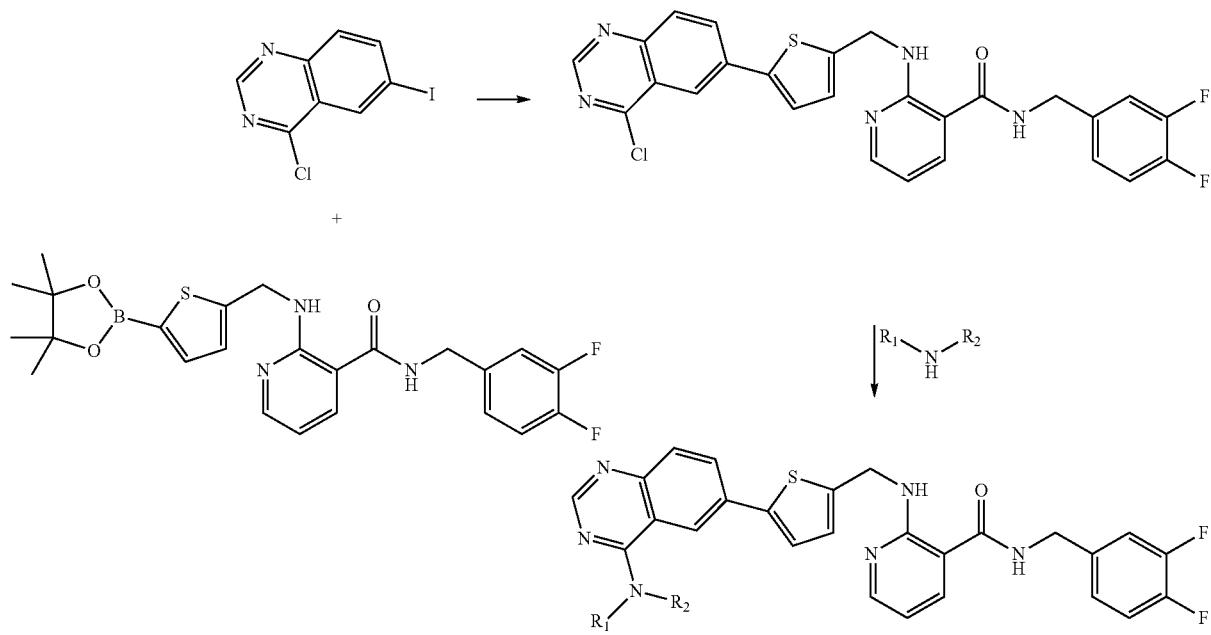

Synthesis of 2-(((5-(4-chloroquinazolin-6-yl)thiophen-2-yl)methyl)amino)-N-(3,4-difluorobenzyl)nicotinamide Into a vial was added N-(3,4-Difluoro-benzyl)-2-{[5-(4,4,5,5-tetramethyl-1,3,2-dioxaborolan-2-yl)-thiophen-2-ylmethyl]-amino}-nicotinamide (50.0 mg, 0.000103 mol), 4-Chloro-6-iodo-quinazoline (36 mg, 0.00012 mol), [1,1'-Bis(diphenylphosphino)ferrocene]-dichloropalladium(II), complex with dichloromethane (1:1) (10.1 mg, 0.0000124 mol), and N,N-Dimethylformamide (0.6 mL, 0.007 mol). The reaction mixture was dissolved under an atmosphere of Nitrogen. Then was added Potassium carbonate (43 mg, 0.00031 mol) and 1.2 M of Sodium bicarbonate in Water (300.0 μL, 0.0003600 mol) The reaction was microwaved on 300 watts, 60° C. for 5 minutes. Crude reaction mixture was washed (brine), was extracted DCM, dried over sodium sulfate and solvent removed in vacuo. A gradient elution (0->50%) EtOAc (B) in hexanes (A) was used to purify the crude product. Collected 27.3 mg of the desired product (50% yield). LC-MS (Agilent 460, acidic method): RT: 1.5 min.; ES (+) MS m/e 522.2 (M+1).

Synthesis of N-(3,4-difluorobenzyl)-2-(((5-(4-(iso-propylamino)quinazolin-6-yl)thiophen-2-yl)methyl)amino)nicotinamide Into a vial was added 2-{[5-(4-Chloro-quinazolin-6-yl)-thiophen-2-ylmethyl]-amino}-N-(3,4-difluoro-benzyl)-nicotinamide (36.00 mg, 0.06897 mmol), 2-Propanamine (41 μL, 0.48 mmol), Methylene chloride (0.159 mL, 2.47 mmol) and Triethylamine (0.0192 mL, 0.138 mmol). The reaction was microwaved on 300 watts, 110° C. for 10 minutes. The reaction mixture was filtered, was washed H$_2$O (DI), was extracted EtOAc, dried over sodium sulfate and solvent removed in vacuo. Purification was done by HPLC to yield desired product as a TFA salt. Collected 17.8 mg solid yellow powder (47% yield). LC-MS (Agilent 460, acidic method): RT: 1.2 min.; ES (+) MS m/e 545.3 (M+1); $^1$H NMR (300 MHz, DMSO-d$_6$) δ 9.86 (d, J=7.55 Hz, 1H), 9.19 (t, J=5.85 Hz, 1H), 8.78-8.92 (m, 2H), 8.66 (d, J=1.51 Hz, 1H), 8.25 (dt, J=1.94, 6.70 Hz, 2H), 8.08 (dd, J=1.70, 7.74 Hz, 1H), 7.77 (d, J=8.69 Hz, 1H), 7.56 (d, J=3.78 Hz, 1H), 7.13 (d, J=3.40 Hz, 1H), 6.99-7.11 (m, 3H), 6.70 (dd, J=4.91, 7.55 Hz, 1H), 4.87 (d, J=5.29 Hz, 2H), 4.73 (dq, J=6.72, 13.83 Hz, 1H), 4.46 (d, J=5.67 Hz, 2H), 1.35 (d, J=6.80 Hz, 6H).

Ex. 4.13 was prepared in a manner consistent with Ex. 4.12 from 1-Propanamine.
Ex. 4.14 was prepared in a manner consistent with Ex. 4.12 from methoxylamine hydrochloride.
Ex. 4.15 was prepared in a manner consistent with Ex. 4.12 from dimethylamine.
Ex. 4.16 was prepared in a manner consistent with Ex. 4.12 from ethylamine.
Ex. 4.17 was prepared in a manner consistent with Ex. 4.12 from diethylamine.
Ex. 4.18 was prepared in a manner consistent with Ex. 4.12 from n-pentylamine.
Ex. 4.19 was prepared in a manner consistent with Ex. 4.12 from pyrrolidine.
Ex. 4.20 was prepared in a manner consistent with Ex. 4.12 from 1-Pyrrolidineethanamine.
Ex. 4.21 was prepared in a manner consistent with Ex. 4.12 from N-methyl-cyclohexanamine.
Ex. 4.22 was prepared in a manner consistent with Ex. 4.12 from 2,2,2-Trifluoro-ethylamine.
Ex. 4.23 was prepared in a manner consistent with Ex. 4.12 from tert-Butylamine.
Ex. 4.24 was prepared in a manner consistent with Ex. 4.12 from methylamine.
Ex. 4.25-32 were prepared in a manner consistent with Ex. 4.12.

Example 5

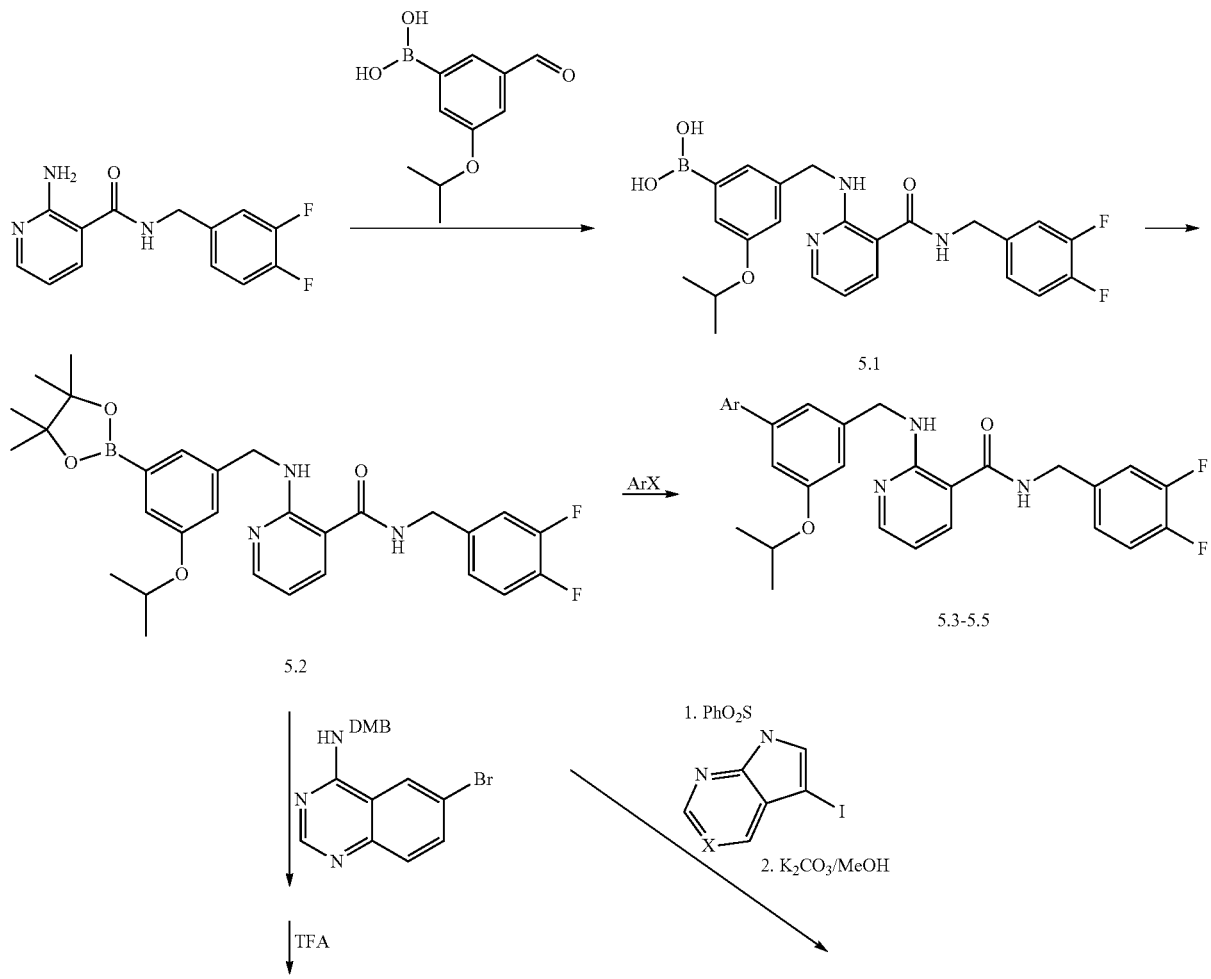

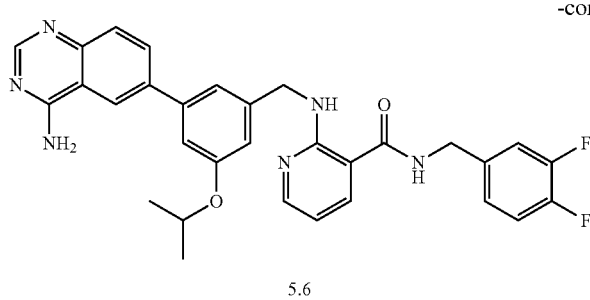

5.6

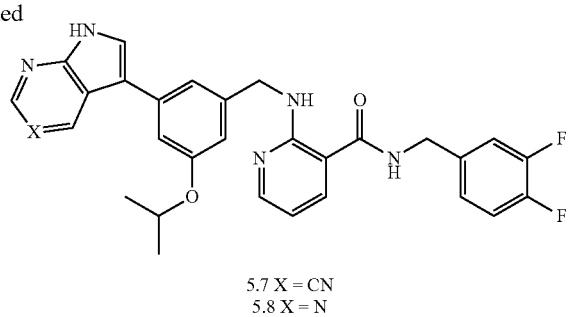

5.7 X = CN
5.8 X = N

Synthesis of 3-((3-(3,4-difluorobenzylcarbamoyl)pyridin-2-ylamino)methyl)-5-isopropoxyphenylboronic acid (5.1)

Compound 5.1 was synthesized in a manner consistent with compound 3.3. Reaction mixture was quenched with 1N HCl$_{(aq)}$ and stirred vigorously. Neutralized with Na$_2$CO$_{3(aq)}$ and diluted with H$_2$O. The organic layer was extracted with EtOAc, washed with a NaHCO$_{3(aq)}$/brine solution, dried over MgSO$_4$ and solvent removed in vacuo to yield relatively pure product. Crude material was carried forward without further purification. LC-MS (Agilent 460, acidic method): RT: 1.2 min.; ES (+) MS m/e 456.2 (M+1).

Synthesis of N-(3,4-difluorobenzyl)-2-(3-isopropoxy-5-(4,4,5,5-tetramethyl-1,3,2-dioxaborolan-2-yl)benzylamino)nicotinamide (5.2)

3-((3-(3,4-difluorobenzylcarbamoyl)pyridin-2-ylamino)methyl)-5-isopropoxyphenylboronic acid (5.1, 1.73 g, 3.80 mmol), 2,3-Dimethyl-2,3-butanediol (1140 mg, 9.65 mmol) were dissolved in tetrahydrofuran (6.6 mL, 82 mmol) and stirred at room temperature overnight. A gradient elution (0-60%) EtOAc (B) in hexane (A) was used to purify the crude product. Final product was purified by precipitation from diethyl ether. Collected 1.35 g white solid (66% yield). LC-MS (Agilent 460, acidic method): RT: 1.6 min.; ES (+) MS m/e 538.4 (M+1); $^1$H NMR (300 MHz, DMSO-d$_6$) δ 9.13 (t, J=5.85 Hz, 1H), 8.68 (t, J=5.85 Hz, 1H), 8.17 (dd, J=1.89, 4.91 Hz, 1H), 8.03 (dd, J=1.70, 7.74 Hz, 1H), 7.19 (s, 1H), 6.94-7.15 (m, 5H), 6.63 (dd, J=4.72, 7.74 Hz, 1H), 4.49-4.63 (m, 3H), 4.45 (d, J=6.04 Hz, 2H), 1.27 (s, 11H), 1.21 (d, 6H).

Ex. 5.3 was synthesized in a manner consistent with Ex. 4.5. Purification was done by HPLC to yield desired product as a TFA salt. Collected 38.7 mg solid yellow powder (77% yield). LC-MS (Agilent 460, acidic method): RT: 1.2 min.

Ex. 5.4 was synthesized in a manner consistent with Ex. 4.5. and Ex. 5.4. Purification was done by HPLC to yield desired product as a TFA salt. Collected 21.4 mg solid off white powder (42% yield). LC-MS (Agilent 460, acidic method): RT: 1.2 min.

Ex. 5.5 was synthesized in a manner consistent with Ex. 4.5. Purification was done by HPLC to yield desired product as a TFA salt. Collected 35.3 mg solid off white powder (64% yield). LC-MS (Agilent 460, acidic method): RT: 1.2 min.

Ex. 5.6: N-(3,4-difluorobenzyl)-2-(3-(4-(2,4-dimethoxybenzylamino)quinazolin-6-yl)-5-isopropoxybenzylamino)nicotinamide was synthesized in a manner consistent with Ex. 4.5. ES (+) MS m/e 705.2 (M+1). The crude was deprotected with TFA in a manner consistent with Ex. 4.4. Purification was done by HPLC to yield desired product as a TFA salt. Collected 30.1 mg solid off white powder (58% yield). LC-MS (Agilent 460, acidic method): RT: 1.2 min.

Ex. 5.7 was synthesized in a manner consistent with Ex. 4.5, from 3-iodo-1-(phenylsulfonyl)-1H-pyrrolo[2,3-b]pyridine, followed with phenylsulfonyl deprotection with potassium in methanol to yield desired product as a TFA salt. Collected 30.6 mg solid yellow powder (62% yield). LC-MS (Agilent 460, acidic method): RT: 1.2 min.

Ex. 5.8 was synthesized in a manner consistent with Ex. 4.5, from 5-iodo-7-(phenylsulfonyl)-7H-pyrrolo[2,3-d]pyrimidine, followed with phenylsulfonyl deprotection with potassium in methanol to yield desired product as a TFA salt. Collected 24.5 mg solid yellow powder (49% yield). LC-MS (Agilent 460, acidic method): RT: 1.1 min.

Example 6

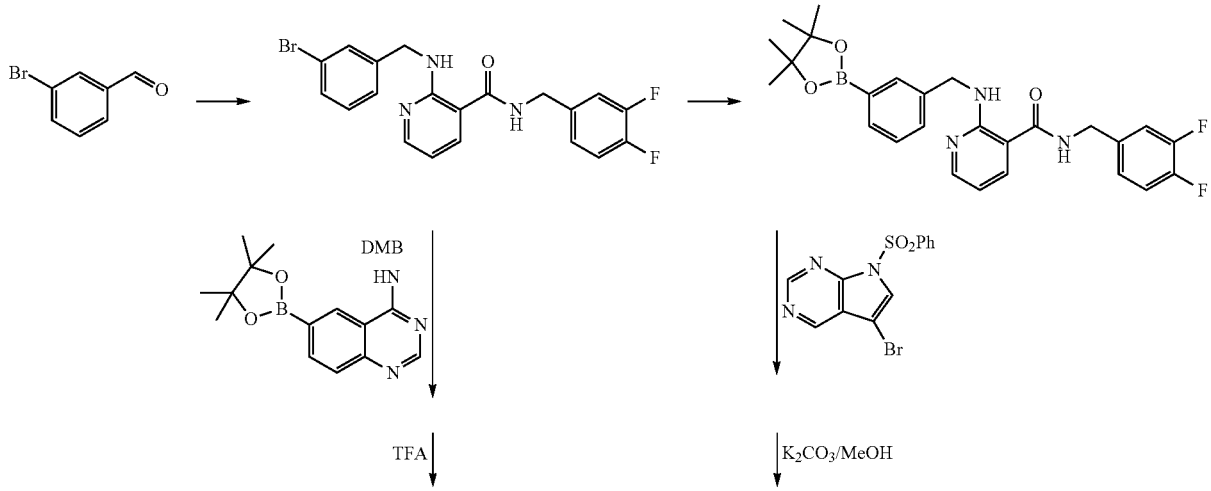

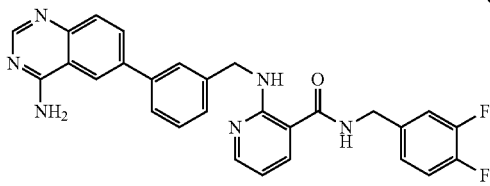

Ex. 6.1

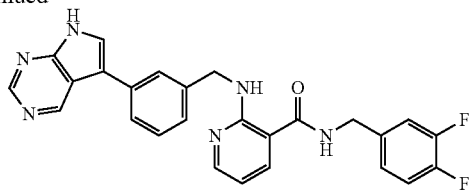

Ex. 6.2

Ex. 6.1

Synthesis of 2-(3-(4-aminoquinazolin-6-yl)benzylamino)-N-(3,4-difluorobenzyl)nicotinamide Step 1: Synthesis of 2-(3-bromobenzylamino)-N-(3,4-difluorobenzyl)nicotinamide 2-Amino-N-(3,4-difluoro-benzyl)-nicotinamide (1.00 g, 3.80 mmol) was dissolved in 1,2-dichloroethane (19.00 mL, 241.2 mmol). To this was added Acetic acid (cat), 3-Bromobenzaldehyde (664 μL, 5.70 mmol), pre-stirred for 60 minutes, and then Sodium triacetoxyborohydride (1.61 g, 7.60 mmol). After 2 hours no progress observed so Acetic acid (216 μL, 3.80 mmol) was added and stirred at room temperature overnight. Reaction mixture was quenched with 1M HCl$_{(aq)}$ and stirred vigorously. Neutralized with Na$_2$CO$_3$ $_{(aq)}$ and diluted with H$_2$O. The organic layer was extracted with EtOAc, washed with a NaHCO$_{3(aq)}$/brine solution, dried over MgSO$_4$ and solvent removed in vacuo. A gradient elution (0->50%) EtOAc (B) in hexanes (A) was used to purify the crude product. Final product was precipitated from DCM/Hexanes solution to give desired intermediate. Collected 1.34 g (80% yield) white powder. LC-MS (Agilent 460, acidic method): RT: 1.3 min.; ES (+) MS m/e 432.1 (M+1); $^1$H NMR (300 MHz, DMSO-d$_6$) δ 9.14 (t, J=5.85 Hz, 1H), 8.71 (t, J=6.04 Hz, 1H), 8.16 (dd, J=1.89, 4.91 Hz, 1H), 8.03 (dd, J=1.89, 7.55 Hz, 1H), 7.46-7.55 (m, 1H), 7.41 (dt, J=1.75, 7.46 Hz, 1H), 7.22-7.35 (m, 2H), 6.99-7.16 (m, 3H), 6.64 (dd, J=4.72, 7.74 Hz, 1H), 4.63 (d, J=6.04 Hz, 2H), 4.47 (d, J=6.04 Hz, 2H).

Step 2: Synthesis of N-(3,4-difluorobenzyl)-2-(3-(4-(2,4-dimethoxybenzylamino)quinazolin-6-yl)benzylamino)nicotinamide Into a vial was added 2-(3-Bromo-benzylamino)-N-(3,4-difluoro-benzyl)-nicotinamide (95.00 mg, 0.2198 mmol), (2,4-Dimethoxy-benzyl)-[6-(4,4,5,5-tetramethyl-1,3,2-dioxaborolan-2-yl)-quinazolin-4-yl]-amine (111 mg, 0.264 mmol) and [1,1'-Bis(diphenylphosphino)ferrocene]dichloropalladium(II), complex with dichloromethane (1:1) (22 mg, 0.026 mmol). The reaction mixture was degassed under an atmosphere of Nitrogen then was added N,N-Dimethylformamide (1.02 mL, 13.2 mmol) and 1.2 M of Sodium bicarbonate in Water (0.549 mL, 0.659 mmol) under an atmosphere of Nitrogen. The reaction was microwaved on 300 watts, 85° C. for 10 minutes. Added EtOAc and filtered through Celite. Washed with NaHCO$_3$, brine, dried over MgSO$_4$, and removed solvent in vacuo to give the desired product without further purifications. LC-MS (Agilent 460, acidic method): RT: 1.26 min.; ES (+) MS m/e 647.4 (M+1).

The above crude reaction mixture was dissolved in Trifluoroacetic Acid (4 mL, 50 mmol) and heated to 40° C. for 1 hr. The crude reaction mixture was dissolved EtOAc, washed NaHCO$_{3(aq)}$ and extracted EtOAc. Solvent removed in vacuo. Purification was done by HPLC to yield the desired product 2-(3-(4-aminoquinazolin-6-yl)benzylamino)-N-(3,4-difluorobenzyl)nicotinamide (Ex. 6.1) as a TFA salt. Collected 86 mg solid white powder (78% yield). LC-MS (Agilent 460, acidic method): RT: 1.0 min.; ES (+) MS m/e 497.3 (M+1); $^1$H NMR (300 MHz, DMSO-d$_6$) δ 9.87 (d, J=17.00 Hz, 2H), 9.18 (t, J=5.85 Hz, 1H), 8.80-8.92 (m, 2H), 8.78 (d, J=1.89 Hz, 1H), 8.37 (dd, J=1.51, 8.69 Hz, 1H), 8.20 (dd, J=1.51, 4.91 Hz, 1H), 8.08 (dd, J=1.70, 7.74 Hz, 1H), 7.86 (d, J=8.69 Hz, 1H), 7.82 (s, 1H), 7.72 (d, J=7.93 Hz, 1H), 7.48-7.57 (m, 1H), 7.39-7.47 (m, 1H), 6.97-7.15 (m, 3H), 6.67 (dd, J=4.91, 7.93 Hz, 1H), 4.75 (d, J=4.91 Hz, 2H), 4.45 (d, J=5.67 Hz, 2H).

Ex. 6.2

Synthesis of 2-(3-(7H-pyrrolo[2,3-d]pyrimidin-5-yl)benzylamino)-N-(3,4-difluorobenzyl)nicotinamide Into a Round bottom flask was added 2-(3-Bromo-benzylamino)-N-(3,4-difluoro-benzyl)-nicotinamide (50 mg, 0.1 mmol), bis(pinacolato)diboron (32 mg, 0.13 mmol), Potassium acetate (34 mg, 0.35 mmol) [1,1'-Bis(diphenylphosphino)ferrocene]-dichloropalladium(II), complex with dichloromethane (1:1) (14 mg, 0.017 mmol) and Dimethyl sulfoxide (0.8 mL, 10 mmol). The reaction mixture was degassed under an atmosphere of Nitrogen (×3) and was stirred for 1.5 hours at 90° C. to give relatively clean crude product without further purifications. LC-MS (Agilent 460, acidic method): RT: 1.5 min.; ES (+) MS m/e 480.3 (M+1).

To the above crude reaction mixture of N-(3,4-Difluoro-benzyl)-2-[3-(4,4,5,5-tetramethyl-1,3,2-dioxaborolan-2-yl)-benzylamino]-nicotinamide (60.0 mg, 0.125 mmol) in solution was added 5-bromo-7-(phenyl sulfonyl)-7H-pyrrolo[2,3-d]pyrimidine (63 mg, 0.19 mmol) and 2 M of Sodium carbonate in water (0.31 mL, 0.62 mmol) and was degassed under an atmosphere of Nitrogen. The reaction mixture was stirred at 90° C. overnight under an atmosphere of Nitrogen. Crude reaction mixture was filtered and solvent volume reduced. Crude reaction mixture was washed (brine), was extracted EtOAc, dried over sodium sulfate and solvent removed in vacuo. Purification was done by HPLC to yield desired product (Ex. 6.2) as a TFA salt. Collected 10.2 mg solid yellow powder (17% yield). LC-MS (Agilent 460, acidic method): RT: 1.0 min.; ES (+) MS m/e 471.2 (M+1); $^1$H NMR (300 MHz, CD$_3$OD) δ 9.48 (s, 1H), 9.03 (s, 1H), 8.25 (dd, J=1.51, 7.55 Hz, 1H), 8.08-8.15 (m, 2H), 7.80 (s, 1H), 7.71 (d, J=7.93 Hz, 1H), 7.53 (t, J=7.74 Hz, 1H), 7.39-7.46 (m, 1H), 6.74-7.00 (m, 4H), 4.78 (s, 2H), 4.55 (s, 2H).

Ex. 6.3 was prepared following the procedure for Ex. 6.1 from (6-Bromo-quinazolin-4-yl)-cyclopropyl-amine.

Ex. 6.4 was prepared following the procedure for Ex. 6.2 from 2-bromobenzaldehyde and 1-(phenylsulfonyl)-3-(4,4,5,5-tetramethyl-1,3,2-dioxaborolan-2-yl)-1H-pyrrolo[2,3-b]pyridine.

Ex. 6.5 was prepared following the procedure for Ex. 6.1 from 2-bromobenzaldehyde and N-(2,4-dimethoxybenzyl)-6-(4,4,5,5-tetramethyl-1,3,2-dioxaborolan-2-yl)quinazolin-4-amine.

Ex. 6.6 was prepared following the procedure for Ex. 6.1 from 2-bromothiazole-5-carbaldehyde and N-(2,4-dimethoxybenzyl)-6-(4,4,5,5-tetramethyl-1,3,2-dioxaborolan-2-yl)quinazolin-4-amine.

Ex. 6.7 was prepared following the procedure for Ex. 6.1 from 4-bromothiazole-2-carbaldehyde and N-(2,4-dimethoxybenzyl)-6-(4,4,5,5-tetramethyl-1,3,2-dioxaborolan-2-yl)quinazolin-4-amine.

Ex. 6.8 was prepared following the procedure for Ex. 6.1 from 2-bromothiazole-4-carbaldehyde and N-(2,4-dimethoxybenzyl)-6-(4,4,5,5-tetramethyl-1,3,2-dioxaborolan-2-yl)quinazolin-4-amine.

Ex. 6.9 was prepared following the procedure for Ex. 6.1 from 2-bromothiazole-4-carbaldehyde and N-cyclopropyl-6-(4,4,5,5-tetramethyl-1,3,2-dioxaborolan-2-yl)quinazolin-4-amine.

Ex. 6.10 was prepared following the procedure for Ex. 6.2 from 2-bromothiazole-5-carbaldehyde and 1-Benzenesulfonyl-3-(4,4,5,5-tetramethyl-1,3,2-dioxaborolan-2-yl)-1H-pyrrolo[2,3-b]pyridine.

Ex. 6.11 was prepared following the procedure for Ex. 6.2 from 4-bromothiazole-2-carbaldehyde and 1-Benzenesulfonyl-3-(4,4,5,5-tetramethyl-1,3,2-dioxaborolan-2-yl)-1H-pyrrolo[2,3-b]pyridine.

Ex. 6.12 was prepared following the procedure for Ex. 6.2 from 2-bromothiazole-4-carbaldehyde and 1-Benzenesulfonyl-3-(4,4,5,5-tetramethyl-1,3,2-dioxaborolan-2-yl)-1H-pyrrolo[2,3-b]pyridine.

Ex. 6.13 was prepared following the procedure for Ex. 6.2 from 5-bromo-7-(phenylsulfonyl)-7H-pyrrolo[2,3-d]pyrimidine and 2-[(2-Bromo-thiazol-4-ylmethyl)-amino]-N-(3,4-difluoro-benzyl)-nicotinamide.

Ex. 6.14 was prepared following the procedure for Ex. 6.1 from 4-bromo-thiophene-2-carbaldehyde and (2,4-dimethoxy-benzyl)-[6-(4,4,5,5-tetramethyl-1,3,2-dioxaborolan-2-yl)-quinazolin-4-yl]-amine.

Ex. 6.15 was prepared following the procedure for Ex. 6.2 from 4-bromothiophene-2-carbaldehyde and 1-Benzenesulfonyl-3-(4,4,5,5-tetramethyl-1,3,2-dioxaborolan-2-yl)-1H-pyrrolo[2,3-b]pyridine.

Example 7

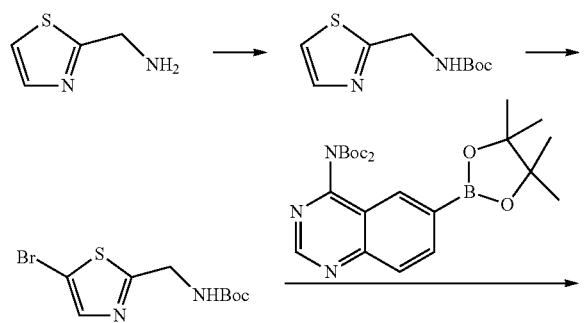

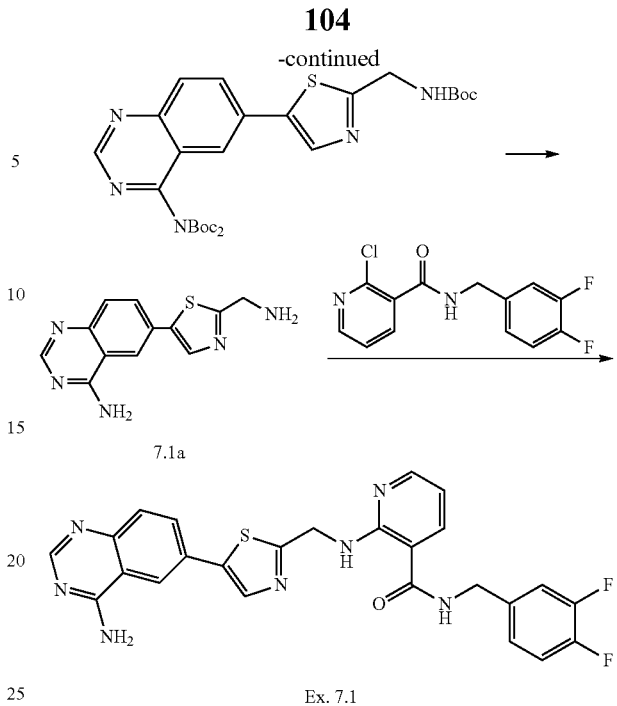

Ex. 7.1

Step 1. Synthesis of tert-butyl thiazol-2-ylmethylcarbamate

To a solution of thiazol-2-ylmethanamine (1.14 g, 10 mmol) in THF (10 mL), was added NaHCO$_3$ (920 mg, 11 mmol, 1.1 equiv) and (Boc)$_2$O (2.18 g, 10 mmol, 1.05 equiv) slowly. The resulted mixture was stirred at rt for 2 h. The reaction was filtrated through a short path of silica gel and concentrated to give tert-butyl thiazol-2-ylmethylcarbamate (2.05 g, 96%). ESI-MS (M+H$^+$): 215.1; $^1$H NMR (400 MHz, CDCl$_3$) δ: 1.47 (s, 9H), 4.64 (d, 2H), 5.39 (s, 1H), 7.28 (d, 1H), 7.71 (d, 1H).

Step 2. Synthesis of tert-butyl (5-bromothiazol-2-yl)methylcarbamate

The mixture of tert-butyl thiazol-2-ylmethylcarbamate (2 g, 9.5 mmol), NBS (1.78 g, 10 mmol, 1.1 equiv) in DMF (20 mL) was stirred at rt for 2 h. The reaction was diluted with ethyl acetate and washed with water for three times. The organic layer was dried over MgSO$_4$ and concentrated in vacuum. The residue was purified by chromatography with silica gel to give the desired product (2.24 g, 80%). ESI-MS (M+H$^+$): 293; $^1$H NMR (400 MHz, CDCl$_3$) δ: 7.57 (s, 1H), 5.39 (s, 1H), 4.55 (d, 2H), 1.47 (s, 9H).

Step 3. Synthesis of tert-butyl (5-(4-(di-Boc-amino)quinazolin-6-yl)thiazol-2-yl)methylcarbamate A flask charged with compound di-Boc-6-(4,4,5,5-tetramethyl-1,3,2-dioxaborolan-2-yl)quinazolin-4-amine (2.35 g, 5 mmol), tert-butyl (5-bromothiazol-2-yl)methylcarbamate (1.46 g, 5 mmol, 1.0 equiv), 2M K$_2$CO$_3$ (5.0 mL, 2.0 equiv) and [1,1-bis (diphenylphosphino) ferrocene]dichloropalladium(II) complex with dichloromethane (1:1) (210 mg, 0.25 mmol, 0.05 equiv) was flushed with nitrogen. 1, 4-Dioxane (30 mL) was added and the reaction was stirred at 90° C. for 2 h. The solution was cooled to room temperature. The solvent was removed and the residue was purified by column chromatography (PE/EA=4:1) to give the product (1.5 g, 55%). ESI-MS (M+H⁺): 558.2; ¹H NMR (400 MHz, CDCl₃) δ: 9.25 (s, 1H), 8.15 (s, 2H), 8.01 (d, 2H), 5.39 (s, 1H), 4.68 (d, 2H), 1.50 (s, 9H), 1.36 (s, 18H).

Step 4. Synthesis of 6-(2-(aminomethyl)thiazol-5-yl)quinazolin-4-amine (7.1a)

A solution of tert-butyl (5-(4-(di-Boc-amino)quinazolin-6-yl)thiazol-2-yl)methylcarbamate: (1.5 g, 2.7 mmol) in DCM/TFA (30 mL, 1:1) was stirred at rt for 30 min, then the solvent was removed and the residue was dissolved in water. Sat aqueous NaHCO₃ was added, white solid was formed, filtered to give the desired product (690 mg, 100%). ESI-MS (M+H⁺): 258; ¹H NMR (400 MHz, DMSO-d₆) δ: 9.89 (s, 2H), 8.85 (s, 1H), 8.75 (d, 1H), 8.68 (s, 2H), 8.45 (s, 1H), 8.37-8.40 (m, 1H), 7.88 (d, 1H), 4.56 (s, 2H).

Ex. 7.1

Synthesis of 2-(((5-(4-aminoquinazolin-6-yl)thiazol-2-yl)methylamino)-N-(3,4-difluorobenzyl)nicotinamide The mixture of 6-(2-(aminomethyl)thiazol-5-yl)quinazolin-4-amine (258 mg, 1 mmol), 2-chloro-N-(3,4-difluorobenzyl)nicotinamide (210 mg, 0.75 mmol, 0.75 equiv) and NaHCO₃ (160 mg, 2 mmol, 2.0 equiv) in 1-pentanol (2 mL) was stirred at 130° C. for 18 h, then the solvent was removed, the residue was purified by prep HPLC to give the product (35 mg, 8%). ESI-MS (M+H⁺): 504.1; ¹H NMR (400 MHz, CD₃OD/CDCl₃) δ: 8.39 (s, 2H), 8.22 (dd, 1H), 8.06 (s, 1H), 7.95-7.98 (m, 2H), 7.73 (d, 1H), 7.14-7.25 (m, 3H), 6.69-6.71 (m, 1H), 5.02 (s, 2H), 4.52 (s, 2H).

Ex. 7.2 was prepared following the procedure for Ex. 7.1 from 1-(thiophen-2-yl)ethanamine.

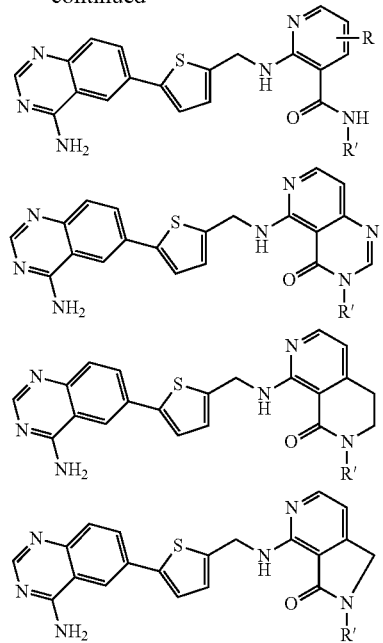

6-(5-(Aminomethyl)thiophen-2-yl)quinazolin-4-amine (7.1b) was prepared following the same as procedure as 6-(2-(aminomethyl)thiazol-5-yl)quinazolin-4-amine (7.1a) in Ex. 7.1.

Ex. 7.3.1 was prepared following the procedure for Ex. 7.1 from 6-(5-(aminomethyl)thiophen-2-yl)quinazolin-4-amine (7.1b) and 2-chloro-N-(3,4-difluorobenzyl)-5-fluoronicotinamide.

Ex. 7.3.2 was prepared by an analogous procedure to Ex. 7.3.1.

Preparation of 2-chloro-N-(3,4-difluorobenzyl)-4-methoxynicotinamide for use in synthesis of Ex. 7.4

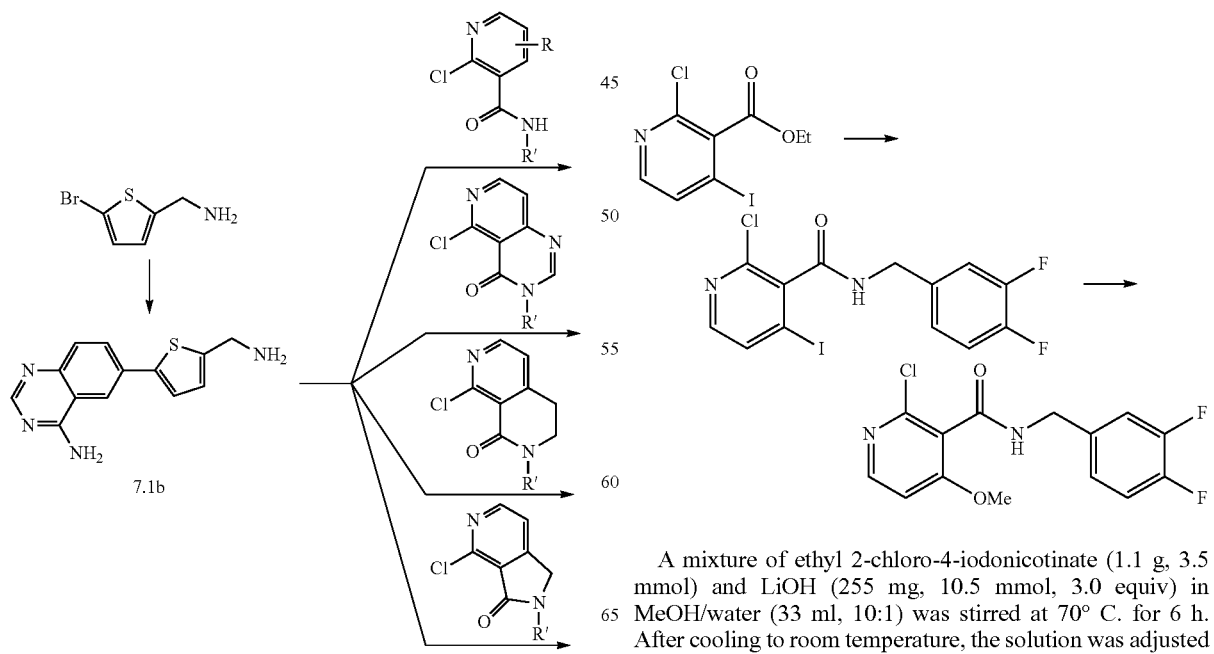

A mixture of ethyl 2-chloro-4-iodonicotinate (1.1 g, 3.5 mmol) and LiOH (255 mg, 10.5 mmol, 3.0 equiv) in MeOH/water (33 ml, 10:1) was stirred at 70° C. for 6 h. After cooling to room temperature, the solution was adjusted to pH=6, then concentrated, dissolved in MeOH/DCM (1:5), filtered and the filtrate was concentrated to give the crude acid product without further purifications. ESI-MS (M+H$^+$): 284.

To a solution of the above product (890 mg, 3.2 mmol) in anhydrous DMF (50 ml), was added DIPEA (830 mg, 6.4 mmol, 2.0 equiv) in one portion. The reaction mixture was stirred at room temperature for 10 min., and then dFBnNH$_2$ (456 mg. 3.2 mmol, 1.0 equiv), HATU (2.4 g. 6.4 mmol, 2.0 equiv) was added. The mixture was stirred at room temperature for 18h. After the reaction ended, the solvent was removed and the residue was purified by column chromatography (PE/EA=4:1) to give 2-chloro-N-(3,4-difluorobenzyl)-4-iodonicotinamide, (1 g, 78%). ESI-MS (M+H$^+$): 409.0.

A mixture of -chloro-N-(3,4-difluorobenzyl)-4-iodonicotinamide (500 mg, 1.2 mmol) and MeONa (65 mg, 1.2 mmol, 1.0 equiv) in MeOH (15 ml) was stirred at 70° C. for 18 h. Then the solvent was removed and the residue was purified by column chromatography (PE/EA=2:1) to give the desired product, 2-chloro-N-(3,4-difluorobenzyl)-4-methoxynicotinamide (188 mg, 50%). ESI-MS (M+H$^+$): 313.0; $^1$H NMR (400 MHz, DMSO-d$_6$) δ: 9.32 (t, 1H), 8.10 (d, 1H), 7.98 (d, 1H), 7.13-7.17 (m, 3H), 4.51 (d, 2H).

2-Chloro-N-(3,4-difluorobenzyl)-4-ethoxynicotinamide was prepared similarly. ESI-MS (M+H$^+$): 327.1.

Ex. 7.4 was prepared following the procedure for Ex. 7.1 from 6-(5-(aminomethyl)thiophen-2-yl)quinazolin-4-amine (7.1b) and 2-chloro-N-(3,4-difluorobenzyl)-4-methoxynicotinamide.

Ex. 7.5 was prepared following the procedure for Ex. 7.1 from 6-(5-(aminomethyl)thiophen-2-yl)quinazolin-4-amine (7.1b) and 2-chloro-N-(3,4-difluorobenzyl)-4-ethoxynicotinamide.

Ex. 7.6 was prepared following the procedure for Ex. 7.1 from 6-(5-(aminomethyl)thiophen-2-yl)quinazolin-4-amine (7.1b) and (S)-2-chloro-N-(1-(4-fluorophenyl)ethyl)-4-methoxynicotinamide.

Ex. 7.7 was prepared following the procedure for Ex. 7.1 from 6-(5-(aminomethyl)thiophen-2-yl)quinazolin-4-amine (7.1b) and (S)-2-chloro-N-(1-(4-fluorophenyl)ethyl)-4-ethoxynicotinamide.

Preparation of 5-chloro-3-(3,4-difluorobenzyl)pyrido[4,3-d]pyrimidin-4(3H)-one for use in synthesis of Ex. 7.8

A mixture of 2-chloro-N-(3,4-difluorobenzyl)-4-iodonicotinamide (1 g, 2.46 mmol), p-methoxybenzylamine (0.62 g, 3.7 mmol), Cs$_2$CO$_3$ (1.6 g, 4.9 mmol) in dioxane was stirred at 90° C. for 4 h, Then the solvent was removed and the residue was purified by column chromatography to give the product, 2-chloro-N-(3,4-difluorobenzyl)-4-(4-methoxybenzylamino)nicotinamide (690 mg, 67.5%). MS (M+H$^+$): 418.1.

A solution of the above product (690 mg, 1.65 mmol) in TFA (50 mL) was stirred at rt. for 2h, then the solvent was removed and the residue was dissolved in water, sat aqueous NaHCO$_3$ was added, white solid was formed, filtered to give 4-amino-2-chloro-N-(3,4-difluorobenzyl)nicotinamide (290 mg, 59.2%). MS (M+H$^+$): 298.1.

A solution of 4-amino-2-chloro-N-(3,4-difluorobenzyl)nicotinamide (290 mg, 0.974 mmol) was dissolved in DMFDMA/Ac$_2$O (50 ml, 1:4) was stirred at 120° C. for overnight, then the solvent was removed and the residue was purified on silica gel to give the product, 5-chloro-3-(3,4-difluorobenzyl)pyrido[4,3-d]pyrimidin-4(3H)-one (150 mg, (yield: 50%). MS (M+H$^+$): 308.0.

Ex. 7.8 was prepared following the procedure for Ex. 7.1 from 6-(5-(aminomethyl)thiophen-2-yl)quinazolin-4-amine (7.1b) and 5-chloro-3-(3,4-difluorobenzyl)pyrido[4,3-d]pyrimidin-4(3H)-one.

Ex. 7.9 was prepared following the procedure for Ex. 7.1 from 6-(5-(aminomethyl)thiophen-2-yl)quinazolin-4-amine (7.1b) and (S)-5-chloro-3-(1-(4-fluorophenyl)ethyl)pyrido[4,3-d]pyrimidin-4(3H)-one.

Examples 7.10-7.16 were prepared in a manner analogous to Ex. 7.1.

Ex. 7.17 was prepared following the procedure for Ex. 7.1 from 6-(5-(aminomethyl)thiophen-2-yl)quinazolin-4-amine (7.1b) and 5,7-dichloro-3-(3,4-difluorobenzyl)pyrido[4,3-d]pyrimidin-4(3H)-one.

5,7-dichloro-3-(3,4-difluorobenzyl)pyrido[4,3-d]pyrimidin-4(3H)-one was prepared according to the procedure for 5-chloro-3-(3,4-difluorobenzyl)pyrido[4,3-d]pyrimidin-4(3H)-one from 4-amino-2,6-dichloronicotinic acid (reference see: Jang, M., et. al, Tetrahedron Letters (2006), 47(50), 8917).

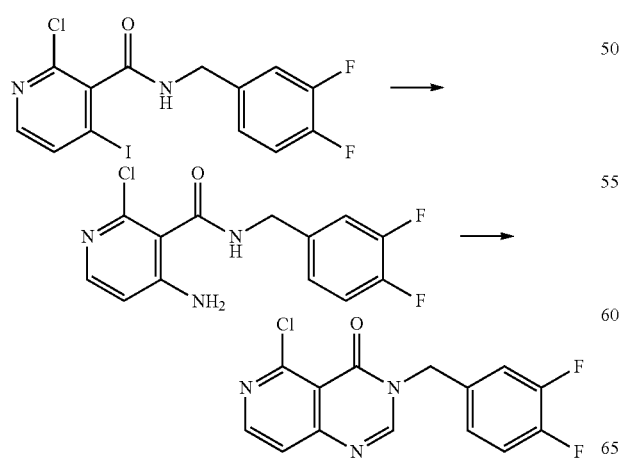

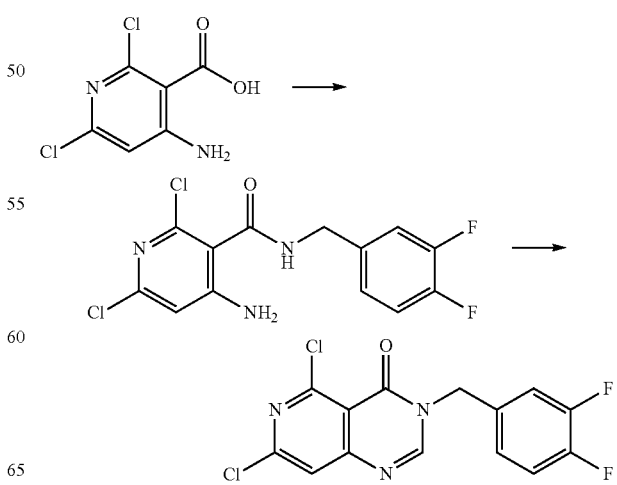

Synthesis of 8-chloro-2-(3,4-difluorobenzyl)-3,4-dihydro-2,7-naphthyridin-1(2H)-one

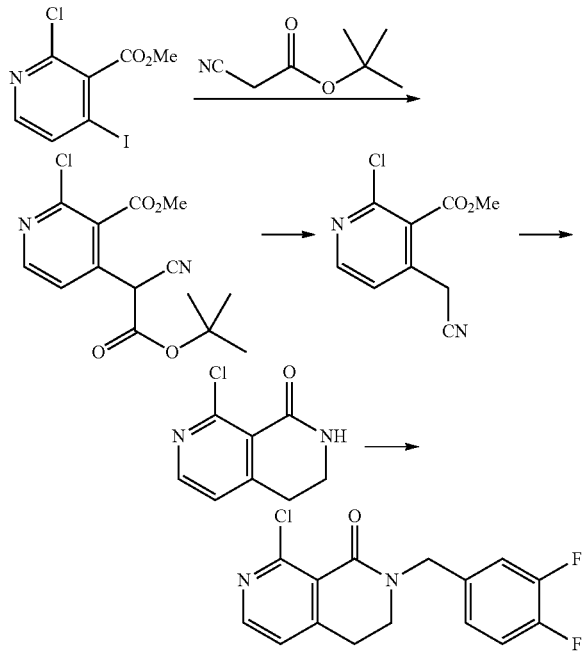

To a solution of methyl 2-chloro-4-iodonicotinate (4 g, 12.87 mmol) in 50 ml DMF, tert-butyl 2-cyanoacetate (3.6 g, 25.75 mmol, equiv), $K_2CO_3$ (7.1 g, 51.5 mmol, 4 equiv) and CuI (13 mg, 0.1 mmol, 0.01 equiv) were added. The result solution was stirred for overnight at 50° C. Then the solvent was removed and the residue was purified on silica gel column to give the product, methyl 4-(2-tert-butoxy-1-cyano-2-oxoethyl)-2-chloronicotinate (2.8 g, 66%). ESI-MS (M+H$^+$): 311.1; $^1$H NMR (400 MHz, CDCl$_3$) δ: 8.56 (d, 1H), 7.54 (d, 1H), 5.13 (s, 1H), 3.99 (s, 3H), 1.48 (s, 9H).

A flask charged with methyl 4-(2-tert-butoxy-1-cyano-2-oxoethyl)-2-chloronicotinate (0.8 g, 2.6 mmol) was added 5 mL DCM and 2 mL TFA. The solution was stirred at room temperature for 6h. The solvent was removed and the residue was purified by column chromatography (PE/EA=3/1) to give the product, methyl 2-chloro-4-(cyanomethyl) nicotinat (370 mg, 64%). ESI-MS (M+H$^+$): 211.0; $^1$H NMR (400 MHz, CD$_3$OD) δ: 8.51 (d, 1H), 7.46 (d, 2H), 4.03 (s, 3H), 3.86 (s, 2H).

To a solution of methyl 2-chloro-4-(cyanomethyl)nicotinat (0.35 g, 1.66 mmol) in EtOH (20 mL), was added 5% Pt/C (0.07 g, 2 equiv) and concentrated HCl (0.2 ml). Hydrogen (1 atm) was introduced at room temperature for 5h. When TLC showed the starting material was disappeared, the catalyst was filtrated through celite and the solvent was removed. The residue was dissolved in saturated NaHCO$_3$ solution (30 ml) and stirred at room temperature for 1 h. The reaction was monitored by LC-MS, after the reaction was complete, the solution was extracted with 150 ml DCM×3. The organic layer was concentrated and purified by silica gel to give the desired product, 8-chloro-3,4-dihydro-2,7-naphthyridin-1(2H)-one (0.2 g, 67%). ESI-MS (M+H$^+$): 183.0; $^1$H NMR (400 MHz, CDCl$_3$) 8.46 (d, 1H), 7.15 (d, 1H), 6.79 (s, 1H), 3.55 (m, 2H), δ: 3.01 (t, 2H).

To a solution of 8-chloro-3,4-dihydro-2,7-naphthyridin-1(2H)-one (0.2 g, 1.1 mmol) in 10 ml DMF, 50% NaH (100 mg, 2.2 mmol, 2.0 equiv) was added and keep stirring for 15 min at room temperature, followed by the addition of 4-(bromomethyl)-1,2-difluorobenzene (0.27 g, 1.3 mmol, 1.2 equiv). When TLC detected the completion of reaction, the mixture was poured into 100 mL ice water and extracted with 200 mL DCM. The organic layer was concentrated and purified by silica gel to obtain pure product, 8-chloro-2-(3,4-difluorobenzyl)-3,4-dihydro-2,7-naphthyridin-1(2H)-one (0.12 g, 35.5%). ESI-MS (M+H$^+$): 309; $^1$H NMR (400 MHz, CDCl$_3$) δ: 2.93 (t, 2H), 3.52 (t, 2H), 4.71 (s, 2H), 7.08-7.19 (m, 4 H), 6.79 (s, 1H), 8.37 (d, 1H).

Ex. 7.18 was prepared following the procedure for Ex. 7.1 from 6-(5-(aminomethyl)thiophen-2-yl)quinazolin-4-amine (7.1b) and 8-chloro-2-(3,4-difluorobenzyl)-3,4-dihydro-2,7-naphthyridin-1 (2H)-one.

Synthesis of 4-chloro-2-(3,4-difluorobenzyl)-1H-pyrrolo[3,4-c]pyridin-3(2H)-one

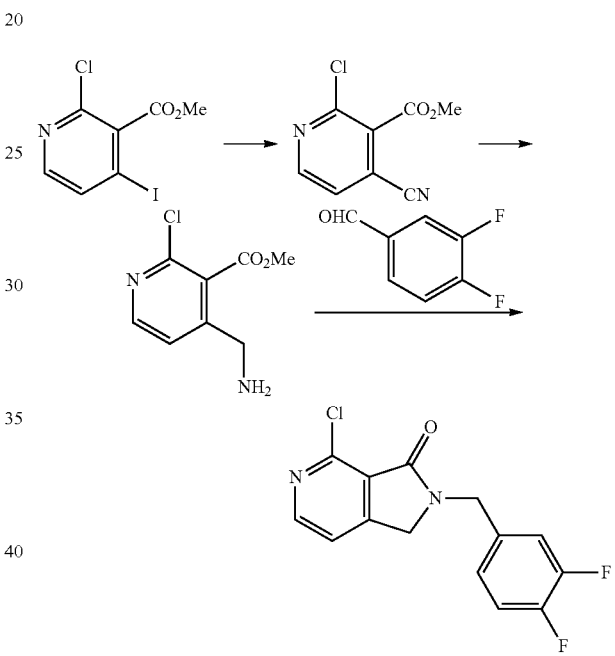

A mixture of methyl 2-chloro-4-iodonicotinate (2.0 g, 6.7 mmol), cuprous cyanide (0.60 g, 6.7 mmol) and NMP (1.0 mL) was heated at 130° C. for 5 h, cooled and dilutes with EtOAc (50 mL). The mixture was filtered and concentrated under reduced pressure. The residue was dissolved in EtOAc (25 mL) and washed with 2×10 mL ammonium hydroxide, dried over MgSO$_4$, and concentrated. The residue was purified by column chromatography on silica gel (mobile phase:EtOAc:petroleum=3%-5%), to give the desired product, methyl 2-chloro-4-cyanonicotinate, as a white solid. (1.0 g, 5.1 mmmol, 56%). ESI-MS (M+H)$^+$: 197.0; $^1$HNMR (400 MHz, CDCl$_3$) δ: 8.65 (d, 1H), 7.57 (d, 1H), 4.075 (s, 3H).

Methyl 2-chloro-4-cyanonicotinate (392 mg, 2 mmol) was hydrogenated in the presence of 10% Pt/C (150 mg) catalyst at atmospheric pressure in abs methanol (25 mL) for 36h. The catalyst was filtered off and the solvent was evaporated off to give methyl 4-(aminomethyl)-2-chloronicotinate as a light yellow solid, (0.472 g, 100%). ESI-MS (M-35)$^+$201.0.

To a solution of methyl 4-(aminomethyl)-2-chloronicotinate (420 mg, 1.78 mmol) and 3,4-difluorobenzaldehyde (379 mg, 2.67 mmol, 1.5 eq) in DCE was slowly added NaBH(OAc)₃ (751 mg, 3.56 mmol, 2.0 eq). Then HOAc (325 mg, 5.34 mmol, 3.0 equiv) was added and stirred at reflux for 15h. TLC showed the reaction was completed. The organic solvent was then removed to give a crude product, which was purified through silica gel column to give 4-chloro-2-(3,4-difluorobenzyl)-1H-pyrrolo[3,4-c]pyridin-3 (2H)-one (240 mg, 45.9%). ESI-MS (M+H)⁺: 294.9; ¹H NMR (400 MHz, CDCl₃) δ: 8.53 (d, 1H), 7.34 (m, 1H), 7.13-7.26 (m, 2H) 7.09 (m, 1H), 4.75 (s, 2H), 4.29 (s, 2H).

Ex. 7.19 was prepared following the procedure for Ex. 7.1 from 6-(5-(aminomethyl)thiophen-2-yl)quinazolin-4-amine (7.1b) and 4-chloro-2-(3,4-difluorobenzyl)-1H-pyrrolo[3,4-c]pyridin-3 (2H)-one.

Ex. 7.20

Synthesis of 4-((5-(4-aminoquinazolin-6-yl)thiophen-2-yl)methyl)amino)-2-(3,4-difluorobenzyl)-1-methylene-1H-pyrrolo[3,4-c]pyridin-3(2H)-one

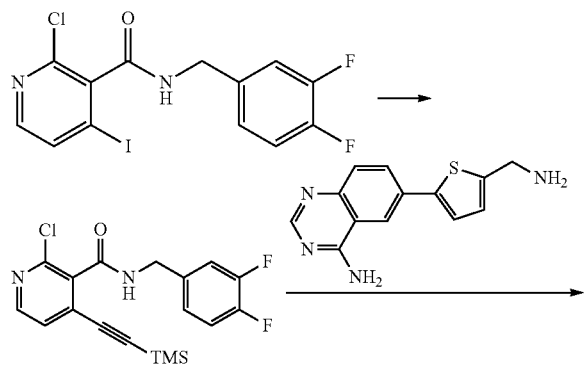

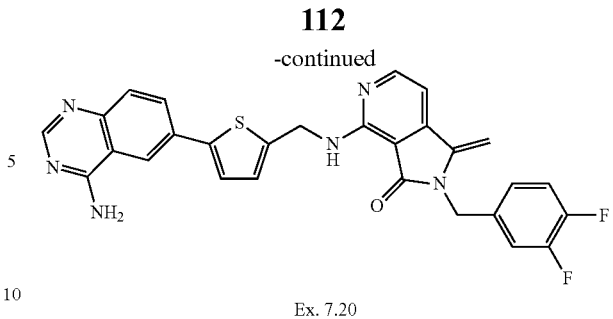

Ex. 7.20

Under nitrogen, ethynyltrimethylsilane (426 mg, 4.4 mmol) was added to a solution of 2-chloro-N-(3,4-difluorobenzyl)-4-iodonicotinamide (1.2 g, 2.9 mmol), PdCl₂(PPh₃)₂ (51 mg, 0.073 mmol), and CuI (55 mg, 0.29 mmol) in DIPEA and DMF (50 mL) at rt and stirred for 3h. The precipitates were collected and washed with EtOAc. The filtrate was concentrated under reduced pressure. The residue was dissolved in EtOAc (200 mL) and washed with water (200 mL) and brine (200 mL). The organic layer was dried over MgSO₄ and concentrated under reduced pressure. The residue was distilled in vacuo to give 2-chloro-N-(3,4-difluorobenzyl)-4-((trimethylsilyl)ethynyl)nicotinamide (650 mg, 60%). ¹H NMR (400 MHz, DMSO-d₆) δ: 9.07 (t, 1H) 8.26 (d, 1H), 7.36 (d, 1H), 7.20-7.27 (m, 2H), 7.06-7.07 (br, 1H), 4.28-4.29 (d, 2H), 0.00 (s, 9H).

A mixture of 2-chloro-N-(3,4-difluorobenzyl)-4-((trimethylsilyl)ethynyl)nicotinamide (650 mg, 1.7 mmol), 6-(5-(aminomethyl)thiophen-2-yl)quinazolin-4-amine (7.1b) (660 mg, 2.6 mmol, 1.5 equiv), and Cs₂CO₃ (1.1 g, 3.4 mmol, 2 equiv) in 1-pentanol (1 ml) was stirred at 130° C. for 16 h, then the solvent was removed, the residue was purified by HPLC-preparation (CH₃CN/H₂O 0.05% CF₃COOH) to give 4-((5-(4-aminoquinazolin-6-yl)thiophen-2-yl)methyl)amino)-2-(3,4-difluorobenzyl)-1-methylene-1H-pyrrolo[3,4-c]pyridin-3 (2H)-one (Ex. 7.20) (70 mg, 6%). ESI-MS (M+H⁺): 527.14; ¹H NMR (400 MHz, DMSO-d₆) δ: 9.86 (bs, 1H), 9.76(bs, 1H), 8.80 (s, 1H), 8.61 (s, 1H), 8.36 (d, 1H), 8.29 (d, 1H), 7.79 (d, 1H), 7.57-7.52 (m, 2H), 7.41-7.36 (m, 2H), 7.17-7.12 (m, 3H), 5.57 (s, 1H), 5.52 (s, 1H), 4.91 (br, 4H).

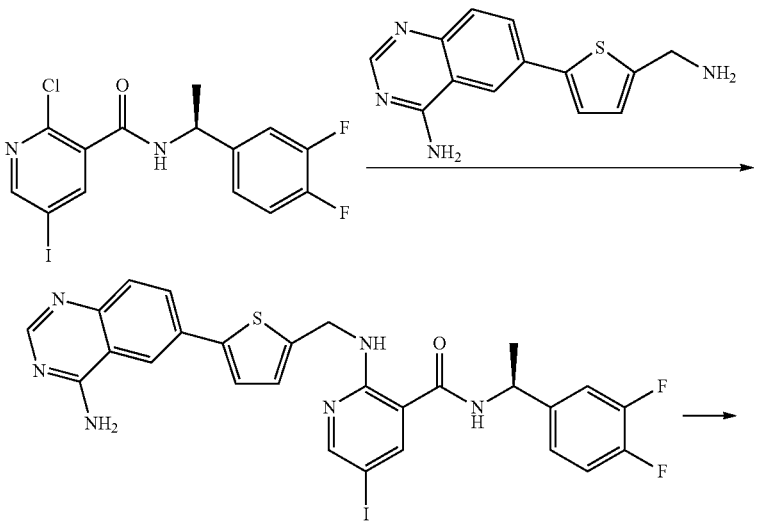

Ex. 7.21.1

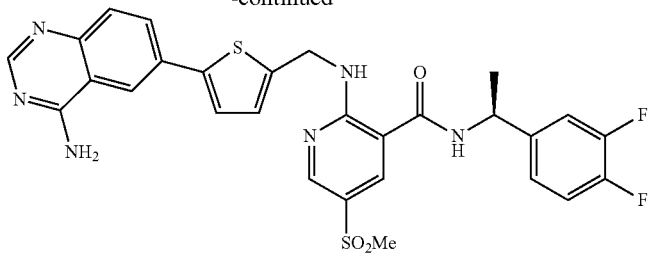
Ex. 7.22.1

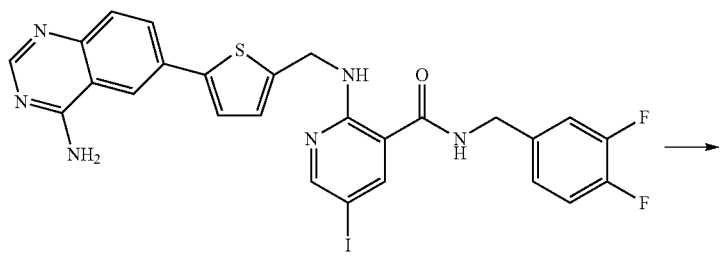
Ex. 8.3

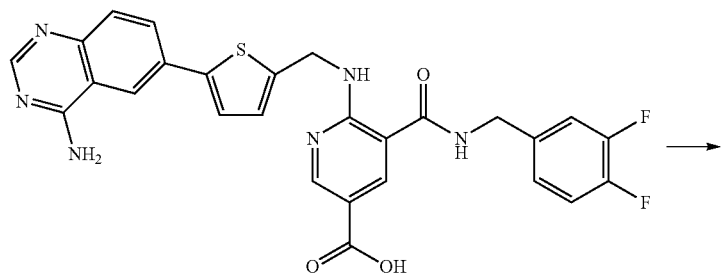
Ex. 7.23.1

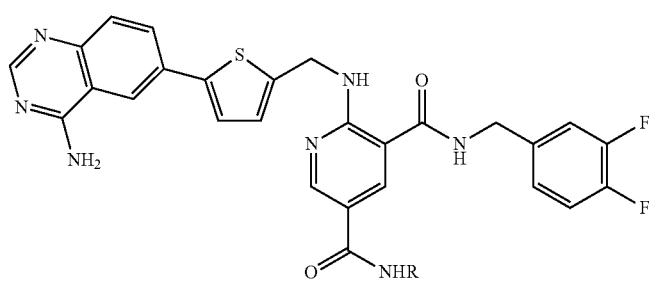

Ex. 7.21.1 was prepared following the procedure for Ex. 7.1 from 6-(5-(aminomethyl)thiophen-2-yl)quinazolin-4-amine (7.1b) and (S)-2-chloro-N-(1-(3,4-difluorophenyl)ethyl)-5-iodonicotinamide. LCMS: RT 1.60 min.

Ex. 7.21.2 was prepared in a manner analogous to Ex. 7.21.1.

Ex. 7.22.1

Synthesis of 2-({[5-(4-aminoquinazolin-6-yl)thiophen-2-yl]methyl}amino)-N-[(1S)-1-(4-fluorophenyl)ethyl]-5-(methylsulfonyl)pyridine-3-carboxamide A solution of 2-{[5-(4-amino-quinazolin-6-yl)-thiophen-2-ylmethyl]-amino}-N-[(S)-1-(3,4-difluoro-phenyl)-ethyl]-5-iodo-nicotinamide (Ex. 7.14, 150.0 mg, 0.23 mmol) in dimethyl sulfoxide (2 mL) in a dry flask was degassing for 10 min. A mixture of methanesulfinic acid sodium salt (159 mg, 1.56 mmol), L-proline sodium salt (21.34 mg, 0.16 mmol, reference see: W. Zhu; J. Org. Chem., 2005, 70 (7), pp 2696-2700), and copper (I) iodide (11.86 mg, 0.006 mmol) was then added. The reaction mixture kept degassing for another 5 min. then heated at 95° C. overnight. The reaction solution was diluted with 30 ml of EtOAc and washed with water (5 times). The organic layer was separated, dried over MaSO$_4$, decolored with charcoal, and filtered. The filtration was concentrated. The crude was purified by HPLC to give product 2-({[5-(4-aminoquinazolin-6-yl)thiophen-2-yl]methyl}amino)-N-[(1S)-1-(4-fluorophenyl)ethyl]-5-(methylsulfonyl)pyridine-3-carboxamide (Ex. 7.22.1) as a light yellow powder (36.7 mg, TFA salt, 26%). LCMS: RT 1.45 min.; MH+ 595.30; $^1$H NMR (400 MHz, DMSO-d$_6$) δ 9.83 (br. s., 2H), 9.41 (t, J=6.15 Hz, 1H), 9.21 (d, J=7.53 Hz, 1H), 8.72-8.89 (m, 1H), 8.66 (d, J=2.26 Hz, 1H), 8.60 (d, J=1.51 Hz, 1H), 8.52 (d, J=2.26 Hz, 1H), 8.26 (dd, J=1.63, 8.66 Hz, 1H), 7.77 (d, J=8.78 Hz, 1H), 7.54 (d, J=3.76 Hz, 1H), 7.28-7.50 (m, 2H), 7.23 (ddd, J=2.26, 4.27, 6.27 Hz, 1H), 7.13 (d, J=3.76 Hz, 1H), 5.11 (quin, J=7.03 Hz, 1H), 4.91 (d, 2H), 3.24 (s, 3H), 1.49 (d, J=7.03 Hz, 3H).

Ex. 7.22.2 was prepared in a manner analogous to Ex. 7.22.1.

Ex. 7.23.1

Synthesis of 6-((5-(4-aminoquinazolin-6-yl)thiophen-2-yl)methyl)amino)-5-(3,4-difluorobenzylcarbamoyl)nicotinic acid A suspension of 2-{[5-(4-amino-quinazolin-6-yl)-thiophen-2-ylmethyl]-amino}-N-(3,4-difluoro-benzyl)-5-iodo-nicotinamide (Ex. 8.3) (1.00 g, 1.59 mmol), triethylamine (1.11 mL, 8.0 mmol) and bis(triphenylphosphine)palladium (II) chloride (60 mg, 0.08 mmol) in methanol (50 mL) and dimethyl sulfoxide (20 mL, 0.2 mol) was degassed for 10 min with nitrogen, purged with carbon monoxide (CO). The mixture was stirred with heating at 70° C. overnight under CO gas at a pressure of 100 psi. Cooled down, diluted with EtOAc (200 ml), washed with water (5 times). The organic layer was dried and concentrated. The crude was purified by precipitation from hexanes/methylene chloride to give product methyl 6-((5-(4-aminoquinazolin-6-yl)thiophen-2-yl)methyl)amino)-5-(3,4-difluorobenzyl-carbamoyl)nicotinate (0.66 g with ~10% impurity as $Ph_3P=O$ based on NMR, the impurity peak right overlap with the product on LCMS) which was used directly without further purifications. LCMS: RT 1.49 min.; MH+ 561.30.

To a stirred solution of 6-{[5-(4-amino-quinazolin-6-yl)-thiophen-2-ylmethyl]-amino}-5-(3,4-difluoro-benzylcarbamoyl)-nicotinic acid methyl ester (1.0 g, 1.8 mmol) in tetrahydrofuran (100 mL) was added 1.0 M of lithium hydroxide in water (40 mL, 0.04 mol), The reaction was stirred at RT overnight. The reaction mixture was cooled down to 0° C., acidified with 2N HCl, concentrated to dryness. The crude was re-dissolved in $CH_2Cl_2$/methanol, and filtered. The filtrate was concentrated to give 0.69 g (71%) of the title compound Ex. 7.23.1 which was used in the next step without further purifications. A small portion of the solid product was purified by HPLC to give a light yellow powder of pure material for testing. LCMS: RT 1.35 min., MH+ 547.20; HPLC; $^1$H NMR (400 MHz, DMSO-$d_6$) δ 12.82 (br. s., 1H), 9.79 (br. s., 2H), 9.24-9.55 (m, 2H), 8.69-8.91 (m, 2H), 8.57 (dd, J=1.88, 16.44 Hz, 2H), 8.27 (dd, J=2.01, 8.78 Hz, 1H), 7.75 (d, J=8.78 Hz, 1H), 7.54 (d, J=3.51 Hz, 1H), 7.27-7.48 (m, 2H), 7.04-7.27 (m, 2H), 4.93 (d, J=5.77 Hz, 2H), 4.41 (d, J=5.77 Hz, 2H).

Ex. 7.23.2 was prepared in a manner analogous to Ex. 7.23.1.

Ex. 7.24.1

Synthesis of 2-({[5-(4-aminoquinazolin-6-yl)thiophen-2-yl]methyl}amino)-N~3~-(3,4-difluorobenzyl)pyridine-3,5-dicarboxamide A stirred solution of 6-{[5-(4-amino-quinazolin-6-yl)-thiophen-2-ylmethyl]-amino}-5-(3,4-difluoro-benzylcarbamoyl)-nicotinic acid (Ex. 7.23.1, 100 mg, 0.18 mmol), N,N,N',N'-tetramethyl-O-(7-azabenzotriazol-1-yl)uronium hexafluorophosphate (118 mg, 0.31 mol) and N,N-diisopropylethylamine (0.0956 mL, 0.549 mmol) in N,N-dimethylformamide (1 mL) was stirred at RT for 1h. 0.5 M of ammonia in dioxane (3.66 mL, 1.8 mmol) was then added. The mixture was stirred at RT overnight, diluted with EtOAc, washed with water (5 times). The organic layer was dried and concentrated. The crude was purified by HPLC to give desired product as a TFA salt (37 mg, 37%). LCMS: RT 1.25 min.; MH+ 546.20; $^1$H NMR (400 MHz, DMSO-$d_6$) δ 9.68 (br. s., 2H), 9.27 (t, J=5.77 Hz, 1H), 9.13 (t, J=5.90 Hz, 1H), 8.69-8.87 (m, 2H), 8.59 (s, 1H), 8.50 (d, J=2.26 Hz, 1H), 8.26 (dd, J=1.76, 8.78 Hz, 1H), 7.76 (d, J=8.78 Hz, 2H), 7.54 (d, J=3.76 Hz, 1H), 7.23-7.47 (m, 3H), 7.09-7.23 (m, 2H), 4.91 (d, J=5.77 Hz, 2H), 4.43 (d, J=5.52 Hz, 2H).

Ex. 7.24.2-7.24.6 were prepared in a manner analogous to Ex. 7.24.1.

Ex. 7.25

(S)-5-(((5-(4-aminoquinazolin-6-yl)thiophen-2-yl)methyl)amino)-3-(1-(3,4-difluorophenyl)ethyl)-4-oxo-3,4-dihydropyrido[4,3-d]pyrimidine-8-carbonitrile

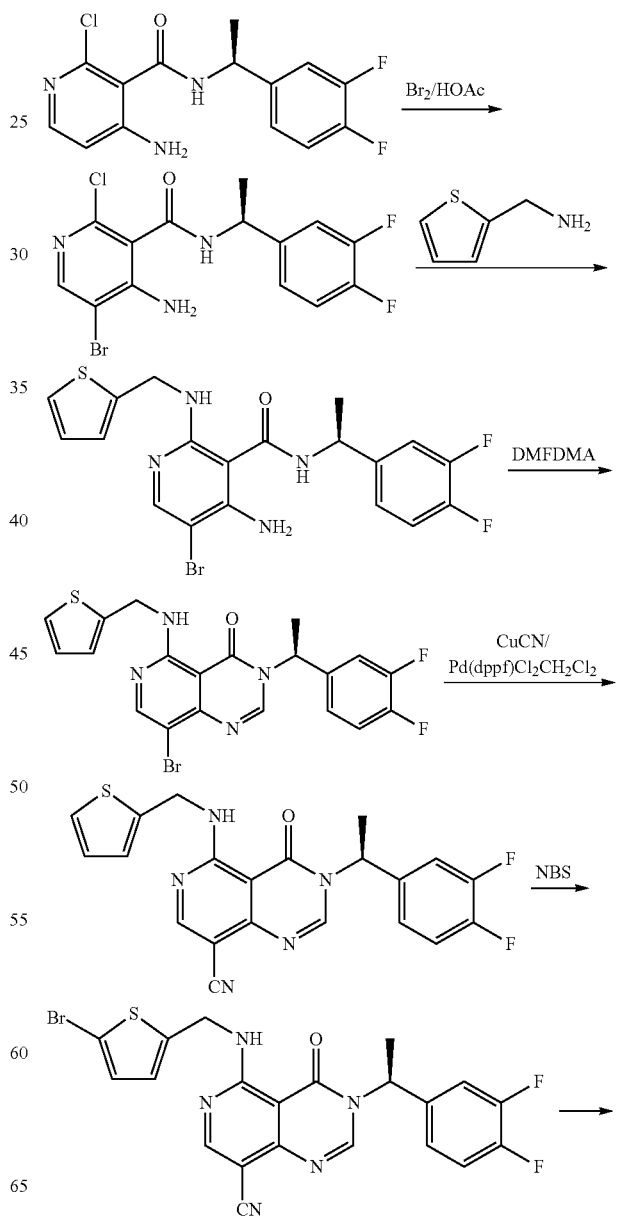

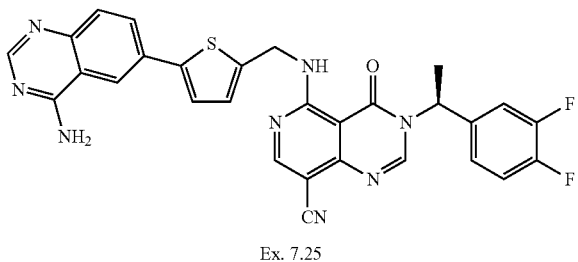

Ex. 7.25

To a solution of (S)-4-amino-2-chloro-N-(1-(3,4-difluorophenyl)ethyl)nicotinamide (3.1 g, 10 mmol) in AcOH was added bromine (3.2 g, 20 mmol). The reaction was stirred at room temperature for 30 min before cooled to 0° C., adjusted pH to 10 with ammonia and extracted with EtOAc (200 mL), and washed with water (200 mL×3). Evaporated off the solvent to give (S)-4-amino-5-bromo-2-chloro-N-(1-(3,4-difluorophenyl)ethyl)nicotinamide as a brown solid (2.88 g, 74%). ESI-MS (M+H+): 392.0; $^1$H NMR (400 MHz, CDCl$_3$) δ: 8.16 (s, 1H), 7.26-7.13 (m, 3H), 6.64 (d, 1H), 6.07 (br, 2H), 5.27-5.22 (m, 1H), 1.59 (d, 3H).

To a solution of (S)-4-amino-5-bromo-2-chloro-N-(1-(3,4-difluorophenyl)ethyl)nicotinamide (1.3 g, 3.3 mmol), thiophen-2-ylmethanamine (0.75 g, 6.6 mmol) in amyl alcohol (10 ml) was added sodium bicarbonate (1.4 g, 16.45 mmol) and the reaction was heated to 130° C. for 16 h. The solvent was removed and the residue was purified on silica gel (PE:EA=3:1) to give (S)-4-amino-5-bromo-N-(1-(3,4-difluorophenyl)ethyl)-2-(thiophen-2-ylmethylamino)nicotinamide as a white solid (1.1 g, 71%). ESI-MS (M+H+): 467.1; $^1$H NMR (400 MHz, CDCl$_3$) δ: 8.00 (s, 1H), 7.22 (d, 1H), 7.10-7.07 (m, 2H), 7.00-6.96 (m, 3H), 6.75 (d, 1H), 5.81 (s, 2H), 5.34-5.29 (m, 1H), 5.19-5.16 (m, 1H), 4.69 (AB, 2H), 1.48 (d, 3H).

A solution of (S)-4-amino-5-bromo-N-(1-(3,4-difluorophenyl)ethyl)-2-(thiophen-2-ylmethylamino)nicotinamide (1.1 g, 2.3 mmol) in DMF/DMA (20 mL) was heated to 120° C. for 30 min, then the solvent was removed and the residue was purified on silica gel (PE: EA=3:1) to give (S)-8-bromo-3-(1-(3,4-difluorophenyl)ethyl)-5-(thiophen-2-ylmethylamino)pyrido[4,3-d]pyrimidin-4(3H)-one as a white solid (180 mg, 46%). ESI-MS (M+H+): 479; $^1$H NMR (400 MHz, CDCl$_3$) δ: 9.10 (m, 1H), 8.47 (s, 1H), 8.08 (s, 1H), 7.21-7.14 (m, 3H), 7.06-7.05 (m, 2H), 6.98-6.95 (m, 1H), 6.12 (q, 1H), 4.93-4.90 (m, 2H), 1.79 (d, 3H).

A mixture of (S)-8-bromo-3-(1-(3,4-difluorophenyl)ethyl)-5-(thiophen-2-ylmethylamino)pyrido[4,3-d]pyrimidin-4-(3H)-one (480 mg, 1 mmol), CuCN (450 mg, 5 mmol), TEA (200 mg, 2 mmol), and [1,1-bis(diphenylphosphino)ferrocene]dichloropalladium (II) complex with dichloromethane (1:1) (4 mg, 0.05 mmol) in DMF (10 ml) was heated to 120° C. under nitrogen for 2 h. Then the solvent was removed and the residue was purified by silica gel column chromatography (PE: EA=3:1) to give (S)-3-(1-(3,4-difluorophenyl)ethyl)-4-oxo-5-(thiophen-2-ylmethylamino)-3,4-dihydropyrido[4,3-d]pyrimidine-8-carbonitrile as a white solid (200 mg, 48%). ESI-MS (M+H+): 423.9; $^1$H NMR (400 MHz, CDCl$_3$) δ: 9.55 (m, 1H), 8.61 (s, 1H), 8.16 (s, 1H), 7.33-7.21 (m, 3H), 7.12-7.11 (m, 2H), 6.97 (t, 1H), 6.11 (q, 1H), 5.01 (d, 2H), 1.81 (d, 3H).

NBS (110 mg, 0.6 mmol) was added to a solution of (S)-3-(1-(3,4-difluorophenyl)ethyl)-4-oxo-5-(thiophen-2-ylmethylamino)-3,4-dihydropyrido[4,3-d]pyrimidine-8-carbonitrile (170 mg, 0.4 mmol) in DMF (10 mL). The reaction was stirred at room temperature for 16 h. Then the reaction mixture was concentrated and used directly for the next step reaction without further purification. ESI-MS (M+H+): 503.9.

A mixture of the above crude material (120 mg, 0.24 mmol), 6-(4,4,5,5-tetramethyl-1,3,2-dioxaborolan-2-yl)quinazolin-4-amine (130 mg, 0.48 mmol), 2M Na$_2$CO$_3$ (0.2 mL), and [1, 1-bis (diphenylphosphino) ferrocene]dichloropalladium (II) complex with dichloromethane (1:1) (10 mg, 0.012 mmol) in DMF (5 mL) was flushed with nitrogen and stirred at 80° C. for 1 h. The solution was cooled to room temperature. The solvent was removed and the residue was purified by HPLC-preparation (0.05% TFA/H$_2$O: CH$_3$OH=3:1) to give (S)-5-(((5-(4-aminoquinazolin-6-yl)thiophen-2-yl)methyl)amino)-3-(1-(3,4-difluorophenyl)ethyl)-4-oxo-3,4-dihydropyrido[4,3-d]pyrimidine-8-carbonitrile Ex. 7.25 as a white solid (12 mg, 5%). ESI-MS (M+H+): 567.0; $^1$H NMR (400 MHz, CDCl$_3$/DMSO-d$_6$) δ: 9.78 (m, 1H), 8.79 (s, 1H), 8.75 (s, 1H), 8.64 (s, 1H), 8.55 (d, 1H), 8.16 (dd, 1H), 7.73 (d, 1H), 7.53-7.52 (m, 2H), 7.44-7.41 (m, 1H), 7.26-7.25 (m, 1H), 7.16-7.12 (m, 2H), 7.00 (s, 1H), 5.91 (q, 1H), 4.99 (d, 2H), 1.83 (d, 3H).

Example 8

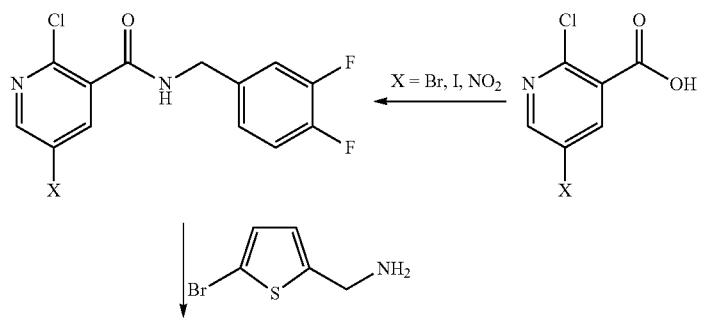

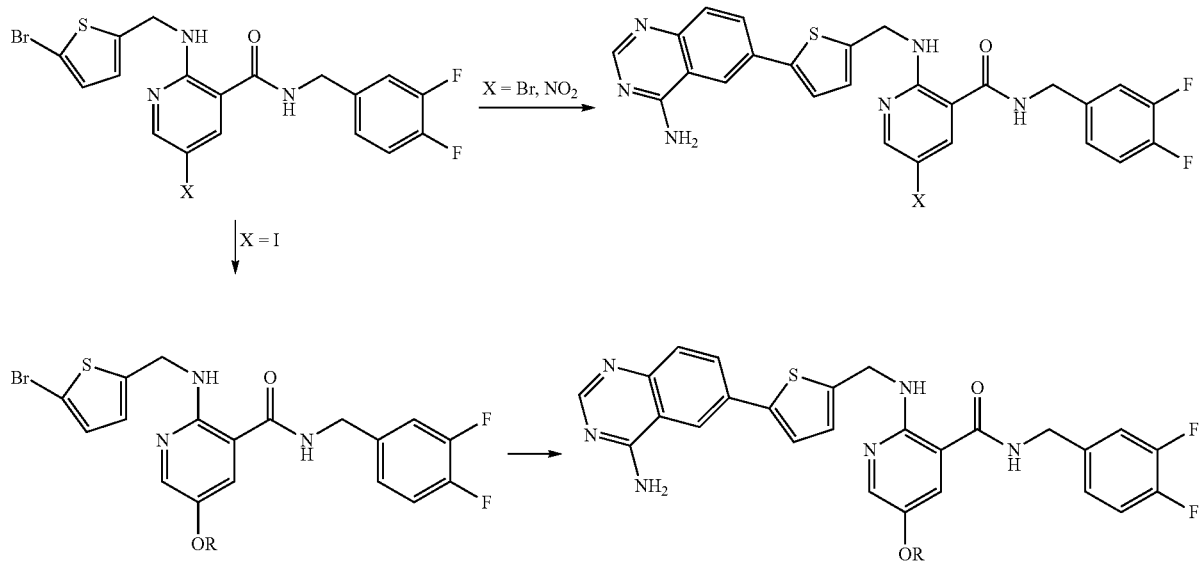

Synthesis of 2-(((5-bromothiophen-2-yl)methyl) amino)-N-(3,4-difluorobenzyl)-5-iodo-nicotinamide Into a vial was added 2-Chloro-5-iodo-nicotinic acid (100.0 mg, 0.3528 mmol) in Methylene chloride (2 mL, 30 mmol) followed by Oxalyl chloride (89.6 μL, 1.06 mmol). To this solution was added N,N-Dimethylformamide (40 μL, 0.5 mmol) and the reaction was stirred at room temperature for 1 hr. Solvent removed in vacuo. To crude acid chloride mixture was added Pyridine (3.79 mL, 46.9 mmol) and 3,4-Difluoro-benzylamine (83.5 μL, 0.706 mmol). The reaction mixture was stirred overnight at room temperature. Solvent was removed in vacuo. The crude reaction mixture was washed with $NaHCO_{3(aq)}$, was extracted with EtOAc dried over $MgSO_4$ and solvent removed in vacuo. Crude material was carried forward with out further purification. LC-MS (Agilent 460, acidic method): RT: 1.5 min.; ES (+) MS m/e 409 (M+1).

The above crude 2-Chloro-N-(3,4-difluoro-benzyl)-5-iodonicotinamide (140 mg, 0.00034 mol), (5-Bromo-thiophen-2-yl)-methylamine (132 mg, 0.000685 mol) Cesium carbonate (450 mg, 0.0014 mol) and 1,4-Dioxane (2.00 mL, 0.0256 mol). The reaction mixture was heated at 130° C. and was stirred overnight. The crude reaction mixture was washed with $NaHCO_{3(aq)}$, was extracted with EtOAc dried over $MgSO_4$ and solvent removed in vacuo. A gradient elution (0->100%) EtOAc (B) in hexanes (A) was used to purify the crude product. Collected 82 mg purified 2-(((5-bromothiophen-2-yl)methyl)amino)-N-(3,4-difluorobenzyl)-5-iodonicotinamide (42% yield). LC-MS (Agilent 460, acidic method): RT: 2.2 min.; ES (+) MS m/e 564 (M+1).

Ex. 8.1.1 was prepared following the procedure for Ex. 6.1 from 2-(((5-bromothiophen-2-yl)methyl)amino)-N-(3,4-difluorobenzyl)-5-iodonicotinamide and N-(2,4-dimethoxy-benzyl)-6-(4,4,5,5-tetramethyl-1,3,2-dioxaborolan-2-yl)quinazolin-4-amine. LC-MS (Agilent 460, acidic method): RT: 1.4 min.

Ex. 8.1.2-8.1.3 were prepared in a manner analogous to Ex. 8.1.1.

Ex. 8.2 was prepared following the procedure for Ex. 6.1 from 2-(((5-bromothiophen-2-yl)methyl)amino)-N-(3,4-difluorobenzyl)-5-nitronicotinamide and N-(2,4-dimethoxy-benzyl)-6-(4,4,5,5-tetramethyl-1,3,2-dioxaborolan-2-yl)quinazolin-4-amine. LC-MS (Agilent 460, acidic method): RT: 1.3 min.

Ex. 8.3 was prepared following the procedure for Ex. 6.1 from 2-(((5-bromothiophen-2-yl)methyl)amino)-N-(3,4-difluorobenzyl)-5-iodonicotinamide and N-(2,4-dimethoxy-benzyl)-6-(4,4,5,5-tetramethyl-1,3,2-dioxaborolan-2-yl)quinazolin-4-amine. LC-MS (Agilent 460, acidic method): RT: 1.4 min.

Ex. 8.4

Synthesis of 2-({[5-(4-aminoquinazolin-6-yl)thiophen-2-yl]methyl}amino)-N-(3,4-difluorobenzyl)-5-aminopyridine-3-carboxamide Into a round bottom flask was added 2-{[5-(4-Aminoquinazolin-6-yl)-thiophen-2-ylmethyl]-amino}-N-(3,4-difluoro-benzyl)-5-nitro-nicotinamide (100 mg, 0.0002 mol). To this was added 10% Palladium on Carbon (1:9, Palladium:carbon black, 40 mg, 0.00004 mol), Methanol (2.0 mL, 0.049 mol), then Ethyl acetate (2.0 mL, 0.020 mol) (due to poor solubility). The crude reaction mixture was degassed, then back flushed with hydrogen. The reaction was stirred at room temperature under an atmosphere of Hydrogen for 1 hour. The crude reaction mixture was filtered and solvent removed in vacuo. Purification was done by HPLC to yield desired product as a TFA salt. Collected 17.3 mg solid yellow powder (18% yield). LC-MS (Agilent 460, acidic method): RT: 1.0 min.; MS m/e 518.3 (M+1); $^1$H NMR (300 MHz, DMSO-$d_6$) δ 9.74 (br. s., 2H), 9.22 (t, J=5.85 Hz, 1H), 8.77-8.83 (m, 1H), 8.61 (d, J=1.89 Hz, 1H), 8.48 (br. s., 1H), 8.26 (dd, J=1.89, 8.69 Hz, 1H), 8.05 (d, J=2.27 Hz, 1H), 7.77 (dd, J=3.40, 5.67 Hz, 2H), 7.51-7.57 (m, 1H), 7.26-7.47 (m, 2H), 7.09-7.20 (m, 2H), 4.81 (s, 2H), 4.42 (d, J=5.67 Hz, 2H).

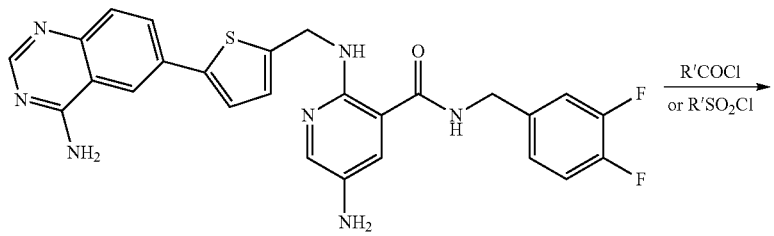

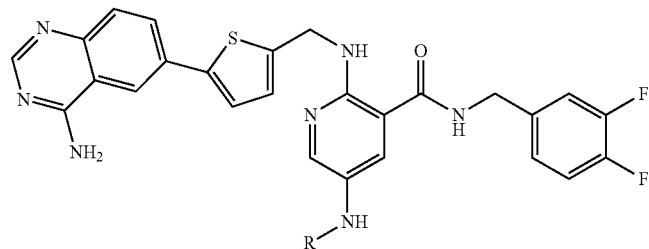

Ex. 8.5.1

Synthesis of 5-(acetylamino)-2-({[5-(4-aminoquinazolin-6-yl)thiophen-2-yl]methyl}amino)-N-(3,4-difluorobenzyl)pyridine-3-carboxamide To a solution of 5-Amino-2-{[5-(4-amino-quinazolin-6-yl)-thiophen-2-ylmethyl]-amino}-N-(3,4-difluoro-benzyl)-nicotinamide (50.000 mg, 9.6608E-5 mol) in Tetrahydrofuran (3.0 mL, 0.037 mol) at 0° C. was added a Acetyl chloride (8.2429 µL, 1.1593E-4 mol), then Triethylamine (13.465 µL, 9.6608E-5 mol) was added dropwise with stirring. The reaction mixture was slowly warmed to RT and was stirred for 1 hour. Solvent removed in vacuo and crude reaction mixture was dissolved in DMSO. Purification was done by HPLC to yield desired product as a TFA salt. Collected 20.7 mg solid yellow powder (38% yield). LC-MS (Agilent 460, acidic method): RT: 1.10 min.; MS m/e 560.3 (M+1); $^1$H NMR (300 MHz, DMSO-$d_6$) δ 9.81 (s, 3H), 9.14 (t, J=6.04 Hz, 1H), 8.80 (s, 1H), 8.60 (d, J=1.89 Hz, 1H), 8.48 (br. s., 1H), 8.24-8.31 (m, 2H), 8.15 (d, J=2.27 Hz, 1H), 7.76 (d, J=9.06 Hz, 1H), 7.54 (d, J=3.78 Hz, 1H), 7.28-7.45 (m, 2H), 7.07-7.20 (m, 2H), 4.83 (d, J=4.15 Hz, 2H), 4.40 (d, J=5.67 Hz, 2H), 2.03 (s, 3H).

Examples 8.5.2-8.5.8 were prepared in a manner analogous to Ex. 8.5.1.

Ex. 8.6.1

Synthesis of 2-({[5-(4-aminoquinazolin-6-yl)thiophen-2-yl]methyl}amino)-N-(3,4-difluorobenzyl)-5-[(methylsulfonyl)amino]pyridine-3-carboxamide To a solution of 5-Amino-2-{[5-(4-amino-quinazolin-6-yl)-thiophen-2-ylmethyl]-amino}-N-(3,4-difluoro-benzyl)-nicotinamide (60.0 mg, 0.000116 mol) in Methylene chloride (7.4310 mL, 0.11593 mol) at 0° C. was added a Methanesulfonyl chloride (50.0 µL, 0.000646 mol), then was added, drop wise with stirring, N,N-Diisopropylethylamine (120 µL, 0.00069 mol). The reaction mixture was slowly warmed to RT and was stirred overnight. Solvent removed in vacuo. Purification was done by HPLC to yield desired product as a TFA salt. Collected 13.8 mg solid yellow powder (20% yield). LC-MS (Agilent 460, acidic method): RT: 1.2 min.; MS m/e 596.3 (M+1); $^1$H NMR (300 MHz, DMSO-$d_6$) δ 9.87 (br. s., 1H), 9.72-9.83 (m, 1H), 9.30 (s, 1H), 9.24 (t, J=5.85 Hz, 1H), 8.80 (s, 1H), 8.76 (t, J=6.04 Hz, 1H), 8.61 (d, J=1.51 Hz, 1H), 8.27 (dd, J=1.89, 8.69 Hz, 1H), 8.13 (d, J=2.64 Hz, 1H), 7.92 (d, J=2.27 Hz, 1H), 7.77 (d, J=8.69 Hz, 1H), 7.52-7.59 (m, 1H), 7.30-7.47 (m, 2H), 7.08-7.22 (m, 2H), 4.85 (d, J=4.15 Hz, 2H), 4.43 (d, J=5.67 Hz, 2H), 2.98 (s, 3H).

Examples 8.6.2-8.6.19 were prepared in a manner analogous to Ex. 8.6.1.

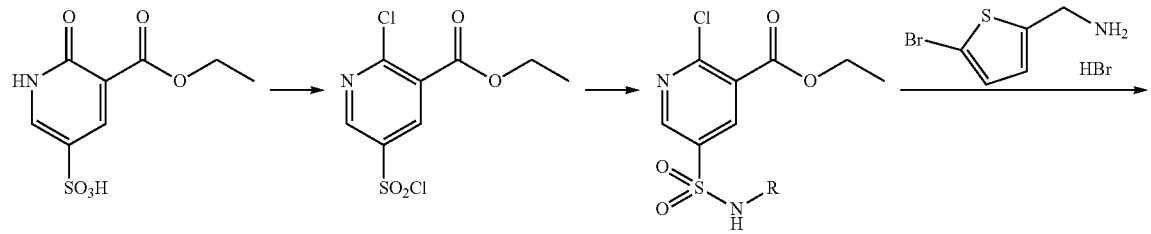

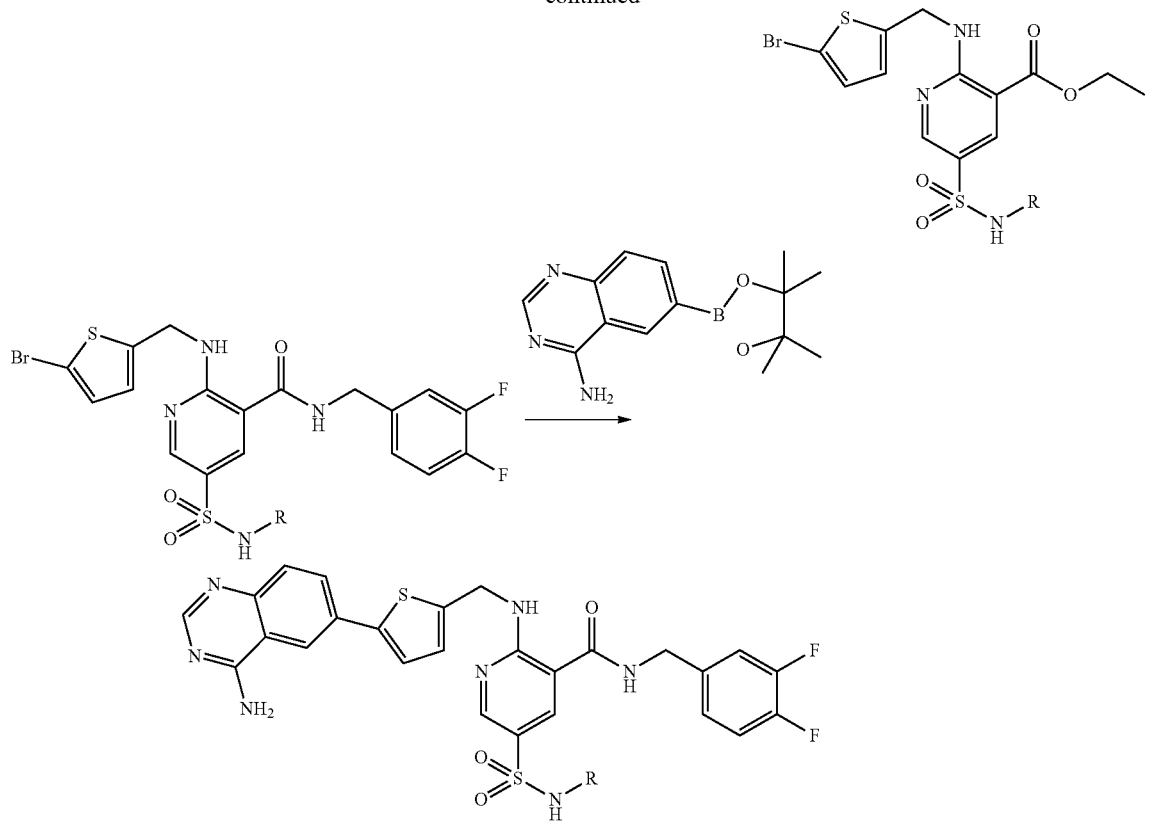

Synthesis of ethyl 2-chloro-5-(chlorosulfonyl)nicotinate

To a flask charged with 2-oxo-5-sulfo-1,2-dihydro-pyridine-3-carboxylic acid ethyl ester (3.18 g, 12.9 mmol) was slurried in thionyl chloride (18.77 mL, 257.3 mmol) and N,N-dimethylformamide (0.1 mL). The reaction was heated at reflux (90° C.) for 2h. Remove the $SOCl_2$ under vacuo. The residual $SOCl_2$ was removed by co-evaporating with toluene (3 times) to give crude product as light yellow oil which was used directly in the next step without further purifications. LCMS:RT:1.60 min; MH+ 284.00.

Synthesis of ethyl 2-chloro-5-(N-methylsulfamoyl)nicotinate

To a solution of 2-Chloro-5-chlorosulfonyl-nicotinic acid ethyl ester (0.50 g, 1.76 mmol) in ethyl acetate (10 mL) at 0° C. was slowly added 2.0 M of methylamine in tetrahydrofuran (0.79 mL, 1.58 mmol) and triethylamine (0.66 mL, 4.75 mmol). The reaction was stirred at 0° C. for 30 min. Remove the solvent under vacuo. The residue was taken into EtOAc, and washed with brine and the water. The organic layer was then separated, dried and concentrated. The crude was then purified by ISCO to give product as a white solid of the title compound (0.29 g, 66%). LCMS: RT 1.19 min.; MH+ 279.10. $^1$H NMR (400 MHz, DMSO-$d_6$) δ 8.07 (d, J=2.51 Hz, 1H); 7.73 (d, J=2.51 Hz, 1H); 3.64 (q, J=7.03 Hz, 2H); 1.80 (s, 3H); 0.61 (t, 3H).

Synthesis of ethyl 2-(((5-bromothiophen-2-yl)methyl)amino)-5-(N-methylsulfamoyl)nicotinate To a solution of 2-chloro-5-methylsulfamoyl-nicotinic acid ethyl ester (0.28 g, 1.0 mmol) in 1,4-dioxane (8 mL) was added a solution of (5-bromo-thiophen-2-yl)-methylamine; hydrobromide (0.41 g, 1.51 mmol) and triethylamine (0.28 mL, 2.0 mmol). The reaction was stirred at 80° C. for 1h. Cooled down, EtOAc was added, and the solution was washed with brine and the water. The organic layer was then separated, dried and concentrated. The crude (0.22 g, 50%, ~90% purity based on HPLC and LCMS) was used directly in the next step without further purifications. LCMS: RT 1.76 min.; MH+ 434.10.

Synthesis of 2-(((5-bromothiophen-2-yl)methyl)amino)-5-(N-methylsulfamoyl)nicotinic acid To a solution of 2-[(5-bromo-thiophen-2-ylmethyl)-amino]-5-methylsulfamoyl-nicotinic acid ethyl ester (0.22 g, 0.51 mmol) in tetrahydrofuran (10 mL) was added 1.0 M of lithium hydroxide in water (1.52 mL, 1.52 mmol). The reaction was stirred at RT overnight. Remove the organic solvent under vacuo. The residue was cooled to 0° C., then acidified with HCl to pH=1. The resulting precipitate was filtered and washed with iced water. The crude was dissolved in $CH_2Cl_2$ and washed with acidified brine solution. The organic layer was separated, dried and concentrated to give desired product as a white solid (153 mg, 74%) which was used directly in the next step without further purifications. HPLC (ACN/water 10/90 to 90/10): 1.417 min.

Synthesis of 2-(((5-bromothiophen-2-yl)methyl)amino)-N-(3,4-difluorobenzyl)-5-(N-methyl-sulfamoyl)nicotinamide A solution of 2-[(5-bromo-thiophen-2-ylmethyl)-amino]-5-methylsulfamoyl-nicotinic acid (0.12 g, 0.30 mmol), N,N- diisopropylethylamine (0.22 mL, 1.26 mmol) and N,N,N',N'-tetramethyl-O-(7-azabenzotriazol-1-yl)uronium hexafluorophosphate (206.8 mg, 0.54 mmol) in N,N-dimethylformamide (5 mL) was stirred at RT for 15 min. 3,4-difluoro-benzylamine (0.06 mL, 0.50 mmol) was then added, and the reaction was stirred at RT for 1h. Diluted with EtOAc, washing brine 2×, water 3×, the organic layer was then separated, dried and concentrated. The crude was purified by precipitation from $CH_2Cl_2$/hexanes to give 54 mg (34%) of desired product as a light yellow powder. LCMS: RT 1.86 min.; MH+ 531.10. $^1$H NMR (400 MHz, $CD_3OD$) δ 8.55-8.65 (m, 1H), 8.23 (d, J=2.26 Hz, 1H), 7.09-7.32 (m, 3H), 6.88-6.96 (m, 1H), 6.84 (d, J=3.76 Hz, 1H), 4.49 (s, 2H), 2.56 (s, 3H).

Ex. 8.7.1

Synthesis of 2-(((5-(4-aminoquinazolin-6-yl)thiophen-2-yl)methyl)amino)-N-(3,4-difluorobenzyl)-5-(N-methylsulfamoyl)nicotinamide To a solution of 6-(4,4,5,5-tetramethyl-1,3,2-dioxaborolan-2-yl)-quinazolin-4-ylamine (38 mg, 0.14 mmol) and 2-[(5-bromo-thiophen-2-ylmethyl)-amino]-N-(3,4-difluoro-benzyl)-5-methylsulfamoyl-nicotinamide (50 mg, 0.09 mmol) in dimethyl sulfoxide (1.0 mL) was added [1,1'-Bis(diphenylphosphino)ferrocene]dichloropalladium(II), complex with dichloromethane (1:1) (9 mg, 0.01 mol) and 1.2 M of saturated aqueous sodium bicarbonate solution (0.24 mL, 0.28 mmol). Degassed with nitrogen for 5 min., seal the tube and heated in microwave at 90° C. for 10 min. The reaction was worked up with EtOAc and aqueous $NaHCO_3$. The organic layers were combined, dried over $MgSO_4$, and concentrated. The crude was purified by HPLC to give the desired product as a TFA salt (15.5 mg, 30%). LCMS: RT 1.25 min.; MH+ 596.20; $^1$H NMR (400 MHz, DMSO-$d_6$) δ 9.77 (br., s, 2H), 9.48 (t, J=5.77 Hz, 1H), 9.35 (t, J=6.02 Hz, 1H), 8.79 (s, 1H), 8.60 (d, J=1.76 Hz, 1H), 8.56 (d, J=2.26 Hz, 1H), 8.33 (d, J=2.26 Hz, 1H), 8.27 (dd, J=2.01, 8.78 Hz, 1H), 7.76 (d, J=8.78 Hz, 1H), 7.55 (d, J=3.76 Hz, 1H), 7.32-7.45 (m, 2H), 7.29 (q, J=4.94 Hz, 1H), 7.10-7.22 (m, 2H), 4.92 (d, J=6.02 Hz, 2H), 4.43 (d, J=5.77 Hz, 2H).

Examples 8.7.2-8.7.13 were prepared in a manner analogous to 8.7.1.

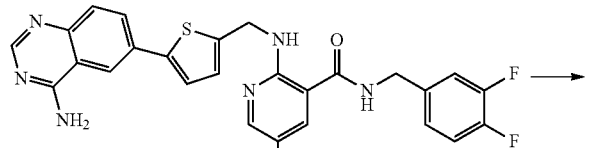

Ex. 8.3

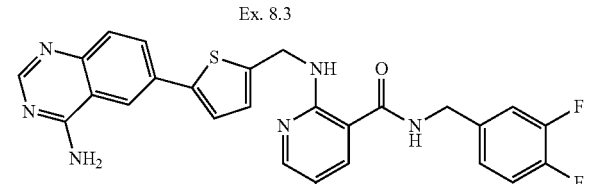

Ex. 8.8

Ex. 8.8.1

Synthesis of 2-(((5-(4-aminoquinazolin-6-yl)thiophen-2-yl)methyl)amino)-5-cyano-N-(3,4-difluorobenzyl)nicotinamide Into a vial was added 2-(((5-(4-aminoquinazolin-6-yl)thiophen-2-yl)methyl)amino)-N-(3,4-difluorobenzyl)-5-iodonicotinamide (90.0 mg, 0.143 mmol), Zinc Cyanide (28 mg, 0.24 mmol), [1,1'-Bis(diphenylphosphino)ferrocene]dichloropalladium(II), complex with dichloromethane (1:1) (24.4 mg, 0.0299 mmol), and N-Methylpyrrolidinone (5 mL, 50 mmol). The crude reaction mixture was purged under an atmosphere of Nitrogen. The reaction was microwaved on 300 watts, 140° C. for 30 minutes. The crude reaction mixture was diluted EtOAc and was filtered. The filtrate was washed (brine), was extracted EtOAc, dried over sodium sulfate and solvent removed in vacuo. Purification was done by HPLC to yield desired product as a TFA salt. Collected 43.0 mg solid yellow powder (56% yield). LC-MS (Agilent 460, acidic method): RT: 1.3 min.; MS m/e 528.3 (M+1); $^1$H NMR (300 MHz, DMSO-$d_6$) δ 9.67 (s, 2H), 9.40-9.48 (m, 1H), 9.24-9.34 (m, J=5.29 Hz, 1H), 8.77 (s, 1H), 8.66 (d, J=1.89 Hz, 1H), 8.59 (s, 1H), 8.44 (d, J=1.89 Hz, 1H), 8.25 (d, J=8.69 Hz, 1H), 7.76 (d, J=8.69 Hz, 1H), 7.54 (d, J=3.78 Hz, 1H), 7.31-7.49 (m, 2H), 7.09-7.24 (m, 2H), 4.92 (d, J=5.29 Hz, 2H), 4.43 (d, J=5.29 Hz, 2H).

Examples 8.8.2 and 8.8.3 were prepared in a manner analogous to Ex. 8.8.1.

Ex. 8.8.4

Synthesis of 2-((5-(4-aminoquinazolin-6-yl)thiophen-2-yl)methylamino)-N-(3,4-difluorobenzyl)-5-(oxetan-3-yl)nicotinamide A mixture of 2-((5-(4-aminoquinazolin-6-yl)thiophen-2-yl)methylamino)-N-(3,4-difluorobenzyl)-5-iodonicotinamide (400 mg, 0.6 mmol), bis(pinacolato)diboron (180 mg, 0.70 mmol) in N,N-dimethylformamide (12 mL) was degassed for 10 min, [1,1'-bis(diphenylphosphino)ferrocene]dichloropalladium(II), complex with dichloromethane (1:1) (52 mg, 0.064 mmol) and potassium acetate (187 mg, 1.91 mmol) were then added. Degas for another 5 min. The reaction was heated in microwave at 90° C. for 20 min. LCMS showed no starting material left. The crude was diluted with EtOAc and washed with saturated $NaHCO_3$. The organic layer was separated, dried over $MaSO_4$, filtered. The filtrate was concentrated. The crude was purified by ISCO (EtOAC/hexane, gradient) to give 125 mg of the intermediate. LCMS: RT 0.98 min.; MH+ not seen. only 547.20 (Boronic acid). Take 60 mg (0.1 mmol) of this intermediate, dissolved in 1,4-dioxane (2 mL), degassed for 10 min. bis(tricyclohexylphosphine)palladium (0) (8 mg, 0.01 mmol) was added under nitrogen, followed by the addition of 3-iodo-oxetane (176 mg, 0.955 mmol). The mixture was then heated at 120° C. in microwave for 20 min. Diluted with EtOAc, washed with brine, then water. The organic phase was dried, filtered and concentrated. The crude was purified by HPLC to give 2-((5-(4-aminoquinazolin-6-yl)thiophen-2-yl)methylamino)-N-(3,4-difluorobenzyl)-5-(oxetan-3-yl)nicotinamide as a light yellow powder (5.5 mg with purity ~90%). LCMS: RT 1.06 min.; MH+ 559.20. $^1$H NMR (400 MHz, DMSO-$d_6$) δ ppm 9.27 (t, J=5.77 Hz, 1 H) 8.80 (s, 2 H) 8.59 (s, 1 H) 8.21-8.32 (m, 2 H) 8.18 (d, J=2.26 Hz, 1 H) 7.76 (d, J=8.78 Hz, 1 H) 7.53 (d, J=3.51 Hz, 1 H) 7.30-7.46 (m, 2 H) 7.06-7.23 (m, 2 H) 4.79-4.94 (m, 4 H) 4.68 (t, J=6.53 Hz, 2 H) 4.36-4.50 (m, 2 H) 4.22 (d, J=8.03 Hz, 1 H).

Ex. 8.9 was prepared following the procedure for Ex. 6.1 from 2-(((5-bromothiophen-2-yl)methyl)amino)-N-(3,4-difluorobenzyl)-5-bromonicotinamide and N-(2,4-dimethoxybenzyl)-6-(4,4,5,5-tetramethyl-1,3,2-dioxaborolan-2-yl)quinazolin-4-amine.

copper(I) iodide (16.4 mg, 0.0861 mmol) were charged to a vial and flushed with nitrogen. Acetonitrile (3.8 mL), (trimethylsilyl)acetylene (98.5 µL, 0.697 mmol), and triethylamine (72.8 µL, 0.523 mmol) were added and the reaction was heated in a microwave reactor at 130° C. for 20 minutes.

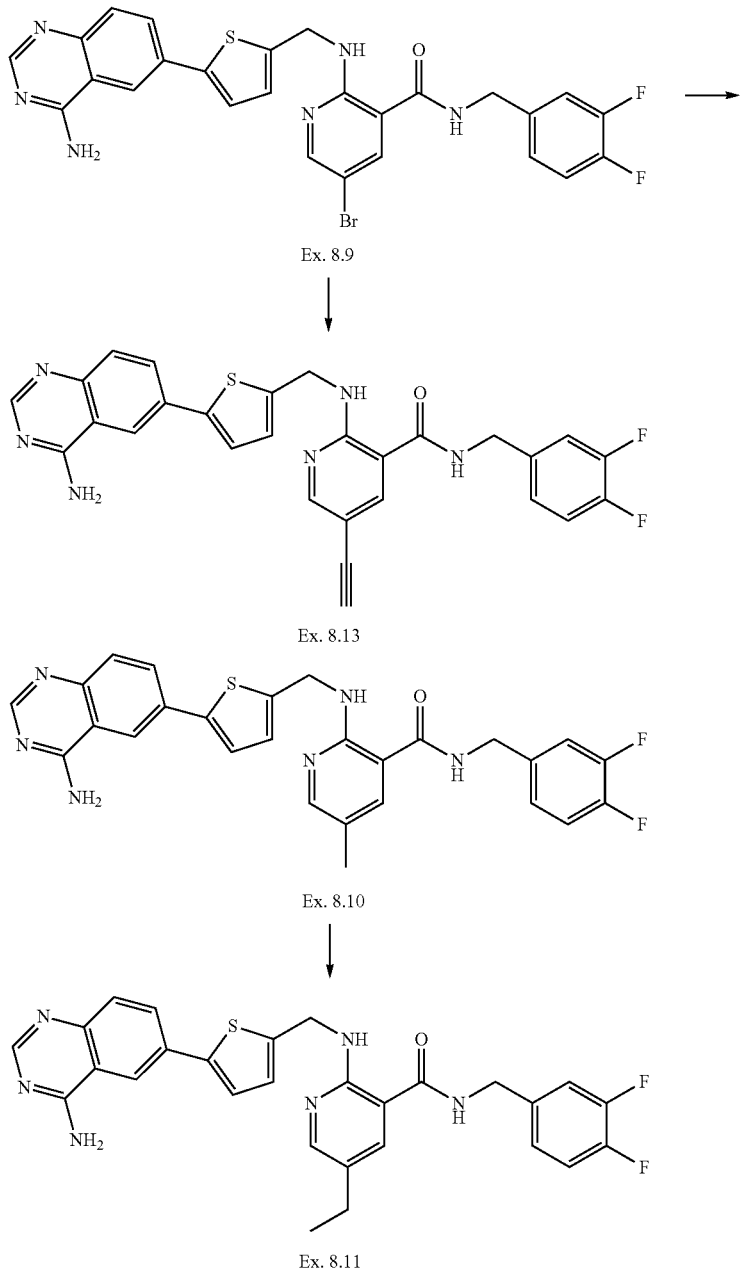

Ex. 8.10

Synthesis of 2-((((5-(4-aminoquinazolin-6-yl)thiophen-2-yl)methyl)amino)-N-(3,4-difluorobenzyl)-5-ethynylnicotinamide 2-({[5-(4-aminoquinazolin-6-yl)thiophen-2-yl] methyl}amino)-N-(3,4-difluorobenzyl)-5-bromopyridine-3-carboxamide (101.3 mg, 0.1742 mmol), tetrakis(triphenylphosphine)palladium(0) (39.3 mg, 0.0340 mmol), and [Bis(diphenylphosphino)ferrocene]dichloropalladium(II) (24 mg) and more (trimethylsilyl)acetylene (24 µL) were added and the reaction was heated again for 30 minutes. Upon completion, the reaction was diluted with ethyl acetate and washed with aqueous sodium bicarbonate, water, then brine. Finally, the organic phase was dried over magnesium sulfate, evaporated, and purified by flash chromatography (0-10% methanol:dichloromethane) to produce 68.2 mg of 2-(((5-(4-aminoquinazolin-6-yl)thiophen-2-yl)methyl)amino)-N-(3,4-difluorobenzyl)-5-((trimethylsilyl)ethynyl)

nicotinamide as a brown solid (65%). ES (+) MS m/e=599.3 (M+1); $^1$H NMR (300 MHz, CDCl$_3$): 8.72 (t, J=5.4 Hz, 1H), 8.54 (s, 1H), 8.39 (d, J=2.1 Hz, 1H), 7.90 (s, 2H), 7.82-7.75 (m, 2H), 7.19 (d, J=3.6 Hz, 1H), 7.03 (t, J=5.4 Hz, 1H), 6.95 (d, J=3.6 Hz, 1H), 6.88-6.78 (m, 2H), 6.69 (tt, J=9.0; 2.2 Hz, 1H), 6.26 (br s, 2H), 4.85 (d, J=5.7 Hz, 2H), 4.53 (d, J=5.4 Hz, 2H), 0.23 (s, 9H).

2-(((5-(4-aminoquinazolin-6-yl)thiophen-2-yl)methyl) amino)-N-(3,4-difluorobenzyl)-5-((trimethylsilyl)ethynyl) nicotinamide (68.2 mg, 0.114 mmol) was dissolved in methanol (1.00 mL). Potassium carbonate (46.8 mg, 0.339 mmol) was added and the reaction was stirred at room temperature for 3 hours. The reaction was diluted with ethyl acetate and washed with aqueous sodium bicarbonate, water, then brine. The organic phase was dried over magnesium sulfate, evaporated, and purified by flash chromatography (0-10% methanol:dichloromethane) to give the desired product. Collected 40.3 mg of a beige powder. ES (+) MS m/e=527.3 (M+1); $^1$H NMR (300 MHz, CD$_3$OD) δ: 8.35-8.31 (m, 3H), 8.04 (s, 1H), 8.03 (dd, J=9.6; 2.1 Hz, 1H), 7.68 (d, J=8.7 Hz, 1H), 7.38 (d, J=3.9 Hz, 1H), 7.04 (d, J=3.9 Hz, 1H), 6.98-6.89 (m, 2H), 6.80 (tt, J=9.1; 2.3 Hz, 1H), 4.89 (s, 2H), 4.50 (s, 2H), 3.49 (s, 1H).

Ex. 8.11

Synthesis of 2-({[5-(4-aminoquinazolin-6-yl)thiophen-2-yl]methyl}amino)-N-(3,4-difluorobenzyl)-5-ethylpyridine-3-carboxamide 2-(((5-(4-aminoquinazolin-6-yl)thiophen-2-yl)methyl) amino)-N-(3,4-difluorobenzyl)-5-ethynylnicotinamide (40.3 mg, 0.0765 mmol), 10% wet palladium on carbon (16 mg, 0.0076 mmol) were combined, evacuated, and flushed with hydrogen gas. Methanol (1.50 mL) was added, and the reaction was stirred at room temperature overnight. More wet palladium on carbon (25 mg) was added and the reaction was heated at 40° C. for 2 hours. The reaction was diluted in methanol, filtered through Celite, evaporated and purified by preparatory reverse-phase HPLC. Collected 13.1 mg of a yellow powder (32%). ES (+) MS m/e=529.3 (M+1). $^1$H NMR (300 MHz, DMSO-d$_6$) δ: 9.86 (br s, 1H), 9.77 (br s, 1H), 9.16 (t, J=5.6 Hz, 1H), 8.80 (s, 1H), 8.68 (t, J=6.0 Hz, 1H), 8.60 (d, J=1.5 Hz, 1H), 8.27 (dd, J=8.7; 1.5 Hz, 1H), 8.12 (d, J=1.8 Hz, 1H), 7.97 (d, J=1.8 Hz, 1H), 7.76 (d, J=8.7 Hz, 1H), 7.54 (d, J=3.6 Hz, 1H), 7.16-7.06 (m, 2H), 7.06-6.97 (m, 2H), 4.84 (d, J=3.9 Hz, 2H), 4.46 (d, J=5.7 Hz, 2H), 1.19 (t, J=7.5 Hz, 3H). (Missing 2Hs buried under DMSO peak).

Ex. 8.12.1

Synthesis of 2-(((5-(4-aminoquinazolin-6-yl)thiophen-2-yl)methyl)amino)-N-(3,4-difluorobenzyl)-5-(trifluoromethyl)nicotinamide A solution of 2-amino-5-trifluoromethyl-nicotinic acid (300.0 mg, 1.46 mmol), N,N-diisopropylethylamine (0.5 mL, 2.92 mmol) and N,N,N',N'-Tetramethyl-O-(7-azabenzotriazol-1-yl)uronium hexafluorophosphate (608.7 mg, 1.60 mmol) in N,N-dimethylformamide (5.00 mL) was stirred at RT for 15 min. 3,4-Difluoro-benzylamine (0.1722 mL, 1.46 mol) was then added, and the reaction mixture was stirred at room temperature for 1h. The reaction mixture was then diluted with EtOAc, washed with brine, then water (5 times). The organic layer was then separated, dried and concentrated. The crude was purified by precipitation from CH$_2$Cl$_2$/ hexanes to give 365 mg (75%) a white powder. LCMS: RT 1.36 min.; MH+ 332.10. $^1$H NMR (400 MHz, DMSO-d$_6$) δ 9.23 (t, J=5.52 Hz, 1H), 8.41 (d, J=1.51 Hz, 1H), 8.30 (d, J=2.26 Hz, 1H), 7.79 (br. s., 2H), 7.28-7.45 (m, 2H), 7.18 (ddd, J=2.26, 3.83, 5.96 Hz, 1H), 4.43 (d, J=5.77 Hz, 2H).

To a suspension of 2-amino-N-(3,4-difluoro-benzyl)-5-trifluoromethyl-nicotinamide (200.00 mg, 0.60 mmol) in trifluoromethyl benzene (7 ml) was added 2-bromo-5-bromomethyl-thiophene (232 mg, 0.91 mmol). The reaction was then heated in microwave at 135° C. for 1 h. The reaction mixture was diluted with EtOAc, washed with aqueous Na$_2$CO$_3$, then water. The organic layer was separated, dried, and concentrated. The crude was purified by HPLC, followed by neutralized with aqueous NaHCO$_3$ to give the desired product as a light yellow solid (113 mg, 37%). LCMS: RT 2.15 min.; MH+ 506.10. $^1$H NMR (400 MHz, DMSO-d$_6$) δ 9.34 (t, J=5.77 Hz, 7H), 9.23 (t, J=5.90 Hz, 1H), 8.50-8.61 (m, 1H), 8.34 (s, 1H), 7.30-7.45 (m, 2H), 7.11-7.23 (m, 1H), 7.03 (d, J=3.77 Hz, 1H), 6.88 (d, J=3.76 Hz, 1H), 4.77 (d, J=6.02 Hz, 2H), 4.43 (d, J=5.77 Hz, 2H).

To a solution of 6-(4,4,5,5-tetramethyl-1,3,2-dioxaborolan-2-yl)-quinazolin-4-ylamine (64 mg, 0.24 mmol) and 2-[(5-bromo-thiophen-2-ylmethyl)-amino]-N-(3,4-difluorobenzyl)-5-trifluoromethyl-nicotinamide (100.00 mg, 0.20 mmol) in dimethyl sulfoxide (2 mL, 0.03 mol) was added [1,1'-bis(diphenylphosphino)ferrocene]dichloro palladium (II), complex with dichloromethane (1:1) (20 mg, 0.02 mmol) and 1.2 M of saturated aqueous NaHCO$_3$ (0.3 mL, 0.0004 mol). Degas with nitrogen for 5 minutes, seal the tube and heated in microwave at 90° C. for 10 min. The reaction was worked up with EtOAc and aqueous NaHCO$_3$. The organic layers were combined and dried over MgSO$_4$. The crude was purified by HPLC to give product as a TFA salt (48.6 mg, 43%). LCMS: RT 1.44 min.; MH+ 571.20; $^1$H NMR (400 MHz, DMSO-d$_6$) δ 9.70 (br. s., 2H), 9.23-9.46 (m, 2H), 8.79 (s, 1H), 8.59 (dd, J=1.51, 7.03 Hz, 2H), 8.38 (d, J=2.01 Hz, 1H), 8.27 (dd, J=2.01, 8.78 Hz, 1H), 7.76 (d, J=8.78 Hz, 1H), 7.54 (d, J=3.76 Hz, 1H), 7.29-7.47 (m, 2H), 7.07-7.24 (m, 2H), 4.92 (d, J=5.77 Hz, 2H), 4.44 (d, J=5.52 Hz, 2H).

Examples 8.12.2-8.12.8 were prepared in a manner analogous to Ex. 8.12.1.

Ex. 8.13

Synthesis of 2-({[5-(4-aminoquinazolin-6-yl)thiophen-2-yl]methyl}amino)-N-(3,4-difluorobenzyl)-5-(prop-1-en-2-yl)pyridine-3-carboxamide 2-({[5-(4-aminoquinazolin-6-yl)thiophen-2-yl] methyl}amino)-N-(3,4-difluorobenzyl)-5-bromopyridine-3-carboxamide (48.3 mg, 0.0831 mmol), isopropenylboronic acid pinacol ester (93.7 μL, 0.498 mmol), and [1,1'-bis (diphenylphosphino)ferrocene]-dichloro-palladium(II), complex with dichloromethane (1:1) (10.1 mg, 0.0124 mmol) were stirred in triethylamine (34.7 μL, 0.249 mmol) and acetonitrile (0.65 mL). The reaction was heated in a microwave reactor at 130° C. for 5 minutes, followed by 150° C. for 10 minutes. The mixture was filtered through Celite and washed with ethyl acetate and dichloromethane. The filtrate was evaporated, purified by preparatory HPLC, and lyophilized. Collected 2.3 mg of a yellow powder (5.1%). ES (+) MS m/e=543.2 (M+1).

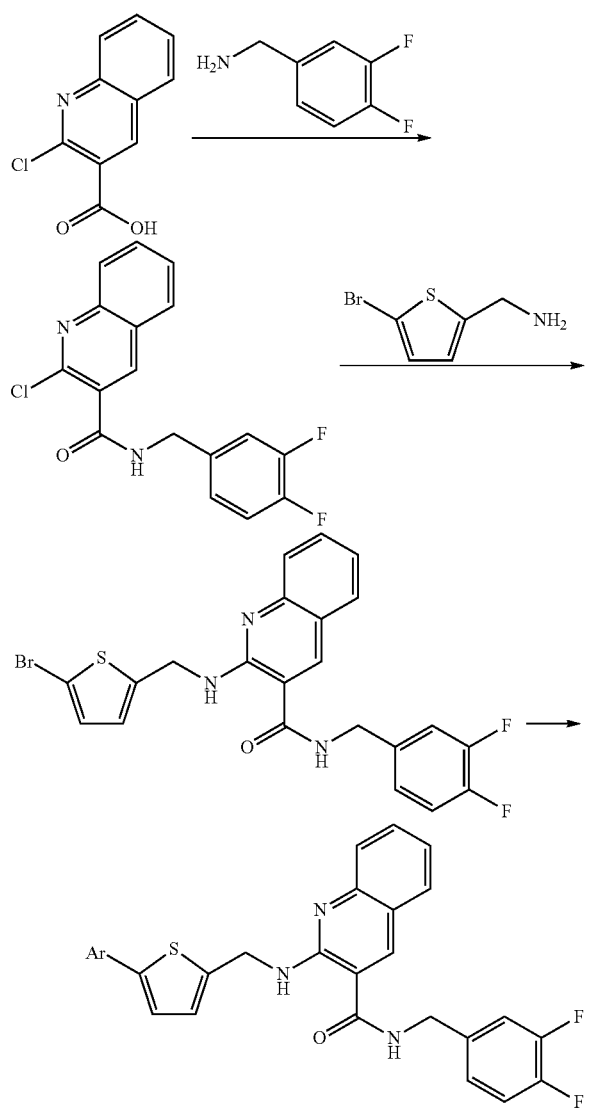

Synthesis of 2-chloro-N-(3,4-difluorobenzyl)quinoline-3-carboxamide, intermediate for Example 8.14.1

To a solution of 2-Chloro-quinoline-3-carboxylic acid (1.0 g, 0.0048 mol) and N,N-Diisopropylethylamine (1.7 mL, 0.0096 mol) in N,N-Dimethylformamide (20 mL, 0.2 mol) was added N,N,N',N'-Tetramethyl-O-(7-azabenzotriazol-1-yl)uronium Hexafluorophosphate (2.7 g, 0.0072 mol) and stirred for 15 min before 3,4-Difluoro-benzylamine (630 µL, 0.0053 mol) was added and stirred for 1 h. LC-MS showed complete reaction. Worked up with EtOAc and sat. sodium bicarbonate, dried over MgSO$_4$. Purified on silica gel column with 0-100% EtOAc/DCM to give the desired product (0.4 g, 20%).

Synthesis of 2-(((5-bromothiophen-2-yl)methyl)amino)-N-(3,4-difluorobenzyl)-quinoline-3-carboxamide, intermediate for Example 8.14.1

A mixture of 2-chloro-N-(3,4-difluorobenzyl)quinoline-3-carboxamide (0.25 g, 0.00075 mol), (5-Bromo-thiophen-2-yl)-methylamine (0.29 g, 0.0015 mol), and Cesium Carbonate (500 mg, 0.002 mol) in N,N-Dimethylformamide (10 mL, 0.2 mol) was The reaction was microwaved on 250 watts, 120° C. for 1 hours and LC-MS showed the major formation of the desired product (1.53 min, ES+/488.09n490.09). Worked up with EtOAc and water. Dried over MgSO$_4$ and concentrated. Purified on silica gel column with 0-75% EtOAc in hexane to give the desired product as a yellow greenish solid (0.18 g, 49%). $^1$H NMR (400 MHz, CDCl$_3$) δ 8.07-8.14 (m, 1H), 7.97 (d, J=5.02 Hz, 1H), 7.67 (dd, J=6.90, 8.34 Hz, 1H), 7.47-7.60 (m, 2H), 6.98-7.17 (m, 4H), 6.80 (d, J=3.70 Hz, 1H), 6.74 (d, J=3.64 Hz, 1H), 6.42-6.56 (m, 1H), 4.80 (d, J=5.40 Hz, 2H), 4.50 (d, J=5.84 Hz, 2H).

Ex. 8.14.1 was prepared following the procedure for Ex. 6.1 from 2-(((5-bromothiophen-2-yl)methyl)amino)-N-(3,4-difluorobenzyl)quinoline-3-carboxamide and 6-(4,4,5,5-Tetramethyl-1,3,2-dioxaborolan-2-yl)-quinazolin-4-ylamine.

Examples 8.14.2-8.14.4 were prepared in a manner analogous to Ex. 8.14.1.

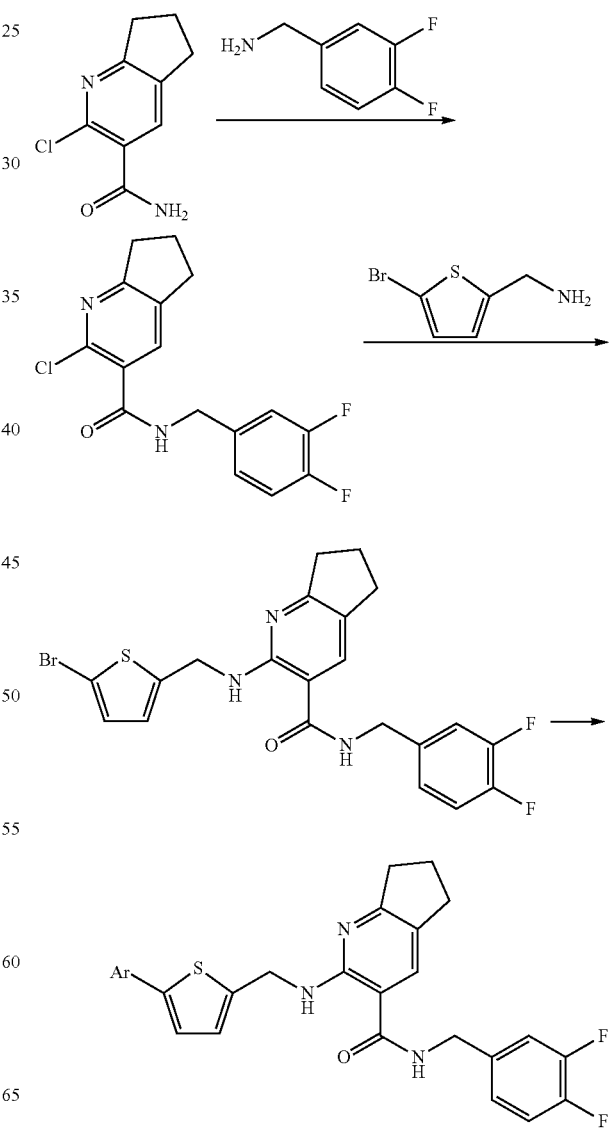

Synthesis of 2-chloro-N-(3,4-difluorobenzyl)-6,7-dihydro-5H-cyclopenta-[b]pyridine-3-carboxamide, intermediate for Example 8.15.1

1 g of 5 Å molecular seives (Aldrich) was heated for 3 min and flushed with nitrogen and cooled to room temperature. To which was added anhydrous Methylene chloride (20 mL, 0.4 mol) and 1,1-Dimethoxy-N,N-dimethylmethanamine (0.844 mL, 0.00636 mol) and stirred at room temperature for 1h until LC-MS showed completed reaction (LC-MS: 0.32 min, ES+/252.18). The reaction mix was then concentrated and purified on a short silica gel column with DCM to give the desired product as a white solid, which was then dissolved back in Methylene chloride (20 mL) and added 3,4-Difluoro-benzylamine (1200 μL, 0.010 mol), followed with addition of a solution of Zirconium tetrachloride (0.5 g, 0.002 mol) in Acetonitrile (5 mL, 0.1 mol) and stirred for 1h. LC-MS showed clean conversion to the desired product (1.58 min, ES+/323.25). The mix was then diluted with EtOAc and filtered thru a silica gel cake and washed with EtOAc. Concentration to give the desired product as a white solid (0.9 g, 50%). $^1$H NMR (400 MHz, CDCl$_3$) δ 7.95 (s, 1H), 7.26 (s, 0H), 7.13-7.20 (m, 1H), 7.01-7.09 (m, 1H), 6.84-7.01 (m, 2H), 4.69 (d, J=5.90 Hz, 2H), 3.04 (t, J=7.78 Hz, 2H), 2.96 (t, J=7.59 Hz, 2H); Ref. A. Myers, J. Am. Chem. Soc., 2006, 128, 16406.

Synthesis of 2-(((5-bromothiophen-2-yl)methyl)amino)-N-(3,4-difluorobenzyl)-6,7-dihydro-5H-cyclopenta[b]pyridine-3-carboxamide, intermediate for Example 8.15.1

Prepared by the same procedure as 2-(((5-bromothiophen-2-yl)methyl)amino)-N-(3,4-difluorobenzyl)quinoline-3-carboxamide. $^1$H NMR (400 MHz, CD$_3$OD) d 8.16 (s, 1H), 7.06-7.15 (m, 2H), 6.96 (d, J=3.76 Hz, 1H), 6.94-7.05 (m, 1H), 6.88 (dt, J=1.00, 3.72 Hz, 1H), 4.88 (s, 4H), 4.72-4.84 (m, 2H), 4.55 (s, 2H), 3.32-3.36 (m, 1H), 3.26-3.32 (m, 1H), 3.05 (t, J=7.72 Hz, 2H), 2.85-2.92 (m, 2H), 2.15-2.28 (m, 2H), 0.00 (s, 1H); MH+: 478.1/480.1.

Ex. 8.15.1 was prepared following the procedure for Ex. 6.1 from 2-(((5-bromothiophen-2-yl)methyl)amino)-N-(3,4-difluorobenzyl)-6,7-dihydro-5H-cyclopenta[b]pyridine-3-carboxamide and 6-(4,4,5,5-Tetramethyl-1,3,2-dioxaborolan-2-yl)-quinazolin-4-ylamine.

Ex. 8.15.2 was prepared in a manner analogous to Ex. 8.15.1.

Example 9

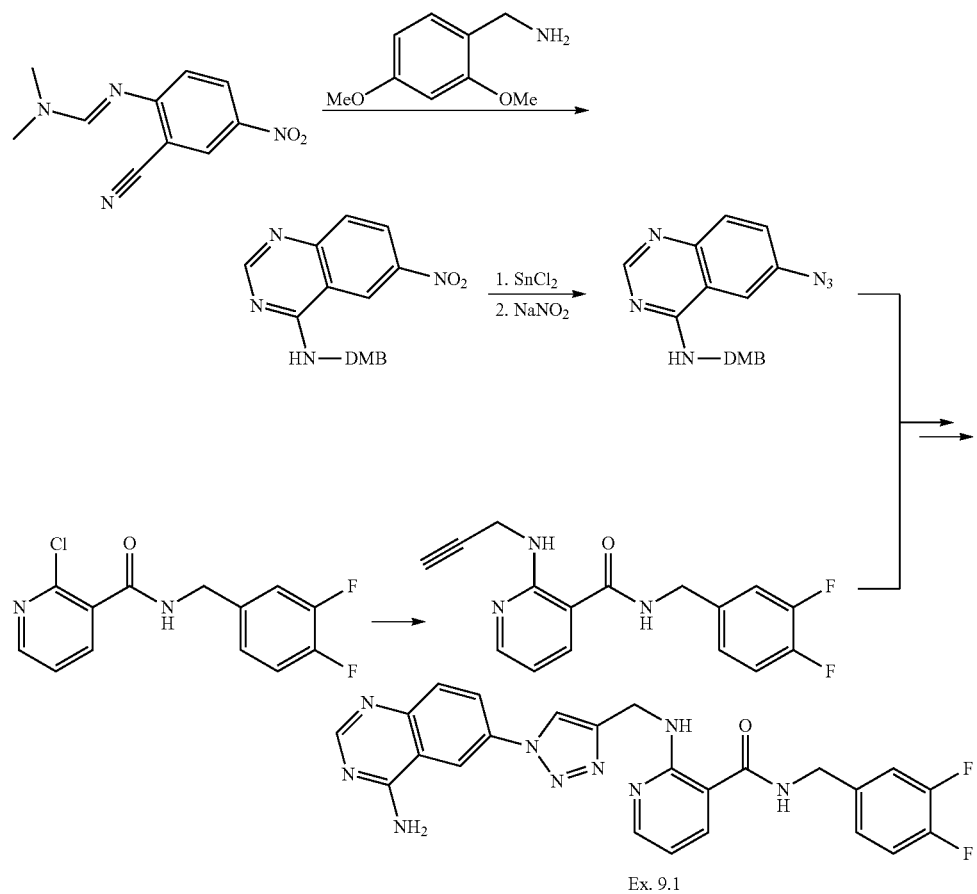

Ex. 9.1

Synthesis of N-(2,4-dimethoxybenzyl)-6-nitroquinazolin-4-amine (E)-N'-(2-cyano-4-nitrophenyl)-N,N-dimethylformimidamide (4.745 g, 0.02174 mol) and 2,4-dimethoxy-benzylamine (4.00 g, 0.0239 mol) were stirred with acetic acid (21.8 mL, 0.383 mol) and heated at reflux for one hour. The reaction became homogeneous, followed by the slow formation of a precipitate. The reaction was cooled to room temperature, filtered, and the filtrant was washed with acetic acid and diethyl ether followed by drying under high-vacuum. Collected 3.745 g of a yellow powder (20%). ES (+) MS m/e=341.1 (M+1); $^1$H NMR (300 MHz, CDCl$_3$) δ 9.47 (d, J=2.64 Hz, 1H), 9.26 (t, J=5.29 Hz, 1H), 8.58 (s, 1H), 8.48 (dd, J=2.45, 9.25 Hz, 1H), 7.83 (d, J=9.06 Hz, 1H), 7.15 (d, J=8.31 Hz, 1H), 6.59 (d, J=2.27 Hz, 1H), 6.46 (dd, J=2.27, 8.31 Hz, 1H), 4.67 (d, J=5.29 Hz, 2H), 3.82 (s, 3H), 3.74 (s, 3H).

Synthesis of N$^4$-(2,4-dimethoxybenzyl)quinazoline-4,6-diamine

N-(2,4-dimethoxybenzyl)-6-nitroquinazolin-4-amine (102.3 mg, 0.3006 mmol), tin dichloride (285 mg, 1.49 mmol), and ethanol (3.00 mL, 51.4 mmol) were combined in a sealed tube and heated at 80° C. for 1.5 hours. The reaction was cooled to room temperature and quenched with 5 mL of 1N KOH. Added 3 mL of dichloromethane, 2 mL of water and stirred vigorously overnight. The mixture was diluted with 30 mL water, extracted thrice with methylene chloride. The organic phase was dried over magnesium sulfate, filtered, evaporated, and purified by flash chromatography (0-10% methanol:dichloromethane, silica). Collected 57.1 mg of an orange residue (61%). ES (+) MS m/e=311.2 (M+1); $^1$H NMR (300 MHz, CDCl$_3$): 8.47 (s, 1H), 7.45 (d, J=95.4 Hz, 1H), 7.17 (d, J=61.5 Hz, 1H), 7.05 (dd, J=8.9; 2.6 Hz, 1H), 6.65 (d, J=99.6 Hz, 1H), 6.47 (d, J=7.2 Hz, 1H), 6.44 (dd, J=8.3; 2.2 Hz, 1H), 6.32 (br s, 1H), 4.45 (d, J=177.6 Hz, 2H), 3.86 (s, 3H), 3.79 (s, 3H), 2.86 (br s, 2H)

Synthesis of 6-azido-N-(2,4-dimethoxybenzyl)quinazolin-4-amine

N$^4$-(2,4-dimethoxybenzyl)quinazoline-4,6-diamine (144.9 mg, 0.4669 mmol) was stirred with methanol (567 μL, 14.0 mmol) followed by 1.0 M aqueous hydrochloric acid (7.4 mL, 7.4 mmol). The reaction was stirred at 0° C. for 15 minutes, then 1.8 M aqueous sodium nitrite (1.3 mL, 2.3 mmol) was added dropwise and stirred for 30 minutes. Finally, 1.3M aqueous sodium azide (3.59 mL, 4.67 mmol) was added in two portions. The reaction became viscous and 0.3 mL of acetonitrile was added, and the reaction was stirred at 0° C. for 1 hour. Afterwards, the reaction was warmed to room temperature and stirred an additional 2 hours before being quenched with aqueous sodium bicarbonate. The reaction was extracted with 3×75 mL ethyl acetate, dried over magnesium sulfate, evaporated, and purified by flash chromatography (0-100% ethyl acetate:hexanes). Collected 126.7 mg of a yellow powder (81%). ES (+) MS m/e=337.2 (M+1); $^1$H NMR (300 MHz, CDCl$_3$): 8.61 (s, 1H), 7.82 (d, J=8.7 Hz, 1H), 7.37 (dd, J=8.8; 2.5 Hz, 1H), 7.31 (d, J=2.4 Hz, 1H), 7.27 (d, J=8.4 Hz, 1H), 6.55 (br tr, J=6 Hz, 1H), 6.48-6.40 (m, 2H), 4.78 (d, J=5.1 Hz, 2H), 3.85 (s, 3H), 3.78 (s, 3H).

Synthesis of N-(3,4-difluorobenzyl)-2-(prop-2-ynylamino)nicotinamide 2-chloro-N-(3,4-difluorobenzyl)nicotinamide (199.8 mg, 0.7068 mmol) and cesium carbonate (0.46 g, 1.4 mmol) were stirred in 1,4-dioxane (2.8 mL, 36 mmol). Added propargylamine (193.9 μL, 2.827 mmol) and stirred at 80° C. overnight. Afterwards, water (30 mL) was added and extracted with ethyl acetate (3×30 mL). The organic extracts were dried over magnesium sulfate, evaporated, and purified by flash chromatography (0-100% ethyl acetate:hexanes). Collected 92.3 mg of a yellow solid (43%). ES (+) MS m/e=302.2 (M+1); $^1$H NMR (300 MHz, CDCl$_3$): 10.79 (br s, 1H), 8.20 (dd, J=7.2; 0.9 Hz, 1H), 8.02 (dd, J=6.9; 1.2 Hz, 1H), 7.39 (d, J=0.9 Hz, 1H), 7.26-7.19 (m, 1H), 7.15-7.07 (m, 2H), 7.01 (t, J=7.0 Hz, 1H), 4.72 (d, J=6.0 Hz, 2H), 2.51 (d, J=0.9 Hz, 3H).

Synthesis of N-(3,4-difluorobenzyl)-2-((1-(4-(2,4-dimethoxybenzylamino) quinazolin-6-yl)-1H-1,2,3-triazol-4-yl)methylamino)nicotinamide N-(3,4-difluorobenzyl)-2-(prop-2-ynylamino)nicotinamide (45.9 mg, 0.152 mmol), 6-azido-N-(2,4-dimethoxybenzyl)quinazolin-4-amine (52.2 mg, 0.155 mmol) were stirred in Water (1.00 mL, 55.5 mmol) and tert-Butyl alcohol (1.00 mL, 10.4 mmol). Added sodium ascorbate (13.8 mg, 0.0696 mmol) followed by 0.2 M aqueous copper(II) sulfate (38.1 μL, 0.00762 mmol). The reaction was stirred at room temperature for 2 hours before being diluted by 4 mL of 1:1 water:tert-butanol and heating at 60° C. for 1 hour. The reaction was cooled to room temperature, diluted with 175 mL ethyl acetate and washed with 75 mL of 1:1 ammonium chloride (saturated, aqueous)/NaOH (1N, aqueous), 75 mL aqueous sodium bicarbonate, and 75 mL brine. The organic phase was dried over magnesium sulfate, evaporated to yield a powder. The powder was triturated with methylene chloride followed by ethyl acetate to yield an off-white powder (67.2 mg). ES (+) MS m/e=638.4 (M+1). $^1$H NMR (300 MHz, DMSO-d$_6$): 9.11 (t, J=5.5 Hz, 1H), 8.86 (d, J=2.4 Hz, 1H), 8.79 (t, J=5.3 Hz, 1H), 8.69 (t, J=5.3 Hz, 1H), 8.63 (s, 1H), 8.49 (s, 1H), 8.29 (dd, J=9.0; 2.1 Hz, 1H), 8.23 (dd, J=5.1; 1.5 Hz, 1H), 8.04 (dd, J=7.9; 1.9 Hz, 1H), 7.86 (d, J=9.0 Hz, 1H), 7.43-7.31 (m, 2H), 7.16 (br s, 1H), 7.16 (d, J=8.4 Hz, 1H), 6.66 (dd, J=7.8; 4.8 Hz, 1H), 6.59 (d, J=2.4 Hz, 1H), 6.46 (dd, J=8.2; 2.3 Hz, 1H), 4.77 (d, J=5.7 Hz, 2H), 4.67 (d, J=4.8 Hz, 2H), 4.41 (d, J=5.7 Hz, 2H), 3.82 (s, 3H), 3.73 (s, 3H).

Ex. 9.1

Synthesis of 2-((1-(4-aminoquinazolin-6-yl)-1H-1,2,3-triazol-4-yl)methylamino)-N-(3,4-difluorobenzyl)nicotinamide N-(3,4-difluorobenzyl)-2-((1-(4-(2,4-dimethoxybenzylamino)quinazolin-6-yl)-1H-1,2,3-triazol-4-yl)methylamino)nicotinamide (67.3 mg, 0.106 mmol) was dissolved in trifluoroacetic acid (3.00 mL) and heated at 60° C. for 3 hours. The reaction was cooled to room temperature, diluted with dichloromethane, and neutralized by slow addition of saturated aqueous sodium carbonate accompanied by vigorous stirring. Ethyl acetate (75 mL) was added to the mixture and washed twice with aqueous sodium bicarbonate, and once with brine. The organic phase was dried over magnesium sulfate, evaporated, and purified by preparatory reverse-phase HPLC. Collected 36.9 mg of a white powder. ES (+) MS m/e=488.3 (M+1); 1H NMR (300 MHz, DMSO): 9.90 (br s, 1H), 9.83 (br s, 1H), 9.17 (s, 1H), 8.97 (s, 1H), 8.88 (s, 2H), 8.66 (s, 1H), 8.56 (d, J=8.7 Hz, 1H), 8.23 (d, J=3.0 Hz, 1H), 8.08 (d, J=7.5 Hz, 1H), 7.96 (d, J=8.7 Hz, 1H), 7.46-7.29 (m, 2H), 7.17 (br s, 1H), 6.69 (t, J=5.8 Hz, 1H), 4.81 (s, 2H), 4.42 (d, J=4.5 Hz, 2H).

Example 9.2 was synthesized in a manner analogous to Ex. 9.1.

Example 10

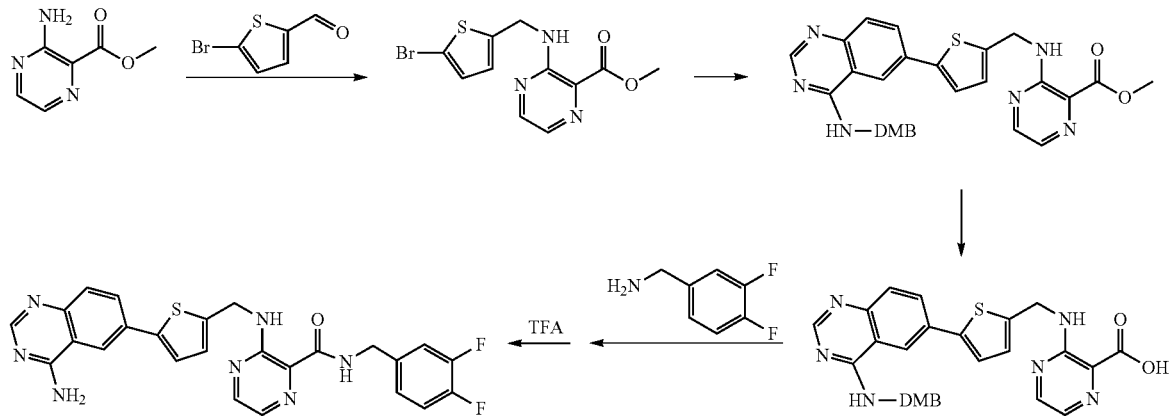

Ex. 10.1

Synthesis of methyl 3-((5-bromothiophen-2-yl)methyl)amino)pyrazine-2-carboxylate Methyl 3-aminopyrazine-2-carboxylate (3.690 g, 24.10 mmol), 5-bromo-thiophene-2-carbaldehyde (13.302 g, 69.627 mmol) were stirred in 1,2-dichloroethane (87.2 mL). Added Acetic acid (2.60 mL, 45.7 mmol) and prestirred for 15 minutes, then sodium triacetoxyborohydride (14.53 g, 68.56 mmol) was added and stirred overnight at room temperature. Some aldehyde was still present by HPLC-MS, and 1 equiv of sodium triacetoxyborohydride was added and the reaction was stirred for 24 hours. The reaction was quenched with 30 mL of 1M HCl, stirred vigorously for 30 minutes, and neutralized with sodium bicarbonate. The reaction was extracted with ethyl acetate and washed with aqueous sodium bicarbonate, water, then brine. Dried over magnesium sulfate and evaporated. The mixture was purified by flash chromatography (0-25% ethyl acetate:hexanes). Collected 1.612 g of a white solid. ES (+) MS m/e=328.0 (M+1).

Synthesis of methyl 3-((5-(4-(2,4-dimethoxybenzylamino)quinazolin-6-yl)thiophen-2-yl)methyl)amino)pyrazine-2-carboxylate Methyl 3-((5-bromothiophen-2-yl)methyl)amino)pyrazine-2-carboxylate (1.612 g, 4.912 mmol), (2,4-dimethoxybenzyl)-[6-(4,4,5,5-tetramethyl-1,3,2-dioxaborolan-2-yl)-quinazolin-4-yl]-amine (2.681 g, 6.363 mmol), [1,1'-bis(diphenylphosphino)-ferrocene]dichloropalladium(II), complex with dichloromethane (1:1) (320 mg, 0.39 mmol) were stirred in 1,4-Dioxane (48.9 mL, 626 mmol). Added saturated sodium carbonate in water (7.84 mL, 14.7 mmol) and heated at 100° C. The reaction was monitored by HPLC-MS and deemed complete after 1.5 hours. The reaction was cooled to room temperature, diluted with ethyl acetate, filtered through Celite and evaporated. The reaction was purified by flash chromatography (0-5% MeOH:DCM). Collected 2.002 g of a brown amorphous solid. ES (+) MS m/e=543.3 (M+1).

Synthesis of 3-((5-(4-(2,4-dimethoxybenzylamino)quinazolin-6-yl)thiophen-2-yl)methyl)amino)pyrazine-2-carboxylic acid Methyl 3-((5-(4-(2,4-dimethoxybenzylamino)quinazolin-6-yl)thiophen-2-yl)methyl)amino)pyrazine-2-carboxylate (270. mg, 0.498 mmol) was stirred in methanol (3.00 mL) and added 1.0 M of aqueous sodium hydroxide (1.49 mL, 1.49 mmol). The compound never dissolved, but was still stirred at 40° C. for 2 hours. Over time, the reaction solidified. Methanol (3 mL) was added to aid solubility and the reaction was heated at 60° C. for 1 hour. Added hydrochloric acid to acidify, and basified with excess sodium bicarbonate. The aqueous phase was extracted thrice with ethyl acetate. neutralize, and added EtOAc (still some solid that doesn't dissolve). Tried acidifying w/HCl, however most of material went to aqueous phase. Neutralized with excess aqueous sodium bicarbonate, and added 300 mL water and 300 mL ethyl acetate. The two phases were shaken vigorously and filtered to collect 138.5 mg of a light yellow solid (53%). ES (+) MS m/e=529.3 (M+1).

Ex. 10.1

Synthesis of 3-((5-(4-aminoquinazolin-6-yl)thiophen-2-yl)methyl)amino)-N-(3,4-difluorobenzyl)pyrazine-2-carboxamide 3-((5-(4-(2,4-dimethoxybenzylamino)quinazolin-6-yl)thiophen-2-yl)methyl)amino)pyrazine-2-carboxylic acid (88.6 mg, 0.168 mmol), N,N,N',N'-tetramethyl-O-(7-azabenzotriazol-1-yl)uronium hexafluorophosphate (83.8 mg, 0.220 mmol) were dissolved in N,N-dimethylformamide (1.7 mL). Added 3,4-difluoro-benzylamine (39.6 µL, 0.335 mmol) followed by N,N-diisopropylethylamine (58.4 µL, 0.335 mmol). The reaction was stirred at room temperature for 1 hour. Added 75 mL ethyl acetate and washed with 2×50 mL aqueous sodium bicarbonate, and 50 mL brine. The organic phase was dried over magnesium sulfate, evaporated, and purified by flash chromatography (0-8% methanol:dichloromethane). Collected 120.9 mg of N-(3,4-difluorobenzyl)-3-((5-(4-(2,4-dimethoxybenzylamino)quinazolin- 6-yl)thiophen-2-yl)methyl)amino)pyrazine-2-carboxamide as a yellow powder (110%, crude). ES (+) MS m/e=654.3 (M+1).

N-(3,4-difluorobenzyl)-3-((5-(4-(2,4-dimethoxybenzylamino)quinazolin-6-yl)thiophen-2-yl)methyl)amino)pyrazine-2-carboxamide (120.9 mg, 0.1849 mmol) was stirred in trifluoroacetic acid (2.0 mL) at 40° C. for 1.5 hours. The reaction was diluted with 2 mL dichloromethane, and slowly quenched with saturated aqueous sodium carbonate. Added 75 mL ethyl acetate and washed twice with 50 mL aqueous sodium bicarbonate, then 50 mL brine. The organic phase was dried over magnesium sulfate, evaporated, and purified by flash chromatography (0-8% methanol:dichloromethane). Collected 41.2 mg of a yellow powder (44%). ES (+) MS m/e=504.2 (M+1); 1H NMR (300 MHz, DMSO): 9.49 (t, J=6.1 Hz, 1H), 9.12 (t, J=5.8 Hz, 1H), 8.40 (d, J=1.8 Hz, 1H), 8.36 (d, J=2.1 Hz, 1H), 8.34 (s, 1H), 7.98 (dd, J=8.7; 1.8 Hz, 1H), 7.89 (d, J=2.1 Hz, 1H), 7.84 (br s, 2H), 7.64 (d, J=8.7 Hz, 1H), 7.47 (d, J=3.6 Hz, 1H), 7.42-7.31 (m, 2H), 7.20-7.13 (m, 1H), 7.10 (d, J=3.6 Hz, 1H), 4.86 (d, J=6.0 Hz, 2H), 4.42 (d, J=6.0 Hz, 2H).

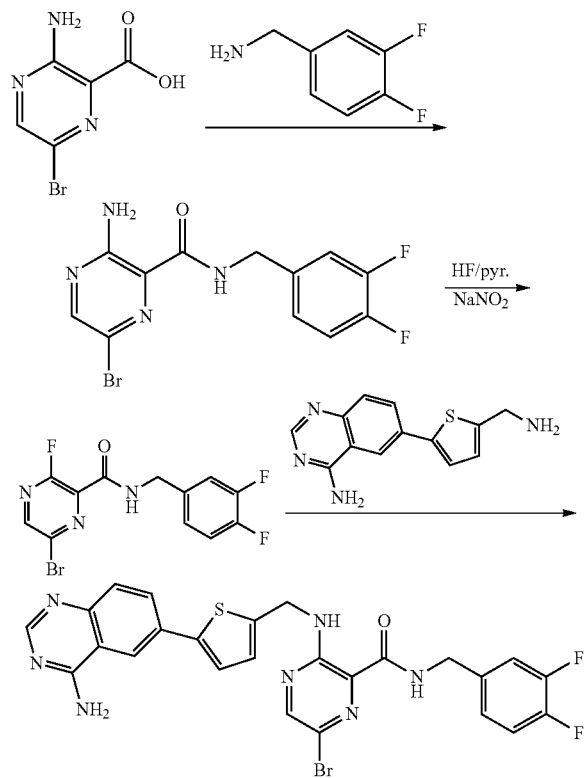

Ex. 10.2

Synthesis of 3-amino-6-bromo-N-(3,4-difluorobenzyl)pyrazine-2-carboxamide

3-Amino-6-bromopyrazine-2-carboxylic acid (1.51 g, 6.93 mmol), N,N-dimethylformamide (30 mL), 3,4-difluoro-benzylamine (1.23 mL, 10.4 mmol), and N,N-Diisopropylethylamine (2.40 mL, 13.8 mmol) were combined and stirred before adding N,N,N',N'-tetramethyl-O-(7-azabenzotriazol-1-yl)uronium hexafluorophosphate (2.89 g, 7.60 mmol) portionwise and stirring for 2 hours. Ethyl acetate (250 mL) and water (150 mL) were added, filtered, and the organic phase was washed further with 150 mL aqueous sodium bicarbonate, and brine. Dried over magnesium sulfate, evaporated, and purified by flash chromatography (0-50% ethyl acetate:hexanes). Collected 0.899 g of a yellow solid (38%). ¹H NMR (300 MHz, CDCl₃) d=8.25 (s, 1H), 8.04 (br. s., 1H), 7.24-7.00 (m, 3H), 4.56 (d, J=6.4 Hz, 2H).

Synthesis of 6-bromo-N-(3,4-difluorobenzyl)-3-fluoropyrazine-2-carboxamide

3-Amino-6-bromo-N-(3,4-difluorobenzyl)pyrazine-2-carboxamide (505 mg, 1.47 mmol) was weighed into a polypropylene reaction vial and dissolved in hydrogen fluoride pyridine (65-70%, 4.5 mL, 160 mmol). Cooled in an ice bath, and added sodium nitrite (113.7 mg, 1.648 mmol). The reaction began to evolve a gas, and the reaction was stirred at 0° C. for 15 min before warming to room temperature. After stirring for an additional hour, the reaction was deemed complete by HPLC-MS, and quenched over ice. Added ethyl acetate (75 mL) and washed twice with water (50 mL), then brine (50 mL). Dried over magnesium sulfate, evaporated, and purified by flash chromatography (0-30% ethyl acetate:hexanes). ES (+) MS m/e=346.0 (M+1); ¹H NMR (CDCl₃) δ: 8.48 (d, J=1.4 Hz, 1H), 7.94 (t, J=6.0 Hz, 1H), 7.03-7.24 (m, 3H), 4.60 (d, J=6.3 Hz, 2H).

Ex. 10.2

Synthesis of 3-({[5-(4-aminoquinazolin-6-yl)thiophen-2-yl]methyl}amino)-6-bromo-N-(3,4-difluorobenzyl)pyrazine-2-carboxamide 6-bromo-N-(3,4-difluorobenzyl)-3-fluoropyrazine-2-carboxamide (99.7 mg, 0.288 mmol), 6-(5-(aminomethyl)thiophen-2-yl)quinazolin-4-amine (90.5 mg, 0.353 mmol), was stirred in 1,4-dioxane (3.00 mL) and triethylamine (80.3 µL, 0.576 mmol). Heated at 50° C. for 1 hour and monitored by HPLC-MS. Added 75 mL ethyl acetate, washed 2×50 mL water, and 1×50 mL brine. Dried over magnesium sulfate, evaporated, and purified by flash chromatography (0-10% methanol:dichloromethane). Collected a yellow powder (139.3 mg, 83%). ES (+) MS m/e=582.2 (M+1); ¹H NMR (300 MHz, DMSO-d₆) δ=9.35 (t, J=6.3 Hz, 1 H), 9.16 (t, J=6.0 Hz, 1 H), 8.51 (s, 1 H), 8.41 (d, J=2.1 Hz, 1 H), 8.34 (s, 1 H), 7.98 (dd, J=2.0, 8.7 Hz, 1 H), 7.83 (br. s., 1 H), 7.64 (d, J=8.7 Hz, 1 H), 7.47 (d, J=3.6 Hz, 1 H), 7.44-7.30 (m, 2 H), 7.22-7.13 (m, 1 H), 7.09 (d, J=3.6 Hz, 1 H), 4.84 (d, J=5.9 Hz, 2 H), 4.42 (d, J=6.3 Hz, 2 H).

Synthesis of Ex. 10.3 was accomplished using an analogous sequence to that of Ex. 10.2 from 3-amino-N-(3,4-difluorobenzyl)-6-phenylpyrazine-2-carboxamide.

Synthesis of 3-amino-N-(3,4-difluorobenzyl)-6-phenylpyrazine-2-carboxamide

3-Amino-6-bromo-N-(3,4-difluorobenzyl)pyrazine-2-carboxamide (98.8 mg, 0.288 mmol), phenylboronic acid (72.5 mg, 0.595 mmol), and [1,1'-bis(diphenylphosphino)ferrocene]-dichloropalladium(II), complex with dichloromethane (1:1) (23.5 mg, 0.0288 mmol) were stirred in N,N-dimethylformamide (2.96 mL). Added 1.04 M of aqueous sodium bicarbonate (0.834 mL, 0.864 mmol) and heated in a microwave reactor at 130° C. for 5 minutes. The reaction was diluted with ethyl acetate and filtered through Celite. The organic phase was washed twice with water, then brine. Dried over magnesium sulfate, evaporated, and purified by flash chromatography (0-30% ethyl acetate:hexanes). Collected 92.7 mg of a white powder (95%). ES (+) MS m/e=341.2 (M+1); $^1$H NMR (300 MHz, CDCl$_3$) δ: 8.68 (s, 1 H), 8.41 (t, J=6.4 Hz, 1 H), 8.19 (d, J=6.4 Hz, 1 H), 7.90-7.79 (m, 2 H), 7.61-7.34 (m, 4 H), 7.26-7.03 (m, 3 H), 4.62 (d, J=6.4 Hz, 2 H).

Synthesis of Ex. 10.4 was accomplished using an analogous sequence to that of Ex. 10.2 by starting with 3-Amino-6-isopropyl-pyrazine-2-carboxylic acid 3,4-difluoro-benzylamide.

Synthesis of
3-Amino-6-isopropyl-pyrazine-2-carboxylic acid
3,4-difluoro-benzylamide 3-Amino-6-isopropenyl-pyrazine-2-carboxylic acid 3,4-difluoro-benzylamide (106.4 mg, 0.3497 mmol), wet 10% palladium on carbon (57.7 mg, 0.0271 mmol), were weighed in a vial that was evacuated and flushed with hydrogen gas three times. Added methanol (3.00 mL) and heated at 50° C. for 1 hour. The reaction was filtered through celite, and washed with EtOAc. Evaporated. LCMS (Agilent 460, 254 nm):M+1=307.2@1.59 min. Crude is clean. Carried onto next reaction. Collected 110.8 mg of a yellow solid. ES (+) MS m/e=307.2 (M+1); $^1$H NMR (300 MHz, CDCl$_3$) δ=8.32 (br. s., 1 H), 8.10 (s, 1 H), 7.23-7.03 (m, 3 H), 4.59 (d, J=6.4 Hz, 2 H), 2.98 (spt, J=6.9 Hz, 1 H), 1.27 (d, J=6.9 Hz, 6 H).

Synthesis of Ex. 10.5 was accomplished using an analogous sequence to that of Ex. 10.2 by starting with 3-amino-N-(3,4-difluorobenzyl)-6-(prop-1-en-2-yl)pyrazine-2-carboxamide.

Synthesis of 3-amino-N-(3,4-difluorobenzyl)-6-(prop-1-en-2-yl)pyrazine-2-carboxamide 3-Amino-6-bromo-N-(3,4-difluorobenzyl)pyrazine-2-carboxamide (299.5 mg, 0.8728 mmol), isopropenylboronic acid pinacol ester (329 µL, 1.75 mmol), and [1,1'-bis(diphenylphosphino)-ferrocene]dichloropalladium(II), complex with dichloromethane (1:1) (36.2 mg, 0.0443 mmol) were stirred in N,N-dimethylformamide (4.5 mL, 58 mmol). Added 1.04 M of aqueous sodium bicarbonate (2.528 mL, 2.618 mmol) and heated at 100° C. for 2.5 hours. The reaction was diluted with ethyl acetate and filtered through Celite. The organic phase was washed twice with water, then brine. Dried over magnesium sulfate, evaporated, and purified by flash chromatography (0-30% ethyl acetate:hexanes). Collected 246.mg of a yellow powder (93%).

Synthesis of Ex. 10.6 was accomplished using an analogous sequence to that of Ex. 10.2 by starting with 3-fluoro-6-((E)-propenyl)-pyrazine-2-carboxylic acid 3,4-difluoro-benzylamide.

Synthesis of 3-fluoro-6-((E)-propenyl)-pyrazine-2-carboxylic acid 3,4-difluoro-benzylamide 3-Amino-6-bromo-N-(3,4-difluorobenzyl)pyrazine-2-carboxamide (107.0 mg, 0.3092 mmol), trans-1-propen-1-ylboronic acid (48.4 mg, 0.563 mmol) [1,1'-bis(diphenylphosphino)ferrocene]dichloropalladium(II), complex with dichloromethane (1:1) (13.3 mg, 0.0163 mmol), 1,4-dioxane (3.00 mL, 38.4 mmol) and triethylamine (129.3 µL, 0.9275 mmol) were combined and heated at 65° C. for 1.5 hours. Added 75 mL ethyl acetate and washed with 75 mL water, 75 mL aqueous sodium bicarbonate, and 75 mL brine. Dried over MgSO4, evaporated, and purified by flash chromatography (10-30% ethyl acetate:hexanes, silica). Collected 90.3 mg of a off-white solid (95%). $^1$H NMR (300 MHz, CDCl$_3$) δ=8.30 (d, J=1.6 Hz, 1 H), 8.18-7.92 (m, 1 H), 7.26-7.05 (m, 3 H), 6.81 (dq, J=6.8, 15.7 Hz, 1 H), 6.52 (dq, J=1.7, 15.7 Hz, 1 H), 4.62 (d, J=6.3 Hz, 2 H), 1.98 (dd, J=1.7, 6.8 Hz, 3 H).

Synthesis of Ex. 10.7

3-({[5-(4-aminoquinazolin-6-yl)thiophen-2-yl] methyl}amino)-N-(3,4-difluorobenzyl)-6-propylpyrazine-2-carboxamide Ex. 10.6 (102.3 mg, 0.1882 mmol), 10% palladium on carbon (wet, 24.4 mg, 0.0115 mmol) were combined in a vial, evacuated, and flushed with hydrogen. Added methanol (2.00 mL), methylene chloride (1.00 mL) and heated under an hydrogen atmosphere at 60° C. for 4 hours. A second portion of 10% palladium on carbon (wet, 40 mg) added and heated overnight. The reaction was filtered through Celite, evaporated, and purified by flash chromatography (0-6% methanol:methylene chloride). Collected 49.2 mg of a white solid (48%). ES (+) MS m/e=546.3 (M+1). $^1$H NMR (300 MHz, CDCl$_3$) δ=8.83 (t, J=5.9 Hz, 1 H), 8.60 (s, 1 H), 8.40 (t, J=6.4 Hz, 1 H), 8.16 (s, 1 H), 7.96 (dd, J=1.9, 8.7 Hz, 1 H), 7.88-7.79 (m, 2 H), 7.24-6.97 (m, 5 H), 5.98 (br. s., 2 H), 4.87 (d, J=6.0 Hz, 2 H), 4.56 (d, J=6.4 Hz, 2 H), 2.69-2.58 (m, 2 H), 1.70 (sxt, J=7.5 Hz, 2 H), 0.97 (t, J=7.4 Hz, 3 H).

Synthesis of Ex. 10.8 was accomplished using an analogous sequence to that of Ex. 10.2 by starting with 3-Fluoro-6-(3-methoxy-prop-1-ynyl)-pyrazine-2-carboxylic acid [(S)-1-(3,4-difluoro-phenyl)-ethyl]-amide.

Synthesis of 3-Fluoro-6-(3-methoxy-prop-1-ynyl)-pyrazine-2-carboxylic acid [(S)-1-(3,4-difluoro-phenyl)-ethyl]-amide (S)-6-bromo-N-(1-(3,4-difluorophenyl)ethyl)-3-fluoro-pyrazine-2-carboxamide (59.6 mg, 0.165 mmol), [1,1'-bis (diphenylphosphino)-ferrocene]dichloropalladium(II), complex with dichloromethane (1:1) (13.6 mg, 0.0166 mmol), and copper(I) iodide (4.8 mg, 0.025 mmol) were stirred in acetonitrile (3.30 mL, 63.2 mmol), triethylamine (69.2 µL, 0.496 mmol), and methyl propargyl ether (55.9 µL, 0.662 mmol). The reaction was heated in a microwave reactor at 130° C. for 10 minutes. After cooling to room temperature, the reaction was filtered through Celite, washed with ethyl acetate, evaporated, and purified by flash chromatography (0-50% ethyl acetate:Hexanes, silica). Collected 38.3 mg of a reddish oil (66%). ES (+) MS m/e=350.2 (M+1); $^1$H NMR (300 MHz, CDCl$_3$) δ=8.46 (d, J=1.5 Hz, 1 H), 7.83 (d, J=7.9 Hz, 1 H), 7.25-7.10 (m, 3 H), 5.25 (quin, J=7.2 Hz, 1 H), 4.38 (s, 2H), 3.49 (s, 3H), 1.61 (d, J=7.2 Hz, 3H).

Synthesis of Ex. 10.9 was accomplished using an analogous sequence to that of Ex. 10.2 by starting with 3-Amino-6-cyano-pyrazine-2-carboxylic acid [(S)-1-(3,4-difluoro-phenyl)-ethyl]-amide.

Synthesis of 3-Amino-6-cyano-pyrazine-2-carboxylic acid [(S)-1-(3,4-difluoro-phenyl)-ethyl]-amide (S)-3-amino-6-bromo-N-(1-(3,4-difluorophenyl)ethyl) pyrazine-2-carboxamide (200.5 mg, 0.5614 mmol), zinc cyanide (136.6 mg, 1.163 mmol), [1,1'-bis(diphenylphosphino)ferrocene]dichloropalladium(II), complex with dichloromethane (1:1) (47.9 mg, 0.0586 mmol), and N-methylpyrrolidinone (4.0 mL, 42 mmol) were combined and heated in a microwave reactor at 125° C. for 15 minutes.

The reaction was dissolved in ethyl acetate and filtered through Celite. The organic washings were washed with aqueous sodium bicarbonate, water, then brine. Dried over magnesium sulfate, evaporated, and purified by flash chromatography (0-25% ethyl acetate:hexanes, silica). Evaporation of fractions yielded 106.3 mg of a white powder (62%). ES (+) MS m/e=304.1 (M+1); 1H NMR (300 MHz, CHLOROFORM-d) d 8.78 (br. s., 1H), 8.45 (s, 1H), 7.94 (d, J=7.18 Hz, 1H), 7.04-7.25 (m, 3H), 5.80 (br. s., 1H), 5.15 (quin, J=7.18 Hz, 1H), 1.61 (d, J=6.80 Hz, 3H).

Ex. 10.10 was prepared in a manner analogous to Ex. 10.2.

Example 11

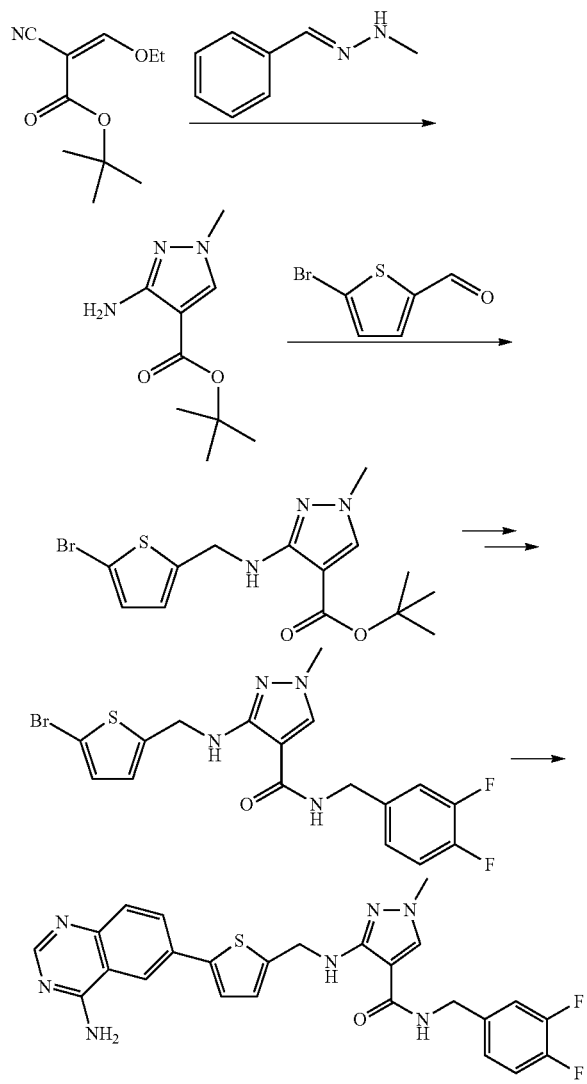

Synthesis of (Z)-tert-butyl 2-cyano-3-ethoxyacrylate

To a solution of 2-cyanoacetic acid (5 g, 0.059 mol) and tert-butanol (5.2 g, 0.07 mmol, 1.2 equiv) in MeCN/MeOH (1:1), DCC (12 g, 0.059 mmol, 1 equiv) was added in portions at 0° C., and stirred for 20 min. The reaction mixture was filtrated, and the organic layer was concentrated by vacuum evaporator. The resulting yellow oil was purified by flash chromatography on silica gel (PE/EA=10/1) to give tert-butyl 2-cyanoacetate 5.4 g (yield: 65%). Triethoxymethane (17 g, 0.115 mol, 1.2 equiv) was added to a solution of tert-butyl 2-cyanoacetate (13.5 g, 0.0957 mol) in 200 ml Ac$_2$O. The reaction mixture was heated to reflux for 15 h, and then remove the solvent under vacuum to give (Z)-tert-butyl 2-cyano-3-ethoxyacrylate as a red oil (16 g, 85%).

Synthesis of tert-butyl 3-amino-1-methyl-1H-pyrazole-4-carboxylate

Compound (Z)-tert-butyl 2-cyano-3-ethoxyacrylate (15 g, 76.14 mmol) and (E)-1-benzylidene-2-methylhydrazine (reference: Y. Xia, J M C, 1997, 40, 4372) (12.3 g, 91.8 mmol, 1.2 equiv) were dissolved in 200 mL of methanol, and stirred for 3 h at rt. Then the reaction mixture was refluxed for 15 h after 5 ml of condensed hydrochloric acid was added. Finally the mixture was purified by silica gel to give product 5 g (yield: 33%) MS (M+H$^+$): 198.1.

Synthesis of tert-butyl 3-((5-bromothiophen-2-yl)methyl)amino)-1-methyl-1H-pyrazole-4-carboxylate Into a solution of tert-butyl 3-amino-1-methyl-1H-pyrazole-4-carboxylate (1.4 g 7.0 mmol) in 5 mL of methanol was added 5-bromothiophene-2-carbaldehyde (1.6 g, 8.4 mmol) at rt. The reaction mixture was heated to refluxing and stirred for 16 h. Then 10 mL of methanol and NaBH$_4$ (266 mg, 7.0 mmol, 1.0 equiv) was added to the reaction mixture at rt. The reaction mixture was stirred of 2 h at rt. The solvent was removed by rotation evaporation, and the residue was purified on silica gel to give product (1.3 g, 49.4%). MS (M+H$^+$): 372.0.

Synthesis of 3-((5-bromothiophen-2-yl)methyl)amino)-N-(3,4-difluorobenzyl)-1-methyl-1H-pyrazole-4-carboxamide To a solution of tert-butyl 3-((5-bromothiophen-2-yl)methyl)amino)-1-methyl-1H-pyrazole-4-carboxylate (1.3 g crude) in methanol and tetrahydrofuran (40 ml, 1/1), sodium hydroxide (4.0 g 0.1 mol) and 0.5 ml water were added with stirring. The reaction mixture was heated to reflux and stirred for 16 h. The solvent was removed by rotation evaporation, and 30 mL water was added with stirring. The byproduct (5-bromothiophen-2-yl) was extracted by CH$_2$Cl$_2$ (20 mL×3). The pH of the aqueous solution was adjusted to 5, and extracted by ethyl acetate (20 mL×3), concentrated to give 3-((5-bromothiophen-2-yl)methyl)amino)-1-methyl-1H-pyrazole-4-carboxylic acid without further purifications (0.3 g, 27%). ESI-MS (M+H$^+$): 316.0.

To a solution of the above crude (110 mg, 0.35 mmol) in 1.0 mL DMF, HATU (265 mg, 0.70 mmol, 2.0 equiv) and DIPEA (250 mg, 1.75 mmol, 5.0 equiv) was added with stirring. Then (3, 4-difluorophenyl) methanamine (50 mg, 0.35 mmol, 1.0 equiv) was added. The reaction mixture was stirred at rt for 16 h, concentrated and the residue was purified on silica gel to give the product (80 mg, 52.6%). ESI-MS (M+H$^+$): 441.0.

Ex. 11.1

Synthesis of 3-((5-(4-aminoquinazolin-6-yl)thiophen-2-yl)methyl)amino)-N-(3,4-difluorobenzyl)-1-methyl-1H-pyrazole-4-carboxamide A flask charged with 6-(4,4,5,5-tetramethyl-1,3,2-dioxaborolan-2-yl)quinazolin-4-amine (45 mg, 0.16 mmol), 3-((5-bromothiophen-2-yl)methyl)amino)-N-(3,4-difluorobenzyl)-1-methyl-1H-pyrazole-4-carboxamide (73 mg, 0.16 mmol, 1.0 equiv), 2M K$_2$CO$_3$ (45.6 mg, 0.32 mmol, 2.0 equiv) and [1,1-Bis (diphenylphosphino)ferrocene]dichloropalladium(II) complex with dichloromethane (1:1) (13.4 mg, 1.6 mmol, 0.10 equiv) was flushed with nitrogen. 1,4-Dioxane (10 mL) was added and the reaction was stirred at 90° C. for 2 h. The solution was cooled to room temperature. The solvent was removed and the residue was purified by HPLC-preparation to give the product (38 mg, 45.4%). ESI-MS (M+H$^+$): 506.1; $^1$H NMR (400 MHz, CD$_3$OD) δ:8.65 (s, 1H) 8.58 (d, 1H), 8.33 (dd, 1H), 7.85 (s, 1H), 7.77 (d, 1H), 7.52 (d, 1H), 7.18-7.25 (m, 2H), 7.11-7.14 (m, 2H), 4.68 (s, 2H), 4.45 (s, 2H), 3.77 (s, 3H).

Ex. 11.2 was prepared in a similar manner as Ex. 11.1 from phenylhydrazine.

Ex. 11.3 was prepared in a similar manner as Ex. 11.1 from 2-hydrazinylpyridine.

Ex. 11.4-11.5 were prepared in a similar manner as Ex. 11.1.

Example 12

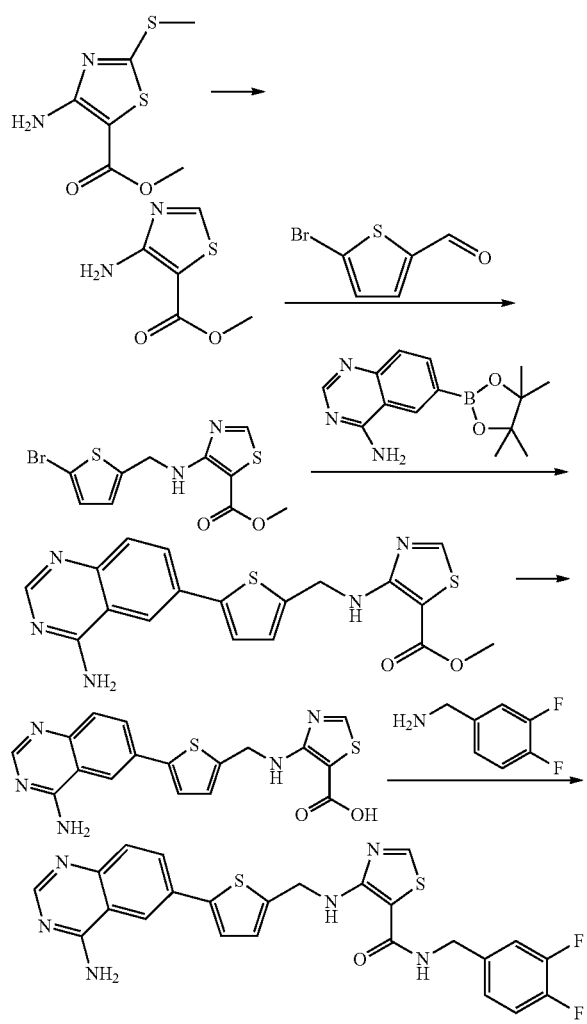

Ex. 12.1

Synthesis of methyl 4-aminothiazole-5-carboxylate

4-Amino-2-methylsulfanyl-thiazole-5-carboxylic acid methyl ester (2.00 g, 9.79 mmol) was dissolved in methanol (40 mL) (may need to warm up). Zinc (3.84 g, 58.8 mmol) dust was then added to the solution. 3 M of hydrogen chloride in MeOH (20 mL) was then dropwise added to the reaction during 10 min. period. During this addition, rapid evolution of gas ensued which was passed from the reaction flask into a bubbler of bleach to capture the evolved methanethiol. The reaction was stirred at room temperature for 1 h. Extra zinc (1 g) was added. The reaction was then stirred at room temperature for overnight. The reaction mixture was poured into a stirring mixture of celite in 200 ml saturated aqueous Na$_2$CO$_3$. The resulting mixture was filtered and the solid were rinsed with minimal MeOH. Water (100 ml) was added to the filtrate, and it was the extracted 3 times with CH$_2$Cl$_2$. Combined extracts were washed with brine, dried over Na$_2$SO$_4$, evaporated in vacuo. The crude was purified by precipitation from ether to yield desired compound as a white solid (0.80 g, 52%). LCMS: RT 0.60 min. MH+ 159.00. $^1$H NMR (400 MHz, DMSO-d$_6$) δ 8.96 (s, 1H), 6.99 (br. s., 2H), 3.73 (s, 3H).

Synthesis of methyl 4-((5-bromothiophen-2-yl)methyl)amino)thiazole-5-carboxylate To a solution of 4-Amino-thiazole-5-carboxylic acid methyl ester (500 mg, 3.0 mmol) in 1,2-dichloroethane (10 mL) was added 5-bromo-thiophene-2-carbaldehyde (906 mg, 4.74 mmol) and acetic acid (0.180 mL, 3.16 mol). The mixture was stirred at room temperature for 1 h. Sodium triacetoxyborohydride (1.34 g, 6.32 mmol) was then added. The reaction was then stirred at room temperature overnight. The reaction was quenched with water, stirred at room temperature for 30 min. then diluted with EtOAc, washed with aqueous NaHCO$_3$. The organic layer was dried over MgSO$_4$ and purified by HPLC to give product as a white powder (0.346 g). LCMS: RT 1.76 min.; MH+ 333.00. $^1$H NMR (400 MHz, DMSO-d$_6$) δ 9.07 (s, 1H), 7.55 (t, J=6.27 Hz, 1H), 7.03 (d, J=3.77 Hz, 1H), 6.83 (d, J=3.51 Hz, 1H), 4.66-4.84 (m, 2H), 3.74 (s, 3H).

Synthesis of methyl 4-((5-bromothiophen-2-yl)methyl)amino)thiazole-5-carboxylate To a solution of 6-(4,4,5,5-tetramethyl-1,3,2-dioxaborolan-2-yl)-quinazolin-4-ylamine (163 mg, 0.000600 mol) and 4-[(5-bromo-thiophen-2-ylmethyl)-amino]-thiazole-5-carboxylic acid methyl ester (200 mg, 0.0006 mol) in DMSO (3 mL) was added [1,1'-bis(diphenylphosphino)-ferrocene]dichloropalladium(II), complex with dichlorometh-ane (1:1) (49.0 mg, 0.0600 mmol) and 1.2 M of saturated aqueous sodium bicarbonate solution (2 mL, 2.0 mmol). After degassed for 5 min., the reaction was heated in microwave at 90° C. for 10 min. The reaction was diluted with EtOAc, washed with water (5 times). The organic layer was then dried and concentrated. The crude was purified by prep-TLC to give product 9.3 (91 mg, 40%). LCMS: RT 1.05 min.; MH+ 398.20. $^1$H NMR (400 MHz, DMSO-d$_6$) δ 9.08 (s, 1H), 8.75 (s, 1H), 8.57 (d, J=2.01 Hz, 1H), 8.25 (dd, J=1.88, 8.66 Hz, 1H), 7.75 (d, J=8.78 Hz, 1H), 7.64 (t, 1H), 7.54 (d, J=3.76 Hz, 1H), 7.10 (d, J=3.51 Hz, 1H), 4.85-4.96 (m, 2H), 3.76 (s, 3H).

Synthesis of 4-((5-(4-aminoquinazolin-6-yl)thiophen-2-yl)methyl)amino)thiazole-5-carboxylic acid To a solution of 4-{[5-(4-amino-quinazolin-6-yl)-thiophen-2-ylmethyl]-amino}-thiazole-5-carboxylic acid methyl ester (90 mg, 0.23 mmol) in tetrahydrofuran (2 mL) was added 1.0 M of lithium hydroxide in water (0.7 mL, 0.7 mmol). The reaction was stirred at rt for 1h. Remove the organic solvent in vacuo, the residue was cooled to 0° C., then acidified with HCl to pH=1. The crude was taken into EtOAc and washed with acidified brine solution. The organic layer was then separated, dried over MgSO₄ and concentrated to give product (84 mg, 97%) which was used directly in the next step without further purifications.

Ex. 12.1

Synthesis of 4-((5-(4-aminoquinazolin-6-yl)thiophen-2-yl)methyl)amino)-N-(3,4-difluorobenzyl)thiazole-5-carboxamide A solution of 4-{[5-(4-Amino-quinazolin-6-yl)-thiophen-2-ylmethyl]-amino}-thiazole-5-carboxylic acid (80 mg, 0.17 mmol), N,N-diisopropylethylamine (0.07 mL, 0.4 mmol) and N,N,N',N'-tetramethyl-O-(7-azabenzotriazol-1-yl)uronium hexafluoropho-sphate (87.26 mg, 0.23 mmol) in N,N-dimethylformamide (2.0 mL) was stirred at RT for 15 min., 3,4-difluoro-benzylamine (0.02468 mL, 0.21 mmol) was then added, and the reaction was stirred at RT for 1h. The reaction mixture was diluted with EtOAc, washing with brine, then water. The organic layer was separated, dried and concentrated. The crude was purified by HPLC to give product as a light yellow powder (18 mg, 21%). LCMS: RT 1.21 min.; MH+ 509.10; ¹H NMR (400 MHz, DMSO-d₆) δ 9.71 (br. s., 2H), 8.90-9.01 (m, 1H), 8.79 (s, 1H), 8.59 (d, J=1.76 Hz, 1H), 8.44 (t, J=6.02 Hz, 1H), 8.27 (dd, J=2.01, 8.78 Hz, 1H), 7.91 (t, J=6.40 Hz, 1H), 7.76 (d, J=8.78 Hz, 1H), 7.47-7.61 (m, 1H), 7.22-7.44 (m, 2H), 6.98-7.19 (m, 2H), 4.73-4.95 (m, 2H), 4.34 (d, J=5.27 Hz, 2H).

Example 13

Synthesis of 2-(4-(4-aminoquinazolin-6-yl)thiazol-2-ylamino)-N-(3,4-difluorobenzyl)-nicotinamide

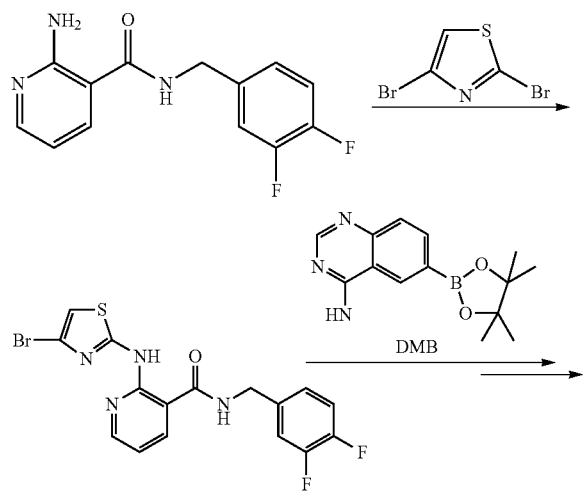

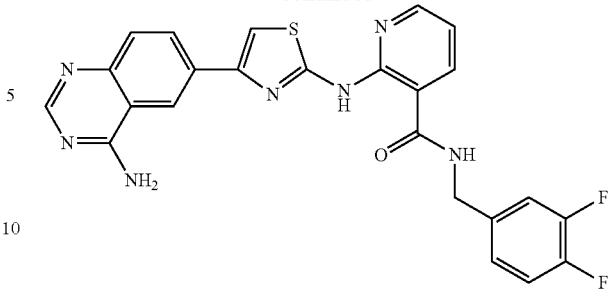

Ex. 13

To a mixture of 2-Amino-N-(3,4-difluoro-benzyl)-nicotinamide (0.500 g, 1.90 mmol), 2,4-Dibromo-thiazole (0.508 g, 2.09 mmol) in 1,4-Dioxane (15 mL, 190 mmol) was added potassium phosphate (605 mg, 2.85 mmol) and a mixture of tris(dibenzylideneacetone)dipalladium(0) (90 mg, 0.09 mmol) and xantphos (130 mg, 0.23 mmol). The mixture was degassed with nitrogen for 10 min. The reaction was then heated in microwave reactor at 150° C. for 30 min. The reaction was diluted with EtOAc and washed with aqueous NaHCO₃, then water. The organic phase was separated, dried, and concentrated. The crude was purified by column (EtOAc/DCM gradient) to give desired product 2-(4-bromothiazol-2-ylamino)-N-(3,4-difluorobenzyl)nicotinamide as a light yellow powder (380 mg, 47%), LCMS: 1.88 min.; MH+ 425.10. ¹H NMR (400 MHz, DMSO-d₆) δ 12.29 (s, 1H), 9.57 (t, J=5.77 Hz, 1H), 8.52 (dd, J=1.63, 4.89 Hz, 1H), 8.39 (dd, J=1.76, 7.78 Hz, 1H), 6.98-7.28 (m, 5H), 4.55 (d, J=6.02 Hz, 2H).

To a suspension of 2-(4-bromo-thiazol-2-ylamino)-N-(3,4-difluoro-benzyl)-nicotinamide (3.1, 100 mg, 0.0002 mol), (2,4-dimethoxy-benzyl)-[6-(4,4,5,5-tetramethyl-1,3,2-dioxaborolan-2-yl)-quinazolin-4-yl]-amine (198 mg, 0.000470 mol) in 1,4-dioxane (4.00 mL, 0.0512 mol) was added a solution of potassium carbonate (97.5 mg, 0.000705 mol) in water (1.00 mL, 0.0555 mol). The mixture was degassed with nitrogen for 15 min. Tetrakis(triphenylphosphine)palladium(0) (41 mg, 0.000035 mol) was added. Degassed for another 5 min. The reaction was heated at 130° C. in microwave (high power) for 1 h. After cooled down, the reaction was diluted with EtOAc, washed with aqueous NaHCO₃ and then water. The organic phase was then dried, concentrated. The crude was purified by prep-TLC to give 35 mg of the desired product 3.2 (with purity about 80% based on LCMS) which was used directly in the next step without further purifications. LCMS: RT 1.55 min.; MH+ 640.30.

A suspension of N-(3,4-difluoro-benzyl)-2-{4-[4-(2,4-dimethoxy-benzylamino)-quinazolin-6-yl]-thiazol-2-ylamino}-nicotinamide (3.2, 25 mg, 0.039 mmol) in trifluoroacetic acid (1.5 mL, 19 mmol) and methylene chloride (0.5 mL). The reaction was heated at 50° C. for 4 h. After cooled down, the reaction was diluted with EtOAc, washed with water. The organic phase was then dried, concentrated. The crude was purified by HPLC to give 2-(4-(4-aminoquinazolin-6-yl)thiazol-2-ylamino)-N-(3,4-difluorobenzyl)nicotinamide (Ex. 13) as a light yellow powder (2.9 mg, 15%). LCMS: RT 1.25 min.; MH+ 490.20. ¹H NMR (400 MHz, DMSO-d₆) δ 12.33 (s, 1H), 9.63 (t, 1H), 8.94 (s, 1H), 8.80 (s, 1H), 8.57 (dd, J=4.89, 1.63 Hz, 2H), 8.43 (dd, J=8.03, 1.76 Hz, 1H), 7.64-7.91 (m, 2H), 7.01-7.26 (m, 4H), 4.57 (d, 2H).

Example 14

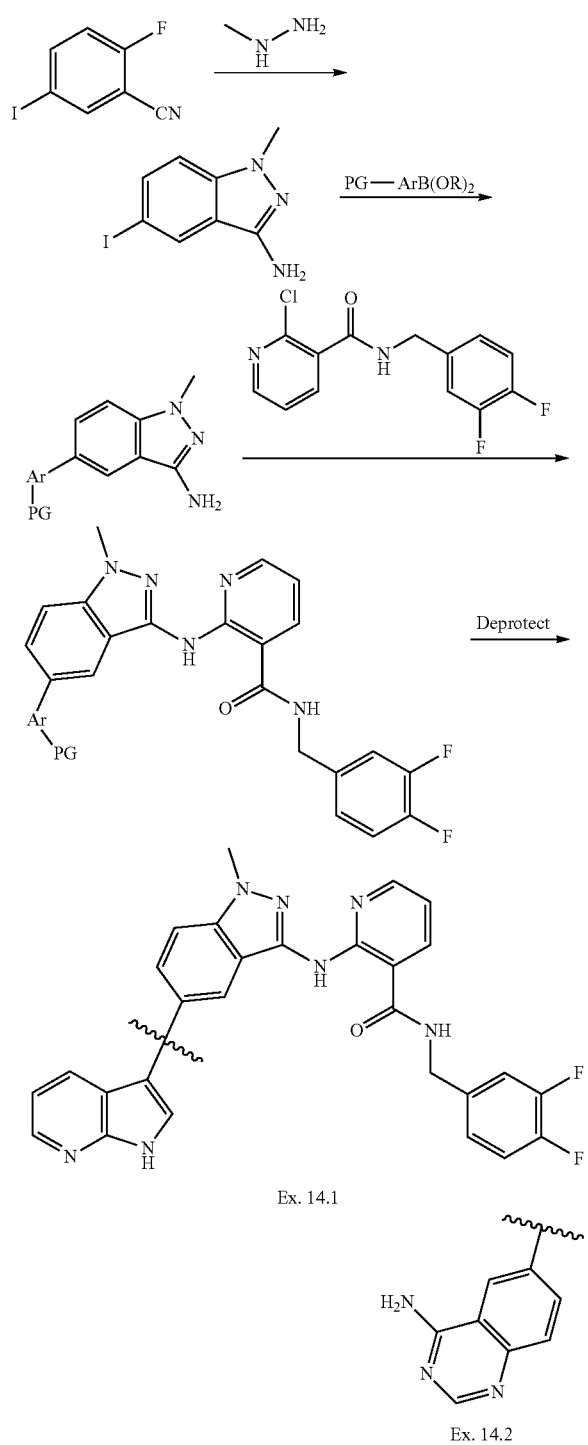

Ex. 14.1

Ex. 14.2

Synthesis of 5-iodo-1-methyl-1H-indazol-3-amine

A mixture of 2-Fluoro-5-iodo-benzonitrile (2.00 g, 8.097 mmol) and N-methylhydrazine (4.308 mL, 80.97 mmol) in 1-butanol (50.0 mL) was stirred at 100° C. to 110° C. for 2h. The reaction was then cooled down and concentrated. The residue was diluted with EtOAc, washed with water, then aqueous NaHCO$_3$, then water. The organic layer was separated, dried over MgSO4, concentrated. The crude was purified by precipitation from ether/hexanes to give the product as an off white powder (1.66 g, 75%). LCMS: RT 1.05 min.; MH+ 274.00. $^1$H NMR (400 MHz, DMSO-d$_6$) δ 8.10 (d, J=1.00 Hz, 1H), 7.47 (dd, J=1.51, 8.78 Hz, 1H), 7.20 (d, J=8.78 Hz, 1H), 5.50 (s, 2H), 3.70 (s, 3H) (*Ref JMC*, 2007, 50, 1584-97).

Synthesis of 1-methyl-5-(1-(phenylsulfonyl)-1H-pyrrolo[2,3-b]pyridin-3-yl)-1H-indazol-3-amine A mixture of 1-benzenesulfonyl-3-(4,4,5,5-tetramethyl-1,3,2-dioxaborolan-2-yl)-1H-pyrrolo[2,3-b]pyridine (600.0 mg, 1.56 mmol) and 5-iodo-1-methyl-1H-indazol-3-ylamine (26.4 mg, 1.561 mmol) in N,N-dimethylformamide (10.00 mL) was degassed with nitrogen for 5 min. Saturated aqueous sodium bicarbonate solution (1.00 mL) was added. Degas for another 5 min. [1,1'-Bis(diphenylphosphino)ferrocene]dichloropalladium(II), complex with dichloromethane (1:1) (128 mg, 0.156 mmol) was added. The reaction vial was then sealed and heated in microwave reactor at 90° C. for 10 min. The reaction was diluted with EtOAc, washed with water (5 times). The organic phase was separated, dried over MgSO$_4$, concentrated. The crude was purified by ISCO (DCM+1%-5% of 2M NH$_3$ in MeOH) to give the product as a light yellow powder (350 mg, 56%). LCMS: RT 1.31 min.; MH+ 404.20. $^1$H NMR (400 MHz, DMSO-d$_6$) δ 8.39-8.52 (m, 2H), 8.02-8.26 (m, 4H), 7.68-7.80 (m, 2H), 7.56-7.68 (m, 2H), 7.34-7.50 (m, 2H), 5.34-5.72 (m, 2H), 3.76 (s, 3H).

Synthesis of N-(3,4-difluorobenzyl)-2-(1-methyl-5-(1-(phenylsulfonyl)-1H-pyrrolo[2,3-b]pyridin-3-yl)-1H-indazol-3-ylamino)nicotinamide To a mixture of 2-chloro-N-(3,4-difluoro-benzyl)-nicotinamide (100.0 mg, 0.35 mmol), in 1,4-dioxane (5.0 mL) was added tris(dibenzylideneacetone)dipalladium(0) (32.4 mg, 0.035 mmol) and xantphos (49.1 mg, 0.085 mmol). The mixture was degassed with nitrogen for 15 min., followed by heating at 150° C. for 1h in microwave. The reaction was diluted with EtOAc and washed with water. The organic phase was separated, dried over MgSO$_4$, and purified by prep-TLC (DCM+5% 2M NH$_3$ in MeOH) to give 117 mg (51%) of the product. LC-MS: RT 1.55 min.; MH+ 650.30. $^1$H NMR (400 MHz, DMSO-d$_6$) δ 10.80 (s, 1H), 9.37 (t, J=5.90 Hz, 1H), 8.43 (dd, J=1.51, 4.77 Hz, 1H), 8.13-8.30 (m, 6H), 8.03 (s, 1H), 7.75-7.84 (m, 1H), 7.66-7.75 (m, 2H), 7.58-7.66 (m, 2H), 7.34-7.48 (m, 3H), 7.22 (ddd, J=2.38, 4.27, 6.40 Hz, 1H), 6.90 (dd, J=4.89, 7.65 Hz, 1H), 4.50 (d, J=5.77 Hz, 2H), 3.99 (s, 3H).

Ex. 14.1 was prepared using the same procedure described for Ex. 5.7 using potassium carbonate was pin methanol. (40%).

Ex. 14.2 was prepared using the same procedure described for Ex. 14.1 from N-(2,4-dimethoxybenzyl)-6-(4,4,5,5-tetramethyl-1,3,2-dioxaborolan-2-yl)quinazolin-4-amine.

Example 15

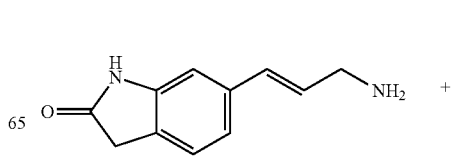

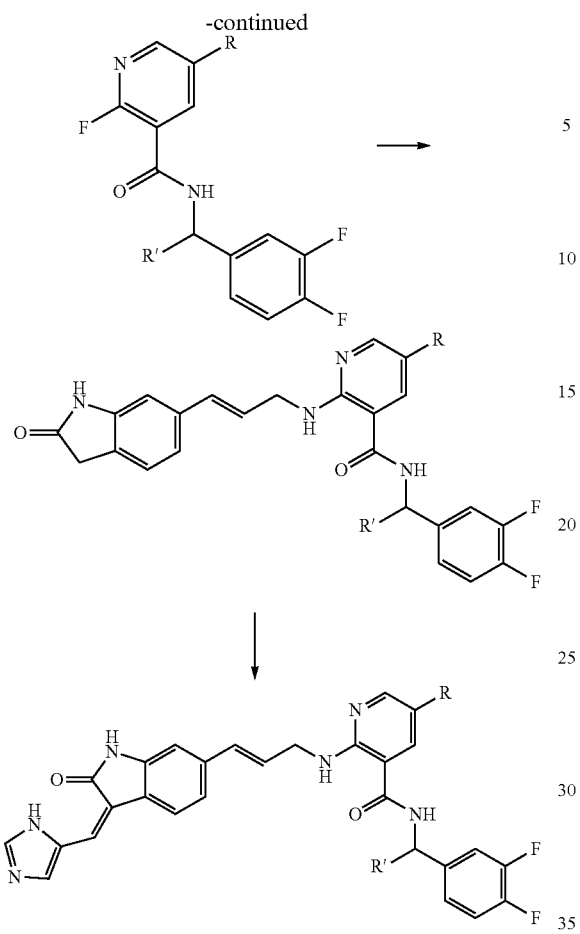

Synthesis of (E)-N-(3,4-difluorobenzyl)-2-(3-(2-oxoindolin-6-yl)allylamino)-nicotinamide A mixture of (E)-6-(3-aminoprop-1-enyl)indolin-2-one (ref. Lind, K. E., WO2008005457) (1.0 g, 0.0053 mol), N-(3,4-Difluoro-benzyl)-2-fluoro-nicotinamide (1.4 g, 0.0053 mol), and Cesium Carbonate (2.6 g, 0.0080 mol) in Dimethyl sulfoxide (50 mL, 0.7 mol) was heated at 130° C. LC-MS showed the formation of the desired product (1.09 min, ES+/435.20). Cooled to room temperature and worked up with EtOAc and water. Dried over MgSO4. Purified on silica gel column with 0-100% EtOAc in DCM and then followed with 0-20% Methanol in DCM to give the desired product (1. g, 48%). $^1$H NMR (300 MHz, DMSO-d$_6$) δ 10.32 (s, 1H), 9.08 (t, J=5.67 Hz, 1H), 8.46 (t, J=5.29 Hz, 1H), 8.20 (dd, J=1.89, 4.91 Hz, 1H), 8.01 (dd, J=1.89, 7.93 Hz, 1H), 7.30-7.45 (m, 2H), 7.09-7.22 (m, 2H), 6.94 (dd, J=1.51, 7.93 Hz, 1H), 6.83 (s, 1H), 6.62 (dd, J=4.91, 7.55 Hz, 1H), 6.51 (d, J=15.86 Hz, 1H), 6.26-6.39 (m, 1H), 4.42 (d, J=6.04 Hz, 2H), 4.19 (t, J=5.67 Hz, 2H), 3.44 (s, 2H)

Ex. 15.1

Synthesis of 2-((E)-3-((Z)-3-((1H-imidazol-5-yl)methylene)-2-oxoindolin-6-yl)allylamino)-N-(3,4-difluorobenzyl)nicotinamide A mix of (E)-N-(3,4-difluorobenzyl)-2-(3-(2-oxoindolin-6-yl)allylamino)nicotinamide (1.1 g, 0.0025 mol), Piperidine (0.50 mL, 0.0051 mol) and Ethanol (10 mL, 0.2 mol) was heated to a solution and then added 1H-imidazole-5-carbaldehyde (290 mg, 0.0030 mol) and heated at 80° C. in a sealed tube for overnight. Cooled to room temperature and the solids were collected and purified on silica gel column with 0-20% MeOH in EtOAc to give the desired product as an orange solid (0.51 mg, 39%). MH+: 513.20; $^1$H NMR (400 MHz, DMSO-d$_6$) d 13.69 (s, 1H), 9.10 (t, J=5.83 Hz, 1H), 8.21 (dd, J=1.76, 4.83 Hz, 1H), 8.01 (dd, J=1.82, 7.78 Hz, 2H), 7.80 (br. s., 1H), 7.61 (d, J=7.91 Hz, 1H), 7.29-7.46 (m, 2H), 7.13-7.23 (m, 1H), 7.01-7.11 (m, 1H), 6.89 (br. s., 1H), 6.63 (dd, J=4.77, 7.65 Hz, 1H), 6.55 (d, J=15.94 Hz, 1H), 6.33-6.47 (m, 1H), 4.43 (d, J=6.09 Hz, 2H), 4.22 (t, J=5.21 Hz, 1H).

Synthesis of (S)-N-(1-(3,4-difluorophenyl)ethyl)-2-fluoro-5-(trifluoromethyl)nicotinamide 2-Amino-N-[(S)-1-(3,4-difluoro-phenyl)-ethyl]-5-trifluoromethyl-nicotinamide (330 mg, 0.96 mmol) was stirred in 30 M of Hydrofluoric acid in Pyridine (3 mL, 90 mmol) in a PTFE vial. Chilled in an ice bath and added Sodium nitrite (76 mg, 1.1 mmol). Stirred in an ice bath for 15 min. LC-MS showed complete conversion (1.65 min, ES+/349.2). Quenched with water with cooling, and extracted with 50 mL EtOAc. Dried over MgSO$_4$ and evaporated. Purified with a short silica gel column with EtOAc to give the desired product as light yellow solid. $^1$H NMR (300 MHz, CDCl$_3$) d 8.69 (dd, J=2.64, 8.69 Hz, 1H), 8.51 (s, 1H), 6.89-7.17 (m, 4H), 5.18 (dt, 1H), 1.52 (d, J=6.80 Hz, 3H).

Synthesis of (S,E)-N-(1-(3,4-difluorophenyl)ethyl)-2-(3-(2-oxoindolin-6-yl)allylamino)-5-(trifluoromethyl)nicotinamide Prepared by the same procedure as (E)-N-(3,4-difluorobenzyl)-2-(3-(2-oxoindolin-6-yl)allylamino)nicotinamide. $^1$H NMR (400 MHz, DMSO-d$_6$) δ 10.34 (s, 1H), 9.07 (d, J=7.47 Hz, 1H), 8.94 (t, J=5.65 Hz, 1H), 8.52 (dd, J=0.88, 2.26 Hz, 1H), 8.40 (d, J=2.07 Hz, 1H), 7.33-7.50 (m, 2H), 7.19-7.26 (m, 1H), 7.13 (d, J=7.65 Hz, 1H), 6.93 (dd, J=1.38, 7.65 Hz, 1H), 6.82 (d, J=1.00 Hz, 1H), 6.48 (d, J=15.94 Hz, 1H), 6.32 (dt, J=5.77, 15.94 Hz, 1H), 5.06-5.16 (m, 1H), 4.20-4.27 (m, 2H), 3.43 (s, 2H); MH+: 517.3.

Ex. 15.2-15.22 were prepared in an analogous manner to Ex. 15.1.

Example 16.1

(R)-N-(3,4-difluorobenzyl)-2-(2-(2-oxo-2,3-dihydro-1H-benzo[d]imidazol-5-yloxy)-1-phenylethylamino)nicotinamide

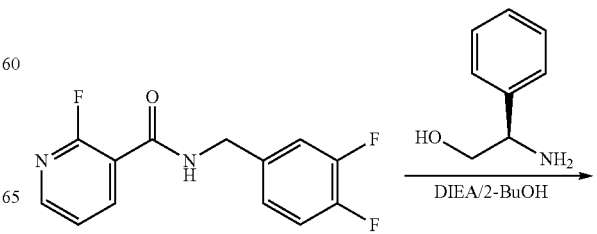

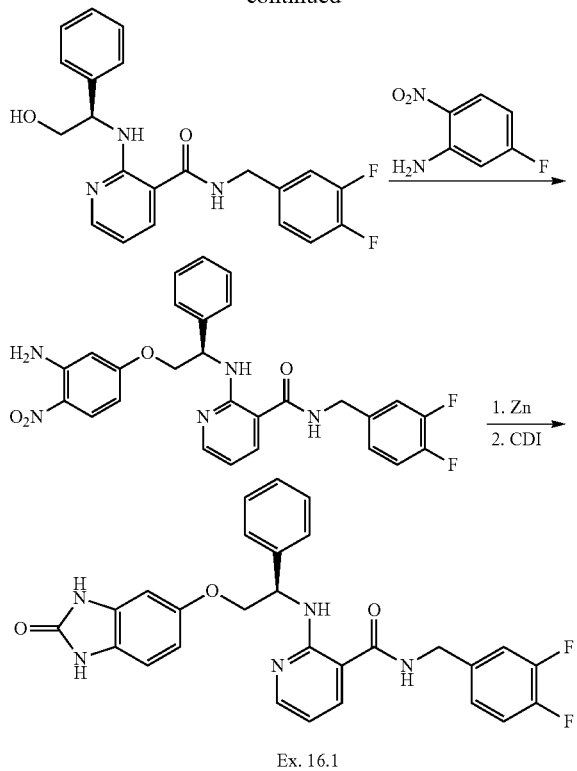

Ex. 16.1

A mixture of 2-Phenylglycinol (1.0 gram, 7.29 mmol), N-(3,4-difluorobenzyl)-2-fluoronicotinamide (1.94 grams, 7.29 mmol), 2-butanol (20 mL), and DIEA (3.81 mL, 21.87 mmol) was heated with stirring at 110° C. for 24 hours. Reaction mixture was then partitioned between ethyl acetate and a saturated solution of sodium bicarbonate. The aqueous layer was extracted an additional time with ethyl acetate, and the organics combined and washed with brine, dried over magnesium sulfate, filtered and concentrated under reduced pressure. Crude product was purified by silica gel chromatography (DCM/MeOH 98:2) to yield (R)-N-(3,4-difluorobenzyl)-2-(2-hydroxy-1-phenylethylamino)nicotinamide as 1.5 grams (69.89%) of an orange oil. E/S MS m/e=384.14 (M+1).

A 250 mL round bottom flask was charged with (R)-N-(3,4-difluorobenzyl)-2-(2-hydroxy-1-phenylethylamino) nicotinamide (2.79 grams, 7.29 mmol) and DMF (25 mL). To the stirring solution was then added sodium hydride (321 mg, 8.02 mmol) and 5-Fluoro-2-nitroaniline (1.78 grams, 11.49 mmol). The reaction flask was closed and placed under a nitrogen atmosphere, then allowed to stir at ambient temperature for 24 hours. Upon completion the reaction mixture was transferred to a separation funnel with ethyl acetate, and was washed with a saturated solution of sodium bicarbonate, followed by brine. The organic layer was dried over magnesium sulfate, filtered and solvents removed under reduced pressure. The crude product was purified by silica gel chromatography (DCM, 100%) to yield (R)-2-(2-(3-amino-4-nitrophenoxy)-1-phenylethylamino)-N-(3,4-difluorobenzyl)nicotinamide as 1.13 grams (29.8%) of a yellow oil. E/S MS m/e=520.17 (M+1).

A 250 mL round bottom flask was charged with (R)-2-(2-(3-amino-4-nitrophenoxy)-1-phenylethylamino)-N-(3,4-difluorobenzyl)nicotinamide (1.13 grams, 21.7 mmol) isopropyl alcohol (40 mL), methanol (20 mL) and 1N hydrochloric acid (21.7 mL, 21.7 mmol). To stirring solution was then added zinc powder (2.83 grams, 43.53 mmol) portion-wise. The reaction mixture was allowed to stir at ambient temperature for 2 hours. Upon completion, reaction mixture was diluted with a saturated solution of sodium bicarbonate (200 mL) and ethyl acetate (160 mL) and mixture was stirred vigorously. The resulting precipitate was filtered through a pad of celite, washing with copious ethyl acetate. The combined organics were then washed with a saturated solution of sodium bicarbonate, followed by brine, and dried over magnesium sulfate. The organic was the filtered and solvent removed under reduced pressure to yield (R)-2-(2-(3,4-diaminophenoxy)-1-phenylethylamino)-N-(3,4-difluorobenzyl)nicotinamide as 840 milligrams (79%) of a yellow oil. E/S MS m/e=490.20 (M+1).

A 50 mL round bottom flask was charged with (R)-2-(2-(3,4-diaminophenoxy)-1-phenylethylamino)-N-(3,4-difluorobenzyl)nicotinamide (840 mg, 1.72 mmol), 1,1'-Carbonyldiimidazole (309 mg, 1.91 mmol) and DMF (6 mL). The reaction mixture was heated at 60° C. for 12 hours. Upon completion the reaction mixture was purified by silica gel chromatography (DCM/MeOH 98:2) to yield (R)-N-(3,4-difluorobenzyl)-2-(2-(2-oxo-2,3-dihydro-1H-benzo[d]imidazol-5-yloxy)-1-phenylethylamino)nicotinamide (Ex. 16.1, 32 mg, 3.6%) of an off white solid. E/S MS m/e=516.18 (M+1); 1H NMR (400 MHz, MeOH-d-4) δ 4.18 (d, 2H), 4.43 (d, 2H), 5.48 (s, 1H), 6.61 (m, 3H), 6.79 (d, 1H), 7.07 (s, 1H), 7.15 (d, 2H), 7.23 (t, 3H), 7.36 (d, 2H), 7.81 (d, 1H), 7.99 (d, 1H).

Ex. 16.2 was prepared following the same procedure as for Ex. 16.1 from aminoethanol.

Ex. 16.3-16.12 were prepared using a procedure analogous to Ex. 16.1.

Ex. 16.13

N—((S)-1-(3,4-difluorophenyl)ethyl)-2-((R)-2-(1-methyl-2-oxo-2,3-dihydro-1H-benzo[d]imidazol-5-yloxy)-1-phenylethylamino)nicotinamide

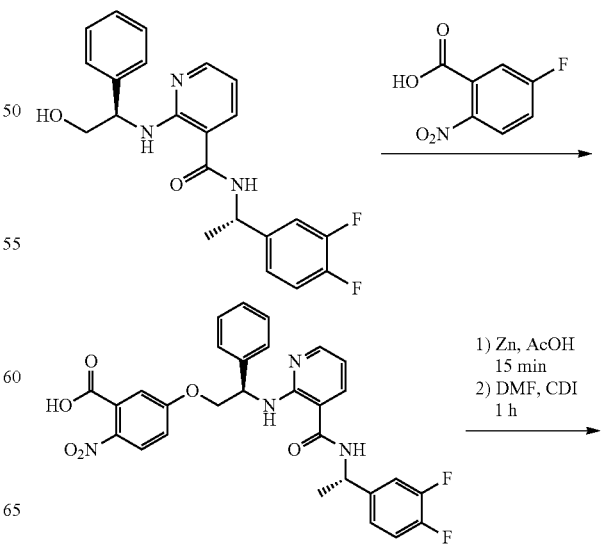

-continued

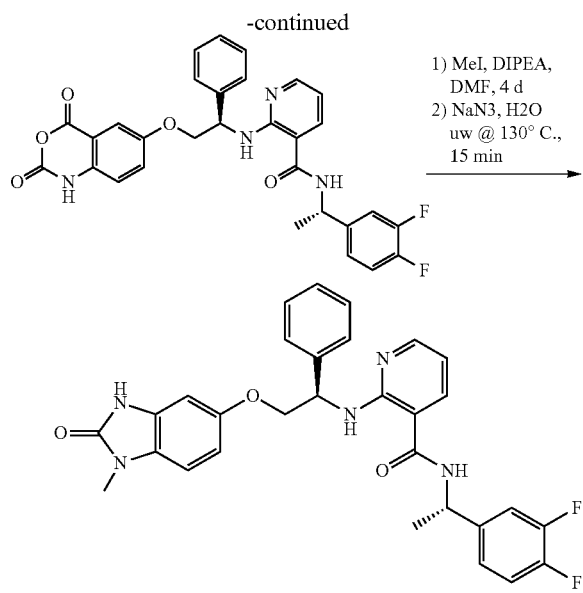

5-((R)-2-{3-[(S)-1-(3,4-Difluoro-phenyl)-ethylcarbamoyl]-pyridin-2-ylamino}-2-phenyl-ethoxy)-2-nitro-benzoic acid N-[(S)-1-(3,4-Difluoro-phenyl)-ethyl]-2-((R)-2-hydroxy-1-phenyl-ethylamino)-nicotinamide (205 mg, 0.515 mmol), and 5-fluoro-2-nitro-benzoic acid (166 mg, 0.894 mmol) were dissolved in N,N-dimethylformamide (5.1 mL). Added 60% sodium hydride dispersion in mineral oil (108 mg, 2.70 mmol) and stirred at rt. The reaction bubbled, turned cloudy, then turned red and clear. The reaction was monitored by LCMS. After 1 hour, the reaction required the addition of a second lot of sodium hydride in mineral oil. The reaction was subsequently quenched with water, acidified with concentrated hydrochloric acid, and extracted with 75 mL ethyl acetate. The organic phase was washed once with brine, dried over magnesium sulfate, evaporated, and purified by flash chromatography (0-100% ethyl acetate:hexanes, silica gel). Collected 258 mg of a yellow solid (89%). ES (+) MS m/e=563.2 (M+1). $^1$H NMR (300 MHz, DMSO-$d_6$) Shift 8.94 (d, J=7.55 Hz, 1H), 8.85 (d, J=7.55 Hz, 1H), 8.16 (dd, J=1.51, 4.91 Hz, 1H), 8.12 (dd, J=1.70, 7.74 Hz, 1H), 8.02 (d, J=9.06 Hz, 1H), 7.16-7.51 (m, 10H), 6.67 (dd, J=4.91, 7.55 Hz, 1H), 5.56-5.68 (m, 1H), 5.14 (quin, J=7.18 Hz, 1H), 4.39-4.60 (m, 2H), 1.44 (d, J=7.18 Hz, 3H).

N-[(S)-1-(3,4-Difluoro-phenyl)-ethyl]-2-[(R)-2-(2,4-dioxo-1,4-dihydro-2H-3,1-benzoxazin-6-yloxy)-1-phenyl-ethylamino]-nicotinamide 5-((R)-2-{3-[(S)-1-(3,4-Difluoro-phenyl)-ethylcarbamoyl]-pyridin-2-ylamino}-2-phenyl-ethoxy)-2-nitro-benzoic acid (258 mg, 0.459 mmol), zinc powder (307 mg, 4.69 mmol), and acetic acid (4.5 mL) were stirred at rt for 15 minutes. The reaction was diluted with ethyl acetate, and filtered through Celite. The filtrant was rinsed thoroughly with ethyl acetate, and the combined organic washes were evaporated to dryness. Collected 0.246 g of a yellow solid. The crude material, 2-amino-5-((R)-2-{3-[(S)-1-(3,4-difluoro-phenyl)-ethylcarbamoyl]-pyridin-2-ylamino}-2-phenyl-ethoxy)-benzoic acid, was used without further purification. ES (+) MS m/e=533.2 (M+1).

2-Amino-5-((R)-2-{3-[(S)-1-(3,4-difluoro-phenyl)-ethylcarbamoyl]-pyridin-2-ylamino}-2-phenyl-ethoxy)-benzoic acid (246 mg, 0.463 mmol) was dissolved in N,N-dimethylformamide (3.0 mL) and chilled in an ice bath. Added N,N-Carbonyldiimidazole (90.0 mg, 0.555 mmol), warmed to rt, and stirred for 30 minutes. The reaction was monitored by LCMS and shown to be incomplete. Therefore more N,N-Carbonyldiimidazole (38 mg) were added and the reaction was complete. Added 75 mL ethyl acetate and washed with 75 mL saturated sodium bicarbonate, water, and brine. The organic phase was dried over magnesium sulfate, filtered, evaporated, and purified by flash chromatography (0-70% ethyl acetate:hexanes, silica). Collected 155 mg of a yellow powder (60%). ES (+) MS m/e=559.2 (M+1). $^1$H NMR (300 MHz, CDCl$_3$) δ 8.77 (d, J=7.18 Hz, 1H), 8.32 (d, J=4.53 Hz, 1H), 7.73 (br. s., 1H), 7.63 (dd, J=1.32, 7.74 Hz, 1H), 7.45 (d, J=7.18 Hz, 2H), 7.35 (t, J=7.36 Hz, 2H), 7.23-7.31 (m, 2H), 7.04-7.22 (m, 3H), 6.97 (d, J=9.06 Hz, 1H), 6.52-6.63 (m, 1H), 6.27 (br. s., 1H), 5.70 (q, J=6.04 Hz, 1H), 5.23 (quin, J=6.99 Hz, 1H), 4.40-4.51 (m, 1H), 4.25-4.40 (m, 1H), 3.00 (s, 1H), 1.57 (d, J=6.80 Hz, 3H).

N—((S)-1-(3,4-difluorophenyl)ethyl)-2-((R)-2-(1-methyl-2-oxo-2,3-dihydro-1H-benzo[d]imidazol-5-yloxy)-1-phenylethylamino)nicotinamide N-[(S)-1-(3,4-Difluoro-phenyl)-ethyl]-2-[(R)-2-(2,4-dioxo-1,4-dihydro-2H-3,1-benzoxazin-6-yloxy)-1-phenyl-ethylamino]-nicotinamide (155 mg, 0.278 mmol) was dissolved in N,N-dimethylformamide (7.0 mL). Added N,N-diisopropylethylamine (193 μL, 1.11 mmol) followed by methyl iodide (69.1 μL, 1.11 mmol). The reaction was stirred at room temperature for 3 days. Afterwards additional methyl iodide (10 μL) and N,N-diisopropylethylamine (28 μL) were added and stirred for 24 hours. The reaction was diluted with ethyl acetate (75 mL) and washed with 75 mL water, and 75 mL of brine. The organic phase was dried over magnesium sulfate and evaporated. Collected 170 mg of a yellow foam, identified as N-[(S)-1-(3,4-Difluoro-phenyl)-ethyl]-2-[(R)-2-(1-methyl-2,4-dioxo-1,4-dihydro-2H-3,1-benzoxazin-6-yloxy)-1-phenyl-ethylamino]-nicotinamide, and carried the crude material to the next step.

N-[(S)-1-(3,4-Difluoro-phenyl)-ethyl]-2-[(R)-2-(1-methyl-2,4-dioxo-1,4-dihydro-2H-3,1-benzoxazin-6-yloxy)-1-phenyl-ethylamino]-nicotinamide (170 mg, 0.297 mmol) and sodium azide (116 mg, 1.78 mmol) were stirred in water (4.0 mL) and heated in a microwave at 130° C. for 15 minutes. Added ethyl acetate and washed with sodium bicarbonate, and brine. The organic phase was dried over magnesium sulfate, evaporated, and purified by Gilson HPLC. Collected 3.0 mg of N—((S)-1-(3,4-difluorophenyl)ethyl)-2-((R)-2-(1-methyl-2-oxo-2,3-dihydro-1H-benzo[d]imidazol-5-yloxy)-1-phenylethylamino)nicotinamide as a white powder as the bis-TFA salt. ES (+) MS m/e=544.2 (M+1). 1H NMR (300 MHz, DMSO-d6) Shift 10.67 (s, 1H), 8.91 (d, J=7.55 Hz, 1H), 8.78 (d, J=7.55 Hz, 1H), 8.03 (dd, J=1.89, 7.55 Hz, 1H), 8.07 (dd, J=1.89, 4.91 Hz, 1H), 7.39 (ddd, J=2.64, 7.55, 11.71 Hz, 1H), 7.29-7.35 (m, 3H), 7.11-7.29 (m, 4H), 6.86 (d, J=9.06 Hz, 1H), 6.57 (dd, J=4.91, 7.55 Hz, 1H), 6.53 (s, 1H), 6.52 (dd, J=2.40, 7.30 Hz, 1H), 5.42-5.54 (m, 1H), 5.09 (quin, J=7.27 Hz, 1H), 4.17 (tt, J=5.15, 9.96 Hz, 2H), 2.47 (s, 3H), 1.38 (d, J=7.18 Hz, 3H).

Example 17.1

N-(3,4-difluorobenzyl)-2-(3-(1-oxoisoindolin-4-yl)phenylamino)-nicotinamide

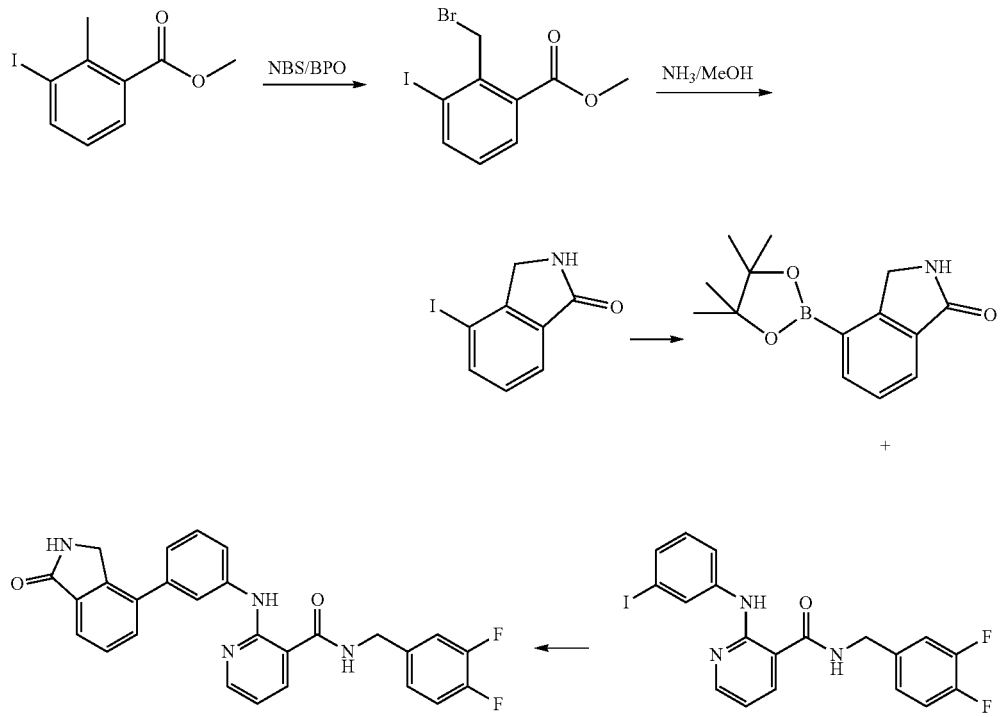

To a solution of 3-Iodo-2-methylbenzoic acid (10 grams, 38.16 mmol) in Dichloromethane (20 mL) and Methanol (5 mL) was added dropwise TMS-diazomethane 2.0M in Hexanes (38.16 mL, 76.32 mmol). Reaction was done when intense yellow color remained, and all solvents were removed to yield 3-iodo-2-methylbenzoate as a yellow oil (10.53 g, 100%) without further purification. E/S MS m/e=277 (M+1).

A solution of methyl 3-iodo-2-methylbenzoate (10.53 grams, 38.16 mmol) in carbon tetrachloride (100 mL) was stirred at ambient temperature until homogenous. To this mixture was then added benzoyl peroxide (184.8 mg, 0.763 mmol) and N-bromosuccinamide (6.79 grams, 38.16 mmol). Reaction solution was heated to reflux for 16 hours. Upon completion, N-bromsuccinamide was filtered from solution through a medium filter frit. All solvents were removed under reduced pressure to yield methyl 2-(bromomethyl)-3-iodobenzoate (9.45 g, 70%) of a yellowish brown solid. E/S MS m/e=354.88 (M+1).

To a solution of yield methyl 2-(bromomethyl)-3-iodobenzoate (9.45 grams, 26.71 mmol) in methanol (30 mL) was added 7N Ammonia in methanol (100 mL). The reaction mixture was allowed to stir at ambient temperature until the formation of a precipitate was observed. Precipitates were collected and washed with dichloromethane, yielding 4-iodoisoindolin-1-one (2.99 g, 43.2%) as a white solid. E/S MS m/e=260 (M+1). $^1$H NMR (400 MHz, DMSO-d$_6$) δ 5.74 (s, 2H), 7.29 (t, 1H), 7.68 (d, 1H), 7.96 (d, 1H), 8.77 (s, 1H).

A mixture of 4-iodoisoindolin-1-one (500 mg, 1.93 mmol), Bis(pinocolato)diboron (538 mg, 2.12 mmol), Bis(triphenylphosphine)palladium (II) dichloride (157.6 mg, 0.193 mmol), Potassium acetate (663 mg, 6.76 mmol), and N,N-dimethylformamide (20 mL). The reaction mixture was heated to 90° C. under a nitrogen atmosphere for 4 hours. Reaction mixture was used without further work up in following Suzuki reaction. E/S MS m/e=260 (M+1).

A mixture of the above product (181.3 mg, 0.700 mmol), N-(3,4-difluorobenzyl)-2-(3-iodophenylamino)nicotinamide (295 mg, 0.634 mmol), Bis(triphenylphosphine)-palladium (II) dichloride (52 mg, 0.0634 mmol), 1.2 M Sodium bicarbonate (1.58 mL, 1.90 mmol), and N,N-Dimethylformamide (15 mL) was heated to 80° C. under a nitrogen atmosphere for 1.5 hours. Reaction mixture was filtered through a Celite pad and washed with ethyl acetate. Washed with saturated sodium bicarbonate, brine, and dried over magnesium sulfate. Solvents were removed under reduced pressure. The resulting residue was purified by HPLC to yield N-(3,4-difluorobenzyl)-2-(3-(1-oxoisoindolin-4-yl)phenylamino)nicotinamide (Ex. 17.1) (20 mg, 6%) as an off white solid. E/S MS m/e=471.47 (M+1); 1H NMR (400 MHz, DMSO-d-6) δ 4.48 (d, 1H), 4.53 (s, 2H), 6.90 (t, 1H), 7.21 (d, 2H), 7.41 (t, 3H), 7.59 (d, 3H), 7.68 (d, 2H), 8.04 (s, 1H), 8.19 (d, 1H), 8.33 (d, 1H), 8.65 (s, 1H), 9.37 (t, 1H), 10.95 (s, 1H).

Ex. 17.2 was prepared following the procedure for Ex. 17.1 from N-(3,4-difluorobenzyl)-2-(3-iodo-4-methylphenylamino)nicotinamide and 4-iodoisoindolin-1-one.

Ex. 17.3 was prepared following the procedure for Ex. 17.1 from N-(3,4-difluorobenzyl)-2-(3-iodophenylamino) nicotinamide and 8-iodo-[1,2,4]triazolo[4,3-a]pyridin-3 (2H)-one (Prepared following procedure reported in reference: Sun, Q., et. al., WO 2006138695).

Example 18.1

2-((4-(1H-pyrrolo[2,3-b]pyridin-3-yl)pyridin-2-ylmethyl)amino)-N-(3,4-difluorobenzyl)nicotinamide Ex. 18.1 was prepared following the procedure for Ex. 7.1 from (4-(1-(phenylsulfonyl)-1H-pyrrolo[2,3-b]pyridin-3-yl)pyridin-2-yl)methanamine and N-(3,4-difluorobenzyl)-2-fluoronicotinamide.

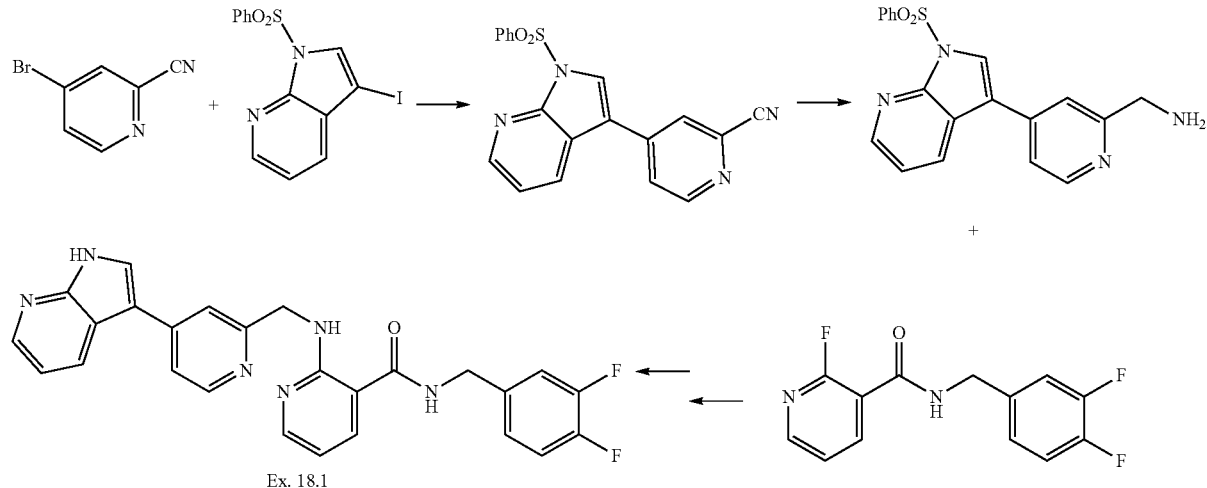

Ex. 18.1

A mixture of 4-Bromopyridine-2-carbonitrile (4.0 grams, 21.85 mmol), Bis(pinocolato)diboron (6.11 grams, 24.04 mmol), Dichloro(bis-diphenylphosphine)palladium (II) (1.78 grams, 2.185 mmol), Potassium acetate (7.51 grams, 76.47 mmol), and N,N-dimethylformamide (60 mL) was heated under a nitrogen atmosphere at 80° C. for 4 hours. Upon completion mixture was filtered through a celite pad and washed with ethyl acetate. Mixture was then partitioned between ethyl acetate and a saturated solution of sodium bicarbonate, the organic was collected and washed with brine, then dried over magnesium sulfate. The organic phase was filtered and evaporated to yield 4-(4,4,5,5-tetramethyl-1,3,2-dioxaborolan-2-yl)picolinonitrile (4.5 g, 89%) as a brown solid. E/S MS m/e=231.07 (M+1).

A mixture of 4-(4,4,5,5-tetramethyl-1,3,2-dioxaborolan-2-yl)picolinonitrile (2.51 grams, 5.91 mmol), Iodoazaindole (3.49 grams, 9.09 mmol), Dichloro(bis-diphenylphosphine)palladium (II) (742 mg, 0.909 mmol), 1.2 M Sodium bicarbonate (22.72 mL, 27.27 mmol), and N,N-dimethylformamide (45.5 mL) was heated at 90° C. under nitrogen for 3 hours. Upon completion reaction mixture was filtered through a Celite pad and washed with ethyl acetate. Reaction mixture was partitioned between ethyl acetate and a saturated solution of sodium bicarbonate. The organic phase was isolated, washed with brine, dried over magnesium sulfate, filtered and evaporated. Crude product was purified by silica gel chromatography (Hexanes/Ethyl Acetate 97:3) to yield 1.77 grams (55.3%) of a peach colored solid. E/S MS m/e=361 (M+1).

A parr shaker flask was charged with 4-(1-(phenylsulfonyl)-1H-pyrrolo[2,3-b]pyridin-3-yl)picolinonitrile (1.10 grams, 2.805 mmol), Methanol (30 mL), conc. HCl (3 mL), and 10% Palladium on carbon (scoop). Placed on Parr apparatus and allowed to react at 35 psi for 30 minutes. The reaction mixture was filtered through a celite pad, and washed with Methanol. The organics were evaporated under reduced pressure, and used without further purification in the next reaction. Yielded (4-(1-(phenylsulfonyl)-1H-pyrrolo[2,3-b]pyridin-3-yl)pyridin-2-yl)methanamine (820 mg, 73.2%) as a white solid. E/S MS m/e=365 (M+1).

Example 19

Ex. 19.1

(S)-2-(2-(1H-indol-6-yloxy)ethylamino)-N-(1-(3,4-difluorophenyl)ethyl)nicotinamide To a mixture of 6-Hydroxyindole (1.0 g, 0.0075 mol) and (2-hydroxy-ethyl) carbamic acid t-butyl ester (2, 1.453 g, 0.009012 mol) in THF (20 mL, 0.2 mol) was added triphenylphosphine (2.955 g, 0.01126 mol) and diisopropyl azodicarboxylate (2.218 mL, 0.01126 mol). The reaction mixture stirred at RT overnight. The crude was diluted with EtOAc and washed with saturated NaHCO$_3$. The organic layer was separated, dried over MgSO$_4$, and filtered. The filtration was concentrated. The crude was purified by ISCO column chromatography (EtOAC/hexane, gradient) to give 0.55 g of desired product, [2-(1H-Indol-6-yloxy)-ethyl]-carbamic acid tert-butyl ester. LCMS: RT 1.51 min.; MH+ 277.10. $^1$H NMR (400 MHz, DMSO-d$_6$) δ 10.84 (br. s., 1H), 7.39 (d, J=8.53 Hz, 1H), 7.13-7.21 (m, 1H), 6.99 (t, J=5.40 Hz, 1H), 6.88 (d, J=2.26 Hz, 1H), 6.64 (dd, J=2.26, 8.53 Hz, 1H), 6.31 (t, J=2.01 Hz, 1H), 3.94 (t, J=6.02 Hz, 2H), 3.27-3.32 (m, 2H), 1.39 (s, 9H).

To a mixture of [2-(1H-Indol-6-yloxy)-ethyl]-carbamic acid tert-butyl ester (500 mg, 0.002 mol) in 1,4-dioxane (9 mL) was added 4 M of hydrogen chloride in 1,4-dioxane (4 mL, 0.004 mol) was heated at 40° C. for 1 h. The solvent was removed under vacuo. The crude (370 mg) was used directly in the next step without further purifications. LCMS: RT 0.71 min.; MH+177.20.

To a mixture of crude 2-(1H-Indol-6-yloxy)-ethylamine hydrochloride (4, 100.0 mg, 0.4702 mmol) in 1-butanol (5 mL, 0.05 mol) was added N,N-diisopropylethylamine (0.2457 mL, 1.410 mmol). Stirred for 5 min, then N-[(S)-1-(3,4-Difluoro-phenyl)-ethyl]-2-fluoro-nicotinamide (5, 131.8 mg, 0.4702 mmol) was added. The reaction was refluxed at 125° C. overnight. The solvent was removed under vacuo. The crude was purified by HPLC followed by prep-TLC (DCM+2% 2M NH$_3$/MeOH) to give desired product, (S)-2-(2-(1H-indol-6-yloxy)ethylamino)-N-(1-(3,4-difluorophenyl)ethyl)nicotinamide as a white powder (110 mg, 54%). LCMS: RT 1.49 min.; MH+ 437.20; $^1$H NMR (400 MHz, DMSO-d$_6$) δ 10.84 (br. s., 1H), 8.79 (d, J=7.53 Hz, 1H), 8.46 (t, J=5.52 Hz, 1H), 8.21 (dd, J=1.76, 4.77 Hz, 1H), 8.06 (dd, J=1.88, 7.66 Hz, 1H), 7.29-7.49 (m, 3H), 7.22 (ddd, J=2.38, 4.33, 6.34 Hz, 1H), 7.14-7.19 (m, 1H), 6.93 (d, J=2.26 Hz, 1H), 6.57-6.67 (m, 2H), 6.31 (t, J=2.13 Hz, 1H), 5.12 (quin, J=7.15 Hz, 1H), 4.10 (t, J=5.77 Hz, 2H), 3.63-3.85 (m, 2H), 1.44 (d, J=7.03 Hz, 3H).

Ex. 19.2

(S,Z)-2-(2-(3-((1H-imidazol-5-yl)methylene)-2-oxoindolin-6-yloxy)ethylamino)-N-(1-(3,4-difluorophenyl)ethyl)nicotinamide To a solution of N-[(S)-1-(3,4-Difluoro-phenyl)-ethyl]-2-[2-(1H-indol-6-yloxy)-ethylamino]-nicotinamide (100 mg, 0.20 mol) in acetonitrile (3.0 mL) was added acetic acid (0.3 mL) and Bu$_4$N-Oxone (0.18 g, 2.2 eq, FW 355.53). The reaction was stirred at RT for 3 days. The solvent was removed under vacuo. The crude was purified by HPLC to give 24 mg (20%) of desired product, N-[(S)-1-(3,4-Difluoro-phenyl)-ethyl]-2-[2-(2-oxo-2,3-dihydro-1H-indol-6-yloxy)-ethylamino]-nicotinamide. LCMS: RT 1.11 min.; MH+ 453.20.
A solution of N-[(S)-1-(3,4-Difluoro-phenyl)-ethyl]-2-[2-(2-oxo-2,3-dihydro-1H-indol-6-yloxy)-ethylamino]-nicotinamide (7, 20 mg, 0.00004 mol), 1H-imidazole-5-carbaldehyde (5.1 mg, 0.053 mmol) and piperidine (0.0087 mL, 0.088 mmol) in ethanol (1 mL, 0.02 mol) was refluxed at 80° C. for 1h. The solvent was removed under vacuo. The crude was purified by HPLC to give the desired product, (S,Z)-2-(2-(3-((1H-imidazol-5-yl)methylene)-2-oxoindolin-6-yloxy)ethylamino)-N-(1-(3,4-difluorophenyl)ethyl)nicotinamide (3.7 mg, 15%). LCMS: RT 0.98 min.; MH+ 531.20; $^1$H NMR (400 MHz, DMSO-d$_6$) δ 11.15 (s, 1H), 8.81 (s, 2H), 8.47 (br. s., 1H), 8.22 (dd, J=1.76, 4.77 Hz, 1H), 8.09 (dd, J=1.76, 7.78 Hz, 2H), 7.64 (s, 1H), 7.58 (d, J=8.28 Hz, 1H), 7.27-7.51 (m, 2H), 7.21 (br. s., 1H), 6.66 (td, J=3.14, 4.58 Hz, 2H), 6.52 (d, J=2.26 Hz, 1H), 5.11 (s, 1H), 4.08-4.20 (m, 2H), 3.76 (br. s., 2H), 1.44 (d, J=7.28 Hz, 3H).

Example 20

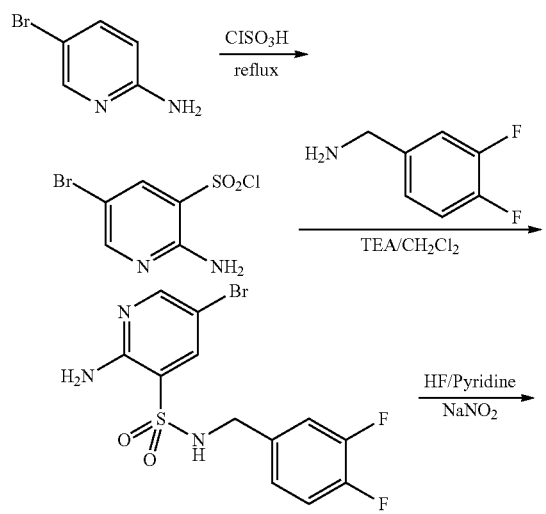

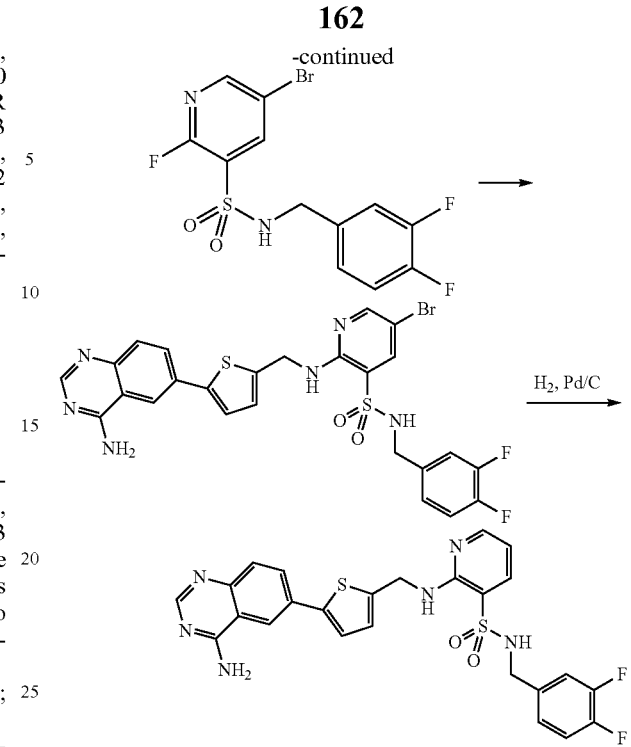

Ex. 20.1

2-(((5-(4-aminoquinazolin-6-yl)thiophen-2-yl)methyl)amino)-5-bromo-N-(3,4-difluorobenzyl)pyridine-3-sulfonamide To a cooled solution of chlorosulfonic acid (58 mL) under vigorous stirring was added 5-bromo-2-pyridinamine (4.3 g, 25 mmol) portionwise at 0° C. The reaction mixture was then heated to reflux for 16 h. Upon cooling to room temperature, the reaction mixture was poured into ice (100 g) with vigorous stirring. The resulting yellow precipitate was collected by suction filtration, washed with cold water and petroleum ether to provide 2-amino-5-bromopyridine-3-sulfonyl chloride as light yellow solid (5.0 g, yield: 74%). ESI-MS (M+H+): 272.8; $^1$H NMR (400 MHz, DMSO-d$_6$) δ: 9.12 (br, 2H), 8.32 (d, 1H), 8.11 (d, 1H).

To a solution of 2-amino-5-bromopyridine-3-sulfonyl chloride (4.08 g, 15.0 mmol) in dry CH$_2$Cl$_2$ (100 mL) was slowly added (3,4-difluorophenyl)methanamine (2.15 g, 15.0 mmol) and triethylamine (5.8 mL, 45.0 mmol). The reaction mixture was stirred at room temperature for 1 h. Solvent was removed and the crude mixture was purified by silica gel chromatography (PE/EA=10/1) to give 2-amino-5-bromo-N-(3,4-difluorobenzyl)pyridine-3-sulfonamide as a pink solid (2.32 g, yield: 40%). ESI-MS (M+H$^+$): 377.8; $^1$H NMR (400 MHz, CDCl$_3$) δ: 8.21 (d, 1H), 7.93 (d, 1H), 7.07-7.01 (m, 2H), 6.93-6.90 (m, 1H), 5.71 (br, 2H), 5.38 (t, 1H), 4.09 (d, 2H).

Sodium nitrite (464 mg, 6.7 mmol) was added in small portions to a solution of 2-amino-5-bromo-N-(3,4-difluorobenzyl)pyridine-3-sulfonamide (2.10 g, 5.6 mmol) in an HF/Pyridine mixture (40 mL) in a polyethylene reaction vessel, cooled at 0° C. The resulting solution was stirred at 0° C. for 1 h, then heated to 40-50° C. and stirred at this temperature for 1 h. The reaction mixture was poured into crushed ice (20 g), neutralized with sodium bicarbonate (pH=5), and extracted with ethyl acetate (50 mL×2). The combined organic phase was washed with water, dried with anhydrous sodium sulfate, and concentrated under the vacuo to give the product, 5-bromo-N-(3,4-difluorobenzyl)-2-fluoropyridine-3-sulfonamide, as a brown solid (1.2 g, yield: 60%). ESI-MS (M+H+): 382.8; $^1$H NMR (400 MHz, CDCl$_3$) δ: 8.42 (d, 1H), 8.30 (dd, 1H), 7.12-7.05 (m, 2H), 6.99-6.96 (m, 1H), 5.42 (t, 1H), 4.26 (d, 2H).

The mixture of 5-bromo-N-(3,4-difluorobenzyl)-2-fluoropyridine-3-sulfonamide (1.20 g, 3.16 mmol), 6-(5-(aminomethyl)thiophen-2-yl)quinazolin-4-amine (1.61 g, 6.32 mmol, 2.0 equiv) and NaHCO$_3$ (531 mg, 6.32 mmol, 2 equiv) in n-pentanol (5 mL) was stirred at 130° C. for 3 h, then the solvent was removed, the residue was purified by column chromatography (PE/EA=2:1) to give the product, 2-(((5-(4-aminoquinazolin-6-yl)thiophen-2-yl)methyl)amino)-5-bromo-N-(3,4-difluorobenzyl)pyridine-3-sulfonamide, as light yellow solid (680 mg, yield: 36%). ESI-MS (M+H+): 618.0; $^1$H NMR (400 MHz, DMSO-d$_6$) δ: 8.64 (t, 1H), 8.42 (d, 1H), 8.34 (d, 2H) 7.98 (dd, 1H), 7.83 (d, 1H), 7.83 (br, 2H), 7.65 (dd, 1H), 7.48 (d, 1H), 7.25-7.18 (m, 2H), 7.12-7.09 (m, 2H), 7.03-7.00 (br, 1H), 4.80 (d, 2H), 4.12 (d, 2H).

Ex. 20.2

2-(((5-(4-aminoquinazolin-6-yl)thiophen-2-yl)methyl)amino)-N-(3,4-difluorobenzyl)pyridine-3-sulfonamide 2-(((5-(4-aminoquinazolin-6-yl)thiophen-2-yl)methyl)amino)-5-bromo-N-(3,4-difluorobenzyl)pyridine-3-sulfonamide (50 mg, 0.16 mmol) was hydrogenated in the presence of Pd/C (25 mg) catalyst under 1 atmosphere of hydrogen in methanol (100 mL) for 24 h. The catalyst was filtered off and the solvent was evaporated, precipitated from methanol to give 2-(((5-(4-aminoquinazolin-6-yl)thiophen-2-yl)methyl)amino)-N-(3,4-difluorobenzyl)pyridine-3-sulfonamide as a light yellow solid (20 mg, yield: 47.0%). ESI-MS (M+H+): 538.8.; $^1$H NMR (400 MHz, DMSO-d$_6$) δ: 9.38 (br, 2H), 8.70 (s, 1H), 8.57 (d, 1H), 8.48 (t, 1H), 8.2 (dd, 1H), 8.18 (dd, 1H), 7.85 (dd, 1H), 7.74 (d, 1H), 7.53 (d, 1H), 7.27-7.13 (m, 2H), 7.14 (d, 1H), 7.05-7.03 (m, 2H), 6.73-6.69 (m, 1H), 4.83 (d, 2H), 4.07 (d, 2H).

Synthesis of 2-(9H-pyrido[2,3-b]indol-7-yloxy)ethanamine, intermediate for Ex. 21

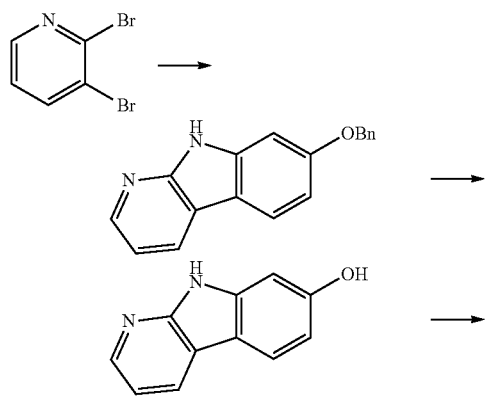

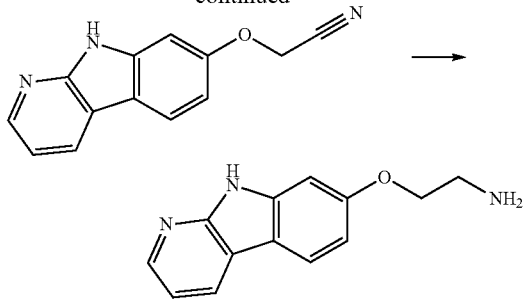

A mixture of 2,3-dibromopyridine (1.01 g, 4.27 mmol), 3-(benzyloxy)aniline (0.93 g, 4.69 mmol, 1.1 eq), Pd(OAc)$_2$ (0.05 g, 0.22 mmol, 0.05 eq), PPh$_3$ (0.17 g, 0.43 mmol, 0.1 eq) and $^t$BuONa (0.49 g, 5.12 mmol, 1.2 eq) in o-xylene. (10 mL) was stirred under nitrogen atmosphere for about 5 min. Then the mixture was heated to 120° C. for 3 h. The reaction mixture was allowed to cool to rt, and then Pd(OAc)$_2$ (0.05 g, 0.22 mmol, 0.05 eq), PCy$_3$.HBF$_4$ (0.16 g, 0.43 mmol, 0.1 eq), DBU (1.30 g, 8.53 mmol, 2.0 eq) and DMA (10 mL) were added to reaction vessel. The reaction mixture was degassed again heated to 145° C. for 30 h. The reaction mixture was concentrated under reduced pressure then dissolved in ethyl acetate (60 mL×4) while heating at 40° C.-50 OC. The mixture was washed with water (10 mL×3), brine (5 mL×1) and concentrated. The residue was purified by column chromatography on silica gel using PE/EA (1/1) to give 7-(benzyloxy)-9H-pyrido[2,3-b]indole as yellow solid (440 mg, yield: 38%). LCMS (M+1+): 275.1. $^1$H NMR: (400 MHz, DMSO-d$_6$) δ: 11.68 (s, 1H), 8.37-8.30 (m, 2H), 8.04 (d, 1H), 7.63-7.34 (m, 5H), 7.15 (t, 1H), 7.13 (s, 1H), 7.05-6.91 (m, 1H), 5.22 (s, 2H).

7-(benzyloxy)-9H-pyrido[2,3-b] (1.12 g, 4.09 mmol, 1.0 eq) was dissolved in THF (30 mL) and MeOH (30 mL), then Pd/C (10%, containing 70% H$_2$O) (1.73 g) was added. The reaction mixture was stirred under H$_2$ atmosphere for 20 h at rt. Then the mixture was filtered and concentrated to give 9H-pyrido[2,3-b]indol-7-ol as pale yellow solid (0.47 g, yield: 63%). ESI-MS (M+1$^+$): 185.2. $^1$H NMR (400 MHz, DMSO-d$_6$) δ: 11.46 (s, 1H), 9.62 (s, 1H), 8.28-8.24 (m, 2H), 7.90 (d, 1H), 7.10 (dd, 1H), 6.85 (d, 1H), 6.68 (dd, 1H).

To a solution of 9H-pyrido[2,3-b]indol-7-ol (211 mg, 1.15 mmol, 1.0 eq) in 2-butanone (6 mL) were added BrCH$_2$CN (206 mg, 1.72 mmol, 1.5 eq), K$_2$CO$_3$ (318 mg, 2.30 mmol, 2.0 eq) and KI (20 mg, 0.12 mmol, 0.1 eq). The mixture was stirred at 60° C. for 3 h. Then H$_2$O (5 mL) was added. The solvent was removed and the residue was dissolved in EtOAc (30 mL), washed with H$_2$O (5 mL×2), concentrated and purified by column chromatography using petroleum ether/ethyl acetate (2/1) to give 2-(9H-pyrido[2,3-b]indol-7-yloxy)acetonitrile as white solid (110 mg, yield: 45%). LCMS (M+H$^+$): 224.0. $^1$H NMR (400 MHz, DMSO-d$_6$) δ: 11.84 (s, 1H), 8.41-8.34 (m, 2H), 8.10 (d, 1H), 7.18-7.14 (m, 2H), 6.94 (dd, 1H), 5.28 (s, 2H).

To a solution of 2-(9H-pyrido[2,3-b]indol-7-yloxy)acetonitrile (70 mg, 0.32 mmol) in MeOH (20 mL) and THF (20 mL) was added Pd/C (10%, containing 70% H$_2$O) (200 mg). Then the mixture was stirred under H$_2$ atmosphere for 25 h. The mixture was filtered and concentrated to give 2-(9H-pyrido[2,3-b]indol-7-yloxy)ethanamine as white solid. LCMS (M+1+): 228.1

Ex. 21-24 were synthesized in a manner consistent with the final step of Ex. 19.2.

Syntheses of Nicotinamide Intermediates

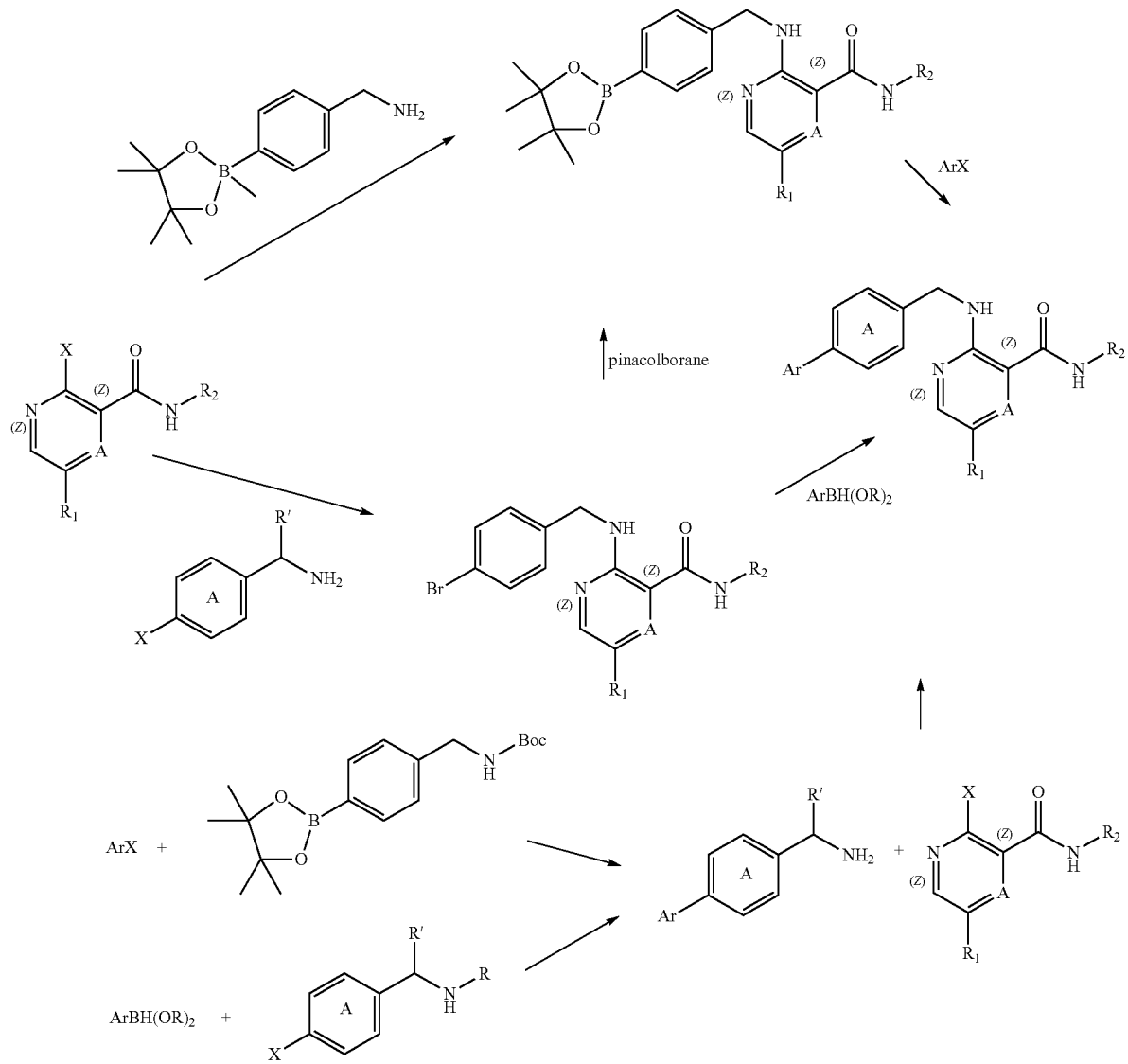

5-cyano-2-fluoro-N-(4-fluorobenzyl)nicotinamide

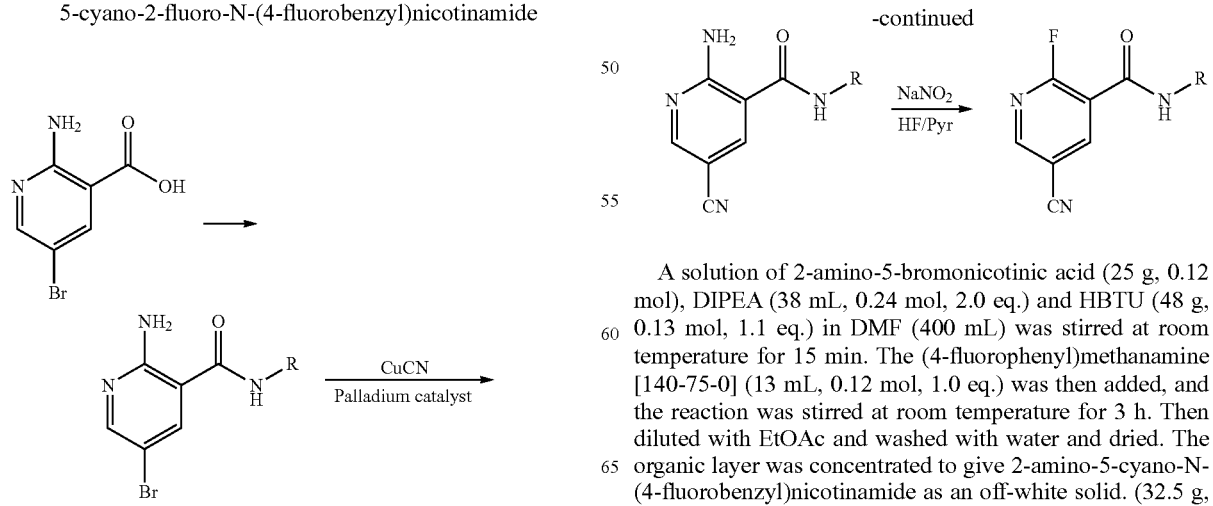

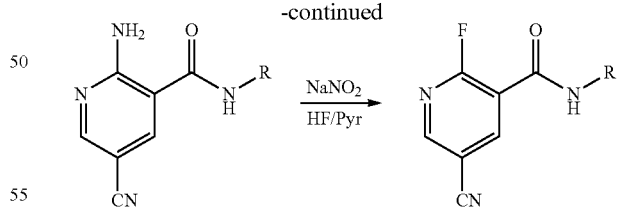

A solution of 2-amino-5-bromonicotinic acid (25 g, 0.12 mol), DIPEA (38 mL, 0.24 mol, 2.0 eq.) and HBTU (48 g, 0.13 mol, 1.1 eq.) in DMF (400 mL) was stirred at room temperature for 15 min. The (4-fluorophenyl)methanamine [140-75-0] (13 mL, 0.12 mol, 1.0 eq.) was then added, and the reaction was stirred at room temperature for 3 h. Then diluted with EtOAc and washed with water and dried. The organic layer was concentrated to give 2-amino-5-cyano-N-(4-fluorobenzyl)nicotinamide as an off-white solid. (32.5 g, yield: 87%). ESI-MS: 325.9 (M+H)$^+$; $^1$H NMR (400 MHz, CDCl$_3$) δ: 8.16 (d, 1H), 7.98 (s, 1H), 7.73 (d, 1H), 7.33-7.29 (m, 2H), 7.06-7.02 (m, 2H), 4.55 (d, 2H).

A mixture of 2-amino-5-bromo-N-(4-fluorobenzyl)nicotinamide (25 g, 77.4 mmol), CuCN (10.3 g, 120 mmol, 1.5 eq.), TEA (32.5 mN, 230 mmol, 3.0 eq.) and PdCl$_2$(dppf) (6.3 g, 7.7 mmol, 0.1 eq.) in DMF (400 mL) was heated at 130° C. 15 h. Then the mixture was cooled to room temperature and extracted with EtOAc and water. The organic layer was concentrated and purified on silica gel column with PE/EA=2/1 to give 2-Fluoro-5-cyano-N-(4-fluorobenzyl)nicotinamide as a yellow solid. (12.3 g, yield: 53%). ESI-MS: 271.0 (M+H)$^+$.

2-amino-5-cyano-N-(4-fluorobenzyl)nicotinamide (12 g, 44.4 mmol) was stirred in 70% HF in pyridine (140 mL, 4 mmol, 90 eq.) in a PTFE vial, chilled in an ice bath and added NaNO$_2$ (7.66 g, 111.2 mmol, 2.5 eq.), stirred in an ice bath for 4 h. Then the mixture was quenched with ice and water, the precipitates were collected and washed with water and dried, purified by silica gel column with PE/EA=5/1 to give 5-cyano-2-fluoro-N-(4-fluorobenzyl)nicotinamide as an off-white solid. (5.1 g, yield: 42%). ESI-MS: 273.9 (M+H)$^+$; $^1$H NMR (400 MHz, CDCl$_3$) δ: 8.90-8.87 (m, 1H), 8.64-8.63 (m, 1H), 7.35-7.31 (m, 2H), 7.09-7.04 (m, 3H), 4.65 (d, 2H).

The following intermediates were prepared analogously from the corresponding starting materials:

(S)-5-cyano-N-(1-(3,4-difluorophenyl)ethyl)-2-fluoronicotinamide from (S)-1-(3,4-difluorophenyl)ethanamine. ESI-MS: 306.0 (M+H)$^+$; $^1$H NMR (400 MHz, CDCl$_3$) δ: 8.84-8.81 (m, 1H), 8.63 (s, 1H), 7.20-7.08 (m, 3H), 6.94 (br, 1H), 5.28-5.24 (m, 1H), 1.59 (d, 3H);

(S)-5-cyano-2-fluoro-N-(1-(4-fluorophenyl)ethyl)nicotinamide from (S)-1-(4-fluorophenyl)ethan amine. $^1$H NMR (400 MHz, CDCl$_3$) δ: 8.85-8.82 (m, 1H), 8.63-8.62 (m, 1H), 7.37-7.33 (m, 2H), 7.06-7.04 (m, 3H), 5.32-5.29 (m, 1H), 1.61 (d, 3H). ESI-MS (M+H$^+$): 288.0;

5-cyano-N-(3,4-difluorobenzyl)-2-fluoronicotinamide from (3,4-difluorophenyl)methanamine. $^1$H NMR (400 MHz, DMSO-d$_6$) δ: 9.23 (t, 1H), 8.92 (d, 1H), 8.78 (dd, 1H), 7.45-7.34 (m, 2H), 7.22-7.19 (m, 1H), 4.48 (d, 2H). ESI-MS (M+H+): 292.0.

Synthesis of 2-chloro-N-(4-fluorophenyl)-5-(trifluoromethyl)nicotinamide

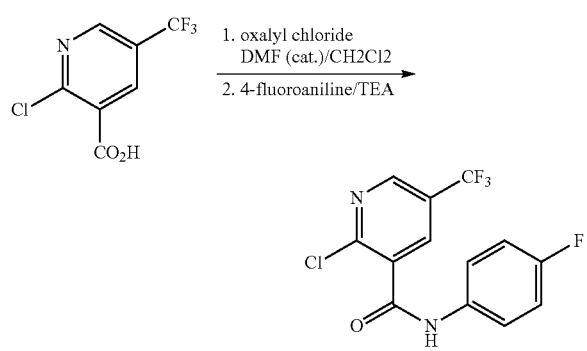

To a solution of 2-chloro-5-(trifluoromethyl)nicotinic acid (9 g, 40 mmol, 1.0 eq) in CH$_2$Cl$_2$ (30 mL) and DMF (15 mL) was added oxalyl chloride (4.7 g, 48 mmol, 1.2 eq) dropwise. The reaction mixture was stirred at rt for 1 h. Then TEA (16.9 mL, 120 mmol, 3 eq) and 4-fluoroaniline (4.89 g, 44 mmol, 1.1 eq) was added. The reaction mixture was stirred for 1 h and then concentrated and purified by silica gel column (PE: EA=10:1) to give 2-chloro-N-(4-fluorophenyl)-5-(trifluoromethyl)nicotinamide as a white solid (10 g, yield: 79%). ESI-MS (M+H$^+$): 318.7; $^1$H NMR (500 MHz, CDCl$_3$) δ: 8.78 (d, 1H), 8.46 (d, 1H), 8.11 (br, 1H), 7.63-7.60 (m, 2H), 7.14-7.11 (m, 2H).

Syntheses of Pyrazine Intermediates

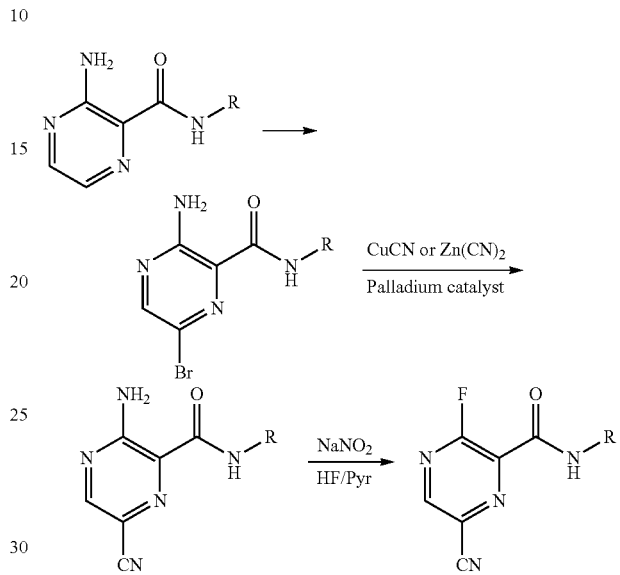

(S)-6-cyano-N-(1-(3,4-difluorophenyl)ethyl)-3-fluoropyrazine-2-carboxamide

A solution of 3-aminopyrazine-2-carboxylic acid (10.1 g, 72.54 mmol), Et$_3$N (41 mL, 290.1 mmol, 4.0 eq) and HBTU (33.1 g, 87.05 mmol, 1.2 eq) in DCM (200 mL) was stirred at room temperature for 15 min. Then (S)-1-(3,4-difluorophenyl)ethanamine hydrochloride (14 g, 72.54 mmol, 1.0 eq) was added and the reaction was stirred at room temperature for 3 h. EtOAc (300 mL) was added and the mixture was washed with water (300 mL×3). The organic layer was dried (Na$_2$SO$_4$), concentrated and purified by silica gel column (PE: EA=5:1) to give (S)-3-amino-N-(1-(3,4-difluorophenyl)ethyl)-pyrazine-2-carboxamide as a red oil. (26 g, yield: 93%). ESI-MS (M+H)$^+$: 279.1; $^1$H NMR (400 MHz, CDCl$_3$) δ: 8.14-8.11 (m, 2H), 7.78 (s, 1H), 7.26-7.09 (m, 3H), 5.17-5.13 (m, 1H), 1.57-1.56 (d, 3H).

To a solution of (S)-3-amino-N-(1-(3,4-difluorophenyl)ethyl)pyrazine-2-carboxamide (26 g, 93.5 mmol) in DMF (250 mL) was added NBS (25 g, 140.3 mmol, 1.5 eq). The mixture was stirred at room temperature for 1 h. Then the mixture was diluted with EtOAc (300 mL) and washed with water (300 mL×3). The organic layer was dried (Na$_2$SO$_4$), concentrated and purified by silica gel column (PE: EA=5:1) to give (S)-3-amino-6-bromo-N-(1-(3,4-difluorophenyl) ethyl)pyrazine-2-carboxamide as a yellow solid (28 g, yield: 84%). ESI-MS (M+H)$^+$: 357.0; $^1$H NMR (400 MHz, DMSO-d$_6$) δ: 8.87 (d, 1H), 8.32 (s, 1H), 7.48 (br, 2H), 7.35-7.30 (m, 2H), 7.23 (br, 1H), 5.10-5.06 (m, 1H), 1.48 (d, 3H).

A mixture of (S)-3-amino-6-bromo-N-(1-(3,4-difluorophenyl)ethyl)pyrazine-2-carboxamide (10 g, 28.1 mmol), CuCN (3 g, 33.7 mmol, 1.2 eq), TEA (11.7 mL, 84.3 mmol, 3.0 eq) and PdCl$_2$(dppf)DCM (2.3 g, 2.8 mmol, 0.1 eq) in anhydrous DMA (30 mL) was heated to 130° C. for 2 h under N$_2$. Then the mixture was cooled to rt, diluted with EtOAc (250 mL) and filtered through Celite. The filtrate was washed with NH$_3$—H$_2$O (250 mL×3) and dried. The organic layer was concentrated and purified by silica gel column (PE: EA=4:1) to give (S)-3-amino-6-cyano-N-(1-(3,4-difluorophenyl)ethyl)pyrazine-2-carboxamide as a yellow solid (3.83 g, yield: 45%). ESI-MS (M+H)$^+$: 304.1; $^1$H NMR (400 MHz, CDCl$_3$) δ: 9.18 (d, 1H), 8.63 (s, 1H), 8.48 (s, 1H), 8.27 (s, 1H), 7.50-7.21 (m, 3H), 5.11-5.07 (m, 1H), 1.48 (d, 3H).

(S)-3-amino-6-cyano-N-(1-(3,4-difluorophenyl)ethyl)pyrazine-2-carboxamide (10 g, 33 mmol) was dissolved in 70% HF in pyridine (40 mL, 45 eq) in a PTFE vial and chilled in ice bath, then NaNO$_2$ (9.1 g, 132 mmol, 4.0 eq) was added slowly. The reaction mixture was stirred for 30 min under ice bath. Then the mixture was quenched with ice and water, the precipitates were collected and washed with water (50 mL), the residue was purified by silica gel column (PE:EA=4:1) to give (S)-6-cyano-N-(1-(3,4-difluorophenyl)ethyl)-3-fluoropyrazine-2-carboxamide as a white solid (5.86 g, yield: 58%). ESI-MS (M+H)$^+$: 307.1. HPLC: 214 nm: 98.69%; 254 nm: 91.23%; $^1$H NMR (400 MHz, DMSO-d$_6$) δ: 9.46-9.44 (m, 1H), 9.17 (s, 1H), 7.52-7.27 (m, 3H), 5.18-5.14 (m, 1H), 1.50 (d, 3H).

The following intermediates were prepared analogously from the corresponding starting materials:

(S)-6-cyano-3-fluoro-N-(1-(4-fluorophenyl)ethyl)pyrazine-2-carboxamide from (S)-1-(4-fluorophenyl)ethanamine. ESI-MS: 289.1 (M+H)$^+$; $^1$H NMR (400 MHz, CDCl$_3$) δ: 8.74 (s, 1H), 7.68-7.66 (m, 1H), 7.39-7.36 (m, 2H), 7.08-7.03 (m, 2H), 5.30-5.27 (m, 1H), 1.64 (d, 3H);

6-cyano-3-fluoro-N-(4-fluorobenzyl)pyrazine-2-carboxamide from (4-fluorophenyl) methanamine. ESI-MS: 275.1 (M+H)$^+$; $^1$H NMR (400 MHz, CDCl$_3$) δ: 8.74 (s, 1H), 7.85 (s, 1H), 7.35-7.31 (m, 2H), 7.06-7.01 (m, 2H), 4.64 (d, 2H);

(6-cyano-N-(3,4-difluorobenzyl)-3-fluoropyrazine-2-carboxamide from (3,4-difluorophenyl) methanamine. ESI-MS: 293.1 (M+H)$^+$; $^1$H NMR (400 MHz, DMSO-d$_6$) δ: 9.60 (s, 1H), 9.18 (s, 1H), 7.44-7.37 (m, 2H), 7.22-7.18 (br, 1), 4.85 (d, 2H);

6-cyano-3-fluoro-N-(4-fluorophenyl)pyrazine-2-carboxamide from 4-fluoroaniline. ESI-MS: 260.9 (M+H)$^+$; $^1$H NMR (500 MHz, CDCl$_3$) δ: 9.25 (s, 1H), 8.82 (s, 1H), 7.74-7.70 (m, 2H), 7.14-7.10 (m, 2H);

5-cyano-2-fluoro-N-((5-fluoropyridin-3-yl)methyl)nicotinamide from (5-fluoropyridin-3-yl)methanamine. ESI-MS (M+1)+: 275.0; $^1$H NMR (400 MHz, CDCl$_3$) δ: 8.88 (dd, 1H), 8.66 (s, 1H), 8.47 (s, 2H), 7.45 (d, 1H), 7.26 (s, 1H), 4.73 (d, 2H).

Synthesis of 3-fluoro-N-(4-fluorophenyl)-6-(trifluoromethyl)pyrazine-2-carboxamide

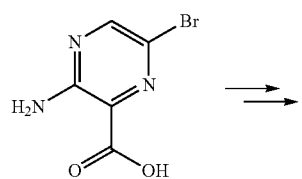

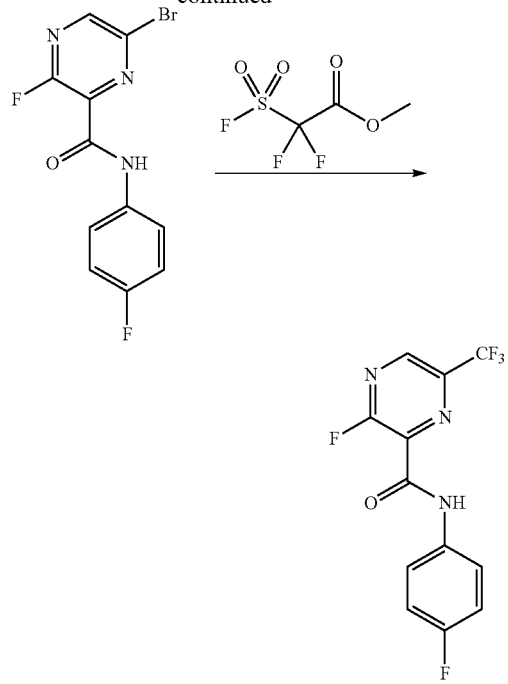

Synthesis of 3-amino-6-bromo-N-(4-fluorophenyl)pyrazine-2-carboxamide

3-Amino-6-bromopyrazine-2-carboxylic acid (2.53 g, 11.6 mmol) and p-fluoroaniline (1270 μL, 13.3 mmol) were stirred in dimethylformamide (57.5 mL) and N,N-diisopropylethylamine (6060 μL, 34.8 mmol). Added N,N,N',N'-tetramethyl-O-(7-azabenzotriazol-1-yl)uronium hexafluorophosphate (4.85 g, 12.8 mmol) and stirred overnight. The reaction was worked-up by diluting with ethyl acetate (250 mL) and washed twice with aqueous sodium bicarbonate (150 mL) and 150 mL brine. The organic phase was dried over magnesium sulfate and evaporated in vacuo. The crude solid was taken up in 40 mL of dichloromethane:hexanes (1:2) and collected by filtration and washed with 20 mL of dichloromethane:hexanes (1:2). Collected 2.49 g of a yellow powder (69%). ES (+) MS m/e=310.8 (M+1). $^1$H NMR (300 MHz, CDCl$_3$) δ 9.44 (br. s., 1H), 8.29 (s, 1H), 7.59-7.72 (m, 2H), 7.00-7.17 (m, 2H).

Synthesis of 6-bromo-3-fluoro-N-(4-fluorophenyl)pyrazine-2-carboxamide 3-amino-6-bromo-N-(4-fluorophenyl)pyrazine-2-carboxamide (0.35 g, 1.1 mmol) was dissolved in 30 M of hydrofluoric acid in pyridine (2.2 mL, 66 mmol). Chilled in an ice bath and added sodium nitrite (85.4 mg, 1.24 mmol). The reaction bubbled and a solid crashed out. The reaction was diluted with pyridine (2 ml) to aid stirring. The reaction was quenched by adding water (15 mL) followed by ethyl acetate (75 mL). The organic phase was washed twice with water (75 mL) and once with brine (75 mL). The organic phase was dried over magnesium sulfate, filtered, and evaporated in vacuo to yield 0.234 g of an orange solid (66%). ES (+) MS m/e=313.8 (M+1).

Synthesis of 3-fluoro-N-(4-fluorophenyl)-6-(trifluoromethyl)pyrazine-2-carboxamide 6-Bromo-3-fluoro-N-(4-fluorophenyl)pyrazine-2-carboxamide (234 mg, 0.745 mmol) and copper(I) iodide (284 mg, 1.49 mmol) were combined with N,N-dimethylformamide (3.9 mL, 51 mmol), hexamethylphosphoramide (648 μL, 3.72 mmol) then methyl fluorosulphonyldifluoroacetate (474 μL, 3.72 mmol). The vial was heated at 80° C. for 3 hours and reaction was monitored by LCMS. Reaction was cooled to rt, and diluted with ethyl acetate (57 mL) before filtering through Celite. The organic phase was washed twice with aqueous sodium bicarbonate (75 mL), then once with water (75 mL), and brine (75 mL). The organic phase was dried over magnesium sulfate, filtered, and evaporated in vacuo. The resulting oil was purified by flash chromatography (5-25% ethyl acetate:hexanes, silica gel). Collected 55.9 mg of a bright yellow powder that predominantly consisted of product by LCMS. ES (+) MS m/e=303.9 (M+1).

Preparation of (S)-5-cyano-2-(2-fluoro-4-(4,4,5,5-tetramethyl-1,3,2-dioxaborolan-2-yl)benzylamino)-N-(1-(4-fluorophenyl)ethyl)nicotinamide and (S)-5-cyano-2-(3-fluoro-4-(4,4,5,5-tetramethyl-1,3,2-dioxaborolan-2-yl)benzylamino)-N-(1-(4-fluorophenyl)ethyl)nicotinamide (4-bromo-2-fluorophenyl)methanamine (1.77 g, 8.71 mmol, 1.0 eq) was dissolved into THF (15 mL), then Et$_3$N (6.49 g, 36.50 mmol, 4.0 eq) was added and stirred for 10 min, then (S)-5-cyano-2-fluoro-N-(1-(4-fluorophenyl)ethyl)nicotinamide (2.5 g, 8.71 mmol, 1.0 eq) was added. The whole mixture was refluxed at 85° C. for 2 h, then THF was evaporated, and the mixture was purified via silica gel column (PE/EA=5:1) to give (S)-2-(4-bromo-2-fluorobenzylamino)-5-cyano-N-(1-(4-fluorophenyl)ethyl)nicotinamide as a white solid (1.64 g, yield: 40%). ESI-MS (M+3$^+$): 472.9. $^1$H NMR (400 MHz, CDCl$_3$) δ: 9.18 (t, 1H), 8.44 (s, 1H), 7.90 (s, 1H), 7.35-7.32 (m, 2H), 7.26-7.21 (m, 3H), 7.06 (t, 2H), 6.64 (d, 1H), 5.22-5.15 (m, 1H), 4.79-4.67 (m, 2H), 1.58 (d, 3H).

To a solution of (S)-2-(4-bromo-2-fluorobenzylamino)-5-cyano-N-(1-(4-fluorophenyl)ethyl)nicotinamide (1.64 g, 3.49 mmol, 1.0 eq) in dioxane (13 mL), KOAc (0.684 g, 6.98 mmol, 2 eq), DMSO (1 mL), and 4,4,4',4',5,5,5',5'-octamethyl-2,2'-bi(1,3,2-dioxaborolane) (2.66 g, 10.47 mmol, 3 eq) was added gradually, then PdCl$_2$(dppf) (0.142 g, 0.175

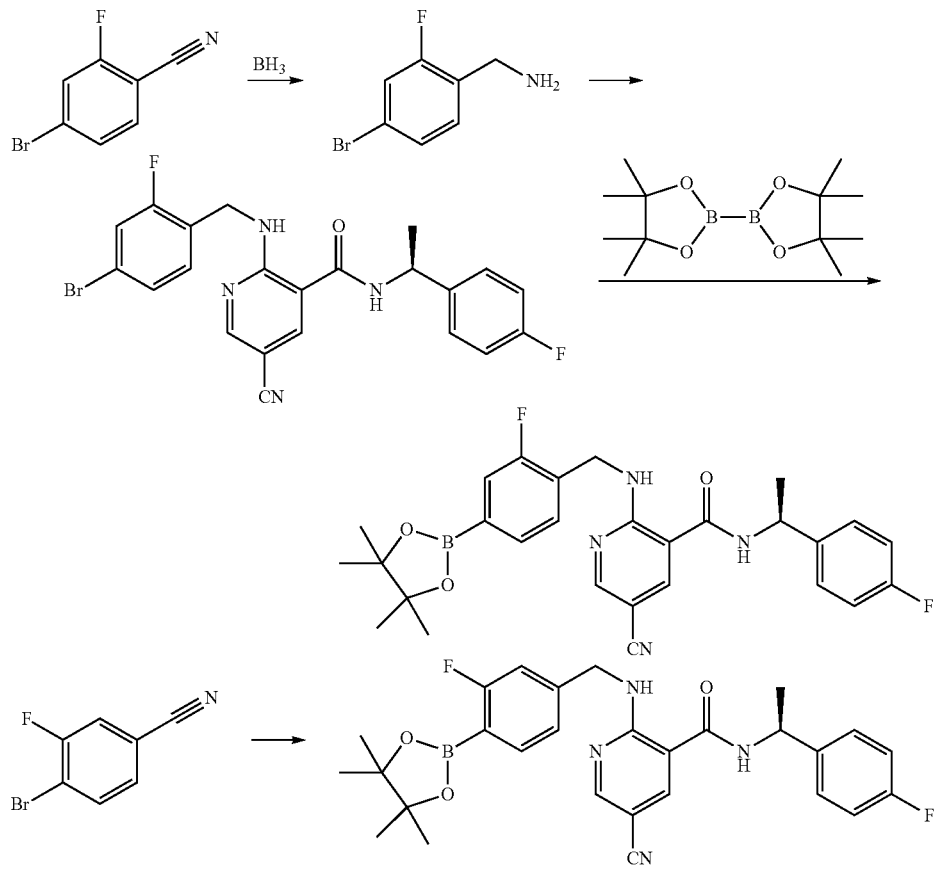

4-bromo-2-fluorobenzonitrile (2 g, 10.05 mmol, 1.0 eq) was dissolved in BH$_3$ (2 M in THF, 8 mL), then the mixture was refluxed at 85° C. for 2 h. TLC showed 27-01SM disappeared, MeOH was added to quench the reaction, then the reaction mixture was concentrated to get (4-bromo-2-fluorophenyl)methanamine as yellow solid (crude: 1.83 g, yield: 90%). ESI-MS (M+3$^+$): 205.9; $^1$H NMR (400 MHz, DMSO-d$_6$) δ: 8.42 (br, 2H), 7.67 (d, 1H), 7.51 (d, 2H), 4.06 (s, 2H).

mmol, 0.05 eq) was added, the reaction mixture was stirred at 90° C. for 4 h under N$_2$ atmosphere, then the mixture was filtered and the filtrate was concentrated and purified via silica gel column (PE/EA=5:1) to obtain (S)-5-cyano-2-(2-fluoro-4-(4,4,5,5-tetramethyl-1,3,2-dioxaborolan-2-yl)benzylamino)-N-(1-(4-fluorophenyl)ethyl)nicotinamide as a white solid (1.40 g, yield: 77%). ESI-MS (M+H$^+$): 519.0. $^1$H NMR (400 MHz, CDCl$_3$) δ: 9.19 (t, 1H), 8.43 (d, 1H), 7.91

(d, 1H), 7.51-7.45 (m, 2H), 7.35-7.30 (m, 3H), 7.04 (t, 2H), 6.59 (d, 1H), 5.22-5.17 (m, 1H), 4.86-4.74 (m 2H), 1.57 (d, 3H), 1.32 (s, 12H).

(S)-5-cyano-2-(3-fluoro-4-(4,4,5,5-tetramethyl-1,3,2-dioxaborolan-2-yl)benzylamino)-N-(1-(4-fluorophenyl)ethyl) nicotinamide was prepared similarly using 4-bromo-3-fluorobenzonitrile as starting material. ESI-MS (M+H$^+$): 519.0; $^1$H NMR (400 MHz, CDCl$_3$) δ: 9.26 (t, 1H), 8.42 (d, 1H), 7.94 (d, 1H), 7.70-7.68 (m, 1H), 7.36-7.32 (m, 2H), 7.09-7.03 (m, 3H), 6.97 (d, 1H), 6.46-6.42 (m, 1H), 5.19-5.14 (m, 1H), 4.76-4.70 (m, 2H), 1.58 (d, 3H), 1.35 (s, 12H).

Example 25

(S)-3-(4-(3-amino-1H-pyrazolo[3,4-b]pyridin-5-yl) benzylamino)-6-cyano-N-(1-(3,4-difluorophenyl) ethyl)pyrazine-2-carboxamide

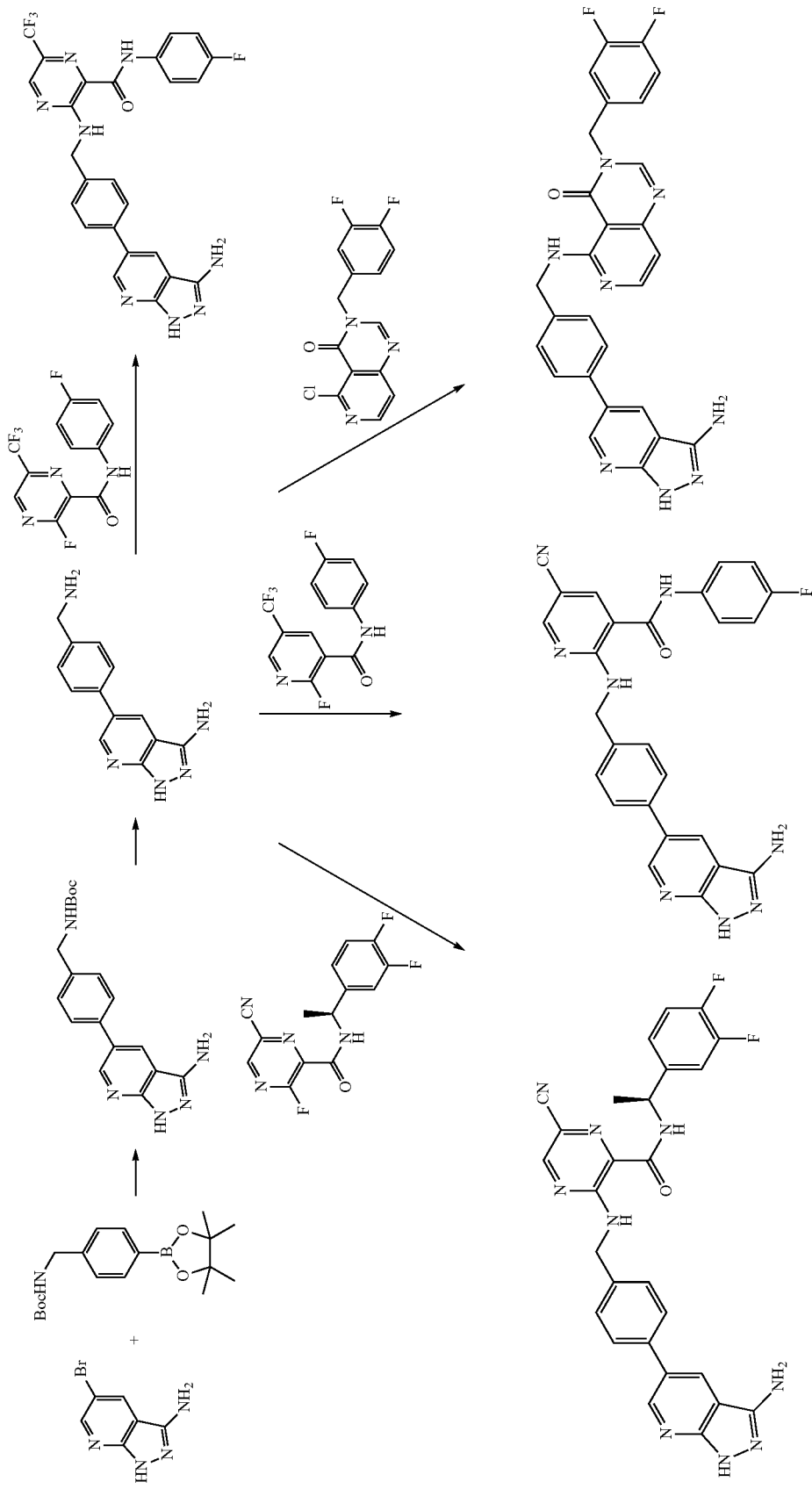

tert-Butyl 4-(3-amino-1H-pyrazolo[3,4-b]pyridin-5-yl)benzylcarbamate

5-Bromo-1H-pyrazolo[3,4-b]pyridin-3-amine (11.5 g, 54 mmol, 1.0 equiv) and tert-butyl 4-(4,4,5,5-tetramethyl-1,3,2-dioxaborolan-2-yl)benzylcarbamate (21.6 g, 65 mmol, 1.25 equiv) were dissolved in dioxane (240 mL). A solution of sodium bicarbonate (11.3 g, 135 mmol, 2.5 equiv) in water (120 mL) was added and the mixture was degassed with a stream of nitrogen for 10 minutes. Pd(cyclohexyl$_3$P)$_2$ (1.8 g, 2.7 mmol, 0.05 equiv) was added and the mixture degassed with a stream of nitrogen for an additional 10 minutes. The solution was refluxed for 48 hours until the bromide starting material consumed. The reaction was cooled to room temperature and diluted with ethyl acetate (600 mL) and saturated brine (250 mL). The layers were separated and the aqueous layer was extracted with ethyl acetate (200 mL). The combined organic layers were dried over sodium sulfate, filtered and concentrated under reduced pressure The residue was triturated with MTBE (100 mL) and collected to give tert-Butyl 4-(3-amino-1H-pyrazolo[3,4-b]pyridin-5-yl)benzylcarbamate (15.9 g, 87% yield) as a yellow solid.

5-(4-(Aminomethyl)phenyl)-1H-pyrazolo[3,4-b]pyridin-3-amine tert-Butyl 4-(3-amino-1H-pyrazolo[3,4-b]pyridin-5-yl)benzylcarbamate (5.0 g, 14.8 mmol, 1.0 equiv) was dissolved in dioxane (100 mL). A 4M solution of HCl in dioxane (18.4 mL, 73.7 mmol, 5.0 equiv) was added over 2 minutes. The reaction became a thick orange suspension which was stirred for 4 hours at which time LC/MS indicated the reaction was complete. The reaction was concentrated under reduced pressure and the residue was triturated with MTBE (250 mL) and filtered. The orange solid was dried in a vacuum oven at 40° C. for 4 hours to give 5-(4-(aminomethyl)phenyl)-1H-pyrazolo[3,4-b]pyridin-3-amine (4.6 g, 95% yield) as the HCl salt.

5-(4-(aminomethyl)phenyl)-1H-pyrazolo[3,4-b]pyridin-3-amine (102 mg, 0.176 mmol), 6-cyano-3-fluoro-pyrazine-2-carboxylic acid [(S)-1-(3,4-difluoro-phenyl)-ethyl]-amide (45.0 mg, 0.147 mmol) were combined and dissolved in dimethyl sulfoxide (2.00 mL). Added triethylamine (81.8 μL, 0.587 mmol) and stirred at room temperature for 3 hours. Diluted with ethyl acetate (75 mL) and washed with aqueous sodium bicarbonate, water, followed by brine. The organic phase was dried over magnesium sulfate, filtered, and evaporated. The material was purified by flash chromatography (50-90% ethyl acetate:hexanes, silica). Collected 43.0 mg of a yellow powder. ES (+) MS m/e=525.9 (M+1). $^1$H NMR (300 MHz, CDCl$_3$) δ 10.55 (br. s., 1H), 9.62 (t, J=5.67 Hz, 1H), 8.64 (d, J=1.89 Hz, 1H), 8.42 (s, 1H), 7.97 (d, J=1.89 Hz, 1H), 7.94 (d, J=7.55 Hz, 1H), 7.41-7.53 (m, 2H), 7.31-7.40 (m, 2H), 6.94-7.16 (m, 3H), 5.04 (quin, J=7.18 Hz, 1H), 4.55-4.82 (m, 2H), 4.23 (br. s., 2H), 1.52 (d, J=7.18 Hz, 3H).

Examples 26-35 were prepared in a manner consistent with Example 25.

Example 36

(S)-ethyl 5-(4-((5-cyano-3-(1-(3,4-difluorophenyl)ethylcarbamoyl)pyrazin-2-ylamino)methyl)phenyl)-1H-pyrazolo[3,4-b]pyridin-3-ylcarbamate (S)-3-(4-(3-amino-1H-pyrazolo[3,4-b]pyridin-5-yl)benzylamino)-6-cyano-N-(1-(3,4-difluorophenyl)ethyl)pyrazine-2-carboxamide (100 mg, 0.190 mmol) was dissolved in pyridine (1.00 mL) before treating with ethyl chloroformate (21.8 μL, 0.228 mmol) and stirring overnight. The reaction was diluted with ethyl acetate (75 mL) and washed with saturated sodium bicarbonate, water, then brine. The organic phase was dried over magnesium sulfate, filtered, evaporated, and purified by flash chromatography (0-100% ethyl acetate:hexanes, silica). Collected 62.8 mg of a powder (55%). ES (+) MS m/e=597.9 (M+1). $^1$H NMR (300 MHz, DMSO-d$_6$) δ 13.20 (br. s, 1H), 10.12 (br. s, 1H), 9.76 (t, J=5.85 Hz, 1H), 9.31 (d, J=8.31 Hz, 1H), 8.76 (d, J=2.27 Hz, 1H), 8.73 (s, 1H), 8.46 (d, J=1.89 Hz, 1H), 7.64 (d, J=7.93 Hz, 2H), 7.47-7.56 (m, 1H), 7.45 (d, J=8.31 Hz, 2H), 7.37 (td, J=8.50, 10.58 Hz, 1H), 7.21-7.30 (m, 1H), 5.12 (quin, J=7.27 Hz, 1H), 4.65-4.82 (m, 2H), 4.16 (q, J=7.18 Hz, 2H), 1.52 (d, J=7.18 Hz, 3H), 1.24 (t, J=6.99 Hz, 3H).

Example 37 was prepared in a manner analogous to Example 36 using benzoyl chloride.

Example 38

2-[4-(3-Amino-1H-pyrazolo[3,4-b]pyridin-5-yl)-benzylamino]-N-(4-fluoro-phenyl)-5-trifluoromethyl-nicotinamide 2-Chloro-N-(4-fluoro-phenyl)-5-trifluoromethyl-nicotinamide (70.0 mg, 0.220 mmol), 5-(4-(aminomethyl)phenyl)-1H-pyrazolo[3,4-b]pyridin-3-amine hydrochloride (57.7 mg, 0.209 mmol), Triethylamine (0.088 mL, 0.63 mmol) and Dimethyl sulfoxide (1.0 mL, 14 mmol) were combined and heated at 45° C. for 48 hours. Added EtOAc (75 mL) then washed with NaHCO$_3$, H$_2$O, and Brine. The organic layer was dried over sodium sulfate and solvent removed in vacuo. Crude compound dissolved (DCM) and purified by gradient elution (24 G column) (0->10%) B (MeOH) in A (DCM). Collected 41.1 mg of offwhite solid powder (38% yield). ESI-MS (M+H+): 522.2. $^1$H NMR (300 MHz, DMSO-d$_6$) δ 11.99 (s, 1H), 10.51 (s, 1H), 8.93 (t, J=5.67 Hz, 1H), 8.65 (d, J=2.27 Hz, 1H), 8.56 (d, J=1.51 Hz, 1H), 8.39 (dd, J=2.27, 4.91 Hz, 2H), 7.67-7.76 (m, 2H), 7.42-7.66 (m, 4H), 7.17-7.28 (m, 2H), 5.61 (s, 2H), 4.77 (d, J=5.67 Hz, 2H).

Example 39

3-(4-(3-amino-1H-pyrazolo[3,4-b]pyridin-5-yl)benzylamino)-N-(4-fluorophenyl)-6-(trifluoromethyl)pyrazine-2-carboxamide Crude 3-fluoro-N-(4-fluorophenyl)-6-(trifluoromethyl)pyrazine-2-carboxamide (55.9 mg, 0.184 mmol) and 5-(4-(aminomethyl)phenyl)-1H-pyrazolo[3,4-b]pyridin-3-amine bis TFA salt (85.4 mg, 0.183 mmol) were dissolved in dimethyl sulfoxide (1.00 mL). Added triethylamine (77.1 μL, 0.553 mmol) and stirred for 30 min. The reaction was diluted with ethyl acetate (75 mL) and washed with aqueous sodium bicarbonate (75 mL), water (75 mL) and brine (75 mL). The organic phase was dried over magnesium sulfate, evaporated and purified by flash chromatography (0-10% methanol:dichloromethane). LCMS revealed a mixture of two compounds so the material was triturated with methanol before drying in vacuo. Collected 65.9 mg of a yellow powder. $^1$H NMR (300 MHz, DMSO-d$_6$) δ 12.00 (s, 1H), 10.49 (s, 1H), 9.44 (t, J=6.04 Hz, 1H), 8.75 (s, 1H), 8.65 (d, J=1.89 Hz, 1H), 8.38 (d, J=1.89 Hz, 1H), 7.75-7.86 (m, 2H), 7.60-7.69 (m, J=8.31 Hz, 2H), 7.44-7.53 (m, 2H), 7.18-7.28 (m, 2H), 5.61 (br. s, 2H), 4.80 (d, J=5.67 Hz, 2H). ES (+) MS m/e=522.9 (M+1).

Example 40

5-(4-(3-amino-1H-pyrazolo[3,4-b]pyridin-5-yl)benzylamino)-3-(3,4-difluorobenzyl)pyrido[4,3-d]pyrimidin-4(3H)-one 5-Chloro-3-(3,4-difluoro-benzyl)-3H-pyrido[4,3-d]pyrimidin-4-one (200.0 mg, 0.6500 mmol), 5-(4-(aminomethyl)phenyl)-1H-pyrazolo[3,4-b]pyridin-3-amine dihydrochloride (155 mg, 0.496 mmol), Dimethyl sulfoxide (2.5 mL, 35 mmol) and Triethylamine (345.4 μL, 2.478 mmol) were combined. Reaction mixture was heated at 110° C. overnight. Solvent removed and residue purified by HPLC to give desired product. Collected 106.2 mg purified compound (42% yld). ESI-MS (M+H$^+$): 510.9; $^1$H NMR (300 MHz, DMSO-d$_6$) δ 9.42 (br. s., 1H), 8.71 (s, 1H), 8.65 (d, J=1.89 Hz, 1H), 8.40 (d, J=1.89 Hz, 1H), 8.14 (d, J=6.04 Hz, 1H), 7.59 (d, J=7.93 Hz, 2H), 7.26-7.53 (m, 4H), 7.20 (br. s., 1H), 6.70 (d, J=5.67 Hz, 1H), 5.09 (s, 2H), 4.72 (d, J=5.29 Hz, 2H), 2.00 (s, 2H).

Synthesis of N-(4-fluorophenyl)-2-(4-(4,4,5,5-tetramethyl-1,3,2-dioxaborolan-2-yl)benzylamino)-5-(trifluoromethyl)nicotinamide To a solution of (4-bromophenyl)methanamine (6.4 g, 35 mmol, 1.1 eq) in THF (25 mL) was added Et$_3$N (12.9 g, 140 mmol, 4.0 eq), after stirring for 10 min, 2-chloro-N-(4-fluorophenyl)-5-(trifluoromethyl)nicotinamide (10 g, 32 mmol, 1.0 eq) was added. The mixture was heated to 80° C. for 2 h and then concentrated to give a crude product which was purified by silica gel column (PE:EA=10:1) to give 2-(4-bromobenzylamino)-N-(4-fluorophenyl)-5-(trifluoromethyl)nicotinamide as a white solid (9.5 g, yield: 64%). ESI-MS (M+2)$^+$: 469.7; $^1$H NMR (500 MHz, CDCl$_3$) δ: 8.74 (br, 1H), 8.50 (s, 1H), 7.89 (s, 1H), 7.67 (br, 1H), 7.51-7.43 (m, 5H), 7.26-7.21 (m, 1H), 7.08 (t, 2H), 4.71 (d, 2H).

To a solution of 2-(4-bromobenzylamino)-N-(4-fluorophenyl)-5-(trifluoromethyl)-nicotinamide (4.5 g, 9.61 mmol, 1.0 eq) in dioxane (35 mL) and DMSO (2.5 mL) were added KOAc (1.87 g, 19 mmol, 2 eq) and 4,4,4',4',5,5,5',5'-octamethyl-2,2'-bi(1,3,2-dioxaborolane) (7.32 g, 28.83 mmol, 3 eq), then PdCl$_2$(dppf)DCM (784 mg, 0.96 mmol, 0.1 eq) was added, the reaction mixture was stirred at 90° C. for 2 h under N$_2$ atmosphere, then the mixture was filtered and the filtrate was concentrated and purified by silica gel column (PE:EA=20:1) to give N-(4-fluorophenyl)-2-(4-(4,4,5,5-tetramethyl-1,3,2-dioxaborolan-2-yl)benzylamino)-5-(trifluoromethyl)nicotinamide as a white solid (3.66 g, yield: 74%). ESI-MS (M+H$^+$): 515.7. HPLC: 4.45% (boron acid)+ 95.54% (boron ester). $^1$H NMR (500 MHz, CDCl$_3$) δ: 8.75 (br, 1H), 8.49 (s, 1H), 7.88 (s, 1H), 7.76 (d, 2H), 7.69 (br, 1H), 7.50-7.48 (m, 2H), 7.35 (d, 2H), 7.08 (t, 2H), 4.77 (d, 2H), 1.32 (s, 12H).

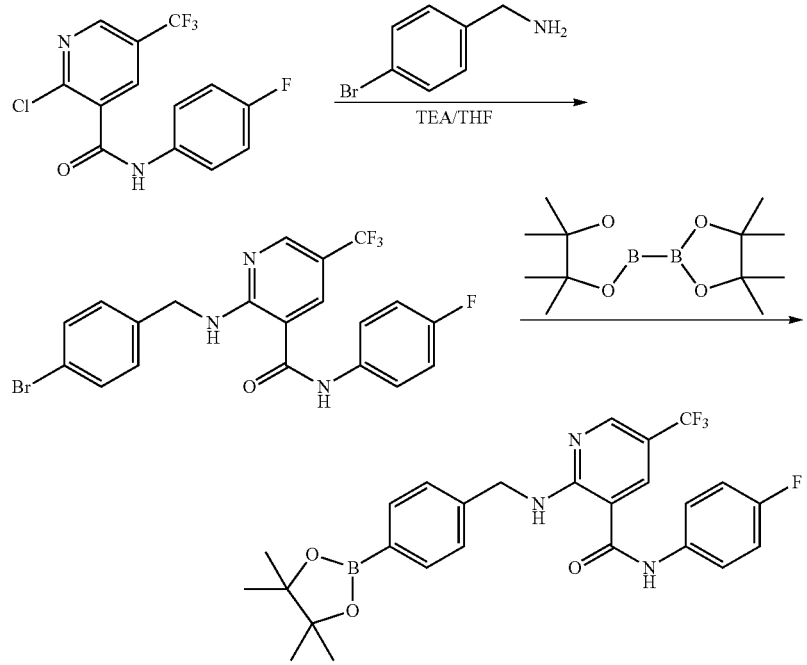

Example 41

2-[4-(4-Amino-7H-pyrrolo[2,3-d]pyrimidin-5-yl)-benzylamino]-5-cyano-N-[(S)-1-(4-fluoro-phenyl)-ethyl]-nicotinamide

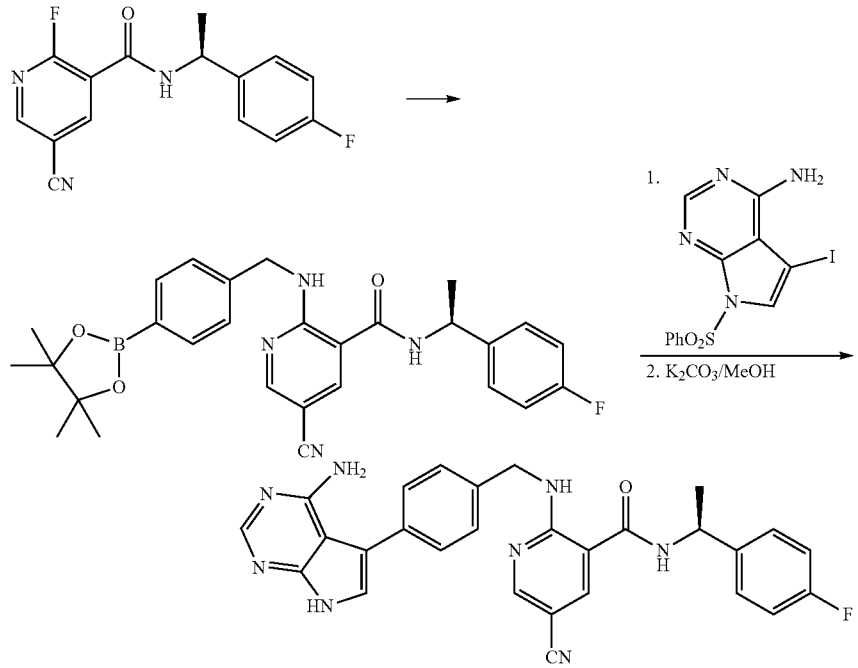

5-Cyano-2-fluoro-N-[(S)-1-(4-fluoro-phenyl)-ethyl]-nicotinamide (4.46 g, 15.5 mmol), 4-(4,4,5,5-Tetramethyl-1,3,2-dioxaborolan-2-yl)-benzylamine; hydrochloride (3.99 g, 14.8 mmol) Dimethyl sulfoxide (40 mL, 600 mmol) and N,N-Diisopropylethylamine (7.73 mL, 44.4 mmol) were combined and stirred at rt for 3 hours. LCMS indicated the complete reaction. Added 100 mL ethyl acetate and washed with sodium bicarbonate solution followed by water, then brine. The organic phase was dried over magnesium sulfate, filtered and concentrated under reduced pressure. The crude product was used without purification. m/z=501.28 [M+1].

Into a vial was added 5-Cyano-N-[(S)-1-(4-fluoro-phenyl)-ethyl]-2-[4-(4,4,5,5-tetramethyl-1,3,2-dioxaborolan-2-yl)-benzylamino]-nicotinamide (60.3 mg, 0.000120 mol), 7-Benzenesulfonyl-5-iodo-7H-pyrrolo[2,3-d]pyrimidin-4-ylamine (72.34 mg, 0.0001808 mol), [1,1'-Bis(diphenyl-phosphino)ferrocene]dichloropalladium(II), complex with dichloromethane (1:1) (11.81 mg, 1.446E-5 mol), N,N-Dimethylformamide (0.6 mL, 0.008 mol) and 1.2 M of Sodium bicarbonate in Water (0.3 mL, 0.0004 mol). The reaction was microwaved on 300 watts, 65° C. for 20 minutes. Solvent removed and residue purified by column chromatography to give desired product. ESI-MS (M+H⁺): 646.9.

Isolated intermediate (S)-2-(4-(4-amino-7-(phenylsulfonyl)-7H-pyrrolo[2,3-d]pyrimidin-5-yl)benzylamino)-5-cyano-N-(1-(4-fluorophenyl)ethyl)nicotinamide was dissolved in Methanol (14.645 mL, 0.36153 mol) then was added Potassium carbonate (83.28 mg, 0.0006026 mol) was heated to reflux (80° C.) for 1 hour. Solvent removed and residue purified by column chromatography to give desired product. Collected 26.9 mg of the purified compound (44% yld). ESI-MS (M+H⁺): 507.0; $^1$H NMR (300 MHz, DMSO-$d_6$) δ 11.78 (br. s., 1H), 9.36 (t, J=5.48 Hz, 1H), 8.99 (d, J=7.18 Hz, 1H), 8.42-8.67 (m, 2H), 8.10 (s, 1H), 7.31-7.59 (m, 6H), 7.00-7.30 (m, 3H), 5.77-6.18 (m, 1H), 5.10 (t, J=7.18 Hz, 1H), 4.72 (d, J=5.29 Hz, 2H), 1.46 (d, J=7.18 Hz, 3H).

Example 42

3-((R)-1-(4-(3-amino-1H-pyrazolo[3,4-b]pyridin-5-yl) phenyl)ethylamino )-6-cyano-N—((S)-1-(3,4-difluorophenyl)ethyl)pyrazine-2-carboxamide

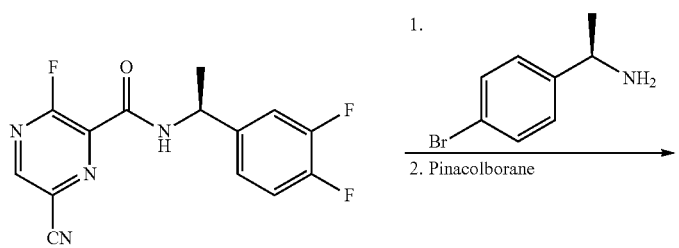

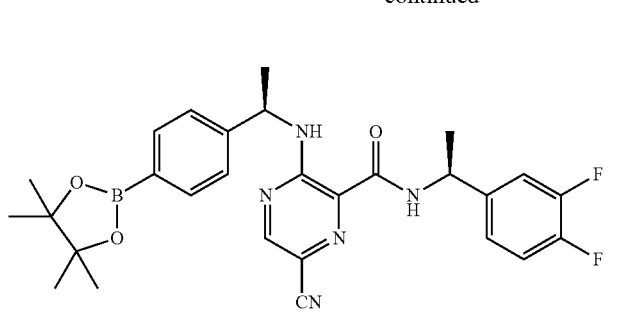
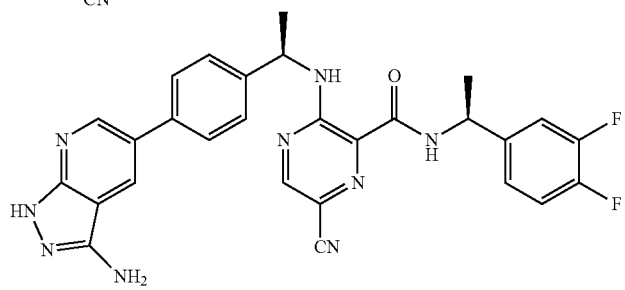

(S)-6-cyano-N-(1-(3,4-difluorophenyl)ethyl)-3-fluoropyrazine-2-carboxamide (500 mg, 1.63 mmol, 1.0 eq) and (R)-1-(4-bromophenyl)ethanamine (358 mg, 1.80 mmol, 1.1 eq) were dissolved in THF (10 mL), then Et$_3$N (330 mg, 3.26 mmol, 2.0 eq) was added, the reaction mixture was refluxed for 2 h. TLC showed AAG-4 disappeared, then the reaction mixture was concentrated and purified by silica gel (PE:EA=4:1) to give 3-((R)-1-(4-bromophenyl)ethylamino)-6-cyano-N—((S)-1-(3,4-difluorophenyl)ethyl)pyrazine-2-carboxamide as a yellow solid (610 mg, yield: 77%). ESI-MS (M+H$^+$): 486.0. $^1$H NMR (400 MHz, DMSO-d$_6$) δ: 9.68 (d, 1H), 9.34 (d, 1H), 8.63 (s, 1H), 7.48-7.44 (m, 3H), 7.34-7.21 (m, 4H), 5.16-5.08 (m, 2H), 1.46-1.42 (m, 6H).

To a solution of 3-((R)-1-(4-bromophenyl)ethylamino)-6-cyano-N—((S)-1-(3,4-difluorophenyl)ethyl)pyrazine-2-carboxamide (600 mg, 1.24 mmol, 1.0 eq) in dioxane (10 mL) and DMSO (1 mL) were added 4,4,4',4',5,5,5',5'-octamethyl-2,2'-bi(1,3,2-dioxaborolane) (472 mg, 1.86 mmol, 1.5 eq) and KOAc (244 mg, 2.48 mmol, 2 eq), then PdCl$_2$(dppf) DCM (101 mg, 0.124 mmol, 0.1 eq) was added, the reaction mixture was stirred at 90° C. for 2 h under N$_2$ atmosphere, then the mixture was filtered and the filtrate was concentrated and purified via silica gel column (PE/EA=6:1) to obtain the desired boronate product as a yellow solid (550 mg, yield: 82%). ESI-MS (M+H$^+$): 534.2. $^1$H NMR (400 MHz, CDCl$_3$) δ: 9.67 (d, 1H), 8.38 (s, 1H), 7.99 (d, 1H), 7.77 (d, 2H), 7.34 (d, 2H), 7.19-7.10 (m, 3H), 5.31-5.26 (m, 1H), 5.15-5.10 (m, 1H), 1.61-1.56 (m, 6H), 1.33 (s, 12H).

5-bromo-1H-pyrazolo[3,4-b]pyridin-3-amine (60 mg, 0.28 mmol), 6-cyano-N—((S)-1-(3,4-difluorophenyl)ethyl)-3-((R)-1-(4-(4,4,5,5-tetramethyl-1,3,2-dioxaborolan-2-yl)phenyl)ethylamino)pyrazine-2-carboxamide (176 mg, 0.312 mmol), Pd(PPh$_3$)$_4$ (32 mg, 0.028 mmol, 0.1 eq) and K$_3$PO$_4$ (120 mg, 0.56 mmol, 2.0 eq) were dissolved in H$_2$O (10 mL) and dioxane (15 mL). The mixture was stirred at 100° C. for 16 h. LCMS showed SM disappeared. The mixture was cooled to rt and concentrated. The residue was purified by silica gel column with (CH$_2$Cl$_2$/CH$_3$OH=20/1) to give 3-((R)-1-(4-(3-amino-1H-pyrazolo[3,4-b]pyridin-5-yl)phenyl)ethylamino)-6-cyano-N—((S)-1-(3,4-difluorophenyl)ethyl)pyrazine-2-carboxamide as a yellow solid (80 mg, yield: 53%). ESI-MS (M+H$^+$): 540.0. $^1$H NMR (400 MHz, DMSO-d$_6$) δ: 12.03 (s, 1H), 9.81 (d, 1H), 9.41 (d, 1H), 8.73 (s, 1H), 8.65 (d, 1H), 8.37 (s, 1H), 7.64 (d, 2H), 7.57-7.49 (m, 3H), 7.42-7.37 (m, 1H), 7.27 (br, 1H), 5.65 (s, 2H), 5.33-5.25 (m, 1H), 5.18-5.13 (m, 1H), 1.57-1.51 (m, 6H).

Synthesis of 2-(2-chloro-5-(trifluoromethyl)pyridin-3-yl)-5-fluoro-1H-benzo[d]imidazole

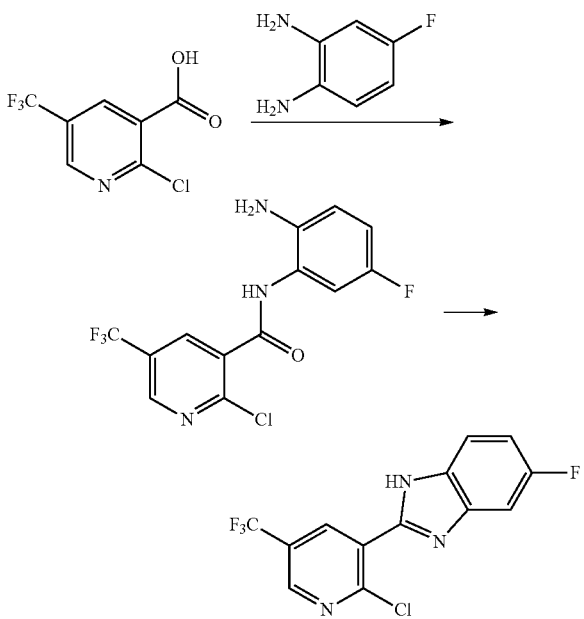

2-chloro-5-(trifluoromethyl)nicotinic acid (450 mg, 2 mmol), 4-fluorobenzene-1,2-diamine (408 mg, 4 mmol, 2 eq), DCC (824 mg, 4 mmol, 2 eq) and DMAP (24 mg, 0.2 mmol, 0.1 eq) were dissolved in DCM (20 mL). The reaction mixture was stirred at rt for 4 h (LCMS show SM disappeared). Then the reaction mixture was concentrated and purified by silica gel column (PE:EA=4:1) to give N-(2-amino-5-fluorophenyl)-2-chloro-5-(trifluoromethyl) nicotinamide as a yellow solid (350 mg, yield: 53%). ESI-MS (M+H)$^+$: 334.0. $^1$H NMR (400 MHz, DMSO-d$_6$) δ: 8.84 (br, 2H), 8.80 (s, 1H), 8.52 (d, 1H), 7.70 (dd, 1H), 6.95-6.85 (m, 2H), 6.45 (s, 1H).

N-(2-amino-5-fluorophenyl)-2-chloro-5-(trifluoromethyl)nicotinamide (350 mg, 1.05 mmol) was dissolved in HOAc (5 mL). Then the reaction mixture was stirred at 90° C. for 2 h (LCMS show the SM disappeared). Then the reaction mixture was concentrated and purified by silica gel column (PE: EA=4:1) to give 2-(2-chloro-5-(trifluoromethyl)pyridin-3-yl)-5-fluoro-1H-benzo[d]imidazole as a yellow solid (200 mg, yield: 60%). ESI-MS (M+H)$^+$: 316.0. $^1$H NMR (400 MHz, CDCl$_3$) δ9.10 (d, 1H), 8.72 (d, 1H), 7.71 (s, 1H), 7.44 (d, 1H), 7.18 (dt, 1H).

Synthesis of 5-fluoro-2-(2-fluoro-5-(trifluoromethyl)pyridin-3-yl)benzo[d]oxazole

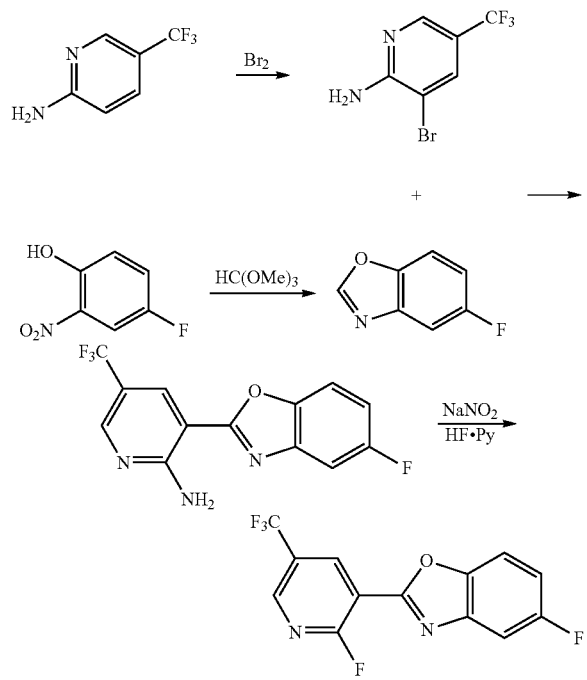

To a solution of 5-(trifluoromethyl)pyridin-2-amine (9 g, 55.6 mmol) in AcOH (75 mL) was added Br$_2$ (5.8 mL, 113.2 mmol, 2 eq) at rt. The mixture was stirred at rt for 2 h and then NaOH (10 N) was added to adjust pH=8 under ice bath. The mixture was filtered and the residue was dissolved in Et$_2$O (60 mL), the solution was washed with sat. Na$_2$CO$_3$ (10 mL), sat. Na$_2$SO$_3$ (10 mL), brine (10 mL) dried over Na$_2$SO$_4$ and concentrated, the residue was dispersed in hexanes (60 mL) and filtered to give 3-bromo-5-(trifluoromethyl)pyridin-2-amine (5.5 g, yield: 42%) as a white solid. $^1$H NMR (400 MHz, CDCl$_3$) δ: 8.27 (s, 1H), 7.86 (s, 1H).

A mixture of 4-fluoro-2-nitrophenol (785 mg, 5 mmol), HC(OMe)$_3$ (2.12 g, 20 mmol, 4 eq), AcOH (3.0 g, 50 mmol, 10 eq) and In (2.29 g, 20 mmol, 4 eq) in benzene (20 mL) was heated to 90° C. for 12 h. The mixture was then filtered, washed with sat. NH$_4$Cl (10 mL) and extracted with DCM (10 mL×2). The combined organics were dried over Na$_2$SO$_4$ and concentrated to give a residue, which was purified by column chromatograph (PE:EA=10:1) to give 5-fluorobenzo[d]oxazole (400 mg, yield: 58%) as a white solid. $^1$H NMR (400 MHz, CDCl$_3$) δ 8.09 (s, 1H), 7.73 (dd, 1H), 7.32 (dd, 1H), 7.14 (dt, 1H).

To a solution of 3-bromo-5-(trifluoromethyl)pyridin-2-amine (300 mg, 2.2 mmol) and 5-fluorobenzo[d]oxazole (528 mg, 2.2 mmol, 1 eq) in DMA (3 mL) were added Pd(PPh$_3$)$_4$ (254 mg, 0.22 mmol, 0.1 eq) and KOAc (431 mg, 4.4 mmol, 2 eq) under nitrogen atmosphere. The mixture was heated to 170° C. for 4 h and then concentrated, the residue was purified by column chromatograph (PE:EA=10:1) to give 3-(5-fluorobenzo[d]oxazol-2-yl)-5-(trifluoromethyl)pyridin-2-amine (550 mg, yield: 83%) as a while solid. LCMS (M+H)$^+$: 298.1. $^1$H NMR (400 MHz, CDCl$_3$) δ8.52 (s, 1H), 8.45 (s, 1H), 7.70 (dd, 1H), 7.35 (dd, 1H), 7.16 (dt, 1H), 2.45 (br, 2H).

3-(5-fluorobenzo[d]oxazol-2-yl)-5-(trifluoromethyl)pyridin-2-amine (90 mg, 0.3 mmol) was dissolved in HF.Py (385 mg, 13.5 mmol, 45 eq) under ice bath. After stirring for 10 min, NaNO$_2$ (52 mg, 0.75 mmol, 2.5 eq) was added and stirred was continued for 3 h. Ice was added to quench the reaction and then the mixture was extracted with EtOAc (10 mL×2). The combined organics were dried over Na$_2$SO$_4$, concentrated and purified by column chromatograph (PE: EA=10:1) to give 5-fluoro-2-(2-fluoro-5-(trifluoromethyl)pyridin-3-yl)benzo[d]oxazole (40 mg, yield: 45%) as a white solid. LCMS (M+H)$^+$: 301. $^1$H NMR (400 MHz, CDCl$_3$) δ: 8.90 (dd, 1H), 8.68 (s, 1H), 7.81 (dd, 1H), 7.40 (dd, 1H), 7.24-7.18 (m, 1H).

Synthesis of 6-fluoro-5-(oxazol-2-yl)nicotinonitrile

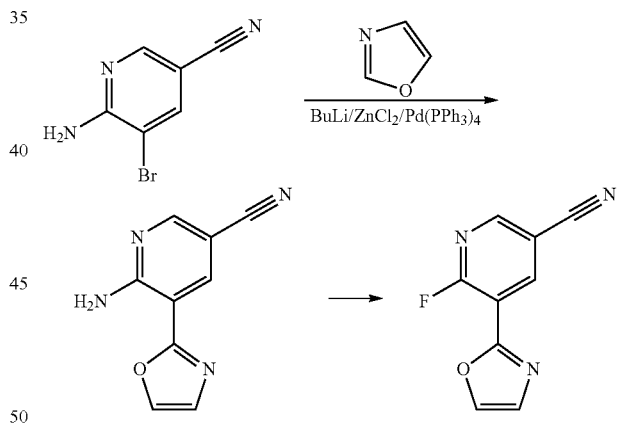

To a solution of oxazole (331 mg, 4.8 mmol) in THF (2 mL) was added n-BuLi (2.5 M in hexane, 2.2 mL, 5.6 mmol) at −60° C. After stirring for 10 min, solid ZnCl$_2$ (1.6 g, 12 mmol) was added portion wise, then the mixture was warmed to rt. Once at ambient temperature, Pd(PPh$_3$)$_4$ (462 mg, 0.4 mmol) and 6-amino-5-bromonicotinonitrile (800 mg, 4 mmol) were added and the mixture was heated to 60° C. for 4 h. NH$_4$Cl (4 mL) was added to quench the reaction and the mixture was extracted with EA (10 mL×3). The combined organics were concentrated and purified by column chromatograph (PE:EA=6:1) to afford 6-amino-5-(oxazol-2-yl)nicotinonitrile as a white solid (400 mg, yield: 50%). LCMS: (M+H)$^+$187.1. $^1$H NMR (400 MHz, CDCl$_3$) δ: 8.41 (d, 1H), 8.31 (d, 1H), 7.76 (s, 1H), 7.29 (s, 1H).

To a mixture of 6-amino-5-(oxazol-2-yl)nicotinonitrile (450 mg, 2.4 mmol) in HF.Py (3.1 g, 108 mmol) was added NaNO$_2$ (500 mg, 7.2 mmol) under ice bath. The resultant mixture was stirred for 3 h. Ice was added to quench the reaction and the mixture was extracted with EA (10 mL×3). The combined organics were concentrated and purified by silica gel column (PE:EA=10:1) to give 6-fluoro-5-(oxazol-2-yl)nicotinonitrile as yellow solid (50 mg, yield: 10%). ESI-MS (M+H$^+$): 190.1. $^1$H NMR (400 MHz, CDCl$_3$) δ: 8.77 (d, 1H), 8.61 (d, 1H), 7.88 (s, 1H), 7.40 (s, 1H).

Example 43

Synthesis of 6-(4-(4-amino-7H-pyrrolo[2,3-d]pyrimidin-5-yl)benzylamino)-5-(oxazol-2-yl)nicotinonitrile

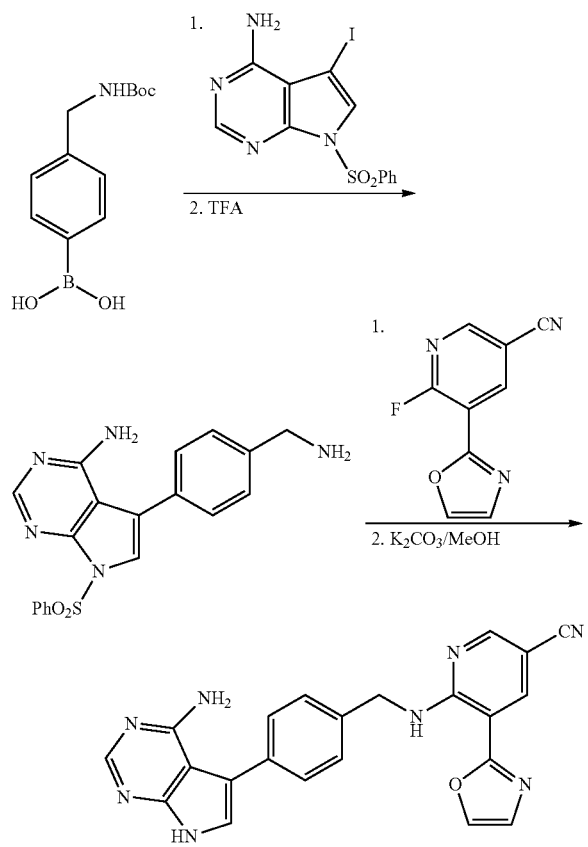

To a solution of 4-((tert-butoxycarbonylamino)methyl) phenylboronic acid (750 mg, 3 mmol) and 5-iodo-7-(phenylsulfonyl)-7H-pyrrolo[2,3-d]pyrimidin-4-amine (1.2 g, 3 mmol) in dioxane (10 mL) and H$_2$O (1 mL) were added PdCl$_2$(dppf) (240 mg, 0.3 mmol) and K$_2$CO$_3$ (828 mg, 6 mmol) under nitrogen. The mixture was heated to 100° C. for 2 h and then concentrated to give a residue, which was purified by column chromatograph (PE:EA=2:1) to give tert-butyl 4-(4-amino-7-(phenylsulfonyl)-7H-pyrrolo[2,3-d]pyrimidin-5-yl)benzylcarbamate (979 mg, Y: 68%) as a brown solid. ESI-MS (M+H$^+$): 519.0. $^1$H NMR (400 MHz, CD$_3$OD) δ: 8.32 (s, 1H), 8.25 (s, 1H), 8.23 (s, 1H), 7.70 (t, 1H), 7.62-7.56 (m, 4H), 7.45-7.37 (m, 5H), 4.98 (br, 1H), 4.39 (d, 2H), 1.48 (s, 9H). To a solution of tert-butyl 4-(4-amino-7-(phenylsulfonyl)-7H-pyrrolo[2,3-d]pyrimidin-5-yl)benzylcarbamate (380 mg, 0.79 mmol) in DCM (1 mL) was added TFA (384 mg, 3.94 mmol, 5 eq). The result mixture was stirred at rt for 12 h and then concentrated to give 5-(4-(aminomethyl)phenyl)-7-(phenylsulfonyl)-7H-pyrrolo[2,3-d]pyrimidin-4-amine (280 mg, yield: 93%) as a brown solid. ESI-MS (M+H$^+$): 380.0.

To a solution of 5-(4-(aminomethyl)phenyl)-7-(phenylsulfonyl)-7H-pyrrolo[2,3-d]pyrimidin-4-amine (200 mg, 0.52 mmol, 2 eq) and 6-fluoro-5-(oxazol-2-yl)nicotinonitrile (50 mg, 0.26 mmol) in DMSO (2 mL) was added Et$_3$N (132 mg, 1.3 mmol, 5 eq). The mixture was heated to 110° C. for 2 h. Water (10 mL) was added and the mixture was extracted with EA (10 mL*3). The combined organics were dried over Na$_2$SO$_4$ and concentrated to give a residue, which was purified by column chromatograph (PE:EA=1:1) to give 6-(4-(4-amino-7-(phenylsulfonyl)-7H-pyrrolo[2,3-d]pyrimidin-5-yl)benzylamino)-5-(oxazol-2-yl)nicotinonitrile (130 mg, yield: 91%) as a white solid. ESI-MS (M+H$^+$): 548.9; $^1$H NMR (400 MHz, CDCl$_3$) δ: 9.56 (t, 1H), 8.48 (d, 1H), 8.42 (s, 1H), 8.31 (d, 1H), 8.26-8.22 (m, 2H), 7.77 (d, 1H), 7.67-7.41 (m, 8H), 7.28 (d, 1H), 5.36 (br, 2H), 4.95 (d, 2H).

To a solution of 6-(4-(4-amino-7-(phenylsulfonyl)-7H-pyrrolo[2,3-d]pyrimidin-5-yl)benzylamino)-5-(oxazol-2-yl)nicotinonitrile (130 mg, 0.24 mmol) in MeOH (5 mL) was added K$_2$CO$_3$ (131 mg, 0.96 mmol, 4 eq). The mixture was heated to 75° C. for 3 h and then filtered. The filtrate was concentrated and purified by column chromatograph (DCM:MeOH=20:1) to give 6-(4-(4-amino-7H-pyrrolo[2,3-d]pyrimidin-5-yl)benzylamino)-5-(oxazol-2-yl)nicotinonitrile (15 mg, yield: 15%) as a white solid. LCMS (M+H$^+$): 409.0; $^1$H NMR (400 MHz, CD$_3$OD/CDCl$_3$) δ: 9.67 (t, 1H), 8.49 (d, 1H), 8.38 (d, 1H), 8.16 (s, 1H), 7.93 (s, 1H), 7.53-7.44 (m, 4H), 7.34 (s, 1H), 7.12 (s, 1H), 4.96 (d, 2H).

Example 44

(R)-methyl 3-(4-(4-amino-7H-pyrrolo[2,3-d]pyrimidin-5-yl)phenyl)-3-(5-cyano-3-((S)-1-(4-fluorophenyl)ethylcarbamoyl)pyridin-2-ylamino)propanoate

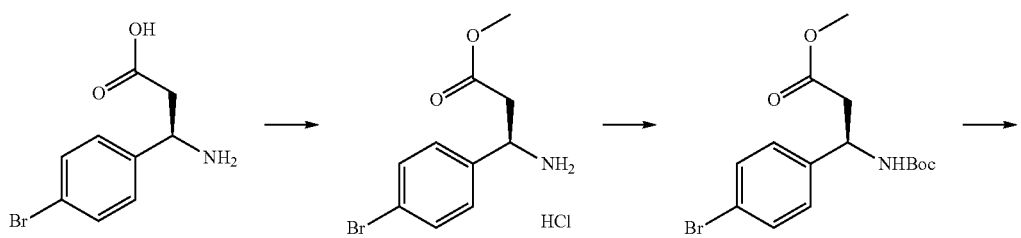

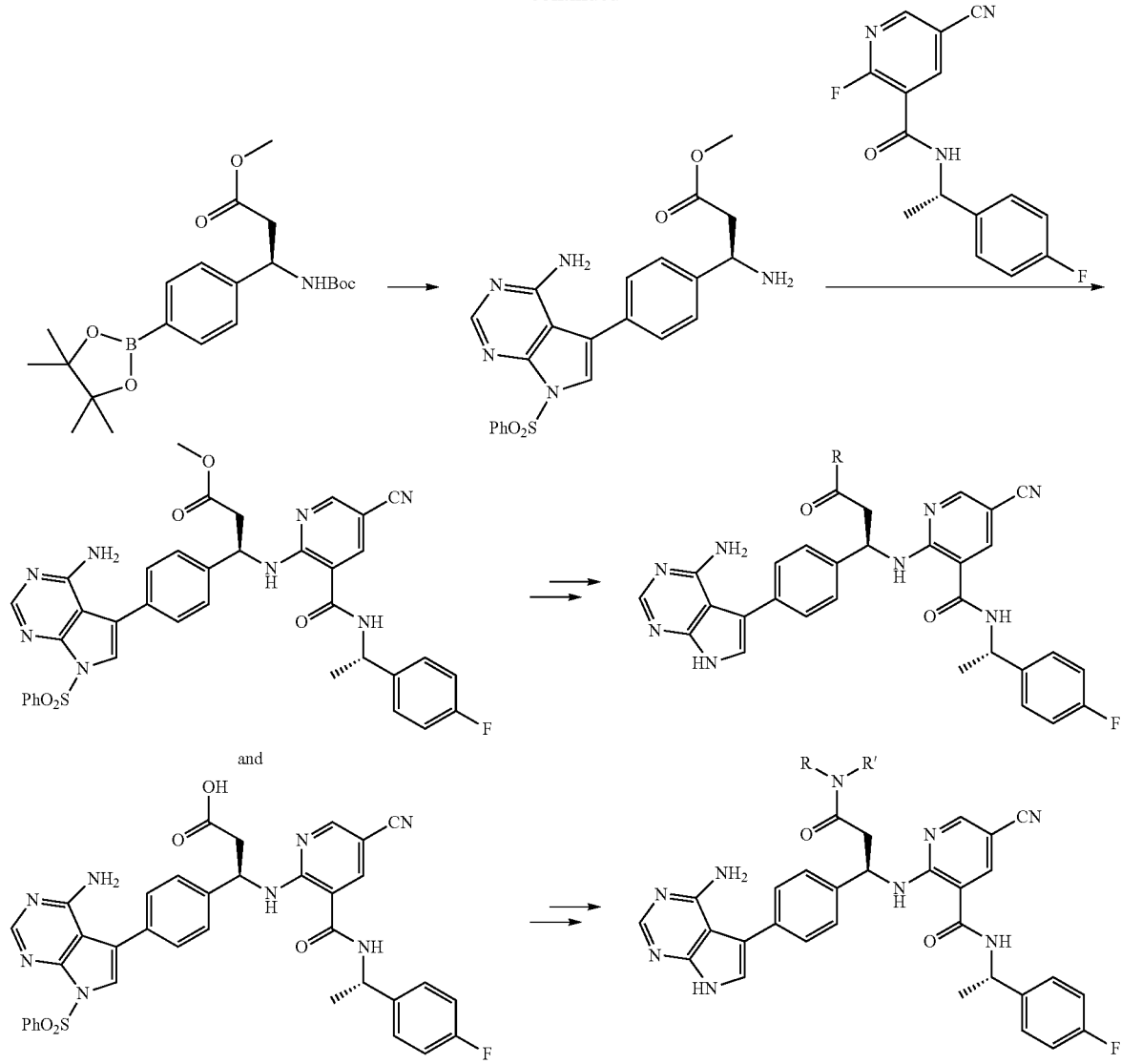

To a solution of compound (R)-3-amino-3-(4-bromophenyl)propanoic acid (3 g, 12 mmol) in MeOH (100 mL) was added SOCl$_2$ (1 mL) slowly. Then the reaction solution was heated under reflux for 16 h. The solvent was removed in vacuo to give (R)-methyl-3-amino-3-(4-bromophenyl)propanoate (3.4 g, yield: 100%) as white solid. ESI-MS (M+H$^+$): 258.0. $^1$H NMR (400 MHz, DMSO-d$_6$) δ: 8.73 (br, 2H), 7.63 (d, 2H), 7.50 (d, 2H), 4.60 (br, 1H), 3.55 (s, 3H) 3.18 (d, 1H), 3.00 (d, 1H).

A mixture of (R)-methyl-3-amino-3-(4-bromophenyl)propanoate (3.4 g, 13 mmol), Boc$_2$O (3.5 g, 16 mmol, 1.2 eq) and NaHCO$_3$ (6.0 g, 18.6 mmol, 2.0 eq) in THF (100 mL) was stirred at rt for 1 h. Then the reaction mixture was filtered and concentrated to give (R)-methyl 3-(4-bromophenyl)-3-(tert-butoxycarbonylamino)propanoate (4.0 g, yield: 94%) as white solid. ESI-MS (M+H$^+$): 358.1. $^1$H NMR (400 MHz, CDCl$_3$) δ: 7.46 (d, 2H), 7.18 (d, 2H), 5.59 (d, 1H), 5.05 (br, 1H), 3.62 (s, 3H), 2.83-2.81 (m, 2H), 1.42 (s, 9H).

A flask charged with (R)-methyl 3-(4-bromophenyl)-3-(tert-butoxycarbonylamino)propanoate (7 g, 19.6 mmol), 4,4,4',4',5,5,5',5'-octamethyl-2,2'-bi(1,3,2-dioxaborolane) (10 g, 40 mmol, 2.0 eq), KOAc (4 g, 40 mmol, 2.0 eq) and [1,1-Bis (diphenylphosphino)ferrocene]dichloropalladium (II) complex with dichloromethane (1:1) (0.8 g, 1 mmol, 0.05 eq) was flushed with nitrogen. Then dioxane (200 mL) was added and the reaction was stirred at 90° C. for 1 h. The solution was cooled to rt. and the residue was purified by silica gel column (EA:PE=1:10) to give the product (R)-methyl 3-(tert-butoxycarbonylamino)-3-(4-(4,4,5,5-tetramethyl-1,3,2-dioxaborolan-2-yl)phenyl)propanoate (7 g, yield: 89%) as a white solid. ESI-MS (M+H$^+$): 406.2. $^1$H NMR (400 MHz, CDCl$_3$) δ: 7.77 (d, 2H), 7.30 (d, 2H), 5.50 (br, 1H), 5.11 (br, 1H), 3.60 (s, 3H), 2.84-2.82 (m, 2H), 1.33 (s, 12H), 1.24 (s, 9H).

A mixture of (R)-methyl 3-(tert-butoxycarbonylamino)-3-(4-(4,4,5,5-tetramethyl-1,3,2-dioxaborolan-2-yl)phenyl)propanoate (1.8 g, 4.4 mmol), 5-iodo-7-(phenylsulfonyl)-7H-pyrrolo[2,3-d]pyrimidin-4-amine (1.8 g, 4.4 mmol, 1.0 eq), K$_2$CO$_3$ (1.2 g, 8.8 mmol, 2.0 eq) and [1,1-Bis (diphenylphosphino)ferrocene]dichloropalladium (II) complex with dichloromethane (1:1) (180 mg, 0.22 mmol, 0.05 eq) was flushed with nitrogen and the reaction was stirred at 100° C. for 2 h. The solution was cooled to room temperature. The solvent was removed and the residue was purified by column chromatography (PE:EA=1:4) to give compound (R)-methyl-3-(4-(4-amino-7-(phenyl sulfonyl)-7H-pyrrolo[2,3-d]pyrimidin-5-yl)phenyl)-3-(tert-butoxycarbonylamino)propanoate (870 mg, yield: 35.6%). ESI-MS (M+H$^+$): 552.2. $^1$H NMR (400 MHz, DMSO-d$_6$) δ: 8.25 (s, 1H), 8.18-8.16 (m, 2H), 7.77-7.75 (m, 2H), 7.67-7.65 (m, 4H), 7.58-7.56 (m, 1H), 7.48 (d, 2H), 7.45 (d, 2H), 5.00 (br, 1H), 3.58 (s, 3H), 2.79-2.75 (m, 2H), 1.37 (s, 9H).

A solution of compound (R)-methyl-3-(4-(4-amino-7-(phenylsulfonyl)-7H-pyrrolo[2,3-d]pyrimidin-5-yl)phenyl)-3-(tert-butoxycarbonylamino)propanoate (1.5 g, 2.7 mmol), conc HCl (0.25 mL, 2.7 mmol, 5 eq) in MeOH (20 mL) was stirred at rt for 1 h, After the reaction completed, the solvent was removed to give the product (R)-methyl 3-amino-3-(4-(4-amino-7-(phenylsulfonyl)-7H-pyrrolo[2,3-d]pyrimidin-5-yl)phenyl)propanoate (1.1 g, yield: 89.4%) as yellow solid. ESI-MS (M+H$^+$): 452.1.

A solution of (R)-methyl 3-amino-3-(4-(4-amino-7-(phenylsulfonyl)-7H-pyrrolo[2,3-d]pyrimidin-5-yl)phenyl)propanoate (1.5 g, 3.3 mmol), (S)-5-cyano-2-fluoro-N-(1-(4-fluorophenyl)ethyl)nicotinamide (0.95 g, 3.3 mmol, 1 eq) and TEA (671 mg, 6.6 mmol, 2 eq) in DMF (20 mL) was stirred at 100° C. for 1 h (LCMS show the SM disappeared and main products were desired product and the corresponding acid. Then EA (60 mL) was added. The organic phase was washed with H$_2$O (20 mL×3) and dried. The organic phases were concentrated and purified on silica gel column (EA:PE=2:1) to give (R)-methyl 3-(4-(4-amino-7-(phenylsulfonyl)-7H-pyrrolo[2,3-d]pyrimidin-5-yl)phenyl)-3-(5-cyano-3-((S)-1-(4-fluorophenyl)ethylcarbamoyl)pyridin-2-ylamino)propanoate (520 mg, yield: 21.8%) as a yellow solid (ESI-MS (M+H$^+$): 719.2) and (R)-3-(4-(4-amino-7-(phenylsulfonyl)-7H-pyrrolo[2,3-d]pyrimidin-5-yl)phenyl)-3-(5-cyano-3-((S)-1-(4-fluorophenyl)ethylcarbamoyl)pyridin-2-ylamino)propanoic acid (1 g, yield: 42%) as a yellow solid (ESI-MS (M+H$^+$): 705.2).

The mixture of (R)-methyl 3-(4-(4-amino-7-(phenylsulfonyl)-7H-pyrrolo[2,3-d]pyrimidin-5-yl)phenyl)-3-(5-cyano-3-((S)-1-(4-fluorophenyl)ethylcarbamoyl)pyridin-2-ylamino)propanoate (520 mg, 0.72 mmol) and K$_2$CO$_3$ (200 mg, 1.45 mmol, 2.0 eq) in MeOH (15 mL) was stirred at 50° C. for 30 min. Then the reaction mixture was concentrated and purified by silica gel column (DCM/MeOH=20:1) to give the desired product (R)-methyl 3-(4-(4-amino-7H-pyrrolo[2,3-d]pyrimidin-5-yl)phenyl)-3-(5-cyano-3-((S)-1-(4-fluorophenyl)ethylcarbamoyl)pyridin-2-ylamino)propanoate as white solid (300 mg, yield: 71.6%). ESI-MS (M+H$^+$): 579.0, $^1$H NMR (400 MHz, DMSO-d$_6$) δ: 11.82 (s, 1H), 9.66 (d, 1H), 9.01 (d, 1H), 8.56 (dd, 2H), 8.11 (s, 1H), 7.45-7.44 (m, 6H), 7.25-7.17 (m, 3H), 5.99 (br, 2H), 5.78-5.72 (m, 1H), 5.15-5.11 (m, 1H), 3.48 (s, 3H), 3.06-2.96 (m, 2H), 1.46 (d, 3H).

Example 45

(R)-3-(4-(4-amino-7H-pyrrolo[2,3-d]pyrimidin-5-yl) phenyl)-3-(5-cyano-3-((S)-1-(4-fluorophenyl)ethylcarbamoyl)pyridin-2-ylamino)propanoic acid The mixture of (R)-methyl 3-(4-(4-amino-7H-pyrrolo[2,3-d]pyrimidin-5-yl)phenyl)-3-(5-cyano-3-((S)-1-(4-fluorophenyl)ethylcarbamoyl)pyridin-2-ylamino)propanoate (200 mg, 0.35 mmol) and K$_2$CO$_3$ (2M, 190 mg, 1.40 mmol, 4.0 eq) in MeOH (15 mL) was stirred at 50° C. for 30 min. Then the reaction mixture was concentrated and purified by silica gel column (DCM/MeOH=10:1) to give the desired product (R)-3-(4-(4-amino-7H-pyrrolo[2,3-d]pyrimidin-5-yl)phenyl)-3-(5-cyano-3-((S)-1-(4-fluorophenyl)ethylcarbamoyl) pyridin-2-ylamino)propanoic acid as white solid (300 mg, yield: 35.9%). ESI-MS (M+H$^+$): 565.2, $^1$H NMR (400 MHz, DMSO-d$_6$) δ: 12.78 (s, 1H), 12.32 (br, 1H), 9.67 (d, 1H), 9.00 (d, 1H), 8.56 (dd, 2H), 8.36 (s, 1H), 7.49-7.44 (m, 9H), 7.17 (t, 2H), 5.77-5.75 (m, 1H), 5.14-5.12 (m, 1H), 2.92-2.90 (m, 2H), 1.47 (d, 3H).

Example 46

2-((R)-3-amino-1-(4-(4-amino-7H-pyrrolo[2,3-d] pyrimidin-5-yl)phenyl)-3-oxopropylamino)-5-cyano-N—((S)-1-(4-fluorophenyl)ethyl)nicotinamide To a solution of (R)-3-(4-(4-amino-7-(phenylsulfonyl)-7H-pyrrolo[2,3-d]pyrimidin-5-yl)phenyl)-3-(5-cyano-3-((S)-1-(4-fluorophenyl)ethylcarbamoyl)pyridin-2-ylamino) propanoic acid (500 mg, 0.71 mmol) in DCM (50 mL), was added HBTU (538 mg, 1.42 mmol, 2.0 eq), NH$_4$Cl (120 mg 2.13 mmol, 3.0 eq.) and TEA (360 mg 3.6 mmol, 5.0 eq). The reaction mixture was stirred at room temperature for 1 h. The solvent was removed and the residue was purified by silica gel column (PE/EA=1:5) to give the corresponding amide as a white solid (300 mg, yield: 60%). ESI-MS (M+H$^+$): 704.2. $^1$H NMR (400 MHz, DMSO-d$_6$) δ: 9.69-9.67 (m, 1H), 9.04-9.02 (m, 1H), 8.54-8.53 (m, 2H), 8.24 (s, 1H), 8.15-8.14 (m, 1H), 7.90-7.88 (m, 2H), 7.76-7.74 (m, 1H), 7.67-7.62 (m, 4H), 7.49-7.40 (m, 6H), 7.34-7.31 (m, 2H), 7.19-7.15 (m, 2H), 5.76-5.71 (m, 1H), 5.16-5.11 (m, 1H), 3.06-3.00 (m, 2H), 1.46 (d, 3H). The phenylsulfonyl was removed under standard condition to give 2-((R)-3-amino-1-(4-(4-amino-7H-pyrrolo[2,3-d]pyrimidin-5-yl) phenyl)-3-oxopropylamino)-5-cyano-N—((S)-1-(4-fluorophenyl)ethyl)nicotinamide as a white solid, yield: 29.2%. ESI-MS (M+H$^+$): 564.2. $^1$H NMR (400 MHz, DMSO-d$_6$) δ: 8.87 (d, 1H), 8.43 (d, 1H), 8.32-8.23 (m, 2H), 7.58-7.40 (m, 4H), 7.44-7.41 (m, 3H), 7.11-7.07 (m, 2H), 5.83 (t, 1H), 5.23-5.19 (m, 1H), 2.97-2.91 (m, 1H), 2.84-2.78 (m, 1H), 1.56 (d, 3H).

Examples 47 and 48 were prepared in a manner consistent with Example 46.

Synthesis of
4-(4-(aminomethyl)phenoxy)pyridin-2-amine

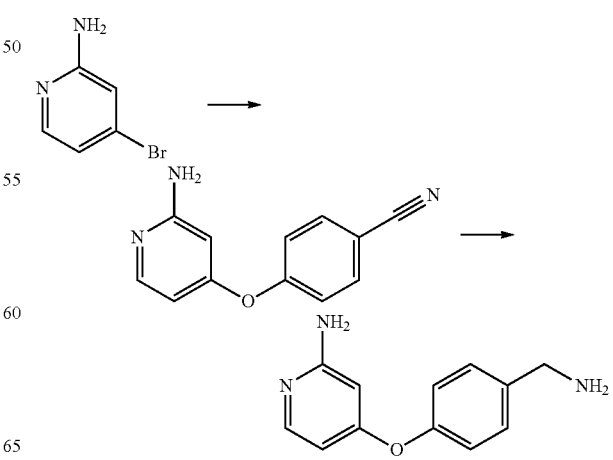

A mixture of 2-Amino-4-bromopyridine (200.0 mg, 1.156 mmol), 4-Hydroxybenzoic acid nitrile (275 mg, 2.31 mmol), Potassium carbonate (319 mg, 2.31 mmol), Copper(I) oxide (33.0 mg, 0.231 mmol) in Pyridine (1.90 mL, 23.5 mmol) was heated at 120° C. for 18 hours. Solvent removed and residue purified by column chromatography to give 4-(2-aminopyridin-4-yloxy)benzonitrile (59.0 mg, 22% yld). ESI-MS (M+H$^+$): 212.1.

To a solution of 4-(2-Amino-pyridin-4-yloxy)-benzonitrile (59.0 mg, 0.279 mmol) in Tetrahydrofuran (2.9 mL, 36 mmol) was added 1.00 M of Borane in Tetrahydrofuran (0.8380 mL, 0.8380 mmol). Reaction mixture was heated to reflux overnight. A second addition of 1.00 M of Borane in Tetrahydrofuran (0.8380 mL, 0.8380 mmol) was added then refluxed for an additional 4 hours. To this reaction mixture was added 1.25 M of Hydrogen chloride in Methanol (2.682 mL, 3.352 mmol) and refluxed for an additional 2 hours. Solvent removed in vacuo. The crude 4-(4-(aminomethyl)phenoxy)pyridin-2-amine was carried onto next step without further purification. ESI-MS (M+H$^+$): 216.1.

Synthesis of 6-(4-(aminomethyl)phenoxy)pyrimidin-4-amine

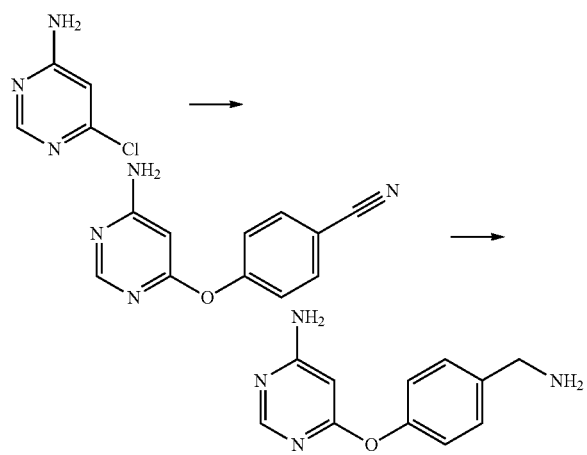

A mixture of 6-chloropyrimidin-4-amine (1.29 g, 10 mmol), 4-hydroxybenzonitrile (1.5 g, 15 mmol, 1.2 eq), Cu$_2$O (0.5 g, 2 mmol, 0.2 eq), K$_2$CO$_3$ (2.76 g, 20 mmol, 2 eq) and pyridine (40 mL) was refluxed at 125° C. for 18 h. Pyridine was removed in vacuum and H$_2$O (20 mL) was added, then extracted with EtOAc (50 mL). The organic layer was washed with 2N NaOH (20 mL) and brine (20 mL), respectively, then dried and concentrated to give crude 4-(6-aminopyrimidin-4-yloxy)benzonitrile as tan solid (1.2 g, yield: 55%). ESI-MS (M+H$^+$): 213.1. $^1$H-NMR (400 MHz, DMSO-d$_6$) δ: 8.16 (s, 1H), 7.90 (d, 2H), 7.35 (d, 2H), 7.01 (s, 1H), 5.95 (s, 2H).

In a round-bottom flask, a mixture of 4-(6-aminopyrimidin-4-yl)oxy)benzonitrile (50 mg, 0.23 mmol), Raney Ni (15 mg, 0.23 mmol, 1 eq), MeOH (20 mL) and 2 drops concentrated HCl was stirred at rt under H$_2$ for 16 h. Then Raney Ni was removed by filtration, the filtrate was concentrated to give crude 6-(4-(aminomethyl)phenoxy)pyrimidin-4-amine as a yellow solid (35 mg, yield: 70%). ESI-MS (M+H$^+$): 217.1.

Synthesis of tert-butyl (5-(7-cyclobutyl-4-(4-methoxybenzylamino)-7H-pyrrolo[2,3-d]pyrimidin-5-yl)thiophen-2-yl)methylcarbamate

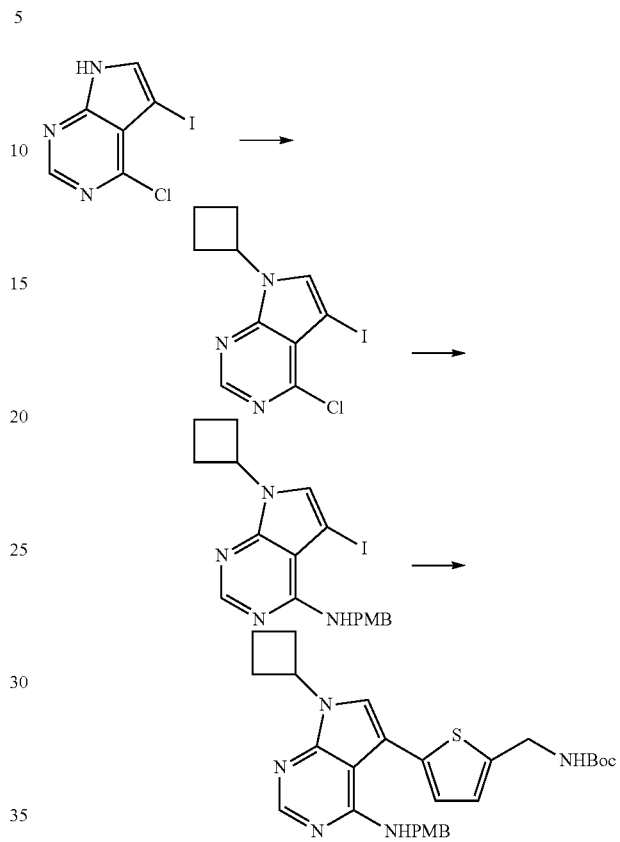

To a mixture of compound 4-chloro-5-iodo-7H-pyrrolo[2,3-d]pyrimidine (5.8 g, 20.8 mmol, 1.0 eq) and Cs$_2$CO$_3$ (33.9 g, 103.9 mmol, 5.0 eq) in anhydrous DMA was added bromocyclobutane (3.4 g, 25.0 mmol, 1.2 eq). The mixture was stirred at 90° C. for 16 h. After the reaction completed, the mixture was diluted with water (200 mL) and extracted with ethyl acetate (3×150 mL). The organic layer was dried over sodium sulfate and concentrated in vacuum to get crude product, which was purified by silica gel chromatography (PE:EA=0~50%) to give product 4-chloro-7-cyclobutyl-5-iodo-7H-pyrrolo[2,3-d]pyrimidine as a white solid (2.0 g, yield: 29%). ESI-MS (M+H$^+$): 331.0. $^1$H NMR (400 MHz, CDCl$_3$) δ: 8.61 (s, 1H), 7.58 (s, 1H), 5.30-5.26 (m, 1H), 2.60-2.54 (m, 2H), 2.50-2.45 (m, 2H), 1.99-1.92 (m, 2H).

To a solution of 4-chloro-7-cyclobutyl-5-iodo-7H-pyrrolo[2,3-d]pyrimidine (400 mg, 1.20 mmol, 1.0 eq) and DIPEA (465 mg, 3.60 mmol, 3.0 eq) in DMSO was added PMBNH$_2$ (165 mg, 1.20 mmol, 1.0 eq). The mixture was stirred at 100° C. for 16 h. Then the mixture was diluted with water (150 mL) and extracted with EA (3×100 mL). The combined organics were dried over magnesium sulfate and concentrated. The mixture was purified by silica gel chromatography (PE:EA=0~10%) to give 7-cyclobutyl-5-iodo-N-(4-methoxybenzyl)-7H-pyrrolo[2,3-d]pyrimidin-4-amine as white solid. (286 mg, yield: 55%). ESI-MS (M+H$^+$): 435.1. $^1$H NMR (400 MHz, CDCl$_3$) δ: 8.35 (s, 1H), 7.34 (d, 2H), 7.20 (s, 1H), 6.91-6.88 (m, 2H), 6.33 (s, 1H), 5.24-5.20 (m, 1H), 4.78 (s, 2H), 3.81 (s, 3H), 2.56-2.49 (m, 2H), 2.44-2.37 (m, 2H), 1.92-1.86 (m, 2H).

To a mixture of tert-butyl (5-(4,4,5,5-tetramethyl-1,3,2-dioxaborolan-2-yl)thiophen-2-yl)methylcarbamate (200 mg, 0.46 mmol, 1.0 eq), K$_2$CO$_3$ (127 mg, 0.92 mmol, 2.0 eq) and PdCl$_2$(dppf)DCM (19 mg, 0.023 mmol, 0.05 eq) in dioxane (10 mL) and H$_2$O (1 mL) was added tert-butyl (5-bromothiophen-2-yl)methylcarbamate (156 mg, 0.46 mmol, 1.0 eq) under nitrogen. The mixture was heated to 90° C. for 2h and then diluted with water (30 mL), extracted with EA (3×20 mL). The combined organic phase was dried over sodium sulfate and concentrated. The residue was purified by silica gel chromatography (PE:EA=0-60%) to give tert-butyl (5-(7-cyclobutyl-4-(4-methoxybenzylamino)-7H-pyrrolo[2,3-d]pyrimidin-5-yl)thiophen-2-yl)methylcarbamate as a light grey solid (86 mg, yield: 36%). ESI-MS (M+H$^+$): 520.2. $^1$H NMR (400 MHz, CDCl$_3$) δ: 8.39 (s, 1H), 7.23 (d, 2H), 7.16 (s, 1H), 6.87-6.82 (m, 3H), 6.81 (s, 1H), 5.67 (s, 1H), 5.29-5.25 (m, 1H), 4.98 (s, 1H), 4.72 (s, 2H), 4.44 (s, 2H), 3.79 (s, 3H), 2.56-2.52 (m, 2H), 2.46-2.41 (m, 2H), 1.92-1.84 (m, 2H), 1.41 (s, 9H).

Synthesis of 9-Iodo-3-methyl-imidazo[1,2-c]quinazoline

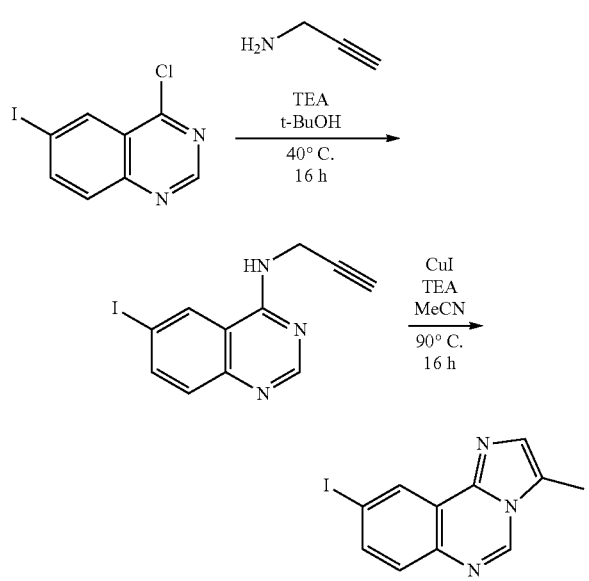

(6-Iodo-quinazolin-4-yl)-prop-2-ynyl-amine

4-Chloro-6-iodo-quinazoline (434 mg, 1.49 mmol) was stirred in tert-butyl alcohol (7.5 mL). Added propargylamine (150 µL, 2.19 mmol) followed by triethylamine (312 µL, 2.24 mmol) and heated at 40° C. for three days. Added ethyl acetate (75 mL) to the reaction and washed with aqueous sodium bicarbonate, and brine. The organic phase was dried over magnesium sulfate, and evaporated. Collected a yellow powder. 1H NMR (300 MHz, CDCl$_3$) δ 8.73 (s, 1H), 8.10 (d, J=1.51 Hz, 1H), 8.01 (dd, J=1.89, 8.69 Hz, 1H), 7.62 (d, J=8.69 Hz, 1H), 5.78 (t, J=4.91 Hz, 1H), 4.48 (dd, J=2.64, 5.29 Hz, 2H), 2.35 (t, J=2.64 Hz, 1H) ES (+) MS m/e=310.0 (M+1).

9-Iodo-3-methyl-imidazo[1,2-c]quinazoline (6-Iodo-quinazolin-4-yl)-prop-2-ynyl-amine (207 mg, 0.670 mmol), and copper(I) iodide (19 mg, 0.099 mmol) were combined with acetonitrile (6.7 mL, 130 mmol) and triethylamine (187 µL, 1.34 mmol) and heated at 90° C. for 16 hours. The reaction was taken up in ethyl acetate (75 ml) and washed with 1M ammonium hydroxide, aqueous sodium bicarbonate, and brine. The organic phase was dried over magnesium sulfate, evaporated, and purified by flash chromatography (0-100% ethyl acetate:hexanes, silica gel). Collected 126.1 mg of a light yellow powder (61%) with a minor amount of undesired regioisomer detected by NMR. $^1$H NMR (300 MHz, CDCl$_3$) δ 8.90 (d, J=1.89 Hz, 1H), 8.75 (s, 1H), 7.96 (dd, J=2.08, 8.50 Hz, 1H), 7.68 (d, J=8.69 Hz, 1H), 7.35-7.40 (m, 1H), 2.62 (d, J=1.13 Hz, 3H).

Example 49 was prepared in a manner analogous to Ex. 2.4 from 9-Iodo-3-methyl-imidazo[1,2-c]quinazoline.

Example 50

2-(3-carbamoyl-4-(1H-imidazol-1-yl)benzylamino)-N-(3,4-difluorobenzyl)nicotinamide

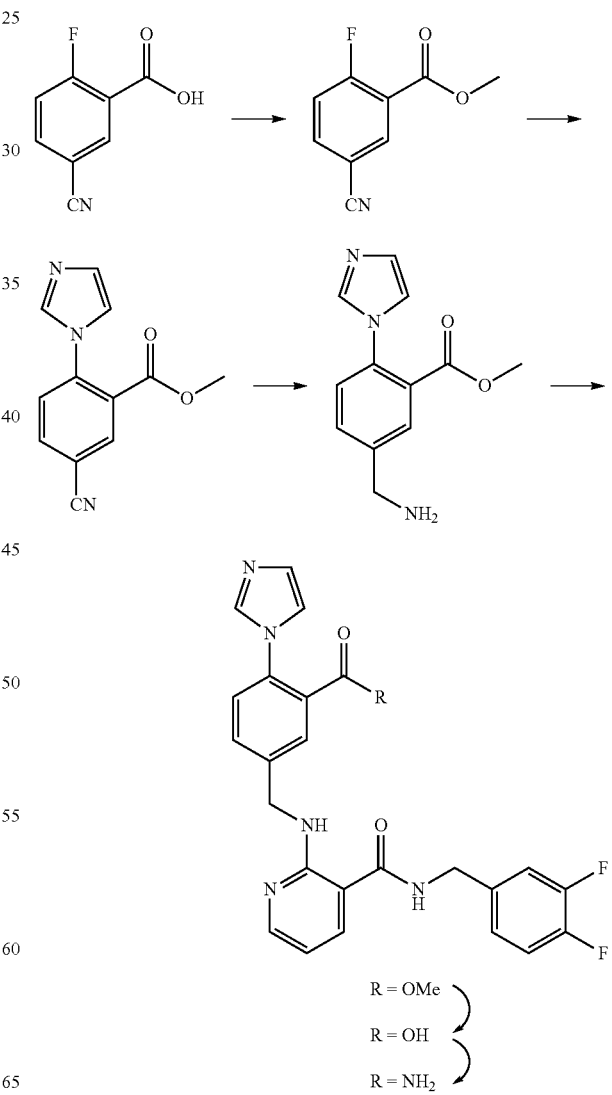

Methyl 5-((3-(3,4-difluorobenzylcarbamoyl)pyridin-2-ylamino)methyl)-2-(1H-imidazol-1-yl)benzoate To a solution of 5-cyano-2-fluorobenzoic acid (2.61 g, 16 mmol) in MeOH (40 mL) was added $SOCl_2$ (0.92 g, 8 mmol, 0.5 eq) at rt, then stirred for 2 h at 85° C. The reaction mixture was concentrated to give the crude product methyl 5-cyano-2-fluorobenzoate as white solid (2.87 g, yield: 100%). ESI-MS (M+H)+: 180.1. $^1$H NMR (400 MHz, $CDCl_3$) δ: 8.24 (dd, 1H), 7.80-7.74 (m, 1H), 7.28-7.20 (m, 1H), 3.92 (s, 3H).

To a solution of methyl 5-cyano-2-fluorobenzoate (3.77 g, 21 mmol) in DMF (30 mL) was added imidazole (2 g, 29 mmol, 1.4 eq) at rt, then stirred for 3 h at 110° C. until the reaction was finished. The mixture was diluted with sat. $NH_4Cl$ (40 mL), extracted with DCM (3×50 mL). The combined organic layer was washed by brine (50 mL), dried over $Na_2SO_4$, concentrated to give the residues which was purified by silica gel column chromatography using petroleum ether/ethyl acetate (2/1) as eluent to give methyl 5-cyano-2-(1H-imidazol-1-yl)benzoate as the slight yellow solid (3.95 g, yield: 83%). ESI-MS (M+H)+: 228.1. $^1$H NMR (400 MHz, $CDCl_3$) δ: 8.25 (d, 1H), 7.79 (dd, 1H), 7.63 (s, 1H), 7.75 (d, 1H), 7.21 (s, 1H), 7.10 (t, 1H), 3.78 (s, 3H).

To a solution of methyl 5-cyano-2-(1H-imidazol-1-yl)benzoate (3.82 g, 16 mmol) in MeOH (100 mL) was added aq. $NH_3$ (30%, 8 mL) at rt, then Raney Ni (~1 g) was added to the mixture under $N_2$. Then the mixture was stirred for 18 h at rt under $H_2$. The reaction mixture was filtered, concentrated to give the crude product methyl 5-(aminomethyl)-2-(1H-imidazol-1-yl)benzoate as slight yellow oil (3.47 g, yield: 63%). ESI-MS (M+H)+: 232.1. $^1$H NMR (400 MHz, DMSO-$d_6$) δ: 7.91-7.58 (m, 3H), 7.46-7.25 (m, 2H), 7.02 (s, 1H), 3.80 (s, 2H), 3.64 (s, 3H).

To a solution of methyl 5-(aminomethyl)-2-(1H-imidazol-1-yl)benzoate (3.27 g, 14 mmol) in DMF (40 mL) was added N-(3, 4-difluorobenzyl)-2-fluoronicotinamide (3.76 g, 14 mmol, 1 eq) and $Et_3N$ (3.56 g, 35 mmol, 2.5 eq) at rt, then stirred for 3 h at 110° C. The reaction mixture was diluted with $H_2O$ (40 mL), extracted with DCM (2×50 mL). The organic layer was washed with brine (60 mL), dried over $Na_2SO_4$, concentrated and purified by silica gel column chromatography using DCM/MeOH (20/1) as eluent to give methyl 5-((3-(3,4-difluorobenzylcarbamoyl)pyridin-2-ylamino)methyl)-2-(1H-imidazol-1-yl)benzoate as yellow oil (3.47 g, yield: 51%). ESI-MS (M+H)+: 478.2. $^1$H NMR (400 MHz, DMSO-$d_6$) δ: 9.14 (t, 1H), 8.83 (t, 1H), 8.18-8.14 (m, 1H), 8.05-7.99 (m, 1H), 7.85-7.82 (m, 1H), 7.78-7.74 (m, 1H), 7.66-7.61 (m, 1H), 7.46-7.34 (m, 4H), 7.20-7.14 (m, 1H), 7.05-7.00 (m, 1H), 6.67-6.62 (m, 1H), 4.73 (d, 2H), 4.44 (d, 2H), 3.63 (s, 3H).

5-((3-(3,4-difluorobenzylcarbamoyl)pyridin-2-ylamino)methyl)-2-(1H-imidazol-1-yl)benzoic acid To a solution of methyl 5-((3-(3,4-difluorobenzylcarbamoyl)pyridin-2-ylamino)methyl)-2-(1H-imidazol-1-yl)benzoate (1.00 g, 2 mmol) in EtOH (40 mL) was added NaOH (419 mg, 10 mmol, 5 eq) and $H_2O$ (4 mL) at rt. The mixture was refluxed for 1 h until the reaction finished. The mixture was adjusted to pH=6 with 5% HCl, then concentrated. The residues was dispersed in DCM/EtOH (4:1, 400 mL), filtered and concentrated to give the crude 5-((3-(3,4-difluorobenzylcarbamoyl)pyridin-2-ylamino)methyl)-2-(1H-imidazol-1-yl)benzoic acid.

2-(3-carbamoyl-4-(1H-imidazol-1-yl)benzylamino)-N-(3,4-difluorobenzyl)nicotinamide 5-((3-(3,4-difluorobenzylcarbamoyl)pyridin-2-ylamino)methyl)-2-(1H-imidazol-1-yl)benzoic acid was converted to 2-(3-carbamoyl-4-(1H-imidazol-1-yl)benzylamino)-N-(3,4-difluorobenzyl)nicotinamide with $NH_4Cl$ and HATU as slight yellow solid (58 mg, yield: 29%). (Mobile phase: MeOH/$H_2O$=0-65%). ESI-MS (M+H+): 463.2. $^1$H NMR (400 MHz, $CD_3OD$) δ: 8.13-8.09 (m, 1H), 7.94-7.89 (m, 1H), 7.79 (s, 1H), 7.62-7.56 (m, 2H), 7.41-7.36 (m, 1H), 7.31-7.04 (m, 5H), 6.66-6.58 (m, 1H), 4.76 (s, 2H), 4.49 (s, 2H).

Example 51

(S)-2-(5-(4-aminoquinazolin-6-yl)thiophen-2-ylamino)-N-(1-(3,4-difluorophenyl)ethyl)nicotinamide

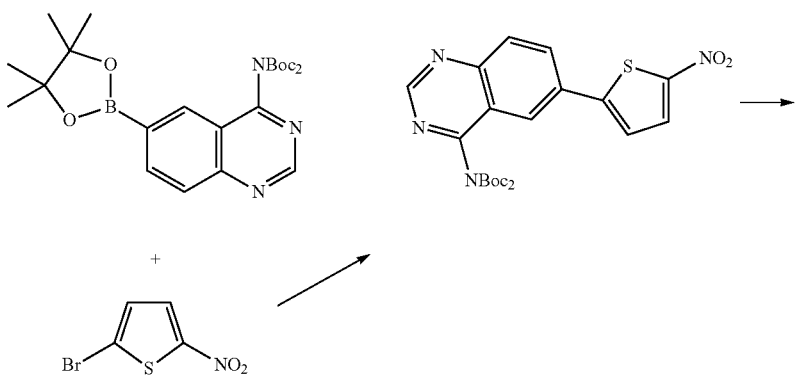

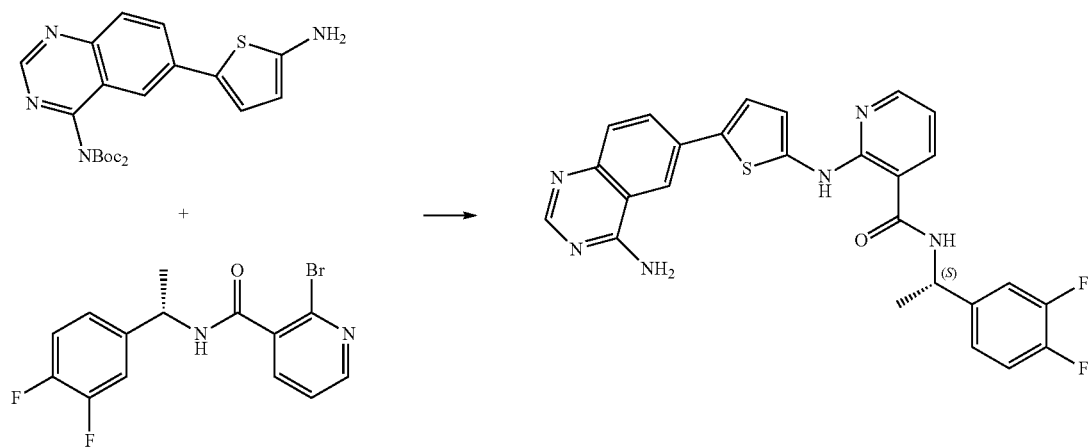

2-Bromo-5-nitrothiophene (500 mg, 2.42 mmol), N,N-di-Boc-6-(4,4,5,5-tetramethyl-1,3,2-dioxaborolan-2-yl)quinazolin-4-amine (1.37 g, 2.90 mmol, 1.2 eq) and $K_2CO_3$ (668 mg, 4.84 mmol, 2.0 eq) were dissolved in dioxane (10 mL). $PdCl_2$ (dppf)$CH_2Cl_2$ (99 mg, 0.12 mmol, 0.05 eq) was added. The reaction mixture was heated to 90° C. for 3 h at the nitrogen atmosphere. Then the reaction mixture was cooled, and evaporated under reduced pressure. The residue was purified by silica gel column (PE/EA=5/1) to give 6-(5-nitrothiophen-2-yl)-N,N-di-Boc-quinazolin-4-amine as yellow solid (650 mg, yield: 57%). ESI-MS (M+H$^+$): 473.1. $^1$H NMR (400 MHz, DMSO-d$_6$) δ: 9.33 (s, 1H), 8.54 (dd, 1H), 8.43 (d, 1H), 8.27-8.22 (m, 2H), 8.02 (d, 1H), 1.31 (s, 18H).

6-(5-Nitrothiophen-2-yl)-N,N-di-Boc-quinazolin-4-amine (350 mg, 0.74 mmol) was dissolved in methanol (10 mL) then Pd/C (35 mg) was added. The reaction was stirred at rt for 16 h under hydrogen atmosphere. The catalyst was removed by filtration and the filtrate was concentrated under reduced pressure to give 6-(5-aminothiophen-2-yl)-N,N-di-Boc-quinazolin-4-amine as brown solid (300 mg, yield: 91%), which was used for the next step without further purification. ESI-MS (M+H$^+$): 443.1.

6-(5-Aminothiophen-2-yl)-N,N-di-Boc-quinazolin-4-amine (300 mg, 0.68 mmol), (S)-2-bromo-N-(1-(3,4-difluorophenyl)ethyl)nicotinamide (277 mg, 0.81 mmol, 1.2 eq) and $Cs_2CO_3$ (443 mg, 1.36 mmol, 2 eq) were added into a sealed tube and dioxane (1 mL). Then $Pd_2$(dba)$_3$ (62 mg, 0.07 mmol, 0.1 eq) and Xantphos (40 mg, 0.07 mmol, 0.1 eq) were added into the mixture under nitrogen protection. The reaction mixture was heated to 160° C. under MW for 70 min. Then the reaction mixture was cooled, evaporated under reduced pressure. The residue was purified by HPLC-preparation (0.05% TFA/100%-50% $H_2O$/0-50% MeOH) to give (S)-2-(5-(4-aminoquinazolin-6-yl)thiophen-2-ylamino)-N-(1-(3,4-difluorophenyl)ethyl)nicotinamide as red solid (13 mg, yield: 3.8%). ESI-MS: (M+H$^+$): 503.0. HPLC: 95.87%. $^1$H NMR (400 MHz, CD$_3$OD) δ: 8.49 (s, 1H), 8.40-8.37 (m, 2H), 8.21 (dd, 1H), 8.14 (dd, 1H), 7.63 (d, 1H), 7.35 (d, 1H), 7.29 (t, 1H), 7.19-7.16 (m, 2H), 6.87-6.84 (m, 1H), 6.60 (d, 1H), 5.19 (q, 1H), 1.52 (d, 3H).

Example 52

Synthesis of (S)-6-cyano-N-(1-(3,4-difluorophenyl)ethyl)-3-(4-(3-(methylamino)-1H-pyrazolo[3,4-b]pyridin-5-yl)benzylamino)pyrazine-2-carboxamide

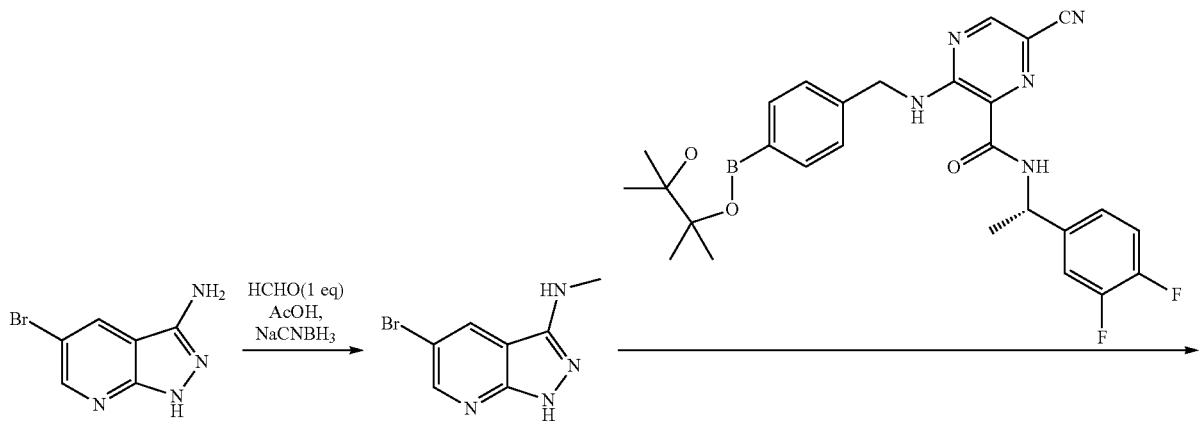

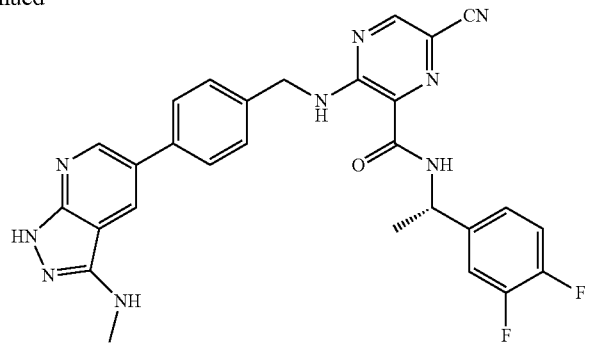

Synthesis of 5-bromo-N-methyl-1H-pyrazolo[3,4-b]pyridin-3-amine

To a mixture of 5-bromo-1H-pyrazolo[3,4-b]pyridin-3-ylamine (0.2 g, 0.9 mmol) and formaldehyde (0.07 mL, 0.9 mmol) in acetic acid (5 mL, 90 mmol) was added a solution of sodium cyanoborohydride (185 mg, 2.95 mmol) in tetrahydrofuran (2 mL). The mixture was then stirred at rt overnight. Quenched with water, extracted with EtOAc, washed with water, brine, then sat'd NaHCO$_3$. The organic phase was dried over MgSO$_4$, filtered, and concentrated. The crude was then purified by prep-TLC to give desired product (38 mg) which was used in the next step without further purifications. LCMS: RT 0.82 min., MH$^+$ 227.6.

Synthesis of (S)-6-cyano-N-(1-(3,4-difluorophenyl)ethyl)-3-(4-(3-(methylamino)-1H-pyrazolo[3,4-b]pyridin-5-yl)benzylamino)pyrazine-2-carboxamide A solution of 6-cyano-3-[4-(4,4,5,5-tetramethyl-1,3,2-dioxaborolan-2-yl)-benzylamino]-pyrazine-2-carboxylic acid [(S)-1-(3,4-difluoro-phenyl)-ethyl]-amide (103 mg, 0.2 mmol) and (5-Bromo-1H-pyrazolo[3,4-b]pyridin-3-yl)-methyl-amine (30 mg, 0.10 mmol) in 1,4-dioxane (2.0 mL) was degassed for 10 min, bis(tricyclohexylphosphine)palladium (0) (8.8 mg, 0.01 mmol) and saturated aqueous NaHCO$_3$ (0.3 mL, 0.4 mmol) were added. The reaction was heated in the microwave at 120° C. for 20 min. The reaction mixture was diluted with EtOAc, washed with water (5×). The organic phase was the separated, dried over MgSO$_4$, and concentrated. The crude was then purified by HPLC to give desired product 38 mg. LCMS: RT 1.66 min.; MH+ 540.6: $^1$H NMR (400 MHz, DMSO-d$_6$) δ ppm 12.05 (br. s., 1 H) 9.76 (t, J=5.77 Hz, 1 H) 9.34 (d, J=8.28 Hz, 1 H) 8.75 (s, 1 H) 8.64 (d, J=2.01 Hz, 1 H) 8.33 (d, J=2.26 Hz, 1 H) 7.61 (d, J=8.03 Hz, 2 H) 7.48-7.56 (m, 1 H) 7.33-7.46 (m, 3 H) 7.27 (br. s., 1 H) 6.23 (d, J=5.02 Hz, 1 H) 4.99-5.22 (m, 1 H) 4.73 (t, J=5.65 Hz, 2 H) 2.87 (d, J=5.02 Hz, 3 H) 1.52 (d, J=7.03 Hz, 3 H); $^{19}$F NMR (376 MHz, DMSO-d$_6$) δ ppm $^-$139.01-$^-$138.68 (m, 1 F), $^-$141.62-$^-$141.28 (m, 1 F).

Example 53

2-(3-(5-(1H-pyrazol-5-yl)-1H-pyrrolo[2,3-b]pyridin-3-yl)-5-isopropoxybenzylamino)-N-(3,4-difluorobenzyl)nicotinamide

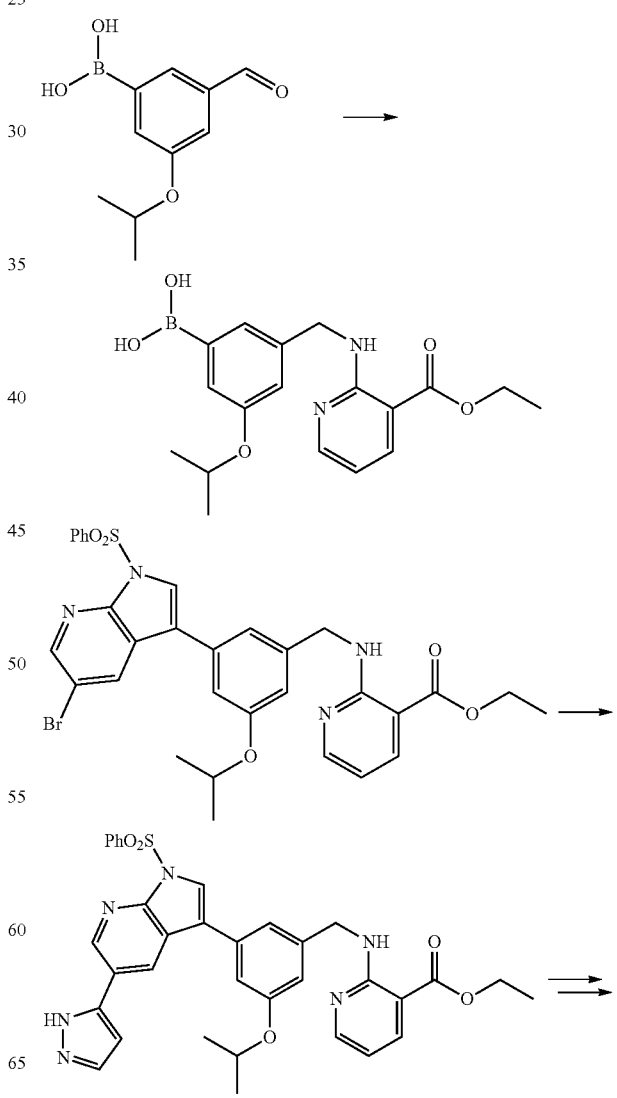

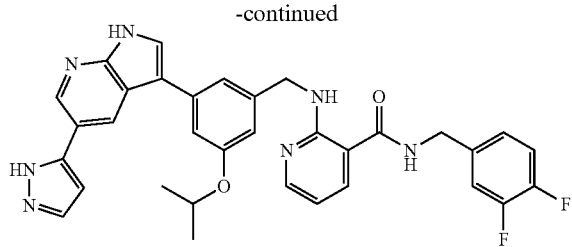

A solution of 3-formyl-5-isopropoxyphenylboronic acid (2.5 g, 12 mmol) and ethyl 2-aminonicotinate (3.0 g, 18 mmol) in toluene (100 mL) was heated to 120° C. for 16 h. Then the solvent was removed and a solution of NaBH$_4$ (2.05 g, 54 mmol, 3 eq) in MeOH (20 mL) was added slowly, the residue was stirred at rt for 2 h. The mixture was diluted with water (100 mL) and adjusted with HCl to pH=3-4. Then extracted with EtOAc (100 mL×3) and washed with saturated NaHCO$_3$ (100 mL×3) and dried. The organic phase was concentrated to give 3-((3-(ethoxycarbonyl)pyridin-2-ylamino)methyl)-5-isopropoxyphenylboronic acid (3.3 g, yield: 76%) as a yellow solid. This crude compound was used to the next step without further purification. ESI-MS (M+H$^+$): 359.2.

A mixture of 3-((3-(ethoxycarbonyl)pyridin-2-ylamino)methyl)-5-isopropoxyphenylboronic acid (3.3 g, 9.2 mmol), 5-bromo-3-iodo-1-(phenylsulfonyl)-1H-pyrrolo[2,3-b]pyridine (5.1 g, 11.1 mmol, 1.2 eq), Pd(dppf)Cl$_2$DCM (380 mg, 0.46 mmol, 0.05 eq), K$_2$CO$_3$ (2.6 g, 18.5 mmol, 2 eq) and H$_2$O (2 mL) in dioxane (100 mL) was stirred at 90° C. for 3 h under N$_2$ atmosphere. After the reaction completed, the solvent was removed and the residue was purified by silica gel (PE/EA=4:1) to give ethyl 2-(3-(5-bromo-1-(phenylsulfonyl)-1H-pyrrolo[2,3-b]pyridin-3-yl)-5-isopropoxybenzylamino)nicotinate (3.2 g, yield: 53%) as yellow solid. ESI-MS (M+H$^+$): 651.0. $^1$H NMR (400 MHz, CDCl$_3$) δ: 8.19-8.13 (m, 5H), 7.89-7.86 (m, 3H), 6.92-6.90 (m, 2H), 6.80 (d, 1H), 6.62-6.59 (m, 3H), 6.42 (s, 1H), 4.58-4.54 (m, 1H), 4.36-4.31 (m, 4H), 1.39-1.35 (m, 9H).

A mixture of compound ethyl 2-(3-(5-bromo-1-(phenylsulfonyl)-1H-pyrrolo[2,3-b]pyridin-3-yl)-5-isopropoxybenzylamino)nicotinate (1 g, 1.54 mmol), 1H-pyrazol-5-ylboronic acid (0.26 g, 2.3 mmol, 1.5 eq), Pd(dppf)Cl$_2$DCM (60 mg, 0.12 mmol, 0.05 eq), Na$_2$CO$_3$ (330 mg, 3.1 mmol, 2 eq) and H$_2$O (1 mL) in DMF (20 mL) was stirred at 80° C. for 1 h. After the reaction completed, the solvent was removed and the residue was purified by silica gel (PE/EA=1:5) to give ethyl 2-(3-isopropoxy-5-(1-(phenylsulfonyl)-5-(1H-pyrazol-5-yl)-1H-pyrrolo[2,3-b]pyridin-3-yl)benzylamino)nicotinate (200 mg, yield: 21%) as yellow solid. ESI-MS (M+H$^+$): 637.2.

To a solution of ethyl 2-(3-isopropoxy-5-(1-(phenylsulfonyl)-5-(1H-pyrazol-5-yl)-1H-pyrrolo[2,3-b]pyridin-3-yl)benzylamino)nicotinate (200 mg, 0.314 mmol) in MeOH—H$_2$O (1:1, 20 mL) was added NaOH (50 mg, 1.26 mmol, 4 eq), then the reaction solution was heated to reflux for 30 min, after the reaction completed, the mixture was cooled to the rt, acidified to pH=3-4, the mixture was filtered to give the corresponding acid with the phenylsulfonyl removed too, which was converted to 2-(3-(5-(1H-pyrazol-5-yl)-1H-pyrrolo[2,3-b]pyridin-3-yl)-5-isopropoxybenzylamino)-N-(3,4-difluorobenzyl)nicotinamide as a white solid. ESI-MS (M+H$^+$): 594.0; $^1$H NMR (400 MHz, CDCl$_3$/CD$_3$OD) δ: 8.62 (br, 1H), 8.56 (s, 1H), 8.21-8.19 (m, 1H), 7.82-7.79 (m, 1H), 7.63 (s, 1H), 7.55 (s, 1H), 7.32 (s, 1H), 7.06-7.02 (m, 4H), 6.88 (s, 1H), 6.62 (br, 1H), 6.59-6.56 (m, 1H), 4.75 (s, 2H), 4.67-4.64 (m, 1H), 4.48 (s, 2H), 1.38 (d, 6H).

Example 54

Synthesis of 2-((4-(5-(1H-pyrazol-5-yl)-1H-pyrrolo[2,3-b]pyridin-3-yl)pyridin-2-yl)methylamino)-N-(3,4-difluorobenzyl)nicotinamide

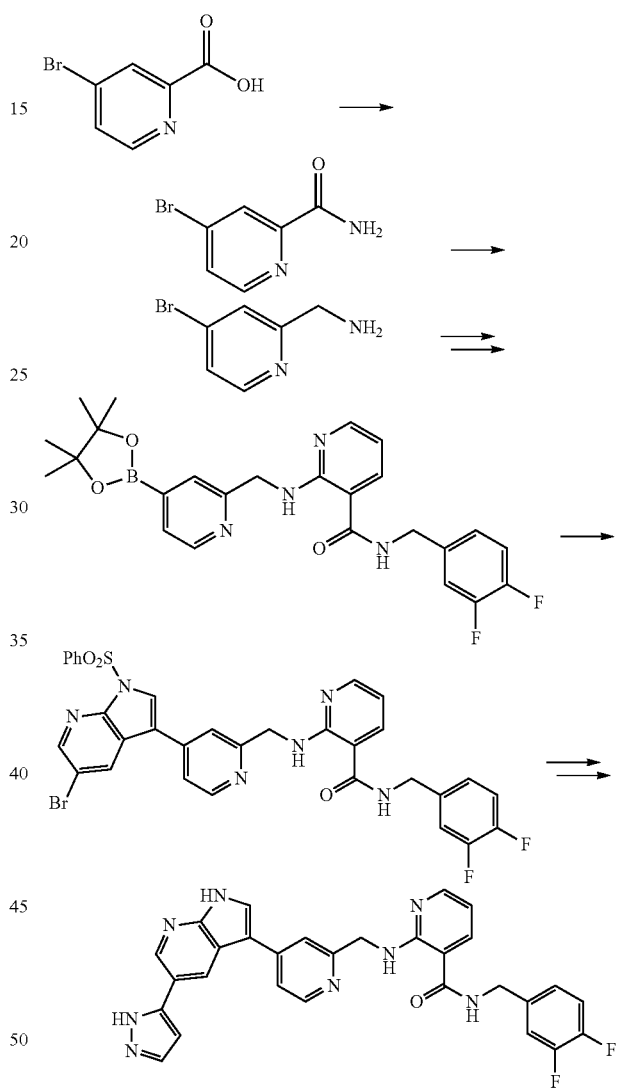

To a solution of 4-bromopicolinic acid (5 g, 24.8 mmol) and NH$_4$Cl (6.7 g, 124 mmol, 5 eq) in DMF (200 mL) was added K$_2$CO$_3$ (34 g, 240 mmol, 10 eq) in one portion. And then HBTU (18.8 g. 240 mmol, 2 eq) was added. The mixture was stirred at rt for 2 h. The solvent was removed and the residue was purified by silica gel column chromatography (EA) to give the 4-bromopicolinamide (2.5 g, yield: 50%) as white solid. ESI-MS (M+H$^+$): 201.1. $^1$H NMR (400 MHz, CDCl$_3$) δ: 9.21 (s, 1H), 8.19 (s, 1H), 8.03 (s, 1H), 6.12 (br, 2H).

A solution of 4-bromopicolinamide (1.85 g, 9.2 mmol) in BH$_3$ (2M in THF, 100 mL) was heated to reflux for 16 h, Then the reaction mixture was cooled to rt and acidified with c-HCl (20 mL) to pH=6. The solvent was removed in vacuo and dissolved in EtOAc (200 mL), washed with sat NaHCO$_3$ (100 mL×3) and dried over anhydrous Na$_2$SO$_4$. The organic layer was concentrated to give (4-bromopyridin-2-yl)methanamine (540 mg, 31%) as white solid. ESI-MS (M+H+): 201.1. $^1$H NMR (400 MHz, CDCl$_3$) δ: 8.53-8.51 (m, 1H), 8.33 (br, 2H), 7.86-7.85 (m, 1H), 7.72-7.70 (m, 1H), 4.23-4.20 (m, 2H).

N-(3,4-difluorobenzyl)-2-((4-(4,4,5,5-tetramethyl-1,3,2-dioxaborolan-2-yl)pyridin-2-yl)methylamino)nicotinamide, prepared from (4-bromopyridin-2-yl)methanamine and N-(3,4-difluorobenzyl)-2-fluoronicotinamide in 2 steps in a similar way as previously described (ESI-MS (M+H+): 481.1), and 5-bromo-3-iodo-1-(phenylsulfonyl)-1H-pyrrolo[2,3-b]pyridine gave 2-((4-(5-bromo-1-(phenylsulfonyl)-1H-pyrrolo[2,3-b]pyridin-3-yl)pyridin-2-yl)methylamino)-N-(3,4-difluorobenzyl)nicotinamide. ESI-MS (M+H$^+$): 691.1. $^1$H NMR (400 MHz, CDCl$_3$) δ: 8.62 (d, 1H), 8.60 (d, 1H), 8.53 (s, 1H), 8.36 (s, 1H), 8.24 (d, 1H), 7.91 (d, 1H), 7.82 (s, 1H), 7.75-7.62 (m, 4H), 7.61-7.55 (m, 3H), 7.54-7.46 (m, 3H), 7.15 (s, 1H), 6.74 (s, 1H), 4.83 (d, 2H), 4.58 (d, 2H).

2-((4-(5-(1H-pyrazol-5-yl)-1H-pyrrolo[2,3-b]pyridin-3-yl)pyridin-2-yl)methylamino)-N-(3,4-difluorobenzyl)nicotinamide was prepared from 2-((4-(5-bromo-1-(phenylsulfonyl)-1H-pyrrolo[2,3-b]pyridin-3-yl)pyridin-2-yl)methylamino)-N-(3,4-difluorobenzyl)nicotinamide and 1H-pyrazol-5-ylboronic acid under standard Suzuki condition and then deprotected with potassium carbonate in methanol. ESI-MS (M+H$^+$): 537.2; $^1$H NMR (400 MHz, CD$_3$OD) δ: 8.75 (s, 1H), 8.71 (s, 1H), 8.39 (s, 1H), 8.37 (s, 1H), 8.27 (d, 1H), 8.13 (d, 1H), 8.04 (d, 1H), 7.90 (d, 1H), 7.65 (s, 1H), 7.17-7.07 (m, 3H), 6.74 (s, 1H), 6.66-6.62 (m, 1H), 4.93 (s, 2H), 4.44 (s, 2H).

Synthesis of 3-iodo-1-methyl-1H-pyrazolo[3,4-d]pyrimidin-4-amine

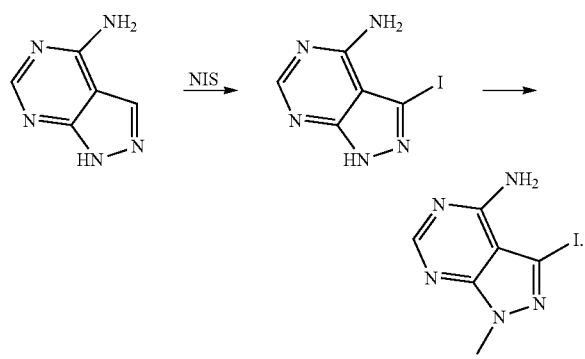

To a solution of 4-Aminopyrazolo[3,4-d]pyrimidine (500.0 mg, 3.700 mmol) in N,N-Dimethylformamide (17.0 mL, 2.20E2 mmol) was added N-Iodosuccinimide (915.7 mg, 4.070 mmol) and was stirred at 80° C. overnight. Solvent removed and residue purified by column chromatography to give 3-iodo-1H-pyrazolo[3,4-d]pyrimidin-4-amine (865 mg, 89% yld). ESI-MS (M+H$^+$): 261.8.

To a solution of 3-Iodo-1H-pyrazolo[3,4-d]pyrimidin-4-ylamine (671.0 mg, 2.571 mmol) in N,N-Dimethylformamide (17 mL, 220 mmol) was added Potassium carbonate (1660 mg, 12.0 mmol). The solution was degassed with N$_2$, the vial was sealed and then was added Methyl iodide (1.2 mL, 2.0E1 mmol). The reaction was stirred at room temperature for 4 hours. Solvent removed and residue purified by HPLC to give desired 3-iodo-1-methyl-1H-pyrazolo[3,4-d]pyrimidin-4-amine. (120 mg, 17% yld). ESI-MS (M+H$^+$): 275.8.

Synthesis of 6-bromo-1-methyl-1H-imidazo[4,5-b]pyridin-2(3H)-one

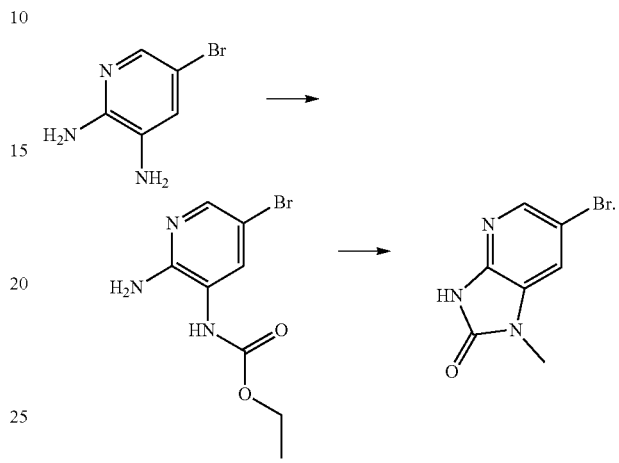

A mixture of 5-bromopyridine-2,3-diamine (10 g, 44 mmol) and pyridine (8.8 g, 88 mmol, 2.0 eq) in THF (80 mL) was stirred at 0° C. for 30 min. Then EtOCOCl (5.8 g, 44 mmol, 1.0 eq) was added into the mixture. The mixture was stirred at rt for 16 h. Then the mixture was concentrated and the crude solid was washed with CH$_3$OH/EtOAc (1:9, 100 mL) to give ethyl 2-amino-5-bromopyridin-3-ylcarbamate as yellow solid (7.2 g, yield: 53%). ESI-MS (M+H$^+$): 261.9; $^1$H-NMR (400 MHz, DMSO-d$_6$) δ: 8.84 (s, 1H), 7.84 (s, 1H), 7.76 (d, 1H), 6.07 (s, 1H), 4.11 (q, 2H), 1.22 (t, 3H).

In a round-bottom flask, NaH (1.92 g, 80 mmol, 60%, 4 eq) was added slowly into a solution of ethyl 2-amino-5-bromopyridin-3-ylcarbamate (5.2 g, 20 mmol) in THF (100 mL) at 0° C. The reaction mixture was stirred at 0° C. for 30 min at N$_2$ atmosphere. MeI (2.84 g, 20 mmol) in THF (5 mL) was added slowly into the above solution, then the reaction mixture was stirred at r.t. for 12 h. The precipitate was filtered and the solid was collected, then the solid was dissolved in H$_2$O (50 mL) and filtered, the filtrate was adjusted pH=6 with dilute HCl (1N), the precipitate was formed and filtered to obtain 6-bromo-1-methyl-1H-imidazo[4,5-b]pyridin-2-(3H)-one as yellow solid (2.3 g, yield: 50%). ESI-MS (M+2): 228.9. $^1$H-NMR (400 MHz, DMSO-d$_6$) δ: 11.71 (s, 1H), 7.95 (d, 1H), 7.70 (d, 1H), 3.25 (s, 3H).

Synthesis of (3-amino-6-bromopyrazin-2-yl)methanol

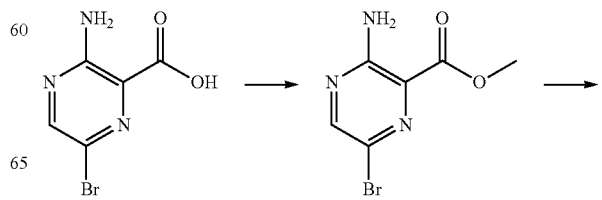

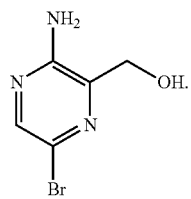

To a mixture of 3-amino-6-bromopyrazine-2-carboxylic acid (500 mg, 2.3 mmol) in DME (15 mL) was added NMM (221 mg, 2.19 mmol, 0.95 eq) and isobutyl carbonochloridate (298 mg, 2.19 mmol, 0.95 eq). The mixture was stirred at −20° C. for 1 h. Then the solid was filtrated and the solution was added MeOH (10 mL). The mixture was stirred at rt for 1 h. Then the solvent was removed and the residue was purified by silica gel column (PE/EA=5/1) to give methyl 3-amino-6-bromopyrazine-2-carboxylate as white solid (377 mg, yield: 71%). ESI-MS (M+3): 233.9. $^1$H NMR (400 MHz, DMSO-$d_6$) δ: 8.43 (s, 1H), 7.56 (br, 2H), 3.85 (s, 3H).

1.0 M lithium aluminium hydride in THF (1.43 mL, 1.43 mmol) was added to a solution of methyl 3-amino-6-bromopyrazine-2-carboxylate (300 mg, 1.29 mmol) in THF (10 mL) at 0° C. under $N_2$ atmosphere. The reaction mixture was stirred at 0° C. for 2 h. Water (2 mL), 2 M sodium hydroxide (0.05 mL) and water (4 mL) were added sequentially and the resultant mixture stirred at 20° C. for 30 min before filtration through Celite. The solution was extracted with ethyl acetate (30 mL×3) and dried. The organic phases were concentrated to afford (3-amino-6-bromopyrazin-2-yl)methanol as a brown solid (180 mg, yield: 59%), which was used in the next step without further purification. ESI-MS (M+3): 205.9. $^1$H NMR (400 MHz, DMSO-$d_6$) δ: 8.00 (s, 1H), 6.44 (br, 2H), 5.39 (t, 1H), 4.43 (d, 2H).

Example 55

Synthesis of 2-(4-(4-amino-7-(3-(dimethylamino) propyl)-7H-pyrrolo[2,3-d]pyrimidin-5-yl)benzylamino)-N-(3,4-difluorobenzyl)-5-(trifluoromethyl) nicotinamide

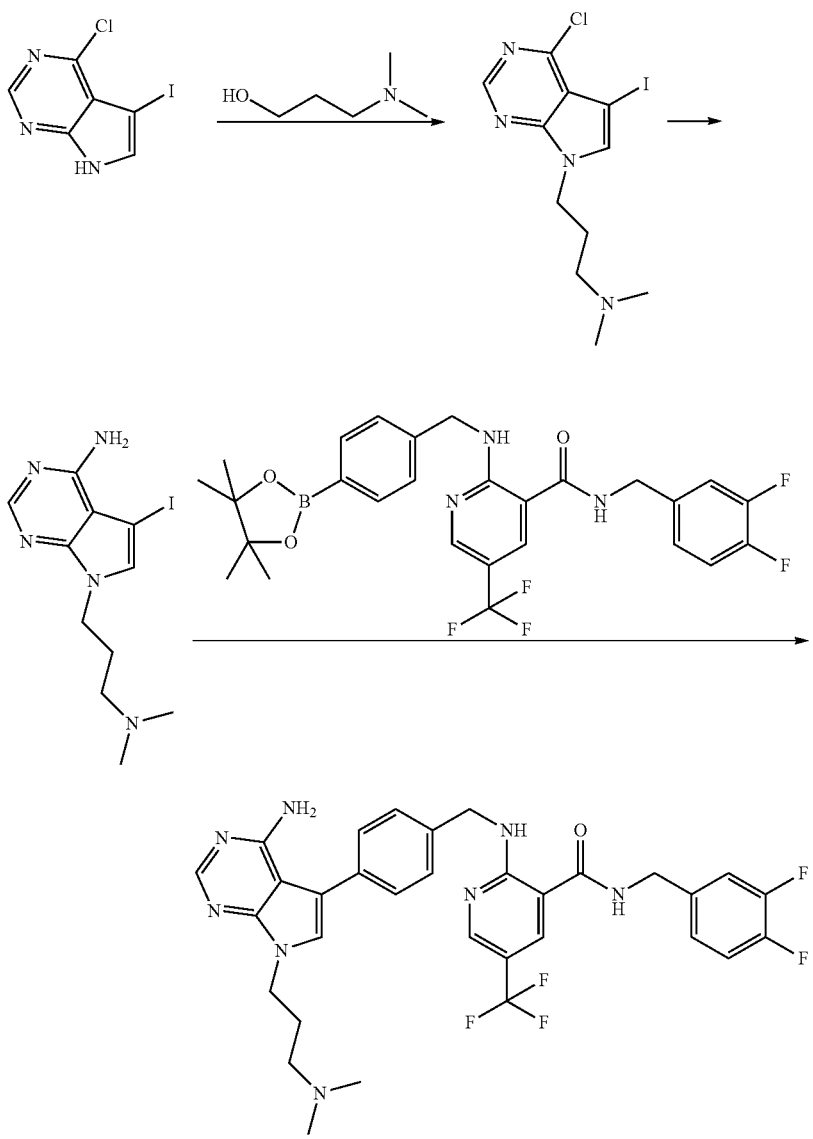

To a solution of 4-chloro-5-iodo-7H-pyrrolo[2,3-d]pyrimidine (40.0 mg, 0.000143 mol), 3-(Dimethylamino)-1-propanol (29.53 µL, 0.0002863 mol), and resin bound triphenylphosphine (1.00 mmol/g loading; 214.7 mg, 0.0002147 mol) in Tetrahydrofuran (10.45 mL, 0.1288 mol) was added Diisopropyl azodicarboxylate (42.27 µL, 0.0002147 mol). The reaction mixture was stirred at room temperature overnight. Reaction mixture was washed, organic layer collected and solvent removed in vacuo. Product carried forwards w/out further purification. ESI-MS (M+H$^+$):364.7.

Into a vial was added [3-(4-Chloro-5-iodo-pyrrolo[2,3-d]pyrimidin-7-yl)-propyl]-dimethyl-amine (52.20 mg, 0.1432 mmol) and 0.5 M of Ammonia in 1,4-Dioxane (2.00 mL, 1.00 mmol). To this was added Ammonium hydroxide (1.00 g, 28.5 mmol) and was stirred at 105° C. overnight. Product was diluted MeOH and solvent removed in vacuo. Product carried forwards w/out further purification. ESI-MS (M+H$^+$):345.9.

Into a vial was added N-(3,4-Difluoro-benzyl)-2-[4-(4,4,5,5-tetramethyl-1,3,2-dioxaborolan-2-yl)-benzylamino]-5-trifluoromethyl-nicotinamide (86.20 mg, 0.1575 mmol), 7-(3-Dimethylamino-propyl)-5-iodo-7H-pyrrolo[2,3-d]pyrimidin-4-ylamine (49.42 mg, 0.1432 mmol), [1,1'-Bis(diphenylphosphino)ferrocene]dichloropalladium(II), complex with dichloromethane (1:1) (14.03 mg, 0.01718 mmol), N,N-Dimethylformamide (1.330 mL, 17.18 mmol) and 1.2 M of Sodium bicarbonate$_{(aq)}$ (596.5 µL, 0.7158 mmol). The reaction was microwaved on 300 W for 30 min at 110 C. Solvent removed and residue purified by HPLC to give desired product. Collected 21.3 mg purified compound (23% yld). ESI-MS (M+H$^+$): 638.9; $^1$H NMR (400 MHz, DMSO-d$_6$) δ 9.34 (td, J=5.52, 22.09 Hz, 2H), 8.53 (s, 1H), 8.37 (s, 1H), 8.14 (s, 1H), 7.29-7.46 (m, 7H), 7.20 (br. s., 1H), 4.75 (d, J=5.77 Hz, 2H), 4.45 (d, J=5.52 Hz, 2H), 4.18 (t, J=7.03 Hz, 2H), 2.35 (br. s., 2H), 2.23 (br. s., 6H), 1.95 (quin, J=6.96 Hz, 2H).

Example 56

Synthesis of 2-(((6-(4-amino-7-methyl-7H-pyrrolo[2,3-d]pyrimidin-5-yl)pyridin-3-yl)methyl)amino)-N-(4-fluorophenyl)-5-(trifluoromethyl)nicotinamide

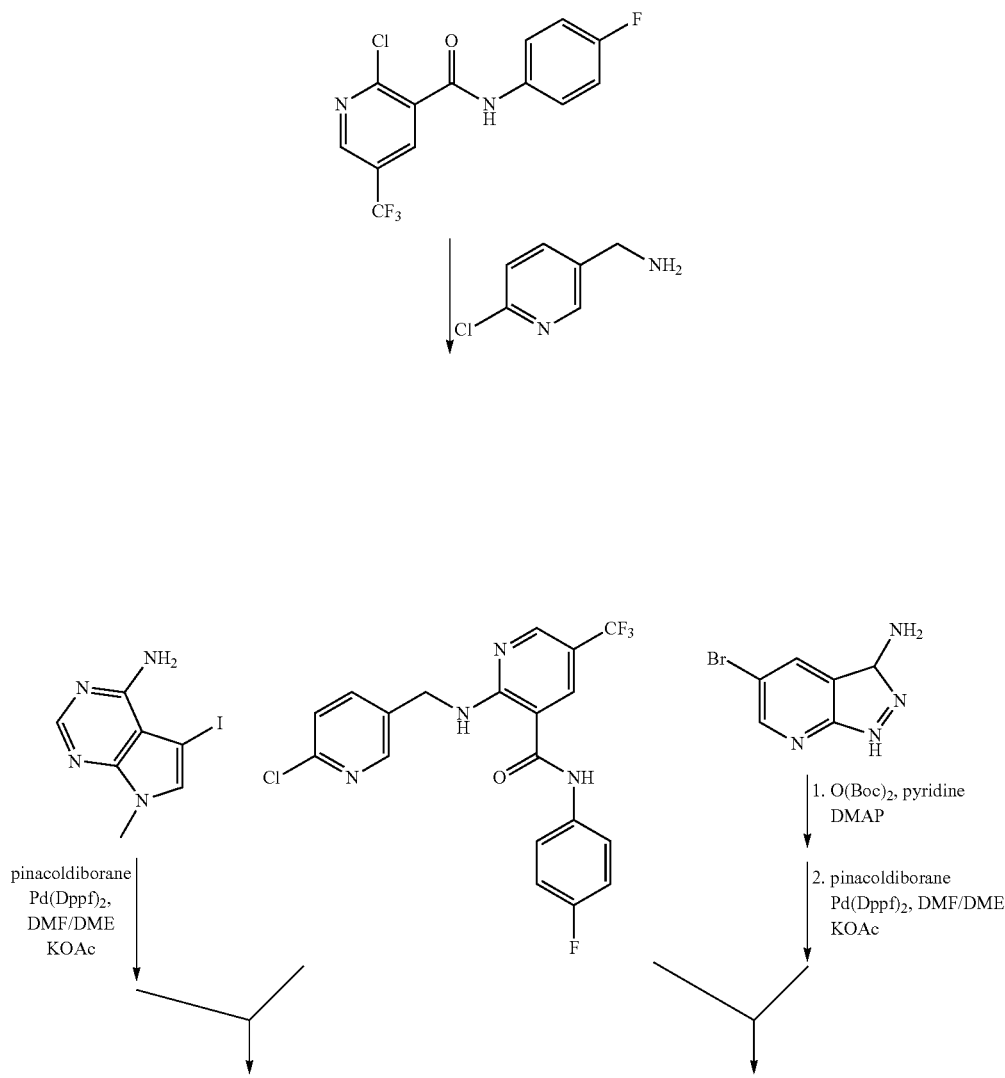

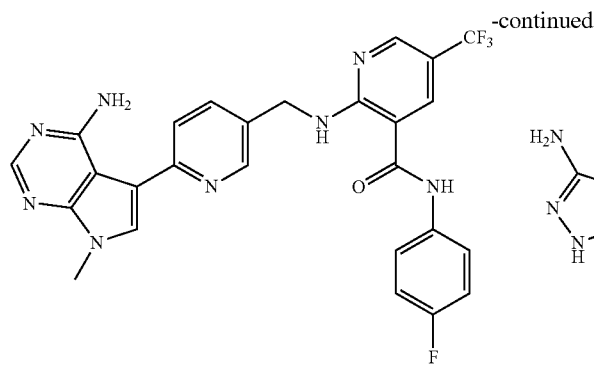
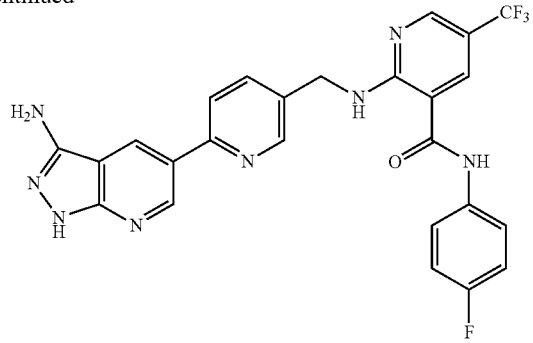

Synthesis of 2-chloro-N-(4-fluorophenyl)-5-(trifluoromethyl)nicotinamide

Oxalyl chloride (2.4 g, 19 mmol) was added dropwise to a suspension of 2-chloro-5-trifluoromethyl-nicotinic acid (1.7 g, 7.5 mmol) in DMF (0.1 mL) and methylene chloride (100 mL) and stirred at RT for 1 h. Evaporated off the solvents and re-dissolved in dichloromethane and added N,N-diisopropylethylamine (13 mL, 75 mmol) and p-fluoroaniline (0.72 mL, 7.5 mmol) and stirred for 1 h at rt. LC-MS showed complete reaction (1.53 min, ES+/318.8). Evaporated off the solvents and worked up with EtOAc and water, dried over MgSO$_4$ to give 2.4 g 2-chloro-N-(4-fluorophenyl)-5-(trifluoromethyl)nicotinamide.

Synthesis of 2-(((6-chloropyridin-3-yl)methyl) amino)-N-(4-fluorophenyl)-5-(trifluoromethyl)nicotinamide To a solution of (6-chloro-pyridin-3-yl)-methylamine (1.00 g, 7.01 mmol) and 2-chloro-N-(4-fluoro-phenyl)-5-trifluoromethyl-nicotinamide (2.23 g, 7.01 mmol) in N,N-dimethylformamide (10 mL, 0.2 mol) was added N,N-diisopropylethylamine (3.66 mL, 21.0 mmol). The reaction was heated at 80° C. overnight. The reaction mixture was diluted with EtOAc, washed with brine, then water. The organic phase was the separated, dried and concentrated. The crude was recrystallized from CH$_2$Cl$_2$/hexane to give desired product as an off white powder (2.84 g) which was used in the next step without further purifications. LCMS: RT 1.70 min., MH+ 424.80; $^1$H NMR (400 MHz, DMSO-d$_6$) δ ppm 10.50 (s, 1 H) 8.89 (t, J=6.02 Hz, 1 H) 8.52 (d, J=1.00 Hz, 1 H) 8.38 (dd, J=16.94, 2.13 Hz, 2 H) 7.81 (dd, J=8.28, 2.51 Hz, 1 H) 7.62-7.75 (m, 2 H) 7.45 (d, J=8.03 Hz, 1 H) 7.15-7.28 (m, 2 H) 4.71 (d, J=6.02 Hz, 2 H); $^{19}$F NMR (376 MHz, DMSO-d$_6$) δ ppm −59.05 (s, 3 F), −118.20 (s, 1 F).

Synthesis of 2-(((6-(4-amino-7-methyl-7H-pyrrolo [2,3-d]pyrimidin-5-yl)pyridin-3-yl)methyl)amino)-N-(4-fluorophenyl)-5-(trifluoromethyl)nicotinamide A mixture of 5-Iodo-7-methyl-7H-pyrrolo[2,3-d]pyrimidin-4-ylamine (50 mg, 0.18 mmol), bis(pinacolato)diboron (56 mg, 0.22 mmol), potassium acetate (72 mg, 0.72 mmol) and 1,4-dioxane (2 mL) was degassed for 10 min. bis (tricyclohexylphosphine)palladium (0) (12.2 mg, 0.02 mmol) was then added. The reaction was heated at 60° C. over the weekend. LCMS showed the desired intermediate (boronate RT 1.05 min., MH+ 275.00). 2-((6-chloropyridin-3-yl)methylamino)-N-(4-fluorophenyl)-5-(trifluoromethyl) nicotinamide (116.2 mg, 0.27 mol) and 1.2 M of saturated aqueous sodium bicarbonate solution in water (0.45 mL, 0.55 mmol) were then added. The reaction was heated in microwave at 120° C. for 20 min. The reaction mixture was diluted with EtOAc, washed with water (3×). The organic phase was separated, dried and concentrated. The crude was purified by HPLC to give the desired product as a TFA salt (23 mg). LCMS: RT 1.41 min.; MH+ 536.90; $^1$H NMR (400 MHz, DMSO-d$_6$) δ ppm 11.70 (br. s., 1H) 10.52 (s, 1 H) 8.96 (t, J=5.90 Hz, 1 H) 8.56 (d, J=11.29 Hz, 3 H) 8.39 (d, J=10.04 Hz, 3 H) 7.96-8.05 (m, 1 H) 7.87-7.95 (m, 1 H) 7.71 (dd, J=8.78, 5.02 Hz, 2 H) 7.23 (t, J=8.91 Hz, 2 H) 4.77 (d, J=5.77 Hz, 2 H) 3.84 (s, 3 H).

Example 57

2-(((6-(3-amino-1H-pyrazolo[3,4-b]pyridin-5-yl) pyridin-3-yl) methyl)amino)-N-(4-fluorophenyl)-5-(trifluoromethyl)nicotinamide Synthesis of (5-Bromo-1H-pyrazolo[3,4-b]pyridin-3-yl)-carbamic acid tert-butyl ester 5-Bromo-1H-pyrazolo[3,4-b]pyridin-3-ylamine (0.500 g, 2.35 mmol) and Di-tert-butyldicarbonate (0.598 g, 2.74 mmol) was stirred in pyridine (10.0 mL, 124 mmol). To the stirred mixture was added 4-dimethylaminopyridine (26 mg, 0.21 mmol). The reaction was stirred at room temperature. After 3 h, the reaction was evaporated to dryness. The residue was taken up in DCM, DMF. Silica gel was added and the solvent removed by evaporation. The residue was purified by silica gel chromatography using 0-100% ethyl acetate in hexanes as eluent to give the product at 1.27. LCMS m/z 312.80, 314.80 (M+1).

Synthesis of [5-(4,4,5,5-Tetramethyl-1,3,2-dioxaborolan-2-yl)-1H-pyrazolo[3,4-b]pyridin-3-yl]-carbamic acid tert-butyl ester Into a Vial (uW) was added (5-bromo-1H-pyrazolo[3,4-b]pyridin-3-yl)-carbamic acid tert-butyl ester (0.126 g, 0.402 mmol) and bis(pinacolato)diboron (0.128 g, 0.505 mmol) and potassium acetate (0.164 g, 1.68 mmol) and 1,2-dimethoxyethane (1.54 mL, 14.8 mmol) and N,N-dimethylformamide (0.768 mL, 9.92 mmol). The reaction mixture was evacuated, then purged with Ar (X5). The reaction was sealed under Ar and was microwaved 110° C. for 10 minutes. LCMS shows good conversion to a new peak consistent with the boronate ester (79%, RT=0.72 min, m/z=179.00). Note that the mass seen is that of the boronic acid, -Boc. The reaction was diluted with ethyl acetate, washed with saturated sodium bicarbonate, washed with saturated sodium chloride, dried with sodium sulfate, filtered and evaporated. LCMS shows that the product is still the major species though the second peak is now larger. The residue was used as is in the next reaction. LCMS m/z 179.00.

Synthesis of 2-(((6-(3-amino-1H-pyrazolo[3,4-b]pyridin-5-yl)pyridin-3-yl)methyl)amino)-N-(4-fluorophenyl)-5-(trifluoromethyl)nicotinamide A solution of 2-((6-chloropyridin-3-yl)methylamino)-5-cyano-N-(4-fluorophenyl)nicotinamide (0.146 g, 0.383 mmol) and [5-(4,4,5,5-Tetramethyl-1,3,2-dioxaborolan-2-yl)-1H-pyrazolo[3,4-b]pyridin-3-yl]-carbamic acid tert-butyl ester (0.145 g, 0.402 mmol) [crude from previous reaction] in 1,4-Dioxane (1.9 mL, 25 mmol). Bis(tricyclohexylphosphine)palladium (0) (32 mg, 0.048 mmol) was then added, followed by 1.2 M of Saturated Aqueous Sodium Bicarbonate Solution in water (1.06 mL, 1.27 mmol). The vessel was sealed under Ar. The reaction was stirred and heated in microwave at 120° C. for 20 min. Note that boronate ester SM is crude from previous reaction, and is likely the boronic acid with no Boc. LCMS shows the major peak at RT=1.36 min (48%, m/z=522.80). The reaction mixture was purified by GILSON preparative HPLC (X4) to give the product. Note that there is no Boc on the product, so this protecting group has fallen off in this reaction (or more likely the previous reaction). LCMS m/z 522.80 (M+1)$^1$H NMR (400 MHz, DMSO-d$_6$) δ 10.51 (s, 1H), 9.06 (d, J=2.01 Hz, 1H), 8.94 (s, 1H), 8.89 (br. s., 1H), 8.69 (s, 1H), 8.55 (s, 1H), 8.38 (d, J=2.01 Hz, 1H), 7.85-8.00 (m, 2H), 7.64-7.76 (m, 2H), 7.22 (t, J=8.91 Hz, 2H), 4.78 (d, J=5.27 Hz, 2H).

Example 58 was synthesized in a manner consistent with Example 57.

Synthesis of tert-butyl 3-(5-bromo-1H-pyrazolo[3,4-b]pyridin-3-yl)propylcarbamate 5-bromo-3-iodo-1H-pyrazolo[3,4-b]pyridine A solution of 5-bromo-1H-pyrazolo[3,4-b]pyridine (10.0 g, 50.5 mmol) and N-iodosuccinimide (11.9 g, 53.0 mmol) in dry 1,2-dichloroethane (300 mL) was heated at reflux for 6 h. Cooled to RT and diluted with THF (300 ml). The resulting solution was washed with saturated aqueous Na$_2$S$_2$SO$_4$, then brine. The organic phase was then dried (MgSO$_4$) and concentrated. The residue was triturated with a 1:1 mixture of DCM/ether, and then ether to give desired product as a yellow solid (12.4 g) which was used in the next step without further purifications. LCMS: RT 1.35 min.; MH+ 323.60. $^1$H NMR (400 MHz, DMSO-d$_6$) δ ppm 14.30 (br. s., 1 H) 8.64 (d, J=2.26 Hz, 1 H) 8.20 (d, J=2.26 Hz, 1 H).

3-(5-bromo-1H-pyrazolo[3,4-b]pyridin-3-yl)-N,N-dimethylprop-2-yn-1-amine

To a mixture of 5-bromo-3-iodo-1H-pyrazolo[3,4-b]pyridine (1.0 g, 3.1 mmol) and copper(I) iodide (29 mg, 0.154 mmol) in N,N-dimethylformamide (10.0 mL) was added N,N-diisopropylethylamine (3.76 mL, 21.6 mmol) degassed for 10 min. propargyl(dimethylamine) (0.57 mL, 5.3 mmol) was then added, followed by [1,1'-bis(diphenylphosphino)ferrocene]dichloropalladium(II), complex with dichloromethane (1:1) (0.126 g, 0.154 mmol), continued degassed for 5 min. The reaction was then stirred at 40° C. for 2h. The reaction was diluted with DCM, washed with sat'd NaHCO$_3$, then brine. The organic phase was then dried (MgSO$_4$) and concentrated. The crude was diluted with small amount of MeOH, and washed with methanol, then hexane to give 3-(5-bromo-1H-pyrazolo[3,4-b]pyridin-3-yl)-N,N-dimethylprop-2-yn-1-amine (355 mg). LCMS: RT 0.69 min.; MH+ 278.90. $^1$H NMR (400 MHz, DMSO-d$_6$) δ ppm 14.18 (br. s., 1 H) 8.66 (d, J=2.26 Hz, 1 H) 8.41 (d, J=2.01 Hz, 1 H) 3.58 (s, 2 H) 2.29 (s, 6 H).

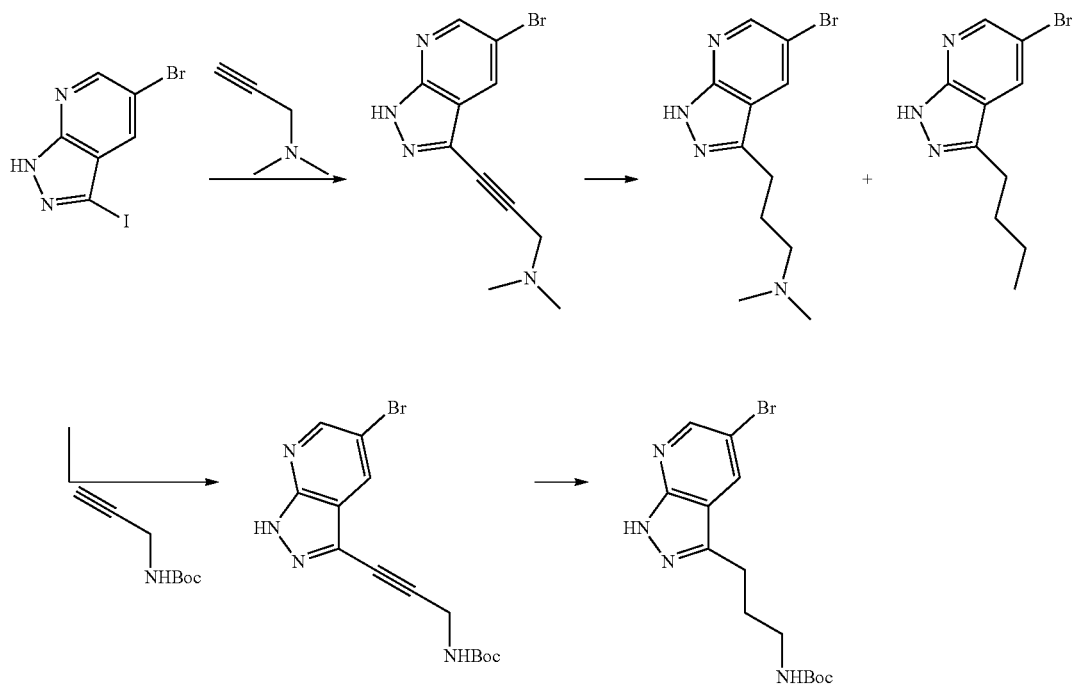

3-(5-bromo-1H-pyrazolo[3,4-b]pyridin-3-yl)-N,N-dimethylpropan-1-amine

To a mixture of 5% Pd/C (7.6 mg, 0.072 mmol) in methanol (10 mL) was added a few drops of triethylamine and a suspension of [3-(5-bromo-1H-pyrazolo[3,4-b]pyridin-3-yl)-prop-2-ynyl]-dimethyl-amine (100 mg, 0.36 mmol) in MeOH (5 ml). The mixture was degassed with nitrogen (3×), then with hydrogen (3×). The reaction was then stirred at RT under hydrogen balloon. After 30 min, the reaction mixture was filtered through celite. The filtrate was concentrated, purified by prep-TLC (5% NH$_3$/MeOH in DCM) to give 3-(5-bromo-1H-pyrazolo[3,4-b]pyridin-3-yl)-N,N-dimethylpropan-1-amine (22 mg). MH+ 282.90

5-bromo-3-butyl-1H-pyrazolo[3,4-b]pyridine

To a mixture of platinum (20 mg, 0.09 mmol) in methanol (5.0 mL) and ethyl acetate (5.0 mL) was added [3-(5-bromo-1H-pyrazolo[3,4-b]pyridin-3-yl)-prop-2-ynyl]-dimethyl-amine (50 mg, 0.0002 mol). The mixture was degassed with hydrogen (3×). The reaction was then stirred at RT under hydrogen balloon overnight. The reaction was filtered through celite. The filtrate was concentrated and purified by prep-TLC to give 5-bromo-3-butyl-1H-pyrazolo[3,4-b]pyridine (30 mg). MH+ 239.90; $^1$H NMR (400 MHz, DMSO-d$_6$) δ ppm 13.18-13.58 (m, 1 H) 8.35-8.71 (m, 2 H) 2.87 (t, J=7.53 Hz, 2 H) 1.63-1.80 (m, 2 H) 0.93 (t, J=7.28 Hz, 3 H).

tert-butyl 3-(5-bromo-1H-pyrazolo[3,4-b]pyridin-3-yl)prop-2-ynylcarbamate

To a mixture of 5-bromo-3-iodo-1H-pyrazolo[3,4-b]pyridine (0.50 g, 1.5 mmol) and copper(I) iodide (29.4 mg, 0.154 mmol) in N,N-dimethylformamide (0.50 mL, 6.4 mmol) was added N,N-diisopropylethylamine (1.88 mL, 10.8 mmol) degassed for 10 min. Prop-2-ynyl-carbamic acid t-butyl ester (0.41 g, 2.6 mmol) was then added, followed by [1,1'-bis(diphenylphosphino)ferrocene]dichloropalladium (II), complex with dichloromethane (1:1) (63 mg, 0.08 mmol). The reaction was then heated at 50° C. for 20 min. The reaction was diluted with EtOAc, washed with saturated aqueous NaHCO$_3$, then brine. The organic phase was then dried (MgSO$_4$) and concentrated. The crude was purified by HPLC to give tert-butyl 3-(5-bromo-1H-pyrazolo[3,4-b]pyridin-3-yl)prop-2-ynylcarbamate (261 mg). LCMS: RT 1.50 min.; MH+ 350.80; $^1$H NMR (400 MHz, DMSO-d$_6$) δ ppm 14.19 (s, 1 H) 8.66 (d, J=2.01 Hz, 1 H) 8.44 (d, J=1.51 Hz, 1 H) 7.36-7.55 (m, 1 H) 4.08 (d, J=5.52 Hz, 2 H) 1.42 (s, 9 H).

tert-butyl 3-(5-bromo-1H-pyrazolo[3,4-b]pyridin-3-yl)propylcarbamate

A flask was charged with 5% Pd/C (7.6 mg, 0.071 mmol). Methanol (10 mL) was added. The mixture was degassed and back filled with nitrogen (3×). The degassed and back filled with hydrogen (3×). The reaction was then stirred at RT under hydrogen balloon. After 1 h, the reaction mixture was filtered through celite. The filtrate was concentrated, purified by prep-TLC (CH$_2$Cl$_2$+5% of 2MNH$_3$/MeOH) to give tert-butyl 3-(5-bromo-1H-pyrazolo[3,4-b]pyridin-3-yl)propylcarbamate (125 mg). LCMS: RT 1.39 min.; MH+ 354.80.

Synthesis of 2-(5-bromo-1H-pyrazolo[3,4-b]pyridin-3-yl)acetonitrile

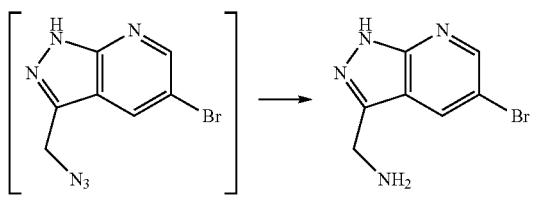

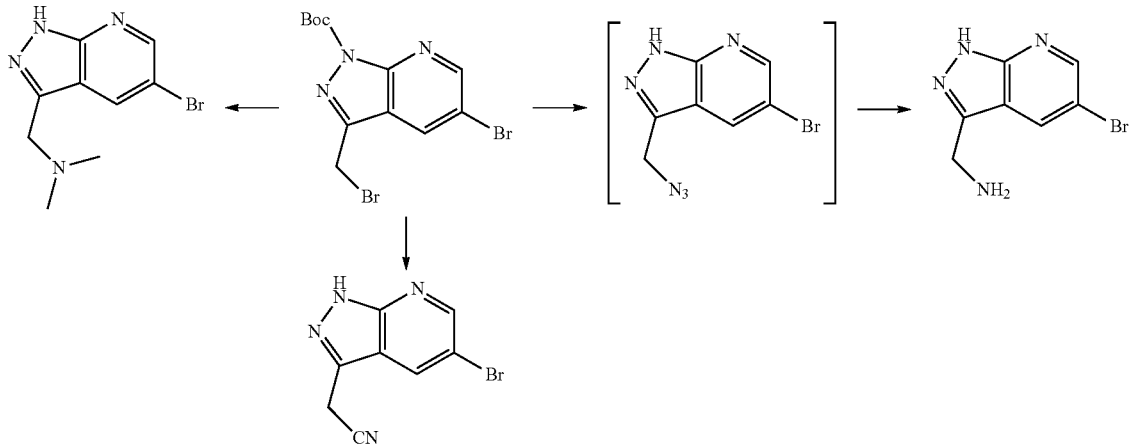

(5-bromo-1H-pyrazolo[3,4-b]pyridin-3-yl)methanamine

To a solution of 5-bromo-3-bromomethyl-pyrazolo[3,4-b]pyridine-1-carboxylic acid tert-butyl ester (100 mg, 0.26 mmol) in N,N-dimethylformamide (3 mL, 0.04 mol) was added sodium azide (18 mg, 0.28 mmol). The reaction was stirred at RT for 1h. LCMS showed no SM left. Triphenylphosphine (141 mg, 0.54 mmol), tetrahydrofuran (3 mL) and water (1 mL) were then added under nitrogen. The reaction was then stirred at RT overnight. The reaction was diluted with EtOAc, filtered through celite. The filtrate was concentrated under vacuo. The crude was purified by HPLC afford 51 mg (5-bromo-1H-pyrazolo[3,4-b]pyridin-3-yl)methanamine. LCMS: RT 0.96 min, MH+ 226.90.

1-(5-bromo-1H-pyrazolo[3,4-b]pyridin-3-yl)-N,N-dimethylmethanamine

To a solution of 5-bromo-3-bromomethyl-pyrazolo[3,4-b]pyridine-1-carboxylic acid tert-butyl ester (100 mg, 0.26 mmol) in N,N-dimethylformamide (2 mL) was added dimethylamine hydrochloride (25 mg, 0.31 mmol). The reaction was heated at 80° C. for 1h. The reaction mixture was diluted with EtOAc, filtered through celite. The filtrate was concentrate to give a crude 1-(5-bromo-1H-pyrazolo[3,4-b]pyridin-3-yl)-N,N-dimethylmethanamine which was used in the next step without further purifications. LCMS: RT 0.28 min.; MH+ 354.90.

2-(5-bromo-1H-pyrazolo[3,4-b]pyridin-3-yl)acetonitrile

To a solution of 5-bromo-3-bromomethyl-pyrazolo[3,4-b]pyridine-1-carboxylic acid tert-butyl ester (100 mg, 0.26 mmol) in ethanol (5 mL) was added a solution of potassium cyanide (18 mg, 0.28 mmol) in water (0.50 mL). The reaction was stirred at 50° C. for 8h. The reaction mixture was diluted with EtOAc, washed with brine. The organic phase was the separated, dried and concentrated. The crude was purified by HPLC afford 26 mg of 2-(5-bromo-1H-pyrazolo[3,4-b]pyridin-3-yl)acetonitrile. LCMS: RT 0.92 min.; MH+ 236.80; $^1$H NMR (400 MHz, DMSO-$d_6$) δ ppm 13.94 (br. s., 1 H) 8.63 (dd, J=11.67, 2.13 Hz, 2 H) 4.40 (s, 2 H).

2-(5-bromo-1H-pyrazolo[3,4-b]pyridin-3-yl)acetonitrile

A mixture of 5-bromo-1H-pyrazolo[3,4-b]pyridin-3-ylamine (1.0 g, 4.7 mmol), (2-oxo-ethyl)carbamic acid t-butyl ester (1.12 g, 7.0 mmol) and acetic acid (0.27 mL, 4.69 mmol) in 1,2-dichloroethane (20 mL) was stirred at RT for 1h. Sodium triacetoxyborohydride (2.0 g, 9.4 mmol) was then added. The reaction was then stirred at RT overnight. The reaction was quenched with water (1 mL), stirred at RT for 30 min., diluted with DCM, washed with sat. NaHCO$_3$. The organic layer was separated, dried (MgSO$_4$), and concentrated. The crude was purified by ISCO (EtOAc/hexane gradient) to afford 2-(5-bromo-1H-pyrazolo[3,4-b]pyridin-3-yl)acetonitrile (0.74 g). LCMS: RT 1.28 min.; MH+ 355.80; $^1$H NMR (400 MHz, DMSO-$d_6$) δ ppm 12.15-12.34 (m, 1 H) 8.40 (d, J=2.26 Hz, 1 H) 8.36 (d, J=2.26 Hz, 1 H) 6.85 (br. s., 2 H) 3.23-3.33 (m, 2 H) 3.18 (d, J=5.77 Hz, 2 H) 1.37 (s, 9 H).

Example 59

Synthesis of 2-(4-(3-amino-1H-pyrazolo[3,4-b]pyridin-5-yl)benzylamino)-N-(5-fluoro pyridin-2-yl)-5-(trifluoromethyl)nicotinamide

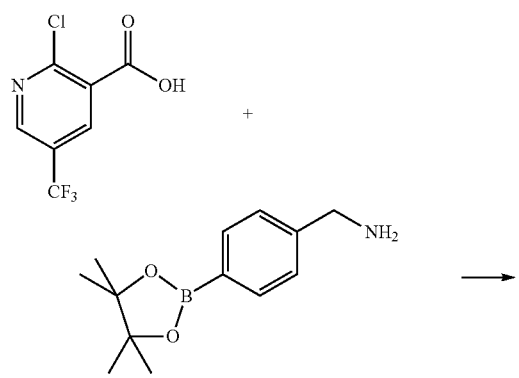

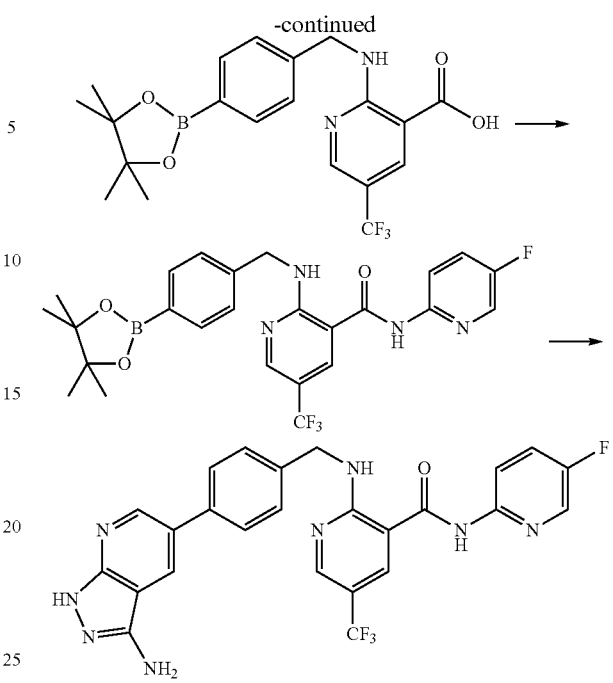

Synthesis of 2-(4-(4,4,5,5-tetramethyl-1,3,2-dioxaborolan-2-yl)benzylamino)-5-(trifluoro methyl) nicotinic acid To a mixture of 2-chloro-5-trifluoromethyl-nicotinic acid (0.5 g, 2.0 mmol) and 4-(4,4,5,5-tetramethyl-1,3,2-dioxaborolan-2-yl)-benzylamine hydrochloride (0.60 g, 2.2 mmol) in dimethyl sulfoxide (5.0 mL) was added N,N-diisopropylethylamine (1.2 mL, 6.6 mmol). The reaction was stirred at 80° C. for 2h. The reaction was diluted with EtOAc, washed with 5% aqueous citric acid solution. The organic layer was then separated, dried and concentrated. The precipitate formed was filtered and washed with hexanes to give 2-(4-(4,4,5,5-tetramethyl-1,3,2-dioxaborolan-2-yl)benzylamino)-5-(trifluoro methyl) nicotinic acid (0.46 g). MH+ 422.90; small portion was purified by HPLC to give: $^1$H NMR (400 MHz, DMSO-$d_6$) δ ppm 13.71 (br. s., 1 H) 8.97 (t, J=5.90 Hz, 1 H) 8.56 (d, J=1.76 Hz, 1 H) 8.26 (d, J=2.26 Hz, 1 H) 7.62 (d, J=8.03 Hz, 2 H) 7.33 (d, J=8.03 Hz, 2 H) 4.78 (d, J=6.02 Hz, 2 H) 1.28 (s, 12 H).

Synthesis of N-(5-fluoropyridin-2-yl)-2-(4-(4,4,5,5-tetramethyl-1,3,2-dioxaborolan-2-yl)benzylamino)-5-(trifluoromethyl)nicotinamide A solution of 2-[4-(4,4,5,5-tetramethyl-1,3,2-dioxaborolan-2-yl)-benzylamino]-5-trifluoromethyl-nicotinic acid (100 mg, 0.24 mmol), N,N,N',N'-tetramethyl-O-(7-azabenzotriazol-1-yl)uronium hexafluorophosphate (0.14 g, 0.38 mmol), N,N-diisopropylethylamine (0.12 mL, 0.71 mmol) in N,N-dimethylformamide (1 mL) was stirred at RT for 15 min. 5-fluoro-pyridin-2-ylamine (53 mg, 0.47 mmol) was then added, and the reaction was stirred at 45° C. overnight. Diluted with EtOAc, washed brine, then water (3×). The organic layer was then separated, dried and concentrated. The crude was used directly in the next step without further purifications (119 mg). LCMS: RT 2.00 min.; MH+ 516.90; $^1$H NMR (400 MHz, DMSO-$d_6$) δ ppm 11.25 (s, 1 H) 8.87 (t, J=5.77 Hz, 1 H) 8.37-8.57 (m, 3 H) 8.11 (dd, J=9.16, 4.14

Hz, 1 H) 7.80 (td, J=8.66, 3.01 Hz, 1 H) 7.62 (d, J=7.78 Hz, 2 H) 7.34 (d, J=8.03 Hz, 2 H) 4.74 (d, J=5.77 Hz, 2 H) 1.28 (s, 12 H); $^{19}$F NMR (376 MHz, DMSO-d$_6$) δ ppm $^-$59.16 (s, 3 F) −132.49 (s, 1 F).

Synthesis of 2-(4-(3-amino-1H-pyrazolo[3,4-b]pyridin-5-yl)benzylamino)-N-(5-fluoro pyridin-2-yl)-5-(trifluoromethyl)nicotinamide A solution of N-(5-fluoro-pyridin-2-yl)-2-[4-(4,4,5,5-tetramethyl-1,3,2-dioxaborolan-2-yl)-benzylamino]-5-trifluoromethyl-nicotinamide (100 mg, 0.2 mmol) and 5-bromo-1H-pyrazolo[3,4-b]pyridin-3-ylamine (49 mg, 0.23 mmol) in 1,4-dioxane (3.0 mL) was degassed for 10 min, bis(tricyclohexylphosphine)palladium (0) (13 mg, 0.019 mmol) and 1.2 M of saturated aqueous sodium bicarbonate solution in water (0.5 mL, 0.58 mmol) were added. The reaction was heated in the microwave at 120° C. for 20 min. The reaction mixture was diluted with EtOAc, washed with water (5×). The organic phase was the separated, dried over MgSO$_4$, filtered and concentrated. The crude was purified by HPLC to give 2-(4-(3-amino-1H-pyrazolo[3,4-b]pyridin-5-yl)benzylamino)-N-(5-fluoro pyridin-2-yl)-5-(trifluoromethyl) nicotinamide (42 mg). MH+ 522.90: $^1$H NMR (400 MHz, DMSO-d$_6$) δ ppm 11.26 (s, 1 H) 8.90 (t, J=5.90 Hz, 1 H) 8.68 (d, J=2.01 Hz, 1 H) 8.34-8.58 (m, 4 H) 8.12 (dd, J=9.16, 4.14 Hz, 1 H) 7.81 (td, J=8.72, 3.14 Hz, 1 H) 7.63 (d, J=8.03 Hz, 2 H) 7.47 (d, J=8.03 Hz, 2 H) 4.77 (d, J=5.77 Hz, 2 H); 19F NMR (376 MHz, DMSO-d$_6$) δ ppm −62.99 (s, 3 F) −78.50 (TFA, s, 4 F) −136.34 (s, 1 F).

Example 60

Synthesis of (S)-3-((4-(3-amino-1H-pyrazolo[3,4-b]pyridin-5-yl)cyclohexyl)methylamino)-6-cyano-N-(1-(3,4-difluorophenyl)ethyl)pyrazine-2-carboxamide

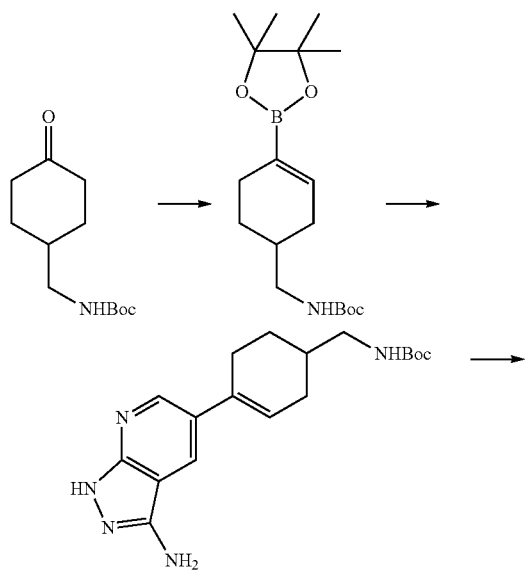

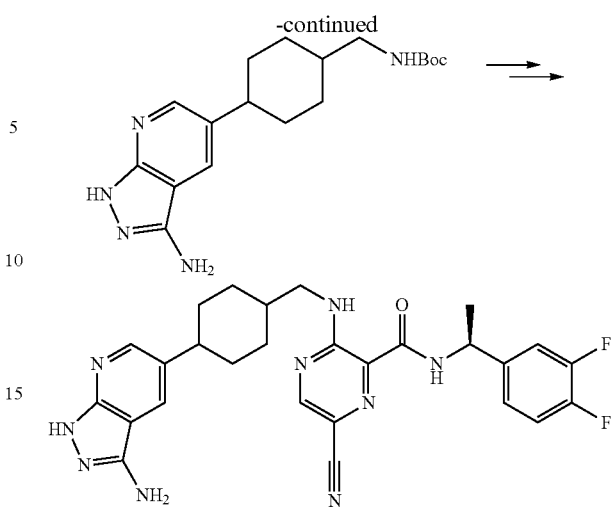

Synthesis of tert-butyl (4-(4,4,5,5-tetramethyl-1,3,2-dioxaborolan-2-yl)cyclohex-3-enyl)methylcarbamate 1.0 M of lithium hexamethyldisilazide in tetrahydrofuran (9.2 mL, 9.24 mmol) and 5 ml of dry THE was cooled to −78° C. A solution of (4-oxo-cyclohexylmethyl)-carbamic acid tert-butyl ester (1.0 g, 4.4 mmol) in dry THF (10 ml) was added dropwise. The reaction mixture was stirred under argon at −78° C. for 1.5h. N-phenylbis(trifluoromethanesulphonimide) (1.57 g, 4.4 mmol) in dry THE (10 ml) was slowly added at −78° C., and the reaction mixture was stirred from −78 to 5° C. over 3h. The reaction mixture was quenched with 2M aq.NH$_4$Cl, extracted with ether, washed with aq. NaHCO$_3$, and brine. The organic phase was separate, dried (MgSO$_4$) and concentrate to give the triflate intermediate as light yellow oil which was then dissolved in dimethyl sulfoxide (10 mL). To this, bis(pinacolato)diboron (1.12 g, 4.4 mmol) was added. The reaction solution was then degassed with argon. [1,1'-bis(diphenylphosphino)ferrocene]dichloropalladium(II), complex with dichloromethane (1:1) (0.36 g, 0.44 mmol), 1,1'-bis(diphenylphosphino)-ferrocene (0.24 g, 0.44 mmol) and potassium acetate (1.73 g, 17.6 mmol) were then added. The reaction was then heated at 80° C. overnight. Cooled down, the reaction mixture was filtered through a silica gel pad, rinsed with excess EtOAc. The filtrate was washed with brine, then water, dried and concentrated. The crude was then loaded on small silica gel column, eluted with 25/75 of EtOAc/hexanes, concentrated. The crude was then purified by HPLC to give tert-butyl (4-(4,4,5,5-tetramethyl-1,3,2-dioxaborolan-2-yl)cyclohex-3-enyl) methylcarbamate as light yellow oil (0.66 g). LCMS: RT 1.94 min; MH+238.00 (Product-Boc) and 360.00 (P+Na). $^1$H NMR (400 MHz, DMSO-d$_6$) δ ppm 6.76-6.88 (m, 1 H) 6.40 (br. s., 1 H) 2.82 (t, J=6.02 Hz, 2 H) 2.02-2.18 (m, 2 H) 1.85-1.99 (m, 1 H) 1.63 (d, J=4.77 Hz, 3 H) 1.37 (s, 9 H) 1.18 (s, 13 H).

Synthesis of tert-butyl (4-(3-amino-1H-pyrazolo[3,4-b]pyridin-5-yl)cyclohex-3-enyl)methylcarbamate A mixture of 5-bromo-1H-pyrazolo[3,4-b]pyridin-3-ylamine (140 mg, 0.68 mmol), [4-(4,4,5,5-tetramethyl-1,3,2-dioxaborolan-2-yl)-cyclohex-3-enylmethyl]-carbamic acid tert-butyl ester (200 mg, 0.59 mmol) and 1,4-dioxane (4.0 mL) was degassed for 10 min. Tetrakis(triphenylphosphine)palladium(0) (69 mg, 0.06 mmol) and a solution of potassium phosphate (504 mg, 2.4 mmol) in water (1.0 mL) were then added. The reaction was heated in microwave at 120° C. for 30 min. The reaction mixture was diluted with EtOAc, washed with water (2×). The organic phase was separated, dried, and concentrate. The crude was purified by HPLC afford tert-butyl (4-(3-amino-1H-pyrazolo[3,4-b] pyridin-5-yl)cyclohex-3-enyl)methylcarbamate (76 mg). LCMS: RT 1.15 min.; MH+ 344.00.

Synthesis of tert-butyl (4-(3-amino-1H-pyrazolo[3, 4-b]pyridin-5-yl)cyclohexyl)methyl carbamate A mixture of [4-(3-Amino-1H-pyrazolo[3,4-b]pyridin-5-yl)-cyclohex-3-enylmethyl]-carbamic acid tert-butyl ester (70 mg, 0.2 mmol) and platinum dioxide (5 mg, 0.02 mmol) in methanol (5 mL) was degassed with argon, then back filled with hydrogen (3×). The reaction was stirred at RT under hydrogen balloon overnight. The solid was then filtered off. The filtrate was concentrated. The crude tert-butyl (4-(3-amino-1H-pyrazolo[3,4-b]pyridin-5-yl)cyclohexyl)methyl carbamate (45 mg) was used in the next step without further purifications. LCMS: RT 1.07 min. (10_90_2 m method); MH+ 246.00 (P-Boc).

Synthesis of 5-(4-(aminomethyl)cyclohexyl)-1H-pyrazolo[3,4-b]pyridin-3-amine

A mixture of [4-(3-Amino-1H-pyrazolo[3,4-b]pyridin-5-yl)-cyclohexylmethyl]-carbamic acid tert-butyl ester (45 mg, 0.13 mmol), methylene chloride (2.0 mL, 0.031 mol) and trifluoroacetic acid (0.2 mL, 2.0 mmol) was stirred at RT for 1h. The reaction was neutralized with 2M $NH_3$ in methanol, the solvent was then removed. The crude (30 mg) was used in the next step without further purifications. LCMS: RT 1.45 min; MH+ 246.00.

Synthesis of (S)-3-((4-(3-amino-1H-pyrazolo[3,4-b] pyridin-5-yl)cyclohexyl)methylamino)-6-cyano-N-(1-(3,4-difluorophenyl)ethyl)pyrazine-2-carboxamide To a solution of 5-(4-aminomethyl-cyclohexyl)-1H-pyrazolo[3,4-b]pyridin-3-ylamine (30 mg, 0.1 mmol) and 6-cyano-3-fluoro-pyrazine-2-carboxylic acid [(S)-1-(3,4-difluoro-phenyl)-ethyl]-amide (87 mg, 0.28 mmol) in dimethyl sulfoxide (1.0 mL) was added N,N-diisopropylethylamine (0.055 g, 0.43 mmol). Stirred at RT for 1 h, the reaction mixture was diluted with EtOAc, washed with brine, then water. The organic phase was the separated, dried and concentrated. The crude was purified by HPLC to give (S)-3-((4-(3-amino-1H-pyrazolo[3,4-b]pyridin-5-yl)cyclohexyl)methylamino)-6-cyano-N-(1-(3,4-difluorophenyl) ethyl)pyrazine-2-carboxamide (15 mg). LCMS: RT 1.29 min.; MH+ 532.00;). $^1$H NMR (400 MHz, DMSO-$d_6$) δ ppm 11.59-12.25 (m, 1 H) 9.39-9.57 (m, 1 H) 9.31 (dd, J=8.28, 3.51 Hz, 1 H) 8.73 (s, 1 H) 8.29 (dd, J=14.81, 1.51 Hz, 1 H) 7.90-8.08 (m, 1 H) 7.45-7.57 (m, 1 H) 7.32-7.44 (m, 1 H) 7.27 (br. s., 1 H) 5.03-5.21 (m, 1 H) 3.61 (dd, J=16.56, 7.53 Hz, 2 H) 2.64-2.79 (m, 1 H) 2.05 (br. s., 1 H) 1.57-1.93 (m, 8 H) 1.36-1.55 (m, 5 H); $^{19}$F NMR (376 MHz, DMSO-$d_6$) d ppm ⁻139.01-⁻138.71 (m, 1 F), ⁻141.60-⁻141.30 (m, 1 F).

Example 61

(S)-2-(((1-(5-aminopyrazin-2-yl)piperidin-4-yl) methyl)amino)-5-cyano-N-(1-(4-fluorophenyl)ethyl) nicotinamide

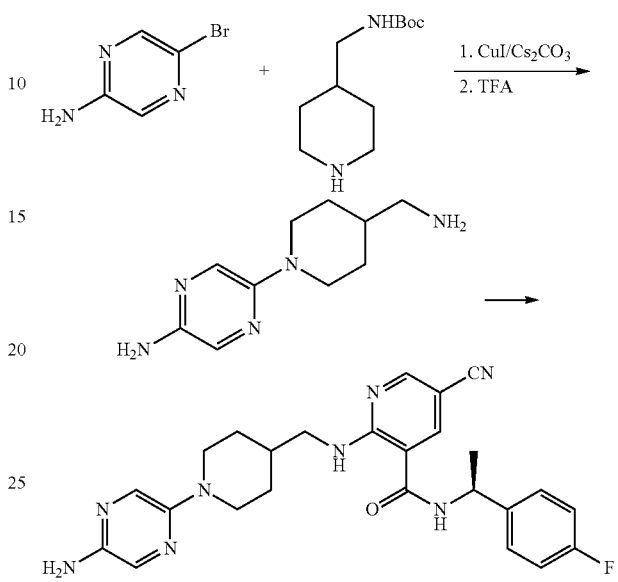

A solid mixture of 5-Bromo-pyrazin-2-ylamine (0.25 g, 1.4 mmol), Piperidin-4-ylmethyl-carbamic acid tert-butyl ester (0.46 g, 2.2 mmol), Copper(I) iodide (0.0055 g, 0.029 mmol), Cesium Carbonate (0.94 g, 2.9 mmol) was degassed and flushed with nitrogen with magnetic stirring. It was added N,N-Dimethylformamide (2 mL, 20 mmol) via syringe and followed with 2-Isobutyryl-cyclohexanone (0.048 g, 0.29 mmol). Heated to at 90° C. for overnight and LC-MS showed no more starting material and the major formation of the desired product (0.81 min, ES+/308.20). Cooled to room temperature and worked up with EtOAc and water. Dried over $MgSO_4$ and purified on silica gel column with 0-100% EtOAc in DCM to give the desired product as a light brown syrup. (note: the starting material appeared from the silica gel column may due to its limited solubility in the reaction mix and LC-MS on the supernatant did not pick up the residual solid starting material.) $^1$H NMR (400 MHz, $CDCl_3$) δ ppm 1.25-1.35 (m, 2 H) 1.43 (s, 9 H) 1.61 (d, J=18.32 Hz, 1 H) 1.77 (d, J=14.05 Hz, 2 H) 2.70 (td, J=12.30, 2.51 Hz, 2 H) 3.03 (t, J=6.27 Hz, 2 H) 3.99 (d, J=12.55 Hz, 2 H) 4.05-4.15 (m, 2 H) 4.73 (br. s., 1 H) 7.65 (dd, J=8.03, 1.51 Hz, 2 H) 7.80-8.08 (m, 1 H).

A solution of [1-(5-Amino-pyrazin-2-yl)-piperidin-4-ylmethyl]-carbamic acid tert-butyl ester (0.10 g, 0.00032 mol) in Trifluoroacetic Acid (1 mL, 0.02 mol) and Methylene chloride (0.9 mL, 0.01 mol) was stirred at room temperature for 30 min and LC-MS showed complete reaction (0.12 min, ES+/20.8.0). Concentrated to give the crude product as a TFA salt without further purifications.

To a solution of the TFA salt of 5-(4-Aminomethyl-piperidin-1-yl)-pyrimidin-2-ylamine (50.0 mg, 0.000241 mol) in Dimethyl sulfoxide (0.6 mL, 0.009 mol) was added N,N-Diisopropylethylamine (0.126 mL, 0.000724 mol), followed by 5-Cyano-2-fluoro-N-[(S)-1-(4-fluoro-phenyl)-ethyl]-nicotinamide (69.3 mg, 0.000241 mol). The reaction was heated at 90° C. for 30 min. LC-MS showed completed reaction (1.24 min, ES+/475.2). Cooled to room temperature and worked up with EtOAc and water, dried over $MgSO_4$. Purified on a silica gel column with 0-100% EtOAc in DCM to give the desired product as a yellow solid. (4 mg, 3%).

MS: ES+/475.2. $^1$H NMR (400 MHz, CDCl$_3$) δ ppm 1.31-1.49 (m, 2 H) 1.60 (d, J=6.78 Hz, 3 H) 1.86 (d, J=12.30 Hz, 3 H) 2.73 (t, J=12.05 Hz, 2 H) 3.33-3.56 (m, 2 H) 3.98-4.07 (m, 4 H) 5.12-5.27 (m, 1 H) 6.61 (d, J=7.53 Hz, 1 H) 7.04 (t, J=8.78 Hz, 1 H) 7.35 (dd, J=7.91, 5.65 Hz, 2 H) 7.67 (d, J=7.53 Hz, 2 H) 7.62-7.73 (m, 1 H) 7.89 (d, J=1.51 Hz, 1 H) 8.43 (s, 1 H) 8.88-9.09 (m, 1 H) 9.00 (t, J=1.00 Hz, 1H) 9.25-9.26 (m, 1 H).

Example 62

Synthesis of (S)-6-cyano-N-(1-(3,4-difluorophenyl)ethyl)-3-(4-(3-(dimethylamino)-1H-pyrazolo[3,4-b]pyridin-5-yl)benzylamino)pyrazine-2-carboxamide

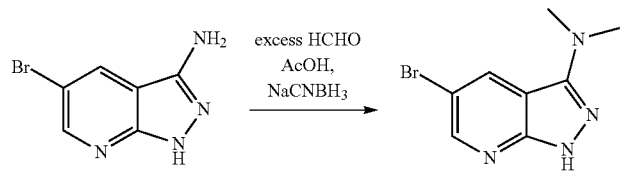

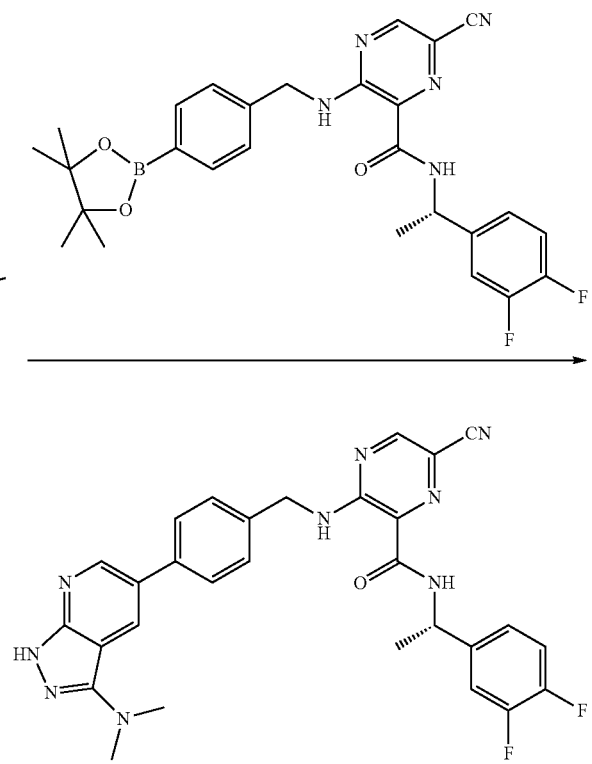

Synthesis of 5-bromo-N,N-dimethyl-1H-pyrazolo[3,4-b]pyridin-3-amine

To a mixture of 5-bromo-1H-pyrazolo[3,4-b]pyridin-3-ylamine (200 mg, 0.9 mmol) and formaldehyde (2.0 mL, 27 mmol) in acetic acid (10 mL, 180 mmol) was added a solution of sodium cyanoborohydride (195 mg, 3.10 mmol) in tetrahydrofuran (2 mL). The mixture was then stirred at 0° C. overnight. Quenched with water, extracted with EtOAc, washed with water (2×), brine, and then sat'd NaHCO$_3$. The organic phase was dried over MgSO$_4$, filtered, and concentrated. The crude was (153 mg, purity ~60%) was used directly in the next step without further purifications. LCMS: RT 1.09 min., MH+ 241.5.

A solution of 6-cyano-3-[4-(4,4,5,5-tetramethyl-1,3,2-dioxaborolan-2-yl)-benzylamino]-pyrazine-2-carboxylic acid [(S)-1-(3,4-difluoro-phenyl)-ethyl]-amide (181 mg, 0.348 mmol) and (5-bromo-1H-pyrazolo[3,4-b]pyridin-3-yl)-dimethyl-amine (140 mg, 0.29 mmol) in 1,4-dioxane (2 mL) was degassed for 10 min, bis(tricyclohexylphosphine)-palladium (0) (19.4 mg, 0.029 mmol) and saturated aqueous NaHCO$_3$ solution in water (0.73 mL, 0.87 mmol) were added. The reaction was heated in the microwave at 120° C. for 20 min. The reaction mixture was diluted with EtOAc, washed with water (5×). The organic phase was the separated, dried (MgSO$_4$), and concentrated. The crude was then purified by HPLC to give desired product 37 mg. LCMS: RT 1.82 min.; MH+ 554.2: $^1$H NMR (400 MHz, DMSO-d$_6$) δ ppm 12.45 (s, 1 H) 9.75 (t, J=5.90 Hz, 1 H) 9.33 (d, J=8.28 Hz, 1 H) 8.75 (s, 1 H) 8.66 (d, J=2.01 Hz, 1 H) 8.40 (d, J=1.76 Hz, 1 H) 7.69 (d, J=8.03 Hz, 2 H) 7.52 (ddd, J=11.92, 7.91, 2.01 Hz, 1 H) 7.43 (d, J=8.03 Hz, 2 H) 7.33-7.40 (m, 1 H) 7.26 (br. s., 1 H) 5.12 (quin, J=7.22 Hz, 1 H) 4.62-4.84 (m, 2 H) 3.05 (s, 6 H) 1.52 (d, J=7.03 Hz, 3 H); $^{19}$F NMR (376 MHz, DMSO-d$_6$) δ ppm $^-$138.99-$^-$138.73 (m, 1 F), $^-$141.59-$^-$141.31 (m, 1 F).

Example 63

5-Cyano-N-[(S)-1-(4-fluoro-phenyl)-ethyl]-2-{[5-(1H-pyrazolo[3,4-b]pyridin-5-yl)-pyrazin-2-ylmethyl]-amino}-nicotinamide

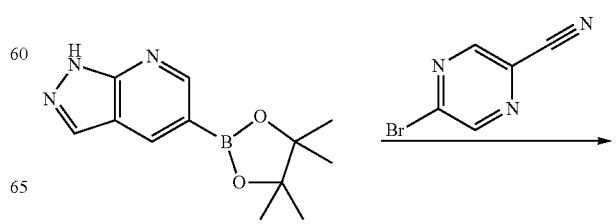

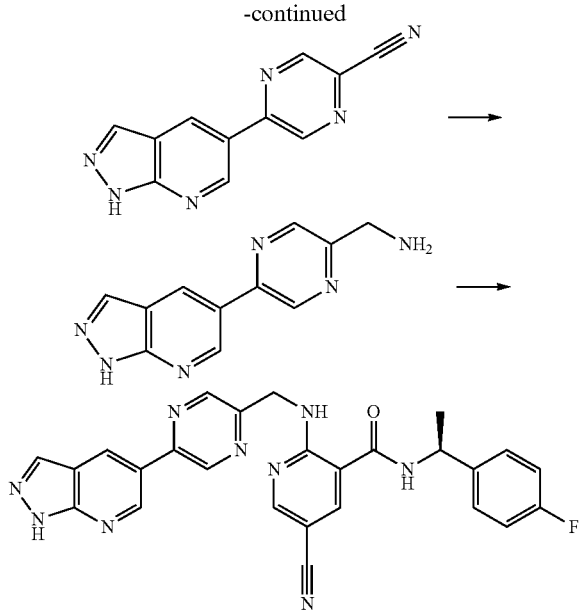

5-(1H-Pyrazolo[3,4-b]pyridin-5-yl)-pyrazine-2-carbonitrile

A solution of 5-Bromo-pyrazine-2-carbonitrile (0.078 g, 0.00042 mol) and 5-(4,4,5,5-Tetramethyl-1,3,2-dioxaborolan-2-yl)-1H-pyrazolo[3,4-b]pyridine (102 mg, 0.000416 mol) in 1,4-Dioxane (1.70 mL) was degassed with argon for 5 min. Bis(tricyclohexylphosphine)-palladium (0) (22 mg, 0.000033 mol) was then added, followed by 1.2 M of Saturated Aqueous Sodium Bicarbonate Solution in water (0.90 mL, 0.0011 mol). The reaction was heated in microwave at 120° C. for 20 min. The reaction mixture was diluted with ethyl acetate, washed with saturated sodium bicarbonate then with saturated sodium chloride. The organics were dried over sodium sulfate, filtered and evaporated. The residue was purified by silica gel chromatography using 0-10% methanol in methylene chloride as eluent. Isolated was 23 mg (25%) of product ($R_f$=0.46 in 10% methanol in methylene chloride). ESI-MS (M+H$^+$): 222.92.

5-Cyano-N-[(S)-1-(4-fluoro-phenyl)-ethyl]-2-{[5-(1H-pyrazolo[3,4-b]pyridin-5-yl)-pyrazin-2-ylm-ethyl]-amino}-nicotinamide Raney nickel catalyst (approx. 50 mg) was washed 5× with methanol. A solution of 5-(1H-Pyrazolo[3,4-b]pyridin-5-yl)-pyrazine-2-carbonitrile (0.0144 g, 0.0648 mmol) in 2.0M of Ammonia in Methanol (2.0 mL, 4.0 mmol) was added. The reaction was evacuated briefly, then was stirred under hydrogen (balloon) for 90 min. The mixture was diluted with methanol, then filtered through a PTFE filter. The filter was then washed with ACN, then with ACN-MeOH, and the filtrate was concentrated in vacuo. The sample was diluted with methanol and evaporated (repeat). The residue was taken up in Dimethyl sulfoxide (1.0 mL) and N,N-Diisopropylethylamine (57 µL, 0.33 mmol), and 5-Cyano-2-fluoro-N-[(S)-1-(4-fluoro-phenyl)-ethyl]-nicotinamide (22 mg, 0.076 mmol) were added. The reaction was stirred at room temperature for 1h. The reaction was diluted in ethyl acetate, washed with water, washed with saturated sodium chloride, dried with sodium sulfate, filtered and evaporated. The residue was purified by preparative HPLC to yield 1.4 mg of product, as TFA salt (3.6%). ESI-MS (M+H$^+$): 493.90; $^1$H NMR (400 MHz, DMSO-d$_6$) δ 13.84 (br. s., 1H), 9.61 (t, J=5.40 Hz, 1H), 9.28 (s, 1H), 9.24 (d, J=1.76 Hz, 1H), 9.01 (d, J=7.28 Hz, 1H), 8.92 (d, J=1.76 Hz, 1H), 8.68 (s, 1H), 8.57 (d, J=1.76 Hz, 1H), 8.51 (d, J=1.76 Hz, 1H), 8.26 (s, 1H), 7.44 (dd, J=5.65, 8.41 Hz, 2H), 7.16 (t, J=8.91 Hz, 2H), 5.13 (quin, J=6.96 Hz, 1H), 4.88 (d, J=5.27 Hz, 2H), 1.47 (d, J=7.03 Hz, 3H). 0.2 TFA per molecule.

Example 64 was synthesized in a manner consistent with Example 63.

Example 65

5-Cyano-N-[(S)-1-(4-fluoro-phenyl)-ethyl]-2-{[6-(1H-pyrazolo[3,4-b]pyridin-5-yl)-pyridin-3-ylm-ethyl]-amino}-nicotinamide

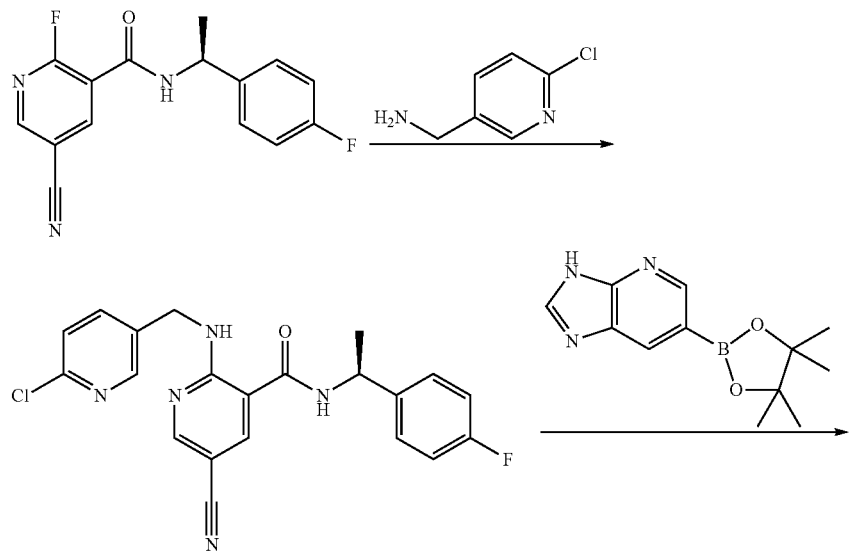

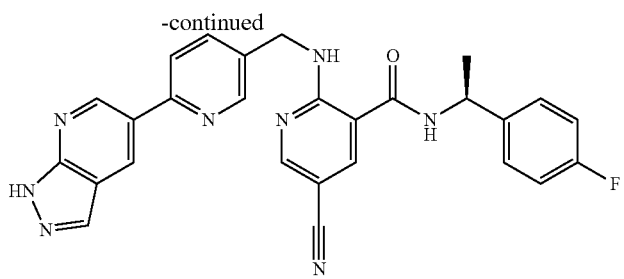

2-[(6-Chloro-pyridin-3-ylmethyl)-amino]-5-cyano-N-[(S)-1-(4-fluoro-phenyl)-ethyl]-nicotinamide To a stirred solution of 5-Cyano-2-fluoro-N-[(S)-1-(4-fluoro-phenyl)-ethyl]-nicotinamide (0.400 g, 0.00139 mol) in Dimethyl sulfoxide (8.5 mL) was added (6-Chloro-pyridin-3-yl)-methylamine (401 mg, 0.00281 mol), followed by N,N-Diisopropylethylamine (1.3 mL, 0.0075 mol). The reaction was stirred at room temperature for 1 hour. The reaction mixture was diluted with ethyl acetate, washed with water, washed with saturated sodium chloride, dried with sodium sulfate, filtered, evaporated. The residue was purified by silica gel chromatography using 0-50% ethyl acetate in hexanes as eluent. Isolated was 492 mg (86%) of product ($R_f$=0.79 in 1:1 hexanes/ethyl acetate). ESI-MS (M+H$^+$): 409.90.

5-Cyano-N-[(S)-1-(4-fluoro-phenyl)-ethyl]-2-{[6-(1H-pyrazolo[3,4-b]pyridin-5-yl)-pyridin-3-ylmethyl]-amino}-nicotinamide A solution of and 5-(4,4,5,5-Tetramethyl-1,3,2-dioxaborolan-2-yl)-1H-pyrazolo[3,4-b]pyridine (43 mg, 0.00018 mol) in 1,4-Dioxane (1.00 mL) was degassed with argon for 5 min. Bis(tricyclohexylphosphine)palladium (0) (7 mg, 0.00001 mol) was then added, followed by 1.2 M of Saturated Aqueous Sodium Bicarbonate Solution in water (0.305 mL). The vessel was evacuated and stirred under Ar. The reaction was sealed, stirred and heated in microwave at 120° C. for 30 min. The reaction mixture was diluted with ethyl acetate, washed with saturated NaHCO3 (+added saturated NaCl to reduce emulsion) then with saturated sodium chloride. Each aqueous wash was extracted with methylene chloride and the organics were combined. The organics were evaporated. The residue was taken up in DMSO, filtered and purified by preparative HPLC. Isolated was 45 mg (60%) of product as TFA salt. ESI-MS (M+H$^+$): 492.90. $^1$H NMR (400 MHz, DMSO-d$_6$) δ 9.38 (t, J=5.90 Hz, 1H), 9.20 (d, J=2.01 Hz, 1H), 9.00 (d, J=7.53 Hz, 1H), 8.82 (d, J=1.76 Hz, 1H), 8.65 (d, J=1.26 Hz, 1H), 8.58 (d, J=1.76 Hz, 1H), 8.47 (d, J=2.01 Hz, 1H), 8.23 (s, 1H), 8.02 (d, J=8.03 Hz, 1H), 7.85 (dd, J=1.76, 8.28 Hz, 1H), 7.42 (dd, J=5.65, 8.41 Hz, 2H), 7.14 (t, J=8.78 Hz, 2H), 5.10 (quin, J=6.96 Hz, 1H), 4.66-4.81 (m, 2H), 1.46 (d, J=7.03 Hz, 3H). 0.9 TFA per molecule.

Example 66

2-{[6-(3-Amino-1H-pyrazolo[3,4-b]pyridin-5-yl)-pyridin-3-ylmethyl]-amino}-5-cyano-N-[(S)-1-(4-fluoro-phenyl)-ethyl]-nicotinamide

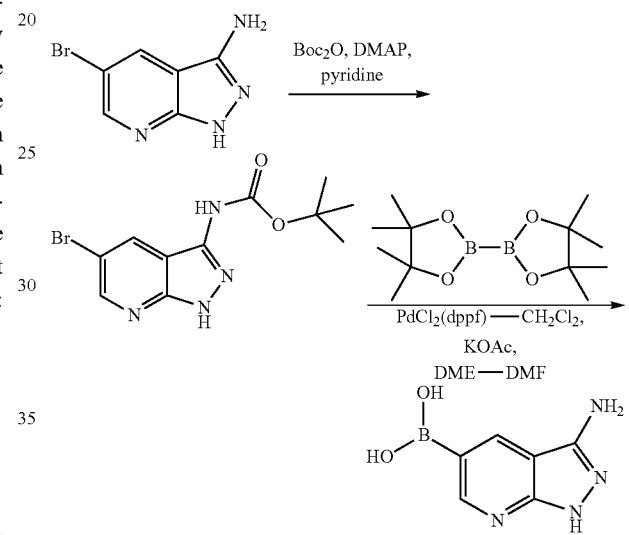

5-Bromo-1H-pyrazolo[3,4-b]pyridin-3-ylamine (0.500 g, 2.35 mmol) and Di-tert-Butyldicarbonate (0.598 g, 2.74 mmol) was stirred in Pyridine (10.0 mL). To the stirred mixture was added 4-Dimethylaminopyridine (26 mg, 0.21 mmol). The reaction was stirred at room temperature. After 3 h, the reaction was evaporated to dryness. The residue was purified by silica gel chromatography using 0-100% ethyl acetate in hexanes as eluent to give the product ($R_f$=0.27 in 1:1 hexanes/ethyl acetate) in 328 mg yield (45%). ESI-MS (M−Boc+H): 212.90/214.80.

3-amino-1H-pyrazolo[3,4-b]pyridin-5-ylboronic acid

Into a Vial was added (5-Bromo-1H-pyrazolo[3,4-b]pyridin-3-yl)-carbamic acid tert-butyl ester (0.212 g, 0.677 mmol) and bis(pinacolato)diboron (0.216 g, 0.850 mmol) and Potassium acetate (0.277 g, 2.82 mmol) and [1,1'-Bis(diphenylphosphino)ferrocene]dichloropalladium(II), complex with dichloromethane (53 mg, 0.065 mmol) and 1,2-Dimethoxyethane (2.58 mL) and N,N-Dimethylformamide (1.29 mL). The reaction mixture was evacuated, then purged with Ar (X5). The reaction was sealed under Ar and was microwaved 110° C. for approx. 2 h (in 30 min intervals). The reaction was diluted with ethyl acetate, washed with saturated sodium bicarbonate, washed with saturated sodium chloride, dried with sodium sulfate, filtered and evaporated. The residue was used as is in the next reaction. ESI-MS (M+H$^+$): 179.00.

229

Examples 67-68 were synthesized in a manner consistent with Example 66.

Example 69

Synthesis of 5-Cyano-N-[(S)-1-(4-fluoro-phenyl)-ethyl]-2-{[2-(1H-pyrazolo[3,4-b]pyridin-5-yl)-pyrimidin-5-ylmethyl]-amino}-nicotinamide

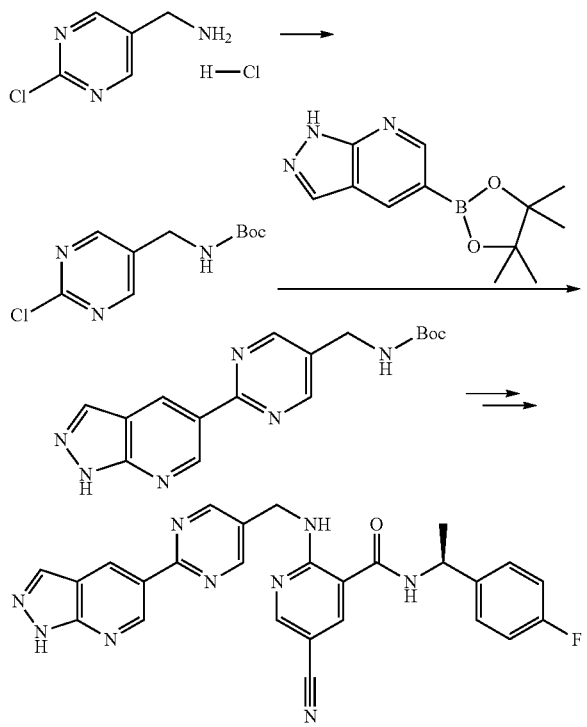

(2-Chloro-pyrimidin-5-ylmethyl)-carbamic acid tert-butyl ester (2-chloropyrimidin-5-yl)methanamine hydrogen chloride salt (0.501 g, 2.78 mmol) and Di-tert-Butyldicarbonate (0.675 g, 3.09 mmol) and 4-Dimethylaminopyridine (38 mg, 0.31 mmol) was stirred in Methylene chloride (12.0 mL). To this was added Triethylamine (1940 µL, 13.9 mmol) and the reaction was stirred at room temperature for 3 days. The reaction was diluted with DMF to aid solubilization and silica gel was added. The solvent was removed and the residue was purified by silica gel chromatography using 0-50% methanol in methylene chloride as eluent. Isolated was 212 mg (31%). ESI-MS (M+H$^+$): 243.9.

230

[2-(1H-Pyrazolo [3,4-b]pyridin-5-yl)-pyrimidin-5-ylmethyl]-carbamic acid

A solution of Chloro-pyrimidin-5-ylmethyl)-carbamic acid tert-butyl ester (0.212 g, 0.000870 mol) and 5-(4,4,5,5-Tetramethyl-1,3,2-dioxaborolan-2-yl)-1H-pyrazolo[3,4-b]pyridine (236 mg, 0.000961 mol) in 1,4-Dioxane (3.5 mL, 0.045 mol) was degassed with argon for 5 min.

Bis(tricyclohexylphosphine)palladium (0) (60.0 mg, 0.0000899 mol) was then added, followed by 1.2 M of Saturated Aqueous Sodium Bicarbonate Solution in water (2.00 mL, 0.00240 mol). The vessel was degassed again and sealed under Ar. The reaction was stirred and heated in microwave at 120° C. for 20 min. The reaction mixture was diluted with ethyl acetate, washed with saturated sodium bicarbonate then with saturated sodium chloride. The organics were dried over sodium sulfate, filtered and evaporated. The residue was purified by silica gel chromatography using 0-100% ethyl acetate in hexanes as eluent. Isolated was 177 mg (62%) of product (R$_f$ 0.45 in ethyl acetate). ESI-MS (M+H$^+$): 327.00.

5-Cyano-N-[(S)-1-(4-fluoro-phenyl)-ethyl]-2-{[2-(1H-pyrazolo[3,4-b]pyridin-5-yl)-pyrimidin-5-ylmethyl]-amino}-nicotinamide To a suspension of 2-(1H-Pyrazolo[3,4-b]pyridin-5-yl)-pyrimidin-5-ylmethyl]-carbamic acid tert-butyl ester (0.078 g, 0.24 mmol) in Methylene chloride (1.0 mL) was added Trifluoroacetic Acid (1.0 mL). The reaction was stirred at room temperature for 30 minutes. The mixture was evaporated under pressure. The residue was taken up in DCM and evaporated. Repeat 2×. The residue was taken up in Dimethyl sulfoxide (2.0 mL) and N,N-Diisopropylethylamine (176 µL, 1.01 mmol) and 5-Cyano-2-fluoro-N-[(S)-1-(4-fluoro-phenyl)-ethyl]-nicotinamide (53 mg, 0.18 mmol) were added. The reaction was stirred at room temperature for 1 h. Trifluoroacetic Acid (150 µL, 1.9 mmol) was added to the reaction and the reaction mixture was purified by preparative HPLC. The fractions were combined and the solvent evaporated. The residue was further purified by silica gel chromatography using 0-100% ethyl acetate in hexanes to give the product in 46.7 mg yield (51%). ESI-MS (M+H$^+$): 493.90. $^1$H NMR (400 MHz, DMSO-d$_6$) δ 13.84 (br. s., 1H), 9.46 (d, J=1.51 Hz, 1H), 9.38 (t, J=5.77 Hz, 1H), 9.10 (d, J=1.51 Hz, 1H), 8.99 (d, J=7.28 Hz, 1H), 8.86 (s, 2H), 8.59 (d, J=1.51 Hz, 1H), 8.46 (d, J=1.76 Hz, 1H), 8.27 (s, 1H), 7.42 (dd, J=5.65, 8.41 Hz, 2H), 7.14 (t, J=8.78 Hz, 2H), 5.10 (quin, J=6.90 Hz, 1H), 4.64-4.79 (m, 2H), 1.46 (d, J=7.03 Hz, 3H). 0.3 TFA per molecule.

Example 70

Synthesis of 2-{4-[5-Amino-6-(3-amino-propyl)-pyrazin-2-yl]-benzylamino}-5-cyano-N-[(S)-1-(4-fluoro-phenyl)-ethyl]-nicotinamide

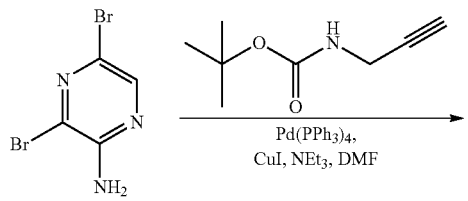

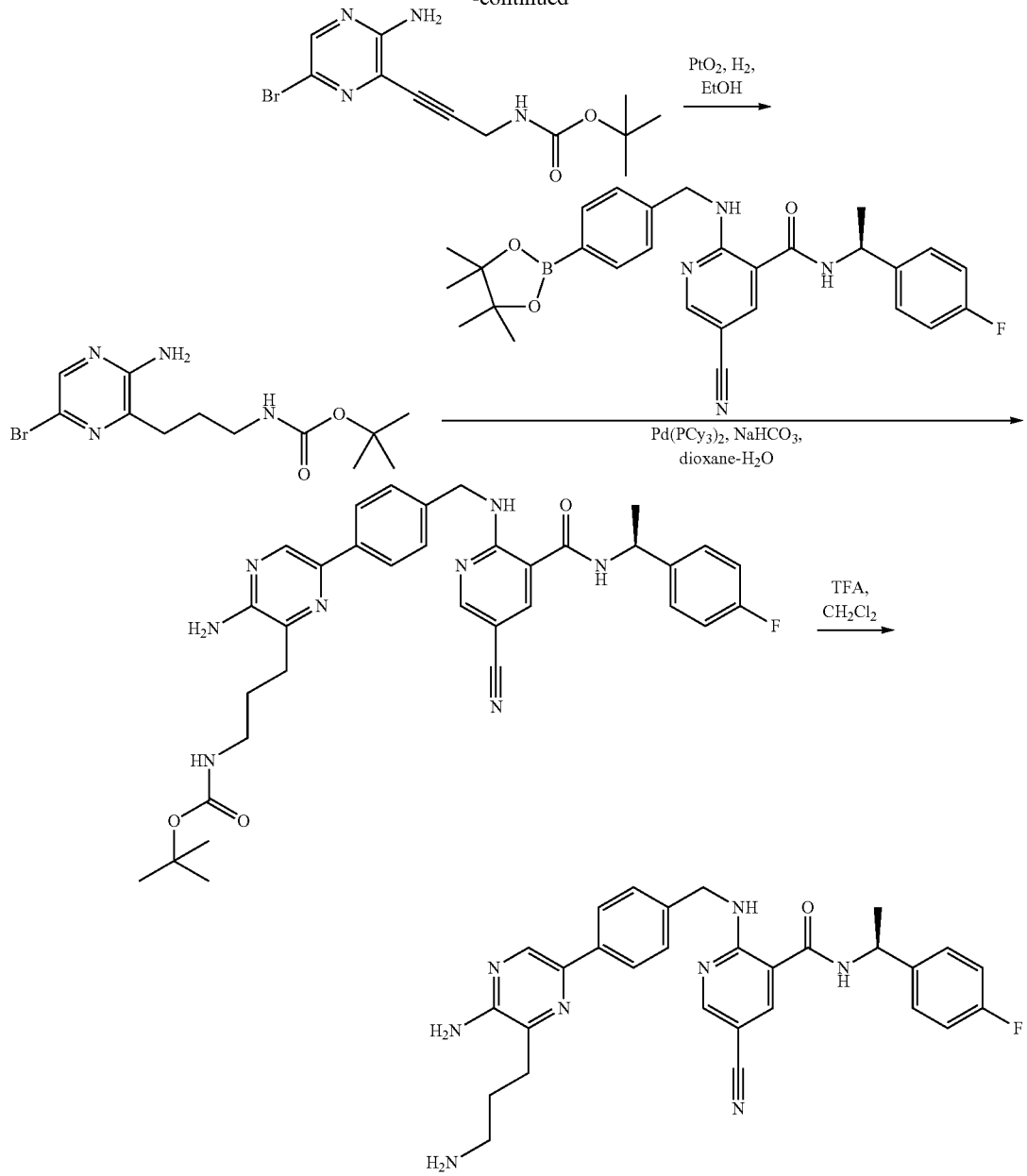

[3-(3-Amino-6-bromo-pyrazin-2-yl)-prop-2-ynyl]-carbamic acid tert-butyl ester 3,5-dibromopyrazin-2-amine (1.002 g, 3.962 mmol) and Prop-2-ynyl-carbamic acid t-butyl ester (0.743 g, 4.79 mmol) and Copper(I) iodide (0.099 g, 0.52 mmol) was dissolved in N,N-Dimethylformamide (14 mL) and Triethylamine (5.6 mL, 40 mmol). The reaction was evacuated and filled with Ar. Repeat 5×. Tetrakis(triphenylphosphine)palladium(0) (0.250 g, 0.216 mmol) was added and the reaction was sealed and was stirred under Ar and was heated at 120° C. for 15 minutes (microwave). The reaction was diluted with DMF and filtered The solvent was evaporated to dryness. The residue was purified by silica gel chromatography using 0-10% methanol in methylene chloride as eluent (Rf=0.19 in 5% methanol/methylene chloride). Isolated was 717 mg (55%) product. ESI-MS (M+H$^+$): 326.90.3

[3-(3-Amino-6-bromo-pyrazin-2-yl)-propyl]-carbamic acid tert-butyl ester

[3-(3-Amino-6-bromo-pyrazin-2-yl)-prop-2-ynyl]-carbamic acid tert-butyl ester (0.107 g, 0.327 mmol) was dissolved in Ethanol (2.0 mL) and the reaction vessel was evacuated, then replaced with nitrogen. Platinum dioxide (5 mg, estimated) was added and the reaction vessel was evacuated, then replaced with hydrogen. The reaction was stirred under balloon pressure of hydrogen at room temperature overnight. The reaction was filtered through a PTFE syringe filter and evaporated to give the product in 118 mg yield (>100%, crude). ESI-MS (M+H$^+$): 332.90.

3-{3-Amino-6-[4-({5-cyano-3-[(S)-1-(4-fluoro-phenyl)-ethylcarbamoyl]-pyridin-2-ylamino}-methyl)-phenyl]-pyrazin-2-yl}-propyl)-carbamic acid tert-butyl ester A solution of 5-Cyano-N-[(S)-1-(4-fluoro-phenyl)-ethyl]-2-[4-(4,4,5,5-tetramethyl-1,3,2-dioxaborolan-2-yl)-benzylamino]-nicotinamide (163.2 mg, 0.0003261 mol) and [3-(3-Amino-6-bromo-pyrazin-2-yl)-propyl]-carbamic acid tert-butyl ester (0.108 g, 0.000326 mol) in 1,4-Dioxane (2.0 mL) was degassed for 10 min, Bis(tricyclohexylphosphine) palladium (0) (22 mg, 0.000033 mol) and 1.2 M of Saturated Aqueous Sodium Bicarbonate Solution in water (0.80 mL, 0.00096 mol) were added. The reaction was heated in the microwave at 120° C. for 10 min. The reaction mixture was diluted with ethyl acetate, washed with water, then with saturated sodium chloride. The organic phase was dried over sodium sulfate, filtered and concentrated. The crude was purified by silica gel chromatography using 0-10% methanol in methylene chloride as eluent to give desired product in 56 mg (27%) yield. ESI-MS (M+H$^+$): 625.00.

2-{4-[5-Amino-6-(3-amino-propyl)-pyrazin-2-yl]-benzylamino}-5-cyano-N-[(S)-1-(4-fluoro-phenyl)-ethyl]-nicotinamide (3-{3-Amino-6-[4-({5-cyano-3-[(S)-1-(4-fluoro-phenyl)-ethylcarbamoyl]-pyridin-2-ylamino}-methyl)-phenyl]-pyrazin-2-yl}-propyl)-carbamic acid tert-butyl ester (0.056 g, 0.090 mmol) was dissolved in Methylene chloride (1.0 mL) and Trifluoroacetic Acid (1.0 mL) and was stirred at room temperature for 1 hour. The solvent was evaporated, then the residue was purified by preparative HPLC to give the product in 28 mg yield as TFA salt. ESI-MS (M+H$^+$): 525.00); $^1$H NMR (400 MHz, DMSO-d$_6$) δ 9.32 (t, J=5.52 Hz, 1H), 9.00 (d, J=7.28 Hz, 1H), 8.57 (s, 1H), 8.48 (s, 1H), 8.38 (s, 1H), 7.87 (d, J=7.78 Hz, 2H), 7.68 (br. s., 2H), 7.37-7.45 (m, 2H), 7.34 (d, J=7.78 Hz, 2H), 7.15 (t, J=8.53 Hz, 2H), 5.08 (quin, J=6.78 Hz, 1H), 4.68 (d, J=5.52 Hz, 2H), 2.86-2.99 (m, 2H), 2.72 (t, J=7.03 Hz, 2H), 2.01 (quin, J=7.22 Hz, 2H), 1.46 (d, J=6.78 Hz, 3H). 1.6 TFA per molecule.

Examples 71-95 were synthesized in a manner consistent with Example 70, using the appropriate alkyne and boronate ester. Deprotection step (last) was omitted when the product of Suzuki coupling was not a tBu carbamate.

Examples 96-157 were synthesized in a manner consistent with Example 41.

Example 158

Synthesis of (S)-2-(4-(5-amino-6-(3-(dimethylamino)propyl)pyrazin-2-yl)benzylamino)-5-cyano-N-(1-(4-fluorophenyl)ethyl) nicotinamide

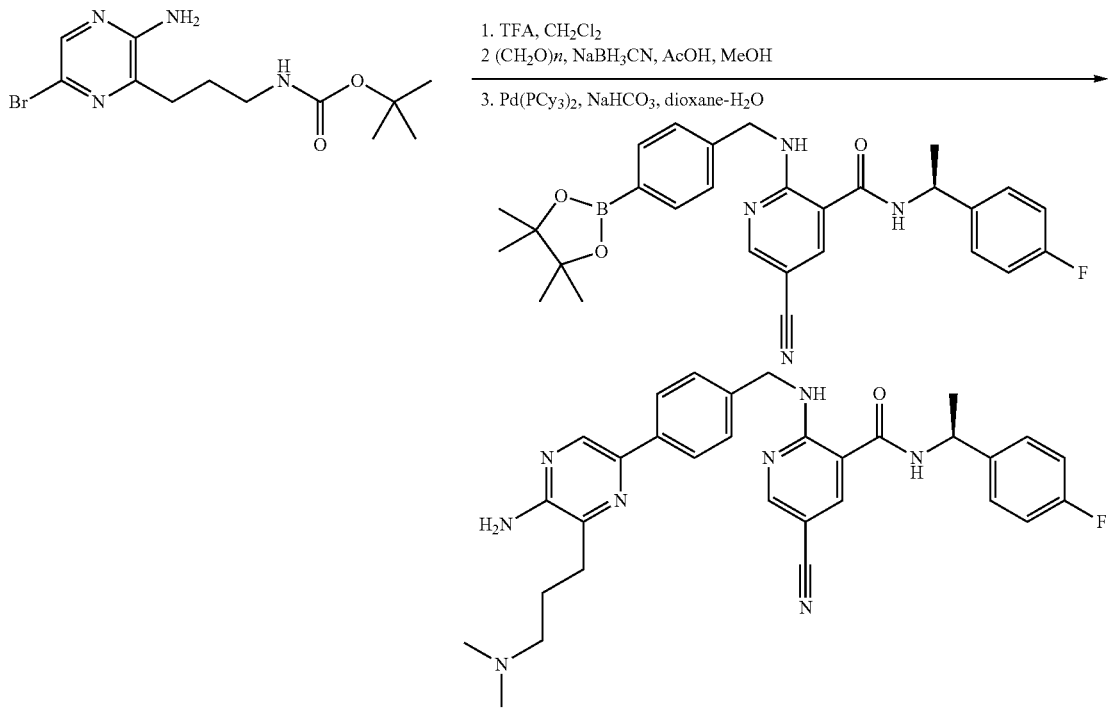

[3-(3-Amino-6-bromo-pyrazin-2-yl)-propyl]-carbamic acid tert-butyl ester (100 mg, 0.302 mmol) was dissolved in Methylene chloride (1.0 mL) and Trifluoroacetic Acid (1.0 mL) and was stirred at room temperature for 1 hour. The reaction was evaporated to dryness (azeotroped 3× methylene chloride) and was dissolved in Methanol (2.00 mL) and Acetic acid (0.200 mL) and Paraformaldehyde (27 mg, 0.90 mmol) was added followed by Sodium cyanoborohydride (101 mg, 1.61 mmol) and the reaction was stirred at room temperature. After 4d, the solvent was evaporated, and the residue was taken up in ethyl acetate, then washed with saturated sodium bicarbonate, then washed with saturated sodium chloride, dried with sodium sulfate, filtered and evaporated. The residue was dissolved along with 5-Cyano-N-[(S)-1-(4-fluoro-phenyl)-ethyl]-2-[4-(4,4,5,5-tetramethyl-1,3,2-dioxaborolan-2-yl)-benzylamino]-nicotinamide (141 mg, 0.000282 mol) in 1,4-Dioxane (1.5 mL). The reaction was degassed by evacuating, then replacing with Ar. (X5). Bis(tricyclohexylphosphine)palladium (0) (28 mg, 0.000042 mol) and 1.2 M of Saturated Aqueous Sodium Bicarbonate Solution in water (0.60 mL, 0.00073 mol) were added. The reaction was heated in the microwave at 120° C. for 10 min. The reaction mixture was evaporated then taken up in DMSO, filtered and purified by preparative HPLC to give desired product in 49 mg yield as bis-TFA salt (25%). ESI-MS (M+H$^+$): 553.00; $^1$H NMR (400 MHz, DMSO-d$_6$) δ 9.43 (br. s., 1H), 9.33 (t, J=5.77 Hz, 1H), 9.01 (d, J=7.28 Hz, 1H), 8.58 (d, J=2.01 Hz, 1H), 8.49 (d, J=2.01 Hz, 1H), 8.39 (s, 1H), 7.88 (d, J=8.03 Hz, 2H), 7.42 (dd, J=5.65, 8.41 Hz, 2H), 7.34 (d, J=8.03 Hz, 2H), 7.15 (t, J=8.78 Hz, 2H), 5.09 (quin, J=7.03 Hz, 1H), 4.69 (d, J=5.52 Hz, 2H), 3.10-3.21 (m, 2H), 2.81 (d, J=4.77 Hz, 6H), 2.70 (t, J=7.03 Hz, 2H), 2.03-2.19 (m, 2H), 1.46 (d, J=7.03 Hz, 3H). 2.2 TFA per molecule.

Example 159

Synthesis of 2-{4-[5-Amino-6-((R)-pyrrolidin-3-yloxy)-pyrazin-2-yl]-benzylamino}-N-(4-fluorophenyl)-5-trifluoromethyl-nicotinamide

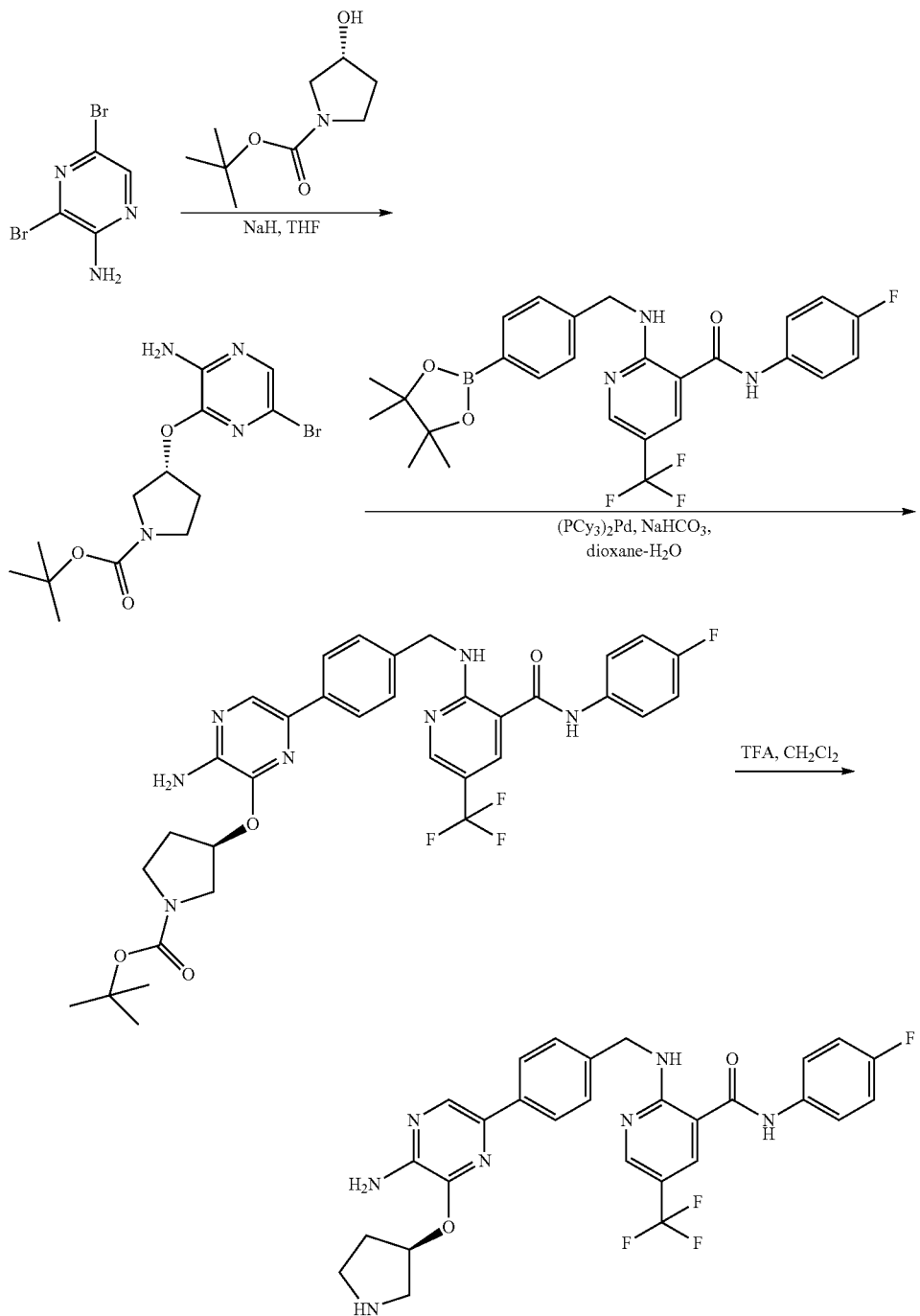

(R)-3-(3-Amino-6-bromo-pyrazin-2-yloxy)-pyrrolidine-1-carboxylic acid tert-butyl ester Sodium hydride/mineral oil (60:40, Sodium hydride:Mineral Oil, 0.105 g, 2.62 mmol) was washed 2× with hexanes, then was taken up in Tetrahydrofuran (2.0 mL). To this was added (R)-3-Hydroxy-pyrrolidine-1-carboxylic acid tert-butyl ester (0.350 g, 1.87 mmol). The reaction mixture was stirred at room temperature for 5 minutes, at which point the reaction has become a gel. A solution of 3,5-dibromopyrazin-2-amine (0.235 g, 0.929 mmol) in Tetrahydrofuran (2.0 mL) was added and the reaction mixture was heated at 50° C. for 2.5 hours. The reaction mixture was cooled to room temperature and saturated sodium bicarbonate was added. The whole was then extracted with ethyl acetate, washed with saturated sodium chloride, dried with sodium sulfate, filtered and concentrated in vacuole. The crude product was purified by flash column chromatography using 0-70% ethyl acetate in hexanes as eluent. Isolated (Rf=0.48 in 1:1 hexanes/ethyl acetate) was 160 mg (48%) product. ESI-MS (M+H$_+$): 358.80.

(R)-3-[3-Amino-6-(4-{[3-(4-fluoro-phenylcarbamoyl)-5-trifluoromethyl-pyridin-2-ylamino]-methyl}-phenyl)-pyrazin-2-yloxy]-pyrrolidine-1-carboxylic acid tert-butyl ester A solution of N-(4-fluorophenyl)-2-(4-(4,4,5,5-tetramethyl-1,3,2-dioxaborolan-2-yl)benzylamino)-5-(trifluoromethyl)nicotinamide (87 mg, 0.00017 mol) and (R)-3-(3-Amino-6-bromo-pyrazin-2-yloxy)-pyrrolidine-1-carboxylic acid tert-butyl ester (0.053 g, 0.00015 mol) in 1,4-Dioxane (1.00 mL) was degassed by evacuating and replacing with Ar (repeat 5×). Bis(tricyclohexylphosphine)palladium (0) (16 mg, 0.000024 mol) and 1.2 M of Saturated Aqueous Sodium Bicarbonate Solution in water (0.35 mL, 0.00042 mol) were added. The reaction was heated in the microwave at 120° C. for 25 min. The reaction mixture was diluted with ethyl acetate, washed with water, then with saturated sodium chloride. The organic phase was dried over sodium sulfate, filtered and concentrated. The crude was purified by silica gel chromatography using 0-100% ethyl acetate in hexanes as eluent to give desired product in 55. mg (56%) yield (R$_f$=0.28 in 1:1 hexanes/ethyl acetate). $^1$H NMR (400 MHz, CDCl$_3$) δ 8.77 (br. s., 1H), 8.53 (s, 1H), 8.02 (d, J=10.54 Hz, 1H), 7.92 (d, J=1.76 Hz, 1H), 7.74-7.86 (m, 3H), 7.49-7.57 (m, 2H), 7.38-7.46 (m, 2H), 7.09 (t, J=8.53 Hz, 2H), 5.62-5.81 (m, 1H), 4.90-5.05 (m, 2H), 4.80 (d, J=5.02 Hz, 2H), 3.43-3.80 (m, 4H), 2.26 (br. s., 2H), 1.49 (br. s., 9H).

2-{4-[5-Amino-6-((R)-pyrrolidin-3-yloxy)-pyrazin-2-yl]-benzylamino}-N-(4-fluoro-phenyl)-5-trifluoromethyl-nicotinamide (R)-3-[3-Amino-6-(4-{[3-(4-fluoro-phenylcarbamoyl)-5-trifluoromethyl-pyridin-2-ylamino]-methyl}-phenyl)-pyrazin-2-yloxy]-pyrrolidine-1-carboxylic acid tert-butyl ester (0.055 g, 0.082 mmol) was dissolved in Methylene chloride (1.5 mL) and Trifluoroacetic Acid (0.50 mL) and was stirred at room temperature for 15 min. The reaction was evaporated to dryness. The residue was purified by preparative HPLC to give the product in 27.5 mg yield (42%) as bis-TFA salt. ESI-MS (M+H$^+$): 568.52. $^1$H NMR (400 MHz, DMSO-d$_6$) δ 10.52 (s, 1H), 9.00 (br. s., 2H), 8.90 (t, J=5.77 Hz, 1H), 8.54 (s, 1H), 8.40 (d, J=1.76 Hz, 1H), 8.12 (s, 1H), 7.86 (d, J=8.28 Hz, 2H), 7.63-7.74 (m, 2H), 7.39 (d, J=8.03 Hz, 2H), 7.22 (t, J=8.91 Hz, 2H), 5.71 (br. s., 1H), 4.73 (d, J=5.52 Hz, 2H), 3.46-3.58 (m, 2H), 3.31-3.45 (m, 2H), 2.16-2.35 (m, 2H). 1.6 TFA per molecule.

Examples 160-173 were synthesized in a manner consistent with Example 159.

Example 174

Synthesis of 2-[4-(4-Amino-pyrrolo[2,1-f][1,2,4]triazin-5-yl)-benzylamino]-5-cyano-N-[(S)-1-(4-fluoro-phenyl)-ethyl]-nicotinamide

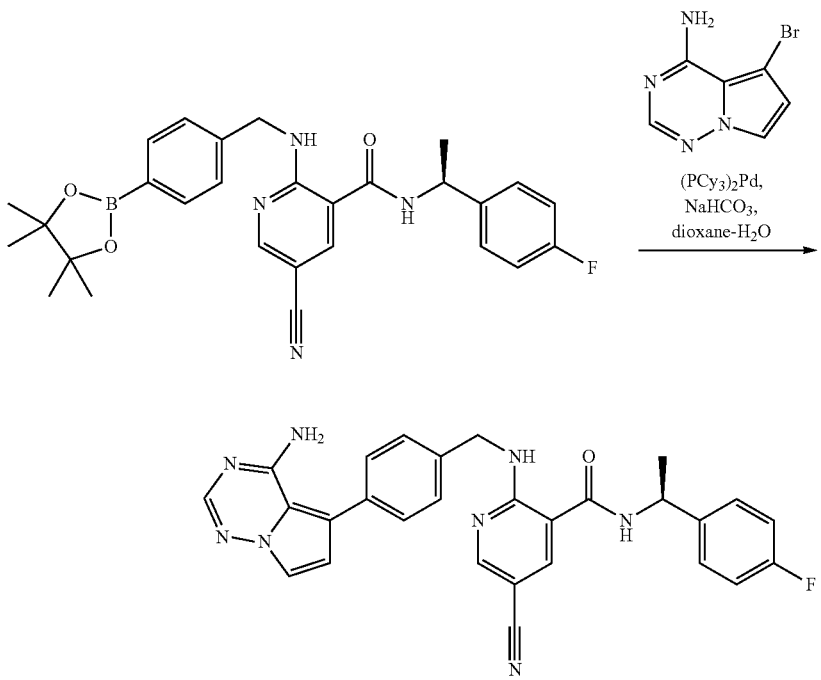

Synthesis of 5-Bromo-pyrrolo[2,1-f][1,2,4]triazin-4-ylamine is described in WO2007056170A2. Synthesis of 7-Bromo-pyrrolo[2,1-f][1,2,4]triazin-4-ylamine is described in WO2007056170A2.

2-[4-(4-Amino-pyrrolo[2,1-f][1,2,4]triazin-5-yl)-benzylamino]-5-cyano-N-[(S)-1-(4-fluoro-phenyl)-ethyl]-nicotinamide A solution of 5-Bromo-pyrrolo[2, 1-f][1,2,4]triazin-4-ylamine (0.0562 g, 0.264 mmol) and 5-Cyano-N-[(S)-1-(4-fluoro-phenyl)-ethyl]-2-[4-(4,4,5,5-tetramethyl-1,3,2-dioxaborolan-2-yl)-benzylamino]-nicotinamide (0.145 g, 0.290 mmol) in 1,4-Dioxane (4.00 mL) was degassed under argon (5×). Bis(tricyclohexylphosphine)palladium (0) (0.0194 g, 0.0290 mmol) and 1.2 M of Sodium bicarbonate in Water (0.660 mL, 0.791 mmol) were added. The mixture was degassed under argon then heated in the microwave at 120° C. for 20 minutes. The reaction mixture was diluted in ethylacetate and washed with water, then brine. The organic phase was dried over MgSO4, filtered and concentrated to dryness under reduced pressure. The crude product was purified by preparative HPLC to give the desired product as a bis-TFA salt. ESI-MS (M+H+): 507.2; $^1$H NMR (400 MHz, CD$_3$OD) δ 8.81-8.87 (m, 1H), 8.47-8.49 (m, 1H), 8.28 (d, J=2.26 Hz, 1H), 7.98 (s, 1H), 7.90 (d, J=2.76 Hz, 1H), 7.50 (s, 4H), 7.38-7.44 (m, 2H), 7.04-7.10 (m, 2H), 6.87 (d, J=2.76 Hz, 1H), 5.14-5.23 (m, 1H), 4.82 (s, 2H), 1.56 (d, J=7.03 Hz, 3H). 2 TFA per molecule.

Examples 175-181 were synthesized in a manner consistent with Example 174.

Example 182

Synthesis of 3-[4-(3-Amino-1H-pyrazolo[3,4-b]pyrazin-5-yl)-benzylamino]-6-cyano-pyrazine-2-carboxylic acid [(S)-1-(3,4-difluoro-phenyl)-ethyl]-amide

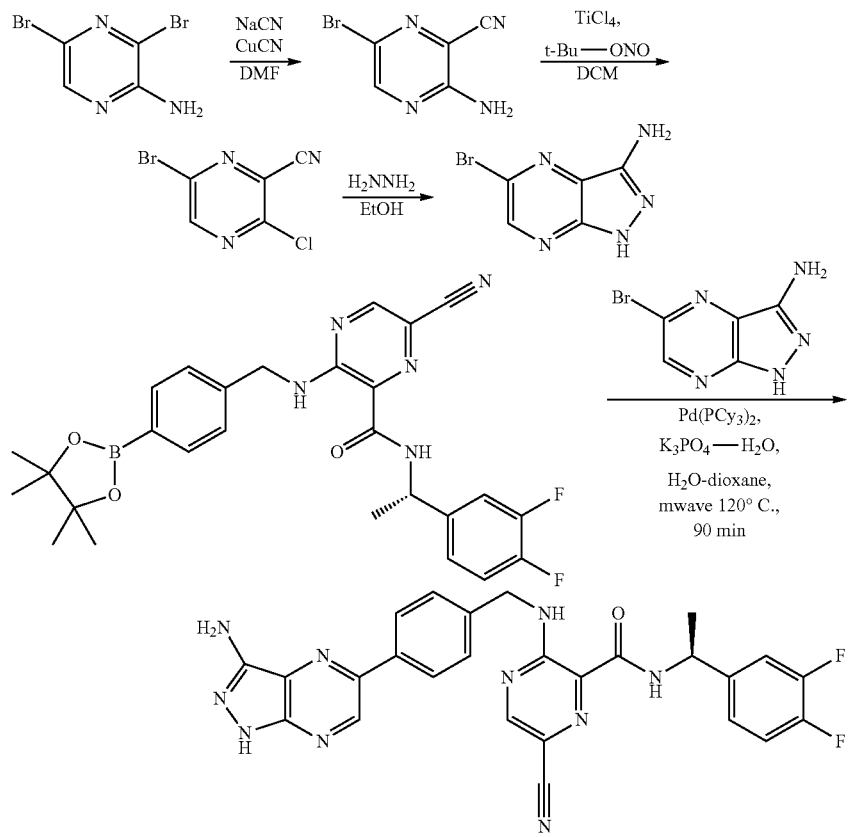

3-Amino-6-bromopyrazine-2-carbonitrile

To a mixture of sodium cyanide (7.7 g, 156 mmol, 1.0 equiv) and copper (I) cyanide (14.0 g, 156 mmol, 1.0 equiv) in DMF (400 mL) was added a solution of 3,5-dibromopyrazin-2-amine (39.5 g, 156 mmol, 1.0 equiv) in DMF (100 mL) through an addition funnel at 120° C. over 20 minutes. The reaction was heated at 120° C. overnight. Upon completion, the reaction was cooled to room temperature and concentrated under reduced pressure. The resulting residue was diluted with ethyl acetate (2 L) and washed with water (1 L). The organic layer was separated, washed with saturated brine (500 mL), dried over sodium sulfate, filtered and concentrated under reduced pressure. The resulting crude product was purified by column chromatography (600 g of silica gel), eluting with 10% ethyl acetate in heptane (4 L) and 20% ethyl acetate in heptane (8 L) to give the title compound (16 g, 52% yield). EI-MS (M+): 197.9; $^1$H NMR (300 MHz, DMSO-d$_6$) δ 8.70 (s, 1H), 8.39 (bs, 2H).

6-Bromo-3-chloropyrazine-2-carbonitrile

To a suspension of 3-Amino-6-bromopyrazine-2-carbonitrile (13.0 g, 65.3 mmol, 1.0 equiv) in dichloromethane (520 mL) was added a 1.0M solution of titanium tetrachloride in dichloromethane (65.3 mL, 65.3 mmol, 1.0 equiv). The mixture was cooled to 0° C. and t-butyl nitrite (20.2 g, 196 mmol, 3.1 equiv) was added at 0° C. After addition, the reaction was warmed up to room temperature and allowed to stir at room temperature for 2 h. Upon completion, the reaction mixture was quenched with water (200 mL). The organic layer was separated, washed with saturated brine, dried over sodium sulfate, filtered and concentrated under reduced pressure. The resulting crude product was purified on an AnaLogix (SF40-115 g) column. The gradient utilized for the purification was 5 minutes isocratic heptanes followed by a 20 minutes ramp to 15% ethyl acetate in heptanes. The pure fractions were combined, concentrated under reduced pressure to give title compound (12.0 g, 85% yield). ESI-MS (M+H$^+$): 217.9; $^1$H NMR (300 MHz, CDCl$_3$) δ 8.68 (s, 1H).

5-Bromo-1H-pyrazolo[3,4-b]pyrazin-3-amine

To a solution of 6-Bromo-3-chloropyrazine-2-carbonitrile (9.6 g, 43.9 mmol, 1.0 equiv) in ethanol (200 mL) was added hydrazine monohydrate (8.8 g, 176 mmol, 4.0 equiv) and the reaction was heated to 80° C. overnight. Upon completion, the reaction mixture was filtered and the filtrate was concentrated under reduced pressure. The resulting residue was diluted with ethyl acetate (500 mL), dried over sodium sulfate, filtered and concentrated under reduced pressure. The resulting solid was triturated with MTBE (30 mL) to give title compound (6.5 g, 69% yield). ESI-MS (M+H$^+$): 213.9; $^1$H NMR (300 MHz, DMSO-d6) δ 12.66 (bs, 1H), 8.54 (s, 1H), 5.84 (bs, 2H).

3-[4-(3-Amino-1H-pyrazolo[3,4-b]pyrazin-5-yl)-benzylamino]-6-cyano-pyrazine-2-carboxylic acid [(S)-1-(3,4-difluoro-phenyl)-ethyl]-amide 5-Bromo-1H-pyrazolo[3,4-b]pyrazin-3-ylamine (0.0699 g, 0.327 mmol) and 6-Cyano-3-[4-(4,4,5,5-tetramethyl-1,3,2-dioxaborolan-2-yl)-benzylamino]-pyrazine-2-carboxylic acid [(S)-1-(3,4-difluoro-phenyl)-ethyl]-amide (0.200 g, 0.385 mmol) were taken up in 1,4-Dioxane (1.7 mL). The reaction mixture was evacuated and replaced with Ar (5×). Potassium Phosphate Monohydrate (0.165 g, 0.718 mmol) in Water (0.42 mL, 23 mmol) was added, and the reaction mixture was again evacuated and replaced with Ar (2×). Bis(tricyclohexylphosphine)palladium (0) (0.0160 g, 0.0239 mmol) was then added, and the reaction was sealed. The reaction mixture was heated in the microwave at 120° C. for 90 minutes. The reaction mixture was cooled to room temperature, diluted with ethyl acetate, washed with water, and then with brine (2×). The organic phase was dried over sodium sulfate and then evaporated to dryness. The residue was purified by preparative HPLC to give the desired product as a yellow solid (66.2 mg, 38.5% yield). ESI-MS (M+H+): 526.9; $^1$H NMR (400 MHz, DMSO-d$_6$) δ 12.41 (s, 1H), 9.77 (t, J=5.90 Hz, 1H), 9.31-9.36 (m, 1H), 8.99 (s, 1H), 8.74 (s, 1H), 8.08 (d, J=8.28 Hz, 2H), 7.52 (ddd, J=2.13, 7.91, 12.05 Hz, 1H), 7.46 (d, J=8.53 Hz, 2H), 7.33-7.42 (m, 1H), 7.24-7.29 (m, 1H), 5.09-5.17 (m, 1H), 4.73-4.78 (m, 2H), 1.49-1.54 (m, 3H). No TFA per molecule (parent).

Examples 183-184 were synthesized in a manner consistent with Example 182.

Example 185

Synthesis of 2-[4-(5-Amino-6-pyrrolidin-3-ylmethyl-pyrazin-2-yl)-benzylamino]-5-cyano-N-[(S)-1-(4-fluoro-phenyl)-ethyl]-nicotinamide Into the reaction was dissolved 3-{3-Amino-6-[4-({5-cyano-3-[(S)-1-(4-fluoro-phenyl)-ethylcarbamoyl]-pyridin-2-ylamino}-methyl)-phenyl]-pyrazin-2-ylmethyl}-pyrrolidine-1-carboxylic acid tert-butyl ester (0.065 g, 0.10 mmol) in Methylene chloride (3.0 mL) and Trifluoroacetic Acid (0.50 mL) and was stirred at room temperature for 15 min. The reaction was evaporated to dryness. The residue was purified by preparative HPLC to give the product in 33.3 mg yield (37%) as tri-TFA salt. ESI-MS (M+H$^+$): 551.00. $^1$H NMR (400 MHz, DMSO-d$_6$) δ 9.33 (t, J=5.77 Hz, 1H), 9.01 (d, J=7.28 Hz, 1H), 8.60-8.77 (m, 2H), 8.58 (d, J=2.01 Hz, 1H), 8.49 (d, J=2.01 Hz, 1H), 8.39 (s, 1H), 7.87 (d, J=8.28 Hz, 2H), 7.42 (dd, J=5.65, 8.66 Hz, 2H), 7.34 (d, J=8.28 Hz, 2H), 7.15 (t, J=8.78 Hz, 2H), 5.09 (quin, J=7.03 Hz, 1H), 4.69 (d, J=5.77 Hz, 2H), 3.44-3.57 (m, 1H), 3.22-3.34 (m, 1H), 3.08-3.21 (m, 1H), 2.68-2.92 (m, 4H), 2.16 (dd, J=5.65, 10.42 Hz, 1H), 1.59-1.72 (m, 1H), 1.46 (d, J=7.03 Hz, 3H). 2.6 TFA per molecule.

Examples 186-187 were prepared in a manner consistent with Example 185.

Example 188

Synthesis of 2-{4-[5-Amino-6-((R)-3-amino-piperidin-1-yl)-pyrazin-2-yl]-benzylamino}-5-cyano-N-[(S)-1-(4-fluoro-phenyl)-ethyl]-nicotinamide

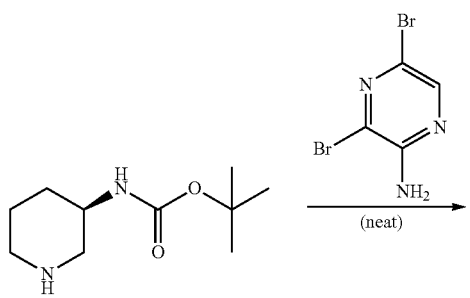

-continued

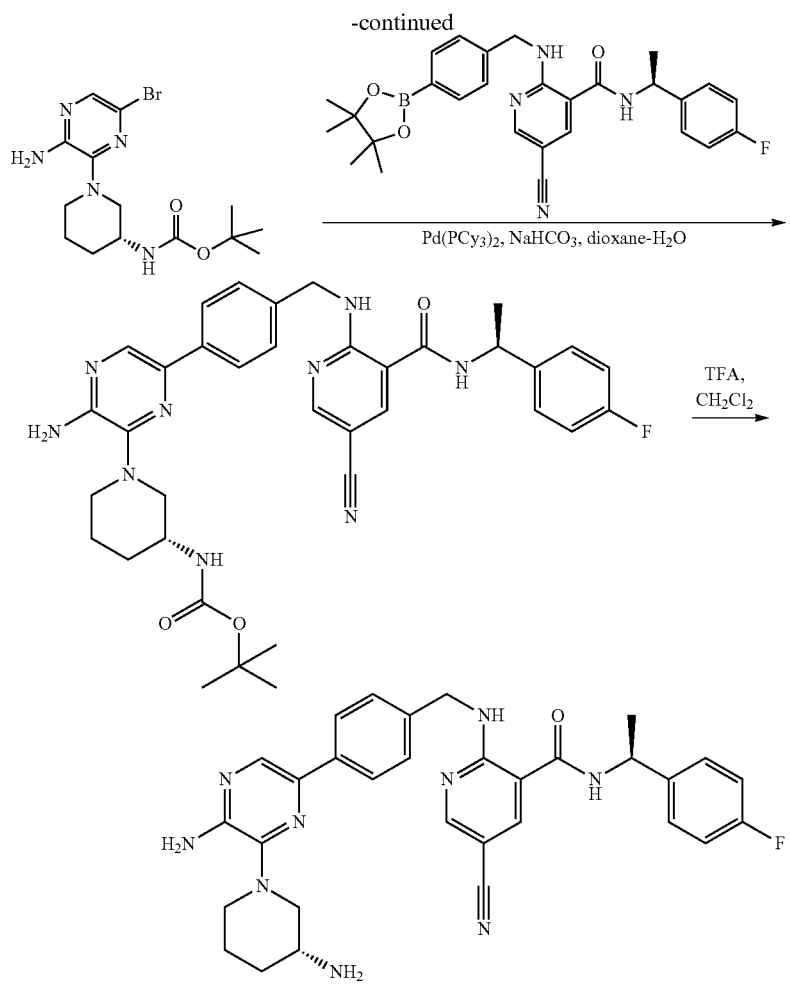

[(R)-1-(3-Amino-6-bromo-pyrazin-2-yl)-piperidin-3-yl]-carbamic acid tert-butyl ester To a solution of (R)-Piperidin-3-yl-carbamic acid tert-butyl ester (0.098 g, 0.49 mmol) in 1,4-Dioxane (0.50 mL) was added 3,5-dibromopyrazin-2-amine (0.121 g, 0.478 mmol) and N,N-Diisopropylethylamine (100 µL, 0.574 mmol). The mixture was microwaved for 3 h at 150° C. The solution was diluted with DCM and silica gel was added. The solvent was removed and the residue was purified by flash chromatography (0-50% EtOAc/hexanes) to afford the title compound as a solid. 138 mg (78%) isolated, Rf=0.08 in 3:1 hexanes/ethyl acetate. ESI-MS (M+H$^+$): 371.90/373.90.

((R)-1-{3-Amino-6-[4-({5-cyano-3-[(S)-1-(4-fluoro-phenyl)-ethylcarbamoyl]-pyridin-2-ylamino}-methyl)-phenyl]-pyrazin-2-yl}-piperidin-3-yl)-carbamic acid tert-butyl ester A solution of 5-Cyano-N-[(S)-1-(4-fluoro-phenyl)-ethyl]-2-[4-(4,4,5,5-tetramethyl-1,3,2-dioxaborolan-2-yl)-benzylamino]-nicotinamide (76 mg, 0.00015 mol) and [(R)-1-(3-Amino-6-bromo-pyrazin-2-yl)-piperidin-3-yl]-carbamic acid tert-butyl ester (0.046 g, 0.00012 mol) in 1,4-Dioxane (1.00 mL) was degassed by evacuating and replacing with Ar (repeat 5x).

Bis(tricyclohexylphosphine)palladium (0) (9.4 mg, 0.000014 mol) and 1.2 M of Saturated Aqueous Sodium Bicarbonate Solution in water (0.35 mL, 0.00042 mol) were added. The reaction was heated in the microwave at 120° C. for 25 min. The reaction mixture was diluted with ethyl acetate, washed with water, then with saturated sodium chloride. The organic phase was dried over sodium sulfate, filtered and concentrated. The crude was purified by silica gel chromatography using 0-75% ethyl acetate in hexanes as eluent to give desired product in 69 mg (84%) yield. ESI-MS (M+H$^+$): 666.00.

2-{4-[5-Amino-6-((R)-3-amino-piperidin-1-yl)-pyrazin-2-yl]-benzylamino}-5-cyano-N-[(S)-1-(4-fluoro-phenyl)-ethyl]-nicotinamide Into the reaction was dissolved ((R)-1-{3-Amino-6-[4-({5-cyano-3-[(S)-1-(4-fluoro-phenyl)-ethylcarbamoyl]-pyridin-2-ylamino}-methyl)-phenyl]-pyrazin-2-yl}-piperidin-3-yl)-carbamic acid tert-butyl ester (0.069 g, 0.10 mmol) in Methylene chloride (3.0 mL) and Trifluoroacetic Acid (0.50 mL) and was stirred at room temperature for 15 min. The reaction was evaporated to dryness. The residue was purified by preparative HPLC to give the product in 55.0 mg yield (66%) as bis-TFA salt. ESI-MS (M+H+): 566.00. $^1$H NMR (400 MHz, DMSO-d$_6$) δ 9.31 (t, J=5.65 Hz, 1H), 9.00 (d, J=7.53 Hz, 1H), 8.57 (d, J=2.01 Hz, 1H), 8.47 (d, J=2.01

Hz, 1H), 8.22 (s, 1H), 7.92 (br. s., 3H), 7.84 (d, J=8.28 Hz, 2H), 7.41 (dd, J=5.77, 8.53 Hz, 2H), 7.33 (d, J=8.28 Hz, 2H), 7.14 (t, J=8.78 Hz, 2H), 5.08 (quin, J=7.03 Hz, 1H), 4.67 (d, J=5.52 Hz, 2H), 3.50-3.60 (m, 1H), 3.47 (d, J=12.55 Hz, 1H), 3.00-3.12 (m, 2H), 2.94 (br. s., 1H), 1.84-1.97 (m, 2H), 1.68 (br. s., 2H), 1.45 (d, J=7.03 Hz, 3H). 2.2 TFA per molecule.

Examples 189-199 were synthesized in a manner consistent with Example 188 from the appropriate N-Boc-diamine and boronate ester.

Example 200

Synthesis of 2-{4-[5-Amino-6-(2-amino-2-methyl-propoxy)-pyrazin-2-yl]-benzylamino}-N-(4-fluoro-phenyl)-5-trifluoromethyl-nicotinamide

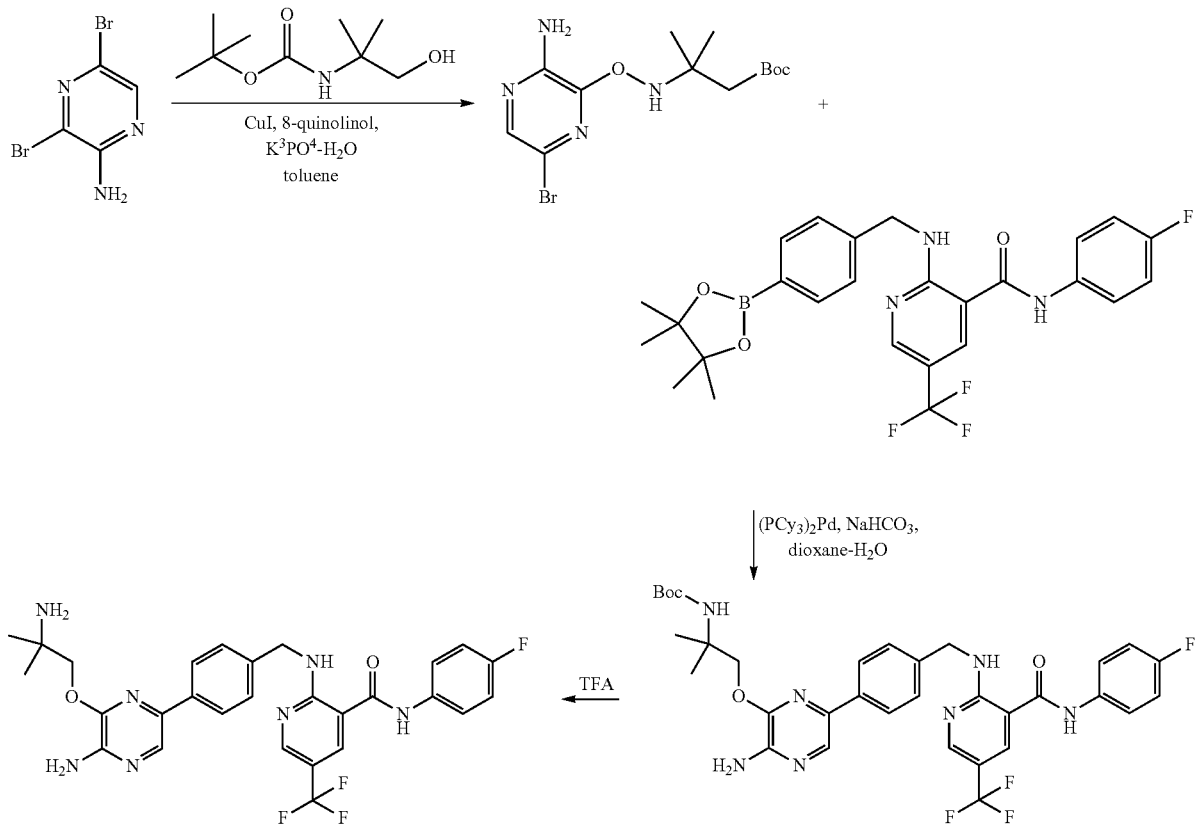

[2-(3-Amino-6-bromo-pyrazin-2-yloxy)-1,1-dimethyl-ethyl]-carbamic acid tert-butyl ester 8-Quinolinol (0.0290 g, 0.200 mmol), 3,5-dibromopyrazin-2-amine (0.253 g, 1.00 mmol), and Potassium Phosphate Monohydrate (0.460 g, 2.00 mmol) were added to a screw cap vial and Toluene (2 mL) was added. The reaction mixture was degassed and replaced with Ar (3×). Copper(I) iodide (0.0190 g, 0.100 mmol) was added to the reaction mixture. The mixture was again degassed and replaced with Ar (2×). A solution of (2-hydroxy-1,1-dimethyl ethyl)-carbamic acid t-butyl ester (0.189 g, 1.00 mmol) in Toluene (1 mL) was added to the reaction mixture. The reaction mixture was stirred at 110° C. for 16 hours, under Argon. The reaction mixture was diluted with DCM and evaporated to dryness. The residue was purified via flash chromatography (0-100% ethyl acetate in Hexanes) to afford the title compound (10.8 mg, 3% yield). ESI-MS (M+H+): 361.07.

{2-[3-Amino-6-(4-{[3-(4-fluoro-phenylcarbamoyl)-5-trifluoromethyl-pyridin-2-ylamino]-methyl}-phenyl)-pyrazin-2-yloxy]-1,1-dimethyl-ethyl}-carbamic acid tert-butyl ester A solution of N-(4-fluorophenyl)-2-(4-(4,4,5,5-tetramethyl-1,3,2-dioxaborolan-2-yl)benzylamino)-5-(trifluoromethyl)nicotinamide (0.0252 g, 0.0000488 mol) and [2-(3-Amino-6-bromo-pyrazin-2-yloxy)-1, 1-dimethyl-ethyl]-carbamic acid tert-butyl ester (0.00980 g, 0.0000271 mol) in 1,4-Dioxane (0.529 mL) was degassed by evacuating and replacing with Ar (repeat 5×). Bis(tricyclohexylphosphine) palladium (0) (0.00181 g, 0.00271 mmol) and 1.2 M of Saturated Aqueous Sodium Bicarbonate Solution in water (154 µL, 0.000184 mol) were added. The reaction was heated in the microwave at 120° C. for 25 min. The reaction mixture was diluted with ethyl acetate, washed with water, then with saturated sodium chloride. The organic phase was dried over sodium sulfate, filtered and concentrated. The residue was purified by silica gel chromatography using 0-50% EtOAc in Hexanes as eluent to give the product in 15.7 mg yield (86.4%). ESI-MS (M+H+): 670.47.

2-{4-[5-Amino-6-(2-amino-2-methyl-propoxy)-pyrazin-2-yl]-benzylamino}-N-(4-fluoro-phenyl)-5-trifluoromethyl-nicotinamide {2-[3-Amino-6-(4-{[3-(4-fluoro-phenyl carbamoyl)-5-trifluoromethyl-pyridin-2-ylamino]-methyl}-phenyl)-pyrazin- 2-yloxy]-1,1-dimethyl-ethyl}-carbamic acid tert-butyl ester (0.0157 g, 0.0234 mmol) was dissolved in Methylene chloride (3.0 mL) and Trifluoroacetic Acid (0.50 mL) and was stirred at room temperature for 15 min. The reaction was evaporated to dryness. The residue was taken up in DMSO and purified by preparative HPLC to give the product in 2.9 mg yield (18%) as mono-TFA salt. ESI-MS (M+H+): 570.16. $^1$H NMR (400 MHz, CD$_3$OD) δ 10.24 (s, 1H), 8.45 (dd, J=1.00, 2.26 Hz, 1H), 8.31-8.33 (m, 1H), 8.04 (s, 1H), 7.86-7.89 (m, 2H), 7.65 (ddd, J=3.01, 4.89, 9.16 Hz, 2H), 7.42 (d, J=8.53 Hz, 2H), 7.06-7.11 (m, 2H), 4.78 (s, 1H), 4.50 (s, 2H), 1.52 (s, 6H). 1.4 TFA per molecule.

Example 201

Synthesis of (S)-2-(4-(6-amino-5-carbamoylpyridin-3-yl)benzylamino)-5-cyano-N-(1-(4-fluorophenyl)ethyl)nicotinamide

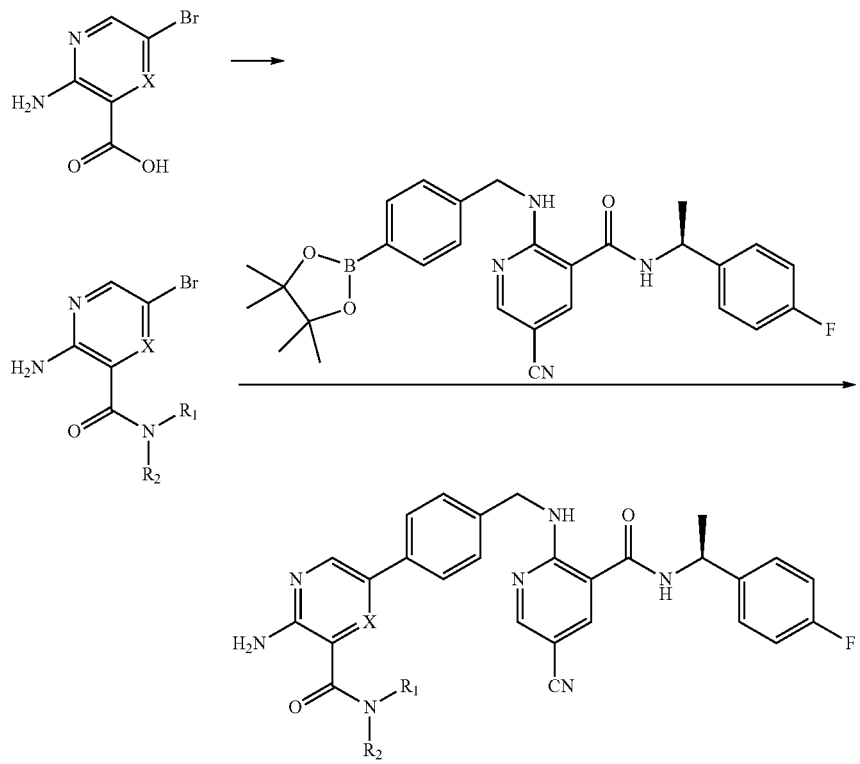

To a solution of 2-amino-5-bromonicotinic acid (216 mg, 1.0 mmol) in THF (4 mL) were added NH$_4$Cl (265 mg, 5.0 mmol, 5.0 eq), TEA (505 mg, 5.0 mmol, 5.0 eq) and HATU (760 mg, 2.0 mmol, 2.0 eq). The reaction mixture was stirred at 45° C. for 30 min. The mixture was cooled to rt and concentrated. H$_2$O (20 mL) was added and the residue was extracted with EA (30 mL*3). The organic layer was washed with brine, dried over Na$_2$SO$_4$ and concentrated. The crude product was purified by silica gel column (PE/EA=1/1) to obtain compound 2-amino-5-bromonicotinamide as yellow solid (54 mg. yield: 25%). ESI-MS (M+H+): 215.9; $^1$HNMR (400 MHz, DMSO-d$_6$) δ: 8.14 (br, 2H), 8.05 (s, 1H), 7.47 (s, 1H), 7.38 (br, 2H).

To a solution of (S)-5-cyano-N-(1-(4-fluorophenyl)ethyl)-2-(4-(4,4,5,5-tetramethyl-1,3,2-dioxaborolan-2-yl)benzylamino)nicotinamide (165 mg, 0.33 mmol, 1.1 eq) in dioxane (2 mL) was added 2-amino-5-bromonicotinamide (65 mg, 0.3 mmol, 1.0 eq), Pd(dppf)Cl$_2$DCM (25 mg, 0.03 mmol, 0.1 eq) and a solution of K$_2$CO$_3$ (82 mg, 0.6 mmol, 2.0 eq) in H$_2$O (0.4 mL). The reaction mixture was stirred at 90° C. for 2 h. The mixture was cooled to rt and concentrated. H$_2$O (30 mL) was added and the residue was extracted with EA (50 mL×3). The organic layer was washed with brine, dried over Na$_2$SO$_4$ and concentrated. The crude product was purified by silica gel column (DCM/MeOH=20/1) to obtain (S)-2-(4-(6-amino-5-carbamoylpyridin-3-yl)benzylamino)-5-cyano-N-(1-(4-fluorophenyl)ethyl)nicotinamide as a white solid (80 mg. yield: 53%). ESI-MS (M+H+): 510.2. HPLC: 90.57%. $^1$HNMR (400 MHz, DMSO-d$_6$) δ: 9.33 (s, 1H), 9.01-9.00 (m, 1H), 8.58 (s, 1H), 8.48 (s, 1H), 8.40 (s, 1H), 8.22 (s, 1H), 8.11 (br, 1H), 7.62-7.60 (m, 2H), 7.43-7.41 (m, 7H), 7.17-7.13 (m, 2H), 5.11-5.07 (m, 1H), 4.68 (s, 2H), 1.46-1.45 (m, 3H).

Examples 202-221 were synthesized in a manner consistent with Example 201 from the appropriate amine and boronate ester. An acidic deprotection was required as a final step. Note that for these reactions, N,N,N',N'-Tetramethyl-O-(7-azabenzotriazol-1-yl)uronium Hexafluorophosphate (HATU) was used in place of O-(Benzotriazol-1-yl)-N,N,N',N'-tetramethyluronium hexafluorophosphate (HBTU) in the amide coupling step, by analogy to the synthesis of Cyclopropane-1,1-dicarboxylic acid [(R)-1-(4-bromo-phenyl)-ethyl]-amide [(S)-1-(3,4-difluoro-phenyl)-ethyl]-amide. Note that for these compounds, the Suzuki coupling step was done with Bis(tricyclohexylphosphine)palladium (0) as catalyst, by analogy to the synthesis of 5-(1H-Pyrazolo[3,4-b]pyridin-5-yl)-pyrazine-2-carbonitrile.

Example 222

Synthesis of 5-Cyano-N-[(S)-1-(4-fluoro-phenyl)-ethyl]-2-{4-[6-(2-hydroxy-ethylamino)-pyridin-3-yl]-benzylamino}-nicotinamide

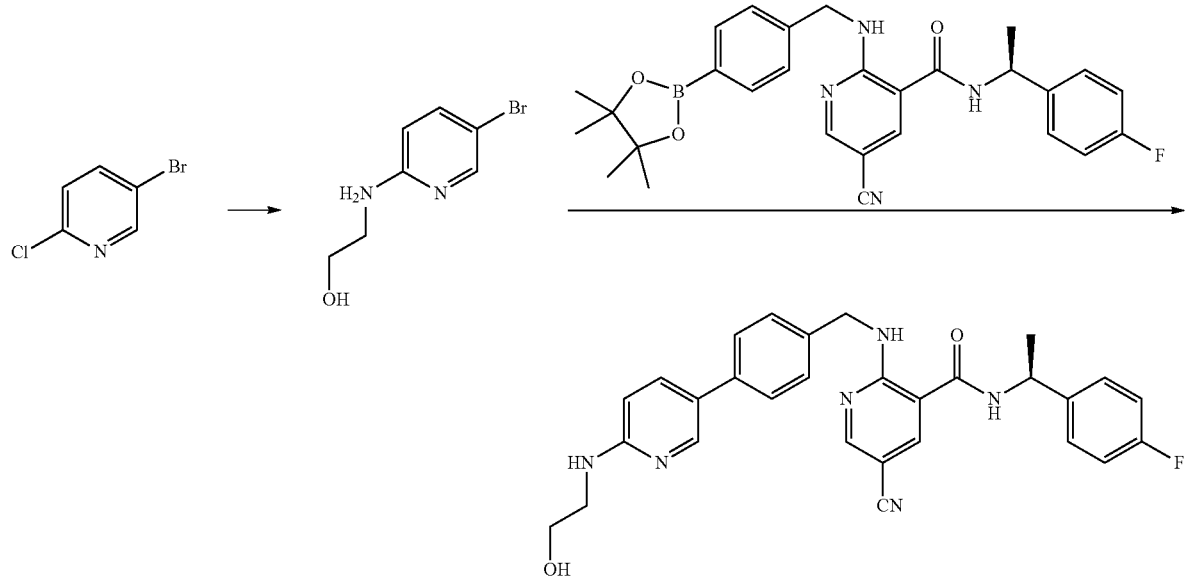

2-(5-Bromo-pyridin-2-ylamino)-ethanol

A mixture of 5-Bromo-2-chloro-pyridine (0.612 g, 3.18 mmol) in ethanolamine (1.92 mL, 31.8 mmol) was heated in a microwave oven for 2 h at 170° C. After cooling to room temperature, the reaction mixture was quenched with water and extracted with ethylacetate. The combined organic layer was washed with water, dried over MgSO$_4$, filtered and concentrated under reduced pressure. The crude product was purified by flash chromatography (methylene chloride) to give the title compound as a white solid in 71% yield. ESI-MS (M+H$^+$): 216.9/218.9.

5-Cyano-N-[(S)-1-(4-fluoro-phenyl)-ethyl]-2-{4-[6-(2-hydroxy-ethylamino)-pyridin-3-yl]-benzylamino}-nicotinamide A solution of 5-Cyano-N-[(S)-1-(4-fluoro-phenyl)-ethyl]-2-[4-(4,4,5,5-tetramethyl-1,3,2-dioxaborolan-2-yl)-benzylamino]-nicotinamide (0.1076 g, 0.2150 mmol) and 2-(5-Bromo-pyridin-2-ylamino)-ethanol (0.05601 g, 0.2580 mmol) in N,N-dimethylformamide (2.00 mL, 25.8 mmol) was degassed under argon. [1,1'-Bis(diphenylphosphino)ferrocene]dichloropalladium(II), complex with dichloromethane (0.0157 g, 0.0192 mmol) and 1.2 M of Sodium carbonate in Water (0.538 mL, 0.645 mmol) were then added and the mixture was heated at 70° C. After 3 hours, the mixture was cooled to room temperature, diluted with ethyl acetate and washed with water. The organic phase was dried over MgSO$_4$, filtered, concentrated under reduced pressure and purified by HPLC to give the title compound. ESI-MS (M+H$^+$): 510.9; $^1$H NMR (400 MHz, CD$_3$OD) δ 8.80-8.87 (m, 1H), 8.43-8.49 (m, 1H), 8.25-8.28 (m, 1H), 8.21-8.25 (m, 1H), 8.03-8.06 (m, 1H), 7.55-7.60 (m, 1H), 7.46 (d, J=8.53 Hz, 2H), 7.38-7.44 (m, 2H), 7.18-7.21 (m, J=0.50 Hz, 1H), 7.04-7.10 (m, 2H), 5.14-5.22 (m, 1H), 4.78 (s, 2H), 3.84 (d, J=10.29 Hz, 2H), 3.57 (d, J=10.29 Hz, 2H), 2.67 (s, 1H), 1.55 (d, J=7.03 Hz, 3H). 2 TFA per molecule.

Examples 223-224 were prepared in a manner consistent with Example 222.

Example 225

Synthesis of 5-Cyano-2-{4-[5-(3-dimethylamino-propylamino)-pyrazin-2-yl]-benzylamino}-N-[(S)-1-(4-fluoro-phenyl)-ethyl]-nicotinamide

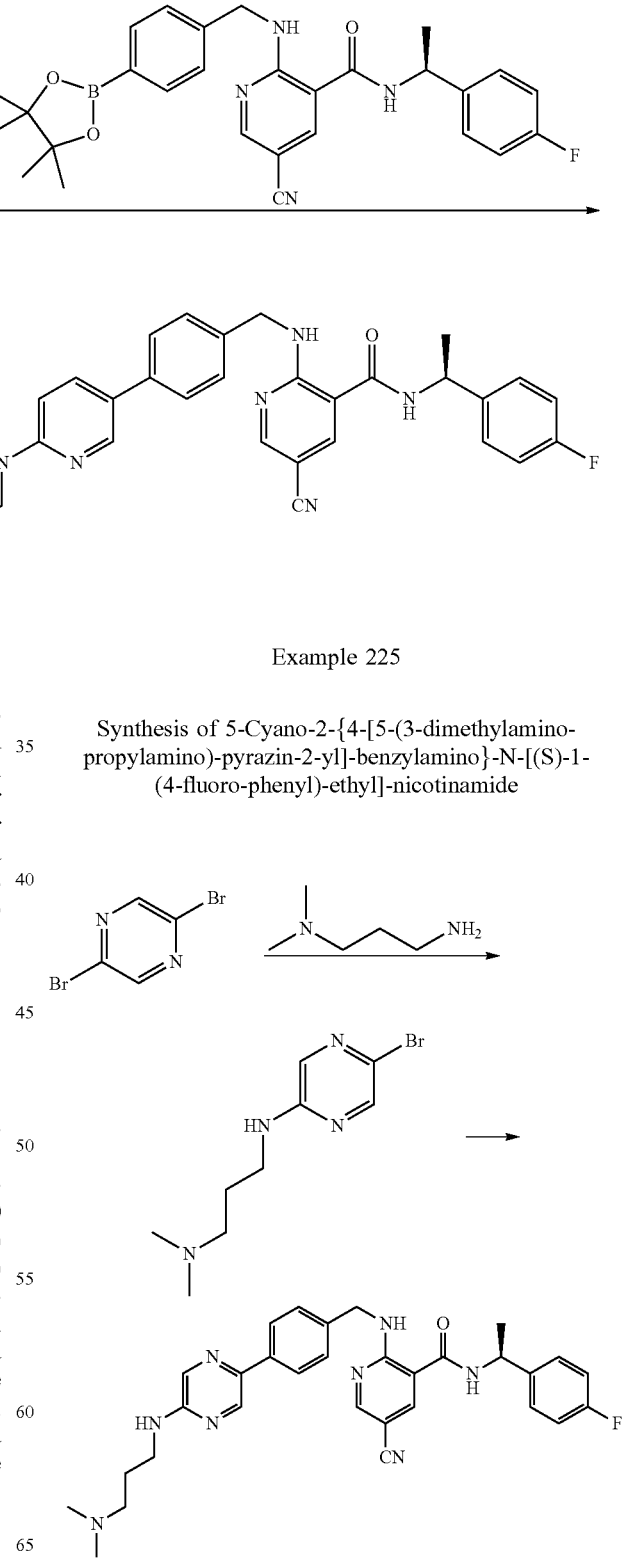

N'-(5-Bromo-pyrazin-2-yl)-N,N-dimethyl-propane-1,3-diamine

N,N-Diisopropylethylamine (0.1740 mL, 0.9988 mmol) was added to a solution of 2,5-Dibromo-pyrazine (0.2376 g, 0.9988 mmol) and 1,3-Propanediamine, N,N-dimethyl- (0.1020 g, 0.9988 mmol) in 1-Butanol (3.00 mL, 32.8 mmol) and the mixture was heated at 160° C. in the microwave for 30 minutes. The reaction mixture was then cooled to room temperature, diluted in ethylacetate and washed with water. The organic phase was dried over MgSO$_4$, filtered and concentrated. The crude product was purified by flash chromatography (0-10% MeOH in methylene chloride) to give N'-(5-Bromo-pyrazin-2-yl)-N,N-dimethyl-propane-1,3-diamine in 34% yield. ESI-MS (M+H$^+$): 260.2.

5-Cyano-2-{4-[5-(3-dimethylamino-propylamino)-pyrazin-2-yl]-benzylamino}-N-[(S)-1-(4-fluoro-phenyl)-ethyl]-nicotinamide A solution of 5-Cyano-N-[(S)-1-(4-fluoro-phenyl)-ethyl]-2-[4-(4,4,5,5-tetramethyl-1,3,2-dioxaborolan-2-yl)-benzylamino]-nicotinamide (0.130 g, 0.260 mmol) and N'-(5-Bromo-pyrazin-2-yl)-N,N-dimethyl-propane-1,3-diamine (0.0808 g, 0.312 mmol) in N,N-Dimethylformamide (5.00 mL, 64.6 mmol) was degassed under argon. [1,1'-Bis(diphenylphosphino)ferrocene]dichloropalladium(II), complex with dichloromethane (0.0380 g, 0.0465 mmol) and a solution of 1.2 M of Sodium carbonate in Water (0.650 mL, 0.779 mmol) were then added and the mixture was heated at 70° C. After 3 hours, the reaction was cooled to room temperature, diluted in ethylacetate and washed with water. The organic phase was dried over MgSO$_4$, filtered and concentrated to dryness under reduced pressure. The crude product was purified by HPLC to give the title compound. ESI-MS (M+H$^+$): 553.32; $^1$H NMR (400 MHz, CD$_3$OD) δ 8.81-8.85 (m, 1H), 8.54 (d, J=1.51 Hz, 1H), 8.48 (d, J=2.01 Hz, 1H), 8.26 (d, J=2.26 Hz, 1H), 8.19 (d, J=1.51 Hz, 1H), 7.82-7.87 (m, 2H), 7.38-7.44 (m, 4H), 7.04-7.10 (m, 2H), 5.16-5.22 (m, 1H), 4.77 (br. s., 2H), 3.77 (t, J=6.53 Hz, 2H), 3.19 (s, 3H), 3.04 (t, J=7.15 Hz, 2H), 2.74 (s, 3H), 2.01-2.11 (m, 2H), 1.55 (d, J=7.03 Hz, 3H). 2 TFA per molecule.

Examples 226-228 were prepared in a manner consistent with Example 225.

Example 229

Synthesis of N-(3,4-difluorobenzyl)-2-(4-(5-(2-hydroxyethylamino)pyrazin-2-yl)benzylamino)-5-(trifluoromethyl)nicotinamide

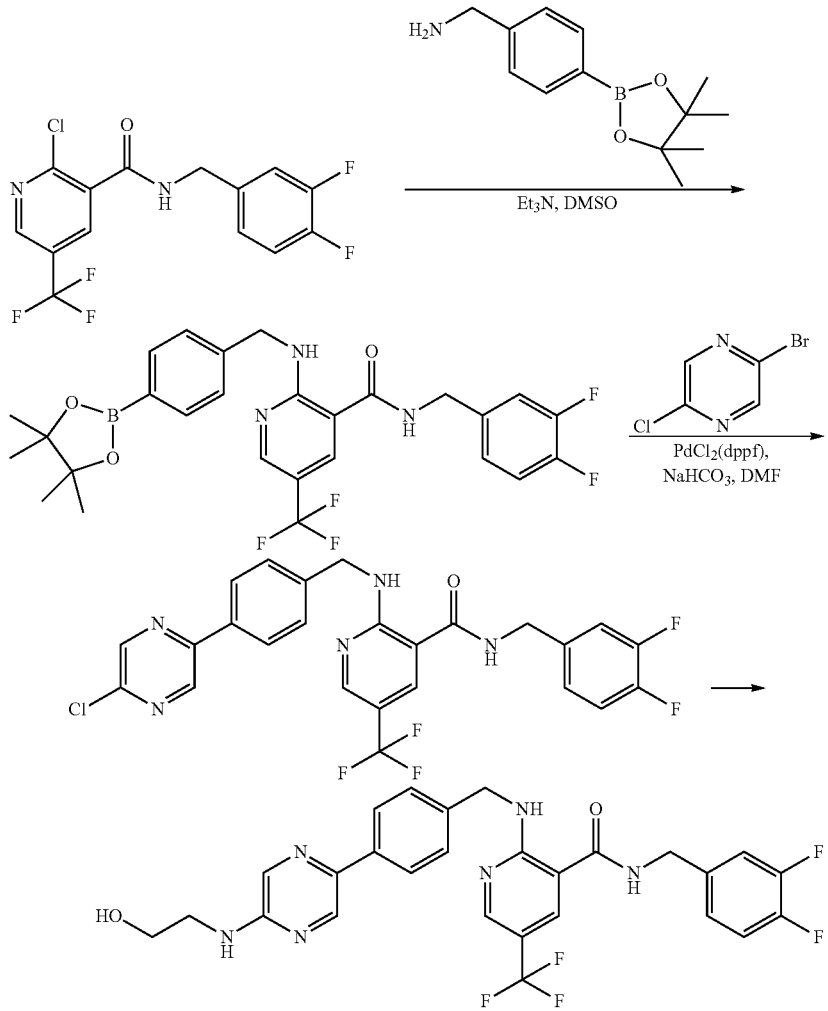

N-(3,4-Difluoro-benzyl)-2-[4-(4,4,5,5-tetramethyl-1,3,2-dioxaborolan-2-yl)-benzylamino]-5-trifluoromethyl-nicotinamide N,N-Diisopropylethylamine (5.0178 mL, 28.808 mmol) was added to a solution of 2-Chloro-N-(3,4-difluoro-benzyl)-5-trifluoromethyl-nicotinamide (2.0204 g, 5.7615 mmol) and 4-(4,4,5,5-Tetramethyl-1,3,2-dioxaborolan-2-yl)-benzylamine; hydrochloride (1.5532 g, 5.7615 mmol) in dimethyl sulfoxide (16.355 mL, 230.46 mmol) and the mixture was heated at 80° C. After 3 hours, the reaction mixture was cooled to room temperature, diluted with ethylacetate and washed consecutively with sat. sodium bicarbonate, water and brine. The organic layer was dried over MgSO₄, filtered and concentrated under reduced pressure to give the title compound in 84% yield. ESI-MS (M+H+): 548.2.

2-[4-(5-Chloro-pyrazin-2-yl)-benzylamino]-N-(3,4-difluoro-benzyl)-5-trifluoromethyl-nicotinamide A solution of N-(3,4-Difluoro-benzyl)-2-[4-(4,4,5,5-tetramethyl-1,3,2-dioxaborolan-2-yl)-benzylamino]-5-trifluoromethyl-nicotinamide (2.64 g, 0.00482 mol) and 2-Bromo-5-chloro-pyrazine (0.933 g, 0.00482 mol) in N,N-Dimethylformamide (37.3 mL, 0.482 mol) was degassed under argon for 10 minutes. [1,1'-Bis(diphenylphosphino)ferrocene]dichloropalladium(II), complex with dichloromethane (0.353 g, 0.000432 mol) and 1.2 M of Saturated Aqueous Sodium Bicarbonate Solution in water (12.0 mL, 0.0145 mol) were added and the reaction was heated at 70° C. in an oil bath. After 3 hours, the reaction mixture was diluted with ethylacetate, then washed with water and saturated ammonium chloride solution. The organic phase was then dried over MgSO₄, filtered and concentrated to dryness under reduced pressure. The crude product was purified by silica gel chromatography, eluted with 0-40% EtOAc in hexanes, to give the title compound. ESI-MS (M+H+): 534.2; ¹H NMR (400 MHz, DMF-d₇) δ 9.30-9.40 (m, 2H), 9.08 (d, J=1.51 Hz, 1H), 8.83 (d, J=1.51 Hz, 1H), 8.49 (d, J=1.25 Hz, 1H), 8.35 (d, J=2.01 Hz, 1H), 8.07 (d, J=8.53 Hz, 2H), 7.47 (d, J=8.28 Hz, 2H), 7.35-7.44 (m, 2H), 7.15-7.22 (m, 1H), 4.77 (d, J=5.77 Hz, 2H), 4.45 (d, J=5.77 Hz, 2H).

Synthesis of N-(3,4-difluorobenzyl)-2-(4-(5-(2-hydroxyethylamino)pyrazin-2-yl)benzylamino)-5-(trifluoromethyl)nicotinamide N,N-Diisopropylethylamine (0.0110 mL, 0.0634 mmol) was added to a solution of 2-[4-(5-Chloro-pyrazin-2-yl)-benzylamino]-N-(3,4-difluoro-benzyl)-5-trifluoromethyl-nicotinamide (0.028 g, 0.053 mmol) and Ethanolamine (0.00383 mL, 0.0634 mmol) in 1-Butanol (2.00 mL, 21.9 mmol). The mixture was heated in the microwave at 170° C. for 30 minutes. HPLC and LCMS analysis showed that the reaction was not complete. Thus, the mixture was heated in the microwave for an additional 45 minutes at 180° C. Still the reaction was not complete. Thus 0.1 mL of N,N-Diisopropylethylamine was added and, the reaction was heated in the microwave in 1 hour intervals at 180° C. and monitored to completion by HPLC. The mixture was then cooled to room temperature, diluted with ethylacetate and washed with water (3×). The organic phase was concentrated to dryness under reduced pressure and purified by prep HPLC to give the title compound as a TFA salt. ESI-MS (M+H+): 559.4; ¹H NMR (400 MHz, CD₃OD) δ 8.81-8.87 (m, 1H), 8.47-8.51 (m, 1H), 8.35-8.39 (m, 1H), 8.23-8.28 (m, 1H), 8.13-8.17 (m, 1H), 7.80-7.86 (m, 2H), 7.38-7.46 (m, 4H), 7.04-7.12 (m, 2H), 5.15-5.24 (m, 1H), 4.75-4.80 (m, 2H), 3.79 (t, 2H), 3.56 (t, J=5.52 Hz, 2H), 2.69 (s, 1H), 1.56 (d, J=7.28 Hz, 3H). 1 TFA per molecule.

Examples 230-231 were prepared in a manner consistent with Example 225.

Example 232

Synthesis of 2-[4-(5-Amino-6-dimethylaminomethyl-pyrazin-2-yl)-benzylamino]-5-cyano-N-[(S)-1-(4-fluoro-phenyl)-ethyl]-nicotinamide

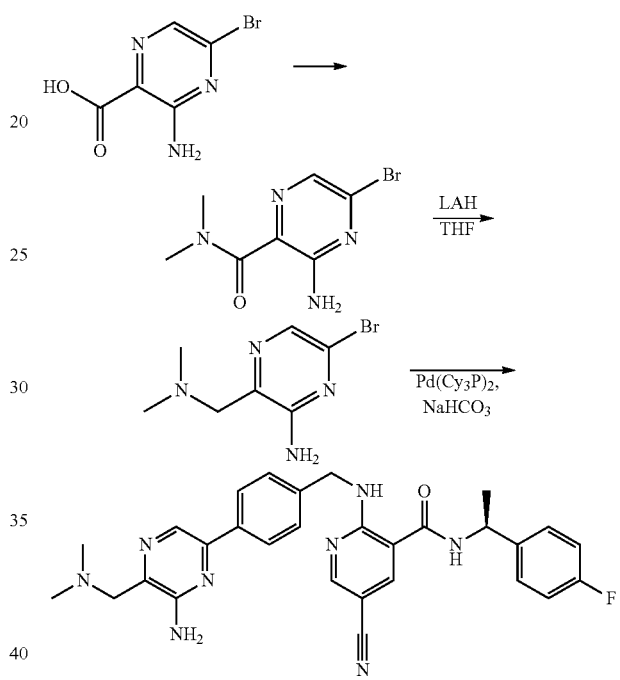

3-Amino-6-bromo-pyrazine-2-carboxylic acid dimethylamide

N,N,N',N'-Tetramethyl-O-(7-azabenzotriazol-1-yl)uronium Hexafluorophosphate (2.36 g, 6.19 mmol) was added to a solution of N,N-Diisopropylethylamine (3.269 mL, 18.77 mmol), 3-Amino-6-bromopyrazine-2-carboxylic acid (0.900 g, 4.13 mmol) and dimethylamine hydrochloride (0.3061 g, 3.754 mmol) in N,N-Dimethylformamide (20.9 mL, 2.70E2 mmol). The mixture was stirred at room temperature for 72 hours, after which it was diluted in ethylacetate and washed with water. The organic phase was then washed with sat. aq. ammonium chloride, dried over MgSO₄, filtered and concentrated to dryness under reduced pressure to give the title compound as a reddish brown solid. ESI-MS (M+H⁺): 244.89.

6-Bromo-3-dimethylaminomethyl-pyrazin-2-ylamine

1 M of Lithium tetrahydroaluminate in Tetrahydrofuran (0.6984 mL, 0.6984 mmol) was added to a solution of 3-Amino-5-bromo-pyrazine-2-carboxylic acid dimethylamide (0.1556 g, 0.6349 mmol) in Tetrahydrofuran (4.00 mL, 49.3 mmol). The mixture was stirred at room temperature for 2 hours. The reaction was then quenched with saturated ammonium chloride solution and extracted with ethyl acetate. The organic phase was washed with brine, then dried over MgSO$_4$, filtered and concentrated to dryness under reduced pressure to give the title compound in 38% yield. ESI-MS (M+H$^+$): 230.8.
m 2-[4-(5-Amino-6-dimethylaminomethyl-pyrazin-2-yl)-benzylamino]-5-cyano-N-[(S)-1-(4-fluoro-phenyl)-ethyl]-nicotinamide A solution of 5-Bromo-3-dimethylaminomethyl-pyrazin-2-ylamine (0.0554 g, 0.240 mmol) and 5-Cyano-N-[(S)-1-(4-fluoro-phenyl)-ethyl]-2-[4-(4,4,5,5-tetramethyl-1,3,2-dioxaborolan-2-yl)-benzylamino]-nicotinamide (0.144 g, 0.288 mmol) in 1,4-Dioxane (4.50 mL, 57.7 mmol) was degassed under argon.

Bis(tricyclohexylphosphine)palladium (0) (0.0176 g, 0.0264 mmol) and 1.2 M of Sodium bicarbonate in Water (0.599 mL, 0.719 mmol) were added. The mixture was degassed under argon, then heated in the microwave at 120° C. for 20 minutes. The reaction mixture was then diluted in ethylacetate and washed with water, then brine. The organic phase was dried over MgSO$_4$, filtered and concentrated to dryness under reduced pressure. The crude product was dissolved in DMSO and purified by prep HPLC to give the title compound. ESI-MS (M+H+): 525.49. $^1$H NMR (400 MHz, CD$_3$OD) δ 8.81-8.86 (m, 1H), 8.55 (br. s., 1H), 8.46-8.48 (m, 1H), 8.25-8.27 (m, 1H), 7.94-7.99 (m, 2H), 7.37-7.46 (m, 4H), 7.03-7.11 (m, 2H), 5.14-5.22 (m, 1H), 4.77 (br. s., 2H), 4.44 (br. s., 2H), 3.11 (s, 6H), 1.55 (d, J=7.28 Hz, 3H). 3 TFA per molecule.

Example 233

Synthesis of 2-{4-[5-Amino-6-(1,2,3,6-tetrahydro-pyridin-4-yl)-pyrazin-2-yl]-benzylamino}-5-cyano-N-[(S)-1-(4-fluoro-phenyl)-ethyl]-nicotinamide

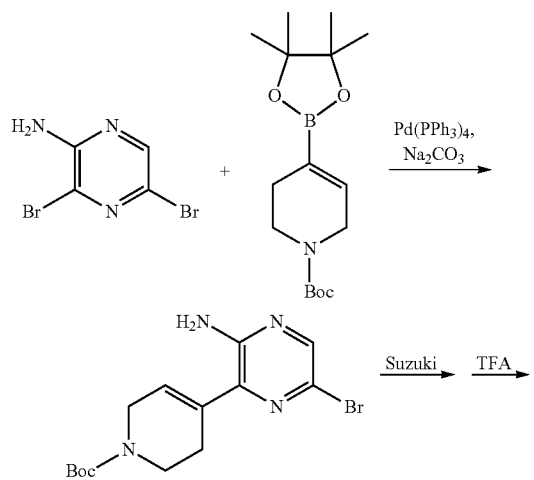

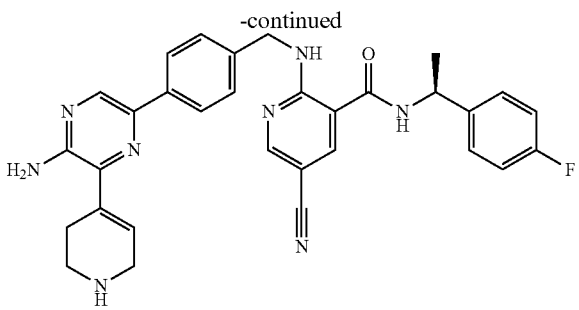

4-(3-Amino-6-bromo-pyrazin-2-yl)-3,6-dihydro-2H-pyridine-1-carboxylic acid tert-butyl ester 3,5-dibromopyrazin-2-amine (0.4164 g, 1.646 mmol), tert-butyl 4-(4,4,5,5-tetramethyl-1,3,2-dioxaborolan-2-yl)-5,6-dihydropyridine-1-(2H)-carboxylate (0.5346 g, 1.729 mmol), and Tetrakis(triphenylphosphine)palladium(0) (0.09513 g, 0.08233 mmol) were combined in a 10 mL microwave tube. The mixture was degassed under argon, then dimethoxymethane (6.00 mL, 67.8 mmol) and 1.2 M of Sodium carbonate in water (3.00 mL, 3.60 mmol) were added. The reaction mixture was degassed under argon, sealed and heated at 130° C. for 45 minutes in the microwave. The mixture was diluted in ethylacetate and washed with water, then brine. The organic phase was dried over MgSO$_4$, filtered and concentrated to dryness under reduced pressure. The crude product was adsorbed onto silica gel and purified by flash chromatography (0-50% EtOAc in hexanes) to give the title compound in 69% yield. ESI-MS (M+H+): 357.21.

4-{3-Amino-6-[4-({5-cyano-3-[(S)-1-(4-fluoro-phenyl)-ethylcarbamoyl]-pyridin-2-ylamino}-methyl)-phenyl]-pyrazin-2-yl}-3,6-dihydro-2H-pyridine-1-carboxylic acid tert-butyl ester A solution of 4-(3-Amino-6-bromo-pyrazin-2-yl)-3,6-dihydro-2H-pyridine-1-carboxylic acid tert-butyl ester (0.0679 g, 0.191 mmol) and 5-Cyano-N-[(S)-1-(4-fluoro-phenyl)-ethyl]-2-[4-(4,4,5,5-tetramethyl-1,3,2-dioxaborolan-2-yl)-benzylamino]-nicotinamide (0.105 g, 0.210 mmol) in 1,4-dioxane (4.50 mL, 57.7 mmol) was degassed under argon. Bis(tricyclohexylphosphine)palladium (0) (0.0128 g, 0.0191 mmol) and a solution of 1.2 M of Sodium bicarbonate in Water (0.478 mL, 0.573 mmol) were added. The mixture was degassed under argon then heated in the microwave at 120° C. for 20 minutes. The reaction mixture was cooled to room temperature, then diluted in ethylacetate and washed with water and then brine. The organic phase was dried over MgSO$_4$, filtered and concentrated to dryness under reduced pressure. The crude product was adsorbed onto silica gel and purified by flash chromatography (0-100% EtOAC in hexanes) to give the title compound in 53% yield. ESI-MS (M+H$^+$): 649.0.

2-{4-[5-Amino-6-(1,2,3,6-tetrahydro-pyridin-4-yl)-pyrazin-2-yl]-benzylamino}-5-cyano-N-[(S)-1-(4-fluoro-phenyl)-ethyl]-nicotinamide Trifluoroacetic Acid (0.50 mL, 6.5 mmol) was added to a solution of 4-{3-Amino-6-[4-({5-cyano-3-[(S)-1-(4-fluoro-phenyl)-ethylcarbamoyl]-pyridin-2-ylamino}-methyl)-phenyl]-pyrazin-2-yl}-3,6-dihydro-2H-pyridine-1-carboxylic acid tert-butyl ester (0.0662 g, 0.102 mmol) in methylene chloride (2.00 mL, 31.2 mmol) and the mixture was stirred for 30 minutes. The solvent was removed under reduced pressure. The crude product was dissolved in DMSO and purified by prep HPLC to give the title compound. ESI-MS (M+H+): 549.4; $^1$H NMR (400 MHz, CD$_3$OD) δ 8.81-8.85 (m, 1H), 8.77-8.89 (m, 1H), 8.47 (d, J=2.01 Hz, 1H), 8.38 (s, 1H), 8.25 (d, J=2.01 Hz, 1H), 7.85-7.90 (m, 2H), 7.37-7.44 (m, 4H), 7.03-7.10 (m, 2H), 6.38-6.42 (m, 1H), 5.13-5.23 (m, 1H), 4.76 (br. s., 2H), 3.89-3.94 (m, 2H), 3.54 (t, J=6.15 Hz, 2H), 2.92-2.98 (m, 2H), 1.55 (d, J=7.03 Hz, 3H). 1 TFA per molecule.

Example 234

Synthesis of 2-{4-[5-Amino-6-(3-hydroxy-phenyl)-pyrazin-2-yl]-benzylamino}-5-cyano-N-[(S)-1-(4-fluoro-phenyl)-ethyl]-nicotinamide

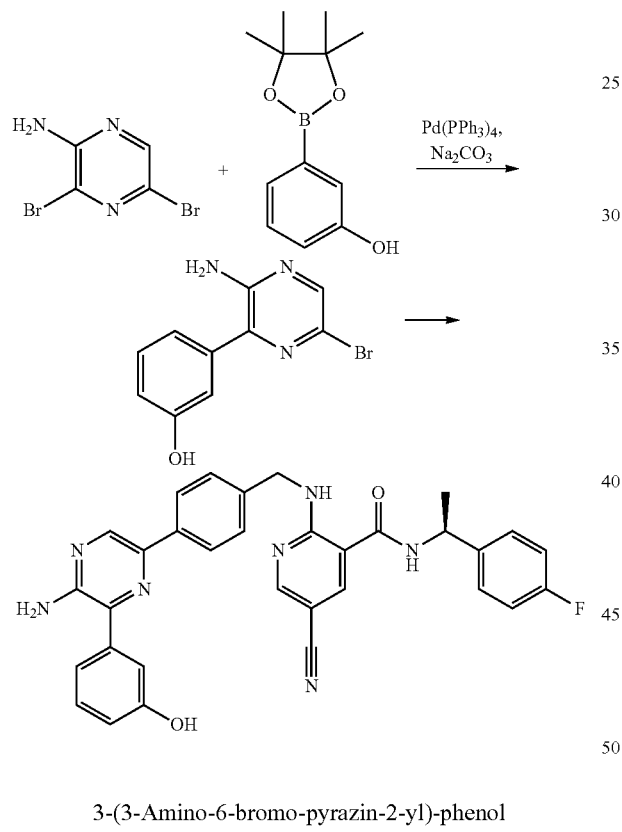

3-(3-Amino-6-bromo-pyrazin-2-yl)-phenol 3,5-dibromopyrazin-2-amine (0.3041 g, 1.202 mmol), 3-(4,4,5,5-Tetramethylborolan-2-yl)phenol (0.2779 g, 1.262 mmol), and tetrakis(triphenylphosphine)palladium(0) (0.06948 g, 0.06012 mmol) were combined in a 10 mL microwave tube. The mixture was degassed under argon, then dimethoxymethane (4.00 mL, 45.2 mmol) and a solution of 1.2 M of Sodium carbonate in water (2.004 mL, 2.405 mmol) were added. The mixture was degassed under argon, sealed and heated in the microwave at 130° C. for 45 minutes. The mixture was diluted in ethylacetate and washed with water, then brine. The organic phase was dried over MgSO$_4$, filtered and concentrated to dryness under reduced pressure. The crude product was adsorbed onto silica gel and purified by flash chromatography (0-50% EtOAc in hexanes) to give the title compound in 60% yield. ESI-MS (M+H+): 268.0.

2-{4-[5-Amino-6-(3-hydroxy-phenyl)-pyrazin-2-yl]-benzylamino}-5-cyano-N-[(S)-1-(4-fluoro-phenyl)-ethyl]-nicotinamide A solution of 3-(3-Amino-6-bromo-pyrazin-2-yl)-phenol (0.0542 g, 0.204 mmol) and 5-Cyano-N-[(S)-1-(4-fluoro-phenyl)-ethyl]-2-[4-(4,4,5,5-tetramethyl-1,3,2-dioxaborolan-2-yl)-benzylamino]-nicotinamide (0.112 g, 0.224 mmol) in 1,4-dioxane (4.00 mL, 51.2 mmol) was degassed under argon. Bis(tricyclohexylphosphine)palladium (0) (0.01359 g, 0.02037 mmol) and a solution of 1.2 M of Sodium bicarbonate in Water (0.5092 mL, 0.6111 mmol) were added. The mixture was degassed under argon then heated in the microwave at 120° C. for 20 minutes. The reaction mixture was then diluted in ethylacetate and washed with water, then brine. The organic phase was dried over MgSO4, filtered and concentrated to dryness under reduced pressure. The crude product was dissolved in DMSO and purified by prep HPLC to give the title compound. ESI-MS (M+H+): 560.5. $^1$H NMR (400 MHz, CD$_3$OD) δ 8.46-8.48 (m, 1H), 8.34 (s, 1H), 8.25 (d, J=2.26 Hz, 1H), 7.90-7.94 (m, 2H), 7.36-7.45 (m, 5H), 7.21-7.28 (m, 2H), 7.03-7.10 (m, 2H), 6.94-6.98 (m, 1H), 5.14-5.21 (m, 1H), 4.75-4.78 (m, 2H), 1.55 (d, J=7.03 Hz, 3H). 2 TFA per molecule.

Examples 235-239 were prepared in a manner consistent with Example 234.

Example 240 was prepared in a manner consistent with Example 225

Examples 241-242 were prepared in a manner consistent with Example 240.

Example 243

Synthesis of 2-{4-[5-Amino-6-(2,3-dihydroxy-propylamino)-pyrazin-2-yl]-benzylamino}-5-cyano-N-[(S)-1-(4-fluoro-phenyl)-ethyl]-nicotinamide

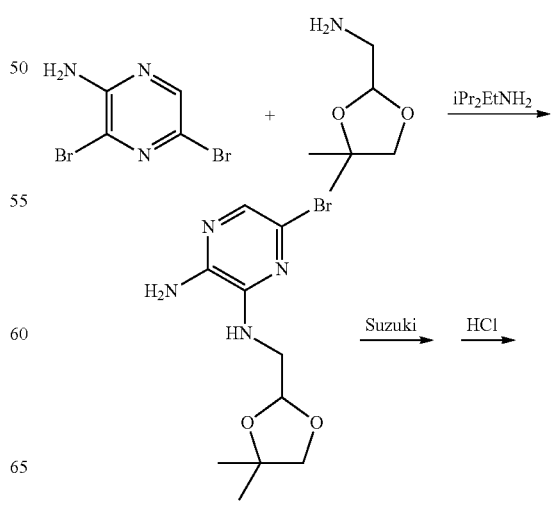

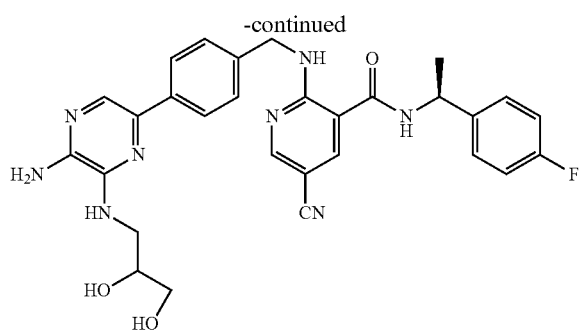

5-Bromo-N(3)-(2,2-dimethyl-[1,3]dioxolan-4-ylmethyl)-pyrazine-2,3-diamine

A mixture of 3,5-dibromopyrazin-2-amine (0.2819 g, 1.115 mmol), (2,2-Dimethyl-[1,3]dioxolan-4-yl)-methylamine (0.1608 g, 1.226 mmol), N,N-Diisopropylethylamine (0.2330 mL, 1.338 mmol) and 1,4-dioxane (3.00 mL, 38.4 mmol) was heated in the microwave at 150° C. for 8 hours. The mixture was cooled to room temperature, diluted in ethylacetate and washed with water, then brine. The organic phase was dried over $MgSO_4$, filtered and concentrated to dryness under reduced pressure to give the title compound in 93% yield. ESI-MS (M+H$^+$): 305.2.

2-(4-{5-Amino-6-[(2,2-dimethyl-1,3-dioxolan-4-ylmethyl)-amino]-pyrazin-2-yl}-benzylamino)-5-cyano-N-[(S)-1-(4-fluoro-phenyl)-ethyl]-nicotinamide A solution of 5-Bromo-N(3)-(2,2-dimethyl-[1,3]dioxolan-4-ylmethyl)-pyrazine-2,3-diamine (0.0984 g, 0.324 mmol) (13538-094) and 5-Cyano-N-[(S)-1-(4-fluoro-phenyl)-ethyl]-2-[4-(4,4,5,5-tetramethyl-1,3,2-dioxaborolan-2-yl)-benzylamino]-nicotinamide (0.148 g, 0.295 mmol) in 1,4-Dioxane (4.0 mL, 51 mmol) was degassed under argon. Bis(tricyclohexylphosphine)palladium (0) (0.0197 g, 0.0295 mmol) and a solution of 1.2 M of Sodium bicarbonate in Water (0.738 mL, 0.885 mmol) were added. The mixture was degassed under argon, then heated in the microwave at 120° C. for 20 minutes. The reaction mixture was then diluted in ethylacetate and washed with water, then brine. The organic phase was dried over MgSO4, filtered and concentrated to dryness under reduced pressure. The crude product was adsorbed onto silica gel and purified by flash chromatography (0-100% EtOAc in hexanes) to give the title compound in 37% yield. ESI-MS (M+H$^+$): 597.38.

2-{4-[5-Amino-6-(2,3-dihydroxy-propylamino)-pyrazin-2-yl]-benzylamino}-5-cyano-N-[(S)-1-(4-fluoro-phenyl)-ethyl]-nicotinamide A solution of 1 M of Hydrogen chloride in Water (2.0 mL, 2.0 mmol) was added to a solution of 2-(4-{5-Amino-6-[(2,2-dimethyl-1,3-dioxolan-4-ylmethyl)-amino]-pyrazin-2-yl}-benzylamino)-5-cyano-N-[(S)-1-(4-fluoro-phenyl)-ethyl]-nicotinamide (0.065 g, 0.11 mmol) in Tetrahydrofuran (0.5 mL, 6 mmol) and the mixture was stirred at room temperature for 1 hour. The solvent was removed under reduced pressure. The crude product was dissolved in DMSO and purified by prep HPLC to give the title compound. ESI-MS (M+H+): 557.3. $^1$H NMR (400 MHz, CD$_3$OD) δ 8.80-8.85 (m, 1H), 8.47 (d, J=2.01 Hz, 1H), 8.25 (d, J=2.01 Hz, 1H), 7.86-7.90 (m, 2H), 7.55 (s, 1H), 7.38-7.44 (m, 4H), 7.03-7.10 (m, 2H), 5.14-5.23 (m, 1H), 4.76 (s, 2H), 3.97-4.04 (m, 1H), 3.89 (dd, J=4.27, 13.80 Hz, 1H), 3.57-3.65 (m, 3H), 1.55 (d, J=7.03 Hz, 3H). 1 TFA per molecule.

Examples 244-245 were prepared in a manner consistent with Example 243.

Example 246

Synthesis of N-[(S)-1-(4-Fluoro-phenyl)-ethyl]-2-[4-(1H-pyrazolo[3,4-b]pyridin-5-yl)-benzylamino]-5-trifluoromethyl-nicotinamide

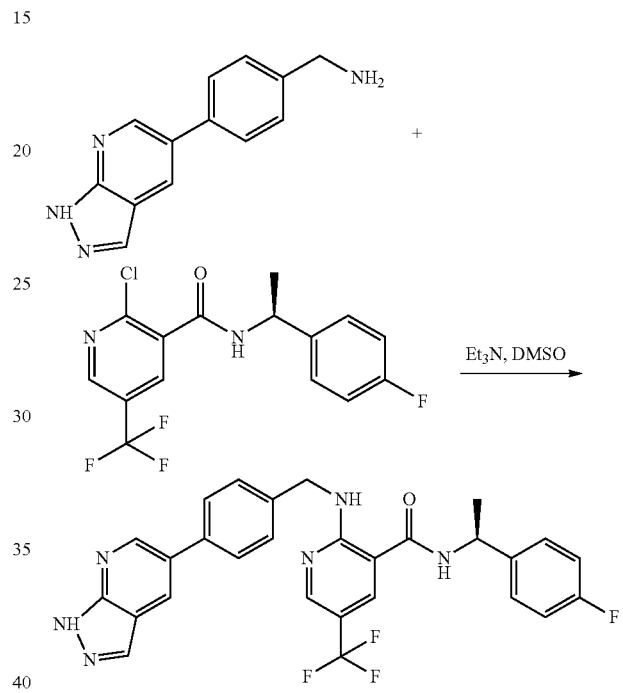

2-Chloro-N-[(S)-1-(4-fluoro-phenyl)-ethyl]-5-trifluoromethyl-nicotinamide

N,N-Diisopropylethylamine (0.280 mL, 1.61 mmol) and N,N,N',N'-Tetramethyl-O-(7-azabenzotriazol-1-yl)uronium Hexafluorophosphate (0.336 g, 0.885 mmol) were added to a solution of 2-Chloro-5-trifluoromethyl-nicotinic acid (0.133 g, 0.590 mmol) in N,N-Dimethylformamide (3.0 mL, 39 mmol) at 0° C. The mixture was stirred for 15 minutes then (S)-1-(4-Fluoro-phenyl)-ethylamine (0.0746 g, 0.536 mmol) was added. The mixture was stirred at 0° C. for 3 hours after which it was adsorbed onto silica gel under reduced pressure and purified by flash chromatography (0-30% EtOAc in hexanes) to give the title compound in 45% yield. ESI-MS (M+H+): 347.1.

N-[(S)-1-(4-Fluoro-phenyl)-ethyl]-2-[4-(1H-pyrazolo[3,4-b]pyridin-5-yl)-benzylamino]-5-trifluoromethyl-nicotinamide A mixture of 2-Chloro-N-[(S)-1-(4-fluoro-phenyl)-ethyl]-5-trifluoromethyl-nicotinamide (0.0410 g, 0.107 mmol) and 4-(1H-Pyrazolo[3,4-b]pyridin-5-yl)-benzylamine (53.2 mg, 0.118 mmol) was dissolved in dimethyl sulfoxide (0.494 mL, 6.96 mmol). Triethylamine (0.0596 mL, 0.428 mmol)

was added and the mixture was heated at 80° C. After 4 hours, the reaction was cooled to room temperature and diluted with ethylacetate. The mixture was washed with NaHCO₃, water, and brine (consecutively). The organic layer was dried over MgSO₄, filtered, adsorbed onto silica gel and purified by flash chromatography (0-100% EtOAc in methylene chloride) to give the title compound. ESI-MS (M+H+): 535.3; ¹H NMR (400 MHz, DMSO-d₆) δ 13.69 (s, 1H), 9.26 (t, J=5.77 Hz, 1H), 9.11 (d, J=7.53 Hz, 1H), 8.81 (d, J=2.26 Hz, 1H), 8.48-8.53 (m, 1H), 8.42-8.46 (m, J=0.75 Hz, 1H), 8.39-8.42 (m, 1H), 8.18 (d, J=1.25 Hz, 1H), 7.69-7.71 (m, 1H), 7.67-7.69 (m, 1H), 7.37-7.46 (m, 4H), 7.11-7.20 (m, 2H), 5.14 (quin, J=7.03 Hz, 1H), 4.66-4.79 (m, 2H), 1.48 (d, 3H).

Example 247

Synthesis of 2-(((5-(4-aminoquinazolin-6-yl)thiophen-2-yl)methyl)amino)-5-cyano-N-(3,4-difluorobenzyl)benzamide

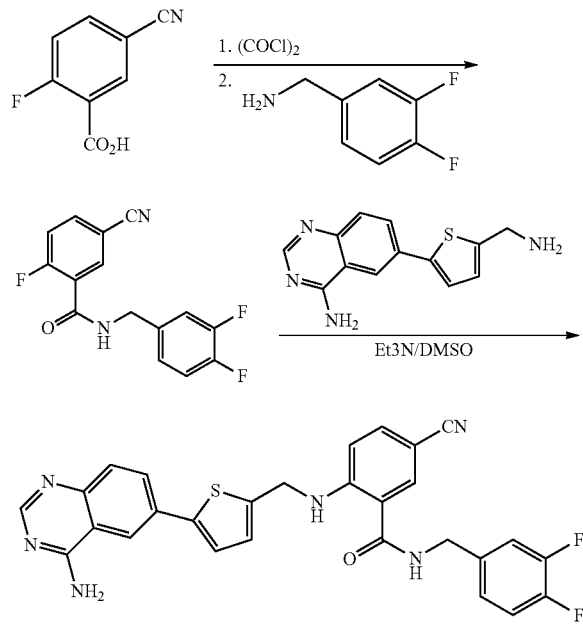

To a suspension of 5-cyano-2-fluorobenzoic acid (1.01 g, 0.00612 mol) in N,N-Dimethylformamide (0.00474 mL, 0.0000612 mol) and Methylene chloride (20 mL, 0.3 mol) was added Oxalyl chloride (0.776 mL, 0.00918 mol) and stirred at rt for 1 h until no more bubbling and it became a clear solution. Evaporated off the solvents. The residue was then dissolved in Pyridine (4 mL, 0.05 mol) and then added 3,4-Difluoro-benzylamine (0.760 mL, 0.00642 mol) and stirred at rt for 1 h. LC-MS showed clean formation of the desired product. (1.39 min, ES+/291.1). Evaporated off the solvents and the residue was worked up with DCM and water. Dried over MgSO₄ and purified on silica gel column with 0-100% EtOAc in DCM to give the desired product 5-Cyano-N-(3,4-difluoro-benzyl)-2-fluoro-benzamide as a white solid (1.5 g, 84%). ¹H NMR (400 MHz, CDCl₃) δ ppm 4.64 (d, J=5.77 Hz, 2 H) 7.01 (br. s., 1 H) 7.04-7.23 (m, 3 H) 7.29 (dd, J=11.17, 8.66 Hz, 1 H) 7.78-7.84 (m, 1 H) 8.49 (dd, J=7.03, 2.26 Hz, 1 H).

5-Cyano-N-(3,4-difluoro-benzyl)-2-fluoro-benzamide (0.1240 g, 0.4273 mmol), 6-(5-(aminomethyl)thiophen-2-yl)quinazolin-4-amine (0.10 g, 0.39 mmol) were dissolved in Dimethyl sulfoxide (3.8 mL, 54 mmol) and Triethylamine (108.8 µL, 0.7802 mmol). The reaction was microwaved on 200 watts, PowerMAX enabled, 120° C. for 25 hours. LCMS indicated the complete reaction (1.34 min, ES+/527.2). The reaction was partitioned between water and ethyl acetate. The organic layer was dried over magnesium sulfate, and evaporated. Purified by flash chromatography (0-20% methanol in ethyl acetate) to give 2-(((5-(4-aminoquinazolin-6-yl)thiophen-2-yl)methyl)amino)-5-cyano-N-(3,4-difluorobenzyl)benzamide as a white solid. ¹H NMR (400 MHz, DMSO-d₆) δ ppm 4.36 (d, J=5.52 Hz, 2 H) 4.67 (d, J=5.52 Hz, 2 H) 6.86 (d, J=8.78 Hz, 1 H) 7.07 (d, J=3.76 Hz, 1 H) 7.10-7.17 (m, 1 H) 7.28-7.38 (m, 2 H) 7.43 (d, J=3.76 Hz, 1 H) 7.54-7.63 (m, 2 H) 7.92 (dd, J=8.66, 2.13 Hz, 1 H) 8.05 (d, J=2.01 Hz, 1 H) 8.28 (s, 1 H) 8.35 (d, J=2.01 Hz, 1 H) 8.98 (t, J=5.90 Hz, 1 H) 9.10 (t, J=5.90 Hz, 1 H); MS:ES+/527.2.

Example 248

Synthesis of (S)-2-(4-(4-amino-7-methyl-7H-pyrrolo[2,3-d]pyrimidin-5-yl)benzylamino)-5-(2,5-dihydrofuran-3-yl)-N-(1-(4-fluorophenyl)ethyl) nicotinamide

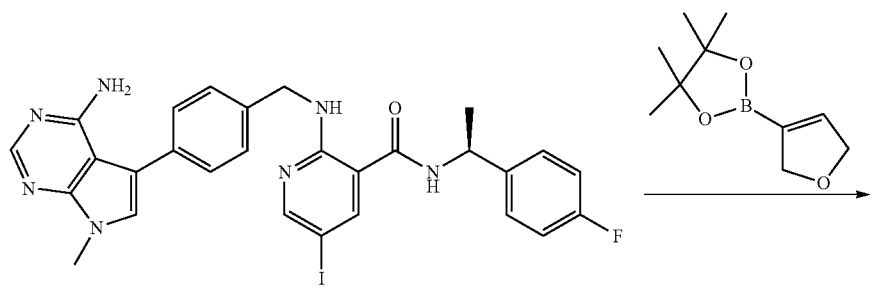

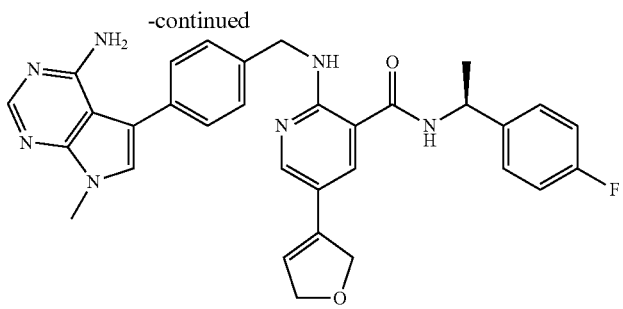

A mixture of 2-[4-(4-amino-7-methyl-7H-pyrrolo[2,3-d]pyrimidin-5-yl)-benzylamino]-N-[(S)-1-(4-fluoro-phenyl)-ethyl]-5-iodo-nicotinamide (100 mg, 0.16 mmol), 2-(2,5-dihydro-furan-3-yl)-4,4,5,5-tetramethyl-1,3,2-dioxaborolane (158 mg, 0.8 mmol) and 1,4-dioxane (3.0 mL) was degassed for 10 min. Bis(tricyclohexylphosphine) palladium (0) (11 mg, 0.016 mmol) and 1.2 M of saturated aqueous sodium bicarbonate solution in water (0.40 mL, 0.48 mmol) were then added. The reaction was heated in microwave at 120° C. for 30 min. The reaction mixture was diluted with EtOAc, washed with water (2×). The organic phase was separate, dried, and concentrate. The crude was purified by HPLC to give compound (S)-2-(4-(4-amino-7-methyl-7H-pyrrolo[2,3-d]pyrimidin-5-yl)benzylamino)-5-(2, 5-dihydrofuran-3-yl)-N-(1-(4-fluorophenyl)ethyl)nicotinamide (32 mg). LCMS: RT 1.24 min.; MH+ 564.00; $^1$H NMR (400 MHz, DMSO-$d_6$) δ ppm 8.94 (d, J=7.53 Hz, 1 H) 8.84 (t, J=5.65 Hz, 1 H) 8.42 (s, 1 H) 8.19 (d, J=3.51 Hz, 2 H) 7.58 (s, 1 H) 7.32-7.48 (m, 6H) 7.16 (t, J=8.78 Hz, 2 H) 6.36 (s, 1 H) 5.10-5.18 (m, 1 H) 4.90 (br. s., 2 H) 4.62-4.78 (m, 4 H) 3.83 (s, 3 H) 1.49 (d, J=7.03 Hz, 3 H); $^{19}$F NMR (376 MHz, DMSO-$d_6$) δ ppm ⁻78.50 (TFA, s, 6F), ⁻120.75 (s, 1 F).

Example 249

Synthesis of (S)-2-(3-(1H-pyrazolo[3,4-b]pyridin-5-yl)prop-2-ynylamino)-5-cyano-N-(1-(4-fluorophenyl)ethyl)nicotinamide

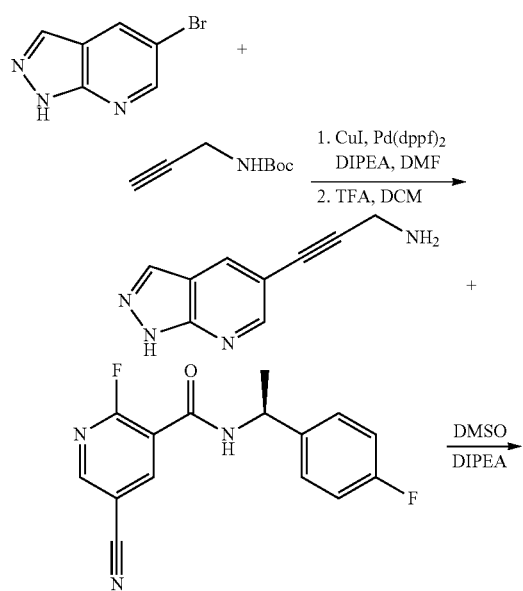

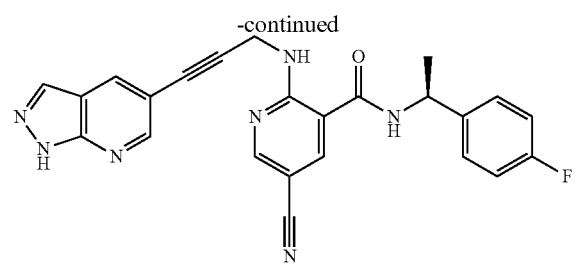

Step 1: Synthesis of tert-butyl 3-(1H-pyrazolo[3,4-b]pyridin-5-yl)prop-2-ynylcarbamate A mixture of 5-Bromo-1H-pyrazolo[3,4-b]pyridine (200.00 mg, 1.0100 mmol), Prop-2-ynyl-carbamic acid t-butyl ester (0.392 g, 2.52 mmol), Copper(I) iodide (9.62 mg, 0.0505 mmol), [1,1'-Bis(diphenylphosphino)ferrocene]dichloropalladium(II), complex with dichloromethane (1:1) (0.0825 g, 0.101 mmol), N,N-Diisopropylethylamine (1210 µL, 6.97 mmol), and N,N-Dimethylformamide (2.00 mL, 25.8 mmol) was dissolved and a bed of argon was added to the top. The reaction was heated at 80 C for 4 h. The reaction was diluted (DCM), washed (NaHCO₃, brine), dried (MgSO₄) and evaporated. Purification SiO₂ DCM→MeOH, 0.193 g of beige solid was recovered. LCMS m/z 273 (M+1).

Step 2: Synthesis of 3-(1H-pyrazolo[3,4-b]pyridin-5-yl)prop-2-yn-1-amine tert-butyl 3-(1H-pyrazolo[3,4-b]pyridin-5-yl)prop-2-ynylcarbamate (0.104 g, 0.382 mmol) was dissolved in methylene chloride (3 mL, 50 mmol) and trifluoroacetic acid (1 mL, 10 mmol) and stirred at room temperature for 1 hour. LC-MS showed the formation of product at the elution time of the HPLC with the correct mass. The crude was concentrated to dryness and methylene chloride was added and concentrated again to remove excess TFA. Once dry the crude was taken directly on to the next step.

Step 3: Synthesis of (S)-2-(3-(1H-pyrazolo[3,4-b]pyridin-5-yl)prop-2-ynylamino)-5-cyano-N-(1-(4-fluorophenyl)ethyl)nicotinamide To a solution of 3-(1H-pyrazolo[3,4-b]pyridin-5-yl)prop-2-yn-1-amine in Dimethyl sulfoxide (1.5 mL, 0.021 mol) was added N,N-Diisopropylethylamine (0.329 mL, 0.00189 mol), followed by 5-Cyano-2-fluoro-N-[(S)-1-(4-fluorophenyl)-ethyl]-nicotinamide (0.108 g, 0.000377 mol). The reaction was stirred at room temperature for 1 hour. LCMS shows complete conversion to a new peak consistent with the product (100%, RT=1.61 min, m/z=440.00). The reaction mixture was directly injected onto HPLC after acidifying with a few drops of TFA. The product was collected and concentrated. LCMS m/z 440.00 (M+1), $^1$H NMR (400 MHz, DMSO-$d_6$) δ 9.16 (t, J=5.65 Hz, 1H), 9.02 (d, J =7.53 Hz, 1H), 8.68 (d, J=2.01 Hz, 1H), 8.51 (dd, J=2.13, 3.14 Hz, 2H), 8.32 (d, J=2.01 Hz, 1H), 8.14 (s, 1H), 7.43 (dd, J=5.52, 8.53 Hz, 2H), 7.15 (t, J=8.91 Hz, 2H), 5.11 (t, J=7.15 Hz, 1H), 4.55 (d, J=5.52 Hz, 2H), 1.47 (d, J=7.03 Hz, 3H).

Example 250

Synthesis of (S)-5-cyano-N-(1-(4-fluorophenyl)ethyl)-2-(2-(2-(methylamino)quinazolin-6-yloxy)ethylamino)nicotinamide

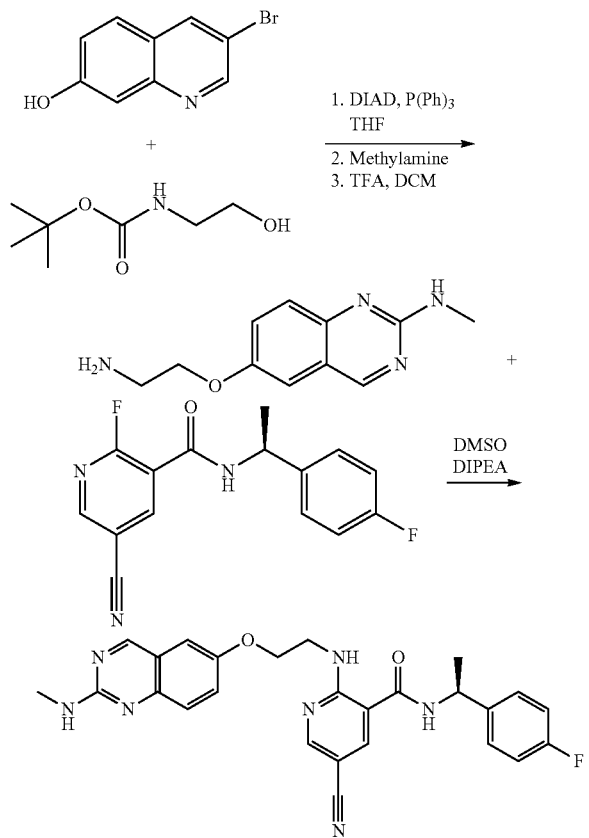

Step 1: Synthesis of tert-butyl 2-(2-bromoquinazolin-6-yloxy)ethylcarbamate

The mixture of (2-hydroxy-ethyl) carbamic acid t-butyl ester (165 µL, 0.00107 mol), 2-Bromo-quinazolin-6-ol (200 mg, 0.0009 mol), Triphenylphosphine (2.80E2 mg, 0.00107 mol) was dissolved in tetrahydrofuran (9 mL, 0.1 mol) and Diisopropyl azodicarboxylate (0.210 mL, 0.00107 mol) was added dropwise and stirred at room temperature. The product appeared at 1.44 (278.9, M+1, 100%). The mixture was diluted with DCM and extracted 1× with 5% citric acid, 1× with sodium bicarbonate, and 1× with brine, the organic layer was then dried and concentrated. The crude was subjected to chromatography purification with hexane/EA (0-100) on silica to give product. LCMS m/z 278.9 (M+1).

Step 2: Synthesis of tert-butyl 2-(2-(methylamino)quinazolin-6-yloxy)ethylcarbamate tert-butyl 2-(2-bromoquinazolin-6-yloxy)ethylcarbamate (0.100 g, 0.272 mmol) and 2.0 M of methylamine in t(0.163 mL, 0.326 mmol) were dissolved in 3-methyl-1-butanol, (3 mL, 30 mmol) and the reaction was heated to 145 degrees for 12 hours. LC-MS showed formation of product at 0.95 319 M+1. The reaction was diluted with methylene chloride and extracted 1× with citric acid, 1× with sodium bicarbonate and 1× with brine. The organic layer was dried with magnesium sulfate and concentrated. The crude was then purified by silica gel chromatography 0-50% methylene chloride methanol to give 60 mgs of product. LCMS m/z 319.00 (M+1).

Step 3: Synthesis of 6-(2-aminoethoxy)-N-methylquinazolin-2-amine tert-butyl 2-(2-(methylamino)quinazolin-6-yloxy)ethylcarbamate (0.060 g, 0.19 mmol) was dissolved in methylene chloride (3 mL, 50 mmol) and trifluoroacetic acid (0.2 mL, 2 mmol) and stirred at room temperature for 1 hour. LC-MS showed the formation of product at the elution time of the HPLC with the correct mass. The crude was concentrated to dryness and methylene chloride was added and concentrated again to remove excess TFA. Once dry the crude was taken directly into the next step. LCMS m/z 219.00 (M+1).

Step 4: Synthesis of (S)-5-cyano-N-(1-(4-fluorophenyl)ethyl)-2-(2-(2-(methylamino)quinazolin-6-yloxy)ethylamino)nicotinamide To a solution of 6-(2-aminoethoxy)-N-methylquinazolin-2-amine (0.041 g, 0.00019 mol) in dimethyl sulfoxide (0.75 mL, 0.010 mol) was added N,N-diisopropylethylamine (0.164 mL, 0.000939 mol), followed by 5-Cyano-2-fluoro-N-[(S)-1-(4-fluoro-phenyl)-ethyl]-nicotinamide (0.0540 g, 0.000188 mol). The reaction was stirred at room temperature for 1 hour. LCMS shows complete conversion to a new peak consistent with the product (100%, RT=1.26 min, m/z=485.9). The reaction mixture was directly injected onto HPLC after acidifying with a few drops of TFA. The product was collected and concentrated. LCMS m/z 485.9 (M+1), $^1$H NMR (400 MHz, DMSO-$d_6$) δ 9.19 (d, J=5.27 Hz, 2H), 8.98 (d, J=7.53 Hz, 1H), 8.63 (d, J=2.01 Hz, 1H), 8.48 (d, J=2.01 Hz, 1H), 7.58 (br. s., 1H), 7.49 (br. s., 2H), 7.41 (dd, J=5.77, 8.53 Hz, 2H), 7.14 (t, J=8.91 Hz, 2H), 5.09 (t, J=7.15 Hz, 1H), 4.22 (t, J=5.65 Hz, 2H), 3.88 (dd, J=2.76, 5.52 Hz, 2H), 2.97 (s, 3H), 1.45 (d, J=7.03 Hz, 3H).

Examples 251-254 were prepared in a manner consistent with Example 250.

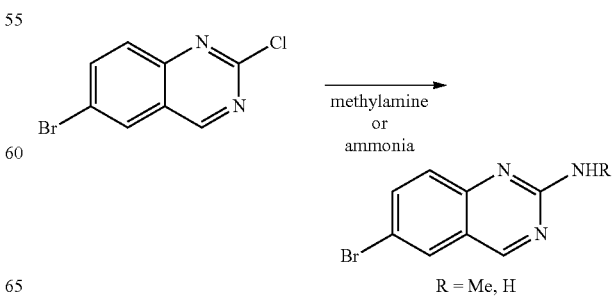

Synthesis of 6-bromo-N-methylquinazolin-2-amine

6-Bromo-2-chloro-quinazoline (0.215 g, 0.883 mmol) and 2.0 M of methylamine in tetrahydrofuran (0.530 mL, 1.06 mmol) were dissolved in 3-methyl-1-butanol, (9 mL, 80 mmol) and the reaction was heated to 145 degrees for 12 hours. LC-MS showed formation of product at 0.95. The reaction was diluted with methylene chloride and extracted 1× with citric acid, 1× with sodium bicarbonate and 1× with brine. The organic layer was dried with magnesium sulfate and concentrated. The crude was then purified by column 0-50% methylene chloride methanol to give 92 mgs of product. LCMS m/z 237.9 (M+1).

Synthesis of 6-bromoquinazolin-2-amine

6-Bromo-2-chloro-quinazoline (0.500 g, 2.05 mmol) and 7 M of ammonia in methanol (0.352 mL, 2.46 mmol) were dissolved in 3-methyl-1-butanol, (20 mL, 200 mmol) and the reaction was heated to 145 degrees for 12 hours. LC-MS showed formation of product at 0.55 241.9 M+NH$_4$$^+$. It appears that the product precipitated after the reaction, therefore the reaction was filtered and washed with water to remove any salts. NMR of the solid was consistent with product therefore it was taken on directly to the next step. LCMS m/z 241.9 M+NH$_4$$^+$.

Examples 255-258 were prepared in an analogous manner to Example 249 from prop-2-ynyl-carbamic acid t-butyl ester, and the appropriate 6-bromoquinazoline and halogenated nicotinamide.

Example 259

Synthesis of 1-(4-(5-aminopyrazin-2-yl)benzyl)-3-(3,4-difluorobenzylamino)-1H-pyrazolo[3,4-b]pyridine-5-carbonitrile

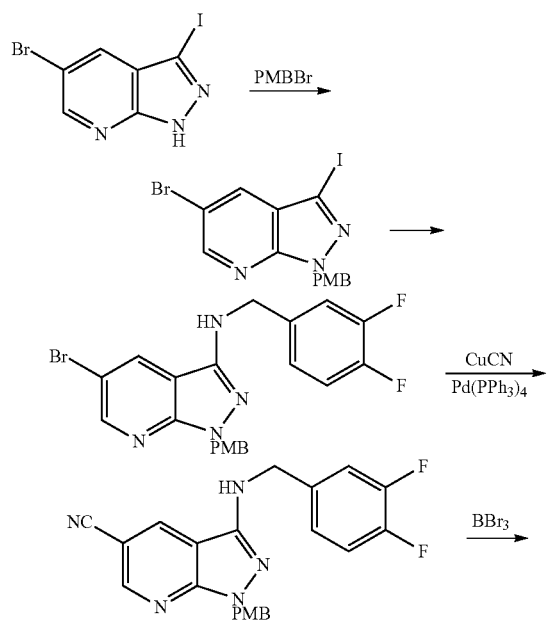

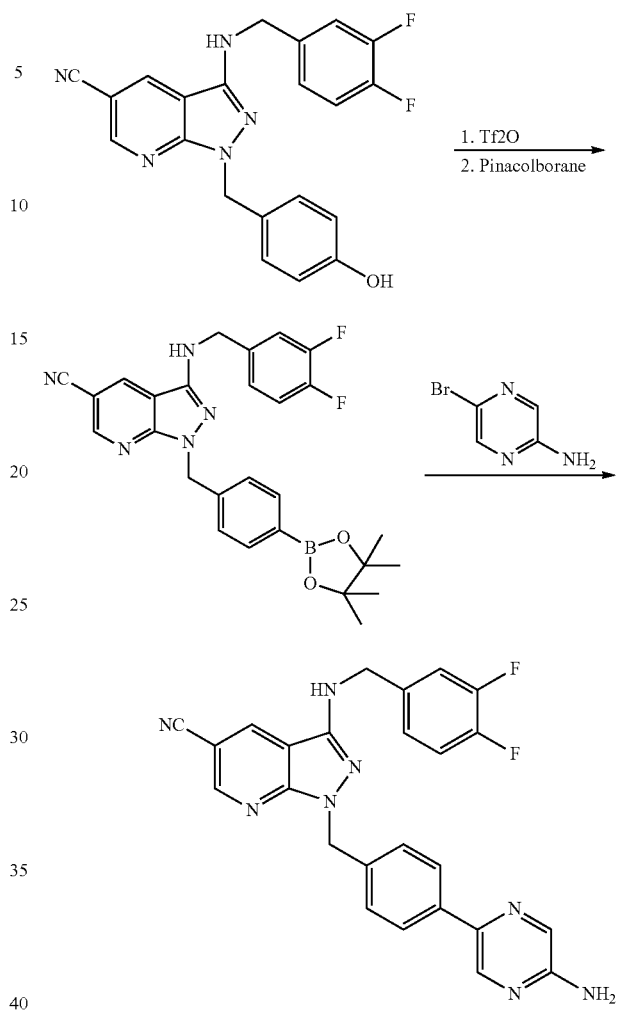

A mixture of 5-bromo-3-iodo-1H-pyrazolo[3,4-b]pyridine (3.0 g, 9.3 mmol), 4-methoxybenzylbromide (2.2 g, 11.1 mmol, 1.2 eq) and NaO$^t$Bu (6.0 g, 18.6 mmol, 2.0 eq) in DMF (100 mL) was stirred at 20° C. for 2 h. Then water was added and the mixture was extracted with EtOAc (200 mL). The organics were washed with water (100 mL×2) and concentrated to give 5-bromo-3-iodo-1-(4-methoxybenzyl)-1H-pyrazolo[3,4-b]pyridine (2.3 g, yield: 43%) as yellow solid. ESI-MS (M+H$^+$): 443.9. $^1$H NMR (400 MHz, DMSO-d$_6$) δ: 8.73 (d, 1H), 8.24 (d, 1H), 7.23 (d, 2H), 6.87 (d, 2H), 5.59 (s, 2H), 3.70 (s, 3H).

A mixture of 5-bromo-3-iodo-1-(4-methoxybenzyl)-1H-pyrazolo[3,4-b]pyridine (1.8 g, 4.1 mmol), CuI (234 mg, 1.2 mmol, 0.3 eq), pyrrolidine-2-carboxylic acid (138 mg, 1.2 mmol, 0.3 eq) and K$_2$CO$_3$ (2.7 g, 20 mmol, 5.0 eq) in DMSO (50 mL) was stirred at 100° C. for 4 h. The mixture was cooled to rt and the residue was diluted with EtOAc (200 mL), washed with water (100 mL×3) and dried. The organic phase was concentrated and purified on silica gel (EA:PE=1:1) to give 5-bromo-N-(3,4-difluorobenzyl)-1-(4-methoxybenzyl)-1H-pyrazolo[3,4-b]pyridin-3-amine (700 mg, yield: 37.6%) as a white solid. ESI-MS (M+H$^+$): 459.1. $^1$H NMR (400 MHz, DMSO-d$_6$) δ: 8.49-8.43 (m, 2H), 7.44-7.33 (m, 2H), 7.23 (s, 1H), 7.09-7.02 (m, 3H), 6.79 (d, 2H), 5.28 (s, 2H), 4.43 (d, 2H), 3.69 (s, 3H).

A mixture of 5-bromo-N-(3,4-difluorobenzyl)-1-(4-methoxybenzyl)-1H-pyrazolo[3,4-b]pyridin-3-amine (300 mg, 0.65 mmol), CuCN (116 mg, 1.3 mmol, 2.0 eq), Pd(PPh$_3$)$_4$ (75 mg, 0.06 mmol, 0.1 eq) and TEA (130 mg, 1.3 mmol, 2.0 eq) in dioxane (100 mL) was stirred at 130° C. for 16 h under N$_2$ atmosphere. After the reaction completed, the solvent was removed and the residue was purified by silica gel (EA:PE=2:1) to give 5-cyano-N-(3,4-difluorobenzyl)-1-(4-methoxybenzyl)-1H-pyrazolo[3,4-b]pyridin-3-amine (150 mg, yield: 56.6%) as yellow solid. ESI-MS (M+H$^+$): 406.1. $^1$H NMR (400 MHz, CDCl$_3$) δ: 8.64 (d, 1H), 8.12 (d, 1H), 7.28-7.26 (m, 3H), 7.12-7.10 (m, 2H), 6.83-6.81 (m, 3H), 5.43 (s, 2H), 4.55 (d, 2H), 3.77 (s, 3H).

A solution of 5-cyano-N-(3,4-difluorobenzyl)-1-(4-methoxybenzyl)-1H-pyrazolo[3,4-b]pyridin-3-amine (400 mg, 1.0 mmol), BBr$_3$ (375 mg, 1.5 mmol, 1.5 eq) and TEA (1.0 g, 10 mmol, 10 eq) in DCM (20 mL) was stirred at −10° C. for 1 h and then warmed to rt for 16 h, After the reaction completed, the solvent was removed and the residue was purified by silica gel (EA:PE=4:1) to give 3-(3,4-difluorobenzylamino)-1-(4-hydroxybenzyl)-1H-pyrazolo[3,4-b]pyridine-5-carbonitrile (230 mg, yield: 46%) as yellow solid. ESI-MS (M+H$^+$): 392.1. $^1$H NMR (400 MHz, DMSO-d$_6$) δ: 9.27 (br, 1H), 8.83 (s, 1H), 8.78 (s, 1H), 7.51-7.41 (m, 2H), 7.31 (br, 1H), 7.07 (d, 2H), 6.70 (d, 2H), 5.34 (s, 2H), 4.51 (d, 2H).

To a solution of 3-(3,4-difluorobenzylamino)-1-(4-hydroxybenzyl)-1H-pyrazolo[3,4-b]pyridine-5-carbonitrile (230 mg, 0.59 mmol) in DCM (20 mL) were added Tf$_2$O (332 mg, 1.2 mmol, 2.0 eq) and TEA (300 mg, 3.0 mmol, 5.0 eq), then the reaction solution was stirred at −78° C. for 30 min, warmed to rt for 1.5 h, after the reaction completed, the mixture was concentrated and purified on silica gel (EA:PE=1:2) to give the corresponding triflate (100 mg, yield: 32.5%) as yellow solid. ESI-MS (M+H$^+$): 524.4.

A flask charged with the above triflate (170 mg, 0.32 mmol), 4,4,4',4',5,5,5',5'-octamethyl-2,2'-bi(1,3,2-dioxaborolane) (163 mg, 0.64 mmol, 2.0 eq), KOAc (63 mg, 0.64 mmol, 2.0 eq) and [1,1-Bis(diphenylphosphino)ferrocene]dichloropalladium(II) complex with dichloromethane (1:1) (26 mg, 0.032 mmol, 0.10 eq) was flushed with nitrogen. Then dioxane (50 mL) was added and the reaction was stirred at 90° C. for 1 h. The solution was cooled to rt and the residue was used directly in the next step. ESI-MS (M+H$^+$): 502.3.

To the above reaction mixture were added 5-bromopyrazin-2-amine (111 mg, 0.64 mmol, 2.0 eq), K$_2$CO$_3$ (88 mg, 0.64 mmol, 2.0 eq) and [1,1-Bis (diphenylphosphino) ferrocene]dichloropalladium (II) complex with dichloromethane (1:1) (26 mg, 0.032 mmol, 0.10 eq). The mixture was charged with nitrogen and heated to 100° C. for 1 h. The solution was cooled to room temperature. The solvent was removed and the residue was purified by column chromatography (PE:EA=1:4) to give 1-(4-(5-aminopyrazin-2-yl)benzyl)-3-(3,4-difluorobenzylamino)-1H-pyrazolo[3,4-b]pyridine-5-carbonitrile as a yellow solid (4 mg, yield: 2.6%). ESI-MS (M+H$^+$): 469.0. $^1$H NMR (400 MHz, DMSO-d$_6$) δ: 8.80 (d, 1H), 8.70 (d, 1H), 8.44 (d, 1H), 7.93 (d, 1H), 7.81-7.79 (m, 2H), 7.45-7.32 (m, 3H), 7.22-7.19 (m, 3H), 6.57 (br, 2H), 5.44 (s, 2H), 4.46 (d, 2H).

Example 260

Synthesis of 2-(4-(3-amino-1H-pyrazolo[3,4-b]pyridin-5-yl)benzylamino)-N-cyclopropyl-5-(trifluoromethyl)nicotinamide

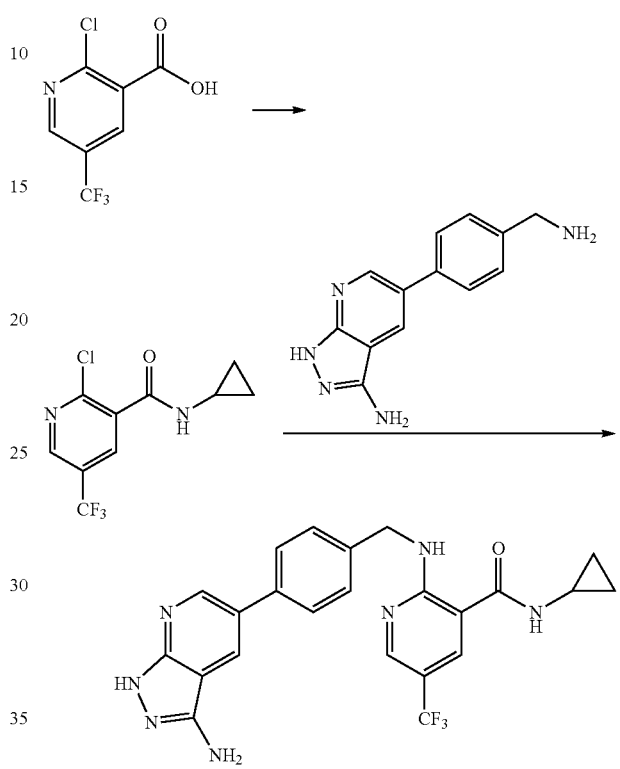

2-chloro-N-cyclopropyl-5-(trifluoromethyl)nicotinamide was prepared from 2-chloro-5-(trifluoromethyl)nicotinic acid via acid chloride using oxalyl chloride. ESI-MS (M+H$^+$): 265.2; $^1$H NMR (400 MHz, DMSO-d$_6$) δ: 8.92-8.91 (m, 1H), 8.76 (d, 1H), 8.41 (d, 1H), 2.84-2.78 (m, 1H), 0.74-0.71 (m, 2H), 0.56-0.55 (m, 2H).

A mixture of 2-chloro-N-cyclopropyl-5-(trifluoromethyl) (200 mg, 0.76 mmol), 5-(4-(aminomethyl)phenyl)-1H-pyrazolo[3,4-b]pyridin-3-amine (200 mg, 0.84 mmol, 1.1 eq), TEA (230 mg, 2.28 mmol, 3.0 eq) in DMSO (5 mL) was stirred at 110° C. for 2 h. Then the mixture was poured into water (20 mL) and filtered to afford crude compound. The crude compound was purified by silica gel column (CH$_2$Cl$_2$/CH$_3$OH=15/1) to give 2-(4-(3-amino-1H-pyrazolo[3,4-b]pyridin-5-yl)benzylamino)-N-cyclopropyl-5-(trifluoromethyl)nicotinamide as a yellow solid (100 mg, yield: 28%). ESI-MS (M+H$^+$): 468.0. $^1$H NMR (400 MHz, DMSO-d$_6$): 12.00 (s, 1H), 9.34 (t, 1H), 8.76 (d, 1H), 8.64 (d, 1H), 8.49 (s, 1H), 8.38 (d, 1H), 8.22 (d, 1H), 7.63 (d, 2H), 7.44 (d, 2H), 5.62 (s, 2H), 4.73 (d, 2H), 2.84-2.80 (m, 1H), 0.71-0.70 (m, 2H), 0.60-0.59 (m, 2H).

Examples 261-309 were prepared in a manner consistent with Example 260.

Examples 310-320 were prepared in a manner consistent with Example 25.

Examples 321-324 were prepared in a manner consistent with Example 38.

Examples 325-328 were prepared in a manner consistent with Example 56.

Examples 329-334 were prepared in a manner consistent with Example 55.

Example 335 was prepared in a manner consistent with Example 53.

Example 337 was prepared in a manner consistent with Example 54.

Example 338 was prepared in a manner consistent with Example 59.

Examples 339-340 were prepared in a manner consistent with Example 60.

Examples 341-344 were prepared in a manner consistent with Example 8.7.1.

Examples 345-346 were prepared in a manner consistent with Example 61.

Example 347 was prepared in a manner consistent with Example 2.20.

Examples 348-352 were prepared in a manner consistent with Example 43.

Example 353 was prepared in a manner consistent with Example 42.

Example 354 was prepared in a manner consistent with Example 3.6.

Example 355

Synthesis of 2-(4-(6-amino-5-methylpyridin-3-yl)benzylamino)-N-(3,4-difluorobenzyl)-5-(trifluoromethyl)nicotinamide

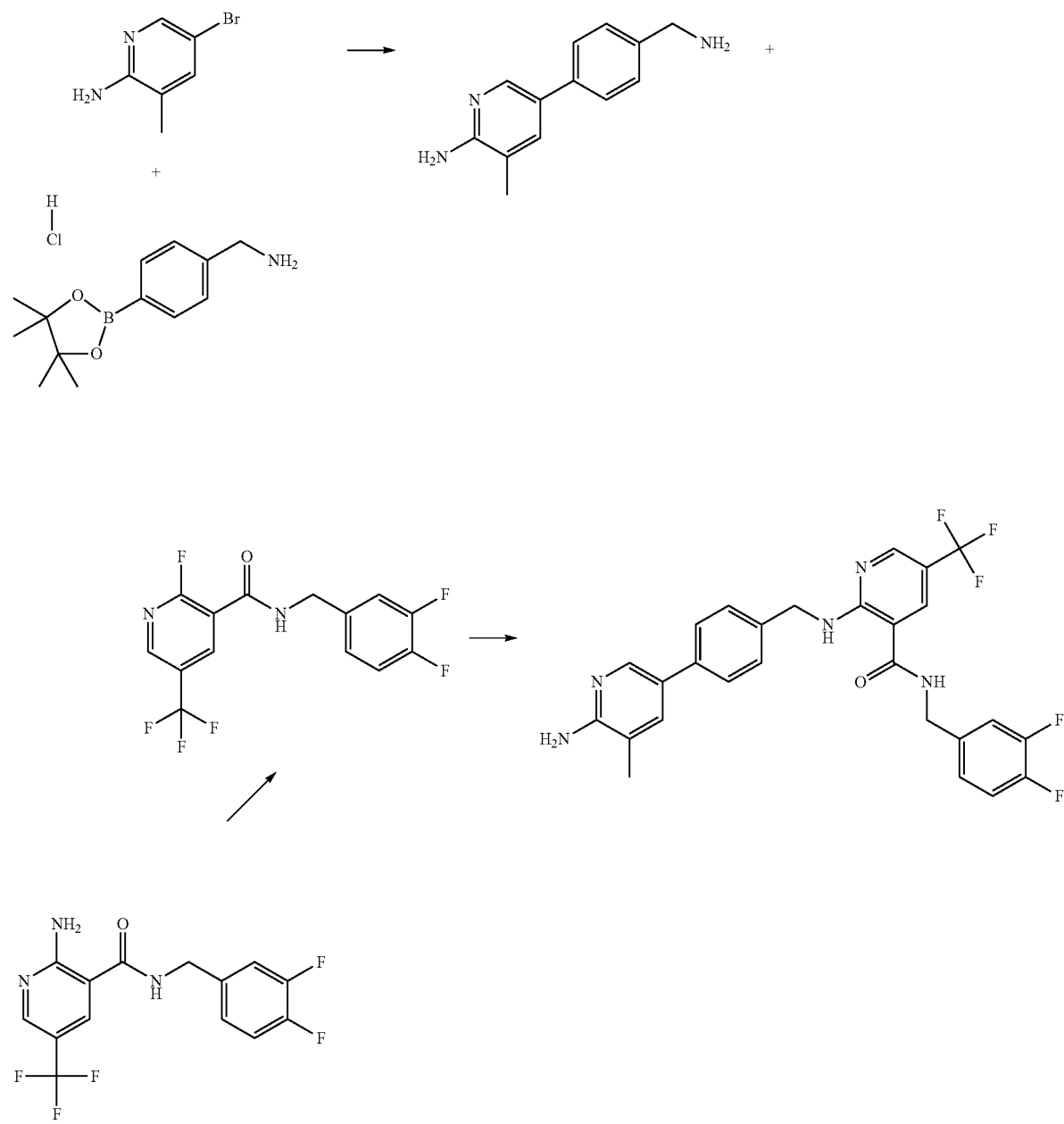

Synthesis of 5-(4-Aminomethyl-phenyl)-3-methyl-pyridin-2-ylamine

5-Bromo-3-methyl-pyridin-2-ylamine (109.5 mg, 0.5854 mmol), and 4-(4,4,5,5-Tetramethyl-1,3,2-dioxaborolan-2-yl)-benzylamine; hydrochloride (144.7 mg, 0.5368 mmol) were stirred in 1,4-Dioxane (3.00 mL, 38.4 mmol) and 1.04 M of Sodium bicarbonate in Water (1.555 mL, 1.610 mmol). The mixture was degassed for 10 minutes. Added Bis(tricyclohexylphosphine)palladium (0) (28.0 mg, 0.0420 mmol) and microwaved at 120° C. for 10 minutes. Added saturated sodium bicarbonate solution (~60 mL) and extracted 3×60 mL ethyl acetate. The combined organic extracts were dried over magnesium sulfate, and evaporated to yield 50.0 mg of a light yellow powder (44%). $^1$H NMR (300 MHz, DMSO-$d_6$) δ 8.10 (d, J=2.27 Hz, 1H), 7.55 (d, J=1.51 Hz, 1H), 7.45-7.53 (m, 2H), 7.30-7.38 (m, J=8.31 Hz, 2H), 5.77 (s, 2H), 3.71 (s, 2H), 2.11 (s, 3H) ES (+) MS m/e=214.1 (M+1).

Synthesis of N-(3,4-Difluoro-benzyl)-2-fluoro-5-trifluoromethyl-nicotinamide 2-Amino-N-(3,4-difluoro-benzyl)-5-trifluoromethyl-nicotinamide (9.5 g, 29 mmol) was stirred in 30 M of Hydrofluoric acid in Pyridine (90 mL, 3000 mmol) in a PTFE vial. Chilled in an ice bath and added Sodium nitrite (2.3 g, 33 mmol). Stirred in an ice bath for 30 min. LC-MS showed complete conversion (1.73 min, ES+/335.1). Quenched with water with cooling, and extracted with EtOAc. Dried over MgSO4 and evaporated. Purified with a short silica gel column with EtOAc to give the desired product as a white solid. $^1$H NMR (400 MHz, CDCl$_3$) δ 8.81 (dd, J=2.32, 8.72 Hz, 1H), 8.56 (s, 1H), 6.96-7.17 (m, 5H), 4.58 (d, J=5.84 Hz, 3H).

Synthesis of 2-(4-(6-amino-5-methylpyridin-3-yl)benzylamino)-N-(3,4-difluorobenzyl)-5-(trifluoromethyl)nicotinamide 5-(4-Aminomethyl-phenyl)-3-methyl-pyridin-2-ylamine (48.6 mg, 0.228 mmol), N-(3,4-Difluoro-benzyl)-2-fluoro-5-trifluoromethyl-nicotinamide (95.6 mg, 0.286 mmol), Dimethyl sulfoxide (1.00 mL, 14.1 mmol) and Triethylamine (98.0 uL, 0.703 mmol) were combined and heated at 100° C. for 2 hours. LCMS-done. Added 10 mL ethyl acetate and washed 3×6 mL saturated sodium bicarbonate solution. The organic phase was flushed through a sodium sulfate plug, rinsed with 2 mL ethyl acetate and evaporated to dryness. The resulting solid was loaded onto a 4 g silica gel column and purified by flash chromatography (20-100% ethyl acetate:hexanes). Evaporated. Collected 95.5 mg of a yellow powder. $^1$H NMR (300 MHz, DMSO-$d_6$) δ 9.35 (t, J=5.67 Hz, 1H), 9.26 (t, J=5.67 Hz, 1H), 8.51 (d, J=1.13 Hz, 1H), 8.34 (d, J=2.27 Hz, 1H), 8.09 (d, J=2.27 Hz, 1H), 7.54 (d, J=2.27 Hz, 1H), 7.51 (d, J=8.31 Hz, 2H), 7.30-7.45 (m, 4H), 7.14-7.24 (m, 1H), 5.80 (s, 2H), 4.70 (d, J=5.67 Hz, 2H), 4.44 (d, J=5.67 Hz, 2H), 2.10 (s, 3H); ES (+) MS m/e=528.2 (M+1).

Example 356

Synthesis of 5-cyano-N-(3,4-difluorobenzyl)-2-(4-(2-oxo-2,3-dihydro-1H-imidazo[4,5-b]pyridin-6-yl)benzylamino)nicotinamide

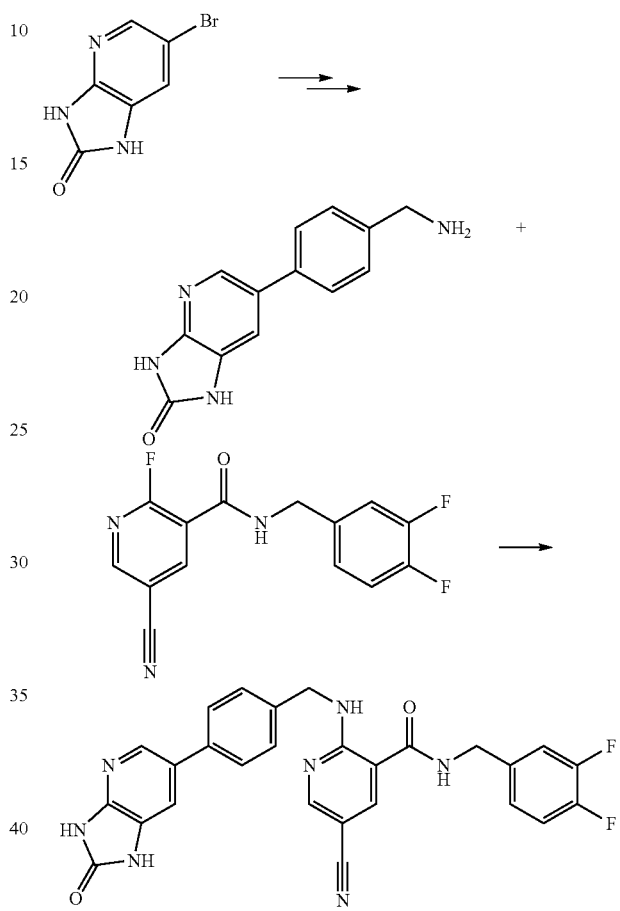

Synthesis of 6-(4-(aminomethyl)phenyl)-1H-imidazo[4,5-b]pyridin-2(3H)-one

6-Bromo-1,3-dihydro-imidazo[4,5-b]pyridin-2-one (2.65 g, 12.4 mmol), and 4-(N-Boc-aminoethyl)phenylboronic acid (3.00 g, 11.9 mmol) were stirred in 1,4-Dioxane (60.0 mL, 769 mmol) and 1.04 M of Sodium bicarbonate in Water (26.0 mL, 26.9 mmol). The mixture was degassed for 10 minutes. Added Bis(tricyclohexylphosphine)palladium (0) (558.1 mg, 0.8364 mmol) and heated at 100° C. overnight. The reaction was treated with 200 mL ethyl acetate, 100 mL water and 100 mL saturated sodium bicarbonate solution. The resulting emulsion/precipitate was filtered, washed twice with water, twice with ethyl acetate, and high-vac'd overnight. Collected 1.967 g of an off-white powder (48%). LCMS (Agilent 460, 254 nm): ES (+) MS m/e=341.2 (M+1) @ 1.15 min. $^1$H NMR (300 MHz, DMSO-$d_6$) δ 11.15 (br. s., 1H), 8.14 (d, J=1.89 Hz, 1H), 7.54-7.65 (m, J=7.93 Hz, 2H), 7.42 (d, J=5.67 Hz, 1H), 7.40 (d, J=1.89 Hz, 1H), 7.26-7.36 (m, 1H), 4.16 (d, J=6.04 Hz, 2H), 1.40 (s, 9H).

Synthesis of 5-cyano-N-(3,4-difluorobenzyl)-2-(4-(2-oxo-2,3-dihydro-1H-imidazo[4,5-b]pyridin-6-yl)benzylamino)nicotinamide 6-(4-(aminomethyl)phenyl)-1H-imidazo[4,5-b]pyridin-2(3H)-one bis-TFA Salt (100.0 mg, 0.2135 mmol), 5-Cyano-N-(3,4-difluoro-benzyl)-2-fluoro-nicotinamide (77.73 mg, 0.2669 mmol), Dimethyl sulfoxide (1.00 mL, 14.1 mmol) and Triethylamine (89.29 uL, 0.6406 mmol) were heated at 100° C. for 1 hour. The reaction was cooled to rt, and treated with 5 mL sodium bicarbonate, and 5 mL ethyl acetate. A solid precipitated out and was collected by filtration. The solid was washed with 10 mL water and 20 mL ethyl acetate. Compound was heated in 10% DMSO/ethyl acetate, cooled to rt, centrifuged, and solvent was decanted. Stirred in DCM, centrifuged, and decanted to remove residual DMSO. Evaporated to dryness. $^1$H NMR (400 MHz, DMSO-$d_6$) δ 11.37 (br. s., 1H), 10.92 (br. s., 1H), 9.38 (t, J=5.77 Hz, 1H), 9.26 (t, J=5.52 Hz, 1H), 8.58 (d, J=1.76 Hz, 1H), 8.40 (d, J=2.01 Hz, 1H), 8.13 (d, J=1.76 Hz, 1H), 7.58 (d, J=8.03 Hz, 2H), 7.38 (d, J=9.29 Hz, 2H), 7.30-7.47 (m, 3H), 7.08-7.24 (m, 1H), 4.72 (d, J=5.77 Hz, 2H), 4.42 (d, J=5.52 Hz, 2H); ES (+) MS m/e=512.2 (M+1).

Examples 357-366 were prepared in a manner consistent with Example 356.

Examples 367-385 were prepared in a manner consistent with Example 355.

Examples 386-387 were prepared in a manner consistent with Example 4.9.

Example 388 was prepared in a manner consistent with Example 25.

Examples 389-399 were prepared in a manner consistent with Example 246.

Examples 400-401 were prepared in a manner consistent with Example 182.

Examples 402 was prepared in a manner consistent with Example 42.

Examples 403-405 were prepared in a manner consistent with Example 38.

Examples 406-408 were prepared in a manner consistent with Example 25.

Examples 409-410 were prepared in a manner consistent with Example 182.

Examples 411-412 were prepared in a manner consistent with Example 42.

Example 413

Synthesis of 3-(4-(3-amino-1H-pyrazolo[3,4-b]pyridin-5-yl)benzylamino)-6-cyano-N-(3,4-difluorobenzyl)-N-methylpyrazine-2-carboxamide

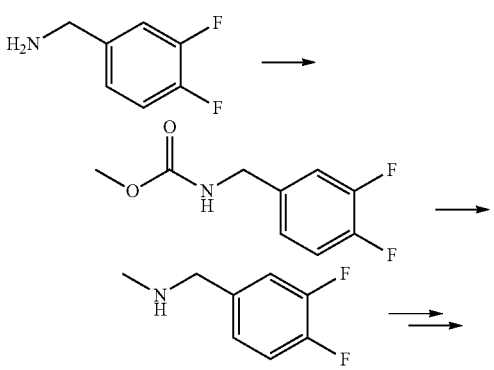

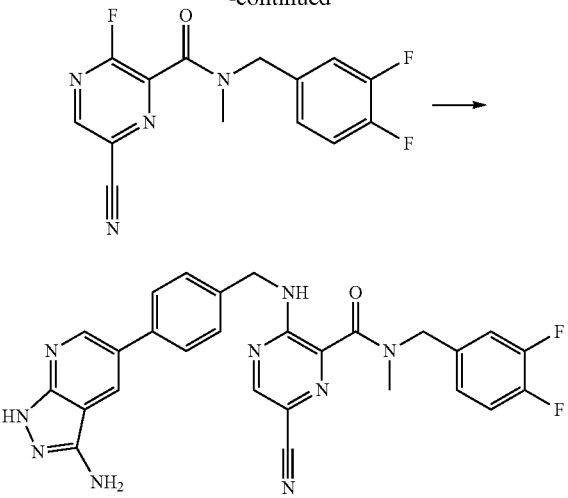

3,4-Difluoro-benzylamine (1.213 g, 8.474 mmol) was dissolved in Methylene chloride (40 mL, 600 mmol). Added Triethylamine (1.18 mL, 8.47 mmol) followed by Methyl chloroformate (0.66 mL, 8.5 mmol). Stirred at room temperature overnight. The solvents were evaporated off and purified on Combiflash(0-30% EtOAc:Hexanes) to give 1.35 g of the desired product (3,4-Difluoro-benzyl)-carbamic acid methyl ester as a white crystalline solid.

(3,4-Difluoro-benzyl)-carbamic acid methyl ester (1.346 g, 6.691 mmol) was heated with 1.0 M of Lithium tetrahydroaluminate in Tetrahydrofuran (23.4 mL, 23.4 mmol) at 60° C. LCMS after 50 minutes inducted the conversion was complete. Poured over ice, and added ether and 1N NaOH. The mixture was stirred well for 10 minutes and filtered. The filtrates were concentrated to give 0.792 g of the desired product as an oil. $^1$H NMR (300 MHz, CDCl$_3$): 7.21-6.98 (m, 3H), 3.71 (s, 2H), 2.45 (s, 3H).

6-Cyano-3-fluoro-pyrazine-2-carboxylic acid (3,4-difluoro-benzyl)-methyl-amide, (prepared from 1-(3,4-difluorophenyl)-N-methylmethanamine analogously to (S)-6-cyano-N-(1-(3,4-difluorophenyl)ethyl)-3-fluoropyrazine-2-carboxamide) (210.4 mg, 0.6870 mmol), 5-(4-(aminomethyl)phenyl)-1H-pyrazolo[3,4-b]pyridin-3-amine dihydrochloride (191.1 mg, 0.6121 mmol) were dissolved in Dimethyl sulfoxide (3.00 mL, 42.3 mmol). Added Triethylamine (259.3 uL, 1.860 mmol) and stirred at rt. Worked up with EtOAc and water. Collected 209.2 mg of 3-(4-(3-amino-1H-pyrazolo[3,4-b]pyridin-5-yl)benzylamino)-6-cyano-N-(3,4-difluorobenzyl)-N-methylpyrazine-2-carboxamide as a yellow powder. $^1$H NMR (300 MHz, DMSO-$d_6$, Two conformers observed) δ 12.01 (br. s., 1H), 8.62-8.69 (m, 1H), 8.61 (s, 0.48H), 8.56 (s, 0.52H), 8.47-8.55 (m, 1H), 8.37 (t, J=2.27 Hz, 1H), 7.56-7.67 (m, 2H), 7.31-7.52 (m, 4H), 7.19-7.27 (m, 0.47H), 7.09-7.19 (m, 0.53H), 5.61 (br. s., 2H), 4.71 (d, 0.95H), 4.70 (s, 0.96H), 4.66 (d, 1.05H), 4.54 (s, 1.04H), 2.97 (s, 1.54H), 2.93 (s, 1.46H); ES (+) MS m/e=525.9 (M+1).

Example 414 was prepared in a manner consistent with Example 182.

Example 415

Synthesis of 3-{(R)-1-[6-(3-Amino-1H-pyrazolo[3,4-b]pyridin-5-yl)-pyridin-3-yl]-ethylamino}-6-cyano-pyrazine-2-carboxylic acid [(S)-1-(3,4-difluoro-phenyl)-ethyl]-amide

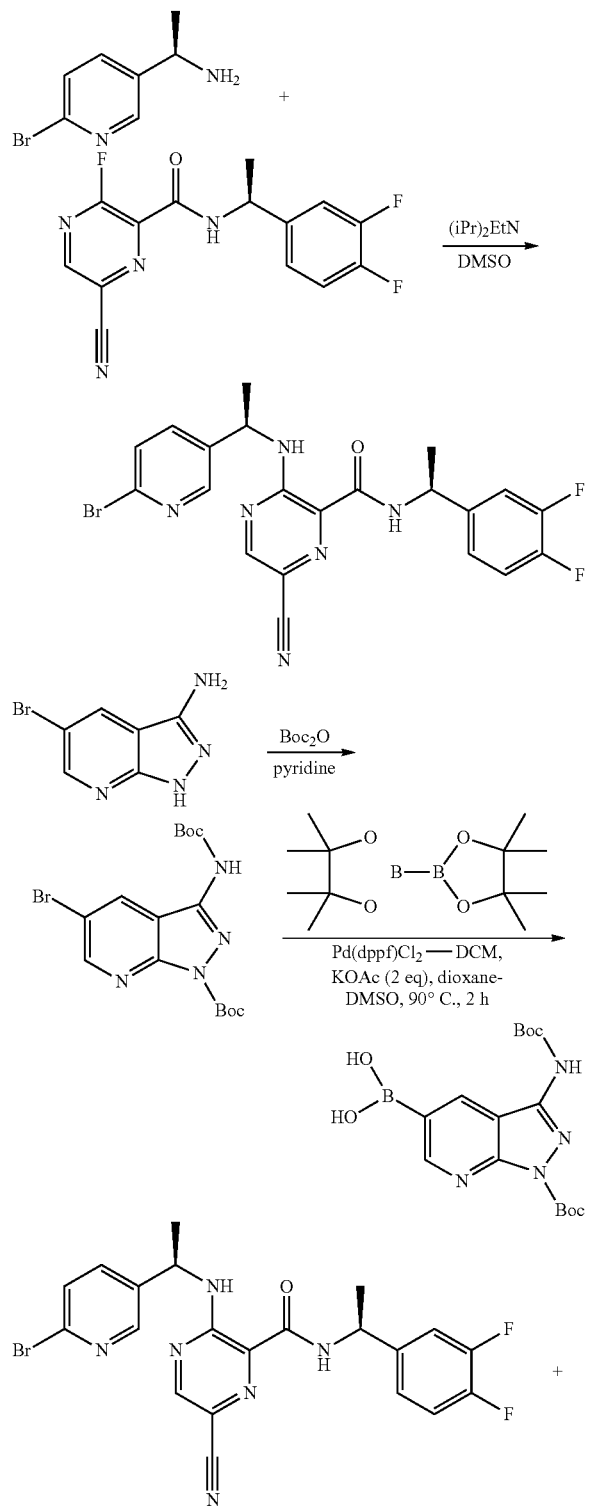

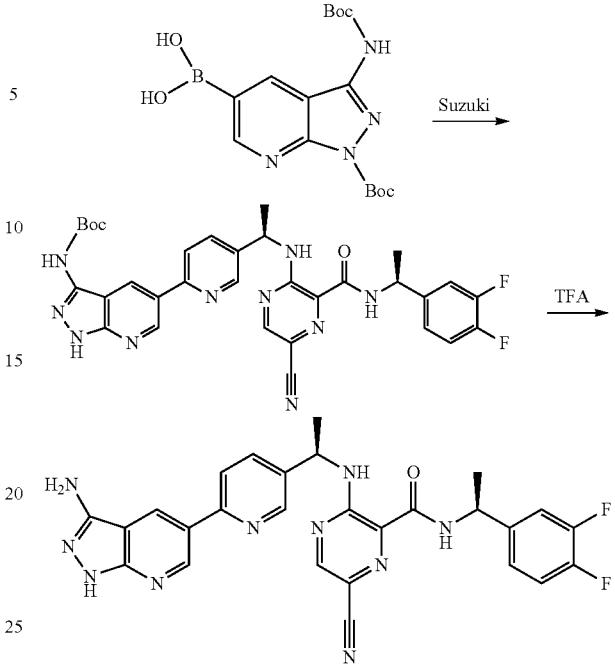

3-[(R)-1-(6-Bromo-pyridin-3-yl)-ethylamino]-6-cyano-pyrazine-2-carboxylic acid [(S)-1-(3,4-difluoro-phenyl)-ethyl]-amide N,N-Diisopropylethylamine (0.9746 mL, 5.595 mmol) was added to a solution of (R)-1-(6-Bromo-pyridin-3-yl)-ethylamine (0.2250 g, 1.119 mmol) and 6-Cyano-3-fluoro-pyrazine-2-carboxylic acid [(S)-1-(3,4-difluoro-phenyl)-ethyl]-amide (0.3770 g, 1.231 mmol) in dimethyl sulfoxide (8 mL, 100 mmol) and the mixture was heated at 80° C. in the microwave for 1 hour. The mixture was cooled to room temperature and diluted in ethylacetate. The mixture was washed with sat. aq. sodium bicarbonate solution, water and brine. The organic phase was dried over MgSO₄, filtered, concentrated to dryness under reduced pressure and purified by flash chromatography (0-10% MeOH in methylene chloride) to give the title compound.

5-Bromo-3-tert-butoxycarbonylamino-pyrazolo[3,4-b]pyridine-1-carboxylic acid tert-butyl ester 5-Bromo-1H-pyrazolo[3,4-b]pyridin-3-ylamine (2.52 g, 11.8 mmol) and Di-tert-Butyldicarbonate (5.42 g, 24.8 mmol; Supplier=Aldrich) was stirred in pyridine (47.8 mL, 591 mmol; Supplier=Acros). To the stirred mixture was added 4-dimethylaminopyridine (0.2312 g, 1.893 mmol). The mixture is homogeneous and becomes a dark yellow in color. The reaction was stirred at room temperature overnight. The reaction mixture was concentrated to dryness under reduced pressure. The residue was adsorbed onto silica gel and purified by flash chromatography using 0-10% MeOH in methylene chloride as eluent.

1-(tert-butoxycarbonyl)-3-(tert-butoxycarbonylamino)-1H-pyrazolo[3,4-b]pyridin-5-ylboronic acid A mixture of 5-Bromo-3-tert-butoxycarbonylamino-pyrazolo[3,4-b]pyridine-1-carboxylic acid tert-butyl ester (0.3124 g, 0.7559 mmol), bis(pinacolato)diboron (0.4031 g, 1.587 mmol), [1,1'-bis(diphenylphosphino)ferrocene]dichloropalladium(II), complex with dichloromethane (1:1) (0.09260 g, 0.1134 mmol; Supplier=Strem) and potassium acetate (0.1558 g, 1.587 mmol; Supplier=Aldrich) was dissolved in 1,4-Dioxane (10 mL, 100 mmol; Supplier=Acros) with stirring. The reaction was degassed by evacuating and replacing with Ar (5×). The reaction was sealed and heated at 90° C. for 1.5 hours in the microwave. The reaction was cooled to room temperature, then diluted with saturated sodium bicarbonate and extracted with ethyl acetate. The organics were washed with saturated sodium chloride, dried with sodium sulfate, filtered and evaporated to dryness under reduced pressure to give the title compound, which was used in the subsequent step without purification.

{5-[5-((R)-1-{5-Cyano-3-[(S)-1-(3,4-difluoro-phenyl)-ethylcarbamoyl]-pyrazin-2-ylamino}-ethyl)-pyridin-2-yl]-1H-pyrazolo[3,4-b]pyridin-3-yl}-carbamic acid tert-butyl ester A solution of 1-(tert-butoxycarbonyl)-3-(tert-butoxycarbonylamino)-1H-pyrazolo[3,4-b]pyridin-5-ylboronic acid (0.06983 g, 0.1846 mmol) and 3-[(R)-1-(6-Bromo-pyridin-3-yl)-ethylamino]-6-cyano-pyrazine-2-carboxylic acid [(S)-1-(3,4-difluoro-phenyl)-ethyl]-amide (0.0818 g, 0.168 mmol) in 1,4-Dioxane (4.0 mL, 51 mmol) was degassed under argon (5×).

Bis(tricyclohexylphosphine)palladium (0) (0.02240 g, 0.03357 mmol) and 1.2 M of Sodium bicarbonate in Water (0.6994 mL, 0.8393 mmol) were added. The mixture was degassed under argon then heated in the microwave at 120° C. for 20 minutes. The reaction mixture was cooled to room temperature, diluted in ethylacetate and washed with water, then brine. The organic phase was dried over MgSO$_4$, filtered and concentrated to dryness under reduced pressure. The crude product was purified by prep HPLC to give the title compound.

3-{(R)-1-[6-(3-Amino-1H-pyrazolo[3,4-b]pyridin-5-yl)-pyridin-3-yl]-ethylamino}-6-cyano-pyrazine-2-carboxylic acid [(S)-1-(3,4-difluoro-phenyl)-ethyl]-amide Trifluoroacetic Acid (0.5 mL, 6 mmol) was added to a solution of {5-[5-((R)-1-{5-Cyano-3-[(S)-1-(3,4-difluoro-phenyl)-ethylcarbamoyl]-pyrazin-2-ylamino}-ethyl)-pyridin-2-yl]-1H-pyrazolo[3,4-b]pyridin-3-yl}-carbamic acid tert-butyl ester (0.0095 g, 0.015 mmol) in Methylene chloride (2 mL, 30 mmol) and the mixture was stirred for 1 hour. The mixture was concentrated to dryness under reduced pressure, dissolved in 1 mL DMSO and purified by prep HPLC to give the title compound as a bis-TFA salt (11 mg). ESI-MS (M+H+): 541.9; $^1$H NMR (400 MHz, CD$_3$OD) δ 9.10-9.13 (m, 1H), 9.07 (d, J=2.01 Hz, 1H), 8.85-8.87 (m, 1H), 8.74-8.76 (m, 1H), 8.52 (s, 1H), 8.11-8.15 (m, 1H), 7.98-8.02 (m, 1H), 7.34-7.41 (m, 1H), 7.22-7.27 (m, 2H), 5.40-5.48 (m, 1H), 5.17-5.26 (m, 1H), 1.71 (d, J=6.78 Hz, 3H), 1.60 (d, J=7.03 Hz, 3H).

Example 416 was prepared in a manner consistent with Example 415.

Example 417 was prepared in a manner consistent with Example 25.

Examples 418-419 were prepared in a manner consistent with Example 38.

Example 420 was prepared in a manner consistent with Example 36.

Example 421 was prepared in a manner consistent with Example 39.

Examples 422-424 were prepared in a manner consistent with Example 42.

Examples 425-426 were prepared in a manner consistent with Example 25.

Examples 427-428 were prepared in a manner consistent with Example 39.

Examples 429-431 were prepared in a manner consistent with Example 174.

Example 432 was prepared in a manner consistent with Example 44.

Example 433 was prepared in a manner consistent with Example 38.

Example 434 was prepared in a manner consistent with Example 44.

Example 435 was prepared in a manner consistent with Example 42.

Example 436 was prepared in a manner consistent with Example 41.

Examples 437-440 were prepared in a manner consistent with Example 38.

Examples 441-443 were prepared in a manner consistent with Example 174.

TABLE 1

| Ex. No. | Structure | Chemical Name | ESI-MS (M + H) | 1H NMR |
|---|---|---|---|---|
| 1.5 | 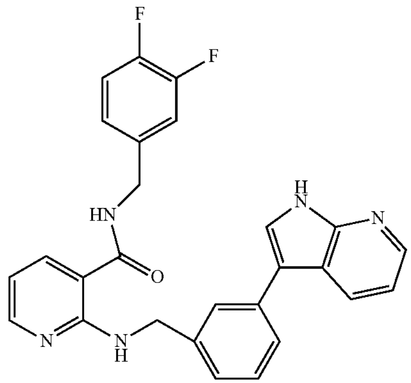 [SMILES: O=C(NCc1ccc(F)c(F)c1)c1cccnc1NCc1cccc(-c2c[nH]c3ncccc23)c1] | 2-(3-(1H-pyrrolo[2,3-b]pyridin-3-yl)benzylamino)-N-(3,4-difluorobenzyl)nicotinamide | 470.2 | 1H NMR (400 MHz, DMSO-d6) δ 9.15-9.30 (m, 2H), 8.16-8.27 (m, 4H), 7.85 (d, 1H), 7.70 (s, 1H), 7.59 (d, 1H), 7.29-7.41 (m, 3H), 7.08-7.22 (m, 3H), 6.73-6.77 (m, 1H), 4.71 (s, 2H), 4.42 (d, 2H), 2.16 (s, 1H) |
| 1.6 | 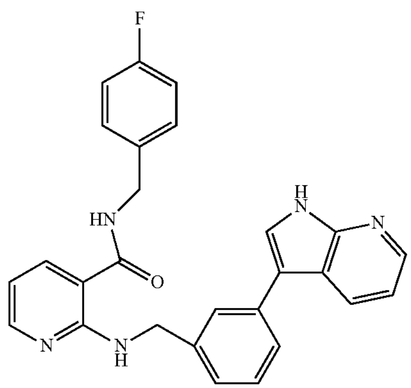 [SMILES: O=C(NCc1ccc(F)cc1)c1cccnc1NCc1cccc(-c2c[nH]c3ncccc23)c1] | 2-(3-(1H-pyrrolo[2,3-b]pyridin-3-yl)benzylamino)-N-(4-fluorobenzyl)nicotinamide | 452 | 1H NMR (400 MHz, DMSO-d6) δ 12.08 (s, 1H), 9.36-9.34 (t, 2H), 8.30-8.16 (m, 4H), 7.87 (s, 1H), 7.72 (s, 1H), 7.61 (d, 1H), 7.42-7.31 (m, 3H), 7.23 (d, 1H), 7.15-7.07 (m, 3H), 6.81-6.76 (m, 1H), 4.48-4.73 (m, 4H) |

TABLE 1-continued

| Ex. No. | Structure | Chemical Name | ESI-MS (M + H) | ¹H NMR |
|---|---|---|---|---|
| 1.7 | 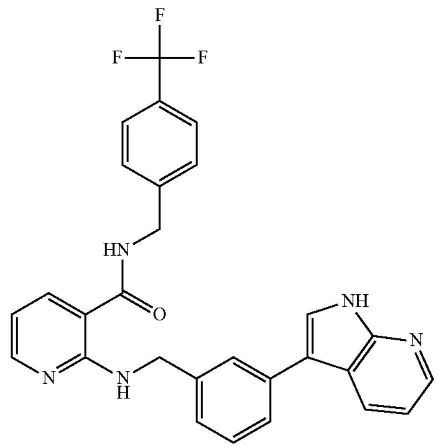 [SMILES: O=C(NCc1ccc(C(F)(F)F)cc1)c1cccnc1NCc1cccc(-c2c[nH]c3ncccc23)c1] | 2-(3-(1H-pyrrolo[2,3-b]pyridin-3-yl)benzylamino)-N-(4-(trifluoromethyl)benzyl)nicotinamide | 502 | ¹H NMR (400 MHz, DMSO-d₆) δ 12.01 (br, 1H), 9.35-9.36 (bs, 2H), 8.18-8.26 (m, 4H), 7.86 (d, 2H), 7.50-7.78 (m, 5H), 7.36-7.41 (m, 1H), 7.20-7.22 (m, 1H), 7.08 (dd, 1H), 6.74-6.79 (m, 1H), 4.71 (s, 2H), 4.50 (d, 2H) |
| 1.8 | 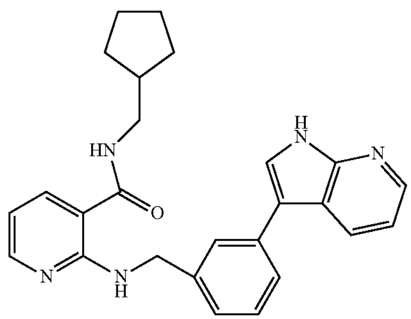 [SMILES: O=C(NCC1CCCC1)c1cccnc1NCc1cccc(-c2c[nH]c3ncccc23)c1] | 2-(3-(1H-pyrrolo[2,3-b]pyridin-3-yl)benzylamino)-N-(cyclopentylmethyl)nicotinamide | 432 | ¹H NMR (400 MHz, DMSO-d₆) δ 12.03 (s, 1H), 9.34-9.32 (bs, 1H), 8.77 (q, 1H), 8.31-8.26 (m, 2H), 8.16-8.12 (m, 2H), 7.87-7.86 (m, 1H), 7.71 (s, 1H), 7.62-7.59 (d, 1H), 7.43-7.37 (t, 1H), 7.23-7.21 (d, 1H), 7.16-7.11 (t, 1H), 6.80-6.78 (t, 1H), 4.71 (s, 2H), 3.15 (t, 2H), 2.10-2.08 (m, 1H), 1.65-1.43 (m, 6H), 1.23-1.19 (m, 2H) |
| 1.9 | 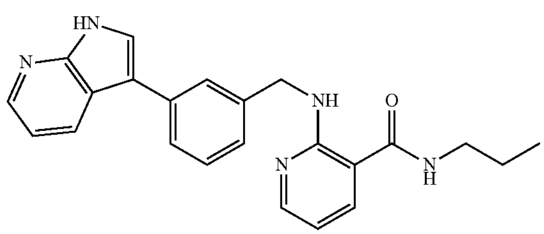 [SMILES: CCCNC(=O)c1cccnc1NCc1cccc(-c2c[nH]c3ncccc23)c1] | N-propyl-2-{[3-(1H-pyrrolo[2,3-b]pyridin-3-yl)benzyl]amino}pyridine-3-carboxamide | 386.3 | ¹H NMR (300 MHz, CDCl₃) δ 10.11 (s, 1H), 9.31 (br. s, 1H), 8.72 (t, J = 5.10 Hz, 1H), 8.24-8.32 (m, 2H), 8.10-8.20 (m, 2H), 7.87 (d, J = 2.64 Hz, 1H), 7.72 (s, 1H), 7.62 (d, J = 7.93 Hz, 1H), 7.41 (t, J = 7.74 Hz, 1H), 7.23 (d, J = 7.55 Hz, 1H), 7.15 (dd, J = 4.91, 7.93 Hz, 1H), 6.77 (dd, J = 5.48, 7.37 Hz, 1H), 4.72 (br. s., 2H), 3.13-3.26 (m, 2H), 1.52 (sxt, J = 7.25 Hz, 2H), 0.87 (t, J = 7.37 Hz, 3H) |

TABLE 1-continued

| Ex. No. | Structure | Chemical Name | ESI-MS (M + H) | ¹H NMR |
|---|---|---|---|---|
| 1.10 | 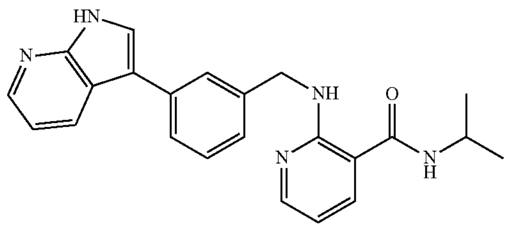 [SMILES: CC(C)NC(=O)c1cccnc1NCc1cccc(-c2c[nH]c3ncccc23)c1] | N-(propan-2-yl)-2-{[3-(1H-pyrrolo[2,3-b]pyridin-3-yl)benzyl]amino}pyridine-3-carboxamide | 386.4 | ¹H NMR (300 MHz, CDCl₃) δ 10.28 (br s, 1H), 8.69 (br t, J = 5.3 Hz, 1H), 8.34 (d, J = 4.8 Hz, 1H), 8.31 (d, J = 8.1 Hz, 1H), 8.24 (dd, J = 5.1; 1.5 Hz, 1H), 7.68 (s, 1H), 7.62 (dd, J = 7.5; 1.5 Hz, 1H), 7.54 (s, 1H), 7.51 (d, J = 7.5 Hz, 1H), 7.42 (t, J = 7.5 Hz, 1H), 7.34 (d, J = 7.5 Hz, 1H), 7.18 (dd, J = 8.0; 4.9 Hz, 1H), 6.54 (dd, J = 7.7; 4.9 Hz, 1H), 5.98 (br d, J = 7.2 Hz, 1H), 4.82 (d, J = 5.4 Hz, 2H), 4.21 (septet, J = 6.7 Hz, 1H), 1.26 (d, J = 6.3 Hz, 6H) |
| 1.11 | 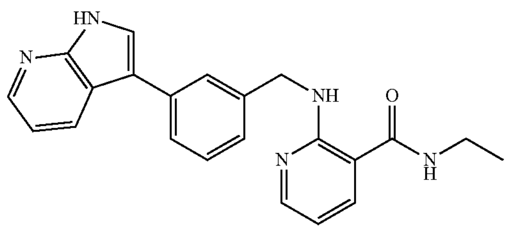 [SMILES: CCNC(=O)c1cccnc1NCc1cccc(-c2c[nH]c3ncccc23)c1] | N-ethyl-2-{[3-(1H-pyrrolo[2,3-b]pyridin-3-yl)benzyl]amino}pyridine-3-carboxamide | 372.2 | ¹H NMR (300 MHz, CDCl₃) δ 10.11 (s, 1H), 9.34 (br. s., 1H), 8.72 (t, J = 4.72 Hz, 1H), 8.24-8.31 (m, 2H), 8.16 (dd, J = 1.70, 5.48 Hz, 1H), 8.12 (d, J = 7.55 Hz, 1H), 7.87 (d, J = 2.64 Hz, 1H), 7.72 (s, 1H), 7.62 (d, J = 7.93 Hz, 1H), 7.41 (t, J = 7.74 Hz, 1H), 7.23 (d, J = 7.93 Hz, 1H), 7.15 (dd, J = 4.72, 7.74 Hz, 1H), 6.77 (dd, J = 5.29, 7.55 Hz, 1H), 4.73 (s, 2H), 3.18-3.38 (m, 2H), 1.11 (t, J = 7.18 Hz, 3H) |
| 1.12 | 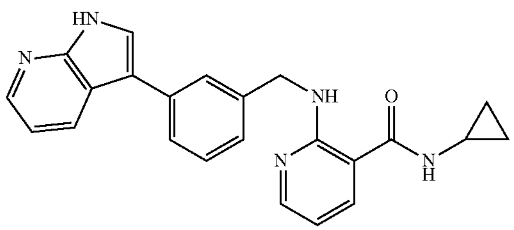 [SMILES: O=C(NC1CC1)c1cccnc1NCc1cccc(-c2c[nH]c3ncccc23)c1] | N-cyclopropyl-2-{[3-(1H-pyrrolo[2,3-b]pyridin-3-yl)benzyl]amino}pyridine-3-carboxamide | 384.3 | ¹H NMR (300 MHz, CDCl₃) δ 10.11 (s, 1H), 9.13 (br. s., 1H), 8.61 (d, J = 3.40 Hz, 1H), 8.28 (dd, J = 1.51, 4.53 Hz, 1H), 8.21-8.26 (m, 1H), 8.16 (dd, J = 1.70, 5.10 Hz, 1H), 8.02 (d, J = 7.55 Hz, 1H), 7.86 (d, J = 2.64 Hz, 1H), 7.72 (s, 1H), 7.61 (d, J = 7.93 Hz, 1H), 7.40 (t, J = 7.55 Hz, 1H), 7.18-7.27 (m, 1H), 7.14 (dd, J = 4.53, 7.93 Hz, 1H), 6.69 (dd, J = 4.91, 7.55 Hz, 1H), 4.72 (s, 2H), 2.81 (tq, J = 3.86, 7.25 Hz, 1H), 0.65-0.77 (m, 2H), 0.51-0.60 (m, 2H) |
| 1.13 | 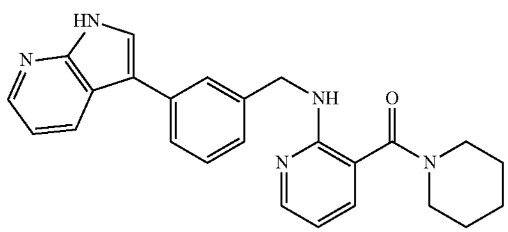 [SMILES: O=C(c1cccnc1NCc1cccc(-c2c[nH]c3ncccc23)c1)N1CCCCC1] | Piperidin-1-yl(2-{[3-(1H-pyrrolo[2,3-b]pyridin-3-yl)benzyl]amino}pyridin-3-yl)methanone | 412.2 | — |

TABLE 1-continued

| Ex. No. | Structure | Chemical Name | ESI-MS (M + H) | ¹H NMR |
|---|---|---|---|---|
| 1.14 | 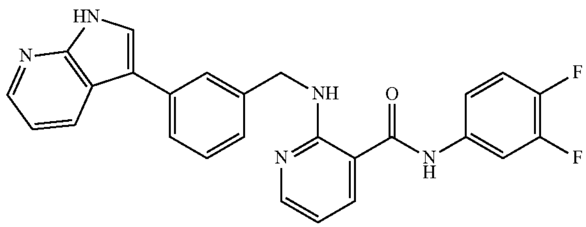 [SMILES: O=C(Nc1ccc(F)c(F)c1)c1cccnc1NCc1cccc(-c2c[nH]c3ncccc23)c1] | N-(3,4-difluorophenyl)-2-{[3-(1H-pyrrolo[2,3-b]pyridin-3-yl)benzyl]amino}pyridine-3-carboxamide | 456.2 | — |
| 1.15 | 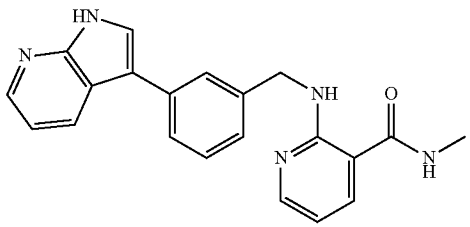 [SMILES: CNC(=O)c1cccnc1NCc1cccc(-c2c[nH]c3ncccc23)c1] | N-methyl-2-{[3-(1H-pyrrolo[2,3-b]pyridin-3-yl)benzyl]amino}pyridine-3-carboxamide | 358.2 | — |
| 1.16 | 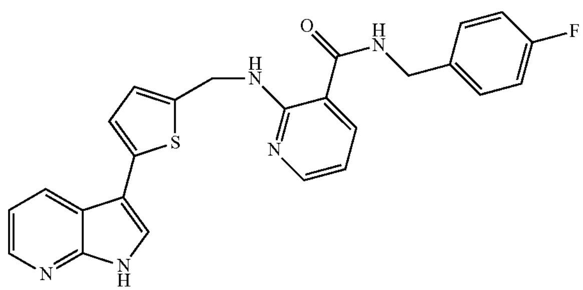 [SMILES: O=C(NCc1ccc(F)cc1)c1cccnc1NCc1ccc(-c2c[nH]c3ncccc23)s1] | 2-(((5-(1H-pyrrolo[2,3-b]pyridin-3-yl)thiophen-2-yl)methyl)amino)-N-(4-fluorobenzyl)nicotinamide | 458.1 | ¹H NMR (400 MHz, DMSO-$d_6$) δ 11.97 (s, 1H), 9.17 (t, 1H), 8.91 (br, 1H), 8.28-8.20 (m, 3H), 8.09-8.06 (d, 1H), 7.78-7.77 (d, 1H), 7.35-7.31 (m, 2H), 7.20-7.02 (m, 5H), 6.72-6.68 (m, 1H), 4.80 (s, 2H), 4.40 (d, 2H) |
| 1.17 | 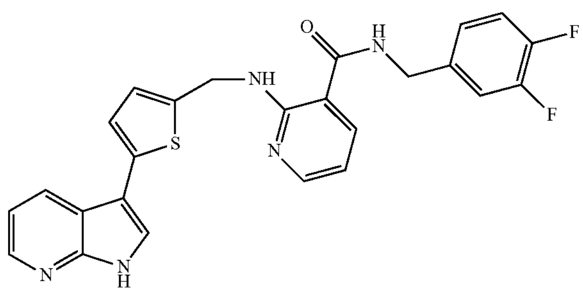 [SMILES: O=C(NCc1ccc(F)c(F)c1)c1cccnc1NCc1ccc(-c2c[nH]c3ncccc23)s1] | 2-(((5-(1H-pyrrolo[2,3-b]pyridin-3-yl)thiophen-2-yl)methyl)amino)-N-(3,4-difluorobenzyl)nicotinamide | 476.1 | ¹H NMR (400 MHz, DMSO-$d_6$) δ 11.97 (s, 1H), 9.19 (q, 1H), 8.90 (bs, 1H), 8.28-8.20 (m, 3H), 8.09 (d, 1H), 7.78 (d, 1H), 7.37-7.31 (m, 2H), 7.20-7.14 (m, 3H), 7.02 (d, 1H), 6.73-6.69 (m, 1H), 4.80 (s, 2H), 4.40 (d, 2H) |

| Ex. No. | Structure | Chemical Name | ESI-MS (M+H) | ¹H NMR |
|---|---|---|---|---|
| 1.18 | 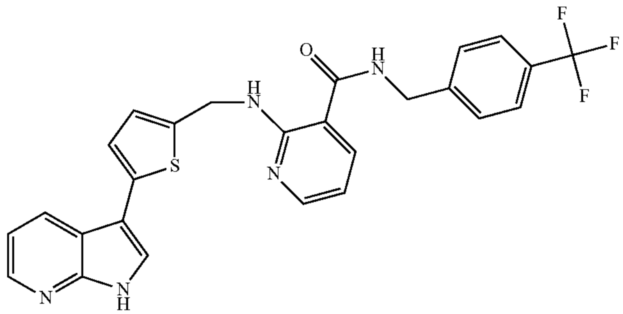 [SMILES: O=C(NCc1ccc(C(F)(F)F)cc1)c1cccnc1NCc1ccc(-c2c[nH]c3ncccc23)s1] | 2-(((5-(1H-pyrrolo[2,3-b]pyridin-3-yl)thiophen-2-yl)methyl)amino)-N-(4-trifluoromethyl)benzyl)nicotinamide | 508 | ¹H NMR (400 MHz, DMSO-d₆) δ 11.96 (s, 1H), 9.25 (m, 1H), 8.80 (bs, 1H), 8.27-8.11 (m, 4H), 7.77 (d, 1H), 7.69 (d, 1H), 7.65 (d, 1H) 7.19-7.13 (m, 2H), 7.18-7.13 (m, 2H), 7.02 (d 1H), 6.71 (m, 1H), 4.79 (s, 2H), 4.62 (br, 2H) |
| 1.19 | 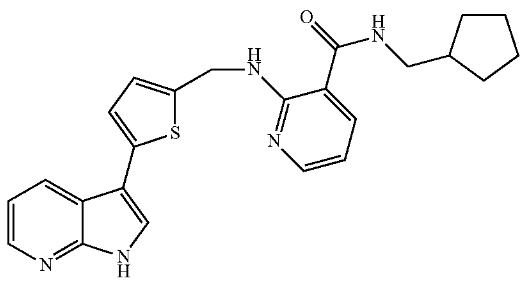 [SMILES: O=C(NCC1CCCC1)c1cccnc1NCc1ccc(-c2c[nH]c3ncccc23)s1] | 2-(((5-(1H-pyrrolo[2,3-b]pyridin-3-yl)thiophen-2-yl)methyl)amino)-N-4-(cyclopentylmethyl)nicotinamide | 432 | ¹H NMR (400 MHz, DMSO-d₆) δ 11.96 (s, 1H), 8.62 (bs, 1H), 8.27-8.26 (bs, 1H), 8.26-8.19 (m, 3H), 8.01 (d, 1H), 7.78 (d, 1H), 7.20-7.02 (m, 3H), 6.72-6.69 (m, 1H), 4.79 (s, 2H), 3.28-3.11 (t, 2H), 2.10-2.08 (m, 1H), 1.67-1.45 (m, 6H), 1.23-1.20 (m, 2H) |
| 1.20 | 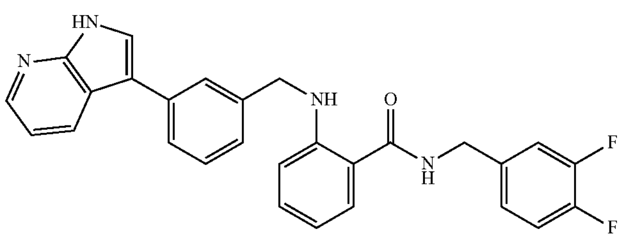 [SMILES: O=C(NCc1ccc(F)c(F)c1)c1ccccc1NCc1cccc(-c2c[nH]c3ncccc23)c1] | 2-(3-(1H-pyrrolo[2,3-b]pyridin-3-yl)benzylamino)-N-(3,4-difluorobenzyl)benzamide | 469.2 | ¹H NMR (300 MHz, CDCl₃) δ 8.69 (s, 1H), 8.43 (t, J = 5.4 Hz, 1H), 8.29 (dd, J = 5.1; 1.5 Hz, 1H), 7.85 (dd, J = 8.7; 1.5 Hz, 1H), 7.77-7.72 (m, 2H), 7.67 (dd, J = 7.6; 1.7 Hz, 1H), 7.08 (d, J = 3.9 Hz, 1H), 6.97-6.90 (m, 2H), 6.85-6.78 (m, 2H), 6.69 (tt, J = 9.0; 2.3 Hz, 1H), 6.62 (br s, 1H), 6.53 (dd, J = 7.9; 5.0 Hz, 1H), 4.81 (d, J = 5.7 Hz, 2H), 4.54 (d, J = 6.0 Hz, 2H), 3.06 (br s, 1H), 1.01-0.93 (m, 2H), 0.78-0.71 (m, 2H) |

TABLE 1-continued

| Ex. No. | Structure | Chemical Name | ESI-MS (M + H) | ¹H NMR |
|---|---|---|---|---|
| 2.4 | 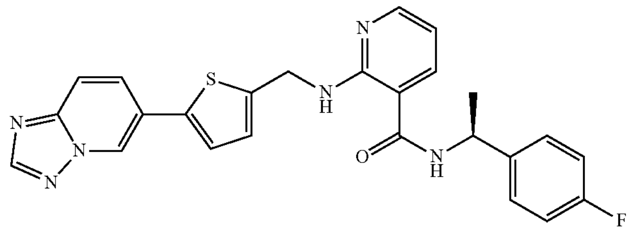 [SMILES: C[C@H](NC(=O)c1cccnc1NCc1ccc(-c2ccc3ncnn3c2)s1)c1ccc(F)cc1] | N-[(1S)-1-(4-fluorophenyl)ethyl]-2-({5-([1,2,4]triazolo[1,5-a]pyridin-6-yl)thiophen-2-yl]methyl}aminopyridine-3-carboxamide | 472.1 | ¹H NMR (400 MHz, CD₃OD) δ 8.93 (br, 1H), 8.35 (br, 1H), 8.23 (d, 1H), 8.01-8.03 (dd, 1H), 7.84 (d, 1H), 7.69 (d, 1H), 7.28-7.31 (m, 3H), 7.03 (d, 1H), 6.91-6.96 (m, 2H), 6.81-6.85 (m, 1H), 5.06-5.11 (q, 1H), 4.77 (s, 2H), 1.44 (d, 3H) |
| 2.5 | 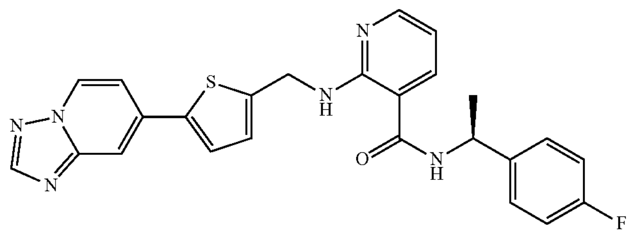 [SMILES: C[C@H](NC(=O)c1cccnc1NCc1ccc(-c2ccn3ncnc3c2)s1)c1ccc(F)cc1] | N-[(1S)-1-(4-fluorophenyl)ethyl]-2-({5-([1,2,4]triazolo[1,5-a]pyridin-7-yl)thiophen-2-yl]methyl}aminopyridine-3-carboxamide | 472.1 | ¹H NMR (400 MHz, CD₃OD) δ 8.93 (s, 1H), 8.04-8.10 (m, 4H), 7.93 (s, 1H), 7.82 (d, 1H), 7.34-7.35 (m, 1H), 7.27-7.31 (m, 2H), 7.02 (d, 1H), 6.91-6.95 (m, 2H), 6.70-6.74 (dd, 1H), 5.05-5.10 (q, 1H), 4.77 (s, 2H), 1.43 (d, 3H) |
| 2.6 | 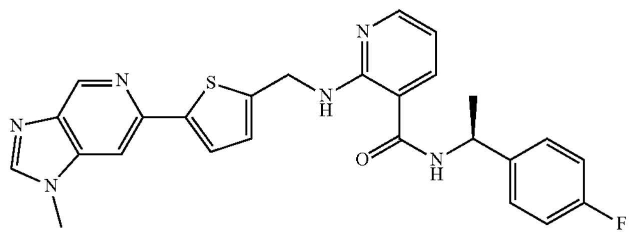 [SMILES: C[C@H](NC(=O)c1cccnc1NCc1ccc(-c2cc3c(cn2)ncn3C)s1)c1ccc(F)cc1] | (S)-N-(1-(4-fluorophenyl)ethyl)-2-((5-(1-methyl-1H-imidazo[4,5-c]pyridin-6-yl)thiophen-2-yl)methyl)aminonicotinamide | 486.16 | ¹H NMR (400 MHz, CD₃OD) δ 8.91 (s, 1H), 8.50 (br, 1H), 8.18 (d, 1H), 8.11 (s, 1H), 8.03-8.05 (dd, 1H), 7.59 (d, 1H), 7.28-7.31 (m, 2H), 7.10 (d, 1H), 6.91-6.96 (m, 2H), 6.78-6.80 (m, 1H), 5.06-5.11 (q, 1H), 4.81 (s, 2H), 3.916 (s, 3H), 1.44 (d, 3H) |
| 2.7 | 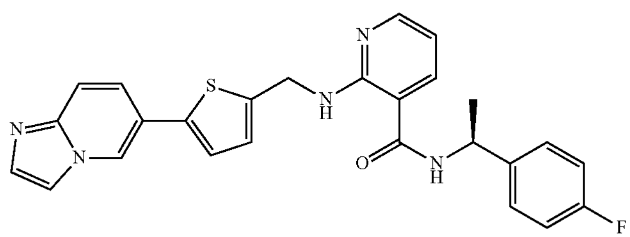 [SMILES: C[C@H](NC(=O)c1cccnc1NCc1ccc(-c2ccc3nccn3c2)s1)c1ccc(F)cc1] | (S)-N-(1-(4-fluorophenyl)ethyl)-2-(((5-(imidazo[1,2-a]pyridin-6-yl)methyl)aminonicotinamide | 471.15 | ¹H NMR (400 MHz, CD₃OD) δ 8.67 (br, 1H), 8.36 (br, 1H), 8.14 (dd, 1H), 8.02 (dd, 1H), 7.78 (br, 1H), 7.48 (d, 1H), 7.40 (d, 1H), 7.29-7.32 (m, 2H), 7.04 (d, 1H), 6.92-6.96 (m, 2H), 6.76-6.80 (m, 1H), 5.07-5.12 (q, 1H), 4.79 (s, 2H), 1.45 (d, 3H) |

TABLE 1-continued

| Ex. No. | Structure | Chemical Name | ESI-MS (M + H) | ¹H NMR |
|---|---|---|---|---|
| 2.8 | 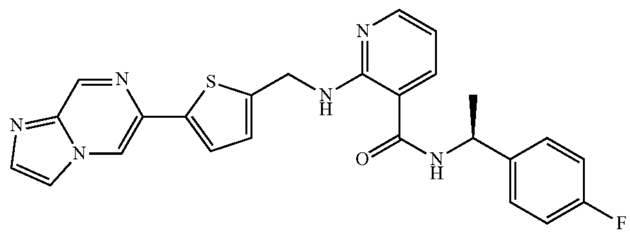 [SMILES: C[C@H](NC(=O)c1cccnc1NCc1ccc(-c2cn3ccnc3cn2)s1)c1ccc(F)cc1] | (S)-N-(1-(4-fluorophenyl)ethyl)-2-(((5-(imidazo[1,2-a]pyrazin-6-yl)thiophen-2-yl)methyl)amino)nicotinamide | 472.1 | ¹H NMR (400 MHz, CD₃OD) δ 9.08 (s, 1H), 9.03 (s, 1H), 8.36 (d, 1H), 8.10-8.14 (m, 2H), 7.97 (br, 1H), 7.56 (d, 1H), 7.39-7.42 (m, 2H), 7.14 (d, 1H), 7.03-7.07 (m, 2H), 6.95 (dd, 1H), 5.18 (q, 1H), 4.91 (s, 2H), 1.56 (d, 3H) |
| 2.9 | 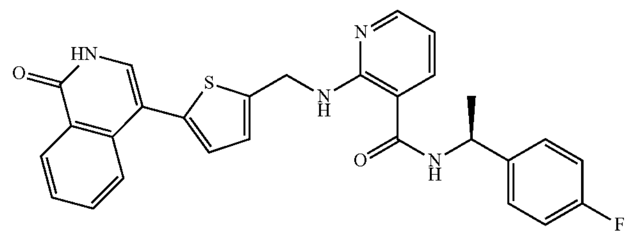 [SMILES: C[C@H](NC(=O)c1cccnc1NCc1ccc(-c2c[nH]c(=O)c3ccccc23)s1)c1ccc(F)cc1] | (S)-N-(1-(4-fluorophenyl)ethyl)-2-(((5-(1-oxo-1,2-dihydroisoquinolin-4-yl)thiophen-2-yl)methyl)amino)nicotinamide | 499.2 | ¹H NMR (400 MHz, CDCl₃) δ 10.97 (br, 1H), 8.55 (br, 1H), 8.46 (d, 1H), 8.28 (br, 1H), 7.89 (d, 1H), 7.70-7.63 (m, 2H), 7.51-7.55 (m, 2H), 7.22 (br, 1H), 7.00-7.05 (m, 3H), 6.94 (d, 1H), 6.56 (br, 1H), 6.31 (br, 1H), 5.23 (t, 1H), 4.83-4.94 (m, 2H), 1.57 (d, 3H) |
| 2.10 | 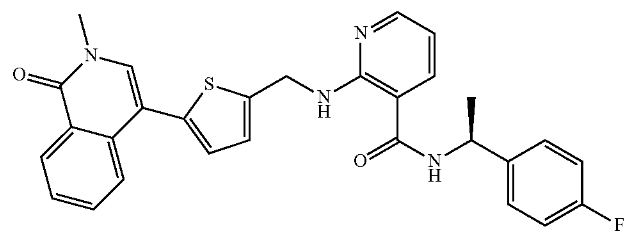 [SMILES: C[C@H](NC(=O)c1cccnc1NCc1ccc(-c2cn(C)c(=O)c3ccccc23)s1)c1ccc(F)cc1] | (S)-N-(1-(4-fluorophenyl)ethyl)-2-(((5-(2-methyl-1-oxo-1,2-dihydroisoquinolin-4-yl)thiophen-2-yl)methyl)amino)nicotinamide | 513.6 | ¹H NMR (400 MHz, CD₃OD) δ 8.83 (d, 1H), 8.67 (t, 1H), 8.30 (d, 1H), 8.23 (dd, 1H), 8.15 (d, 1H), 7.77-7.70 (m, 2H), 7.63 (s, 1H), 7.54-7.57 (m, 1H), 7.42-7.18 (m, 2H), 7.15-6.65 (m, 4H), 6.68 (dd, 1H), 5.12-5.09 (m, 1H), 4.81 (d, 2H), 3.53 (s, 3H), 1.43 (d, 3H) |
| 2.11 | 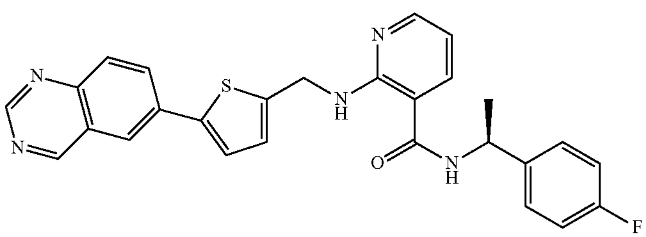 [SMILES: C[C@H](NC(=O)c1cccnc1NCc1ccc(-c2ccc3ncncc3c2)s1)c1ccc(F)cc1] | (S)-N-(1-(4-fluorophenyl)ethyl)-2-(((5-(quinazolin-6-yl)thiophen-2-yl)methyl)amino)nicotinamide | 484.1 | ¹H NMR (400 MHz, CD₃OD) δ 9.37 (d, 1H), 9.06 (d, 1H), 8.14-8.17 (m, 1H), 8.08-8.10 (m, 2H), 7.85-7.89 (m, 2H), 7.26-7.35 (m, 2H), 6.89-6.94 (m, 3H), 6.57 (dd, 1H), 5.06 (q, 1H), 4.73 (s, 2H), 1.42 (d, 3H) |

TABLE 1-continued

| Ex. No. | Structure | Chemical Name | ESI-MS (M + H) | $^1$H NMR |
|---|---|---|---|---|
| 2.12 | 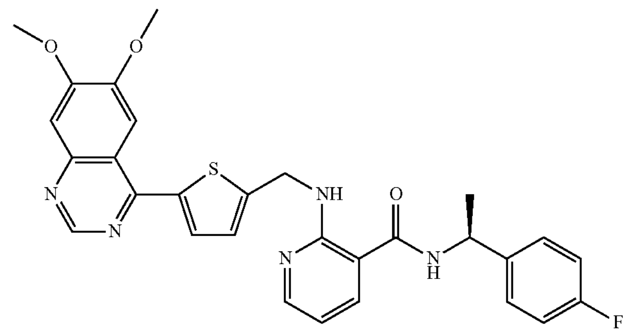 [SMILES: COc1cc2ncnc(-c3ccc(CNc4ncccc4C(=O)N[C@@H](C)c4ccc(F)cc4)s3)c2cc1OC] | (S)-2-(((5-(6,7-dimethoxyquinazolin-4-yl)thiophen-2-yl)methyl)amino)-N-(1-(4-fluorophenyl)ethyl)nicotinamide | 544.2 | $^1$H NMR (400 MHz, CDCl$_3$) δ 9.04 (s, 1H), 8.26 (d, 1H), 7.72 (s, 1H), 8.62 (t, 1H), 7.63 (m, 2H), 7.32 (m, 3H), 7.14 (d, 1H), 7.02 (t, 2H), 6.55 (m, 1H), 5.20 (m, 1H), 4.94 (m, 2H), 4.06 (s, 3H), 4.01 (s, 3H), 1.55 (d, 3H) |
| 2.13.1 | 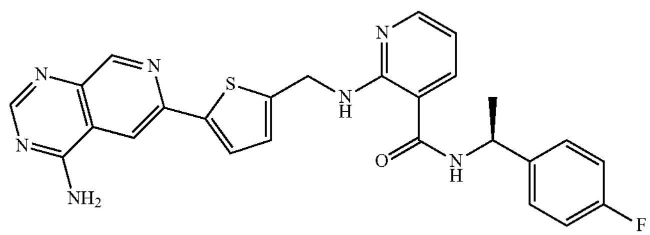 [SMILES: C[C@H](NC(=O)c1cccnc1NCc1ccc(-c2cc3c(N)ncnc3cn2)s1)c1ccc(F)cc1] | (S)-2-(((5-(4-aminopyrido[3,4-d]pyrimidin-6-yl)thiophen-2-yl)methyl)amino)-N-(1-(4-fluorophenyl)ethyl)nicotinamide | 499.2 | $^1$H NMR (400 MHz, CD$_3$OD) δ 8.97 (s, 1H), 8.41 (s, 1H), 8.34 (s, 1H), 8.17-8.15 (dd, 1H), 7.93 (d, 1H), 7.67 (s, 1H), 7.54 (m, 1H), 7.34-7.32 (m, 2H), 7.01-6.96 (m, 3H), 6.62 (m, 1H), 5.16-5.12 (q, 1H), 4.81 (s, 2H), 1.52-1.51 (d, 3H) |
| 2.13.2 | 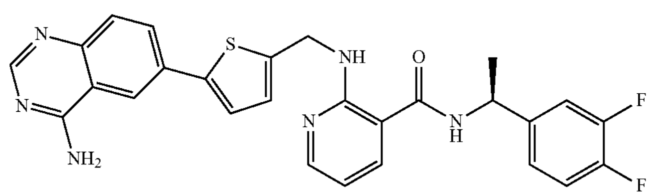 [SMILES: C[C@H](NC(=O)c1cccnc1NCc1ccc(-c2ccc3ncnc(N)c3c2)s1)c1ccc(F)c(F)c1] | 2-{[5-(4-aminopyrido[3,4-d]pyrimidin-2-yl)thiophen-2-yl]methyl}amino)-N-(1-(4-fluorophenyl)ethyl)nicotinamide | 504.3 | $^1$H NMR (300 MHz, DMSO-d$_6$) δ 9.17 (m, br, 3H), 9.03 (s, 1H), 8.76-8.90 (m, 1H), 8.65 (d, J = 11.33 Hz, 2H), 8.26 (dd, J = 1.89, 4.91 Hz, 1H), 8.08 (dd, J = 1.70, 7.74 Hz, 1H), 7.60 (d, J = 3.78 Hz, 1H), 6.96-7.18 (m, 4H), 6.70 (dd, J = 4.72, 7.74 Hz, 1H), 4.80-4.89 (m, 2H), 4.40-4.50 (m, 2H) |
| 2.14 | 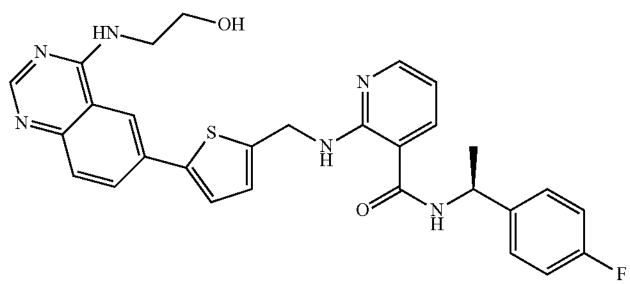 [SMILES: C[C@H](NC(=O)c1cccnc1NCc1ccc(-c2ccc3ncnc(NCCO)c3c2)s1)c1ccc(F)cc1] | (S)-N-(1-(4-fluorophenyl)ethyl)-2-(((5-(4-(2-hydroxyethyl)amino)quinazolin-6-yl)thiophen-2-yl)methyl)amino)nicotinamide | 542 | $^1$H NMR (400 MHz, CD$_3$OD) δ 8.28 (s, 1H), 8.23 (d, 1H), 8.08 (m, 1H), 7.85-7.91 (m, 2H), 7.57 (d, 1H), 7.27-7.30 (m, 3H), 6.91-6.95 (m, 3H), 6.55-6.58 (dd, 1H), 5.05-5.10 (q, 1H), 4.72 (d, 2H), 3.64-3.74 (m, 4H), 1.42 (d, 3H) |

TABLE 1-continued

| Ex. No. | Structure | Chemical Name | ESI-MS (M + H) | ¹H NMR |
|---|---|---|---|---|
| 2.15 | 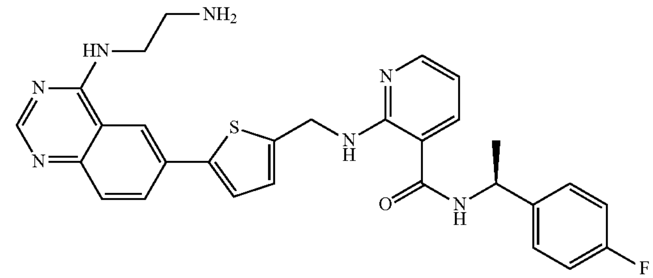 [SMILES: C[C@H](NC(=O)c1cccnc1NCc1ccc(-c2ccc3ncnc(NCCN)c3c2)s1)c1ccc(F)cc1] | (S)-2-(((5-(4-(2-aminoethylamino)quinazolin-6-yl)thiophen-2-yl)methyl)amino)-N-(1-(4-fluorophenyl)ethyl)nicotinamide | 542.0 | ¹H NMR (400 MHz, CD₃OD) δ 8.48 (s, 1H), 8.29 (d, 1H), 8.19 (dd, 1H), 8.05 (dd, 1H), 7.96 (dd, 1H), 7.72 (d, 1H), 7.41-7.37 (m, 3H), 7.06-7.02 (m, 3H), 6.66 (dd, 1H), 5.18 (q, 1H), 4.83 (s, 2H), 3.93 (t, 1H), 3.29 (t, 1H), 1.53 (d, 3H) |
| 2.16 | 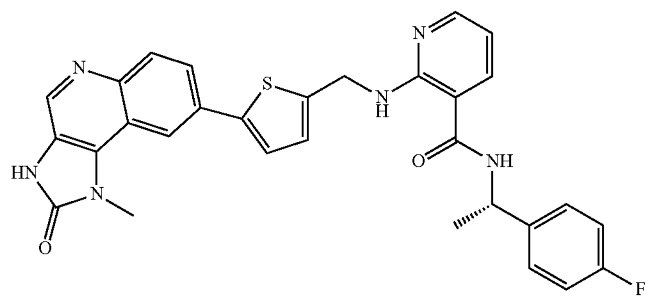 [SMILES: C[C@H](NC(=O)c1cccnc1NCc1ccc(-c2ccc3ncc4[nH]c(=O)n(C)c4c3c2)s1)c1ccc(F)cc1] | (S)-N-(1-(4-fluorophenyl)ethyl)-2-(((5-(1-methyl-2-oxo-2,3-dihydro-1H-imidazo[4,5-c]quinolin-8-yl)methyl)amino)nicotinamide | 552.9 | ¹H NMR (400 MHz, DMSO-d₆) δ 11.52 (br, 1H), 8.66 (t, 1H), 8.61 (s, 1H), 8.38 (d, 1H), 8.23 (t, 1H), 8.09 (dd, 1H), 8.00 (d, 1H), 7.83 (dd, 1H), 7.53 (d, 1H), 7.41 (dd, 2H), 7.15-7.01 (m, 3H), 6.68 (dd, 1H), 5.12 (t, 1H), 4.81 (d, 2H), 3.83 (s, 3H), 1.45 (d, 3H) |
| 2.17 | 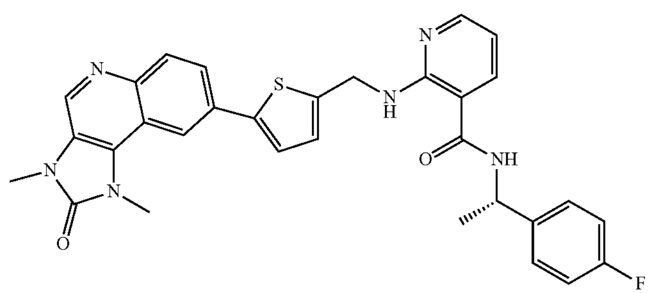 [SMILES: C[C@H](NC(=O)c1cccnc1NCc1ccc(-c2ccc3ncc4c(c3c2)n(C)c(=O)n4C)s1)c1ccc(F)cc1] | (S)-2-(((5-(1,3-dimethyl-2-oxo-2,3-dihydro-1H-imidazo[4,5-c]quinolin-8-yl)thiophen-2-yl)methyl)amino)-N-(1-(4-fluorophenyl)ethyl)nicotinamide | 566.9 | ¹H NMR (400 MHz, DMSO-d₆) δ 8.56 (t, 2H), 8.28 (t, 1H), 8.09 (d, 1H), 8.03 (d, 1H), 7.75 (dd, 1H), 7.67 (dd, 1H), 7.32 (dd, 2H), 7.23 (d, 1H), 7.02-6.98 (m, 3H), 6.55 (dd, 2H), 5.20 (t, 1H), 4.86 (t, 2H), 3.82 (s, 3H), 3.48 (s, 3H), 1.56 (d, 3H) |

TABLE 1-continued

| Ex. No. | Structure | Chemical Name | ESI-MS (M + H) | ¹H NMR |
|---|---|---|---|---|
| 2.18 | 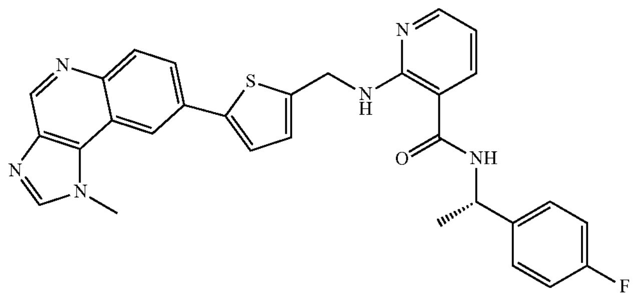 [SMILES: C[C@H](NC(=O)c1cccnc1NCc1ccc(-c2ccc3ncc4ncn(C)c4c3c2)s1)c1ccc(F)cc1] | (S)-N-(1-(4-fluorophenyl)ethyl-2-(((5-(1-methyl-1H-imidazo[4,5-c]quinolin-8-yl)thiophen-2-yl)methyl)amino)nicotinamide | 536.9 | ¹H NMR (400 MHz, DMSO-d₆) δ 9.15 (s, 1H), 8.56 (t, 1H), 8.27 (dd, 1H), 8.17 (d, 1H), 8.09 (d, 1H), 8.32 (s, 1H), 7.76 (dd, 1H), 7.70 (dd, 1H), 7.32-7.28 (m, 2H), 7.18 (d, 1H), 7.00-6.96 (m, 3H), 6.77 (d, 1H), 6.51 (d, 1H), 5.20 (t, 1H), 4.85 (t, 2H), 4.15 (s, 3H), 1.53 (d, 3H) |
| 2.19 | 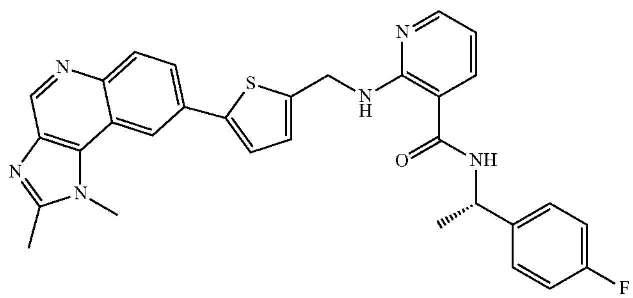 [SMILES: Cc1nc2cnc3ccc(-c4ccc(CNc5ncccc5C(=O)N[C@@H](C)c5ccc(F)cc5)s4)cc3c2n1C] | (S)-2-(((5-(1,2-dimethyl-1H-imidazo[4,5-c]quinolin-8-yl)thiophen-2-yl)methyl)amino)-N-(1-(4-fluorophenyl)ethyl)nicotinamide | 550.9 | ¹H NMR (400 MHz, CDCl₃) δ 9.11 (s, 1H), 8.55 (t, 1H), 8.28 (d, 1H), 8.24 (s, 1H), 8.14 (d, 1H), 7.78 (d, 1H), 7.66 (d, 1H), 7.31 (m, 1H), 7.21 (d, 1H), 7.01 (m, 3H), 6.54 (m, 2H), 5.21 (m, 1H), 4.86 (m, 2H), 4.08 (s, 3H), 2.66 (s, 3H), 1.54 (d, 3H) |
| 2.20 | 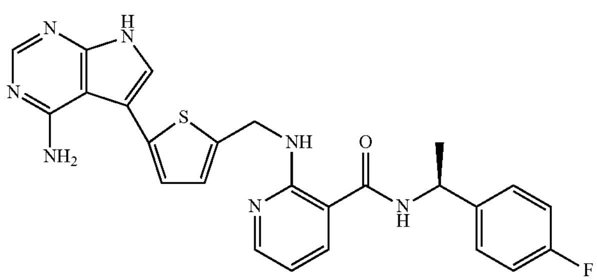 [SMILES: C[C@H](NC(=O)c1cccnc1NCc1ccc(-c2c[nH]c3ncnc(N)c23)s1)c1ccc(F)cc1] | (S)-2-(((5-(4-amino-7H-pyrrolo[2,3-d]pyrimidin-5-yl)thiophen-2-yl)methyl)amino)-N-(1-(4-fluorophenyl)ethyl)nicotinamide | 488.2 | ¹H NMR (400 MHz, CD₃OD) δ 8.19-8.17 (dd, 2H), 8.13 (br, 1H), 7.89-7.75 (m, 2H), 7.34-7.31 (m, 2H), 7.09 (s, 1H), 6.99-6.97 (m, 3H), 6.89 (d, 1H), 6.62-6.58 (m, 1H), 5.20-5.15 (m, 1H), 4.79 (q, 2H), 1.52 (d, 3H) |

TABLE 1-continued

| Ex. No. | Structure | Chemical Name | ESI-MS (M + H) | ¹H NMR |
|---|---|---|---|---|
| 2.21 | 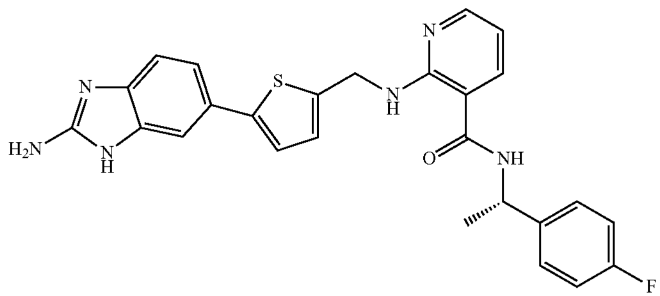 [SMILES: C[C@H](NC(=O)c1cccnc1NCc1ccc(-c2ccc3nc(N)[nH]c3c2)s1)c1ccc(F)cc1] | (S)-2-(((5-(2-amino-1H-benzo[d]imidazol-6-yl)thiophen-2-yl)methyl)amino)-N-(1-(4-fluorophenyl)ethyl)nicotinamide | 487.2 | ¹H NMR (400 MHz, DMSO-d₆) δ 12.68 (br, 1H), 8.74 (br, 1H), 8.59 (br, 2H), 8.24 (d, 1H), 8.14 (d, 1H), 7.49 (s, 1H), 7.39-7.42 (m, 3 H), 7.34 (d, 1 H), 7.29 (d, 1H), 7.14 (m, 2H), 7.01 (d, 1H), 6.69-6.72 (dd, 1H), 5.07-5.14 (m, 1H), 4.77 (s, 2H), 1.46 (d, 3H) |
| 2.22 | 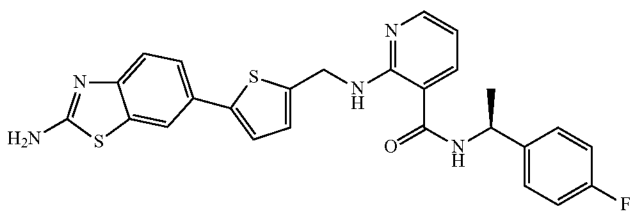 [SMILES: C[C@H](NC(=O)c1cccnc1NCc1ccc(-c2ccc3nc(N)sc3c2)s1)c1ccc(F)cc1] | (S)-2-(((5-(2-aminobenzo[d]thiazol-6-yl)thiophen-2-yl)methyl)amino)-N-(1-(4-fluorophenyl)ethyl)nicotinamide | 504.1 | ¹H NMR (400 MHz, DMSO-d₆) δ 8.90 (d, 1H), 8.70-8.72 (bs, 1H), 8.22-8.23 (m, 3H), 8.14 (dd, 1H), 7.97-7.96 (d, 1H), 7.48 (dd, 1H), 7.42-7.39 (m, 2 H), 7.35 (d, 1H), 7.24 (d, 1H), 7.16-7.11 (m, 2H), 6.99 (d, 1H), 6.72-6.69 (m, 1H), 5.10 (m, 1H), 4.77 (s, 2H), 1.44 (d, 3H) |
| 2.23 | 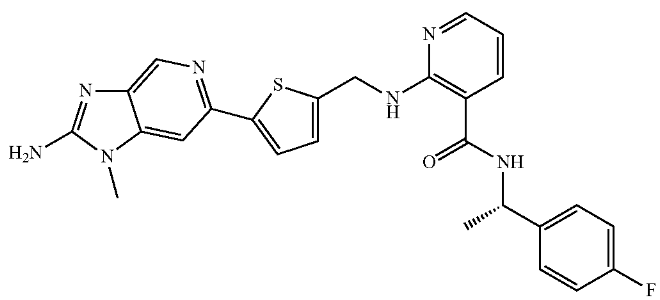 [SMILES: C[C@H](NC(=O)c1cccnc1NCc1ccc(-c2cc3c(cn2)nc(N)n3C)s1)c1ccc(F)cc1] | (S)-2-(((5-(2-amino-1-methyl-1H-imidazo[4,5-c]pyridin-6-yl)thiophen-2-yl)methyl)amino)-N-(1-(4-fluorophenyl)ethyl)nicotinamide | 502.2 | ¹H NMR (400 MHz, DMSO-d₆) δ 8.75-8.91 (br, 4H), 8.47 (s, 1H), 8.24 (d, 1H), 8.13 (d, 1H), 8.06 (s, 1H), 7.65 (d, 1H), 7.16-7.43 (m, 2H), 7.13 (m, 2H), 7.06 (d, 1H), 6.80 (dd, 1H), 5.11 (m, 1H), 4.80 (s, 2H), 3.64 (s, 3H), 1.46 (d, 3H) |

| Ex. No. | Structure | Chemical Name | ESI-MS (M + H) | ¹H NMR |
|---|---|---|---|---|
| 2.24 | 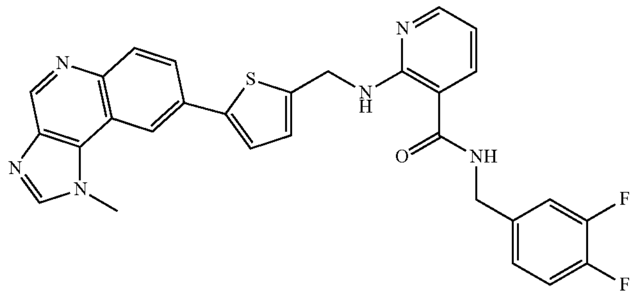 [SMILES: Cn1cnc2cnc3ccc(-c4ccc(CNc5ncccc5C(=O)NCc5ccc(F)c(F)c5)s4)cc3c21] | N-(1-(3,4-difluorophenyl)ethyl)-2-(((5-(1-methyl-1H-imidazo[4,5-c]quinolin-8-yl)thiophen-2-yl)methyl)amino)nicotinamide | 541.2 | ¹H NMR (300 MHz, CDCl₃) δ 9.27 (s, 1H), 8.59 (t, J = 5.67 Hz, 1H), 8.40 (d, J = 1.51 Hz, 1H), 8.32 (dd, J = 1.89, 4.91 Hz, 1H), 8.23 (d, J = 8.69 Hz, 1H), 7.93 (s, 1H), 7.90 (dd, J = 2.27, 8.69 Hz, 1H), 7.65 (dd, J = 1.89, 7.93 Hz, 1H), 7.30 (d, J = 3.78 Hz, 1H), 7.00-7.20 (m, 4H), 6.49-6.62 (m, 2H), 4.93 (d, J = 5.67 Hz, 2H), 4.55 (d, J = 6.04 Hz, 2H), 4.33 (s, 3H) |
| 2.25 | 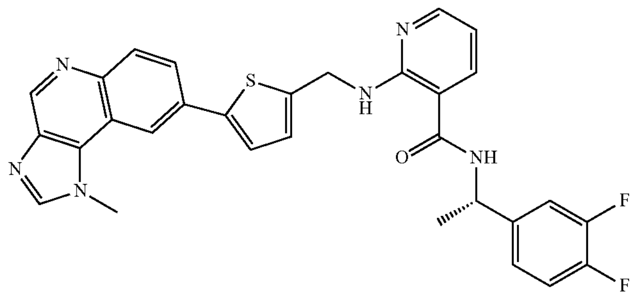 [SMILES: C[C@H](NC(=O)c1cccnc1NCc1ccc(-c2ccc3ncc4ncn(C)c4c3c2)s1)c1ccc(F)c(F)c1] | (S)-N-(1-(3,4-difluorophenyl)ethyl)-2-(((5-(1-methyl-1H-imidazo[4,5-c]quinolin-8-yl)thiophen-2-yl)methyl)amino)nicotinamide | 555.2 | ¹H NMR (300 MHz, CDCl₃) δ 9.28 (s, 1H), 8.53 (t, J = 5.48 Hz, 1H), 8.41 (d, J = 1.89 Hz, 1H), 8.32 (dd, J = 1.89, 4.91 Hz, 1H), 8.24 (d, J = 8.69 Hz, 1H), 7.94 (s, 1H), 7.91 (dd, J = 2.08, 8.88 Hz, 1H), 7.64 (dd, J = 1.89, 7.93 Hz, 1H), 7.29 (d, J = 3.40 Hz, 1H), 7.03-7.22 (m, 4H), 6.59 (dd, J = 4.72, 7.74 Hz, 1H), 6.24 (d, J = 7.18 Hz, 1H), 5.19 (quin, J = 6.99 Hz, 1H), 4.83-4.99 (m, 2H), 4.34 (s, 3H), 1.57 (d, J = 7.18 Hz, 3H) |
| 2.26 | 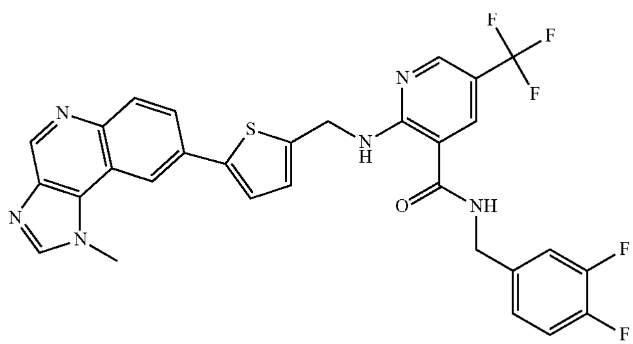 [SMILES: Cn1cnc2cnc3ccc(-c4ccc(CNc5ncc(C(F)(F)F)cc5C(=O)NCc5ccc(F)c(F)c5)s4)cc3c21] | N-(3,4-difluorobenzyl)-2-(((5-(1-methyl-1H-imidazo[4,5-c]quinolin-8-yl)thiophen-2-yl)methyl)amino)-5-(trifluoromethyl)nicotinamide | 609.2 | ¹H NMR (300 MHz, CDCl₃) δ 9.21 (t, J = 5.67 Hz, 1H), 9.17 (s, 1H), 8.71 (t, J = 5.67 Hz, 1H), 8.41 (s, 1H), 8.34 (d, J = 1.89 Hz, 1H), 8.09-8.18 (m, 2H), 7.90 (s, 1H), 7.82 (dd, J = 1.89, 8.69 Hz, 1H), 7.22 (d, J = 3.40 Hz, 1H), 6.93-7.16 (m, 4H), 4.85 (d, J = 6.04 Hz, 2H), 4.39 (d, J = 6.04 Hz, 2H), 4.27 (s, 3H) |

TABLE 1-continued

| Ex. No. | Structure | Chemical Name | ESI-MS (M + H) | ¹H NMR |
|---|---|---|---|---|
| 2.27 | 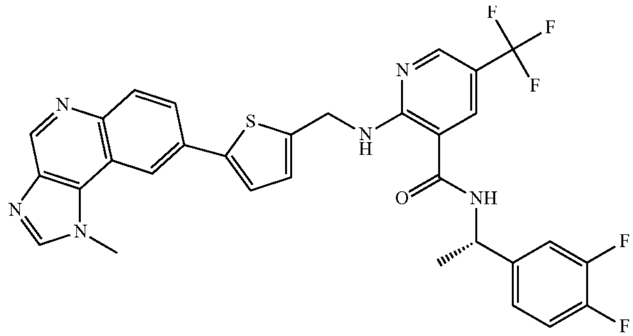 [SMILES: C[C@H](NC(=O)c1cc(C(F)(F)F)cnc1NCc1ccc(-c2ccc3ncc4ncn(C)c4c3c2)s1)c1ccc(F)c(F)c1] | (S)-5-trifluoromethyl-N-(1-(3,4-difluorophenyl)ethyl)-2-(((5-(1-methyl-1H-imidazo[4,5-c]quinolin-8-yl)thiophen-2-yl)methyl)amino)nicotinamide | 623.2 | ¹H NMR (300 MHz, CDCl₃) δ 9.19 (s, 1H), 9.05 (t, J = 5.67 Hz, 1H), 8.49 (d, J = 1.51 Hz, 1H), 8.30 (d, J = 1.89 Hz, 1H), 8.16 (d, J = 8.69 Hz, 1H), 8.04 (d, J = 2.27 Hz, 1H), 7.88 (s, 1H), 7.83 (dd, J = 1.89, 8.69 Hz, 1H), 7.57 (d, J = 7.18 Hz, 1H), 7.04-7.26 (m, 4H), 7.01 (d, J = 3.78 Hz, 1H), 5.18 (quin, J = 6.99 Hz, 1H), 4.79-4.98 (m, 2H), 4.25 (s, 3H), 1.54 (d, J = 7.18 Hz, 3H) |
| 2.28 | 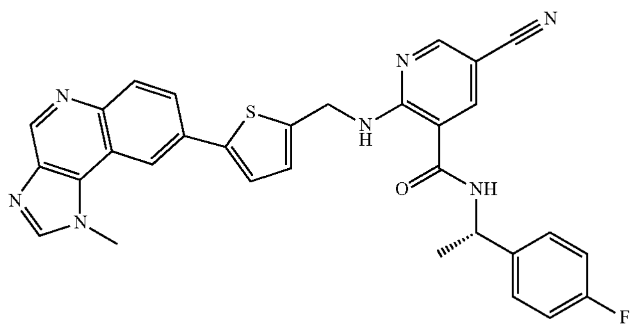 [SMILES: C[C@H](NC(=O)c1cc(C#N)cnc1NCc1ccc(-c2ccc3ncc4ncn(C)c4c3c2)s1)c1ccc(F)cc1] | (S)-5-cyano-N-(1-(4-fluorophenyl)ethyl)-2-(((5-(1-methyl-1H-imidazo[4,5-c]quinolin-8-yl)thiophen-2-yl)methyl)amino)nicotinamide | 562.2 | ¹H NMR (300 MHz, DMSO-d₆) δ 9.37 (t, J = 5.85 Hz, 1H), 9.15 (s, 1H), 9.00 (d, J = 7.55 Hz, 1H), 8.67 (d, J = 1.89 Hz, 1H), 8.51 (dd, J = 1.89, 9.44 Hz, 2H), 8.38 (s, 1H), 8.14 (d, J = 8.69 Hz, 1H), 7.92 (dd, J = 2.08, 8.88 Hz, 1H), 7.58 (d, J = 3.40 Hz, 1H), 7.36-7.47 (m, 2H), 7.07-7.19 (m, 3H), 5.09 (quin, J = 7.08 Hz, 1H), 4.80-4.96 (m, 2H), 4.36 (s, 3H), 1.46 (d, J = 7.18 Hz, 3H) |
| 2.29 | 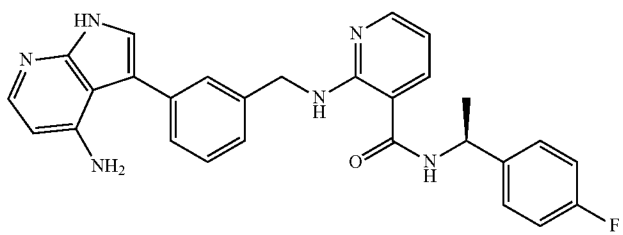 [SMILES: C[C@H](NC(=O)c1cccnc1NCc1cccc(-c2c[nH]c3nccc(N)c23)c1)c1ccc(F)cc1] | (S)-2-(3-(4-amino-7H-pyrrolo[2,3-d]pyrimidin-5-yl)benzylamino)-N-(1-(4-fluorophenyl)ethyl)nicotinamide | 482.0 | ¹H NMR (400 MHz, DMSO-d₆) δ 11.80 (s, 1H), 8.66 (t, 1H), 8.17 (dd, 1H), 8.10 (s, 1H), 8.05 (dd, 1H), 7.43-7.37 (m, 4H), 7.31 (d, 1H), 7.25 (d, 1H), 7.19 (d, 1H), 7.11 (t, 2H), 6.62 (dd, 1H), 5.95 (br, 2H), 5.11 (t, 1H), 4.64 (dd, 2H), 1.43 (d, 3H) |

TABLE 1-continued

| Ex. No. | Structure | Chemical Name | ESI-MS (M + H) | ¹H NMR |
|---|---|---|---|---|
| 2.30 | 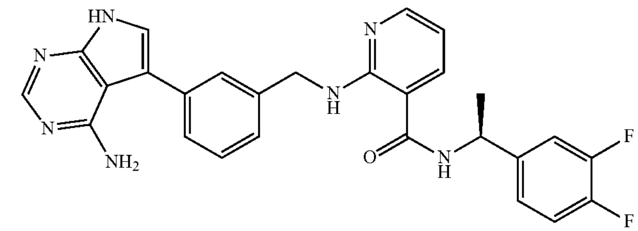 [SMILES: C[C@H](NC(=O)c1cccnc1NCc1cccc(-c2c[nH]c3ncnc(N)c23)c1)c1ccc(F)c(F)c1] | (S)-2-(3-(4-amino-7H-pyrrolo[2,3-d]pyrimidin-5-yl)benzylamino)-N-(1-(3,4-difluorophenyl)ethyl)nicotinamide | 500.0 | ¹H NMR (400 MHz, DMSO-d₆) δ 11.78 (s, 1H), 8.64 (t, 1H), 8.18 (d, 1H), 8.10 (s, 1H), 8.07 (dd, 1H), 7.46-7.31 (m, 5H), 7.25 (d, 1H), 7.20 (d, 2H), 6.63 (q, 1H), 5.97 (br, 2H), 5.10 (t, 1H), 4.67-4.63 (AB, 2H), 1.43 (d, 3H) |
| 2.31 | 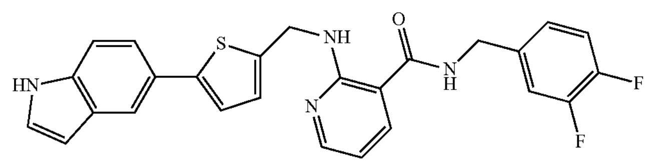 [SMILES: O=C(NCc1ccc(F)c(F)c1)c1cccnc1NCc1ccc(-c2ccc3[nH]ccc3c2)s1] | 2-(((5-(1H-pyrrolo[2,3-b]pyridin-5-yl)thiophen-2-yl)methyl)amino)-N-(3,4-difluorobenzyl)nicotinamide | 476.2 | ¹H NMR (400 MHz, DMSO-d₆) δ 11.72 (br. s., 1H), 8.84 (br. s., 1H), 8.46 (d, J = 2.01 Hz, 1H), 8.25 (dd, J = 1.76, 4.77 Hz, 1H), 8.11 (d, J = 1.76 Hz, 1H), 8.07 (dd, J = 1.76, 7.78 Hz, 1H), 7.53 Hz, 1H), 7.45-7.56 (m, 1H), 7.32-7.43 (m, 2H), 7.31 (d, J = 3.51 Hz, 1H), 7.11-7.24 (m, 1H), 7.04 (d, J = 3.76 Hz, 1H), 6.70 (dd, J = 5.02, 7.53 Hz, 1H), 6.46 (dd, J = 1.76, 3.51 Hz, 1H), 4.81 (br. s., 2H), 4.42 (d, 2H) |
| 2.32 | 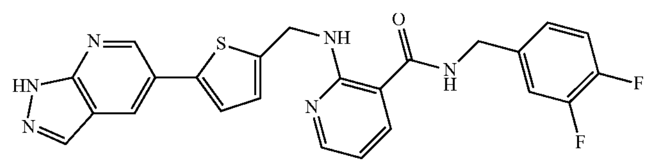 [SMILES: O=C(NCc1ccc(F)c(F)c1)c1cccnc1NCc1ccc(-c2cnc3[nH]ncc3c2)s1] | 2-(((5-(1H-pyrazolo[3,4-b]pyridin-5-yl)thiophen-2-yl)methyl)amino)-N-(3,4-difluorobenzyl)nicotinamide | 477.1 | ¹H NMR (400 MHz, DMSO-d₆) δ 13.71 (s, 1H), 9.12 (t, J = 5.90 Hz, 1H), 8.79 (d, J = 2.26 Hz, 1H), 8.75 (t, J = 5.77 Hz, 1H), 8.35 (d, J = 2.01 Hz, 1H), 8.25 (dd, J = 1.76, 4.77 Hz, 1H), 8.14 (d, J = 1.26 Hz, 1H), 8.03 (dd, J = 1.76, 7.78 Hz, 1H), 7.26-7.46 (m, 3H), 7.16 (ddd, J = 1.88, 4.20, 6.21 Hz, 1H), 7.05 (d, J = 3.51 Hz, 1H), 6.67 (dd, J = 4.77, 7.78 Hz, 1H), 4.81 (d, J = 5.77 Hz, 2H), 4.42 (d, 2H) |
| 2.33 | 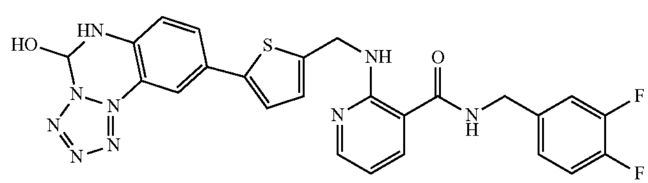 | N-(3,4-difluorobenzyl)-2-((5-(5-hydroxy-5,6-dihydrotetrazolo[1,5-c]quinazolin-9-yl)thiophen-2-yl)methylamino)nicotinamide | 546.56 | ¹H NMR (300 MHz, DMSO-d₆) δ 10.61 (br. s., 1H), 9.17 (t, J = 5.67 Hz, 1H), 8.83 (br. s., 1H), 8.51 (s, 1H), 8.44 (d, J = 8.69 Hz, 1H), 8.25 (dd, J = 1.51, 4.91 Hz, 1H), 8.11 (d, J = 1.89 Hz, 1H), 8.08 (dd, J = 1.70, 7.74 Hz, 1H), 7.79 (dd, J = 1.89, 8.69 Hz, 1H), 7.39 (d, J = 3.40 Hz, 1H), 6.89-7.16 (m, 5H), 6.71 (dd, J = 4.91, 7.55 Hz, 1H), 4.83 (br. s., 2H), 4.46 (d, J = 5.67 Hz, 2H) |

TABLE 1-continued

| Ex. No. | Structure | Chemical Name | ESI-MS (M + H) | ¹H NMR |
|---|---|---|---|---|
| 2.34 | 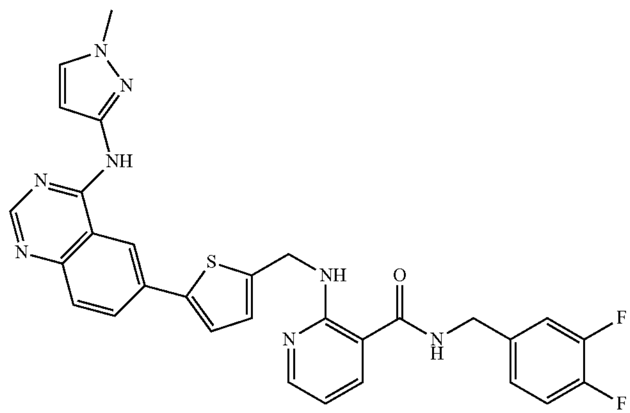 [SMILES: Cn1ccc(Nc2ncnc3ccc(-c4ccc(CNc5ncccc5C(=O)NCc5ccc(F)c(F)c5)s4)cc23)n1] | N-(3,4-difluorobenzyl)-2-(((5-(4-(1-methyl-1H-pyrazol-3-ylamino)quinazolin-6-yl)thiophen-2-yl)methyl)amino)nicotinamide | 583.2 | ¹H NMR (300 MHz, DMSO-d₆) δ 9.17 (t, J = 5.67 Hz, 1H), 9.00 (s, 1H), 8.92 (s, 1H), 8.83 (t, J = 5.48 Hz, 1H), 8.22-8.32 (m, 2H), 8.08 (d, J = 6.42 Hz, 1H), 7.76-7.87 (m, 2H), 7.63 (d, J = 3.78 Hz, 1H), 6.98-7.17 (m, 4H), 6.87 (d, J = 1.89 Hz, 1H), 6.70 (dd, J = 4.91, 7.55 Hz, 1H), 4.87 (d, J = 4.91 Hz, 2H), 4.46 (d, J = 5.29 Hz, 2H), 3.89 (s, 3H) |
| 2.35 | 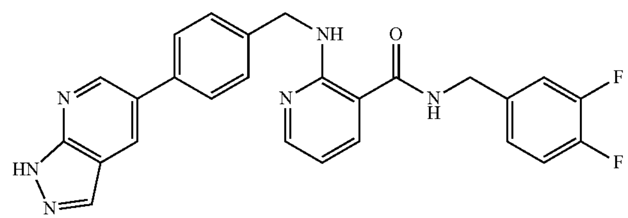 [SMILES: O=C(NCc1ccc(F)c(F)c1)c1cccnc1NCc1ccc(-c2cnc3[nH]ncc3c2)cc1] | 2-(4-(1H-pyrazolo[3,4-b]pyridin-5-yl)benzylamino)-N-(3,4-difluorobenzyl)nicotinamide | 471.2 | ¹H NMR (400 MHz, DMSO-d₆) δ 13.72 (s, 1H), 9.23 (br. s., 1H), 9.04 (br. s., 1H), 8.82 (d, J = 2.26 Hz, 1H), 8.45 (d, J = 2.26 Hz, 1H), 8.19 (s, 1H), 8.16-8.20 (m, 1H), 8.13 (d, J = 7.28 Hz, 1H), 7.67-7.75 (m, 2H), 7.33-7.50 (m, 4H), 7.13-7.21 (m, 1H), 6.72 (dd, J = 5.27, 7.53 Hz, 1H), 4.70 (br. s., 2H), 4.44 (d, J = 5.77 Hz, 2H) |
| 2.36 | 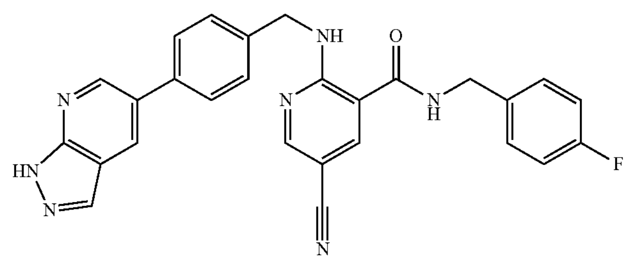 [SMILES: N#Cc1cnc(NCc2ccc(-c3cnc4[nH]ncc4c3)cc2)c(C(=O)NCc2ccc(F)cc2)c1] | 5-Cyano-N-[(S)-1-(4-fluorophenyl)-ethyl]-2-[4-(1H-pyrazolo[3,4-b]pyridin-5-yl)-benzylamino]-nicotinamide | 492.20 | ¹H NMR (400 MHz, DMSO-d₆) δ 9.36 (t, J = 5.90 Hz, 1H), 8.97-9.03 (m, 1H), 8.80 (d, J = 2.26 Hz, 1H), 8.58 (d, J = 2.26 Hz, 1H), 8.48 (d, J = 2.26 Hz, 1H), 8.43 (d, J = 2.26 Hz, 1H), 8.19 (s, 1H), 7.69 (d, J = 8.28 Hz, 2H), 7.35-7.47 (m, 4H), 7.09-7.20 (m, 2H), 5.11 (quin, 1H), 4.64-4.79 (m, 2H), 1.46 (d, 3H) |

TABLE 1-continued

| Ex. No. | Structure | Chemical Name | ESI-MS (M + H) | ¹H NMR |
|---|---|---|---|---|
| 2.37 | 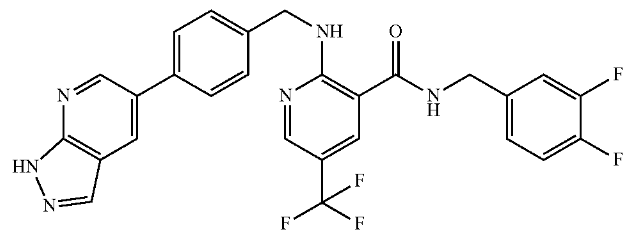 [SMILES: O=C(NCc1ccc(F)c(F)c1)c1cc(C(F)(F)F)cnc1NCc1ccc(-c2cnc3[nH]ncc3c2)cc1] | N-(3,4-Difluoro-benzyl)-2-[4-(1H-pyrazolo[3,4-b]pyridin-5-yl)-benzylamino]-5-trifluoromethyl-nicotinamide | 539.20 | ¹H NMR (400 MHz, DMSO-d₆) δ 9.37 (t, J = 5.90 Hz, 1H), 9.32 (t, J = 5.90 Hz, 1H), 8.81 (d, J = 2.26 Hz, 1H), 8.52 (d, J = 1.51 Hz, 1H), 8.44 (d, J = 2.26 Hz, 1H), 8.36 (d, J = 2.26 Hz, 1H), 8.19 (s, 1H), 7.70 (d, J = 8.28 Hz, 2H), 7.33-7.49 (m, 4H), 7.19 (ddd, J = 1.88, 4.20, 6.21 Hz, 1H), 4.76 (d, J = 5.52 Hz, 2H), 4.45 (d, J = 5.77 Hz, 2H) |
| 2.38 | 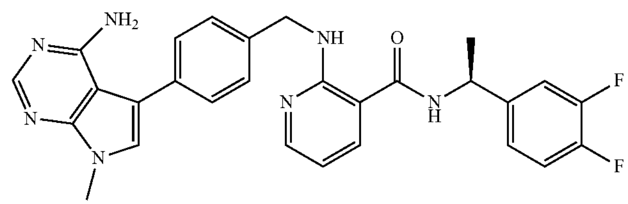 [SMILES: C[C@H](NC(=O)c1cccnc1NCc1ccc(-c2cn(C)c3ncnc(N)c23)cc1)c1ccc(F)c(F)c1] | 2-[4-(4-Amino-7-methyl-7H-pyrrolo[2,3-d]pyrimidin-5-yl)-benzylamino]-N-[(S)-1-(3,4-difluoro-phenyl)-ethyl]-nicotinamide | 514.30 | ¹H NMR (400 MHz, DMSO-d₆) δ 8.92 (d, J = 7.78 Hz, 1H), 8.80 (br. s., 1H), 8.46 (s, 1H), 8.10-8.24 (m, 2H), 7.61 (s, 1H), 7.31-7.52 (m, 6H), 7.22 (ddd, J = 2.26, 4.20, 6.34 Hz, 1H), 6.70 (dd, J = 5.02, 7.53 Hz, 1H), 5.10 (quin, J = 7.15 Hz, 1H), 4.69 (d, J = 4.02 Hz, 2H), 3.84 (s, 3H), 1.46 (d, J = 7.03 Hz, 3H) |
| 2.39 | 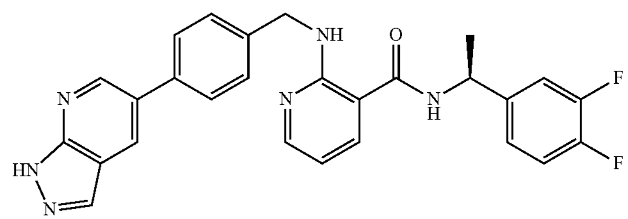 [SMILES: C[C@H](NC(=O)c1cccnc1NCc1ccc(-c2cnc3[nH]ncc3c2)cc1)c1ccc(F)c(F)c1] | N-[(S)-1-(3,4-Difluoro-phenyl)-ethyl]-2-[4-(1H-pyrazolo[3,4-b]pyridin-5-yl) benzyl-amino]-nicotinamide | 485.20 | ¹H NMR (400 MHz, DMSO-d₆) δ 9.06 (d, J = 7.53 Hz, 2H), 8.45 (d, J = 2.26 Hz, 1H), 8.22-8.35 (m, 1H), 8.08-8.22 (m, 2H), 7.71 (d, J = 8.28 Hz, 2H), 7.29-7.55 (m, 4H), 7.23 (ddd, J = 2.26, 4.20, 6.34 Hz, 1H), 6.81 (dd, J = 5.52, 7.53 Hz, 1H), 5.12 (quin, J = 7.03 Hz, 1H), 4.70 (s, 2H), 1.46 (d, J = 7.03 Hz, 3H) |
| 3.6 | 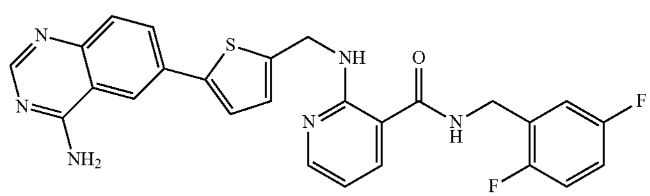 [SMILES: Nc1ncnc2ccc(-c3ccc(CNc4ncccc4C(=O)NCc4cc(F)ccc4F)s3)cc12] | 2-({[5-(4-aminoquinazolin-6-yl)thiophen-2-yl]methyl}amino)-N-(2,5-difluorobenzyl)pyridine-3-carboxamide (TFA salt) | 503.2 | ¹H NMR (300 MHz, DMSO-d₆) δ 9.83 (br s, 1H), 9.75 (br s, 1H), 9.11 (t, J = 6.0 Hz, 1H), 8.65-8.75 (m, 2H), 8.59 (s, 1H), 8.26 (d, J = 12.0 Hz, 1H), 8.25 (s, 1H), 8.06 (d, J = 6.0 Hz, 1H), 7.76 (d, J = 9.0 Hz, 1H), 7.54 (s, 1H), 7.27-7.11 (m, 5H), 6.69 (dd, J = 3.0, 3.0 Hz, 1H), 4.85 (d, J = 6.0 Hz, 2H), 4.46 (d, J = 6.0 Hz, 2H) |

TABLE 1-continued

| Ex. No. | Structure | Chemical Name | ESI-MS (M + H) | $^1$H NMR |
|---|---|---|---|---|
| 3.7 | 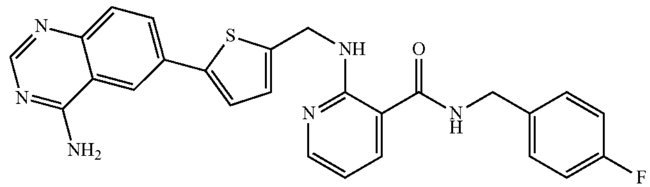 [SMILES: Nc1ncnc2ccc(-c3ccc(CNc4ncccc4C(=O)NCc4ccc(F)cc4)s3)cc12] | 2-({[5-(4-aminoquinazolin-6-yl)thiophen-2-yl]methyl}amino)-N-(4-fluorobenzyl)pyridine-3-carboxamide (TFA salt) | 485.2 | $^1$H NMR (300 MHz, DMSO-d$_6$) δ 9.86 (br. s., 1H), 9.76 (br. s., 1H), 9.13 (t, J = 5.85 Hz, 1H), 8.87 (d, J = 6.04 Hz, 1H), 8.80 (s, 1H), 8.60 (d, J = 1.89 Hz, 1H), 8.18-8.31 (m, 2H), 8.04 (dd, J = 1.89, 7.93 Hz, 1H), 7.76 (d, J = 8.69 Hz, 1H), 7.54 (d, J = 3.78 Hz, 1H), 7.35 (dd, J = 5.67, 8.69 Hz, 2H), 7.05-7.23 (m, 3H), 6.68 (dd, J = 4.72, 7.74 Hz, 1H), 4.86 (d, J = 5.67 Hz, 2H), 4.42 (d, J = 6.04 Hz, 2H) |
| 3.8 | 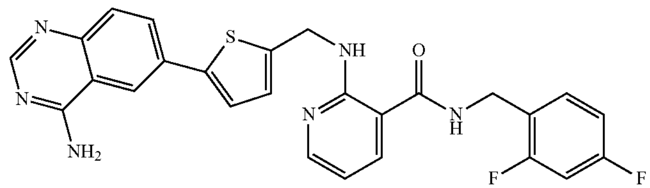 [SMILES: Nc1ncnc2ccc(-c3ccc(CNc4ncccc4C(=O)NCc4ccc(F)cc4F)s3)cc12] | 2-({[5-(4-aminoquinazolin-6-yl)thiophen-2-yl]methyl}amino)-N-(2,4-difluorobenzyl)pyridine-3-carboxamide (TFA salt) | 503.2 | $^1$H NMR (300 MHz, DMSO-d$_6$) δ 9.84 (br. s., 1H), 9.75 (br. s., 1H), 9.12 (t, J = 5.72 Hz, 1H), 8.80 (s, 1H), 8.81 (t, J = 5.85 Hz, 1H), 8.60 (d, J = 1.13 Hz, 1H), 8.26 (d, J = 1.51 Hz, 0H), 8.26 (dd, J = 1.82, 13.40 Hz, 1H), 8.07 (dd, J = 1.69, 7.66 Hz, 1H), 7.76 (d, J = 8.69 Hz, 1H), 7.54 (d, J = 3.78 Hz, 1H), 7.04-7.34 (m, 5H), 6.69 (dd, J = 4.72, 7.74 Hz, 1H), 4.86 (d, J = 6.04 Hz, 2H), 4.46 (d, J = 5.67 Hz, 2H) |
| 3.9 | 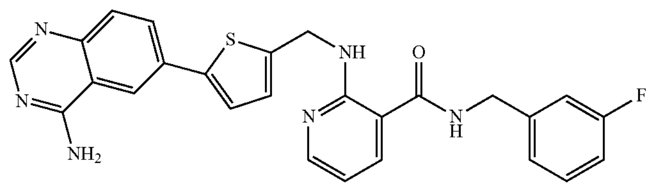 [SMILES: Nc1ncnc2ccc(-c3ccc(CNc4ncccc4C(=O)NCc4cccc(F)c4)s3)cc12] | 2-({[5-(4-aminoquinazolin-6-yl)thiophen-2-yl]methyl}amino)-N-(3-fluorobenzyl)pyridine-3-carboxamide (TFA salt) | 485.2 | $^1$H NMR (300 MHz, DMSO-d$_6$) δ 9.85 (br. s., 1H), 9.75 (br. s., 1H), 9.15 (t, J = 5.67 Hz, 1H), 8.84 (t, J = 6.04 Hz, 1H), 8.80 (s, 1H), 8.60 (d, J = 1.89 Hz, 1H), 8.25 (t, J = 1.13 Hz, 1H), 8.26 (dd, J = 1.70, 14.92 Hz, 1H), 8.06 (dd, J = 2.08, 7.74 Hz, 1H), 7.76 (d, J = 8.69 Hz, 1H), 7.54 (d, J = 3.40 Hz, 1H), 7.27-7.44 (m, 1H), 6.99-7.20 (m, 4H), 6.69 (dd, J = 4.91, 7.55 Hz, 1H), 4.86 (d, J = 6.04 Hz, 2H), 4.46 (d, J = 6.04 Hz, 2H) |
| 3.10 | 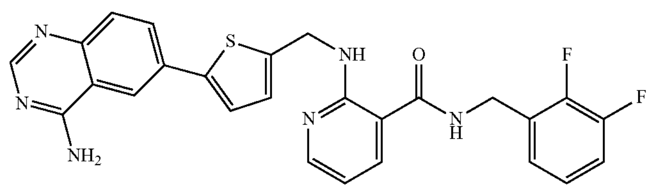 [SMILES: Nc1ncnc2ccc(-c3ccc(CNc4ncccc4C(=O)NCc4cccc(F)c4F)s3)cc12] | 2-({[5-(4-aminoquinazolin-6-yl)thiophen-2-yl]methyl}amino)-N-(2,3-difluorobenzyl)pyridine-3-carboxamide (TFA salt) | 503.2 | $^1$H NMR (300 MHz, DMSO-d$_6$) δ 9.85 (br. s., 1H), 9.76 (br. s., 1H), 9.15 (t, J = 5.73 Hz, 1H), 8.76-8.88 (m, 2H), 8.59 (d, J = 1.92 Hz, 1H), 8.26 (t, J = 1.51 Hz, 1H), 8.26 (dd, J = 2.08, 14.92 Hz, 1H), 8.06 (dd, J = 1.70, 7.74 Hz, 1H), 7.76 (d, J = 8.69 Hz, 1H), 7.54 (d, J = 3.40 Hz, 1H), 7.25-7.39 (m, 1H), 7.08-7.24 (m, 3H), 6.69 (dd, J = 4.72, 7.74 Hz, 1H), 4.85 (d, J = 6.04 Hz, 2H), 4.51 (d, J = 6.04 Hz, 2H) |
| 3.11 | 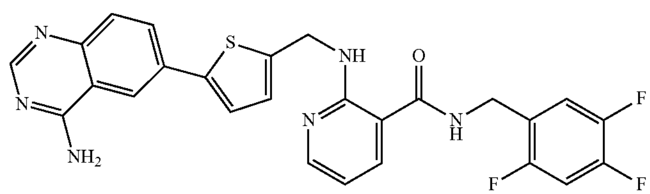 [SMILES: Nc1ncnc2ccc(-c3ccc(CNc4ncccc4C(=O)NCc4cc(F)c(F)cc4F)s3)cc12] | 2-({[5-(4-aminoquinazolin-6-yl)thiophen-2-yl]methyl}amino)-N-(2,4,5-trifluorobenzyl)pyridine-3-carboxamide (TFA salt) | 521.2 | $^1$H NMR (300 MHz, DMSO-d$_6$) δ 9.87(br. s., 1H), 9.78 (br. s., 1H), 9.11 (t, J = 5.67 Hz, 1H), 8.72-8.94 (m, 2H), 8.60 (s, 1H), 8.18-8.36 (m, 2H), 8.06 (d, J = 6.42 Hz, 1H), 7.77 (d, J = 9.06 Hz, 1H), 7.33-7.65 (m, 3H), 7.12 (s, 1H), 6.69 (dd, J = 4.72, 7.74 Hz, 1H), 4.73-5.00 (m, J = 2.64 Hz, 2H), 4.34-4.52 (m, J = 3.02 Hz, 2H) |

TABLE 1-continued

| Ex. No. | Structure | Chemical Name | ESI-MS (M + H) | ¹H NMR |
|---|---|---|---|---|
| 3.12 | 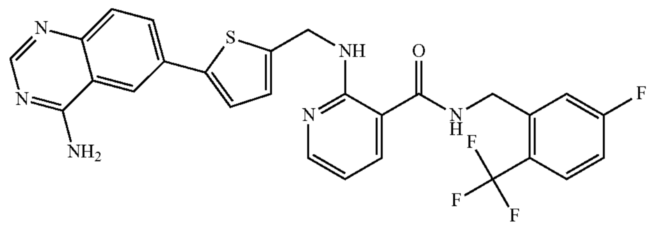 [SMILES: Nc1ncnc2ccc(-c3ccc(CNc4ncccc4C(=O)NCc4cc(F)ccc4C(F)(F)F)s3)cc12] | 2-({[5-(4-aminoquinazolin-6-yl)thiophen-2-yl]methyl}amino)-N-[5-fluoro-2-(trifluoromethyl)benzyl]pyridine-3-carboxamide (TFA salt) | 553.2 | ¹H NMR (300 MHz, DMSO-d₆) δ 9.86 (br. s., 1H), 9.78 (br. s., 1H), 9.21 (t, J = 5.85 Hz, 1H), 8.72-8.90 (m, 2H), 8.60 (s, 1H), 8.21-8.34 (m, 2H), 8.13 (dd, J = 1.70, 7.74 Hz, 1H), 7.83 (dd, J = 5.48, 9.25 Hz, 1H), 7.76 (d, J = 8.69 Hz, 1H), 7.54 (dd, J = 3.40 Hz, 1H), 7.25-7.44 (m, 2H), 7.12 (d, J = 3.78 Hz, 1H), 6.73 (dd, J = 4.91, 7.55 Hz, 1H), 4.86 (d, J = 5.29 Hz, 2H), 4.62 (d, J = 4.91 Hz, 2H) |
| 3.13 | 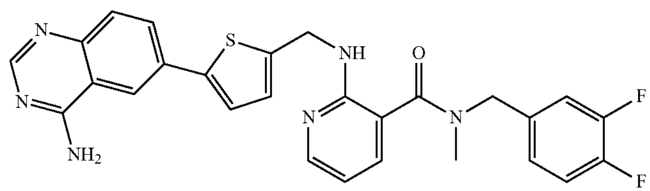 [SMILES: CN(Cc1ccc(F)c(F)c1)C(=O)c1cccnc1NCc1ccc(-c2ccc3ncnc(N)c3c2)s1] | 2-({[5-(4-aminoquinazolin-6-yl)thiophen-2-yl]methyl}amino)-N-(3,4-difluorobenzyl)-N-methylpyridine-3-carboxamide (TFA salt) | 517.2 | ¹H NMR (300 MHz, DMSO-d₆) δ 9.89 (br. s., 1H), 9.80 (br. s., 1H), 8.80 (s, 1H), 8.60 (d, J = 1.89 Hz, 1H), 8.23 (dd, J = 2.08, 8.88 Hz, 1H), 8.14 (dd, J = 1.89, 5.29 Hz, 1H), 7.77 (d, J = 8.69 Hz, 1H), 7.48-7.58 (m, 2H), 7.27-7.46 (m, 2H), 7.00-7.20 (m, 3H), 6.67 (dd, J = 5.10, 7.37 Hz, 1H), 4.72-4.85 (m, 2H), 4.38-4.67 (m, 2H), 2.85 (s, 3H) |
| 3.14 | 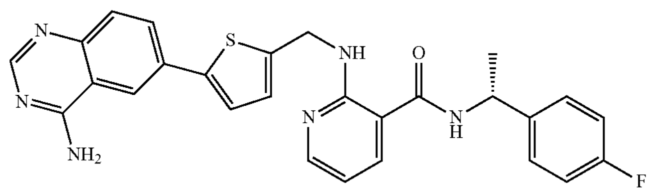 [SMILES: C[C@@H](NC(=O)c1cccnc1NCc1ccc(-c2ccc3ncnc(N)c3c2)s1)c1ccc(F)cc1] | 2-({[5-(4-aminoquinazolin-6-yl)thiophen-2-yl]methyl}amino)-N-[(1R)-1-(4-fluorophenyl)ethyl]pyridine-3-carboxamide (TFA salt) | 499.2 | ¹H NMR (300 MHz, DMSO-d₆) δ 9.88 (br. s., 1H), 9.79 (br. s., 1H), 8.88 (d, J = 7.55 Hz, 1H), 8.70-8.83 (m, 2H), 8.59 (d, J = 1.13 Hz, 1H), 8.27 (dd, J = 1.32, 8.88 Hz, 1H), 8.23 (dd, J = 1.32, 4.72 Hz, 1H), 8.12 (dd, J = 1.13, 7.55 Hz, 1H), 7.77 (d, J = 8.69 Hz, 1H), 7.53 (d, J = 3.40 Hz, 1H), 7.41 (dd, J = 5.29, 8.69 Hz, 2H), 7.01-7.22 (m, 3H), 6.69 (dd, J = 4.91, 7.55 Hz, 1H), 5.11 (quin, J = 7.18 Hz, 1H), 4.83 (d, J = 4.53 Hz, 2H), 1.45 (d, J = 7.18 Hz, 3H) |
| 3.15 | 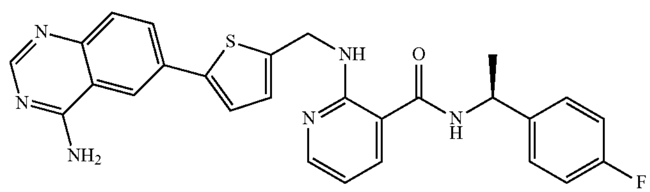 [SMILES: C[C@H](NC(=O)c1cccnc1NCc1ccc(-c2ccc3ncnc(N)c3c2)s1)c1ccc(F)cc1] | 2-({[5-(4-aminoquinazolin-6-yl)thiophen-2-yl]methyl}amino)-N-[(1S)-1-(4-fluorophenyl)ethyl]pyridine-3-carboxamide (TFA salt) | 499.3 | ¹H NMR (300 MHz, DMSO-d₆) δ 8.84 (d, J = 8.1 Hz, 1H), 8.70 (t, J = 5.8 Hz, 1H), 8.40 (d, J = 1.5 Hz, 1H), 8.34 (s, 1H), 8.24 (dd, J = 4.5; 1.5 Hz, 1H), 8.10 (dd, J = 7.8; 1.5 Hz, 1H), 7.96 (dd, J = 9.0; 1.8 Hz, 1H), 7.83 (br s, 2H), 7.64 (d, J = 8.4 Hz, 1H), 7.45 (dd, J = 3.9 Hz, 2H), 7.41 (dd, J = 8.7; 5.7 Hz, 2H), 7.13 (t, J = 8.9 Hz, 2H), 7.05 (d, J = 3.6 Hz, 1H), 6.68 (dd, J = 7.8; 4.8 Hz, 1H), 5.11 (quintet, J = 7.0 Hz, 1H), 4.80 (dd, J = 5.7 Hz, 2H), 1.45 (d, J = 7.2 Hz, 3H) |
| 3.16 | 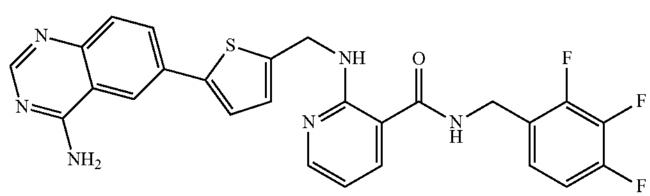 [SMILES: Nc1ncnc2ccc(-c3ccc(CNc4ncccc4C(=O)NCc4ccc(F)c(F)c4F)s3)cc12] | 2-({[5-(4-aminoquinazolin-6-yl)thiophen-2-yl]methyl}amino)-N-(2,3,4-trifluorobenzyl)pyridine-3-carboxamide (TFA salt) | 521.2 | ¹H NMR (300 MHz, DMSO-d₆) δ 9.87 (br. s., 1H), 9.78 (br. s., 1H), 9.15 (t, J = 6.03 Hz, 1H), 8.80 (br. s., 2H), 8.60 (br. s., 1H), 8.16-8.39 (m, 2H), 8.04 (d, J = 7.55 Hz, 1H), 7.77 (d, J = 9.06 Hz, 1H), 7.54 (br. s., 1H), 7.17-7.43 (m, 2H), 7.12 (br. s., 1H), 6.68 (dd, J = 3.97, 6.99 Hz, 1H), 4.74-5.07 (m, 2H), 4.33-4.64 (m, 2H) |

TABLE 1-continued

| Ex. No. | Structure | Chemical Name | ESI-MS (M + H) | ¹H NMR |
|---|---|---|---|---|
| 3.17 | 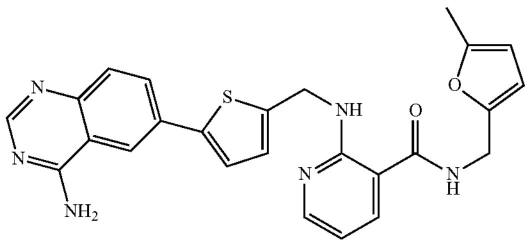 [SMILES: Cc1ccc(CNC(=O)c2cccnc2NCc2ccc(-c3ccc4ncnc(N)c4c3)s2)o1] | 2-({[5-(4-aminoquinazolin-6-yl)thiophen-2-yl]methyl}amino)-N-[(5-methylfuran-2-yl)methyl]pyridine-3-carboxamide (TFA salt) | 471.2 | ¹H NMR (300 MHz, DMSO-$d_6$) δ 9.89 (br. s., 1H), 9.79 (br. s., 1H), 9.00 (br. s., 1H), 8.90 (br. s., 1H), 8.60 (br. s., 1H), 8.14-8.41 (m, 2H), 7.93-8.12 (m, J = 5.29 Hz, 1H), 7.77 (d, J = 6.80 Hz, 1H), 7.55 (br. s., 1H), 7.13 (br. s., 1H), 6.67 (br. s., 1H), 6.14 (br. s., 1H), 5.98 (br. s., 1H), 4.87 (br. s., 2H), 4.37 (br. s., 2H), 2.22 (br. s., 3H) |
| 3.18 | 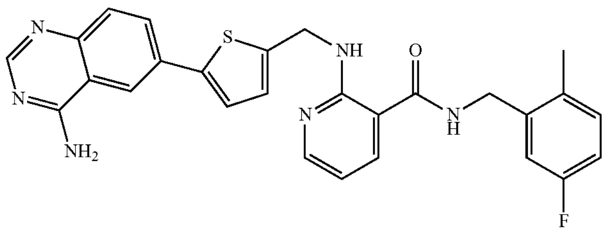 [SMILES: Cc1ccc(F)cc1CNC(=O)c1cccnc1NCc1ccc(-c2ccc3ncnc(N)c3c2)s1] | 2-({[5-(4-aminoquinazolin-6-yl)thiophen-2-yl]methyl}amino)-N-(5-fluoro-2-methylbenzyl)pyridine-3-carboxamide (TFA salt) | 499.3 | ¹H NMR (300 MHz, DMSO-$d_6$) δ 9.87 (br. s., 1H), 9.79 (br. s., 1H), 9.06 (t, J = 5.67 Hz, 1H), 8.84 (br. s., 1H), 8.80 (br. s., 1H), 8.60 (br. s., 1H), 8.19-8.34 (m, 2H), 8.09 (d, J = 6.80 Hz, 1H), 7.76 (d, J = 8.69 Hz, 1H), 7.54 (dd, J = 3.02 Hz, 1H), 7.20 (t, J = 6.99 Hz, 1H), 7.08-7.16 (m, 1H), 6.89-7.08 (m, 2H), 6.70 (dd, J = 4.91, 7.18 Hz, 1H), 4.78-4.95 (m, J = 3.78 Hz, 2H), 4.40 (d, J = 4.91 Hz, 2H), 2.28 (br. s., 3H) |
| 3.19 | 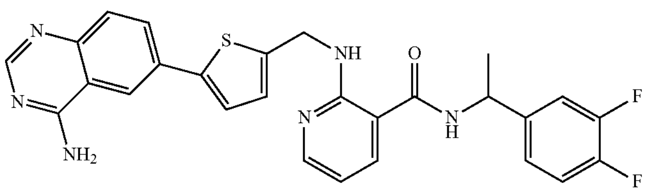 [SMILES: CC(NC(=O)c1cccnc1NCc1ccc(-c2ccc3ncnc(N)c3c2)s1)c1ccc(F)c(F)c1] | 2-({[5-(4-aminoquinazolin-6-yl)thiophen-2-yl]methyl}amino)-N-[1-(3,4-difluorophenyl)ethyl]pyridine-3-carboxamide (TFA salt) | 517.3 | ¹H NMR (300 MHz, DMSO-$d_6$) δ 9.86 (br. s., 1H), 9.78 (br. s., 1H), 8.86 (d, J = 7.93 Hz, 1H), 8.80 (s, 1H), 8.73 (t, J = 5.67 Hz, 1H), 8.59 (d, J = 1.51 Hz, 1H), 8.25 (s, 1H), 8.25 (dd, J = 1.70, 14.92 Hz, 1H), 8.12 (dd, J = 1.89, 7.55 Hz, 1H), 7.76 (d, J = 8.69 Hz, 1H), 7.53 (d, J = 3.78 Hz, 1H), 7.30-7.50 (m, 2H), 7.16-7.28 (m, 1H), 7.10 (d, J = 3.40 Hz, 1H), 6.70 (dd, J = 4.91, 7.93 Hz, 1H), 5.09 (quin, J = 6.89 Hz, 1H), 4.83 (d, J = 5.29 Hz, 2H), 1.45 (d, J = 7.18 Hz, 3H) |
| 3.20 | 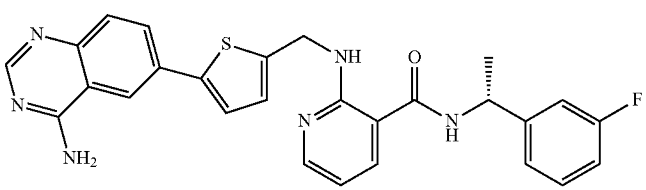 [SMILES: C[C@@H](NC(=O)c1cccnc1NCc1ccc(-c2ccc3ncnc(N)c3c2)s1)c1cccc(F)c1] | 2-({[5-(4-aminoquinazolin-6-yl)thiophen-2-yl]methyl}amino)-N-[(1R)-1-(3-fluorophenyl)ethyl]pyridine-3-carboxamide (TFA salt) | 499.3 | ¹H NMR (300 MHz, DMSO-$d_6$) δ 9.87 (br. s., 1H), 9.78 (br. s., 1H), 8.88 (d, J = 7.55 Hz, 1H), 8.80 (s, 1H), 8.75 (t, J = 6.04 Hz, 1H), 8.59 (s, 1H), 8.20-8.39 (m, 2H), 8.14 (dd, J = 1.70, 7.74 Hz, 1H), 7.76 (d, J = 8.69 Hz, 1H), 7.53 (d, J = 3.78 Hz, 1H), 7.36 (td, J = 5.85, 8.03 Hz, 1H), 7.16-7.29 (m, 2H), 6.99-7.15 (m, 2H), 6.70 (dd, J = 4.72, 7.74 Hz, 1H), 5.12 (quin, J = 7.08 Hz, 1H), 4.83 (d, J = 5.29 Hz, 2H), 1.46 (d, J = 7.18 Hz, 3H) |

TABLE 1-continued

| Ex. No. | Structure | Chemical Name | ESI-MS (M + H) | ¹H NMR |
|---|---|---|---|---|
| 3.21 | 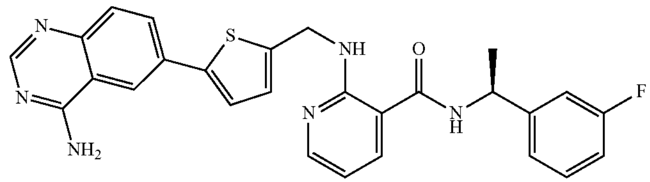 [SMILES: C[C@H](NC(=O)c1cccnc1NCc1ccc(-c2ccc3ncnc(N)c3c2)s1)c1cccc(F)c1] | 2-({[5-(4-aminoquinazolin-6-yl)thiophen-2-yl]methyl}amino)-N-[(1S)-1-(3-fluorophenyl)ethyl]pyridine-3-carboxamide (TFA salt) | 499.3 | ¹H NMR (300 MHz, DMSO-$d_6$) δ 9.87 (br. s., 1H), 9.79 (br. s., 1H), 8.89 (d, J = 7.55 Hz, 1H), 8.68-8.84 (m, 2H), 8.59 (br. s., 1H), 8.20-8.36 (m, 2H), 8.14 (d, J = 6.80 Hz, 1H), 7.76 (d, J = 9.06 Hz, 1H), 7.53 (d, J = 3.02 Hz, 1H), 7.29-7.43 (m, 1H), 7.15-7.27 (m, 2H), 7.08-7.14 (m, 1H), 6.97-7.08 (m, 1H), 6.71 (dd, J = 4.91, 6.80 Hz, 1H), 5.12 (quin, J = 6.80 Hz, 1H), 4.73-4.93 (m, 2H), 1.46 (d, J = 7.18 Hz, 3H) |
| 3.22 | 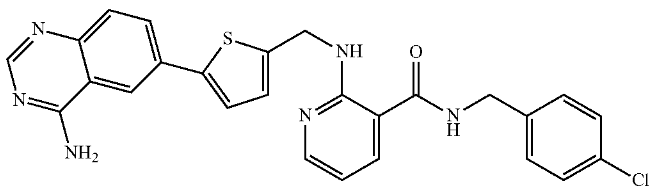 [SMILES: Nc1ncnc2ccc(-c3ccc(CNc4ncccc4C(=O)NCc4ccc(Cl)cc4)s3)cc12] | 2-({[5-(4-aminoquinazolin-6-yl)thiophen-2-yl]methyl}amino)-N-(4-chlorobenzyl)pyridine-3-carboxamide (TFA salt) | 501.2 | ¹H NMR (300 MHz, DMSO-$d_6$) δ 9.83 (br. s., 1H), 9.73 (br. s., 1H), 9.15 (t, J = 6.04 Hz, 1H), 8.85 (t, J = 6.04 Hz, 1H), 8.79 (s, 1H), 8.60 (d, J = 1.51 Hz, 1H), 8.25 (d, J = 1.51 Hz, 1H), 8.26 (dd, J = 1.89, 14.73 Hz, 1H), 8.05 (dd, J = 1.89, 7.55 Hz, 1H), 7.77 (d, J = 8.69 Hz, 1H), 7.54 (d, J = 3.78 Hz, 1H), 7.27-7.43 (m, 4H), 7.12 (d, J = 3.74 Hz, 1H), 6.68 (dd, J = 4.72, 7.74 Hz, 1H), 4.85 (d, J = 5.67 Hz, 2H), 4.42 (d, J = 6.04 Hz, 2H). |
| 3.23 | 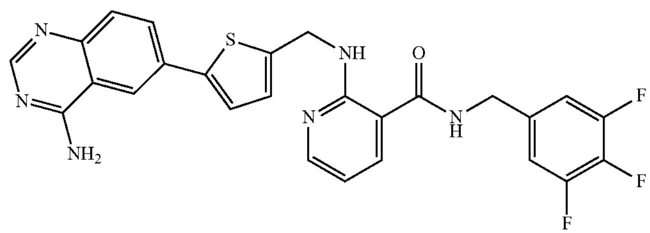 [SMILES: Nc1ncnc2ccc(-c3ccc(CNc4ncccc4C(=O)NCc4cc(F)c(F)c(F)c4)s3)cc12] | 2-({[5-(4-aminoquinazolin-6-yl)thiophen-2-yl]methyl}amino)-N-(3,4,5-trifluorobenzyl)pyridine-3-carboxamide (TFA salt) | 521.2 | ¹H NMR (300 MHz, DMSO-$d_6$) δ 9.87 (br. s., 1H), 9.78 (br. s., 1H), 9.16 (t, J = 6.04 Hz, 1H), 8.73-8.90 (m, 2H), 8.60 (d, J = 1.13 Hz, 1H), 8.21-8.36 (m, 2H), 8.07 (dd, J = 1.13, 7.93 Hz, 1H), 7.77 (d, J = 9.06 Hz, 1H), 7.54 (d, J = 3.40 Hz, 1H), 7.27 (d, J = 7.20 Hz, 1H), 7.24 (d, J = 6.81 Hz, 1H), 7.12 (d, J = 3.74 Hz, 1H), 6.70 (dd, J = 4.91, 7.55 Hz, 1H), 4.86 (d, J = 5.29 Hz, 2H), 4.42 (d, J = 5.29 Hz, 2H). |
| 3.24 | 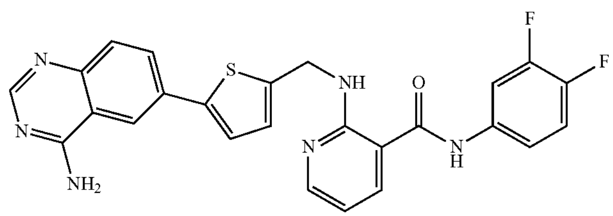 [SMILES: Nc1ncnc2ccc(-c3ccc(CNc4ncccc4C(=O)Nc4ccc(F)c(F)c4)s3)cc12] | 2-({[5-(4-aminoquinazolin-6-yl)thiophen-2-yl]methyl}amino)-N-(3,4-difluorophenyl)pyridine-3-carboxamide (TFA salt) | 489.2 | ¹H NMR (300 MHz, DMSO-$d_6$) δ 10.44 (s, 1H), 9.88 (br. s., 1H), 9.78 (br. s., 1H), 8.80 (s, 1H), 8.61 (d, J = 1.51 Hz, 1H), 8.46 (t, J = 5.80 Hz, 1H), 8.23-8.35 (m, 2H), 8.12 (dd, J = 1.81, 7.75 Hz, 1H), 7.81-7.93 (m, 1H), 7.77 (d, J = 8.69 Hz, 1H), 7.55 (d, J = 3.78 Hz, 1H), 7.37-7.51 (m, 2H), 7.14 (d, J = 3.78 Hz, 1H), 6.76 (dd, J = 4.91, 7.55 Hz, 1H), 4.88 (d, J = 5.29 Hz, 2H). |
| 3.25 | 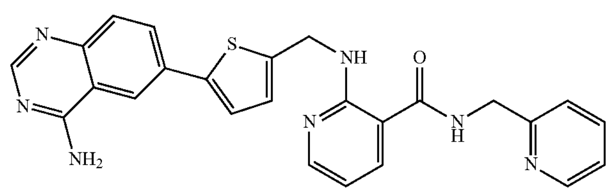 [SMILES: Nc1ncnc2ccc(-c3ccc(CNc4ncccc4C(=O)NCc4ccccn4)s3)cc12] | 2-({[5-(4-aminoquinazolin-6-yl)thiophen-2-yl]methyl}amino)-N-(pyridin-2-ylmethyl)pyridine-3-carboxamide (TFA salt) | 468.3 | ¹H NMR (300 MHz, DMSO-$d_6$) δ 9.90 (br. s., 1H), 9.81 (br. s., 1H), 9.31 (t, J = 5.48 Hz, 1H), 8.87 (br. s., 1H), 8.81 (s, 1H), 8.63 (d, J = 4.91 Hz, 1H), 8.60 (s, 1H), 8.22-8.35 (m, 2H), 8.14 (d, J = 7.18 Hz, 1H), 8.05 (t, J = 7.55 Hz, 1H), 7.77 (d, J = 8.69 Hz, 1H), 7.46-7.66 (m, 3H), 7.12 (d, J = 3.40 Hz, 1H), 6.73 (dd, J = 4.91, 7.18 Hz, 1H), 4.86 (br. s., 2H), 4.64 (d, J = 5.29 Hz, 2H). |

TABLE 1-continued

| Ex. No. | Structure | Chemical Name | ESI-MS (M + H) | ¹H NMR |
|---|---|---|---|---|
| 3.26 | 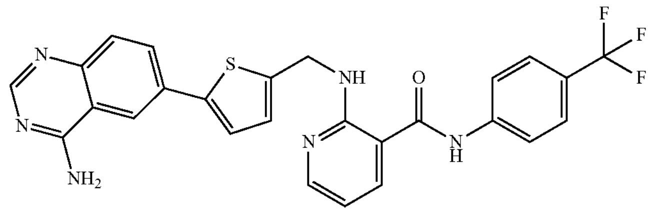 [SMILES: Nc1ncnc2ccc(-c3ccc(CNc4ncccc4C(=O)Nc4ccc(C(F)(F)F)cc4)s3)cc12] | 2-({[5-(4-aminoquinazolin-6-yl)thiophen-2-yl]methyl}amino)-N-[4-(trifluoromethyl)phenyl]pyridine-3-carboxamide (TFA salt) | 521.2 | ¹H NMR (300 MHz, DMSO-d₆) δ 10.56 (s, 1H), 9.85 (br. s., 1H), 9.75 (br. s., 1H), 8.80 (s, 1H), 8.60 (d, J = 1.13 Hz, 1H), 8.47 (s, 1H), 8.30 (t, J = 5.85 Hz, 1H), 8.29 (dd, J = 1.70, 5.85 Hz, 1H), 8.16 (dd, J = 1.70, 15.67 Hz, 1H), 8.16 (dd, J = 1.70, 7.74 Hz, 1H), 7.94 (d, J = 8.69 Hz, 2H), 7.62-7.82 (m, 4H), 7.55 (d, J = 3.40 Hz, 1H), 7.15 (d, J = 3.78 Hz, 1H), 6.77 (dd, J = 4.91, 7.55 Hz, 1H), 4.89 (d, J = 5.67 Hz, 2H). |
| 3.27 | 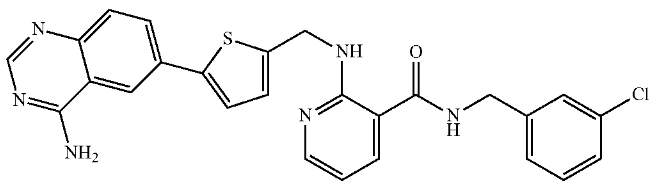 [SMILES: Nc1ncnc2ccc(-c3ccc(CNc4ncccc4C(=O)NCc4cccc(Cl)c4)s3)cc12] | 2-({[5-(4-aminoquinazolin-6-yl)thiophen-2-yl]methyl}amino)-N-(3-chlorobenzyl)pyridine-3-carboxamide (TFA salt) | 501.2 | ¹H NMR (300 MHz, DMSO-d₆) δ 9.87 (br. s., 1H), 9.78 (br. s., 1H), 9.16 (t, J = 6.04 Hz, 1H), 8.86 (t, J = 5.67 Hz, 1H), 8.80 (s, 1H), 8.60 (d, J = 1.51 Hz, 1H), 8.28 (dd, J = 1.86, 8.76 Hz, 1H), 8.25 (dd, J = 1.70, 4.85 Hz, 1H), 8.06 (dd, J = 1.70, 7.74 Hz, 1H), 7.76 (d, J = 8.69 Hz, 1H), 7.54 (d, J = 3.78 Hz, 1H), 7.33-7.40 (m, 2H), 7.29 (tt, J = 1.56, 7.51 Hz, 2H), 7.12 (d, J = 3.40 Hz, 1H), 6.69 (dd, J = 4.72, 7.74 Hz, 1H), 4.86 (d, J = 5.29 Hz, 2H), 4.44 (d, J = 5.67 Hz, 2H). |
| 3.28 | 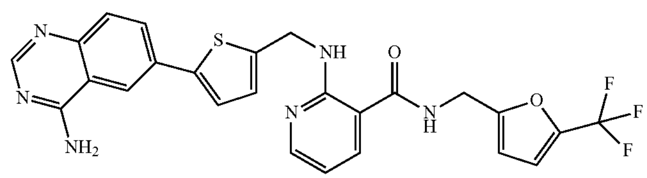 [SMILES: Nc1ncnc2ccc(-c3ccc(CNc4ncccc4C(=O)NCc4ccc(C(F)(F)F)o4)s3)cc12] | 2-({[5-(4-aminoquinazolin-6-yl)thiophen-2-yl]methyl}amino)-N-{[5-(trifluoromethyl)furan-2-yl]methyl}pyridine-3-carboxamide (bis TFA salt) | 525.2 | ¹H NMR (300 MHz, DMSO-d₆) δ 9.87 (br. s., 1H), 9.78 (br. s., 1H), 9.16 (t, J = 5.67 Hz, 1H), 8.83 (t, J = 6.04 Hz, 1H), 8.80 (s, 1H), 8.60 (d, J = 1.89 Hz, 1H), 8.28 (dd, J = 1.89, 8.69 Hz, 1H), 8.25 (dd, J = 1.89, 4.91 Hz, 1H), 8.03 (dd, J = 1.70, 7.74 Hz, 1H), 7.76 (d, J = 8.69 Hz, 1H), 7.54 (d, J = 3.78 Hz, 1H), 7.14-7.19 (m, J = 1.13, 3.40 Hz, 1H), 7.13 (d, J = 3.78 Hz, 1H), 6.69 (dd, J = 4.91, 7.93 Hz, 1H), 6.53 (d, J = 3.02 Hz, 1H), 4.86 (d, J = 5.29 Hz, 2H), 4.51 (d, J = 5.29 Hz, 2H). |
| 3.29 | 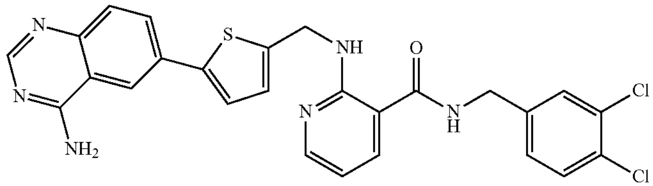 [SMILES: Nc1ncnc2ccc(-c3ccc(CNc4ncccc4C(=O)NCc4ccc(Cl)c(Cl)c4)s3)cc12] | 2-({[5-(4-aminoquinazolin-6-yl)thiophen-2-yl]methyl}amino)-N-(3,4-dichlorobenzyl)pyridine-3-carboxamide (TFA salt) | 535.2 | ¹H NMR (300 MHz, DMSO-d₆) δ 9.85 (br. s., 1H), 9.76 (br. s., 1H), 9.16 (t, J = 5.85 Hz, 1H), 8.82 (t, J = 6.04 Hz, 1H), 8.80 (s, 1H), 8.60 (d, J = 1.89 Hz, 1H), 8.25-8.31 (m, J = 1.89, 8.69 Hz, 1H), 8.05 (dd, J = 1.89, 4.91 Hz, 1H), 7.76 (d, J = 8.69 Hz, 1H), 7.47-7.65 (m, 3H), 7.31 (dd, J = 2.08, 8.12 Hz, 1H), 7.12 (d, J = 3.78 Hz, 1H), 6.69 (dd, J = 4.72, 7.74 Hz, 1H), 4.86 (d, J = 5.29 Hz, 2H), 4.43 (d, J = 5.67 Hz, 2H). |
| 3.30 | 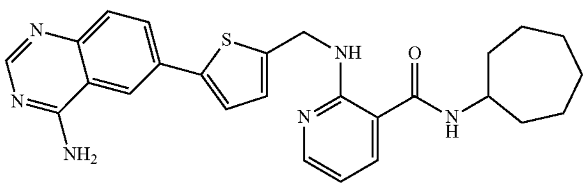 [SMILES: Nc1ncnc2ccc(-c3ccc(CNc4ncccc4C(=O)NC4CCCCCC4)s3)cc12] | 2-({[5-(4-aminoquinazolin-6-yl)thiophen-2-yl]methyl}amino)-N-cycloheptylpyridine-3-carboxamide (TFA salt) | 473.3 | ¹H NMR (300 MHz, DMSO-d₆) δ 9.88 (br. s., 1H), 9.79 (br. s., 1H), 8.82 (t, J = 5.29 Hz, 1H), 8.80 (s, 1H), 8.61 (d, J = 1.89 Hz, 1H), 8.33 (d, J = 7.55 Hz, 1H), 8.28 (dd, J = 1.70, 8.88 Hz, 1H), 8.20 (dd, J = 1.51, 4.91 Hz, 1H), 7.98 (dd, J = 1.70, 7.74 Hz, 1H), 7.77 (d, J = 8.69 Hz, 1H), 7.55 (d, J = 3.78 Hz, 1H), 7.13 (d, J = 3.78 Hz, 1H), 6.66 (dd, J = 4.91, 7.55 Hz, 1H), 4.84 (d, J = 4.53 Hz, 2H), 1.74-1.92 (m, 11H), 1.33-1.72 (m, 11H). |

TABLE 1-continued

| Ex. No. | Structure | Chemical Name | ESI-MS (M + H) | ¹H NMR |
|---|---|---|---|---|
| 3.31 | 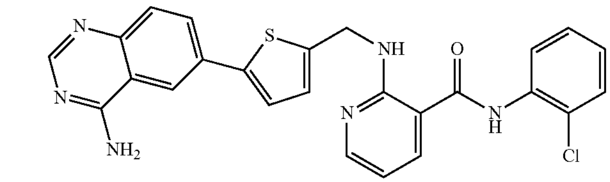 [SMILES: Nc1ncnc2ccc(-c3ccc(CNc4ncccc4C(=O)Nc4ccccc4Cl)s3)cc12] | 2-({[5-(4-aminoquinazolin-6-yl)thiophen-2-yl]methyl}amino)-N-(2-chlorophenyl)pyridine-3-carboxamide (TFA salt) | 487.2 | ¹H NMR (300 MHz, DMSO-d₆) δ 10.14 (s, 1H), 9.84 (br. s., 1H), 9.76 (br. s., 1H), 8.80 (s, 1H), 8.66 (t, J = 5.85 Hz, 1H), 8.60 (d, J = 1.51 Hz, 1H), 8.31 (dd, J = 1.70, 4.72 Hz, 1H), 8.28 (dd, J = 1.70, 8.88 Hz, 1H), 8.22 (dd, J = 1.70, 7.74 Hz, 1H), 7.76 (d, J = 8.69 Hz, 1H), 7.48-7.60 (m, 3H), 7.35-7.44 (m, 1H), 7.55, 7.55 Hz, 1H), 7.31 (td, J = 1.89, 7.55 Hz, 1H), 7.13 (d, J = 3.78 Hz, 1H), 6.76 (dd, J = 4.72, 7.74 Hz, 1H), 4.88 (d, J = 5.29 Hz, 2H). |
| 3.32 | 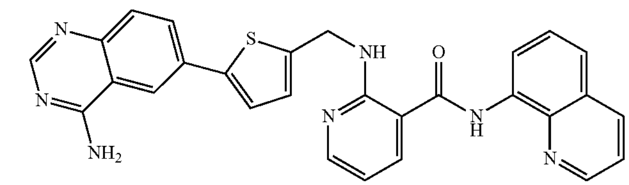 [SMILES: Nc1ncnc2ccc(-c3ccc(CNc4ncccc4C(=O)Nc4cccc5cccnc45)s3)cc12] | 2-({[5-(4-aminoquinazolin-6-yl)thiophen-2-yl]methyl}amino)-N-(quinolin-8-yl)pyridine-3-carboxamide (TFA salt) | 504.2 | ¹H NMR (300 MHz, DMSO-d₆) δ 10.65 (s, 1H), 9.86 (br. s., 1H), 9.76 (br. s., 1H), 8.97 (dd, J = 1.70, 4.34 Hz, 1H), 8.80 (s, 1H), 8.68 (t, J = 5.85 Hz, 1H), 8.57-8.64 (m, 2H), 8.47 (dd, J = 1.51, 8.31 Hz, 1H), 8.36 (dd, J = 1.70, 4.72 Hz, 1H), 8.29 (dd, J = 1.89, 8.69 Hz, 1H), 8.23 (dd, J = 1.70, 7.74 Hz, 1H), 7.73-7.80 (m, 2H), 7.60-7.72 (m, 2H), 7.56 (d, J = 3.78 Hz, 1H), 7.17 (d, J = 3.78 Hz, 1H), 6.85 (dd, J = 4.72, 7.74 Hz, 1H), 4.93 (d, J = 5.67 Hz, 2H). |
| 3.33 | 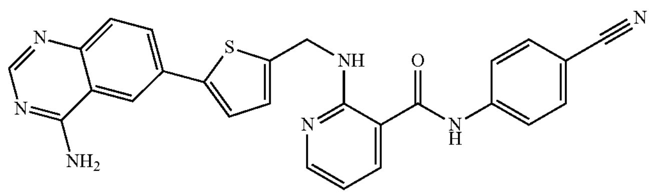 [SMILES: N#Cc1ccc(NC(=O)c2cccnc2NCc2ccc(-c3ccc4ncnc(N)c4c3)s2)cc1] | 2-({[5-(4-aminoquinazolin-6-yl)thiophen-2-yl]methyl}amino)-N-(4-cyanophenyl)pyridine-3-carboxamide (TFA salt) | 478.2 | ¹H NMR (300 MHz, DMSO-d₆) δ 10.60 (s, 1H), 9.83 (br. s., 1H), 9.75 (br. s., 1H), 8.60 (s, 1H), 8.31 (dd, J = 1.89, 4.91 Hz, 1H), 8.27 (dd, J = 1.89, 8.69 Hz, 1H), 8.15 (dd, J = 1.89, 7.93 Hz, 1H), 7.88-7.95 (m, 2H), 7.79-7.86 (m, 2H), 7.76 (d, J = 8.69 Hz, 1H), 7.55 (d, J = 3.78 Hz, 1H), 7.14 (d, J = 3.78 Hz, 1H), 6.77 (dd, J = 4.91, 7.55 Hz, 1H), 4.89 (d, J = 6.04 Hz, 2H). |
| 3.34 | 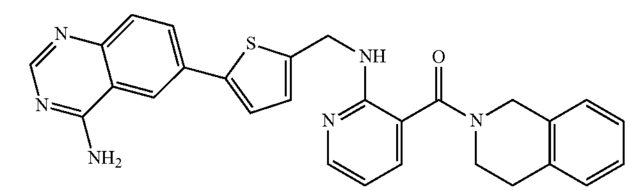 [SMILES: Nc1ncnc2ccc(-c3ccc(CNc4ncccc4C(=O)N4CCc5ccccc5C4)s3)cc12] | 2-({[5-(4-aminoquinazolin-6-yl)thiophen-2-yl]methyl}amino)pyridin-3-yl](3,4-dihydroisoquinolin-2(1H)-yl)methanone (TFA salt) | 493.3 | ¹H NMR (300 MHz, DMSO-d₆) δ 9.96 (br. s., 1H), 8.79 (s, 1H), 8.23 (d, J = 8.69 Hz, 1H), 8.16 (d, J = 3.78 Hz, 1H), 7.81 (d, J = 9.06 Hz, 1H), 7.55 (d, J = 3.40 Hz, 1H), 7.51 (d, J = 6.80 Hz, 1H), 7.16 (br. s., 3H), 7.03-7.24 (m, 3H), 6.70 (dd, J = 4.94, 7.32 Hz, 1H), 4.78 (br. s., 2H), 4.68 (s, 2H), 3.64 (s, 2H), 2.84 (t, J = 5.32 Hz, 2H). |
| 3.35 | 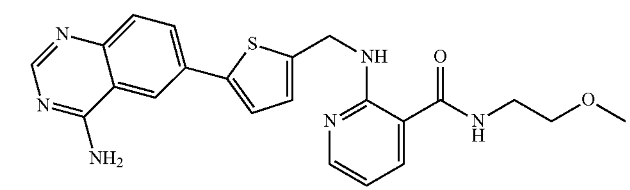 [SMILES: COCCNC(=O)c1cccnc1NCc1ccc(-c2ccc3ncnc(N)c3c2)s1] | 2-({[5-(4-aminoquinazolin-6-yl)thiophen-2-yl]methyl}amino)-N-(2-methoxyethyl)pyridine-3-carboxamide (TFA salt) | 432.2 | ¹H NMR (300 MHz, DMSO-d₆) δ 9.88 (br. s., 1H), 9.79 (br. s., 1H), 8.88 (t, J = 5.89 Hz, 1H), 8.81 (s, 1H), 8.54-8.65 (m, 2H), 8.29 (dd, J = 1.70, 8.88 Hz, 1H), 8.22 (dd, J = 1.51, 4.91 Hz, 1H), 7.99 (dd, J = 1.70, 7.74 Hz, 1H), 7.77 (d, J = 8.69 Hz, 1H), 7.55 (d, J = 4.91, 7.55 Hz, 1H), 7.13 (d, J = 3.78 Hz, 1H), 6.67 (dd, J = 4.91, 7.55 Hz, 1H), 4.86 (d, J = 4.91 Hz, 2H), 3.34-3.50 (m, 4H), 3.26 (s, 3H). |

TABLE 1-continued

| Ex. No. | Structure | Chemical Name | ESI-MS (M + H) | 1H NMR |
|---|---|---|---|---|
| 3.36 | 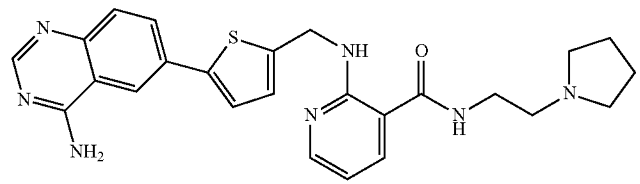 [SMILES: Nc1ncnc2ccc(-c3ccc(CNc4ncccc4C(=O)NCCN4CCCC4)s3)cc12] | 2-({[5-(4-aminoquinazolin-6-yl)thiophen-2-yl]methyl}amino)-N-[2-(pyrrolidin-1-yl)ethyl]pyridine-3-carboxamide (TFA salt) | 474.3 | 1H NMR (300 MHz, DMSO-d6) δ 9.88 (br. s., 1H), 9.80 (br. s., 1H), 8.78-8.86 (m, 2H), 8.74 (t, J = 5.48 Hz, 1H), 8.61 (d, J = 1.51 Hz, 1H), 8.27-8.31 (m, 1H), 8.00 (dd, J = 1.89, 7.93 Hz, 1H), 7.77 (d, J = 8.69 Hz, 1H), 7.55 (d, J = 3.78 Hz, 1H), 7.14 (d, J = 5.67 Hz, 2H), 6.71 (dd, J = 4.91, 7.55 Hz, 1H), 4.87 (d, J = 5.67 Hz, 2H), 3.52-3.68 (m, 4H), 3.32 (q, J = 5.92 Hz, 2H), 2.97-3.13 (m, 2H), 1.94-2.10 (m, 2H), 1.76-1.94 (m, 2H). |
| 3.37 | 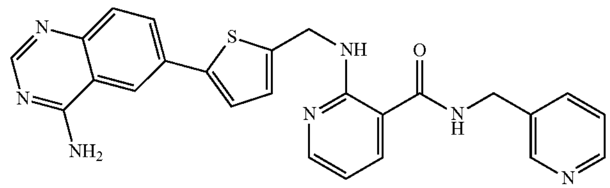 [SMILES: Nc1ncnc2ccc(-c3ccc(CNc4ncccc4C(=O)NCc4cccnc4)s3)cc12] | 2-({[5-(4-aminoquinazolin-6-yl)thiophen-2-yl]methyl}amino)-N-(pyridin-3-ylmethyl)pyridine-3-carboxamide (TFA salt) | 468.2 | 1H NMR (300 MHz, DMSO-d6) δ 9.88 (br. s., 1H), 9.80 (br. s., 1H), 9.24 (t, J = 5.48 Hz, 1H), 8.76-8.92 (m, 2H), 8.73 (s, 1H), 8.65 (d, J = 4.91 Hz, 1H), 8.60 (s, 1H), 8.20-8.33 (m, 2H), 8.14 (d, J = 7.55 Hz, 1H), 8.07 (d, J = 7.18 Hz, 2H), 7.76 (d, J = 8.69 Hz, 1H), 7.71 (dd, J = 5.29, 7.55 Hz, 1H), 7.54 (d, J = 3.40 Hz, 1H), 7.12 (d, J = 3.40 Hz, 1H), 6.71 (dd, J = 5.29, 7.55 Hz, 1H), 4.74-4.95 (m, J = 4.53 Hz, 2H), 4.55 (d, J = 5.29 Hz, 2H). |
| 3.38 | 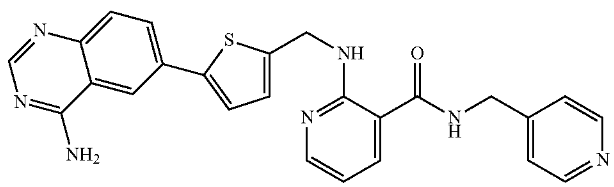 [SMILES: Nc1ncnc2ccc(-c3ccc(CNc4ncccc4C(=O)NCc4ccncc4)s3)cc12] | 2-({[5-(4-aminoquinazolin-6-yl)thiophen-2-yl]methyl}amino)-N-(pyridin-4-ylmethyl)pyridine-3-carboxamide (TFA salt) | 468.3 | 1H NMR (300 MHz, DMSO-d6) δ 9.88 (br. s., 1H), 9.80 (br. s., 1H), 9.35 (t, J = 4.91 Hz, 1H), 8.68-8.96 (m, 4H), 8.60 (br. s., 1H), 8.22-8.37 (m, 2H), 8.13 (d, J = 7.18 Hz, 1H), 7.69-7.88 (m, 3H), 7.54 (d, J = 3.40 Hz, 1H), 7.06-7.17 (m, J = 2.64 Hz, 1H), 6.73 (dd, J = 4.91, 7.18 Hz, 1H), 4.81-4.89 (m, J = 3.40 Hz, 2H), 4.64 (d, J = 4.53 Hz, 2H). |
| 3.39 | 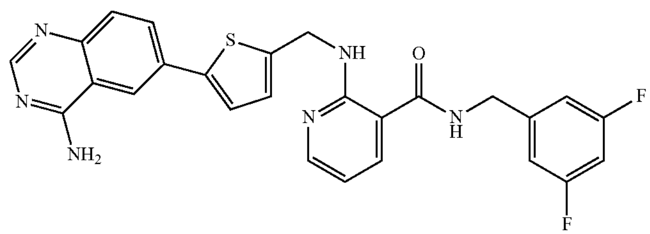 [SMILES: Nc1ncnc2ccc(-c3ccc(CNc4ncccc4C(=O)NCc4cc(F)cc(F)c4)s3)cc12] | 2-({[5-(4-aminoquinazolin-6-yl)thiophen-2-yl]methyl}amino)-N-(3,5-difluorobenzyl)pyridine-3-carboxamide (TFA salt) | 503.2 | 1H NMR (300 MHz, DMSO-d6) δ 9.87 (br. s., 1H), 9.78 (br. s., 1H), 9.17 (br. s., 1H), 8.71-8.91 (m, 2H), 8.51-8.66 (m, 1H), 8.18-8.35 (m, 2H), 8.07 (d, J = 5.67 Hz, 1H), 7.76 (d, J = 7.18 Hz, 1H), 7.54 (br. s., 1H), 7.08-7.21 (m, 2H), 6.93-7.08 (m, 2H), 6.70 (t, J = 6.80 Hz, 1H), 4.86 (d, 2H), 4.46 (d, 2H). |
| 3.40 | 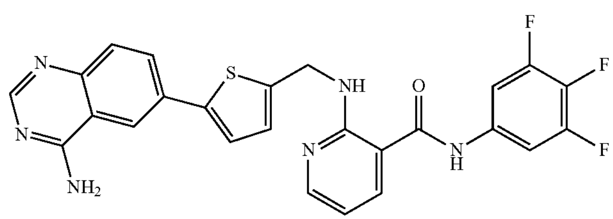 [SMILES: Nc1ncnc2ccc(-c3ccc(CNc4ncccc4C(=O)Nc4cc(F)c(F)c(F)c4)s3)cc12] | 2-({[5-(4-aminoquinazolin-6-yl)thiophen-2-yl]methyl}amino)-N-(3,4,5-trifluorophenyl)pyridine-3-carboxamide (TFA salt) | 507.2 | 1H NMR (300 MHz, DMSO-d6) δ 10.53 (s, 1H), 9.86 (br. s., 1H), 9.76 (br. s., 1H), 8.80 (s, 1H), 8.60 (d, J = 1.51 Hz, 1H), 8.42 (t, J = 6.04 Hz, 1H), 8.31 (dd, J = 1.51, 4.91 Hz, 1H), 8.28 (dd, J = 1.89, 9.06 Hz, 1H), 8.10 (dd, J = 1.89, 7.55 Hz, 1H), 7.76 (d, J = 8.69 Hz, 1H), 7.60-7.72 (m, 2H), 7.55 (d, J = 3.78 Hz, 1H), 7.14 (d, J = 3.40 Hz, 1H), 6.77 (dd, J = 4.72, 7.74 Hz, 1H), 4.89 (d, J = 5.67 Hz, 2H). |

TABLE 1-continued

| Ex. No. | Structure | Chemical Name | ESI-MS (M + H) | ¹H NMR |
|---|---|---|---|---|
| 3.41 | 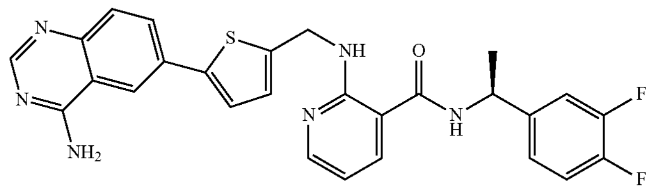 [SMILES: C[C@H](NC(=O)c1cccnc1NCc1ccc(-c2ccc3ncnc(N)c3c2)s1)c1ccc(F)c(F)c1] | (S)-2-(((5-(4-aminoquinazolin-6-yl)thiophen-2-yl)methyl)amino)-N-(1-(3,4-difluorophenyl)ethyl)nicotinamide (TFA salt) | 517.2 | ¹H NMR (300 MHz, DMSO-d₆) δ 9.87 (br. s., 1H), 8.87 (d, J = 7.55 Hz, 1H), 8.80 (s, 1H), 8.74 (t, J = 5.85 Hz, 1H), 8.54-8.64 (m, J = 1.51 Hz, 1H), 8.25 (s, 1H), 8.13 (dd, J = 1.89, 15.11 Hz, 1H), 8.13 (d, J = 1.84, 7.72 Hz, 1H), 7.76 (d, J = 8.69 Hz, 1H), 7.53 (d, J = 3.78 Hz, 1H), 7.29-7.49 (m, 2H), 7.16-7.28 (m, 1H), 7.10 (d, J = 3.78 Hz, 1H), 6.70 (dd, J = 4.72, 7.74 Hz, 1H), 5.09 (quin, J = 7.27 Hz, 1H), 4.83 (d, J = 4.15 Hz, 2H), 1.45 (d, J = 7.18 Hz, 3H). |
| 3.42 | 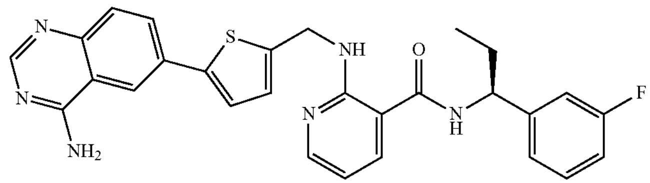 [SMILES: CC[C@H](NC(=O)c1cccnc1NCc1ccc(-c2ccc3ncnc(N)c3c2)s1)c1cccc(F)c1] | (S)-2-((5-(4-aminoquinazolin-6-yl)thiophen-2-yl)methylamino)-N-(1-(3-fluorophenyl)propyl)nicotinamide (TFA salt) | 513.3 | ¹H NMR (300 MHz, DMSO-d₆) δ 9.88 (br. s., 1H), 9.79 (br. s., 1H), 8.67-8.96 (m, 3H), 8.59 (s, 1H), 8.19-8.32 (m, 2H), 8.15 (d, J = 7.18 Hz, 1H), 7.77 (d, J = 8.69 Hz, 1H), 7.53 (d, J = 3.02 Hz, 1H), 7.29-7.43 (m, J = 7.18, 7.18, 7.18 Hz, 1H), 7.20 (d, J = 7.93 Hz, 2H), 6.97-7.15 (m, 2H), 6.71 (dd, J = 4.91, 7.18 Hz, 1H), 4.75-4.96 (m, 3H), 1.66-1.99 (m, 2H), 0.89 (t, J = 7.18 Hz, 3H). |
| 3.43 | 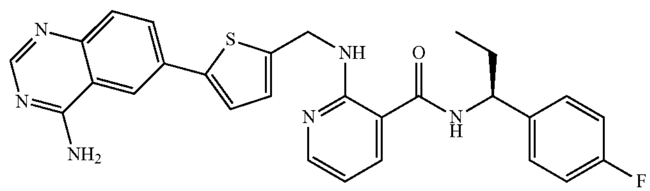 [SMILES: CC[C@H](NC(=O)c1cccnc1NCc1ccc(-c2ccc3ncnc(N)c3c2)s1)c1ccc(F)cc1] | (S)-2-((5-(4-aminoquinazolin-6-yl)thiophen-2-yl)methylamino)-N-(1-(4-fluorophenyl)propyl)nicotinamide (TFA salt) | 513.3 | ¹H NMR (300 MHz, DMSO-d₆) δ 9.87 (br. s., 1H), 8.77-8.91 (m, 2H), 8.74 (t, J = 5.67 Hz, 1H), 8.59 (d, J = 1.13 Hz, 1H), 8.24-8.31 (m, J = 1.51, 8.69 Hz, 1H), 8.23 (dd, J = 1.51, 4.91 Hz, 1H), 8.12 (dd, J = 1.32, 7.74 Hz, 1H), 7.76 (d, J = 8.69 Hz, 1H), 7.53 (d, J = 3.40 Hz, 1H), 7.40 (dd, J = 5.67, 8.31 Hz, 2H), 7.05-7.22 (m, 3H), 6.70 (dd, J = 4.91, 7.55 Hz, 1H), 4.74-4.93 (m, 3H), 1.65-1.96 (m, 2H), 0.88 (t, J = 7.18 Hz, 3H). |
| 3.44 | 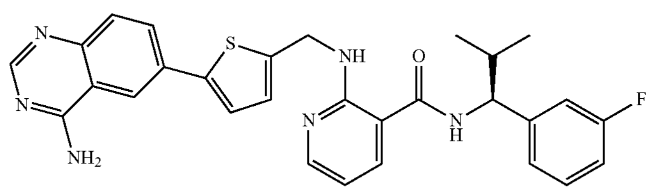 [SMILES: CC(C)[C@H](NC(=O)c1cccnc1NCc1ccc(-c2ccc3ncnc(N)c3c2)s1)c1cccc(F)c1] | (S)-2-((5-(4-aminoquinazolin-6-yl)thiophen-2-yl)methylamino)-N-(1-(3-fluorophenyl)-2-methylpropyl)nicotinamide (TFA salt) | 527.3 | ¹H NMR (300 MHz, DMSO-d₆) δ 9.85 (br. s., 1H), 9.77 (br. s., 1H), 8.75-8.85 (m, 2H), 8.67 (t, J = 6.04 Hz, 1H), 8.59 (d, J = 1.89 Hz, 1H), 8.19-8.30 (m, 2H), 8.10 (dd, J = 1.89, 7.55 Hz, 1H), 7.76 (d, J = 8.69 Hz, 1H), 7.52 (d, J = 3.78 Hz, 1H), 7.36 (td, J = 6.42, 7.93 Hz, 1H), 7.17-7.28 (m, 2H), 7.09 (d, J = 3.40 Hz, 1H), 7.00-7.08 (m, 1H), 6.71 (dd, J = 4.91, 7.55 Hz, 1H), 4.81 (d, J = 5.29 Hz, 2H), 4.63 (t, J = 8.88 Hz, 1H), 2.02-2.22 (m, 1H), 1.00 (d, J = 6.42 Hz, 3H), 0.71 (d, J = 6.80 Hz, 3H). |
| 3.45 | 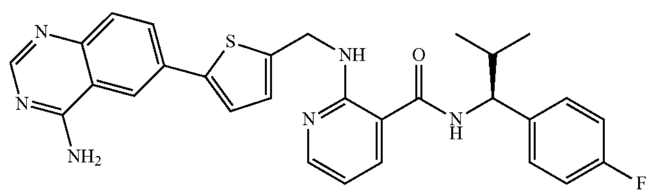 [SMILES: CC(C)[C@H](NC(=O)c1cccnc1NCc1ccc(-c2ccc3ncnc(N)c3c2)s1)c1ccc(F)cc1] | (S)-2-((5-(4-aminoquinazolin-6-yl)thiophen-2-yl)methylamino)-N-(1-(4-fluorophenyl)-2-methylpropyl)nicotinamide (TFA salt) | 527.3 | ¹H NMR (300 MHz, DMSO-d₆) δ 9.87 (br. s., 1H), 8.76-8.85 (m, 2H), 8.70 (t, J = 6.04 Hz, 1H), 8.59 (d, J = 1.51 Hz, 1H), 8.26 (dd, J = 1.51, 9.06 Hz, 1H), 8.22 (dd, J = 1.51, 4.91 Hz, 1H), 8.10 (dd, J = 1.32, 7.74 Hz, 1H), 7.76 (d, J = 8.69 Hz, 1H), 7.53 (d, J = 3.40 Hz, 1H), 7.41 (dd, J = 5.85, 8.50 Hz, 2H), 7.04-7.20 (m, 3H), 6.70 (dd, J = 4.91, 7.55 Hz, 1H), 4.81 (d, J = 4.53 Hz, 2H), 4.60 (t, J = 9.25 Hz, 1H), 2.01-2.21 (m, 1H), 1.00 (d, J = 6.42 Hz, 3H), 0.69 (d, J = 6.42 Hz, 3H). |

TABLE 1-continued

| Ex. No. | Structure | Chemical Name | ESI-MS (M + H) | ¹H NMR |
|---|---|---|---|---|
| 3.46 | 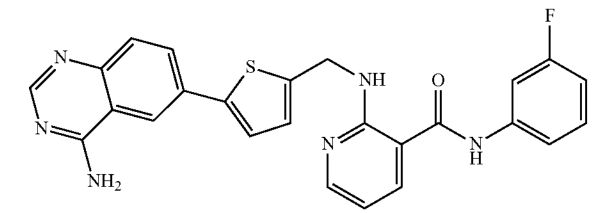 [SMILES: Nc1ncnc2ccc(-c3ccc(CNc4ncccc4C(=O)Nc4cccc(F)c4)s3)cc12] | 2-({[5-(4-aminoquinazolin-6-yl)thiophen-2-yl]methyl}amino)-N-(3-fluorophenyl)pyridine-3-carboxamide (TFA salt) | 471.2 | ¹H NMR (300 MHz, DMSO-d₆) δ 10.42 (s, 1H), 9.88 (br. s., 1H), 9.78 (br. s., 1H), 8.80 (s, 1H), 8.61 (d, J = 1.89 Hz, 1H), 8.46 (t, J = 5.85 Hz, 1H), 8.24-8.33 (m, 2H), 8.13 (dd, J = 1.51, 7.93 Hz, 1H), 7.76 (d, J = 8.69 Hz, 1H), 7.68 (dt, J = 2.08, 11.71 Hz, 1H), 7.55 (d, J = 3.40 Hz, 1H), 7.46-7.52 (m, 1H), 7.33-7.45 (m, 1H), 7.15 (d, J = 3.40 Hz, 1H), 6.94 (td, J = 3.02, 8.31 Hz, 1H), 6.76 (dd, J = 4.91, 7.55 Hz, 1H), 4.89 (d, J = 4.91 Hz, 2H). |
| 3.47 | 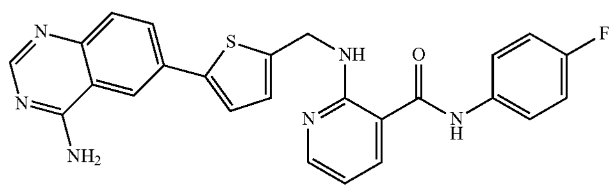 [SMILES: Nc1ncnc2ccc(-c3ccc(CNc4ncccc4C(=O)Nc4ccc(F)cc4)s3)cc12] | 2-({[5-(4-aminoquinazolin-6-yl)thiophen-2-yl]methyl}amino)-N-(4-fluorophenyl)pyridine-3-carboxamide (TFA salt) | 471.2 | ¹H NMR (300 MHz, DMSO-d₆) δ 10.32 (s, 1H), 9.89 (br. s., 1H), 9.79 (br. s., 1H), 8.80 (s, 1H), 8.57-8.65 (m, J = 1.51 Hz, 1H), 8.51 (t, J = 5.67 Hz, 1H), 8.24-8.32 (m, 2H), 8.13 (dd, J = 1.51, 7.93 Hz, 1H), 7.77 (d, J = 8.69 Hz, 1H), 7.65-7.74 (m, 2H), 7.55 (d, J = 3.40 Hz, 1H), 7.19 (t, J = 8.88 Hz, 2H), 7.14 (d, J = 3.78 Hz, 1H), 6.75 (dd, J = 4.91, 7.55 Hz, 1H), 4.88 (d, J = 4.53 Hz, 2H). |
| 3.48 | 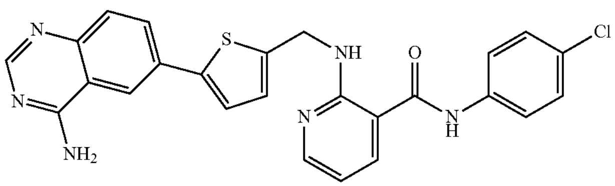 [SMILES: Nc1ncnc2ccc(-c3ccc(CNc4ncccc4C(=O)Nc4ccc(Cl)cc4)s3)cc12] | 2-({[5-(4-aminoquinazolin-6-yl)thiophen-2-yl]methyl}amino)-N-(4-chlorophenyl)pyridine-3-carboxamide (TFA salt) | 487.2 | ¹H NMR (300 MHz, DMSO-d₆) δ 10.37 (br. s., 1H), 9.88 (br. s., 1H), 9.79 (br. s., 1H), 8.80 (s, 1H), 8.61 (br. s., 1H), 8.49 (t, J = 5.67 Hz, 1H), 8.23-8.35 (m, 2H), 8.13 (d, J = 7.18 Hz, 1H), 7.69-7.82 (m, 3H), 7.55 (d, J = 3.02, 2H), 7.41 (d, J = 8.31 Hz, 2H), 7.09-7.18 (m, 1H), 7.14 (d, J = 2.27 Hz, 1H), 6.75 (dd, J = 4.91, 7.18 Hz, 1H), 4.80-4.95 (m, J = 3.78 Hz, 2H). |
| 3.49 | 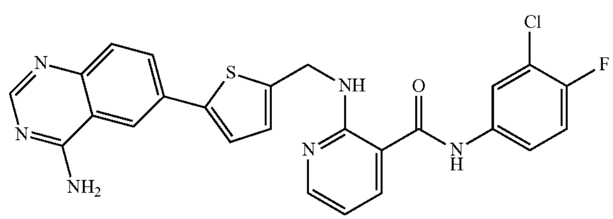 [SMILES: Nc1ncnc2ccc(-c3ccc(CNc4ncccc4C(=O)Nc4ccc(F)c(Cl)c4)s3)cc12] | 2-({[5-(4-aminoquinazolin-6-yl)thiophen-2-yl]methyl}amino)-N-(3-chloro-4-fluorophenyl)pyridine-3-carboxamide (TFA salt) | 505.3 | ¹H NMR (300 MHz, DMSO-d₆) δ 10.43 (s, 1H), 9.89 (br. s., 1H), 9.79 (br. s., 1H), 8.80 (s, 1H), 8.61 (d, J = 1.51 Hz, 1H), 8.48 (t, J = 5.85 Hz, 1H), 8.23-8.34 (m, 2H), 8.12 (dd, J = 1.70, 7.74 Hz, 1H), 8.02 (dd, J = 2.45, 6.99 Hz, 1H), 7.77 (d, J = 9.06 Hz, 1H), 7.63 (ddd, J = 2.64, 4.15, 9.06 Hz, 1H), 7.55 (d, J = 3.78 Hz, 1H), 7.37-7.47 (m, 1H), 7.14 (d, J = 3.78 Hz, 1H), 6.76 (dd, J = 4.91, 7.55 Hz, 1H), 4.88 (d, J = 5.29 Hz, 2H). |
| 3.50 | 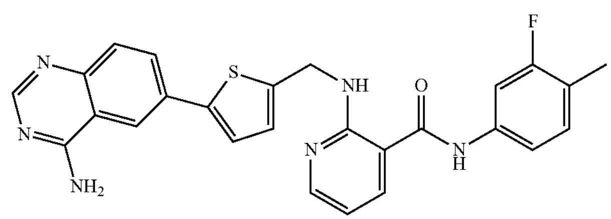 [SMILES: Cc1ccc(NC(=O)c2cccnc2NCc2ccc(-c3ccc4ncnc(N)c4c3)s2)cc1F] | 2-({[5-(4-aminoquinazolin-6-yl)thiophen-2-yl]methyl}amino)-N-(3-fluoro-4-methylphenyl)pyridine-3-carboxamide (TFA salt) | 489.3 | ¹H NMR (300 MHz, DMSO-d₆) δ 10.34 (s, 1H), 9.88 (br. s., 1H), 9.79 (br. s., 1H), 8.80 (s, 1H), 8.56-8.67 (m, J = 1.51 Hz, 1H), 8.50 (t, J = 4.53 Hz, 1H), 8.21-8.33 (m, 2H), 8.06-8.17 (m, J = 1.51, 7.55 Hz, 1H), 7.77 (d, J = 8.69 Hz, 1H), 7.62 (dd, J = 1.70, 12.27 Hz, 1H), 7.55 (d, J = 3.40 Hz, 1H), 7.38 (dd, J = 1.51, 8.31 Hz, 1H), 7.24 (t, J = 8.69 Hz, 1H), 7.14 (d, J = 3.40 Hz, 1H), 6.75 (dd, J = 4.91, 7.55 Hz, 1H), 4.88 (d, J = 4.53 Hz, 2H), 2.20 (s, 3H). |

TABLE 1-continued

| Ex. No. | Structure | Chemical Name | ESI-MS (M + H) | ¹H NMR |
|---|---|---|---|---|
| 3.51 | 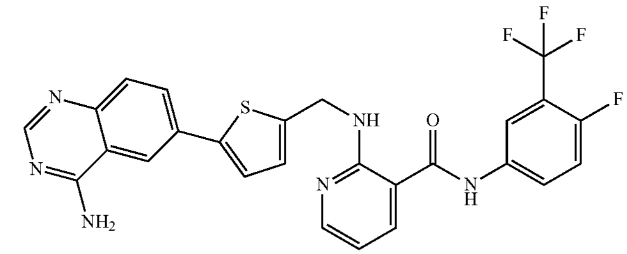 [SMILES: Nc1ncnc2ccc(-c3ccc(CNc4ncccc4C(=O)Nc4ccc(F)c(C(F)(F)F)c4)s3)cc12] | 2-({[5-(4-aminoquinazolin-6-yl)thiophen-2-yl]methyl}amino)-N-[4-fluoro-3-(trifluoromethyl)phenyl]pyridine-3-carboxamide (TFA salt) | 539.4 | ¹H NMR (300 MHz, DMSO-d₆) δ 10.55 (s, 1H), 9.87 (br. s., 1H), 9.78 (br. s., 1H), 8.80 (s, 1H), 8.60 (d, J = 1.89 Hz, 1H), 8.49 (t, J = 5.67 Hz, 1H), 8.29-8.34 (m, 1H), 8.28 (dd, J = 1.89, 8.69 Hz, 1H), 8.22 (dd, J = 2.45, 6.61 Hz, 1H), 8.15 (dd, J = 1.70, 7.74 Hz, 1H), 7.98 (ddd, J = 3.02, 4.25, 8.97 Hz, 1H), 7.76 (d, J = 9.06 Hz, 1H), 7.55 (d, J = 3.78 Hz, 1H), 7.53 (t, J = 9.82 Hz, 1H), 7.14 (d, J = 3.78 Hz, 1H), 6.77 (dd, J = 4.91, 7.55 Hz, 1H), 4.89 (d, J = 5.29 Hz, 2H). |
| 3.52 | 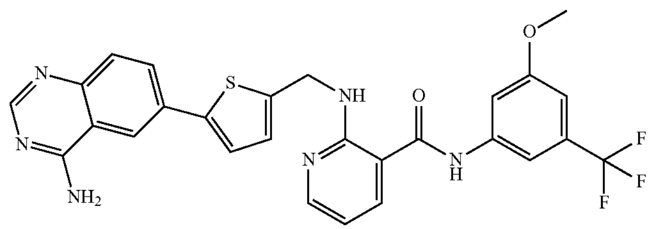 [SMILES: COc1cc(NC(=O)c2cccnc2NCc2ccc(-c3ccc4ncnc(N)c4c3)s2)cc(C(F)(F)F)c1] | 2-({[5-(4-aminoquinazolin-6-yl)thiophen-2-yl]methyl}amino)-N-[3-methoxy-5-(trifluoromethyl)phenyl]pyridine-3-carboxamide (TFA salt) | 551.4 | ¹H NMR (300 MHz, DMSO-d₆) δ 10.48 (s, 1H), 9.87 (br. s., 1H), 9.78 (br. s., 1H), 8.80 (s, 1H), 8.60 (d, J = 1.89 Hz, 1H), 8.49 (t, J = 6.04 Hz, 1H), 8.30 (dd, J = 1.51, 4.91 Hz, 1H), 8.28 (dd, J = 1.89, 9.30 Hz, 1H), 8.15 (dd, J = 1.70, 7.74 Hz, 1H), 7.79-7.84 (m, 1H), 7.76 (d, J = 8.69 Hz, 1H), 7.60 (t, J = 1.89 Hz, 1H), 7.55 (d, J = 3.40 Hz, 1H), 7.14 (d, J = 3.78 Hz, 1H), 6.96-7.03 (m, 1H), 6.76 (dd, J = 4.91, 7.55 Hz, 1H), 4.89 (d, J = 5.29 Hz, 2H), 3.83 (s, 3H). |
| 3.53 | 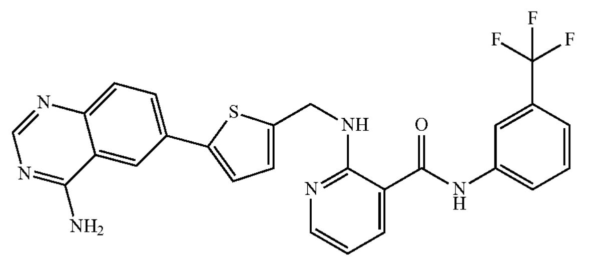 [SMILES: Nc1ncnc2ccc(-c3ccc(CNc4ncccc4C(=O)Nc4cccc(C(F)(F)F)c4)s3)cc12] | 2-({[5-(4-aminoquinazolin-6-yl)thiophen-2-yl]methyl}amino)-N-[3-(trifluoromethyl)phenyl]pyridine-3-carboxamide (TFA salt) | 521.3 | ¹H NMR (300 MHz, DMSO-d₆) δ 10.53 (s, 1H), 9.86 (br. s., 1H), 9.77 (br. s., 1H), 8.80 (s, 1H), 8.60 (d, J = 1.89 Hz, 1H), 8.50 (t, J = 6.04 Hz, 1H), 8.30 (dd, J = 1.89, 4.91 Hz, 1H), 8.25-8.29 (m, J = 1.89, 9.06 Hz, 1H), 8.22 (t, J = 2.08 Hz, 1H), 8.16 (dd, J = 1.89, 7.93 Hz, 1H), 7.89-7.98 (m, 1H), 7.76 (d, J = 8.69 Hz, 1H), 7.60 (t, J = 7.93 Hz, 1H), 7.55 (d, J = 3.78 Hz, 1H), 7.47 (d, J = 7.93 Hz, 1H), 7.14 (d, J = 3.78 Hz, 1H), 6.76 (dd, J = 4.91, 7.55 Hz, 1H), 4.89 (d, J = 5.67 Hz, 2H). |
| 3.54 | 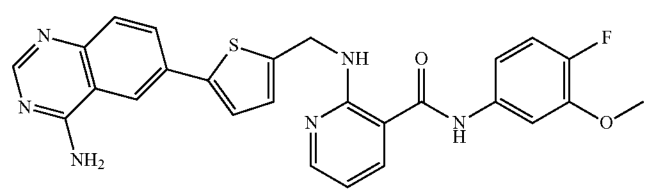 [SMILES: COc1cc(NC(=O)c2cccnc2NCc2ccc(-c3ccc4ncnc(N)c4c3)s2)ccc1F] | 2-({[5-(4-aminoquinazolin-6-yl)thiophen-2-yl]methyl}amino)-N-(4-fluoro-3-methoxyphenyl)pyridine-3-carboxamide (TFA salt) | 501.4 | ¹H NMR (300 MHz, DMSO-d₆) δ 10.27 (s, 1H), 9.88 (br s, 1H), 9.78 (br s, 1H), 8.80 (s, 1H), 8.60 (s, 1H), 8.50 (t, J = 5.3 Hz, 1H), 8.29 (s, 1H), 8.28-8.24 (m, 1H), 8.12 (d, J = 7.5 Hz, 1H), 7.76 (d, J = 8.7 Hz, 1H), 7.61-7.52 (m, 2H), 7.29-7.23 (m, 1H), 7.22-7.11 (m, 2H), 6.75 (dd, J = 7.5; 4.8 Hz, 1H), 4.89 (d, J = 4.8 Hz, 2H), 3.82 (s, 3H). |

TABLE 1-continued

| Ex. No. | Structure | Chemical Name | ESI-MS (M + H) | ¹H NMR |
|---|---|---|---|---|
| 3.55 | 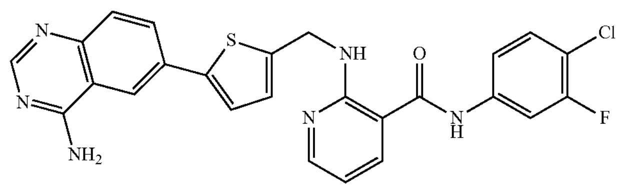 [SMILES: Nc1ncnc2ccc(-c3ccc(CNc4ncccc4C(=O)Nc4ccc(Cl)c(F)c4)s3)cc12] | 2-({[5-(4-aminoquinazolin-6-yl)thiophen-2-yl]methyl}amino)-N-(4-chloro-3-fluorophenyl)pyridine-3-carboxamide (TFA salt) | 505.3 | ¹H NMR (300 MHz, DMSO-d₆) δ 10.52 (s, 1H), 9.86 (br s, 1H), 9.77 (br s, 1H), 8.80 (s, 1H), 8.61 (d, J = 1.5 Hz, 1H), 8.44 (t, J = 5.8 Hz, 1H), 8.29 (d, J = 1.5 Hz, 1H), 8.29 (dd, J = 14.1; 1.5 Hz, 1H), 8.12 (dd, J = 7.7; 1.7 Hz, 1H), 7.88 (dd, J = 12.1; 1.9 Hz, 1H), 7.76 (d, J = 9.0 Hz, 1H), 7.61-7.49 (m, 3H), 7.14 (d, J = 3.9 Hz, 1H), 6.76 (dd, J = 7.7; 4.9 Hz, 1H), 4.89 (d, J = 5.7 Hz, 2H). |
| 3.56 | 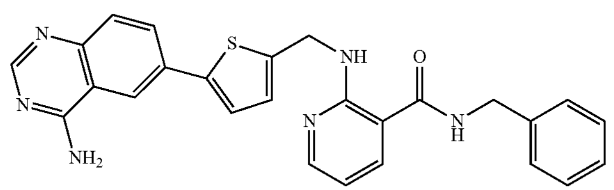 [SMILES: Nc1ncnc2ccc(-c3ccc(CNc4ncccc4C(=O)NCc4ccccc4)s3)cc12] | 2-({[5-(4-aminoquinazolin-6-yl)thiophen-2-yl]methyl}amino)-N-benzylpyridine-3-carboxamide (TFA salt) | 467.2 | ¹H NMR (300 MHz, DMSO-d₆) δ 9.11 (br t, J = 5.3 Hz, 1H), 8.83 (br t, J = 5.6 Hz, 1H), 8.41 (s, 1H), 8.34 (s, 1H), 8.24 (d, J = 3.9 Hz, 1H), 8.04 (d, J = 6.9 Hz, 1H), 7.97 (d, J = 8.7 Hz, 1H), 7.85 (br s, 2H), 7.64 (d, J = 8.7 Hz, 1H), 7.46 (d, J = 3.3 Hz, 1H), 7.38-7.18 (m, 5H), 7.07 (d, J = 3.0 Hz, 1H), 6.67 (dd, J = 7.5; 4.8 Hz, 1H), 4.84 (d, J = 5.7 Hz, 2H), 4.45 (d, J = 5.7 Hz, 2H). |
| 3.57 | 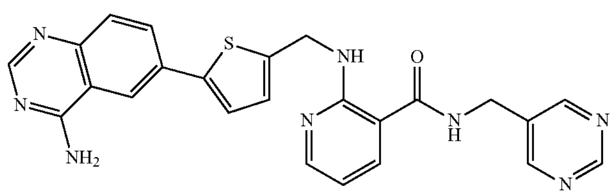 [SMILES: Nc1ncnc2ccc(-c3ccc(CNc4ncccc4C(=O)NCc4cncnc4)s3)cc12] | 2-({[5-(4-aminoquinazolin-6-yl)thiophen-2-yl]methyl}amino)-N-(pyrimidin-5-ylmethyl)pyridine-3-carboxamide (TFA salt) | 469.3 | — |
| 3.58 | 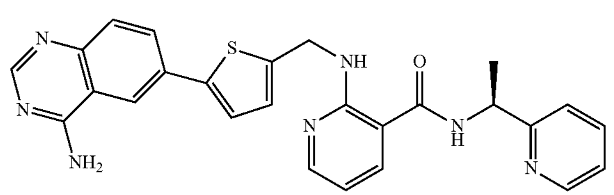 [SMILES: C[C@H](NC(=O)c1cccnc1NCc1ccc(-c2ccc3ncnc(N)c3c2)s1)c1ccccn1] | (S)-2-(((5-(4-aminoquinazolin-6-yl)thiophen-2-yl)methyl)amino)-N-(1-(pyridin-2-yl)ethyl)nicotinamide (TFA salt) | 482.3 | ¹H NMR (300 MHz, DMSO-d₆) δ 9.85 (br. s., 1H), 9.02 (d, J = 6.71 Hz, 1H), 8.77 (s, 1H), 8.75 (br. s., 1H), 8.60 (dt, J = 1.06, 5.53 Hz, 1H), 8.56 (d, J = 8.77 Hz, 1H), 8.14-8.27 (m, 3H), 7.98-8.10 (m, 1H), 7.73 (d, J = 8.77 Hz, 1H), 7.64 (d, J = 7.95 Hz, 1H), 7.43-7.55 (m, 2H), 7.07 (d, J = 3.64 Hz, 1H), 6.71 (dd, J = 4.97, 7.62 Hz, 1H), 5.10-5.26 (m, 1H), 1.50 (d, J = 7.08 Hz, 3H). |
| 3.59 | 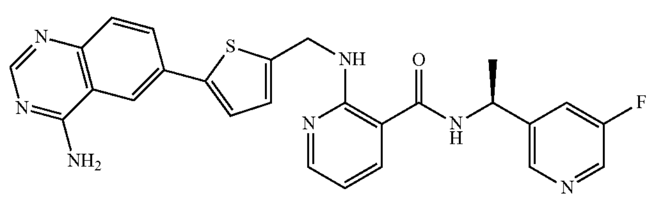 [SMILES: C[C@H](NC(=O)c1cccnc1NCc1ccc(-c2ccc3ncnc(N)c3c2)s1)c1cncc(F)c1] | (S)-2-(((5-(4-aminoquinazolin-6-yl)thiophen-2-yl)methyl)amino)-N-(1-(5-(fluoropyridin-3-yl)ethyl)nicotinamide (TFA salt) | 500.3 | ¹H NMR (300 MHz, DMSO-d₆) δ 9.87 (br. s., 1 H), 8.94 (d, J = 7.4 Hz, 1 H), 8.80 (s, 1 H), 8.72 (br. s., 1 H), 8.59 (d, J = 1.9 Hz, 1 H), 8.49 (t, J = 1.8 Hz, 1 H), 8.45 (d, J = 2.7 Hz, 1 H), 8.30-8.20 (m, 2 H), 8.14 (dd, J = 1.8, 7.7 Hz, 1 H), 7.81-7.68 (m, 2 H), 7.52 (d, J = 3.7 Hz, 1 H), 7.10 (d, J = 3.7 Hz, 1 H), 6.71 (dd, J = 4.9, 7.7 Hz, 1 H), 5.18 (quin, J = 7.0 Hz, 1 H), 4.83 (d, J = 4.5 Hz, 2 H), 1.50 (d, J = 7.1 Hz, 3H). |

TABLE 1-continued

| Ex. No. | Structure | Chemical Name | ESI-MS (M + H) | $^1$H NMR |
|---|---|---|---|---|
| 3.60 | 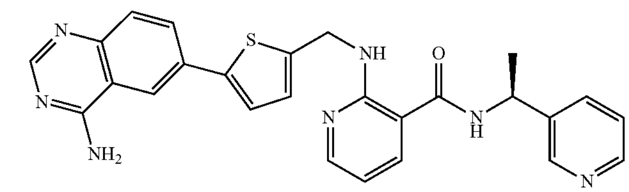 [SMILES: C[C@H](NC(=O)c1cccnc1NCc1ccc(-c2ccc3ncnc(N)c3c2)s1)c1cccnc1] | (S)-2-(((5-(4-aminoquinazolin-6-yl)thiophen-2-yl)methyl)amino)-N-(1-(pyridin-3-yl)ethyl)nicotinamide (TFA salt) | 482.3 | $^1$H NMR (300 MHz, DMSO-d$_6$) δ 9.87 (br. s., 1 H), 9.78 (br. s., 1 H), 8.98 (d, J = 7.2 Hz, 1 H), 8.80 (s, 1 H), 8.78-8.74 (m, 1 H), 8.69 (t, J = 5.8 Hz, 1 H), 8.65-8.60 (m, 1 H), 8.59 (dd, J = 0.7, 1.8 Hz, 1 H), 8.30-8.21 (m, 2 H), 8.20-8.10 (m, 2 H), 7.76 (d, J = 8.8 Hz, 1 H), 7.67 (dd, J = 5.2, 8.0 Hz, 1 H), 7.52 (d, J = 3.7 Hz, 1 H), 7.09 (d, J = 3.7 Hz, 1 H), 6.71 (dd, J = 4.9, 7.7 Hz, 1 H), 5.20 (quin, J = 7.1 Hz, 1 H), 4.92-4.72 (m, 2 H), 1.52 (d, J = 7.1 Hz, 3 H). |
| 3.61 | 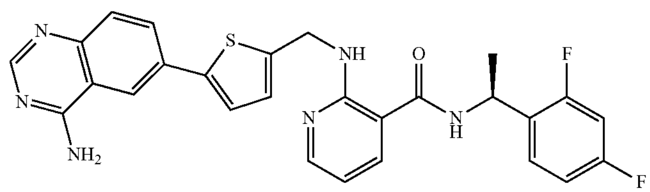 [SMILES: C[C@H](NC(=O)c1cccnc1NCc1ccc(-c2ccc3ncnc(N)c3c2)s1)c1ccc(F)cc1F] | (S)-2-(((5-(4-aminoquinazolin-6-yl)thiophen-2-yl)methyl)amino)-N-(1-(2,4-difluorophenyl)ethyl)nicotinamide (TFA salt) | 517.3 | $^1$H NMR (300 MHz, DMSO-d$_6$) δ = 9.85 (br. s., 1 H), 8.90 (d, J = 7.3 Hz, 1 H), 8.79 (s, 1 H), 8.70 (t, J = 5.9 Hz, 1 H), 8.61-8.55 (m, 1 H), 8.29-8.19 (m, 2 H), 8.13 (dd, J = 1.8, 7.7 Hz, 1 H), 7.75 (d, J = 8.8 Hz, 1 H), 7.55-7.42 (m, 2 H), 7.23-7.12 (m, 1 H), 7.12-7.00 (m, 2 H), 6.69 (dd, J = 4.8, 7.7 Hz, 1 H), 5.30 (quin, J = 7.1 Hz, 1 H), 4.81 (d, J = 5.4 Hz, 2 H), 1.45 (d, J = 7.0 Hz, 3 H). |
| 3.62 | 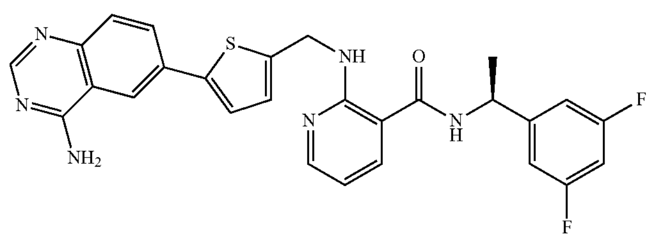 [SMILES: C[C@H](NC(=O)c1cccnc1NCc1ccc(-c2ccc3ncnc(N)c3c2)s1)c1cc(F)cc(F)c1] | (S)-2-(((5-(4-aminoquinazolin-6-yl)thiophen-2-yl)methyl)amino)-N-(1-(3,5-difluorophenyl)ethyl)nicotinamide (TFA salt) | 517.3 | $^1$H NMR (300 MHz, DMSO-d$_6$) δ = 9.85 (br. s., 1 H), 9.77 (br. s., 1 H), 8.87 (d, J = 7.4 Hz, 1 H), 8.79 (s, 1 H), 8.70 (t, J = 6.1 Hz, 1 H), 8.59 (d, J = 1.7 Hz, 1 H), 8.29-8.21 (m, 2 H), 8.13 (dd, J = 1.8, 7.8 Hz, 1 H), 7.75 (d, J = 8.7 Hz, 1 H), 7.52 (d, J = 3.8 Hz, 1 H), 7.15-7.01 (m, 4 H), 6.70 (dd, J = 4.9, 7.7 Hz, 1 H), 5.10 (quin, J = 7.1 Hz, 1 H), 4.83 (d, J = 5.9 Hz, 2 H), 1.45 (d, J = 7.2 Hz, 3 H). |
| 3.63 | 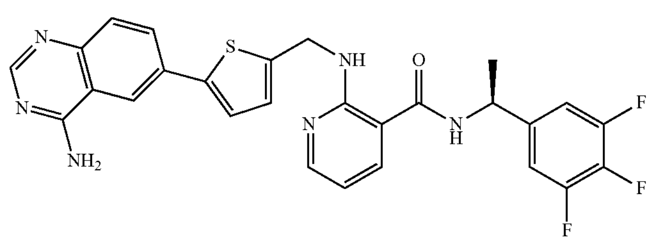 [SMILES: C[C@H](NC(=O)c1cccnc1NCc1ccc(-c2ccc3ncnc(N)c3c2)s1)c1cc(F)c(F)c(F)c1] | (S)-2-(((5-(4-aminoquinazolin-6-yl)thiophen-2-yl)methyl)amino)-N-(1-(3,4,5-trifluorophenyl)ethyl)nicotinamide (TFA salt) | 535.3 | $^1$H NMR (300 MHz, DMSO-d$_6$) δ 9.87 (br. s., 1 H), 9.78 (br. s., 1 H), 8.86 (d, J = 7.4 Hz, 1 H), 8.79 (s, 1 H), 8.71 (t, J = 6.2 Hz, 1 H), 8.59 (d, J = 2.1 Hz, 1 H), 8.29-8.20 (m, 2 H), 8.13 (dd, J = 1.9, 7.7 Hz, 1 H), 7.76 (d, J = 8.9 Hz, 1 H), 7.52 (d, J = 3.8 Hz, 1 H), 7.39-7.26 (m, 2 H), 7.10 (d, J = 3.8 Hz, 1 H), 6.70 (dd, J = 4.9, 7.7 Hz, 1 H), 5.07 (quin, J = 7.0 Hz, 1 H), 4.83 (d, J = 5.5 Hz, 2 H), 1.44 (d, J = 7.0 Hz, 3 H). |

| Ex. No. | Structure | Chemical Name | ESI-MS (M + H) | ¹H NMR |
|---|---|---|---|---|
| 3.64 | 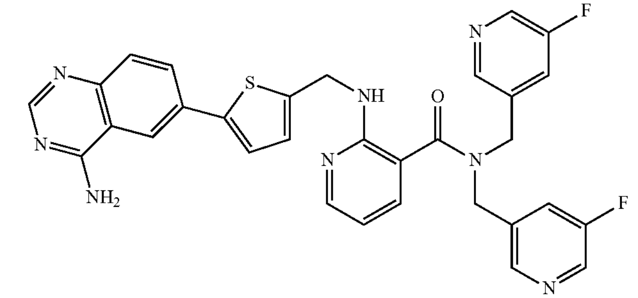 [SMILES: Nc1ncnc2ccc(-c3ccc(CNc4ncccc4C(=O)N(Cc4cncc(F)c4)Cc4cncc(F)c4)s3)cc12] | 2-(((5-(4-aminoquinazolin-6-yl)thiophen-2-yl)methyl)amino)-N,N-bis((5-fluoropyridin-3-yl)methyl)nicotinamide (TFA salt) | 595.3 | ¹H NMR (300 MHz, DMSO-d₆) δ 9.88 (br. s., 1 H), 9.80 (br. s., 1 H), 8.80 (s, 1 H), 8.59 (d, J = 1.9 Hz, 1 H), 8.48-8.37 (m, 2 H), 8.27 (br. s., 2 H), 8.20 (dd, J = 1.9, 8.8 Hz, 1 H), 8.13 (dd, J = 1.8, 5.1 Hz, 1 H), 7.76 (d, J = 8.8 Hz, 1 H), 7.68 (dd, J = 1.8, 7.4 Hz, 1 H), 7.57 (br. s., 1 H), 7.60 (br. s., 1 H), 7.51 (d, J = 3.7 Hz, 1 H), 7.18 (s, 1 H), 7.07 (d, J = 3.7 Hz, 1 H), 6.68 (dd, J = 5.1, 7.3 Hz, 1 H), 4.77-4.71 (m, 2 H) 4.67 (br. s, 4 H). |
| 3.65 | 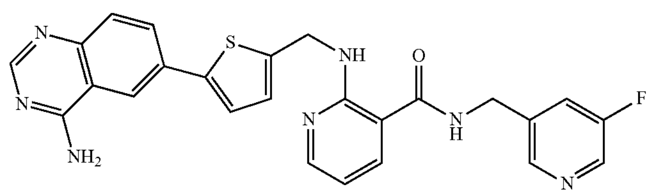 [SMILES: Nc1ncnc2ccc(-c3ccc(CNc4ncccc4C(=O)NCc4cncc(F)c4)s3)cc12] | 2-({[5-(4-aminoquinazolin-6-yl)thiophen-2-yl]methyl}amino)-N-[(5-fluoropyridin-3-yl)methyl]pyridine-3-carboxamide (TFA salt) | 586.2 | ¹H NMR (300 MHz, DMSO-d₆) δ 9.89 (br. s., 1 H), 9.79 (br. s., 1 H), 9.20 (t, J = 5.9 Hz, 1 H), 8.84 (t, J = 7.6 Hz, 1 H), 8.80 (s, 1 H), 8.61 (d, J = 1.1 Hz, 1 H), 8.52-8.41 (m, 2 H), 8.32-8.20 (m, 2 H), 8.07 (dd, J = 1.7, 7.7 Hz, 1 H), 7.77 (d, J = 8.7 Hz, 1 H), 7.66 (dt, J = 2.5, 9.6 Hz, 1 H), 7.54 (d, J = 3.8 Hz, 1 H), 7.12 (d, J = 3.8 Hz, 1 H), 6.70 (dd, J = 4.7, 7.7 Hz, 1 H), 4.86 (d, J = 2.3 Hz, 2 H), 4.50 (d, J = 6.0 Hz, 2 H). ¹⁹F NMR-TFA ratio is 3:1 by integration. |
| 3.66 | 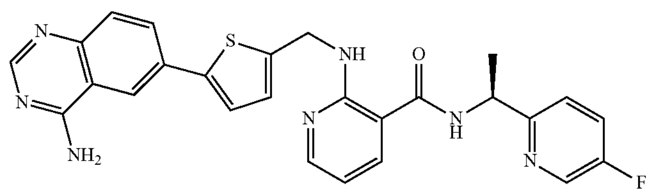 [SMILES: C[C@H](NC(=O)c1cccnc1NCc1ccc(-c2ccc3ncnc(N)c3c2)s1)c1ccc(F)cn1] | 2-({[5-(4-aminoquinazolin-6-yl)thiophen-2-yl]methyl}amino)-N-[(1S)-1-(5-fluoropyridin-2-yl)ethyl]pyridine-3-carboxamide (TFA salt) | 500.3 | ¹H NMR (300 MHz, DMSO-d₆) δ 9.88 (br. s., 1 H), 9.79 (br. s., 1 H), 8.92 (d, J = 7.6 Hz, 1 H), 8.84-8.70 (m, 2 H), 8.60 (d, J = 1.9 Hz, 1 H), 8.49 (d, J = 3.0 Hz, 1 H), 8.32-8.21 (m, 2 H), 8.17 (dd, J = 1.9, 7.9 Hz, 1 H), 7.77 (d, J = 8.7 Hz, 1 H), 7.68 (td, J = 3.0, 8.9 Hz, 1 H), 7.53 (d, J = 3.4 Hz, 1 H), 7.48 (dd, J = 4.5, 8.7 Hz, 1 H), 7.11 (d, J = 3.8 Hz, 1 H), 6.70 (dd, J = 4.9, 7.9 Hz, 1 H), 5.17 (quin, J = 7.2 Hz, 1 H), 4.93-4.73 (m, 2 H), 1.49 (d, J = 7.2 Hz, 3 H). ¹⁹F NMR-TFA ratio is 2:1. |
| 3.67 | 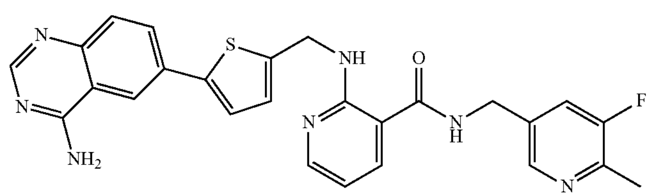 [SMILES: Cc1ncc(CNC(=O)c2cccnc2NCc2ccc(-c3ccc4ncnc(N)c4c3)s2)cc1F] | 2-(((5-(4-aminoquinazolin-6-yl)thiophen-2-yl)methyl)amino)-N-((5-fluoro-6-methylpyridin-3-yl)methyl)nicotinamide (TFA salt) | 500.2 | ¹H NMR (300 MHz, DMSO-d₆) δ 9.91 (br. s., 1H), 9.80 (br. s., 1H), 9.21 (t, J = 5.29 Hz, 1H), 8.89 (br. s., 1H), 8.80 (s, 1H), 8.56-8.67 (m, J = 1.13 Hz, 1H), 8.19-8.38 (m, 3H), 8.07 (d, J = 6.42 Hz, 1H), 7.78 (d, J = 9.06 Hz, 1H), 7.58 (d, J = 10.58 Hz, 1H), 7.54 (d, J = 3.78 Hz, 1H), 7.12 (d, J = 3.40 Hz, 1H), 6.71 (dd, J = 4.91, 7.55 Hz, 1H), 4.86 (br. s., 2H), 4.46 (d, J = 5.67 Hz, 2H), 2.41 (d, J = 2.64 Hz, 3H). |

TABLE 1-continued

| Ex. No. | Structure | Chemical Name | ESI-MS (M + H) | ¹H NMR |
|---|---|---|---|---|
| 3.68 | 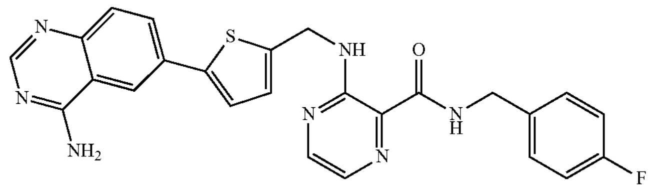 | 3-({[5-(4-aminoquinazolin-6-yl)thiophen-2-yl]methyl}amino)-N-(4-fluorobenzyl)pyrazine-2-carboxamide (TFA salt) | 486.3 | ¹H NMR (300 MHz, DMSO-d₆) δ 9.84 (br. s., 1H), 9.77 (br. s., 1H), 9.46 (t, J = 6.42 Hz, 1H), 9.18 (t, J = 6.04 Hz, 1H), 8.80 (s, 1H), 8.56-8.63 (m, J = 1.13 Hz, 1H), 8.34 (d, J = 2.27 Hz, 1H), 8.28 (dd, J = 1.51, 8.69 Hz, 1H), 7.89 (d, J = 2.64 Hz, 1H), 7.76 (d, J = 8.69 Hz, 1H), 7.55 (d, J = 3.40 Hz, 1H), 7.36 (dd, J = 5.67, 8.31 Hz, 2H), 7.06-7.21 (m, 3H), 4.88 (d, J = 6.04 Hz, 2H), 4.43 (d, J = 6.04 Hz, 2H). |
| 3.69 | 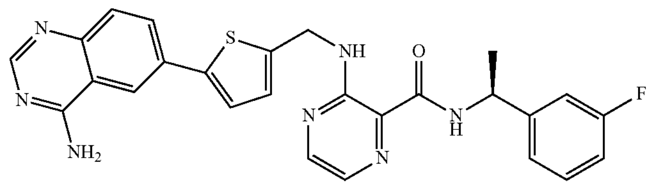 | 3-({[5-(4-aminoquinazolin-6-yl)thiophen-2-yl]methyl}amino)-N-[(1S)-1-(3-fluorophenyl)ethyl]pyrazine-2-carboxamide (TFA salt) | 500.2 | ¹H NMR (300 MHz, DMSO-d₆) δ 9.85 (br. s., 1H), 9.22 (d, J = 8.31 Hz, 1H), 9.12 (t, J = 5.85 Hz, 1H), 8.80 (s, 1H), 8.54-8.62 (m, J = 1.51 Hz, 1H), 8.35 (d, J = 2.27 Hz, 1H), 8.28 (dd, J = 1.51, 8.69 Hz, 1H), 7.92 (d, J = 2.27 Hz, 1H), 7.76 (d, J = 8.69 Hz, 1H), 7.54 (d, J = 3.40 Hz, 1H), 7.30-7.41 (m, 1H), 7.18-7.30 (m, 2H), 7.13 (d, J = 3.78 Hz, 1H), 7.05 (td, J = 2.08, 8.40 Hz, 1H), 5.12 (quin, J = 7.27 Hz, 1H), 4.86 (d, J = 6.04 Hz, 2H), 1.51 (d, J = 6.80 Hz, 3H). |
| 3.70 | 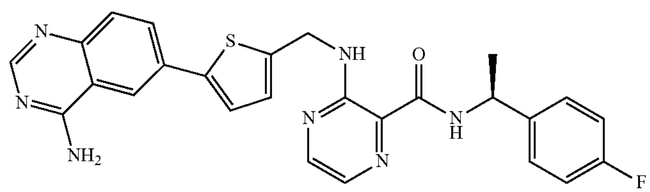 | 3-({[5-(4-aminoquinazolin-6-yl)thiophen-2-yl]methyl}amino)-N-[(1S)-1-(4-fluorophenyl)ethyl]pyrazine-2-carboxamide (TFA salt) | 500.2 | ¹H NMR (300 MHz, DMSO-d₆) δ 9.85 (br. s., 1H), 9.06-9.23 (m, 2H), 8.80 (s, 1H), 8.34 (d, J = 2.64 Hz, 1H), 8.28 (dd, J = 1.51, 8.69 Hz, 1H), 7.91 (d, J = 2.64 Hz, 1H), 7.76 (d, J = 8.69 Hz, 1H), 7.54 (d, J = 3.40 Hz, 1H), 7.45 (dd, J = 5.67, 8.31 Hz, 2H), 7.13 (t, J = 9.06 Hz, 3H), 5.11 (quin, J = 7.37 Hz, 1H), 4.86 (d, J = 6.04 Hz, 2H), 1.50 (d, J = 7.18 Hz, 3H). |
| 3.71 | 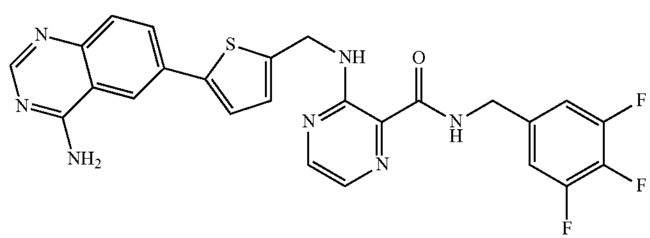 | 3-({[5-(4-aminoquinazolin-6-yl)thiophen-2-yl]methyl}amino)-N-(3,4,5-trifluorobenzyl)pyrazine-2-carboxamide (TFA salt) | 522.2 | ¹H NMR (300 MHz, DMSO-d₆) δ 9.83 (br. s., 1H), 9.75 (br. s., 1H), 9.53 (t, J = 6.23 Hz, 1H), 9.11 (t, J = 5.67 Hz, 1H), 8.80 (s, 1H), 8.60 (s, 1H), 8.36 (d, J = 2.27 Hz, 1H), 8.27 (d, J = 9.06 Hz, 1H), 7.91 (d, J = 2.27 Hz, 1H), 7.76 (d, J = 8.69 Hz, 1H), 7.55 (d, J = 3.78 Hz, 1H), 7.20-7.36 (m, J = 7.18, 8.69 Hz, 2H), 7.15 (d, J = 3.40 Hz, 1H), 4.88 (d, J = 5.67 Hz, 2H), 4.42 (d, J = 6.04 Hz, 2H). |
| 3.72 | 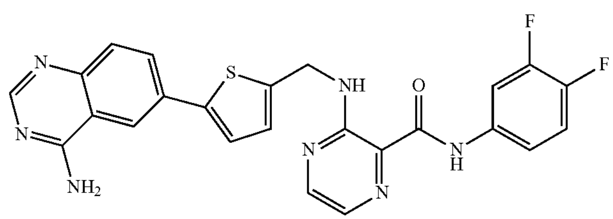 [SMILES: Nc1ncnc2ccc(-c3ccc(CNc4nccnc4C(=O)Nc4ccc(F)c(F)c4)s3)cc12] | 3-({[5-(4-aminoquinazolin-6-yl)thiophen-2-yl]methyl}amino)-N-(3,4-difluorophenyl)pyrazine-2-carboxamide (TFA salt) | 490.2 | ¹H NMR (300 MHz, DMSO-d₆) δ 10.88 (s, 1H), 9.81 (br. s., 1H), 9.73 (br. s., 1H), 9.06 (t, J = 5.85 Hz, 1H), 8.79 (s, 1H), 8.60 (s, 1H), 8.49 (m, J = 1.89 Hz, 1H), 8.28 (d, J = 9.44 Hz, 1H), 7.92-8.10 (m, 2H), 7.76 (d, J = 9.06 Hz, 1H), 7.63-7.73 (m, 1H), 7.56 (d, J = 2.64 Hz, 1H), 7.43 (q, J = 9.95 Hz, 1H), 7.18 (d, J = 3.02 Hz, 1H), 4.94 (d, J = 5.67 Hz, 2H). |

TABLE 1-continued

| Ex. No. | Structure | Chemical Name | ESI-MS (M + H) | $^1$H NMR |
|---|---|---|---|---|
| 3.73 | 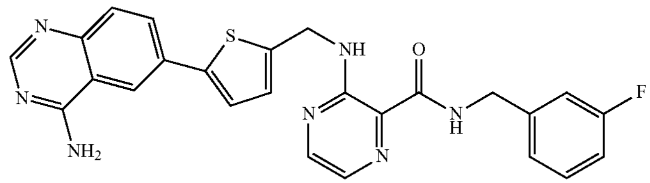 | 3-({[5-(4-aminoquinazolin-6-yl)thiophen-2-yl]methyl}amino)-N-(3-fluorobenzyl)pyrazine-2-carboxamide (TFA salt) | 486.2 | $^1$H NMR (300 MHz, DMSO-d$_6$) δ 9.59 (br. s., 2H), 9.50 (t, J = 6.42 Hz, 1H), 9.16 (t, J = 6.23 Hz, 1H), 8.75 (s, 1H), 8.57 (d, J = 1.89 Hz, 1H), 8.35 (d, J = 2.64 Hz, 1H), 8.25 (dd, J = 1.51, 8.69 Hz, 1H), 7.90 (d, J = 2.27 Hz, 1H), 7.75 (d, J = 8.69 Hz, 1H), 7.54 (d, J = 3.78 Hz, 1H), 7.28-7.47 (m, 1H), 6.98-7.20 (m, 4H), 4.88 (d, J = 6.42 Hz, 2H), 4.46 (d, J = 6.42 Hz, 2H). |
| 3.74 | 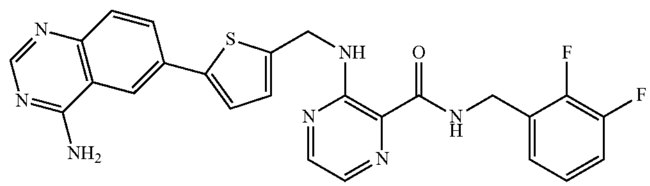 [SMILES: Nc1ncnc2ccc(-c3ccc(CNc4nccnc4C(=O)NCc4cccc(F)c4F)s3)cc12] | 3-({[5-(4-aminoquinazolin-6-yl)thiophen-2-yl]methyl}amino)-N-(2,3-difluorobenzyl)pyrazine-2-carboxamide (TFA salt) | 504.3 | $^1$H NMR (300 MHz, DMSO-d$_6$) δ 9.65 (br s, 1H), 9.48 (t, J = 6.3 Hz, 1H), 9.12 (t, J = 6.2 Hz, 1H), 8.76 (s, 1H), 8.58 (d, J = 1.8 Hz, 1H), 8.36 (d, J = 2.7 Hz, 1H), 8.25 (dd, J = 1.8 Hz, 8.7 Hz, 1H), 7.91 (d, J = 2.1 Hz, 1H), 7.75 (d, J = 9.3 Hz, 1H), 7.54 (d, J = 3.6 Hz, 1H), 7.37-7.26 (m, 1H), 7.22-7.11 (m, 3H), 4.88 (d, J = 6.0 Hz, 2H), 4.54 (d, J = 6.0 Hz, 2H). |
| 3.75 | 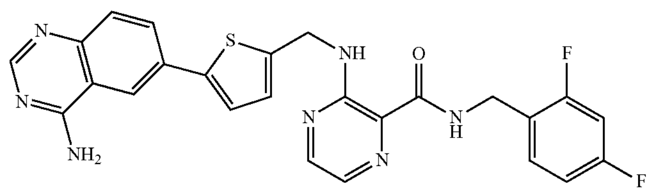 [SMILES: Nc1ncnc2ccc(-c3ccc(CNc4nccnc4C(=O)NCc4ccc(F)cc4F)s3)cc12] | 3-({[5-(4-aminoquinazolin-6-yl)thiophen-2-yl]methyl}amino)-N-(2,4-difluorobenzyl)pyrazine-2-carboxamide (TFA salt) | 504.3 | $^1$H NMR (300 MHz, DMSO-d$_6$) δ 9.61 (br s, 2H), 9.41 (t, J = 6.2 Hz, 1H), 9.14 (t, J = 5.8 Hz, 1H), 8.75 (s, 1H), 8.58 (s, 1H), 8.36 (d, J = 1.8 Hz, 1H), 8.25 (d, J = 8.7 Hz, 1H), 7.90 (d, J = 2.4 Hz, 1H), 7.75 (d, J = 1.8 Hz, 1H), 7.91 (d, J = 2.1 Hz, 1H), 7.54 (d, J = 3.6 Hz, 1H), 7.41 (q, J = 8.0 Hz, 1H), 7.27-6.92 (m, 3H), 4.88 (d, J = 6.0 Hz, 2H), 4.47 (d, J = 6.0 Hz, 2H). |
| 3.76 | 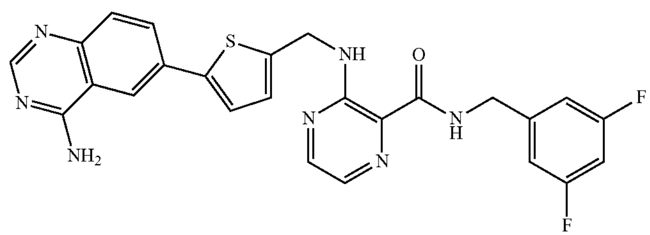 [SMILES: Nc1ncnc2ccc(-c3ccc(CNc4nccnc4C(=O)NCc4cc(F)cc(F)c4)s3)cc12] | 3-({[5-(4-aminoquinazolin-6-yl)thiophen-2-yl]methyl}amino)-N-(3,5-difluorobenzyl)pyrazine-2-carboxamide (TFA salt) | 504.3 | $^1$H NMR (300 MHz, DMSO-d$_6$) δ 9.53 (t, J = 6.4 Hz, 1H), 9.51 (br s, 2H), 9.12 (t, J = 6.2 Hz, 1H), 8.73 (s, 1H), 8.57 (d, J = 1.8 Hz, 1H), 8.36 (d, J = 2.7 Hz, 1H), 8.23 (dd, J = 8.7; 1.8 Hz, 1H), 7.91 (d, J = 2.7 Hz, 1H), 7.74 (d, J = 9.0 Hz, 1H), 7.54 (d, J = 3.6 Hz, 1H), 7.18-6.97 (m, 4H), 4.88 (d, J = 6.0 Hz, 2H), 4.46 (d, J = 6.0 Hz, 2H). |
| 3.77 | 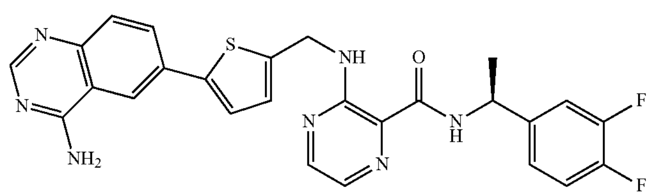 [SMILES: C[C@H](NC(=O)c1nccnc1NCc1ccc(-c2ccc3ncnc(N)c3c2)s1)c1ccc(F)c(F)c1] | 3-({[5-(4-aminoquinazolin-6-yl)thiophen-2-yl]methyl}amino)-N-[(1S)-1-(3,4-difluorophenyl)ethyl]pyrazine-2-carboxamide (TFA salt) | 518.3 | $^1$H NMR (300 MHz, DMSO-d$_6$) δ 9.76 (br s, 1H), 9.69 (br s, 1H), 9.23 (d, J = 8.4 Hz, 1H), 9.11 (t, J = 6.1 Hz, 1H), 8.78 (s, 1H), 8.58 (d, J = 1.8 Hz, 1H), 8.35 (d, J = 2.1 Hz, 1H), 8.26 (dd, J = 8.7; 1.8 Hz, 1H), 7.91 (d, J = 2.7 Hz, 1H), 7.76 (d, J = 9.3 Hz, 1H), 7.54 (d, J = 3.9 Hz, 1H), 7.55-7.46 (m, 1H), 7.42-7.31 (m, 1H), 7.29-7.21 (m, 1H), 7.13 (d, J = 3.9 Hz, 1H), 5.10 (quintet, J = 7.3 Hz, 1H), 4.86 (d, J = 6.3 Hz, 2H), 1.50 (d, J = 7.2 Hz, 3H). |

TABLE 1-continued

| Ex. No. | Structure | Chemical Name | ESI-MS (M + H) | ¹H NMR |
|---|---|---|---|---|
| 3.78 | 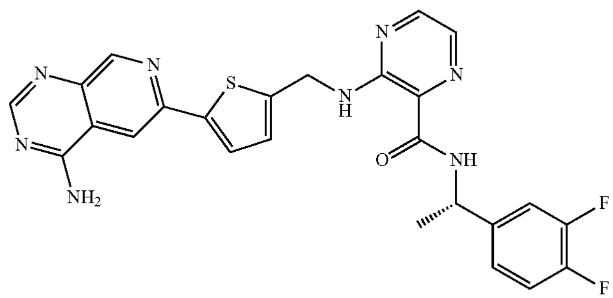 [SMILES: C[C@H](NC(=O)c1nccnc1NCc1ccc(-c2cc3c(N)ncnc3cn2)s1)c1ccc(F)c(F)c1] | 3-({[5-(4-aminopyrido[3,4-d]pyrimidin-6-yl)methyl]-thiophen-2-yl]methyl}amino)-N-[(1S)-1-(3,4-difluorophenyl)ethyl]pyrazine-2-carboxamide (TFA salt) | 519.1 | ¹H NMR (400 MHz, DMSO-d₆) δ 9.24 (d, 1H), 9.10 (t, 1H), 8.96 (s, 1H), 8.55 (s, 1H), 8.45 (s, 1H), 8.37 (d, 1H), 8.16 (bs, 2H), 7.91 (d, 1H), 7.58 (d, 1H), 7.52 (m, 1H), 7.33 (m, 1H), 7.24 (br, 1H) 7.11 (d, 1H), 5.08-5.15 (m, 1H), 4.82-4.85 (m, 2H), 1.50 (d, 3H). |
| 3.79 | 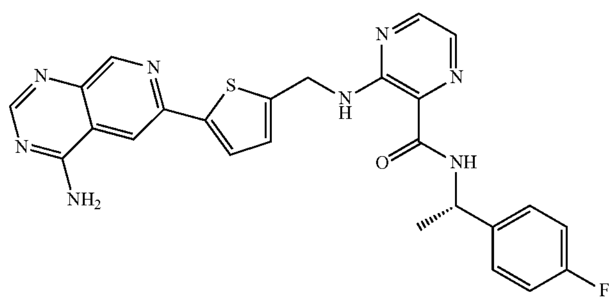 [SMILES: C[C@H](NC(=O)c1nccnc1NCc1ccc(-c2cc3c(N)ncnc3cn2)s1)c1ccc(F)cc1] | 3-({[5-(4-aminopyrido[3,4-d]pyrimidin-6-yl)thiophen-2-yl]methyl}amino)-N-[(1S)-1-(4-fluorophenyl)ethyl]pyrazine-2-carboxamide (TFA salt) | 500.2 | ¹H NMR (400 MHz, DMSO-d₆) δ 9.18 (d, 1H), 9.12 (t, 1H), 8.96 (s, 1H), 8.55 (s, 1H), 8.45 (s, 1H), 8.37 (d, 1H), 8.17 (bs, 2H), 7.90 (d, 1H), 7.57 (d, 1H), 7.44-7.47 (m, 2H), 7.11-7.15 (m, 3H), 5.09-5.15 (m, 1H), 4.82-4.85 (m, 2H), 1.50 (d, 3H). |
| 3.80 | 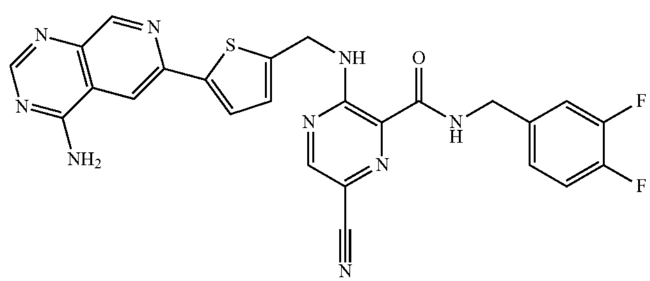 [SMILES: N#Cc1cnc(NCc2ccc(-c3cc4c(N)ncnc4cn3)s2)c(C(=O)NCc2ccc(F)c(F)c2)n1] | 3-(((5-(4-aminoquinazolin-6-yl)thiophen-2-yl)methyl)amino)-6-cyano-N-(3,4-difluorobenzyl)pyrazine-2-carboxamide (TFA salt) | 529.1 | ¹H NMR (300 MHz, DMSO-d₆) δ 9.82 (t, J = 5.85 Hz, 1H), 9.59 (t, J = 6.42 Hz, 1H), 8.82 (s, 1H), 8.42 (d, J = 1.89 Hz, 1H), 8.35 (s, 1H), 7.98 (dd, J = 1.89, 8.69 Hz, 1H), 7.87 (br. s., 2H), 7.65 (d, J = 8.69 Hz, 1H), 7.47 (d, J = 3.78 Hz, 1H), 7.30-7.44 (m, 2H), 7.14-7.23 (m, 1H), 7.12 (d, J = 3.40 Hz, 1H), 4.91 (d, J = 6.04 Hz, 2H), 4.42 (d, J = 6.04 Hz, 2H). |

TABLE 1-continued

| Ex. No. | Structure | Chemical Name | ESI-MS (M + H) | ¹H NMR |
|---|---|---|---|---|
| 3.81 | 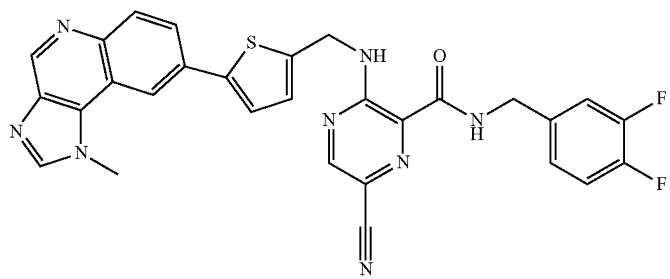 [SMILES: Cn1cnc2cnc3ccc(-c4ccc(CNc5ncc(C#N)nc5C(=O)NCc5ccc(F)c(F)c5)s4)cc3c21] | 6-cyano-N-(3,4-difluorobenzyl)-3-(((5-(1-methyl-1H-imidazo[4,5-c]quinolin-8-yl)thiophen-2-yl)methyl)amino)pyrazine-2-carboxamide (TFA salt) | 567.2 | ¹H NMR (300 MHz, DMSO-d₆) δ 9.83 (t, J = 6.04 Hz, 1H), 9.59 (t, J = 6.23 Hz, 1H), 9.16 (s, 1H), 8.84 (s, 1H), 8.54 (d, J = 1.89 Hz, 1H), 8.39 (s, 1H), 8.15 (d, J = 8.69 Hz, 1H), 7.94 (dd, J = 1.89, 8.69 Hz, 1H), 7.61 (d, J = 3.40 Hz, 1H), 7.37 (dt, J = 8.59, 10.76 Hz, 2H), 7.17 (d, J = 3.78 Hz, 2H), 4.93 (d, J = 6.04 Hz, 2H), 4.43 (d, J = 6.04 Hz, 2H), 4.37 (s, 3H). |
| 3.82 | 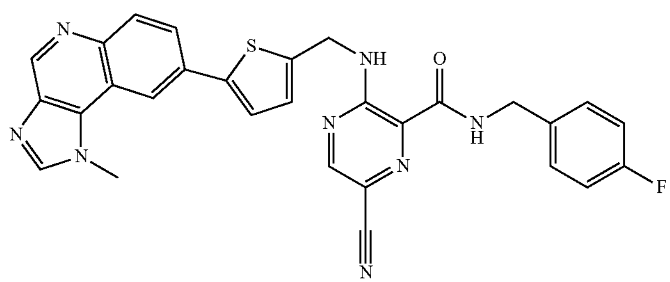 [SMILES: Cn1cnc2cnc3ccc(-c4ccc(CNc5ncc(C#N)nc5C(=O)NCc5ccc(F)cc5)s4)cc3c21] | 6-cyano-N-(4-fluorobenzyl)-3-(((5-(1-methyl-1H-imidazo[4,5-c]quinolin-8-yl)thiophen-2-yl)methyl)amino)pyrazine-2-carboxamide (TFA salt) | 549.2 | ¹H NMR (300 MHz, DMSO-d₆) δ 9.86 (t, J = 6.04 Hz, 1H), 9.58 (t, J = 6.23 Hz, 1H), 9.15 (s, 1H), 8.83 (s, 1H), 8.54 (d, J = 1.89 Hz, 1H), 8.36-8.42 (m, 1H), 8.15 (d, J = 8.69 Hz, 1H), 7.93 (dd, 1H), 7.61 (d, J = 3.40 Hz, 1H), 7.33-7.43 (m, 2H), 7.09-7.20 (m, 3H), 4.93 (d, J = 5.67 Hz, 2H), 4.43 (d, J = 6.04 Hz, 2H), 4.37 (s, 3H). |
| 3.83 | 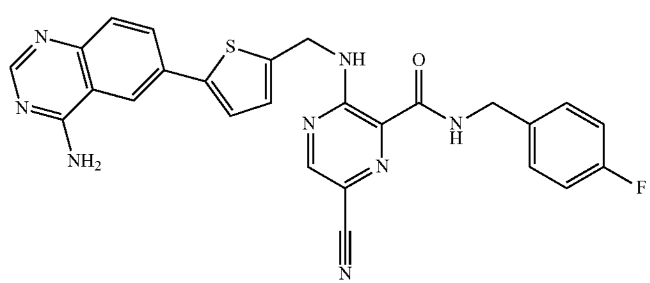 [SMILES: N#Cc1cnc(NCc2ccc(-c3ccc4ncnc(N)c4c3)s2)c(C(=O)NCc2ccc(F)cc2)n1] | 3-(((5-(4-aminoquinazolin-6-yl)thiophen-2-yl)methyl)amino)-6-cyano-N-(4-fluorobenzyl)pyrazine-2-carboxamide (TFA salt) | 511.2 | ¹H NMR (300 MHz, DMSO-d₆) δ 9.86 (t, J = 6.04 Hz, 1H), 9.58 (t, J = 6.23 Hz, 1H), 8.82 (s, 1H), 8.42 (d, J = 1.89 Hz, 1H), 8.35 (s, 1H), 7.95-8.01 (m, 1H), 7.77-7.90 (m, 2H), 7.62-7.67 (m, 1H), 7.47 (d, J = 3.78 Hz, 1H), 7.31-7.42 (m, 2H), 7.07-7.19 (m, 3H), 4.91 (d, J = 6.04 Hz, 2H), 4.38-4.47 (m, 2H). |
| 3.84 | 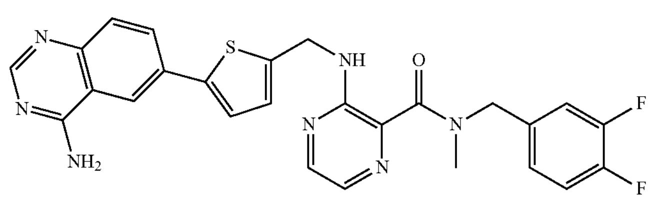 [SMILES: CN(Cc1ccc(F)c(F)c1)C(=O)c1nccnc1NCc1ccc(-c2ccc3ncnc(N)c3c2)s1] | 3-({[5-(4-aminoquinazolin-6-yl)thiophen-2-yl]methyl}amino)-N-(3,4-difluorobenzyl)-N-methylpyrazine-2-carboxamide (TFA salt) | 518.2 | ¹H NMR (300 MHz, DMSO-d₆) δ 9.85 (br s, 1H), 9.77 (br s, 1H), 8.80 (s, 1H), 8.60 (br t, J = 2.2 Hz, 1H), 8.26 (ddd, J = 8.4; 5.6; 1.7 Hz, 1H), 8.17 (dd, J = 12.6; 2.7 Hz, 1H), 7.82 (dd, J = 18.5; 2.6 Hz, 1H), 7.76 (d, J = 8.7 Hz, 1H), 7.63 (br t, J = 5.7 Hz, 1H), 7.54 (t, J = 3.6 Hz, 1H), 7.50-7.29 (m, 2H), 7.25-7.08 (m, 1H), 7.12 (dd, J = 7.3; 3.8 Hz, 1H), 4.78 (dd, J = 12.1; 5.8 Hz, 2H), 4.70 (s, 1H), 4.53 (s, 1H), 2.92 (d, J = 6.9 Hz, 3H). Rotational isomers possibly observed by NMR. |

TABLE 1-continued

| Ex. No. | Structure | Chemical Name | ESI-MS (M + H) | ¹H NMR |
|---|---|---|---|---|
| 3.85 | 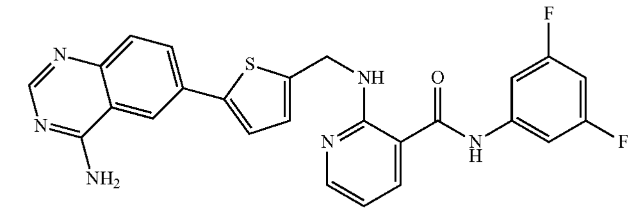 [SMILES: Nc1ncnc2ccc(-c3ccc(CNc4ncccc4C(=O)Nc4cc(F)cc(F)c4)s3)cc12] | 2-({[5-(4-aminoquinazolin-6-yl)thiophen-2-yl]methyl}amino)-N-(3,5-difluorophenyl)pyridine-3-carboxamide (TFA salt) | 489.3 | ¹H NMR (300 MHz, DMSO-d₆) δ 10.54 (s, 1H), 9.85 (br. s., 1H), 9.76 (br. s., 1H), 8.80 (s, 1H), 8.60 (d, J = 1.51 Hz, 1H), 8.42 (t, J = 5.85 Hz, 1H), 8.23-8.34 (m, 2H), 8.11 (dd, J = 1.70, 7.74 Hz, 1H), 7.76 (d, J = 8.69 Hz, 1H), 7.55 (d, J = 3.78 Hz, 1H), 7.43-7.53 (m, 2H), 7.14 (d, J = 3.78 Hz, 1H), 6.98 (tt, J = 2.64, 9.06 Hz, 1H), 6.77 (dd, J = 4.72, 7.74 Hz, 1H), 4.89 (d, J = 6.04 Hz, 2H). |
| 3.86 | 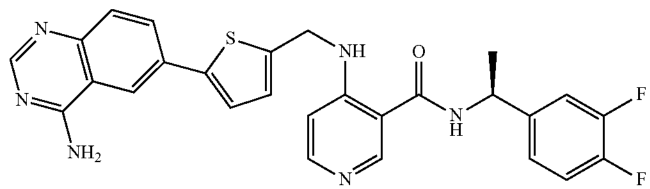 [SMILES: C[C@H](NC(=O)c1cnccc1NCc1ccc(-c2ccc3ncnc(N)c3c2)s1)c1ccc(F)c(F)c1] | (S)-4-(((5-(4-aminoquinazolin-6-yl)thiophen-2-yl)methyl)amino)-N-1-(3,4-difluorophenyl)ethyl)nicotinamide | 517.1 | ¹H NMR (300 MHz, CDCl₃) δ 9.87 (t, J = 5.67 Hz, 1H), 9.49 (br. s., 2H), 9.26 (d, J = 6.80 Hz, 1H), 8.82 (s, 1H), 8.73 (s, 1H), 8.60 (s, 1H), 8.35 (d, J = 7.18 Hz, 1H), 8.22 (d, J = 8.69 Hz, 1H), 7.77 (d, J = 8.69 Hz, 1H), 7.58 (d, J = 3.40 Hz, 1H), 7.33-7.54 (m, 2H), 7.16-7.30 (m, 3H), 5.10 (quin, J = 6.99 Hz, 1H), 4.93 (d, J = 6.04 Hz, 2H), 1.48 (d, J = 6.80 Hz, 3H). |
| 3.87 | 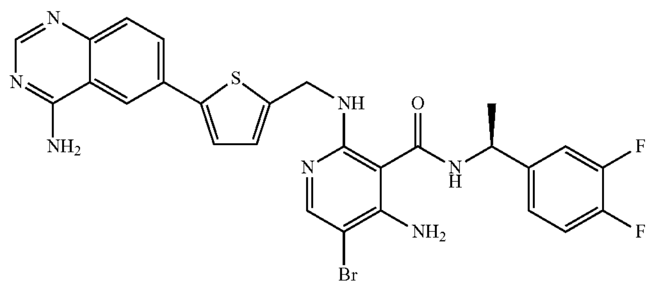 [SMILES: C[C@H](NC(=O)c1c(NCc2ccc(-c3ccc4ncnc(N)c4c3)s2)ncc(Br)c1N)c1ccc(F)c(F)c1] | (S)-4-amino-2-((5-(4-aminoquinazolin-6-yl)thiophen-2-yl)methyl)amino)-5-bromo-N-1-(3,4-difluorophenyl)ethyl)nicotinamide | 609.8 | 1H NMR (400 MHz, CD₃OD) δ 8.66 (s, 1H), 8.61 (d, 1H), 8.25 (d, 1H), 7.96 (s, 1H), 7.80 (d, 1H), 7.53 (d, 1H), 7.27 (q, 1H), 7.17-7.11 (m, 3H), 5.16 (q, 1H), 4.76 (AB, 2H), 1.51 (d, 3H). |
| 4.1.1 | 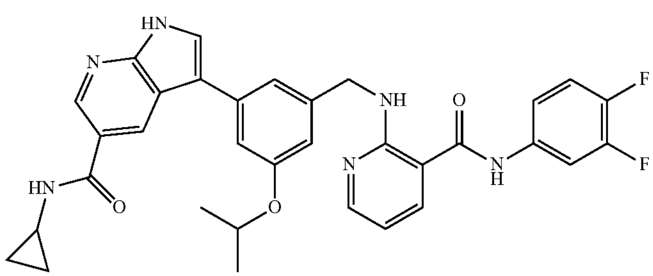 [SMILES: CC(C)Oc1cc(CNc2ncccc2C(=O)Nc2ccc(F)c(F)c2)cc(-c2c[nH]c3ncc(C(=O)NC4CC4)cc23)c1] | N-cyclopropyl-3-(3-((3-(3,4-difluorophenyl)carbamoyl)pyridin-2-yl)aminomethyl)-5-isopropoxyphenyl)-1H-pyrrolo[2,3-b]pyridine-5-carboxamide | 593.3 | ¹H NMR (300 MHz, DMSO-d₆) δ 12.13 (d, J = 2.27 Hz, 1H), 10.45 (s, 1H), 8.71 (d, J = 1.89 Hz, 1H), 8.60 (d, J = 1.89 Hz, 1H), 8.55 (d, J = 3.78 Hz, 1H), 8.44 (br. s., 1H), 8.26 (dd, J = 1.89, 4.91 Hz, 1H), 8.11 (dd, J = 1.51, 7.55 Hz, 1H), 7.90 (d, J = 2.64 Hz, 1H), 7.84 (ddd, J = 1.70, 7.65, 13.31 Hz, 1H), 7.37-7.47 (m, 2H), 7.28 (s, 1H), 7.06-7.11 (m, 1H), 6.80-6.87 (m, 1H), 6.72 (dd, J = 4.91, 7.55 Hz, 1H), 4.61-4.75 (m, 3H), 2.80-2.93 (m, 1H), 1.28 (d, J = 6.04 Hz, 6H), 0.66-0.76 (m, 2H), 0.53-0.62 (m, 2H). |

TABLE 1-continued

| Ex. No. | Structure | Chemical Name | ESI-MS (M + H) | ¹H NMR |
|---|---|---|---|---|
| 4.1.2 | 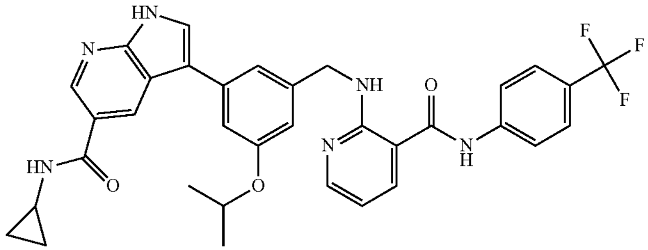 [SMILES: CC(C)Oc1cc(CNc2ncccc2C(=O)Nc2ccc(C(F)(F)F)cc2)cc(-c2c[nH]c3ncc(C(=O)NC4CC4)cc23)c1] | N-cyclopropyl-3-[3-(propan-2-yloxy)-5-{[({3-[(4-trifluoromethyl)phenyl]carbamoyl}pyridin-2-yl)amino]methyl}phenyl]-1H-pyrrolo[2,3-b]pyridine-5-carboxamide | 629.9 | ¹H NMR (300 MHz, DMSO-d₆) δ 12.14 (d, J = 2.1 Hz, 1H), 10.61 (s, 1H), 8.71 (d, J = 2.1 Hz, 1H), 8.60 (d, J = 2.1 Hz, 1H), 8.55 (d, J = 4.2 Hz, 2H), 8.52 (br s, 1H), 8.27 (dd, J = 4.9; 1.7 Hz, 1H), 8.19 (dd, J = 7.5; 1.5 Hz, 1H), 7.93 (d, J = 8.1 Hz, 2H), 7.91 (s, 1H), 7.71 (d, J = 8.7 Hz, 2H), 7.30 (s, 1H), 7.10 (s, 1H), 6.84 (s, 1H), 6.76 (dd, J = 7.7; 4.9 Hz, 1H), 4.71 (br s, 1H), 4.68 (septet, J = 6.0 Hz, 1H), 2.91-2.82 (m, 1H), 1.29 (d, J = 6.0 Hz, 6H), 0.74-0.66 (m, 2H), 0.61-0.55 (m, 2H). |
| 4.1.3 | 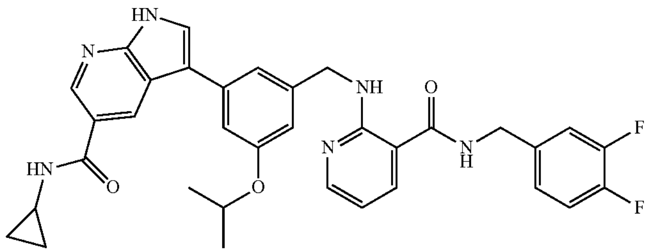 [SMILES: CC(C)Oc1cc(CNc2ncccc2C(=O)NCc2ccc(F)c(F)c2)cc(-c2c[nH]c3ncc(C(=O)NC4CC4)cc23)c1] | N-cyclopropyl-3-[3-[({3-[(3,4-difluorobenzyl)carbamoyl]pyridin-2-yl}amino)methyl]-5-(propan-2-yloxy)phenyl]-1H-pyrrolo[2,3-b]pyridine-5-carboxamide | 611.4 | ¹H NMR (300 MHz, DMSO-d₆) δ 12.14 (d, J = 2.1 Hz, 1H), 9.19 (br t, J = 5.9 Hz, 1H), 8.95 (br s, 1H), 8.71 (d, J = 2.1 Hz, 1H), 8.59 (d, J = 2.1 Hz, 1H), 8.55 (d, J = 4.2 Hz, 1H), 8.21 (dd, J = 5.3; 1.6 Hz, 1H), 8.10 (d, J = 7.5 Hz, 1H), 7.90 (d, J = 2.7 Hz, 1H), 7.40-7.30 (m, 2H), 7.27 (s, 1H), 7.18-7.11 (m, 1H), 7.09 (s, 1H), 6.80 (s, 1H), 6.70 (dd, J = 7.6; 5.0 Hz, 1H), 4.71-4.61 (m, 3H), 4.42 (d, J = 5.7 Hz, 2H), 2.93-2.83 (m, 1H), 1.28 (d, J = 6.3 Hz, 6H), 0.75-0.67 (m, 2H), 0.62-0.55 (m, 2H). |
| 4.1.4 | 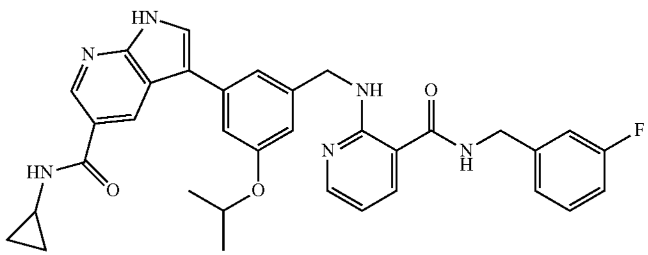 [SMILES: CC(C)Oc1cc(CNc2ncccc2C(=O)NCc2cccc(F)c2)cc(-c2c[nH]c3ncc(C(=O)NC4CC4)cc23)c1] | N-cyclopropyl-3-{3-[({3-[(3-fluorobenzyl)carbamoyl]pyridin-2-yl}amino)methyl]-5-(propan-2-yloxy)phenyl}-1H-pyrrolo[2,3-b]pyridine-5-carboxamide | 593.4 | ¹H NMR (300 MHz, DMSO-d₆) δ 12.08-12.20 (m, 1H), 9.25 (t, J = 5.85 Hz, 1H), 9.11 (br s, 1H), 8.71 (d, J = 1.89 Hz, 1H), 8.60 (d, J = 1.51 Hz, 1H), 8.55 (d, J = 4.15 Hz, 1H), 8.21 (dd, J = 1.51, 5.29 Hz, 1H), 8.16 (dd, J = 1.32, 7.74 Hz, 1H), 7.91 (d, J = 2.64 Hz, 1H), 7.22-7.45 (m, 2H), 6.99-7.20 (m, 4H), 6.81 (s, 1H), 6.74 (dd, J = 5.10, 7.74 Hz, 1H), 4.59-4.74 (m, 3H), 4.46 (d, J = 6.04 Hz, 2H), 2.80-2.93 (m, 1H), 1.28 (d, J = 6.04 Hz, 6H), 0.66-0.76 (m, 2H), 0.53-0.63 (m, 2H). |
| 4.1.5 | 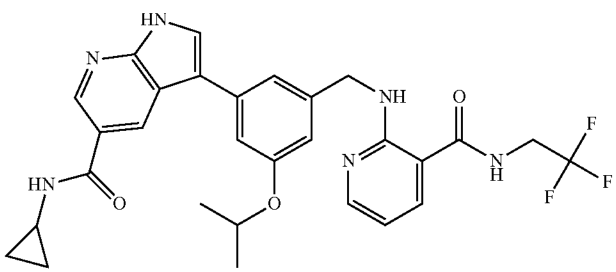 [SMILES: CC(C)Oc1cc(CNc2ncccc2C(=O)NCC(F)(F)F)cc(-c2c[nH]c3ncc(C(=O)NC4CC4)cc23)c1] | N-cyclopropyl-3-{3-[(propan-2-yloxy)-5-[({3-[(2,2,2-trifluoroethyl)carbamoyl]pyridin-2-yl}amino)methyl]phenyl]-1H-pyrrolo[2,3-b]pyridine-5-carboxamide | 567.3 | ¹H NMR (300 MHz, DMSO-d₆) δ 12.14 (br s., 1H), 9.09-9.26 (m, 1H), 8.83 (br s., 1H), 8.71 (s, 1H), 8.60 (s, 1H), 8.55 (d, J = 3.78 Hz, 1H), 8.19-8.29 (m, 1H), 8.01-8.15 (m, 1H), 7.90 (d, J = 2.27 Hz, 1H), 7.27 (s, 1H), 7.10 (s, 1H), 6.81 (s, 1H), 6.63-6.77 (m, 1H), 4.58-4.80 (m, 3H), 3.99-4.15 (m, 2H), 2.79-2.96 (m, 1H), 1.29 (d, J = 6.04 Hz, 6H), 0.68-0.78 (m, 2H), 0.51-0.63 (m, 2H). |

TABLE 1-continued

| Ex. No. | Structure | Chemical Name | ESI-MS (M + H) | ¹H NMR |
|---|---|---|---|---|
| 4.1.6 | 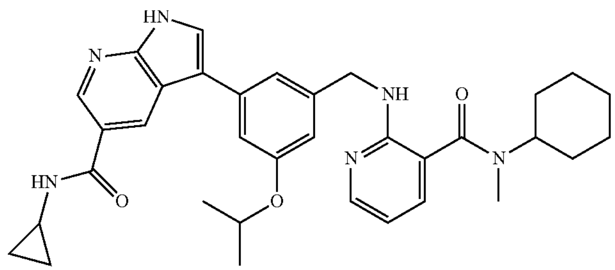 [SMILES: CC(C)Oc1cc(CNc2ncccc2C(=O)N(C)C2CCCCC2)cc(-c2c[nH]c3ncc(C(=O)NC4CC4)cc23)c1] | 3-{3-[({3-[cyclohexyl(methyl) carbamoyl]pyridin-2-yl}amino) methyl]-5-(propan-2-yloxy) phenyl}-N-cyclopropyl-1H-pyrrolo[2,3-b]pyridine-5-carboxamide | 581.4 | ¹H NMR (300 MHz, DMSO-$d_6$) δ 12.06-12.23 (m, J = 1.89 Hz, 1H), 8.71 (d, J = 4.15 Hz, 1H), 8.59 (d, J = 1.89 Hz, 1H), 8.54 (d, J = 4.15 Hz, 1H), 8.05 (dd, J = 1.51, 5.67 Hz, 1H), 7.87 (d, J = 2.27 Hz, 1H), 7.64 (d, J = 6.80 Hz, 1H), 7.24 (s, 1H), 7.09 (s, 1H), 6.73-6.84 (m, 2H), 4.61-4.71 (m, 4H), 2.68-2.96 (m, 4H), 1.62 (br. s., 4H), 1.34-1.53 (m, 4H), 1.28 (d, J = 5.67 Hz, 6H), 0.97 (br. s., 3H), 0.68-0.77 (m, 2H), 0.54-0.63 (m, 2H). |
| 4.1.7 | 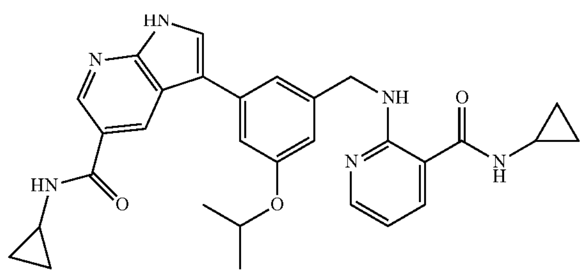 [SMILES: CC(C)Oc1cc(CNc2ncccc2C(=O)NC2CC2)cc(-c2c[nH]c3ncc(C(=O)NC4CC4)cc23)c1] | N-cyclopropyl-3-{3-({[3-(cyclopropylcarbamoyl) pyridin-2-yl]amino} methyl)phenyl}-5-(propan-2-yloxy)-1H-pyrrolo[2,3-b]pyridine-5-carboxamide | 525.4 | ¹H NMR (300 MHz, DMSO-$d_6$) δ 12.10 (br. s., 1H), 9.19 (br. s., 1H), 8.69-8.77 (m, J = 1.89 Hz, 1H), 8.65 (br. s., 1H), 8.58-8.62 (m, J = 1.51 Hz, 1H), 8.55 (d, J = 4.15 Hz, 1H), 8.12-8.21 (m, 1H), 8.05 (d, J = 7.55 Hz, 1H), 7.92 (d, J = 2.27 Hz, 1H), 7.28 (s, 1H), 7.12 (s, 1H), 6.83 (s, 1H), 6.66-6.78 (m, 1H), 4.61-4.77 (m, 3H), 2.84-2.95 (m, 1H), 2.74-2.84 (m, 1H), 1.30 (d, J = 6.04 Hz, 6H), 0.64-0.77 (m, 4H), 0.50-0.64 (m, 4H). |
| 4.1.8 | 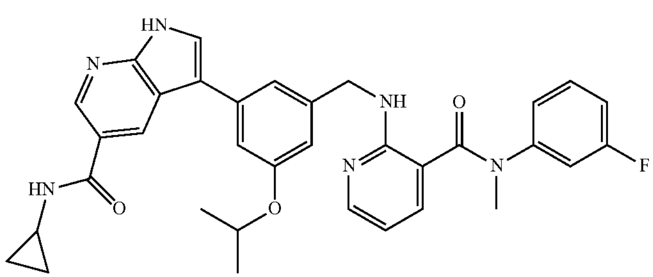 [SMILES: CC(C)Oc1cc(CNc2ncccc2C(=O)N(C)c2cccc(F)c2)cc(-c2c[nH]c3ncc(C(=O)NC4CC4)cc23)c1] | N-cyclopropyl-3-{3-[({3-[(3-fluorophenyl)(methyl) carbamoyl]pyridin-2-yl} amino)methyl]phenyl}-5-(propan-2-yloxy)-1H-pyrrolo[2,3-b] pyridine-5-carboxamide | 593.4 | ¹H NMR (300 MHz, DMSO-$d_6$) δ 12.15 (br. s., 1H), 8.72 (s, 1H), 8.62 (s, 1H), 8.55 (d, J = 4.15 Hz, 1H), 7.87-7.95 (m, 2H), 7.80 (br. s., 1H), 7.40 (d, J = 7.18 Hz, 1H), 7.08-7.29 (m, 4H), 6.93-7.08 (m, 2H), 6.80 (s, 1H), 6.50 (t, J = 6.23 Hz, 1H), 4.62-4.73 (m, 3H), 3.36 (s, 3H), 2.87 (tq, J = 3.73, 7.25 Hz, 1H), 1.30 (d, J = 5.67 Hz, 6H), 0.67-0.77 (m, 2H), 0.53-0.62 (m, 2H). |

TABLE 1-continued

| Ex. No. | Structure | Chemical Name | ESI-MS (M + H) | ¹H NMR |
|---|---|---|---|---|
| 4.1.9 | 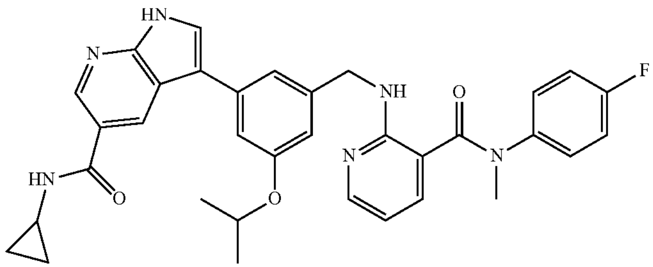 [SMILES: CC(C)Oc1cc(CNc2ncccc2C(=O)N(C)c2ccc(F)cc2)cc(-c2c[nH]c3ncc(C(=O)NC4CC4)cc23)c1] | N-cyclopropyl-3-{3-[({3-[(4-fluorophenyl)(methyl) carbamoyl]pyridin-2-yl}amino)methyl]-5-(propan-2-yloxy)phenyl}-1H-pyrrolo[2,3-b]pyridine-5-carboxamide | 593.4 | ¹H NMR (300 MHz, DMSO-d₆) δ 12.17 (d, J = 2.27 Hz, 1H), 8.72 (d, J = 1.89 Hz, 1H), 8.63 (d, J = 1.89 Hz, 1H), 8.55 (d, J = 3.78 Hz, 1H), 7.91 (d, J = 2.64 Hz, 1H), 7.89 (dd, J = 1.70, 5.48 Hz, 1H), 7.84 (br. s., 1H), 7.40 (d, J = 6.80 Hz, 1H), 7.24-7.35 (m, 3H), 7.11 (s, 1H), 6.99 (t, J = 8.69 Hz, 2H), 6.77 (s, 1H), 6.46-6.54 (m, 1H), 4.62-4.73 (m, 3H), 3.33 (s, 3H), 2.82-2.94 (m, 1H), 1.30 (d, J = 6.04 Hz, 6H), 0.67-0.77 (m, 2H), 0.54-0.63 (m, 2H). |
| 4.1.10 | 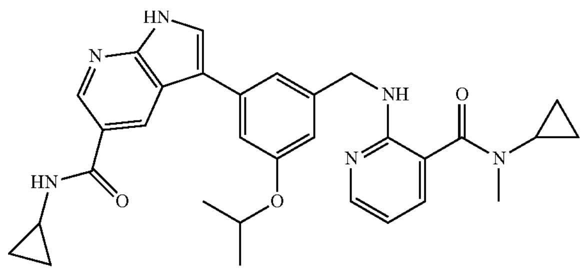 [SMILES: CC(C)Oc1cc(CNc2ncccc2C(=O)N(C)C2CC2)cc(-c2c[nH]c3ncc(C(=O)NC4CC4)cc23)c1] | N-cyclopropyl-3-{3-[({3-[cyclopropyl(methyl) carbamoyl]pyridin-2-yl}amino)methyl]-5-(propan-2-yloxy)phenyl}-1H-pyrrolo[2,3-b]pyridine-5-carboxamide | 539.4 | ¹H NMR (300 MHz, DMSO-d₆) δ 12.10-12.22 (m, 1H), 8.68-8.75 (m, 1H), 8.61 (d, J = 1.51 Hz, 1H), 8.55 (d, J = 4.15 Hz, 1H), 8.02-8.09 (m, 1H), 7.89 (d, J = 2.27 Hz, 1H), 7.82 (d, J = 6.80 Hz, 1H), 7.27 (s, 1H), 7.10 (s, 1H), 6.73-6.87 (m, 2H), 4.61-4.75 (m, 3H), 2.97 (s, 3H), 2.79-2.93 (m, 2H), 1.28 (d, J = 6.04 Hz, 6H), 0.68-0.77 (m, 2H), 0.55-0.63 (m, 2H), 0.40-0.55 (m, 4H). |
| 4.1.11 | 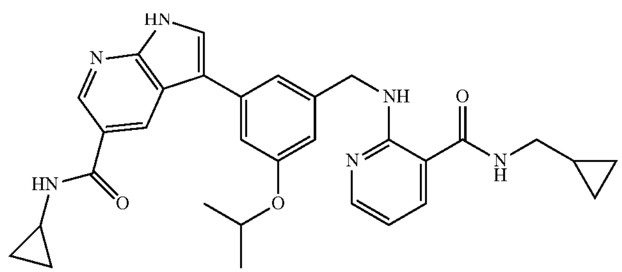 [SMILES: CC(C)Oc1cc(CNc2ncccc2C(=O)NCC2CC2)cc(-c2c[nH]c3ncc(C(=O)NC4CC4)cc23)c1] | N-cyclopropyl-3-{3-[({3-[(cyclopropylmethyl)carbamoyl]pyridin-2-yl}amino)methyl]-5-(propan-2-yloxy)phenyl}-1H-pyrrolo[2,3-b]pyridine-5-carboxamide | 539.4 | ¹H NMR (300 MHz, DMSO-d₆) δ 12.11-12.20 (m, 1H), 9.27 (br. s., 1H), 8.82 (t, J = 4.91 Hz, 1H), 8.72 (d, J = 1.89 Hz, 1H), 8.60 (d, J = 1.89 Hz, 1H), 8.55 (d, J = 4.15 Hz, 1H), 8.16-8.23 (m, 1H), 8.14 (d, J = 7.18 Hz, 1H), 7.92 (d, J = 2.64 Hz, 1H), 7.28 (s, 1H), 7.12 (s, 1H), 6.83 (s, 1H), 6.77 (dd, J = 5.48, 7.37 Hz, 2H), 4.63-4.75 (m, 3H), 3.11 (t, J = 6.23 Hz, 2H), 2.88 (tq, J = 3.75, 7.41 Hz, 1H), 1.29 (d, J = 6.04 Hz, 6H), 0.91-1.06 (m, 1H), 0.67-0.77 (m, 2H), 0.55-0.63 (m, 2H), 0.37-0.46 (m, 2H), 0.15-0.24 (m, 2H). |

| Ex. No. | Structure | Chemical Name | ESI-MS (M + H) | ¹H NMR |
|---|---|---|---|---|
| 4.1.12 | 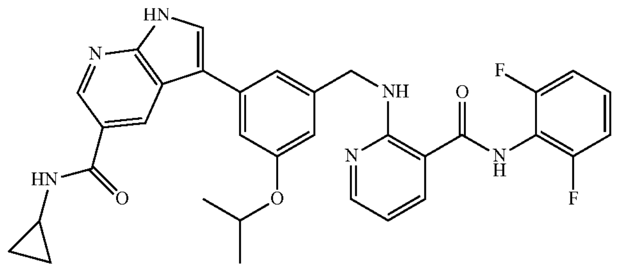 [SMILES: CC(C)Oc1cc(CNc2ncccc2C(=O)Nc2c(F)cccc2F)cc(-c2c[nH]c3ncc(C(=O)NC4CC4)cc23)c1] | N-cyclopropyl-3-[3-[({3-[(2,6-difluorophenyl)carbamoyl]pyridin-2-yl}amino)methyl]-5-(propan-2-yloxy)phenyl]-1H-pyrrolo[2,3-b]pyridine-5-carboxamide | 597.4 | ¹H NMR (300 MHz, DMSO-d₆) δ 12.13 (d, J = 2.27 Hz, 1H), 10.18 (s, 1H), 8.71 (d, J = 1.89 Hz, 1H), 8.69 (br. s., 1H), 8.59 (d, J = 1.89 Hz, 1H), 8.54 (d, J = 4.15 Hz, 1H), 8.31 (dd, J = 1.51, 4.91 Hz, 1H), 8.23 (dd, J = 1.70, 7.74 Hz, 1H), 7.89 (d, J = 2.64 Hz, 1H), 7.33-7.47 (m, 1H), 7.26 (s, 1H), 7.16-7.24 (m, 2H), 7.08 (s, 1H), 6.80 (s, 1H), 6.73 (dd, J = 4.91, 7.93 Hz, 1H), 4.60-4.72 (m, 3H), 2.79-2.92 (m, 1H), 1.28 (d, J = 6.04 Hz, 6H), 0.64-0.75 (m, 2H), 0.50-0.64 (m, 2H). |
| 4.1.13 | 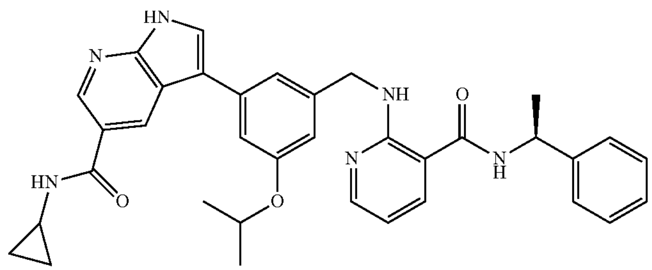 [SMILES: CC(C)Oc1cc(CNc2ncccc2C(=O)N[C@@H](C)c2ccccc2)cc(-c2c[nH]c3ncc(C(=O)NC4CC4)cc23)c1] | N-cyclopropyl-3-[3-{[(3-{[(1S)-1-phenylethyl]carbamoyl}pyridin-2-yl)amino]methyl}-5-(propan-2-yloxy)phenyl]-1H-pyrrolo[2,3-b]pyridine-5-carboxamide | 589.4 | ¹H NMR (300 MHz, DMSO-d₆) δ 12.14 (d, J = 2.27 Hz, 1H), 8.96 (d, J = 7.55 Hz, 1H), 8.91 (br. s., 1H), 8.72 (d, J = 2.27 Hz, 1H), 8.59 (d, J = 1.89 Hz, 1H), 8.55 (d, J = 4.15 Hz, 1H), 8.19 (d, J = 5.29 Hz, 1H), 8.14 (br. s., 1H), 7.89 (d, J = 2.64 Hz, 1H), 7.16-7.39 (m, 6H), 7.09 (s, 1H), 6.79 (s, 1H), 6.69-6.76 (m, 1H), 5.11 (quin, J = 7.18 Hz, 1H), 4.65 (quin, J = 6.04 Hz, 3H), 2.82-2.93 (m, 1H), 1.45 (d, J = 7.18 Hz, 3H), 1.27 (d, J = 6.04 Hz, 6H), 0.67-0.77 (m, 2H), 0.54-0.62 (m, 2H). |
| 4.1.14 | 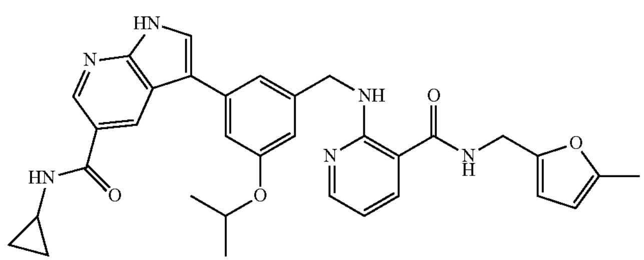 [SMILES: Cc1ccc(CNC(=O)c2cccnc2NCc2cc(OC(C)C)cc(-c3c[nH]c4ncc(C(=O)NC5CC5)cc34)c2)o1] | N-cyclopropyl-3-[3-{[({3-[(5-methylfuran-2-yl)methyl carbamoyl]pyridin-2-yl}amino)methyl]-5-(propan-2-yloxy)phenyl]-1H-pyrrolo[2,3-b]pyridine-5-carboxamide | 579.4 | ¹H NMR (300 MHz, DMSO-d₆) δ 12.15 (d, J = 2.27 Hz, 1H), 8.95-9.19 (m, 2H), 8.72 (d, J = 1.89 Hz, 1H), 8.60 (d, J = 1.89 Hz, 1H), 8.55 (d, J = 3.78 Hz, 1H), 8.19 (dd, J = 1.70, 5.10 Hz, 1H), 8.09 (d, J = 6.80 Hz, 1H), 7.91 (d, J = 2.64 Hz, 1H), 7.27 (s, 1H), 7.10 (s, 1H), 6.82 (s, 1H), 6.69 (dd, J = 5.10, 7.37 Hz, 1H), 6.12 (d, J = 3.02 Hz, 1H), 5.96 (dd, J = 0.94, 2.83 Hz, 1H), 4.67 (quin, J = 5.95 Hz, 3H), 4.37 (d, J = 5.29 Hz, 2H), 2.88 (tq, J = 3.86, 7.44 Hz, 1H), 2.20 (s, 3H), 1.29 (d, J = 6.04 Hz, 6H), 0.64-0.77 (m, 2H), 0.54-0.64 (m, 2H). |

TABLE 1-continued

| Ex. No. | Structure | Chemical Name | ESI-MS (M + H) | ¹H NMR |
|---|---|---|---|---|
| 4.1.15 | 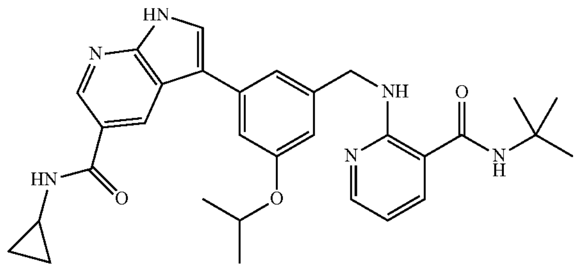 [SMILES: CC(C)Oc1cc(CNc2ncccc2C(=O)NC(C)(C)C)cc(-c2c[nH]c3ncc(C(=O)NC4CC4)cc23)c1] | 3-[3-({[(3-tert-butylcarbamoyl)pyridin-2-yl]amino}methyl)-5-(propan-2-yloxy)phenyl]-N-cyclopropyl-1H-pyrrolo[2,3-b]pyridine-5-carboxamide | 541.3 | ¹H NMR (300 MHz, DMSO-d₆) δ 12.16 (d, J = 2.27 Hz, 1H), 8.97 (br. s., 1H), 8.71 (d, J = 1.89 Hz, 1H), 8.59 (d, J = 1.89 Hz, 1H), 8.55 (d, J = 4.15 Hz, 1H), 8.15 (dd, J = 1.51, 5.29 Hz, 1H), 7.96-8.10 (m, 2H), 7.91 (d, J = 2.64 Hz, 1H), 7.27 (s, 1H), 7.11 (s, 1H), 6.83 (s, 1H), 6.61-6.78 (m, 1H), 4.62-4.77 (m, 3H), 2.78-2.98 (m, 1H), 1.35 (s, 9H), 1.30 (d, J = 6.04 Hz, 6H), 0.66-0.78 (m, 2H), 0.50-0.66 (m, 2H). |
| 4.1.16 | 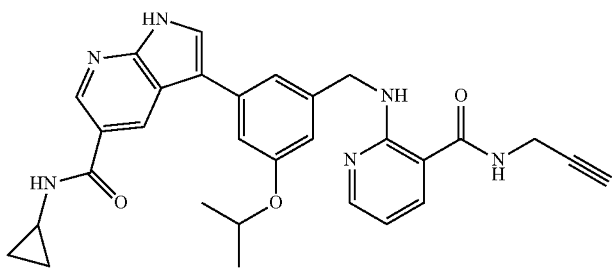 [SMILES: C#CCNC(=O)c1cccnc1NCc1cc(OC(C)C)cc(-c2c[nH]c3ncc(C(=O)NC4CC4)cc23)c1] | N-cyclopropyl-3-[3-(propan-2-yloxy)-5-({[3-(prop-2-yn-1-ylcarbamoyl)pyridin-2-yl]amino}methyl)phenyl]-1H-pyrrolo[2,3-b]pyridine-5-carboxamide | 523.3 | ¹H NMR (300 MHz, DMSO-d₆) δ 12.07-12.18 (m, 1H), 9.00-9.09 (m, 1H), 8.71 (d, J = 2.27 Hz, 1H), 8.60 (d, J = 1.89 Hz, 1H), 8.55 (d, J = 3.78 Hz, 1H), 8.21 (dd, J = 1.70, 5.10 Hz, 1H), 8.02 (d, J = 7.93 Hz, 1H), 7.90 (d, J = 2.27 Hz, 1H), 7.27 (s, 1H), 7.10 (s, 1H), 6.81 (s, 1H), 6.68 (dd, J = 5.29, 7.55 Hz, 1H), 4.68 (quin, J = 6.04 Hz, 3H), 4.02 (dd, J = 2.45, 5.48 Hz, 3H), 3.12 (t, J = 2.45 Hz, 1H), 2.81-2.96 (m, 1H), 1.29 (d, J = 6.04 Hz, 6H), 0.65-0.78 (m, 2H), 0.52-0.65 (m, 2H). |
| 4.20 | 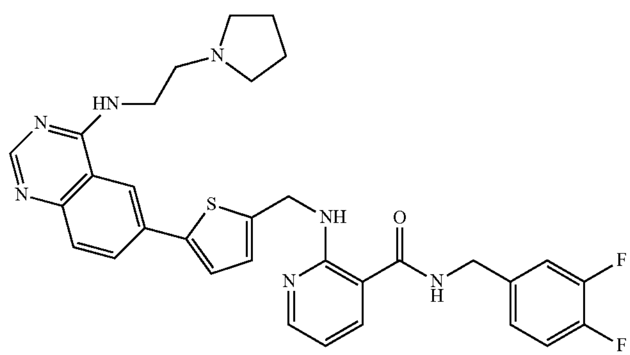 [SMILES: O=C(NCc1ccc(F)c(F)c1)c1cccnc1NCc1ccc(-c2ccc3ncnc(NCCN4CCCC4)c3c2)s1] | N-(3,4-difluorobenzyl)-2-(((5-(4-(2-(pyrrolidin-1-yl)ethylamino)quinazolin-6-yl)thiophen-2-yl)methyl)amino)nicotinamide | 600.3 | ¹H NMR (300 MHz, DMSO-d₆) δ 10.29 (t, J = 6.42 Hz, 1H), 9.20 (t, J = 5.85 Hz, 1H), 8.92 (s, 1H), 8.85 (t, J = 5.29 Hz, 1H), 8.54 (d, J = 1.89 Hz, 1H), 8.30 (dd, J = 1.70, 8.88 Hz, 1H), 8.25 (dd, J = 1.51, 4.91 Hz, 1H), 8.09 (dd, J = 1.70, 7.74 Hz, 1H), 7.84 (d, J = 9.06 Hz, 1H), 7.56 (d, J = 3.40 Hz, 1H), 6.99-7.16 (m, 4H), 6.71 (dd, J = 4.91, 7.93 Hz, 1H), 4.87 (d, J = 4.91 Hz, 2H), 4.46 (d, J = 5.67 Hz, 2H), 4.08 (q, J = 5.41 Hz, 2H), 3.66 (br. s., 2H), 3.48-3.58 (m, 2H), 3.13 (br. s., 2H), 1.80-2.06 (m, 4H). |

TABLE 1-continued

| Ex. No. | Structure | Chemical Name | ESI-MS (M + H) | ¹H NMR |
|---|---|---|---|---|
| 4.21 | 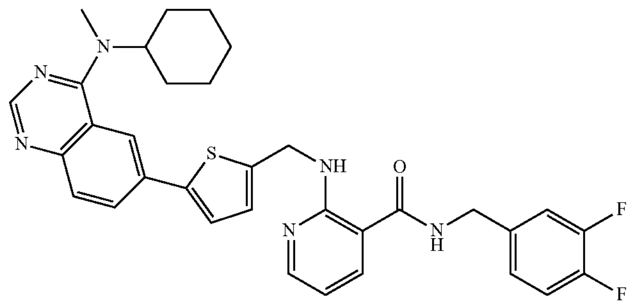 [SMILES: CN(c1ncnc2ccc(-c3ccc(CNc4ncccc4C(=O)NCc4ccc(F)c(F)c4)s3)cc12)C1CCCCC1] | 2-(((5-(4-(cyclohexyl(methyl)amino)quinazolin-6-yl)thiophen-2-yl)methyl)amino)-N-(3,4-difluorobenzyl)nicotinamide | 599.4 | ¹H NMR (300 MHz, DMSO-d₆) δ 9.19 (t, J = 5.85 Hz, 1H), 8.80-8.88 (m, 1H), 8.78 (s, 1H), 8.18-8.30 (m, 3H), 8.08 (dd, J = 1.70, 7.74 Hz, 1H), 7.77 (d, J = 9.06 Hz, 1H), 7.55 (d, J = 3.78 Hz, 1H), 6.97-7.15 (m, 4H), 6.71 (dd, J = 4.91, 7.55 Hz, 1H), 4.84 (d, J = 4.53 Hz, 2H), 4.45 (d, J = 6.04 Hz, 2H), 3.47 (s, 3H), 1.06-1.96 (m, 11H). |
| 4.22 | 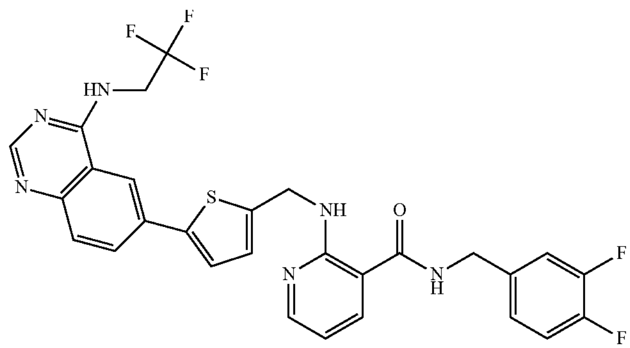 [SMILES: O=C(NCc1ccc(F)c(F)c1)c1cccnc1NCc1ccc(-c2ccc3ncnc(NCC(F)(F)F)c3c2)s1] | N-(3,4-difluorobenzyl)-2-(((5-(4-(2,2,2-trifluoroethyl)amino)quinazolin-6-yl)thiophen-2-yl)methyl)amino)nicotinamide | 585.2 | ¹H NMR (300 MHz, DMSO-d₆) δ 10.10 (br. s., 1H), 9.17 (t, J = 5.67 Hz, 1H), 8.90 (s, 1H), 8.83 (br. s., 1H), 8.66 (s, 1H), 8.22-8.34 (m, 2H), 8.04-8.11 (m, 1H), 7.83 (d, J = 8.69 Hz, 1H), 7.57 (d, J = 3.78 Hz, 1H), 6.98-7.18 (m, 4H), 6.70 (dd, J = 4.91, 7.55 Hz, 1H), 4.87 (d, J = 4.91 Hz, 2H), 4.56-4.73 (m, 2H), 4.46 (d, J = 5.67 Hz, 2H). |
| 4.23 | 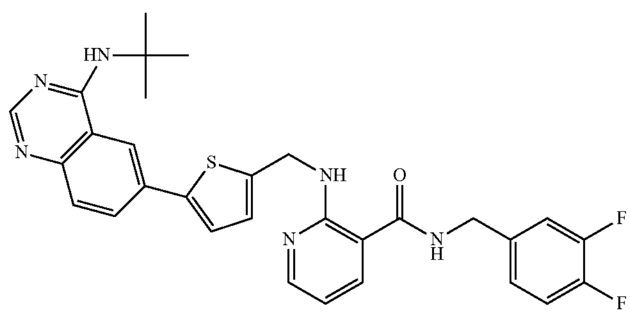 [SMILES: CC(C)(C)Nc1ncnc2ccc(-c3ccc(CNc4ncccc4C(=O)NCc4ccc(F)c(F)c4)s3)cc12] | N-(3,4-difluorobenzyl)-2-(((5-(4-(tert-butylamino)quinazolin-6-yl)thiophen-2-yl)methyl)amino)nicotinamide | 559.3 | ¹H NMR (300 MHz, DMSO-d₆) δ 9.15-9.24 (m, 2H), 8.90 (s, 1H), 8.83-8.89 (m, 1H), 8.74 (d, J = 1.51 Hz, 1H), 8.20-8.28 (m, 2H), 8.09 (dd, J = 1.89, 7.93 Hz, 1H), 7.76 (d, J = 8.69 Hz, 1H), 7.60 (d, J = 3.78 Hz, 1H), 6.99-7.16 (m, 4H), 6.71 (dd, J = 4.91, 7.55 Hz, 1H), 4.87 (d, J = 3.78 Hz, 2H), 4.46 (d, J = 5.67 Hz, 2H), 1.62 (s, 9H). |

TABLE 1-continued

| Ex. No. | Structure | Chemical Name | ESI-MS (M + H) | ¹H NMR |
|---|---|---|---|---|
| 4.24 | 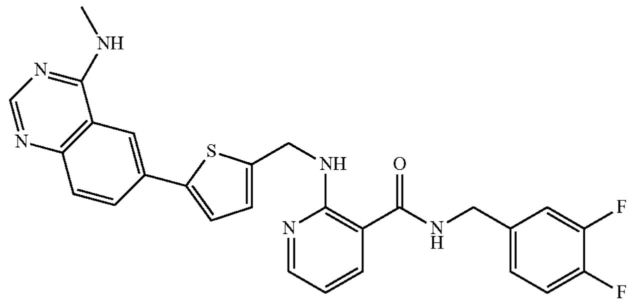 [SMILES: CNc1ncnc2ccc(-c3ccc(CNc4ncccc4C(=O)NCc4ccc(F)c(F)c4)s3)cc12] | N-(3,4-difluorobenzyl)-2-(((5-(4-(methylamino)quinazolin-6-yl)thiophen-2-yl)methyl)amino)nicotinamide | 517.2 | ¹H NMR (300 MHz, DMSO-d₆) δ 10.30 (d, J = 4.53 Hz, 1H), 9.19 (t, J = 5.67 Hz, 1H), 8.81-8.91 (m, 2H), 8.58 (s, 1H), 8.22-8.29 (m, 2H), 8.08 (dd, J = 1.51, 7.55 Hz, 1H), 7.78 (d, J = 8.69 Hz, 1H), 7.54 (d, J = 3.78 Hz, 1H), 6.97-7.16 (m, 4H), 6.70 (dd, J = 4.91, 7.55 Hz, 1H), 4.86 (d, J = 4.53 Hz, 2H), 4.45 (d, J = 5.67 Hz, 2H), 3.20 (d, J = 4.53 Hz, 3H). |
| 4.25 | 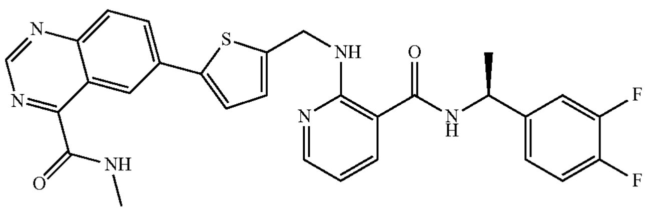 [SMILES: CNC(=O)c1ncnc2ccc(-c3ccc(CNc4ncccc4C(=O)N[C@@H](C)c4ccc(F)c(F)c4)s3)cc12] | (S)-6-(5-(3-(1-(3,4-difluorophenyl)ethyl-carbamoyl)pyridin-2-ylamino)methyl)thiophen-2-yl)-N-methylquinazoline-4-carboxamide | 559.2 | ¹H NMR (400 MHz, DMSO-d₆) δ 9.32 (s, 1H), 9.12 (d, J = 4.52 Hz, 1H), 9.07 (d, J = 1.76 Hz, 1H), 8.90 (d, J = 7.53 Hz, 1H), 8.77 (br. s., 1H), 8.38 (dd, J = 2.13, 8.91 Hz, 1H), 8.25 (dd, J = 1.76, 5.02 Hz, 1H), 8.15 (dd, J = 1.63, 7.66 Hz, 1H), 8.08 (d, J = 8.78 Hz, 1H), 7.57 (d, J = 3.77 Hz, 1H), 7.39-7.50 (m, 1H), 7.31-7.39 (m, 1H), 7.17-7.26 (m, 1H), 7.10 (d, J = 3.76 Hz, 1H), 6.73 (dd, J = 4.89, 7.65 Hz, 1H), 5.11 (quin, J = 7.15 Hz, 1H), 4.73-4.91 (m, 2H), 2.89 (d, J = 5.02 Hz, 3H), 1.46 (d, J = 7.03 Hz, 3H). |
| 4.26 | 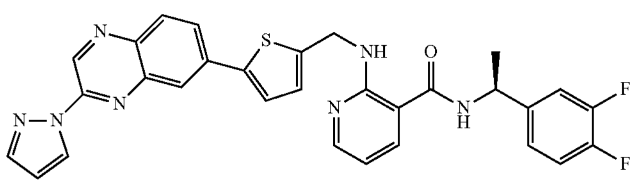 [SMILES: C[C@H](NC(=O)c1cccnc1NCc1ccc(-c2ccc3ncc(-n4cccn4)nc3c2)s1)c1ccc(F)c(F)c1] | (S)-2-(((5-(3-(1H-pyrazol-1-yl)quinoxalin-6-yl)thiophen-2-yl)methyl)amino)-N-(1-(3,4-difluorophenyl)ethyl)nicotinamide | 568.2 | ¹H NMR (400 MHz, DMSO-d₆) δ 9.52 (s, 1H), 8.89 (d, J = 7.53 Hz, 1H), 8.81 (d, J = 3.26 Hz, 1H), 8.67-8.79 (m, 1H), 8.26 (dd, J = 1.88, 4.89 Hz, 1H), 8.03-8.18 (m, 2H), 8.01 (d, J = 2.26 Hz, 1H), 7.68 (d, J = 3.51 Hz, 1H), 7.30-7.50 (m, 2H), 7.16-7.27 (m, 1H), 7.11 (d, J = 3.51 Hz, 1H), 6.66-6.78 (m, 2H), 5.02-5.20 (m, 1H), 4.84 (br. s., 2H), 1.46 (d, J = 7.03 Hz, 3H). |
| 4.27 | 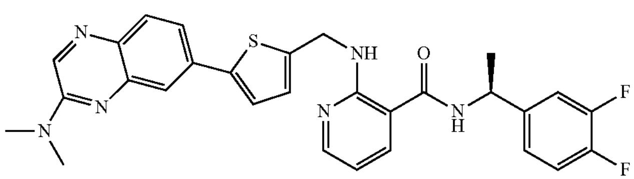 [SMILES: C[C@H](NC(=O)c1cccnc1NCc1ccc(-c2ccc3ncc(N(C)C)nc3c2)s1)c1ccc(F)c(F)c1] | (S)-N-(1-(3,4-difluorophenyl)ethyl)-2-((5-(3-(dimethylamino)quinoxalin-6-yl)thiophen-2-yl)methyl)aminonicotinamide | 545.2 | ¹H NMR (400 MHz, DMSO-d₆) δ 8.84 (d, J = 7.78 Hz, 1H), 8.52-8.68 (m, 2H), 8.26 (dd, J = 1.76, 4.77 Hz, 1H), 8.10 (dd, J = 1.88, 7.66 Hz, 1H), 7.77 (d, J = 8.53 Hz, 1H), 7.67 (d, J = 2.01 Hz, 1H), 7.58 (dd, J = 2.26, 8.53 Hz, 1H), 7.51 (d, J = 3.76 Hz, 1H), 7.39-7.48 (m, 1H), 7.28-7.39 (m, 1H), 7.21 (ddd, J = 2.38, 4.33, 6.34 Hz, 1H), 7.03 (d, J = 3.77 Hz, 1H), 6.69 (dd, J = 4.89, 7.65 Hz, 1H), 5.10 (quin, J = 7.09 Hz, 1H), 4.69-4.87 (m, 3H), 3.22 (s, 6H), 1.45 (d, J = 7.03 Hz, 3H). |

TABLE 1-continued

| Ex. No. | Structure | Chemical Name | ESI-MS (M + H) | ¹H NMR |
|---|---|---|---|---|
| 4.28 | 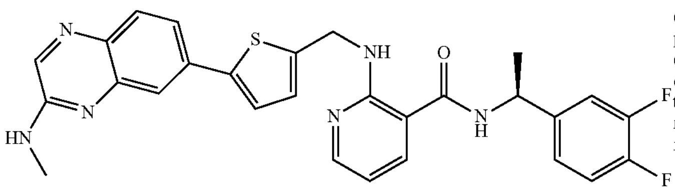 [SMILES: CNc1cnc2ccc(-c3ccc(CNc4ncccc4C(=O)N[C@@H](C)c4ccc(F)c(F)c4)s3)cc2n1] | (S)-N-(1-(3,4-difluorophenyl)ethyl)-2-(((5-(3-(methyl)amino)quinoxalin-6-yl)thiophen-2-yl)methyl)amino)nicotinamide | 531.2 | ¹H NMR (400 MHz, DMSO-d₆) δ 8.90 (d, J = 7.53 Hz, 1H), 8.77 (br. s., 1H), 8.20-8.41 (m, 2H), 8.14 (dd, J = 1.76, 7.78 Hz, 1H), 7.69-7.88 (m, 2H), 7.61 (dd, J = 2.01, 8.53 Hz, 1H), 7.52 (d, J = 3.51 Hz, 1H), 7.30-7.49 (m, 2H), 7.22 (ddd, J = 2.13, 4.27, 6.40 Hz, 1H), 7.06 (d, J = 3.76 Hz, 1H), 6.73 (dd, J = 5.02, 7.78 Hz, 1H), 5.10 (t, J = 7.15 Hz, 1H), 4.81 (br. s., 2H), 2.96 (s, 3H), 1.45 (d, J = 7.03 Hz, 3H). |
| 4.29 | 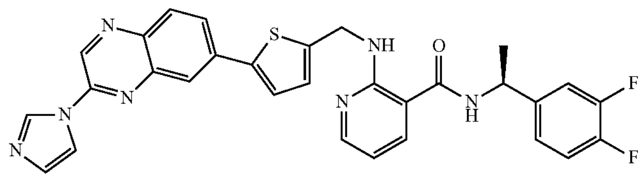 [SMILES: C[C@H](NC(=O)c1cccnc1NCc1ccc(-c2ccc3ncc(-n4ccnc4)nc3c2)s1)c1ccc(F)c(F)c1] | (S)-2-(((5-(3-(1H-imidazol-1-yl)quinoxalin-6-yl)thiophen-2-yl)methyl)amino)-N-(1-(3,4-difluorophenyl)ethyl)nicotinamide | 568.2 | ¹H NMR (300 MHz, DMSO-d₆) δ 9.39-9.55 (m, 2H), 8.87 (d, J = 7.55 Hz, 1H), 8.73 (br. s., 1H), 8.42 (s, 1H), 8.26 (dd, J = 1.70, 4.72 Hz, 1H), 8.05-8.22 (m, 4H), 7.70 (d, J = 3.78 Hz, 1H), 7.61 (s, 1H), 7.29-7.53 (m, 2H), 7.17-7.29 (m, 1H), 7.12 (d, J = 3.40 Hz, 1H), 6.72 (dd, J = 4.91, 7.55 Hz, 1H), 5.11 (quin, J = 7.18 Hz, 1H), 4.84 (d, J = 3.40 Hz, 2H), 1.46 (d, J = 7.18 Hz, 3H). |
| 4.30 | 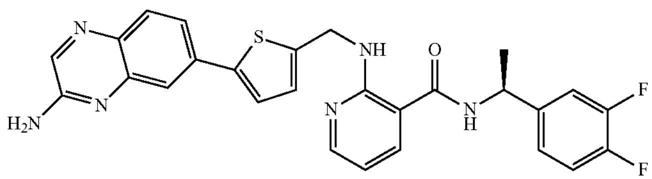 [SMILES: C[C@H](NC(=O)c1cccnc1NCc1ccc(-c2ccc3ncc(N)nc3c2)s1)c1ccc(F)c(F)c1] | (S)-2-(((5-aminoquinoxalin-6-yl)thiophen-2-yl)methyl)amino)-N-(1-(3,4-difluorophenyl)ethyl)nicotinamide | 517.2 | ¹H NMR (400 MHz, DMSO-d₆) δ 8.86 (d, J = 7.53 Hz, 1H), 8.64 (t, J = 5.77 Hz, 1H), 8.21-8.27 (m, 2H), 8.11 (dd, J = 1.76, 7.78 Hz, 1H), 7.74 (d, J = 8.28 Hz, 1H), 7.50-7.63 (m, 2H), 7.30-7.50 (m, 3H), 7.06-7.26 (m, 2H), 7.04 (d, J = 3.76 Hz, 1H), 6.69 (dd, J = 4.89, 7.65 Hz, 1H), 5.10 (quin, J = 7.22 Hz, 1H), 4.69-4.86 (m, 2H), 1.45 (d, J = 7.03 Hz, 3H). |
| 4.31 | 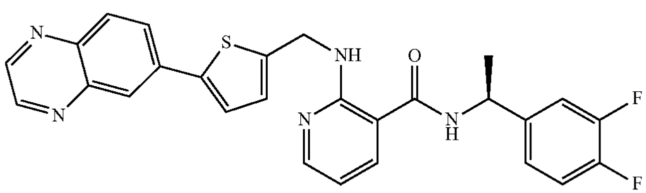 [SMILES: C[C@H](NC(=O)c1cccnc1NCc1ccc(-c2ccc3nccnc3c2)s1)c1ccc(F)c(F)c1] | (S)-N-(1-(3,4-difluorophenyl)ethyl)-2-(((5-(3-quinoxalin-2-yl)thiophen-2-yl)methyl)amino)nicotinamide | 502.2 | ¹H NMR (400 MHz, DMSO-d₆) δ 8.78-8.97 (m, 3H), 8.66 (t, J = 6.02 Hz, 1H), 8.26 (dd, J = 1.76, 5.02 Hz, 1H), 8.00-8.19 (m, 4H), 7.65 (d, J = 3.51 Hz, 1H), 7.29-7.49 (m, 2H), 7.21 (ddd, J = 2.26, 4.27, 6.27 Hz, 1H), 7.09 (d, J = 3.51 Hz, 1H), 6.69 (dd, J = 4.89, 7.65 Hz, 1H), 5.10 (quin, J = 7.15 Hz, 1H), 4.70-4.91 (m, 2H), 1.45 (d, J = 7.15 Hz, 3H). |
| 4.32 | 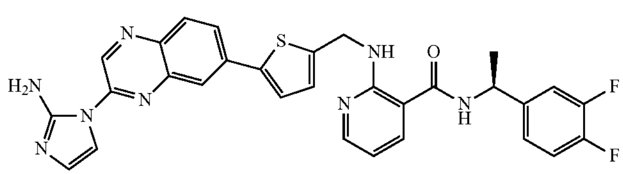 [SMILES: C[C@H](NC(=O)c1cccnc1NCc1ccc(-c2ccc3ncc(-n4ccnc4N)nc3c2)s1)c1ccc(F)c(F)c1] | (S)-2-(((5-(3-(2-amino-1H-imidazol-1-yl)quinoxalin-6-yl)thiophen-2-yl)methyl)amino)-N-(1-(3,4-difluorophenyl)ethyl)nicotinamide | 583.3 | ¹H NMR (400 MHz, DMSO-d₆) δ 9.38 (s, 1H), 9.01 (s, 2H), 8.86 (d, J = 7.53 Hz, 1H), 8.72 (s, 1H), 8.50 (d, J = 1.76 Hz, 1H), 8.25 (dd, J = 1.76, 4.77 Hz, 1H), 8.16-8.21 (m, 1H), 8.10-8.15 (m, 2H), 8.08 (d, J = 2.76 Hz, 1H), 7.66 (d, J = 3.76 Hz, 1H), 7.32-7.49 (m, 2H), 7.28 (d, J = 2.76 Hz, 1H), 7.24 (br. s., 1H), 7.12 (d, J = 3.51 Hz, 1H), 6.70 (dd, J = 4.77, 7.53 Hz, 1H), 5.10 (t, J = 7.53 Hz, 1H), 4.84 (d, J = 5.77 Hz, 2H), 1.45 (d, J = 7.03 Hz, 3H). |

TABLE 1-continued

| Ex. No. | Structure | Chemical Name | ESI-MS (M + H) | ¹H NMR |
|---|---|---|---|---|
| 4.33 | 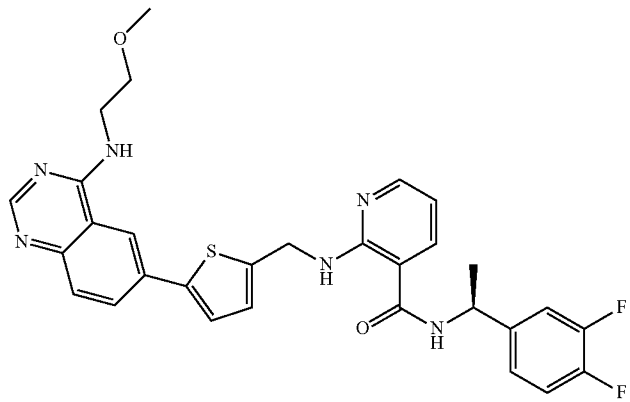 [SMILES: COCCNc1ncnc2ccc(-c3ccc(CNc4ncccc4C(=O)N[C@@H](C)c4ccc(F)c(F)c4)s3)cc12] | N-[(S)-1-(3,4-Difluoro-phenyl)-ethyl]-2-({5-[4-(2-methoxy-ethylamino)-quinoxalin-6-yl]-thiophen-2-ylmethyl}-amino)-nicotinamide | 575.2 | ¹H NMR (300 MHz, DMSO-$d_6$) δ 10.34 (t, J = 5.29 Hz, 1H), 8.83-8.93 (m, 2H), 8.76 (t, J = 6.04 Hz, 1H), 8.65 (d, J = 1.51 Hz, 1H), 8.22-8.30 (m, 2H), 8.14 (dd, J = 1.70, 7.74 Hz, 1H), 7.78 (d, J = 8.69 Hz, 1H), 7.55 (d, J = 3.40 Hz, 1H), 7.31-7.49 (m, 2H), 7.18-7.26 (m, 1H), 7.12 (d, J = 3.40 Hz, 1H), 6.71 (dd, J = 4.91, 7.55 Hz, 1H), 5.10 (quin, J = 7.18 Hz, 1H), 4.85 (d, J = 4.91 Hz, 2H), 3.91 (q, J = 5.29 Hz, 2H), 3.61-3.68 (m, 2H), 3.30 (s, 3H), 1.46 (d, 3H |
| 4.34 | 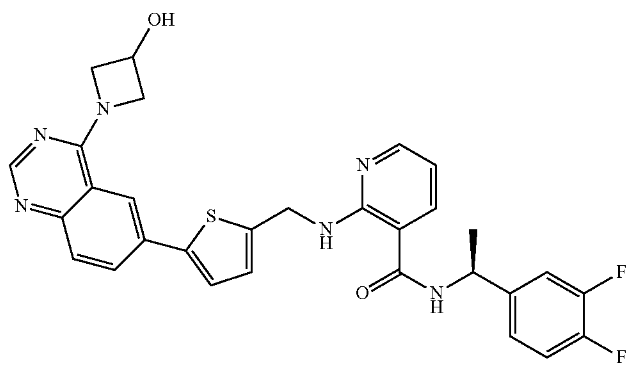 [SMILES: C[C@H](NC(=O)c1cccnc1NCc1ccc(-c2ccc3ncnc(N4CC(O)C4)c3c2)s1)c1ccc(F)c(F)c1] | N-[(S)-1-(3,4-Difluoro-phenyl)-ethyl]-2-({5-[4-(3-hydroxy-azetidin-1-yl)-quinoxalin-6-yl]-thiophen-2-ylmethyl}-amino)-nicotinamide | 573.2 | ¹HNMR (300 MHz, DMSO-$d_6$) δ 8.88 (d, J = 7.55 Hz, 1H), 8.78 (s, 1H), 8.72 (br. s., 1H), 8.10-8.28 (m, 3H), 8.05 (s, 1H), 7.78 (d, J = 8.69 Hz, 1H), 7.58 (d, J = 3.78 Hz, 1H), 7.31-7.49 (m, 2H), 7.16-7.27 (m, 1H), 7.10 (d, J = 3.78 Hz, 1H), 6.71 (dd, J = 4.91, 7.55 Hz, 1H), 5.27 (br. s., 1H), 5.09 (quin, J = 6.99 Hz, 2H), 4.65-4.99 (m, 5H), 4.27 (br. s., 1H), 1.45 (d, J = 6.80 Hz, 3H) |

TABLE 1-continued

| Ex. No. | Structure | Chemical Name | ESI-MS (M + H) | ¹H NMR |
|---|---|---|---|---|
| 4.35 | 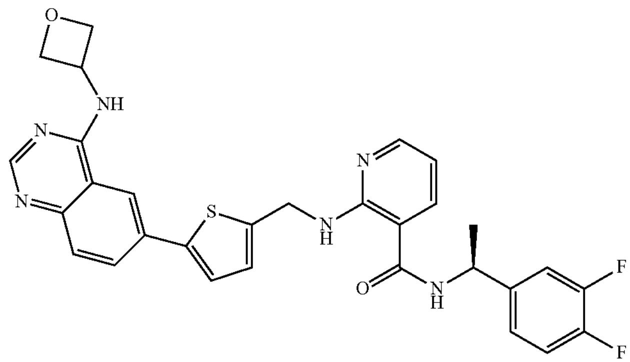 [SMILES: C[C@H](NC(=O)c1cccnc1NCc1ccc(-c2ccc3ncnc(NC4COC4)c3c2)s1)c1ccc(F)c(F)c1] | N-[(S)-1-(3,4-Difluorophenyl)-ethyl]-2-({5-[4-(oxetan-3-ylamino)quinazolin-6-yl]-thiophen-2-ylmethyl}-amino)-nicotinamide | 573.2 | ¹H NMR (300 MHz, DMSO-d₆) δ 8.79-8.94 (m, 2H), 8.69 (t, J = 5.85 Hz, 1H), 8.49 (d, J = 1.89 Hz, 1H), 8.41 (s, 1H), 8.25 (dd, J = 1.89, 4.91 Hz, 1H), 8.11 (dd, J = 1.70, 7.74 Hz, 1H), 8.01 (dd, J = 2.08, 8.88 Hz, 1H), 7.68 (d, J = 8.69 Hz, 1H), 7.30-7.51 (m, 3H), 7.17-7.26 (m, 1H), 7.07 (d, J = 3.78 Hz, 1H), 6.69 (dd, J = 4.91, 7.55 Hz, 1H), 5.03-5.28 (m, 2H), 4.89 (t, J = 6.99 Hz, 2H), 4.83 (d, J = 5.67 Hz, 2H), 4.68 (t, J = 6.42 Hz, 2H), 1.45 (d, J = 7.18 Hz, 3H) |
| 4.36 | 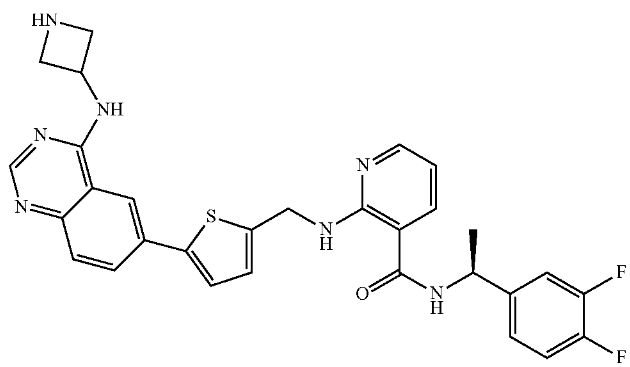 [SMILES: C[C@H](NC(=O)c1cccnc1NCc1ccc(-c2ccc3ncnc(NC4CNC4)c3c2)s1)c1ccc(F)c(F)c1] | 2-({5-[4-(Azetidin-3-ylamino)-quinazolin-6-yl]-thiophen-2-ylmethyl}-amino)-N-[(S)-1-(3,4-difluoro-phenyl)-ethyl]-nicotinamide | 572.2 | ¹H NMR (300 MHz, DMSO-d₆) δ 8.83 (d, J = 7.55 Hz, 1H), 8.61 (t, J = 5.85 Hz, 1H), 8.36-8.45 (m, 1H), 8.24 (dd, J = 1.51, 4.91 Hz, 1H), 8.09 (dd, J = 1.70, 7.74 Hz, 1H), 7.91-8.02 (m, 2H), 7.67 (d, J = 9.44 Hz, 1H), 7.28-7.52 (m, 3H), 7.15-7.26 (m, 1H), 7.03 (d, J = 3.78 Hz, 1H), 6.68 (dd, J = 4.72, 7.74 Hz, 1H), 5.09 (quin, J = 7.08 Hz, 1H), 4.59-4.87 (m, 4H), 4.13 (br. s., 2H), 3.81-3.99 (m, 1H), 2.60 (br. s., 1H), 1.44 (d, J = 6.80 Hz, 3H). |

TABLE 1-continued

| Ex. No. | Structure | Chemical Name | ESI-MS (M + H) | ¹H NMR |
|---|---|---|---|---|
| 4.37 | 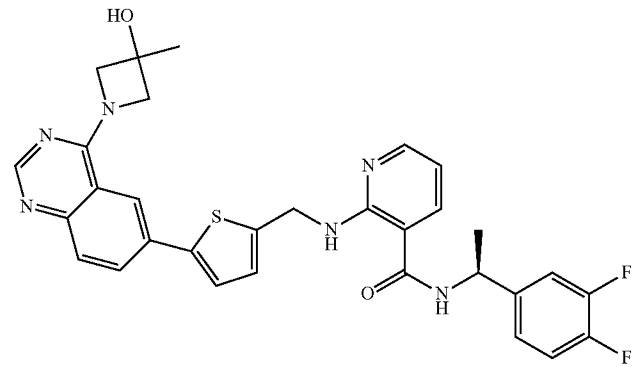 [SMILES: C[C@H](NC(=O)c1cccnc1NCc1ccc(-c2ccc3ncnc(N4CC(C)(O)C4)c3c2)s1)c1ccc(F)c(F)c1] | N-[(S)-1-(3,4-Difluorophenyl)-ethyl]-2-({5-[4-(3-hydroxy-3-methyl-azetidin-1-yl)-quinazolin-6-yl]-thiophen-2-ylmethyl}-amino)-nicotinamide | 587.3 | ¹H NMR (300 MHz, DMSO-d₆) δ 8.77 (d, J = 7.55 Hz, 1H), 8.55 (t, J = 5.85 Hz, 1H), 8.35 (s, 1H), 8.18 (dd, J = 1.70, 4.72 Hz, 1H), 8.02 (dd, J = 1.70, 7.74 Hz, 1H), 7.86-7.95 (m, 2H), 7.59-7.67 (m, 1H), 7.22-7.44 (m, 3H), 7.14 (ddd, J = 2.27, 4.25, 6.33 Hz, 1H), 6.98 (d, J = 3.78 Hz, 1H), 6.62 (dd, J = 4.72, 7.74 Hz, 1H), 5.71 (s, 1H), 5.03 (quin, J = 7.18 Hz, 1H), 4.72 (d, J = 5.67 Hz, 2H), 4.22-4.47 (m, 3H), 1.42 (s, 3H), 1.38 (d, J = 6.80 Hz, 3H). |
| 4.38 | 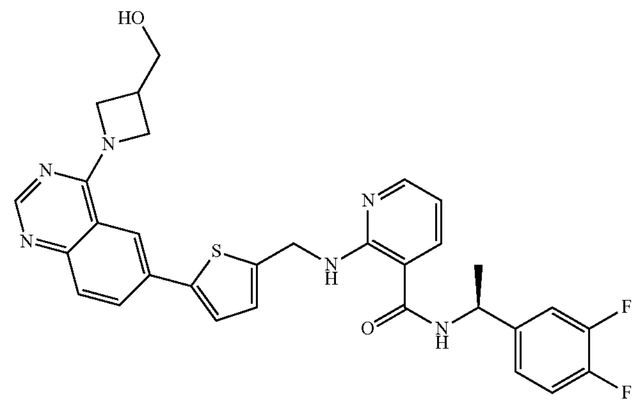 [SMILES: C[C@H](NC(=O)c1cccnc1NCc1ccc(-c2ccc3ncnc(N4CC(CO)C4)c3c2)s1)c1ccc(F)c(F)c1] | N-[(S)-1-(3,4-Difluorophenyl)-ethyl]-2-({5-[4-(3-hydroxymethyl-azetidin-1-yl)-quinazolin-6-yl]-thiophen-2-ylmethyl}-amino)-nicotinamide | 587.2 | ¹H NMR (300 MHz, DMSO-d₆) δ 8.76 (d, J = 7.55 Hz, 1H), 8.54 (t, J = 5.85 Hz, 1H), 8.34 (s, 1H), 8.17 (dd, J = 1.70, 4.72 Hz, 1H), 8.02 (dd, J = 1.70, 7.74 Hz, 1H), 7.87-7.95 (m, 2H), 7.61 (d, J = 9.44 Hz, 1H), 7.23-7.42 (m, 3H), 7.14 (ddd, J = 2.27, 4.25, 6.33 Hz, 1H), 6.97 (d, J = 3.78 Hz, 1H), 6.61 (dd, J = 4.91, 7.55 Hz, 1H), 5.03 (quin, J = 7.18 Hz, 1H), 4.80 (t, J = 1.00 Hz, 1H), 4.71 (d, J = 4.53 Hz, 2H), 4.10-4.59 (m, 2H), 3.57 (t, J = 5.67 Hz, 2H), 2.74-2.97 (m, 1H), 1.38 (d, J = 7.18 Hz, 3H) |
| 5.3 | 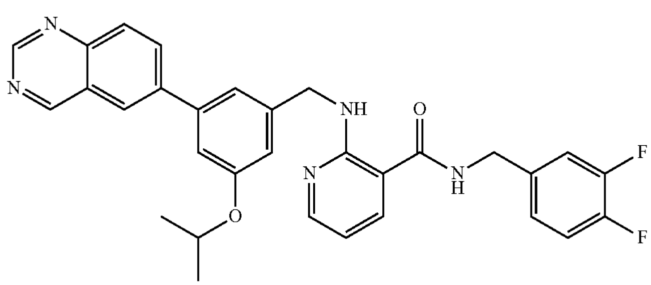 [SMILES: CC(C)Oc1cc(CNc2ncccc2C(=O)NCc2ccc(F)c(F)c2)cc(-c2ccc3ncncc3c2)c1] | N-(3,4-difluorobenzyl)-2-(3-isopropoxy-5-(quinazolin-6-yl)benzylamino)-nicotinamide | 540.3 | ¹H NMR (300 MHz, DMSO-d₆) δ 9.64 (s, 2H), 9.22-9.37 (m, 4H), 9.10 (br. s., 1H), 8.46 (d, J = 1.89 Hz, 1H), 8.34 (dd, J = 2.08, 8.88 Hz, 1H), 8.14-8.23 (m, 2H), 8.08 (d J = 8.69 Hz, 1H), 7.39 (s, 1H), 7.26 (t, J = 1.89 Hz, 1H), 6.99-7.14 (m, 3H), 6.97 (s, 1H), 6.76 (dd, J = 5.29, 7.55 Hz, 1H), 4.72 (t, J = 6.04 Hz, 3H), 4.48 (d, J = 5.67 Hz, 2H), 1.22-1.34 (m, 6H). |

| Ex. No. | Chemical Name | Structure | ESI-MS (M + H) | ¹H NMR |
|---|---|---|---|---|
| 5.4 | N-(3,4-difluorobenzyl)-2-(3-isopropoxy-5-(quinolin-6-yl)benzylamino)nicotinamide | 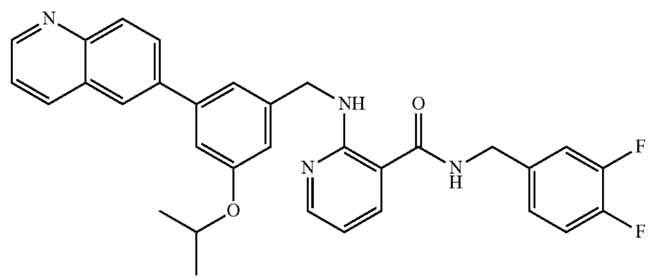 [SMILES: CC(C)Oc1cc(CNc2ncccc2C(=O)NCc2ccc(F)c(F)c2)cc(-c2ccc3ncccc3c2)c1] | 539.3 | ¹H NMR (300 MHz, DMSO-d₆) δ 9.34 (t, J = 5.85 Hz, 1H), 9.07-9.12 (m, 1H), 8.76 (d, J = 7.93 Hz, 1H), 8.43-8.49 (m, 1H), 8.17-8.26 (m, 2H), 7.82 (dd, J = 4.53, 8.31 Hz, 1H), 7.40 (s, 1H), 7.26 (s, 1H), 7.00-7.16 (m, 2H), 6.98 (s, 1H), 6.71-6.82 (m, 1H), 4.66-4.78 (m, 2H), 4.47 (d, J = 6.04 Hz, 2H), 1.29 (d, J = 6.04 Hz, 6H). |
| 5.5 | 2-(3-(4-(cyclopropylamino)quinazolin-6-yl)-5-isopropoxybenzylamino)-N-(3,4-difluorobenzyl)nicotinamide | 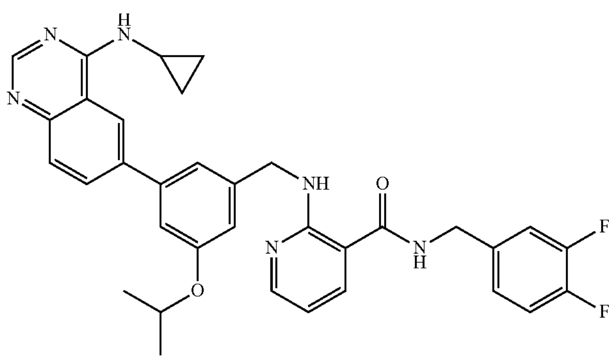 [SMILES: CC(C)Oc1cc(CNc2ncccc2C(=O)NCc2ccc(F)c(F)c2)cc(-c2ccc3ncnc(NC4CC4)c3c2)c1] | 595.4 | ¹H NMR (300 MHz, DMSO-d₆) δ 10.19 (d, J = 4.15 Hz, 1H), 9.27 (t, J = 5.85 Hz, 1H), 8.87-9.04 (m, 2H), 8.79 (d, J = 1.51 Hz, 1H), 8.32 (dd, J = 1.70, 8.88 Hz, 1H), 8.20 (dd, J = 1.70, 5.10 Hz, 1H), 8.13 (dd, J = 1.70, 7.74 Hz, 1H), 7.88 (d, J = 8.69 Hz, 1H), 7.36 (s, 1H), 7.25 (s, 1H), 6.96-7.15 (m, 4H), 6.71 (dd, J = 5.10, 7.74 Hz, 1H), 4.63-4.76 (m, 4H), 4.46 (d, J = 6.04 Hz, 2H), 3.34-3.48 (m, 1H), 1.27 (d, J = 6.04 Hz, 6H), 0.85-1.05 (m, 4H). |
| 5.6 | 2-(3-(4-(aminoquinazolin-6-yl)-5-isopropoxybenzylamino)-N-(3,4-difluorobenzyl)nicotinamide | 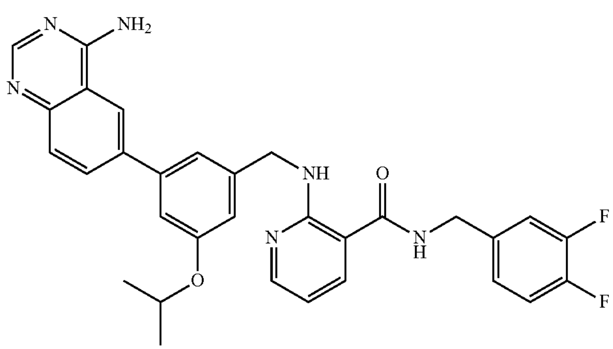 [SMILES: CC(C)Oc1cc(CNc2ncccc2C(=O)NCc2ccc(F)c(F)c2)cc(-c2ccc3ncnc(N)c3c2)c1] | 555.3 | ¹H NMR (300 MHz, DMSO-d₆) δ 9.87 (d, J = 18.51 Hz, 1H), 9.19 (t, J = 5.85 Hz, 1H), 8.85 (s, 1H), 8.81 (t, J = 5.29 Hz, 1H), 8.75 (d, J = 1.51 Hz, 1H), 8.36 (dd, J = 1.51, 8.69 Hz, 1H), 8.20 (dd, J = 1.51, 4.91 Hz, 1H), 8.07 (dd, J = 1.70, 7.74 Hz, 1H), 7.84 (d, J = 8.69 Hz, 1H), 7.36 (s, 1H), 7.24 (s, 1H), 6.99-7.14 (m, 2H), 6.98 (s, 1H), 6.67 (dd, J = 4.91, 7.93 Hz, 1H), 4.63-4.73 (m, 2H), 4.46 (d, J = 5.67 Hz, 2H), 1.28 (d, J = 6.04 Hz, 6H). |

TABLE 1-continued

| Ex. No. | Structure | Chemical Name | ESI-MS (M + H) | ¹H NMR |
|---|---|---|---|---|
| 5.7 | 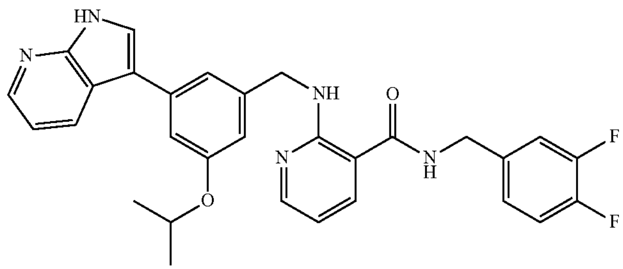 [SMILES: CC(C)Oc1cc(CNc2ncccc2C(=O)NCc2ccc(F)c(F)c2)cc(-c2c[nH]c3ncccc23)c1] | N-(3,4-difluorobenzyl)-2-(3-isopropoxy-5-(1H-pyrrolo[2,3-b]pyridin-3-yl)benzylamino)nicotinamide | 528.3 | ¹H NMR (300 MHz, DMSO-d₆) δ 11.97 (br. s., 1H), 9.22-9.35 (m, 1H), 9.08 (d, J = 7.93 Hz, 1H), 8.13-8.35 (m, 4H), 7.88 (d, J = 2.27 Hz, 1H), 7.26 (s, 1H), 6.98-7.16 (m, 5H), 6.67-6.84 (m, 2H), 4.64-4.72 (m, 3H), 4.48 (d, J = 6.04 Hz, 2H), 1.28 (d, J = 6.04 Hz, 6H). |
| 5.8 | 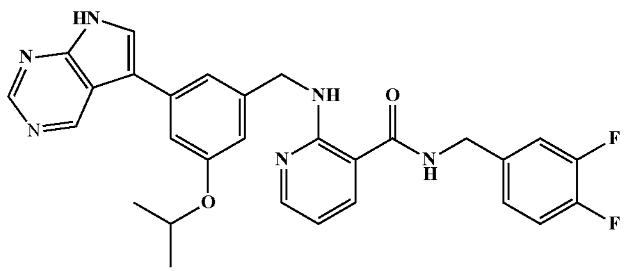 | N-(3,4-difluorobenzyl)-2-{[3-(propan-2-yloxy)-5-(7H-pyrrolo[2,3-d]pyrimidin-5-yl)benzyl]amino}pyridine-3-carboxamide | 529.3 | ¹H NMR (300 MHz, DMSO-d₆) δ 12.99 (br. s., 1H), 9.44 (s, 1H), 9.21 (t, J = 6.04 Hz, 1H), 9.00 (s, 1H), 8.84-8.96 (m, 1H), 8.18-8.24 (m, 1H), 8.10 (dd, J = 1.89, 7.55 Hz, 1H), 7.34 (s, 1H), 7.17 (s, 1H), 6.97-7.14 (m, 2H), 6.85 (s, 1H), 6.65-6.74 (m, 1H), 4.69 (quin, J = 6.04 Hz, 3H), 4.47 (d, J = 5.67 Hz, 2H), 1.27 (d, J = 6.04 Hz, 6H). |
| 6.1 | 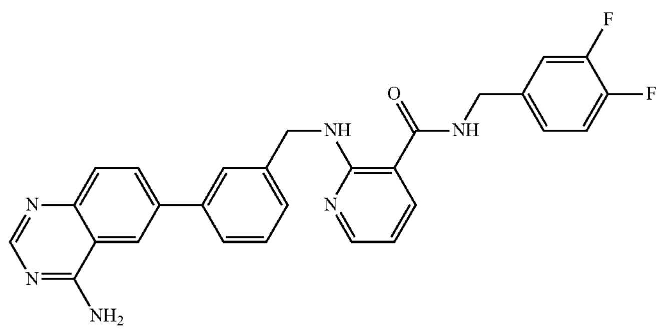 [SMILES: Nc1ncnc2ccc(-c3cccc(CNc4ncccc4C(=O)NCc4ccc(F)c(F)c4)c3)cc12] | 2-(3-(4-(aminoquinazolin-6-yl)benzylamino)-N-(3,4-difluorobenzyl)nicotinamide | 497.3 | ¹H NMR (300 MHz, DMSO-d₆) δ 9.87 (d, J = 17.00 Hz, 2H), 9.18 (t, J = 5.85 Hz, 1H), 8.80-8.92 (m, 2H), 8.78 (d, J = 1.89 Hz, 1H), 8.37 (dd, J = 1.51, 8.69 Hz, 1H), 8.20 (dd, J = 1.51, 4.91 Hz, 1H), 8.08 (dd, J = 1.70, 7.74 Hz, 1H), 7.86 (d, J = 8.69 Hz, 1H), 7.82 (s, 1H), 7.72 (d, J = 7.93 Hz, 1H), 7.48-7.57 (m, 1H), 7.39-7.47 (m, 1H), 6.97-7.15 (m, 3H), 6.67 (dd, J = 4.91, 7.93 Hz, 1H), 4.75 (d, J = 4.91 Hz, 2H), 4.45 (d, J = 5.67 Hz, 2H). |

TABLE 1-continued

| Ex. No. | Structure | Chemical Name | ESI-MS (M + H) | ¹H NMR |
|---|---|---|---|---|
| 6.2 | 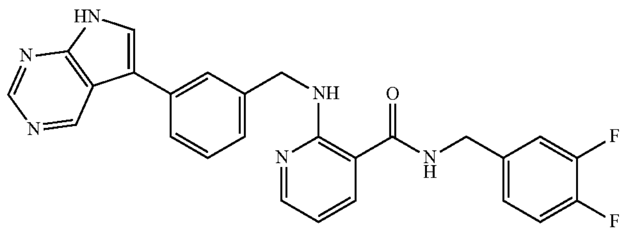 [SMILES: O=C(NCc1ccc(F)c(F)c1)c1cccnc1NCc1cccc(-c2c[nH]c3ncncc23)c1] | 2-(3-(7H-pyrrolo[2,3-d]pyrimidin-5-yl)benzylamino)-N-(3,4-difluorobenzyl)nicotinamide | 471.2 | ¹H NMR (300 MHz, CD₃OD) δ 9.48 (s, 1H), 9.03 (s, 1H), 8.25 (dd, J = 1.51, 7.55 Hz, 1H), 8.08-8.15 (m, 2H), 7.80 (s, 1H), 7.71 (d, J = 7.93 Hz, 1H), 7.53 (t, J = 7.74 Hz, 1H), 7.39-7.46 (m, 1H), 6.74-7.00 (m, 4H), 4.78 (s, 2H), 4.55 (s, 2H). |
| 6.3 | 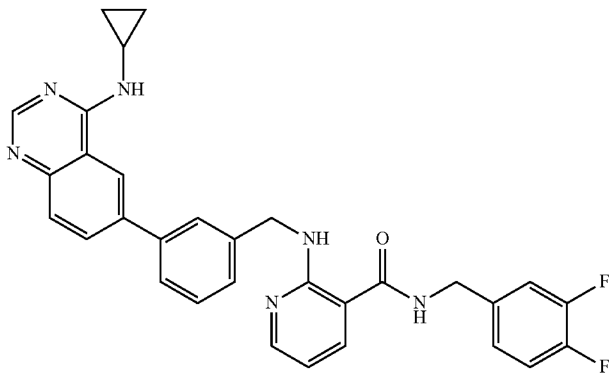 [SMILES: O=C(NCc1ccc(F)c(F)c1)c1cccnc1NCc1cccc(-c2ccc3ncnc(NC4CC4)c3c2)c1] | 2-(3-(4-(cyclopropylamino)quinazolin-6-yl)benzylamino)-N-(3,4-difluorobenzyl)-nicotinamide | 537.3 | ¹H NMR (300 MHz, DMSO-d₆) δ 10.06 (d, J = 3.78 Hz, 1H), 9.18 (t, J = 5.67 Hz, 1H), 8.97 (s, 1H), 8.81 (br. s., 1H), 8.75 (s, 1H), 8.32 (d, J = 8.69 Hz, 1H), 8.19 (d, J = 3.40 Hz, 1H), 8.07 (d, J = 6.42 Hz, 1H), 7.87 (d, J = 8.69 Hz, 1H), 7.78 (s, 1H), 7.69 (d, J = 7.55 Hz, 1H), 7.51 (t, J = 7.55 Hz, 1H), 7.39-7.46 (m, 1H), 6.94-7.16 (m, 3H), 6.66 (dd, J = 4.91, 7.55 Hz, 1H), 4.74 (d, J = 4.53 Hz, 2H), 4.45 (d, J = 5.67 Hz, 2H), 3.33-3.45 (m, 1H), 0.83-1.04 (m, 4H). |
| 6.4 | 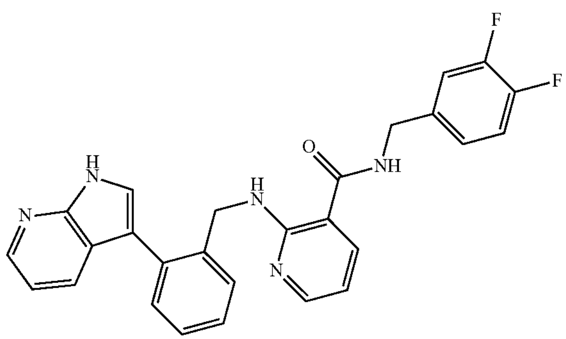 [SMILES: O=C(NCc1ccc(F)c(F)c1)c1cccnc1NCc1ccccc1-c1c[nH]c2ncccc12] | N-(3,4-difluorobenzyl)-2-{[2-(1H-pyrrolo[2,3-b]pyridin-3-yl)benzyl]amino}-pyridine-3-carboxamide | 470.3 | ¹H NMR (300 MHz, DMSO-d₆) δ 11.95-12.15 (m, 1H), 9.26 (br. s., 1H), 9.00 (br. s., 1H), 8.30 (d, J = 4.53 Hz, 1H), 8.16 (d, J = 6.80 Hz, 1H), 8.08 (d, J = 4.53 Hz, 1H), 7.94 (d, J = 7.93 Hz, 1H), 7.62 (s, 1H), 7.26-7.54 (m, 4H), 6.94-7.24 (m, 4H), 6.67-6.79 (m, 1H), 4.64 (br. s., 1H), 4.44 (d, J = 5.29 Hz, 2H). |

TABLE 1-continued

| Ex. No. | Structure | Chemical Name | ESI-MS (M + H) | ¹H NMR |
|---|---|---|---|---|
| 6.5 | 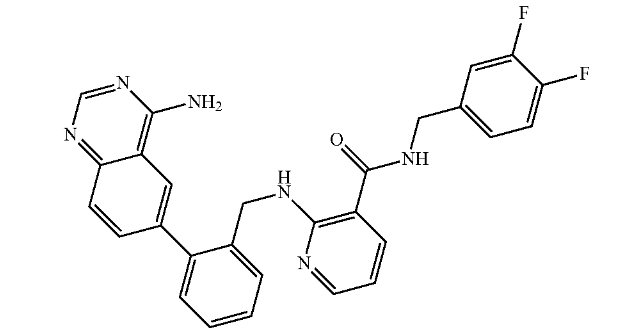 [SMILES: Nc1ncnc2ccc(-c3ccccc3CNc3ncccc3C(=O)NCc3ccc(F)c(F)c3)cc12] | 2-{[2-(4-aminoquinazolin-6-yl)benzyl]amino}-N-(3,4-difluorobenzyl)pyridine-3-carboxamide | 497.3 | ¹H NMR (300 MHz, DMSO-d₆) δ 9.82 (br. s., 1H), 9.72 (br. s., 1H), 9.08 (t, J = 5.85 Hz, 1H), 8.87 (s, 1H), 8.57 (t, J = 5.10 Hz, 1H), 8.45 (s, 1H), 8.07 (dd, J = 1.51, 8.69 Hz, 1H), 8.03 (dd, J = 1.89, 4.91 Hz, 1H), 7.96 (dd, J = 1.70, 7.74 Hz, 1H), 7.79 (d, J = 8.69 Hz, 1H), 7.27-7.55 (m, 4H), 6.94-7.17 (m, 3H), 6.55 (dd, J = 4.72, 7.74 Hz, 1H), 4.63 (d, J = 5.29 Hz, 2H), 4.40 (d, J = 5.67 Hz, 3H). |
| 6.6 | 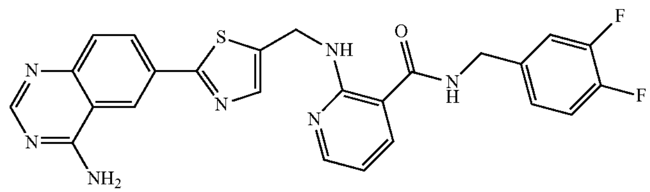 [SMILES: Nc1ncnc2ccc(-c3ncc(CNc4ncccc4C(=O)NCc4ccc(F)c(F)c4)s3)cc12] | 2-({[2-(4-aminoquinazolin-6-yl)-1,3-thiazol-5-yl]methyl}amino)-N-(3,4-difluoro-benzyl)pyridine-3-carboxamide | 504.2 | ¹H NMR (300 MHz, DMSO-d₆) δ 9.80-10.03 (m, 2H), 9.25 (t, J = 5.67 Hz, 1H), 8.96-9.10 (m, 2H), 8.84 (s, 1H), 8.60 (d, J = 9.06 Hz, 1H), 8.21 (d, J = 3.78 Hz, 1H), 8.07-8.15 (m, 2H), 7.85 (d, J = 8.69 Hz, 1H), 7.01-7.17 (m, 3H), 6.74 (dd, J = 4.91, 7.55 Hz, 1H), 5.02 (d, J = 5.67 Hz, 2H), 4.50 (d, J = 5.67 Hz, 2H). |
| 6.7 | 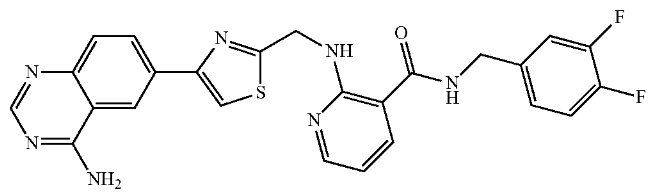 [SMILES: Nc1ncnc2ccc(-c3csc(CNc4ncccc4C(=O)NCc4ccc(F)c(F)c4)n3)cc12] | 2-({[4-(4-aminoquinazolin-6-yl)-1,3-thiazol-2-yl]methyl}amino)-N-(3,4-difluoro-benzyl)pyridine-3-carboxamide | 504.2 | ¹H NMR (300 MHz, DMSO-d₆) δ 9.80-10.03 (m, 2H), 9.25 (t, J = 5.67 Hz, 1H), 8.96-9.10 (m, 2H), 8.84 (s, 1H), 8.60 (d, J = 9.06 Hz, 1H), 8.21 (d, J = 3.78 Hz, 1H), 8.07-8.15 (m, 2H), 7.85 (d, J = 8.69 Hz, 1H), 7.01-7.17 (m, 3H), 6.74 (dd, J = 4.91, 7.55 Hz, 1H), 5.02 (d, J = 5.67 Hz, 2H), 4.50 (d, J = 5.67 Hz, 2H). |
| 6.8 | 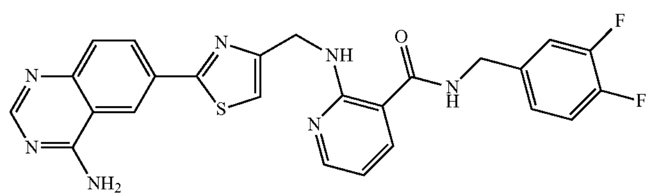 | 2-({[2-(4-aminoquinazolin-6-yl)-1,3-thiazol-4-yl]methyl}amino)-N-(3,4-difluoro-benzyl)pyridine-3-carboxamide | 504.2 | ¹H NMR (300 MHz, DMSO-d₆) δ 10.10 (br. s., 2H), 9.89 (br. s., 1H), 9.20 (t, J = 6.04 Hz, 1H), 8.97 (d, J = 1.51 Hz, 1H), 8.82-8.93 (m, 2H), 8.58 (dd, J = 1.70, 8.88 Hz, 1H), 8.21 (dd, J = 1.70, 4.72 Hz, 1H), 8.10 (dd, J = 1.70, 7.74 Hz, 1H), 7.87 (d, J = 9.06 Hz, 1H), 7.56 (s, 1H), 6.93-7.15 (m, 4H), 6.69 (dd, J = 4.72, 7.74 Hz, 1H), 4.82 (d, J = 4.53 Hz, 2H), 4.47 (d, J = 6.04 Hz, 2H). |

TABLE 1-continued

| Ex. No. | Structure | Chemical Name | ESI-MS (M + H) | ¹H NMR |
|---|---|---|---|---|
| 6.9 | 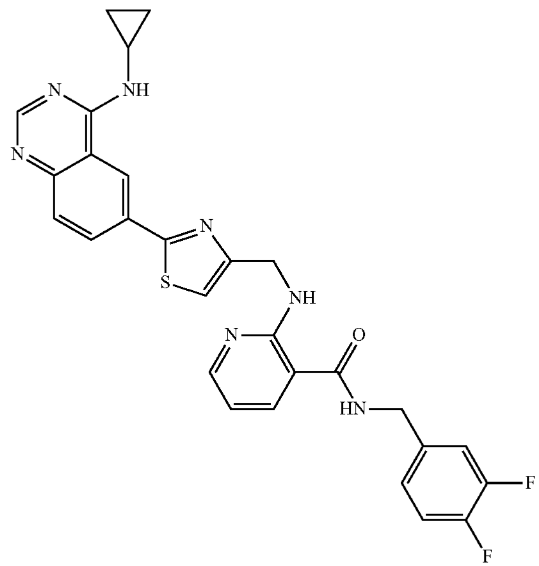 [SMILES: O=C(NCc1ccc(F)c(F)c1)c1cccnc1NCc1csc(-c2ccc3ncnc(NC4CC4)c3c2)n1] | 2-[({2-[4-(cyclopropyl-amino)quinazolin-6-yl]-1,3-thiazol-4-yl}methyl)amino]-N-(3,4-difluorobenzyl)pyridine-3-carboxamide | 544.3 | — |
| 6.10 | 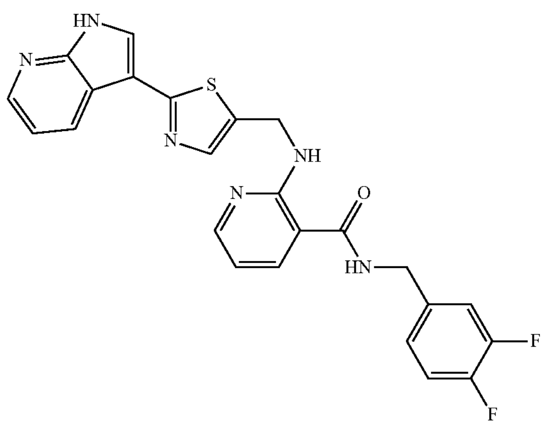 [SMILES: O=C(NCc1ccc(F)c(F)c1)c1cccnc1NCc1cnc(-c2c[nH]c3ncccc23)s1] | N-(3,4-difluorobenzyl)-2-({[2-(1H-pyrrolo[2,3-b]pyridin-3-yl)-1,3-thiazol-5-yl]methyl}amino)pyridine-3-carboxamide | 477.2 | ¹H NMR (300 MHz, DMSO-d₆) δ 12.27 (br. s., 1H), 9.21 (t, J = 5.85 Hz, 1H), 8.89 (br. s., 1H), 8.46-8.53 (m, 1H), 8.30 (ddd, J = 1.51, 4.82, 12.94 Hz, 1H), 8.09-8.15 (m, 1H), 7.74 (s, 1H), 7.24 (dd, J = 4.91, 7.93 Hz, 1H), 7.01-7.14 (m, 2H), 6.76 (dd, J = 5.10, 7.74 Hz, 1H), 4.86 (s, 1H), 4.46 (d, J = 6.04 Hz, 2H). |

TABLE 1-continued

| Ex. No. | Structure | Chemical Name | ESI-MS (M + H) | ¹H NMR |
|---|---|---|---|---|
| 6.11 | 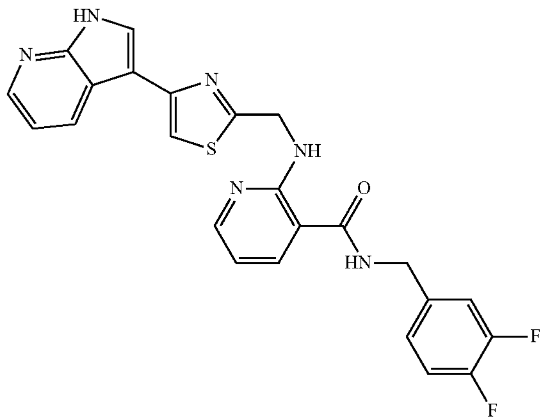 [SMILES: O=C(NCc1ccc(F)c(F)c1)c1cccnc1NCc1nc(-c2c[nH]c3ncccc23)cs1] | N-(3,4-difluorobenzyl)-2-({[4-(1H-pyrrolo[2,3-b]pyridin-3-yl)-1,3-thiazol-2-yl]methyl}amino)pyridine-3-carboxamide | 477.2 | ¹H NMR (300 MHz, DMSO-d$_6$) δ 11.97 (br. s., 1H), 9.24 (t, J = 5.85 Hz, 1H), 9.12 (br. s., 1H), 8.56 (d, J = 6.80 Hz, 1H), 8.29 (dd, J = 1.51, 4.53 Hz, 1H), 8.21 (dd, J = 1.89, 4.91 Hz, 1H), 8.13 (dd, J = 1.70, 7.74 Hz, 1H), 7.99 (d, J = 2.64 Hz, 1H), 7.70 (s, 1H), 7.03-7.20 (m, 4H), 6.75 (dd, J = 4.91, 7.55 Hz, 1H), 5.01 (d, J = 3.02 Hz, 2H), 4.51 (d, J = 5.67 Hz, 2H). |
| 6.12 | 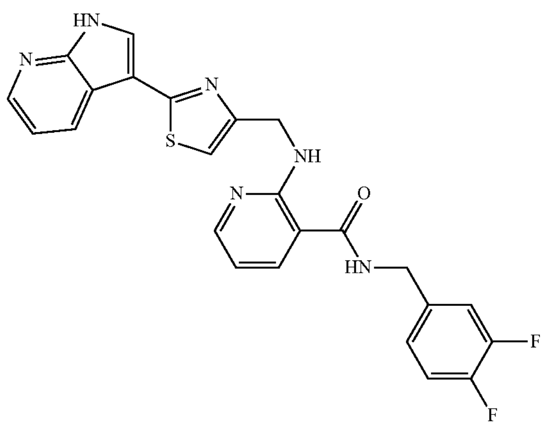 [SMILES: O=C(NCc1ccc(F)c(F)c1)c1cccnc1NCc1csc(-c2c[nH]c3ncccc23)n1] | N-(3,4-difluorobenzyl)-2-({[2-(1H-pyrrolo[2,3-b]pyridin-3-yl)-1,3-thiazol-4-yl]methyl}amino)pyridine-3-carboxamide | 477.2 | ¹H NMR (300 MHz, DMSO-d$_6$) δ 12.28 (br. s., 1H), 9.44 (br. s., 1H), 9.33 (t, J = 5.67 Hz, 1H), 8.58 (dd, J = 1.51, 7.93 Hz, 1H), 8.32 (dd, J = 1.51, 4.53 Hz, 1H), 8.18-8.28 (m, 3H), 7.32 (s, 1H), 7.03-7.20 (m, 4H), 6.82 (dd, J = 5.67, 7.18 Hz, 1H), 4.79 (s, 2H), 4.51 (d, J = 6.04 Hz, 2H). |

TABLE 1-continued

| Ex. No. | Structure | Chemical Name | ESI-MS (M + H) | ¹H NMR |
|---|---|---|---|---|
| 6.13 | 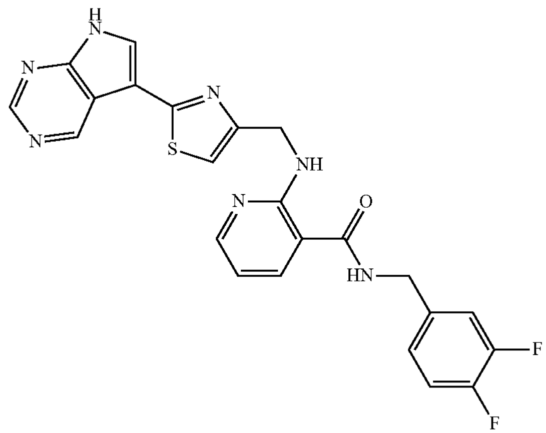 [SMILES: O=C(NCc1ccc(F)c(F)c1)c1cccnc1NCc1csc(-c2c[nH]c3ncncc23)n1] | N-(3,4-difluorobenzyl)-2-({[2-(7H-pyrrolo[2,3-d]pyrimidin-5-yl)-1,3-thiazol-4-yl]methyl}amino)pyridine-3-carboxamide | 478.2 | — |
| 6.14 | 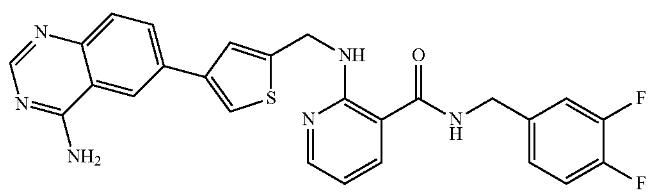 [SMILES: Nc1ncnc2ccc(-c3csc(CNc4ncccc4C(=O)NCc4ccc(F)c(F)c4)c3)cc12] | 2-({[4-(4-aminoquinazolin-6-yl)thiophen-2-yl]methyl}amino)-N-(3,4-difluoro-benzyl)pyridine-3-carboxamide | 503.3 | ¹H NMR (400 MHz, DMSO-d₆) δ 9.16 (t, J = 5.90 Hz, 1H), 8.76 (t, J = 5.90 Hz, 1H), 8.54 (d, J = 4.77 Hz, 1H), 8.38 (s, 1H), 8.26 (dd, J = 1.76, 4.77 Hz, 1H), 8.02-8.17 (m, 2H), 7.80 (d, J = 1.76 Hz, 1H), 7.56-7.72 (m, 2H), 6.94-7.17 (m, 3H), 6.69 (dd, J = 4.77, 7.78 Hz, 1H), 4.86 (d, J = 5.77 Hz, 2H), 4.45 (d, J = 6.02 Hz, 2H). |
| 6.15 | 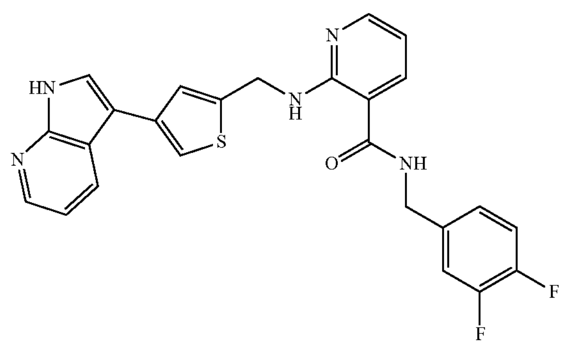 [SMILES: O=C(NCc1ccc(F)c(F)c1)c1cccnc1NCc1cc(-c2c[nH]c3ncccc23)cs1] | N-(3,4-difluorobenzyl)-2-({[4-(1H-pyrrolo[2,3-b]pyridin-3-yl)thiophen-2-yl]methyl}amino)pyridine-3-carboxamide | 476.2 | ¹H NMR (400 MHz, DMSO-d₆) δ 11.87 (d, J = 1.00 Hz, 1H), 9.20 (s, 1H), 8.72-8.99 (m, 1H), 8.31-8.42 (m, 1H), 8.26 (ddd, J = 1.51, 4.83, 9.98 Hz, 2H), 8.10 (dd, J = 1.63, 7.65 Hz, 1H), 7.83 (d, J = 2.76 Hz, 1H), 7.57 (d, J = 1.51 Hz, 1H), 7.48 (d, J = 1.51 Hz, 1H), 7.17 (dd, J = 4.77, 7.78 Hz, 1H), 7.06-7.14 (m, 1H), 7.03 (dd, J = 2.13, 8.66 Hz, 2H), 6.72 (dd, J = 5.77 Hz, 2H), 4.84 (s, 2H), 4.446 (d, J = 5.77 Hz, 2H). |

TABLE 1-continued

| Ex. No. | Structure | Chemical Name | ESI-MS (M + H) | ¹H NMR |
|---|---|---|---|---|
| 7.1 | 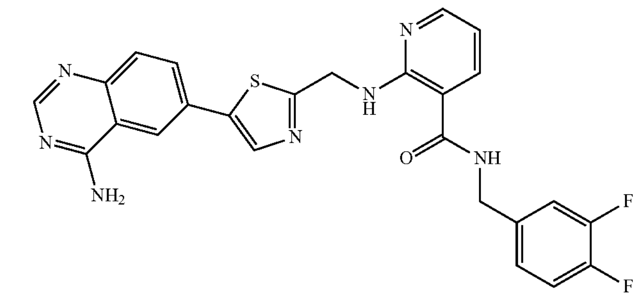 [SMILES: Nc1ncnc2ccc(-c3cnc(CNc4ncccc4C(=O)NCc4ccc(F)c(F)c4)s3)cc12] | 2-((5-(4-aminoquinazolin-6-yl)thiazol-2-yl)methyl)amino)-N-(3,4-difluorobenzyl)nicotinamide | 504.1 | ¹H NMR (400 MHz, CD₃OD/CDCl₃) δ 8.39 (s, 2H), 8.22 (dd, 1H), 8.06 (s, 1H), 7.95-7.98 (m, 2H), 7.73 (d, 1H), 7.14-7.25 (m, 3H), 6.69-6.71 (m, 1H), 5.02 (s, 2H), 4.52 (s, 2H). |
| 7.2 | 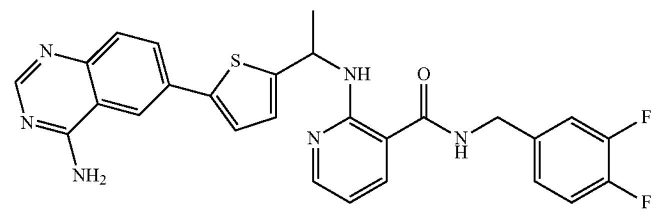 [SMILES: CC(Nc1ncccc1C(=O)NCc1ccc(F)c(F)c1)c1ccc(-c2ccc3ncnc(N)c3c2)s1] | 2-({[1-[5-(4-aminoquinazolin-6-yl)thiophen-2-yl]ethyl]amino)-N-(3,4-difluorobenzyl)pyridine-3-carboxamide | 517.3 | ¹H NMR (400 MHz, DMSO-d₆) δ 9.69-10.02 (m, 2H), 9.18 (t, J = 5.90 Hz, 1H), 8.89 (d, J = 7.78 Hz, 1H), 8.61 (d, J = 2.01 Hz, 1H), 8.29 (dd, J = 2.01, 8.78 Hz, 1H), 8.21 (dd, J = 1.76, 4.77 Hz, 1H), 8.09 (dd, J = 1.76, 7.78 Hz, 1H), 7.77 (d, J = 8.78 Hz, 1H), 7.56 (d, J = 3.76 Hz, 1H), 7.31-7.47 (m, 2H), 7.07-7.22 (m, 2H), 6.69 (dd, J = 4.89, 7.65 Hz, 1H), 5.54-5.71 (m, 1H), 4.43 (d, J = 5.77 Hz, 2H), 1.61 (d, J = 7.03 Hz, 3H). |
| 7.3.1 | 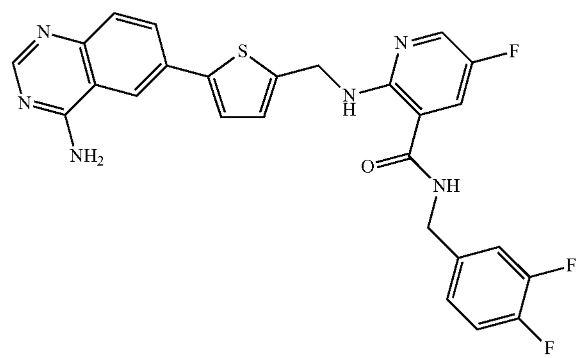 [SMILES: Nc1ncnc2ccc(-c3ccc(CNc4ncc(F)cc4C(=O)NCc4ccc(F)c(F)c4)s3)cc12] | 2-((5-(4-aminoquinazolin-6-yl)thiophen-2-yl)methyl)amino)-N-(3,4-difluorobenzyl)fluoronicotinamide | 521.1 | ¹H NMR (400 MHz, CD₃OD) δ 8.53 (s, 1H), 8.42 (d, 1H), 8.16 (dd, 1H), 8.06 (d, 1H), 7.72 (dd, 1H), 7.64 (d, 1H), 7.36 (d, 1H), 7.04-7.17 (m, 3H), 6.97 (d, 1H), 4.76 (s, 2H), 4.38 (s, 2H). |

TABLE 1-continued

| Ex. No. | Structure | Chemical Name | ESI-MS (M + H) | ¹H NMR |
|---|---|---|---|---|
| 7.3.2 | 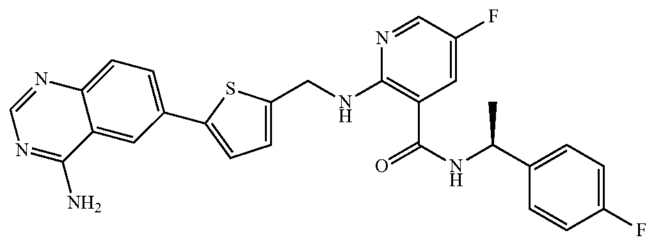 [SMILES: C[C@H](NC(=O)c1cc(F)cnc1NCc1ccc(-c2ccc3ncnc(N)c3c2)s1)c1ccc(F)cc1] | (S)-2-(((5-(4-aminoquinazolin-6-yl)thiophen-2-yl]methyl)amino)-5-fluoro-N-(1-(4-fluorophenyl)ethyl)nicotinamide | 517.2 | ¹H NMR (400 MHz, CD₃OD) δ 8.64 (s, 1H), 8.53 (d, 1H), 8.27 (dd, 1H), 8.16 (d, 1H), 7.90 (dd, 1H), 7.75 (d, 1H), 7.47 (d, 2H), 7.41 (m, 2H), 7.03-7.07 (m, 3H), 5.18 (q, 1H), 4.84 (s, 2H), 1.54 (d, 3H). |
| 7.4 | 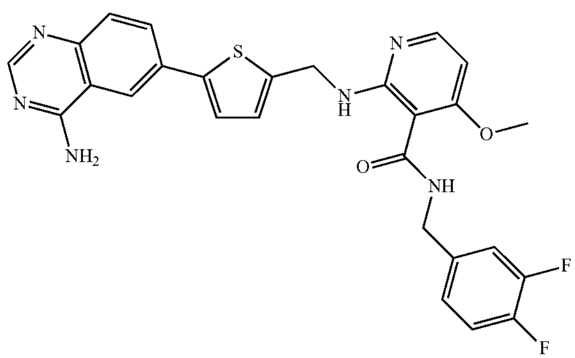 [SMILES: COc1ccnc(NCc2ccc(-c3ccc4ncnc(N)c4c3)s2)c1C(=O)NCc1ccc(F)c(F)c1] | 2-({[5-(4-aminoquinazolin-6-yl)thiophen-2-yl]methyl}amino)-N-(3,4-difluorobenzyl)-4-methoxypyridine-3-carboxamide | 533.2 | ¹H NMR (400 MHz, CD₃OD) δ 8.54 (s, 1H), 8.49 (d, 1H), 8.17 (dd, 1H), 7.95 (d, 1H), 7.68 (d, 1H), 7.44 (d, 1H), 7.05-7.19 (m, 4H), 6.83 (d, 1H), 4.79 (s, 2H), 4.44 (s, 2H), 4.03 (d, 3H). |
| 7.5 | 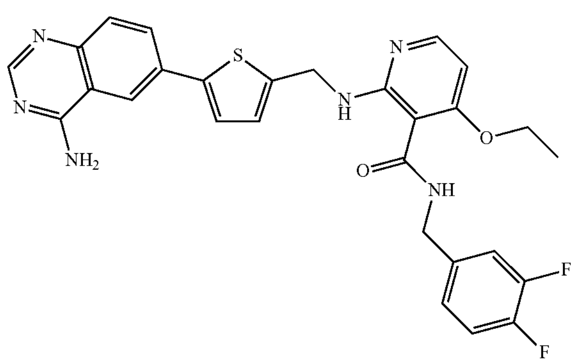 [SMILES: CCOc1ccnc(NCc2ccc(-c3ccc4ncnc(N)c4c3)s2)c1C(=O)NCc1ccc(F)c(F)c1] | 2-({[5-(4-aminoquinazolin-6-yl)thiophen-2-yl]methyl}amino)-N-(3,4-difluorobenzyl)-4-ethoxypyridine-3-carboxamide | 547.2 | ¹H NMR (400 MHz, CD₃OD) δ 8.70 (t, 1H), 8.42-8.45 (m, 2H), 8.12 (t, 1H), 8.06 (d, 1H), 8.01 (dd, 1H), 7.66 (d, 1H), 7.46 (d, 1H), 7.35-7.39 (m, 2H), 7.20 (br, 1H), 7.04 (d, 1H), 6.47 (d, 1H), 4.78 (d, 2H), 4.46 (d, 2H), 4.15 (d, 2H), 1.32 (t, 3H). |

TABLE 1-continued

| Ex. No. | Structure | Chemical Name | ESI-MS (M + H) | $^1$H NMR |
|---|---|---|---|---|
| 7.6 | 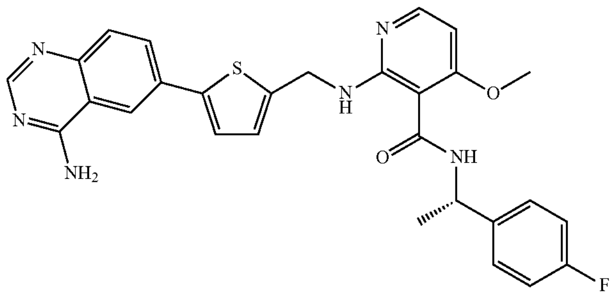 [SMILES: COc1ccnc(NCc2ccc(-c3ccc4ncnc(N)c4c3)s2)c1C(=O)N[C@@H](C)c1ccc(F)cc1] | (S)-2-(((5-(4-aminoquinazolin-6-yl)thiophen-2-yl)methyl)amino)-N-(1-(4-fluoro-phenyl)ethyl)-4-methoxynicotinamide | 529 | $^1$H NMR (400 MHz, CD$_3$OD) δ 8.66 (s, 1H), 8.59 (d, 1H), 8.28 (dd, 1H), 8.03 (d, 1H), 7.78 (d, 1H), 7.54 (d, 1H), 7.40-7.43 (m, 2H), 7.16 (d, 1H), 7.06 (m, 2H), 6.92 (d, 1H), 5.21 (q, 1H), 4.87 (d, 2H), 4.11 (s, 3H), 1.53 (d, 3H). |
| 7.7 | 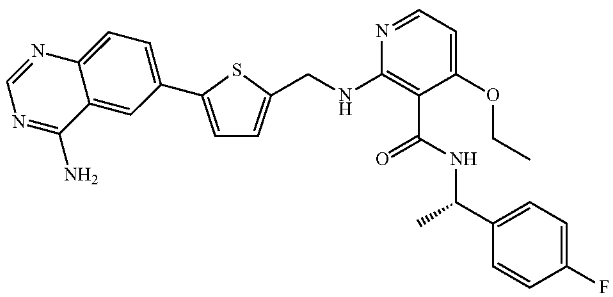 [SMILES: CCOc1ccnc(NCc2ccc(-c3ccc4ncnc(N)c4c3)s2)c1C(=O)N[C@@H](C)c1ccc(F)cc1] | (S)-2-(((5-(4-aminoquinazolin-6-yl)thiophen-2-yl)methyl)amino)-N-(1-(4-fluoro-phenyl)ethyl)-4-ethoxynicotinamide | 543.2 | $^1$H NMR (400 MHz, CD$_3$OD) δ 8.66 (s, 1H), 8.61 (d, 1H), 8.28 (dd, 1H), 8.02 (d, 1H), 7.79 (d, 1H), 7.55 (d, 1H), 7.42-7.46 (m, 2H), 7.18 (d, 1H), 7.04-7.09 (m, 2H), 6.90 (d, 1H), 5.23 (q, 1H), 4.35-4.41 (m, 2H), 1.55 (s, 3H), 1.45 (d, 3H). |
| 7.8 | 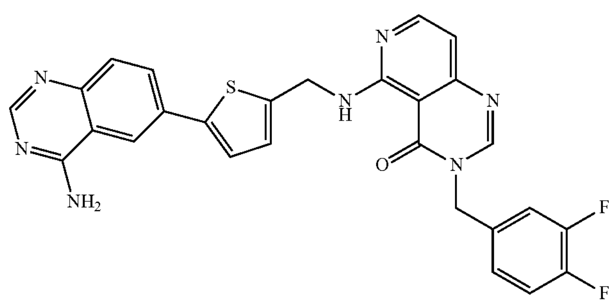 [SMILES: Nc1ncnc2ccc(-c3ccc(CNc4nccc5ncn(Cc6ccc(F)c(F)c6)c(=O)c45)s3)cc12] | 5-((5-(4-aminoquinazolin-6-yl)thiophen-2-yl)methyl)amino)-3-(3,4-difluorobenzyl)pyrido[4,3-d]pyrimidin-4(3H)-one | 528.1 | $^1$H NMR (400 MHz, CDCl$_3$—D$_2$O) δ 4.85 (d, 2H), 4.99 (d, 2H), 6.67 (d, 1H), 7.08 (m, 4H), 7.20 (d, 1H), 7.74 (d, 1H), 7.89 (d, 1H), 7.96 (d, 1H), 8.10 (s, 1H), 8.24 (d, 1H), 8.36 (s, 1H). |

TABLE 1-continued
| Ex. No. | Structure | Chemical Name | ESI-MS (M + H) | ¹H NMR |
|---|---|---|---|---|
| 7.9 | 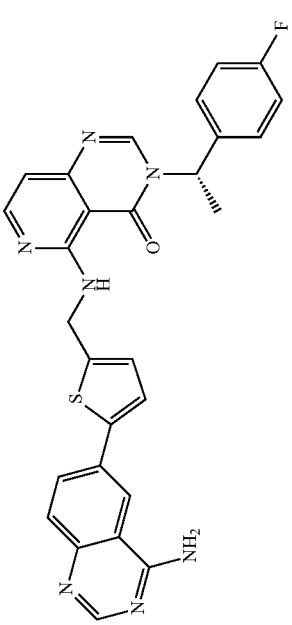 | (S)-5-((5-(4-aminoquinazolin-6-yl)thiophen-2-yl)methyl)amino)-3-(1-(4-fluorophenyl)ethyl)pyrido[4,3-d]pyrimidin-4(3H)-one | 524.2 | ¹H NMR (400 MHz, CDCl₃) δ 9.19 (t, 1H), 8.59 (s, 1H), 8.34 (d, 1H), 7.98-8.00 (dd, 1H), 7.94 (s, 1H), 7.84 (m, 2H), 7.33 (m, 2H), 7.24 (d, 1H), 7.08 (m, 3H), 6.72 (d, 1H), 6.21 (q, 1H), 5.87 (br, 1H), 4.96-4.98 (m, 2H), 1.81 (d, 3H). |
| 7.10 | 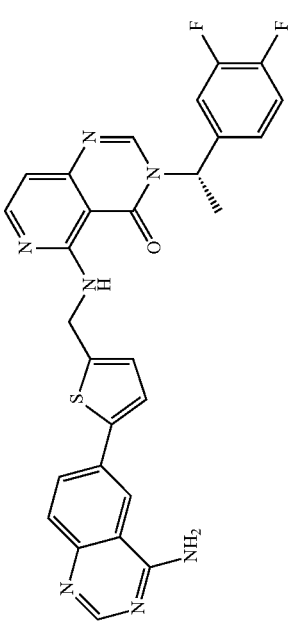 | 5-({[5-(4-aminoquinazolin-6-yl)thiophen-2-yl]methyl}amino)-3-[(1S)-1-(3,4-difluorophenyl)ethyl]pyrido[4,3-d]pyrimidin-4(3H)-one | 542.2 | ¹H NMR (400 MHz, DMSO-d₆) δ 9.17 (t, 1H), 8.57 (s, 1H), 8.41 (s, 1H), 8.34 (s, 1H), 8.31 (d, 1H), 7.96 (dd, 1H), 7.80 (br, 2H), 7.55-7.65 (m, 2H), 7.55-7.65 (m, 2H), 7.24 (bs, 1H), 7.12 (d, 1H), 6.70 (d, 1H), 5.94 (q, 1H), 4.90-4.96 (m, 2H), 1.82 (d, 3H). |

TABLE 1-continued

| Ex. No. | Structure | Chemical Name | ESI-MS (M + H) | ¹H NMR |
|---|---|---|---|---|
| 7.11 | 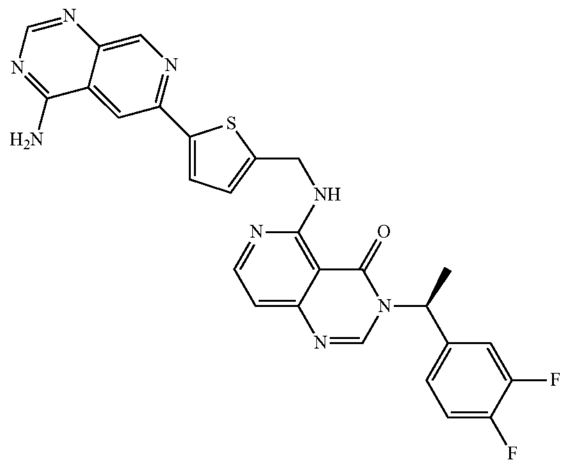 [SMILES: C[C@@H](c1ccc(F)c(F)c1)n1cnc2ccnc(NCc3ccc(-c4cc5c(N)ncnc5cn4)s3)c2c1=O] | 5-({[5-(4-aminopyrido[3,4-d]pyrimidin-6-yl)thiophen-2-yl]methyl}amino)-3-[(1S)-1-(3,4-difluorophenyl)ethyl]pyrido[4,3-d]pyrimidin-4(3H)-one | 543.1 | ¹H NMR (400 MHz, DMSO-d₆) δ 9.17 (t, 1H), 8.95 (s, 1H), 8.56 (d, 2H), 8.43 (s, 1H), 8.29 (d, 1H), 8.18 (br, 2H), 7.53-7.59 (m, 2H), 7.40 (q, 1H), 7.24 (br, 1H), 7.12 (d, 1H), 6.69 (d, 1H), 5.93 (q, 1H), 4.90-4.96 (m, 2H), 1.81 (d, 3H). |
| 7.12 | 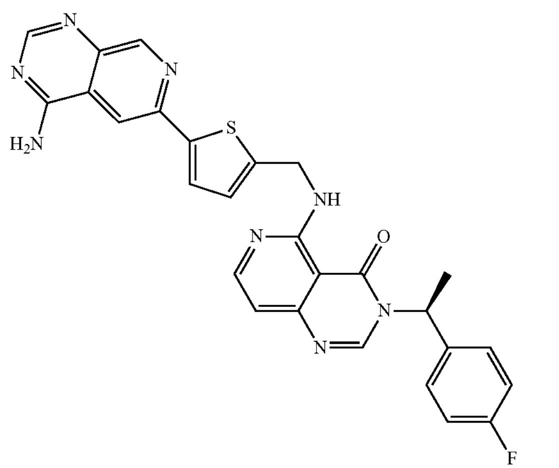 [SMILES: C[C@@H](c1ccc(F)cc1)n1cnc2ccnc(NCc3ccc(-c4cc5c(N)ncnc5cn4)s3)c2c1=O] | 5-({[5-(4-aminopyrido[3,4-d]pyrimidin-6-yl)thiophen-2-yl]methyl}amino)-3-[(1S)-1-(4-fluorophenyl)ethyl]pyrido[4,3-d]pyrimidin-4(3H)-one | 525.2 | ¹H NMR (400 MHz, DMSO-d₆) δ 9.20 (t, 1H), 8.96 (s, 1H), 8.55 (s, 2H), 8.45 (s, 1H), 8.30 (d, 1H), 8.15 (br, 2H), 7.58 (d, 1H), 7.46 (m, 2H), 7.13-7.21 (m, 3H), 6.70 (d, 1H), 5.98 (q, 1H), 4.90-4.92 (m, 2H), 1.82 (d, 3H). |

TABLE 1-continued

| Ex. No. | Structure | Chemical Name | ESI-MS (M + H) | ¹H NMR |
|---|---|---|---|---|
| 7.13 | 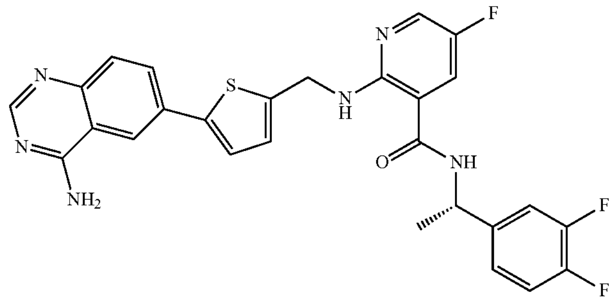 [SMILES: C[C@H](NC(=O)c1cc(F)cnc1NCc1ccc(-c2ccc3ncnc(N)c3c2)s1)c1ccc(F)c(F)c1] | 2-({[5-(4-aminoquinazolin-6-yl)thiophen-2-yl]methyl}amino)-N-[(1S)-1-(3,4-difluorophenyl)ethyl]-5-fluoropyridine-3-carboxamide | 535.1 | ¹H NMR (400 MHz, CD₃OD) δ 8.24 (s, 1H), 8.16 (d, 1H), 8.07 (d, 1H), 7.79-7.85 (m, 2H), 7.54 (d, 1H), 7.17-7.23 (m, 2H), 7.06-7.10 (m, 2H), 6.87 (d, 1H), 5.07 (q, 1H), 4.69 (s, 2H), 1.88 (d, 3H). |
| 7.14 | 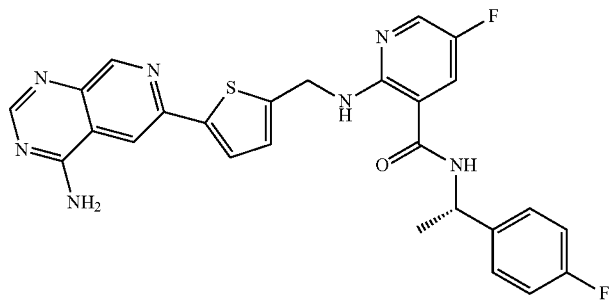 [SMILES: C[C@H](NC(=O)c1cc(F)cnc1NCc1ccc(-c2cc3c(N)ncnc3cn2)s1)c1ccc(F)cc1] | 2-({[5-(4-aminopyrido[3,4-d]pyrimidin-6-yl)thiophen-2-yl]methyl}amino)-5-fluoro-N-[(1S)-1-(4-fluorophenyl)ethyl]pyridine-3-carboxamide | 518.2 | ¹H NMR (400 MHz, CD₃OD/CDCl₃) δ 9.00 (s, 1H), 8.42 (s, 1H), 8.29 (s, 1H), 8.09 (d, 1H), 7.78-7.81 (dd, 1H), 7.54 (d, 1H), 7.32-7.35 (m, 2H), 6.97-7.01 (m, 3H), 5.15 (q, 1H), 4.80 (m, 2H), 1.52 (d, 3H). |
| 7.15 | 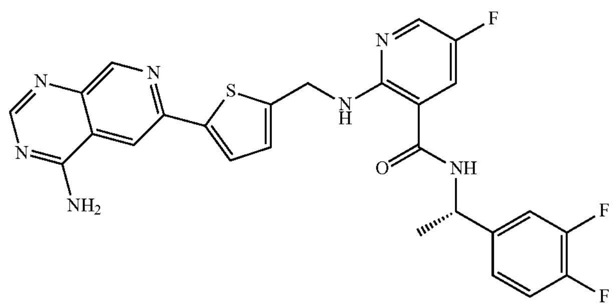 [SMILES: C[C@H](NC(=O)c1cc(F)cnc1NCc1ccc(-c2cc3c(N)ncnc3cn2)s1)c1ccc(F)c(F)c1] | 2-({[5-(4-aminopyrido[3,4-d]pyrimidin-6-yl)thiophen-2-yl]methyl}amino)-N-[(1S)-1-(3,4-difluorophenyl)ethyl]-5-fluoropyridine-3-carboxamide | 536.1 | ¹H NMR (400 MHz, CD₃OD/CDCl₃) δ 9.00 (s, 1H), 8.42 (s, 1H), 8.30 (s, 1H), 8.10 (s, 1H), 7.81 (d, 1H), 7.54 (s, 1H), 7.10-7.22 (m, 3H), 7.01 (d, 1H), 5.12 (q, 1H), 4.80 (m, 2H), 1.52 (d, 3H). |

TABLE 1-continued

| Ex. No. | Structure | Chemical Name | ESI-MS (M + H) | ¹H NMR |
|---|---|---|---|---|
| 7.16 | 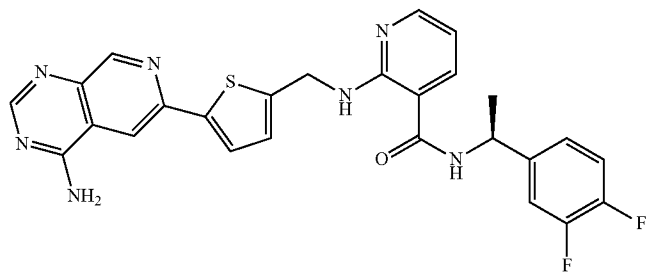 [SMILES: C[C@H](NC(=O)c1cccnc1NCc1ccc(-c2cc3c(N)ncnc3cn2)s1)c1ccc(F)c(F)c1] | 2-({[5-(4-aminopyrido[3,4-d]pyrimidin-6-yl)thiophen-2-yl]methyl}amino)-N-[(1S)-1-(3,4-difluorophenyl)ethyl]pyridine-3-carboxamide | 518.2 | ¹H NMR (400 MHz, DMSO-d₆) δ 9.01 (s, 1H), 8.98 (bs, 1H), 8.89 (d, 1H), 8.71 (t, 1H), 8.62 (s, 2H), 8.26 (dd, 1H), 8.13 (dd, 1H), 7.59 (d, 1H), 7.47-7.36 (m, 2H), 7.23-7.21 (bs, 1H), 7.10 (d, 1H), 6.89 (dd, 1H), 5.10 (m, 1H), 4.82 (d, 2H), 1.46 (d, 3H) |
| 7.17 | 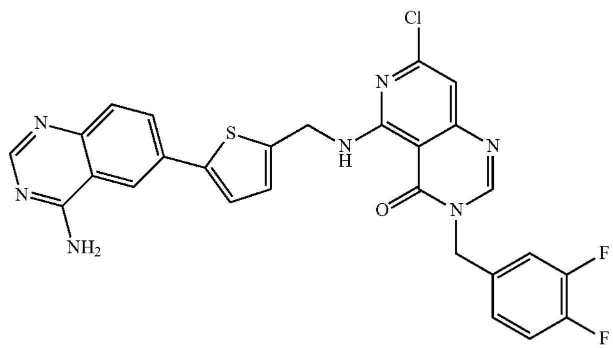 [SMILES: Nc1ncnc2ccc(-c3ccc(CNc4nc(Cl)cc5ncn(Cc6ccc(F)c(F)c6)c(=O)c45)s3)cc12] | 5-({[5-(4-aminoquinazolin-6-yl)thiophen-2-yl]methyl}amino)-7-chloro-N-3-(3,4-difluorobenzyl)pyrido[4,3-d]pyrimidin-4(3H)-one | 562.1 | ¹H NMR (400 MHz, DMSO-d₆) δ 9.31 (t, 1H), 8.68 (s, 1H), 8.44 (d, 1H), 8.35 (s, 1H), 7.98 (dd, 2H), 7.95 (bs, 1H), 7.65 (d, 1H), 7.48 (d, 1H), 7.15-7.13 (m, 4H), 6.76 (s, 1H), 5.14 (s, 2H), 4.87 (d, 2H). |
| 7.18 | 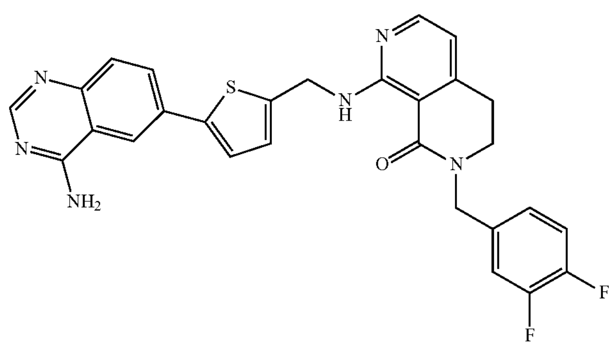 [SMILES: Nc1ncnc2ccc(-c3ccc(CNc4nccc5c4C(=O)N(Cc4ccc(F)c(F)c4)CC5)s3)cc12] | 8-({[5-(4-aminoquinazolin-6-yl)thiophen-2-yl]methyl}amino)-2-(3,4-difluorobenzyl)-3,4-dihydro-2,7-naphthyridin-1(2H)-one | 529 | ¹H NMR (400 MHz, CDCl₃) δ 2.84 (t, 2H), 3.45 (t, 2H), 4.69 (s, 2H), 4.89 (d, 2H), 6.13 (s, 2H), 6.36 (s, 1H), 6.98 (d, 1H), 7.09-7.16 (m, 4H), 7.78-7.83 (m, 2H), 7.92 (d, 1H), 8.18 (d, 1H), 8.58 (s, 1H), 9.26 (t, 1H). |

TABLE 1-continued

| Ex. No. | Structure | Chemical Name | ESI-MS (M + H) | ¹H NMR |
|---|---|---|---|---|
| 7.19 | 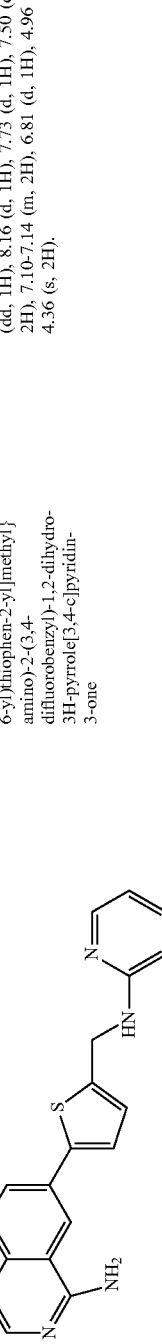 | 4-({[5-(4-aminoquinazolin-6-yl)thiophen-2-yl]methyl}amino)-2-(3,4-difluorobenzyl)-1,2-dihydro-3H-pyrrolo[3,4-c]pyridin-3-one | 515.1 | ¹H NMR (400 MHz, CH₃OD) δ 8.62 (s, 1H), 8.55 (d, 1H), 8.27 (dd, 1H), 8.16 (d, 1H), 7.73 (d, 1H), 7.50 (d, 1H), 7.20-7.25 (m, 2H), 7.10-7.14 (m, 2H), 6.81 (d, 1H), 4.96 (s, 2H), 4.69 (s, 2H), 4.36 (s, 2H). |
| 7.20 | 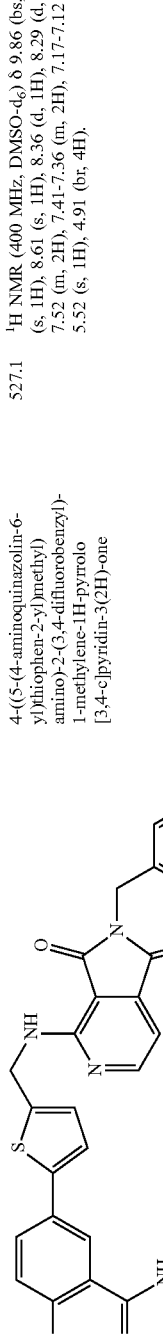 | 4-((5-(4-aminoquinazolin-6-yl)thiophen-2-yl)methyl)amino)-2-(3,4-difluorobenzyl)-1-methylene-1H-pyrrolo[3,4-c]pyridin-3(2H)-one | 527.1 | ¹H NMR (400 MHz, DMSO-d₆) δ 9.86 (bs, 1H), 9.76 (bs, 1H), 8.80 (s, 1H), 8.61 (s, 1H), 8.36 (d, 1H), 8.29 (d, 1H), 7.79 (d, 1H), 7.57-7.52 (m, 2H), 7.41-7.36 (m, 2H), 7.17-7.12 (m, 3H), 5.57 (s, 1H), 5.52 (s, 1H), 4.91 (br, 4H). |
| 7.21.1 | 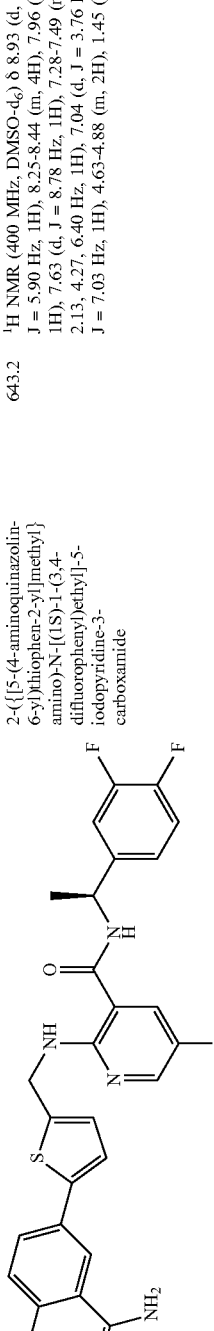 | 2-({[5-(4-aminoquinazolin-6-yl)thiophen-2-yl]methyl}amino)-N-[(1S)-1-(3,4-difluorophenyl)ethyl]-5-iodopyridine-3-carboxamide | 643.2 | ¹H NMR (400 MHz, DMSO-d₆) δ 8.93 (d, J = 7.28 Hz, 1H), 8.75 (t, J = 5.90 Hz, 1H), 8.25-8.44 (m, 4H), 7.96 (dd, J = 2.01, 8.78 Hz, 1H), 7.63 (d, J = 8.78 Hz, 1H), 7.28-7.49 (m, 3H), 7.21 (ddd, J = 2.13, 4.27, 6.40 Hz, 1H), 7.04 (d, J = 3.76 Hz, 1H), 5.07 (quin, J = 7.03 Hz, 1H), 4.63-4.88 (m, 2H), 1.45 (d, J = 7.03 Hz, 3H). |

TABLE 1-continued

| Ex. No. | Structure | Chemical Name | ESI-MS (M + H) | ¹H NMR |
|---|---|---|---|---|
| 7.21.2 | 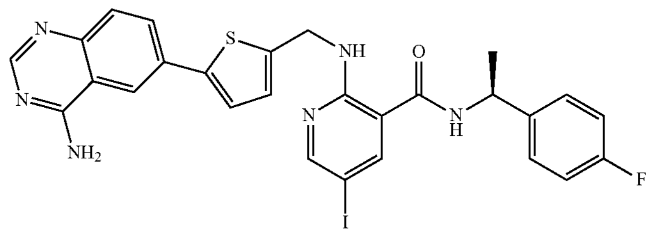 [SMILES: C[C@H](NC(=O)c1cc(I)cnc1NCc1ccc(-c2ccc3ncnc(N)c3c2)s1)c1ccc(F)cc1] | 2-({[5-(4-aminoquinazolin-6-yl)thiophen-2-yl]methyl}amino)-N-[(1S)-1-(4-fluorophenyl)ethyl]-5-iodopyridine-3-carboxamide | 625.2 | ¹H NMR (400 MHz, DMSO-d$_6$) δ 8.94 (d, J = 7.53 Hz, 1H), 8.73-8.84 (m, 1H), 8.39 (ddd, J = 8.47, 10.73 Hz, 4H), 7.99 (dd, J = 1.88, 8.66 Hz, 1H), 7.65 (d, J = 8.78 Hz, 1H), 7.33-7.50 (m, 3H), 7.09-7.23 (m, 2H), 7.05 (d, J = 3.76 Hz, 1H), 5.09 (t, J = 7.15 Hz, 1H), 4.77 (br. s., 2H), 1.45 (d, J = 7.28 Hz, 3H). |
| 7.22.1 | 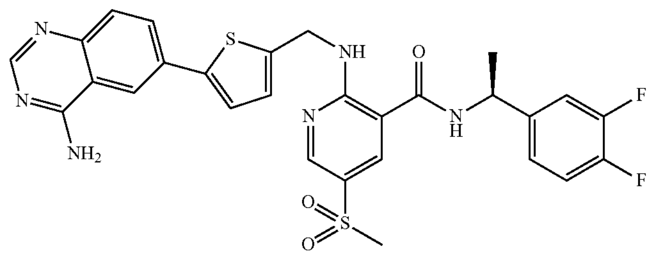 [SMILES: C[C@H](NC(=O)c1cc(S(C)(=O)=O)cnc1NCc1ccc(-c2ccc3ncnc(N)c3c2)s1)c1ccc(F)c(F)c1] | (S)-2-(((5-(4-aminoquinazolin-6-yl)thiophen-2-yl)methyl)amino)-N-(1-(3,4-difluorophenyl)ethyl)-5-(methylsulfonyl)nicotinamide | 595.3 | ¹H NMR (400 MHz, DMSO-d$_6$) δ 9.83 (br. s., 2H), 9.41 (t, J = 6.15 Hz, 1H), 9.21 (d, J = 7.53 Hz, 1H), 8.72-8.89 (m, 1H), 8.66 (d, J = 2.26 Hz, 1H), 8.60 (d, J = 1.51 Hz, 1H), 8.52 (d, J = 2.26 Hz, 1H), 8.26 (dd, J = 1.63, 8.66 Hz, 1H), 7.77 (d, J = 8.78 Hz, 1H), 7.54 (d, J = 3.76 Hz, 1H), 7.28-7.50 (m, 2H), 7.23 (ddd, J = 2.26, 4.27, 6.27 Hz, 1H), 7.13 (d, J = 3.76 Hz, 1H), 5.11 (quin, J = 7.03 Hz, 1H), 4.91 (d, 2H), 3.24 (s, 3H), 1.49 (d, J = 7.03 Hz, 3H). |
| 7.22.2 | 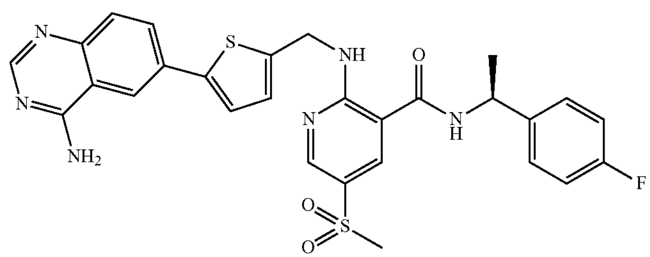 [SMILES: C[C@H](NC(=O)c1cc(S(C)(=O)=O)cnc1NCc1ccc(-c2ccc3ncnc(N)c3c2)s1)c1ccc(F)cc1] | 2-({[5-(4-aminoquinazolin-6-yl)thiophen-2-yl]methyl}amino)-N-[(1S)-1-(4-fluorophenyl)ethyl]-5-(methylsulfonyl)pyridine-3-carboxamide | 577.3 | ¹H NMR (400 MHz, DMSO-d$_6$) δ 9.82 (br. s., 2H), 9.44 (t, J = 5.90 Hz, 1H), 9.20 (d, J = 7.78 Hz, 1H), 8.81 (br. s., 1H), 8.55-8.69 (m, 2H), 8.51 (d, J = 2.26 Hz, 1H), 8.21-8.33 (m, 1H), 7.78 (br. s., 1H), 7.54 (d, J = 3.51 Hz, 1H), 7.35-7.49 (m, 2H), 7.06-7.24 (m, 3H), 5.13 (t, J = 7.15 Hz, 1H), 4.92 (d, J = 5.52 Hz, 2H), 3.12-3.33 (m, 3H), 1.49 (d, J = 7.03 Hz, 3H). |
| 7.23.1 | 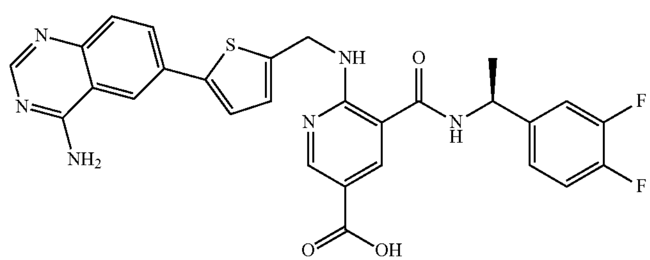 [SMILES: C[C@H](NC(=O)c1cc(C(=O)O)cnc1NCc1ccc(-c2ccc3ncnc(N)c3c2)s1)c1ccc(F)c(F)c1] | 6-((5-(4-aminoquinazolin-6-yl)thiophen-2-yl)methyl)amino)-5-(3,4-difluorobenzyl-carbamoyl)nicotinic acid | 547.2 | ¹H NMR (400 MHz, DMSO-d$_6$) δ 12.82 (br. s., 1H), 9.79 (br. s., 2H), 9.24-9.55 (m, 2H), 8.69-8.91 (m, 2H), 8.57 (dd, J = 1.88, 16.44 Hz, 2H), 8.27 (dd, J = 2.01, 8.78 Hz, 1H), 7.75 (d, J = 8.78 Hz, 1H), 7.54 (d, J = 3.51 Hz, 1H), 7.27-7.48 (m, 2H), 7.04-7.27 (m, 2H), 4.93 (d, J = 5.77 Hz, 2H), 4.41 (d, J = 5.77 Hz, 2H). |

TABLE 1-continued

| Ex. No. | Structure | Chemical Name | ESI-MS (M + H) | ¹H NMR |
|---|---|---|---|---|
| 7.23.2 | 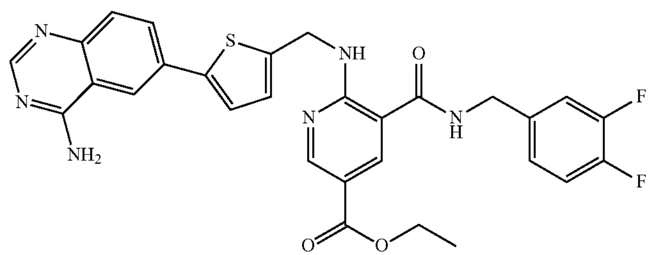 [SMILES: CCOC(=O)c1cnc(NCc2ccc(-c3ccc4ncnc(N)c4c3)s2)c(C(=O)NCc2ccc(F)c(F)c2)c1] | Ethyl 6-({[5-(4-aminoquinazolin-6-yl)thiophen-2-yl]methyl}amino)-5-(3,4-difluorobenzyl)carbamoyl]pyridine-3-carboxylate | 575.3 | ¹H NMR (400 MHz, DMSO-d$_6$) δ 9.33-9.52 (m, 2H), 8.71-8.88 (m, 2H), 8.41-8.67 (m, 2H), 8.26 (dd, J = 2.01, 8.78 Hz, 1H), 7.75 (d, J = 8.78 Hz, 1H), 7.54 (d, J = 3.51 Hz, 1H), 7.26-7.48 (m, 2H), 7.15 (d, J = 3.76 Hz, 2H), 4.93 (d, J = 5.77 Hz, 2H), 4.43 (d, J = 5.77 Hz, 2H), 4.31 (q, J = 7.19 Hz, 2H), 1.32 (t, J = 7.15 Hz, 3H). |
| 7.24.1 | 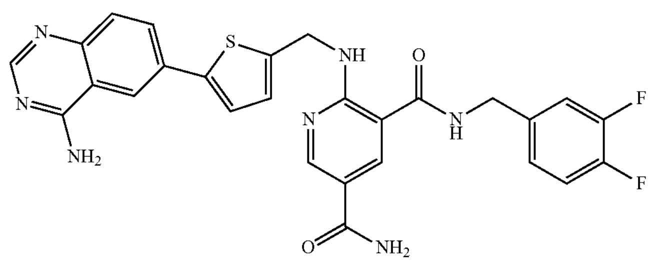 [SMILES: NC(=O)c1cnc(NCc2ccc(-c3ccc4ncnc(N)c4c3)s2)c(C(=O)NCc2ccc(F)c(F)c2)c1] | 2-({[5-(4-aminoquinazolin-6-yl)thiophen-2-yl]methyl}amino)-N³-(3,4-difluorobenzyl)pyridine-3,5-dicarboxamide | 546.2 | ¹H NMR (400 MHz, DMSO-d$_6$) δ 9.68 (br. s., 2H), 9.27 (t, J = 5.77 Hz, 1H), 9.13 (t, J = 5.90 Hz, 1H), 8.69-8.87 (m, 2H), 8.59 (s, 1H), 8.50 (d, J = 2.26 Hz, 1H), 8.26 (dd, J = 1.76, 8.78 Hz, 1H), 7.76 (d, J = 8.78 Hz, 2H), 7.54 (d, J = 3.76 Hz, 1H), 7.23-7.47 (m, 3H), 7.09-7.23 (m, 2H), 4.91 (d, J = 5.77 Hz, 2H), 4.43 (d, J = 5.52 Hz, 2H). |
| 7.24.2 | 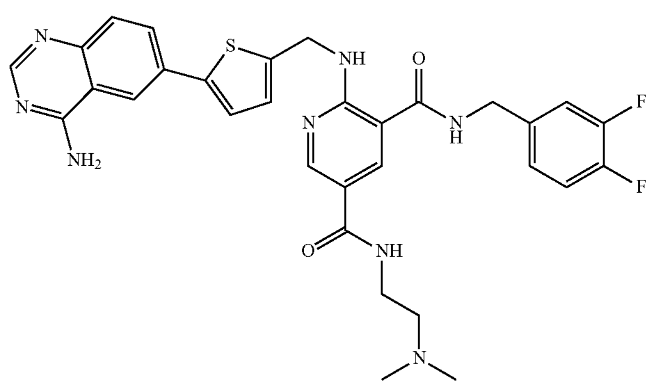 [SMILES: CN(C)CCNC(=O)c1cnc(NCc2ccc(-c3ccc4ncnc(N)c4c3)s2)c(C(=O)NCc2ccc(F)c(F)c2)c1] | 2-({[5-(4-aminoquinazolin-6-yl)thiophen-2-yl]methyl}amino)-N³-(3,4-difluorobenzyl)-N⁵-[2-(dimethylamino)ethyl]pyridine-3,5-dicarboxamide | 617.3 | ¹H NMR (400 MHz, DMSO-d$_6$) δ 9.34 (m, 3H), 9.17 (t, J = 6.02 Hz, 1H), 8.79 (s, 1H), 8.74 (d, J = 2.26 Hz, 1H), 8.60 (d, J = 1.76 Hz, 1H), 8.55 (t, J = 5.65 Hz, 1H), 8.48 (d, J = 2.01 Hz, 1H), 8.24 (dd, J = 2.01, 8.78 Hz, 1H), 7.76 (d, J = 8.53 Hz, 1H), 7.54 (d, J = 3.76 Hz, 1H), 7.31-7.45 (m, 2H), 7.11-7.22 (m, 2H), 4.91 (d, J = 5.77 Hz, 2H), 4.43 (d, J = 5.77 Hz, 2H), 3.60 (q, J = 5.77 Hz, 2H), 3.19-3.31 (m, 2H), 2.85 (d, J = 3.51 Hz, 6H) |

TABLE 1-continued

| Ex. No. | Structure | Chemical Name | ESI-MS (M + H) | $^1$H NMR |
|---|---|---|---|---|
| 7.24.3 | 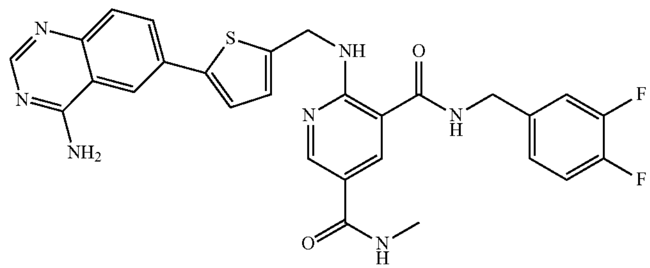 [SMILES: CNC(=O)c1cnc(NCc2ccc(-c3ccc4ncnc(N)c4c3)s2)c(C(=O)NCc2ccc(F)c(F)c2)c1] | 2-({[5-(4-aminoquinazolin-6-yl)thiophen-2-yl]methyl}amino)-N$^3$-(3,4-difluorobenzyl)-N$^5$-methylpyridine-3,5-dicarboxamide | 560.3 | $^1$H NMR (400 MHz, DMSO-d$_6$) δ 9.84 (br. s., 2H), 9.28 (t, J = 5.77 Hz, 1H), 9.09 (t, J = 6.02 Hz, 1H), 8.80 (s, 1H), 8.69 (d, J = 2.01 Hz, 1H), 8.60 (d, J = 2.01 Hz, 1H), 8.46 (d, J = 2.26 Hz, 1H), 8.21-8.33 (m, 2H), 7.76 (d, J = 8.78 Hz, 1H), 7.54 (d, J = 3.51 Hz, 1H), 7.31-7.45 (m, 2H), 7.14 (d, J = 3.76 Hz, 2H), 4.81-4.98 (m, 2H), 4.35-4.50 (m, 2H), 2.78 (d, J = 4.52 Hz, 3H). |
| 7.24.4 | 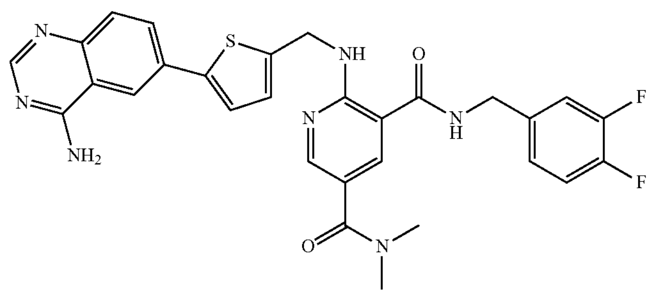 [SMILES: CN(C)C(=O)c1cnc(NCc2ccc(-c3ccc4ncnc(N)c4c3)s2)c(C(=O)NCc2ccc(F)c(F)c2)c1] | 2-({[5-(4-aminoquinazolin-6-yl)thiophen-2-yl]methyl}amino)-N$^3$-(3,4-difluorobenzyl)-N$^5$,N$^5$-dimethylpyridine-3,5-dicarboxamide | 574.3 | $^1$H NMR (400 MHz, DMSO-d$_6$) δ 9.64-9.96 (m, 2H), 9.20-9.35 (m, 1H), 9.06-9.20 (m, 1H), 8.79 (s, 1H), 8.60 (s, 1H), 8.37 (d, J = 2.27 Hz, 1H), 8.23-8.33 (m, 1H), 8.19 (d, J = 2.27 Hz, 1H), 7.76 (d, J = 8.69 Hz, 1H), 7.55 (d, J = 3.78 Hz, 1H), 7.40 (s, 2H), 7.14 (d, J = 3.78 Hz, 2H), 4.80-4.98 (m, 2H), 4.34-4.49 (m, 2H), 3.01 (s, 6H). |
| 7.24.5 | 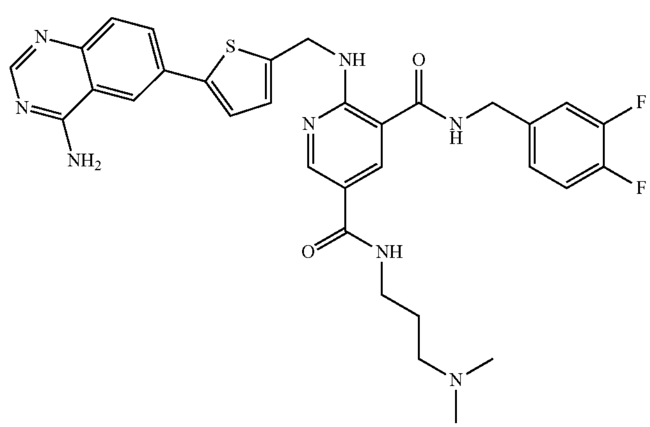 [SMILES: CN(C)CCCNC(=O)c1cnc(NCc2ccc(-c3ccc4ncnc(N)c4c3)s2)c(C(=O)NCc2ccc(F)c(F)c2)c1] | 2-({[5-(4-aminoquinazolin-6-yl)thiophen-2-yl]methyl}amino)-N$^3$-(3,4-difluorobenzyl)-N$^5$-[3-(dimethylamino)propyl]pyridine-3,5-dicarboxamide | 631.3 | $^1$H NMR (400 MHz, DMSO-d$_6$) δ 9.62-9.92 (m, 2H), 9.24-9.36 (m, 1H), 9.07-9.21 (m, 1H), 8.76-8.85 (m, 1H), 8.70-8.76 (m, 1H), 8.57-8.64 (m, 1H), 8.40-8.51 (m, 2H), 8.21-8.29 (m, 1H), 7.70-7.83 (m, 1H), 7.50-7.58 (m, 1H), 7.31-7.47 (m, 2H), 7.10-7.24 (m, 2H), 4.77-5.06 (m, 2H), 4.28-4.53 (m, 2H), 3.23-3.42 (m, 2H), 3.01-3.16 (m, 2H), 2.74-2.84 (m, 6H), 1.73-1.98 (m, 2H). |

TABLE 1-continued

| Ex. No. | Structure | Chemical Name | ESI-MS (M + H) | $^1$H NMR |
|---|---|---|---|---|
| 7.24.6 | 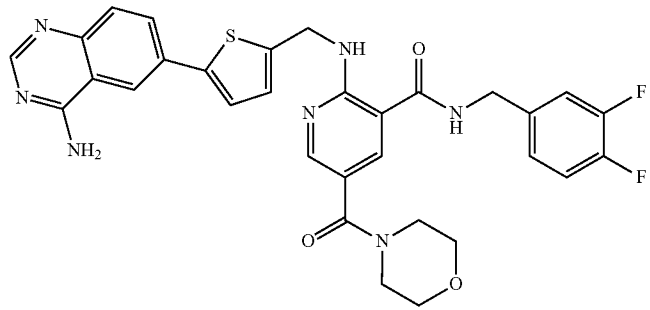 [SMILES: Nc1ncnc2ccc(-c3ccc(CNc4ncc(C(=O)N5CCOCC5)cc4C(=O)NCc4ccc(F)c(F)c4)s3)cc12] | 2-({[5-(4-aminoquinazolin-6-yl)thiophen-2-yl]methyl}amino)-N³-(3,4-difluorobenzyl)-5-(morpholin-4-ylcarbonyl)pyridine-3-carboxamide | 616.3 | $^1$H NMR (400 MHz, DMSO-d$_6$) δ 9.62-9.91 (m, 2H), 9.27 (s, 1H), 9.15 (s, 1H), 8.79 (s, 1H), 8.60 (d, J = 1.76 Hz, 1H), 8.36 (d, J = 2.26 Hz, 1H), 8.22-8.31 (m, 1H), 8.17 (d, J = 2.26 Hz, 1H), 7.76 (d, J = 8.78 Hz, 1H), 7.55 (d, J = 3.76 Hz, 1H), 7.38 (d, J = 10.79 Hz, 2H), 7.14 (d, J = 3.77 Hz, 2H), 4.82-4.98 (m, 2H), 4.34-4.49 (m, 2H), 3.32-3.75 (m, 8H). |
| 7.25 | 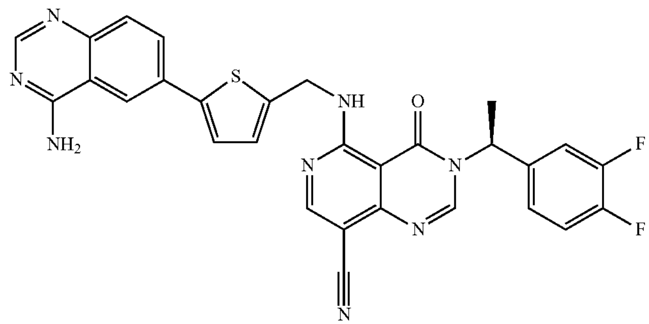 [SMILES: C[C@@H](c1ccc(F)c(F)c1)n1cnc2c(C#N)cnc(NCc3ccc(-c4ccc5ncnc(N)c5c4)s3)c2c1=O] | (S)-5-(((5-(4-aminoquinazolin-6-yl)thiophen-2-yl)methyl)amino)-3-(1-(3,4-difluorophenyl)ethyl)-4-oxo-3,4-dihydropyrido[4,3-d]pyrimidine-8-carbonitrile | 567.0 | $^1$H NMR (400 MHz, CDCl$_3$/DMSO-d$_6$) δ 9.78 (m, 1H), 8.79 (s, 1H), 8.75 (s, 1H), 8.64 (s, 1H), 8.55 (d, 1H), 8.16 (dd, 1H), 7.73 (d, 1H), 7.53-7.52 (m, 2H), 7.44-7.41 (m, 1H), 7.26-7.25 (m, 1H), 7.16-7.12 (m, 2H), 7.00 (s, 1H), 5.91 (q, 1H), 4.99 (d, 2H), 1.83 (d, 3H). |
| 8.1.1 | 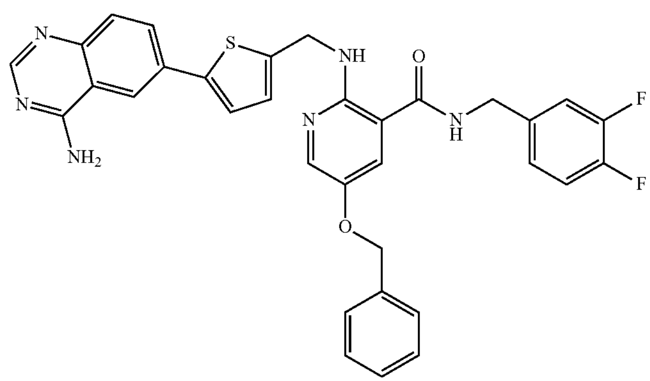 [SMILES: Nc1ncnc2ccc(-c3ccc(CNc4ncc(OCc5ccccc5)cc4C(=O)NCc4ccc(F)c(F)c4)s3)cc12] | 2-({[5-(4-aminoquinazolin-6-yl)thiophen-2-yl]methyl}amino)-5-(benzyloxy)-N-(3,4-difluorobenzyl)pyridine-3-carboxamide | 609.2 | $^1$H NMR (300 MHz, DMSO-d$_6$) δ 9.77 (d, 2H), 9.16 (br. s., 1H), 8.79 (s, 1H), 8.59 (s, 1H), 8.47 (br. s., 1H), 8.26 (d, J = 8.50 Hz, 1H), 8.10 (br. s., 1H), 7.90 (br. s., 1H), 7.76 (d, J = 8.69 Hz, 1H), 7.53 (d, J = 3.21 Hz, 1H), 7.28-7.50 (m, 7H), 7.18 (br. s., 1H), 7.10 (br. s., 1H), 5.10 (s, 2H), 4.80 (d, J = 1.13 Hz, 2H), 4.43 (d, J = 4.91 Hz, 2H). |

| Ex. No. | Structure | Chemical Name | ESI-MS (M + H) | ¹H NMR |
|---|---|---|---|---|
| 8.1.2 | 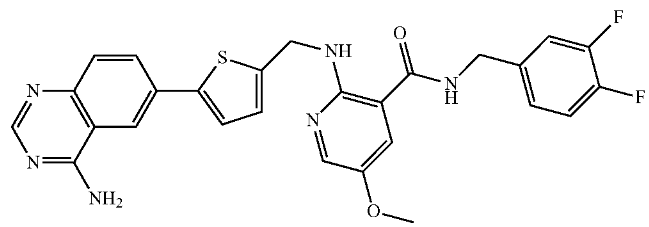 [SMILES: COc1cnc(NCc2ccc(-c3ccc4ncnc(N)c4c3)s2)c(C(=O)NCc2ccc(F)c(F)c2)c1] | 2-({[5-(4-aminoquinazolin-6-yl)thiophen-2-yl]methyl}amino)-N-(3,4-difluorobenzyl)-5-methoxypyridine-3-carboxamide | 533.3 | ¹H NMR (300 MHz, CD₃CN) δ 8.51 (s, 1H), 8.15-8.28 (m, 2H), 8.03 (d, J = 2.64 Hz, 1H), 7.91 (d, J = 9.06 Hz, 1H), 7.61-7.74 (m, 1H), 7.50-7.57 (m, 1H), 7.39-7.46 (m, 1H), 6.91-7.13 (m, 4H), 6.82 (tt, J = 2.31, 9.40 Hz, 1H), 4.83 (s, 2H), 4.47-4.55 (m, 2H), 3.78-3.85 (m, 3H). |
| 8.1.3 | 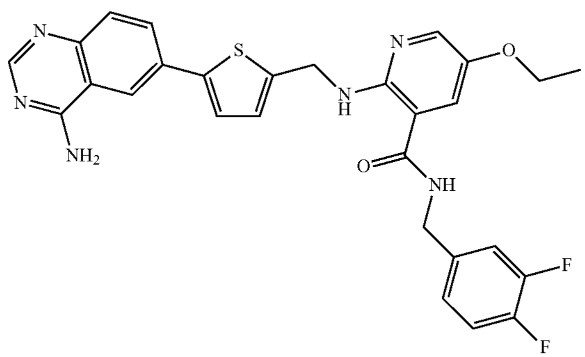 [SMILES: CCOc1cnc(NCc2ccc(-c3ccc4ncnc(N)c4c3)s2)c(C(=O)NCc2ccc(F)c(F)c2)c1] | 2-({[5-(4-aminoquinazolin-6-yl)thiophen-2-yl]methyl}amino)-N-(3,4-difluorobenzyl)-5-ethoxypyridine-3-carboxamide | 547.2 | ¹H NMR (300 MHz, CD₃CN) δ 8.49 (s, 1H), 8.22 (d, J = 1.89 Hz, 1H), 8.16 (dd, J = 1.89, 8.69 Hz, 1H), 8.00 (d, J = 2.64 Hz, 1H), 7.88 (d, J = 9.06 Hz, 1H), 7.64-7.77 (m, 1H), 7.50-7.57 (m, 1H), 7.40 (d, J = 3.78 Hz, 1H), 6.87-7.21 (m, 4H), 6.82 (tt, J = 2.41, 9.30 Hz, 1H), 4.82 (s, 2H), 4.46-4.55 (m, 2H), 3.97-4.10 (m, 2H), 1.29-1.41 (m, 3H). |
| 8.2 | 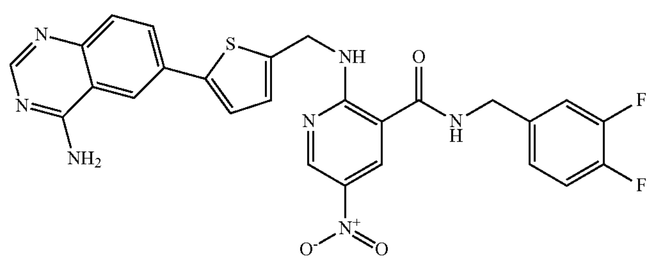 [SMILES: Nc1ncnc2ccc(-c3ccc(CNc4ncc([N+](=O)[O-])cc4C(=O)NCc4ccc(F)c(F)c4)s3)cc12] | 2-({[5-(4-aminoquinazolin-6-yl)thiophen-2-yl]methyl}amino)-N-(3,4-difluorobenzyl)-5-nitropyridine-3-carboxamide | 548.2 | ¹H NMR (300 MHz, DMSO-d₆) δ 9.86 (t, J = 5.85 Hz, 1H), 9.59 (t, J = 5.85 Hz, 1H), 9.38-9.56 (m, 1H), 9.14 (d, J = 2.64 Hz, 1H), 8.90 (d, J = 2.64 Hz, 1H), 8.72 (s, 1H), 8.57 (d, J = 1.51 Hz, 1H), 8.23 (dd, J = 1.70, 8.88 Hz, 1H), 7.74 (d, J = 8.69 Hz, 1H), 7.46-7.70 (m, 2H), 7.34-7.46 (m, 2H), 7.14-7.23 (m, 2H), 4.99 (d, J = 6.04 Hz, 2H), 4.45 (d, J = 5.29 Hz, 2H). |

TABLE 1-continued

| Ex. No. | Structure | Chemical Name | ESI-MS (M + H) | ¹H NMR |
|---|---|---|---|---|
| 8.3 | 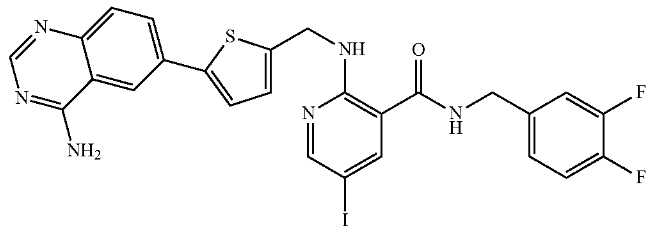 | 2-({[5-(4-aminoquinazolin-6-yl)thiophen-2-yl]methyl}amino)-N-(3,4-difluorobenzyl)-5-iodopyridine-3-carboxamide | 629.2 | ¹H NMR (300 MHz, DMSO-d₆) δ 9.70-9.96 (m, 2H), 9.21 (t, J = 5.85 Hz, 1H), 8.86 (t, J = 6.04 Hz, 1H), 8.77-8.82 (m, 1H), 8.60 (d, J = 1.51 Hz, 1H), 8.40 (d, J = 2.27 Hz, 1H), 8.31 (d, J = 1.89 Hz, 1H), 8.27 (dd, J = 1.89, 9.06 Hz, 1H), 7.77 (d, J = 9.06 Hz, 1H), 7.54 (d, J = 3.40 Hz, 1H), 7.29-7.45 (m, 2H), 7.08-7.21 (m, 2H), 4.82 (d, J = 5.29 Hz, 2H), 4.40 (d, J = 5.67 Hz, 2H). |
| 8.4 | 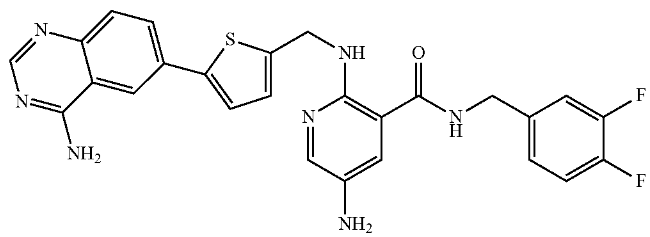 [SMILES: Nc1cnc(NCc2ccc(-c3ccc4ncnc(N)c4c3)s2)c(C(=O)NCc2ccc(F)c(F)c2)c1] | 2-({[5-(4-aminoquinazolin-6-yl)thiophen-2-yl]methyl}amino)-N-(3,4-difluorobenzyl)-5-aminopyridine-3-carboxamide | 518.3 | ¹H NMR (300 MHz, DMSO-d₆) δ 9.74 (br. s., 2H), 9.22 (t, J = 5.85 Hz, 1H), 8.77-8.83 (m, 1H), 8.61 (d, J = 1.89 Hz, 1H), 8.48 (br. s., 1H), 8.26 (dd, J = 1.89, 8.69 Hz, 1H), 8.05 (d, J = 2.27 Hz, 1H), 7.77 (dd, J = 3.40, 5.67 Hz, 2H), 7.51-7.57 (m, 1H), 7.26-7.47 (m, 2H), 7.09-7.20 (m, 2H), 4.81 (s, 2H), 4.42 (d, J = 5.67 Hz, 2H). |
| 8.5.1 | 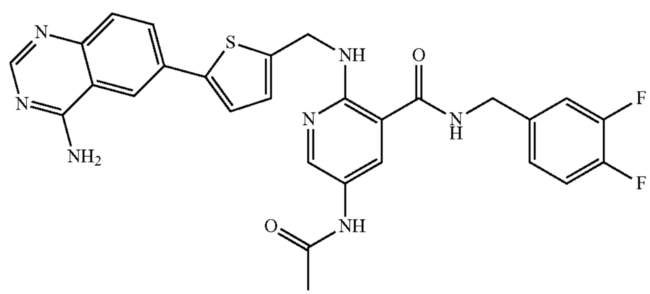 [SMILES: CC(=O)Nc1cnc(NCc2ccc(-c3ccc4ncnc(N)c4c3)s2)c(C(=O)NCc2ccc(F)c(F)c2)c1] | 5-(acetylamino)-2-({[5-(4-aminoquinazolin-6-yl)thiophen-2-yl]methyl}amino)-N-(3,4-difluorobenzyl)pyridine-3-carboxamide | 560.3 | ¹H NMR (300 MHz, DMSO-d₆) δ 9.81 (s, 3H), 9.14 (t, J = 6.04 Hz, 1H), 8.80 (s, 1H), 8.60 (d, J = 1.89 Hz, 1H), 8.48 (br. s., 1H), 8.24-8.31 (m, 2H), 8.15 (d, J = 2.27 Hz, 1H), 7.76 (d, J = 9.06 Hz, 1H), 7.54 (d, J = 3.78 Hz, 1H), 7.28-7.45 (m, 2H), 7.07-7.20 (m, 2H), 4.83 (d, J = 4.15 Hz, 2H), 4.40 (d, J = 5.67 Hz, 2H), 2.03 (s, 3H). |

| Ex. No. | Structure | Chemical Name | ESI-MS (M + H) | ¹H NMR |
|---|---|---|---|---|
| 8.5.2 | 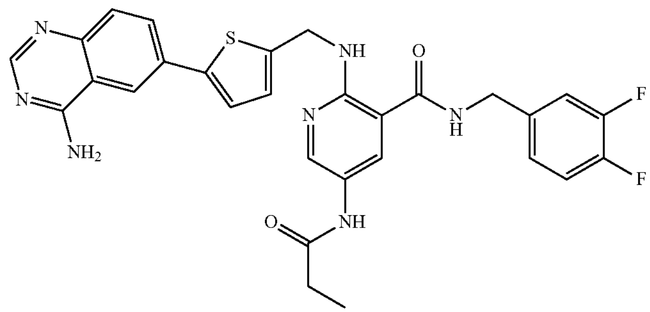 [SMILES: CCC(=O)Nc1cnc(NCc2ccc(-c3ccc4ncnc(N)c4c3)s2)c(C(=O)NCc2ccc(F)c(F)c2)c1] | 2-({[5-(4-aminoquinazolin-6-yl)thiophen-2-yl]methyl}amino)-N-(3,4-difluorobenzyl)-5-(propanoylamino)pyridine-3-carboxamide | 574.3 | ¹H NMR (300 MHz, DMSO-d₆) δ 9.86 (br. s, 1H), 9.71-9.80 (m, 2H), 9.15 (t, J = 6.04 Hz, 1H), 8.80 (s, 1H), 8.60 (d, J = 1.51 Hz, 1H), 8.48 (t, J = 5.85 Hz, 1H), 8.24-8.32 (m, 2H), 8.19 (d, J = 2.27 Hz, 1H), 7.76 (d, J = 8.69 Hz, 1H), 7.54 (d, J = 3.40 Hz, 1H), 7.27-7.44 (m, 2H), 7.09-7.20 (m, 2H), 4.83 (d, J = 4.15 Hz, 2H), 4.40 (d, J = 6.04 Hz, 2H), 2.30 (q, J = 7.55 Hz, 2H), 1.09 (t, J = 7.55 Hz, 3H). |
| 8.5.3 | 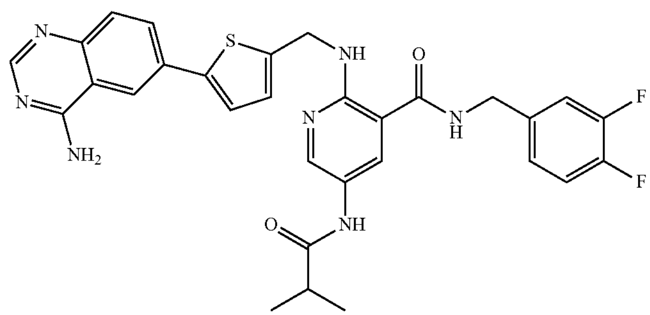 [SMILES: CC(C)C(=O)Nc1cnc(NCc2ccc(-c3ccc4ncnc(N)c4c3)s2)c(C(=O)NCc2ccc(F)c(F)c2)c1] | 2-({[5-(4-aminoquinazolin-6-yl)thiophen-2-yl]methyl}amino)-N-(3,4-difluorobenzyl)-5-[(2-methylpropanoyl)amino]pyridine-3-carboxamide | 588.3 | ¹H NMR (300 MHz, DMSO-d₆) δ 9.85 (br. s, 1H), 9.71 (s, 1H), 9.16 (t, J = 5.85 Hz, 1H), 8.80 (s, 1H), 8.60 (d, J = 1.89 Hz, 1H), 8.48 (br. s., 1H), 8.31 (d, J = 2.27 Hz, 1H), 8.27 (dd, J = 1.89, 8.69 Hz, 1H), 8.21 (d, J = 3.40 Hz, 1H), 7.76 (d, J = 8.69 Hz, 1H), 7.54 (d, J = 3.40 Hz, 1H), 7.27-7.45 (m, 2H), 7.07-7.20 (m, 2H), 4.83 (d, J = 4.15 Hz, 2H), 4.40 (d, J = 5.67 Hz, 2H), 2.55-2.62 (m, 1H), 1.11 (d, J = 6.80 Hz, 6H). |
| 8.5.4 | 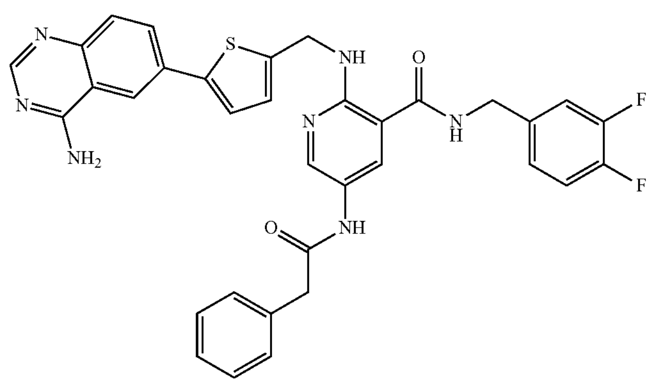 [SMILES: Nc1ncnc2ccc(-c3ccc(CNc4ncc(NC(=O)Cc5ccccc5)cc4C(=O)NCc4ccc(F)c(F)c4)s3)cc12] | 2-({[5-(4-aminoquinazolin-6-yl)thiophen-2-yl]methyl}amino)-N-(3,4-difluorobenzyl)-5-[(phenylacetyl)amino]pyridine-3-carboxamide | 636.3 | ¹H NMR (300 MHz, DMSO-d₆) δ 10.07 (s, 1H), 9.85 (br. s, 1H), 9.77 (br. s., 1H), 9.16 (t, J = 5.85 Hz, 1H), 8.80 (s, 1H), 8.59 (d, J = 1.89 Hz, 1H), 8.49 (br. s., 1H), 8.34 (d, J = 2.64 Hz, 1H), 8.27 (dd, J = 1.89, 8.69 Hz, 1H), 8.18 (d, J = 2.27 Hz, 1H), 7.76 (d, J = 8.69 Hz, 1H), 7.51-7.56 (m, 1H), 7.21-7.40 (m, 7H), 7.08-7.19 (m, 2H), 4.82 (d, J = 3.78 Hz, 2H), 4.39 (d, J = 5.67 Hz, 2H), 3.59-3.65 (m, 2H). |

TABLE 1-continued

TABLE 1-continued

| Ex. No. | Structure | Chemical Name | ESI-MS (M + H) | ¹H NMR |
|---|---|---|---|---|
| 8.5.5 | 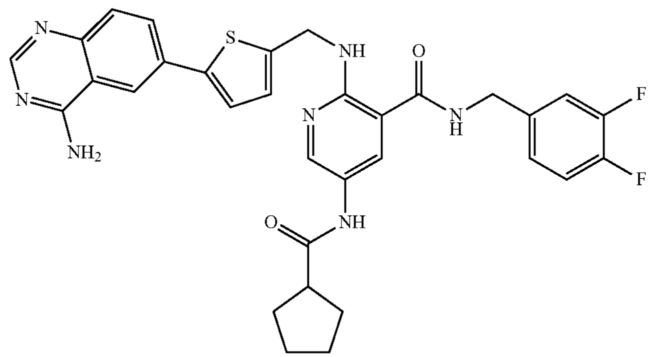 [SMILES: Nc1ncnc2ccc(-c3ccc(CNc4ncc(NC(=O)C5CCCC5)cc4C(=O)NCc4ccc(F)c(F)c4)s3)cc12] | 2-({[5-(4-aminoquinazolin-6-yl)thiophen-6-yl]methyl}amino)-5-[(cyclopentylcarbonyl)amino]-N-(3,4-difluorobenzyl)pyridine-3-carboxamide | 614.3 | ¹H NMR (300 MHz, DMSO-d$_6$) δ 9.87 (br. s., 1H), 9.69-9.83 (m, 2H), 9.16 (t, J = 5.67 Hz, 1H), 8.80 (s, 1H), 8.60 (s, 1H), 8.48 (br. s., 1H), 8.18-8.35 (m, 3H), 7.77 (d, J = 8.69 Hz, 1H), 7.54 (d, J = 3.40 Hz, 1H), 7.26-7.46 (m, 2H), 7.05-7.22 (quin, J = 7.74 Hz, 1H), 4.83 (br. s., 2H), 4.40 (d, J = 5.67 Hz, 2H), 2.75 (quin, J = 7.74 Hz, 1H), 1.42-1.97 (m, 8H). |
| 8.5.6 | 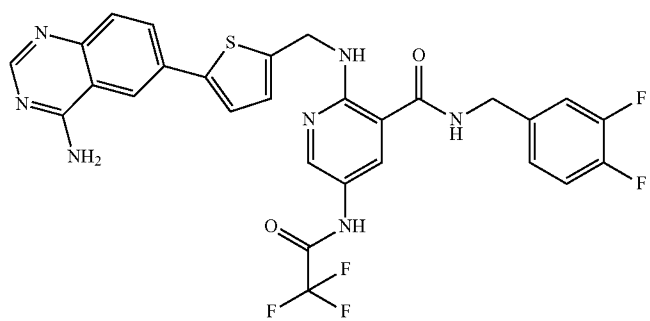 [SMILES: Nc1ncnc2ccc(-c3ccc(CNc4ncc(NC(=O)C(F)(F)F)cc4C(=O)NCc4ccc(F)c(F)c4)s3)cc12] | 2-({[5-(4-aminoquinazolin-6-yl)thiophen-6-yl]methyl}amino)-N-(3,4-difluorobenzyl)-5-[(trifluoroacetyl)amino]pyridine-3-carboxamide | 614.2 | ¹H NMR (300 MHz, DMSO-d$_6$) δ 11.24 (s, 1H), 9.68 (br. s., 2H), 9.20 (t, J = 5.85 Hz, 1H), 8.70-8.82 (m, 2H), 8.60 (d, J = 1.51 Hz, 1H), 8.39 (d, J = 2.27 Hz, 1H), 8.20-8.30 (m, 2H), 7.76 (d, J = 8.69 Hz, 1H), 7.54 (d, J = 3.40 Hz, 1H), 7.30-7.46 (m, 2H), 7.08-7.21 (m, 2H), 4.86 (d, J = 5.67 Hz, 2H), 4.42 (d, J = 5.67 Hz, 2H). |

TABLE 1-continued

| Ex. No. | Structure | Chemical Name | ESI-MS (M + H) | ¹H NMR |
|---|---|---|---|---|
| 8.5.7 | 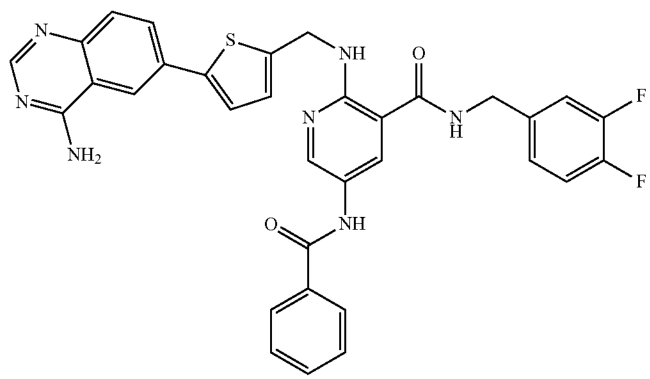 [SMILES: Nc1ncnc2ccc(-c3ccc(CNc4ncc(NC(=O)c5ccccc5)cc4C(=O)NCc4ccc(F)c(F)c4)s3)cc12] | 2-({[5-(4-aminoquinazolin-6-yl)thiophen-2-yl]methyl}amino)-N-(3,4-difluorobenzyl)-5-[(phenylcarbonyl)amino]pyridine-3-carboxamide | 622.3 | ¹H NMR (300 MHz, DMSO-d₆) δ 10.23 (s, 1H), 9.83 (d, 2H), 9.19 (t, J = 5.48 Hz, 1H), 8.80 (s, 1H), 8.62 (br. s., 2H), 8.45 (s, 1H), 8.36 (br. s., 1H), 8.28 (d, J = 8.69 Hz, 1H), 7.98 (d, J = 6.80 Hz, 2H), 7.78 (d, J = 8.69 Hz, 1H), 7.47-7.68 (m, 4H), 7.27-7.46 (m, 2H), 7.05-7.24 (m, 2H), 4.87 (br. s., 2H), 4.43 (d, J = 5.29 Hz, 2H). |
| 8.5.8 | 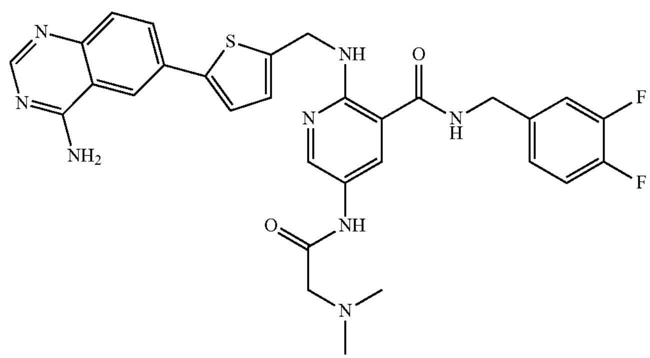 [SMILES: CN(C)CC(=O)Nc1cnc(NCc2ccc(-c3ccc4ncnc(N)c4c3)s2)c(C(=O)NCc2ccc(F)c(F)c2)c1] | 2-({[5-(4-aminoquinazolin-6-yl)thiophen-2-yl]methyl}amino)-N-(3,4-difluorobenzyl)-5-[(N,N-dimethylglycyl)amino]pyridine-3-carboxamide | 603.3 | ¹H NMR (300 MHz, DMSO-d₆) δ 10.50 (s, 1H), 9.83 (br. s., 2H), 9.21 (t, J = 5.85 Hz, 1H), 8.80 (s, 1H), 8.61 (d, J = 1.51 Hz, 1H), 8.53 (t, J = 5.85 Hz, 1H), 8.39 (d, J = 2.27 Hz, 1H), 8.26 (dd, J = 1.89, 8.69 Hz, 1H), 8.10 (d, J = 2.64 Hz, 1H), 7.77 (d, J = 8.69 Hz, 1H), 7.55 (d, J = 3.78 Hz, 1H), 7.31-7.45 (m, 2H), 7.09-7.22 (m, 2H), 4.84 (d, J = 5.29 Hz, 2H), 4.43 (d, J = 5.67 Hz, 2H), 4.12 (s, 2H), 2.84-2.93 (m, 6H). |
| 8.6.1 | 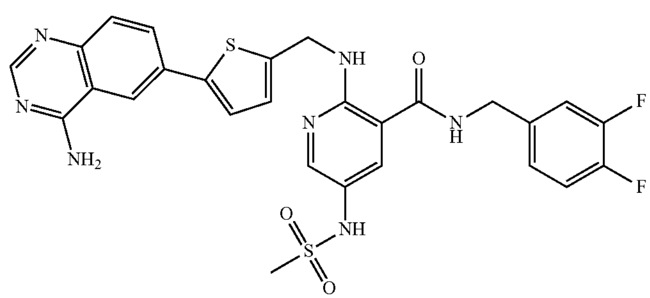 [SMILES: CS(=O)(=O)Nc1cnc(NCc2ccc(-c3ccc4ncnc(N)c4c3)s2)c(C(=O)NCc2ccc(F)c(F)c2)c1] | 2-({[5-(4-aminoquinazolin-6-yl)thiophen-2-yl]methyl}amino)-N-(3,4-difluorobenzyl)-5-[(methylsulfonyl)amino]pyridine-3-carboxamide | 596.3 | ¹H NMR (300 MHz, DMSO-d₆) δ 9.87 (br. s, 1H), 9.72-9.83 (m, 1H), 9.30 (s, 1H), 9.24 (t, J = 5.85 Hz, 1H), 8.80 (s, 1H), 8.76 (t, J = 6.04 Hz, 1H), 8.61 (d, J = 1.51 Hz, 1H), 8.27 (dd, J = 1.89, 8.69 Hz, 1H), 8.13 (d, J = 2.64 Hz, 1H), 7.92 (d, J = 2.27 Hz, 1H), 7.77 (d, J = 8.69 Hz, 1H), 7.52-7.59 (m, 1H), 7.30-7.47 (m, 2H), 7.08-7.22 (m, 2H), 4.85 (d, J = 4.15 Hz, 2H), 4.43 (d, J = 5.67 Hz, 2H), 2.98 (s, 3H). |

TABLE 1-continued

| Ex. No. | Structure | Chemical Name | ESI-MS (M + H) | ¹H NMR |
|---|---|---|---|---|
| 8.6.2 | 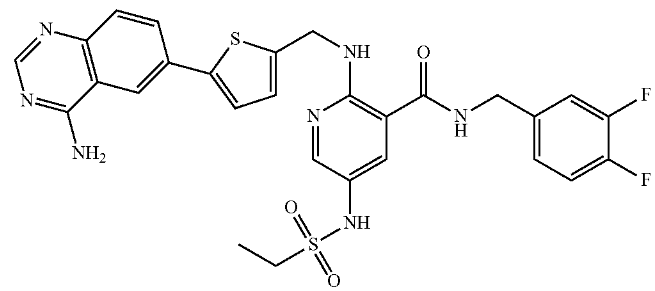 [SMILES: CCS(=O)(=O)Nc1cnc(NCc2ccc(-c3ccc4ncnc(N)c4c3)s2)c(C(=O)NCc2ccc(F)c(F)c2)c1] | 2-({[5-(4-aminoquinazolin-6-yl)thiophen-2-yl]methyl}amino)-N-(3,4-difluorobenzyl)-5-[(ethylsulfonyl)amino]pyridine-3-carboxamide | 610.3 | ¹H NMR (300 MHz, DMSO-d₆) δ 9.76 (br. s., 1H), 9.36 (s, 1H), 9.25 (t, J = 5.48 Hz, 1H), 8.73 (t, J = 5.29 Hz, 1H), 8.61 (s, 1H), 8.27 (d, J = 8.69 Hz, 1H), 8.11 (d, J = 1.89 Hz, 1H), 7.91 (d, J = 2.27 Hz, 1H), 7.77 (d, J = 9.06 Hz, 1H), 7.54 (d, J = 3.40 Hz, 1H), 7.28-7.46 (m, 2H), 7.12 (d, J = 3.78 Hz, 2H), 4.84 (d, J = 4.91 Hz, 2H), 4.43 (d, J = 5.29 Hz, 2H), 3.06 (q, J = 7.18 Hz, 2H), 1.26 (t, J = 7.18 Hz, 3H). |
| 8.6.3 | 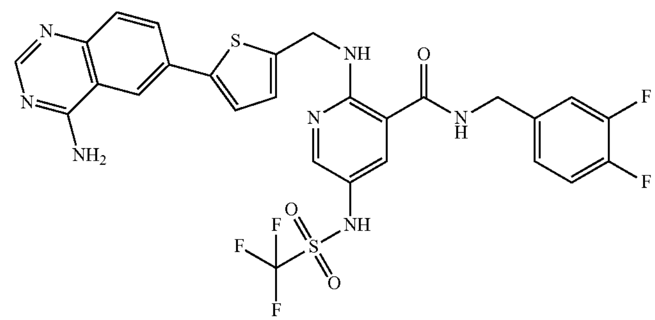 [SMILES: Nc1ncnc2ccc(-c3ccc(CNc4ncc(NS(=O)(=O)C(F)(F)F)cc4C(=O)NCc4ccc(F)c(F)c4)s3)cc12] | 2-({[5-(4-aminoquinazolin-6-yl)thiophen-2-yl]methyl}amino)-N-(3,4-difluorobenzyl)-5-[(trifluoromethyl)sulfonyl]amino}pyridine-3-carboxamide | 650.2 | ¹H NMR (300 MHz, DMSO-d₆) δ 9.81 (d, 2H), 9.29 (t, J = 5.85 Hz, 1H), 9.03 (t, J = 4.72 Hz, 1H), 8.80 (s, 1H), 8.61 (d, J = 1.89 Hz, 1H), 8.27 (dd, J = 1.70, 8.88 Hz, 1H), 8.12 (d, J = 2.64 Hz, 1H), 8.02 (d, J = 2.27 Hz, 1H), 7.77 (d, J = 8.69 Hz, 1H), 7.55 (d, J = 3.78 Hz, 1H), 7.30-7.46 (m, 2H), 7.09-7.22 (m, 2H), 4.86 (d, J = 4.53 Hz, 2H), 4.43 (d, J = 5.67 Hz, 2H), 2.69 (s, 1H). |
| 8.6.4 | 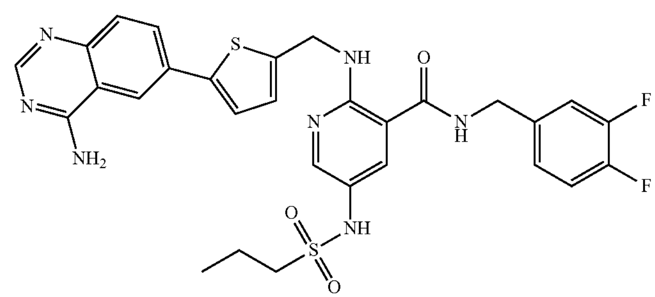 [SMILES: CCCS(=O)(=O)Nc1cnc(NCc2ccc(-c3ccc4ncnc(N)c4c3)s2)c(C(=O)NCc2ccc(F)c(F)c2)c1] | 2-({[5-(4-aminoquinazolin-6-yl)thiophen-2-yl]methyl}amino)-N-(3,4-difluorobenzyl)-5-[(propylsulfonyl)amino]pyridine-3-carboxamide | 624.3 | ¹H NMR (300 MHz, DMSO-d₆) δ 9.83 (br. s., 2H), 9.36 (s, 1H), 9.24 (t, J = 6.04 Hz, 1H), 8.80 (s, 1H), 8.69-8.77 (m, 1H), 8.61 (d, J = 1.89 Hz, 1H), 8.27 (dd, J = 1.70, 8.88 Hz, 1H), 8.11 (d, J = 2.27 Hz, 1H), 7.91 (d, J = 2.64 Hz, 1H), 7.77 (d, J = 8.69 Hz, 1H), 7.54 (d, J = 3.78 Hz, 1H), 7.30-7.45 (m, 2H), 7.09-7.21 (m, 2H), 4.84 (d, J = 4.91 Hz, 2H), 4.42 (d, J = 5.67 Hz, 2H), 2.97-3.07 (m, 2H), 1.73 (sxt, J = 7.55 Hz, 2H), 0.97 (t, J = 7.37 Hz, 3H). |

TABLE 1-continued

| Ex. No. | Structure | Chemical Name | ESI-MS (M + H) | $^1$H NMR |
|---|---|---|---|---|
| 8.6.5 | 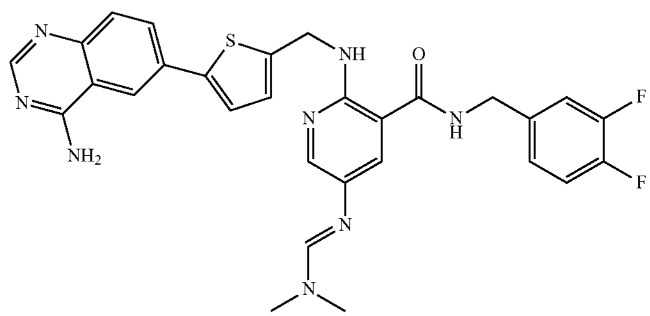 [SMILES: CN(C)/C=N/c1cnc(NCc2ccc(-c3ccc4ncnc(N)c4c3)s2)c(C(=O)NCc2ccc(F)c(F)c2)c1] | 2-({[5-(4-aminoquinazolin-6-yl)thiophen-2-yl]methyl}amino)-N-(3,4-difluorobenzyl)-5-{[(E)-(dimethylamino)methylidene]amino}pyridine-3-carboxamide | 573.3 | $^1$H NMR (300 MHz, DMSO-d$_6$) δ 9.71 (br. s., 2H), 9.20 (t, J = 5.85 Hz, 1H), 8.69-8.84 (m, 2H), 8.61 (d, J = 1.89 Hz, 1H), 8.51 (br. s., 1H), 8.30 (d, J = 2.64 Hz, 1H), 8.24 (dd, J = 1.89, 8.69 Hz, 1H), 8.09 (d, J = 2.64 Hz, 1H), 7.77 (d, J = 8.69 Hz, 1H), 7.54 (d, J = 3.78 Hz, 1H), 7.32-7.48 (m, 2H), 7.06-7.23 (m, 2H), 4.86 (d, J = 5.67 Hz, 2H), 4.46 (d, J = 5.67 Hz, 2H), 3.32 (s, 3H), 3.19 (s, 3H). |
| 8.6.6 | 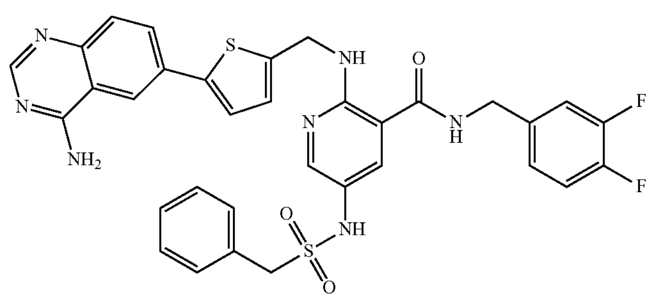 [SMILES: Nc1ncnc2ccc(-c3ccc(CNc4ncc(NS(=O)(=O)Cc5ccccc5)cc4C(=O)NCc4ccc(F)c(F)c4)s3)cc12] | 2-({[5-(4-aminoquinazolin-6-yl)thiophen-2-yl]methyl}amino)-5-[(benzylsulfonyl)amino]-N-(3,4-difluorobenzyl)pyridine-3-carboxamide | 672.3 | $^1$H NMR (300 MHz, DMSO-d$_6$) δ 9.67-9.89 (m, 2H), 9.45 (s, 1H), 9.22 (t, J = 6.04 Hz, 1H), 8.79 (s, 1H), 8.70 (t, J = 5.85 Hz, 1H), 8.61 (d, J = 1.89 Hz, 1H), 8.27 (dd, J = 1.70, 8.88 Hz, 1H), 8.04-8.09 (m, 1H), 7.88-7.94 (m, 1H), 7.76 (d, J = 9.06 Hz, 1H), 7.55 (d, 1H), 7.29-7.47 (m, 7H), 7.08-7.22 (m, 2H), 4.85 (d, J = 5.67 Hz, 2H), 4.38-4.50 (m, 4H). |
| 8.6.7 | 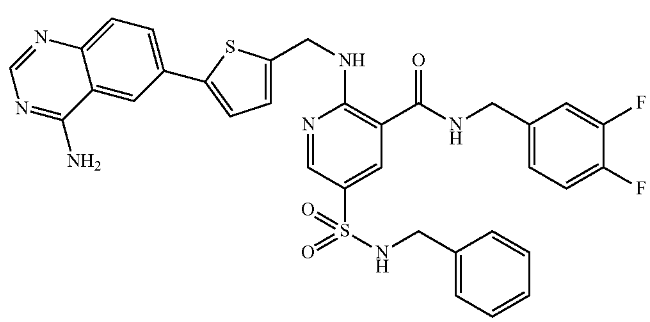 [SMILES: Nc1ncnc2ccc(-c3ccc(CNc4ncc(S(=O)(=O)NCc5ccccc5)cc4C(=O)NCc4ccc(F)c(F)c4)s3)cc12] | 2-((5-(4-aminoquinazolin-6-yl)thiophen-2-yl)methyl)amino)-5-(N-benzylsulfamoyl)-N-(3,4-difluorobenzyl)nicotinamide | 671.8 | $^1$H NMR (400 MHz, DMSO-d$_6$) δ 9.75 (s, 1H), 9.64 (s, 1H), 9.44 (t, 1H), 9.35 (s, 1H), 8.77 (s, 1H), 8.62 (s, 1H), 8.54 (d, 1H), 8.31 (d, 1H), 8.26 (d, 1H), 8.04 (t, 1H), 7.77 (d, 1H), 7.56 (d, 1H), 7.44-7.37 (m, 2H), 7.23-7.14 (m, 7H), 4.91 (d, 2H), 4.43 (d, 2H), 4.04 (d, 2H). |

TABLE 1-continued

| Ex. No. | Structure | Chemical Name | ESI-MS (M + H) | ¹H NMR |
|---|---|---|---|---|
| 8.6.8 | 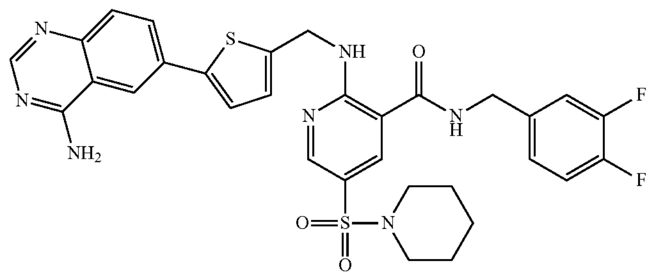 [SMILES: Nc1ncnc2ccc(-c3ccc(CNc4ncc(S(=O)(=O)N5CCCCC5)cc4C(=O)NCc4ccc(F)c(F)c4)s3)cc12] | 2-(((5-(4-aminoquinazolin-6-yl)thiophen-2-yl)methyl)amino)-N-(3,4-difluorobenzyl)-5-(piperidin-1-ylsulfonyl)nicotinamide | 650.1 | ¹H NMR (400 MHz, DMSO-d₆) δ 9.50 (s, 2H), 8.52 (d, 1H), 8.42 (d, 1H), 8.34 (s, 1H), 8.30 (d, 1H), 7.97 (dd, 1H), 7.85 (br, 2H), 7.64 (d, 1H), 7.48 (d, 1H), 7.38 (q, 2H), 7.18 (br, 1H), 7.12 (d, 1H), 4.91 (d, 2H), 4.44 (d, 2H), 2.91 (t, 4H), 1.55 (m, 4H), 1.38 (m, 2H). |
| 8.6.9 | 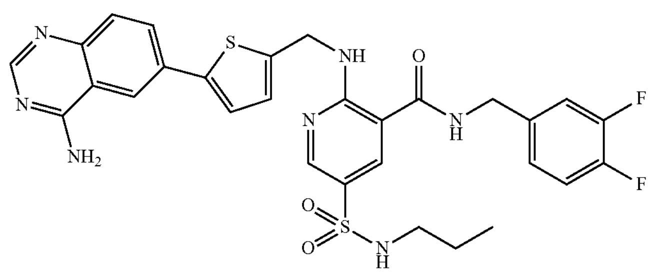 [SMILES: CCCNS(=O)(=O)c1cnc(NCc2ccc(-c3ccc4ncnc(N)c4c3)s2)c(C(=O)NCc2ccc(F)c(F)c2)c1] | 2-(((5-(4-aminoquinazolin-6-yl)thiophen-2-yl)methyl)amino)-N-(3,4-difluorobenzyl)-5-(N-propylsulfamoyl)nicotinamide | 623.9 | ¹H NMR (400 MHz, DMSO-d₆) δ 9.48 (t, 1H), 9.32 (t, 1H), 8.58 (s, 1H), 8.45 (s, 1H), 8.40 (s, 1H), 8.34 (s, 1H), 8.05 (br, 2H), 8.00 (d, 1H), 7.65 (d, 1H), 7.48 (d, 1H), 7.42-7.40 (m, 3H), 7.19 (s, 1H), 7.11 (d, 1H), 4.90 (d, 2H), 4.43 (d, 2H), 2.73 (q, 2H), 1.42-1.37 (m, 2H), 0.80 (t, 3H). |
| 8.6.10 | 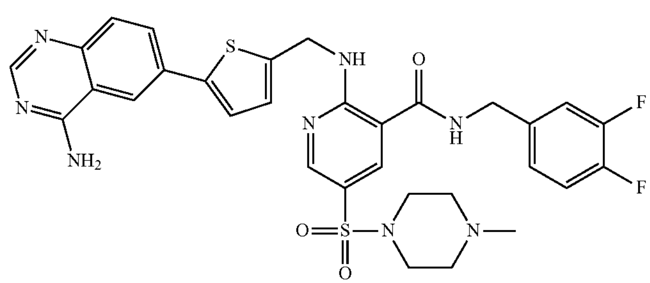 [SMILES: CN1CCN(S(=O)(=O)c2cnc(NCc3ccc(-c4ccc5ncnc(N)c5c4)s3)c(C(=O)NCc3ccc(F)c(F)c3)c2)CC1] | 2-(((5-(4-aminoquinazolin-6-yl)thiophen-2-yl)methyl)amino)-N-(3,4-difluorobenzyl)-5-((4-methylpiperazin-1-yl)sulfonyl)nicotinamide | 664.9 | ¹H NMR (400 MHz, CD₃OD) δ 8.62 (d, 1H), 8.41 (d, 1H), 8.37 (s, 1H), 8.25 (d, 1H), 8.10 (dd, 1H), 7.74 (d, 1H), 7.46 (d, 1H), 7.33-7.22 (m, 3H), 7.12 (d, 1H), 5.01 (s, 2H), 4.54 (s, 2H), 3.10 (s, 4H), 2.56 (t, 4H), 2.31 (s, 3H). |

| Ex. No. | Structure | Chemical Name | ESI-MS (M + H) | ¹H NMR |
|---|---|---|---|---|
| 8.6.11 | 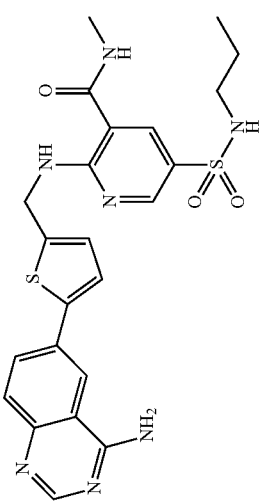 | 2-(((5-(4-aminoquinazolin-6-yl)thiophen-2-yl)methyl)amino)-N-methyl-5-(N-propylsulfamoyl)nicotinamide | 511.9 | ¹H NMR (400 MHz, DMSO-d₆) δ 9.33 (t, 1H), 8.84 (d, 1H), 8.55 (s, 1H), 8.43 (s, 1H), 8.35 (s, 1H), 8.24 (s, 1H), 8.00 (d, 1H), 7.85 (br, 2H), 7.64 (d, 1H), 7.48 (d, 1H), 7.39 (t, 1H), 7.11 (d, 1H), 4.90 (d, 2H), 2.76 (d, 3H), 2.72 (t, 2H), 1.42-1.36 (m, 2H), 0.80 (t, 3H). |
| 8.6.12 | 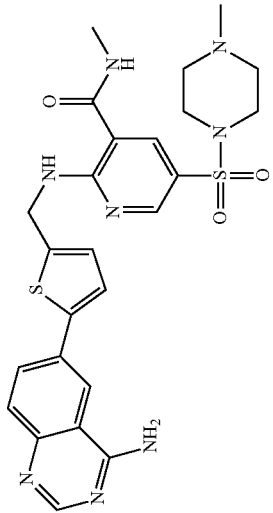 | 2-(((5-(4-aminoquinazolin-6-yl)thiophen-2-yl)methyl)amino)-N-methyl-5-(4-methylpiperazin-1-ylsulfonyl)nicotinamide | 553.0 | ¹H NMR (400 MHz, CD₃OD) δ 8.56 (d, 1H), 8.37 (d, 1H), 8.33 (s, 1H), 8.13 (d, 1H), 8.07 (dd, 1H), 7.70 (d, 1H), 7.42 (d, 1H), 7.09 (d, 1H), 4.96 (s, 2H), 3.06 (m, 4H), 2.88 (s, 3H), 2.54 (t, 4H), 2.28 (s, 3H). |
| 8.6.13 | 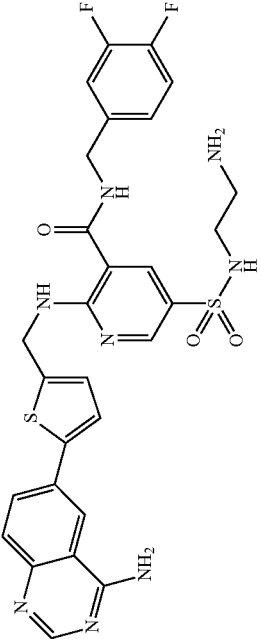 | 5-(N-(2-aminoethyl)sulfamoyl)-2-(((5-(4-aminoquinazolin-6-yl)thiophen-2-yl)methyl)amino)-N-(3,4-difluorobenzyl)nicotinamide | 624.9 | ¹H NMR (400 MHz, DMSO-d₆) δ 9.51 (t, 2H), 9.36 (t, 1H), 8.74 (s, 5H), 8.59 (d, 2H), 8.36 (d, 1H), 8.22 (d, 1H), 7.79-7.73 (m, 5H), 7.54 (d, 1H), 7.39 (q, 2H), 7.18 (q, 2H), 4.92 (d, 2H), 4.43 (d, 2H), 2.96 (t, 2H), 2.89 (t, 2H). |

TABLE 1-continued

| Ex. No. | Structure | Chemical Name | ESI-MS (M + H) | ¹H NMR |
|---|---|---|---|---|
| 8.6.14 | 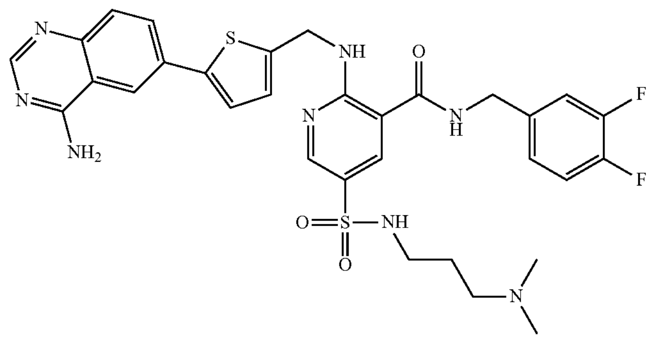 [SMILES: CN(C)CCCNS(=O)(=O)c1cnc(NCc2ccc(-c3ccc4ncnc(N)c4c3)s2)c(C(=O)NCc2ccc(F)c(F)c2)c1] | 2-(((5-(4-aminoquinazolin-6-yl)thiophen-2-yl)methyl)amino)-N-(3,4-difluorobenzyl)-5-(N-(3-(dimethylamino)propyl)sulfamoyl)nicotinamide | 666.9 | ¹H NMR (400 MHz, CD₃OD) δ 8.65 (t, 2H), 8.57 (d, 1H), 8.30 (d, 2H), 8.28 (d, 1 H), 7.77 (d, 1H), 7.51 (d, 1H), 7.29-7.14 (m, 4H), 4.99 (s, 2H), 4.51 (s, 2H), 3.23 (t, 2H), 3.00 (t, 2H), 2.90 (s, 6H), 1.98-1.91 (m, 2H). |
| 8.6.15 | 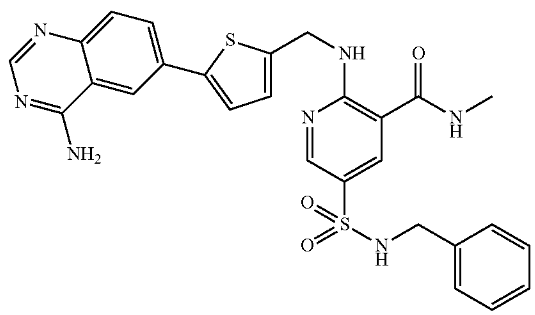 [SMILES: CNC(=O)c1cc(S(=O)(=O)NCc2ccccc2)cnc1NCc1ccc(-c2ccc3ncnc(N)c3c2)s1] | 2-(((5-(4-aminoquinazolin-6-yl)thiophen-2-yl)methyl)amino)-5-(N-benzylsulfamoyl)-N-methylnicotinamide | 559.9 | ¹H NMR (400 MHz, DMSO-d₆) δ 9.37 (t, 3H), 8.82 (d, 1H), 8.70 (s, 1H), 8.58 (d, 1H), 8.52 (d, 1H), 8.23 (q, 2H), 8.00 (t, 1H), 7.74 (d, 1H), 7.55 (d, 1H), 7.25-7.14 (m, 6H), 4.91 (d, 2H), 4.02 (d, 2H), 2.76 (d, 3H). |
| 8.6.16 | 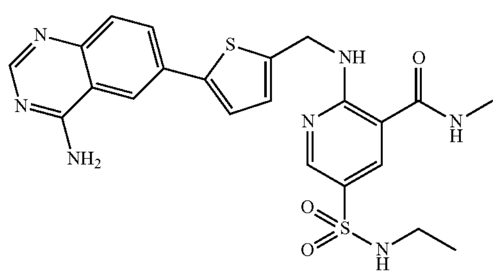 [SMILES: CCNS(=O)(=O)c1cnc(NCc2ccc(-c3ccc4ncnc(N)c4c3)s2)c(C(=O)NC)c1] | 2-(((5-(4-aminoquinazolin-6-yl)thiophen-2-yl)methyl)amino)-5-(N-ethylsulfamoyl)-N-methylnicotinamide | 497.9 | ¹H NMR (400 MHz, DMSO-d₆) δ 9.33 (t, 1H), 8.86 (d, 1H), 8.55 (d, 1H), 8.42 (d, 1H), 8.34 (s, 1H), 8.23 (d, 1H), 8.00 (d, 1H), 7.92 (br, 2H), 7.64 (d, 1H), 7.47 (d, 1H), 7.37 (t, 1H), 7.11 (d, 1H), 4.90 (d, 2H), 2.84-2.76 (m, 5H), 0.99 (t, 3H). |

TABLE 1-continued

| Ex. No. | Structure | Chemical Name | ESI-MS (M + H) | $^1$H NMR |
|---|---|---|---|---|
| 8.6.17 | 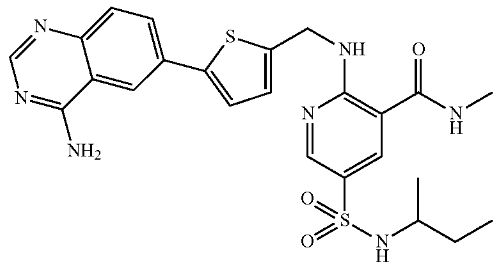 [SMILES: CCC(C)NS(=O)(=O)c1cnc(NCc2ccc(-c3ccc4ncnc(N)c4c3)s2)c(C(=O)NC)c1] | 2-(((5-(4-aminoquinazolin-6-yl)thiophen-2-yl)methyl)amino)-5-(N-sec-butylsulfamoyl)-N-methylnicotinamide | 526.1 | $^1$H NMR (400 MHz, DMSO-d$_6$) δ 9.33 (s, 1H), 8.85 (s, 1H), 8.57 (s, 1H), 8.42 (s, 1H), 8.34 (s, 1H), 8.25 (s, 1H), 7.96 (d, 1H), 7.80 (br, 2H), 7.64 (d, 1H), 7.47 (d, 1H), 7.35 (d, 1H), 7.10 (s, 1H), 4.90 (d, 2H), 3.11-3.09 (m, 1H), 2.75 (d, 3H), 1.31 (t, 2H), 0.92 (d, 3H), 0.72 (t, 3H). |
| 8.6.18 | 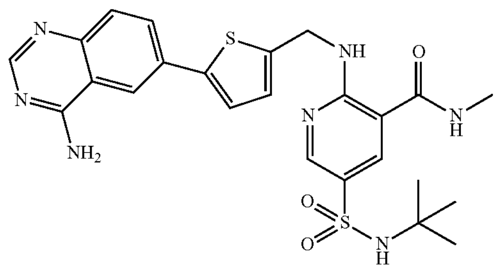 [SMILES: CNC(=O)c1cc(S(=O)(=O)NC(C)(C)C)cnc1NCc1ccc(-c2ccc3ncnc(N)c3c2)s1] | 2-(((5-(4-aminoquinazolin-6-yl)thiophen-2-yl)methyl)amino)-5-(N-t-butylsulfamoyl)-N-methylnicotinamide | 526.1 | $^1$H NMR (400 MHz, DMSO-d$_6$) δ 9.29 (t, 1H), 8.84 (d, 1H), 8.60 (s, 1H), 8.43 (s, 1H), 8.34 (s, 1H), 8.25 (d, 1H), 7.97 (d, 1H), 7.80 (br, 2H), 7.64 (d, 1H), 7.47 (d, 1H), 7.35 (s, 1H), 7.10 (d, 1H), 4.90 (d, 2H), 2.75 (d, 3H), 1.12 (s, 9H). |
| 8.6.19 | 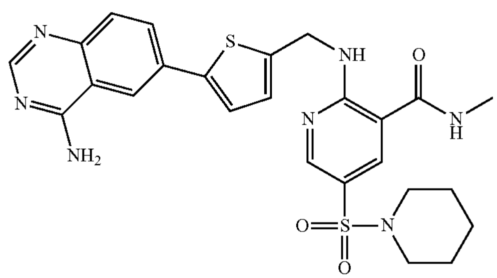 [SMILES: CNC(=O)c1cc(S(=O)(=O)N2CCCCC2)cnc1NCc1ccc(-c2ccc3ncnc(N)c3c2)s1] | 2-(((5-(4-aminoquinazolin-6-yl)thiophen-2-yl)methyl)amino)-N-methyl-5-(piperidin-1-ylsulfonyl)nicotinamide | 538.1 | $^1$H NMR (400 MHz, CD$_3$OD) δ 8.65 (s, 1H), 8.58 (d, 1H), 8.57 (d, 1H), 8.32 (dd, 1H), 8.16 (d, 1H), 7.78 (d, 1H), 7.54 (d, 1H), 7.17 (d, 1H), 5.01 (s, 2H), 3.06-3.03 (m, 4H), 2.91 (s, 3H), 1.70-1.66 (m, 4H), 1.51-1.49 (m, 2H). |

TABLE 1-continued

| Ex. No. | Structure | Chemical Name | ESI-MS (M + H) | ¹H NMR |
|---|---|---|---|---|
| 8.6.20 | 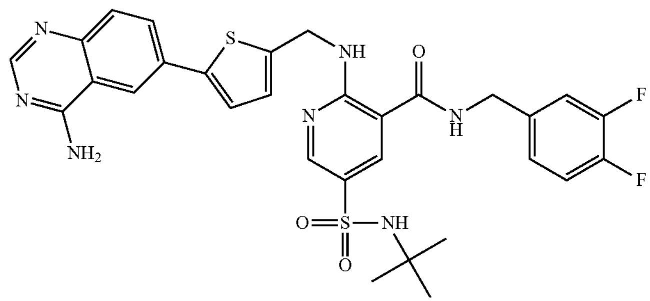 [SMILES: CC(C)(C)NS(=O)(=O)c1cnc(NCc2ccc(-c3ccc4ncnc(N)c4c3)s2)c(C(=O)NCc2ccc(F)c(F)c2)c1] | 2-(((5-(4-aminoquinazolin-6-yl)thiophen-2-yl)methyl)amino)-5-(N-tert-butylsulfamoyl)-N-(3,4-difluorobenzyl)nicotinamide | 637.9 | ¹H NMR (400 MHz, CD₃OD) δ 8.68 (d, 1H), 8.39 (d, 1H), 8.34 (s, 1H), 8.29 (d, 1H), 8.05 (dd, 1H), 7.70 (d, 1H), 7.42 (d, 1H), 7.18-7.26 (m, 3H), 7.10 (d, 1H), 4.64 (s, 2H), 4.51 (s, 2H), 1.24 (s, 9H). |
| 8.7.1 | 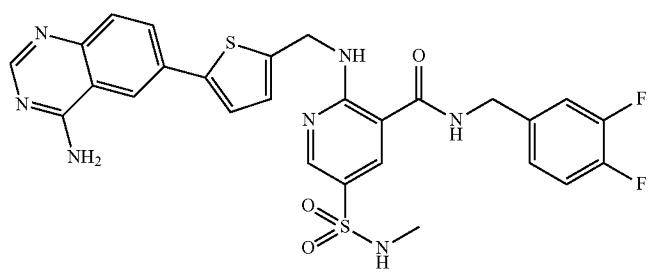 [SMILES: CNS(=O)(=O)c1cnc(NCc2ccc(-c3ccc4ncnc(N)c4c3)s2)c(C(=O)NCc2ccc(F)c(F)c2)c1] | 2-(((5-(4-aminoquinazolin-6-yl)thiophen-2-yl)methyl)amino)-N-(3,4-difluorobenzyl)-5-(N-methylsulfamoyl)nicotinamide | 596.2 | ¹H NMR (400 MHz, DMSO-d₆) δ 9.77 (br, s, 2H), 9.48 (t, J = 5.77 Hz, 1H), 9.35 (t, J = 6.02 Hz, 1H), 8.79 (s, 1H), 8.60 (d, J = 1.76 Hz, 1H), 8.56 (d, J = 2.26 Hz, 1H), 8.33 (d, J = 2.26 Hz, 1H), 8.27 (dd, J = 2.01, 8.78 Hz, 1H), 7.76 (d, J = 8.78 Hz, 1H), 7.55 (d, J = 3.76 Hz, 1H), 7.32-7.45 (m, 2H), 7.29 (q, J = 4.94 Hz, 1H), 7.10-7.22 (m, 2H), 4.92 (d, J = 6.02 Hz, 2H), 4.43 (d, J = 5.77 Hz, 2H). |
| 8.7.2 | 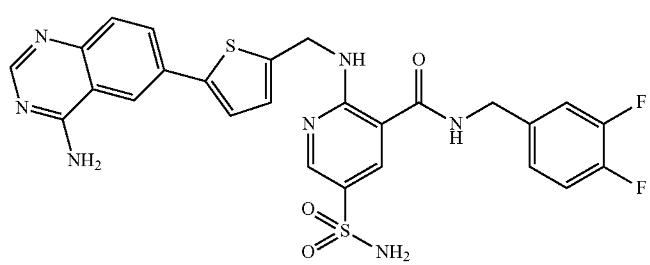 [SMILES: Nc1ncnc2ccc(-c3ccc(CNc4ncc(S(N)(=O)=O)cc4C(=O)NCc4ccc(F)c(F)c4)s3)cc12] | 2-({[5-(4-aminoquinazolin-6-yl)thiophen-2-yl]methyl}amino)-N-(3,4-difluorobenzyl)-5-sulfamoylpyridine-3-carboxamide | 582.3 | ¹H NMR (400 MHz, DMSO-d₆) δ 9.46 (t, J = 5.90 Hz, 1H), 9.27 (t, J = 5.90 Hz, 1H), 8.78 (s, 1H), 8.53-8.64 (m, 2H), 8.38 (d, J = 2.26 Hz, 1H), 8.26 (dd, J = 2.01, 8.78 Hz, 1H), 7.75 (d, J = 8.78 Hz, 1H), 7.54 (d, J = 3.76 Hz, 1H), 7.30-7.44 (m, 2H), 7.25 (s, 2H), 7.08-7.21 (m, 2H). |

TABLE 1-continued

| Ex. No. | Structure | Chemical Name | ESI-MS (M + H) | ¹H NMR |
|---|---|---|---|---|
| 8.7.3 | 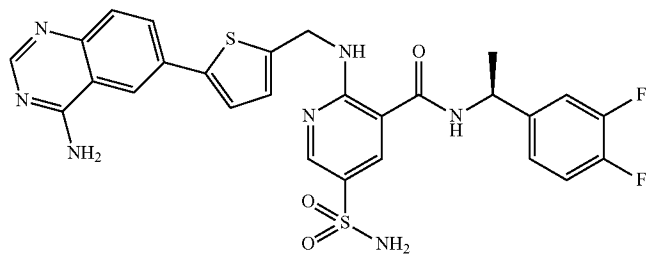 [SMILES: C[C@H](NC(=O)c1cc(S(N)(=O)=O)cnc1NCc1ccc(-c2ccc3ncnc(N)c3c2)s1)c1ccc(F)c(F)c1] | 2-({[5-(4-aminoquinazolin-6-yl)thiophen-2-yl]methyl}amino)-N-[(1S)-1-(3,4-difluorophenyl)ethyl]-5-sulfamoylpyridine-3-carboxamide | 596.3 | ¹H NMR (400 MHz, DMSO-d₆) δ 9.74 (br. s., 2H), 9.25 (d, J = 7.53 Hz, 1H), 9.17 (t, J = 6.02 Hz, 1H), 8.80 (s, 1H), 8.60 (d, J = 2.51 Hz, 2H), 8.44 (d, J = 2.26 Hz, 1H), 8.26 (dd, J = 1.88, 8.66 Hz, 1H), 7.76 (d, J = 8.78 Hz, 1H), 7.53 (d, J = 3.51 Hz, 1H), 7.32-7.49 (m, 2H), 7.16-7.32 (m, 3H), 7.13 (d, J = 3.76 Hz, 1H), 5.02-5.19 (m, 1H), 4.89 (d, J = 5.77 Hz, 2H), 1.47 (d, J = 7.28 Hz, 3H). |
| 8.7.4 | 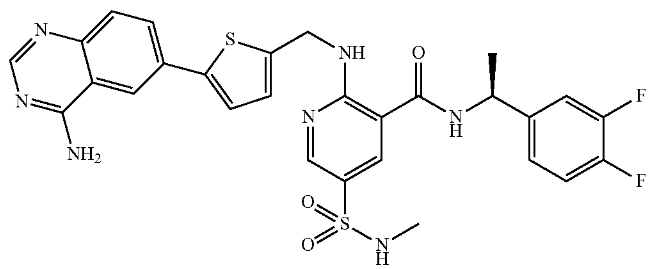 [SMILES: CNS(=O)(=O)c1cnc(NCc2ccc(-c3ccc4ncnc(N)c4c3)s2)c(C(=O)N[C@@H](C)c2ccc(F)c(F)c2)c1] | 2-({[5-(4-aminoquinazolin-6-yl)thiophen-2-yl]methyl}amino)-N-[(1S)-1-(3,4-difluorophenyl)ethyl]-5-(methylsulfamoyl)pyridine-3-carboxamide | 610.3 | ¹H NMR (400 MHz, DMSO-d₆) δ 9.16-9.31 (m, 2H), 8.79 (s, 1H), 8.59 (d, J = 1.76 Hz, 1H), 8.55 (d, J = 2.26 Hz, 1H), 8.39 (d, J = 2.51 Hz, 1H), 8.26 (dd, J = 1.76, 8.78 Hz, 1H), 7.76 (d, J = 8.78 Hz, 1H), 7.54 (d, J = 3.51 Hz, 1H), 7.27-7.50 (m, 3H), 7.24 (br. s., 1H), 7.13 (d, J = 3.51 Hz, 1H), 5.11 (t, J = 7.15 Hz, 1H), 4.90 (d, J = 6.02 Hz, 2H), 2.45 (d, J = 5.02 Hz, 3H), 1.48 (d, J = 7.03 Hz, 3H). |
| 8.7.5 | 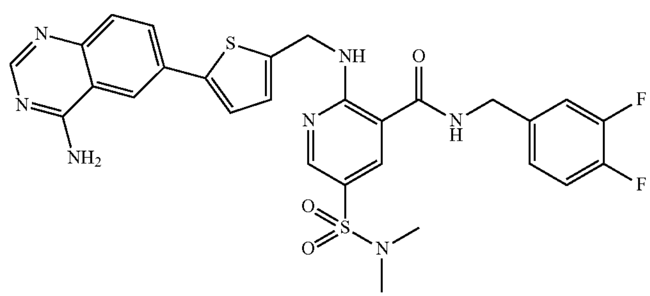 [SMILES: CN(C)S(=O)(=O)c1cnc(NCc2ccc(-c3ccc4ncnc(N)c4c3)s2)c(C(=O)NCc2ccc(F)c(F)c2)c1] | 2-({[5-(4-aminoquinazolin-6-yl)thiophen-2-yl]methyl}amino)-N-(3,4-difluorophenyl)-5-(dimethylsulfamoyl)pyridine-3-carboxamide | 610.3 | ¹H NMR (400 MHz, DMSO-d₆) δ 9.70 (br. s., 2H), 9.44-9.60 (m, 2H), 8.79 (s, 1H), 8.61 (d, J = 1.76 Hz, 2H), 8.55 (d, J = 2.26 Hz, 2H), 8.32-8.37 (m, 1H), 8.27 (dd, J = 1.76, 8.78 Hz, 1H), 7.77 (d, J = 8.53 Hz, 1H), 7.55 (d, J = 3.77 Hz, 1H), 7.34-7.44 (m, 2H), 7.10-7.22 (m, 2H), 4.94 (d, J = 5.52 Hz, 2H), 4.44 (d, J = 5.52 Hz, 2H), 2.64 (s, 6H). |

| Ex. No. | Structure | Chemical Name | ESI-MS (M + H) | ¹H NMR |
|---|---|---|---|---|
| 8.7.6 | 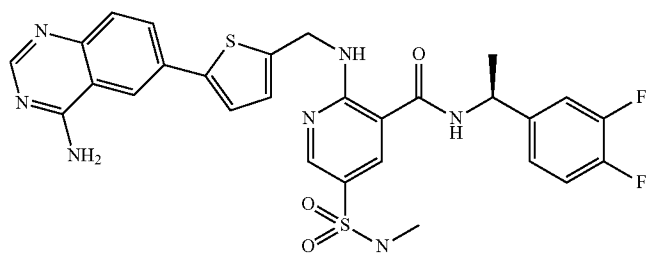 [SMILES: CNS(=O)(=O)c1cnc(NCc2ccc(-c3ccc4ncnc(N)c4c3)s2)c(C(=O)N[C@@H](C)c2ccc(F)c(F)c2)c1] | 2-({[5-(4-aminoquinazolin-6-yl)thiophen-2-yl]methyl}amino)-N-[(1S)-1-(3,4-difluorophenyl)ethyl]-5-(dimethylsulfamoyl)pyridine-3-carboxamide | 624.3 | ¹H NMR (400 MHz, DMSO-d₆) δ 9.72 (br. s., 2H), 9.45 (t, J = 5.90 Hz, 1H), 9.25 (d, J = 7.53 Hz, 1H), 8.79 (s, 1H), 8.60 (d, J = 1.76 Hz, 1H), 8.55 (d, J = 2.26 Hz, 1H), 8.41 (d, J = 2.51 Hz, 1H), 8.26 (dd, J = 2.01, 8.78 Hz, 1H), 7.76 (d, J = 8.78 Hz, 1H), 7.54 (d, J = 3.51 Hz, 1H), 7.34-7.49 (m, 2H), 7.22 (ddd, J = 2.38, 4.33, 6.34 Hz, 1H), 7.14 (d, J = 3.76 Hz, 1H), 5.12 (quin, J = 7.09 Hz, 1H), 4.91 (d, J = 5.27 Hz, 2H), 2.65 (s, 6H), 1.49 (d, J = 7.03 Hz, 3H). |
| 8.7.7 | 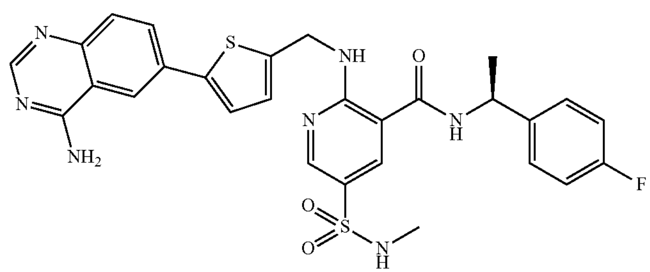 [SMILES: CNS(=O)(=O)c1cnc(NCc2ccc(-c3ccc4ncnc(N)c4c3)s2)c(C(=O)N[C@@H](C)c2ccc(F)cc2)c1] | 2-({[5-(4-aminoquinazolin-6-yl)thiophen-2-yl]methyl}amino)-N-[(1S)-1-(4-fluorophenyl)ethyl]-5-(methylsulfamoyl)pyridine-3-carboxamide | 592.3 | ¹H NMR (400 MHz, DMSO-d₆) δ 9.71 (br., 2H), 9.18-9.33 (m, 2H), 8.79 (s, 1H), 8.60 (d, J = 1.88 Hz, 1H), 8.54 (d, J = 2.32 Hz, 1H), 8.39 (d, J = 2.32 Hz, 1H), 8.26 (dd, J = 1.94, 8.78 Hz, 1H), 7.76 (d, J = 8.78 Hz, 1H), 7.54 (d, J = 3.64 Hz, 1H), 7.37-7.46 (m, 2H), 7.31 (m, 1H), 7.07-7.20 (m, 3H), 5.13 (t, 1H), 4.90 (d, J = 5.65 Hz, 1H), 2.44 (d, J = 5.14 Hz, 3H), 1.48 (d, J = 7.03 Hz, 3H). |
| 8.7.8 | 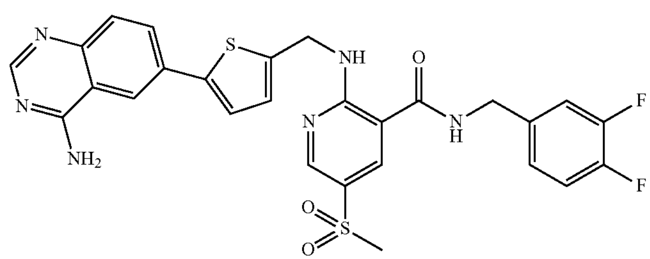 [SMILES: CS(=O)(=O)c1cnc(NCc2ccc(-c3ccc4ncnc(N)c4c3)s2)c(C(=O)NCc2ccc(F)c(F)c2)c1] | 2-({[5-(4-aminoquinazolin-6-yl)thiophen-2-yl]methyl}amino)-N-[(1S)-1-(4-fluorophenyl)ethyl]-5-(methylsulfamoyl)pyridine-3-carboxamide | 581.2 | ¹H NMR (400 MHz, DMSO-d₆) δ 9.44 (dt, J = 5.77, 11.04 Hz, 2H), 8.66 (d, J = 2.26 Hz, 1H), 8.44 (d, J = 2.51 Hz, 1H), 8.42 (d, J = 2.01 Hz, 1H), 8.35 (s, 1H), 7.99 (dd, J = 2.13, 8.66 Hz, 1H), 7.64 (d, J = 8.78 Hz, 1H), 7.47 (d, J = 3.51 Hz, 1H), 7.33-7.45 (m, 2H), 7.14-7.25 (m, 1H), 7.11 (d, J = 3.51 Hz, 1H), 4.93 (d, J = 6.02 Hz, 2H), 4.45 (d, J = 5.77 Hz, 2H), 3.22 (s, 3H). |

TABLE 1-continued

| Ex. No. | Structure | Chemical Name | ESI-MS (M + H) | ¹H NMR |
|---|---|---|---|---|
| 8.7.9 | 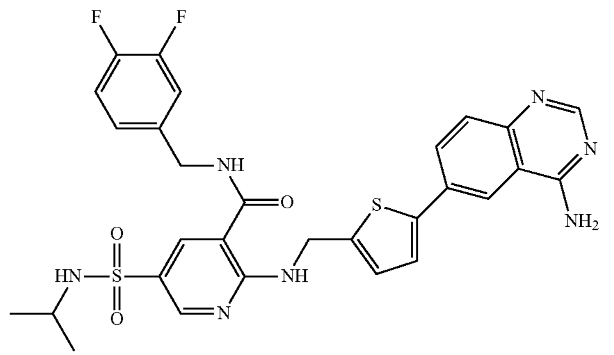 [SMILES: CC(C)NS(=O)(=O)c1cnc(NCc2ccc(-c3ccc4ncnc(N)c4c3)s2)c(C(=O)NCc2ccc(F)c(F)c2)c1] | 2-({[5-(4-aminoquinazolin-6-yl)thiophen-2-yl]methyl}amino)-N-(3,4-difluorobenzyl)-5-(propan-2-ylsulfamoyl)pyridine-3-carboxamide | 624.2 | ¹H NMR (400 MHz, DMSO-$d_6$) δ 9.56 (t, 1H), 9.36 (t, 1H), 8.67 (d, 1H), 8.49 (d, 1H), 8.43 (d, 2H), 8.04 (dd, 1H), 7.72 (dd, 1H), 7.54-7.43 (m, 4H), 7.18 (d, 1H), 4.98 (d, 2H), 4.50 (d, 2H), 3.38-3.33 (m, 1H), 1.06 (d, 6H). |
| 8.7.10 | 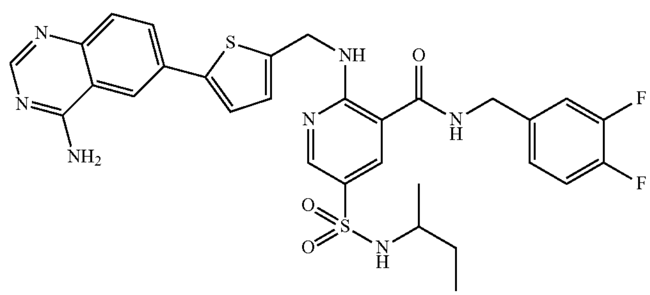 [SMILES: CCC(C)NS(=O)(=O)c1cnc(NCc2ccc(-c3ccc4ncnc(N)c4c3)s2)c(C(=O)NCc2ccc(F)c(F)c2)c1] | 2-({[5-(4-aminoquinazolin-6-yl)thiophen-2-yl]methyl}amino)-5-(butan-2-ylsulfamoyl)-N-(3,4-difluorobenzyl)pyridine-3-carboxamide | 638.2 | ¹H NMR (400 MHz, CD3OD) δ 8.67 (d, 1H), 8.38 (d, 1H), 8.35 (s, 1H), 8.30 (d, 1H), 8.06 (dd, 1H), 7.71 (d, 1H), 7.42 (d, 1H), 7.17-7.30 (m, 3H), 7.08 (d, 1H), 4.96 (s, 2H), 4.51 (s, 2H), 3.19 (q, 1H), 1.42 (m, 2H), 1.04 (d, 3H), 0.82 (t, 3H). |
| 8.7.11 | 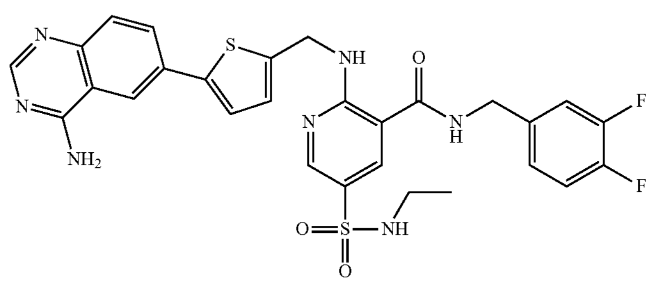 [SMILES: CCNS(=O)(=O)c1cnc(NCc2ccc(-c3ccc4ncnc(N)c4c3)s2)c(C(=O)NCc2ccc(F)c(F)c2)c1] | 2-({[5-(4-aminoquinazolin-6-yl)thiophen-2-yl]methyl}amino)-N-(3,4-difluorobenzyl)-5-(ethylsulfamoyl)pyridine-3-carboxamide | 543.1 | ¹H NMR (400 MHz, DMSO-$d_6$) δ 9.17 (t, 1H), 8.95 (s, 1H), 8.56 (d, 2H), 8.43 (s, 1H), 8.29 (d, 1H), 8.18 (br, 2H), 7.53-7.59 (m, 2H), 7.40 (q, 1H), 7.24 (br, 1H), 7.12 (d, 1H), 6.69 (d, 1H), 5.93 (q, 1H), 4.90-4.96 (m, 2H), 1.81 (d, 3H). |

TABLE 1-continued

| Ex. No. | Structure | Chemical Name | ESI-MS (M + H) | ¹H NMR |
|---|---|---|---|---|
| 8.7.12 | 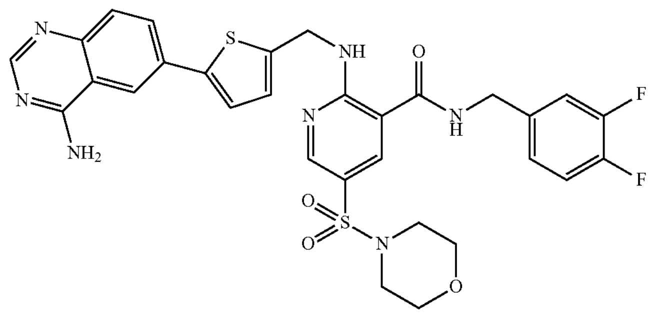 [SMILES: Nc1ncnc2ccc(-c3ccc(CNc4ncc(S(=O)(=O)N5CCOCC5)cc4C(=O)NCc4ccc(F)c(F)c4)s3)cc12] | 2-(((5-(4-aminoquinazolin-6-yl)thiophen-2-yl)methyl)amino)-N-(3,4-difluorobenzyl)-5-(morpholinosulfonyl)nicotinamide | 651.8 | ¹H NMR (400 MHz, DMSO-d₆) δ 9.51-9.49 (m, 2H), 8.55 (s, 1H), 8.43 (s, 1H), 8.35 (s, 1H), 8.30 (s, 1H), 7.98 (d, 1H), 7.87 (br, 2H), 7.64 (d, 1H), 7.48 (d, 1H), 7.40 (q, 2H), 7.12 (s, 1H), 7.12 (d, 1H), 4.93 (d, 2H), 4.44 (d, 2H), 3.66 (s, 4H), 2.93 (s, 4H). |
| 8.7.13 | 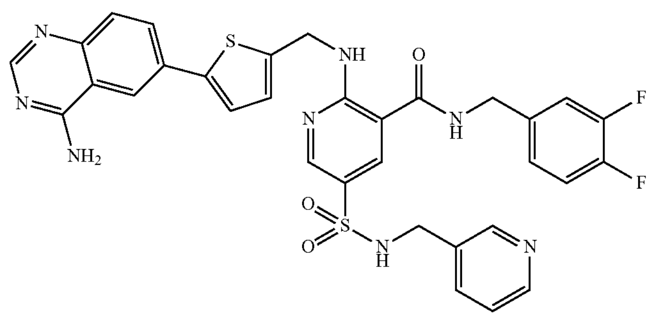 [SMILES: Nc1ncnc2ccc(-c3ccc(CNc4ncc(S(=O)(=O)NCc5cccnc5)cc4C(=O)NCc4ccc(F)c(F)c4)s3)cc12] | 2-(((5-(4-aminoquinazolin-6-yl)thiophen-2-yl)methyl)amino)-N-(3,4-difluorobenzyl)-5-(N-(pyridin-3-ylmethyl)sulfamoyl)nicotinamide | 672.8 | ¹H NMR (400 MHz, DMSO-d₆) δ 9.44 (t, 1H), 9.35 (t, 1H), 8.55 (s, 1H), 8.46 (s, 2H), 8.41 (s, 2H), 8.31 (d, 1H), 8.20 (br, 2H), 8.12 (t, 1H), 8.03 (dd, 1H), 7.67 (s, 1H), 7.49 (d, 1H), 7.42-7.37 (m, 2H), 7.25 (q, 1H), 7.19 (s, 1H), 7.11 (d, 1H), 4.89 (d, 2H), 4.43 (d, 2H), 4.09 (d, 2H). |
| 8.8.1 | 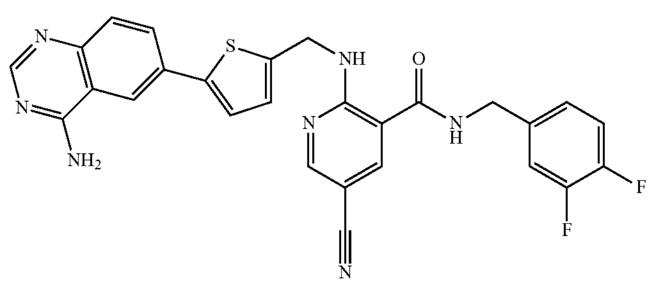 [SMILES: N#Cc1cnc(NCc2ccc(-c3ccc4ncnc(N)c4c3)s2)c(C(=O)NCc2ccc(F)c(F)c2)c1] | 2-(((5-(4-aminoquinazolin-6-yl)thiophen-2-yl)methyl)amino)-5-cyano-N-(3,4-difluorobenzyl)nicotinamide | 528.3 | ¹H NMR (300 MHz, DMSO-d₆) δ 9.67 (s, 2H), 9.40-9.48 (m, 1H), 9.24-9.34 (m, J = 5.29 Hz, 2H), 8.77 (s, 1H), 8.66 (d, J = 1.89 Hz, 1H), 8.59 (s, 1H), 8.44 (d, J = 1.89 Hz, 1H), 8.25 (d, J = 8.69 Hz, 1H), 7.76 (d, J = 8.69 Hz, 1H), 7.54 (d, J = 3.78 Hz, 1H), 7.31-7.49 (m, 2H), 7.09-7.24 (m, 2H), 4.92 (d, J = 5.29 Hz, 2H), 4.43 (d, J = 5.29 Hz, 2H). |

| Ex. No. | Structure | Chemical Name | ESI-MS (M + H) | ¹H NMR |
|---|---|---|---|---|
| 8.8.2 | 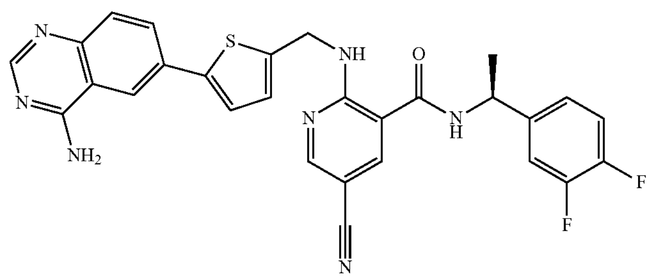 [SMILES: C[C@H](NC(=O)c1cc(C#N)cnc1NCc1ccc(-c2ccc3ncnc(N)c3c2)s1)c1ccc(F)c(F)c1] | 2-({[5-(4-aminoquinazolin-6-yl)thiophen-2-yl]methyl}amino)-N-[(1S)-1-(3,4-difluorophenyl)ethyl]pyridine-3-carboxamide | 542.3 | ¹H NMR (400 MHz, DMSO-d₆) δ 9.68-9.89 (m, 2H), 9.37 (t, J = 6.15 Hz, 1H), 9.03 (d, J = 7.03 Hz, 1H), 8.80 (s, 1H), 8.66 (d, J = 2.01 Hz, 1H), 8.60 (d, J = 1.76 Hz, 1H), 8.53 (d, J = 2.01 Hz, 1H), 8.26 (dd, J = 1.76, 8.78 Hz, 1H), 7.77 (d, J = 8.78 Hz, 1H), 7.54 (d, J = 3.76 Hz, 1H), 7.33-7.50 (m, 2H), 7.19-7.28 (m, 1H), 7.12 (d, J = 3.51 Hz, 1H), 5.07 (quin, J = 7.03 Hz, 1H), 4.89 (d, J = 6.02 Hz, 2H), 1.46 (d, J = 7.03 Hz, 3H). |
| 8.8.3 | 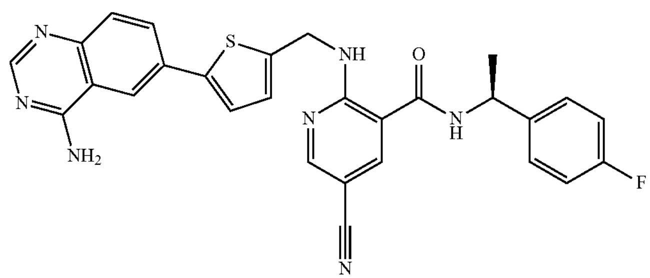 [SMILES: C[C@H](NC(=O)c1cc(C#N)cnc1NCc1ccc(-c2ccc3ncnc(N)c3c2)s1)c1ccc(F)cc1] | 2-({[5-(4-aminoquinazolin-6-yl)thiophen-2-yl]methyl]amino)-N-[(1S)-5-cyano-N-[(1S)-1-(4-fluorophenyl)ethyl]pyridine-3-carboxamide | 524.3 | ¹H NMR (300 MHz, DMSO-d₆) δ 9.59-9.86 (m, 2H), 9.41 (t, J = 6.04 Hz, 1H), 9.02 (d, J = 7.18 Hz, 1H), 8.78 (s, 1H), 8.65 (d, J = 1.89 Hz, 1H), 8.59 (s, 1H), 8.51 (d, J = 1.89 Hz, 1H), 8.25 (dd, J = 1.32, 8.88 Hz, 1H), 7.77 (d, J = 8.69 Hz, 1H), 7.53 (d, J = 3.78 Hz, 1H), 7.42 (dd, J = 5.67, 8.69 Hz, 2H), 7.07-7.22 (m, 3H), 5.08 (quin, J = 6.99 Hz, 1H), 4.89 (d, J = 5.67 Hz, 2H), 1.46 (d, J = 7.18 Hz, 3H). |
| 8.8.4 | 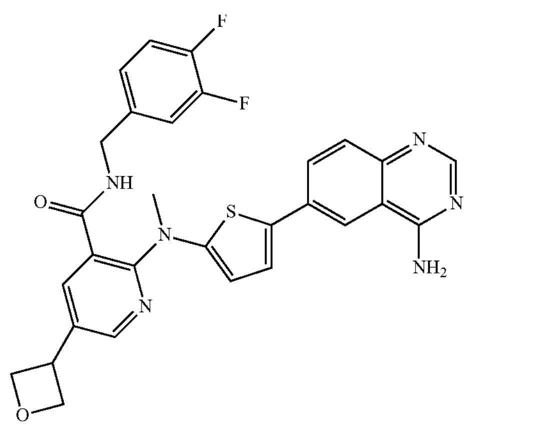 [SMILES: CN(c1ccc(-c2ccc3ncnc(N)c3c2)s1)c1ncc(C2COC2)cc1C(=O)NCc1ccc(F)c(F)c1] | 2-(5-(4-aminoquinazolin-6-yl)methylamino)-N-(3,4-difluoro benzyl)-5-(oxetan-3-yl)nicotinamide | 559.20 | ¹H NMR (400 MHz, DMSO-d₆) δ ppm 9.27 (t, J = 5.77 Hz, 1 H) 8.80 (s, 2 H) 8.59 (s, 1 H) 8.21-8.32 (m, 2 H) 8.18 (d, J = 2.26 Hz, 1 H) 7.76 (d, J = 8.78 Hz, 1 H) 7.53 (d, J = 3.51 Hz, 1 H) 7.30-7.46 (m, 2 H) 7.06-7.23 (m, 2 H) 4.79-4.94 (m, 4 H) 4.68 (t, J = 6.53 Hz, 2 H) 4.36-4.50 (m, 2 H) 4.22 (d, J = 8.03 Hz, 1 H). |

TABLE 1-continued

| Ex. No. | Structure | Chemical Name | ESI-MS (M + H) | $^1$H NMR |
|---|---|---|---|---|
| 8.9 | 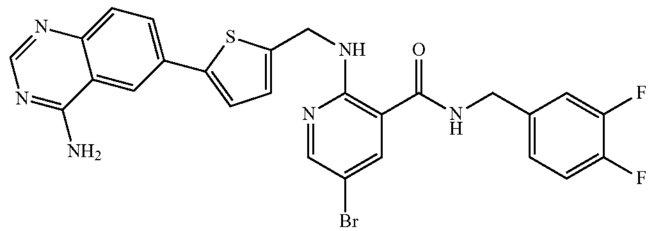 [SMILES: Nc1ncnc2ccc(-c3ccc(CNc4ncc(Br)cc4C(=O)NCc4ccc(F)c(F)c4)s3)cc12] | 2-({[5-(4-aminoquinazolin-6-yl)thiophen-2-yl]methyl}amino)-N-(3,4-difluorobenzyl)-5-bromopyridine-3-carboxamide | 581.1 | $^1$H NMR (300 MHz, DMSO-d$_6$) δ 9.77 (br s, 1H), 9.69 (br s, 1H), 9.26 (t, J = 5.7 Hz, 1H), 8.86 (t, J = 5.8 Hz, 1H), 8.78 (s, 1H), 8.59 (d, J = 1.5 Hz, 1H), 8.33 (d, J = 2.1 Hz, 1H), 8.28 (d, J = 2.1 Hz, 1H), 8.26 (dd, J = 9.6; 1.8 Hz, 1H), 7.76 (d, J = 9.0 Hz, 1H), 7.53 (d, J = 3.9 Hz, 1H), 7.15-7.01 (m, 4H), 4.83 (d, J = 5.4 Hz, 2H), 4.44 (d, J = 5.7 Hz, 2H). |
| 8.10 | 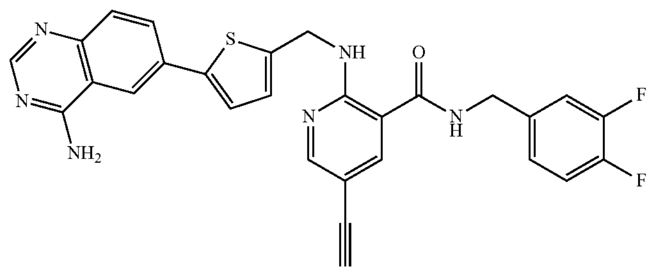 [SMILES: C#Cc1cnc(NCc2ccc(-c3ccc4ncnc(N)c4c3)s2)c(C(=O)NCc2ccc(F)c(F)c2)c1] | 2-({5-(4-aminoquinazolin-6-yl)thiophen-2-yl)methyl}amino)-N-(3,4-difluorobenzyl)-5-ethynylnicotinamide | 527.3 | $^1$H NMR (300 MHz, CD$_3$OD) δ 8.35-8.31 (m, 3H), 8.04 (s, 1H), 8.03 (dd, J = 9.6; 2.1 Hz, 1H), 7.68 (d, J = 8.7 Hz, 1H), 7.38 (d, J = 3.9 Hz, 1H), 7.04 (d, J = 3.9 Hz, 1H), 6.98-6.89 (m, 2H), 6.80 (tt, J = 9.1; 2.3 Hz, 1H), 4.89 (s, 2H), 4.50 (s, 2H), 3.49 (s, 1H). |
| 8.11 | 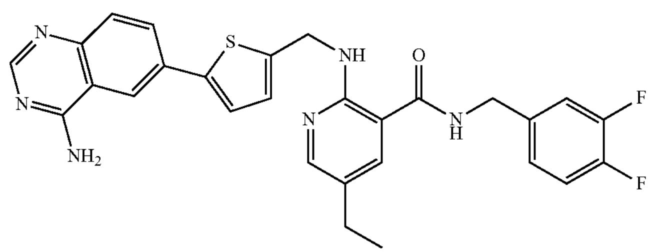 [SMILES: CCc1cnc(NCc2ccc(-c3ccc4ncnc(N)c4c3)s2)c(C(=O)NCc2ccc(F)c(F)c2)c1] | 2-({[5-(4-aminoquinazolin-6-yl)thiophen-2-yl]methyl}amino)-N-(3,4-difluorobenzyl)-5-ethylpyridine-3-carboxamide | 529.3 | $^1$H NMR (300 MHz, DMSO-d$_6$) δ 9.86 (br s, 1H), 9.77 (br s, 1H), 9.16 (t, J = 5.6 Hz, 1H), 8.80 (s, 1H), 8.68 (t, J = 6.0 Hz, 1H), 8.60 (d, J = 1.5 Hz, 1H), 8.27 (dd, J = 8.7; 1.5 Hz, 1H), 8.12 (d, J = 1.8 Hz, 1H), 7.97 (d, J = 1.8 Hz, 1H), 7.76 (d, J = 8.7 Hz, 1H), 7.54 (d, J = 3.6 Hz, 1H), 7.16-7.06 (m, 2H), 7.06-6.97 (m, 2H), 4.84 (d, J = 3.9 Hz, 2H), 4.46 (d, J = 5.7 Hz, 2H), 1.19 (t, J = 7.5 Hz, 3H). (Missing 2Hs buried under DMSO peak). |
| 8.12.1 | 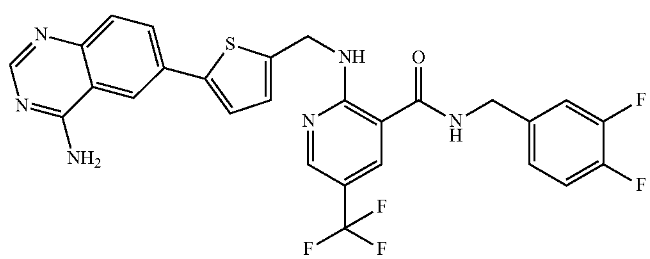 [SMILES: Nc1ncnc2ccc(-c3ccc(CNc4ncc(C(F)(F)F)cc4C(=O)NCc4ccc(F)c(F)c4)s3)cc12] | 2-(((5-(4-aminoquinazolin-6-yl)thiophen-2-yl)methyl)amino)-N-(3,4-difluorobenzyl)-5-(trifluoromethyl)nicotinamide | 571.2 | $^1$H NMR (400 MHz, DMSO-d$_6$) δ 9.70 (br. s., 2H), 9.23-9.46 (m, 2H), 8.79 (s, 1H), 8.59 (dd, J = 1.51, 7.03 Hz, 2H), 8.38 (d, J = 2.01 Hz, 1H), 8.27 (dd, J = 2.01, 8.78 Hz, 1H), 7.76 (d, J = 8.78 Hz, 1H), 7.54 (d, J = 3.76 Hz, 1H), 7.29-7.47 (m, 2H), 7.07-7.24 (m, 2H), 4.92 (d, J = 5.77 Hz, 2H), 4.44 (d, J = 5.52 Hz, 2H). |

TABLE 1-continued

| Ex. No. | Structure | Chemical Name | ESI-MS (M + H) | 1H NMR |
|---|---|---|---|---|
| 8.12.2 | 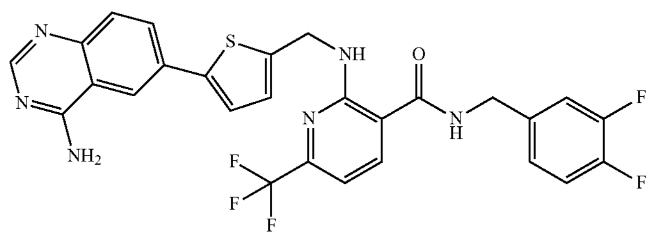 [SMILES: Nc1ncnc2ccc(-c3ccc(CNc4nc(C(F)(F)F)ccc4C(=O)NCc4ccc(F)c(F)c4)s3)cc12] | 2-({[5-(4-aminoquinazolin-6-yl)thiophen-2-yl]methyl}amino)-N-(3,4-difluorobenzyl)-6-(trifluoromethyl)pyridine-3-carboxamide | 571.2 | 1H NMR (400 MHz, DMSO-$d_6$) δ 9.61 (br. s., 2H), 9.36 (s, 1H), 8.91 (s, 1H), 8.75 (s, 1H), 8.60 (d, J = 1.76 Hz, 1H), 8.10-8.32 (m, 2H), 7.76 (d, J = 8.78 Hz, 1H), 7.53 (d, J = 3.76 Hz, 1H), 7.31-7.46 (m, 2H), 7.04-7.25 (m, 3H), 4.84 (d, J = 5.77 Hz, 2H), 4.44 (d, J = 5.77 Hz, 2H). |
| 8.12.3 | 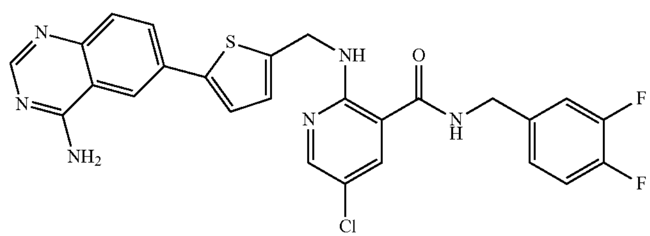 [SMILES: Nc1ncnc2ccc(-c3ccc(CNc4ncc(Cl)cc4C(=O)NCc4ccc(F)c(F)c4)s3)cc12] | 2-({[5-(4-aminoquinazolin-6-yl)thiophen-2-yl]methyl}amino)-5-chloro-N-(3,4-difluorobenzyl)pyridine-3-carboxamide | 537.2 | 1H NMR (400 MHz, DMSO-$d_6$) δ 9.37 (t, J = 5.77 Hz, 1H), 8.76 (s, 1H), 8.58 (d, J = 1.76 Hz, 1H), 8.22-8.29 (m, 1H), 8.03 (s, 2H), 7.75 (d, J = 8.78 Hz, 1H), 7.67 (s, 1H), 7.58 (d, J = 3.51 Hz, 1H), 7.33-7.45 (m, 2H), 7.20 (d, J = 3.76 Hz, 2H), 4.73-4.78 (m, 2H), 4.40-4.46 (m, 2H). |
| 8.12.4 | 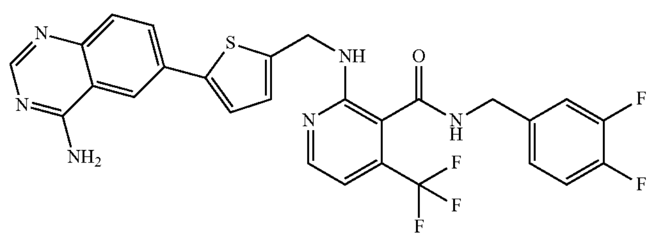 [SMILES: Nc1ncnc2ccc(-c3ccc(CNc4nccc(C(F)(F)F)c4C(=O)NCc4ccc(F)c(F)c4)s3)cc12] | 2-({[5-(4-aminoquinazolin-6-yl)thiophen-2-yl]methyl}amino)-N-(3,4-difluorobenzyl)-4-(trifluoromethyl)pyridine-3-carboxamide | 571.2 | 1H NMR (400 MHz, DMSO-$d_6$) δ 9.64 (br. s., 2H), 9.18 (t, J = 5.90 Hz, 1H), 8.77 (s, 1H), 8.60 (d, J = 1.76 Hz, 1H), 8.32 (d, J = 4.77 Hz, 1H), 8.22 (dd, J = 2.01, 8.78 Hz, 1H), 7.77 (d, J = 8.78 Hz, 1H), 7.53 (d, J = 3.51 Hz, 1H), 7.28-7.46 (m, 2H), 7.03-7.28 (m, 3H), 6.87 (d, J = 5.52 Hz, 1H), 4.78 (d, J = 5.77 Hz, 2H), 4.45 (d, J = 5.77 Hz, 2H). |
| 8.12.5 | 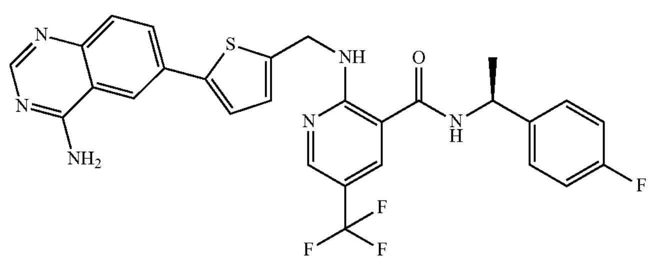 [SMILES: C[C@H](NC(=O)c1cc(C(F)(F)F)cnc1NCc1ccc(-c2ccc3ncnc(N)c3c2)s1)c1ccc(F)cc1] | 2-({[5-(4-aminoquinazolin-6-yl)thiophen-2-yl]methyl}amino)-N-[(1S)-1-(4-fluorophenyl)ethyl]-5-(trifluoromethyl)pyridine-3-carboxamide | 567.3 | 1H NMR (400 MHz, DMSO-$d_6$) δ 9.79 (br. s., 2H), 9.31 (t, J = 6.02 Hz, 1H), 9.13 (d, J = 7.53 Hz, 1H), 8.81 (s, 1H), 8.58 (dd, J = 1.63, 13.93 Hz, 2H), 8.44 (d, J = 2.01 Hz, 1H), 8.27 (dd, J = 1.76, 8.78 Hz, 1H), 7.77 (d, J = 8.78 Hz, 1H), 7.54 (d, J = 3.51 Hz, 1H), 7.32-7.47 (m, 2H), 7.03-7.23 (m, 3H), 5.12 (quin, J = 7.03 Hz, 1H), 4.89 (d, J = 5.77 Hz, 2H). |

TABLE 1-continued

| Ex. No. | Structure | Chemical Name | ESI-MS (M + H) | ¹H NMR |
|---|---|---|---|---|
| 8.12.6 | 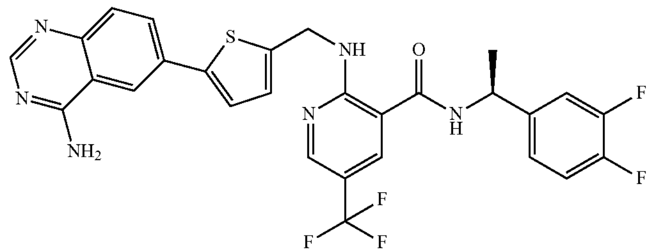 [SMILES: C[C@H](NC(=O)c1cc(C(F)(F)F)cnc1NCc1ccc(-c2ccc3ncnc(N)c3c2)s1)c1ccc(F)c(F)c1] | 2-({[5-(4-aminoquinazolin-6-yl)thiophen-2-yl]methyl}amino)-N-[(1S)-1-(3,4-difluorophenyl)ethyl]-5-(trifluoromethyl)pyridine-3-carboxamide | 585.4 | ¹H NMR (400 MHz, DMSO-d₆) δ 9.77 (br. s., 2H), 9.27 (t, J = 6.02 Hz, 1H), 9.11 (d, J = 7.28 Hz, 1H), 8.80 (s, 1H), 8.58 (dd, J = 1.51, 10.29 Hz, 2H), 8.45 (d, J = 2.01 Hz, 1H), 8.27 (dd, J = 1.76, 8.78 Hz, 1H), 7.76 (d, J = 8.78 Hz, 1H), 7.54 (d, J = 3.76 Hz, 1H), 7.29-7.50 (m, 2H), 7.22 (ddd, J = 2.01, 4.27, 6.27 Hz, 1H), 7.13 (d, J = 3.76 Hz, 1H), 5.10 (quin, J = 7.09 Hz, 1H), 4.89 (d, J = 5.77 Hz, 2H). |
| 8.12.7 | 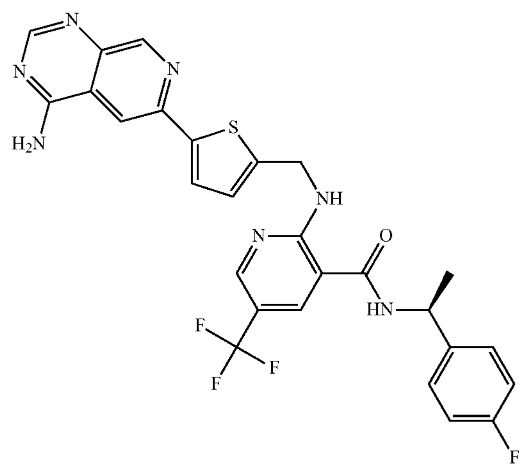 [SMILES: C[C@H](NC(=O)c1cc(C(F)(F)F)cnc1NCc1ccc(-c2cc3c(N)ncnc3cn2)s1)c1ccc(F)cc1] | 2-({[5-(4-aminopyrido[3,4-d]pyrimidin-6-yl)thiophen-2-yl]methyl}amino)-N-[(1S)-1-(4-fluorophenyl)ethyl]-5-(trifluoromethyl)pyridine-3-carboxamide | 568.2 | ¹H NMR (400 MHz, CDCl₃) δ 9.28 (t, 1H), 8.96 (s, 1H), 8.59 (s, 1H), 8.55 (d, 1H), 8.45 (s, 1H), 8.17 (bs, 2H), 7.57 (d, 1H), 7.41 (m, 2H), 7.16 (m, 3H), 5.12 (m, 1H), 4.86 (m, 2H), 1.47 (d, 3). |

TABLE 1-continued

| Ex. No. | Structure | Chemical Name | ESI-MS (M + H) | ¹H NMR |
|---|---|---|---|---|
| 8.12.8 | 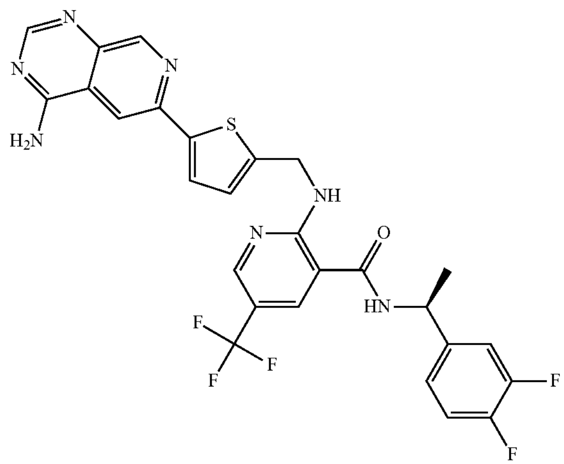 [SMILES: C[C@H](NC(=O)c1cc(C(F)(F)F)cnc1NCc1ccc(-c2cc3c(N)ncnc3cn2)s1)c1ccc(F)c(F)c1] | 2-({[5-(4-aminopyrido[3,4-d]pyrimidin-6-yl)thiophen-2-yl]methyl}amino)-N-[(1S)-1-(3,4-difluorophenyl)ethyl]-5-(trifluoromethyl)pyridine-3-carboxamide | 586.1 | ¹H NMR (400 MHz, CDCl₃) δ 9.26 (t, 1H), 9.17 (d, 1H), 9.97 (s, 1H), 8.60 (d, 1H), 8.59 (m, 1H), 8.45-8.44 (m, 1H), 8.19 (bs, 2H), 7.57 (d, 1H), 7.45-7.35 (m, 2H), 7.21 (bs, 1H), 7.10 (d, 1H), 5.10 (m, 1), 4.87 (m, 2H), 1.48 (d, 3). |
| 8.13 | 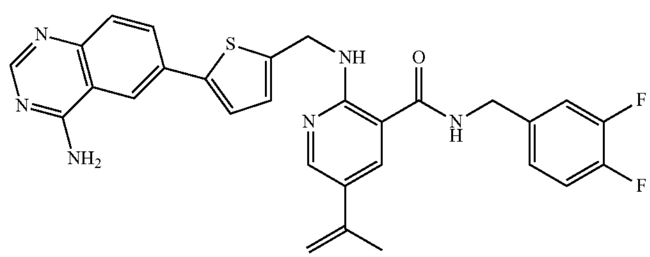 | 2-({[5-(4-aminoquinazolin-6-yl)thiophen-2-yl]methyl}amino)-N-(3,4-difluorobenzyl)-5-(prop-1-en-2-yl)pyridine-3-carboxamide | 543.2 | — |

TABLE 1-continued

| Ex. No. | Structure | Chemical Name | ESI-MS (M + H) | ¹H NMR |
|---|---|---|---|---|
| 8.14.1 | 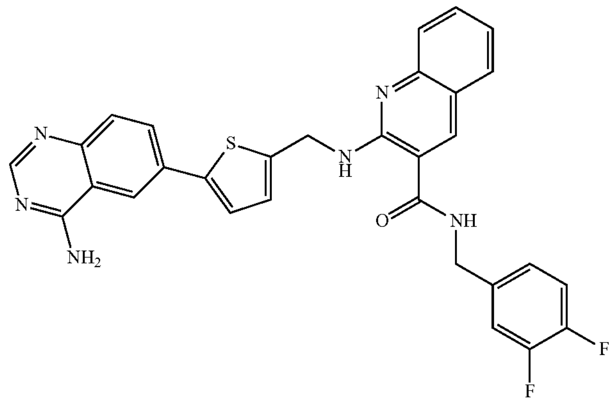 [SMILES: Nc1ncnc2ccc(-c3ccc(CNc4nc5ccccc5cc4C(=O)NCc4ccc(F)c(F)c4)s3)cc12] | 2-({[5-(4-aminoquinazolin-6-yl)thiophen-2-yl]methyl}amino)-N-(3,4-difluorobenzyl)quinoline-3-carboxamide | 553.3 | ¹H NMR (400 MHz, DMSO-d₆) δ 9.77 (br. s., 1H), 9.72 (br. s., 1H), 9.64-9.81 (m, 1H), 9.36 (t, J = 5.71 Hz, 1H), 8.73 (s, 1H), 8.72 (s, 1H), 8.54 (d, J = 1.88 Hz, 1H), 8.51 (s, 1H), 8.17 (dd, J = 1.95, 8.78 Hz, 1H), 7.70 (dd, J = 5.46, 7.97 Hz, 2H), 7.58 (d, J = 3.51 Hz, 2H), 7.29-7.41 (m, 2H), 7.19-7.26 (m, 1H), 7.11-7.18 (m, 2H), 4.90 (d, J = 5.46 Hz, 2H), 4.41 (d, J = 5.84 Hz, 2H). |
| 8.14.2 | 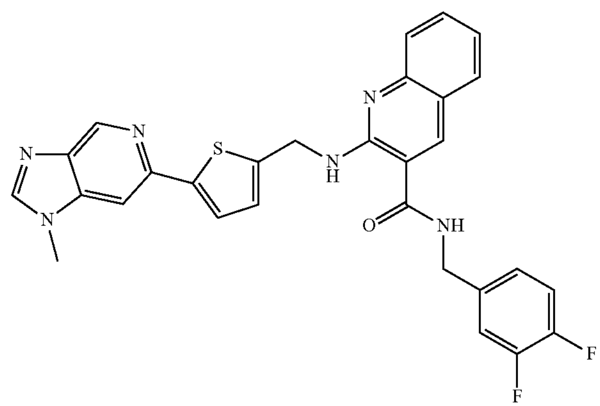 [SMILES: Cn1cnc2cnc(-c3ccc(CNc4nc5ccccc5cc4C(=O)NCc4ccc(F)c(F)c4)s3)cc21] | N-(3,4-difluorobenzyl)-2-({[5-(1-methyl-1H-imidazo[4,5-c]pyridin-6-yl)thiophen-2-yl]methyl}aminoquinoline-3-carboxamide | 541.3 | ¹H NMR (400 MHz, CD₃OD) δ 8.95 (s, 1H), 8.84 (s, 1H), 8.50 (s, 1H), 8.19 (d, J = 0.94 Hz, 1H), 7.89 (dd, 1H), 7.83-8.02 (m, 2H), 7.72 (d, J = 3.76 Hz, 1H), 7.52-7.60 (m, OH), 7.30-7.37 (m, 2H), 7.16-7.21 (m, 2H), 5.13 (s, 2H), 4.56 (s, 2H), 4.00 (s, 3H). |

TABLE 1-continued

| Ex. No. | Structure | Chemical Name | ESI-MS (M + H) | ¹H NMR |
|---|---|---|---|---|
| 8.14.3 | 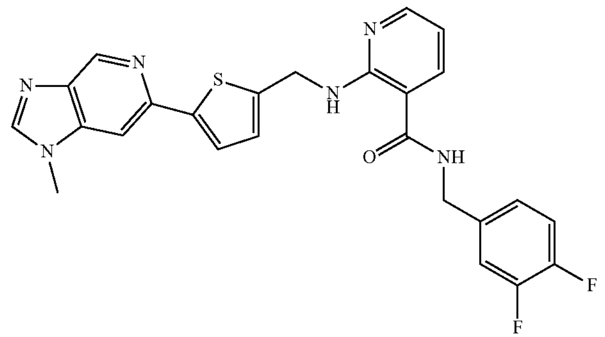 [SMILES: Cn1cnc2cnc(-c3ccc(CNc4ncccc4C(=O)NCc4ccc(F)c(F)c4)s3)cc21] | N-(3,4-difluorobenzyl)-2-({[5-(1-methyl-1H-imidazo[4,5-c]pyridin-6-yl)thiophen-2-yl]methyl}amino)pyridine-3-carboxamide | 491.2 | ¹H NMR (400 MHz, CD₃OD) δ 9.09 (s, 1H), 8.72 (s, 1H), 8.37 (dd, J = 1.60, 7.62 Hz, 1H), 8.30 (s, 1H), 8.16 (d, 1H), 7.77 (d, J = 3.83 Hz, 1H), 7.29 (d, J = 3.89 Hz, 1H), 6.89-7.01 (m, 3H), 6.82 (tt, J = 2.40, 9.14 Hz, 1H), 5.00 (s, 2H), 4.55 (s, 2H), 3.31 (s, 3H), 1.20-1.33 (m, 4H). |
| 8.14.4 | 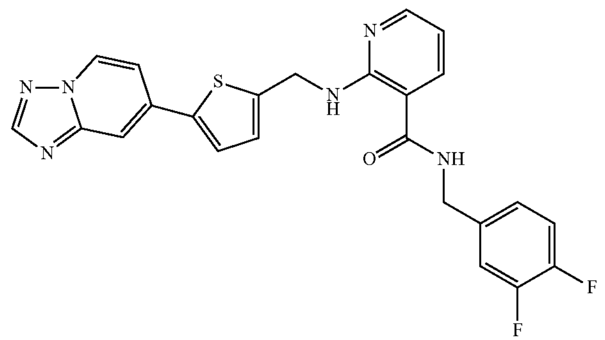 [SMILES: O=C(NCc1ccc(F)c(F)c1)c1cccnc1NCc1ccc(-c2ccn3ncnc3c2)s1] | N-(3,4-difluorobenzyl)-2-({[5-([1,2,4]triazolo[1,5-a]pyridin-7-yl)thiophen-2-yl]methyl}amino)pyridine-3-carboxamide | 477.2 | ¹H NMR (400 MHz, CD₃OD) δ 8.76 (dd, 1H), 8.43 (s, 1H), 8.23-8.28 (m, 1H), 8.15-8.17 (m, 1H), 7.88-7.91 (m, 1H), 7.60 (d, J = 3.76 Hz, 1H), 7.49-7.54 (m, 1H), 7.18 (d, J = 3.76 Hz, 1H), 6.94-7.04 (m, 2H), 6.88-6.94 (m, 1H), 6.78-6.87 (m, 1H), 4.93 (s, 2H), 4.55 (s, 2H). |
| 8.15.1 | 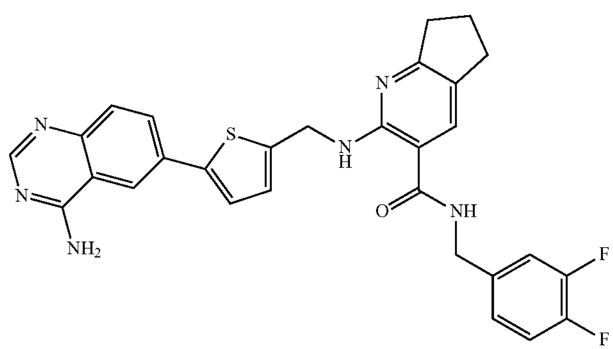 [SMILES: Nc1ncnc2ccc(-c3ccc(CNc4nc5c(cc4C(=O)NCc4ccc(F)c(F)c4)CCC5)s3)cc12] | 2-({[5-(4-aminoquinazolin-6-yl)thiophen-2-yl]methyl}amino)-N-(3,4-difluorobenzyl)-6,7-dihydro-5H-cyclopenta[b]pyridine-3-carboxamide | 543.3 | ¹H NMR (400 MHz, CD₃OD) δ 8.63 (s, 1H), 8.54 (d, J = 1.88 Hz, 1H), 8.24 (dd, J = 1.94, 8.78 Hz, 1H), 8.14 (s, 1H), 7.75 (d, J = 8.78 Hz, 1H), 7.50 (d, J = 3.70 Hz, 1H), 7.05-7.17 (m, 3H), 6.96-7.03 (m, 1H), 4.83-4.95 (m, 12H), 4.56 (s, 2H), 3.25-3.37 (m, 2H), 3.04 (t, J = 7.75 Hz, 2H), 2.91 (t, J = 7.47 Hz, 2H), 2.15-2.28 (m, 2H). |

TABLE 1-continued

| Ex. No. | Structure | Chemical Name | ESI-MS (M + H) | ¹H NMR |
|---|---|---|---|---|
| 8.15.2 | 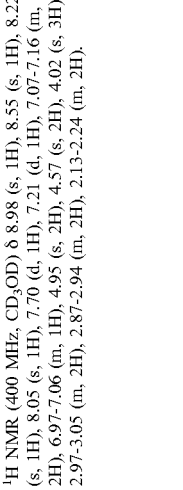 | N-(3,4-difluorobenzyl)-2-({[5-(1-methyl-1H-imidazo[4,5-c]pyridin-6-yl)thiophen-2-yl]methyl}amino)-6,7-dihydro-5H-cyclopenta[b]pyridine-3-carboxamide | 531.1 | ¹H NMR (400 MHz, CD₃OD) δ 8.98 (s, 1H), 8.55 (s, 1H), 8.22 (s, 1H), 8.05 (s, 1H), 7.70 (d, 1H), 7.21 (d, 1H), 7.07-7.16 (m, 2H), 6.97-7.06 (m, 1H), 4.95 (s, 2H), 4.57 (s, 2H), 4.02 (s, 3H), 2.97-3.05 (m, 2H), 2.87-2.94 (m, 2H), 2.13-2.24 (m, 2H). |
| 9.1 | 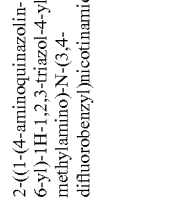 | 2-((1-(4-aminoquinazolin-6-yl)-1H-1,2,3-triazol-4-yl)methylamino)-N-(3,4-difluorobenzyl)nicotinamide | 488.3 | ¹H NMR (300 DMSO-d₆) δ 9.90 (br s, 1H), 9.17 (s, 1H), 8.97 (s, 1H), 8.88 (s, 2H), 8.66 (s, 1H), 8.56 (d, J = 8.7 Hz, 1H), 8.23 (d, J = 3.0 Hz, 1H), 8.08 (d, J = 7.5 Hz, 1H), 7.96 (d, J = 8.7 Hz, 1H), 7.46-7.29 (m, 2H), 7.17 (br s, 1H), 6.69 (t, J = 5.8 Hz, 1H), 4.81 (s, 2H), 4.42 (d, J = 4.5 Hz, 2H |
| 9.2 | 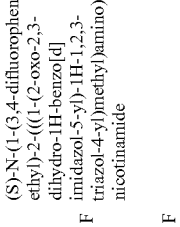 | (S)-N-(1-(3,4-difluorophenyl)ethyl)-2-((1-(2-oxo-2,3-dihydro-1H-benzo[d]imidazol-5-yl)-1H-1,2,3-triazol-4-yl)methyl)amino)nicotinamide | 491.2 | ¹H NMR (300 MHz, DMSO-d₆) δ 10.89 (br. s., 2H), 8.81 (d, J = 7.55 Hz, 1H), 8.61 (t, J = 5.10 Hz, 1H), 8.53 (s, 1H), 8.22 (dd, J = 1.70, 4.72 Hz, 1H), 8.10 (dd, J = 1.70, 7.74 Hz, 1H), 7.30-7.50 (m, 4H), 7.16-7.26 (m, 1H), 7.04 (d, J = 9.06 Hz, 1H), 6.66 (dd, J = 4.72, 7.74 Hz, 1H), 5.10 (quin, J = 7.18 Hz, 1H), 4.60-4.76 (m, 2H), 1.44 (d, J = 6.80 Hz, 3H). |
| 10.1 | 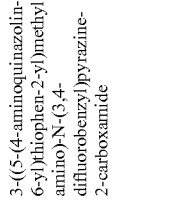 | 3-((5-(4-aminoquinazolin-6-yl)thiophen-2-yl)methyl)amino)-N-(3,4-difluorobenzyl)pyrazine-2-carboxamide | 504.2 | ¹H NMR (300 MHz, DMSO-d₆) δ 9.49 (t, J = 6.1 Hz, 1H), 9.12 (t, J = 5.8 Hz, 1H), 8.40 (d, J = 1.8 Hz, 1H), 8.36 (d, J = 2.1 Hz, 1H), 8.34 (s, 1H), 7.98 (dd, J = 8.7; 1.8 Hz, 1H), 7.89 (d, J = 2.1 Hz, 1H), 7.84 (br s, 2H), 7.64 (d, J = 8.7 Hz, 1H), 7.47 (d, J = 3.6 Hz, 1H), 7.42-7.31 (m, 2H), 7.20-7.13 (m, 1H), 7.10 (d, J = 3.6 Hz, 1H), 4.86 (d, J = 6.0 Hz, 2H), 4.42 (d, J = 6.0 Hz, 2H). |

| Ex. No. | Structure | Chemical Name | ESI-MS (M + H) | ¹H NMR |
|---|---|---|---|---|
| 10.2 | 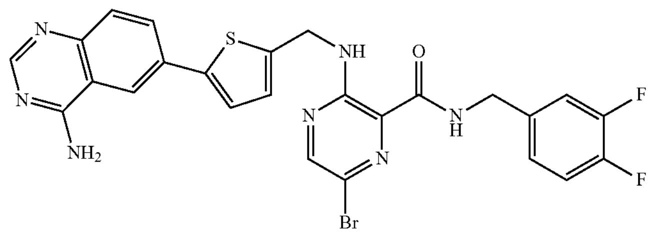 [SMILES: Nc1ncnc2ccc(-c3ccc(CNc4ncc(Br)nc4C(=O)NCc4ccc(F)c(F)c4)s3)cc12] | 3-({[5-(4-aminoquinazolin-6-yl)thiophen-2-yl]methyl}amino)-6-bromo-N-(3,4-difluorobenzyl)pyrazine-2-carboxamide | 582.2 | ¹H NMR (300 MHz, DMSO-d₆) δ 9.35 (t, J = 6.3 Hz, 1 H), 9.16 (t, J = 6.0 Hz, 1 H), 8.51 (s, 1 H), 8.41 (d, J = 2.1 Hz, 1 H), 8.34 (s, 1 H), 7.98 (dd, J = 2.0, 8.7 Hz, 1 H), 7.83 (br. s., 1 H), 7.64 (d, J = 8.7 Hz, 1 H), 7.47 (d, J = 3.6 Hz, 1 H), 7.44-7.30 (m, 2 H), 7.22-7.13 (m, 1 H), 7.09 (d, J = 3.6 Hz, 1 H), 4.84 (d, J = 5.9 Hz, 2 H), 4.42 (d, J = 6.3 Hz, 2 H). |
| 10.3 | 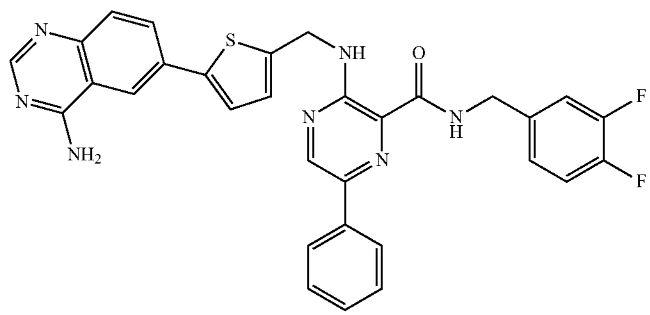 [SMILES: Nc1ncnc2ccc(-c3ccc(CNc4ncc(-c5ccccc5)nc4C(=O)NCc4ccc(F)c(F)c4)s3)cc12] | 3-({[5-(4-aminoquinazolin-6-yl)thiophen-2-yl]methyl}amino)-N-(3,4-difluorobenzyl)-6-phenylpyrazine-2-carboxamide | 580.3 | ¹H NMR (300 MHz, DMSO-d₆) δ 9.28 (t, J = 6.4 Hz, 1 H), 8.91 (t, J = 6.0 Hz, 1 H), 8.39 (d, J = 1.9 Hz, 1 H), 8.33 (s, 1 H), 8.29 (s, 1 H), 7.96 (dd, J = 1.9, 8.7 Hz, 1 H), 7.82 (br. s., 1 H), 7.63 (d, J = 8.7 Hz, 1 H), 7.45 (d, J = 3.8 Hz, 1 H), 7.42-7.29 (m, 2 H), 7.22-7.12 (m, 1 H), 7.07 (d, J = 3.8 Hz, 1 H), 4.83 (d, J = 6.0 Hz, 2 H), 4.46 (d, J = 6.8 Hz, 2 H), 2.99 (spt, J = 6.9 Hz, 1 H), 1.26 (d, J = 6.8 Hz, 6 H). |
| 10.4 | 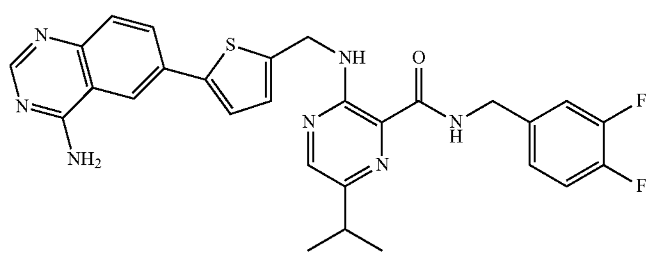 [SMILES: CC(C)c1cnc(NCc2ccc(-c3ccc4ncnc(N)c4c3)s2)c(C(=O)NCc2ccc(F)c(F)c2)n1] | 3-({[5-(4-aminoquinazolin-6-yl)thiophen-2-yl]methyl}amino)-N-(3,4-difluorobenzyl)-6-(propan-2-yl)pyrazine-2-carboxamide | 546.3 | ¹H NMR (300 MHz, DMSO-d₆) δ 9.28 (t, J = 6.4 Hz, 1 H), 8.91 (t, J = 6.0 Hz, 1 H), 8.39 (d, J = 1.9 Hz, 1 H), 8.33 (s, 1 H), 8.29 (s, 1 H), 7.96 (dd, J = 1.9, 8.7 Hz, 1 H), 7.82 (br. s., 1 H), 7.63 (d, J = 8.7 Hz, 1 H), 7.45 (d, J = 3.8 Hz, 1 H), 7.42-7.29 (m, 2 H), 7.22-7.12 (m, 1 H), 7.07 (d, J = 3.8 Hz, 1 H), 4.83 (d, J = 6.0 Hz, 2 H), 4.46 (d, J = 6.8 Hz, 2 H), 2.99 (spt, J = 6.9 Hz, 1 H), 1.26 (d, J = 6.8 Hz, 6 H). |

TABLE 1-continued

| Ex. No. | Structure | Chemical Name | ESI-MS (M + H) | ¹H NMR |
|---|---|---|---|---|
| 10.5 | 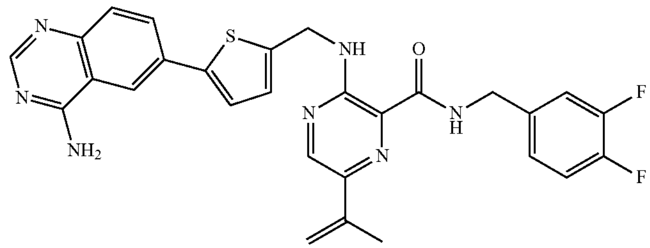 [SMILES: C=C(C)c1cnc(NCc2ccc(-c3ccc4ncnc(N)c4c3)s2)c(C(=O)NCc2ccc(F)c(F)c2)n1] | 3-({[5-(4-aminoquinazolin-6-yl)thiophen-2-yl]methyl}amino)-N-(3,4-difluorobenzyl)-6-(prop-1-en-1-yl)pyrazine-2-carboxamide | 544.3 | ¹H NMR (300 MHz, DMSO-d$_6$) δ 9.32 (t, J = 6.4 Hz, 1 H), 9.13 (t, J = 6.0 Hz, 1 H), 8.61 (s, 1 H), 8.39 (d, J = 2.1 Hz, 1 H), 8.33 (s, 1 H), 7.97 (dd, J = 2.0, 8.7 Hz, 1 H), 7.81 (br. s., 2 H), 7.63 (d, J = 8.7 Hz, 1 H), 7.46 (d, J = 3.6 Hz, 1 H), 7.43-7.30 (m, 2 H), 7.22-7.13 (m, 1 H), 7.09 (d, J = 3.6 Hz, 1 H), 5.96 (s, 1 H), 5.18 (t, J = 1.6 Hz, 1 H), 4.88 (d, J = 6.0 Hz, 2 H), 4.47 (d, J = 6.4 Hz, 2 H), 2.17 (s, 3 H). |
| 10.6 | 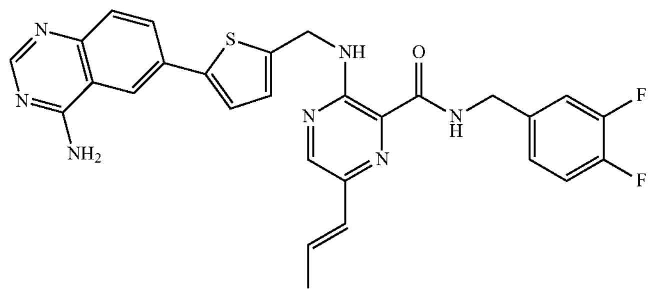 [SMILES: C/C=C/c1cnc(NCc2ccc(-c3ccc4ncnc(N)c4c3)s2)c(C(=O)NCc2ccc(F)c(F)c2)n1] | 3-({[5-(4-aminoquinazolin-6-yl)thiophen-2-yl]methyl}amino)-N-(3,4-difluorobenzyl)-6-[(1E)-prop-1-en-1-yl]pyrazine-2-carboxamide | 544.3 | ¹H NMR (300 MHz, CDCl$_3$) δ 8.96 (t, J = 5.8 Hz, 1 H), 8.61 (s, 1 H), 8.39 (t, J = 6.4 Hz, 1 H), 8.28 (s, 1 H), 7.96 (dd, J = 1.8, 8.9 Hz, 1 H), 7.88-7.76 (m, 2 H), 7.24-6.96 (m, 5 H), 6.51 (dq, J = 6.4, 15.7 Hz, 1 H), 6.38 (dd, J = 1.6, 15.7 Hz, 1 H), 5.88 (br. s., 2 H), 4.88 (d, J = 5.9 Hz, 2 H), 4.56 (d, J = 6.3 Hz, 2 H), 1.92 (dd, J = 1.4, 6.5 Hz, 3 H) |
| 10.7 | 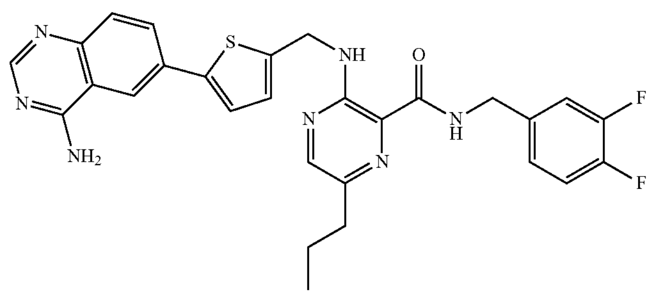 [SMILES: CCCc1cnc(NCc2ccc(-c3ccc4ncnc(N)c4c3)s2)c(C(=O)NCc2ccc(F)c(F)c2)n1] | 3-({[5-(4-aminoquinazolin-6-yl)thiophen-2-yl]methyl}amino)-N-(3,4-difluorobenzyl)-6-propylpyrazine-2-carboxamide | 546.3 | ¹H NMR (300 MHz, CDCl$_3$) δ 8.83 (t, J = 5.9 Hz, 1 H), 8.60 (s, 1 H), 8.40 (t, J = 6.4 Hz, 1 H), 8.16 (s, 1 H), 7.96 (dd, J = 1.9, 8.7 Hz, 1 H), 7.88-7.79 (m, 2 H), 7.24-6.97 (m, 5 H), 5.98 (br. s., 2 H), 4.87 (d, J = 6.0 Hz, 2 H), 4.56 (d, J = 6.4 Hz, 2 H), 2.69-2.58 (m, 2 H), 1.70 (sxt, J = 7.5 Hz, 2 H), 0.97 (t, J = 7.4 Hz, 3 H). |

TABLE 1-continued

| Ex. No. | Structure | Chemical Name | ESI-MS (M + H) | $^1$H NMR |
|---|---|---|---|---|
| 10.8 | 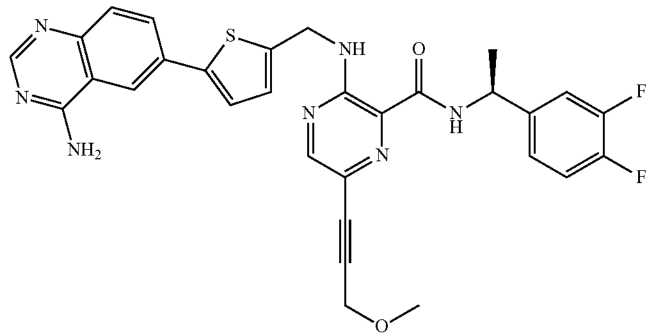 [SMILES: COCC#Cc1cnc(NCc2ccc(-c3ccc4ncnc(N)c4c3)s2)c(C(=O)N[C@@H](C)c2ccc(F)c(F)c2)n1] | 3-({[5-(4-aminoquinazolin-6-yl)thiophen-2-yl]methyl}amino)-N-[(1S)-1-(3,4-difluorophenyl)ethyl]-6-(3-methoxyprop-1-yn-1-yl)pyrazine-2-carboxamide | 586.3 | $^1$H NMR (300 MHz, CDCl$_3$) δ 9.23 (t, J = 6.0 Hz, 1 H), 8.61 (s, 1 H), 8.39 (s, 1 H), 8.14 (d, J = 7.6 Hz, 1 H), 7.95 (dd, J = 2.3, 8.7 Hz, 1 H), 7.84 (d, J = 8.7 Hz, 1 H), 7.81 (d, J = 1.9 Hz, 1 H), 7.22-7.04 (m, 4 H), 6.99 (d, J = 3.8 Hz, 1 H), 5.89 (br. s., 2 H), 5.13 (quin, J = 7.2 Hz, 1 H), 4.86 (ddd, J = 6.0, 15.5, 24.6 Hz, 2 H), 4.37 (s, 2 H), 3.48 (s, 3 H), 1.58 (d, J = 7.2 Hz, 3 H). |
| 10.9 | 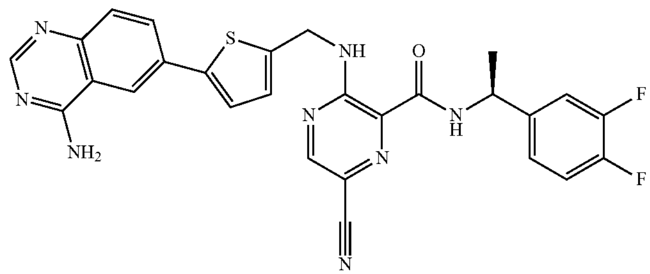 [SMILES: C[C@H](NC(=O)c1nc(C#N)cnc1NCc1ccc(-c2ccc3ncnc(N)c3c2)s1)c1ccc(F)c(F)c1] | 3-({[5-(4-aminoquinazolin-6-yl)thiophen-2-yl]methyl}amino)-6-cyano-N-[(1S)-1-(3,4-difluorophenyl)ethyl]pyrazine-2-carboxamide | 543.2 | $^1$H NMR (300 MHz, DMSO-d$_6$) δ 9.77 (t, J = 6.0 Hz, 1 H), 9.34 (d, J = 8.3 Hz, 1 H), 8.82 (s, 1 H), 8.41 (d, J = 1.5 Hz, 1 H), 8.35 (s, 1 H), 7.97 (dd, J = 1.9, 8.7 Hz, 1 H), 7.83 (br. s., 2 H), 7.64 (d, J = 8.7 Hz, 1 H), 7.57-7.44 (m, 2 H), 7.37 (dt, J = 8.3, 10.6 Hz, 1 H), 7.30-7.22 (m, 1 H), 7.11 (d, J = 3.4 Hz, 1 H), 5.12 (quin, J = 7.3 Hz, 1 H), 4.98-4.81 (m, 2 H), 1.52 (d, J = 7.2 Hz, 3 H). |
| 10.10 | 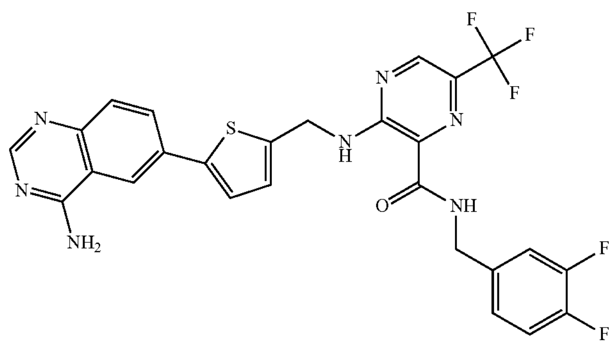 [SMILES: Nc1ncnc2ccc(-c3ccc(CNc4ncc(C(F)(F)F)nc4C(=O)NCc4ccc(F)c(F)c4)s3)cc12] | 3-(((5-(4-aminoquinazolin-6-yl)thiophen-2-yl)methyl)amino)-N-(3,4-difluorobenzyl)-6-(trifluoromethyl)pyrazine-2-carboxamide | 572.1 | $^1$H NMR (300 MHz, CDCl$_3$) δ 9.45 (t, J = 5.48 Hz, 1H), 8.55 (s, 1H), 8.53 (s, 1H), 8.29 (t, J = 5.67 Hz, 1H), 8.03 (d, J = 1.51 Hz, 1H), 7.90 (dd, J = 2.08, 8.88 Hz, 1H), 7.77 (d, J = 8.69 Hz, 1H), 7.24 (d, J = 3.40 Hz, 1H), 6.94-7.19 (m, 4H), 6.33 (br. s., 2H), 4.89 (d, J = 6.04 Hz, 2H), 4.52 (d, J = 6.42 Hz, 2H) |

TABLE 1-continued

| Ex. No. | Structure | Chemical Name | ESI-MS (M + H) | ¹H NMR |
|---|---|---|---|---|
| 11.1 | 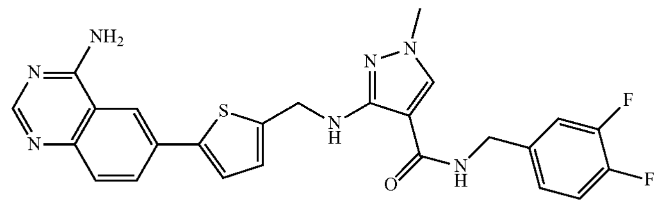 [SMILES: Cn1cc(C(=O)NCc2ccc(F)c(F)c2)c(NCc2ccc(-c3ccc4ncnc(N)c4c3)s2)n1] | 3-((5-(4-aminoquinazolin-6-yl)thiophen-2-yl)methyl)amino)-N-(3,4-difluorobenzyl)-1-methyl-1H-pyrazole-4-carboxamide | 506.1 | ¹H NMR (400 MHz, CD₃OD) δ 8.65 (s, 1H) 8.58 (d, 1H), 8.33 (dd, 1H), 7.85 (s, 1H), 7.77 (d, 1H), 7.52 (d, 1H), 7.18-7.25 (m, 2H), 7.11-7.14 (m, 2H), 4.68 (s, 2H), 4.45 (s, 2H), 3.77 (s, 3H). |
| 11.2 | 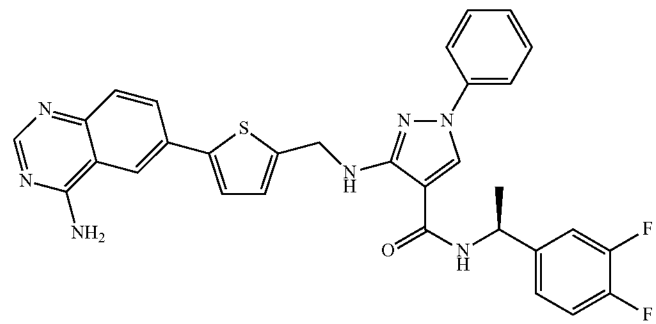 [SMILES: C[C@H](NC(=O)c1cn(-c2ccccc2)nc1NCc1ccc(-c2ccc3ncnc(N)c3c2)s1)c1ccc(F)c(F)c1] | (S)-3-((5-(4-aminoquinazolin-6-yl)thiophen-2-yl)methyl)amino)-N-(1-(3,4-difluorophenyl)ethyl)-1-phenyl-1H-pyrazole-4-carboxamide | 582 | ¹H NMR (400 MHz, DMSO-d₆) δ 8.57 (s, 1H), 8.06 (s, 1H), 7.89 (d, 1H), 7.79-7.78 (m, 2H), 7.60 (d, 2H), 7.40 (t, 2H), 7.22 (s, 1H), 7.20-6.88 (m, 5H), 6.28-6.20 (m, 4H), 5.18 (m, 1H), 4.68 (AB, 2H), 1.52 (d, 3H). |
| 11.3 | 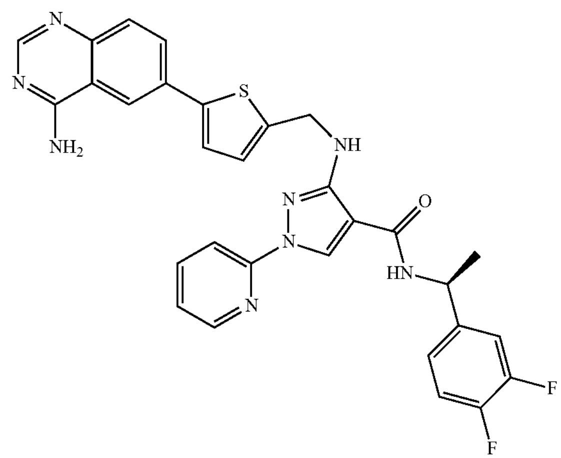 [SMILES: C[C@H](NC(=O)c1cn(-c2ccccn2)nc1NCc1ccc(-c2ccc3ncnc(N)c3c2)s1)c1ccc(F)c(F)c1] | (S)-3-((5-(4-aminoquinazolin-6-yl)thiophen-2-yl)methyl)amino)-N-(1-(3,4-difluorophenyl)ethyl)-1-(pyridin-2-yl)-1H-pyrazole-4-carboxamide | 583.0 | ¹H NMR (400 MHz, DMSO-d₆) δ 9.30 (s, 1H), 8.62 (d, 1H), 8.43-8.41 (m, 2H), 8.33 (s, 1H), 7.98-7.96 (m, 2H), 7.95-7.70 (m, 3H), 7.64 (d, 1H), 7.47-7.39 (m, 4H), 7.30 (s, 1H), 7.12 (d, 1H), 6.75 (t, 1H), 5.08 (m, 1H), 4.68 (s, 2H), 1.43 (d, 3H). |

TABLE 1-continued

| Ex. No. | Structure | Chemical Name | ESI-MS (M + H) | ¹H NMR |
|---|---|---|---|---|
| 11.4 | 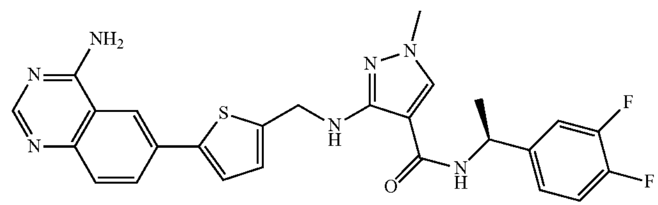 [SMILES: C[C@H](NC(=O)c1cn(C)nc1NCc1ccc(-c2ccc3ncnc(N)c3c2)s1)c1ccc(F)c(F)c1] | (S)-3-(((5-(4-aminoquinazolin-6-yl)thiophen-2-yl)methyl)amino)-N-(1-(3,4-difluorophenyl)ethyl)-1-methyl-1H-pyrazole-4-carboxamide | 520.0 | ¹H NMR (400 MHz, CD₃OD) δ: 8.40 (s, 2H), 8.28 (br, 1H), 8.11 (dd, 1H), 7.96 (s, 1H), 7.72 (d, 1H), 7.42 (d, 1H), 7.17-7.29 (m, 3H), 7.05 (d, 1H), 5.10 (q, 1H), 4.64 (s, 2H), 3.78 (s, 3H), 1.51 (d, 3H) |
| 11.5 | 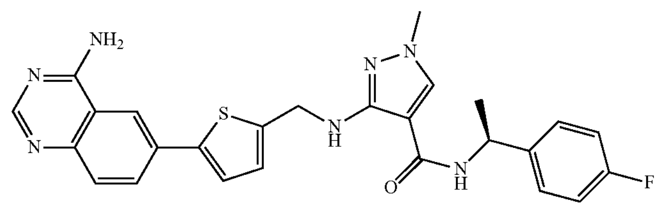 [SMILES: C[C@H](NC(=O)c1cn(C)nc1NCc1ccc(-c2ccc3ncnc(N)c3c2)s1)c1ccc(F)cc1] | 3-({[5-(4-aminoquinazolin-6-yl)thiophen-2-yl]methyl}amino)-N-[(1S)-1-(4-fluorophenyl)ethyl]-1-methyl-1H-pyrazole-4-carboxamide | 502.1 | ¹H NMR (400 MHz, CD₃OD) δ 8.59 (s, 1H), 8.39 (s, 1H), 8.13 (d, 1H), 7.95 (s, 1H), 7.66 (d, 1H), 7.32-7.35 (m, 3H), 6.96-7.00 (m, 3H), 5.13 (q, 1H), 4.60 (s, 2H), 3.74 (s, 3H), 1.48 (d, 3H). |
| 12.1 | 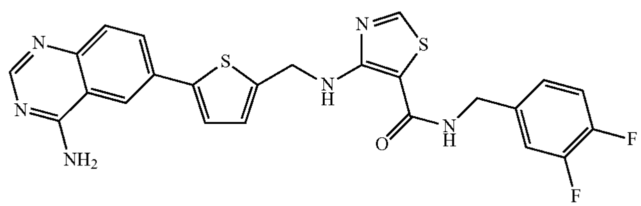 [SMILES: Nc1ncnc2ccc(-c3ccc(CNc4ncsc4C(=O)NCc4ccc(F)c(F)c4)s3)cc12] | 4-((5-(4-aminoquinazolin-6-yl)thiophen-2-yl)methyl)amino)-N-(3,4-difluorobenzyl)thiazole-5-carboxamide | 509.1 | ¹H NMR (400 MHz, DMSO-d₆) δ 9.71 (br. s., 2H), 8.90-9.01 (m, 1H), 8.79 (s, 1H), 8.59 (s, 1H), 8.44 (t, J = 6.02 Hz, 1H), 8.27 (dd, J = 2.01, 8.78 Hz, 1H), 7.91 (t, J = 6.40 Hz, 1H), 7.76 (d, J = 8.78 Hz, 1H), 7.47-7.61 (m, 1H), 7.22-7.44 (m, 2H), 6.98-7.19 (m, 2H), 4.73-4.95 (m, 2H), 4.34 (d, J = 3.27 Hz, 2H). |
| 13 | 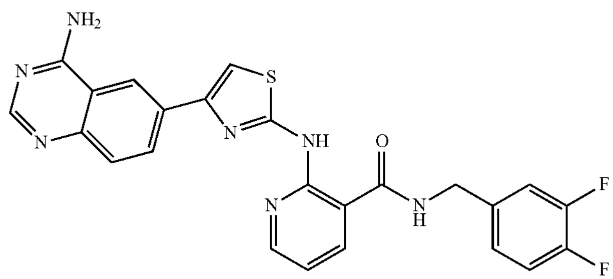 [SMILES: Nc1ncnc2ccc(-c3csc(Nc4ncccc4C(=O)NCc4ccc(F)c(F)c4)n3)cc12] | 2-(4-(4-aminoquinazol-2-yl)amino)-N-(3,4-difluorobenzyl)-nicotinamide | 490.2 | ¹H NMR (400 MHz, DMSO-d₆) δ 12.33 (s, 1H), 9.63 (t, 1H), 8.94 (s, 1H), 8.80 (s, 1H), 8.57 (dd, J = 4.89, 1.63 Hz, 2H), 8.43 (dd, J = 8.03, 1.76 Hz, 1H), 7.64-7.91 (m, 2H), 7.01-7.26 (m, 4H), 4.57 (d, 2H). |

TABLE 1-continued

| Ex. No. | Structure | Chemical Name | ESI-MS (M + H) | ¹H NMR |
|---|---|---|---|---|
| 14.1 | 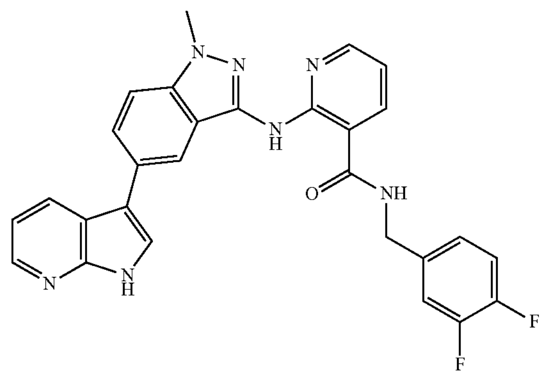 [SMILES: Cn1nc(Nc2ncccc2C(=O)NCc2ccc(F)c(F)c2)c2cc(-c3c[nH]c4ncccc34)ccc21] | N-(3,4-difluorobenzyl)-2-(1-methyl-5-(1H-pyrrolo[2,3-b]pyridin-3-yl)-1H-indazol-3-ylamino)nicotinamide | 510.3 | ¹H NMR (400 MHz, DMSO-$d_6$) δ 11.94 (br. s., 1H), 10.97 (br. s., 1H), 9.32-9.51 (m, 1H), 8.18-8.36 (m, 4H), 7.94 (s, 1H), 7.83 (d, J = 2.51 Hz, 1H), 7.71-7.79 (m, 1H), 7.62-7.71 (m, 1H), 7.34-7.49 (m, 2H), 7.13-7.29 (m, 2H), 6.96 (dd, J = 5.02, 7.53 Hz, 1H), 4.52 (d, J = 5.52 Hz, 2H), 4.00 (s, 3H). |
| 14.2 | 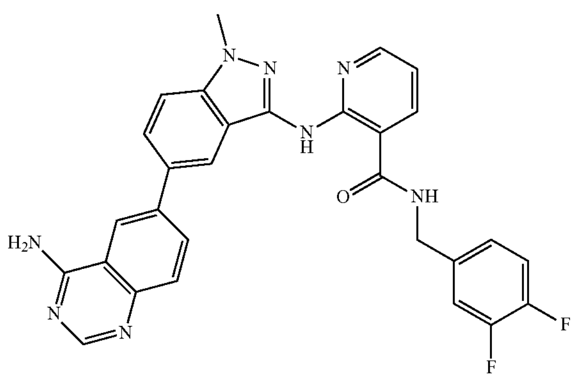 [SMILES: Cn1nc(Nc2ncccc2C(=O)NCc2ccc(F)c(F)c2)c2cc(-c3ccc4ncnc(N)c4c3)ccc21] | 2-(5-(4-aminoquinazolin-6-yl)-1-methyl-1H-indazol-3-ylamino)-N-(3,4-difluorobenzyl)-nicotinamide | 537.3 | ¹H NMR (400 MHz, DMSO-$d_6$) δ 10.78 (s, 1H), 9.85 (br. s., 2H), 9.32-9.48 (m, 1H), 8.84 (s, 1H), 8.73 (d, J = 1.51 Hz, 1H), 8.38 (dd, J = 1.88, 8.66 Hz, 1H), 8.16-8.29 (m, 2H), 8.10 (s, 1H), 7.71-7.94 (m, 3H), 7.33-7.51 (m, 2H), 7.23 (d, J = 9.29 Hz, 1H), 6.89 (dd, J = 4.77, 7.78 Hz, 1H), 4.51 (d, J = 6.02 Hz, 2H), 4.02 (s, 3H). |

TABLE 1-continued

| Ex. No. | Structure | Chemical Name | ESI-MS (M + H) | ¹H NMR |
|---|---|---|---|---|
| 15.1 | 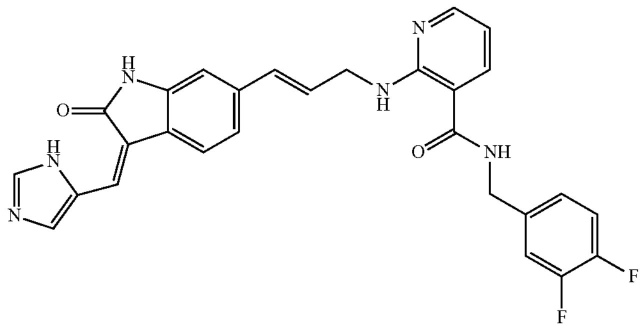 [SMILES: O=C1Nc2cc(/C=C/CNc3ncccc3C(=O)NCc3ccc(F)c(F)c3)ccc2/C1=C/c1cnc[nH]1] | 2-(E)-3-((Z)-((1H-imidazol-5-yl)methylene)-2-oxoindolin-6-yl)allylamino)-N-(3,4-difluorobenzyl)nicotinamide | 513.2 | ¹H NMR (400 MHz, DMSO-d₆) δ 13.69 (s, 1H), 9.10 (t, J = 5.83 Hz, 1H), 8.21 (dd, J = 1.76, 4.83 Hz, 1H), 8.01 (dd, J = 1.82, 7.78 Hz, 2H), 7.80 (br. s., 1H), 7.61 (d, J = 7.91 Hz, 1H), 7.29-7.46 (m, 2H), 7.13-7.23 (m, 1H), 7.01-7.11 (m, 1H), 6.89 (br. s., 1H), 6.63 (dd, J = 4.77, 7.65 Hz, 1H), 6.55 (d, J = 15.94 Hz, 1H), 6.33-6.47 (m, 1H), 4.43 (d, J = 6.09 Hz, 2H), 4.22 (t, J = 5.21 Hz, 1H). |
| 15.2 | 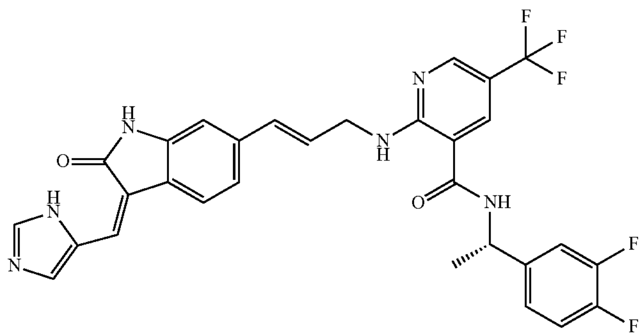 [SMILES: C[C@H](NC(=O)c1cc(C(F)(F)F)cnc1NC/C=C/c1ccc2c(c1)NC(=O)/C2=C\c1cnc[nH]1)c1ccc(F)c(F)c1] | 2-(E)-3-((Z)-((1H-imidazol-5-yl)methylene)-2-oxoindolin-6-yl)allylamino)-N-((S)-1-(3,4-difluorophenyl)ethyl)-5-(trifluoromethyl)nicotinamide | 595.3 | ¹H NMR (400 MHz, DMSO-d₆) δ 10.95 (br. s., 1H), 9.07 (d, J = 7.28 Hz, 1H), 8.95 (t, J = 5.90 Hz, 1H), 8.50-8.57 (m, 1H), 8.39-8.42 (m, 1H), 8.01-8.07 (m, 1H), 7.79 (br. s., 1H), 7.60 (d, J = 7.91 Hz, 1H), 7.34-7.50 (m, 2H), 7.03-7.09 (m, 1H), 6.89 (br. s., 1H), 6.54 (d, J = 16.13 Hz, 1H), 6.32-6.42 (m, 1H), 5.12 (t, J = 7.09 Hz, 1H), 4.21-4.31 (m, 2H), 1.48 (d, J = 7.03 Hz, 3H). |
| 15.3 | 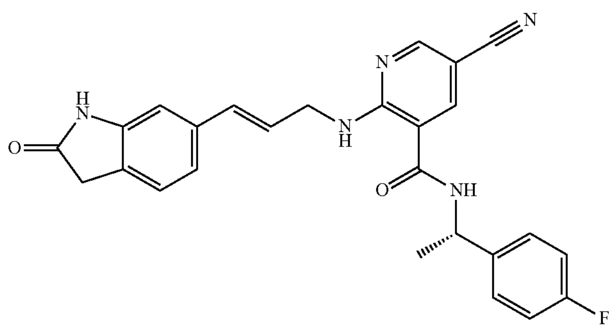 [SMILES: C[C@H](NC(=O)c1cc(C#N)cnc1NC/C=C/c1ccc2c(c1)NC(=O)C2)c1ccc(F)cc1] | (S,E)-5-cyano-N-(1-(4-fluorophenyl)ethyl)-2-(3-(2-oxoindolin-6-yl)allylamino)nicotinamide | 456.5 | ¹H NMR (400 MHz, DMSO-d₆) δ 10.33 (s, 1H), 9.07 (t, J = 5.71 Hz, 1H), 8.97 (d, J = 7.53 Hz, 1H), 8.58 (d, J = 2.13 Hz, 1H), 8.45 (d, J = 2.13 Hz, 1H), 7.36-7.46 (m, 2H), 7.07-7.19 (m, 3H), 6.92 (dd, J = 1.38, 7.72 Hz, 1H), 6.81 (br. s., 1H), 6.48 (d, J = 15.94 Hz, 1H), 6.27 (dt, J = 5.84, 15.81 Hz, 1H), 5.03-5.14 (m, 1H), 4.17-4.26 (m, 2H), 3.43 (s, 2H), 1.45 (d, J = 7.03 Hz, 3H). |

TABLE 1-continued

| Ex. No. | Structure | Chemical Name | ESI-MS (M + H) | ¹H NMR |
|---|---|---|---|---|
| 15.4 | 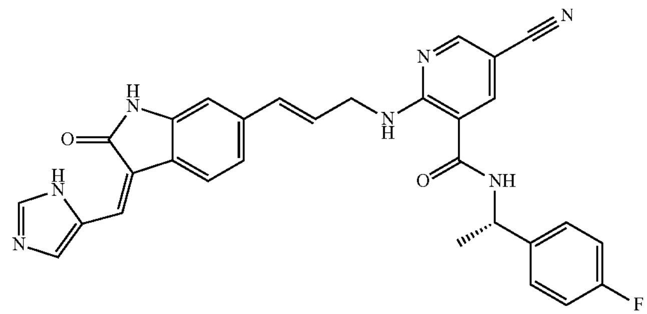 [SMILES: C[C@H](NC(=O)c1cc(C#N)cnc1NC/C=C/c1ccc2c(c1)NC(=O)/C2=C\c1cnc[nH]1)c1ccc(F)cc1] | 2-(E)-3-((Z)-3-((1H-imidazol-5-yl)methylene)-2-oxoindolin-6-yl)allylamino)-5-cyano-N-((S)-1-(4-fluorophenyl)ethyl)nicotinamide | 534.2 | ¹H NMR (400 MHz, DMSO-d₆) δ 10.89 (br. s., 1H), 9.09 (t, J = 5.58 Hz, 1H), 8.97 (d, J = 7.53 Hz, 1H), 8.59 (d, J = 2.20 Hz, 1H), 8.46 (d, J = 2.13 Hz, 1H), 7.99 (s, 1H), 7.78 (s, 1H), 7.59 (d, J = 7.91 Hz, 1H), 7.40-7.44 (m, 2H), 7.09-7.21 (m, 2H), 7.04 (dd, J = 0.88, 6.96 Hz, 1H), 6.88 (dd, J = 0.28, 1.29 Hz, 1H), 6.51 (d, J = 15.81 Hz, 1H), 6.32 (dt, J = 5.90, 15.87 Hz, 1H), 1.46 (d, J = 7.09 Hz, 3H). |
| 15.5 | 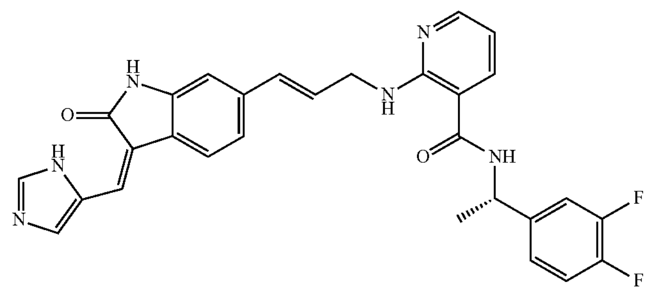 [SMILES: C[C@H](NC(=O)c1cccnc1NC/C=C/c1ccc2c(c1)NC(=O)/C2=C\c1cnc[nH]1)c1ccc(F)c(F)c1] | 2-(E)-3-((Z)-3-((1H-imidazol-5-yl)methylene)-2-oxoindolin-6-yl)allylamino)-N-((S)-1-(3,4-difluorophenyl)ethyl)nicotinamide | 527.2 | ¹H NMR (400 MHz, DMSO-d₆) δ 11.24 (s, 1H), 8.96 (s, 1H), 8.90 (d, J = 7.72 Hz, 1H), 8.53 (br. s., 1H), 8.21 (s, 1H), 8.19 (dd, J = 1.79, 4.99 Hz, 1H), 8.15 (dd, J = 1.63, 7.72 Hz, 1H), 7.80 (s, 1H), 7.62 (d, J = 7.91 Hz, 1H), 7.32-7.50 (m, 2H), 7.18-7.27 (m, 1H), 7.11 (dd, J = 1.19, 8.03 Hz, 1H), 6.94 (s, 1H), 6.69 (dd, J = 5.02, 7.59 Hz, 1H), 6.54 (d, J = 15.94 Hz, 1H), 6.45 (d, J = 5.58, 16.00 Hz, 1H), 5.11 (dt, J = 7.09, 14.43 Hz, 1H), 4.21 (br. s., 2H), 1.46 (d, J = 7.09 Hz, 3H). |
| 15.6 | 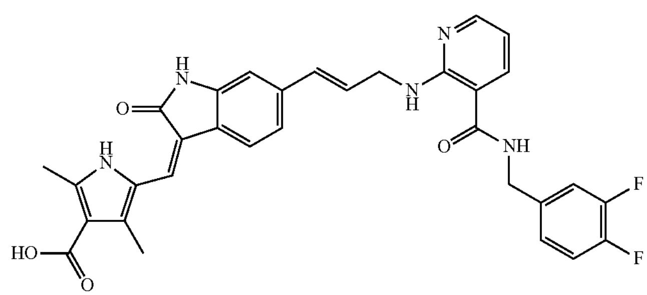 [SMILES: Cc1[nH]c(/C=C2\C(=O)Nc3cc(/C=C/CNc4ncccc4C(=O)NCc4ccc(F)c(F)c4)ccc32)c(C)c1C(=O)O] | 5-((Z)-6-((E)-3-(3-(3,4-difluorobenzyl(carbamoyl)pyridin-2-ylamino)prop-1-enyl)-2-oxoindolin-3-ylidene)methyl)-2,4-dimethyl-1H-pyrrole-3-carboxylic acid | 584.3 | 1H NMR (300 MHz, DMSO-d6) d 13.78 (s, 1H), 10.92 (s, 1H), 9.10 (t, J = 5.85 Hz, 1H), 8.49 (t, J = 5.48 Hz, 1H), 8.21 (dd, J = 1.70, 4.72 Hz, 1H), 8.02 (dd, J = 1.70, 7.74 Hz, 1H), 7.74 (d, J = 7.93 Hz, 1H), 7.64 (s, 1H), 7.31-7.46 (m, 2H), 7.13-7.23 (m, 1H), 7.01-7.09 (m, 1H), 6.90 (s, 1H), 6.63 (dd, J = 4.91, 7.55 Hz, 1H), 6.56 (d, J = 1.00 Hz, 1H), 6.37 (q, J = 1.00 Hz, 1H), 4.43 (d, J = 5.67 Hz, 2H), 4.22 (t, J = 5.29 Hz, 2H), 2.53 (s, 3H), 2.49 (s, 3H) |

TABLE 1-continued

| Ex. No. | Structure | Chemical Name | ESI-MS (M + H) | ¹H NMR |
|---|---|---|---|---|
| 15.7 | 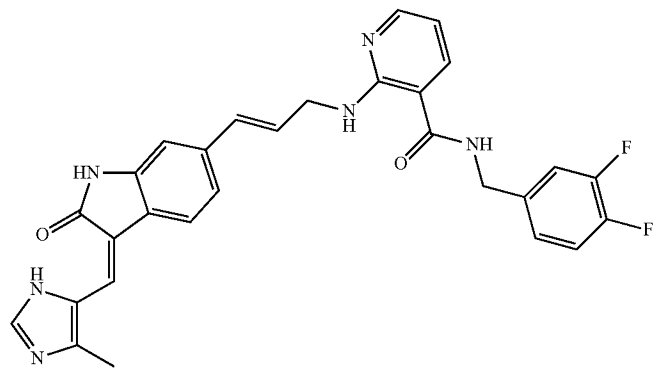 [SMILES: Cc1nc[nH]c1/C=C1\C(=O)Nc2cc(/C=C/CNc3ncccc3C(=O)NCc3ccc(F)c(F)c3)ccc21] | N-(3,4-Difluoro-benzyl)-2-((E)-3-{3-[1-(5-methyl-3H-imidazol-4-yl)-meth-(Z)-ylidene]-2-oxo-2,3-dihydro-1H-indol-6-yl}-allylamino)-nicotinamide | 527.3 | 1H NMR (300 MHz, DMSO-d6) Shift 13.77 (s, 1H), 10.96 (s, 1H), 9.10 (t, J = 5.85 Hz, 1H), 8.49 (t, J = 5.48 Hz, 1H), 8.21 (dd, J = 1.51, 4.91 Hz, 1H), 8.02 (dd, J = 1.70, 7.74 Hz, 1H), 7.91 (s, 1H), 7.77 (dd, J = 7.55 Hz, 1H), 7.72 (s, 1H), 7.31-7.45 (m, 2H), 7.13-7.22 (m, 1H), 7.07 (dd, J = 4.91, 7.55 Hz, 1H), 6.90 (s, 1H), 6.63 (dd, J = 4.91, 7.55 Hz, 1H), 6.52-6.60 (m, 1H), 6.33-6.45 (m, 1H), 4.43 (d, J = 5.67 Hz, 2H), 4.22 (t, J = 5.29 Hz, 2H), 2.44 (s, 3H) |
| 15.8 | 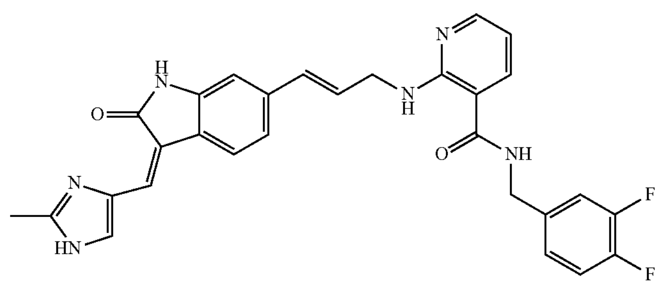 [SMILES: Cc1nc(/C=C2\C(=O)Nc3cc(/C=C/CNc4ncccc4C(=O)NCc4ccc(F)c(F)c4)ccc32)c[nH]1] | N-(3,4-Difluoro-benzyl)-2-((E)-3-{3-[1-(2-methyl-1H-imidazol-4-yl)-meth-(Z)-ylidene]-2-oxo-2,3-dihydro-1H-indol-6-yl}-allylamino)-nicotinamide | 527.2 | 1H NMR (300 MHz, DMSO-d6) Shift 13.44 (s, 1H), 10.95 (br. s., 1H), 9.10 (t, J = 5.85 Hz, 1H), 8.48 (t, J = 5.48 Hz, 1H), 8.21 (dd, J = 1.70, 4.72 Hz, 1H), 8.02 (dd, J = 1.89, 7.93 Hz, 1H), 7.71 (s, 1H), 7.57 (d, J = 7.93 Hz, 1H), 7.52 (s, 1H), 7.31-7.41 (m, 2H), 7.12-7.22 (m, 1H), 7.06 (d, J = 7.93 Hz, 1H), 6.91 (s, 1H), 6.63 (dd, J = 4.91, 7.55 Hz, 1H), 6.56 (d, J = 1.00 Hz, 1H), 6.31-6.45 (m, 1H), 4.43 (d, J = 5.67 Hz, 2H), 4.22 (t, J = 5.29 Hz, 2H), 2.46 (s, 3H) |
| 15.9 | 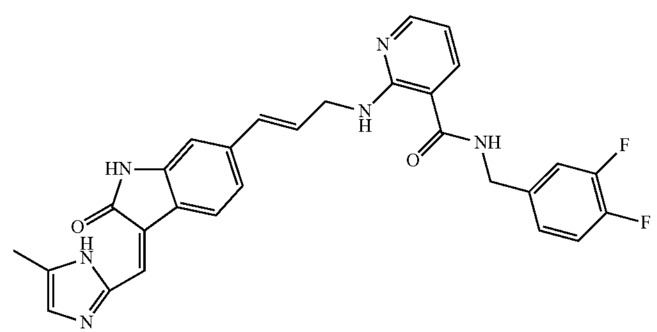 [SMILES: Cc1cnc(/C=C2\C(=O)Nc3cc(/C=C/CNc4ncccc4C(=O)NCc4ccc(F)c(F)c4)ccc32)[nH]1] | N-(3,4-Difluoro-benzyl)-2-((E)-3-{3-[1-(5-methyl-1H-imidazol-2-yl)-meth-(Z)-ylidene]-2-oxo-2,3-dihydro-1H-indol-6-yl}-allylamino)-nicotinamide | 527.3 | 1H NMR (300 MHz, DMSO-d6) Shift 13.77-14.01 (m, 1H), 11.09 (br. s., 1H), 9.10 (t, J = 5.85 Hz, 1H), 8.49 (t, J = 5.48 Hz, 1H), 8.21 (dd, J = 1.70, 4.72 Hz, 1H), 8.02 (dd, J = 1.70, 7.74 Hz, 1H), 7.68-7.77 (m, 1H), 7.66 (s, 1H), 7.32-7.46 (m, 2H), 7.09-7.31 (m, 1H), 7.09-7.31 (m, J = 1.51, 2.64, 12.46 Hz, 1H), 7.09-7.31 (m, J = 1.32, 3.02, 6.61 Hz, 1H), 7.07 (dd, J = 1.13, 8.31 Hz, 1H), 6.92 (s, 1H), 6.63 (dd, J = 4.72, 7.74 Hz, 1H), 6.53-6.60 (m, 1H), 6.41 (dd, J = 5.67, 15.86 Hz, 1H), 4.43 (d, J = 5.67 Hz, 2H), 4.23 (t, J = 5.48 Hz, 2H), 2.20-2.40 (m, 3H) |

TABLE 1-continued

| Ex. No. | Chemical Name | Structure | ESI-MS (M + H) | ¹H NMR |
|---|---|---|---|---|
| 15.10 | N-(3,4-Difluoro-benzyl)-2-((E)-3-{1-(3-methyl-1H-pyrazol-4-yl)-meth-(Z)-ylidene]-2-oxo-2,3-dihydro-1H-indol-6-yl}-allylamino)-nicotinamide | 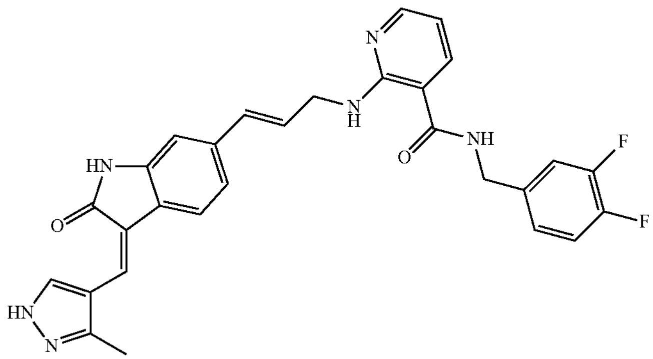 [SMILES: Cc1n[nH]cc1/C=C1\C(=O)Nc2cc(/C=C/CNc3ncccc3C(=O)NCc3ccc(F)c(F)c3)ccc21] | 527.2 | 1H NMR (300 MHz, DMSO-d6) Shift 12.99 (br. s., 1H), 10.45 (s, 1H), 8.99-9.19 (m, 2H), 8.48 (t, J = 5.48 Hz, 1H), 8.21 (dd, J = 1.51, 4.53 Hz, 1H), 8.01 (dd, J = 1.70, 7.74 Hz, 1H), 7.66 (d, J = 7.93 Hz, 1H), 7.51 (s, 1H), 7.31-7.45 (m, 2H), 7.18 (br. s., 1H), 7.00 (d, J = 7.93 Hz, 1H), 6.84 (s, 1H), 6.63 (dd, J = 4.72, 7.74 Hz, 1H), 6.55 (d, J = 15.86 Hz, 1H), 6.36 (td, J = 5.67, 15.49 Hz, 1H), 4.43 (d, J = 5.67 Hz, 2H), 4.21 (t, J = 5.10 Hz, 2H), 2.44 (s, 3H) |
| 15.11 | N-(3,4-Difluoro-benzyl)-2-((E)-3-{1-(2-ethyl-5-methyl-3H-imidazol-4-yl)-2-oxo-2,3-dihydro-1H-indol-6-yl}-meth-(Z)-ylidene]-allylamino)-nicotinamide | 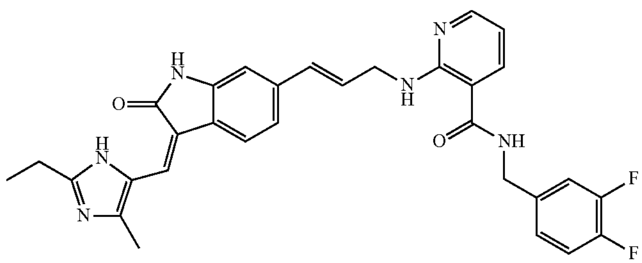 [SMILES: CCc1nc(C)c(/C=C2\C(=O)Nc3cc(/C=C/CNc4ncccc4C(=O)NCc4ccc(F)c(F)c4)ccc32)[nH]1] | 555.3 | 1H NMR (300 MHz, DMSO-d6) Shift 13.74 (s, 1H), 10.91 (s, 1H), 9.10 (t, J = 5.85 Hz, 1H), 8.49 (t, J = 5.48 Hz, 1H), 8.21 (dd, J = 1.70, 4.72 Hz, 1H), 8.02 (dd, J = 1.70, 7.74 Hz, 1H), 7.74 (d, J = 7.93 Hz, 1H), 7.67 (s, 1H), 7.31-7.46 (m, 2H), 7.12-7.23 (m, 1H), 7.06 (dd, J = 1.32, 8.12 Hz, 1H), 6.90 (s, 1H), 6.63 (dd, J = 4.72, 7.74 Hz, 1H), 6.56 (d, J = 15.86 Hz, 1H), 6.37 (td, J = 5.67, 15.86 Hz, 1H), 4.43 (d, J = 6.04 Hz, 2H), 4.22 (t, J = 5.48 Hz, 2H), 2.76 (q, J = 7.55 Hz, 2H), 2.40 (s, 3H), 1.27 (t, J = 7.55 Hz, 3H |
| 15.12 | N-(3,4-Difluoro-benzyl)-2-((E)-3-{1-(1H-imidazol-2-yl)-meth-(Z)-ylidene]-2-oxo-2,3-dihydro-1H-indol-6-yl}-allylamino)-nicotinamide | 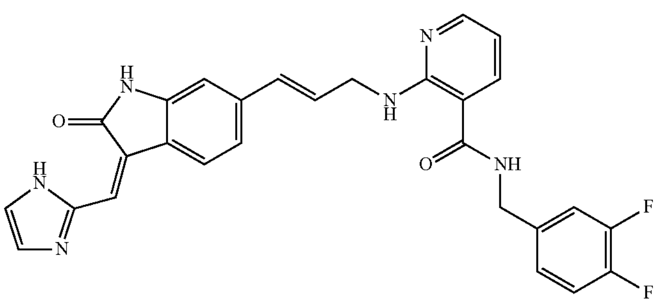 [SMILES: O=C1Nc2cc(/C=C/CNc3ncccc3C(=O)NCc3ccc(F)c(F)c3)ccc2/C1=C/c1ncc[nH]1] | | 1H NMR (300 MHz, DMSO-d6) Shift 14.03 (br. s., 1H), 11.13 (s, 1H), 9.10 (t, J = 5.85 Hz, 1H), 8.49 (t, J = 5.67 Hz, 1H), 8.21 (dd, J = 1.70, 4.72 Hz, 1H), 8.02 (dd, J = 1.89, 7.93 Hz, 1H), 7.71-7.82 (m, 2H), 7.55 (d, J = 2.27 Hz, 1H), 7.30-7.46 (m, 3H), 7.17 (ddd, J = 2.46, 4.15, 6.23 Hz, 1H), 7.08 (dd, J = 1.32, 8.12 Hz, 1H), 6.93 (s, 1H), 6.52-6.67 (m, 2H), 6.43 (td, J = 5.67, 15.86 Hz, 1H), 4.43 (d, J = 6.04 Hz, 2H), 4.23 (t, J = 5.29 Hz, 2H) |

TABLE 1-continued

| Ex. No. | Structure | Chemical Name | ESI-MS (M + H) | ¹H NMR |
|---|---|---|---|---|
| 15.13 | 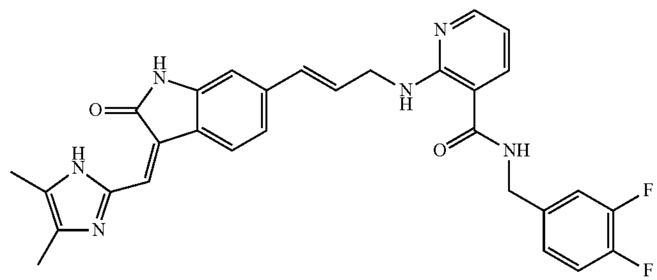 [SMILES: Cc1nc(/C=C2\C(=O)Nc3cc(/C=C/CNc4ncccc4C(=O)NCc4ccc(F)c(F)c4)ccc32)[nH]c1C] | N-(3,4-Difluoro-benzyl)-2-((E)-3-{1-(4,5-dimethyl-1H-imidazol-2-yl)-meth-(Z)-ylidene]-2-oxo-2,3-dihydro-1H-indol-6-yl]-allylamino)-nicotinamide | | 1H NMR (300 MHz, DMSO-d6) Shift 13.78 (s, 1H), 10.98 (s, 1H), 9.03 (t, J = 5.85 Hz, 1H), 8.42 (t, J = 5.48 Hz, 1H), 8.14 (dd, J = 1.70, 4.72 Hz, 1H), 7.95 (dd, J = 1.70, 7.74 Hz, 1H), 7.61 (d, J = 7.93 Hz, 1H), 7.51 (s, 1H), 7.24-7.38 (m, 2H), 7.10 (ddd, J = 2.08, 4.15, 6.23 Hz, 1H), 6.99 (dd, J = 1.13, 7.93 Hz, 1H), 6.85 (s, 1H), 6.45-6.59 (m, 2H), 6.33 (td, J = 5.67, 15.86 Hz, 1H), 4.36 (d, J = 6.04 Hz, 2H), 4.15 (t, J = 5.29 Hz, 2H), 2.05-2.29 (m, 6H) |
| 15.14 | 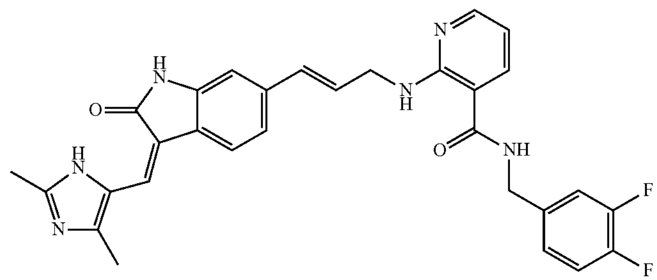 [SMILES: Cc1nc(C)c(/C=C2\C(=O)Nc3cc(/C=C/CNc4ncccc4C(=O)NCc4ccc(F)c(F)c4)ccc32)[nH]1] | N-(3,4-Difluoro-benzyl)-2-((E)-3-{3-[1-(2,5-dimethyl-3H-imidazol-4-yl)-meth-(Z)-ylidene]-2-oxo-2,3-dihydro-1H-indol-6-yl]-allylamino)-nicotinamide | 541.2 | 1H NMR (300 MHz, DMSO-d6) Shift 13.56 (s, 1H), 10.91 (s, 1H), 9.10 (t, J = 6.04 Hz, 1H), 8.49 (t, J = 5.48 Hz, 1H), 8.21 (dd, J = 1.89, 4.91 Hz, 1H), 8.02 (dd, J = 1.70, 7.74 Hz, 1H), 7.73 (d, J = 7.93 Hz, 1H), 7.65 (s, 1H), 7.31-7.45 (m, 2H), 7.17 (ddd, J = 2.08, 4.15, 6.23 Hz, 1H), 7.06 (dd, J = 1.13, 8.31 Hz, 1H), 6.90 (s, 1H), 6.63 (dd, J = 4.91, 7.55 Hz, 1H), 6.51-6.60 (m, 1H), 6.37 (td, J = 5.67, 15.86 Hz, 1H), 4.43 (d, J = 6.04 Hz, 2H), 4.22 (t, J = 5.29 Hz, 2H), 2.40 (d, J = 4.15 Hz, 6H) |
| 15.15 | 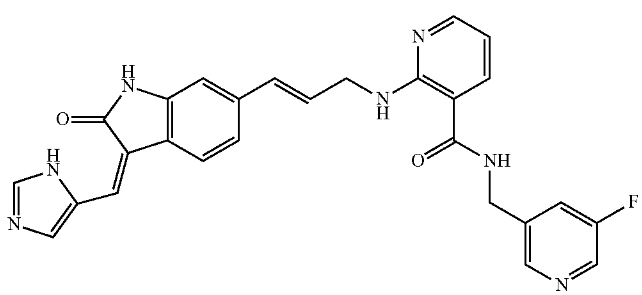 [SMILES: O=C1Nc2cc(/C=C/CNc3ncccc3C(=O)NCc3cncc(F)c3)ccc2/C1=C/c1cnc[nH]1] | 2-((E)-3-((Z)-3-((1H-imidazol-5-yl)methylene)-2-oxoindolin-6-yl)allylamino)-N-(5-fluoropyridin-3-yl)methyl)nicotinamide | 496.2 | 1H NMR (300 MHz, DMSO-d6) Shift 13.66 (br. s., 1H), 10.99 (br. s., 1H), 9.14 (t, J = 5.67 Hz, 1H), 8.47 (d, J = 2.64 Hz, 1H), 8.37-8.56 (m, 2H), 8.21 (dd, J = 1.51, 4.91 Hz, 1H), 8.01 (dd, J = 1.70, 7.74 Hz, 1H), 8.00 (br. s., 1H), 7.80 (br. s., 1H), 7.66 (d, J = 2.70, 9.82 Hz, 1H), 7.63 (br. s., 1H), 7.60 (d, J = 7.93 Hz, 1H), 7.06 (d, J = 7.93 Hz, 1H), 6.90 (s, 1H), 6.63 (dd, J = 4.72, 7.74 Hz, 1H), 6.56 (d, J = 15.86 Hz, 1H), 6.39 (td, J = 5.52, 15.77 Hz, 1H), 4.51 (d, J = 5.67 Hz, 2H), 4.22 (t, J = 5.29 Hz, 2H). |

TABLE 1-continued

| Ex. No. | Structure | Chemical Name | ESI-MS (M + H) | $^1$H NMR |
|---|---|---|---|---|
| 15.16 | 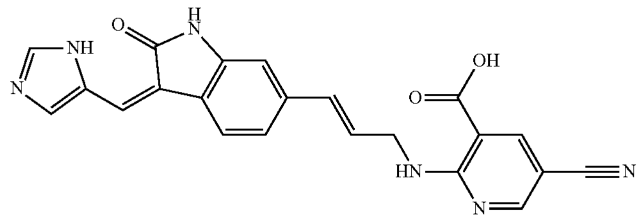 [SMILES: N#Cc1cnc(NC/C=C/c2ccc3c(c2)NC(=O)/C3=C\c2cnc[nH]2)c(C(=O)O)c1] | 2-(E)-3-((Z)-3-((1H-imidazol-5-yl)methylene)-2-oxoindolin-6-yl)allylamino)-5-cyanonicotinic acid | 413.0 | $^1$H NMR (300 MHz, DMSO-d$_6$) δ: 11.25 (s, 1H), 10.42 (s, 1H), 8.94 (br, 1H), 8.90-8.89 (m, 1H), 8.66 (s, 1H), 8.38-8.37 (m, 1H), 8.37 (s, 1H), 7.94 (s, 1H), 7.80 (s, 1H), 7.40 (s, 1H), 6.85 (t, 1H), 6.56-6.38 (m, 2H), 4.33 (s, 2H). |
| 15.17 | 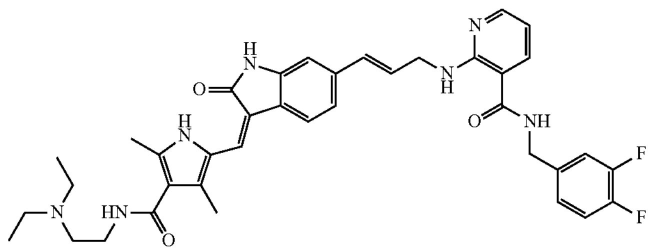 [SMILES: CCN(CC)CCNC(=O)c1c(C)[nH]c(/C=C2\C(=O)Nc3cc(/C=C/CNc4ncccc4C(=O)NCc4ccc(F)c(F)c4)ccc32)c1C] | 2-(E)-3-(Z)-3-((4-(2-(diethylamino)ethylcarbamoyl)-3,5-dimethyl-1H-pyrrol-2-yl)methylene)-2-oxoindolin-6-yl)allylamino)-N-(3,4-difluorobenzyl)nicotinamide | 682.4 | 1H NMR (300 MHz, DMSO-d6) Shift 13.57 (s, 1H), 9.10 (t, J = 5.85 Hz, 1H), 8.48 (t, J = 5.48 Hz, 1H), 8.21 (dd, J = 1.70, 4.72 Hz, 1H), 8.02 (dd, J = 1.89, 7.55 Hz, 1H), 7.72 (d, J = 7.93 Hz, 1H), 7.59 (s, 1H), 7.30-7.47 (m, 3H), 7.13-7.22 (m, 1H), 7.04 (d, J = 8.31 Hz, 1H), 6.90 (s, 1H), 6.63 (dd, J = 4.91, 7.55 Hz, 1H), 6.56 (d, J = 15.86 Hz, 1H), 6.36 (td, J = 5.67, 15.86 Hz, 1H), 4.43 (d, J = 6.04 Hz, 2H), 4.34 (t, J = 4.72 Hz, 1H), 4.22 (t, J = 5.29 Hz, 2H), 3.39-3.53 (m, 3H), 3.17 (d, J = 4.15 Hz, 1H), 2.42 (d, J = 10.58 Hz, 6H), 1.51 (br. s., 1H), 1.06 (t, J = 6.99 Hz, 3H), 0.98 (t, J = 6.99 Hz, 6H) |
| 15.18 | 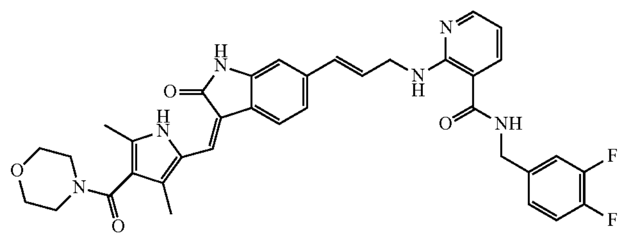 [SMILES: Cc1[nH]c(/C=C2\C(=O)Nc3cc(/C=C/CNc4ncccc4C(=O)NCc4ccc(F)c(F)c4)ccc32)c(C)c1C(=O)N1CCOCC1] | N-(3,4-Difluoro-benzyl)-2-((E)-3-{3-[1-[3,5-dimethyl-4-(morpholine-4-carbonyl)-1H-pyrrol-2-yl]-meth-(Z)-ylidene]-2-oxo-2,3-dihydro-1H-indol-6-yl}-allylamino)-nicotinamide | 653.4 | 1H NMR (300 MHz, DMSO-d6) Shift 13.53 (br. s., 1H), 10.86 (s, 1H), 9.10 (t, J = 5.29 Hz, 1H), 8.48 (t, J = 4.91 Hz, 1H), 8.21 (d, J = 3.78 Hz, 1H), 8.02 (d, J = 6.42 Hz, 1H), 7.70 (d, J = 7.93 Hz, 1H), 7.58 (s, 1H), 7.30-7.46 (m, 2H), 7.17 (br. s., 1H), 7.04 (d, J = 7.93 Hz, 1H), 6.90 (s, 1H), 6.47-6.69 (m, 2H), 6.36 (td, J = 4.91, 15.11 Hz, 1H), 4.43 (d, J = 5.67 Hz, 2H), 4.22 (br. s., 2H), 3.38-3.78 (m, 7H), 2.28 (d, J = 11.71 Hz, 6H) |
| 15.19 | 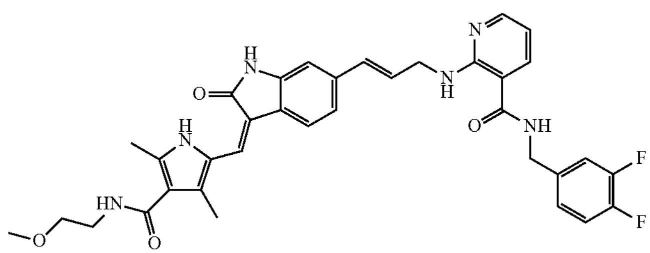 [SMILES: COCCNC(=O)c1c(C)[nH]c(/C=C2\C(=O)Nc3cc(/C=C/CNc4ncccc4C(=O)NCc4ccc(F)c(F)c4)ccc32)c1C] | N-(3,4-difluorobenzyl)-2-((E)-3-((Z)-3-((4-(2-methoxyethylcarbamoyl)-3,5-dimethyl-1H-pyrrol-2-yl]-methylene)-2-oxoindolin-6-yl)allylamino) nicotinamide | 641.4 | 1H NMR (300 MHz, DMSO-d6) Shift 13.57 (s, 1H), 10.87 (s, 1H), 9.10 (t, J = 5.85 Hz, 1H), 8.48 (t, J = 5.48 Hz, 1H), 8.21 (dd, J = 1.70, 4.72 Hz, 1H), 8.02 (dd, J = 1.70, 7.74 Hz, 1H), 7.72 (d, J = 7.93 Hz, 1H), 7.54-7.67 (m, 2H), 7.31-7.46 (m, 2H), 7.17 (ddd, J = 2.27, 4.06, 6.14 Hz, 1H), 7.04 (dd, J = 1.13, 7.93 Hz, 1H), 6.90 (s, 1H), 6.63 (dd, J = 4.91, 7.55 Hz, 1H), 6.56 (d, J = 15.86 Hz, 1H), 6.36 (td, J = 5.67, 15.86 Hz, 1H), 4.43 (d, J = 5.67 Hz, 2H), 4.22 (t, J = 5.29 Hz, 2H), 3.42-3.47 (m, 2H), 3.35-3.42 (m, 2H), 3.22-3.30 (m, 3H), 2.41 (d, J = 11.33 Hz, 6H) |

| Ex. No. | Structure | Chemical Name | ESI-MS (M + H) | ¹H NMR |
|---|---|---|---|---|
| 15.20 | 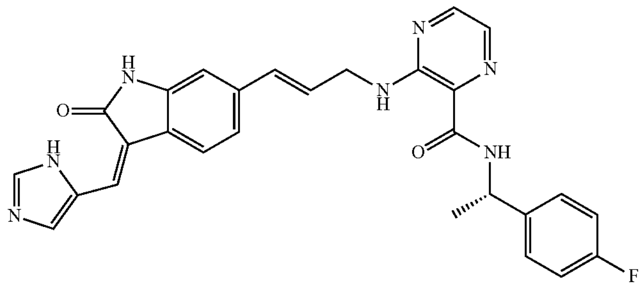 [SMILES: C[C@H](NC(=O)c1nccnc1NC/C=C/c1ccc2c(c1)NC(=O)/C2=C\c1cnc[nH]1)c1ccc(F)cc1] | 3-(E)-3-((Z)-((1H-imidazol-5-yl)methylene)-2-oxoindolin-6-yl)allylamino)-N-(S)-1-(4-fluorophenyl)ethyl)pyrazine-2-carboxamide | 510.2 | 1H NMR (300 MHz, DMSO-d6) Shift 13.66 (br. s., 1H), 10.99 (br. s., 1H), 9.11 (d, J = 8.31 Hz, 1H), 8.81 (t, J = 5.67 Hz, 1H), 8.30 (d, J = 2.27 Hz, 1H), 8.00 (br. s., 1H), 7.85 (d, J = 2.27 Hz, 1H), 7.79 (br. s., 1H), 7.63 (br. s., 2H), 7.60 (d, J = 7.93 Hz, 1H), 7.38-7.52 (m, 2H), 7.14 (tt, J = 2.50, 9.06 Hz, 2H), 7.06 (d, J = 7.55 Hz, 1H), 6.90 (s, 1H), 6.57 (d, J = 15.86 Hz, 1H), 6.37 (td, J = 5.85, 15.86 Hz, 1H), 5.13 (quin, J = 7.27 Hz, 1H), 4.13-4.31 (m, J = 5.70, 5.70 Hz, 2H), 1.51 (d, J = 6.80 Hz, 3H). |
| 15.21 | 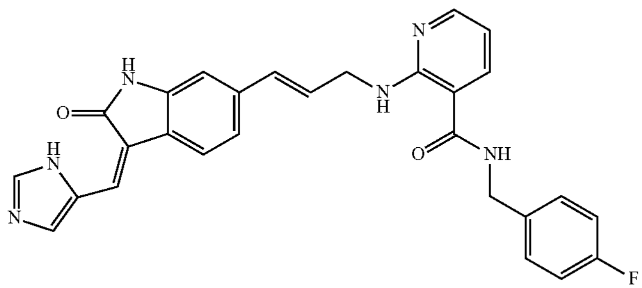 [SMILES: O=C1Nc2cc(/C=C/CNc3ncccc3C(=O)NCc3ccc(F)cc3)ccc2/C1=C/c1cnc[nH]1] | 2-(E)-3-((Z)-((1H-imidazol-5-yl)methylene)-2-oxoindolin-6-yl)allylamino)-N-(4-fluorobenzyl)nicotinamide | 495.2 | 1H NMR (300 MHz, DMSO-d6) Shift 13.66 (br. s., 1H), 10.99 (br. s., 1H), 9.08 (t, J = 5.85 Hz, 1H), 8.51 (t, J = 5.48 Hz, 1H), 8.20 (dd, J = 1.70, 4.72 Hz, 1H), 8.00 (dd, J = 1.70, 7.74 Hz, 1H), 8.00 (br. s., 0H), 7.79 (br. s., 1H), 7.60 (d, J = 7.93 Hz, 1H), 7.62 (br. s., 0H), 7.30-7.41 (m, 2H), 7.15 (tt, J = 2.64, 9.06 Hz, 2H), 7.06 (d, J = 7.93 Hz, 1H), 6.90 (s, 1H), 6.62 (dd, J = 4.91, 7.55 Hz, 1H), 6.56 (d, J = 15.86 Hz, 1H), 6.39 (td, J = 5.67, 15.86 Hz, 1H), 4.43 (d, J = 6.04 Hz, 2H), 4.22 (t, J = 5.29 Hz, 2H). |
| 15.22 | 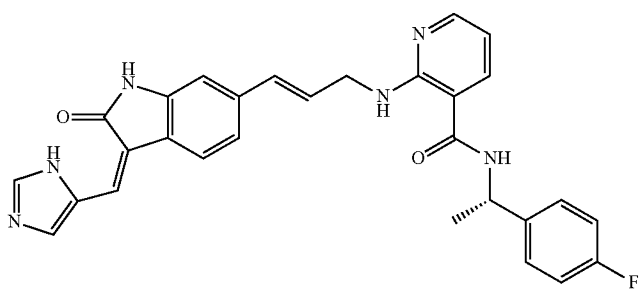 [SMILES: C[C@H](NC(=O)c1cccnc1NC/C=C/c1ccc2c(c1)NC(=O)/C2=C\c1cnc[nH]1)c1ccc(F)cc1] | 2-((E)-3-((Z)-((1H-imidazol-5-yl)methylene)-2-oxoindolin-6-yl)allylamino)-N-((S)-1-(4-fluorophenyl)ethyl)nicotinamide | 509.3 | 1H NMR (300 MHz, DMSO-d6) Shift 13.66 (br. s., 1H), 11.00 (br. s., 1H), 8.82 (d, J = 7.93 Hz, 1H), 8.38 (t, J = 5.48 Hz, 1H), 8.19 (dd, J = 1.70, 4.72 Hz, 1H), 8.07 (dd, J = 1.70, 7.74 Hz, 1H), 8.00 (br. s., 0H), 7.79 (br. s., 1H), 7.60 (d, J = 7.93 Hz, 1H), 7.62 (br. s., 0H), 7.36-7.48 (m, 2H), 7.10-7.21 (m, 2H), 7.05 (d, J = 7.55 Hz, 1H), 6.89 (s, 1H), 6.63 (dd, J = 4.91, 7.55 Hz, 1H), 6.54 (d, J = 15.86 Hz, 1H), 6.37 (td, J = 5.71, 15.77 Hz, 1H), 5.13 (quin, J = 7.27 Hz, 1H), 4.19 (t, J = 5.67 Hz, 2H), 1.46 (d, J = 7.18 Hz, 3H). |

TABLE 1-continued

| Ex. No. | Structure | Chemical Name | ESI-MS (M + H) | ¹H NMR |
|---|---|---|---|---|
| 16.1 | 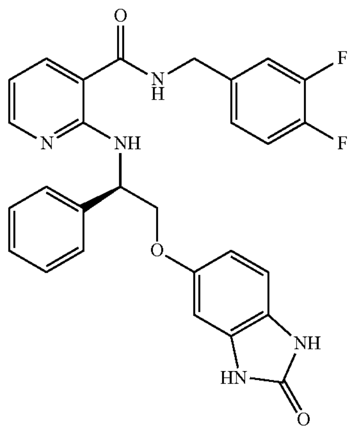 [SMILES: O=C(NCc1ccc(F)c(F)c1)c1cccnc1N[C@@H](COc1ccc2[nH]c(=O)[nH]c2c1)c1ccccc1] | (R)-N-(3,4-difluorobenzyl)-2-(2-(2-oxo-2,3-dihydro-1H-benzo[d]imidazol-5-yloxy)-1-phenylethylamino)nicotinamide | 516.2 | ¹H NMR (400 MHz, CD$_3$OD) δ 4.18 (d, 2H), 4.43 (d, 2H), 5.48 (s, 1H), 6.61 (m, 3H), 6.79 (d, 1H), 7.07 (s, 1H), 7.15 (d, 2H), 7.23 (t, 3H), 7.36 (d, 2H), 7.81 (d, 1H), 7.99 (d, 1H). |
| 16.2 | 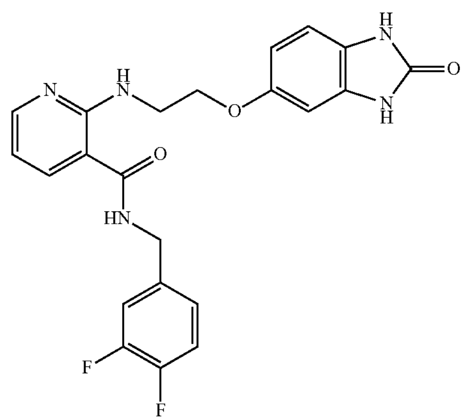 [SMILES: O=C(NCc1ccc(F)c(F)c1)c1cccnc1NCCOc1ccc2[nH]c(=O)[nH]c2c1] | N-(3,4-difluorobenzyl)-2-(2-(2-oxo-2,3-dihydro-1H-benzo[d]imidazol-5-yloxy)-ethylamino)nicotinamide | 440.4 | ¹H NMR (400 MHz, DMSO-d$_6$) δ 4.06 (d, 3H), 4.41 (t, 2H), 6.56 (s, 1H), 6.70 (t, 1H), 6.77 (d, 1H), 7.16 (s, 1H), 7.38 (m, 3H), 8.11 (d, 1H), 8.20 (t, 2H), 9.18 (s, 1H). |

| Ex. No. | Structure | Chemical Name | ESI-MS (M + H) | ¹H NMR |
|---|---|---|---|---|
| 16.3 | 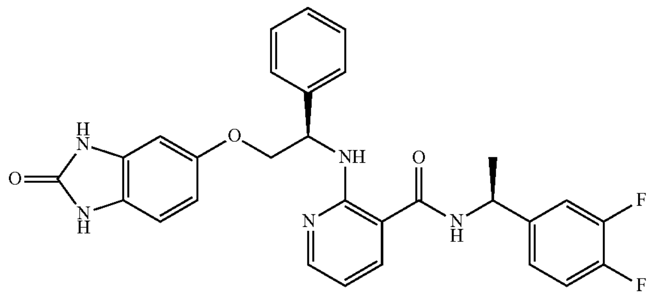 [SMILES: C[C@H](NC(=O)c1cccnc1N[C@@H](COc1ccc2[nH]c(=O)[nH]c2c1)c1ccccc1)c1ccc(F)c(F)c1] | N-((S)-1-(3,4-difluorophenyl)ethyl)-2-((R)-(2-(2-oxo-2,3-dihydro-1H-benzo[d]imidazol-5-yloxy)-1-phenylethylamino)nicotinamide | 530.2 | ¹H NMR (300 MHz, CDCl₃) δ 8.79 (d, J = 7.93 Hz, 1H), 8.74 (s, 1H), 8.49 (s, 1H), 8.19 (dd, J = 1.70, 4.72 Hz, 1H), 7.60 (dd, J = 1.70, 7.74 Hz, 1H), 7.45 (d, J = 7.18 Hz, 2H), 7.04-7.36 (m, 5H), 6.82 (d, J = 8.31 Hz, 1H), 6.64 (d, J = 2.27 Hz, 1H), 6.56-6.63 (m, J = 2.27, 8.31 Hz, 1H), 6.51 (dd, J = 4.91, 7.55 Hz, 1H), 6.26 (d, J = 7.55 Hz, 1H), 5.69 (dt, J = 5.62, 7.65 Hz, 1H), 5.23 (quin, J = 6.99 Hz, 1H), 4.19-4.32 (m, 2H), 3.50 (d, J = 5.29 Hz, 1H), 1.55 (d, J = 6.80 Hz, 3H) |
| 16.4 | 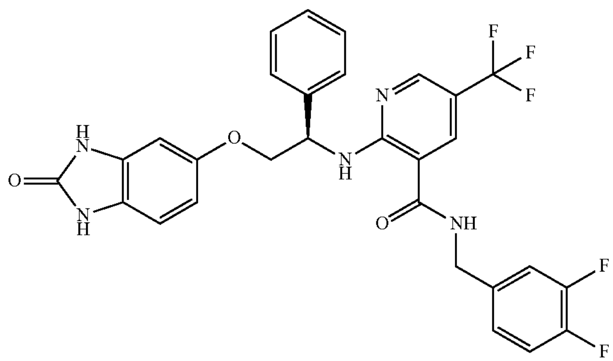 [SMILES: O=C(NCc1ccc(F)c(F)c1)c1cc(C(F)(F)F)cnc1N[C@@H](COc1ccc2[nH]c(=O)[nH]c2c1)c1ccccc1] | (R)-N-(3,4-difluorobenzyl)-2-(2-(2-oxo-2,3-dihydro-1H-benzo[d]imidazol-5-yloxy)-1-phenylethylamino)-5-(trifluoromethyl)nicotinamide | 584.2 | ¹H NMR (300 MHz, DMSO-d₆) δ 10.49 (s, 1H), 10.31 (s, 1H), 9.64 (d, J = 7.55 Hz, 1H), 9.30 (t, J = 5.67 Hz, 1H), 8.44 (s, 1H), 8.32 (d, J = 2.27 Hz, 1H), 7.07-7.50 (m, 9H), 6.69 (d, J = 8.31 Hz, 1H), 6.51 (d, J = 2.27 Hz, 1H), 6.43 (dd, J = 2.27, 8.31 Hz, 1H), 5.68 (s, 1H), 5.49-5.60 (m, 1H), 4.40 (d, J = 5.67 Hz, 2H), 4.10-4.29 (m, 2H). |
| 16.5 | 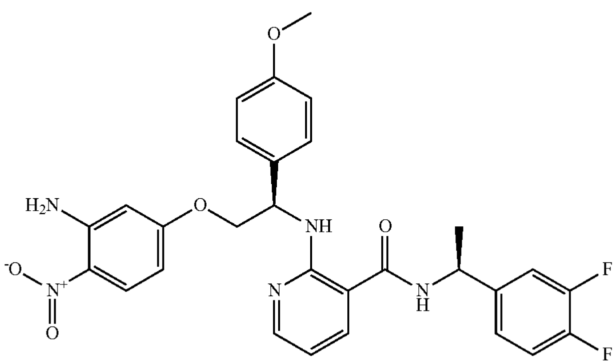 | 2-((R)-2-(3-amino-4-nitrophenoxy)-1-(4-methoxyphenyl)ethylamino)-N-((S)-1-(3,4-difluorophenyl)ethyl)nicotinamide | 564.2 | ¹H NMR (300 MHz, CD₂Cl₂) δ 8.74 (d, J = 7.55 Hz, 1H), 8.20 (dd, J = 1.89, 4.91 Hz, 1H), 7.98-8.04 (m, 1H), 7.66 (dd, J = 1.70, 7.74 Hz, 1H), 7.31-7.37 (m, 2H), 7.07-7.24 (m, 3H), 6.84-6.91 (m, 2H), 6.57 (dd, J = 4.91, 7.55 Hz, 1H), 6.25-6.34 (m, 3H), 6.16 (br. s., 2H), 5.56-5.65 (m, 1H), 5.17 (quin, J = 6.99 Hz, 1H), 4.22-4.39 (m, 2H), 3.77 (s, 3H), 1.54 (d, 3H). |

| Ex. No. | Structure | Chemical Name | ESI-MS (M+H) | ¹H NMR |
|---|---|---|---|---|
| 16.6 | 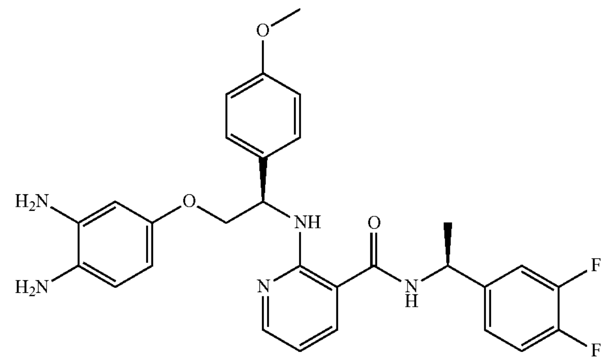 [SMILES: COc1ccc([C@H](COc2ccc(N)c(N)c2)Nc2ncccc2C(=O)N[C@@H](C)c2ccc(F)c(F)c2)cc1] | 2-((R)-2-(3,4-diaminophenoxy)-1-(4-methoxyphenyl)ethylamino)-N-((S)-1-(3,4-difluorophenyl)ethyl)nicotinamide | 534.3 | ¹H NMR (300 MHz, CD$_2$Cl$_2$) δ 8.73 (d, J = 7.18 Hz, 1H), 8.16 (dd, J = 1.89, 4.91 Hz, 1H), 7.59-7.68 (m, 1H), 7.29-7.39 (m, 2H), 7.09-7.27 (m, 3H), 6.79-6.89 (m, 2H), 6.58 (d, J = 8.31 Hz, 1H), 6.53 (dd, J = 4.72, 7.74 Hz, 1H), 6.25-6.33 (m, 2H), 6.22 (dd, J = 2.83, 8.50 Hz, 1H), 5.48-5.56 (m, 1H), 5.21 (quin, J = 6.99 Hz, 1H), 4.12-4.17 (m, 2H), 3.76 (s, 3H), 3.38-3.68 (m, 2H), 3.12 (d, J = 5.29 Hz, 2H), 1.56 (s, 3H). |
| 16.7 | 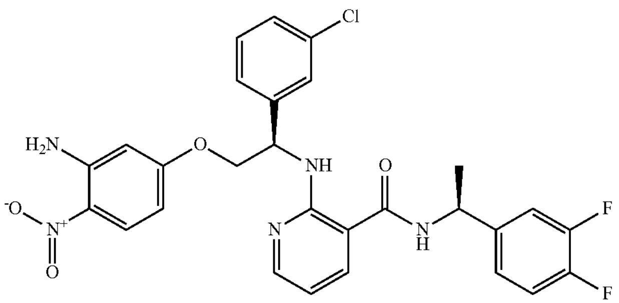 | 2-((R)-2-(3-amino-4-nitrophenoxy)-1-(3-chlorophenyl)ethylamino)-N-((S)-1-(3,4-difluorophenyl)ethyl)nicotinamide | 568.2 | ¹H NMR (300 MHz, CDCl$_3$) δ 8.82 (d, J = 7.55 Hz, 1H), 8.21 (dd, J = 1.70, 4.72 Hz, 1H), 8.06 (d, J = 9.44 Hz, 1H), 7.62 (dd, J = 1.70, 7.74 Hz, 1H), 7.43 (s, 1H), 7.06-7.38 (m, 6H), 6.58 (dd, J = 4.91, 7.55 Hz, 1H), 6.32 (dd, J = 2.64, 9.44 Hz, 1H), 6.22 (d, J = 2.27 Hz, 1H), 6.18 (br. s., 1H), 6.13 (br. s., 2H), 5.70 (dt, J = 5.48, 7.55 Hz, 1H), 5.23 (quin, J = 6.89 Hz, 1H), 4.23-4.39 (m, 2H), 1.51-1.62 (m, 3H). |
| 16.8 | 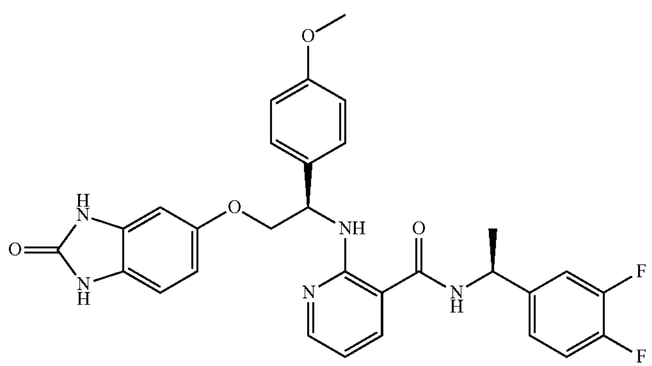 [SMILES: COc1ccc([C@H](COc2ccc3[nH]c(=O)[nH]c3c2)Nc2ncccc2C(=O)N[C@@H](C)c2ccc(F)c(F)c2)cc1] | N-((S)-1-(3,4-difluorophenyl)ethyl)-2-((R)-1-(4-methoxyphenyl)-2-(2-oxo-2,3-dihydro-1H-benzo[d]imidazol-5-yloxy)ethyl)aminonicotinamide | 560.2 | ¹H NMR (300 MHz, DMSO-d$_6$) δ 10.43 (d, 2H), 8.85 (dd, J = 7.74, 16.05 Hz, 2H), 8.15 (dd, J = 1.51, 4.91 Hz, 1H), 8.09 (dd, J = 1.70, 7.74 Hz, 1H), 7.33-7.51 (m, 2H), 7.30 (J = 8.69 Hz, 2H), 7.19-7.27 (m, 1H), 6.86 (d, J = 8.69 Hz, 2H), 6.76 (d, J = 8.31 Hz, 1H), 6.63 (dd, J = 4.72, 7.74 Hz, 1H), 6.55 (d, J = 2.27 Hz, 1H), 6.49 (dd, J = 2.45, 8.50 Hz, 1H), 5.40-5.54 (m, 1H), 5.14 (quin, J = 7.08 Hz, 1H), 4.10-4.26 (m, 2H), 3.70 (s, 3H), 1.45 (d, 3H). |

TABLE 1-continued

| Ex. No. | Structure | Chemical Name | ESI-MS (M + H) | ¹H NMR |
|---|---|---|---|---|
| 16.9 | 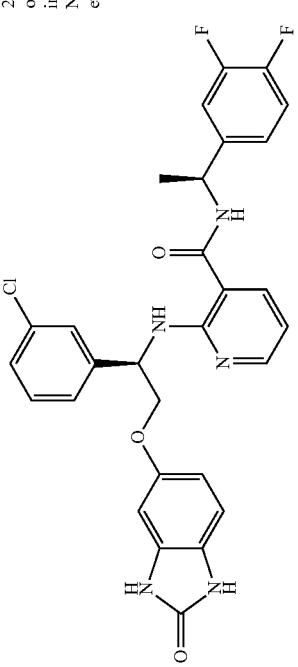 | 2-((R)-1-(3-chlorophenyl)-2-(2-oxo-2,3-dihydro-1H-benzo[d]imidazol-5-yloxy)ethylamino)-N-((S)-1-(3,4-difluorophenyl)ethyl)nicotinamide | 564.2 | ¹H NMR (300 MHz, CDCl₃) δ 9.34 (s, 1H), 9.06 (s, 1H), 8.81 (d, J = 7.18 Hz, 1H), 8.16 (dd, J = 1.89, 4.91 Hz, 1H), 7.62 (dd, J = 1.70, 7.74 Hz, 1H), 7.42 (s,1H), 7.28-7.37 (m, 1H), 7.03-7.26 (m, 5H), 6.78 (d, J = 8.31 Hz, 1H), 6.59 (d, J = 1.89 Hz, 1H), 6.47-6.57 (m, 2H), 6.35 (d, J = 7.18 Hz, 1H), 5.56-5.67 (m, 1H), 5.22 (quin, J = 6.99 Hz, 1H), 4.18 (d, J = 5.29 Hz, 2H), 1.53 (d, J = 6.80 Hz, 3H) |
| 16.10 | 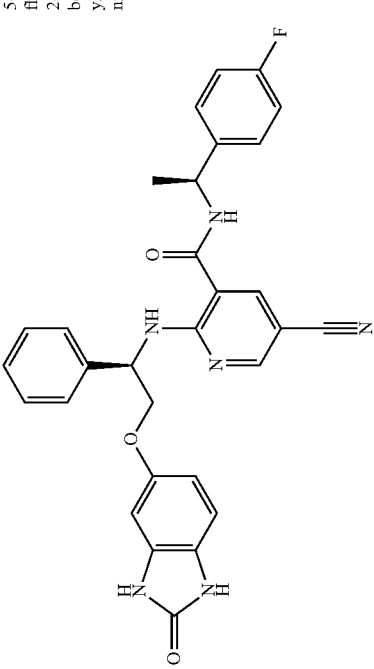 | 5-cyano-N-((S)-1-(4-fluorophenyl)ethyl)-2-(((R)-2-(2-oxo-2,3-dihydro-1H-benzo[d]imidazol-5-yloxy)ethyl)amino)nicotinamide | 537.2 | ¹H NMR (300 MHz, CDCl₃) δ 9.49 (d, J = 7.55 Hz, 1H), 8.49 (d, J = 1.89 Hz, 1H), 8.47 (br. s., 1H), 7.92 (br. s., 1H), 7.81 (d, J = 1.89 Hz, 1H), 7.28-7.47 (m, 7H), 7.01-7.12 (m, 2H), 6.89 (d, J = 8.31 Hz, 1H), 6.74 (d, J = 2.27 Hz, 1H), 6.64 (dd, J = 2.45, 8.50 Hz, 1H), 6.34 (d, J = 7.55 Hz, 1H), 5.72 (dt, J = 5.62, 7.65 Hz, 1H), 5.24 (quin, J = 6.89 Hz, 1H), 4.29 (d, J = 5.67 Hz, 2H), 1.60 (d, J = 7.18 Hz, 3H). |

TABLE 1-continued

| Ex. No. | Structure | Chemical Name | ESI-MS (M + H) | ¹H NMR |
|---|---|---|---|---|
| 16.11 | 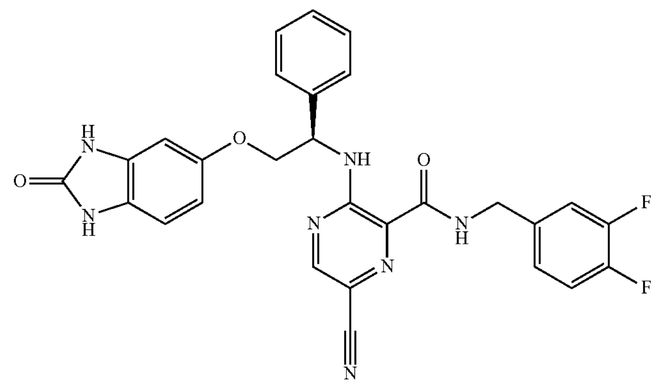 [SMILES: N#Cc1cnc(N[C@@H](COc2ccc3[nH]c(=O)[nH]c3c2)c2ccccc2)c(C(=O)NCc2ccc(F)c(F)c2)n1] | (R)-6-cyano-N-(3,4-difluorobenzyl)-3-(2-(2-oxo-2,3-dihydro-1H-benzo[d]imidazol-5-yloxy)-1-phenylethylamino)pyrazine-2-carboxamide | 542.2 | ¹H NMR (300 MHz, DMSO-d₆) δ 10.52 (s, 1H), 10.38 (s, 1H), 10.16 (d, J = 7.93 Hz, 1H), 9.62 (t, J = 6.23 Hz, 1H), 8.73 (s, 1H), 7.15-7.51 (m, 8H), 6.73-6.80 (m, 1H), 6.56 (d, J = 2.27 Hz, 1H), 6.50 (dd, J = 2.27, 8.31 Hz, 1H), 5.48-5.63 (m, 1H), 4.46 (d, J = 6.42 Hz, 2H), 4.25-4.40 (m, 2H). |
| 16.12 | 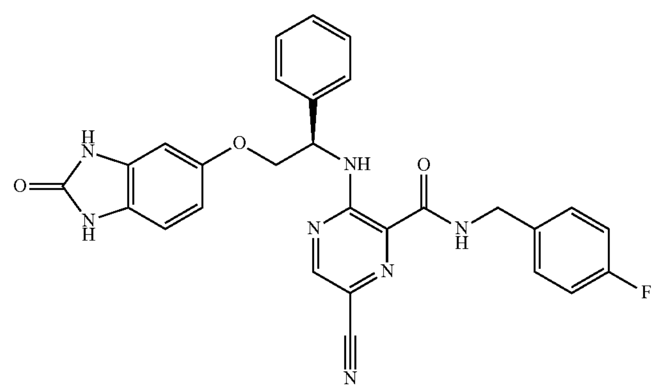 [SMILES: N#Cc1cnc(N[C@@H](COc2ccc3[nH]c(=O)[nH]c3c2)c2ccccc2)c(C(=O)NCc2ccc(F)cc2)n1] | (R)-6-cyano-N-(4-fluorobenzyl)-3-(2-(2-oxo-2,3-dihydro-1H-benzo[d]imidazol-5-yloxy)-1-phenylethylamino)pyrazine-2-carboxamide | 524.2 | ¹H NMR (300 MHz, DMSO-d₆) δ 10.52 (s, 1H), 10.38 (s, 1H), 10.19 (d, J = 7.93 Hz, 1H), 9.61 (t, J = 6.23 Hz, 1H), 8.73 (s, 1H), 7.43-7.52 (m, 2H), 7.23-7.43 (m, 5H), 7.14 (t, J = 8.88 Hz, 2H), 6.70-6.82 (m, 1H), 6.56 (s, 1H), 6.50 (dd, J = 2.08, 8.50 Hz, 1H), 5.48-5.63 (m, 1H), 4.46 (d, J = 6.42 Hz, 2H), 4.25-4.40 (m, 2H). |

TABLE 1-continued

| Ex. No. | Structure | Chemical Name | ESI-MS (M + H) | ¹H NMR |
|---|---|---|---|---|
| 16.13 | 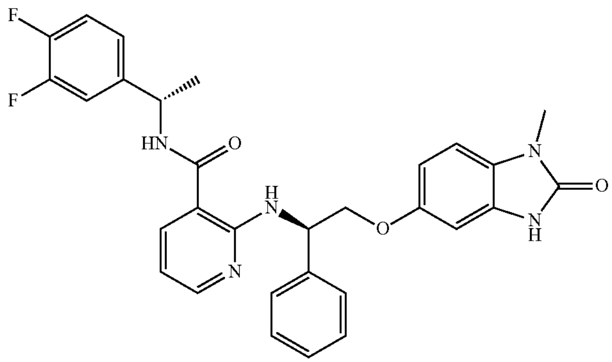 [SMILES: C[C@H](NC(=O)c1cccnc1N[C@@H](COc1ccc2c(c1)[nH]c(=O)n2C)c1ccccc1)c1ccc(F)c(F)c1] | N-((S)-1-(3,4-difluorophenyl)ethyl)-2-((R)-(2-(1-methyl-2-oxo-2,3-dihydro-1H-benzo[d]imidazol-5-yloxy)-1-phenylethylamino)nicotinamide | | ¹H NMR (300 MHz, DMSO-d₆) δ 10.67 (s, 1H), 8.91 (d, J = 7.55 Hz, 1H), 8.78 (d, J = 7.55 Hz, 1H), 8.03 (dd, J = 1.89, 7.55 Hz, 1H), 8.07 (dd, J = 1.89, 4.91 Hz, 1H), 7.39 (ddd, J = 2.64, 7.55, 11.71 Hz, 1H), 7.29-7.35 (m, 3H), 7.11-7.29 (m, 4H), 6.86 (d, J = 9.06 Hz, 1H), 6.57 (dd, J = 4.91, 7.55 Hz, 1H), 6.53 (s, 1H), 6.52 (dd, J = 2.40, 7.30 Hz, 1H), 5.42-5.54 (m, 1H), 5.09 (quin, J = 7.27 Hz, 1H), 4.17 (tt, J = 5.15, 9.96 Hz, 2H), 2.47 (s, 3H), 1.38 (d, J = 7.18 Hz, 3H). |
| 17.1 | 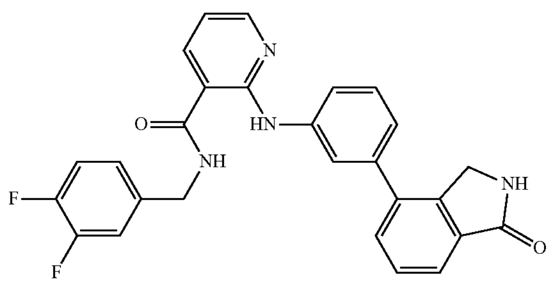 [SMILES: O=C(NCc1ccc(F)c(F)c1)c1cccnc1Nc1cccc(-c2cccc3c2CNC3=O)c1] | N-(3,4-difluorobenzyl)-2-(3-(1-oxoisoindolin-4-yl)phenylamino)nicotinamide | 471.5 | ¹H NMR (400 MHz, DMSO-d₆) δ 4.48 (d, 1H), 4.53 (s, 2H), 6.90 (t, 1H), 7.21 (d, 2H), 7.41 (t, 3H), 7.59 (d, 3H),7.68 (d, 2H), 8.04 (s, 1H), 8.19 (d, 1H), 8.33 (d, 1H), 8.65 (s, 1H), 9.37 (t, 1H), 10.95 (s, 1H) |
| 17.2 | 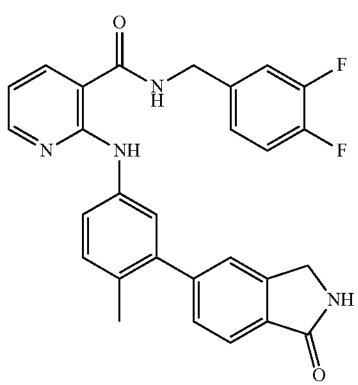 [SMILES: Cc1ccc(Nc2ncccc2C(=O)NCc2ccc(F)c(F)c2)cc1-c1ccc2c(c1)CNC2=O] | N-(3,4-difluorobenzyl)-2-{[4-methyl-(3-(1-oxo-2,3-dihydro-1H-isoindol-5-yl)phenyl]amino}pyridine-3-carboxamide | 485.5 | ¹H NMR (400 MHz, DMSO-d₆) δ 4.16 (s, 3H), 4.44 (d, 2H), 7.39 (t, 2H), 7.45 (d, 2H), 8.16 (m, 3H), 8.27 (d, 1H), 8.35 (d, 1H), 8.56 (s, 1H), 9.08 (s, 1H), 9.33 (t, 1H). |

| Ex. No. | Structure | Chemical Name | ESI-MS (M + H) | ¹H NMR |
|---|---|---|---|---|
| 17.3 | 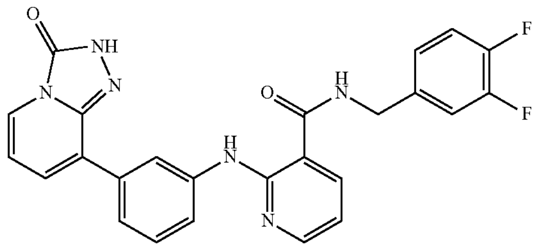 [SMILES: O=C(NCc1ccc(F)c(F)c1)c1cccnc1Nc1cccc(-c2cccn3c(=O)[nH]nc23)c1] | N-(3,4-difluorobenzyl)-2-(3-(3-oxo-2,3-dihydro-[1,2,4]triazolo[4,3-a]pyridin-8-yl)phenyl)aminonicotinamide | 473.2 | ¹H NMR (400 MHz, DMSO-d₆) δ 12.57 (s, 1H), 10.93 (s, 1H), 9.34 (s, 1H), 8.31 (d, J = 4 Hz, 1H), 8.17 (d, J = 8 Hz, 1H), 8.11 (s, 1H), 7.88 (d, J = 8 Hz, 1H), 7.81 (d, J = 8 Hz, 1H), 7.52 (d, J = 8 Hz, 1H), 7.46 (d, J = 4 Hz, 1H), 7.38 (m, 3H), 7.18 (bs, 1H), 6.87 (dd, J = 8 Hz, 1H), 6.68 (dd, J = 8 Hz, 1H), 4.46 (s, 2H) |
| 18.1 | 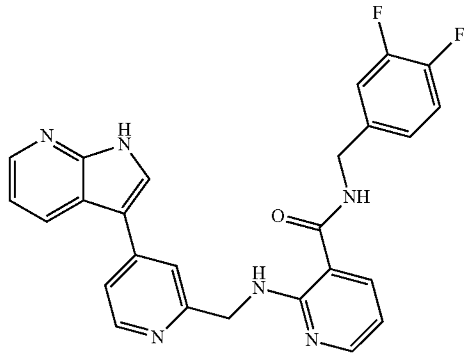 [SMILES: O=C(NCc1ccc(F)c(F)c1)c1cccnc1NCc1cc(-c2c[nH]c3ncccc23)ccn1] | 2-((4-(1H-pyrrolo[2,3-b]pyridin-3-yl)pyridin-2-ylmethyl)amino)-N-(3,4-difluorobenzyl)nicotinamide | 471.2 | ¹H NMR (400 MHz, DMSO-d₆) δ 4.48 (d, 2H), 4.95 (d, 2H), 6.73 (1H), 7.24 (m, 1H), 7.40 (t, 1H), 8.13 (m, 3H), 8.41 (t, 2H), 8.56 (d, 1H), 8.70 (s, 1H), 9.01 (s, 1H), 9.25 (d, 1H), 13.0 (s, 1H) |
| 19.1 | 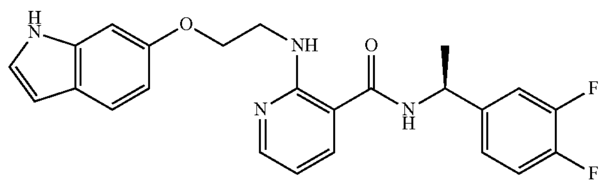 [SMILES: C[C@H](NC(=O)c1cccnc1NCCOc1ccc2cc[nH]c2c1)c1ccc(F)c(F)c1] | (S)-2-(2-(1H-indol-6-yloxy)ethylamino)-N-(1-(3,4-difluorophenyl)ethyl)nicotinamide | 437.2 | ¹H NMR (400 MHz, DMSO-d₆) δ 10.84 (br. s., 1H), 8.79 (d, J = 7.53 Hz, 1H), 8.46 (t, J = 5.52 Hz, 1H), 8.21 (dd, J = 1.76, 4.77 Hz, 1H), 8.06 (dd, J = 1.88, 7.66 Hz, 1H), 7.29-7.49 (m, 3H), 7.22 (ddd, J = 2.38, 4.33, 6.34 Hz, 1H), 7.14-7.19 (m, 1H), 6.93 (d, J = 2.26 Hz, 1H), 6.57-6.67 (m, 2H), 6.31 (t, J = 2.13 Hz, 1H), 5.12 (quin, J = 7.15 Hz, 1H), 4.10 (t, J = 5.77 Hz, 2H), 3.63-3.85 (m, 2H), 1.44 (d, J = 7.03 Hz, 3H). |
| 19.2 | 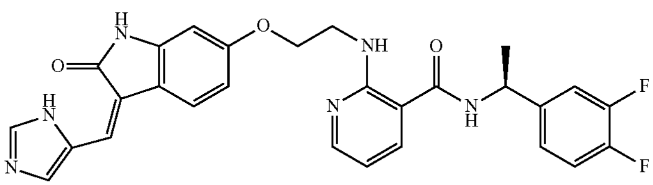 [SMILES: C[C@H](NC(=O)c1cccnc1NCCOc1ccc2c(c1)NC(=O)/C2=C\c1cnc[nH]1)c1ccc(F)c(F)c1] | (S,Z)-2-(2-(3-((1H-imidazol-5-yl)methylene)-2-oxoindolin-6-yloxy)ethylamino)-N-(1-(3,4-difluorophenyl)ethyl)nicotinamide | 531.2 | ¹H NMR (400 MHz, DMSO-d₆) δ 11.15 (s, 1H), 8.81 (s, 2H), 8.47 (br. s., 1H), 8.22 (dd, J = 1.76, 4.77 Hz, 1H), 8.09 (dd, J = 1.76, 7.78 Hz, 2H), 7.64 (s, 1H), 7.58 (d, J = 8.28 Hz, 1H), 7.27-7.51 (m, 2H), 7.21 (br. s., 1H), 6.66 (td, J = 3.14, 4.58 Hz, 2H), 6.52 (d, J = 2.26 Hz, 1H), 5.11 (s, 1H), 4.08-4.20 (m, 2H), 3.76 (br. s., 2H), 1.44 (d, J = 7.28 Hz, 3H) |

| Ex. No. | Structure | Chemical Name | ESI-MS (M + H) | ¹H NMR |
|---|---|---|---|---|
| 20.1 | 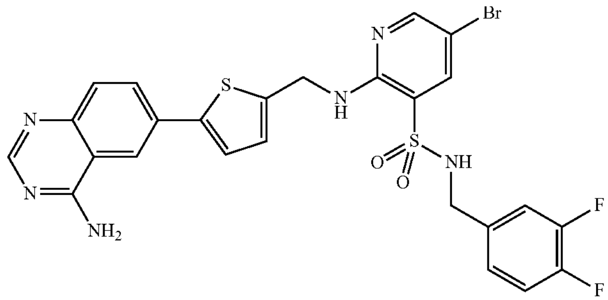 [SMILES: Nc1ncnc2ccc(-c3ccc(CNc4ncc(Br)cc4S(=O)(=O)NCc4ccc(F)c(F)c4)s3)cc12] | 2-(((5-(4-aminoquinazolin-6-yl)thiophen-2-yl)methyl)amino)-5-bromo-N-(3,4-difluorobenzyl)pyridine-3-sulfonamide | 618.0 | ¹H NMR (400 MHz, DMSO-$d_6$) δ 8.64 (t, 1H), 8.42 (d, 1H), 8.34 (d, 2H) 7.98 (dd, 1H), 7.83 (d, 1H), 7.83 (br, 2H), 7.65 (dd, 1H), 7.48 (d, 1H), 7.25-7.18 (m, 2H), 7.12-7.09 (m, 2H), 7.03-7.00 (br, 1H), 4.80 (d, 2H), 4.12 (d, 2H). |
| 20.2 | 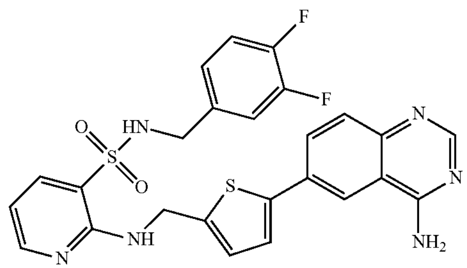 [SMILES: Nc1ncnc2ccc(-c3ccc(CNc4ncccc4S(=O)(=O)NCc4ccc(F)c(F)c4)s3)cc12] | 2-(((5-(4-aminoquinazolin-6-yl)thiophen-2-yl)methyl)amino)-N-(3,4-difluorobenzyl)pyridine-3-sulfonamide | 538.8 | ¹H NMR (400 MHz, DMSO-$d_6$) δ: 9.38 (br, 2H), 8.57 (d, 1H), 8.48 (t, 1H), 8.2 (dd, 1H), 8.18 (dd, 1H), 7.85 (dd, 1H), 7.74 (d, 1H), 7.53 (d, 1H), 7.27-7.13 (m, 2H), 7.14 (d, 1H), 7.05-7.03 (m, 2H), 6.73-6.69 (m, 1H), 4.83 (d, 2H), 4.07 (d, 2H). |
| 21 | 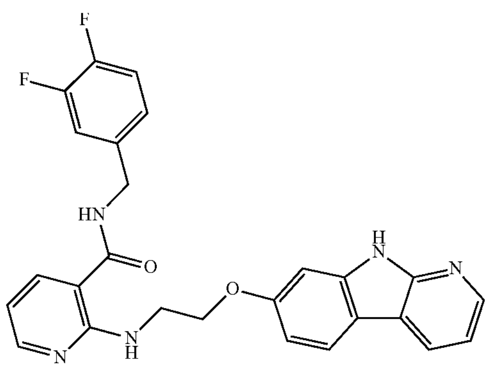 [SMILES: O=C(NCc1ccc(F)c(F)c1)c1cccnc1NCCOc1ccc2c(c1)[nH]c1ncccc12] | 2-(2-(9H-pyrido[2,3-b]indol-7-yloxy)ethylamino)-N-(3,4-difluorobenzyl)nicotinamide | 474.2 | ¹H NMR (400 MHz, DMSO-$d_6$) δ: 11.76 (s, 1H), 9.17 (t, 1H), 8.82 (s, 1H), 8.40 (d, 1H), 8.32 (s, 1H), 8.26-8.22 (m, 1H), 8.07 (dd, 1H), 8.03 (d, 1H), 7.42-7.33 (m, 2H), 7.21-7.14 (m, 2H), 7.03 (d, 1H), 6.88-6.84 (dd, 1H), 6.72-6.66 (dd, 1H), 4.44-4.41 (m, 2H), 4.26-4.22 (m, 2H), 3.87-3.82 (m, 2H). |

TABLE 1-continued

| Ex. No. | Structure | Chemical Name | ESI-MS (M + H) | ¹H NMR |
|---|---|---|---|---|
| 22 | 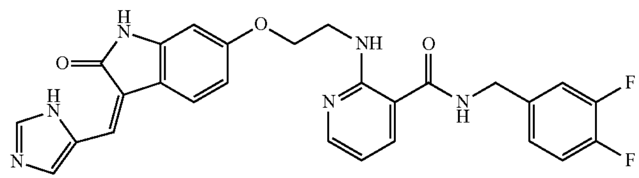 [SMILES: O=C1Nc2cc(OCCNc3ncccc3C(=O)NCc3ccc(F)c(F)c3)ccc2/C1=C/c1cnc[nH]1] | (Z)-2-(3-((1H-imidazol-5-yl)methylene)-2-oxoindolin-6-yloxy)ethylamino)-N-(3,4-difluorobenzyl)nicotinamide | 516.9 | ¹H NMR (400 MHz, DMSO-d$_6$) δ: 11.19 (s, 1H), 9.12 (s, 1H), 8.91 (s, 1H), 8.62 (s, 1H), 8.22 (t, 1H), 8.14 (s, 1H), 8.04-8.02 (m, 1H), 7.65 (s, 1H), 7.59 (d, 1H), 7.39-7.34 (m, 2H), 7.16 (s, 1H), 6.69-6.54 (m, 2H), 6.53 (s, 1H), 4.42 (d, 2H), 4.17 (t, 2H), 3.80-3.78 (m, 2H). |
| 23 | 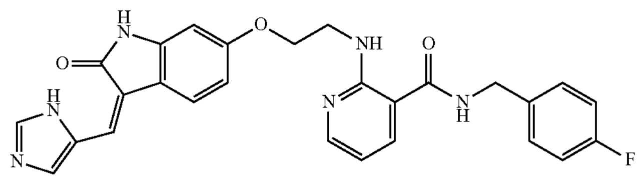 [SMILES: O=C1Nc2cc(OCCNc3ncccc3C(=O)NCc3ccc(F)cc3)ccc2/C1=C/c1cnc[nH]1] | (Z)-2-(2-((1H-imidazol-5-yl)methylene)-2-oxoindolin-6-yloxy)ethylamino)-N-(4-fluorobenzyl)nicotinamide | 499.0 | ¹H NMR (400 MHz, DMSO-d$_6$) δ: 13.57 (s, 1H), 10.90 (s, 1H), 9.06 (t, 1H), 8.58 (t, 1H), 8.21 (t, 1H), 8.00-7.94 (m, 2H), 7.64 (s, 1H), 7.55 (d, 1H), 7.36-7.32 (m, 2H), 7.13 (t, 2H), 6.63-6.50 (m, 2H), 6.49 (d, 1H), 4.41 (d, 2H), 4.13 (t, 2H), 3.79-3.75 (m, 2H). |
| 24 | 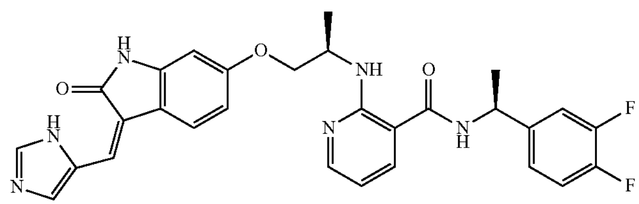 [SMILES: C[C@H](COc1ccc2c(c1)NC(=O)/C2=C\c1cnc[nH]1)Nc1ncccc1C(=O)N[C@@H](C)c1ccc(F)c(F)c1] | (R,Z)-2-(1-(3-((1H-imidazol-5-yl)methylene)-2-oxoindolin-6-yloxy)propan-2-ylamino)-N-(3,4-difluorobenzyl)nicotinamide | 531.2 | ¹H NMR (400 MHz, DMSO-d$_6$) δ: 10.47 (s, 1H), 8.23 (dd, J = 4.77, 1.51 Hz, 1H), 8.05 (d, J = 7.28 Hz, 1H), 7.89 (d, J = 2.01 Hz, 1H), 7.23-7.42 (m, 3H), 7.15 (br, s., 1H), 6.74 (d, J = 2.01 Hz, 1H), 6.62-6.69 (m, 1H), 6.56 (dd, J = 8.66, 2.38 Hz, 1H), 6.47 (d, J = 2.26 Hz, 1H), 4.41 (d, J = 5.27 Hz, 2H), 4.13 (dd, J = 9.41, 4.39 Hz, 1H), 3.88-4.02 (m, 1H), 1.30 (d, J = 6.53 Hz, 4H). |
| 25 | 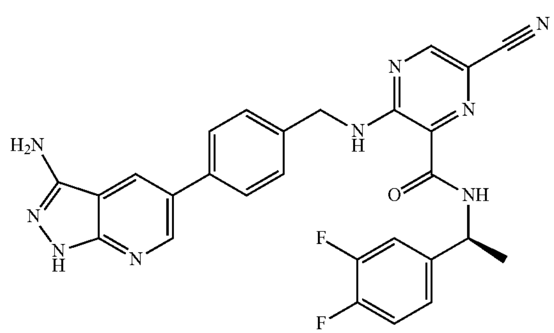 [SMILES: C[C@H](NC(=O)c1nc(C#N)cnc1NCc1ccc(-c2cnc3[nH]nc(N)c3c2)cc1)c1ccc(F)c(F)c1] | (S)-3-(4-(3-amino-1H-pyrazolo[3,4-b]pyridin-5-yl)benzylamino)-6-cyano-N-(1-(3,4-difluorophenyl)ethyl)pyrazine-2-carboxamide | 525.9 | ¹H NMR (300 MHz, CDCl$_3$) δ 10.55 (br. s., 1H), 9.62 (t, J = 5.67 Hz, 1H), 8.64 (d, J = 1.89 Hz, 1H), 8.42 (s, 1H), 7.97 (d, J = 1.89 Hz, 1H), 7.94 (d, J = 7.55 Hz, 1H), 7.41-7.53 (m, 2H), 7.31-7.40 (m, 2H), 6.94-7.16 (m, 3H), 5.04 (quin, J = 7.18 Hz, 1H), 4.55-4.82 (m, 2H), 4.23 (br. s., 2H), 1.52 (d, J = 7.18 Hz, 3H). |

TABLE 1-continued

| Ex. No. | Structure | Chemical Name | ESI-MS (M + H) | ¹H NMR |
|---|---|---|---|---|
| 26 | 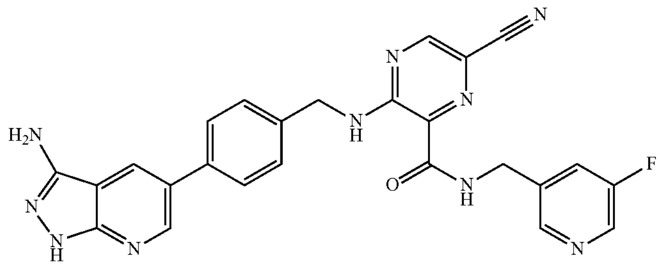 [SMILES: N#Cc1cnc(NCc2ccc(-c3cnc4[nH]nc(N)c4c3)cc2)c(C(=O)NCc2cncc(F)c2)n1] | 3-(4-(3-amino-1H-pyrazolo[3,4-b]pyridin-5-yl)benzylamino)-6-cyano-N-((5-fluoropyridin-3-yl)methyl)pyrazine-2-carboxamide | 494.9 | ¹H NMR (300 MHz, DMSO-d₆) δ 12.00 (s, 1H), 9.79 (t, J = 5.85 Hz, 1H), 9.63 (t, J = 6.04 Hz, 1H), 8.76 (s, 1H), 8.64 (d, J = 2.27 Hz, 1H), 8.42-8.54 (m, 2H), 8.38 (d, J = 1.89 Hz, 1H), 7.68 (td, J = 2.17, 10.01 Hz, 1H), 7.63 (d, J = 7.93 Hz, 2H), 7.46 (d, J = 8.31 Hz, 2H), 5.61 (s, 2H), 4.76 (d, J = 6.04 Hz, 2H), 4.53 (d, J = 6.04 Hz, 2H). |
| 27 | 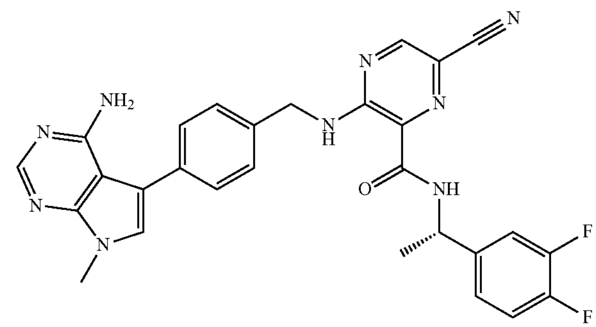 [SMILES: C[C@H](NC(=O)c1nc(C#N)cnc1NCc1ccc(-c2cn(C)c3ncnc(N)c23)cc1)c1ccc(F)c(F)c1] | (S)-3-(4-(4-amino-7-methyl-7H-pyrrolo[2,3-d]pyrimidin-5-yl)benzylamino)-6-cyano-N-(1-(3,4-difluorophenyl)ethyl)pyrazine-2-carboxamide | 539.9 | ¹H NMR (300 MHz, CDCl₃) δ 9.68 (t, J = 5.67 Hz, 1H), 8.51 (s, 1H), 8.27-8.38 (m, 1H), 8.01 (d, J = 7.55 Hz, 1H), 7.37-7.63 (m, 5H), 7.01-7.25 (m, 3H), 6.93 (s, 1H), 5.03-5.26 (m, 2H), 4.68-4.88 (m, 2H), 3.74-3.91 (m, 3H), 1.61 (d, J = 7.18 Hz, 3H). |
| 28 | 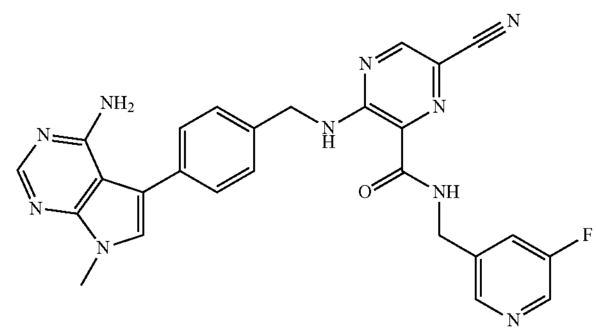 [SMILES: Cn1cc(-c2ccc(CNc3ncc(C#N)nc3C(=O)NCc3cncc(F)c3)cc2)c2c(N)ncnc21] | 3-(4-(4-amino-7-methyl-7H-pyrrolo[2,3-d]pyrimidin-5-yl)benzylamino)-6-cyano-N-((5-fluoropyridin-3-yl)methyl)pyrazine-2-carboxamide | 508.9 | ¹H NMR (300 MHz, CDCl₃) δ 9.67 (t, J = 5.29 Hz, 1H), 8.53 (s, 1H), 8.41-8.49 (m, 2H), 8.37 (s, 1H), 8.25 (t, J = 6.61 Hz, 1H), 7.60 (dd, J = 6.80, 12.09 Hz, 1H), 7.34-7.54 (m, 6H), 6.94 (s, 1H), 5.07 (br. s., 2H), 4.82 (d, J = 6.04 Hz, 2H), 4.65 (d, J = 6.04 Hz, 2H), 3.86 (s, 3H). |

TABLE 1-continued

| Ex. No. | Structure | Chemical Name | ESI-MS (M + H) | ¹H NMR |
|---|---|---|---|---|
| 29 | 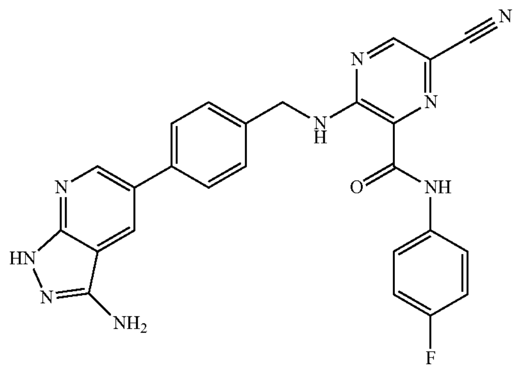 [SMILES: N#Cc1cnc(NCc2ccc(-c3cnc4[nH]nc(N)c4c3)cc2)c(C(=O)Nc2ccc(F)cc2)n1] | 3-(4-(3-amino-1H-pyrazolo[3,4-b]pyridin-5-yl)benzylamino)-6-cyano-N-(4-fluorophenyl)pyrazine-2-carboxamide | 479.9 | ¹H NMR (400 MHz, DMSO-d₆) δ 12.00 (s, 1H), 10.73 (s, 1H), 9.68 (t, J = 5.65 Hz, 1H), 8.79 (s, 1H), 8.64 (d, J = 1.76 Hz, 1H), 8.37 (d, J = 1.76 Hz, 1H), 7.83 (dd, J = 5.02, 8.78 Hz, 2H), 7.57-7.72 (m, J = 8.28 Hz, 2H), 7.40-7.54 (m, J = 8.03 Hz, 2H), 7.21 (t, J = 8.78 Hz, 2H), 5.61 (br. s., 2H), 4.79 (d, J = 5.77 Hz, 2H). |
| 30 | 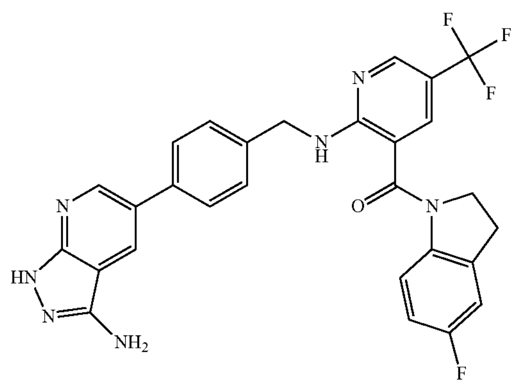 [SMILES: Nc1n[nH]c2ncc(-c3ccc(CNc4ncc(C(F)(F)F)cc4C(=O)N4CCc5cc(F)ccc54)cc3)cc12] | (2-(4-(3-amino-1H-pyrazolo[3,4-b]pyridin-5-yl)benzylamino)-5-(trifluoromethyl)pyridin-3-yl)(5-fluoroindolin-1-yl)methanone | 547.8 | ¹H NMR (400 MHz, DMSO-d₆) δ 11.99 (br. s., 1H), 8.62 (s, 1H), 8.45 (s, 1H), 8.36 (s, 1H), 7.92 (s, 1H), 7.78 (t, J = 5.52 Hz, 1H), 7.52-7.64 (m, J = 7.53 Hz, 2H), 7.31-7.47 (m, J = 7.03 Hz, 2H), 7.17 (d, J = 7.53 Hz, 1H), 7.03 (t, J = 8.53 Hz, 1H), 5.60 (br. s., 2H), 4.66 (d, J = 5.02 Hz, 2H), 4.01 (t, J = 7.53 Hz, 2H), 3.11 (t, J = 7.65 Hz, 2H). |

TABLE 1-continued

| Ex. No. | Structure | Chemical Name | ESI-MS (M + H) | ¹H NMR |
|---|---|---|---|---|
| 31 | 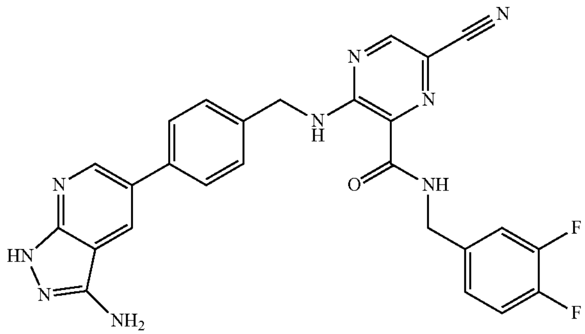 [SMILES: N#Cc1cnc(NCc2ccc(-c3cnc4[nH]nc(N)c4c3)cc2)c(C(=O)NCc2ccc(F)c(F)c2)n1] | 3-(4-(3-amino-1H-pyrazolo[3,4-b]pyridin-5-yl)benzylamino)-6-cyano-N-(3,4-difluorobenzyl)pyrazine-2-carboxamide | 511.9 | ¹H NMR (400 MHz, DMSO-d₆) δ 12.00 (s, 1H), 9.81 (t, J = 5.90 Hz, 1H), 9.58 (t, J = 6.40 Hz, 1H), 8.75 (s, 1H), 8.63 (d, J = 2.01 Hz, 1H), 8.37 (d, J = 2.01 Hz, 1H), 7.55-7.68 (m, J = 8.28 Hz, 2H), 7.42-7.48 (m, J = 8.03 Hz, 2H), 7.29-7.42 (m, 2H), 7.12-7.23 (m, 1H), 5.61 (br. s, 2H), 4.75 (d, J = 5.77 Hz, 2H), 4.43 (d, J = 6.27 Hz, 2H). |
| 32 | 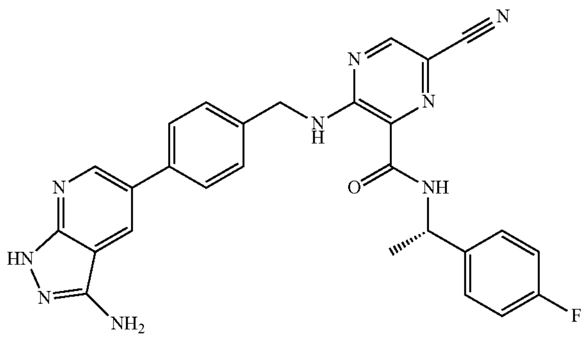 [SMILES: C[C@H](NC(=O)c1nc(C#N)cnc1NCc1ccc(-c2cnc3[nH]nc(N)c3c2)cc1)c1ccc(F)cc1] | (S)-3-(4-(3-amino-1H-pyrazolo[3,4-b]pyridin-5-yl)benzylamino)-6-cyano-N-(1-(4-fluorophenyl)ethyl)pyrazine-2-carboxamide | 507.9 | ¹H NMR (400 MHz, DMSO-d₆) δ 12.00 (s, 1H), 9.78 (t, J = 5.90 Hz, 1H), 9.30 (d, J = 8.28 Hz, 1H), 8.73 (s, 1H), 8.63 (d, J = 2.01 Hz, 1H), 8.36 (d, J = 2.01 Hz, 1H), 7.62 (d, J = 8.03 Hz, 2H), 7.33-7.51 (m, 2H), 7.43 (d, J = 7.78 Hz, 2H), 7.14 (t, J = 8.78 Hz, 2H), 5.61 (br. s, 2H), 5.13 (quin, J = 7.28 Hz, 1H), 4.63-4.82 (m, 2H), 1.51 (d, J = 7.03 Hz, 3H). |
| 33 | 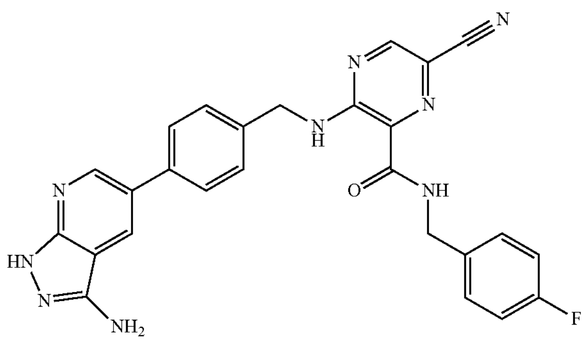 [SMILES: N#Cc1cnc(NCc2ccc(-c3cnc4[nH]nc(N)c4c3)cc2)c(C(=O)NCc2ccc(F)cc2)n1] | 3-(4-(3-amino-1H-pyrazolo[3,4-b]pyridin-5-yl)benzylamino)-6-cyano-N-(4-fluorobenzyl)pyrazine-2-carboxamide | 493.9 | ¹H NMR (400 MHz, DMSO-d₆) δ 12.00 (s, 1H), 9.84 (t, J = 5.90 Hz, 1H), 9.57 (t, J = 6.27 Hz, 1H), 8.74 (s, 1H), 8.63 (d, J = 2.01 Hz, 1H), 8.37 (d, J = 1.76 Hz, 1H), 7.57-7.70 (m, J = 8.28 Hz, 2H), 7.41-7.49 (m, J = 8.28 Hz, 2H), 7.37 (dd, J = 8.41 Hz, 2H), 7.13 (t, J = 8.91 Hz, 2H), 5.61 (br. s, 2H), 4.75 (d, J = 6.02 Hz, 2H), 4.42 (d, J = 6.27 Hz, 2H). |

TABLE 1-continued

| Ex. No. | Structure | Chemical Name | ESI-MS (M + H) | ¹H NMR |
|---|---|---|---|---|
| 34 | 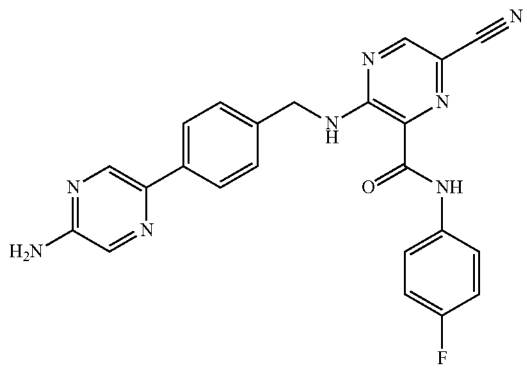 [SMILES: N#Cc1cnc(NCc2ccc(-c3cnc(N)cn3)cc2)c(C(=O)Nc2ccc(F)cc2)n1] | 3-(4-(5-aminopyrazin-2-yl)benzylamino)-6-cyano-N-(4-fluorophenyl)pyrazine-2-carboxamide | 440.9 | ¹H NMR (400 MHz, DMSO-d$_6$) δ 10.72 (s, 1H), 9.65 (t, J = 5.65 Hz, 1H), 8.77 (s, 1H), 8.46 (d, J = 1.26 Hz, 1H), 7.93 (d, J = 1.25 Hz, 1H), 7.86 (d, J = 8.28 Hz, 2H), 7.76-7.84 (m, 2H), 7.40 (d, J = 8.28 Hz, 2H), 7.20 (t, J = 8.91 Hz, 2H), 6.52 (s, 2H), 4.76 (d, J = 5.77 Hz, 2H) |
| 35 | 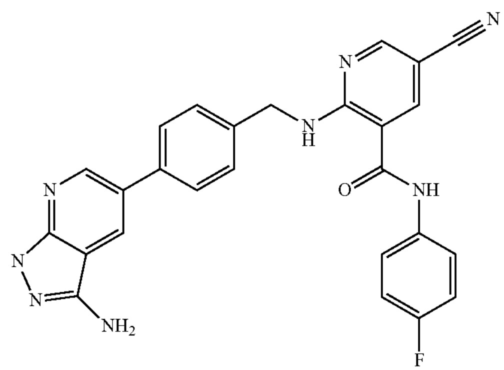 [SMILES: N#Cc1cnc(NCc2ccc(-c3cnc4[nH]nc(N)c4c3)cc2)c(C(=O)Nc2ccc(F)cc2)c1] | 2-(4-(3-amino-1H-pyrazolo[3,4-b]pyridin-5-yl)benzylamino)-5-cyano-N-(4-fluorophenyl)nicotinamide | 478.9 | ¹H NMR (300 MHz, DMSO-d$_6$) δ 12.06 (s, 1H), 10.50 (s, 1H), 9.12 (t, J = 5.67 Hz, 1H), 8.70 (dd, J = 2.08, 5.10 Hz, 2H), 8.53 (d, J = 2.27 Hz, 1H), 8.44 (d, J = 2.27 Hz, 1H), 7.73-7.88 (m, 2H), 7.62-7.73 (m, J = 8.31 Hz, 2H), 7.44-7.58 (m, J = 8.31 Hz, 2H), 7.28 (t, J = 9.06 Hz, 2H), 5.67 (s, 2H), 4.83 (d, J = 5.67 Hz, 2H). |

TABLE 1-continued

| Ex. No. | Structure | Chemical Name | ESI-MS (M + H) | ¹H NMR |
|---|---|---|---|---|
| 36 | 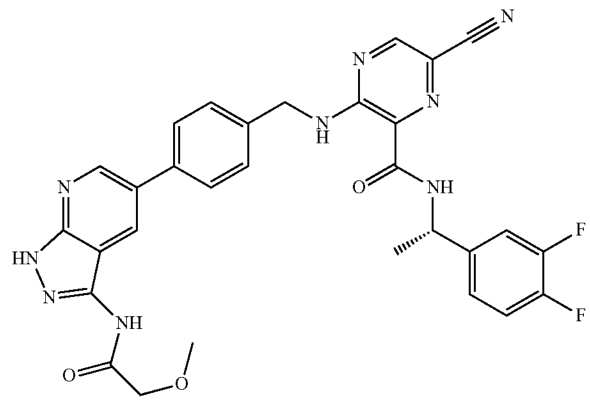 [SMILES: COCC(=O)Nc1n[nH]c2ncc(-c3ccc(CNc4ncc(C#N)nc4C(=O)N[C@@H](C)c4ccc(F)c(F)c4)cc3)cc12] | (S)-ethyl 5-(4-((5-cyano-3-((1-(3,4-difluorophenyl)ethyl)carbamoyl)pyrazin-2-ylamino)methyl)phenyl)-1H-pyrazolo[3,4-b]pyridin-3-ylcarbamate | 597.9 | ¹H NMR (300 MHz, DMSO-d₆) δ 13.20 (br. s, 1H), 10.12 (br. s, 1H), 9.76 (t, J = 5.85 Hz, 1H), 9.31 (d, J = 8.31 Hz, 1H), 8.76 (d, J = 2.27 Hz, 1H), 8.73 (s, 1H), 8.46 (d, J = 1.89 Hz, 1H), 7.64 (d, J = 7.93 Hz, 2H), 7.47-7.56 (m, 1H), 7.45 (d, J = 8.31 Hz, 2H), 7.37 (td, J = 8.50, 10.58 Hz, 1H), 7.21-7.30 (m, 1H), 5.12 (quin, J = 7.27 Hz, 1H), 4.65-4.82 (m, 2H), 4.16 (q, J = 7.18 Hz, 2H), 1.52 (d, J = 7.18 Hz, 3H), 1.24 (t, J = 6.99 Hz, 3H). |
| 37 | 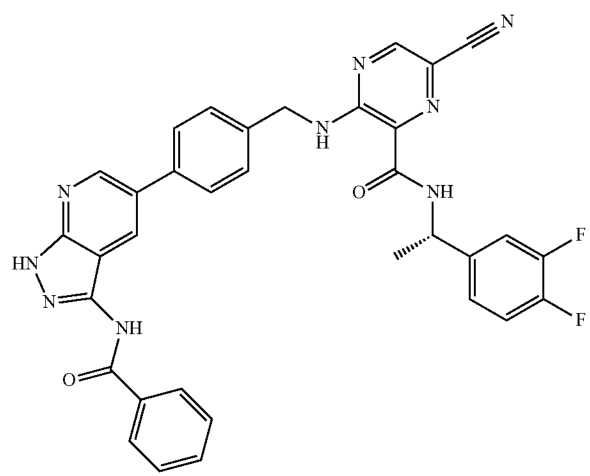 [SMILES: C[C@H](NC(=O)c1nc(C#N)cnc1NCc1ccc(-c2cnc3[nH]nc(NC(=O)c4ccccc4)c3c2)cc1)c1ccc(F)c(F)c1] | (S)-3-(4-(3-benzamido-1H-pyrazolo[3,4-b]pyridin-5-yl)benzylamino)-6-cyano-N-(1-(3,4-difluorophenyl)ethyl)pyrazine-2-carboxamide | 629.9 | ¹H NMR (300 MHz, DMSO-d₆) δ 13.43 (br. s., 1H), 11.09 (s, 1H), 9.76 (t, J = 5.85 Hz, 1H), 9.31 (d, J = 8.31 Hz, 1H), 8.81 (d, J = 2.27 Hz, 1H), 8.73 (s, 1H), 8.49 (d, J = 2.27 Hz, 1H), 8.02-8.16 (m, 2H), 7.42-7.74 (m, 8H), 7.36 (td, J = 8.45, 10.67 Hz, 1H), 7.20-7.30 (m, 1H), 5.12 (quin, J = 7.27 Hz, 1H), 4.65-4.83 (m, 2H), 1.51 (d, J = 7.18 Hz, 3H). |

TABLE 1-continued

| Ex. No. | Structure | Chemical Name | ESI-MS (M + H) | ¹H NMR |
|---|---|---|---|---|
| 38 | 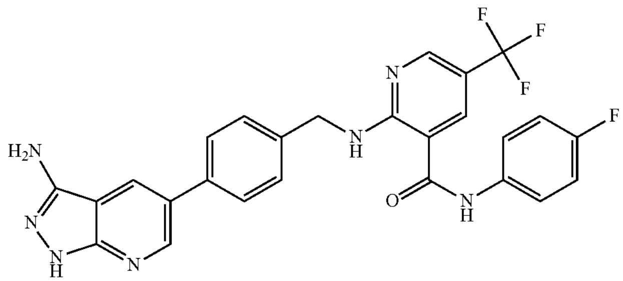 [SMILES: Nc1n[nH]c2ncc(-c3ccc(CNc4ncc(C(F)(F)F)cc4C(=O)Nc4ccc(F)cc4)cc3)cc12] | 2-[4-(3-Amino-1H-pyrazolo [3,4-b]pyridin-5-yl)-benzylamino]-N-(4-fluorophenyl)-5-trifluoromethyl-nicotinamide | 522.2 | ¹H NMR (300 MHz, DMSO-$d_6$) δ 11.99 (s, 1H), 10.51 (s, 1H), 8.93 (t, J = 5.67 Hz, 1H), 8.65 (d, J = 2.27 Hz, 1H), 8.56 (d, J = 1.51 Hz, 1H), 8.39 (dd, J = 2.27, 4.91 Hz, 2H), 7.67-7.76 (m, 4H), 7.42-7.66 (m, 4H), 7.17-7.28 (m, 2H), 5.61 (s, 2H), 4.77 (d, J = 5.67 Hz, 2H) |
| 39 | 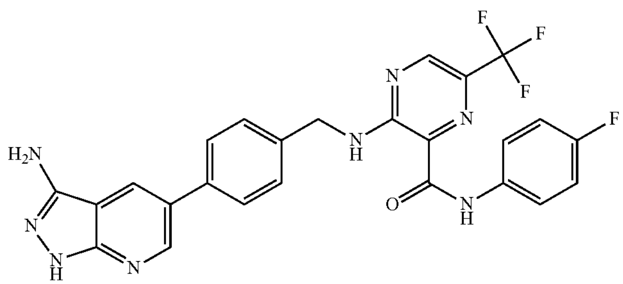 [SMILES: Nc1n[nH]c2ncc(-c3ccc(CNc4ncc(C(F)(F)F)nc4C(=O)Nc4ccc(F)cc4)cc3)cc12] | 3-(4-(3-amino-1H-pyrazolo [3,4-b]pyridin-5-yl) benzylamino)-N-(4-fluorophenyl)-6-(trifluoromethyl)pyrazine-2-carboxamide | 522.9 | ¹H NMR (300 MHz, DMSO-$d_6$) δ 12.00 (s, 1H), 10.49 (s, 1H), 9.44 (t, J = 6.04 Hz, 1H), 8.75 (s, 1H), 8.65 (d, J = 1.89 Hz, 1H), 8.38 (d, J = 1.89 Hz, 1H), 7.75-7.86 (m, 2H), 7.60-7.69 (m, J = 8.31 Hz, 2H), 7.44-7.53 (m, 2H), 7.18-7.28 (m, 2H), 5.61 (br. s, 2H), 4.80 (d, J = 5.67 Hz, 2H). |
| 40 | 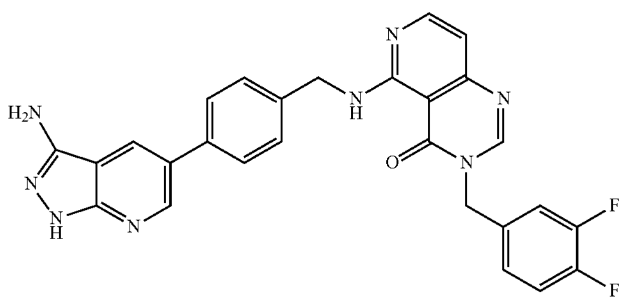 [SMILES: Nc1n[nH]c2ncc(-c3ccc(CNc4nccc5ncn(Cc6ccc(F)c(F)c6)c(=O)c45)cc3)cc12] | 5-(4-(3-amino-1H-pyrazolo [3,4-b]pyridin-5-yl) benzylamino)-3-(3,4-difluorobenzyl)pyrido [4,3-d]pyrimidin-4(3H)-one | 510.9 | ¹H NMR (300 MHz, DMSO-$d_6$) δ 9.42 (br. s., 1H), 8.71 (s, 1H), 8.65 (d, J = 1.89 Hz, 1H), 8.40 (d, J = 1.89 Hz, 1H), 8.14 (d, J = 6.04 Hz, 1H), 7.59 (d, J = 7.93 Hz, 2H), 7.26-7.53 (m, 4H), 7.20 (br. s., 1H), 6.70 (d, J = 5.67 Hz, 1H), 5.09 (s, 2H), 4.72 (d, J = 5.29 Hz, 2H), 2.00 (s, 2H) |

TABLE 1-continued

| Ex. No. | Structure | Chemical Name | ESI-MS (M + H) | ¹H NMR |
|---|---|---|---|---|
| 41 | 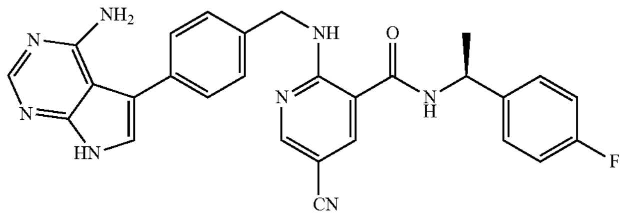 [SMILES: C[C@H](NC(=O)c1cc(C#N)cnc1NCc1ccc(-c2c[nH]c3ncnc(N)c23)cc1)c1ccc(F)cc1] | 2-[4-(4-Amino-7H-pyrrolo [2,3-d]pyrimidin-5-yl)-benzylamino]-5-cyano-N-[(S)-1-(4-fluoro-phenyl)-ethyl]-nicotinamide | 507.0 | ¹H NMR (300 MHz, DMSO-d₆) δ 11.78 (br. s., 1H), 9.36 (t, J = 5.48 Hz, 1H), 8.99 (d, J = 7.18 Hz, 1H), 8.42-8.67 (m, 2H), 8.10 (s, 1H), 7.31-7.59 (m, 6H), 7.00-7.30 (m, 3H), 5.77-6.18 (m, 1H), 5.10 (t, J = 7.18 Hz, 1H), 4.72 (d, J = 5.29 Hz, 2H), 1.46 (d, J = 7.18 Hz, 3H) |
| 42 | 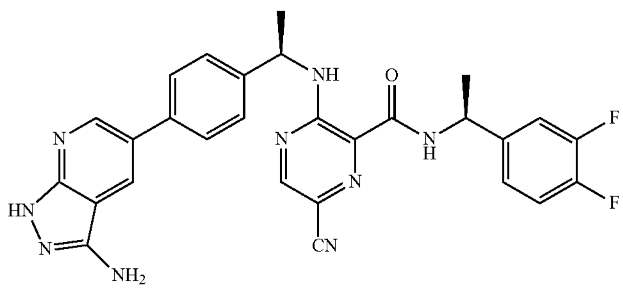 [SMILES: C[C@H](NC(=O)c1nc(C#N)cnc1N[C@H](C)c1ccc(-c2cnc3[nH]nc(N)c3c2)cc1)c1ccc(F)c(F)c1] | 3-((R)-1-(4-(3-amino-1H-pyrazolo[3,4-b]pyridin-5-yl) phenyl)ethylamino)-6-cyano-N-((S)-1-(3,4-difluorophenyl) ethyl)pyrazine-2-carboxamide | 540.0 | ¹H NMR (400 MHz, DMSO-d₆) δ: 12.03 (s, 1H), 9.81 (d, 1H), 9.41 (d, 1H), 8.73 (s, 1H), 8.65 (d, 1H), 8.37 (s, 1H), 7.64 (d, 2H), 7.57-7.49 (m, 3H), 7.42-7.37 (m, 1H), 7.27 (br, 1H), 5.65 (s, 2H), 5.33-5.25 (m, 1H), 5.18-5.13 (m, 1H), 1.57-1.51 (m, 6H). |
| 43 | 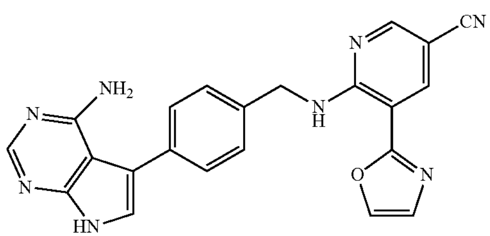 [SMILES: N#Cc1cnc(NCc2ccc(-c3c[nH]c4ncnc(N)c34)cc2)c(-c2ncco2)c1] | 6-(4-(4-amino-7H-pyrrolo [2,3-d]pyrimidin-5-yl) benzylamino)-5-(oxazol-2-yl)nicotinitrile | 409.0 | ¹H NMR (400 MHz, CD₃OD/CDCl₃) δ: 9.67 (t, 1H), 8.49 (d, 1H), 8.38 (d, 1H), 8.16 (s, 1H), 7.93 (s, 1H), 7.53-7.44 (m, 4H), 7.34 (s, 1H), 7.12 (s, 1H), 4.96 (d, 2H). |

TABLE 1-continued

| Ex. No. | Structure | Chemical Name | ESI-MS (M + H) | ¹H NMR |
|---|---|---|---|---|
| 44 | 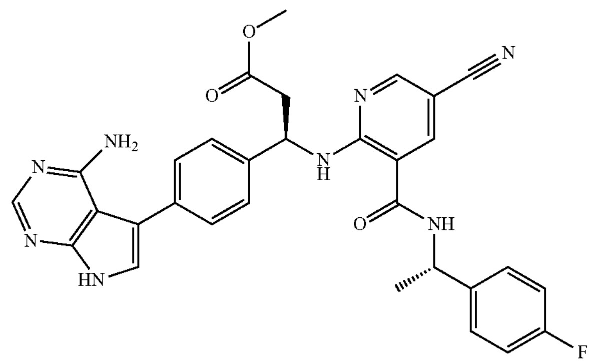 [SMILES: COC(=O)C[C@@H](Nc1ncc(C#N)cc1C(=O)N[C@@H](C)c1ccc(F)cc1)c1ccc(-c2c[nH]c3ncnc(N)c23)cc1] | (R)-methyl 3-(4-(4-amino-7H-pyrrolo[2,3-d]pyrimidin-5-yl)phenyl)-3-(5-cyano-3-((S)-1-(4-fluorophenyl)ethylcarbamoyl)pyridin-2-ylamino)propanoate | 579.0 | ¹H NMR (400 MHz, DMSO-$d_6$) δ: 11.82 (s, 1H), 9.66 (d, 1H), 9.01 (d, 1H), 8.56 (dd, 2H), 8.11 (s, 1H), 7.45-7.44 (m, 6H), 7.25-7.17 (m, 3H), 5.99 (br, 2H), 5.78-5.72 (m, 1H), 5.15-5.11 (m, 1H), 3.48 (s, 3H), 3.06-2.96 (m, 2H), 1.46 (d, 3H). |
| 45 | 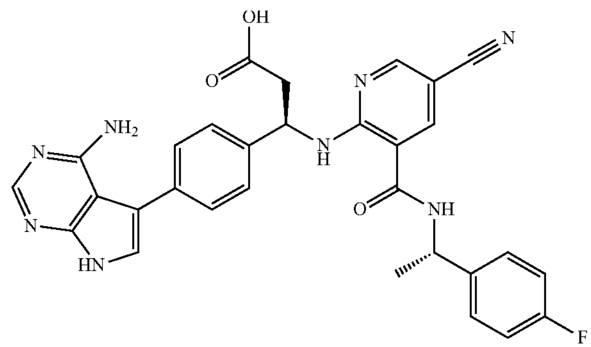 [SMILES: C[C@H](NC(=O)c1cc(C#N)cnc1N[C@H](CC(=O)O)c1ccc(-c2c[nH]c3ncnc(N)c23)cc1)c1ccc(F)cc1] | (R)-3-(4-(4-amino-7H-pyrrolo[2,3-d]pyrimidin-5-yl)phenyl)-3-(5-cyano-3-((S)-1-(4-fluorophenyl)ethylcarbamoyl)pyridin-2-ylamino)propanoic acid | 565.2 | ¹H NMR (400 MHz, DMSO-$d_6$) δ: 12.78 (s, 1H), 12.32 (br, 1H), 9.67 (d, 1H), 9.00 (d, 1H), 8.56 (dd, 2H), 8.36 (s, 1H), 7.49-7.44 (m, 9H), 7.17 (t, 2H), 5.77-5.75 (m, 1H), 5.14-5.12 (m, 1H), 2.92-2.90 (m, 2H), 1.47 (d, 3H). |
| 46 | 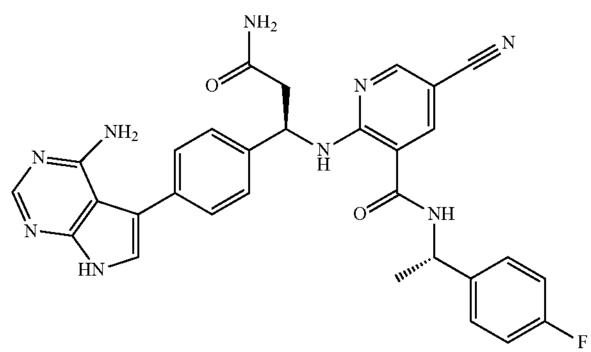 [SMILES: C[C@H](NC(=O)c1cc(C#N)cnc1N[C@H](CC(N)=O)c1ccc(-c2c[nH]c3ncnc(N)c23)cc1)c1ccc(F)cc1] | 2-((R)-3-amino-1-(4-(4-amino-7H-pyrrolo[2,3-d]pyrimidin-5-yl)phenyl)-3-oxopropylamino)-5-cyano-N-((S)-1-(4-fluorophenyl)ethyl)nicotinamide | 564.2 | ¹H NMR (400 MHz, DMSO-$d_6$) δ: 8.87 (d, 1H), 8.43 (d, 1H), 8.32-8.23 (m, 2H), 7.58-7.40 (m, 4H), 7.44-7.41 (m, 3H), 7.11-7.07 (m, 2H), 5.83 (t, 1H), 5.23-5.19 (m, 1H), 2.97-2.91 (m, 1H), 2.84-2.78 (m, 1H), 1.56 (d, 3H). |

TABLE 1-continued

| Ex. No. | Structure | Chemical Name | ESI-MS (M + H) | $^1$H NMR |
|---|---|---|---|---|
| 47 | 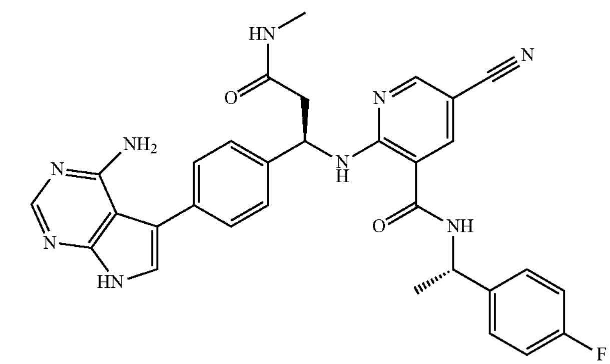 [SMILES: CNC(=O)C[C@@H](Nc1ncc(C#N)cc1C(=O)N[C@@H](C)c1ccc(F)cc1)c1ccc(-c2c[nH]c3ncnc(N)c23)cc1] | 2-((R)-1-(4-(4-amino-7H-pyrrolo[2,3-d]pyrimidin-5-yl)phenyl)-3-(methylamino)-3-oxopropylamino)-5-cyano-N-((S)-1-(4-fluorophenyl)ethyl)nicotinamide | 578.0 | $^1$H NMR (400 MHz, CD$_3$OD) δ: 8.34 (d, 1H), 8.28-8.26 (m, 2H), 7.52-7.45 (m, 4H), 7.41-7.36 (m, 3H), 7.03 (t, 2H), 5.79-5.75 (m, 1H), 5.17-5.15 (m, 1H), 2.84-2.76 (m, 2H), 2.57 (s, 3H), 1.52 (d, 3H). |
| 48 | 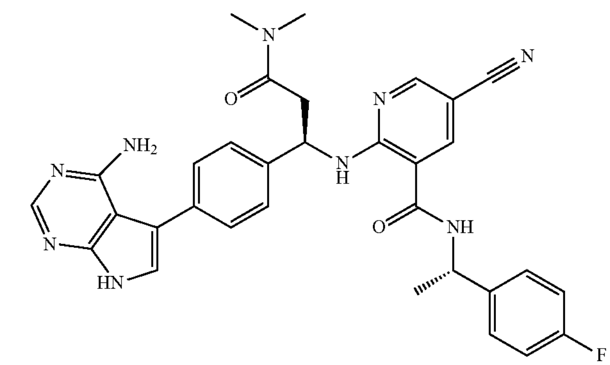 [SMILES: C[C@H](NC(=O)c1cc(C#N)cnc1N[C@H](CC(=O)N(C)C)c1ccc(-c2c[nH]c3ncnc(N)c23)cc1)c1ccc(F)cc1] | 2-((R)-1-(4-(4-amino-7H-pyrrolo[2,3-d]pyrimidin-5-yl)phenyl)-3-(dimethylamino)-3-oxopropylamino)-5-cyano-N-((S)-1-(4-fluorophenyl)ethyl)nicotinamide | 592.3 | $^1$H NMR (400 MHz, DMSO-d$_6$) δ: 11.81 (s, 1H), 9.66 (d, 1H), 8.99 (d, 1H), 8.56 (s, 1H), 8.51 (s, 1H), 8.10 (s, 1H), 7.46-7.39 (m, 6H), 7.23-7.14 (m, 3H), 5.99 (br, 2H), 5.78-5.73 (m, 1H), 5.14-5.10 (m, 1H), 3.10-3.14 (m, 1H), 2.92-2.88 (m, 1H), 2.87 (s, 3H), 2.70 (s, 3H), 1.46 (d, 3H). |
| 49 | 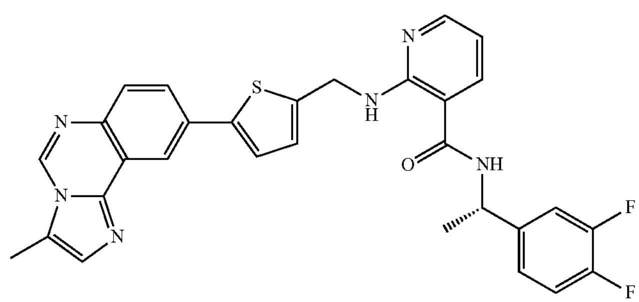 [SMILES: Cc1cnc2c3cc(-c4ccc(CNc5ncccc5C(=O)N[C@@H](C)c5ccc(F)c(F)c5)s4)ccc3ncn12] | (S)-N-(1-(3,4-difluorophenyl)ethyl)-2-((5-(3-methyl-imidazo[1,2-c]quinazolin-9-yl)thiophen-2-yl)methyl)amino)nicotinamide | 555.2 | $^1$H NMR (300 MHz, CDCl$_3$) δ 8.69 (s, 1H), 8.65 (s, 1H), 8.53 (t, J = 5.29 Hz, 1H), 8.32 (d, J = 4.53 Hz, 1H), 7.82-7.95 (m, 2H), 7.63 (d, J = 7.93 Hz, 1H), 7.32-7.41 (m, 2H), 7.05-7.23 (m, 3H), 7.01 (d, J = 3.40 Hz, 1H), 6.59 (dd, J = 4.91, 7.18 Hz, 1H), 6.23 (d, J = 6.80 Hz, 1H), 5.21 (quin, J = 6.80 Hz, 1H), 4.79-5.01 (m, 2H), 2.62 (s, 3H), 1.57 (d, J = 6.42 Hz, 3H). |

TABLE 1-continued

| Ex. No. | Structure | Chemical Name | ESI-MS (M + H) | ¹H NMR |
|---|---|---|---|---|
| 50 | 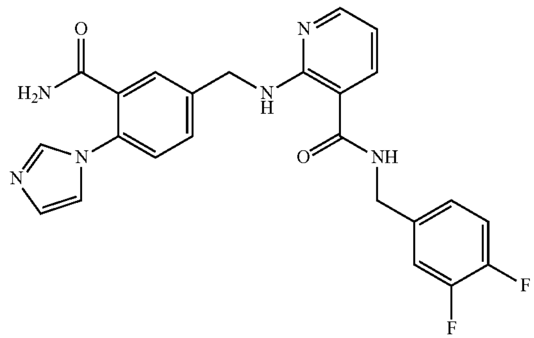 [SMILES: NC(=O)c1cc(CNc2ncccc2C(=O)NCc2ccc(F)c(F)c2)ccc1-n1ccnc1] | 2-(3-carbamoyl-4-(1H-imidazol-1-yl)benzylamino)-N-(3,4-difluorobenzyl) nicotinamide | 463.2 | ¹H NMR (400 MHz, CD₃OD) δ: 8.13-8.09 (m, 1H), 7.94-7.89 (m, 1H), 7.79 (s, 1H), 7.62-7.56 (m, 2H), 7.41-7.36 (m, 1H), 7.31-7.04 (m, 5H), 6.66-6.58 (m, 1H), 4.76 (s, 2H), 4.49 (s, 2H). |
| 51 | 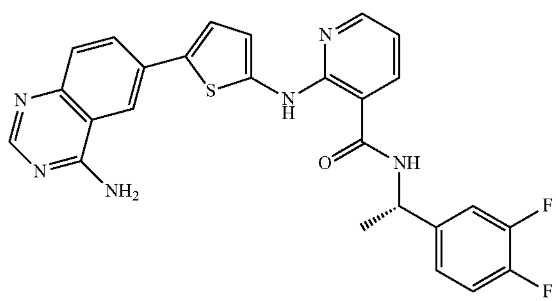 [SMILES: C[C@H](NC(=O)c1cccnc1Nc1ccc(-c2ccc3ncnc(N)c3c2)s1)c1ccc(F)c(F)c1] | (S)-2-(5-(4-aminoquinazolin-6-yl)thiophen-2-ylamino)-N-(1-(3,4-difluorophenyl)ethyl) nicotinamide | 503.0 | ¹H NMR (400 MHz, CD₃OD) δ: 8.49 (s, 1H), 8.40-8.37 (m, 2H), 8.21 (dd, 1H), 8.14 (dd, 1H), 7.63 (d, 1H), 7.35 (d, 1H), 7.29 (t, 1H), 7.19-7.16 (m, 2H), 6.87-6.84 (m, 1H), 6.60 (d, 1H), 5.19 (q, 1H), 1.52 (d, 3H) |
| 52 | 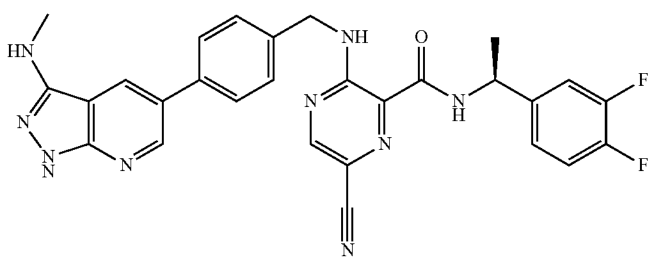 | (S)-6-cyano-N-(1-(3,4-difluorophenyl)ethyl)-3-(4-(3-(methylamino)-1H-pyrazolo[3,4-b]pyridin-5-yl)benzylamino) pyrazine-2-carboxamide | 540.6 | ¹H NMR (400 MHz, DMSO-d₆) δ ppm 12.05 (br. s., 1 H) 9.76 (t, J = 5.11 Hz, 1 H) 9.34 (d, J = 8.28 Hz, 1 H) 8.75 (s, 1 H) 8.64 (d, J = 2.01 Hz, 1 H) 8.33 (d, J = 2.26 Hz, 1 H) 7.61 (d, J = 8.03 Hz, 2 H) 7.48-7.56 (m, 1 H) 7.33-7.46 (m, 3 H) 7.27 (br. s., 1 H) 6.23 (d, J = 5.02 Hz, 1 H) 4.99-5.22 (m, 1 H) 4.73 (t, J = 5.65 Hz, 2 H) 2.87 (d, J = 5.02 Hz, 3 H) 1.52 (d, J = 7.03 Hz, 3 H); ¹⁹F NMR (376 MHz, DMSO-d₆) δ ppm −139.01−−138.68 (m, 1 F)−141.62−−141.28 (m, 1 F). |

TABLE 1-continued

| Ex. No. | Structure | Chemical Name | ESI-MS (M + H) | ¹H NMR |
|---|---|---|---|---|
| 53 | 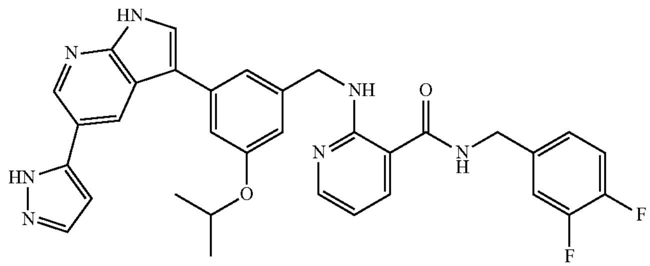 [SMILES: CC(C)Oc1cc(CNc2ncccc2C(=O)NCc2ccc(F)c(F)c2)cc(-c2c[nH]c3ncc(-c4ccn[nH]4)cc23)c1] | 2-(3-(5-(1H-pyrazol-5-yl)-1H-pyrrolo[2,3-b]pyridin-3-yl)-5-isopropoxybenzylamino)-N-(3,4-difluorobenzyl)nicotinamide | 594.0 | ¹H NMR (400 MHz, CDCl₃/CD₃OD) δ: 8.62 (br, 1H), 8.56 (s, 1H), 8.21-8.19 (m, 1H), 7.82-7.79 (m, 1H), 7.63 (s, 1H), 7.55 (s, 1H), 7.32 (s, 1H), 7.06-7.02 (m, 4H), 6.88 (s, 1H), 6.62 (br, 1H), 6.59-6.56 (m, 1H), 4.75 (s, 2H), 4.67-4.64 (m, 1H), 4.48 (s, 2H), 1.38 (d, 6H). |
| 54 | 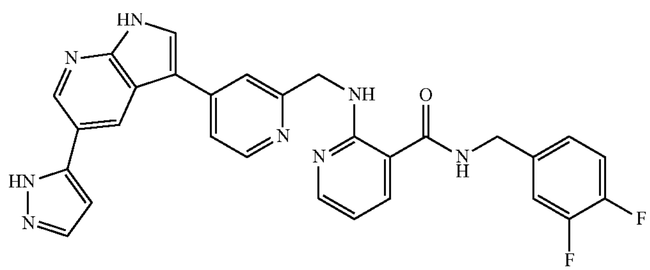 [SMILES: O=C(NCc1ccc(F)c(F)c1)c1cccnc1NCc1cc(-c2c[nH]c3ncc(-c4ccn[nH]4)cc23)ccn1] | 2-(((4-(5-(1H-pyrazol-5-yl)-1H-pyrrolo[2,3-b]pyridin-3-yl)pyridin-2-yl)methyl)amino)-N-(3,4-difluorobenzyl)nicotinamide | 537.2 | ¹H NMR (400 MHz, CD₃OD) δ: 8.75 (s, 1H), 8.71 (s, 1H), 8.39 (s, 1H), 8.37 (s, 1H), 8.27 (d, 1H), 8.13 (d, 1H), 8.04 (d, 1H), 7.90 (d, 1H), 7.65 (s, 1H), 7.17-7.07 (m, 3H), 6.74 (s, 1H), 6.66-6.62 (m, 1H), 4.93 (s, 2H), 4.44 (s, 2H). |
| 55 | 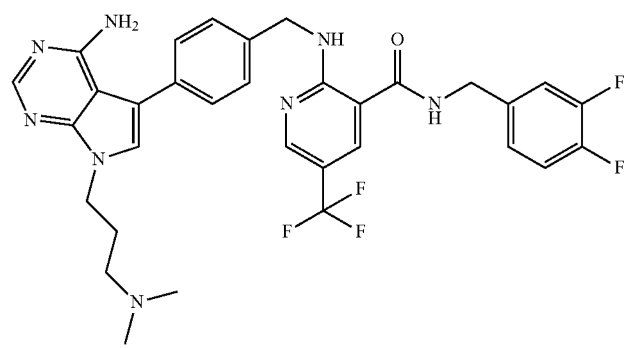 [SMILES: CN(C)CCCn1cc(-c2ccc(CNc3ncc(C(F)(F)F)cc3C(=O)NCc3ccc(F)c(F)c3)cc2)c2c(N)ncnc21] | 2-(4-(4-amino-7-(3-(dimethylamino)propyl)-7H-pyrrolo[2,3-d]pyrimidin-5-yl)benzylamino)-N-(3,4-difluorobenzyl)-5-(trifluoromethyl)nicotinamide | 638.9 | ¹H NMR (400 MHz, DMSO-d₆) δ 9.34 (td, J = 5.52, 22.09 Hz, 2H), 8.53 (s, 1H), 8.37 (s, 1H), 8.14 (s, 1H), 7.29-7.46 (m, 7H), 7.20 (br. s., 1H), 4.75 (d, J = 5.77 Hz, 2H), 4.45 (d, J = 5.52 Hz, 2H), 4.18 (t, J = 7.03 Hz, 2H), 2.35 (br. s., 2H), 2.23 (br. s., 6H), 1.95 (quin, J = 6.96 Hz, 2H) |

TABLE 1-continued

| Ex. No. | Structure | Chemical Name | ESI-MS (M + H) | ¹H NMR |
|---|---|---|---|---|
| 56 | 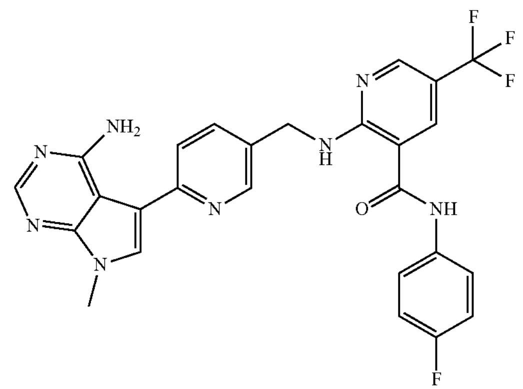 [SMILES: Cn1cc(-c2ccc(CNc3ncc(C(F)(F)F)cc3C(=O)Nc3ccc(F)cc3)cn2)c2c(N)ncnc21] | 2-(((6-(4-amino-7-methyl-7H-pyrrolo[2,3-d]pyrimidin-5-yl)pyridin-3-yl)methyl)amino)-N-(4-fluorophenyl)-5-(trifluoromethyl)nicotinamide | 536.9 | ¹H NMR (400 MHz, DMSO-d$_6$) δ ppm 11.61 (br. s., 1 H) 10.53 (s, 1 H) 8.96 (t, J = 5.90 Hz, 1 H) 8.49-8.78 (m, 3 H) 8.37 (d, J = 15.81 Hz, 3 H) 7.83-8.05 (m, 2 H) 7.61-7.78 (m, 2 H) 7.22 (t, J = 8.91 Hz, 2 H) 4.76 (d, J = 5.77 Hz, 2 H) 3.83 (s, 3 H). ¹⁹F NMR (376 MHz, DMSO-d$_6$) δ ppm −63.71 (s, 3F) −78.50 (TFA, s, 3F) −122.84 (s, 1F). |
| 57 | 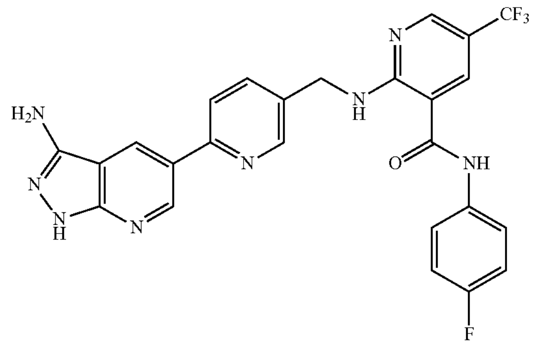 [SMILES: Nc1n[nH]c2ncc(-c3ccc(CNc4ncc(C(F)(F)F)cc4C(=O)Nc4ccc(F)cc4)cn3)cc12] | 2-(((6-(3-amino-1H-pyrazolo[3,4-b]pyridin-5-yl)methyl)amino)-N-(4-fluorophenyl)-5-(trifluoromethyl)nicotinamide | 522.8 | ¹H NMR (400 MHz, DMSO-d$_6$) δ 10.51 (s, 1H), 9.06 (d, J = 2.01 Hz, 1H), 8.94 (s, 1H), 8.89 (br. s., 1H), 8.69 (s, 1H), 8.55 (s, 1H), 8.38 (d, J = 2.01 Hz, 1H), 7.85-8.00 (m, 2H), 7.64-7.76 (m, 2H), 7.22 (t, J = 8.91 Hz, 2H), 4.78 (d, J = 5.27 Hz, 2H) |
| 58 | 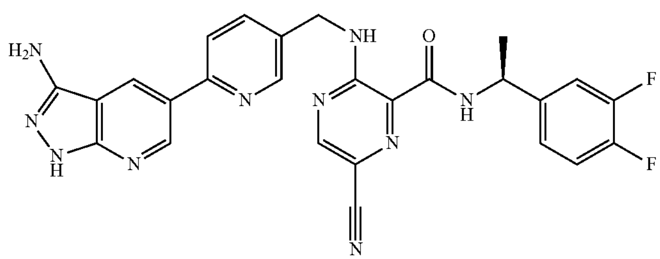 [SMILES: C[C@H](NC(=O)c1nc(C#N)cnc1NCc1ccc(-c2cnc3[nH]nc(N)c3c2)nc1)c1ccc(F)c(F)c1] | (S)-3-(((6-(3-amino-1H-pyrazolo[3,4-b]pyridin-5-yl)pyridin-3-yl)methyl)amino)-6-cyano-N-(1-(3,4-difluorophenyl)ethyl)pyrazine-2-carboxamide | 526.9 | ¹H NMR (400 MHz, CD$_3$OD) δ 9.04 (d, J = 2.01 Hz, 2H), 8.84 (d, J = 2.01 Hz, 1H), 8.70 (s, 1H), 8.56 (s, 1H), 8.07-8.17 (m, 1H), 7.99 (s, 1H), 7.28-7.40 (m, 1H), 7.13-7.25 (m, 2H), 5.18 (t, J = 7.40 Hz, 1H), 1.51-1.64 (m, 2H) |

TABLE 1-continued

| Ex. No. | Structure | Chemical Name | ESI-MS (M + H) | ¹H NMR |
|---|---|---|---|---|
| 59 | 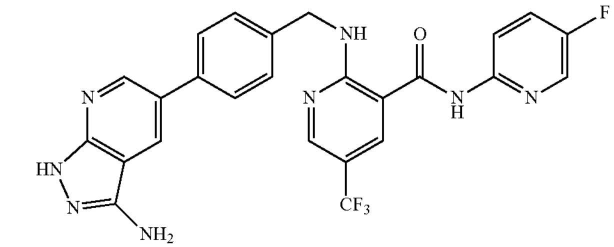 [SMILES: Nc1n[nH]c2ncc(-c3ccc(CNc4ncc(C(F)(F)F)cc4C(=O)Nc4ccc(F)cn4)cc3)cc12] | 2-(4-(3-amino-1H-pyrazolo[3,4-b]pyridin-5-yl)benzylamino)-N-(5-fluoropyridin-2-yl)-5-(trifluoromethyl)nicotinamide | 522.9 | ¹H NMR (400 MHz, DMSO-$d_6$) δ ppm 11.26 (s, 1 H) 8.90 (t, J = 5.90 Hz, 1 H) 8.68 (d, J = 2.01 Hz, 1 H) 8.34-8.58 (m, 4 H) 8.12 (dd, J = 9.16, 4.14 Hz, 1 H) 7.81 (td, J = 8.72, 3.14 Hz, 1 H) 7.63 (d, J = 8.03 Hz, 2 H) 7.47 (d, J = 8.03 Hz, 2 H) 4.77 (d, J = 5.77 Hz, 2 H) |
| 60 | 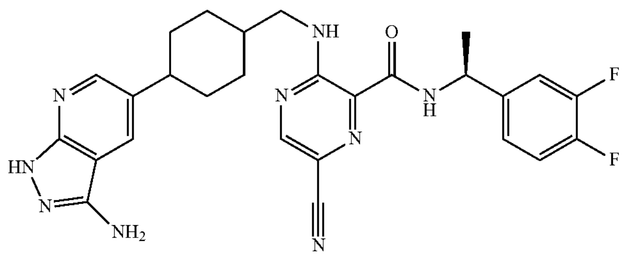 [SMILES: C[C@H](NC(=O)c1nc(C#N)cnc1NCC1CCC(c2cnc3[nH]nc(N)c3c2)CC1)c1ccc(F)c(F)c1] | (S)-3-((4-(3-amino-1H-pyrazolo[3,4-b]pyridin-5-yl)cyclohexyl)methylamino)-6-cyano-N-(1-(3,4-difluorophenyl)ethyl)pyrazine-2-carboxamide | 531.6 | ¹H NMR (400 MHz, DMSO-$d_6$) δ ppm 11.59-12.25 (m, 1 H) 9.39-9.57 (m, 1 H) 9.31 (dd, J = 8.28, 3.51 Hz, 1 H) 8.73 (s, 1 H) 8.29 (dd, J = 14.81, 1.51 Hz, 1 H) 7.90-8.08 (m, 1 H) 7.45-7.57 (m, 1 H) 7.32-7.44 (m, 1 H) 7.27 (br. s., 1 H) 5.03-5.21 (m, 1 H) 3.61 (dd, J = 16.56, 7.53 Hz, 2 H) 2.64-2.79 (m, 1 H) 2.05 (br. s., 1 H) 1.57-1.93 (m, 8 H) 1.36-1.55 (m, 5 H); ¹⁹F NMR (376 MHz, DMSO-$d_6$) δ ppm -139.01--138.71 (m, 1 F) -141.60--141.30 (m, 1 F). |
| 61 | 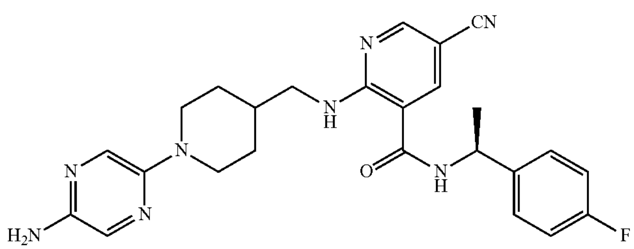 [SMILES: C[C@H](NC(=O)c1cc(C#N)cnc1NCC1CCN(c2cnc(N)cn2)CC1)c1ccc(F)cc1] | (S)-2-(((1-(5-aminopyrazin-2-yl)piperidin-4-yl)methyl)amino)-5-cyano-N-(1-(4-fluorophenyl)ethyl)nicotinamide | 475.2 | ¹H NMR (400 MHz, CDCl$_3$) δ ppm 1.31-1.49 (m, 2 H) 1.60 (d, J = 6.78 Hz, 3 H) 1.86 (d, J = 12.30 Hz, 3 H) 2.73 (t, J = 12.05 Hz, 2 H) 3.33-3.56 (m, 2 H) 3.98-4.07 (m, 4 H) 5.12-5.27 (m, 1 H) 6.61 (d, J = 7.53 Hz, 1 H) 7.04 (t, J = 8.78 Hz, 1 H) 7.35 (dd, J = 7.91, 5.65 Hz, 2 H) 7.67 (d, J = 7.53 Hz, 2 H) 7.62-7.73 (m, 1 H) 7.89 (d, J = 1.51 Hz, 1 H) 8.43 (s, 1 H) 8.88-9.09 (m, 1 H) 9.00 (t, J = 1.00 Hz, 1 H) 9.25-9.26 (m, 1 H); |
| 62 | 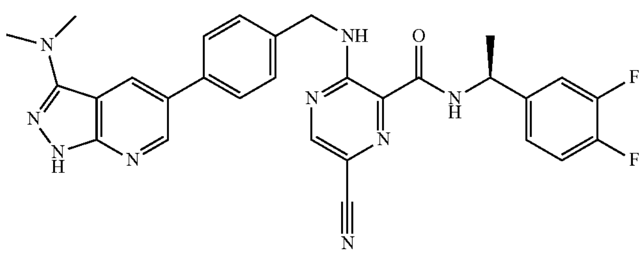 [SMILES: C[C@H](NC(=O)c1nc(C#N)cnc1NCc1ccc(-c2cnc3[nH]nc(N(C)C)c3c2)cc1)c1ccc(F)c(F)c1] | (S)-6-cyano-N-(1-(3,4-difluorophenyl)ethyl)-3-(4-(3-(dimethylamino)-1H-pyrazolo[3,4-b]pyridin-5-yl)benzylamino)pyrazine-2-carboxamide | 554.2 | ¹H NMR (400 MHz, DMSO-$d_6$) δ ppm 12.45 (s, 1 H) 9.75 (t, J = 5.90 Hz, 1 H) 9.33 (d, J = 8.28 Hz, 1 H) 8.75 (s, 1 H) 8.66 (d, J = 2.01 Hz, 1 H) 8.40 (d, J = 1.76 Hz, 1 H) 7.69 (d, J = 8.03 Hz, 2 H) 7.52 (ddd, J = 11.92, 7.91, 2.01 Hz, 1 H) 7.43 (d, J = 8.03 Hz, 2 H) 7.33-7.40 (m, 1 H) 7.26 (br. s., 1 H) 5.12 (quin, J = 7.22 Hz, 1 H) 4.62-4.84 (m, 2 H) 3.05 (s, 6 H) 1.52 (d, J = 7.03 Hz, 3 H); ¹⁹F NMR (376 MHz, DMSO-$d_6$) δ ppm -138.99--138.73 (m, 1 F) -141.59--141.31 (m, 1 F). |

TABLE 1-continued

| Ex. No. | Structure | Chemical Name | ESI-MS (M + H) | ¹H NMR |
|---|---|---|---|---|
| 63 | 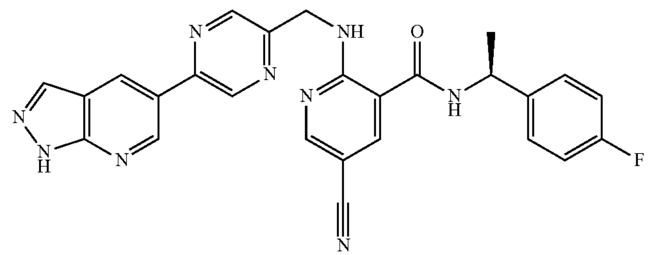 [SMILES: C[C@H](NC(=O)c1cc(C#N)cnc1NCc1cnc(-c2cnc3[nH]ncc3c2)cn1)c1ccc(F)cc1] | 5-Cyano-N-[(S)-1-(4-fluoro-phenyl)-ethyl]-2-{[5-(1H-pyrazolo[3,4-b]pyridin-5-yl)-pyrazin-2-ylmethyl]-amino}-nicotinamide | 493.9 | ¹H NMR (400 MHz, DMSO-d₆) δ 13.84 (br. s., 1H), 9.61 (t, J = 5.40 Hz, 1H), 9.28 (s, 1H), 9.24 (d, J = 1.76 Hz, 1H), 9.01 (d, J = 7.28 Hz, 1H), 8.92 (d, J = 1.76 Hz, 1H), 8.68 (s, 1H), 8.57 (d, J = 1.76 Hz, 1H), 8.51 (d, J = 1.76 Hz, 1H), 8.26 (s, 1H), 7.44 (dd, J = 5.65, 8.41 Hz, 2H), 7.16 (t, J = 8.91 Hz, 2H), 5.13 (quin, J = 6.96 Hz, 1H), 4.88 (d, J = 5.27 Hz, 2H), 1.47 (d, J = 7.03 Hz, 3H) |
| 64 | 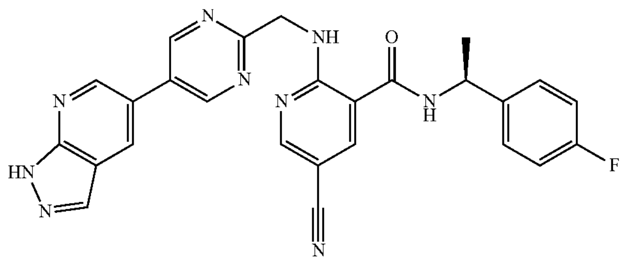 [SMILES: C[C@H](NC(=O)c1cc(C#N)cnc1NCc1ncc(-c2cnc3[nH]ncc3c2)cn1)c1ccc(F)cc1] | 5-Cyano-N-[(S)-1-(4-fluoro-phenyl)-ethyl]-2-{[5-(1H-pyrazolo[3,4-b]pyridin-5-yl)-pyridin-2-ylmethyl]-amino}-nicotinamide | 493.9 | ¹H NMR (400 MHz, DMSO-d₆) δ 13.83 (s, 1H), 9.76 (t, J = 5.27 Hz, 1H), 9.19 (s, 2H), 9.00 (d, J = 7.28 Hz, 1H), 8.92 (d, J = 2.01 Hz, 1H), 8.64 (d, J = 1.76 Hz, 1H), 8.57 (d, J = 2.01 Hz, 1H), 8.52 (d, J = 2.01 Hz, 1H), 8.24 (d, J = 1.26 Hz, 1H), 7.45 (dd, J = 5.52, 8.53 Hz, 2H), 7.16 (t, J = 8.91 Hz, 2H), 5.15 (quin, J = 7.09 Hz, 1H), 4.93 (d, J = 5.27 Hz, 2H), 1.48 (d, J = 7.03 Hz, 3H). |
| 65 | 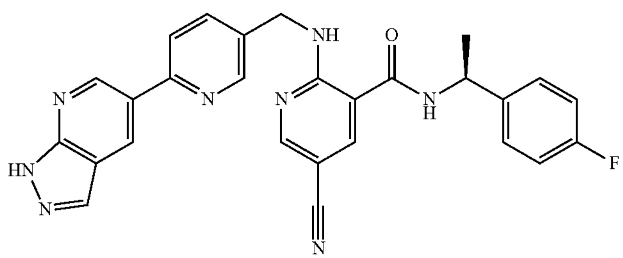 [SMILES: C[C@H](NC(=O)c1cc(C#N)cnc1NCc1ccc(-c2cnc3[nH]ncc3c2)nc1)c1ccc(F)cc1] | 5-Cyano-N-[(S)-1-(4-fluoro-phenyl)-ethyl]-2-{[6-(1H-pyrazolo[3,4-b]pyridin-5-yl)-pyridin-3-ylmethyl]-amino}-nicotinamide | 492.9 | ¹H NMR (400 MHz, DMSO-d₆) δ 9.38 (t, J = 5.90 Hz, 1H), 9.20 (d, J = 2.01 Hz, 1H), 9.00 (d, J = 7.53 Hz, 1H), 8.82 (d, J = 1.76 Hz, 1H), 8.65 (d, J = 1.26 Hz, 1H), 8.58 (d, J = 1.76 Hz, 1H), 8.47 (d, J = 2.01 Hz, 1H), 8.23 (s, 1H), 8.02 (dd, J = 8.03 Hz, 1H), 7.85 (d, J = 1.76, 8.28 Hz, 1H), 7.42 (dd, J = 5.65, 8.41 Hz, 2H), 7.14 (t, J = 8.78 Hz, 2H), 5.10 (quin, J = 6.96 Hz, 1H), 4.66-4.81 (m, 2H), 1.46 (d, J = 7.03 Hz, 3H). |
| 66 | 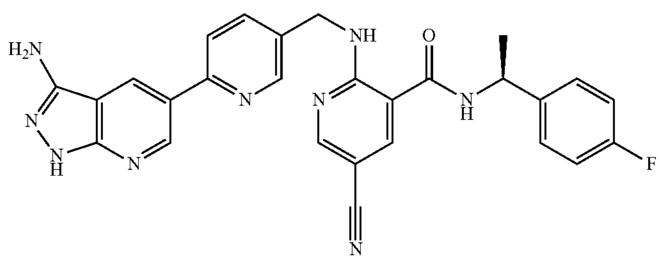 [SMILES: C[C@H](NC(=O)c1cc(C#N)cnc1NCc1ccc(-c2cnc3[nH]nc(N)c3c2)nc1)c1ccc(F)cc1] | 2-{[6-(3-Amino-1H-pyrazolo[3,4-b]pyridin-5-yl)-pyridin-3-ylmethyl]-amino}-5-cyano-N-[(S)-1-(4-fluoro-phenyl)-ethyl]-nicotinamide | 507.9 | ¹H NMR (400 MHz, DMSO-d₆) δ 9.37 (t, J = 5.90 Hz, 1H), 9.04 (d, J = 2.01 Hz, 1H), 9.00 (d, J = 7.53 Hz, 1H), 8.87 (br. s., 1H), 8.63 (d, J = 1.51 Hz, 1H), 8.58 (d, J = 2.01 Hz, 1H), 8.47 (dd, J = 2.01 Hz, 1H), 7.92 (d, J = 8.28 Hz, 1H), 7.83 (dd, J = 1.88, 8.16 Hz, 1H), 7.42 (dd, J = 5.52, 8.53 Hz, 2H), 7.14 (t, J = 8.78 Hz, 2H), 5.09 (quin, J = 7.03 Hz, 1H), 4.65-4.79 (m, 2H), 1.46 (d, J = 7.03 Hz, 3H). |

| Ex. No. | Structure | Chemical Name | ESI-MS (M + H) | ¹H NMR |
|---|---|---|---|---|
| 67 | 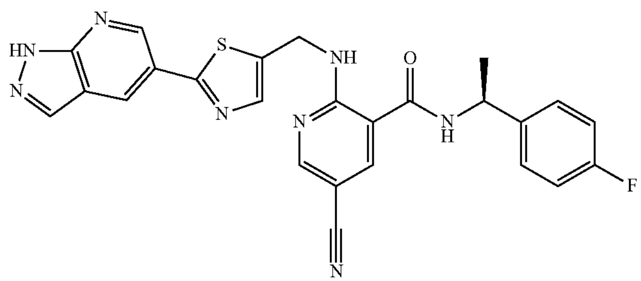 [SMILES: C[C@H](NC(=O)c1cc(C#N)cnc1NCc1cnc(-c2cnc3[nH]ncc3c2)s1)c1ccc(F)cc1] | 5-Cyano-N-[(S)-1-(4-fluoro-phenyl)-ethyl]-2-{[2-(1H-pyrazolo[3,4-b]pyridin-5-yl)-thiazol-5-ylmethyl]-amino}-nicotinamide | 498.9 | ¹H NMR (400 MHz, DMSO-$d_6$) δ 13.88 (br. s., 1H), 9.35 (t, J = 6.02 Hz, 1H), 9.04 (d, J = 2.01 Hz, 1H), 9.00 (d, J = 7.28 Hz, 1H), 8.69 (d, J = 2.26 Hz, 1H), 8.68 (d, J = 2.26 Hz, 1H), 8.49 (d, J = 2.01 Hz, 1H), 8.23 (s, 1H), 7.82 (s, 1H), 7.41 (dd, J = 5.52, 8.53 Hz, 2H), 7.14 (t, J = 8.91 Hz, 2H), 5.08 (quin. J = 7.09 Hz, 1H), 4.90 (d, J = 6.02 Hz, 2H), 1.46 (d, J = 7.03 Hz, 3H). |
| 68 | 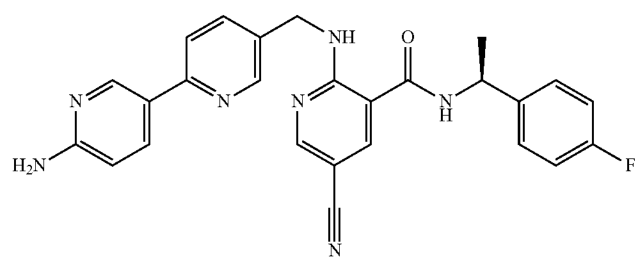 [SMILES: C[C@H](NC(=O)c1cc(C#N)cnc1NCc1ccc(-c2ccc(N)nc2)nc1)c1ccc(F)cc1] | 2-[(6-Amino-[2,3']bipyridinyl-5-ylmethyl)-amino]-5-cyano-N-[(S)-1-(4-fluoro-phenyl)-ethyl]-nicotinamide | 467.9 | ¹H NMR (400 MHz, DMSO-$d_6$) δ 9.29 (t, J = 5.90 Hz, 1H), 8.94 (d, J = 7.28 Hz, 1H), 8.43-8.57 (m, 4H), 8.41 (d, J = 2.26 Hz, 1H), 8.01 (br. s., 1H), 7.78-7.84 (m, 1H), 7.71-7.77 (m, 1H), 7.35 (dd, J = 5.65, 8.41 Hz, 2H), 7.08 (t, J = 8.78 Hz, 2H), 6.97 (d, J = 9.29 Hz, 1H), 5.02 (quin, J = 7.03 Hz, 1H), 4.65 (d, J = 5.77 Hz, 2H), 1.39 (d, J = 7.03 Hz, 3H). |
| 69 | 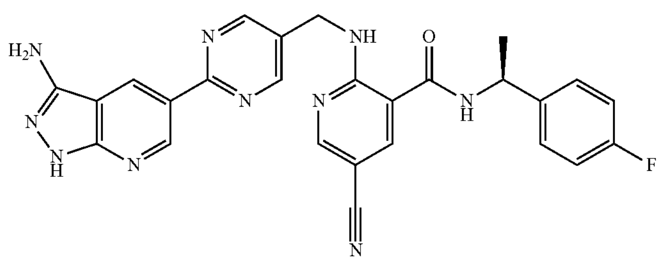 [SMILES: C[C@H](NC(=O)c1cc(C#N)cnc1NCc1cnc(-c2cnc3[nH]nc(N)c3c2)nc1)c1ccc(F)cc1] | 5-Cyano-N-[(S)-1-(4-fluoro-phenyl)-ethyl]-2-{[2-(1H-pyrazolo[3,4-b]pyrimidin-5-yl)-methyl]-amino}-nicotinamide | 493.9 | ¹H NMR (400 MHz, DMSO-$d_6$) δ 13.84 (br. s., 1H), 9.46 (d, J = 1.51 Hz, 1H), 9.38 (t, J = 5.77 Hz, 1H), 9.10 (d, J = 1.51 Hz, 1H), 8.99 (d, J = 7.28 Hz, 1H), 8.86 (s, 2H), 8.59 (d, J = 1.51 Hz, 1H), 8.46 (d, J = 1.76 Hz, 1H), 8.27 (s, 1H), 7.42 (dd, J = 5.65, 8.41 Hz, 2H), 7.14 (t, J = 8.78 Hz, 2H), 5.10 (quin, J = 6.90 Hz, 1H), 4.64-4.79 (m, 2H), 1.46 (d, J = 7.03 Hz, 3H). |

TABLE 1-continued

| Ex. No. | Structure | Chemical Name | ESI-MS (M+H) | ¹H NMR |
|---|---|---|---|---|
| 70 | 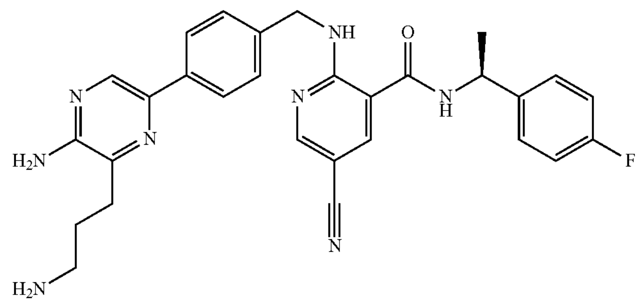 | 2-{4-[5-Amino-6-(3-aminopropyl)-pyrazin-2-yl]-benzylamino}-5-cyano-N-[(S)-1-(4-fluoro-phenyl)-ethyl]-nicotinamide | 525.0 | ¹H NMR (400 MHz, DMSO-d₆) δ 9.32 (t, J = 5.52 Hz, 1H), 9.00 (d, J = 7.28 Hz, 1H), 8.57 (s, 1H), 8.48 (s, 1H), 8.38 (s, 1H), 7.87 (d, J = 7.78 Hz, 2H), 7.68 (br. s., 2H), 7.37-7.45 (m, 2H), 7.34 (d, J = 7.78 Hz, 2H), 7.15 (t, J = 8.53 Hz, 2H), 5.08 (quin, J = 6.78 Hz, 1H), 4.68 (d, J = 5.52 Hz, 2H), 2.86-2.99 (m, 2H), 2.72 (t, J = 7.03 Hz, 2H), 2.01 (quin, J = 7.22 Hz, 2H), 1.46 (d, J = 6.78 Hz, 3H). |
| 71 | 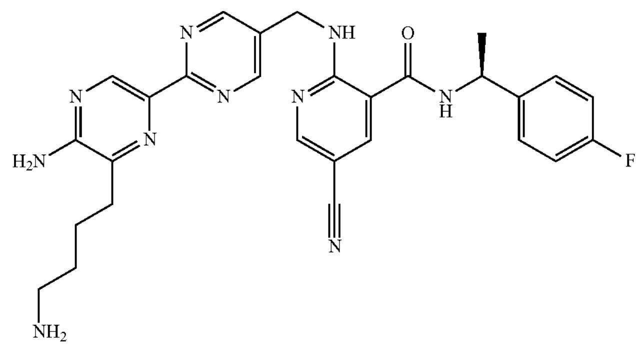 [SMILES: C[C@H](NC(=O)c1cc(C#N)cnc1NCc1cnc(-c2cnc(N)c(CCCCN)n2)nc1)c1ccc(F)cc1] | 2-{4-[5-Amino-6-(4-aminobutyl)-pyrazin-2-yl]-benzylamino}-5-cyano-N-[(S)-1-(4-fluoro-phenyl)-ethyl]-nicotinamide | 539.0 | ¹H NMR (400 MHz, DMSO-d₆) δ 9.32 (t, J = 5.90 Hz, 1H), 9.00 (d, J = 7.53 Hz, 1H), 8.58 (d, J = 2.01 Hz, 1H), 8.48 (d, J = 2.01 Hz, 1H), 8.35 (s, 1H), 7.87 (d, J = 8.28 Hz, 2H), 7.63 (br. s., 2H), 7.42 (dd, J = 5.65, 8.41 Hz, 2H), 7.34 (d, J = 8.28 Hz, 2H), 7.15 (t, J = 8.91 Hz, 2H), 5.09 (quin, J = 6.96 Hz, 1H), 4.68 (d, J = 5.77 Hz, 2H), 2.78-2.89 (m, 2H), 2.69 (t, J = 7.28 Hz, 2H), 1.72-1.84 (m, 2H), 1.57-1.69 (m, 2H), 1.46 (d, J = 7.03 Hz, 3H) |
| 72 | 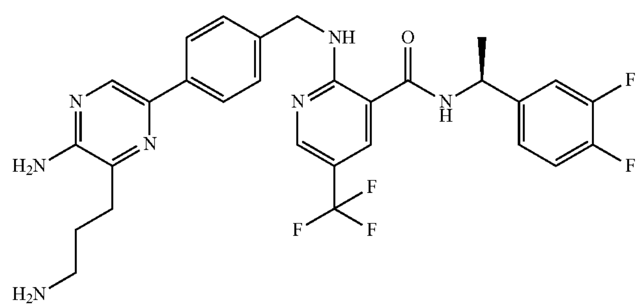 [SMILES: C[C@H](NC(=O)c1cc(C(F)(F)F)cnc1NCc1ccc(-c2cnc(N)c(CCCN)n2)cc1)c1ccc(F)c(F)c1] | 2-{4-[5-Amino-6-(3-aminopropyl)-pyrazin-2-yl]-benzylamino}-N-(3,4-difluorobenzyl)-5-trifluoromethyl-nicotinamide | 571.9 | ¹H NMR (400 MHz, DMSO-d₆) δ 9.39 (t, J = 5.65 Hz, 1H), 9.28 (t, J = 5.65 Hz, 1H), 8.51 (s, 1H), 8.38 (s, 1H), 8.36 (d, J = 2.01 Hz, 1H), 7.89 (d, J = 8.28 Hz, 2H), 7.75 (br. s., 3H), 7.32-7.44 (m, 4H), 7.11-7.22 (m, 1H), 4.72 (d, J = 5.52 Hz, 2H), 4.44 (d, J = 5.52 Hz, 2H), 2.84-3.01 (m, 2H), 2.74 (t, J = 7.15 Hz, 2H), 1.97-2.06 (m, 2H) |

TABLE 1-continued

| Ex. No. | Structure | Chemical Name | ESI-MS (M + H) | ¹H NMR |
|---|---|---|---|---|
| 73 | (structure) | 2-{4-[5-Amino-6-(3-amino-propyl)-pyrazin-2-yl]-benzyl-amino}-N-(4-fluoro-phenyl)-5-trifluoromethyl-nicotinamide | 539.9 | ¹H NMR (400 MHz, DMSO-d₆) δ 10.54 (s, 1H), 8.91 (t, J = 5.52 Hz, 1H), 8.54 (s, 1H), 8.40 (d, J = 1.76 Hz, 1H), 8.39 (s, 1H), 7.90 (d, J = 8.28 Hz, 2H), 7.77 (br. s., 3H), 7.64-7.72 (m, 2H), 7.40 (d, J = 8.03 Hz, 2H), 7.21 (t, J = 8.91 Hz, 2H), 4.74 (d, J = 5.52 Hz, 2H), 2.88-3.01 (m, 2H), 2.74 (t, J = 7.15 Hz, 2H), 2.03 (quin, J = 7.40 Hz, 2H) |
| 74 | (structure) | 2-({6-[5-Amino-6-(3-amino-propyl)-pyrazin-2-yl]-pyridin-3-ylmethyl}-amino)-5-cyano-N-[(S)-1-(4-fluoro-phenyl)-ethyl]-nicotinamide | 526 | ¹H NMR (400 MHz, DMSO-d₆) δ 9.36 (t, J = 5.90 Hz, 1H), 9.01 (d, J = 7.53 Hz, 1H), 8.73 (s, 1H), 8.58 (d, J = 2.01 Hz, 1H), 8.53 (d, J = 1.51 Hz, 1H), 8.48 (d, J = 2.26 Hz, 1H), 8.07 (d, J = 8.28 Hz, 1H), 7.81 (d, J = 8.28 Hz, 2H), 7.72 (br. s., 2H), 7.42 (dd, J = 5.65, 8.66 Hz, 2H), 7.15 (t, J = 8.91 Hz, 2H), 6.66 (br. s., 1H), 5.09 (quin, J = 7.09 Hz, 1H), 4.71 (d, J = 6.02 Hz, 2H), 2.86-3.00 (m, 2H), 2.74 (t, J = 7.15 Hz, 2H), 2.03 (quin, J = 7.34 Hz, 2H), 1.46 (d, J = 7.03 Hz, 3H) |
| 75 | (structure) | 2-{4-[5-Amino-6-((S)-2-pyrrolidin-2-yl-ethyl)-pyrazin-2-yl]-benzylamino}-N-(4-fluoro-phenyl)-5-trifluoromethyl-nicotinamide | 579.9 | ¹H NMR (400 MHz, DMSO-d₆) δ 10.52 (s, 1H), 8.82-8.99 (m, 2H), 8.54 (s, 1H), 8.44 (br. s., 1H), 8.33-8.42 (m, 2H), 7.89 (d, J = 8.28 Hz, 2H), 7.69 (dd, J = 5.02, 9.04 Hz, 2H), 7.40 (d, J = 5.52 Hz, 2H), 7.21 (t, J = 8.78 Hz, 2H), 4.73 (d, J = 5.52 Hz, 2H), 3.55 (td, J = 7.03, 14.06 Hz, 1H), 3.10-3.27 (m, 2H), 2.65-2.83 (m, 2H), 1.79-2.26 (m, 5H), 1.62 (qd, J = 8.63, 12.77 Hz, 1H) |

| Ex. No. | Structure | Chemical Name | ESI-MS (M + H) | ¹H NMR |
|---|---|---|---|---|
| 76 | 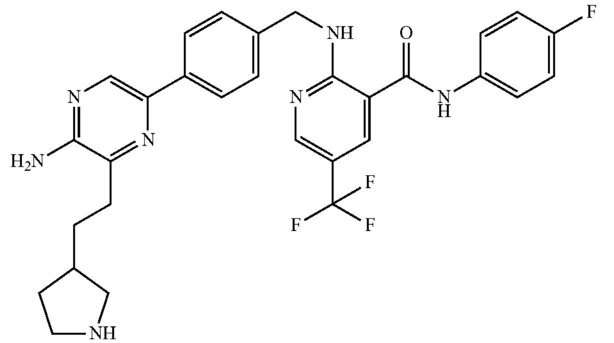 [SMILES: Nc1ncc(-c2ccc(CNc3ncc(C(F)(F)F)cc3C(=O)Nc3ccc(F)cc3)cc2)nc1CCC1CCNC1] | 2-{4-[5-Amino-6-(2-pyrrolidin-3-yl-ethyl)-pyrazin-2-yl]-benzyl}amino}-N-(4-fluoro-phenyl)-5-trifluoromethyl-nicotinamide | 579.9 | ¹H NMR (400 MHz, DMSO-d₆) δ 10.51 (s, 1H), 8.90 (t, J = 5.77 Hz, 1H), 8.54 (s, 1H), 8.40 (d, J = 1.76 Hz, 1H), 8.36 (s, 1H), 7.89 (d, J = 8.28 Hz, 2H), 7.69 (dd, J = 5.02, 9.04 Hz, 1H), 7.39 (d, J = 8.28 Hz, 2H), 7.21 (t, J = 8.78 Hz, 2H), 4.73 (d, J = 5.77 Hz, 2H), 3.17-3.39 (m, 2H), 3.01-3.16 (m, 1H), 2.74-2.82 (m, 1H), 2.70 (t, J = 7.40 Hz, 2H), 2.45 (br. s., 1H), 2.18-2.30 (m, 1H), 2.02-2.15 (m, 1H), 1.77-1.95 (m, 2H), 1.48-1.64 (m, 1H) |
| 77 | 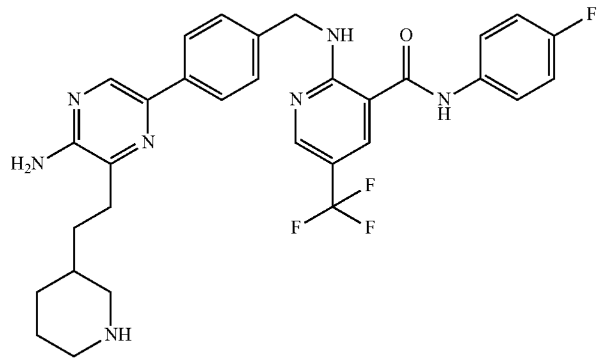 [SMILES: Nc1ncc(-c2ccc(CNc3ncc(C(F)(F)F)cc3C(=O)Nc3ccc(F)cc3)cc2)nc1CCC1CCCNC1] | 2-{4-[5-Amino-6-(2-piperidin-3-yl-ethyl)-pyrazin-2-yl]-benzyl}amino}-N-(4-fluoro-phenyl)-5-trifluoromethyl-nicotinamide | 594 | ¹H NMR (400 MHz, DMSO-d₆) δ 10.52 (s, 1H), 8.91 (t, J = 5.65 Hz, 1H), 8.59 (d, J = 10.00 Hz, 1H), 8.54 (s, 1H), 8.40 (d, J = 1.76 Hz, 1H), 8.36 (s, 1H), 8.29 (d, J = 10.00 Hz, 1H), 7.89 (d, J = 8.03 Hz, 2H), 7.69 (dd, J = 5.02, 9.04 Hz, 2H), 7.40 (d, J = 8.28 Hz, 2H), 7.22 (t, J = 8.91 Hz, 2H), 4.73 (d, J = 5.52 Hz, 2H), 3.29 (d, J = 12.05 Hz, 1H), 3.21 (d, J = 11.80 Hz, 1H), 2.53-2.83 (m, 4H), 1.92 (d, J = 12.80 Hz, 1H), 1.62-1.85 (m, 4H), 1.46-1.62 (m, 1H), 1.11-1.27 (m, 1H) |
| 78 | 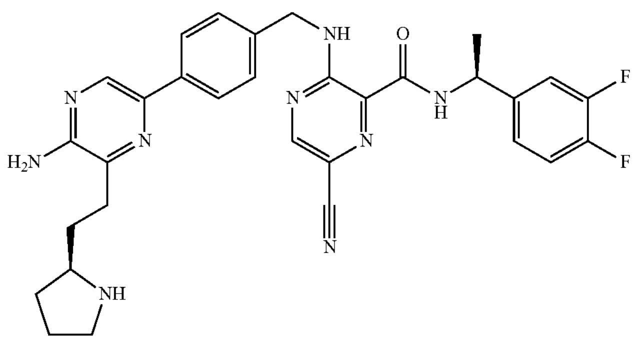 [SMILES: C[C@H](NC(=O)c1nc(C#N)cnc1NCc1ccc(-c2cnc(N)c(CC[C@@H]3CCCN3)n2)cc1)c1ccc(F)c(F)c1] | 3-{4-[5-Amino-6-((S)-2-pyrrolidin-2-yl-ethyl)-pyrazin-2-yl]-benzyl}amino}-6-cyano-pyrazine-2-carboxylic acid [(S)-1-(3,4-difluoro-phenyl)-ethyl]-amide | 584 | ¹H NMR (400 MHz, DMSO-d₆) δ 9.72 (t, J = 5.90 Hz, 1H), 9.35 (d, J = 8.28 Hz, 1H), 8.89 (br. s., 1H), 8.74 (s, 1H), 8.34-8.48 (m, 2H), 7.88 (d, J = 8.28 Hz, 2H), 7.51 (ddd, J = 1.88, 7.97, 11.98 Hz, 1H), 7.32-7.43 (m, 3H), 7.19-7.30 (m, 1H), 5.11 (quin, J = 7.28 Hz, 1H), 4.60-4.82 (m, 2H), 3.48-3.63 (m, 1H), 3.11-3.31 (m, 2H), 2.68-2.84 (m, 2H), 1.79-2.25 (m, 5H), 1.54-1.70 (m, 1H), 1.51 (d, J = 7.03 Hz, 3H) |

TABLE 1-continued

| Ex. No. | Structure | Chemical Name | ESI-MS (M + H) | ¹H NMR |
|---|---|---|---|---|
| 79 | 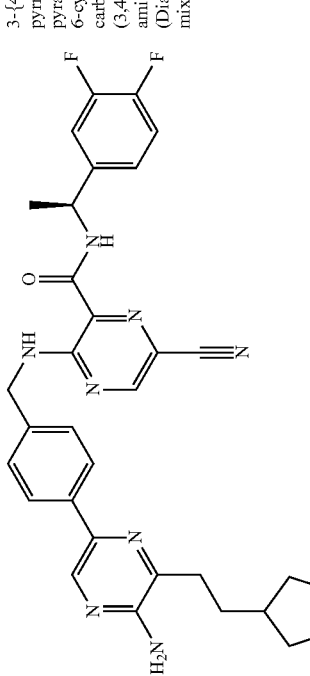 | 3-{4-[5-Amino-6-(2-pyrrolidin-3-yl-ethyl)-pyrazin-2-yl]-benzylamino}-6-cyano-pyrazine-2-carboxylic acid [(S)-1-(3,4-difluoro-phenyl)-ethyl]-amide (Diastereomer 1 Estimated 20:3 mixture of diastereomers) | 584 | ¹H NMR (400 MHz, DMSO-d₆) δ 9.72 (t, J = 5.90 Hz, 1H), 9.26-9.40 (m, 1H), 8.74 (s, 1H), 8.52-8.71 (m, 2H), 8.36 (s, 1H), 7.88 (d, J = 8.28 Hz, 2H), 7.51 (ddd, J = 1.88, 7.97, 11.98 Hz, 1H), 7.31-7.44 (m, 3H), 7.21-7.29 (m, 1H), 5.04-5.19 (m, 1H), 4.60-4.77 (m, 2H), 3.17-3.37 (m, 2H), 3.01-3.16 (m, 1H), 2.74-2.83 (m, 1H), 2.70 (t, J = 7.40 Hz, 2H), 2.17-2.31 (m, 1H), 2.02-2.15 (m, 1H), 1.74-1.94 (m, 2H), 1.53-1.63 (m, 1H), 1.51 (d, J = 7.03 Hz, 3H) |
| 80 | 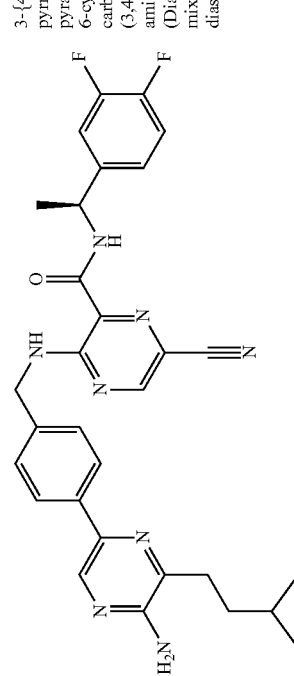 | 3-{4-[5-Amino-6-(2-pyrrolidin-3-yl-ethyl)-pyrazin-2-yl]-benzylamino}-6-cyano-pyrazine-2-carboxylic acid [(S)-1-(3,4-difluoro-phenyl)-ethyl]-amide (Diastereomer 2 Estimated 4:1 mixture of diastereomers (20% diastereomer 1) | 584 | ¹H NMR (400 MHz, DMSO-d₆) δ 9.35-9.41 (m, 1H), 9.28-9.34 (m, 1H), 8.78 (s, 1H), 8.36 (s, 1H), 7.97 (s, 1H), 7.88 (d, J = 8.28 Hz, 2H), 7.46-7.56 (m, 1H), 7.33-7.46 (m, 3H), 7.20-7.30 (m, 1H), 5.08-5.20 (m, 1H), 4.71 (d, J = 5.77 Hz, 2H), 3.19-3.39 (m, 2H), 3.05-3.17 (m, 1H), 2.74-2.83 (m, 1H), 2.63-2.74 (m, 2H), 2.17-2.36 (m, 1H), 2.02-2.14 (m, 1H), 1.78-1.93 (m, 2H), 1.48-1.64 (m, 4H) |

| Ex. No. | Structure | Chemical Name | ESI-MS (M + H) | ¹H NMR |
|---|---|---|---|---|
| 81 | 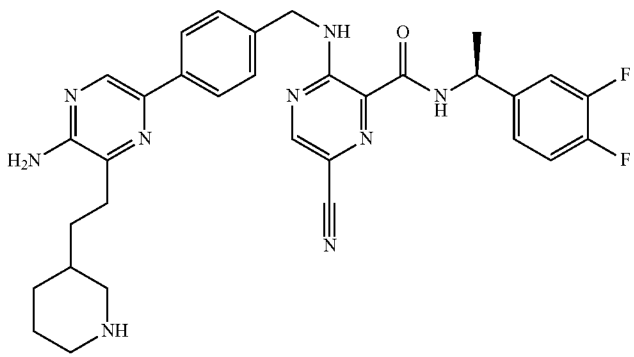 [SMILES: C[C@H](NC(=O)c1nc(C#N)cnc1NCc1ccc(-c2cnc(N)c(CCC3CCCNC3)n2)cc1)c1ccc(F)c(F)c1] | 3-{4-[5-Amino-6-(2-pyrrolidin-3-yl-ethyl)-pyrazin-2-yl]-benzylamino}-6-cyano-pyrazine-2-carboxylic acid [(S)-1-(3,4-difluoro-phenyl)-ethyl]-amide | 598 | ¹H NMR (400 MHz, DMSO-d₆) δ 9.73 (t, J = 5.90 Hz, 1H), 9.35 (d, J = 8.28 Hz, 1H), 8.74 (s, 1H), 8.61 (d, J = 9.79 Hz, 1H), 8.36 (s, 1H), 8.23-8.33 (m, 1H), 7.88 (d, J = 8.28 Hz, 2H), 7.51 (ddd, J = 1.76, 7.97, 11.86 Hz, 1H), 7.32-7.43 (m, 3H), 7.26 (br. s., 1H), 5.12 (quin, J = 7.28 Hz, 1H), 4.63-4.78 (m, 2H), 3.29 (d, J = 11.80 Hz, 1H), 3.21 (d, J = 12.05 Hz, 1H), 2.74-2.83 (m, 1H), 2.71 (t, J = 6.78 Hz, 2H), 2.61 (q, J = 10.71 Hz, 1H), 1.92 (d, J = 12.80 Hz, 1H), 1.62-1.84 (m, 4H), 1.55-1.62 (m, 1H), 1.52 (d, J = 7.03 Hz, 3H), 1.08-1.27 (m, 1H) |
| 82 | 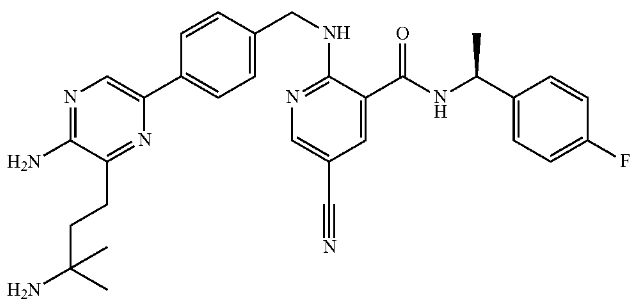 [SMILES: C[C@H](NC(=O)c1cc(C#N)cnc1NCc1ccc(-c2cnc(N)c(CCC(C)(C)N)n2)cc1)c1ccc(F)cc1] | 2-{4-[5-Amino-3-methyl-butyl)-pyrazin-2-yl]-benzylamino}-5-cyano-N-[(S)-1-(4-fluoro-phenyl)-ethyl]-nicotinamide | 553 | ¹H NMR (400 MHz, DMSO-d₆) δ 9.32 (t, J = 5.65 Hz, 1H), 9.01 (d, J = 7.53 Hz, 1H), 8.58 (d, J = 2.01 Hz, 1H), 8.49 (d, J = 2.01 Hz, 1H), 8.38 (s, 1H), 7.80-7.99 (m, 5H), 7.42 (t, J = 5.52, 8.53 Hz, 2H), 7.35 (d, J = 8.28 Hz, 2H), 7.15 (t, J = 8.91 Hz, 2H), 5.09 (quin, J = 7.09 Hz, 1H), 4.68 (d, J = 5.77 Hz, 2H), 2.65-2.75 (m, 2H), 2.02-2.11 (m, 2H), 1.46 (d, J = 7.03 Hz, 3H), 1.31 (s, 6H) |
| 83 | 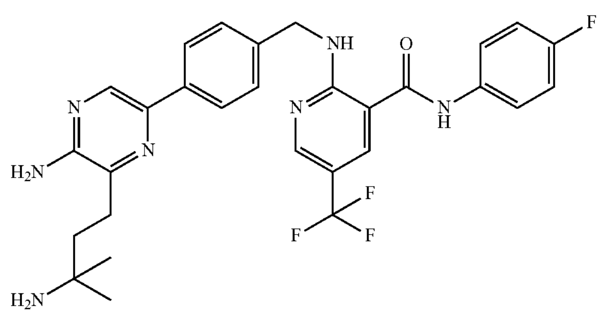 [SMILES: CC(C)(N)CCc1nc(-c2ccc(CNc3ncc(C(F)(F)F)cc3C(=O)Nc3ccc(F)cc3)cc2)cnc1N] | 2-{4-[5-Amino-3-methyl-butyl)-pyrazin-2-yl]-benzylamino}-N-(4-fluoro-phenyl)-5-trifluoromethyl-nicotinamide | 567.9 | ¹H NMR (400 MHz, DMSO-d₆) δ 10.52 (s, 1H), 8.90 (t, J = 5.65 Hz, 1H), 8.54 (s, 1H), 8.40 (d, J = 2.01 Hz, 1H), 8.38 (s, 1H), 7.82-7.97 (m, 5H), 7.65-7.73 (m, 2H), 7.40 (d, J = 8.28 Hz, 2H), 7.16-7.26 (m, 2H), 4.73 (d, J = 5.77 Hz, 2H), 2.67-2.75 (m, 2H), 2.03-2.13 (m, 2H), 1.31 (s, 6H) |

| Ex. No. | Structure | Chemical Name | ESI-MS (M + H) | ¹H NMR |
|---|---|---|---|---|
| 84 | 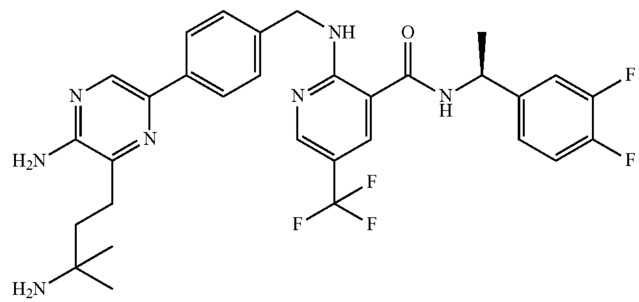 [SMILES: C[C@H](NC(=O)c1cc(C(F)(F)F)cnc1NCc1ccc(-c2cnc(N)c(CCC(C)(C)N)n2)cc1)c1ccc(F)c(F)c1] | 3-{4-[5-Amino-6-(3-amino-3-methyl-butyl)-pyrazin-2-yl]-benzylamino}-6-cyano-pyrazine-2-carboxylic acid [(S)-1-(3,4-difluoro-phenyl)-ethyl]-amide | 572 | ¹H NMR (400 MHz, DMSO-d₆) δ 9.72 (t, J = 5.90 Hz, 1H), 9.35 (d, J = 8.28 Hz, 1H), 8.74 (s, 1H), 8.38 (s, 1H), 7.79-7.92 (m, 5H), 7.51 (ddd, J = 2.01, 8.03, 11.80 Hz, 1H), 7.31-7.42 (m, 3H), 7.21-7.29 (m, 1H), 5.11 (quin, J = 7.28 Hz, 1H), 4.62-4.78 (m, 2H), 2.64-2.76 (m, 2H), 1.99-2.11 (m, 2H), 1.52 (d, J = 7.03 Hz, 3H), 1.31 (s, 6H) |
| 85 | 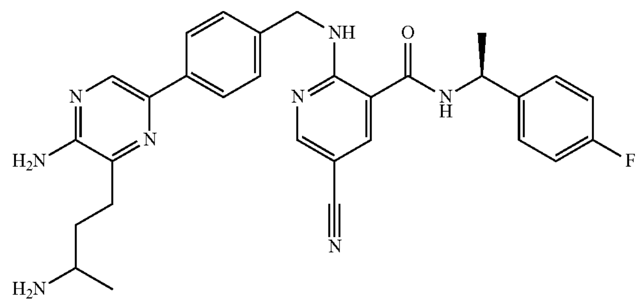 [SMILES: CC(N)CCc1nc(-c2ccc(CNc3ncc(C#N)cc3C(=O)N[C@@H](C)c3ccc(F)cc3)cc2)cnc1N] | 2-{4-[5-Amino-6-(3-amino-butyl)-pyrazin-2-yl]-benzylamino}-5-cyano-N-[(S)-1-(4-fluoro-phenyl)-ethyl]-nicotinamide | 539 | ¹H NMR (400 MHz, DMSO-d₆) δ 9.32 (t, J = 5.65 Hz, 1H), 9.01 (d, J = 7.28 Hz, 1H), 8.58 (d, J = 1.76 Hz, 1H), 8.49 (d, J = 1.76 Hz, 1H), 8.38 (s, 1H), 7.87 (d, J = 8.03 Hz, 2H), 7.76 (br. s., 3H), 7.42 (dd, J = 5.77, 8.28 Hz, 2H), 7.34 (d, J = 8.03 Hz, 2H), 7.15 (t, J = 8.78 Hz, 2H), 5.09 (quin, J = 6.96 Hz, 1H), 4.69 (d, J = 5.52 Hz, 2H), 3.25-3.40 (m, 1H), 2.63-2.83 (m, 2H), 2.05-2.18 (m, 1H), 1.80-1.93 (m, 1H), 1.46 (d, J = 6.78 Hz, 3H), 1.25 (d, J = 6.53 Hz, 3H) |
| 86 | 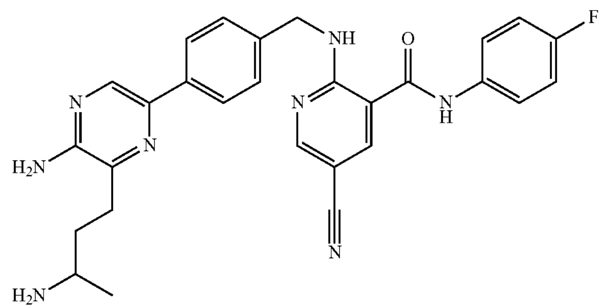 [SMILES: CC(N)CCc1nc(-c2ccc(CNc3ncc(C#N)cc3C(=O)Nc3ccc(F)cc3)cc2)cnc1N] | 2-{4-[5-Amino-6-(3-amino-butyl)-pyrazin-2-yl]-benzylamino}-N-(4-fluoro-phenyl)-5-trifluoromethyl-nicotinamide | 553.9 | ¹H NMR (400 MHz, DMSO-d₆) δ 10.51 (s, 1H), 8.90 (t, J = 5.77 Hz, 1H), 8.54 (s, 1H), 8.40 (d, J = 2.01 Hz, 1H), 8.39 (s, 1H), 7.89 (d, J = 8.28 Hz, 2H), 7.73 (br. s.., 2H), 7.65-7.71 (m, 2H), 7.40 (d, J = 8.28 Hz, 2H), 7.22 (t, J = 8.91 Hz, 2H), 4.73 (d, J = 5.52 Hz, 2H), 3.26-3.39 (m, 1H), 2.62-2.83 (m, 2H), 2.05-2.18 (m, 1H), 1.79-1.93 (m, 1H), 1.25 (d, J = 6.53 Hz, 3H) |

TABLE 1-continued

| Ex. No. | Structure | Chemical Name | ESI-MS (M + H) | ¹H NMR |
|---|---|---|---|---|
| 87 | 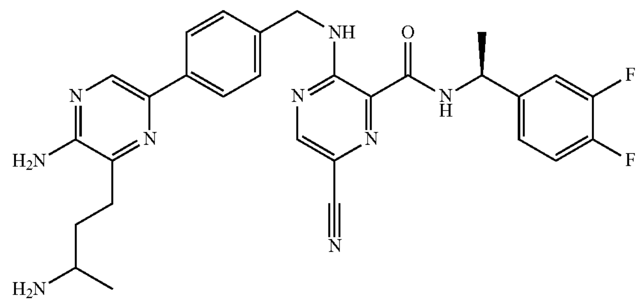 [SMILES: CC(N)CCc1nc(-c2ccc(CNc3ncc(C#N)nc3C(=O)N[C@@H](C)c3ccc(F)c(F)c3)cc2)cnc1N] | 3-{4-[5-Amino-6-(3-amino-butyl)-pyrazin-2-yl]-benzylamino}-6-cyano-pyrazine-2-carboxylic acid [(S)-1-(3,4-difluoro-phenyl)-ethyl]-amide | 558 | ¹H NMR (400 MHz, DMSO-$d_6$) δ 9.72 (t, J = 5.90 Hz, 1H), 9.35 (d, J = 8.03 Hz, 1H), 8.74 (s, 1H), 8.39 (s, 1H), 7.88 (d, J = 8.03 Hz, 2H), 7.77 (br. s., 3H), 7.51 (ddd, J = 1.76, 7.91, 11.92 Hz, 1H), 7.31-7.44 (m, 3H), 7.19-7.29 (m, 1H), 5.11 (quin, J = 7.22 Hz, 1H), 4.63-4.77 (m, 2H), 3.24-3.39 (m, 1H), 2.63-2.83 (m, 2H), 2.02-2.18 (m, 1H), 1.79-1.94 (m, 1H), 1.52 (d, J = 7.03 Hz, 3H), 1.26 (d, J = 6.53 Hz, 3H) |
| 88 | 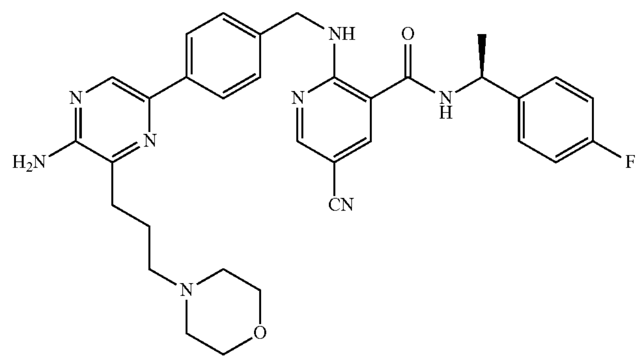 [SMILES: C[C@H](NC(=O)c1cc(C#N)cnc1NCc1ccc(-c2cnc(N)c(CCCN3CCOCC3)n2)cc1)c1ccc(F)cc1] | 2-{4-[5-Amino-6-(3-morpholin-4-yl-propyl)-pyrazin-2-yl]-benzylamino}-5-cyano-N-[(S)-1-(4-fluoro-phenyl)-ethyl]-nicotinamide | 595.5 | ¹H NMR (400 MHz, CD$_3$OD) δ 8.81-8.85 (m, 1H), 8.47 (d, J = 2.01 Hz, 1H), 8.30 (s, 1H), 8.26 (d, 1H), 7.83-7.90 (m, 2H), 7.37-7.45 (m, 4H), 7.03-7.12 (m, 2H), 5.15-5.23 (m, 1H), 4.77 (br. s., 2H), 4.01-4.10 (m, 2H), 3.63-3.77 (m, 2H), 3.52-3.60 (m, 2H), 3.47-3.53 (m, 1H), 3.14-3.24 (m, 2H), 2.83-2.90 (m, 2H), 2.33-2.43 (m, 2H), 1.55 (d, J = 7.03 Hz, 3H) |

TABLE 1-continued

| Ex. No. | Structure | Chemical Name | ESI-MS (M + H) | ¹H NMR |
|---|---|---|---|---|
| 89 | 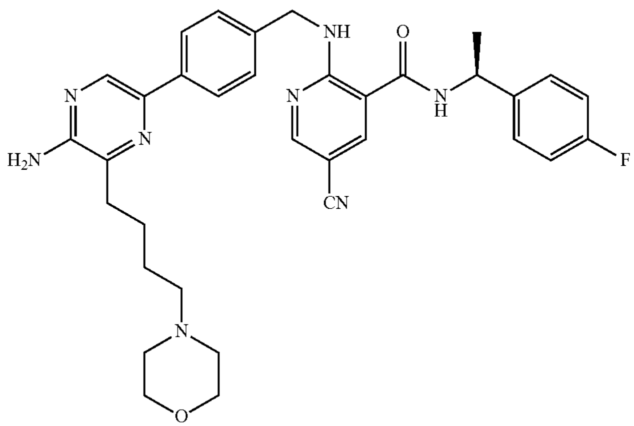 [SMILES: C[C@H](NC(=O)c1cc(C#N)cnc1NCc1ccc(-c2cnc(N)c(CCCCN3CCOCC3)n2)cc1)c1ccc(F)cc1] | 2-{4-[5-Amino-6-(4-morpholin-4-yl-butyl)-pyrazin-2-yl]-benzyl-amino}-5-cyano-N-[(S)-1-(4-fluoro-phenyl)-ethyl]-nicotinamide | 609.5 | ¹H NMR (400 MHz, CD₃OD) δ 8.83-8.87 (m, 1H), 8.49 (d, J = 2.26 Hz, 1H), 8.25-8.29 (m, 2H), 7.87-7.91 (m, 2H), 7.40-7.47 (m, 4H), 7.06-7.13 (m, 2H), 5.16-5.25 (m, 1H), 4.79 (br. s., 2H), 4.00-4.08 (m, 2H), 3.66-3.76 (m, 2H), 3.46-3.53 (m, 2H), 3.09-3.19 (m, 2H), 2.86-2.93 (m, 2H), 1.97-2.08 (m, 2H), 1.86-1.97 (m, 2H), 1.57 (d, J = 7.03 Hz, 3H) |
| 90 | 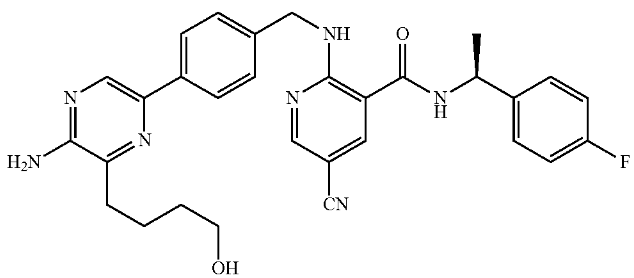 [SMILES: C[C@H](NC(=O)c1cc(C#N)cnc1NCc1ccc(-c2cnc(N)c(CCCCO)n2)cc1)c1ccc(F)cc1] | 2-{4-[5-Amino-6-(4-hydroxy-butyl)-pyrazin-2-yl]-benzyl-amino}-5-cyano-N-[(S)-1-(4-fluoro-phenyl)-ethyl]-nicotinamide | 540.5 | ¹H NMR (400 MHz, CD₃OD) δ 8.80-8.85 (m, 1H), 8.47 (d, J = 2.26 Hz, 1H), 8.25 (d, J = 2.26 Hz, 1H), 8.19 (br. s., 1H), 7.86-7.91 (m, 2H), 7.39-7.44 (m, 4H), 7.04-7.10 (m, 2H), 5.14-5.23 (m, 1H), 4.77 (br. s., 2H), 3.66-3.69 (m, 2H), 2.82-2.88 (m, 2H), 1.90-1.99 (m, 2H), 1.67-1.76 (m, 2H), 1.58-1.58 (m, 0H), 1.55 (d, J = 7.03 Hz, 3H) |
| 91 | 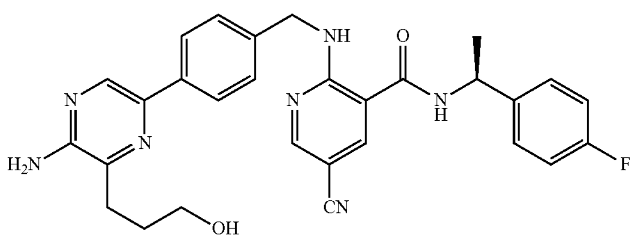 [SMILES: C[C@H](NC(=O)c1cc(C#N)cnc1NCc1ccc(-c2cnc(N)c(CCCO)n2)cc1)c1ccc(F)cc1] | 2-{4-[5-Amino-6-(3-hydroxy-propyl)-pyrazin-2-yl]-benzyl-amino}-5-cyano-N-[(S)-1-(4-fluoro-phenyl)-ethyl]-nicotinamide | 526.5 | ¹H NMR (400 MHz, CD₃OD) δ 8.80-8.85 (m, 1H), 8.48 (d, J = 2.26 Hz, 1H), 8.25 (d, J = 2.26 Hz, 1H), 8.20 (br. s., 1H), 7.86-7.91 (m, 2H), 7.38-7.44 (m, 4H), 7.03-7.10 (m, 2H), 5.15-5.22 (m, 1H), 4.77 (br. s., 2H), 3.72-3.77 (m, 2H), 2.86-2.92 (m, 2H), 2.07-2.15 (m, 2H), 1.55 (d, J = 7.03 Hz, 3H) |

| Ex. No. | Structure | Chemical Name | ESI-MS (M + H) | $^1$H NMR |
|---|---|---|---|---|
| 92 | 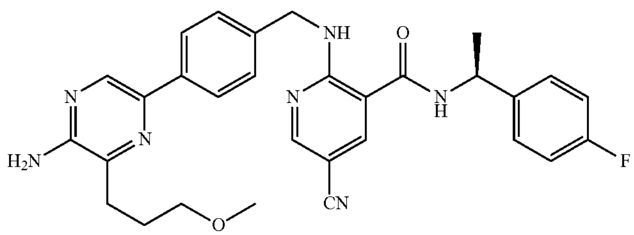 [SMILES: COCCCc1nc(-c2ccc(CNc3ncc(C#N)cc3C(=O)N[C@@H](C)c3ccc(F)cc3)cc2)cnc1N] | 2-{4-[5-Amino-6-(3-methoxy-propyl)-pyrazin-2-yl]-benzyl-amino}-5-cyano-N-[(S)-1-(4-fluoro-phenyl)-ethyl]-nicotinamide | 540.2 | $^1$H NMR (400 MHz, CD$_3$OD) δ 8.80-8.85 (m, J = 6.53 Hz, 1H), 8.47 (d, J = 2.01 Hz, 1H), 8.25 (d, J = 2.01 Hz, 1H), 8.17-8.20 (m, 1H), 7.87-7.92 (m, 2H), 7.38-7.45 (m, J = 6.02 Hz, 4H), 7.03-7.10 (m, 2H), 5.15-5.22 (m, 1H), 4.77 (s, 2H), 3.57 (t, J = 6.15 Hz, 2H), 3.37 (s, 3H), 2.90 (t, J = 7.40 Hz, 2H), 2.12-2.20 (m, 2H), 1.55 (d, J = 7.03 Hz, 3H) |
| 93 | 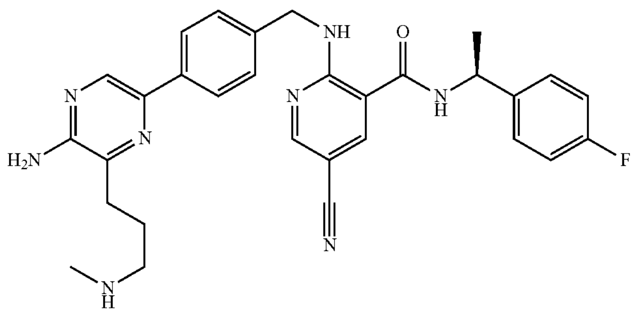 [SMILES: CNCCCc1nc(-c2ccc(CNc3ncc(C#N)cc3C(=O)N[C@@H](C)c3ccc(F)cc3)cc2)cnc1N] | 2-{4-[5-Amino-6-(3-methylamino-propyl)-pyrazin-2-yl]-benzyl-amino}-5-cyano-N-[(S)-1-(4-fluoro-phenyl)-ethyl]-nicotinamide | 539.5 | $^1$H NMR (400 MHz, CD$_3$OD) δ 8.79-8.86 (m, 1H), 8.29-8.30 (m, 1H), 8.25-8.27 (m, 1H), 7.85-7.90 (m, 2H), 7.38-7.44 (m, 4H), 7.04-7.11 (m, 2H), 5.14-5.22 (m, 1H), 4.76 (s, 2H), 3.14-3.21 (m, 2H), 2.84-2.90 (m, 2H), 2.73 (s, 3H), 2.22-2.34 (m, 2H), 1.55 (d, J = 7.03 Hz, 3H) |
| 94 | 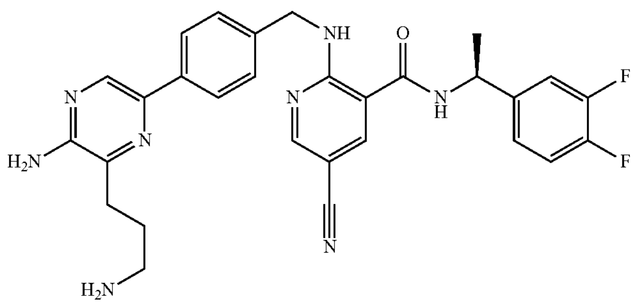 [SMILES: C[C@H](NC(=O)c1cc(C#N)cnc1NCc1ccc(-c2cnc(N)c(CCCN)n2)cc1)c1ccc(F)c(F)c1] | 3-{4-[5-Amino-6-(3-amino-propyl)-pyrazin-2-yl]-benzyl-amino}-6-cyano-pyrazine-2-carboxylic acid [(S)-1-(3,4-difluoro-phenyl)-ethyl]-amide | 544 | $^1$H NMR (400 MHz, CD$_3$OD) δ 9.02-9.08 (m, 1H), 8.57 (s, 1H), 8.26-8.30 (m, 1H), 7.87-7.92 (m, 2H), 7.41-7.47 (m, 2H), 7.31-7.39 (m, 1H), 7.16-7.25 (m, 2H), 5.13-5.22 (m, 1H), 4.79 (s, 2H), 3.08-3.16 (m, 2H), 2.88 (t, J = 7.53 Hz, 2H), 2.18-2.36 (m, 2H), 1.58 (d, J = 7.15 Hz, 2H, 3H) |

| Ex. No. | Structure | Chemical Name | ESI-MS (M + H) | ¹H NMR |
|---|---|---|---|---|
| 95 | 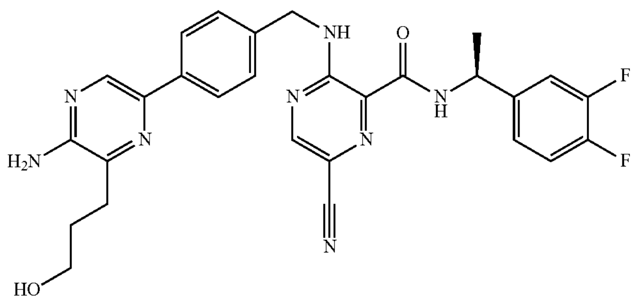 [SMILES: C[C@H](NC(=O)c1nc(C#N)cnc1NCc1ccc(-c2cnc(N)c(CCCO)n2)cc1)c1ccc(F)c(F)c1] | 3-{4-[5-Amino-6-(3-hydroxy-propyl)-pyrazin-2-yl]-benzyl-amino}-6-cyano-pyrazine-2-carboxylic acid [(S)-1-(3,4-difluoro-phenyl)-ethyl]-amide | 545.3 | ¹H NMR (400 MHz, DMSO-d₆) δ 9.73 (t, J = 5.90 Hz, 1H), 9.33 (d, J = 8.53 Hz, 1H), 8.74 (s, 1H), 8.33 (s, 1H), 7.87 (d, J = 8.28 Hz, 2H), 7.51 (ddd, J = 2.13, 7.97, 11.98 Hz, 1H), 7.33-7.42 (m, 3H), 7.23-7.28 (m, 1H), 5.08-5.17 (m, 1H), 4.64-4.76 (m, 2H), 3.53 (t, J = 6.53 Hz, 2H), 2.71 (t, J = 7.40 Hz, 2H), 1.85-1.95 (m, 2H), 1.52 (d, J = 7.03 Hz, 3H). 0.7 TFA per molecule. |
| 96 | 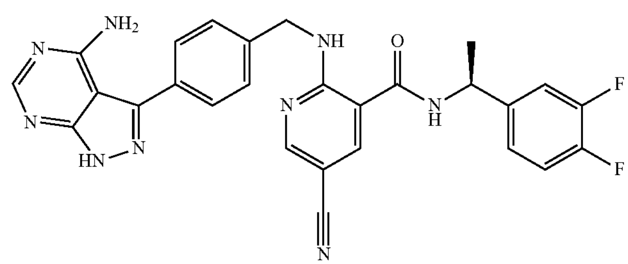 [SMILES: C[C@H](NC(=O)c1cc(C#N)cnc1NCc1ccc(-c2n[nH]c3ncnc(N)c23)cc1)c1ccc(F)c(F)c1] | 2-[4-(4-Amino-1H-pyrazolo[3,4-d]pyrimidin-3-yl)benzylamino]-5-cyano-N-[(S)-1-(4-fluoro-phenyl)-ethyl]-nicotinamide | 507.9 | ¹H NMR (300 MHz, DMSO-d₆) δ 9.41 (t, J = 6.04 Hz, 1H), 9.01 (d, J = 7.55 Hz, 1H), 8.59 (d, J = 2.27 Hz, 1H), 8.50 (d, J = 1.89 Hz, 1H), 8.37 (br. s., 1H), 7.58-7.69 (m, 2H), 7.37-7.54 (m, 4H), 7.07-7.23 (m, 2H), 5.10 (quin, J = 7.08 Hz, 1H), 4.78 (d, J = 5.67 Hz, 2H), 1.47 (d, J = 7.18 Hz, 3H) |
| 97 | 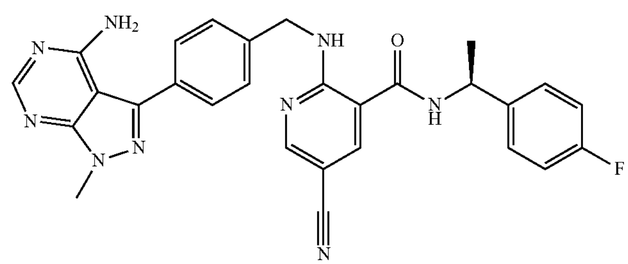 [SMILES: C[C@H](NC(=O)c1cc(C#N)cnc1NCc1ccc(-c2nn(C)c3ncnc(N)c23)cc1)c1ccc(F)cc1] | (S)-2-(4-(4-amino-7-methyl-7H-pyrrolo[2,3-d]pyrimidin-5-yl)benzylamino)-5-cyano-N-(1-(4-fluorophenyl)ethyl)nicotinamide | 521.0 | ¹H NMR (300 MHz, DMSO-d₆) δ 9.29 (t, J = 5.85 Hz, 1H), 8.92 (d, J = 7.55 Hz, 1H), 8.52 (d, J = 1.89 Hz, 1H), 8.42 (d, J = 2.27 Hz, 1H), 8.08 (s, 1H), 6.98-7.41 (m, 9H), 5.96 (br. s., 1H), 5.03 (quin, J = 7.08 Hz, 1H), 4.56-4.74 (m, 2H), 3.53-3.76 (m, 3H), 1.39 (d, J = 6.80 Hz, 3H) |

TABLE 1-continued

| Ex. No. | Structure | Chemical Name | ESI-MS (M + H) | ¹H NMR |
|---|---|---|---|---|
| 98 | 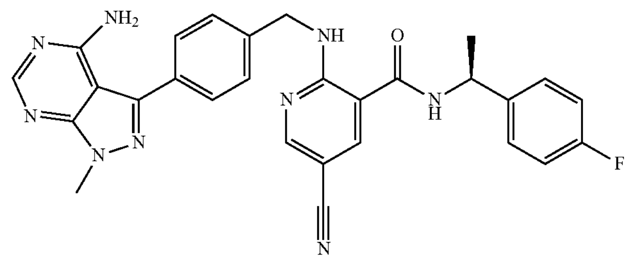 [SMILES: C[C@H](NC(=O)c1cc(C#N)cnc1NCc1ccc(-c2nn(C)c3ncnc(N)c23)cc1)c1ccc(F)cc1] | (S)-2-(4-(4-amino-1-methyl-1H-pyrazolo[3,4-d]pyrimidin-3-yl)benzylamino)-5-cyano-N-(1-(4-fluorophenyl)ethyl)nicotinamide | 521.9 | ¹H NMR (300 MHz, DMSO-d₆) δ 9.33 (t, J = 5.85 Hz, 1H), 8.93 (d, J = 7.55 Hz, 1H), 8.38-8.57 (m, 2H), 8.15-8.23 (m, 1H), 7.54 (d, J = 8.31 Hz, 2H), 7.30-7.45 (m, 4H), 7.01-7.18 (m, 2H), 5.04 (quin, J = 7.08 Hz, 1H), 4.62-4.78 (m, 2H), 3.18-3.31 (m, 3H), 1.33-1.44 (m, 3H) |
| 99 | 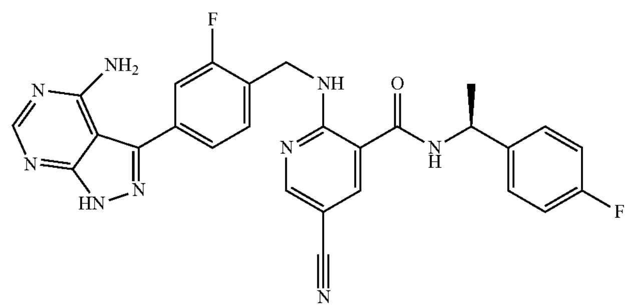 [SMILES: C[C@H](NC(=O)c1cc(C#N)cnc1NCc1ccc(-c2n[nH]c3ncnc(N)c23)cc1F)c1ccc(F)cc1] | (S)-2-(4-(4-amino-7H-pyrrolo[2,3-d]pyrimidin-5-yl)-2-fluorobenzylamino)-5-cyano-N-(1-(4-fluorophenyl)ethyl)nicotinamide | 524.9 | ¹H NMR (300 MHz, DMSO-d₆) δ 11.80 (br. s., 1H), 9.27 (t, J = 5.85 Hz, 1H), 8.94 (d, J = 1.18 Hz, 1H), 8.40-8.57 (m, 2H), 8.04 (s, 1H), 7.01-7.42 (m, 8H), 6.03 (br. s., 2H), 5.04 (quin, J = 7.08 Hz, 1H), 4.60-4.77 (m, 2H), 1.40 (d, J = 6.80 Hz, 3H) |
| 100 | 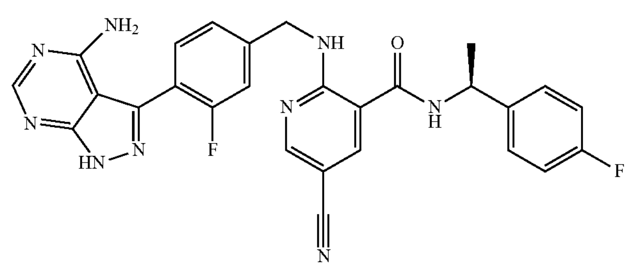 [SMILES: C[C@H](NC(=O)c1cc(C#N)cnc1NCc1ccc(-c2n[nH]c3ncnc(N)c23)c(F)c1)c1ccc(F)cc1] | (S)-2-(4-(4-amino-7H-pyrrolo[2,3-d]pyrimidin-5-yl)-3-fluorobenzylamino)-5-cyano-N-(1-(4-fluorophenyl)ethyl)nicotinamide | 524.9 | ¹H NMR (300 MHz, DMSO-d₆) δ 11.78 (br. s., 1H), 9.30 (t, J = 5.85 Hz, 1H), 8.93 (d, J = 7.18 Hz, 1H), 8.47 (dd, J = 2.27, 30.97 Hz, 2H), 7.99-8.06 (m, 1H), 7.23-7.43 (m, 3H), 7.03-7.21 (m, 5H), 5.81 (br. s., 2H), 5.04 (quin, J = 7.08 Hz, 1H), 4.60-4.73 (m, 2H), 1.40 (d, J = 7.18 Hz, 3H) |

| Ex. No. | Structure | Chemical Name | ESI-MS (M + H) | ¹H NMR |
|---|---|---|---|---|
| 101 | 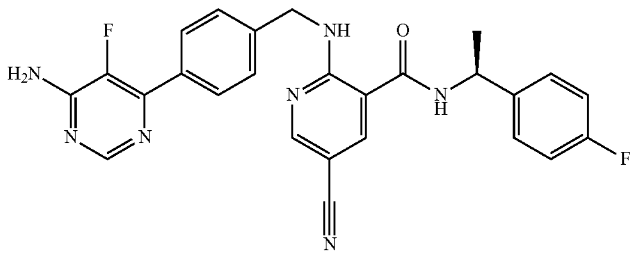 [SMILES: C[C@H](NC(=O)c1cc(C#N)cnc1NCc1ccc(-c2ncnc(N)c2F)cc1)c1ccc(F)cc1] | (S)-2-(4-(6-amino-5-fluoropyrimidin-4-yl)-benzylamino)-5-cyano-N-(1-(4-fluorophenyl)ethyl)nicotinamide | 486.2 | ¹H NMR (400 MHz, DMSO-d₆) δ 9.38 (t, J = 6.02 Hz, 1H), 9.00 (d, J = 7.53 Hz, 1H), 8.56 (d, J = 2.01 Hz, 1H), 8.48 (d, J = 2.01 Hz, 1H), 8.26 (d, J = 2.01 Hz, 1H), 7.87 (d, J = 7.53 Hz, 2H), 7.34-7.51 (m, 6H), 7.15 (t, J = 8.91 Hz, 2H), 5.10 (t, J = 7.15 Hz, 1H), 4.74 (t, J = 4.77 Hz, 2H), 1.46 (d, J = 7.03 Hz, 3H). |
| 102 | 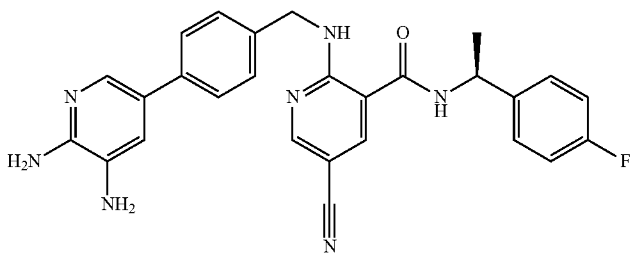 [SMILES: C[C@H](NC(=O)c1cc(C#N)cnc1NCc1ccc(-c2cnc(N)c(N)c2)cc1)c1ccc(F)cc1] | (S)-5-cyano-2-(4-(5,6-diaminopyridin-3-yl)benzylamino)-N-(1-(4-fluorophenyl)ethyl)nicotinamide | 482.0 | ¹H NMR (400 MHz, DMSO-d₆) δ 9.28 (t, J = 5.90 Hz, 1H), 8.94 (d, J = 7.53 Hz, 1H), 8.50 (d, J = 2.01 Hz, 1H), 8.42 (d, J = 2.26 Hz, 1H), 7.47-7.58 (m, 3H), 7.43 (s, 2H), 7.23-7.39 (m, 5H), 7.08 (t, J = 8.91 Hz, 2H), 5.02 (quin, J = 7.03 Hz, 1H), 4.63 (d, J = 5.77 Hz, 2H), 1.39 (d, J = 7.03 Hz, 3H). |
| 103 | 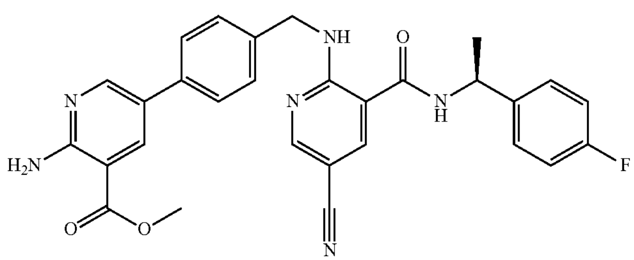 [SMILES: COC(=O)c1cc(-c2ccc(CNc3ncc(C#N)cc3C(=O)N[C@@H](C)c3ccc(F)cc3)cc2)cnc1N] | (S)-methyl 2-amino-5-(4-((5-cyano-3-(1-(4-fluorophenyl)ethylcarbamoyl)pyridin-2-ylamino)methyl)phenyl)nicotinate | 525.2 | ¹H NMR (400 MHz, DMSO-d₆) δ 9.27 (t, J = 5.77 Hz, 1H), 8.93 (d, J = 7.28 Hz, 1H), 8.49 (dd, J = 2.38, 7.65 Hz, 2H), 8.41 (d, J = 2.01 Hz, 1H), 8.30 (d, J = 2.51 Hz, 1H), 7.50 (d, J = 8.28 Hz, 2H), 7.22-7.41 (m, 4H), 7.08 (t, J = 8.91 Hz, 2H), 5.03 (quin, J = 7.03 Hz, 1H), 4.63 (d, J = 5.52 Hz, 2H), 3.80 (s, 3H), 1.39 (d, J = 7.03 Hz, 3H). |
| 104 | 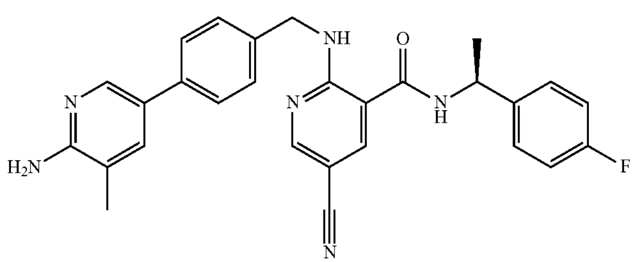 [SMILES: Cc1cc(-c2ccc(CNc3ncc(C#N)cc3C(=O)N[C@@H](C)c3ccc(F)cc3)cc2)cnc1N] | (S)-2-(4-(6-amino-5-methylpyridin-3-yl)benzylamino)-5-cyano-N-(1-(4-fluorophenyl)ethyl)nicotinamide | 481.30 | ¹H NMR (400 MHz, DMSO-d₆) δ ppm 9.34 (t, J = 5.90 Hz, 1 H) 9.00 (d, J = 7.53 Hz, 1 H) 8.57 (d, J = 2.01 Hz, 1 H) 8.48 (d, J = 2.01 Hz, 1 H) 8.14 (d, J = 16.31 Hz, 2 H) 7.52-7.73 (m, 3 H) 7.31-7.47 (m, 4 H) 7.15 (t, J = 8.78 Hz, 2 H) 5.09 (quin, J = 7.09 Hz, 1 H) 4.70 (d, J = 5.77 Hz, 2 H) 2.24 (s, 3 H) 1.46 (d, J = 7.03 Hz, 3 H) |

TABLE 1-continued

| Ex. No. | Structure | Chemical Name | ESI-MS (M + H) | ¹H NMR |
|---|---|---|---|---|
| 105 | 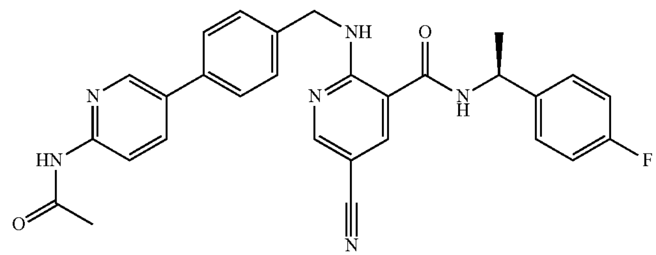 [SMILES: CC(=O)Nc1ccc(-c2ccc(CNc3ncc(C#N)cc3C(=O)N[C@@H](C)c3ccc(F)cc3)cc2)cn1] | (S)-2-(4-(6-acetamidopyridin-3-yl)benzylamino)-5-cyano-N-(1-(4-fluorophenyl)ethyl)nicotinamide | 509.3 | ¹H NMR (400 MHz, DMSO-d₆) δ ppm 10.57 (s, 1 H) 9.35 (t, J = 5.77 Hz, 1 H) 9.00 (d, J = 7.28 Hz, 1 H) 8.58 (dd, J = 7.53, 2.01 Hz, 2 H) 8.48 (d, J = 2.01 Hz, 1 H) 8.09-8.18 (m, 1 H) 8.00-8.08 (m, 1 H) 7.64 (d, J = 8.28 Hz, 2 H) 7.32-7.47 (m, 4 H) 7.15 (t, J = 8.78 Hz, 2 H) 5.02-5.17 (m, 1 H) 4.70 (d, J = 4.02 Hz, 2 H) 2.11 (s, 3 H) 1.46 (d, J = 7.03 Hz, 3 H). |
| 106 | 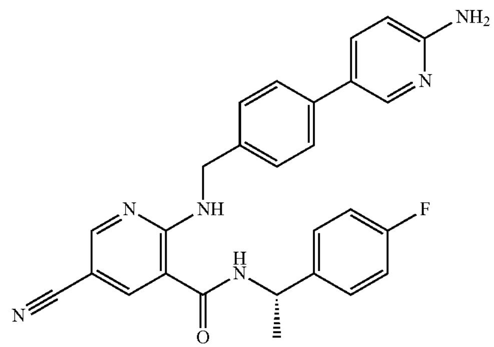 | (S)-2-(4-(6-aminopyridin-3-yl)benzylamino)-5-cyano-N-(1-(4-fluorophenyl)ethyl)nicotinamide | 467.2 | ¹H NMR (400 MHz, DMSO-d₆) δ ppm 9.34 (t, J = 5.90 Hz, 1 H) 9.01 (d, J = 7.28 Hz, 1 H) 8.56 (d, J = 2.01 Hz, 1 H) 8.48 (d, J = 2.01 Hz, 1 H) 8.16-8.30 (m, 2 H) 8.01 (br. s., 2 H) 7.59 (d, J = 8.28 Hz, 2 H) 7.32-7.47 (m, 4 H) 7.15 (t, J = 8.91 Hz, 2 H) 7.04 (d, J = 10.04 Hz, 1 H) 5.09 (quin, J = 7.03 Hz, 1 H) 4.70 (d, J = 5.77 Hz, 2 H) 1.46 (d, J = 7.03 Hz, 3 H) |
| 107 | 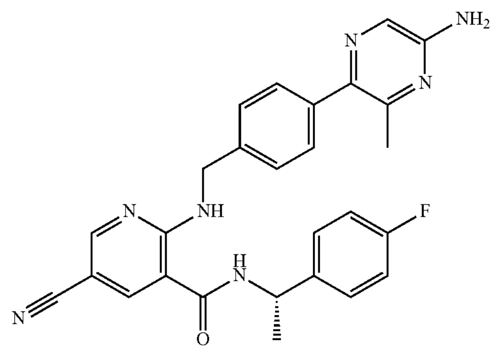 [SMILES: Cc1nc(N)cnc1-c1ccc(CNc2ncc(C#N)cc2C(=O)N[C@@H](C)c2ccc(F)cc2)cc1] | (S)-2-(4-(5-amino-3-methylpyrazin-2-yl)benzylamino)-5-cyano-N-(1-(4-fluorophenyl)ethyl)nicotinamide | 481.30 | ¹H NMR (400 MHz, DMSO-d₆) δ ppm 9.36 (t, J = 5.90 Hz, 1 H) 9.01 (d, J = 7.53 Hz, 1 H) 8.58 (d, J = 2.01 Hz, 1 H) 8.49 (d, J = 2.26 Hz, 1 H) 7.75-8.04 (m, 3 H) 7.35-7.47 (m, 4 H) 7.28-7.34 (m, 2 H) 7.15 (t, J = 8.91 Hz, 2 H) 6.88 (d, J = 9.04 Hz, 1 H) 5.09 (quin, J = 7.03 Hz, 1 H) 4.73 (d, J = 5.77 Hz, 2 H) 2.37 (s, 3 H) 1.46 (d, J = 7.03 Hz, 3 H). |

| Ex. No. | Structure | Chemical Name | ESI-MS (M + H) | ¹H NMR |
|---|---|---|---|---|
| 108 | 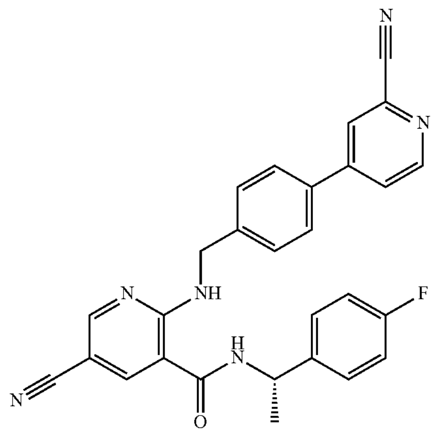 [SMILES: C[C@H](NC(=O)c1cc(C#N)cnc1NCc1ccc(-c2ccnc(C#N)c2)cc1)c1ccc(F)cc1] | (S)-5-cyano-2-(4-(2-cyanopyridin-4-yl)benzylamino)-N-(1-(4-fluorophenyl)ethyl)nicotinamide | 477.2 | ¹H NMR (400 MHz, DMSO-d₆) δ ppm 9.38 (t, J = 5.90 Hz, 1 H) 9.00 (d, J = 7.53 Hz, 1 H) 8.77 (d, J = 5.02 Hz, 1 H) 8.56 (d, J = 2.01 Hz, 1 H) 8.48 (d, J = 2.01 Hz, 1 H) 8.40 (d, J = 1.26 Hz, 1 H) 8.04 (dd, J = 5.27, 1.76 Hz, 1 H) 7.85 (d, J = 8.28 Hz, 2 H) 7.34-7.50 (m, 4 H) 7.15 (t, J = 8.91 Hz, 2 H) 5.10 (quin, J = 7.09 Hz, 1 H) 4.74 (d, J = 6.02 Hz, 2 H) 1.46 (d, J = 7.03 Hz, 3 H). |
| 109 | 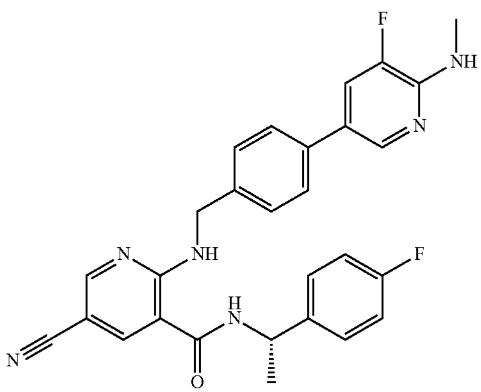 [SMILES: CNc1ncc(-c2ccc(CNc3ncc(C#N)cc3C(=O)N[C@@H](C)c3ccc(F)cc3)cc2)cc1F] | (S)-5-cyano-2-(4-(5-fluoro-6-methylamino)pyridin-3-yl)benzylamino)-N-(1-(4-fluorophenyl)ethyl)nicotinamide | 499.2 | ¹H NMR (400 MHz, DMSO-d₆) δ ppm 9.33 (t, J = 5.77 Hz, 1 H) 8.99 (d, J = 7.53 Hz, 1 H) 8.57 (d, J = 2.01 Hz, 1 H) 8.47 (d, J = 2.01 Hz, 1 H) 8.15 (d, J = 1.26 Hz, 1 H) 7.78 (dd, J = 12.67, 1.38 Hz, 1 H) 7.57 (d, J = 8.28 Hz, 2 H) 7.27-7.47 (m, 4 H) 7.15 (t, J = 8.91 Hz, 2 H) 5.09 (quin, J = 7.09 Hz, 1 H) 4.68 (d, J = 5.27 Hz, 2 H) 2.90 (s, 3 H) 1.46 (d, J = 7.03 Hz, 3 H). |

TABLE 1-continued

| Ex. No. | Structure | Chemical Name | ESI-MS (M + H) | ¹H NMR |
|---|---|---|---|---|
| 110 | 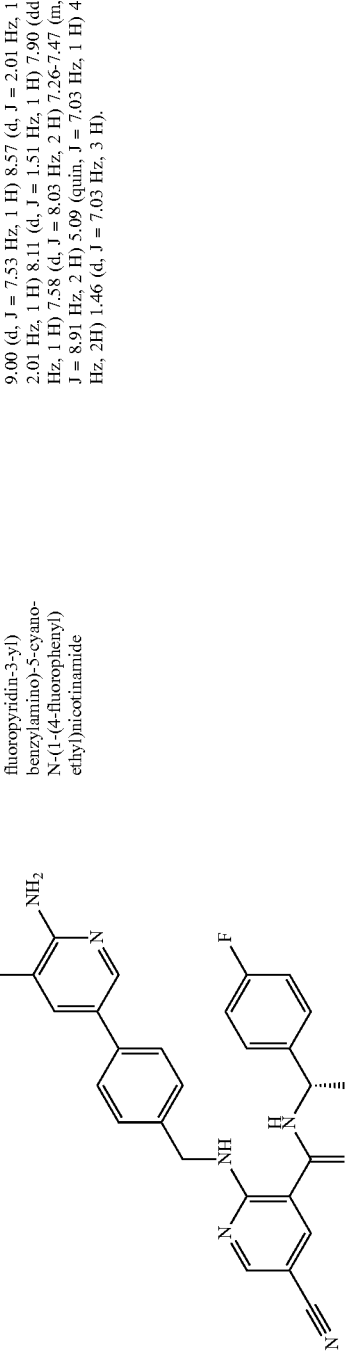 | (S)-2-(4-(6-amino-5-fluoropyridin-3-yl)benzylamino)-5-cyano-N-(1-(4-fluorophenyl)ethyl)nicotinamide | 485.30 | ¹H NMR (400 MHz, DMSO-$d_6$) δ ppm 9.33 (t, J = 5.77 Hz, 1 H) 9.00 (d, J = 7.53 Hz, 1 H) 8.57 (d, J = 2.01 Hz, 1 H) 8.47 (d, J = 2.01 Hz, 1 H) 8.11 (d, J = 1.51 Hz, 1 H) 7.90 (dd, J = 12.30, 1.51 Hz, 1 H) 7.58 (d, J = 8.03 Hz, 2 H) 7.26-7.47 (m, 4 H) 7.15 (t, J = 8.91 Hz, 2 H) 5.09 (quin, J = 7.03 Hz, 1 H) 4.68 (d, J = 5.52 Hz, 2H) 1.46 (d, J = 7.03 Hz, 3 H). |
| 111 | 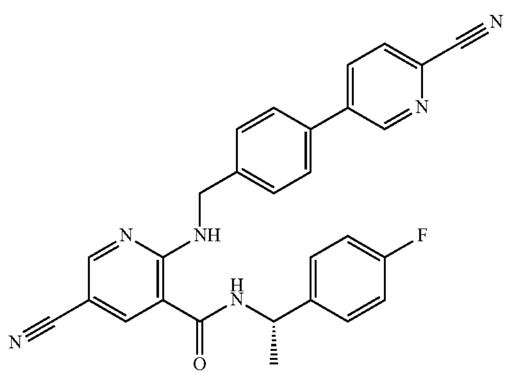 [SMILES: C[C@H](NC(=O)c1cc(C#N)cnc1NCc1ccc(-c2ccc(C#N)nc2)cc1)c1ccc(F)cc1] | (S)-5-cyano-2-(4-(6-cyanopyridin-3-yl)benzylamino)-N-(1-(4-fluorophenyl)ethyl)nicotinamide | 477.2 | ¹H NMR (400 MHz, DMSO-$d_6$) δ ppm 9.37 (t, J = 5.90 Hz, 1 H) 8.93-9.13 (m, 2H) 8.48 (d, J = 2.26 Hz, 1 H) 8.32 (dd, J = 8.03, 2.26 Hz, 1 H) 8.11 (d, J = 8.28 Hz, 1 H) 7.78 (d, J = 8.28 Hz, 2 H) 7.30-7.50 (m, 4 H) 7.15 (t, J = 8.91 Hz, 2 H) 5.10 (quin, J = 7.03 Hz, 1 H) 4.64-4.81 (m, 2 H) 1.46 (d, J = 7.03 Hz, 3 H). |

TABLE 1-continued

| Ex. No. | Structure | Chemical Name | ESI-MS (M + H) | 1H NMR |
|---|---|---|---|---|
| 112 | 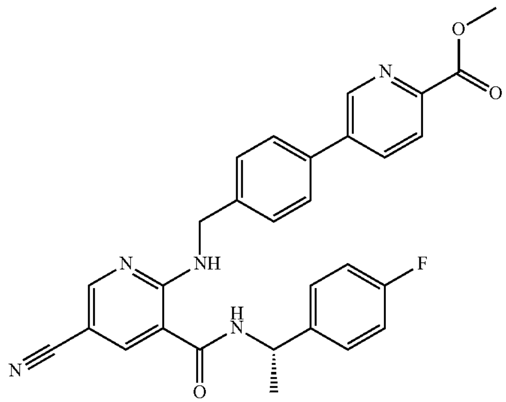 [SMILES: COC(=O)c1ccc(-c2ccc(CNc3ncc(C#N)cc3C(=O)N[C@@H](C)c3ccc(F)cc3)cc2)cn1] | (S)-methyl 5-(4-((5-cyano-3-(1-(4-fluorophenyl)ethylcarbamoyl)pyridin-2-ylamino)methyl)phenyl)picolinate | 510.2 | 1H NMR (400 MHz, DMSO-d6) δ ppm 9.37 (t, J = 5.90 Hz, 1 H) 8.94-9.07 (m, 2 H) 8.57 (d, J = 2.01 Hz, 1 H) 8.48 (d, J = 2.01 Hz, 1 H) 8.25 (dd, J = 8.03, 2.26 Hz, 1 H) 8.11 (d, J = 8.28 Hz, 1 H) 7.76 (d, J = 8.28 Hz, 2 H) 7.35-7.52 (m, 4 H) 7.15 (t, J = 8.91 Hz, 2 H) 5.10 (t, J = 7.15 Hz, 1 H) 4.74 (d, J = 4.77 Hz, 2 H) 3.79-3.99 (m, 3 H) 1.46 (d, J = 7.03 Hz, 3 H). |
| 113 | 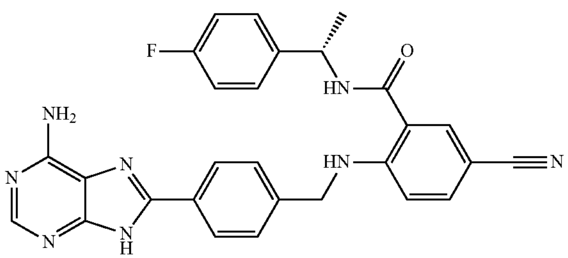 [SMILES: C[C@H](NC(=O)c1cc(C#N)ccc1NCc1ccc(-c2nc3c(N)ncnc3[nH]2)cc1)c1ccc(F)cc1] | (S)-2-(4-(6-amino-9H-purin-8-yl)benzylamino)-5-cyano-N-(1-(4-fluorophenyl)ethyl)nicotinamide | 508.20 | 1H NMR (400 MHz, DMSO-d6) δ ppm 9.39 (t, J = 5.90 Hz, 1 H) 9.02 (d, J = 7.53 Hz, 1 H) 8.57 (d, J = 2.01 Hz, 1H) 8.50 (d, J = 2.01 Hz, 1 H) 8.38 (br. s., 1H) 8.07 (d, J = 8.03 Hz, 2 H) 7.32-7.54 (m, 4 H) 7.15 (t, J = 8.91 Hz, 2 H) 5.10 (quin, J = 7.03 Hz, 1 H) 4.76 (d, J = 5.52 Hz, 2 H) 1.47 (d, J = 7.03 Hz, 3 H). |
| 114 | 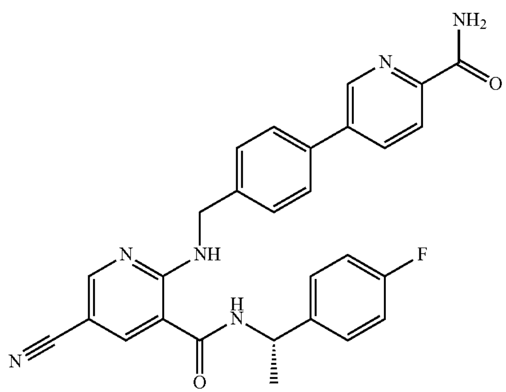 [SMILES: C[C@H](NC(=O)c1cc(C#N)cnc1NCc1ccc(-c2ccc(C(N)=O)nc2)cc1)c1ccc(F)cc1] | (S)-5-(4-((5-cyano-3-(1-(4-fluorophenyl)ethylcarbamoyl)pyridin-2-ylamino)methyl)phenyl)picolinamide | 495.2 | 1H NMR (400 MHz, DMSO-d6) δ ppm 9.32 (t, J = 5.90 Hz, 1 H) 8.94 (d, J = 7.53 Hz, 1 H) 8.60 (d, J = 5.02 Hz, 1 H) 8.50 (d, J = 2.01 Hz, 1 H) 8.41 (d, J = 2.01 Hz, 1 H) 8.20 (d, J = 1.25 Hz, 1 H) 8.09 (br. s., 1 H) 7.81 (dd, J = 5.02, 1.76 Hz, 1 H) 7.73 (d, J = 8.28 Hz, 2 H) 7.63 (br. s., 1 H) 7.25-7.43 (m, 4 H) 7.08 (t, J = 8.91 Hz, 2 H) 5.04 (quin, J = 7.03 Hz, 1 H) 4.68 (dd, J = 5.65, 2.64 Hz, 2 H) 1.40 (d, J = 7.03 Hz, 3 H). |

TABLE 1-continued

| Ex. No. | Structure | Chemical Name | ESI-MS (M + H) | ¹H NMR |
|---|---|---|---|---|
| 115 | 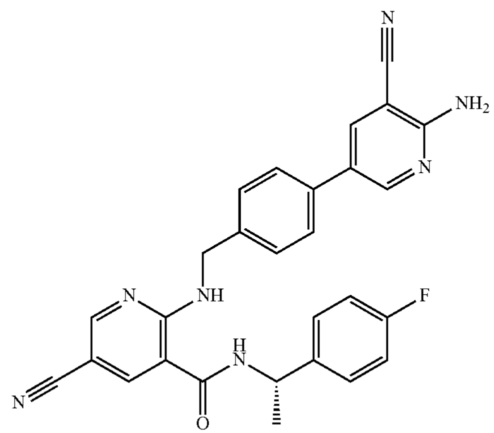 [SMILES: C[C@H](NC(=O)c1cc(C#N)cnc1NCc1ccc(-c2cnc(N)c(C#N)c2)cc1)c1ccc(F)cc1] | (S)-2-(4-(6-amino-5-cyanopyridin-3-yl)benzylamino)-5-cyano-N-(1-(4-fluorophenyl)ethyl)nicotinamide | 492.3 | ¹H NMR (400 MHz, DMSO-d₆) δ ppm 9.32 (t, J = 5.77 Hz, 1 H) 8.99 (d, J = 7.53 Hz, 1 H) 8.41-8.63 (m, 3 H) 8.18 (d, J = 2.51 Hz, 1 H) 7.58 (d, J = 8.28 Hz, 2 H) 7.28-7.47 (m, 4 H) 7.15 (t, J = 8.91 Hz, 2 H) 7.01 (br. s., 1 H) 5.09 (quin, J = 7.09 Hz, 1 H) 4.68 (d, J = 4.27 Hz, 2 H) 1.46 (d, J = 7.03 Hz, 3 H) |
| 116 | 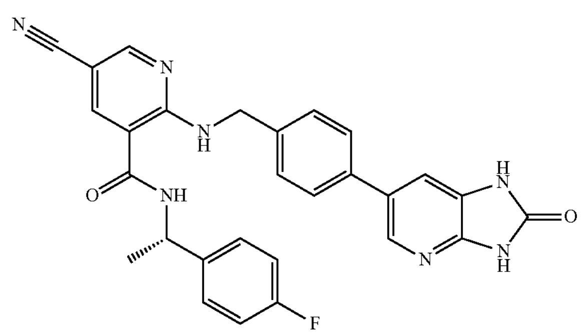 [SMILES: C[C@H](NC(=O)c1cc(C#N)cnc1NCc1ccc(-c2cnc3[nH]c(=O)[nH]c3c2)cc1)c1ccc(F)cc1] | (S)-5-cyano-N-(1-(4-fluorophenyl)ethyl)-2-(4-(2-oxo-2,3-dihydro-1H-imidazo[4,5-b]pyridin-6-yl)benzylamino)nicotinamide | 508.20 | ¹H NMR (400 MHz, DMSO-d₆) δ ppm 11.37 (s, 1 H) 10.92 (s, 1 H) 9.35 (t, J = 5.90 Hz, 1 H) 9.00 (d, J = 7.53 Hz, 1 H) 8.58 (d, J = 2.01 Hz, 1 H) 8.48 (d, J = 2.01 Hz, 1 H) 8.13 (d, J = 2.01 Hz, 1 H) 7.58 (d, J = 8.28 Hz, 2 H) 7.29-7.47 (m, 5 H) 7.15 (t, J = 8.91 Hz, 2 H) 5.10 (quin, J = 7.03 Hz, 1 H) 4.59-4.79 (m, 2 H) 1.46 (d, J = 7.03 Hz, 3 H) |

TABLE 1-continued

| Ex. No. | Structure | Chemical Name | ESI-MS (M + H) | ¹H NMR |
|---|---|---|---|---|
| 117 | 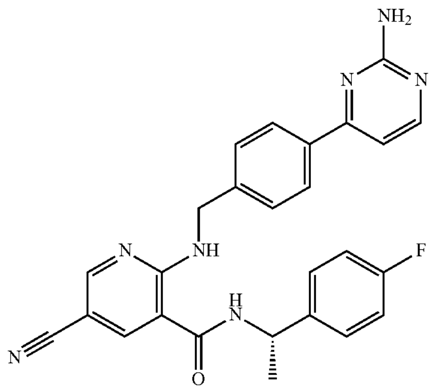 [SMILES: C[C@H](NC(=O)c1cc(C#N)cnc1NCc1ccc(-c2ccnc(N)n2)cc1)c1ccc(F)cc1] | (S)-2-(4-(2-amino-pyrimidin-4-yl)benzylamino)-5-cyano-N-(1-(4-fluorophenyl)ethyl)nicotinamide | 468.2 | ¹H NMR (400 MHz, DMSO-$d_6$) δ ppm 9.38 (t, J = 5.90 Hz, 1 H) 9.01 (d, J = 7.53 Hz, 1 H) 8.55 (d, J = 2.26 Hz, 1 H) 8.49 (d, J = 2.01 Hz, 1 H) 8.36 (d, J = 5.77 Hz, 1 H) 8.06 (d, J = 8.28 Hz, 2 H) 7.36-7.49 (m, 4 H) 7.28 (d, J = 6.02 Hz, 1 H) 7.15 (t, J = 8.91 Hz, 2 H) 5.10 (quin, J = 7.09 Hz, 1 H) 4.75 (d, J = 5.27 Hz, 2 H) 1.46 (d, J = 7.03 Hz, 3 H) |
| 118 | 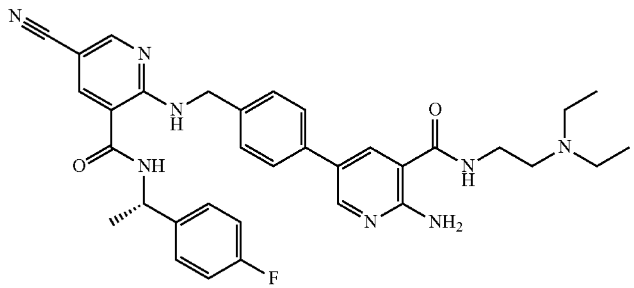 [SMILES: CCN(CC)CCNC(=O)c1cc(-c2ccc(CNc3ncc(C#N)cc3C(=O)N[C@@H](C)c3ccc(F)cc3)cc2)cnc1N] | (S)-2-amino-5-(4-((5-cyano-3-(1-(4-fluorophenyl)ethyl-carbamoyl)pyridin-2-yl)amino)methyl)phenyl)-N-(2-diethylamino)ethyl)nicotinamide | 609.4 | ¹H NMR (400 MHz, DMSO-$d_6$) δ ppm 9.34 (t, J = 5.65 Hz, 2 H) 8.92-9.12 (m, 2 H) 8.57 (d, J = 2.01 Hz, 1 H) 8.48 (dd, J = 5.65, 2.13 Hz, 2 H) 8.38 (d, J = 1.76 Hz, 1 H) 7.64 (d, J = 8.28 Hz, 2 H) 7.30-7.47 (m, 4 H) 7.15 (t, J = 8.91 Hz, 2 H) 5.09 (quin, J = 7.03 Hz, 1 H) 4.70 (d, J = 5.77 Hz, 2 H) 3.62 (q, J = 6.11 Hz, 2 H) 3.07-3.34 (m, 6 H) 1.46 (d, J = 7.03 Hz, 3 H) 1.22 (t, J = 7.28 Hz, 6 H) |
| 119 | 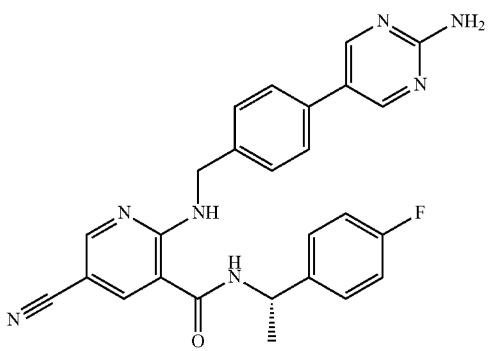 [SMILES: C[C@H](NC(=O)c1cc(C#N)cnc1NCc1ccc(-c2cnc(N)nc2)cc1)c1ccc(F)cc1] | (S)-2-(4-(2-amino-pyrimidin-5-yl)benzylamino)-5-cyano-N-(1-(4-fluorophenyl)ethyl)nicotinamide | 468.2 | ¹H NMR (400 MHz, DMSO-$d_6$) δ ppm 9.33 (t, J = 5.77 Hz, 1 H) 8.99 (d, J = 7.53 Hz, 1 H) 8.54-8.65 (m, 3 H) 8.47 (d, J = 2.01 Hz, 1 H) 7.57 (d, J = 8.03 Hz, 2 H) 7.27-7.47 (m, 4 H) 7.15 (t, J = 8.91 Hz, 2 H) 5.09 (quin, J = 7.09 Hz, 1 H) 4.68 (d, J = 5.27 Hz, 2 H) 1.46 (d, J = 7.03 Hz, 3 H). |

TABLE 1-continued

| Ex. No. | Structure | Chemical Name | ESI-MS (M + H) | ¹H NMR |
|---|---|---|---|---|
| 120 | 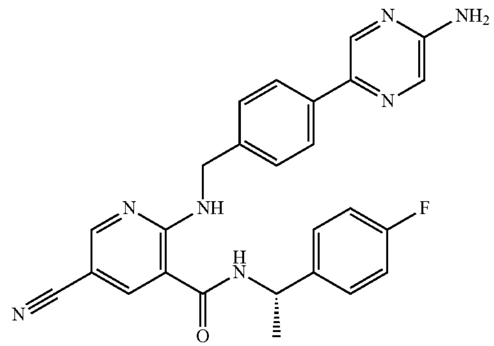 [SMILES: C[C@H](NC(=O)c1cc(C#N)cnc1NCc1ccc(-c2cnc(N)cn2)cc1)c1ccc(F)cc1] | (S)-2-(4-(5-amino-pyrazin-2-yl)benzylamino)-5-cyano-N-(1-(4-fluorophenyl)ethyl)nicotinamide | 468.3 | ¹H NMR (400 MHz, DMSO-$d_6$) δ ppm 9.33 (t, J = 5.90 Hz, 1 H) 8.99 (d, J = 7.28 Hz, 1 H) 8.57 (d, J = 2.01 Hz, 1 H) 8.46 (dd, J = 7.78, 1.76 Hz, 2 H) 7.97 (d, J = 1.51 Hz, 1 H) 7.84 (d, J = 8.28 Hz, 2 H) 7.42 (dd, J = 8.53, 5.52 Hz, 2 H) 7.33 (d, J = 8.28 Hz, 2 H) 7.14 (t, J = 8.78 Hz, 2 H) 5.09 (quin, J = 7.09 Hz, 1 H) 4.57-4.77 (m, 2 H) 1.46 (d, J = 7.03 Hz, 3 H) |
| 121 | 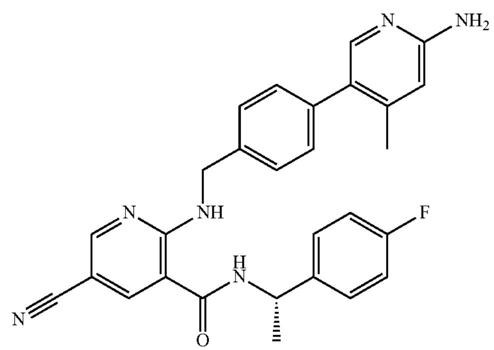 [SMILES: Cc1cc(N)ncc1-c1ccc(CNc2ncc(C#N)cc2C(=O)N[C@@H](C)c2ccc(F)cc2)cc1] | (S)-2-(4-(6-amino-4-methylpyridin-3-yl)benzylamino)-5-cyano-N-(1-(4-fluorophenyl)ethyl)nicotinamide | 481.2 | ¹H NMR (400 MHz, DMSO-$d_6$) δ ppm 9.36 (t, J = 5.90 Hz, 1 H) 9.01 (d, J = 7.53 Hz, 1 H) 8.58 (d, J = 2.01 Hz, 1 H) 8.49 (d, J = 2.01 Hz, 1 H) 7.90 (br. s., 2 H) 7.78 (s, 1 H) 7.35-7.48 (m, 4 H) 7.26-7.35 (m, 2 H) 7.15 (t, J = 8.91 Hz, 2 H) 6.87 (s, 1 H) 5.09 (quin, J = 7.03 Hz, 2 H) 4.73 (d, J = 5.77 Hz, 2 H) 2.23 (s, 3 H) 1.46 |
| 122 | 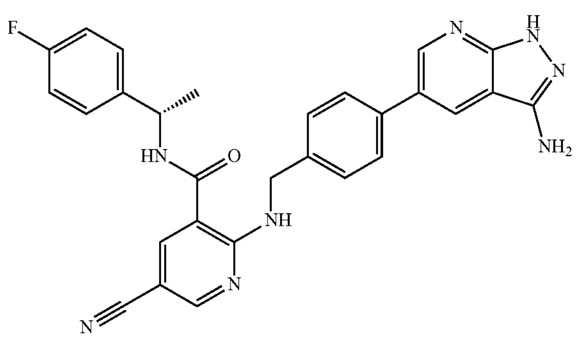 [SMILES: C[C@H](NC(=O)c1cc(C#N)cnc1NCc1ccc(-c2cnc3[nH]nc(N)c3c2)cc1)c1ccc(F)cc1] | (S)-2-(4-(3-amino-1H-pyrazolo[3,4-b]pyridin-5-yl)benzylamino)-5-cyano-N-(1-(4-fluorophenyl)ethyl)nicotinamide | 507.20 | ¹H NMR (400 MHz, DMSO-$d_6$) δ ppm 9.36 (t, J = 5.77 Hz, 1 H) 9.00 (d, J = 7.28 Hz, 1 H) 8.66 (d, J = 2.26 Hz, 1 H) 8.59 (d, J = 2.01 Hz, 1 H) 8.48 (d, J = 2.01 Hz, 1 H) 8.40 (d, J = 2.01 Hz, 1 H) 7.53-7.66 (m, 2 H) 7.31-7.46 (m, 4 H) 7.06-7.20 (m, 2 H) 5.10 (quin, J = 7.03 Hz, 1 H) 4.72 (dd, J = 5.65, 3.14 Hz, 2 H) 1.46 (d, J = 7.03 Hz, 3 H). |

TABLE 1-continued

| Ex. No. | Structure | Chemical Name | ESI-MS (M + H) | ¹H NMR |
|---|---|---|---|---|
| 123 | 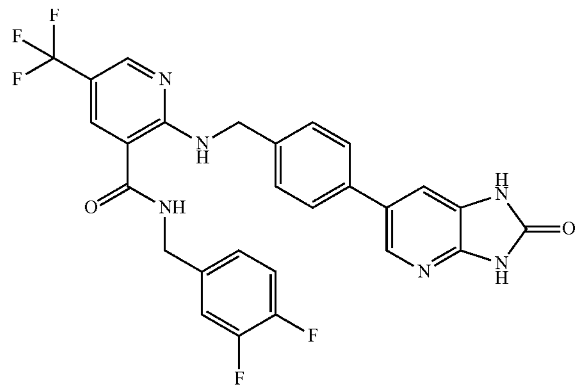 [SMILES: O=C(NCc1ccc(F)c(F)c1)c1cc(C(F)(F)F)cnc1NCc1ccc(-c2cnc3[nH]c(=O)[nH]c3c2)cc1] | N-(3,4-difluorobenzyl)-2-(4-(2-oxo-2,3-dihydro-1H-imidazo[4,5-b]pyridin-6-yl)benzylamino)-5-(trifluoromethyl)nicotinamide | 555.2 | ¹H NMR (400 MHz, DMSO-$d_6$) δ ppm 11.36 (br. s., 1 H) 10.92 (s, 1 H) 9.21-9.43 (m, 2 H) 8.51 (s, 1 H) 8.35 (d, J = 1.76 Hz, 1 H) 8.13 (d, J = 2.01 Hz, 1 H) 7.58 (d, J = 8.03 Hz, 2 H) 7.28-7.46 (m, 5 H) 7.19 (br. s., 1 H) 4.72 (d, J = 5.77 Hz, 2 H) 4.44 (d, J = 5.52 Hz, 2 H). |
| 124 | 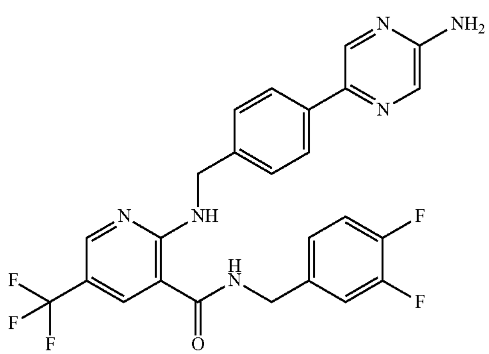 [SMILES: Nc1cnc(-c2ccc(CNc3ncc(C(F)(F)F)cc3C(=O)NCc3ccc(F)c(F)c3)cc2)cn1] | 2-(4-(5-aminopyrazin-2-yl)benzylamino)-N-(3,4-difluorobenzyl)-5-(trifluoromethyl)nicotinamide | 515.2 | ¹H NMR (400 MHz, DMSO-$d_6$) δ ppm 9.34 (t, J = 5.65 Hz, 1 H) 9.27 (t, J = 5.77 Hz, 1 H) 8.42-8.55 (m, 2 H) 8.34 (d, J = 1.76 Hz, 1 H) 7.93 (d, J = 1.25 Hz, 1 H) 7.84 (d, J = 8.28 Hz, 2 H) 7.29-7.45 (m, 4 H) 7.18 (br. s., 1 H) 6.51 (s, 2 H) 4.70 (d, J = 5.77 Hz, 2 H) 4.43 (d, J = 5.52 Hz, 2 H) |

TABLE 1-continued

| Ex. No. | Structure | Chemical Name | ESI-MS (M + H) | ¹H NMR |
|---|---|---|---|---|
| 125 | 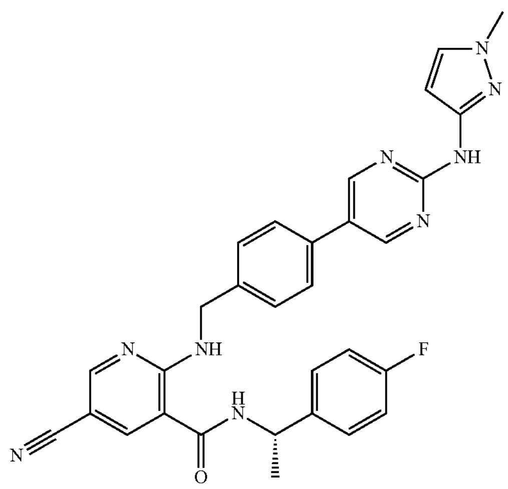 [SMILES: C[C@H](NC(=O)c1cc(C#N)cnc1NCc1ccc(-c2cnc(Nc3ccn(C)n3)nc2)cc1)c1ccc(F)cc1] | (S)-5-cyano-N-(1-(4-fluorophenyl)ethyl)-2-(4-(2-(1-methyl-1H-pyrazol-3-ylamino)pyrimidin-5-yl)benzylamino)nicotinamide | 548.30 | ¹H NMR (400 MHz, DMSO-$d_6$) δ ppm 9.91 (s, 1 H) 9.34 (t, J = 5.90 Hz, 1 H) 9.00 (d, J = 7.28 Hz, 1 H) 8.73 (s, 2 H) 8.57 (d, J = 2.01 Hz, 1 H) 8.47 (d, J = 2.01 Hz, 1 H) 7.49-7.68 (m, 3 H) 7.29-7.46 (m, 4 H) 7.15 (t, J = 8.78 Hz, 2 H) 6.58 (d, J = 2.26 Hz, 1 H) 5.10 (quin, J = 7.03 Hz, 1 H) 4.70 (d, J = 3.76 Hz, 2 H) 1.46 (d, J = 7.03 Hz, 3 H); ¹⁹F-NMR (CFCl$_3$ as zero ref, TFA @ −78.50) ppm: −119.85 (s, 1F). |
| 126 | 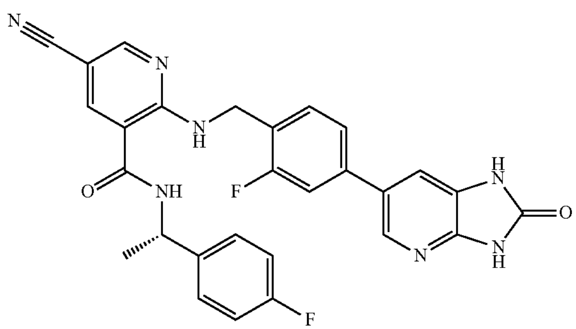 [SMILES: C[C@H](NC(=O)c1cc(C#N)cnc1NCc1ccc(-c2cnc3[nH]c(=O)[nH]c3c2)cc1F)c1ccc(F)cc1] | (S)-5-cyano-2-(2-fluoro-4-(2-oxo-2,3-dihydro-1H-imidazo[4,5-b]pyridin-6-yl)benzylamino)-N-(1-(4-fluorophenyl)ethyl)nicotinamide | 526.2 | ¹H NMR (400 MHz, DMSO-$d_6$) δ ppm 11.42 (s, 1 H) 10.98 (d, J = 1.26 Hz, 1 H) 9.33 (t, J = 6.02 Hz, 1 H) 9.01 (d, J = 7.53 Hz, 1 H) 8.58 (d, J = 2.26 Hz, 1 H) 8.50 (d, J = 2.01 Hz, 1 H) 8.18 (d, J = 2.01 Hz, 1 H) 7.52 (dd, J = 11.80, 1.76 Hz, 1 H) 7.37-7.46 (m, 4 H) 7.29-7.37 (m, 1 H) 7.08-7.19 (m, 2 H) 5.10 (t, J = 7.15 Hz, 1 H) 4.74 (dd, J = 5.77, 2.51 Hz, 2 H) 1.46 (d, J = 7.03 Hz, 3 H); ¹⁹F-NMR (CFCl$_3$ as zero ref, TFA @ −78.50) ppm: −120.61 (s, 1F); −122.75 (s, 1F). |

| Ex. No. | Structure | Chemical Name | ESI-MS (M + H) | ¹H NMR |
|---|---|---|---|---|
| 127 | 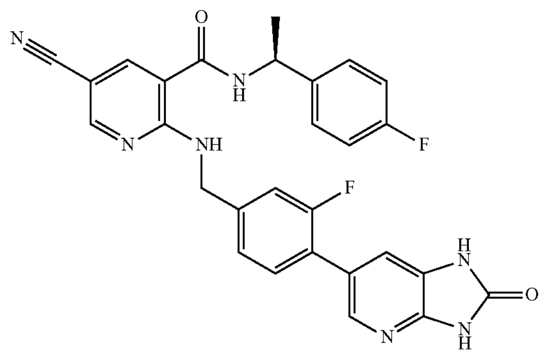 | (S)-5-cyano-2-(3-fluoro-4-(2-oxo-2,3-dihydro-1H-imidazo[4,5-b]pyridin-6-yl)benzyl-amino)-N-(1-(4-fluorophenyl)ethyl)nicotinamide | 526.2 | ¹H NMR (400 MHz, DMSO-d₆) δ ppm 11.43 (s, 1 H) 10.92 (s, 1 H) 9.36 (t, J = 6.02 Hz, 1 H) 9.01 (d, J = 7.28 Hz, 1 H) 8.58 (d, J = 2.01 Hz, 1 H) 8.48 (d, J = 2.01 Hz, 1 H) 8.00 (s, 1 H) 7.37-7.53 (m, 3 H) 7.32 (s, 1 H) 7.09-7.26 (m, 4 H) 5.11 (t, J = 7.15 Hz, 1 H) 4.72 (d, J = 4.52 Hz, 2 H) 1.47 (d, J = 7.03 Hz, 3 H); ¹⁹F-NMR (CFCl₃ as zero ref, TFA @ −78.50) ppm: −120.40 (s, 1F); −122.79 (s, 1F). |
| 128 | 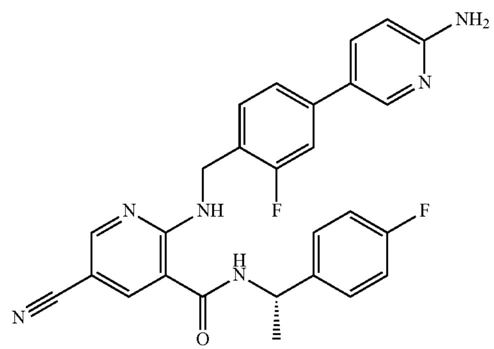 [SMILES: C[C@H](NC(=O)c1cc(C#N)cnc1NCc1ccc(-c2ccc(N)nc2)cc1F)c1ccc(F)cc1] | (S)-2-(4-(4-aminopyridin-3-yl)-2-fluorobenzylamino)-5-cyano-N-(1-(4-fluorophenyl)ethyl)nicotinamide | 484.9 | ¹H NMR (400 MHz, DMSO-d₆) δ ppm 9.33 (t, J = 5.77 Hz, 1 H) 9.02 (d, J = 7.53 Hz, 1 H) 8.42-8.63 (m, 2 H) 8.23-8.36 (m, 2 H) 8.10 (br. s., 2 H) 7.56 (dd, J = 11.55, 1.26 Hz, 1 H) 7.29-7.47 (m, 4 H) 7.15 (t, J = 8.91 Hz, 2 H) 7.04 (d, J = 9.29 Hz, 2 H) 5.00-5.18 (m, 1 H) 4.74 (d, J = 5.77 Hz, 2 H) 1.46 (d, J = 7.03 Hz, 3 H). ¹⁹F-NMR (CFCl₃ as zero ref, TFA @ −78.50) ppm: −120.57 (s, 1F); −122.34 (s, 1F). |
| 129 | 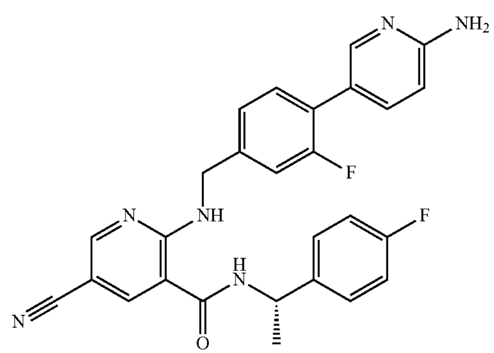 [SMILES: C[C@H](NC(=O)c1cc(C#N)cnc1NCc1ccc(-c2ccc(N)nc2)c(F)c1)c1ccc(F)cc1] | (S)-2-(4-(6-aminopyridin-3-yl)-3-fluorobenzylamino)-5-cyano-N-(1-(4-fluorophenyl)ethyl)nicotinamide | 484.9 | ¹H NMR (400 MHz, DMSO-d₆) δ ppm 9.36 (t, J = 6.02 Hz, 1 H) 9.02 (d, J = 7.28 Hz, 1 H) 8.56 (d, J = 2.26 Hz, 1 H) 8.48 (d, J = 2.01 Hz, 1 H) 7.93-8.19 (m, 4 H) 7.34-7.55 (m, 3 H) 7.09-7.31 (m, 4 H) 7.04 (d, J = 9.29 Hz, 1 H) 4.99-5.17 (m, 1 H) 4.71 (d, J = 6.02 Hz, 2 H) 1.47 (d, J = 7.03 Hz, 3 H); ¹⁹F-NMR (CFCl₃ as zero ref, TFA @ −78.50) ppm: −120.68 (s, 1F); −122.61 (s, 1F). |

TABLE 1-continued

| Ex. No. | Structure | Chemical Name | ESI-MS (M + H) | ¹H NMR |
|---|---|---|---|---|
| 130 | 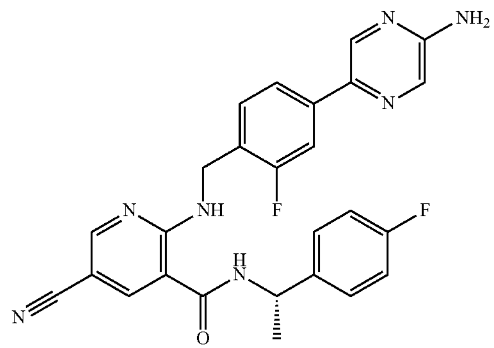 [SMILES: C[C@H](NC(=O)c1cc(C#N)cnc1NCc1ccc(-c2cnc(N)cn2)cc1F)c1ccc(F)cc1] | (S)-2-(4-(5-aminopyrazin-2-yl)-2-fluorobenzylamino)-5-cyano-N-(1-(4-fluorophenyl)ethyl) nicotinamide | 485.9 | ¹H NMR (400 MHz, DMSO-d$_6$) δ ppm 9.32 (t, J = 5.90 Hz, 1 H) 9.00 (d, J = 7.28 Hz, 1 H) 8.40-8.63 (m, 3 H) 7.97 (d, J = 1.25 Hz, 1 H) 7.59-7.77 (m, 2 H) 7.42 (dd, J = 8.66, 5.65 Hz, 2 H) 7.31 (t, J = 8.16 Hz, 1 H) 7.15 (t, J = 8.91 Hz, 2 H) 5.10 (quin, J = 7.03 Hz, 1 H) 4.54-4.83 (m, 2 H) 1.46 (d, J = 7.03 Hz, 3 H); ¹⁹F-NMR (CFCl$_3$ as zero ref, TFA @ −78.50) ppm: −119.84 (s, 1F), −122.21 (s, 1F). |
| 131 | 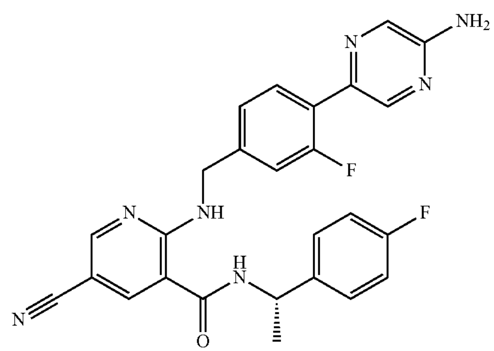 [SMILES: C[C@H](NC(=O)c1cc(C#N)cnc1NCc1ccc(-c2cnc(N)cn2)c(F)c1)c1ccc(F)cc1] | (S)-2-(4-(5-aminopyrazin-2-yl)-3-fluorobenzylamino)-5-cyano-N-(1-(4-fluorophenyl)ethyl) nicotinamide | 486.00 | ¹H NMR (400 MHz, DMSO-d$_6$) δ ppm 9.34 (t, J = 6.02 Hz, 1 H) 9.00 (d, J = 7.28 Hz, 1 H) 8.57 (d, J = 2.01 Hz, 1 H) 8.47 (d, J = 2.01 Hz, 1 H) 8.28 (d, J = 1.76 Hz, 1 H) 8.01 (d, J = 1.26 Hz, 1 H) 7.77 (t, J = 8.28 Hz, 1 H) 7.42 (dd, J = 8.53, 5.77 Hz, 2 H) 7.05-7.26 (m, 4 H) 5.11 (t, J = 7.15 Hz, 1 H) 4.59-4.80 (m, 2 H) 1.46 (d, J = 7.03 Hz, 3 H); ¹⁹F-NMR (CFCl$_3$ as zero ref, TFA @ −78.50) ppm: −120.57 (s, 1F), −122.34 (s, 1F). |

TABLE 1-continued

| Ex. No. | Structure | Chemical Name | ESI-MS (M + H) | ¹H NMR |
|---|---|---|---|---|
| 132 | 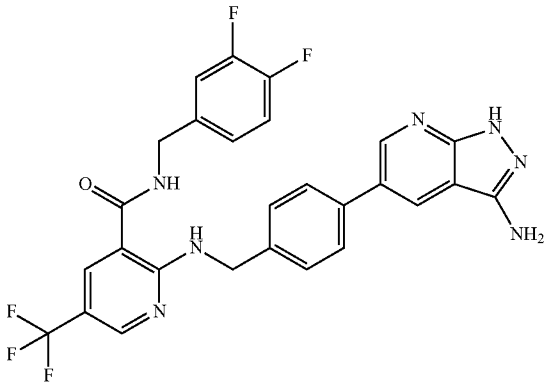 [SMILES: Nc1n[nH]c2ncc(-c3ccc(CNc4ncc(C(F)(F)F)cc4C(=O)NCc4ccc(F)c(F)c4)cc3)cc12] | 2-(4-(3-amino-1H-pyrazolo[3,4-b]pyridin-5-yl)benzylamino)-N-(3,4-difluorobenzyl)-5-(trifluoromethyl)nicotinamide | 53.9 | ¹H NMR (400 MHz, DMSO-d₆) δ ppm 9.19-9.47 (m, 2 H) 8.71 (d, J = 2.01 Hz, 1 H) 8.28-8.58 (m, 3 H) 7.64 (d, J = 8.03 Hz, 2 H) 7.31-7.51 (m, 4 H) 7.12-7.24 (m, 1 H) 4.75 (d, J = 5.77 Hz, 2 H) 4.45 (d, J = 5.77 Hz, 2 H); ¹⁹F NMR (376 MHz, DMSO-d₆, CFCl₃ as zero ref, TFA @ −78.50) δ ppm −62.75 (s, 3 F) −78.50 (s, 3 F) −142.85−−142.50 (m, 1 F) −145.31−−144.94 (m, 1 F). |
| 133 | 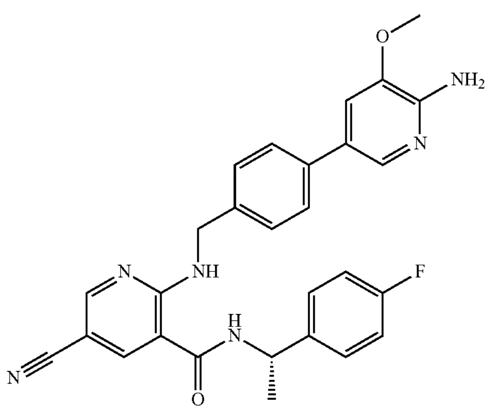 [SMILES: COc1cc(-c2ccc(CNc3ncc(C#N)cc3C(=O)N[C@@H](C)c3ccc(F)cc3)cc2)cnc1N] | (S)-2-(4-(6-amino-5-methoxypyridin-3-yl)benzylamino)-5-cyano-N-(1-(4-fluorophenyl)ethyl)nicotinamide | 496.9 | ¹H NMR (400 MHz, DMSO-d₆) δ ppm 9.34 (t, J = 5.90 Hz, 1 H) 9.01 (d, J = 7.53 Hz, 1 H) 8.57 (d, J = 2.01 Hz, 1 H) 8.48 (d, J = 2.01 Hz, 1 H) 7.73-8.12 (m, 3 H) 7.57-7.70 (m, 3 H) 7.30-7.49 (m, 4 H) 7.15 (t, J = 8.91 Hz, 2 H) 5.09 (quin, J = 7.03 Hz, 1 H) 4.70 (d, J = 5.77 Hz, 2 H) 4.01 (s, 3 H) 1.46 (d, J = 7.03 Hz, 3 H); ¹⁹F NMR (376 MHz, DMSO-d₆) (CFCl₃ as zero ref, TFA @ −78.50) δ ppm −78.50 (s, 3 F) −120.88 (s, 1 F). |

TABLE 1-continued

| Ex. No. | Structure | Chemical Name | ESI-MS (M + H) | ¹H NMR |
|---|---|---|---|---|
| 134 | 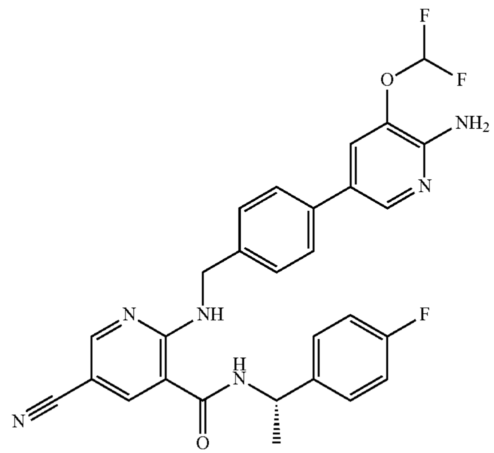 [SMILES: C[C@H](NC(=O)c1cc(C#N)cnc1NCc1ccc(-c2cnc(N)c(OC(F)F)c2)cc1)c1ccc(F)cc1] | (S)-2-(4-(6-amino-5-(difluoromethoxy)pyridin-3-yl)benzylamino)-5-cyano-N-(1-(4-fluorophenyl)ethyl)nicotinamide | 532.90 | ¹H NMR (400 MHz, DMSO-d₆) δ ppm 9.33 (t, J = 5.90 Hz, 1 H) 9.00 (d, J = 7.53 Hz, 1 H) 8.57 (d, J = 2.01 Hz, 1 H) 8.48 (d, J = 2.26 Hz, 1 H) 8.13 (d, J = 1.76 Hz, 1 H) 7.77 (s, 1 H) 7.57 (d, J = 8.28 Hz, 2 H) 7.22-7.49 (m, 5 H) 7.05-7.20 (m, 2 H) 4.99-5.19 (m, 1 H) 4.69 (d, J = 5.77 Hz, 2 H) 1.46 (d, J = 7.03 Hz, 3 H); ¹⁹F NMR (376 MHz, DMSO-d₆) δ ppm −78.50 (s, 3 F) −86.30 (br. s., 3 F) −120.41−120.30 (m, 1 F) (CFCl₃ as zero ref, TFA @ −78.50). |
| 135 | 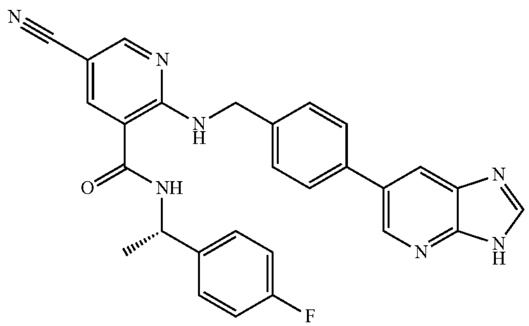 [SMILES: C[C@H](NC(=O)c1cc(C#N)cnc1NCc1ccc(-c2cnc3[nH]cnc3c2)cc1)c1ccc(F)cc1] | (S)-2-(4-(3H-imidazo[4,5-b]pyridin-6-yl)benzylamino)-5-cyano-N-(1-(4-fluorophenyl)ethyl)nicotinamide | 491.9 | ¹H NMR (400 MHz, DMSO-d₆) δ ppm 9.37 (t, J = 5.90 Hz, 1 H) 9.01 (d, J = 7.53 Hz, 1 H) 8.68-8.84 (m, 2 H) 8.59 (d, J = 2.01 Hz, 1 H) 8.49 (d, J = 2.01 Hz, 1 H) 8.30 (s, 1 H) 7.71 (d, J = 8.28 Hz, 2 H) 7.42 (dt, J = 8.47, 2.67 Hz, 4 H) 7.15 (t, J = 8.91 Hz, 2 H) 5.10 (dt, J = 14.06, 7.03 Hz, 1 H) 4.63-4.83 (m, 2H) 1.46 (d, J = 7.03 Hz, 3 H); ¹⁹F NMR (376 MHz, DMSO-d₆) δ ppm −78.50 (s, 109 F, 1TFA) −120.37 (s, 1 F). |
| 136 | 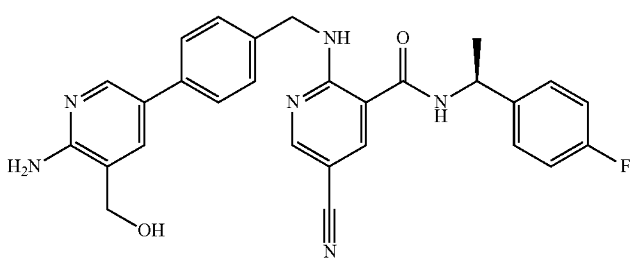 [SMILES: C[C@H](NC(=O)c1cc(C#N)cnc1NCc1ccc(-c2cnc(N)c(CO)c2)cc1)c1ccc(F)cc1] | (S)-2-(4-(6-amino-5-(hydroxymethyl)pyridin-3-yl)benzylamino)-5-cyano-N-(1-(4-fluorophenyl)ethyl)nicotinamide | 497 | ¹H NMR (400 MHz, DMSO-d₆) δ ppm 9.32 (t, J = 5.90 Hz, 1 H) 8.99 (d, J = 7.53 Hz, 1 H) 8.58 (d, J = 2.01 Hz, 1 H) 8.47 (d, J = 2.01 Hz, 1 H) 8.16 (d, J = 2.26 Hz, 1 H) 7.73 (s, 1 H) 7.51 (d, J = 8.28 Hz, 2 H) 7.42 (dd, J = 8.53, 5.77 Hz, 2 H) 7.33 (d, J = 8.03 Hz, 2 H) 7.15 (t, J = 8.91 Hz, 2 H) 5.99 (br. s., 2 H) 5.25 (t, J = 5.27 Hz, 1 H) 5.09 (quin, J = 7.03 Hz, 1 H) 4.68 (dd, J = 5.27, 3.26 Hz, 2 H) 4.41 (d, J = 5.02 Hz, 2 H) 1.46 (d, J = 7.03 Hz, 3 H); ¹⁹F NMR (376 MHz, DMSO-d₆) δ ppm −78.50 (s, 0.36F, TFA) −121.32 (s, 1 F). |

| Ex. No. | Structure | Chemical Name | ESI-MS (M + H) | ¹H NMR |
|---|---|---|---|---|
| 137 | 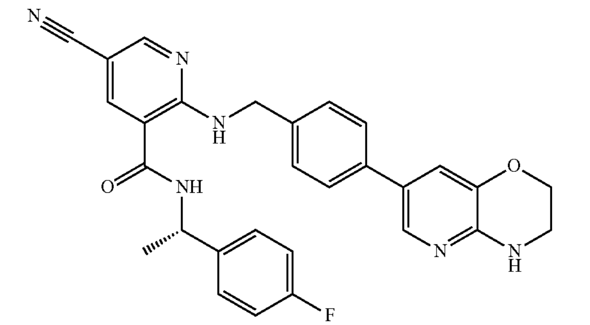 [SMILES: C[C@H](NC(=O)c1cc(C#N)cnc1NCc1ccc(-c2cnc3c(c2)OCCN3)cc1)c1ccc(F)cc1] | (S)-5-cyano-2-(4-(3,4-dihydro-2H-pyrido[3,2-b][1,4]oxazin-7-yl)benzylamino)-N-(1-(4-fluorophenyl)ethyl)nicotinamide | 508.9 | ¹H NMR (400 MHz, DMSO-d₆) δ ppm 9.33 (t, J = 5.77 Hz, 1 H) 9.00 (d, J = 7.28 Hz, 1 H) 8.57 (d, J = 2.01 Hz, 1 H) 8.48 (d, J = 2.26 Hz, 1 H) 7.91 (d, J = 2.01 Hz, 1 H) 7.48-7.65 (m, 3 H) 7.28-7.47 (m, 4 H) 7.15 (t, J = 8.91 Hz, 2 H) 5.09 (quin, J = 7.09 Hz, 1 H) 4.69 (d, J = 5.77 Hz, 2 H) 4.24 (t, J = 4.39 Hz, 2 H) 3.48-3.58 (m, 2 H) 1.46 (d, J = 7.03 Hz, 3 H); ¹⁹F NMR (376 MHz, DMSO-d₆) δ ppm −78.50 (s, 3 F, TFA) −120.69 (s, 1 F). |
| 138 | 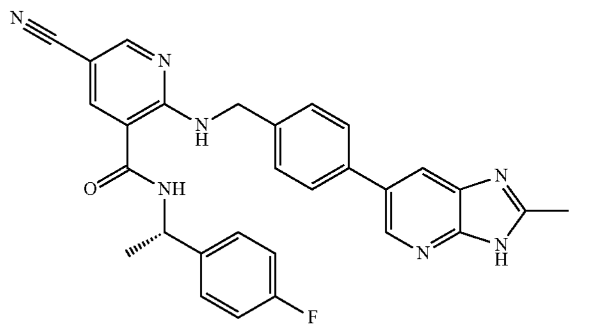 [SMILES: Cc1nc2cc(-c3ccc(CNc4ncc(C#N)cc4C(=O)N[C@@H](C)c4ccc(F)cc4)cc3)cnc2[nH]1] | (S)-5-cyano-N-(1-(4-fluorophenyl)ethyl)-2-(4-(2-methyl-3H-imidazo[4,5-b]pyridin-6-yl)benzylamino)nicotinamide | 505.9 | ¹H NMR (400 MHz, DMSO-d₆) δ ppm 12.31-13.03 (m, 1 H) 9.36 (t, J = 5.77 Hz, 1 H) 9.01 (d, J = 7.28 Hz, 1 H) 8.34-8.66 (m, 3 H) 7.87-8.18 (m, 1 H) 7.66 (d, J = 8.03 Hz, 2 H) 7.30-7.52 (m, 4 H) 7.15 (t, J = 8.91 Hz, 2 H) 5.10 (quin, J = 7.09 Hz, 1 H) 4.59-4.82 (m, 2 H) 2.53 (d, J = 7.53 Hz, 3 H) 1.46 (d, J = 7.03 Hz, 3 H); ¹⁹F NMR (376 MHz, DMSO-d₆) δ ppm −78.50 (s, 0.03 F, trace amount TFA) −121.3 (s, 1 F). |
| 139 | 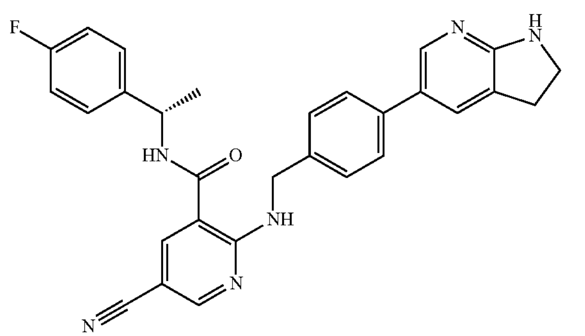 [SMILES: C[C@H](NC(=O)c1cc(C#N)cnc1NCc1ccc(-c2cnc3c(c2)CCN3)cc1)c1ccc(F)cc1] | (S)-5-cyano-2-(4-(3,4-dihydro-1H-pyrrolo[2,3-b]pyridin-5-yl)benzylamino)-N-(1-(4-fluorophenyl)ethyl)nicotinamide | 493 | ¹H NMR (400 MHz, DMSO-d₆) δ ppm 9.34 (t, J = 5.90 Hz, 1 H) 9.01 (d, J = 7.28 Hz, 1 H) 8.72 (br. s., 1 H) 8.57 (d, J = 2.01 Hz, 1 H) 8.48 (d, J = 2.26 Hz, 1 H) 7.96 (d, J = 1.51 Hz, 1 H) 7.88 (s, 1 H) 7.56 (d, J = 8.28 Hz, 2 H) 7.29-7.48 (m, 4 H) 7.15 (t, J = 8.91 Hz, 2 H) 5.09 (quin, J = 7.09 Hz, 1 H) 4.70 (d, J = 6.02 Hz, 2 H) 3.82 (t, J = 8.28 Hz, 2 H) 3.19 (t, J = 8.16 Hz, 2 H) 1.46 (d, J = 7.03 Hz, 3 H); ¹⁹F NMR (376 MHz, DMSO-d₆) δ ppm −78.50 (s, 3 F) −120.75 (s, 1 F). |

TABLE 1-continued

| Ex. No. | Structure | Chemical Name | ESI-MS (M + H) | ¹H NMR |
|---|---|---|---|---|
| 140 | 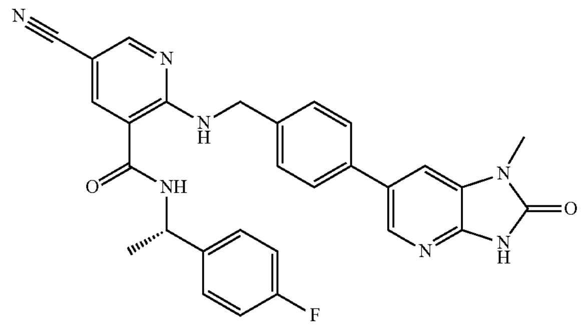 [SMILES: C[C@H](NC(=O)c1cc(C#N)cnc1NCc1ccc(-c2cnc3[nH]c(=O)n(C)c3c2)cc1)c1ccc(F)cc1] | (S)-5-cyano-N-(1-(4-fluorophenyl)ethyl)-2-(4-(1-methyl-2-oxo-2,3-dihydro-1H-imidazo[4,5-b]pyridin-6-yl)benzylamino)nicotinamide | 522.9 | ¹H NMR (400 MHz, DMSO-$d_6$) δ ppm 11.58 (s, 1 H) 9.35 (t, J = 5.90 Hz, 1 H) 9.00 (d, J = 7.53 Hz, 1 H) 8.58 (d, J = 2.26 Hz, 1 H) 8.48 (d, J = 2.26 Hz, 1 H) 8.19 (d, J = 2.01 Hz, 1 H) 7.71 (d, J = 1.76 Hz, 1 H) 7.64 (d, J = 8.03 Hz, 2 H) 7.34-7.47 (m, 4 H) 7.11-7.19 (m, 2 H) 5.09 (t, J = 7.15 Hz, 1 H) 4.71 (d, J = 5.27 Hz, 2 H) 3.34 (s, 3 H) 1.46 (d, J = 7.03 Hz, 3 H); ¹⁹F NMR (376 MHz, DMSO-$d_6$) δ ppm −78.50 (s, 3 F) −120.31 (s, 1 F). |
| 141 | 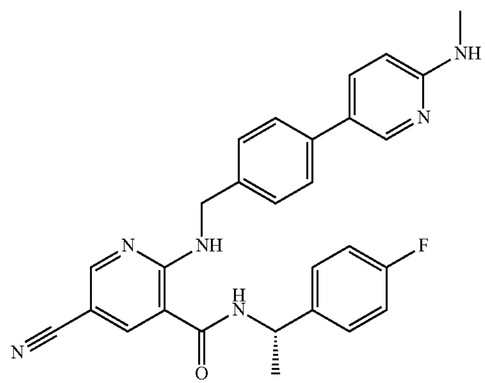 [SMILES: CNc1ccc(-c2ccc(CNc3ncc(C#N)cc3C(=O)N[C@@H](C)c3ccc(F)cc3)cc2)cn1] | (S)-5-cyano-N-(1-(4-fluorophenyl)ethyl)-2-(4-(6-methylamino)pyridin-3-yl)benzylamino)nicotinamide | 481 | ¹H NMR (400 MHz, DMSO-$d_6$) δ ppm 9.34 (t, J = 5.90 Hz, 1 H) 9.00 (d, J = 7.28 Hz, 1 H) 8.57 (d, J = 2.01 Hz, 1 H) 8.48 (d, J = 2.26 Hz, 1 H) 8.09-8.21 (m, 2 H) 7.59 (d, J = 8.28 Hz, 2 H) 7.33-7.48 (m, 4 H) 7.15 (t, J = 8.91 Hz, 2 H) 7.02 (d, J = 9.54 Hz, 1 H) 5.09 (quin, J = 7.09 Hz, 1 H) 4.70 (d, J = 5.77 Hz, 2 H) 2.95 (s, 3 H) 1.46 (d, J = 7.03 Hz, 3 H); ¹⁹F NMR (376 MHz, DMSO-$d_6$) δ ppm −78.50 (s, 3 F) −120.84 (s, 1 F). |
| 142 | 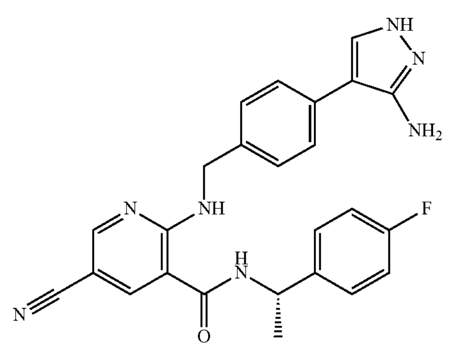 [SMILES: C[C@H](NC(=O)c1cc(C#N)cnc1NCc1ccc(-c2c[nH]nc2N)cc1)c1ccc(F)cc1] | (S)-2-(4-(3-amino-1H-pyrazol-4-yl)benzylamino)-5-cyano-N-(1-(4-fluorophenyl)ethyl)nicotinamide | 455.9 | ¹H NMR (400 MHz, DMSO-$d_6$) δ ppm 11.65 (br. s., 1 H) 9.28 (t, J = 5.65 Hz, 1 H) 8.98 (d, J = 7.53 Hz, 1 H) 8.58 (d, J = 2.01 Hz, 1 H) 8.47 (d, J = 2.01 Hz, 1 H) 7.61 (br. s., 1 H) 7.33-7.48 (m, 4 H) 7.25 (d, J = 8.28 Hz, 2 H) 7.14 (t, J = 8.91 Hz, 2 H) 5.08 (quin, J = 7.09 Hz, 1 H) 4.36-4.92 (m, 4 H) 1.45 (d, J = 7.03 Hz, 3 H); ¹⁹F NMR (376 MHz, DMSO-$d_6$) δ ppm −121.32 (s, 1 F). |

| Ex. No. | Structure | Chemical Name | ESI-MS (M + H) | ¹H NMR |
|---|---|---|---|---|
| 143 | 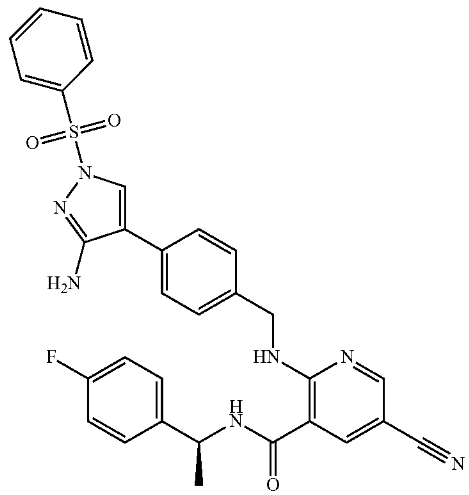 [SMILES: C[C@H](NC(=O)c1cc(C#N)cnc1NCc1ccc(-c2cn(S(=O)(=O)c3ccccc3)nc2N)cc1)c1ccc(F)cc1] | (S)-2-(4-(3-amino-1-(phenylsulfonyl)-1H-pyrazol-4-yl)benzylamino)-5-cyano-N-(1-(4-fluorophenyl)ethyl)nicotinamide | 595.9 | ¹H NMR (400 MHz, DMSO-d₆) δ ppm 9.31 (t, J = 5.77 Hz, 1 H) 8.99 (d, J = 7.28 Hz, 1 H) 8.53-8.60 (m, 1 H) 8.41-8.51 (m, 1 H) 8.33 (s, 1 H) 7.84-7.92 (m, 2 H) 7.70-7.79 (m, 1 H) 7.58-7.67 (m, 2 H) 7.37-7.49 (m, 4 H) 7.26-7.34 (m, 2 H) 7.10-7.19 (m, 2 H) 5.08 (quin, J = 7.09 Hz, 1 H) 4.58-4.75 (m, 2 H) 1.38-1.50 (m, 3 H); ¹⁹F NMR (376 MHz, DMSO-d₆) δ ppm −78.50 (s, 3 F, TFA) −119.94-−119.85 (m, 1 F). |
| 144 | 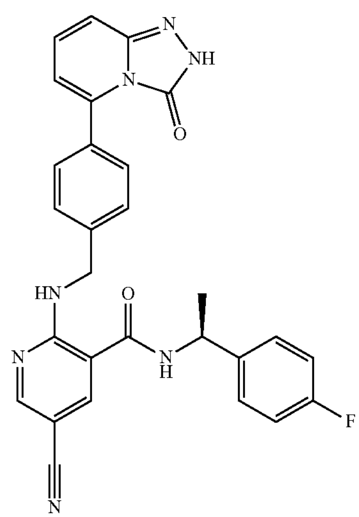 [SMILES: C[C@H](NC(=O)c1cc(C#N)cnc1NCc1ccc(-c2cccc3n[nH]c(=O)n23)cc1)c1ccc(F)cc1] | (S)-5-cyano-N-(1-(4-fluorophenyl)ethyl)-2-(4-(3-oxo-2,3-dihydro-[1,2,4]triazolo[4,3-a]pyridin-5-yl)benzylamino)nicotinamide | 507.9 | ¹H NMR (400 MHz, DMSO-d₆) δ ppm 12.52 (br. s., 1 H) 9.25-9.44 (m, 1 H) 9.00 (d, J = 7.53 Hz, 1 H) 8.57 (d, J = 2.01 Hz, 1 H) 8.48 (d, J = 2.01 Hz, 1 H) 7.99 (s, 1 H) 7.64 (d, J = 8.28 Hz, 2 H) 7.56 (dd, J = 9.79, 1.76 Hz, 1 H) 7.26-7.47 (m, 5 H) 7.15 (t, J = 8.78 Hz, 2 H) 5.10 (t, J = 7.15 Hz, 1 H) 4.56-4.80 (m, 2 H) 1.46 (d, J = 7.03 Hz, 3 H); ¹⁹F NMR (376 MHz, DMSO-d₆) δ ppm −78.50 (s, 0.28 F, TFA) −120.98 (s, 1 F). |

| Ex. No. | Structure | Chemical Name | ESI-MS (M + H) | 1H NMR |
|---|---|---|---|---|
| 145 | 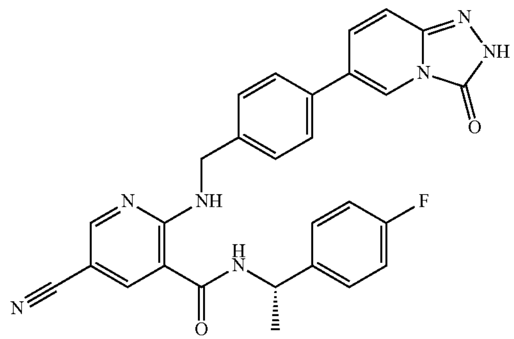 [SMILES: C[C@H](NC(=O)c1cc(C#N)cnc1NCc1ccc(-c2ccc3n[nH]c(=O)n3c2)cc1)c1ccc(F)cc1] | (S)-5-cyano-N-(1-(4-fluorophenyl)ethyl)-2-(4-(3-oxo-2,3-dihydro-[1,2,4]triazolo[4,3-a]pyridin-6-yl)benzyl)aminonicotinamide | 507.9 | 1H NMR (400 MHz, DMSO-$d_6$) δ ppm 12.52 (br. s., 1 H) 9.35 (t, J = 5.90 Hz, 1 H) 9.00 (d, J = 7.53 Hz, 1 H) 8.57 (d, J = 2.01 Hz, 1 H) 8.48 (d, J = 2.01 Hz, 1 H) 7.99 (s, 1 H) 7.49-7.72 (m, 3 H) 7.25-7.47 (m, 5 H) 7.15 (t, J = 8.91 Hz, 2 H) 5.10 (t, J = 7.03 Hz, 1 H) 4.59-4.79 (m, 2 H) 1.46 (d, J = 7.28 Hz, 3 H); 19F NMR (376 MHz, DMSO-$d_6$) δ ppm −78.50 (TFA, s, 0.5F) −120.97 (s, 1 F). |
| 146 | 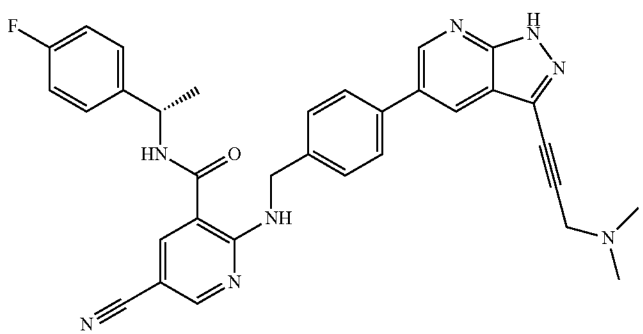 [SMILES: C[C@H](NC(=O)c1cc(C#N)cnc1NCc1ccc(-c2cnc3[nH]nc(C#CCN(C)C)c3c2)cc1)c1ccc(F)cc1] | (S)-5-cyano-2-(4-(3-(3-(dimethylamino)prop-1-ynyl)-1H-pyrazolo[3,4-b]pyridin-5-yl)benzyl)amino)-N-(1-(4-fluorophenyl)ethyl)nicotinamide | 572.9 | 1H NMR (400 MHz, DMSO-$d_6$) δ ppm 14.20-14.56 (m, 1H) 9.37 (t, J = 5.90 Hz, 1 H) 9.01 (d, J = 7.28 Hz, 1 H) 8.92 (d, J = 2.26 Hz, 1 H) 8.59 (d, J = 2.01 Hz, 1 H) 8.49 (d, J = 2.26 Hz, 1 H) 8.40 (d, J = 2.01 Hz, 1 H) 7.72 (d, J = 8.28 Hz, 2 H) 7.34-7.50 (m, 4 H) 7.15 (t, J = 8.91 Hz, 2 H) 5.10 (s, 1 H) 4.74 (d, J = 5.77 Hz, 2 H) 4.40-4.50 (m, 2 H) 2.94 (s, 6 H) 1.47 (d, J = 7.03 Hz, 3 H); 19F NMR (376 MHz, DMSO-$d_6$) δ ppm −73.62 (TFA, s, 5 F) −116.24 (s, 1 F). |
| 147 | 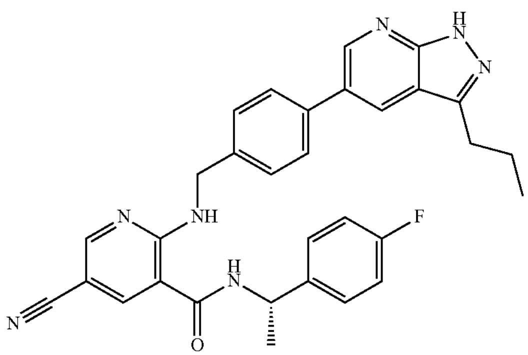 [SMILES: CCCc1n[nH]c2ncc(-c3ccc(CNc4ncc(C#N)cc4C(=O)N[C@@H](C)c4ccc(F)cc4)cc3)cc12] | (S)-5-cyano-N-(1-(4-fluorophenyl)ethyl)-2-(4-(3-propyl-1H-pyrazolo[3,4-b]pyridin-5-yl)benzyl)aminonicotinamide | 534 | 1H NMR (400 MHz, DMSO-$d_6$) δ ppm 13.25 (s, 1 H) 9.36 (t, J = 5.77 Hz, 1 H) 9.00 (d, J = 7.53 Hz, 1 H) 8.76 (d, J = 2.01 Hz, 1 H) 8.59 (d, J = 2.01 Hz, 1 H) 8.48 (d, J = 2.01 Hz, 1 H) 8.43 (d, J = 2.01 Hz, 1 H) 7.70 (d, J = 8.28 Hz, 2 H) 7.33-7.48 (m, 4 H) 7.15 (t, J = 8.91 Hz, 2 H) 5.10 (t, J = 7.03 Hz, 1 H) 4.72 (d, J = 5.27 Hz, 2 H) 2.92 (t, J = 7.40 Hz, 2 H) 1.70-1.85 (m, 2 H) 1.46 (d, J = 7.03 Hz, 3 H) 0.95 (t, J = 7.40 Hz, 3 H); 19F NMR (376 MHz, DMSO-$d_6$) δ ppm −78.50 (TFA, s, 0.17 F) −121.34 (m, 1 F). |

TABLE 1-continued

| Ex. No. | Structure | Chemical Name | ESI-MS (M + H) | ¹H NMR |
|---|---|---|---|---|
| 148 | 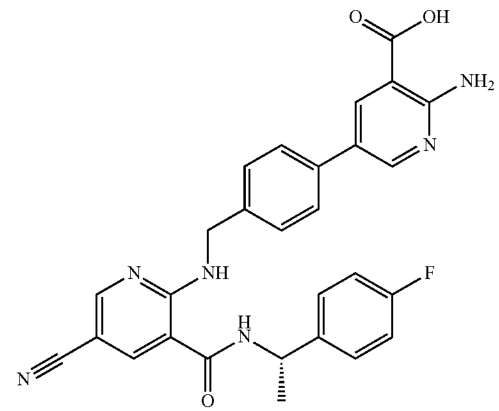 [SMILES: C[C@H](NC(=O)c1cc(C#N)cnc1NCc1ccc(-c2cnc(N)c(C(=O)O)c2)cc1)c1ccc(F)cc1] | (S)-2-amino-5-(4-((5-cyano-3-(1-(4-fluorophenyl)ethyl)carbamoyl)pyridin-2-yl)amino)methyl)phenyl)nicotinic acid | 510.9 | ¹H NMR (400 MHz, DMSO-d₆) δ ppm 9.34 (t, J = 5.77 Hz, 1 H) 9.00 (d, J = 7.53 Hz, 1 H) 8.57 (d, J = 2.01 Hz, 1 H) 8.51 (d, J = 2.51 Hz, 1 H) 8.47 (d, J = 2.01 Hz, 1 H) 8.35 (d, J = 2.51 Hz, 1 H) 7.57 (d, J = 8.28 Hz, 2 H) 7.28-7.46 (m, 4 H) 7.15 (t, J = 8.78 Hz, 2 H) 5.09 (quin, J = 7.09 Hz, 1 H) 4.69 (d, J = 3.76 Hz, 2 H) 1.46 (d, J = 7.03 Hz, 3 H); ¹⁹F NMR (376 MHz, DMSO-d₆) δ ppm −78.50 (TFA, s, 5 F) −120.35 (s, 1 F). |
| 149 | 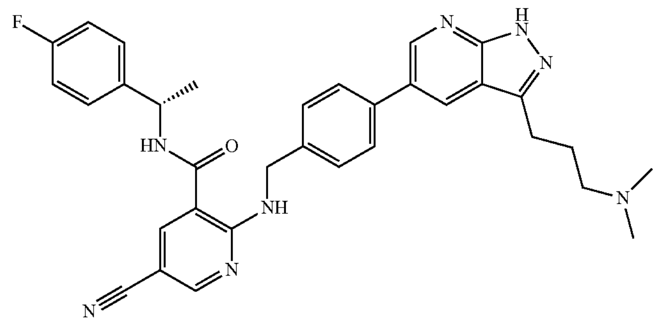 [SMILES: C[C@H](NC(=O)c1cc(C#N)cnc1NCc1ccc(-c2cnc3[nH]nc(CCCN(C)C)c3c2)cc1)c1ccc(F)cc1] | (S)-5-cyano-2-(4-(3-(3-(dimethylamino)propyl)-1H-pyrazolo[3,4-b]pyridin-5-yl)benzyl-amino)-N-(1-(4-fluorophenyl)ethyl)nicotinamide | 577 | ¹H NMR (400 MHz, DMSO-d₆) δ ppm 13.31 (br. s., 1 H) 9.36 (t, J = 5.77 Hz, 1 H) 9.01 (d, J = 7.28 Hz, 1 H) 8.77 (d, J = 2.01 Hz, 1 H) 8.59 (d, J = 1.76 Hz, 1 H) 8.46 (dd, J = 19.58, 2.01 Hz, 2 H) 7.70 (d, J = 8.03 Hz, 5H) 7.31-7.52 (m, 4 H) 7.15 (t, J = 8.78 Hz, 2 H) 5.10 (quin, J = 7.03 Hz, 1 H) 4.72 (d, J = 5.77 Hz, 2 H) 2.97 (t, J = 7.40 Hz, 2 H) 2.53-2.64 (m, 2 H) 2.35 (br. s., 6 H) 1.86-2.07 (m, 2 H) 1.46 (d, J = 7.03 Hz, 3 H); ¹⁹F NMR (376 MHz, DMSO-d₆) δ ppm −78.50 (TFA, s, 0.6 F) −121.32 (s, 1 F). |
| 150 | 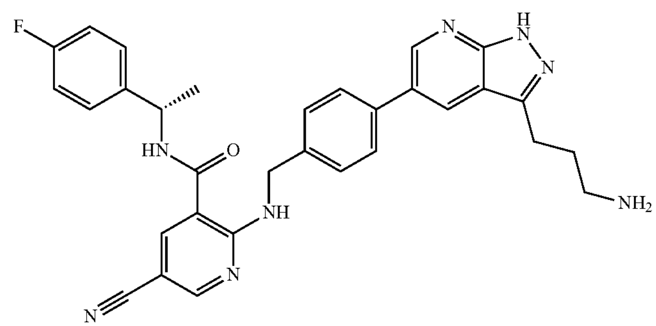 [SMILES: C[C@H](NC(=O)c1cc(C#N)cnc1NCc1ccc(-c2cnc3[nH]nc(CCCN)c3c2)cc1)c1ccc(F)cc1] | (S)-2-(4-(3-(aminopropyl)-1H-pyrazolo[3,4-b]pyridin-5-yl)benzyl-amino)-N-(1-(4-fluorophenyl)ethyl)nicotinamide | 549 | ¹H NMR (400 MHz, DMSO-d₆) δ ppm 13.39 (br. s., 1 H) 9.36 (t, J = 5.90 Hz, 1 H) 9.01 (d, J = 7.53 Hz, 1 H) 8.80 (d, J = 2.01 Hz, 1 H) 8.59 (d, J = 2.01 Hz, 1 H) 8.47 (dd, J = 15.18, 2.13 Hz, 1H) 7.70 (d, J = 8.03 Hz, 5H) 7.34-7.47 (m, 4 H) 7.15 (t, J = 8.78 Hz, 2 H) 5.09 (quin, J = 7.03 Hz, 1 H) 4.73 (d, J = 5.77 Hz, 2 H) 3.04 (t, J = 7.40, 2H) 2.90 (d, J = 8.28 Hz, 2H) 2.04 (quin, J = 7.53 Hz, 2H) 1.46 (d, J = 7.03 Hz, 3 H); ¹⁹F NMR (376 MHz, DMSO-d₆) δ ppm −78.50 (TFA, s, 1 F) −120.38 (s, 1 F). ¹⁹F NMR (376 MHz, DMSO-d₆) δ ppm −78.50 (TFA, s, 5 F) −120.65 (s, 1 F). |

| Ex. No. | Structure | Chemical Name | ESI-MS (M + H) | ¹H NMR |
|---|---|---|---|---|
| 151 | 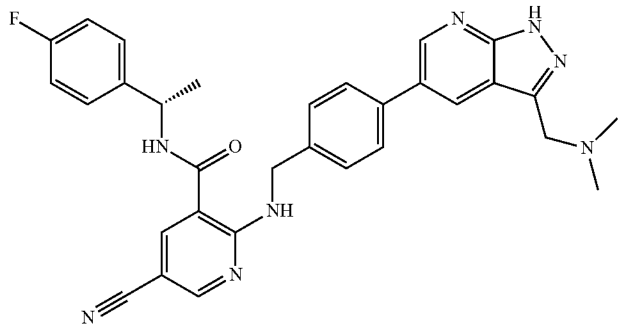 [SMILES: C[C@H](NC(=O)c1cc(C#N)cnc1NCc1ccc(-c2cnc3[nH]nc(CN(C)C)c3c2)cc1)c1ccc(F)cc1] | (S)-5-cyano-2-(4-(3-((dimethylamino)methyl)-1H-pyrazolo[3,4-b]pyridin-5-yl)benzyl-amino)-N-(1-(4-fluorophenyl)ethyl)nicotinamide | 549 | ¹H NMR (400 MHz, DMSO-d₆) δ ppm 14.16 (s, 1 H) 9.37 (t, J = 5.77 Hz, 1 H) 9.02 (d, J = 7.53 Hz, 1 H) 8.91 (d, J = 2.01 Hz, 1 H) 8.74 (d, J = 2.01 Hz, 1 H) 8.59 (d, J = 2.01 Hz, 1 H) 8.50 (d, J = 2.01 Hz, 1 H) 7.73 (d, J = 8.28 Hz, 2 H) 7.37-7.51 (m, 4 H) 7.07-7.20 (m, 2 H) 5.01-5.17 (m, 1 H) 4.61-4.81 (m, 4 H) 2.83 (br. s., 6 H) 1.46 (d, J = 7.03 Hz, 3 H); ¹⁹F NMR (376 MHz, DMSO-d₆) δ ppm -78.50 (TFA, s, 2 F) -121.01 (s, 1 F). |
| 152 | 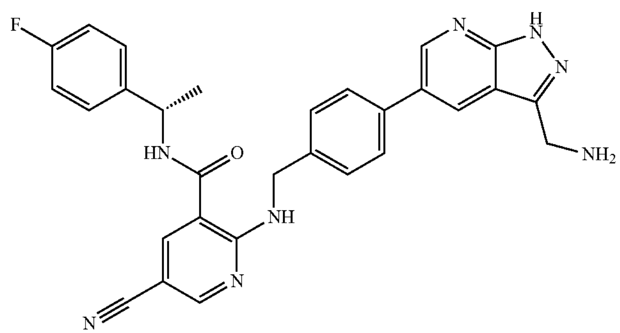 [SMILES: C[C@H](NC(=O)c1cc(C#N)cnc1NCc1ccc(-c2cnc3[nH]nc(CN)c3c2)cc1)c1ccc(F)cc1] | (S)-2-(4-(3-(aminomethyl)-1H-pyrazolo[3,4-b]pyridin-5-yl)benzyl-amino)-5-cyano-N-(1-(4-fluorophenyl)ethyl)nicotinamide | 521.00 | ¹H NMR (400 MHz, DMSO-d₆) δ ppm 13.91 (s, 1 H) 9.37 (t, J = 5.77 Hz, 1 H) 9.01 (d, J = 7.53 Hz, 1 H) 8.88 (d, J = 2.26 Hz, 1 H) 8.67 (d, J = 2.01 Hz, 1 H) 8.59 (d, J = 2.01 Hz, 1 H) 8.49 (d, J = 2.01 Hz, 1 H) 8.37 (br. s., 2 H) 7.72 (d, J = 8.03 Hz, 2 H) 7.34-7.50 (m, 4 H) 7.15 (t, J = 8.91 Hz, 2 H) 5.10 (t, J = 7.15 Hz, 1 H) 4.73 (d, J = 5.77 Hz, 2 H) 4.41-4.53 (m, 2 H) 1.46 (d, J = 7.03 Hz, 3 H); ¹⁹F NMR (376 MHz, DMSO-d₆) δ ppm -78.50 (TFA, s, 3 F) -120.89 (s, 1 F). |

TABLE 1-continued

| Ex. No. | Structure | Chemical Name | ESI-MS (M + H) | ¹H NMR |
|---|---|---|---|---|
| 153 | 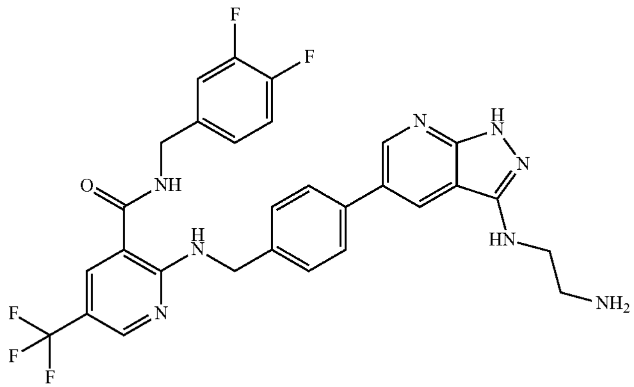 [SMILES: NCCNc1n[nH]c2ncc(-c3ccc(CNc4ncc(C(F)(F)F)cc4C(=O)NCc4ccc(F)c(F)c4)cc3)cc12] | 2-(4-(3-(2-amino-ethylamino)-1H-pyrazolo[3,4-b]pyridin-5-yl)benzylamino)-N-(3,4-difluorobenzyl)-5-(trifluoromethyl)nicotinamide | 596.90 | ¹H NMR (400 MHz, DMSO-d₆) δ ppm 12.25 (s, 1 H) 9.20-9.49 (m, 2 H) 8.70 (d, J = 2.26 Hz, 1 H) 8.52 (s, 1 H) 8.36 (dd, J = 7.78, 2.01 Hz, 2 H) 7.79 (br. s., 3 H) 7.62 (d, J = 8.03 Hz, 2 H) 7.45 (d, J = 8.28 Hz, 4 H) 7.12-7.25 (m, 1 H) 4.75 (d, J = 5.77 Hz, 2 H) 4.45 (d, J = 5.77 Hz, 2 H) 3.51 (t, J = 6.02 Hz, 2 H) 3.02-3.18 (m, 2 H); ¹⁹F NMR (376 MHz, DMSO-d₆) δ ppm −63.15 (s, 3 F) −78.50 (s, 6 F) −143.19−142.95 (m, 1 F) −145.65−145.43 (m, 1 F). |
| 154 | 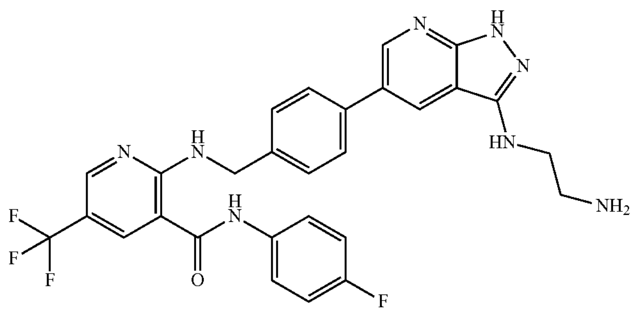 [SMILES: NCCNc1n[nH]c2ncc(-c3ccc(CNc4ncc(C(F)(F)F)cc4C(=O)Nc4ccc(F)cc4)cc3)cc12] | 2-(4-(3-(2-amino-ethylamino)-1H-pyrazolo[3,4-b]pyridin-5-yl)benzylamino)-N-(4-fluorophenyl)-5-(trifluoromethyl)nicotinamide | 564.9 | ¹H NMR (400 MHz, DMSO-d₆) δ ppm 12.25 (s, 1 H) 10.52 (s, 1 H) 8.93 (t, J = 5.11 Hz, 1 H) 8.70 (d, J = 2.01 Hz, 1 H) 8.55 (s, 1 H) 8.27-8.46 (m, 2 H) 7.56-7.91 (m, 7 H) 7.47 (d, J = 8.28 Hz, 2 H) 7.22 (t, J = 8.91 Hz, 2 H) 4.77 (d, J = 5.52 Hz, 2 H) 3.03-3.19 (m, 2 H); ¹⁹F NMR (376 MHz, DMSO-d₆) δ ppm −63.33 (s, 3 F) −78.50 (TFA, s, 5 F) −122.53 (s, 1 F). |
| 155 | 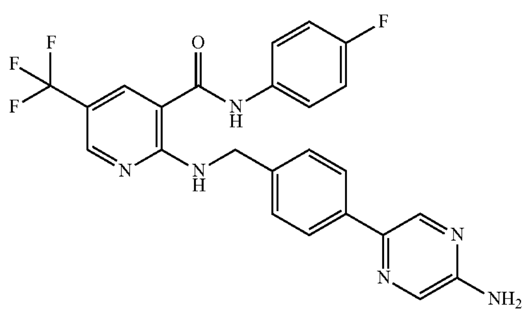 [SMILES: Nc1cnc(-c2ccc(CNc3ncc(C(F)(F)F)cc3C(=O)Nc3ccc(F)cc3)cc2)cn1] | 2-(4-(5-aminopyrazin-2-yl)benzylamino)-N-(4-fluorophenyl)-5-(trifluoromethyl)nicotinamide | 482.9 | ¹H NMR (400 MHz, DMSO-d₆) δ ppm 10.50 (s, 1 H) 8.90 (t, J = 5.65 Hz, 1 H) 8.54 (d, J = 1.00 Hz, 1 H) 8.46 (d, J = 1.26 Hz, 1 H) 8.39 (d, J = 2.01 Hz, 1 H) 7.98 (d, J = 1.25 Hz, 1 H) 7.86 (d, J = 8.28 Hz, 2 H) 7.63-7.76 (m, 2 H) 7.39 (d, J = 8.28 Hz, 2 H) 7.21 (t, J = 8.91 Hz, 2 H) 4.73 (d, J = 5.52 Hz, 2 H); ¹⁹F NMR (376 MHz, DMSO-d₆) δ ppm −62.64 (s, 3 F) −78.50 (TFA, s, 3 F) −121.88 (s, 1 F). |

| Ex. No. | Structure | Chemical Name | ESI-MS (M + H) | ¹H NMR |
|---|---|---|---|---|
| 156 | 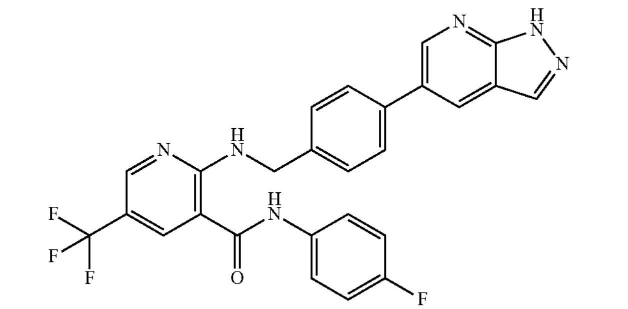 [SMILES: O=C(Nc1ccc(F)cc1)c1cc(C(F)(F)F)cnc1NCc1ccc(-c2cnc3[nH]ncc3c2)cc1] | 2-(4-(1H-pyrazolo[3,4-b]pyridin-5-yl)benzylamino)-N-(4-fluorophenyl)-5-(trifluoromethyl)nicotinamide | 506.9 | ¹H NMR (400 MHz, DMSO-d₆) δ ppm 13.70 (br. s., 1 H) 10.51 (s, 1 H) 8.93 (t, J = 5.90 Hz, 1 H) 8.81 (d, J = 2.01 Hz, 1 H) 8.55 (s, 1 H) 8.32-8.48 (m, 2 H) 8.18 (d, J = 1.25 Hz, 1 H) 7.60-7.77 (m, 4 H) 7.47 (d, J = 8.03 Hz, 2 H) 7.13-7.29 (m, 2 H) 4.77 (d, J = 5.77 Hz, 2 H); ¹⁹F NMR (376 MHz, DMSO-d₆) δ ppm −58.95 (s, 3 F) −118.19 (s, 1 F). |
| 157 | 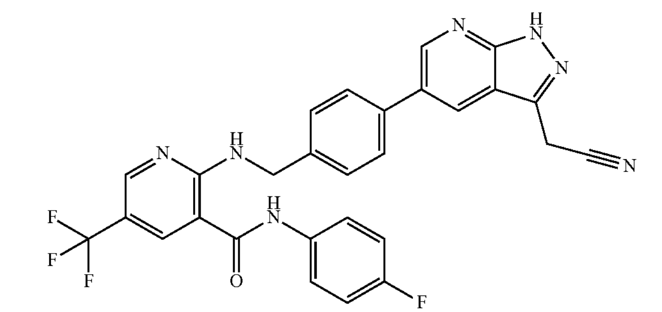 [SMILES: N#CCc1n[nH]c2ncc(-c3ccc(CNc4ncc(C(F)(F)F)cc4C(=O)Nc4ccc(F)cc4)cc3)cc12] | 2-(4-(3-(cyanomethyl)-1H-pyrazolo[3,4-b]pyridin-5-yl)benzylamino)-N-(4-fluorophenyl)-5-(trifluoromethyl)nicotinamide | 545.9 | ¹H NMR (400 MHz, DMSO-d₆) δ ppm 13.77 (s, 1 H) 10.51 (s, 1 H) 8.94 (t, J = 5.77 Hz, 1 H) 8.87 (d, J = 2.01 Hz, 1 H) 8.48-8.62 (m, 2 H) 8.39 (d, J = 2.01 Hz, 1 H) 7.62-7.77 (m, 4 H) 7.49 (d, J = 8.28 Hz, 2 H) 7.22 (t, J = 8.91 Hz, 2 H) 4.78 (d, J = 5.77 Hz, 2 H) 4.44 (s, 2 H); ¹⁹F NMR (376 MHz, DMSO-d₆) δ ppm −58.96 (s, 3 F) −118.19 (s, 1 F). |
| 158 | 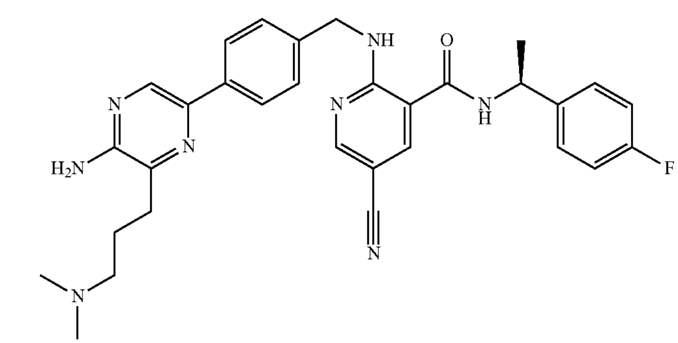 [SMILES: C[C@H](NC(=O)c1cc(C#N)cnc1NCc1ccc(-c2cnc(N)c(CCCN(C)C)n2)cc1)c1ccc(F)cc1] | (S)-2-(4-(5-amino-6-(3-(dimethylamino)propyl)pyrazin-2-yl)benzylamino)-5-cyano-N-(1-(4-fluorophenyl)ethyl)nicotinamide | 553.0 | ¹H NMR (400 MHz, DMSO-d₆) δ 9.43 (br. s., 1 H), 9.33 (t, J = 5.77 Hz, 1 H), 9.01 (d, J = 7.28 Hz, 1H), 8.58 (d, J = 2.01 Hz, 1H), 8.49 (d, J = 2.01 Hz, 1H), 8.39 (s, 1H), 7.88 (d, J = 8.03 Hz, 2H), 7.42 (dd, J = 5.65, 8.41 Hz, 2H), 7.34 (d, J = 8.03 Hz, 2H), 7.15 (t, J = 8.78 Hz, 2H), 5.09 (quin, J = 7.03 Hz, 1H), 4.69 (d, J = 5.52 Hz, 2H), 3.10-3.21 (m, 2H), 2.81 (d, J = 4.77 Hz, 6H), 2.70 (t, J = 7.03 Hz, 2H), 2.03-2.19 (m, 2H), 1.46 (d, J = 7.03 Hz, 3H). |

| Ex. No. | Structure | Chemical Name | ESI-MS (M + H) | 1H NMR |
|---|---|---|---|---|
| 159 | 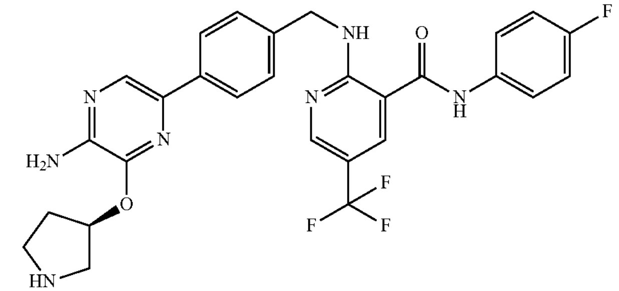 [SMILES: Nc1ncc(-c2ccc(CNc3ncc(C(F)(F)F)cc3C(=O)Nc3ccc(F)cc3)cc2)nc1O[C@@H]1CCNC1] | 2-{4-[5-Amino-6-((R)-pyrrolidin-3-yloxy)-pyrazin-2-yl]-benzylamino}-N-(4-fluoro-phenyl)-5-trifluoromethyl-nicotinamide | 568.52 | 1H NMR (400 MHz, DMSO-d6) δ 10.52 (s, 1H), 9.00 (br. s., 2H), 8.90 (t, J = 5.77 Hz, 1H), 8.54 (s, 1H), 8.40 (d, J = 1.76 Hz, 1H), 8.12 (s, 1H), 7.86 (d, J = 8.28 Hz, 2H), 7.63-7.74 (m, 2H), 7.39 (d, J = 8.03 Hz, 2H), 7.22 (t, J = 8.91 Hz, 2H), 5.71 (br. s., 1H), 4.73 (d, J = 5.52 Hz, 2H), 3.46-3.58 (m, 2H), 3.31-3.45 (m, 2H), 2.16-2.35 (m, 2H). |
| 160 | 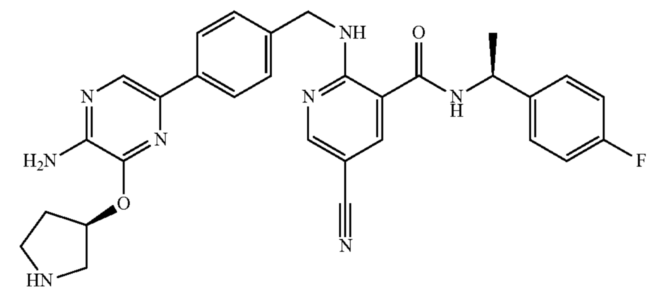 [SMILES: C[C@H](NC(=O)c1cc(C#N)cnc1NCc1ccc(-c2cnc(N)c(O[C@@H]3CCNC3)n2)cc1)c1ccc(F)cc1] | 2-{4-[5-Amino-6-((R)-pyrrolidin-3-yloxy)-pyrazin-2-yl]-benzylamino}-5-cyano-N-[(S)-1-(4-fluoro-phenyl)-ethyl]-nicotinamide | 553.56 | 1H NMR (400 MHz, DMSO-d6) δ 9.32 (t, J = 5.65 Hz, 1H), 8.86-9.06 (m, 3H), 8.57 (d, J = 1.76 Hz, 1H), 8.48 (d, J = 1.76 Hz, 1H), 8.12 (s, 1H), 7.84 (d, J = 8.03 Hz, 2H), 7.42 (dd, J = 5.52, 8.28 Hz, 2H), 7.33 (d, J = 8.03 Hz, 2H), 7.15 (t, J = 8.91 Hz, 2H), 5.70 (br. s., 1H), 5.09 (quin, J = 6.96 Hz, 1H), 4.68 (d, J = 5.77 Hz, 2H), 3.47-3.57 (m, 2H), 3.30-3.46 (m, 2H), 2.16-2.35 (m, 2H), 1.46 (d, J = 7.03 Hz, 3H) |
| 161 | 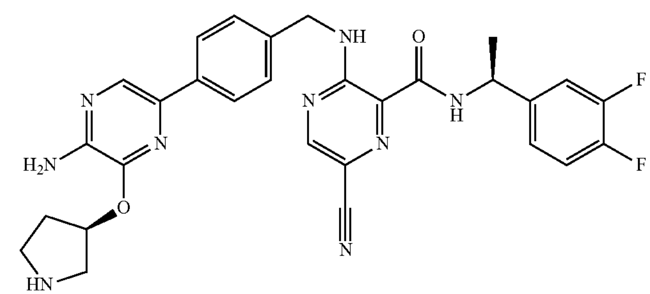 [SMILES: C[C@H](NC(=O)c1nc(C#N)cnc1NCc1ccc(-c2cnc(N)c(O[C@@H]3CCNC3)n2)cc1)c1ccc(F)c(F)c1] | 3-{4-[5-Amino-6-((R)-pyrrolidin-3-yloxy)-pyrazin-2-yl]-benzylamino}-6-cyano-pyrazine-2-carboxylic acid [(S)-1-(3,4-difluoro-phenyl)-ethyl]-amide | 572.55 | 1H NMR (400 MHz, DMSO-d6) δ 9.73 (t, J = 5.90 Hz, 1H), 9.34 (d, J = 8.28 Hz, 1H), 8.97 (br. s., 2H), 8.74 (s, 1H), 8.12 (s, 1H), 7.85 (d, J = 8.28 Hz, 2H), 7.51 (ddd, J = 1.76, 7.97, 11.86 Hz, 1H), 7.31-7.42 (m, 3H), 7.21-7.29 (m, 1H), 5.70 (br. s., 1H), 5.12 (quin, J = 7.28 Hz, 1H), 4.62-4.76 (m, 2H), 3.47-3.57 (m, 2H), 3.30-3.47 (m, 2H), 2.18-2.34 (m, 2H), 1.52 (d, J = 7.03 Hz, 3H) |

TABLE 1-continued

| Ex. No. | Structure | Chemical Name | ESI-MS (M + H) | ¹H NMR |
|---|---|---|---|---|
| 162 | 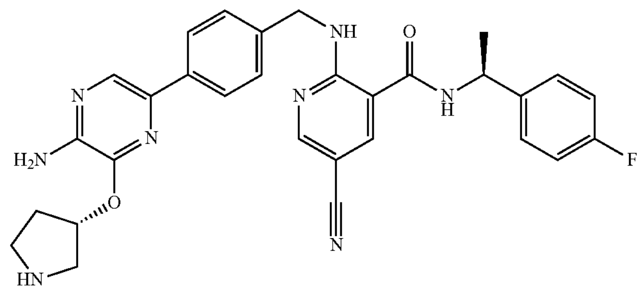 | 2-{4-[5-Amino-6-((S)-pyrrolidin-3-yloxy)-pyrazin-2-yl]-benzylamino}-5-cyano-N-[(S)-1-(4-fluoro-phenyl)-ethyl]-nicotinamide | 553.2 | ¹H NMR (400 MHz, DMSO-d₆) δ 9.33 (t, J = 5.65 Hz, 1H), 8.96-9.12 (m, 3H), 8.57 (d, J = 1.76 Hz, 1H), 8.49 (d, J = 2.01 Hz, 1H), 8.12 (s, 1H), 7.85 (d, J = 8.28 Hz, 2H), 7.42 (dd, J = 5.65, 8.41 Hz, 2H), 7.34 (d, J = 8.28 Hz, 2H), 7.15 (t, J = 8.91 Hz, 2H), 5.72 (br. s., 1H), 5.09 (quin, J = 6.96 Hz, 1H), 4.68 (d, J = 5.52 Hz, 2H), 3.48-3.58 (m, 2H), 3.31-3.47 (m, 2H), 2.18-2.35 (m, 2H), 1.46 (d, J = 7.03 Hz, 3H) |
| 163 | 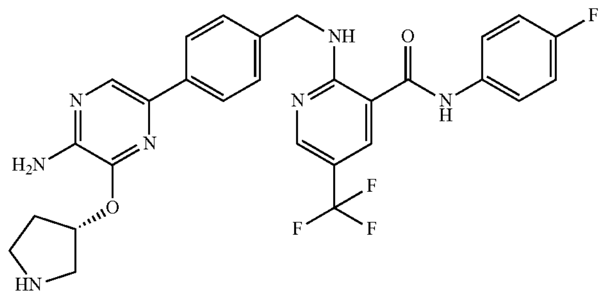 [SMILES: Nc1ncc(-c2ccc(CNc3ncc(C(F)(F)F)cc3C(=O)Nc3ccc(F)cc3)cc2)nc1O[C@H]1CCNC1] | 2-{4-[5-Amino-6-((S)-pyrrolidin-3-yloxy)-pyrazin-2-yl]-benzylamino}-N-(4-fluoro-phenyl)-5-trifluoromethyl-nicotinamide | 568.26 | ¹H NMR (400 MHz, DMSO-d₆) δ 10.52 (s, 1H), 8.97 (br. s., 2H), 8.90 (t, J = 5.65 Hz, 1H), 8.54 (s, 1H), 8.40 (d, J = 1.76 Hz, 1H), 8.12 (s, 1H), 7.86 (d, J = 8.28 Hz, 2H), 7.64-7.74 (m, 2H), 7.39 (d, J = 8.28 Hz, 2H), 7.22 (t, J = 8.91 Hz, 2H), 5.71 (br. s., 1H), 4.73 (d, J = 5.52 Hz, 2H), 3.47-3.58 (m, 2H), 3.29-3.46 (m, 2H), 2.16-2.35 (m, 2H) |
| 164 | 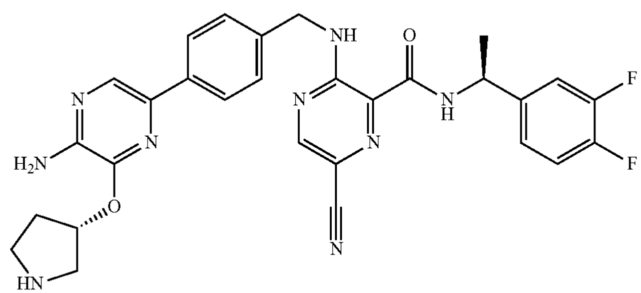 | 3-{4-[5-Amino-6-((S)-pyrrolidin-3-yloxy)-pyrazin-2-yl]-benzylamino}-6-cyano-pyrazine-2-carboxylic acid [(S)-1-(3,4-difluoro-phenyl)-ethyl]-amide | 572.39 | ¹H NMR (400 MHz, DMSO-d₆) δ 9.73 (t, J = 5.90 Hz, 1H), 9.34 (d, J = 8.28 Hz, 1H), 9.01 (br. s., 2H), 8.74 (s, 1H), 8.12 (s, 1H), 7.85 (d, J = 8.28 Hz, 2H), 7.51 (ddd, J = 2.01, 7.97, 11.86 Hz, 1H), 7.32-7.42 (m, 3H), 7.18-7.30 (m, 1H), 5.71 (br. s., 1H), 5.12 (quin, J = 7.28 Hz, 1H), 4.62-4.77 (m, 2H), 3.48-3.56 (m, 2H), 3.30-3.47 (m, 2H), 2.16-2.35 (m, 2H), 1.46-1.58 (m, 3H), |

TABLE 1-continued

| Ex. No. | Structure | Chemical Name | ESI-MS (M + H) | ¹H NMR |
|---|---|---|---|---|
| 165 | 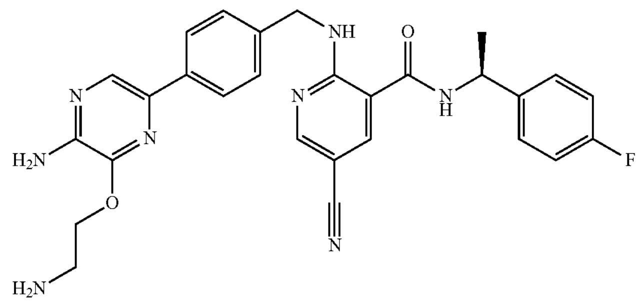 [SMILES: C[C@H](NC(=O)c1cc(C#N)cnc1NCc1ccc(-c2cnc(N)c(OCCN)n2)cc1)c1ccc(F)cc1] | 2-{4-[5-Amino-6-(2-amino-ethoxy)-pyrazin-2-yl]-benzylamino}-5-cyano-N-[(S)-1-(4-fluoro-phenyl)-ethyl]-nicotinamide | 527 | ¹H NMR (400 MHz, DMSO-d₆) δ 9.32 (t, J = 5.77 Hz, 1H), 9.00 (d, J = 7.28 Hz, 1H), 8.57 (d, J = 2.01 Hz, 1H), 8.48 (d, J = 2.01 Hz, 1H), 8.12 (s, 1H), 7.94 (br. s., 3H), 7.84 (d, J = 8.03 Hz, 2H), 7.42 (dd, J = 5.52, 8.53 Hz, 2H), 7.33 (d, J = 8.03 Hz, 2H), 7.15 (t, J = 8.78 Hz, 2H), 5.09 (quin, J = 7.03 Hz, 1H), 4.67 (d, J = 5.52 Hz, 2H), 4.42-4.56 (m, 2H), 3.31 (d, J = 4.77 Hz, 2H), 1.46 (d, J = 7.03 Hz, 3H) |
| 166 | 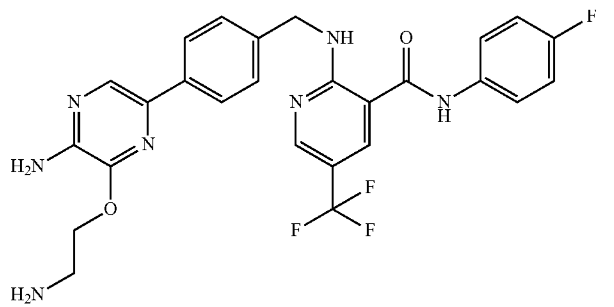 [SMILES: NCCOc1nc(-c2ccc(CNc3ncc(C(F)(F)F)cc3C(=O)Nc3ccc(F)cc3)cc2)cnc1N] | 2-{4-[5-Amino-6-(2-amino-ethoxy)-pyrazin-2-yl]-benzylamino}-N-(4-fluoro-phenyl)-5-trifluoromethyl-nicotinamide | 541.9 | ¹H NMR (400 MHz, DMSO-d₆) δ 10.51 (s, 1H), 8.90 (t, J = 5.65 Hz, 1H), 8.54 (s, 1H), 8.40 (d, J = 2.01 Hz, 1H), 8.13 (s, 1H), 7.95 (br. s., 3H), 7.86 (d, J = 8.28 Hz, 2H), 7.64-7.74 (m, 2H), 7.39 (d, J = 8.28 Hz, 2H), 7.21 (t, J = 8.91 Hz, 2H), 4.72 (d, J = 5.52 Hz, 2H), 4.51 (t, J = 5.02 Hz, 2H), 3.25-3.36 (m, 2H) |
| 167 | 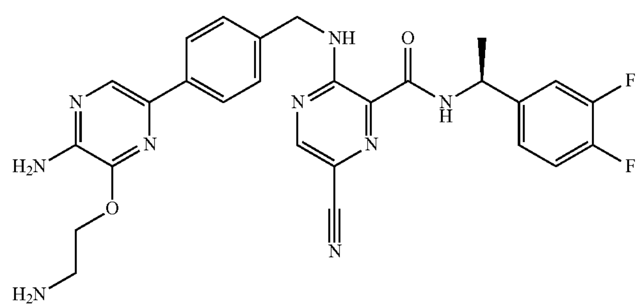 [SMILES: C[C@H](NC(=O)c1nc(C#N)cnc1NCc1ccc(-c2cnc(N)c(OCCN)n2)cc1)c1ccc(F)c(F)c1] | 3-{4-[5-Amino-6-(2-amino-ethoxy)-pyrazin-2-yl]-benzylamino}-6-cyano-pyrazine-2-carboxylic acid [(S)-1-(3,4-difluoro-phenyl)-ethyl]-amide | 545.9 | ¹H NMR (400 MHz, DMSO-d6) δ 9.72 (t, J = 5.90 Hz, 1H), 9.34 (d, J = 8.28 Hz, 1H), 8.74 (s, 1H), 8.13 (s, 1H), 7.95 (br. s., 3H), 7.85 (d, J = 8.28 Hz, 2H), 7.51 (ddd, J = 2.01, 7.91, 11.92 Hz, 1H), 7.31-7.42 (m, 3H), 7.20-7.30 (m, 1H), 5.11 (quin, J = 7.22 Hz, 1H), 4.62-4.76 (m, 2H), 4.50 (t, J = 4.89 Hz, 2H), 3.24-3.37 (m, 2H), 1.51 (d, J = 7.03 Hz, 3H) |

| Ex. No. | Structure | Chemical Name | ESI-MS (M + H) | ¹H NMR |
|---|---|---|---|---|
| 168 | 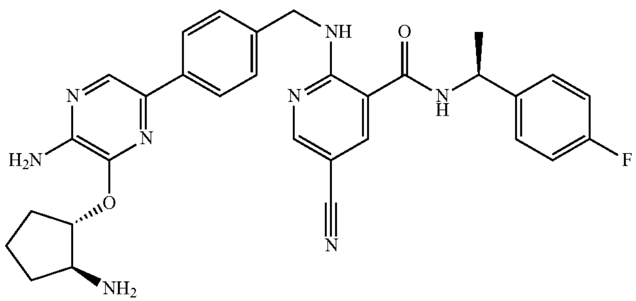 [SMILES: C[C@H](NC(=O)c1cc(C#N)cnc1NCc1ccc(-c2cnc(N)c(O[C@H]3CCC[C@@H]3N)n2)cc1)c1ccc(F)cc1] | 2-{4-[5-Amino-6-((1S,2S)-2-amino-cyclopentyloxy)-pyrazin-2-yl]-benzylamino}-5-cyano-N-[(S)-1-(4-fluoro-phenyl)-ethyl]-nicotinamide | 567.4 | ¹H NMR (400 MHz, CD₃OD) δ 8.80-8.88 (m, 1H), 8.47 (d, 1H), 8.26 (d, J = 2.01 Hz, 1H), 7.98 (s, 1H), 7.82-7.85 (m, 2H), 7.35-7.46 (m, 4H), 7.02-7.12 (m, 2H), 5.48-5.55 (m, 1H), 5.13-5.23 (m, 1H), 4.76 (br. s., 2H), 3.80-3.90 (m, 1H), 2.44-2.53 (m, 1H), 2.30-2.42 (m, 1H), 1.92-2.03 (m, 3H), 1.73-1.84 (m, 1H), 1.55 (d, 3H) |
| 169 | 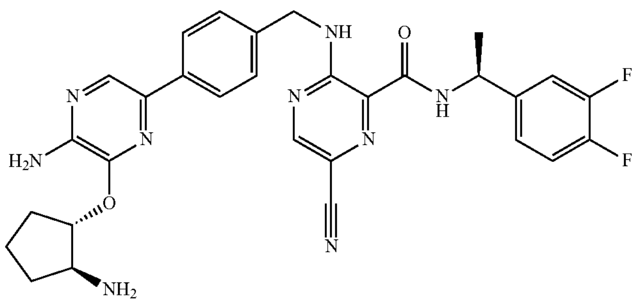 [SMILES: C[C@H](NC(=O)c1nc(C#N)cnc1NCc1ccc(-c2cnc(N)c(O[C@H]3CCC[C@@H]3N)n2)cc1)c1ccc(F)c(F)c1] | 3-{4-[5-Amino-6-((1S,2S)-2-amino-cyclopentyloxy)-pyrazin-2-yl]-benzylamino}-6-cyano-pyrazine-2-carboxylic acid [(S)-1-(3,4-difluoro-phenyl)-ethyl]-amide | 586.4 | ¹H NMR (400 MHz, CD₃OD) δ 11.06 (none, 1H), 9.03-9.08 (m, 1H), 8.57 (s, 1H), 7.99 (s, 1H), 7.83-7.87 (m, 2H), 7.43 (d, J = 8.53 Hz, 2H), 7.31-7.39 (m, 1H), 7.19-7.24 (m, 2H), 5.48-5.54 (m, 1H), 5.13-5.22 (m, 1H), 4.78 (s, 2H), 3.81-3.89 (m, 1H), 2.43-2.53 (m, 1H), 2.30-2.41 (m, 1H), 1.91-2.03 (m, 3H), 1.72-1.84 (m, 1H), 1.58 (d, J = 7.03 Hz, 3H) |
| 170 | 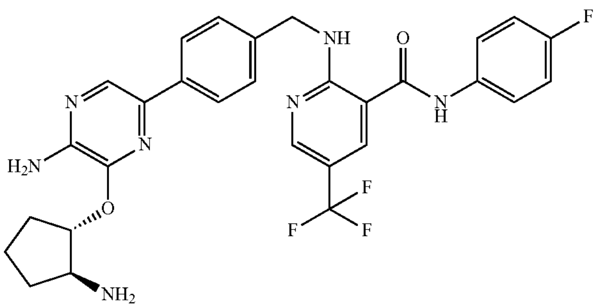 [SMILES: Nc1ncc(-c2ccc(CNc3ncc(C(F)(F)F)cc3C(=O)Nc3ccc(F)cc3)cc2)nc1O[C@H]1CCC[C@@H]1N] | 2-{4-[5-Amino-6-((1S,2S)-2-amino-cyclopentyloxy)-pyrazin-2-yl]-benzylamino}-N-(4-fluoro-phenyl)-5-trifluoromethyl-nicotinamide | 582.4 | ¹H NMR (400 MHz, CD₃OD) δ 8.46-8.48 (m, 1H), 8.33-8.35 (m, 2H), 7.99 (s, 1H), 7.84-7.88 (m, 2H), 7.64-7.70 (m, 2H), 7.47 (d, J = 8.53 Hz, 2H), 7.08-7.14 (m, 2H), 5.49-5.55 (m, 1H), 4.81 (br. s., 2H), 3.80-3.90 (m, 1H), 2.43-2.53 (m, 1H), 2.30-2.41 (m, 1H), 1.93-2.03 (m, 3H), 1.73-1.84 (m, 1H) |

TABLE 1-continued

| Ex. No. | Structure | Chemical Name | ESI-MS (M + H) | ¹H NMR |
|---|---|---|---|---|
| 171 | 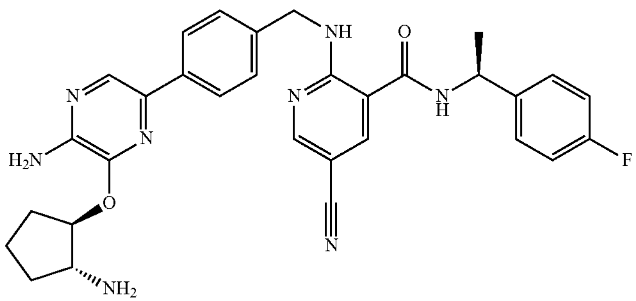 [SMILES: C[C@H](NC(=O)c1cc(C#N)cnc1NCc1ccc(-c2cnc(N)c(O[C@@H]3CCC[C@H]3N)n2)cc1)c1ccc(F)cc1] | 2-{4-[5-Amino-6-((1R,2R)-2-amino-cyclopentyloxy)-pyrazin-2-yl]-benzylamino}-5-cyano-N-[(S)-1-(4-fluoro-phenyl)-ethyl]-nicotinamide | 567.3 | ¹H NMR (400 MHz, CD₃OD) δ 8.82-8.86 (m, 0H), 8.47 (d, J = 2.26 Hz, 1H), 8.26 (d, J = 2.01 Hz, 1H), 7.98 (s, 1H), 7.81-7.87 (m, J = 4.77 Hz, 2H), 7.38-7.45 (m, 4H), 7.03-7.11 (m, 2H), 5.50-5.56 (m, 1H), 5.13-5.23 (m, 1H), 4.76 (s, 2H), 3.82-3.90 (m, 1H), 2.44-2.53 (m, 1H), 2.31-2.41 (m, 1H), 1.93-2.04 (m, 3H), 1.73-1.84 (m, 1H), 1.55 (d, 3H) |
| 172 | 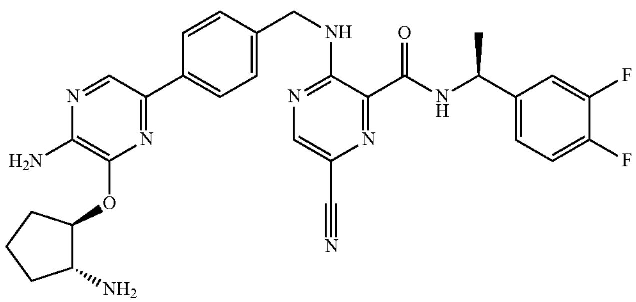 [SMILES: C[C@H](NC(=O)c1nc(C#N)cnc1NCc1ccc(-c2cnc(N)c(O[C@@H]3CCC[C@H]3N)n2)cc1)c1ccc(F)c(F)c1] | 3-{4-[5-Amino-6-((1R,2R)-2-amino-cyclopentyloxy)-pyrazin-2-yl]-benzylamino}-pyrazine-2-carboxylic acid [(S)-1-(3,4-difluoro-phenyl)-ethyl]-amide | 586.3 | ¹H NMR (400 MHz, CD₃OD) δ 9.02-9.07 (m, 1H), 8.57 (s, 1H), 7.99 (s, 1H), 7.83-7.87 (m, J = 5.02 Hz, 2H), 7.41-7.46 (m, 2H), 7.31-7.39 (m, 1H), 7.18-7.25 (m, 2H), 5.48-5.54 (m, 1H), 5.13-5.22 (m, 1H), 4.78 (br. s., 2H), 3.81-3.89 (m, 1H), 2.43-2.54 (m, 1H), 2.30-2.42 (m, 1H), 1.91-2.04 (m, 3H), 1.72-1.83 (m, 1H), 1.58 (d, J = 7.28 Hz, 3H) |
| 173 | 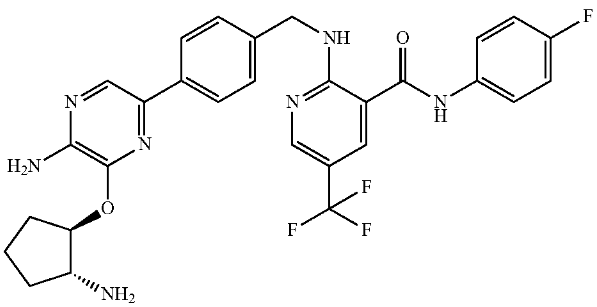 [SMILES: Nc1ncc(-c2ccc(CNc3ncc(C(F)(F)F)cc3C(=O)Nc3ccc(F)cc3)cc2)nc1O[C@@H]1CCC[C@H]1N] | 2-{4-[5-Amino-6-((1R,2R)-2-amino-cyclopentyloxy)-pyrazin-2-yl]-benzylamino}-N-(4-fluoro-phenyl)-5-trifluoromethyl-nicotinamide | 582.4 | ¹H NMR (400 MHz, CD₃OD) δ 8.45-8.48 (m, 1H), 8.32-8.36 (m, 1H), 7.97 (br. s., 1H), 7.84-7.88 (m, 2H), 7.64-7.70 (m, 2H), 7.45-7.49 (m, 2H), 7.07-7.14 (m, 2H), 5.51-5.57 (m, 1H), 4.81 (br. s., 2H), 3.82-3.89 (m, 1H), 2.42-2.55 (m, 1H), 2.30-2.41 (m, 1H), 1.93-2.03 (m, 3H), 1.72-1.83 (m, 1H) |

TABLE 1-continued

| Ex. No. | Structure | Chemical Name | ESI-MS (M + H) | 1H NMR |
|---|---|---|---|---|
| 174 | 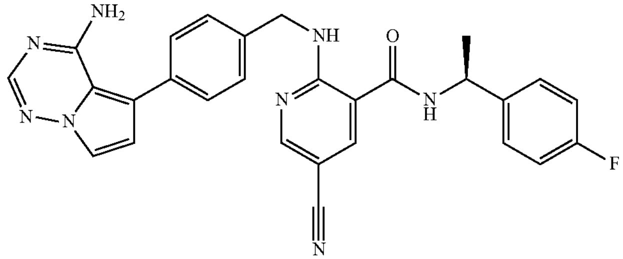 [SMILES: C[C@H](NC(=O)c1cc(C#N)cnc1NCc1ccc(-c2ccn3ncnc(N)c23)cc1)c1ccc(F)cc1] | 2-[4-(4-Amino-pyrrolo[2,1-f][1,2,4]triazin-5-yl)-benzylamino]-5-cyano-N-[(S)-1-(4-fluoro-phenyl)-ethyl]-nicotinamide | 507.2 | 1H NMR (400 MHz, CD3OD) δ 8.81-8.87 (m, 1H), 8.47-8.49 (m, 1H), 8.28 (d, J = 2.26 Hz, 1H), 7.98 (s, 1H), 7.90 (d, J = 2.76 Hz, 1H), 7.50 (s, 4H), 7.38-7.44 (m, 2H), 7.04-7.10 (m, 2H), 6.87 (d, J = 2.76 Hz, 1H), 5.14-5.23 (m, 1H), 4.82 (s, 2H), 1.56 (d, J = 7.03 Hz, 3H). |
| 175 | 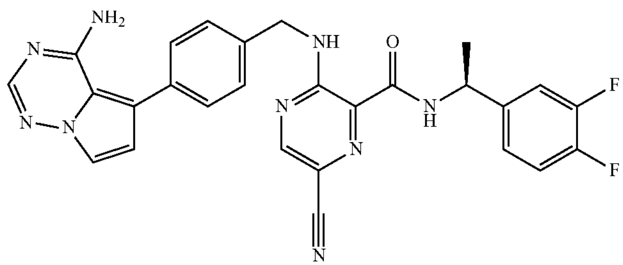 [SMILES: C[C@H](NC(=O)c1nc(C#N)cnc1NCc1ccc(-c2ccn3ncnc(N)c23)cc1)c1ccc(F)c(F)c1] | 3-[4-(4-Amino-pyrrolo[2,1-f][1,2,4]triazin-5-yl)-benzylamino]-6-cyano-pyrazine-2-carboxylic acid [(S)-1-(3,4-difluoro-phenyl)-ethyl]-amide | 526.2 | 1H NMR (400 MHz, CD3OD) δ 9.01-9.15 (m, 1H), 8.58-8.59 (m, 1H), 7.97-8.00 (m, 1H), 7.88-7.92 (m, 1H), 7.49-7.56 (m, 3H), 7.31-7.39 (m, 1H), 7.19-7.25 (m, 2H), 6.85-6.89 (m, 1H), 5.14-5.23 (m, 1H), 4.85 (s, 2H), 1.50-1.67 (m, 3H) |
| 176 | 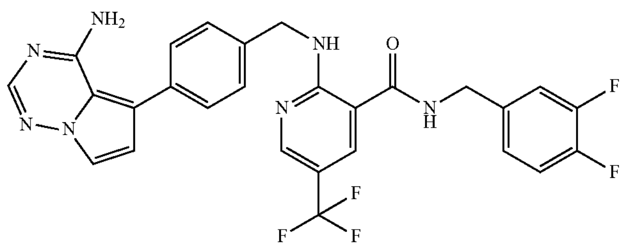 [SMILES: Nc1ncnn2ccc(-c3ccc(CNc4ncc(C(F)(F)F)cc4C(=O)NCc4ccc(F)c(F)c4)cc3)c12] | 2-[4-(4-Amino-pyrrolo[2,1-f][1,2,4]triazin-5-yl)-benzylamino]-N-(3,4-difluoro-benzyl)-5-trifluoromethyl-nicotinamide | 554.4 | 1H NMR (400 MHz, CD3OD) δ 9.15-9.22 (m, 1H), 8.43-8.45 (m, 1H), 8.21-8.23 (m, 1H), 7.99 (s, 1H), 7.92 (d, J = 2.76 Hz, 1H), 7.50-7.57 (m, 4H), 7.15-7.32 (m, 3H), 6.89 (d, J = 2.76 Hz, 1H), 4.85 (br. s., 2H), 4.45-4.56 (m, 2H) |
| 177 | 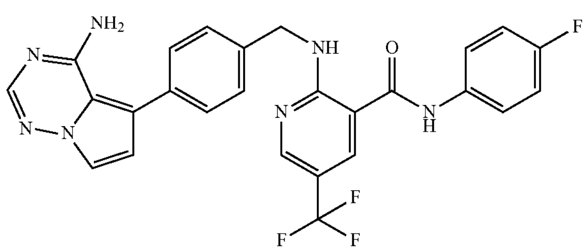 [SMILES: Nc1ncnn2ccc(-c3ccc(CNc4ncc(C(F)(F)F)cc4C(=O)Nc4ccc(F)cc4)cc3)c12] | 2-[4-(4-Amino-pyrrolo[2,1-f][1,2,4]triazin-5-yl)-benzylamino]-N-(4-fluoro-phenyl)-5-trifluoromethyl-nicotinamide | 522.4 | 1H NMR (400 MHz, CD3OD) δ 8.45-8.48 (m, 1H), 8.34-8.36 (m, 1H), 7.99-8.00 (m, 1H), 7.92-7.94 (m, 1H), 7.65-7.71 (m, 2H), 7.50-7.59 (m, 4H), 7.08-7.14 (m, 2H), 6.88-6.90 (m, 1H) |

TABLE 1-continued

| Ex. No. | Structure | Chemical Name | ESI-MS (M + H) | ¹H NMR |
|---|---|---|---|---|
| 178 | 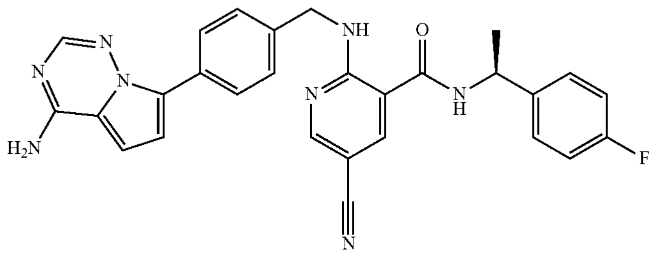 [SMILES: C[C@H](NC(=O)c1cc(C#N)cnc1NCc1ccc(-c2ccc3c(N)ncnn23)cc1)c1ccc(F)cc1] | 2-[4-(4-Amino-pyrrolo[2,1-f][1,2,4]triazin-7-yl)-benzylamino]-5-cyano-N-[(S)-1-(4-fluoro-phenyl)-ethyl]-nicotinamide | 506.9 | ¹H NMR (400 MHz, DMSO-d₆) δ 9.36 (t, J = 5.77 Hz, 1H), 9.00 (d, J = 7.28 Hz, 1H), 8.58 (d, J = 2.01 Hz, 1H), 8.48 (d, J = 2.01 Hz, 1H), 8.05 (s, 1H), 7.95 (d, J = 8.28 Hz, 2H), 7.31-7.48 (m, 5H), 7.26 (d, J = 4.52 Hz, 1H), 7.15 (t, J = 8.91 Hz, 2H), 7.09 (d, J = 4.52 Hz, 1H), 5.10 (quin, J = 7.03 Hz, 1H), 4.64-4.78 (m, 2H), 1.46 (d, J = 7.03 Hz, 3H) |
| 179 | 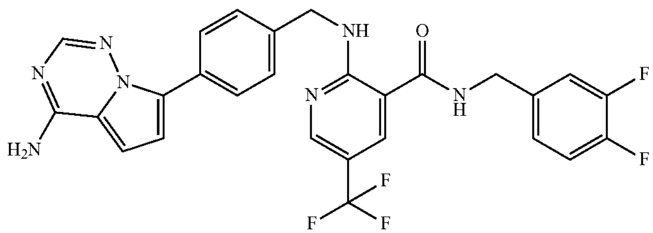 [SMILES: Nc1ncnn2c(-c3ccc(CNc4ncc(C(F)(F)F)cc4C(=O)NCc4ccc(F)c(F)c4)cc3)ccc12] | 2-[4-(4-Amino-pyrrolo[2,1-f][1,2,4]triazin-7-yl)-benzylamino]-N-(3,4-difluoro-benzyl)-5-trifluoromethyl-nicotinamide | 553.9 | ¹H NMR (400 MHz, DMSO-d₆) δ 9.37 (t, J = 5.65 Hz, 1H), 9.32 (t, J = 5.90 Hz, 1H), 8.51 (s, 1H), 8.36 (d, J = 2.01 Hz, 1H), 8.08 (s, 1H), 7.96 (d, J = 8.28 Hz, 2H), 7.34-7.49 (m, 5H), 7.30 (d, J = 4.77 Hz, 1H), 7.15-7.23 (m, 1H), 7.11 (d, J = 4.77 Hz, 1H), 4.74 (d, J = 5.77 Hz, 2H), 4.45 (d, J = 5.77 Hz, 2H) |
| 180 | 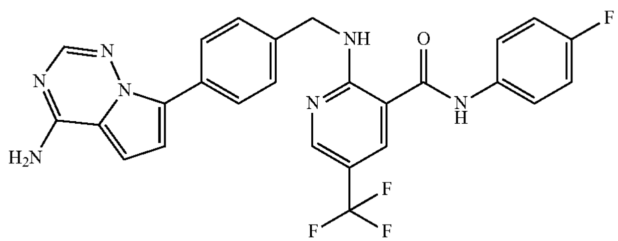 [SMILES: Nc1ncnn2c(-c3ccc(CNc4ncc(C(F)(F)F)cc4C(=O)Nc4ccc(F)cc4)cc3)ccc12] | 2-[4-(4-Amino-pyrrolo[2,1-f][1,2,4]triazin-7-yl)-benzylamino]-N-(4-fluoro-phenyl)-5-trifluoromethyl-nicotinamide | 521.9 | ¹H NMR (400 MHz, DMSO-d₆) δ 10.51 (s, 1H), 8.93 (t, J = 5.77 Hz, 1H), 8.54 (s, 1H), 8.39 (d, J = 2.01 Hz, 1H), 8.04 (s, 1H), 7.91-8.00 (m, 2H), 7.63-7.76 (m, 2H), 7.39-7.50 (m, 2H), 7.15-7.29 (m, 3H), 7.09 (d, J = 4.77 Hz, 1H), 4.70-4.83 (m, 2H) |
| 181 | 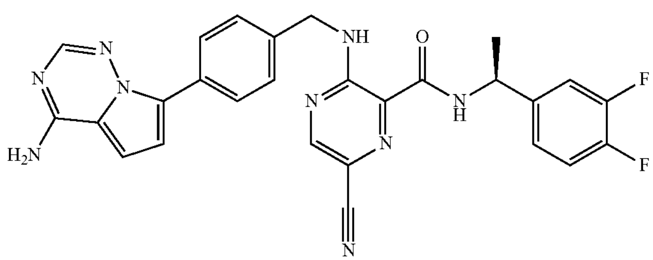 [SMILES: C[C@H](NC(=O)c1nc(C#N)cnc1NCc1ccc(-c2ccc3c(N)ncnn23)cc1)c1ccc(F)c(F)c1] | 3-[4-(4-Amino-pyrrolo[2,1-f][1,2,4]triazin-7-yl)-benzylamino]-6-cyano-pyrazine-2-carboxylic acid [(S)-1-(3,4-difluoro-phenyl)-ethyl]-amide | 525.9 | ¹H NMR (400 MHz, DMSO-d₆) δ 9.76 (t, J = 6.02 Hz, 1H), 9.34 (d, J = 8.28 Hz, 1H), 8.74 (s, 1H), 8.03 (s, 1H), 7.96 (d, J = 8.28 Hz, 2H), 7.52 (ddd, J = 2.01, 7.84, 11.98 Hz, 1H), 7.43 (d, J = 8.28 Hz, 2H), 7.32-7.40 (m, 1H), 7.24-7.30 (m, 1H), 7.22 (d, J = 4.52 Hz, 1H), 7.08 (d, J = 4.52 Hz, 1H), 5.12 (quin, J = 7.28 Hz, 1H), 4.60-4.81 (m, 2H), 1.52 (d, J = 7.03 Hz, 3H) |

TABLE 1-continued

| Ex. No. | Structure | Chemical Name | ESI-MS (M + H) | ¹H NMR |
|---|---|---|---|---|
| 182 | 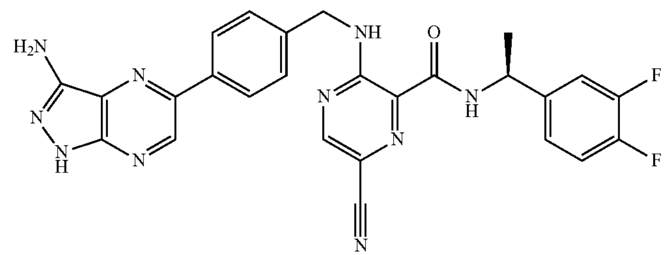 [SMILES: C[C@H](NC(=O)c1nc(C#N)cnc1NCc1ccc(-c2cnc3[nH]nc(N)c3n2)cc1)c1ccc(F)c(F)c1] | 3-[4-(3-Amino-1H-pyrazolo[3,4-b]pyrazin-5-yl)-benzylamino]-6-cyano-pyrazine-2-carboxylic acid [(S)-1-(3,4-difluoro-phenyl)-ethyl]-amide | 526.9 | ¹H NMR (400 MHz, DMSO-d₆) δ 12.41 (s, 1H), 9.77 (t, J = 5.90 Hz, 1H), 9.31-9.36 (m, 1H), 8.99 (s, 1H), 8.74 (s, 1H), 8.08 (d, J = 8.28 Hz, 2H), 7.52 (ddd, J = 2.13, 7.91, 12.05 Hz, 1H), 7.46 (d, J = 8.53 Hz, 2H), 7.33-7.42 (m, 1H), 7.24-7.29 (m, 1H), 5.09-5.17 (m, 1H), 4.73-4.78 (m, 2H), 1.49-1.54 (m, 3H) |
| 183 | 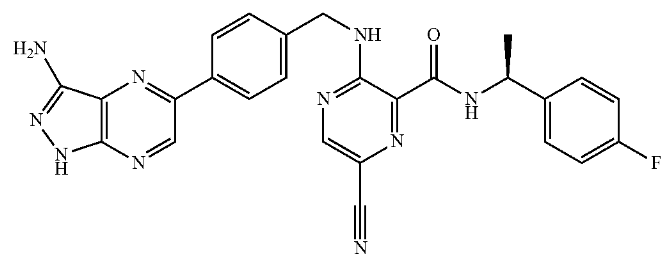 [SMILES: C[C@H](NC(=O)c1nc(C#N)cnc1NCc1ccc(-c2cnc3[nH]nc(N)c3n2)cc1)c1ccc(F)cc1] | 2-[4-(3-Amino-1H-pyrazolo[3,4-b]pyrazin-5-yl)-benzylamino]-5-cyano-N-[(S)-1-(4-fluoro-phenyl)-ethyl]-nicotinamide | 508.4 | ¹H NMR (400 MHz, DMSO-d₆) δ 9.32-9.39 (m, 1H), 8.96-9.02 (m, 2H), 8.58 (s, 1H), 8.48 (d, J = 2.26 Hz, 1H), 8.07 (d, J = 8.28 Hz, 2H), 7.38-7.44 (m, 4H), 7.11-7.17 (m, 2H), 5.72 (s, 2H), 5.06-5.14 (m, 1H), 4.63-4.80 (m, 2H), 1.46 (d, J = 7.03 Hz, 3H) |
| 184 | 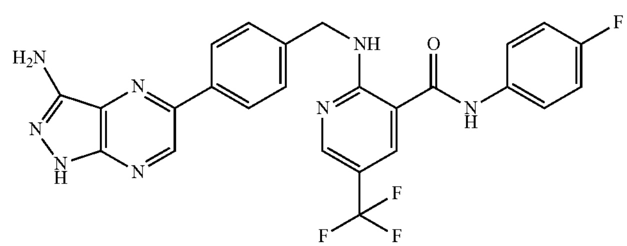 [SMILES: Nc1n[nH]c2ncc(-c3ccc(CNc4ncc(C(F)(F)F)cc4C(=O)Nc4ccc(F)cc4)cc3)nc12] | 2-[4-(3-Amino-1H-pyrazolo[3,4-b]pyrazin-5-yl)-benzylamino]-5-cyano-N-(4-fluoro-phenyl)-5-trifluoromethyl-nicotinamide | 523.4 | ¹H NMR (400 MHz, DMSO-d₆) δ 10.49-10.52 (m, 1H), 8.97-9.00 (m, 1H), 8.92 (br. s., 1H), 8.52-8.55 (m, 1H), 8.37-8.40 (m, 1H), 8.53 Hz, 2H), 7.66-7.72 (m, 2H), 7.48 (d, J = 8.28 Hz, 2H), 7.16-7.26 (m, 2H), 4.71-4.84 (m, 2H) |

TABLE 1-continued

| Ex. No. | Structure | Chemical Name | ESI-MS (M + H) | ¹H NMR |
|---|---|---|---|---|
| 185 | 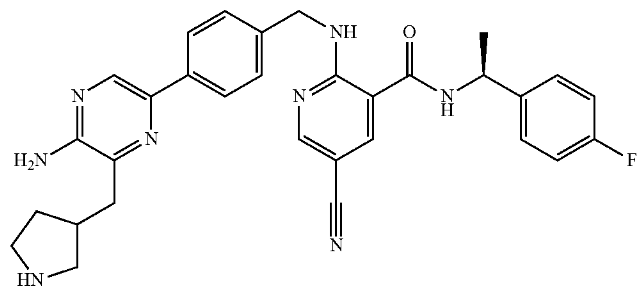 [SMILES: C[C@H](NC(=O)c1cc(C#N)cnc1NCc1ccc(-c2cnc(N)c(CC3CCNC3)n2)cc1)c1ccc(F)cc1] | 2-[4-(5-Amino-6-pyrrolidin-3-ylmethyl-pyrazin-2-yl)-benzylamino]-5-cyano-N-[(S)-1-(4-fluoro-phenyl)-ethyl]-nicotinamide | 551.0 | ¹H NMR (400 MHz, DMSO-d₆) δ 9.33 (t, J = 5.77 Hz, 1H), 9.01 (d, J = 7.28 Hz, 1H), 8.60-8.77 (m, 2H), 8.58 (d, J = 2.01 Hz, 1H), 8.49 (d, J = 2.01 Hz, 1H), 8.39 (s, 1H), 7.87 (d, J = 8.28 Hz, 2H), 7.42 (dd, J = 5.65, 8.66 Hz, 2H), 7.34 (d, J = 8.28 Hz, 2H), 7.15 (t, J = 8.78 Hz, 2H), 5.09 (quin, J = 7.03 Hz, 1H), 4.69 (d, J = 5.77 Hz, 2H), 3.44-3.57 (m, 1H), 3.22-3.34 (m, 1H), 3.08-3.21 (m, 1H), 2.68-2.92 (m, 4H), 2.16 (dd, J = 5.65, 10.42 Hz, 1H), 1.59-1.72 (m, 1H), 1.46 (d, J = 7.03 Hz, 3H) |
| 186 | 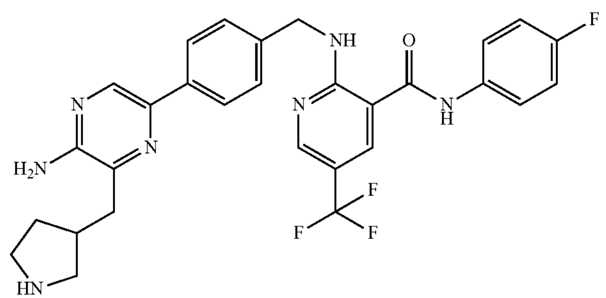 [SMILES: Nc1ncc(-c2ccc(CNc3ncc(C(F)(F)F)cc3C(=O)Nc3ccc(F)cc3)cc2)nc1CC1CCNC1] | 2-[4-(5-Amino-6-pyrrolidin-3-ylmethyl-pyrazin-2-yl)-benzylamino]-N-(4-fluoro-phenyl)-5-trifluoromethyl-nicotinamide | 565.9 | ¹H NMR (400 MHz, DMSO-d₆) δ 10.53 (s, 1H), 8.91 (t, J = 5.65 Hz, 1H), 8.71 (br. s., 2H), 8.54 (s, 1H), 8.37-8.43 (m, 2H), 7.89 (d, J = 8.28 Hz, 2H), 7.62-7.74 (m, 2H), 7.40 (d, J = 8.03 Hz, 2H), 7.22 (t, J = 8.78 Hz, 2H), 4.74 (d, J = 5.52 Hz, 2H), 3.45-3.58 (m, 1H), 3.23-3.34 (m, 1H), 3.09-3.22 (m, 1H), 2.71-2.93 (m, 4H), 2.10-2.22 (m, 1H), 1.60-1.73 (m, 1H) |
| 187 | 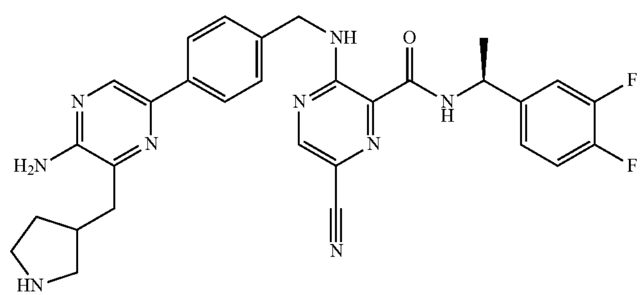 [SMILES: C[C@H](NC(=O)c1nc(C#N)cnc1NCc1ccc(-c2cnc(N)c(CC3CCNC3)n2)cc1)c1ccc(F)c(F)c1] | 3-[4-(5-Amino-6-pyrrolidin-3-ylmethyl-pyrazin-2-yl)-benzylamino]-6-cyano-pyrazine-2-carboxylic acid [(S)-1-(3,4-difluoro-phenyl)-ethyl]-amide | 570 | ¹H NMR (400 MHz, DMSO-d₆) δ 9.73 (t, J = 5.90 Hz, 1H), 9.35 (d, J = 8.03 Hz, 1H), 8.74 (s, 1H), 8.55-8.69 (m, 2H), 8.39 (s, 1H), 7.88 (d, J = 8.28 Hz, 2H), 7.51 (ddd, J = 1.76, 7.91, 11.92 Hz, 1H), 7.32-7.43 (m, 3H), 7.22-7.28 (m, 1H), 5.11 (quin, J = 7.22 Hz, 1H), 4.63-4.77 (m, 2H), 3.43-3.55 (m, 1H), 3.22-3.34 (m, 1H), 3.07-3.21 (m, 1H), 2.69-2.91 (m, 4H), 2.16 (d, J = 5.02 Hz, 1H), 1.65 (dd, J = 8.03, 12.80 Hz, 1H), 1.52 (d, J = 7.03 Hz, 3H) |

| Ex. No. | Structure | Chemical Name | ESI-MS (M + H) | ¹H NMR |
|---|---|---|---|---|
| 188 | 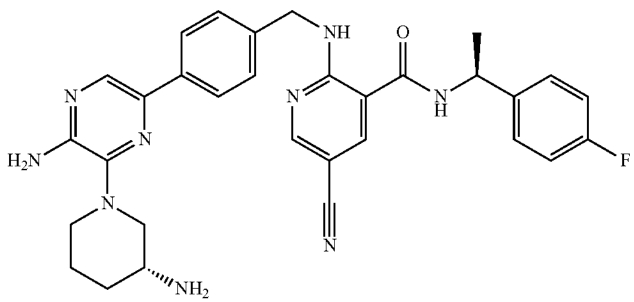 [SMILES: C[C@H](NC(=O)c1cc(C#N)cnc1NCc1ccc(-c2cnc(N)c(N3CCC[C@@H](N)C3)n2)cc1)c1ccc(F)cc1] | 2-{4-[5-Amino-6-((R)-3-amino-piperidin-1-yl)-pyrazin-2-yl]-benzylamino}-N-[(S)-1-(4-fluoro-phenyl)-ethyl]-5-cyano-nicotinamide | 566.00 | ¹H NMR (400 MHz, DMSO-d₆) δ 9.31 (t, J = 5.65 Hz, 1H), 9.00 (d, J = 7.53 Hz, 1H), 8.57 (d, J = 2.01 Hz, 1H), 8.47 (d, J = 2.01 Hz, 1H), 8.22 (s, 1H), 7.92 (br. s., 3H), 7.84 (d, J = 8.28 Hz, 2H), 7.41 (dd, J = 5.77, 8.53 Hz, 2H), 7.33 (d, J = 8.28 Hz, 2H), 7.14 (t, J = 8.78 Hz, 2H), 5.08 (quin, J = 7.03 Hz, 1H), 4.67 (d, J = 5.52 Hz, 2H), 3.50-3.60 (m, 1H), 3.47 (d, J = 12.55 Hz, 1H), 3.00-3.12 (m, 2H), 2.94 (br. s., 1H), 1.84-1.97 (m, 2H), 1.68 (br. s., 2H), 1.45 (d, J = 7.03 Hz, 3H). |
| 189 | 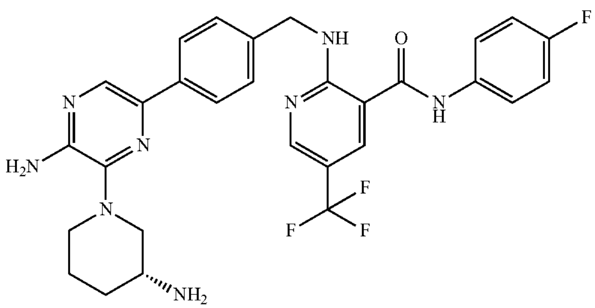 [SMILES: Nc1ncc(-c2ccc(CNc3ncc(C(F)(F)F)cc3C(=O)Nc3ccc(F)cc3)cc2)nc1N1CCC[C@@H](N)C1] | 2-{4-[5-Amino-6-((R)-3-amino-piperidin-1-yl)-pyrazin-2-yl]-benzylamino}-N-(4-fluoro-phenyl)-5-trifluoromethyl-nicotinamide | 580.9 | ¹H NMR (400 MHz, DMSO-d₆) δ 10.45 (s, 1H), 8.83 (t, J = 5.65 Hz, 1H), 8.47 (s, 1H), 8.33 (d, J = 1.76 Hz, 1H), 8.16 (s, 1H), 7.86 (br. s., 3H), 7.80 (d, J = 8.28 Hz, 2H), 7.58-7.67 (m, 2H), 7.33 (d, J = 8.28 Hz, 2H), 7.15 (t, J = 8.91 Hz, 2H), 4.66 (d, J = 5.52 Hz, 2H), 3.48 (br. s., 1H), 3.42 (d, J = 12.55 Hz, 1H), 2.94-3.08 (m, 2H), 2.89 (br. s., 1H), 1.77-1.93 (m, 2H), 1.62 (br. s., 2H) |
| 190 | 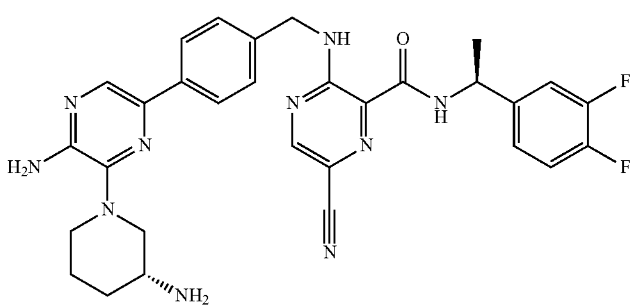 [SMILES: C[C@H](NC(=O)c1nc(C#N)cnc1NCc1ccc(-c2cnc(N)c(N3CCC[C@@H](N)C3)n2)cc1)c1ccc(F)c(F)c1] | 3-{4-[5-Amino-6-((R)-3-amino-piperidin-1-yl)-pyrazin-2-yl]-benzylamino}-6-cyano-pyrazine-2-carboxylic acid [(S)-1-(3,4-difluoro-phenyl)-ethyl]-amide | 584.9 | ¹H NMR (400 MHz, DMSO-d₆) δ 9.72 (t, J = 5.77 Hz, 1H), 9.34 (d, J = 8.28 Hz, 1H), 8.74 (s, 1H), 8.23 (s, 1H), 7.92 (br. s., 3H), 7.86 (d, J = 8.28 Hz, 2H), 7.51 (ddd, J = 2.01, 7.91, 11.92 Hz, 1H), 7.32-7.42 (m, 3H), 7.19-7.29 (m, 1H), 5.12 (quin, J = 7.28 Hz, 1H), 4.63-4.75 (m, 2H), 3.51-3.61 (m, 1H), 3.47 (d, J = 12.55 Hz, 1H), 3.00-3.13 (m, 2H), 2.93 (br. s., 1H), 1.84-1.99 (m, 2H), 1.69 (br. s., 2H), 1.52 (d, J = 7.03 Hz, 3H) |

TABLE 1-continued

| Ex. No. | Structure | Chemical Name | ESI-MS (M + H) | ¹H NMR |
|---|---|---|---|---|
| 191 | 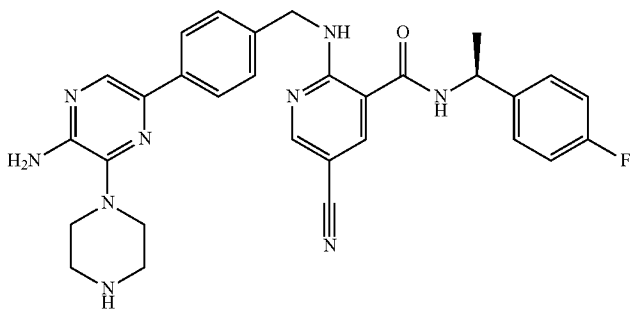 | 2-[4-(3'-Amino-3,4,5,6-tetrahydro-2H-[1,2']bipyrazinyl-6'-yl)-benzylamino]-5-cyano-N-[(S)-1-(4-fluorophenyl)-ethyl]-nicotinamide | 552.3 | ¹H NMR (400 MHz, CD₃OD) δ 8.81-8.85 (m, 1H), 8.79-8.87 (m, 1H), 8.47 (d, J = 2.01 Hz, 1H), 8.25 (d, J = 2.01 Hz, 1H), 8.16 (s, 1H), 7.89 (d, J = 8.53 Hz, 2H), 7.37-7.44 (m, 4H), 7.03-7.10 (m, 2H), 5.13-5.22 (m, 1H), 4.75 (s, 2H), 3.52-3.59 (m, 4H), 3.45-3.51 (m, 4H), 1.55 (d, J = 7.03 Hz, 3H) |
| 192 | 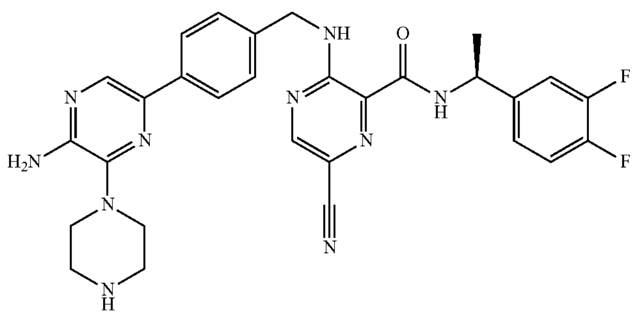 [SMILES: C[C@H](NC(=O)c1nc(C#N)cnc1NCc1ccc(-c2cnc(N)c(N3CCNCC3)n2)cc1)c1ccc(F)c(F)c1] | 3-[4-(3'-Amino-3,4,5,6-tetrahydro-2H-[1,2']bipyrazinyl-6'-yl)-benzylamino]-6-cyano-pyrazine-2-carboxylic acid [(S)-1-(3,4-difluorophenyl)-ethyl]-amide | 571.3 | ¹H NMR (400 MHz, CD₃OD) δ 8.98-9.10 (m, 1H), 8.58 (s, 1H), 8.17 (s, 1H), 7.90 (d, J = 8.28 Hz, 2H), 7.42 (d, J = 8.53 Hz, 2H), 7.31-7.39 (m, 1H), 7.18-7.25 (m, 2H), 5.13-5.23 (m, 1H), 4.78 (br. s., 2H), 3.45-3.56 (m, 8H), 1.59 (d, J = 7.03 Hz, 3H) |
| 193 | 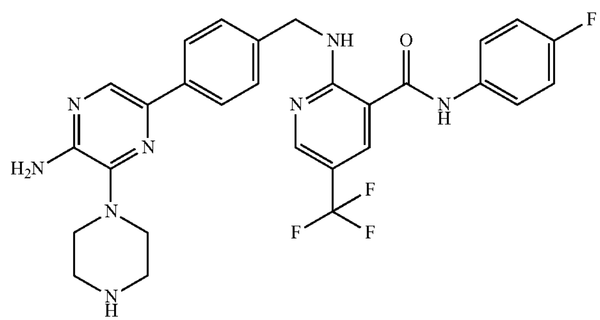 [SMILES: Nc1ncc(-c2ccc(CNc3ncc(C(F)(F)F)cc3C(=O)Nc3ccc(F)cc3)cc2)nc1N1CCNCC1] | 2-[4-(3'-Amino-3,4,5,6-tetrahydro-2H-[1,2']bipyrazinyl-6'-yl)-benzylamino]-N-(4-fluoro-phenyl)-5-trifluoromethyl-nicotinamide | 567.2 | ¹H NMR (400 MHz, CD₃OD) δ 8.44-8.49 (m, 1H), 8.33-8.35 (m, 1H), 8.17 (s, 1H), 7.89-7.93 (m, 2H), 7.64-7.70 (m, 2H), 7.44-7.47 (m, 2H), 7.08-7.14 (m, 2H), 4.81 (br. s., 2H), 3.51-3.59 (m, 4H), 3.45-3.51 (m, 4H) |

TABLE 1-continued

| Ex. No. | Structure | Chemical Name | ESI-MS (M + H) | ¹H NMR |
|---|---|---|---|---|
| 194 | 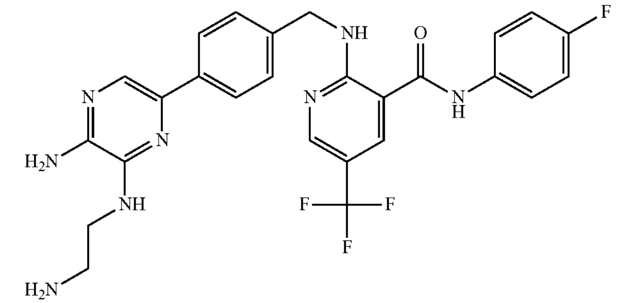 [SMILES: NCCNc1nc(-c2ccc(CNc3ncc(C(F)(F)F)cc3C(=O)Nc3ccc(F)cc3)cc2)cnc1N] | 2-{4-[5-Amino-6-(2-amino-ethylamino)-pyrazin-2-yl]-benzylamino}-N-(4-fluoro-phenyl)-5-trifluoromethyl-nicotinamide | 541.4 | ¹H NMR (400 MHz, DMSO-$d_6$) δ 10.51 (s, 1H), 8.89 (t, J = 5.65 Hz, 1H), 8.53 (d, J = 1.51 Hz, 1H), 8.39 (d, J = 2.01 Hz, 1H), 7.87 (d, J = 8.28 Hz, 2H), 7.73-7.82 (m, 3H), 7.62-7.71 (m, 2H), 7.37 (d, J = 8.53 Hz, 2H), 7.15-7.26 (m, 2H), 4.72 (d, J = 5.77 Hz, 2H), 3.62-3.71 (m, 2H), 3.11 (q, J = 6.11 Hz, 2H) |
| 195 | 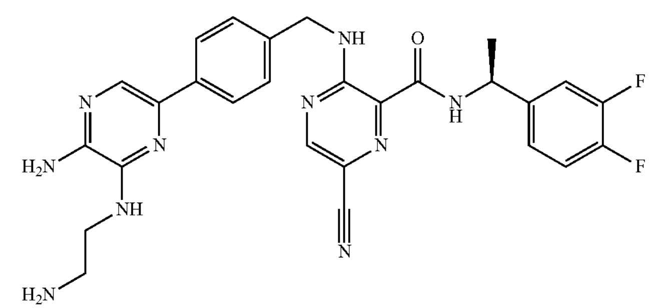 | 3-{4-[5-Amino-6-(2-amino-ethylamino)-pyrazin-2-yl]-benzylamino}-6-cyano-pyrazine-2-carboxylic acid [(S)-1-(3,4-difluoro-phenyl)-ethyl]-amide | 545.5 | ¹H NMR (400 MHz, DMSO-$d_6$) δ 9.66 (t, J = 6.02 Hz, 1H), 9.28 (d, J = 8.28 Hz, 1H), 8.67 (s, 1H), 7.80 (d, J = 8.28 Hz, 2H), 7.71-7.73 (m, 2H), 7.44 (ddd, J = 2.13, 7.72, 11.98 Hz, 1H), 7.27-7.33 (m, 3H), 7.16-7.21 (m, 1H), 5.04 (quin, J = 7.22 Hz, 1H), 4.63 (d, J = 5.77 Hz, 2H), 3.57-3.64 (m, 2H), 3.05 (q, J = 6.11 Hz, 2H), 1.45 (d, J = 7.03 Hz, 3H) |
| 196 | 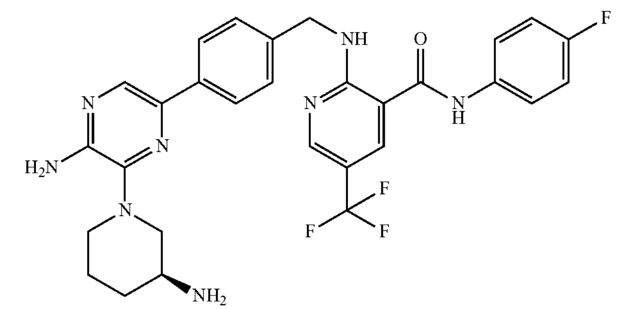 [SMILES: Nc1ncc(-c2ccc(CNc3ncc(C(F)(F)F)cc3C(=O)Nc3ccc(F)cc3)cc2)nc1N1CCC[C@H](N)C1] | 2-{4-[5-Amino-6-((S)-(3-amino-piperidin-1-yl)-pyrazin-2-yl]-benzylamino}-N-(4-fluoro-phenyl)-5-trifluoromethyl-nicotinamide | 581.2 | ¹H NMR (400 MHz, DMSO-$d_6$) δ 10.45 (s, 1H), 8.83 (t, J = 5.90 Hz, 1H), 8.47 (dd, J = 0.88, 2.13 Hz, 1H), 8.33 (d, J = 2.01 Hz, 1H), 8.16 (s, 1H), 7.86 (br. s., 2H), 7.80 (d, J = 8.53 Hz, 2H), 7.59-7.66 (m, 2H), 7.32 (d, J = 8.53 Hz, 2H), 7.11-7.18 (m, 2H), 4.66 (d, J = 5.52 Hz, 2H), 3.37-3.52 (m, 1H), 2.95-3.05 (m, 2H), 1.85 (d, J = 10.79 Hz, 2H), 1.62 (br. s., 2H) |

| Ex. No. | Structure | Chemical Name | ESI-MS (M + H) | ¹H NMR |
|---|---|---|---|---|
| 197 | 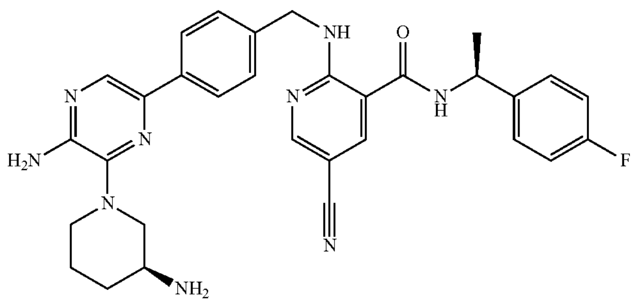 [SMILES: C[C@H](NC(=O)c1cc(C#N)cnc1NCc1ccc(-c2cnc(N)c(N3CCC[C@H](N)C3)n2)cc1)c1ccc(F)cc1] | 2-{4-[5-Amino-6-((S)-(3-amino-piperidin-1-yl)-pyrazin-2-yl]-benzylamino}-5-cyano-N-[(S)-1-(4-fluoro-phenyl)-ethyl]-nicotinamide | 566.4 | ¹H NMR (400 MHz, DMSO-d₆) δ 9.25 (t, J = 6.02 Hz, 1H), 8.94 (d, J = 7.53 Hz, 1H), 8.51 (d, J = 2.26 Hz, 1H), 8.41 (d, J = 2.26 Hz, 1H), 8.16 (s, 1H), 7.85 (br. s., 2H), 7.76-7.80 (m, 2H), 7.32-7.38 (m, 2H), 7.27 (d, J = 8.53 Hz, 2H), 7.04-7.11 (m, 2H), 5.02 (quin, J = 7.22 Hz, 1H), 4.61 (d, J = 6.02 Hz, 2H), 3.37-3.51 (m, 1H), 2.95-3.05 (m, 2H), 1.81-1.89 (m, 2H), 1.57-1.66 (m, 2H), 1.39 (d, J = 7.28 Hz, 3H) |
| 198 | 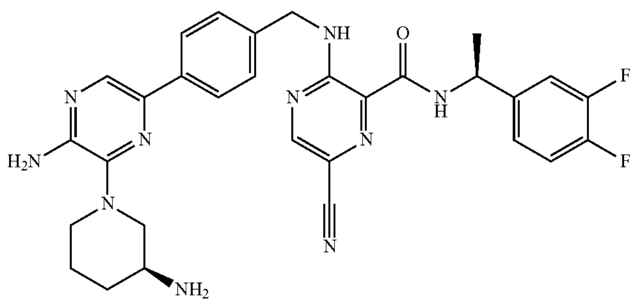 [SMILES: C[C@H](NC(=O)c1nc(C#N)cnc1NCc1ccc(-c2cnc(N)c(N3CCC[C@H](N)C3)n2)cc1)c1ccc(F)c(F)c1] | 3-{4-[5-Amino-6-((S)-(3-amino-piperidin-1-yl)-pyrazin-2-yl]-benzylamino}-6-cyano-pyrazine-2-carboxylic acid [(S)-1-(3,4-difluoro-phenyl)-ethyl]-amide | 585.2 | ¹H NMR (400 MHz, DMSO-d₆) δ 9.65 (t, J = 6.02 Hz, 1H), 9.27 (d, J = 8.28 Hz, 1H), 8.67 (s, 1H), 8.16 (s, 1H), 7.82-7.91 (m, 3H), 7.79 (d, J = 8.53 Hz, 2H), 7.44 (ddd, J = 2.13, 7.91, 12.05 Hz, 1H), 7.26-7.32 (m, 3H), 7.16-7.21 (m, 1H), 5.00-5.09 (m, J = 7.30, 7.30, 7.30, 7.30 Hz, 1H), 4.57-4.68 (m, 2H), 2.96-3.05 (m, 2H), 1.80-1.89 (m, 2H), 1.63 (br. s., 2H), 1.45 (d, J = 7.03 Hz, 3H) |
| 199 | 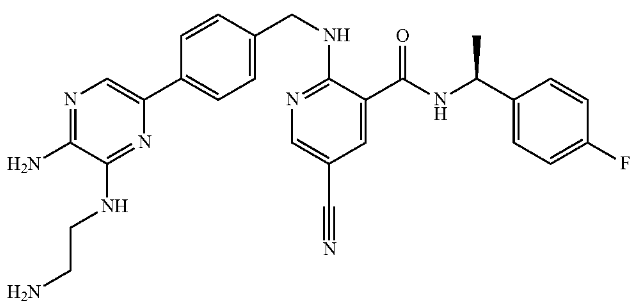 [SMILES: C[C@H](NC(=O)c1cc(C#N)cnc1NCc1ccc(-c2cnc(N)c(NCCN)n2)cc1)c1ccc(F)cc1] | 2-{4-[5-Amino-6-(2-amino-ethylamino)-pyrazin-2-yl]-benzylamino}-5-cyano-N-[(S)-1-(4-fluoro-phenyl)-ethyl]-nicotinamide | 526.5 | ¹H NMR (400 MHz, DMSO-d₆) δ 9.33 (t, J = 5.77 Hz, 1H), 9.01 (d, J = 7.53 Hz, 1H), 8.57 (d, J = 2.26 Hz, 1H), 8.49 (d, J = 2.01 Hz, 1H), 7.76-7.89 (m, 6H), 7.38-7.45 (m, 2H), 7.33 (d, J = 8.53 Hz, 2H), 7.05-7.18 (m, 4H), 5.09 (quin, J = 7.09 Hz, 1H), 4.69 (d, J = 5.77 Hz, 2H), 3.66-3.73 (m, 2H), 3.12 (q, J = 5.69 Hz, 2H), 1.46 (d, J = 7.03 Hz, 3H) |

| Ex. No. | Structure | Chemical Name | ESI-MS (M + H) | ¹H NMR |
|---|---|---|---|---|
| 200 | 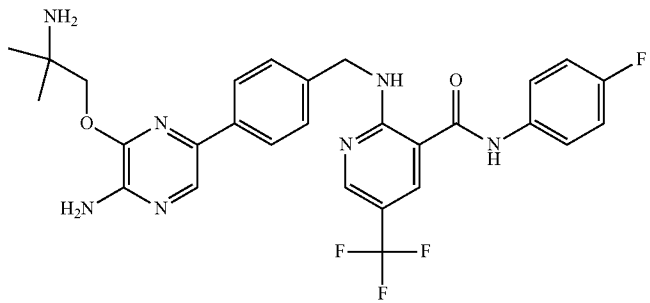 [SMILES: CC(C)(N)COc1nc(-c2ccc(CNc3ncc(C(F)(F)F)cc3C(=O)Nc3ccc(F)cc3)cc2)cnc1N] | 2-{4-[5-Amino-6-(2-amino-2-methyl-propoxy)-pyrazin-2-yl]-benzylamino}-N-(4-fluoro-phenyl)-5-trifluoromethyl-nicotinamide | 570.2 | ¹H NMR (400 MHz, CD₃OD) δ 10.24 (s, 1H), 8.45 (dd, J = 1.00, 2.26 Hz, 1H), 8.31-8.33 (m, 1H), 8.04 (s, 1H), 7.86-7.89 (m, 2H), 7.65 (ddd, J = 3.01, 4.89, 9.16 Hz, 2H), 7.42 (d, J = 8.53 Hz, 2H), 7.06-7.11 (m, 2H), 4.78 (s, 1H), 4.50 (s, 2H), 1.52 (s, 6H). |
| 201 | 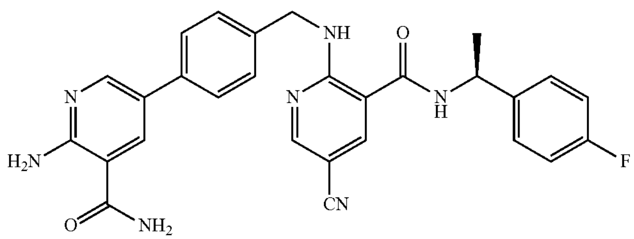 [SMILES: C[C@H](NC(=O)c1cc(C#N)cnc1NCc1ccc(-c2cnc(N)c(C(N)=O)c2)cc1)c1ccc(F)cc1] | (S)-2-(4-(6-amino-5-carbamoylpyridin-3-yl)benzylamino)-5-cyano-N-(1-(4-fluorophenyl)ethyl)nicotinamide | 510.2 | ¹HNMR (400 MHz, DMSO-d₆) δ: 9.33 (s, 1H), 9.01-9.00 (m, 1H), 8.58 (s, 1H), 8.48 (s, 1H), 8.40 (s, 1H), 8.22 (s, 1H), 8.11 (br, 1H), 7.62-7.60 (m, 2H), 7.43-7.41 (m, 7H), 7.17-7.13 (m, 2H), 5.11-5.07 (m, 1H), 4.68 (s, 2H), 1.46-1.45 (m, 3H). |
| 202 | 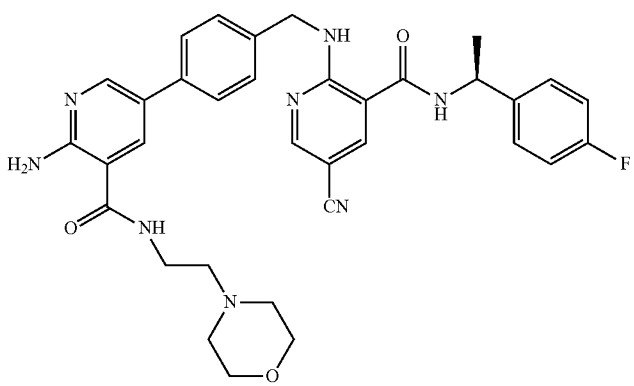 [SMILES: C[C@H](NC(=O)c1cc(C#N)cnc1NCc1ccc(-c2cnc(N)c(C(=O)NCCN3CCOCC3)c2)cc1)c1ccc(F)cc1] | (S)-2-amino-5-(4-(5-cyano-3-(1-(4-fluorophenyl)ethylcarbamoyl)pyridin-2-ylamino)methyl)phenyl)-N-(2-morpholinoethyl)nicotinamide | 623.0 | ¹H NMR (400 MHz, DMSO-d₆) δ: 9.33 (t, 1H), 9.02 (d, 1H), 8.58 (d, 1H), 8.55 (d, 1H), 8.48 (d, 1H), 8.39 (d, 1H), 8.12 (d, 1H), 7.60 (d, 2H), 7.43-7.36 (m, 4H), 7.17-7.13 (m, 4H), 5.10-5.06 (m, 1H), 4.68 (d, 2H), 3.59-3.55 (m, 4H), 3.34-3.32 (m, 2H), 2.52-2.51 (m, 2H), 2.47-2.42 (m, 4H), 1.45 (d, 3H). |

TABLE 1-continued

| Ex. No. | Structure | Chemical Name | ESI-MS (M + H) | ¹H NMR |
|---|---|---|---|---|
| 203 | 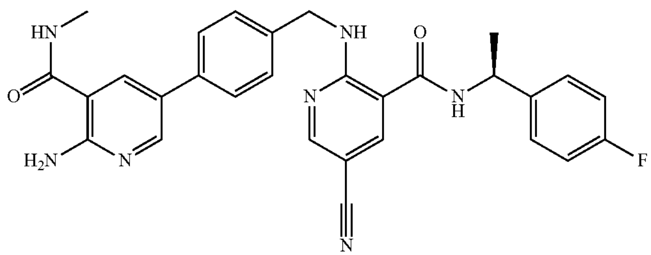 [SMILES: CNC(=O)c1cc(-c2ccc(CNc3ncc(C#N)cc3C(=O)N[C@@H](C)c3ccc(F)cc3)cc2)cnc1N] | (S)-2-amino-5-(4-((5-cyano-3-(1-(4-fluorophenyl)ethylcarbamoyl)pyridin-2-ylamino)methyl)phenyl)-N-methylnicotinamide | 524 | ¹H NMR (400 MHz, DMSO-d₆) δ: 9.33 (t, 1H), 9.01 (d, 1H), 8.58 (dd, 1H), 8.54 (dd, 1H), 8.48 (dd, 1H), 8.39 (dd, 1H), 8.15 (dd, 1H), 7.61 (d, 2H), 7.43-7.41 (m, 2H), 7.35 (d, 2H), 7.19-7.15 (m, 4H), 5.11-5.08 (m, 1H), 4.68 (d, 2H), 2.77 (d, 3H), 1.45 (d, 3H). |
| 204 | 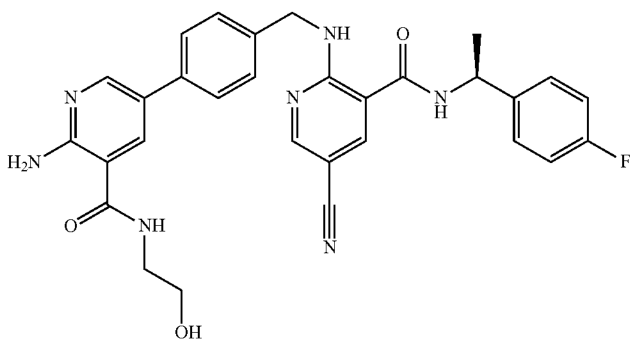 [SMILES: C[C@H](NC(=O)c1cc(C#N)cnc1NCc1ccc(-c2cnc(N)c(C(=O)NCCO)c2)cc1)c1ccc(F)cc1] | (S)-2-amino-5-(4-((5-cyano-3-(1-(4-fluorophenyl)ethylcarbamoyl)pyridin-2-ylamino)methyl)phenyl)-N-(2-hydroxyethyl)nicotinamide | 554 | ¹H NMR (400 MHz, DMSO-d₆) δ: 9.33 (d, 1H), 8.58 (d, 2H), 8.48-8.39 (m, 2H), 8.19 (d, 1H), 7.62 (d, 2H), 7.43-7.35 (m, 4H), 7.35-7.13 (m, 4H), 5.11-5.07 (m, 1H), 4.76 (t, 1H), 4.68 (d, 2H), 3.51-3.48 (m, 2H), 3.34-3.30 (m, 2H), 1.45 (d, 3H). |
| 205 | 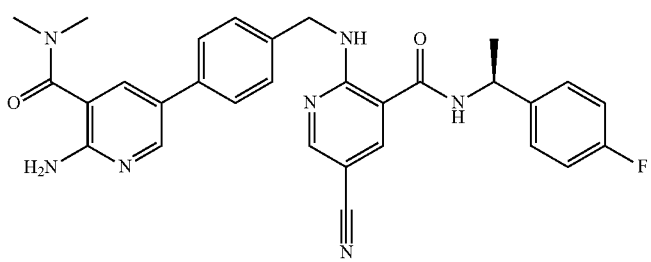 [SMILES: C[C@H](NC(=O)c1cc(C#N)cnc1NCc1ccc(-c2cnc(N)c(C(=O)N(C)C)c2)cc1)c1ccc(F)cc1] | (S)-2-amino-5-(4-((5-cyano-3-(1-(4-fluorophenyl)ethylcarbamoyl)pyridin-2-ylamino)methyl)phenyl)-N,N-dimethylnicotinamide | 538.3 | ¹HNMR (400 MHz, DMSO-d₆) δ: 9.34-9.33 (m, 1H), 9.01 (d, 1H), 8.58 (s, 1H), 8.48 (s, 1H), 8.32 (s, 1H), 7.66 (s, 1H), 7.56-7.54 (m, 2H), 7.44-7.40 (m, 2H), 7.33-7.31 (m, 2H), 7.17-7.13 (m, 2H), 6.11 (s, 2H), 5.11-5.07 (m, 1H), 4.68 (s, 2H), 2.95 (s, 6H), 1.46 (d, 3H). |

| Ex. No. | Structure | Chemical Name | ESI-MS (M + H) | ¹H NMR |
|---|---|---|---|---|
| 206 | 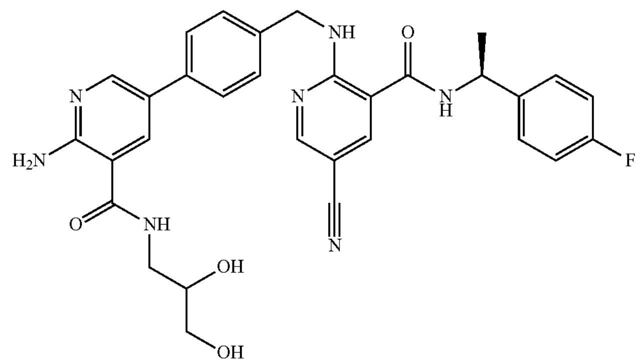 [SMILES: C[C@H](NC(=O)c1cc(C#N)cnc1NCc1ccc(-c2cnc(N)c(C(=O)NCC(O)CO)c2)cc1)c1ccc(F)cc1] | 2-amino-5-(4-((5-cyano-3-((S)-1-(4-fluorophenyl)ethylcarbamoyl)pyridin-2-ylamino)methyl)phenyl)-N-(2,3-dihydroxypropyl)nicotinamide | 584.0 | ¹H NMR (400 MHz, DMSO-d₆) δ: 9.34 (s, 1H), 9.02 (d,1H), 8.87 (s, 1H), 8.58 (d, 1H), 8.54 (s, 1H), 8.49 (d, 1H), 8.43 (d, 1H), 7.95 (br, 2H), 7.67 (d, 2H), 7.44-7.40 (m, 4H), 7.15 (t, 2H), 5.09-5.07 (m, 1H), 4.71-4.69 (m, 2H), 3.95-3.93 (m, 1H), 3.67-3.64 (m, 2H), 3.46-3.41 (m, 1H), 3.37-3.35 (m, 2H), 3.20-3.12 (m, 1H), 1.46 (d, 3H). |
| 207 | 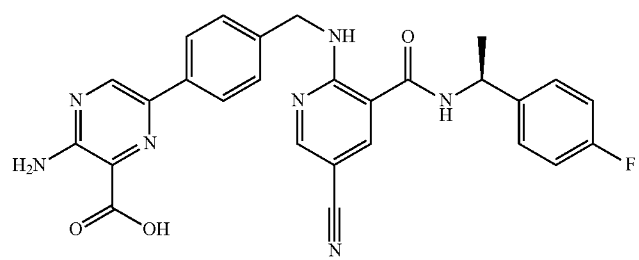 [SMILES: C[C@H](NC(=O)c1cc(C#N)cnc1NCc1ccc(-c2cnc(N)c(C(=O)O)n2)cc1)c1ccc(F)cc1] | (S)-3-amino-6-(4-((5-cyano-3-(1-(4-fluorophenyl)ethylcarbamoyl)pyridin-2-ylamino)methyl)phenyl)pyrazine-2-carboxylic acid | 512 | ¹H NMR (400 MHz, CD₃OD/CDCl₃) δ: 8.41 (br, 2H), 8.21 (s, 1H), 7.74 (br, 2H), 7.34 (br, 4H), 6.70 (t, 2H), 5.16-5.12 (m, 1H), 4.72 (s, 2H), 1.52 (d, 3H). |
| 208 | 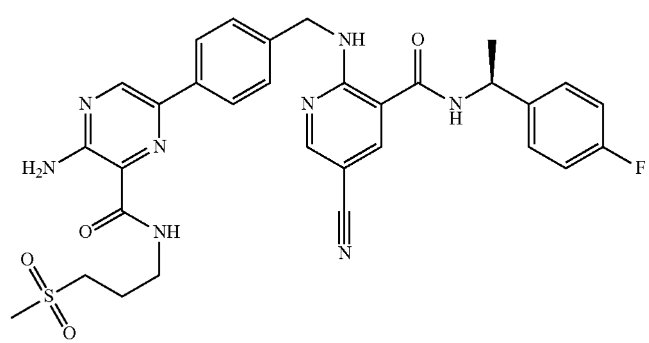 [SMILES: C[C@H](NC(=O)c1cc(C#N)cnc1NCc1ccc(-c2cnc(N)c(C(=O)NCCCS(C)(=O)=O)n2)cc1)c1ccc(F)cc1] | (S)-3-amino-6-(4-((5-cyano-3-(1-(4-fluorophenyl)ethylcarbamoyl)pyridin-2-ylamino)methyl)phenyl)-N-(3-methylsulfonyl)propyl)pyrazine-2-carboxamide | 631.2 | ¹H NMR (400 MHz, DMSO-d₆) δ: 9.35 (t, 1H), 9.03-8.97 (m, 2H), 8.81 (s, 1H), 8.58 (s, 1H), 8.49 (s, 1H), 8.10 (d, 2H), 7.51 (br, 2H), 7.44-7.37 (m, 4H), 7.15 (t, 2H), 5.09 (m, 1H), 4.71 (d, 2H), 3.45-3.39 (m, 2H), 3.16 (t, 2H), 2.98 (s, 3H), 2.00-1.96 (m, 2H), 1.46 (d, 3H). |

| Ex. No. | Structure | Chemical Name | ESI-MS (M + H) | ¹H NMR |
|---|---|---|---|---|
| 209 | 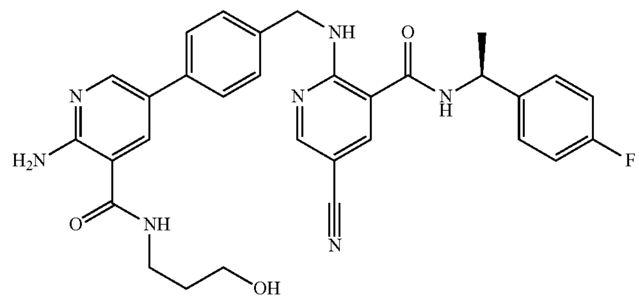 [SMILES: C[C@H](NC(=O)c1cc(C#N)cnc1NCc1ccc(-c2cnc(N)c(C(=O)NCCCO)c2)cc1)c1ccc(F)cc1] | (S)-3-amino-6-(4-((5-cyano-3-(1-(4-fluorophenyl)ethylcarbamoyl)pyridin-2-ylamino)methyl)phenyl)-N-(3-hydroxypropyl)pyrazine-2-carboxamide | 569 | ¹H NMR (400 MHz, DMSO-d₆) δ: 9.36 (t, 1H), 9.02 (d, 1H), 8.95 (t, 1H), 8.80 (s, 1H), 8.58 (d, 1H), 8.48 (d, 1H), 8.07 (d, 2H), 7.44-7.36 (m, 4H), 7.16 (t, 2H), 5.11-5.09 (m, 1H), 4.71 (d, 2H), 4.68-4.65 (m, 1H), 3.53-3.49 (m, 2H), 3.38-3.34 (m, 2H), 1.72-1.67 (m, 2H), 1.45 (d, 3H). |
| 210 | 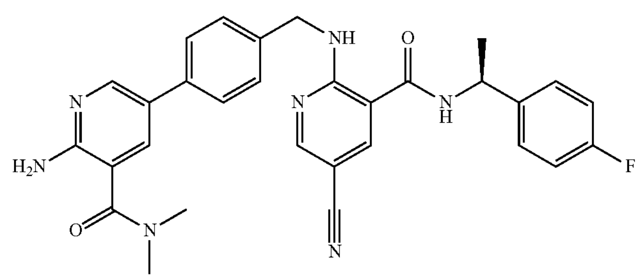 [SMILES: C[C@H](NC(=O)c1cc(C#N)cnc1NCc1ccc(-c2cnc(N)c(C(=O)N(C)C)c2)cc1)c1ccc(F)cc1] | (S)-3-amino-6-(4-((5-cyano-3-(1-(4-fluorophenyl)ethylcarbamoyl)pyridin-2-ylamino)methyl)phenyl)-N,N-dimethylpyrazine-2-carboxamide | 539.1 | ¹H NMR (400 MHz, DMSO-d₆) δ: 9.35 (t, 1H), 9.01 (d, 1H), 8.61 (s, 1H), 8.57 (s, 1H), 8.47 (d, 1H), 7.85 (d, 2H), 7.43-7.40 (m, 2H), 7.35 (d, 2H), 7.17 (t, 2H), 6.65 (s, 2H), 5.11-5.09 (m, 1H), 4.68 (d, 2H), 3.02 (s, 6H), 1.46 (d, 3H). |
| 211 | 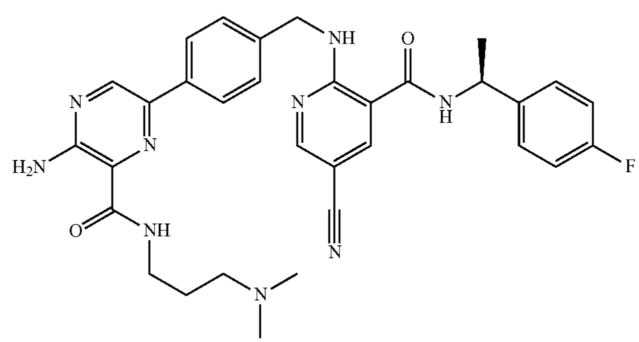 [SMILES: C[C@H](NC(=O)c1cc(C#N)cnc1NCc1ccc(-c2cnc(N)c(C(=O)NCCCN(C)C)n2)cc1)c1ccc(F)cc1] | (S)-3-amino-6-(4-((5-cyano-3-(1-(4-fluorophenyl)ethylcarbamoyl)pyridin-2-ylamino)methyl)phenyl)-N-(3-dimethylamino)propyl)pyrazine-2-carboxamide | 596 | ¹H NMR (400 MHz, DMSO-d₆) δ: 9.36 (t, 1H), 9.05-9.01 (m, 2H), 8.81 (s, 1H), 8.58 (d, 1H), 8.49 (d, 1H), 8.06 (d, 2H), 7.44-7.37 (m, 4H), 7.15 (t, 2H), 5.11-5.09 (m, 1H), 4.71 (d, 2H), 3.37-3.32 (m, 2H), 2.44 (t, 2H), 2.25 (s, 6H), 1.75-1.72 (m, 2H), 1.46 (d, 3H). |

| Ex. No. | Structure | Chemical Name | ESI-MS (M + H) | ¹H NMR |
|---|---|---|---|---|
| 212 | 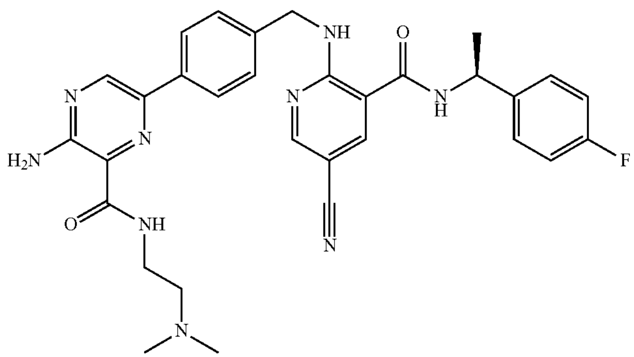 [SMILES: C[C@H](NC(=O)c1cc(C#N)cnc1NCc1ccc(-c2cnc(N)c(C(=O)NCCN(C)C)n2)cc1)c1ccc(F)cc1] | (S)-3-amino-6-(4-((5-cyano-3-(1-(4-fluorophenyl)ethylcarbamoyl)pyridin-2-ylamino)methyl)phenyl)-N-(2-dimethylamino)ethyl)pyrazine-2-carboxamide | 582 | ¹H NMR (400 MHz, CDCl₃) δ: 9.20 (t, 1H), 8.46 (s, 1H), 8.45 (s, 2H), 7.89-7.85 (m, 3H), 7.43 (d, 2H), 7.36-7.32 (m, 2H), 7.06 (t, 2H), 6.48 (d, 1H), 5.20-5.16 (m, 1H), 4.78-4.74 (m, 2H), 3.63 (t, 2H), 2.72 (t, 2H), 2.44 (s, 6H), 1.58 (d, 3H). |
| 213 | 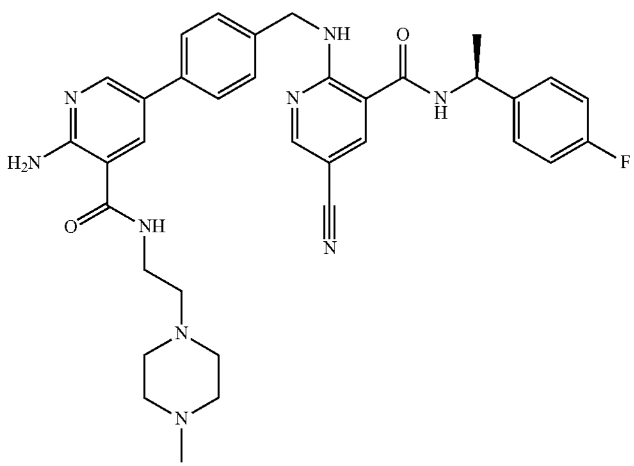 [SMILES: C[C@H](NC(=O)c1cc(C#N)cnc1NCc1ccc(-c2cnc(N)c(C(=O)NCCN3CCN(C)CC3)c2)cc1)c1ccc(F)cc1] | (S)-3-amino-6-(4-((5-cyano-3-(1-(4-fluorophenyl)ethylcarbamoyl)pyridin-2-ylamino)methyl)phenyl)-N-(2-(4-methylpiperazin-1-yl)ethyl)pyrazine-2-carboxamide | 637.2 | ¹H NMR (400 MHz, CDCl₃) δ: 9.28 (t, 1H), 8.63-8.62 (m, 2H), 8.46 (d, 1H), 7.95 (d, 1H), 7.91 (d, 2H), 7.44 (d, 2H), 7.36-7.32 (m, 2H), 7.08-7.04 (m, 2H), 6.64 (d, 1H), 5.20-5.18 (m, 1H), 4.82-4.76 (m, 2H), 3.55-3.54 (m, 2H), 2.67-2.64 (m, 10H), 2.32 (s, 3H), 1.58 (d, 3H). |

TABLE 1-continued

| Ex. No. | Structure | Chemical Name | ESI-MS (M + H) | ¹H NMR |
|---|---|---|---|---|
| 214 | 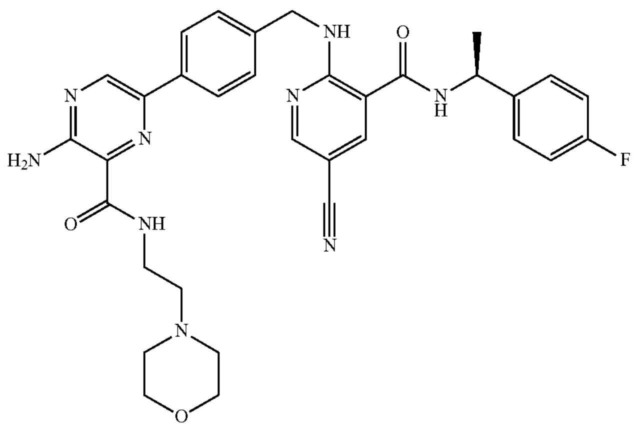 [SMILES: C[C@H](NC(=O)c1cc(C#N)cnc1NCc1ccc(-c2cnc(N)c(C(=O)NCCN3CCOCC3)n2)cc1)c1ccc(F)cc1] | (S)-3-amino-6-(4-((5-cyano-3-(1-(4-fluorophenyl)ethylcarbamoyl)pyridin-2-ylamino)methyl)phenyl)-N-(2-morpholinoethyl)pyrazine-2-carboxamide | 624 | ¹H NMR (400 MHz, DMSO-d₆) δ: 9.36 (t, 1H), 9.00 (d, 1H), 8.82-8.78 (m, 2H), 8.57 (d, 1H), 8.48 (d, 1H), 8.06 (d, 2H), 7.62 (br, 2H), 7.44-7.37 (m, 4H), 7.15 (t, 2H), 5.11-5.08 (m, 1H), 4.70 (d, 2H), 3.59 (t, 4H), 3.44-3.42 (m, 2H), 2.52-2.50 (m, 2H), 2.44 (s, 4H), 1.46 (d, 3H). |
| 215 | 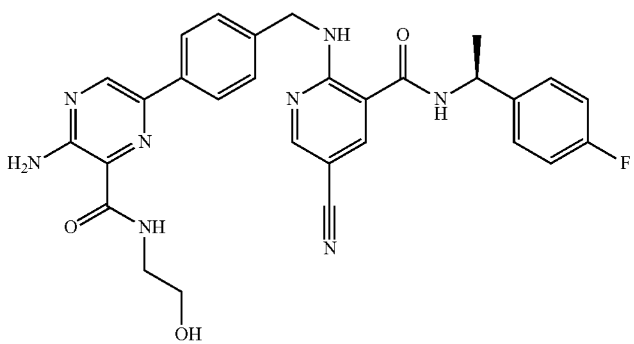 [SMILES: C[C@H](NC(=O)c1cc(C#N)cnc1NCc1ccc(-c2cnc(N)c(C(=O)NCCO)n2)cc1)c1ccc(F)cc1] | (S)-3-amino-6-(4-((5-cyano-3-(1-(4-fluorophenyl)ethylcarbamoyl)pyridin-2-ylamino)methyl)phenyl)-N-(2-hydroxyethyl)pyrazine-2-carboxamide | 555.3 | ¹H NMR (400 MHz, DMSO-d₆) δ: 9.33 (t, 1H), 9.01 (d, 1H), 8.81 (s, 1H), 8.75 (t, 1H), 8.58 (d, 1H), 8.48 (d, 1H), 8.06 (d, 2H), 7.65 (br, 2H), 7.44-7.37 (m, 4H), 7.15 (t, 2H), 5.11-5.08 (m, 1H), 4.81 (t, 1H), 4.71 (d, 2H), 3.55-3.52 (m, 2H), 3.40-3.38 (m, 2H), 1.46 (d, 3H). |
| 216 | 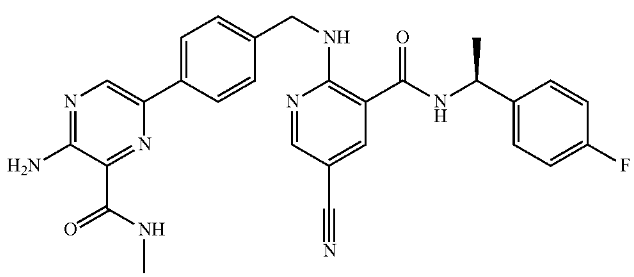 [SMILES: CNC(=O)c1nc(-c2ccc(CNc3ncc(C#N)cc3C(=O)N[C@@H](C)c3ccc(F)cc3)cc2)cnc1N] | (S)-3-amino-6-(4-((5-cyano-3-(1-(4-fluorophenyl)ethylcarbamoyl)pyridin-2-ylamino)methyl)phenyl)-N-methylpyrazine-2-carboxamide | 525 | ¹H NMR (400 MHz, DMSO-d₆) δ: 9.35 (t, 1H), 9.00 (d, 1H), 8.80 (s, 1H), 8.78 (s, 1H), 8.58 (d, 1H), 8.48 (d, 1H), 8.09 (d, 2H), 7.60 (br, 2H), 7.44-7.36 (m, 4H), 7.15 (t, 2H), 5.11-5.08 (m, 1H), 4.70 (d, 2H), 2.83 (d, 3H), 1.45 (d, 3H). |

TABLE 1-continued

| Ex. No. | Structure | Chemical Name | ESI-MS (M + H) | ¹H NMR |
|---|---|---|---|---|
| 217 | 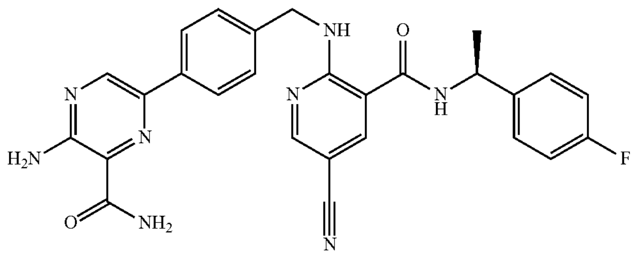 | (S)-3-amino-6-(4-((5-cyano-3-(1-(4-fluorophenyl)ethylcarbamoyl)pyridin-2-ylamino)methyl)phenyl)pyrazine-2-carboxamide | 511 | ¹HNMR (400 MHz, DMSO-$d_6$) δ: 9.35 (t, 1H), 9.01 (d, 1H), 8.80 (s, 1H), 8.58 (d, 1H), 8.48 (d, 1H), 8.21 (s, 1H), 8.10 (d, 2H), 7.69 (s, 1H), 7.65 (br, 2H), 7.44-7.41 (m, 2H), 7.35 (d, 2H), 7.16 (t, 2H), 5.12-5.09 (m, 1H), 4.70 (d, 2H), 1.46 (d, 3H). |
| 218 | 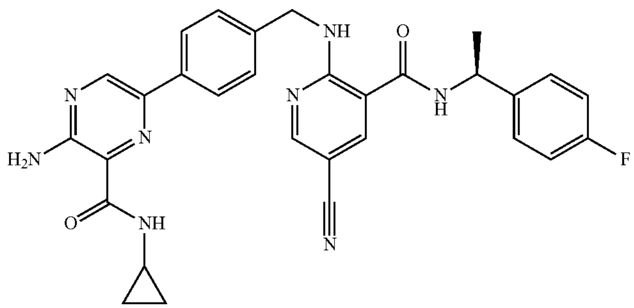 [SMILES: C[C@H](NC(=O)c1cc(C#N)cnc1NCc1ccc(-c2cnc(N)c(C(=O)NC3CC3)n2)cc1)c1ccc(F)cc1] | (S)-3-amino-6-(4-((5-cyano-3-(1-(4-fluorophenyl)ethylcarbamoyl)pyridin-2-ylamino)methyl)phenyl)-N-cyclopropylpyrazine-2-carboxamide | 551.3 | ¹H NMR (400 MHz, DMSO-$d_6$) δ: 9.35 (t, 1H), 9.01 (d, 1H), 8.78 (s, 1H), 8.63 (d, 1H), 8.57 (d, 1H), 8.48 (d, 1H), 8.05 (d, 2H), 7.45 (br, 2H), 7.44-7.40 (m, 2H), 7.35 (d, 2H), 7.17-7.13 (m, 2H), 5.11-5.08 (m, 1H), 4.70 (d, 2H), 2.85-2.83 (m, 1H), 1.45 (d, 3H), 0.74-0.69 (m, 4H). |
| 219 | 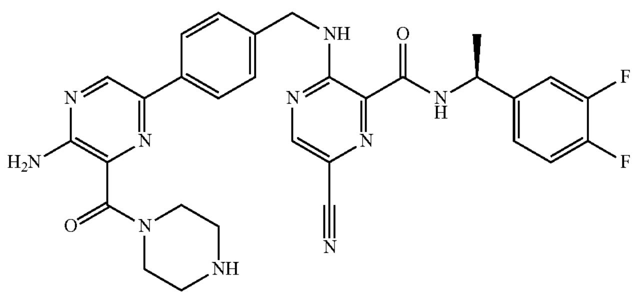 [SMILES: C[C@H](NC(=O)c1nc(C#N)cnc1NCc1ccc(-c2cnc(N)c(C(=O)N3CCNCC3)n2)cc1)c1ccc(F)c(F)c1] | 3-{4-[5-Amino-6-(piperazine-1-carbonyl)-pyrazin-2-yl]-benzylamino}-6-cyano-pyrazine-2-carboxylic acid [(S)-1-(3,4-difluoro-phenyl)-ethyl]-amide | 599.47 | ¹H NMR (400 MHz, DMSO-$d_6$) δ 9.74 (t, J = 6.02 Hz, 1H), 9.35 (d, J = 8.28 Hz, 1H), 8.89 (br. s., 2H), 8.74 (s, 1H), 8.68 (s, 1H), 7.86 (d, J = 8.28 Hz, 2H), 7.51 (ddd, J = 2.13, 7.78, 11.92 Hz, 1H), 7.34-7.43 (m, 3H), 7.23-7.29 (m, 1H), 5.07-5.16 (m, 1H), 4.66-4.77 (m, 2H), 3.86 (br. s., 2H), 3.75 (br. s., 2H), 3.27 (br. s., 2H), 3.16 (br. s., 2H), 1.52 (d, J = 7.03 Hz, 3H) |

TABLE 1-continued

| Ex. No. | Structure | Chemical Name | ESI-MS (M + H) | $^1$H NMR |
|---|---|---|---|---|
| 220 | 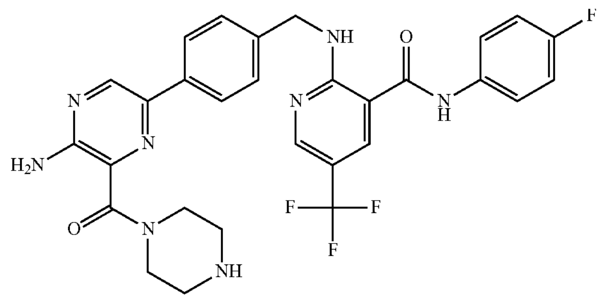 [SMILES: Nc1ncc(-c2ccc(CNc3ncc(C(F)(F)F)cc3C(=O)Nc3ccc(F)cc3)cc2)nc1C(=O)N1CCNCC1] | 2-{4-[5-Amino-6-(piperazine-1-carbonyl)-pyrazin-2-yl]-benzylamino}-N-(4-fluoro-phenyl)-5-trifluoromethyl-nicotinamide | 595.45 | $^1$H NMR (400 MHz, DMSO-d$_6$) δ 10.52 (s, 1H), 8.85-8.94 (m, 3H), 8.68 (s, 1H), 8.54 (d, J = 1.26 Hz, 1H), 8.40 (d, J = 2.26 Hz, 1H), 7.87 (d, J = 8.53 Hz, 2H), 7.66-7.72 (m, 2H), 7.42 (d, J = 8.28 Hz, 2H), 7.18-7.25 (m, 2H), 4.75 (d, J = 5.77 Hz, 2H), 3.86 (br. s., 2H), 3.76 (br. s., 2H), 3.17 (br. s., 2H) |
| 221 | 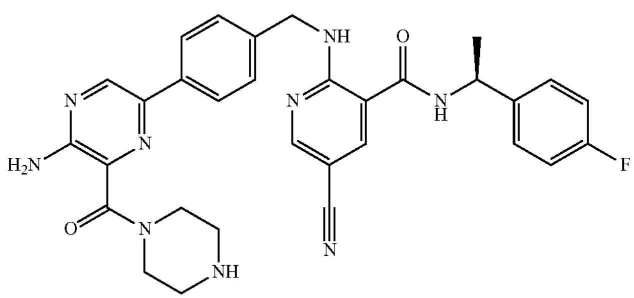 [SMILES: C[C@H](NC(=O)c1cc(C#N)cnc1NCc1ccc(-c2cnc(N)c(C(=O)N3CCNCC3)n2)cc1)c1ccc(F)cc1] | 2-{4-[5-Amino-6-(piperazine-1-carbonyl)-pyrazin-2-yl]-benzylamino}-5-cyano-N-[(S)-1-(4-fluoro-phenyl)-ethyl]-nicotinamide | 580 | $^1$H NMR (400 MHz, DMSO-d$_6$) δ 9.31-9.36 (m, 1H), 9.01 (d, J = 7.53 Hz, 1H), 8.90 (br. s., 2H), 8.67 (s, 1H), 8.57 (d, J = 2.26 Hz, 1H), 8.49 (d, J = 2.01 Hz, 1H), 7.85 (d, J = 8.53 Hz, 2H), 7.39-7.44 (m, 2H), 7.36 (d, J = 8.28 Hz, 2H), 7.11-7.18 (m, 2H), 6.78 (br. s., 1H), 5.05-5.13 (m, 1H), 4.70 (d, J = 6.02 Hz, 2H), 3.86 (br. s., 2H), 3.75 (br. s., 2H), 3.27 (br. s., 2H), 3.17 (br. s., 2H), 1.46 (d, J = 7.03 Hz, 3H) |
| 222 | 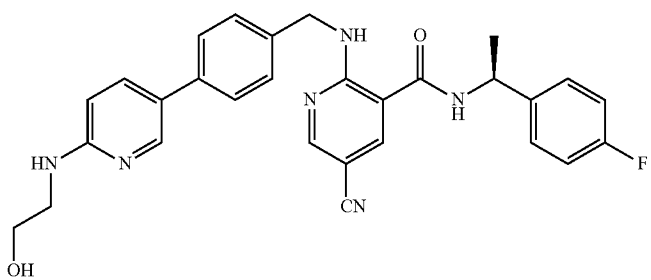 [SMILES: C[C@H](NC(=O)c1cc(C#N)cnc1NCc1ccc(-c2ccc(NCCO)nc2)cc1)c1ccc(F)cc1] | 5-Cyano-N-[(S)-1-(4-fluoro-phenyl)-ethyl]-2-{4-[6-(2-hydroxy-ethylamino)-pyridin-3-yl]-benzylamino}-nicotinamide | 510.9 | $^1$H NMR (400 MHz, CD$_3$OD) δ 8.80-8.87 (m, 1H), 8.43-8.49 (m, 1H), 8.25-8.28 (m, 1H), 8.21-8.25 (m, 1H), 8.03-8.06 (m, 1H), 7.55-7.60 (m, 1H), 7.46 (d, J = 8.53 Hz, 2H), 7.38-7.44 (m, 2H), 7.18-7.21 (m, J = 0.50 Hz, 1H), 7.04-7.10 (m, 2H), 5.14-5.22 (m, 1H), 4.78 (s, 2H), 3.84 (d, J = 10.29 Hz, 2H), 3.57 (d, J = 10.29 Hz, 2H), 2.67 (s, 1H), 1.55 (d, J = 7.03 Hz, 3H) |

| Ex. No. | Structure | Chemical Name | ESI-MS (M + H) | ¹H NMR |
|---|---|---|---|---|
| 223 | 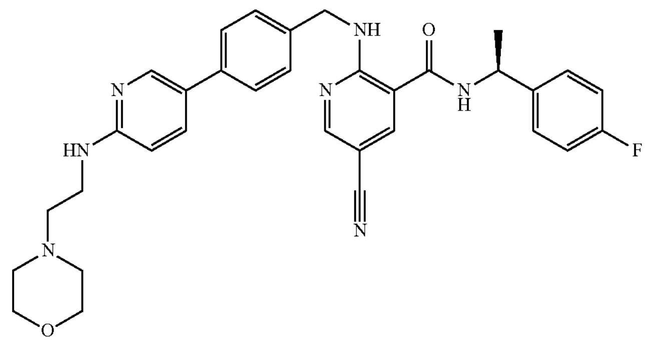 [SMILES: C[C@H](NC(=O)c1cc(C#N)cnc1NCc1ccc(-c2ccc(NCCN3CCOCC3)nc2)cc1)c1ccc(F)cc1] | 5-Cyano-N-[(S)-1-(4-fluoro-phenyl)-ethyl]-2-{4-[6-(2-morpholin-4-yl-ethylamino)-pyridin-3-yl]-benzylamino}-nicotinamide | 580 | ¹H NMR (400 MHz, CD₃OD) δ 8.81-8.85 (m, 0H), 8.47 (d, J = 2.26 Hz, 1H), 8.28-8.30 (m, 1H), 8.26 (d, J = 2.01 Hz, 1H), 7.99-8.05 (m, 1H), 7.54-7.58 (m, 2H), 7.38-7.46 (m, 4H), 7.03-7.10 (m, 2H), 6.94 (d, J = 8.78 Hz, 1H), 5.13-5.22 (m, 1H), 4.77 (br. s., 2H), 3.96-4.01 (m, 4H), 3.77-3.81 (m, 2H), 3.38-3.43 (m, 6H), 1.55 (d, J = 7.03 Hz, 3H) |
| 224 | 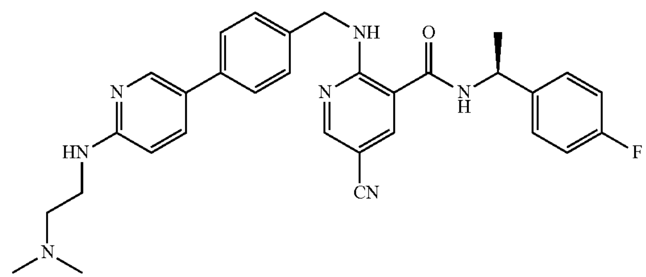 [SMILES: C[C@H](NC(=O)c1cc(C#N)cnc1NCc1ccc(-c2ccc(NCCN(C)C)nc2)cc1)c1ccc(F)cc1] | 5-Cyano-2-{4-[6-(2-dimethylamino-ethylamino)-pyridin-3-yl]-benzylamino}-N-[(S)-1-(4-fluoro-phenyl)-ethyl]-nicotinamide | 538 | ¹H NMR (400 MHz, CD₃OD) δ 8.80-8.86 (m, 1H), 8.45-8.49 (m, 1H), 8.29-8.33 (m, 1H), 8.24-8.28 (m, 1H), 7.93-8.00 (m, 1H), 7.51-7.57 (m, 2H), 7.37-7.45 (m, 4H), 7.02-7.11 (m, 2H), 6.89 (d, J = 9.04 Hz, 1H), 6.82 (none, 1H), 5.14-5.22 (m, 1H), 4.76 (s, 2H), 3.77 (t, 2H), 3.39-3.45 (m, J = 5.52 Hz, 2H), 3.00 (s, 6H), 2.65-2.69 (m, 1H), 1.55 (d, J = 7.03 Hz, 3H) |
| 225 | 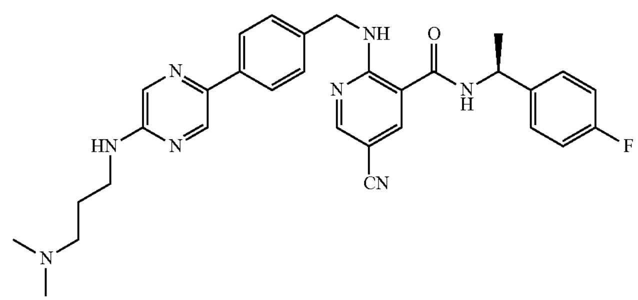 [SMILES: C[C@H](NC(=O)c1cc(C#N)cnc1NCc1ccc(-c2cnc(NCCCN(C)C)cn2)cc1)c1ccc(F)cc1] | 5-Cyano-2-{4-[5-(3-dimethylamino-propylamino)-pyrazin-2-yl]-benzylamino}-N-[(S)-1-(4-fluoro-phenyl)-ethyl]-nicotinamide | 553.3 | ¹H NMR (400 MHz, CD₃OD) δ 8.81-8.85 (m, 1H), 8.54 (d, J = 1.51 Hz, 1H), 8.48 (d, J = 2.01 Hz, 1H), 8.26 (d, J = 2.26 Hz, 1H), 8.19 (d, J = 1.51 Hz, 1H), 7.82-7.87 (m, 2H), 7.38-7.44 (m, 4H), 7.04-7.10 (m, 2H), 5.16-5.22 (m, 1H), 4.77 (br. s., 2H), 3.77 (t, J = 6.53 Hz, 2H), 3.19 (s, 3H), 3.04 (t, J = 7.15 Hz, 2H), 2.74 (s, 3H), 2.01-2.11 (m, 2H), 1.55 (d, J = 7.03 Hz, 3H) |

TABLE 1-continued

| Ex. No. | Structure | Chemical Name | ESI-MS (M + H) | ¹H NMR |
|---|---|---|---|---|
| 226 | 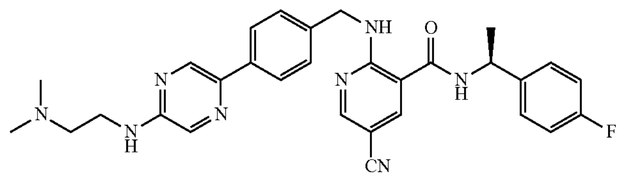 [SMILES: C[C@H](NC(=O)c1cc(C#N)cnc1NCc1ccc(-c2cnc(NCCN(C)C)cn2)cc1)c1ccc(F)cc1] | 5-Cyano-2-{4-[5-(2-dimethylamino-ethylamino)-pyrazin-2-yl]-benzylamino}-N-[(S)-1-(4-fluoro-phenyl)-ethyl]-nicotinamide | 539.2 | ¹H NMR (400 MHz, CD₃OD) δ 8.80-8.86 (m, 1H), 8.45-8.49 (m, 1H), 8.22-8.28 (m, 1H), 8.05-8.10 (m, 1H), 7.81-7.87 (m, 2H), 7.37-7.45 (m, 4H), 7.02-7.11 (m, 2H), 5.13-5.23 (m, 1H), 4.74-4.79 (m, 2H), 3.78-3.84 (m, 2H), 3.40-3.47 (m, 2H), 2.98-3.03 (m, 6H), 1.51-1.58 (m, 3H) |
| 227 | 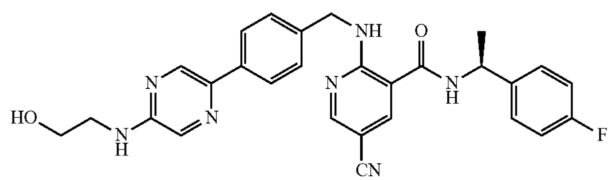 [SMILES: C[C@H](NC(=O)c1cc(C#N)cnc1NCc1ccc(-c2cnc(NCCO)cn2)cc1)c1ccc(F)cc1] | 5-Cyano-N-[(S)-1-(4-fluoro-phenyl)-ethyl]-2-{4-[5-(2-hydroxy-ethylamino)-pyrazin-2-yl]-benzylamino}-nicotinamide | 512.5 | ¹H NMR (400 MHz, CD₃OD) δ 8.81-8.87 (m, 1H), 8.47-8.51 (m, 1H), 8.35-8.39 (m, 1H), 8.23-8.28 (m, 1H), 8.13-8.17 (m, 1H), 7.80-7.86 (m, 2H), 7.38-7.46 (m, 4H), 7.04-7.12 (m, 2H), 5.15-5.24 (m, 1H), 4.75-4.80 (m, 2H), 3.79 (t, J = 5.52 Hz, 2H), 3.56 (t, J = 5.52 Hz, 2H), 2.69 (s, 1H), 1.56 (d, J = 7.28 Hz, 3H) |
| 228 | 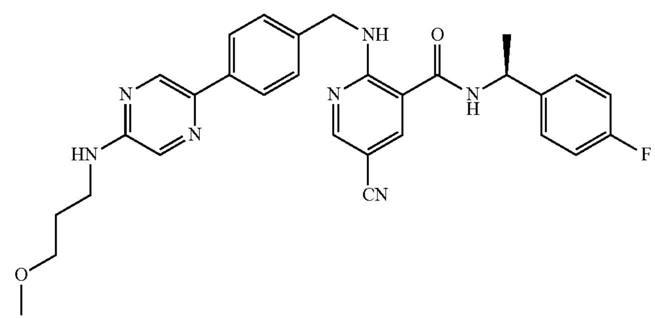 [SMILES: COCCCNc1cnc(-c2ccc(CNc3ncc(C#N)cc3C(=O)N[C@@H](C)c3ccc(F)cc3)cc2)cn1] | 5-Cyano-N-[(S)-1-(4-fluoro-phenyl)-ethyl]-2-{4-[5-(3-methoxy-propylamino)-pyrazin-2-yl]-benzylamino}-nicotinamide | 540.5 | ¹H NMR (400 MHz, CD₃OD) δ 8.76-8.86 (m, 1H), 8.45-8.50 (m, 1H), 8.19-8.24 (m, 1H), 7.76-7.83 (m, 1H), 7.35-7.45 (m, 4H), 7.13-7.18 (m, 2H), 7.02-7.11 (m, 3H), 6.70-6.77 (m, 2H), 5.10-5.23 (m, 1H), 4.54-4.65 (m, 2H), 3.44-3.57 (m, 2H), 1.48-1.58 (m, 3H) |
| 229 | 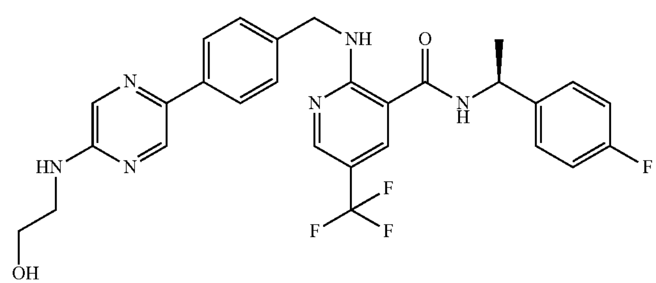 [SMILES: C[C@H](NC(=O)c1cc(C(F)(F)F)cnc1NCc1ccc(-c2cnc(NCCO)cn2)cc1)c1ccc(F)cc1] | N-(3,4-Difluoro-benzyl)-2-{4-[5-(2-hydroxy-ethylamino)-pyrazin-2-yl]-benzylamino}-5-trifluoromethyl-nicotinamide | 559.4 | ¹H NMR (400 MHz, CD₃OD) δ 8.81-8.87 (m, 1H), 8.47-8.51 (m, 1H), 8.35-8.39 (m, 1H), 8.23-8.28 (m, 1H), 8.13-8.17 (m, 1H), 7.80-7.86 (m, 2H), 7.38-7.46 (m, 4H), 7.04-7.12 (m, 2H), 5.15-5.24 (m, 1H), 4.75-4.80 (m, 2H), 3.79 (t, J = 5.52 Hz, 2H), 3.56 (t, J = 5.52 Hz, 2H), 2.69 (s, 1H), 1.56 (d, J = 7.28 Hz, 3H) |

| Ex. No. | Chemical Name | Structure | ESI-MS (M + H) | 1H NMR |
|---|---|---|---|---|
| 230 | 6-Cyano-3-{4-[5-(2-hydroxy-ethylamino)-pyrazin-2-yl]-benzylamino}-pyrazine-2-carboxylic acid [(S)-1-(3,4-difluoro-phenyl)-ethyl]-amide | 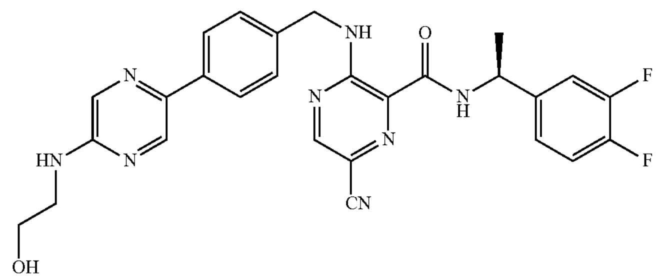 [SMILES: C[C@H](NC(=O)c1nc(C#N)cnc1NCc1ccc(-c2cnc(NCCO)cn2)cc1)c1ccc(F)c(F)c1] | 531.4 | 1H NMR (400 MHz, CD3OD) δ 9.00-9.06 (m, 1H), 8.54-8.59 (m, 1H), 8.31-8.37 (m, 1H), 8.13-8.17 (m, 1H), 7.80-7.86 (m, 2H), 7.44 (d, J = 8.53 Hz 2H), 7.31-7.39 (m, 1H), 2.38, 9.41 Hz, 1H), 7.19-7.25 (m, J = 0.75 Hz, 2H), 5.13-5.23 (m, 1H), 4.77-4.81 (m, 2H), 3.75-3.80 (m, 2H), 3.55 (t, J = 5.65 Hz, 2H), 1.58 (d, J = 7.03 Hz, 3H) |
| 231 | N-(3,4-Difluoro-benzyl)-2-{4-[5-(3-hydroxy-propylamino)-pyrazin-2-yl]-benzylamino}-5-trifluoromethyl-nicotinamide | 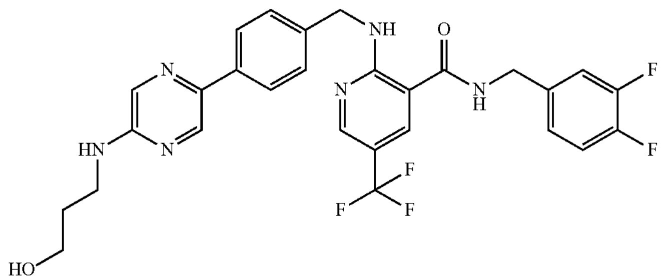 [SMILES: O=C(NCc1ccc(F)c(F)c1)c1cc(C(F)(F)F)cnc1NCc1ccc(-c2cnc(NCCCO)cn2)cc1] | 573.5 | 1H NMR (400 MHz, CD3OD) δ 9.12-9.19 (m, 1H), 8.41-8.46 (m, 1H), 8.32-8.37 (m, 1H), 8.18-8.23 (m, 1H), 8.11-8.16 (m, 1H), 7.80-7.87 (m, 2H), 7.45 (d, J = 8.53 Hz, 2H), 7.13-7.32 (m, 3H), 4.79 (s, 2H), 4.48-4.53 (m, 2H), 3.70 (t, J = 6.27 Hz, 2H), 3.48-3.54 (m, J = 6.90, 6.90 Hz, 2H), 1.90 (quin, J = 6.53 Hz, 2H) |
| 232 | 2-[4-(5-Amino-6-dimethyl-aminomethyl-pyrazin-2-yl)-benzylamino]-5-cyano-N-[(S)-1-(4-fluoro-phenyl)-ethyl]-nicotinamide | 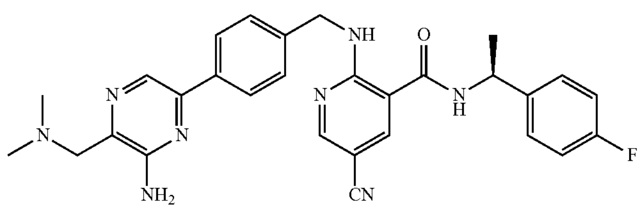 [SMILES: C[C@H](NC(=O)c1cc(C#N)cnc1NCc1ccc(-c2cnc(CN(C)C)c(N)n2)cc1)c1ccc(F)cc1] | 525.5 | 1H NMR (400 MHz, CD3OD) δ 8.81-8.86 (m, 1H), 8.55 (br. s., 1H), 8.46-8.48 (m, 1H), 8.25-8.27 (m, 1H), 7.94-7.99 (m, 2H), 7.37-7.46 (m, 4H), 7.03-7.11 (m, 2H), 5.14-5.22 (m, 1H), 4.77 (br. s., 2H), 4.44 (br. s., 2H), 3.11 (s, 6H), 1.55 (d, J = 7.28 Hz, 3H) |

| Ex. No. | Structure | Chemical Name | ESI-MS (M + H) | ¹H NMR |
|---|---|---|---|---|
| 233 | 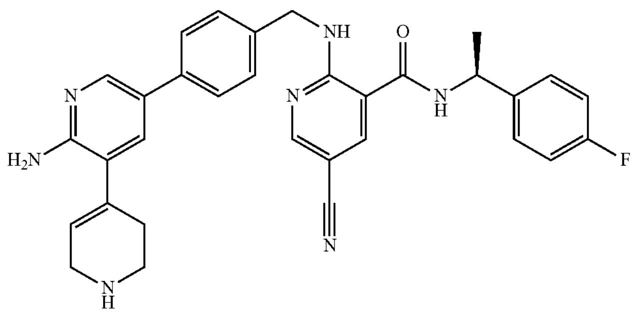 [SMILES: C[C@H](NC(=O)c1cc(C#N)cnc1NCc1ccc(-c2cnc(N)c(C3=CCNCC3)c2)cc1)c1ccc(F)cc1] | 2-{4-[5-Amino-6-(1,2,3,6-tetrahydro-pyridin-4-yl)-pyrazin-2-yl]-benzylamino}-5-cyano-N-[(S)-1-(4-fluoro-phenyl)-ethyl]-nicotinamide | 549.4 | ¹H NMR (400 MHz, CD₃OD) δ 8.81-8.85 (m, 1H), 8.77-8.89 (m, 1H), 8.47 (d, J = 2.01 Hz, 1H), 8.38 (s, 1H), 8.25 (d, J = 2.01 Hz, 1H), 7.85-7.90 (m, 2H), 7.37-7.44 (m, 4H), 7.03-7.10 (m, 2H), 6.38-6.42 (m, 1H), 5.13-5.23 (m, 1H), 4.76 (br. s., 2H), 3.89-3.94 (m, 2H), 3.54 (t, J = 6.15 Hz, 2H), 2.92-2.98 (m, 2H), 1.55 (d, J = 7.03 Hz, 3H). |
| 234 | 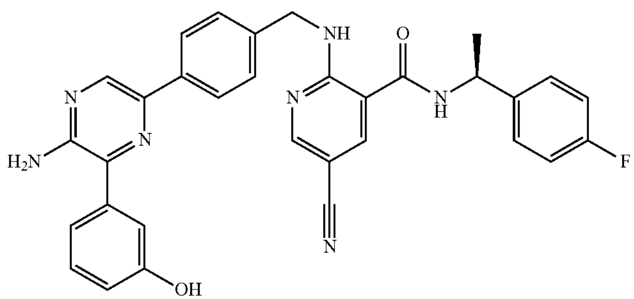 [SMILES: C[C@H](NC(=O)c1cc(C#N)cnc1NCc1ccc(-c2cnc(N)c(-c3cccc(O)c3)n2)cc1)c1ccc(F)cc1] | 2-{4-[5-Amino-6-(3-hydroxy-phenyl)-pyrazin-2-yl]-benzylamino}-5-cyano-N-[(S)-1-(4-fluoro-phenyl)-ethyl]-nicotinamide | 560.5 | ¹H NMR (400 MHz, CD₃OD) δ 8.46-8.48 (m, 1H), 8.34 (s, 1H), 8.25 (d, J = 2.26 Hz, 1H), 7.90-7.94 (m, 2H), 7.36-7.45 (m, 5H), 7.21-7.28 (m, 2H), 7.03-7.10 (m, 2H), 6.94-6.98 (m, 1H), 5.14-5.21 (m, 1H), 4.75-4.78 (m, 2H), 1.55 (d, J = 7.03 Hz, 3H) |
| 235 | 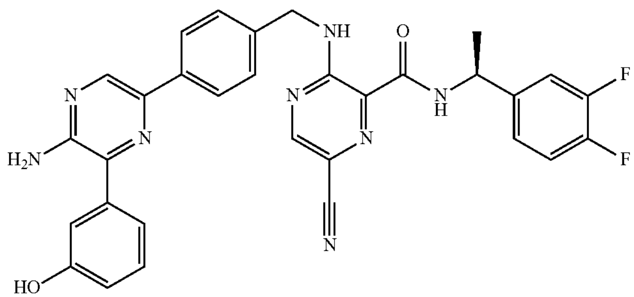 [SMILES: C[C@H](NC(=O)c1nc(C#N)cnc1NCc1ccc(-c2cnc(N)c(-c3cccc(O)c3)n2)cc1)c1ccc(F)c(F)c1] | 3-(4-[5-Amino-6-(3-hydroxy-phenyl)-pyrazin-2-yl]-benzylamino}-6-cyano-pyrazine-2-carboxylic acid [(S)-1-(3,4-difluoro-phenyl)-ethyl]-amide | 579.5 | ¹H NMR (400 MHz, CD₃OD) δ 8.99-9.05 (m, 1H), 8.57 (s, 1H), 8.35 (s, 1H), 7.91-7.95 (m, 2H), 7.45 (d, J = 8.28 Hz, 2H), 7.30-7.41 (m, 2H), 7.16-7.28 (m, 4H), 6.93-6.98 (m, 1H), 5.13-5.22 (m, 1H), 4.77-4.82 (m, 2H), 1.54-1.61 (m, 3H) |

TABLE 1-continued

| Ex. No. | Structure | Chemical Name | ESI-MS (M + H) | ¹H NMR |
|---|---|---|---|---|
| 236 | 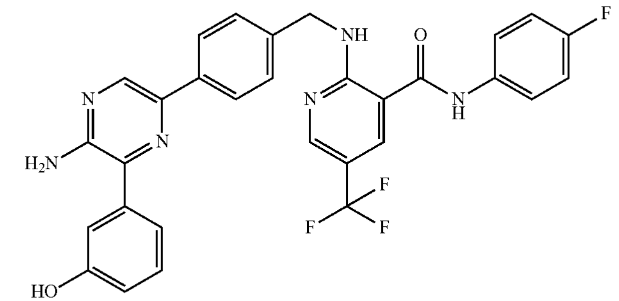 [SMILES: Nc1ncc(-c2ccc(CNc3ncc(C(F)(F)F)cc3C(=O)Nc3ccc(F)cc3)cc2)nc1-c1cccc(O)c1] | 2-{4-[5-Amino-6-(3-hydroxy-phenyl)-pyrazin-2-yl]-benzylamino}-N-(4-fluoro-phenyl)-5-trifluoromethyl-nicotinamide | 575.4 | ¹H NMR (400 MHz, CD₃OD) δ 8.45-8.48 (m, 1H), 8.33 (s, 2H), 7.92-7.97 (m, 2H), 7.63-7.70 (m, 2H), 7.46-7.51 (m, 2H), 7.37-7.42 (m, 1H), 7.19-7.28 (m, 2H), 7.06-7.14 (m, 2H), 6.94-6.99 (m, 1H), 4.82 (br. s., 2H) |
| 237 | 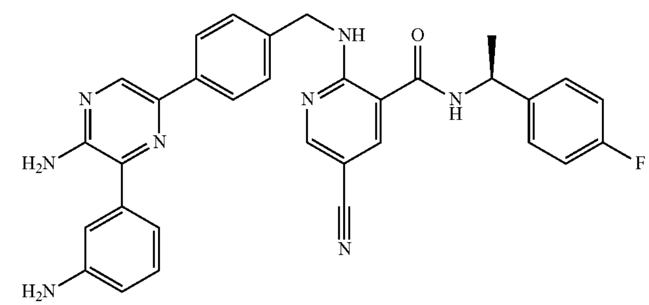 [SMILES: C[C@H](NC(=O)c1cc(C#N)cnc1NCc1ccc(-c2cnc(N)c(-c3cccc(N)c3)n2)cc1)c1ccc(F)cc1] | 2-(4-[5-Amino-6-(3-amino-phenyl)-pyrazin-2-yl]-benzylamino}-5-cyano-N-[(S)-1-(4-fluoro-phenyl)-ethyl]-nicotinamide | 559.5 | ¹H NMR (400 MHz, CD₃OD) δ 8.74-8.89 (m, 1H), 8.46-8.48 (m, 2H), 8.24-8.26 (m, 1H), 7.91-7.96 (m, 2H), 7.83-7.87 (m, 1H), 7.75-7.78 (m, 1H), 7.61-7.67 (m, 1H), 7.36-7.45 (m, 5H), 7.03-7.10 (m, 2H), 5.14-5.22 (m, 1H), 4.77 (br. s., 2H), 1.55 (d, J = 7.03 Hz, 3H) |
| 238 | 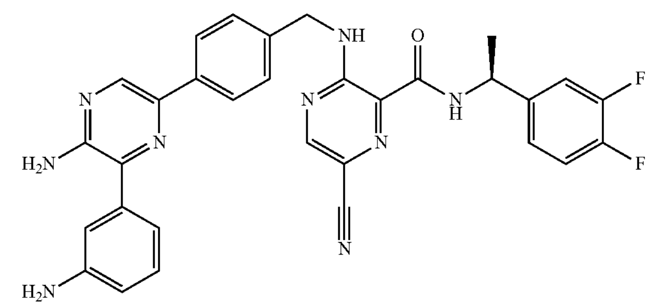 [SMILES: C[C@H](NC(=O)c1nc(C#N)cnc1NCc1ccc(-c2cnc(N)c(-c3cccc(N)c3)n2)cc1)c1ccc(F)c(F)c1] | 3-{4-[5-Amino-6-(3-amino-phenyl)-pyrazin-2-yl]-benzylamino}-6-cyano-pyrazine-2-carboxylic acid [(S)-1-(3,4-difluoro-phenyl)-ethyl]-amide | 578.5 | ¹H NMR (400 MHz, CD₃OD) δ 8.57 (s, 1H), 8.48 (s, 1H), 7.92-7.97 (m, 2H), 7.86-7.90 (m, 1H), 7.78-7.81 (m, 1H), 7.66 (t, J = 7.65 Hz, 1H), 7.31-7.47 (m, 4H), 7.18-7.24 (m, 2H), 5.13-5.23 (m, 1H), 4.80 (br. s., 2H), 1.56-1.61 (m, 3H) |

TABLE 1-continued

| Ex. No. | Structure | Chemical Name | ESI-MS (M + H) | ¹H NMR |
|---|---|---|---|---|
| 239 | 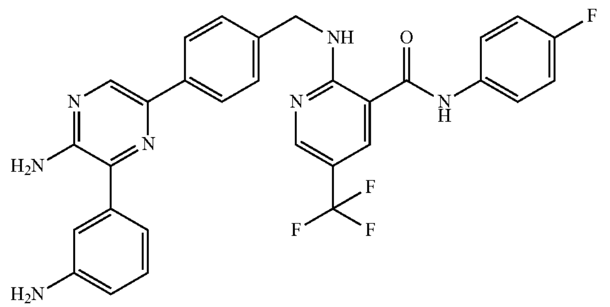 [SMILES: Nc1cccc(-c2nc(-c3ccc(CNc4ncc(C(F)(F)F)cc4C(=O)Nc4ccc(F)cc4)cc3)cnc2N)c1] | 2-[4-[5-amino-phenyl)-pyrazin-2-yl]-benzylamino]-N-(4-fluoro-phenyl)-5-trifluoromethyl-nicotinamide | 574.5 | ¹H NMR (400 MHz, CD₃OD) δ 8.44-8.49 (m, 2H), 8.32-8.35 (m, 1H), 7.93-7.97 (m, 2H), 7.88-7.93 (m, 1H), 7.81-7.84 (m, 1H), 7.63-7.70 (m, 3H), 7.45-7.50 (m, 2H), 7.40-7.45 (m, 1H), 7.06-7.13 (m, 2H), 4.82 (br. s., 2H). |
| 240 | 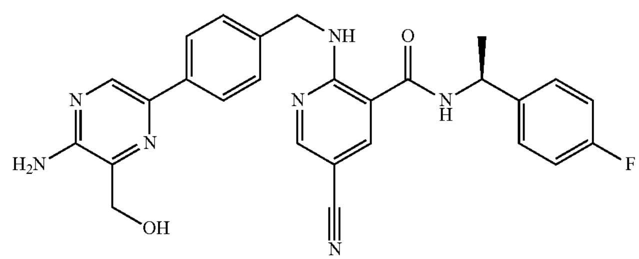 [SMILES: C[C@H](NC(=O)c1cc(C#N)cnc1NCc1ccc(-c2cnc(N)c(CO)n2)cc1)c1ccc(F)cc1] | (S)-2-(4-(5-amino-6-(hydroxymethyl)pyrazin-2-yl)benzylamino)-5-cyano-N-(1-(4-fluorophenyl)ethyl)nicotinamide | 498.1 | ¹H NMR (400 MHz, DMSO-d6) δ: 9.33 (t, 1H), 9.01 (d, 1H), 8.57 (d, 1H), 8.48 (d, 1H), 8.45 (s, 1H), 7.88 (d, 2H), 7.44-7.40 (m, 2H), 7.33 (d, 2H), 7.15 (t, 2H), 6.33 (s, 2H), 5.34 (t, 1H), 5.11-5.08 (m, 1H), 4.69 (d, 2H), 4.56 (d, 2H), 1.45 (d, 3H). |
| 241 | 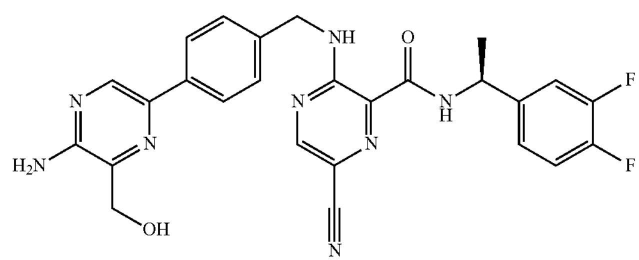 [SMILES: C[C@H](NC(=O)c1nc(C#N)cnc1NCc1ccc(-c2cnc(N)c(CO)n2)cc1)c1ccc(F)c(F)c1] | 3-[4-(5-Amino-6-hydroxy-methyl-pyrazin-2-yl)-benzylamino]-6-cyano-pyrazine-2-carboxylic acid [(S)-1-(3,4-difluoro-phenyl)-ethyl]-amide | 517.4 | ¹H NMR (400 MHz, CD₃OD) δ 9.00-9.05 (m, 1H), 8.57 (s, 1H), 8.32 (d, 1H), 7.90 (d, J = 8.53 Hz, 2H), 7.41-7.46 (m, 2H), 7.32-7.39 (m, 1H), 7.19-7.24 (m, 2H), 5.14-5.22 (m, 1H), 4.79 (d, J = 4.27 Hz, 2H), 4.77 (s, 2H), 1.58 (d, J = 7.03 Hz, 3H). |

TABLE 1-continued

| Ex. No. | Structure | Chemical Name | ESI-MS (M + H) | ¹H NMR |
|---|---|---|---|---|
| 242 | 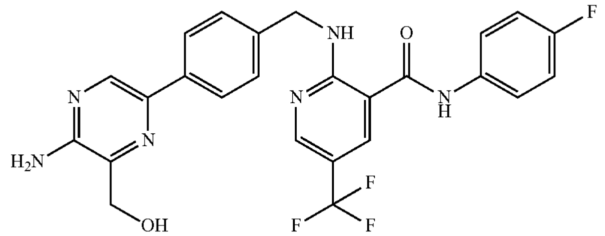 [SMILES: Nc1ncc(-c2ccc(CNc3ncc(C(F)(F)F)cc3C(=O)Nc3ccc(F)cc3)cc2)nc1CO] | 2-[4-[5-Amino-6-hydroxymethyl-pyrazin-2-yl]-benzylamino]-N-(4-fluoro-phenyl)-5-trifluoromethyl-nicotinamide | 513.4 | ¹H NMR (400 MHz, CD₃OD) δ 8.45-8.48 (m, 1H), 8.32-8.35 (m, 1H), 8.30 (s, 1H), 7.89-7.94 (m, 2H), 7.64-7.70 (m, 2H), 7.45-7.50 (m, 2H), 7.07-7.14 (m, 2H), 4.82 (br. s., 2H), 4.80 (s, 2H) |
| 243 | 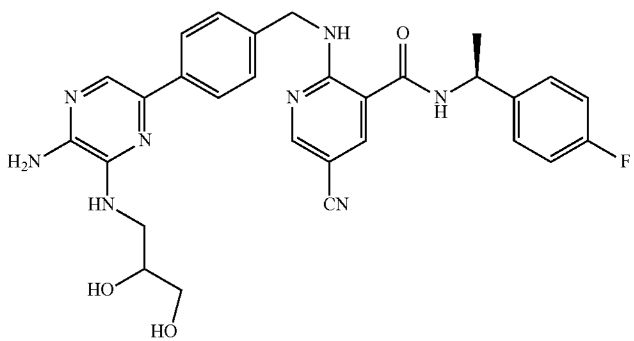 [SMILES: C[C@H](NC(=O)c1cc(C#N)cnc1NCc1ccc(-c2cnc(N)c(NCC(O)CO)n2)cc1)c1ccc(F)cc1] | 2-{4-[5-Amino-6-(2,3-dihydroxy-propylamino)-pyrazin-2-yl]-benzylamino}-5-cyano-N-[(S)-1-(4-fluoro-phenyl)-ethyl]-nicotinamide | 557.3 | ¹H NMR (400 MHz, CD₃OD) δ 8.80-8.85 (m, 1H), 8.47 (d, J = 2.01 Hz, 1H), 8.25 (d, J = 2.01 Hz, 1H), 7.86-7.90 (m, 2H), 7.55 (s, 1H), 7.38-7.44 (m, 4H), 7.03-7.10 (m, 2H), 5.14-5.23 (m, 1H), 4.76 (s, 2H), 3.97-4.04 (m, 1H), 3.89 (dd, J = 4.27, 13.80 Hz, 1H), 3.57-3.65 (m, 3H), 1.55 (d, J = Hz, 3H) |
| 244 | 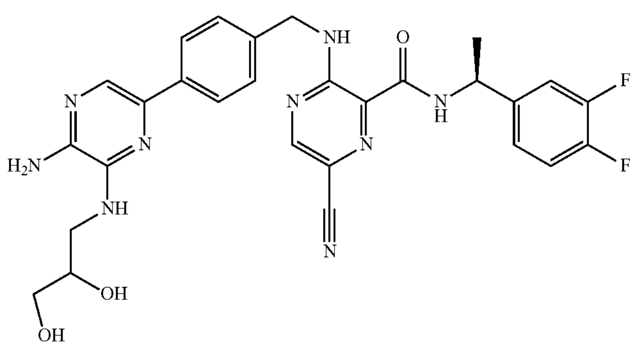 [SMILES: C[C@H](NC(=O)c1nc(C#N)cnc1NCc1ccc(-c2cnc(N)c(NCC(O)CO)n2)cc1)c1ccc(F)c(F)c1] | 3-{4-[5-Amino-6-(2,3-dihydroxy-propylamino)-pyrazin-2-yl]-benzylamino}-6-cyano-pyrazine-2-carboxylic acid [(S)-1-(3,4-difluoro-phenyl)-ethyl]-amide | 576.3 | ¹H NMR (400 MHz, CD₃OD) δ 9.02-9.06 (m, 1H), 8.57 (s, 1H), 7.87-7.92 (m, J = 5.02 Hz, 2H), 7.55 (s, 1H), 7.41-7.46 (m, 2H), 7.32-7.39 (m, 1H), 7.19-7.24 (m, 2H), 5.13-5.23 (m, 1H), 4.79 (br. s., 2H), 3.97-4.04 (m, 1H), 3.89 (dd, J = 4.27, 13.80 Hz, 1H), 3.56-3.65 (m, 3H), 1.58 (d, J = 7.28 Hz, 3H) |

TABLE 1-continued

| Ex. No. | Structure | Chemical Name | ESI-MS (M + H) | 1H NMR |
|---|---|---|---|---|
| 245 | 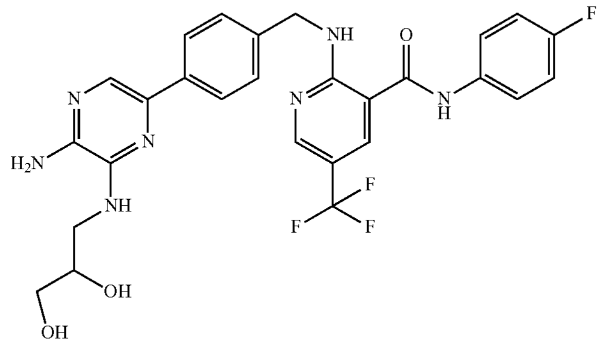 [SMILES: Nc1ncc(-c2ccc(CNc3ncc(C(F)(F)F)cc3C(=O)Nc3ccc(F)cc3)cc2)nc1NCC(O)CO] | 2-[4-[5-Amino-6-(2,3-dihydroxy-propylamino)-pyrazin-2-yl]-benzylamino]-N-(4-fluoro-phenyl)-5-trifluoromethyl-nicotinamide | 572.3 | 1H NMR (400 MHz, CD3OD) δ 8.45-8.48 (m, 1H), 8.33-8.35 (m, 1H), 7.89-7.93 (m, 2H), 7.65-7.70 (m, 2H), 7.54 (br. s., 1H), 7.47 (d, J = 8.53 Hz, 2H), 7.08-7.14 (m, 2H), 4.82 (br. s., 4H), 3.98-4.05 (m, 1H), 3.91 (dd, J = 4.27, 13.80 Hz, 1H), 3.57-3.65 (m, 3H) |
| 246 | 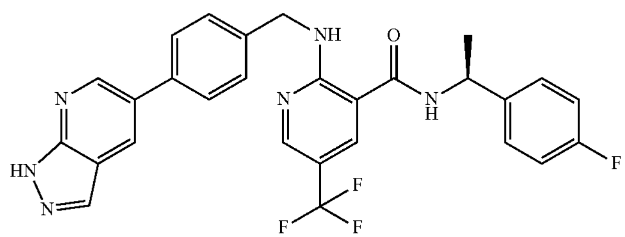 [SMILES: C[C@H](NC(=O)c1cc(C(F)(F)F)cnc1NCc1ccc(-c2cnc3[nH]ncc3c2)cc1)c1ccc(F)cc1] | N-[(S)-1-(4-Fluoro-phenyl)-ethyl]-2-[4-((1H-pyrazolo[3,4-b]pyridin-5-yl)benzylamino]-5-trifluoromethyl-nicotinamide | 535.3 | 1H NMR (400 MHz, DMSO-d6) δ 13.69 (s, 1H), 9.26 (t, J = 5.77 Hz, 1H), 9.11 (d, J = 7.53 Hz, 1H), 8.81 (d, J = 2.26 Hz, 1H), 8.48-8.53 (m, 1H), 8.42-8.46 (m, J = 0.75 Hz, 1H), 8.39-8.42 (m, 1H), 8.18 (d, J = 1.25 Hz, 1H), 7.69-7.71 (m, 1H), 7.67-7.69 (m, 1H), 7.37-7.46 (m, 4H), 7.11 -7.20 (m, 2H), 5.14 (quin, J = 7.03 Hz, 1H), 4.66-4.79 (m, 2H), 1.48 (d, 3H) |
| 247 | 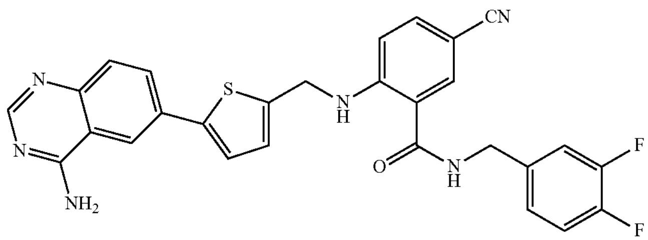 [SMILES: N#Cc1ccc(NCc2ccc(-c3ccc4ncnc(N)c4c3)s2)c(C(=O)NCc2ccc(F)c(F)c2)c1] | 2-(((5-(4-aminoquinazolin-6-yl)thiophen-2-yl)methyl)amino)-5-cyano-N-(3,4-difluorobenzyl)benzamide | 527.2 | 1H NMR (400 MHz, DMSO-d6) δ ppm 4.36 (d, J = 5.52 Hz, 2 H) 4.67 (d, J = 5.52 Hz, 2 H) 6.86 (d, J = 8.78 Hz, 1 H) 7.07 (d, J = 3.76 Hz, 1 H) 7.10-7.17 (m, 1 H) 7.28-7.38 (m, 2 H) 7.43 (d, J = 3.76 Hz, 1 H) 7.54-7.63 (m, 2 H) 7.92 (dd, J = 8.66, 2.13 Hz, 1 H) 8.05 (d, J = 2.01 Hz, 1 H) 8.28 (s, 1 H) 8.35 (d, J = 2.01 Hz, 1 H) 8.98 (t, J = 5.90 Hz, 1 H) 9.10 (t, J = 5.90 Hz, 1 H); MS: ES+/ |

TABLE 1-continued

| Ex. No. | Structure | Chemical Name | ESI-MS (M + H) | ¹H NMR |
|---|---|---|---|---|
| 248 | 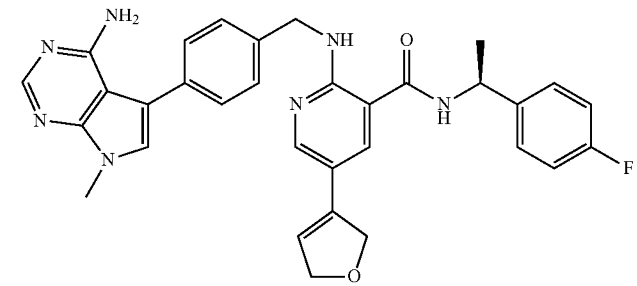 [SMILES: C[C@H](NC(=O)c1cc(C2=CCOC2)cnc1NCc1ccc(-c2cn(C)c3ncnc(N)c23)cc1)c1ccc(F)cc1] | (S)-2-(4-(4-amino-7-methyl-7H-pyrrolo[2,3-d]pyrimidin-5-yl)benzylamino)-5-(2,5-dihydrofuran-3-yl)-N-(1-(4-fluorophenyl)ethyl)nicotinamide | 563.64 | ¹H NMR (400 MHz, DMSO-d₆) δ ppm 8.94 (d, J = 7.53 Hz, 1 H) 8.84 (t, J = 5.65 Hz, 1 H) 8.42 (s, 1 H) 8.19 (d, J = 3.51 Hz, 2 H) 7.58 (s, 1 H) 7.32-7.48 (m, 6 H) 7.16 (t, J = 8.78 Hz, 2 H) 6.36 (s, 1 H) 5.10-5.18 (m, 1 H) 4.90 (br. s., 2 H) 4.62-4.78 (m, 4 H) 3.83 (s, 3 H) 1.49 (d, J = 7.03 Hz, 3 H); ¹⁹F NMR (376 MHz, DMSO-d₆) δ ppm −78.50 (TFA, s, 6 F) −120.75 (s, 1 F). |
| 249 | 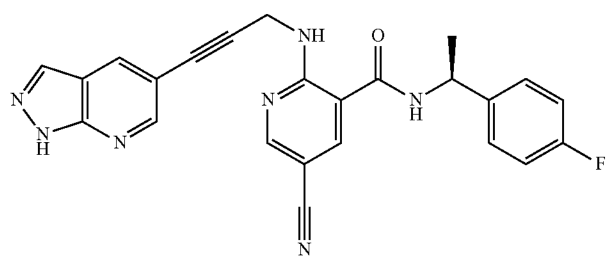 [SMILES: C[C@H](NC(=O)c1cc(C#N)cnc1NCC#Cc1cnc2[nH]ncc2c1)c1ccc(F)cc1] | (S)-2-(3-(1H-pyrazolo[3,4-b]pyridin-5-yl)prop-2-ynylamino)-5-cyano-N-(1-(4-fluorophenyl)ethyl)nicotinamide | 440 | ¹H NMR (400 MHz, DMSO-d₆) δ 9.16 (t, J = 5.65 Hz, 1H), 9.02 (d, J = 7.53 Hz, 1H), 8.68 (d, J = 2.01 Hz, 1H), 8.51 (dd, J = 2.13, 3.14 Hz, 2H), 8.32 (d, J = 2.01 Hz, 1H), 8.14 (s, 1H), 7.43 (dd, J = 5.52, 8.53 Hz, 2H), 7.15 (t, J = 8.91 Hz, 2H), 5.11 (t, J = 7.15 Hz, 1H), 4.55 (d, J = 5.52 Hz, 2H), 1.47 (d, J = 7.03 Hz, 3H) |
| 250 | 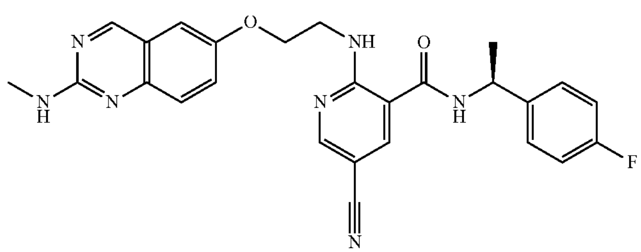 [SMILES: CNc1ncc2cc(OCCNc3ncc(C#N)cc3C(=O)N[C@@H](C)c3ccc(F)cc3)ccc2n1] | (S)-5-cyano-N-(1-(4-fluorophenyl)ethyl)-2-(2-(2-(methylamino)quinazolin-6-yloxy)ethylamino)nicotinamide | 485.9 | ¹H NMR (400 MHz, DMSO-d₆) δ 9.19 (d, J = 5.27 Hz, 2H), 8.98 (d, J = 7.53 Hz, 1H), 8.63 (d, J = 2.01 Hz, 1H), 8.48 (d, J = 2.01 Hz, 1H), 7.58 (br. s., 1H), 7.49 (br. s., 2H), 7.41 (dd, J = 5.77, 8.53 Hz, 2H), 7.14 (t, J = 8.91 Hz, 2H), 5.09 (t, J = 7.15 Hz, 1H), 4.22 (t, J = 5.65 Hz, 2H), 3.88 (dd, J = 2.76, 5.52 Hz, 2H), 2.97 (s, 3H), 1.45 (d, J = 7.03 Hz, 3H) |
| 251 | 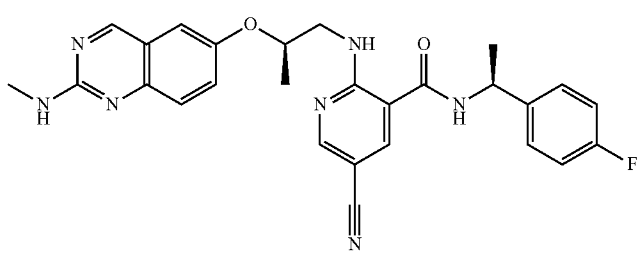 [SMILES: CNc1ncc2cc(O[C@H](C)CNc3ncc(C#N)cc3C(=O)N[C@@H](C)c3ccc(F)cc3)ccc2n1] | 5-cyano-N-((S)-1-(4-fluorophenyl)ethyl)-2-((R)-2-(2-(methylamino)quinazolin-6-yloxy)propylamino)nicotinamide | 500 | ¹H NMR (400 MHz, DMSO-d₆) δ 9.22 (d, J = 6.02 Hz, 2H), 8.93 (s, 1H), 8.65 (d, J = 2.01 Hz, 1H), 8.45 (d, J = 2.01 Hz, 1H), 7.55 (br. s., 3H), 7.38 (dd, J = 5.52, 8.53 Hz, 2H), 7.11 (t, J = 8.91 Hz, 2H), 5.07 (t, J = 7.15 Hz, 1H), 4.68-4.80 (m, 1H), 3.61-3.84 (m, 2H), 2.97 (br. s., 3H), 1.44 (d, J = 7.03 Hz, 3H), 1.31 (d, J = 6.02 Hz, 4H) |

| Ex. No. | Structure | Chemical Name | ESI-MS (M + H) | ¹H NMR |
|---|---|---|---|---|
| 252 | 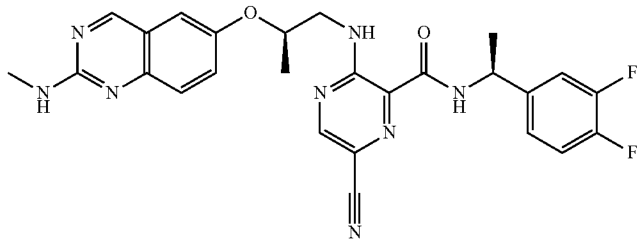 [SMILES: CNc1ncc2cc(O[C@H](C)CNc3ncc(C#N)nc3C(=O)N[C@@H](C)c3ccc(F)c(F)c3)ccc2n1] | 6-cyano-N-((S)-1-(3,4-difluorophenyl)ethyl)-3-((R)-2-(methylamino)quinazolin-6-yloxy)propylamino)pyrazine-2-carboxamide | 519 | ¹H NMR (400 MHz, DMSO-d₆) δ 9.59 (s, 1H), 9.29 (d, J = 8.28 Hz, 1H), 9.19 (br. s., 1H), 8.80 (s, 1H), 7.40-7.63 (m, 4H), 7.35 (td, J = 8.53, 10.79 Hz, 1H), 7.23 (br. s., 1H), 5.09 (t, J = 7.53 Hz, 1H), 4.72-4.84 (m, 1H), 3.68-3.87 (m, 2H), 2.97 (s, 3H), 1.49 (d, J = 7.03 Hz, 3H), 1.33 (d, J = 6.02 Hz, 3H) |
| 253 | 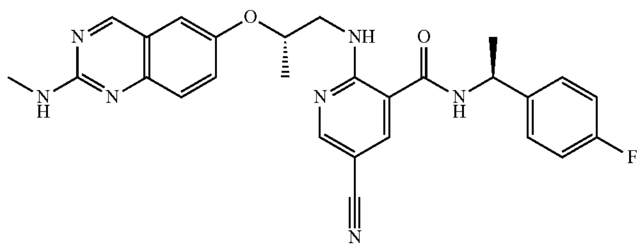 [SMILES: CNc1ncc2cc(O[C@@H](C)CNc3ncc(C#N)cc3C(=O)N[C@@H](C)c3ccc(F)cc3)ccc2n1] | 5-cyano-N-((S)-1-(4-fluorophenyl)ethyl)-2-((S)-2-(methylamino)quinazolin-6-yloxy)propylamino)nicotinamide | 499.9 | ¹H NMR (400 MHz, DMSO-d₆) δ 9.13-9.26 (m, 2H), 8.92 (s, 1H), 8.64 (d, J = 2.01 Hz, 1H), 8.45 (d, J = 2.01 Hz, 1H), 7.53 (br. s., 3H), 7.40 (dd, J = 5.52, 8.53 Hz, 2H), 7.14 (t, J = 8.78 Hz, 2H), 4.95-5.12 (m, 1H), 4.66-4.80 (m, 1H), 3.64-3.84 (m, 2H), 2.97 (br. s., 3H), 1.42 (d, J = 7.03 Hz, 3H), 1.30 (d, J = 6.27 Hz, 3H) |
| 254 | 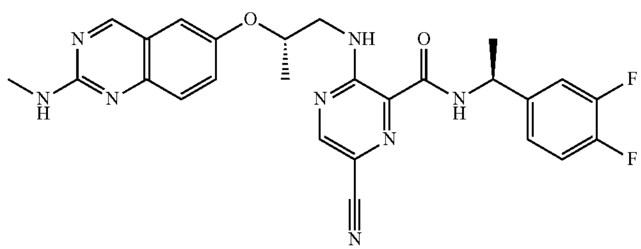 [SMILES: CNc1ncc2cc(O[C@@H](C)CNc3ncc(C#N)nc3C(=O)N[C@@H](C)c3ccc(F)c(F)c3)ccc2n1] | 6-cyano-N-((S)-1-(3,4-difluorophenyl)ethyl)-3-((S)-2-(methylamino)quinazolin-6-yloxy)propylamino)pyrazine-2-carboxamide | 518.9 | ¹H NMR (400 MHz, DMSO-d₆) δ 9.58 (t, J = 5.90 Hz, 1H), 9.29 (d, J = 8.53 Hz, 1H), 9.20 (br. s., 1H), 8.80 (s, 1H), 7.43-7.65 (m, 4H), 7.37 (td, J = 8.44, 10.73 Hz, 1H), 7.24 (br. s., 1H), 5.09 (t, J = 7.53 Hz, 1H), 4.73-4.83 (m, 1H), 3.67-3.88 (m, 2H), 2.97 (s, 3H), 1.48 (d, J = 7.03 Hz, 3H) |
| 255 | 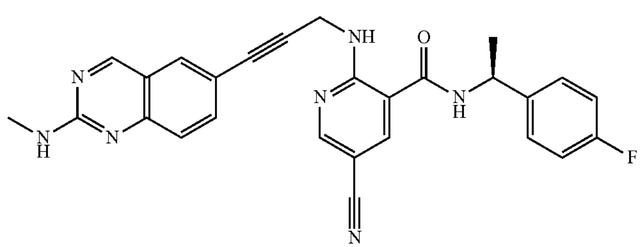 [SMILES: CNc1ncc2cc(C#CCNc3ncc(C#N)cc3C(=O)N[C@@H](C)c3ccc(F)cc3)ccc2n1] | (S)-5-cyano-N-(1-(4-fluorophenyl)ethyl)-2-(3-(2-(methylamino)quinazolin-6-yl)prop-2-ynylamino)nicotinamide | 479.9 | ¹H NMR (400 MHz, DMSO-d₆) δ 9.08-9.21 (m, 2H), 9.02 (d, J = 7.53 Hz, 1H), 8.68 (d, J = 2.01 Hz, 1H), 8.51 (d, J = 2.01 Hz, 1H), 7.95 (s, 1H), 7.69 (d, J = 8.03 Hz, 1H), 7.46-7.56 (m, 1H), 7.43 (dd, J = 5.65, 8.66 Hz, 2H), 7.10-7.21 (m, J = 8.91, 8.91 Hz, 2H), 5.11 (t, J = 7.15 Hz, 1H), 4.53 (d, J = 5.27 Hz, 2H), 2.93 (br. s., 3H), 1.47 (d, J = 7.03 Hz, 3H). |

TABLE 1-continued

| Ex. No. | Structure | Chemical Name | ESI-MS (M + H) | $^1$H NMR |
|---|---|---|---|---|
| 256 | 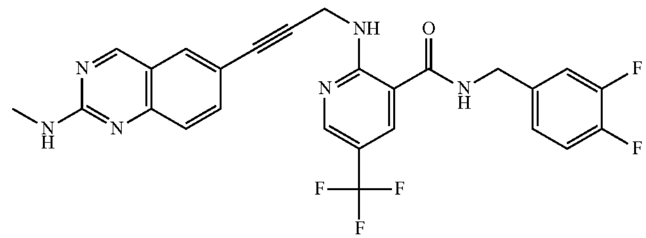 [SMILES: CNc1ncc2cc(C#CCNc3ncc(C(F)(F)F)cc3C(=O)NCc3ccc(F)c(F)c3)ccc2n1] | N-(3,4-difluorobenzyl)-2-(2-(2-(methylamino)quinazolin-6-yl)prop-2-ynylamino)-5-(trifluoromethyl)nicotinamide | 526.8 | 1H NMR (400 MHz, DMSO-d$_6$) δ 9.39 (t, J = 5.65 Hz, 1H), 9.11 (s, 1H), 8.61 (s, 1H), 8.39 (d, J = 2.01 Hz, 1H), 7.96 (s, 1H), 7.66-7.74 (m, 1H), 7.49 (br. s., 1H), 7.34-7.46 (m, 3H), 7.20 (br. s., 1H), 4.56 (d, J = 5.52 Hz, 2H), 4.45 (d, J = 5.52 Hz, 2H), 2.94 (br. s., 3H) |
| 257 | 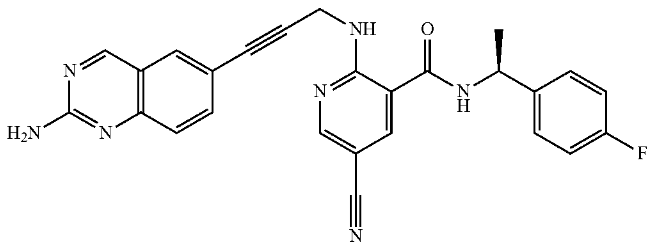 [SMILES: C[C@H](NC(=O)c1cc(C#N)cnc1NCC#Cc1ccc2nc(N)ncc2c1)c1ccc(F)cc1] | (S)-2-(3-(2-aminoquinazolin-6-yl)prop-2-ynylamino)-5-cyano-N-(1-(4-fluorophenyl)ethyl)nicotinamide | 466.8 | 1H NMR (400 MHz, DMSO-d$_6$) d 9.22-9.30 (m, 1H), 9.16 (s, 1H), 9.02 (d, J = 7.53 Hz, 1H), 8.68 (d, J = 2.01 Hz, 1H), 8.51 (d, J = 2.01 Hz, 1H), 8.02 (s, 1H), 7.76 (d, J = 8.78 Hz, 1H), 7.35-7.50 (m, 3H), 7.15 (t, J = 8.78 Hz, 2H), 5.10 (t, J = 7.15 Hz, 1H), 4.54 (d, J = 5.27 Hz, 2H), 1.47 (d, J = 7.03 Hz, 3H) |
| 258 | 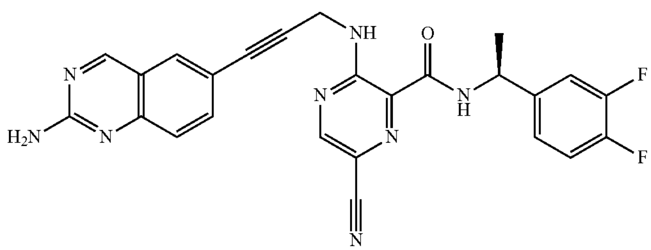 [SMILES: C[C@H](NC(=O)c1nc(C#N)cnc1NCC#Cc1ccc2nc(N)ncc2c1)c1ccc(F)c(F)c1] | (S)-3-(3-(2-aminoquinazolin-6-yl)prop-2-ynylamino)-6-cyano-N-(1-(3,4-difluorophenyl)ethyl)pyrazine-2-carboxamide | 485.9 | 1H NMR (400 MHz, DMSO-d$_6$) δ 9.56 (s, 1H), 9.36 (d, J = 8.28 Hz, 1H), 9.22 (s, 1H), 8.85 (s, 1H), 7.99 (s, 1H), 7.73 (d, J = 8.78 Hz, 1H), 7.47-7.58 (m, 1H), 7.31-7.47 (m, 2H), 7.27 (br. s., 1H), 5.13 (t, J = 7.40 Hz, 1H), 4.55 (d, J = 5.77 Hz, 2H), 1.52 (d, J = 7.03 Hz, 3H) |

TABLE 1-continued

| Ex. No. | Structure | Chemical Name | ESI-MS (M + H) | ¹H NMR |
|---|---|---|---|---|
| 259 | 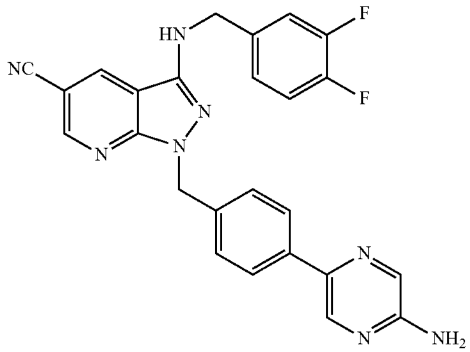 [SMILES: N#Cc1cnc2c(c1)c(NCc1ccc(F)c(F)c1)nn2Cc1ccc(-c2cnc(N)cn2)cc1] | 1-(4-(5-aminopyrazin-2-yl)benzyl)-3-(3,4-difluorobenzylamino)-1H-pyrazolo[3,4-b]pyridine-5-carbonitrile | 469.0 | ¹H NMR (400 MHz, DMSO-d₆) δ: 8.80 (d, 1H), 8.70 (d, 1H), 8.44 (d, 1H), 7.93 (d, 1H), 7.81-7.79 (m, 2H), 7.45-7.32 (m, 3H), 7.22-7.19 (m, 3H), 6.57 (br, 2H), 5.44 (s, 2H), 4.46 (d, 2H). |
| 260 | 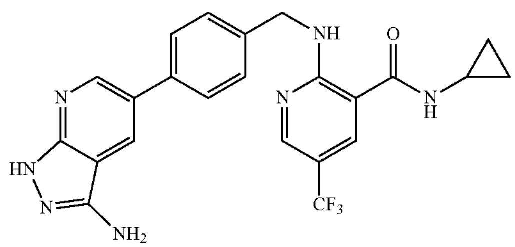 [SMILES: Nc1n[nH]c2ncc(-c3ccc(CNc4ncc(C(F)(F)F)cc4C(=O)NC4CC4)cc3)cc12] | 2-(4-(3-amino-1H-pyrazolo[3,4-b]pyridin-5-yl)benzylamino)-N-cyclopropyl-5-(trifluoromethyl)nicotinamide | 468 | ¹H NMR (400 MHz, DMSO-d₆) δ: 12.00 (s, 1H), 9.34 (t, 1H), 8.76 (d, 1H), 8.64 (d, 1H), 8.49 (s, 1H), 8.38 (d, 1H), 8.22 (d, 1H), 7.63 (d, 2H), 7.44 (d, 2H), 5.62 (s, 2H), 4.73 (d, 2H), 2.84-2.80 (m, 1H), 0.71-0.70 (m, 2H), 0.60-0.59 (m, 2H). |
| 261 | 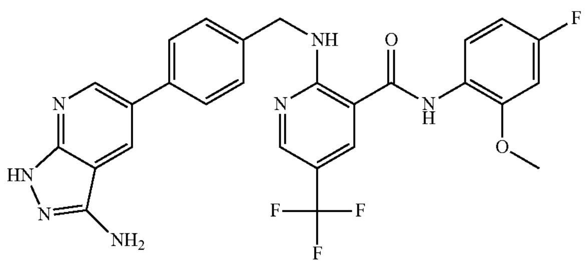 [SMILES: COc1cc(F)ccc1NC(=O)c1cc(C(F)(F)F)cnc1NCc1ccc(-c2cnc3[nH]nc(N)c3c2)cc1] | 2-(4-(3-amino-1H-pyrazolo[3,4-b]pyridin-5-yl)benzylamino)-N-(4-fluoro-2-methoxyphenyl)-5-(trifluoromethyl)nicotinamide | 551.9 | ¹H NMR (400 MHz, DMSO-d₆) δ: 10.02 (s, 1H), 9.09 (t, 1H), 8.66 (d, 1H), 8.55 (d, 1H), 8.46 (s, 1H), 8.40 (d, 1H), 7.63 (d, 2H), 7.47-7.44 (m, 3H), 7.04 (dd, 1H), 6.82-6.78 (m, 1H), 4.74 (d, 2H), 3.82 (s, 3H). |

| Ex. No. | Structure | Chemical Name | ESI-MS (M + H) | ¹H NMR |
|---|---|---|---|---|
| 262 | 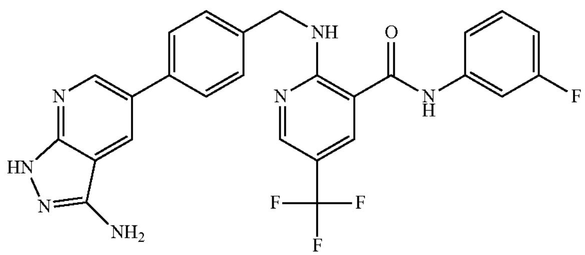 [SMILES: Nc1n[nH]c2ncc(-c3ccc(CNc4ncc(C(F)(F)F)cc4C(=O)Nc4cccc(F)c4)cc3)cc12] | 2-(4-(3-amino-1H-pyrazolo[3,4-b]pyridin-5-yl)benzylamino)-N-(3-fluorophenyl)-5-(trifluoromethyl)nicotinamide | 522 | ¹H NMR (400 MHz, CD₃OD) δ: 8.66 (d, 1H), 8.47 (d, 1H), 8.37 (d, 1H), 8.33 (d, 1H), 7.65-7.62 (m, 3H), 7.50 (d, 2H), 7.42 (d, 1H), 7.34 (d, 1H), 6.90-6.85 (m, 1H), 4.82 (s, 2H). |
| 263 | 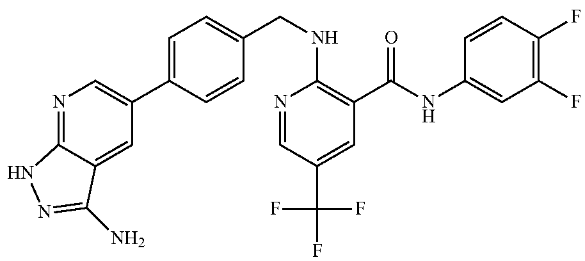 [SMILES: Nc1n[nH]c2ncc(-c3ccc(CNc4ncc(C(F)(F)F)cc4C(=O)Nc4ccc(F)c(F)c4)cc3)cc12] | 2-(4-(3-amino-1H-pyrazolo[3,4-b]pyridin-5-yl)benzylamino)-N-(3,4-difluorophenyl)-5-(trifluoromethyl)nicotinamide | 540 | ¹H NMR (400 MHz, DMSO-d₆) δ: 10.63 (s, 1H), 8.87 (t, 1H), 8.64 (d, 1H), 8.56 (s, 1H), 8.38-8.37 (m, 2H), 7.83-7.81 (m, 1H), 7.63 (d, 2H), 7.48-7.65 (m, 4H), 5.62 (s, 2H), 4.76 (d, 2H). |
| 264 | 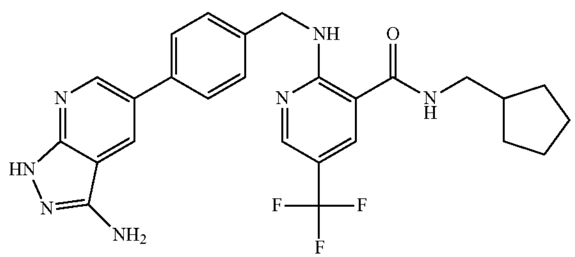 [SMILES: Nc1n[nH]c2ncc(-c3ccc(CNc4ncc(C(F)(F)F)cc4C(=O)NCC4CCCC4)cc3)cc12] | 2-(4-(3-amino-1H-pyrazolo[3,4-b]pyridin-5-yl)benzylamino)-N-(cyclopentylmethyl)-5-(trifluoromethyl)nicotinamide | 510.1 | ¹H NMR (400 MHz, DMSO-d₆) δ: 12.02 (s, 1H), 8.84 (t, 1H), 8.64 (d, 1H), 8.50 (d, 1H), 8.38 (d, 1H), 8.27 (d, 1H), 7.62 (d, 2H), 7.43 (d, 2H), 5.64 (s, 2H), 4.73 (d, 2H), 3.19-3.16 (m, 2H), 2.03-2.01 (m, 1H), 1.68-1.50 (m, 6H), 1.24 (m, 2H). |
| 265 | 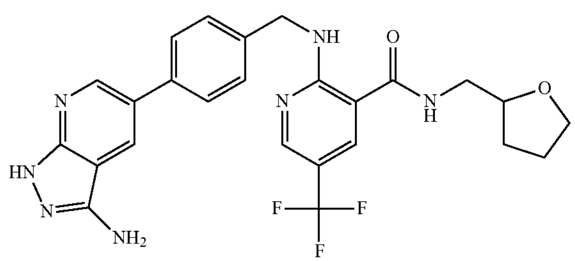 [SMILES: Nc1n[nH]c2ncc(-c3ccc(CNc4ncc(C(F)(F)F)cc4C(=O)NCC4CCCO4)cc3)cc12] | 2-(4-(3-amino-1H-pyrazolo[3,4-b]pyridin-5-yl)benzylamino)-N-((tetrahydrofuran-2-yl)methyl)-5-(trifluoromethyl)nicotinamide | 512.1 | ¹H NMR (400 MHz, DMSO-d₆) δ: 12.02 (s, 1H), 9.30 (t, 1H), 8.95 (t, 1H), 8.65 (d, 1H), 8.51 (s, 1H), 8.38 (d, 1H), 8.31 (d, 1H), 7.63 (d, 2H), 7.43 (d, 2H), 5.64 (s, 2H), 4.74 (d, 2H), 3.99-3.96 (m, 1H), 3.78-3.75 (m, 1H), 3.66-3.63 (m, 1H), 3.34-3.29 (m, 2H), 1.94-1.80 (m, 3H), 1.59-1.56 (m, 1H). |

TABLE 1-continued

| Ex. No. | Structure | Chemical Name | ESI-MS (M + H) | ¹H NMR |
|---|---|---|---|---|
| 266 | 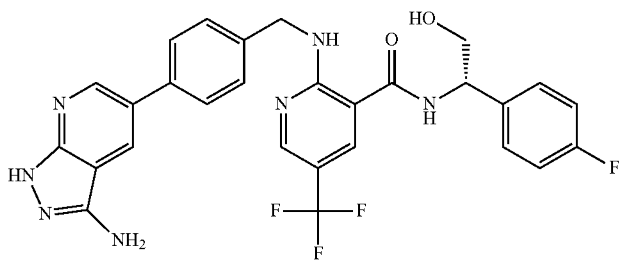 [SMILES: Nc1n[nH]c2ncc(-c3ccc(CNc4ncc(C(F)(F)F)cc4C(=O)N[C@H](CO)c4ccc(F)cc4)cc3)cc12] | (S)-2-(4-(3-amino-1H-pyrazolo[3,4-b]pyridin-5-yl)benzylamino)-N-1-(4-fluorophenyl)-2-hydroxyethyl)-5-(trifluoromethyl)nicotinamide | 566.1 | ¹H NMR (400 MHz, CD₃OD) δ: 8.65 (d, 1H), 8.43 (s, 1H), 8.38 (d, 1H), 8.32 (d, 1H), 7.61 (d, 2H), 7.46-7.40 (m, 4H), 7.08 (t, 2H), 5.17 (t, 1H), 4.76 (d, 2H), 3.86-3.83 (m, 2H). |
| 267 | 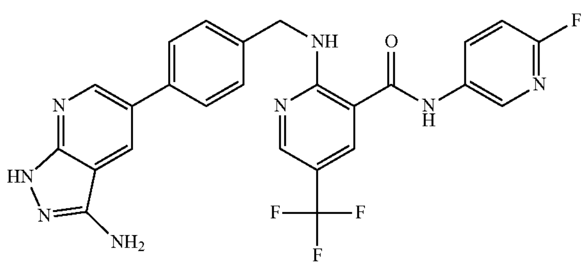 [SMILES: Nc1n[nH]c2ncc(-c3ccc(CNc4ncc(C(F)(F)F)cc4C(=O)Nc4ccc(F)nc4)cc3)cc12] | 2-(4-(3-amino-1H-pyrazolo[3,4-b]pyridin-5-yl)benzylamino)-N-(6-fluoropyridin-3-yl)-5-(trifluoromethyl)nicotinamide | 523 | ¹H NMR (400 MHz, CD₃OD) δ: 8.65 (s, 1H), 8.49 (br, 2H), 8.38 (br, 2H), 8.30-8.26 (m, 1H), 7.62 (d, 2H), 7.49 (d, 2H), 7.09 (d, 1H), 4.82 (s, 2H). |
| 268 | 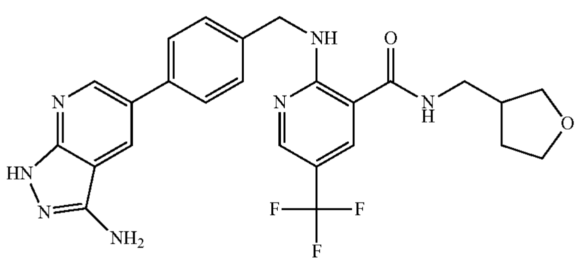 [SMILES: Nc1n[nH]c2ncc(-c3ccc(CNc4ncc(C(F)(F)F)cc4C(=O)NCC4CCOC4)cc3)cc12] | 2-(4-(3-amino-1H-pyrazolo[3,4-b]pyridin-5-yl)benzylamino)-N-((tetrahydrofuran-3-yl)methyl)-5-(trifluoromethyl)nicotinamide | 512 | ¹H NMR (400 MHz, DMSO-d₆) δ: 12.01 (s, 1H), 9.30 (t, 1H), 8.92 (t, 1H), 8.64 (d, 1H), 8.50 (s, 1H), 8.38 (d, 1H), 8.27 (d, 1H), 7.63 (d, 2H), 7.43 (d, 2H), 5.63 (s, 2H), 4.73 (d, 2H), 3.75-3.65 (m, 3H), 3.64-3.61 (m, 1H), 3.33-3.21 (m, 2H) 1.98-1.95 (m, 1H), 1.92-1.90 (m, 1H), 1.19-1.17 (m, 1H). |

TABLE 1-continued

| Ex. No. | Structure | Chemical Name | ESI-MS (M + H) | ¹H NMR |
|---|---|---|---|---|
| 269 | 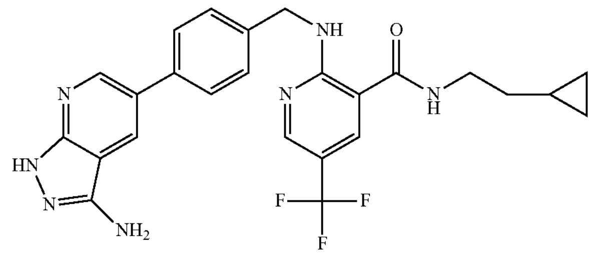 [SMILES: Nc1n[nH]c2ncc(-c3ccc(CNc4ncc(C(F)(F)F)cc4C(=O)NCCC4CC4)cc3)cc12] | 2-(4-(3-amino-1H-pyrazolo[3,4-b]pyridin-5-yl)benzylamino)-N-(2-cyclopropylethyl)-5-(trifluoromethyl)nicotinamide | 496.1 | ¹H NMR (400 MHz, DMSO-d₆) δ: 12.01 (s, 1H), 9.32 (t, 1H), 8.83 (t, 1H), 8.64 (d, 1H), 8.49 (d, 1H), 8.38 (d, 1H), 8.25 (d, 1H), 7.63 (d, 2H), 7.43 (d, 2H), 5.63 (s, 2H), 4.73 (d, 2H), 3.32-3.30 (m, 2H), 1.46-1.41 (m, 2H), 0.74-0.71 (m, 1H), 0.43-0.40 (m, 2H), 0.07-0.05 (m, 2H). |
| 270 | 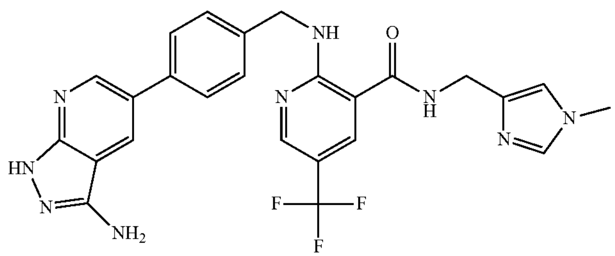 [SMILES: Cn1cnc(CNC(=O)c2cc(C(F)(F)F)cnc2NCc2ccc(-c3cnc4[nH]nc(N)c4c3)cc2)c1] | 2-(4-(3-amino-1H-pyrazolo[3,4-b]pyridin-5-yl)benzylamino)-N-((1-methyl-1H-imidazol-4-yl)methyl)-5-(trifluoromethyl)nicotinamide | 522 | ¹H NMR (400 MHz, DMSO-d₆) δ: 12.02 (s, 1H), 9.21 (t, 1H), 8.65 (d, 1H), 8.50 (d, 1H), 8.39 (d, 1H), 8.33 (d, 1H), 7.63 (d, 2H), 7.50 (s, 1H), 7.44 (d, 2H), 7.01 (s, 1H), 5.64 (s, 2H), 4.75 (d, 2H), 4.31 (d, 2H), 3.60 (s, 3H). |
| 271 | 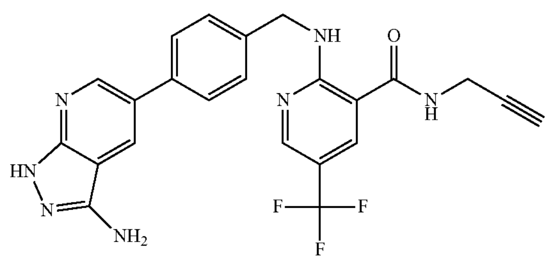 [SMILES: C#CCNC(=O)c1cc(C(F)(F)F)cnc1NCc1ccc(-c2cnc3[nH]nc(N)c3c2)cc1] | 2-(4-(3-amino-1H-pyrazolo[3,4-b]pyridin-5-yl)benzylamino)-N-(prop-2-ynyl)-5-(trifluoromethyl)nicotinamide | 466 | ¹H NMR (400 MHz, DMSO-d₆) δ: 12.02 (s, 1H), 9.39 (dd, 2H), 8.65 (d, 1H), 8.53 (d, 1H), 8.38 (d, 1H), 8.32 (d, 1H), 7.63 (d, 2H), 7.44 (d, 2H), 5.64 (s, 2H), 4.75 (d, 2H), 4.06 (dd, 2H), 3.20 (t, 1H). |
| 272 | 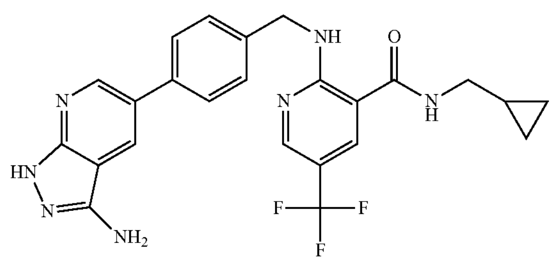 [SMILES: Nc1n[nH]c2ncc(-c3ccc(CNc4ncc(C(F)(F)F)cc4C(=O)NCC4CC4)cc3)cc12] | 2-(4-(3-amino-1H-pyrazolo[3,4-b]pyridin-5-yl)benzylamino)-N-(cyclopropylmethyl)-5-(trifluoromethyl)nicotinamide | 482 | ¹H NMR (400 MHz, DMSO-d₆) δ: 12.02 (s, 1H), 9.35 (t, 1H), 8.94 (t, 1H), 8.65 (s, 1H), 8.50 (d, 1H), 8.39 (d, 1H), 8.31 (d, 1H), 7.63 (d, 2H), 7.45 (d, 2H), 5.64 (s, 2H), 4.74 (d, 2H), 3.13 (t, 2H), 1.05-1.04 (m, 1H), 0.46-0.44 (m, 2H), 0.23-0.22 (m, 2H). |

TABLE 1-continued

| Ex. No. | Structure | Chemical Name | ESI-MS (M + H) | 1H NMR |
|---|---|---|---|---|
| 273 | 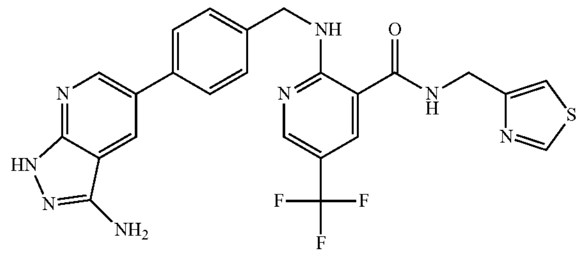 [SMILES: Nc1n[nH]c2ncc(-c3ccc(CNc4ncc(C(F)(F)F)cc4C(=O)NCc4cscn4)cc3)cc12] | 2-(4-(3-amino-1H-pyrazolo[3,4-b]pyridin-5-yl)benzylamino)-N-(thiazol-4-ylmethyl)-5-(trifluoromethyl)nicotinamide | 525 | 1H NMR (400 MHz, CD3OD/CDCl3) δ: 8.94 (d, 1H), 8.64 (d, 1H), 8.42 (s, 1H), 8.36 (d, 1H), 8.22 (d, 1H), 7.61 (d, 2H), 7.48 (d, 2H), 7.43 (s, 1H), 4.80 (s, 2H), 4.70 (s, 2H). |
| 274 | 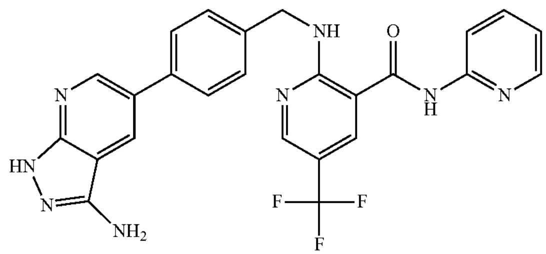 [SMILES: Nc1n[nH]c2ncc(-c3ccc(CNc4ncc(C(F)(F)F)cc4C(=O)Nc4ccccn4)cc3)cc12] | 2-(4-(3-amino-1H-pyrazolo[3,4-b]pyridin-5-yl)benzylamino)-N-(pyridin-2-yl)-5-(trifluoromethyl)nicotinamide | 505.1 | 1H NMR (400 MHz, CD3OD) δ: 8.71 (s, 1H), 8.54 (s, 1H), 8.44-8.40 (m, 3H), 8.19 (d, 1H), 7.87 (t, 1H), 7.69 (d, 2H), 7.55 (d, 2H), 7.21 (t, 1H), 4.66 (s, 2H). |
| 275 | 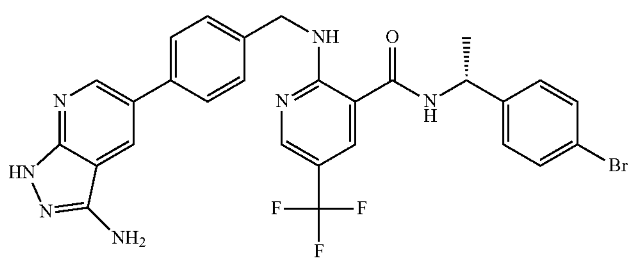 [SMILES: C[C@@H](NC(=O)c1cc(C(F)(F)F)cnc1NCc1ccc(-c2cnc3[nH]nc(N)c3c2)cc1)c1ccc(Br)cc1] | (R)-2-(4-(3-amino-1H-pyrazolo[3,4-b]pyridin-5-yl)benzylamino)-N-(1-(4-bromophenyl)ethyl)-5-(trifluoromethyl)nicotinamide | 609.9 | 1H NMR (400 MHz, DMSO-d6) δ: 12.01 (s, 1H), 9.24 (t, 1H), 9.14 (d, 1H), 8.64 (d, 1H), 8.52 (s, 1H), 8.43 (d, 1H), 8.37 (d, 1H), 7.61 (d, 2H), 7.53 (d, 2H), 7.40 (d, 2H), 7.34 (d, 2H), 5.63 (s, 2H), 5.11-5.09 (m, 1H), 4.72 (t, 2H), 1.47 (d, 3H). |

TABLE 1-continued

| Ex. No. | Structure | Chemical Name | ESI-MS (M + H) | ¹H NMR |
|---|---|---|---|---|
| 276 | 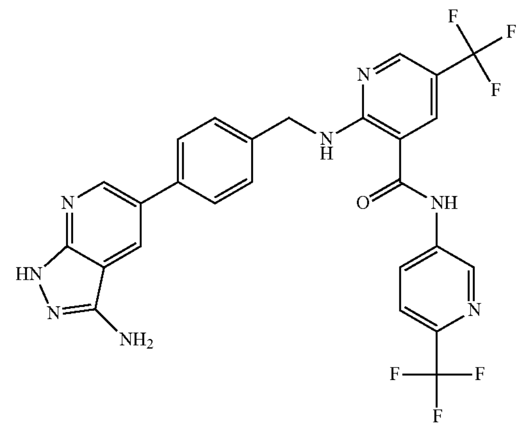 [SMILES: Nc1n[nH]c2ncc(-c3ccc(CNc4ncc(C(F)(F)F)cc4C(=O)Nc4ccc(C(F)(F)F)nc4)cc3)cc12] | 2-(4-(3-amino-1H-pyrazolo[3,4-b]pyridin-5-yl)benzylamino)-N-(6-(trifluoromethyl)pyridin-3-yl)nicotinamide | 573.1 | ¹H NMR (400 MHz, DMSO-d$_6$) δ: 10.96 (s, 1H), 9.04 (d, 1H), 8.89 (t, 1H), 8.67 (d, 1H), 8.60 (s, 1H), 8.48 (s, 1H), 8.43-8.38 (m, 2H), 7.95 (s, 1H), 7.64 (d, 2H), 7.47 (d, 2H), 4.79 (d, 2H), 3.60 (br, 2H). |
| 277 | 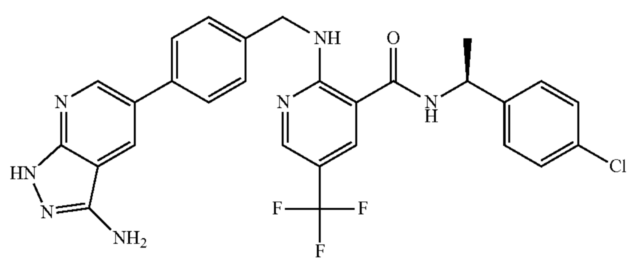 [SMILES: C[C@H](NC(=O)c1cc(C(F)(F)F)cnc1NCc1ccc(-c2cnc3[nH]nc(N)c3c2)cc1)c1ccc(Cl)cc1] | 2-(4-(3-amino-1H-pyrazolo[3,4-b]pyridin-5-yl)benzylamino)-N-(1-(4-chlorophenyl)ethyl)-5-(trifluoromethyl)nicotinamide | 565.9 | ¹H NMR (400 MHz, DMSO-d$_6$) δ: 9.25 (t, 1H), 9.14 (d, 1H), 8.65 (s, 1H), 8.52 (s, 1H), 8.40 (s, 1H), 8.39 (s, 1H), 7.60 (d, 2H), 7.42-7.40 (m, 6H), 5.13-5.10 (m, 1H), 4.73-4.70 (m, 2H), 1.48 (d, 3H). |
| 278 | 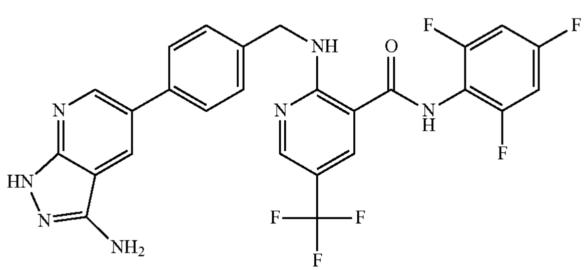 [SMILES: Nc1n[nH]c2ncc(-c3ccc(CNc4ncc(C(F)(F)F)cc4C(=O)Nc4c(F)cc(F)cc4F)cc3)cc12] | 2-(4-(3-amino-1H-pyrazolo[3,4-b]pyridin-5-yl)benzylamino)-5-(trifluoromethyl)-N-(2,4,6-trifluorophenyl)nicotinamide | 557.9 | ¹H NMR (400 MHz, DMSO-d$_6$) δ: 12.01 (s, 1H), 10.46 (s, 1H), 9.15 (t, 1H), 8.64-8.63 (m, 2H), 8.54 (s, 1H), 8.38 (d, 1H), 7.63 (d, 2H), 7.44 (d, 2H), 7.40-7.35 (m, 2H), 5.62 (s, 2H), 4.76 (d, 2H). |

TABLE 1-continued

| Ex. No. | Structure | Chemical Name | ESI-MS (M + H) | ¹H NMR |
|---|---|---|---|---|
| 279 | 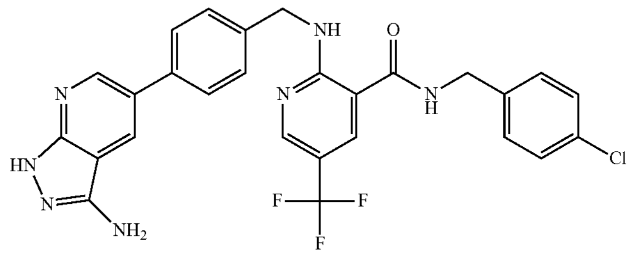 | 2-(4-(3-amino-1H-pyrazolo[3,4-b]pyridin-5-yl)benzylamino)-N-(4-chlorobenzyl)-5-(trifluoromethyl)nicotinamide | 551.9 | ¹H NMR (400 MHz, CD$_3$OD) δ: 8.75 (d, 1H), 8.53 (d, 1H), 8.44 (d, 1H), 8.20 (d, 1H), 7.65 (d, 2H), 7.50 (d, 2H), 7.38-7.32 (m, 4H), 4.81 (s, 2H), 4.53 (s, 2H). |
| 280 | 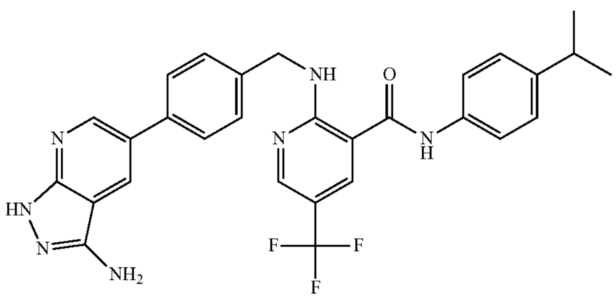 [SMILES: CC(C)c1ccc(NC(=O)c2cc(C(F)(F)F)cnc2NCc2ccc(-c3cnc4[nH]nc(N)c4c3)cc2)cc1] | 2-(4-(3-amino-1H-pyrazolo[3,4-b]pyridin-5-yl)benzylamino)-N-(4-isopropylphenyl)-5-(trifluoromethyl)nicotinamide | 546.1 | ¹H NMR (400 MHz, DMSO-d$_6$) δ: 10.41 (s, 1H), 8.66 (d, 1H), 8.55 (s, 1H), 8.39 (s, 2H), 7.64-7.61 (m, 4H), 7.46 (d, 2H), 7.24 (d, 2H), 4.77 (d, 2H), 2.89-2.84 (m, 1H), 1.20 (d, 6H). |
| 281 | 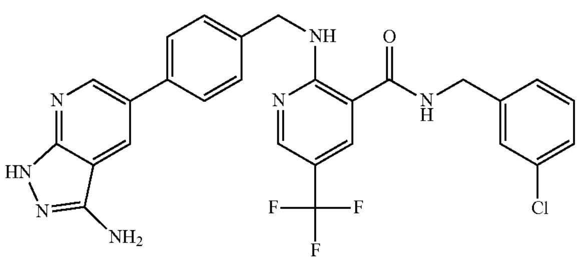 [SMILES: Nc1n[nH]c2ncc(-c3ccc(CNc4ncc(C(F)(F)F)cc4C(=O)NCc4cccc(Cl)c4)cc3)cc12] | 2-(4-(3-amino-1H-pyrazolo[3,4-b]pyridin-5-yl)benzylamino)-N-(3-chlorobenzyl)-5-(trifluoromethyl)nicotinamide | 551.9 | ¹H NMR (400 MHz, DMSO-d$_6$) δ: 9.38-9.34 (m, 2H), 8.65 (d, 1H), 8.52 (d, 1H), 8.40-8.36 (m, 2H), 7.64-7.62 (m, 2H), 7.45-7.35 (m, 6H), 4.74 (d, 2H), 4.45 (d, 2H). |

TABLE 1-continued

| Ex. No. | Structure | Chemical Name | ESI-MS (M + H) | ¹H NMR |
|---|---|---|---|---|
| 282 | 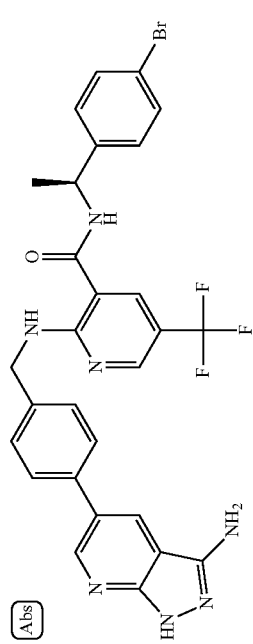 | (S)-2-(4-(3-amino-1H-pyrazolo[3,4-b]pyridin-5-yl)benzylamino)-N-(1-(4-bromophenyl)ethyl)-5-(trifluoromethyl)nicotinamide | 611.8 (M+2) | ¹H NMR (400 MHz, CD$_3$OD) δ: 8.67 (d, 1H), 8.43 (d, 1H), 8.39 (s, 1H), 8.25 (d, 1H), 7.62 (d, 2H), 7.51-7.45 (m, 4H), 7.32 (d, 2H), 5.16 (q, 1H), 4.77 (s, 2H), 1.56 (d, 3H). |
| 283 | 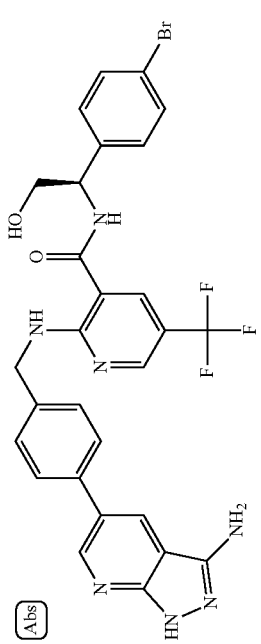 | (R)-2-(4-(3-amino-1H-pyrazolo[3,4-b]pyridin-5-yl)benzylamino)-N-(1-(4-bromophenyl)-2-hydroxyethyl)-5-(trifluoromethyl)nicotinamide | 625.8 | ¹H NMR (400 MHz, CD$_3$OD) δ: 8.65 (s, 1H), 8.44 (s, 1H), 8.37 (s, 1H), 8.33 (s, 1H), 7.60 (d, 2H), 7.51 (s, 2H), 7.44 (d, 2H), 7.33 (d, 2H), 5.17-5.14 (m, 1H), 4.76 (s, 2H), 3.85 (d, 2H). |
| 284 | 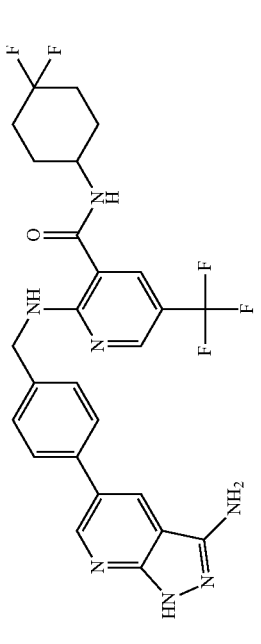 | 2-(4-(3-amino-1H-pyrazolo[3,4-b]pyridin-5-yl)benzylamino)-N-(4,4-difluorocyclohexyl)-5-(trifluoromethyl)nicotinamide | 546 | ¹H NMR (400 MHz, DMSO-d$_6$) δ: 12.01 (s, 1H), 9.26 (t, 1H), 8.65-8.61 (m, 2H), 8.51 (d, 1H), 8.39 (d, 1H), 8.29 (d, 1H), 7.64 (d, 2H), 7.44 (d, 2H), 5.64 (br, 2H), 4.74 (d, 2H), 4.00-3.99 (m, 1H), 2.06-1.89 (m, 6H), 1.65-1.61 (m, 2H). |
| 285 | 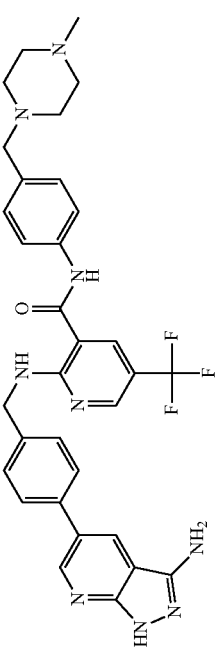 | 2-(4-(3-amino-1H-pyrazolo[3,4-b]pyridin-5-yl)benzylamino)-N-(4-((4-methylpiperazin-1-yl)methyl)phenyl)-5-(trifluoromethyl)nicotinamide | 616.0 | ¹H NMR (400 MHz, CD$_3$OD/CDCl$_3$) δ: 8.63 (d, 1H), 8.45 (s, 1H), 8.33 (d, 2H), 7.68 (s, 1H), 7.62-7.59 (m, 3H), 7.49 (d, 2H), 7.33 (d, 2H), 4.80 (s, 2H), 3.58 (s, 2H), 2.85-2.61 (m, 8H), 2.51 (s, 3H). |

TABLE 1-continued

| Ex. No. | Structure | Chemical Name | ESI-MS (M + H) | ¹H NMR |
|---|---|---|---|---|
| 286 | 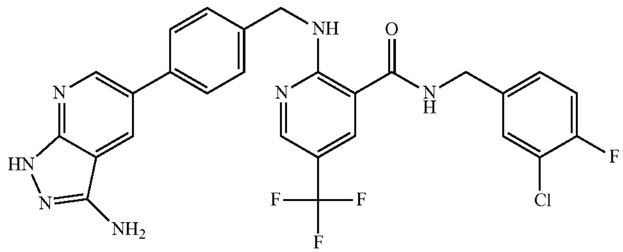 [SMILES: Nc1n[nH]c2ncc(-c3ccc(CNc4ncc(C(F)(F)F)cc4C(=O)NCc4ccc(F)c(Cl)c4)cc3)cc12] | 2-(4-(3-amino-1H-pyrazolo[3,4-b]pyridin-5-yl)benzylamino)-N-(3-chloro-(4-fluorobenzyl)-5-(trifluoromethyl)nicotinamide | 570.1 | ¹H NMR (400 MHz, DMSO-d₆) δ: 9.39-9.31 (m, 2H), 8.67 (d, 1H), 8.53 (s, 1H), 8.41 (d, 1H), 8.36 (d, 1H), 7.63 (d, 2H), 7.56 (d, 1H), 7.45 (d, 2H), 7.41-7.37 (m, 2H), 4.75 (d, 2H), 4.45 (d, 2H). |
| 287 | 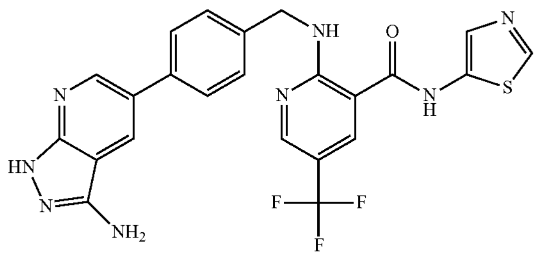 [SMILES: Nc1n[nH]c2ncc(-c3ccc(CNc4ncc(C(F)(F)F)cc4C(=O)Nc4cncs4)cc3)cc12] | 2-(4-(3-amino-1H-pyrazolo[3,4-b]pyridin-5-yl)benzylamino)-N-(thiazol-4-yl)-5-(trifluoromethyl)nicotinamide | ESI-MS (M+2): 512.0 | ¹H NMR (400 MHz, CD₃OD) δ: 8.56 (d, 1H), 8.49 (s, 1H), 8.41 (s, 1H), 8.34 (d, 1H), 8.28 (d, 1H), 7.71 (s, 1H), 7.54 (d, 2H), 7.41 (d, 2H), 4.78 (s, 2H). |
| 288 | 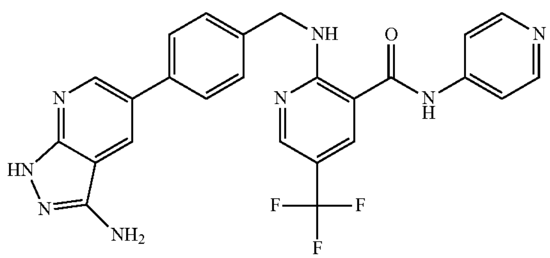 [SMILES: Nc1n[nH]c2ncc(-c3ccc(CNc4ncc(C(F)(F)F)cc4C(=O)Nc4ccncc4)cc3)cc12] | 2-(4-(3-amino-1H-pyrazolo[3,4-b]pyridin-5-yl)benzylamino)-N-(pyridin-4-yl)-5-(trifluoromethyl)nicotinamide | 505.0 | ¹H NMR (400 MHz, CD₃OD) δ: 8.62 (d, 1H), 8.56 (d, 2H), 8.48-8.38 (m, 3H), 8.22 (d, 2H), 7.55 (d, 2H), 7.42 (d, 2H), 4.78 (s, 2H). |
| 289 | 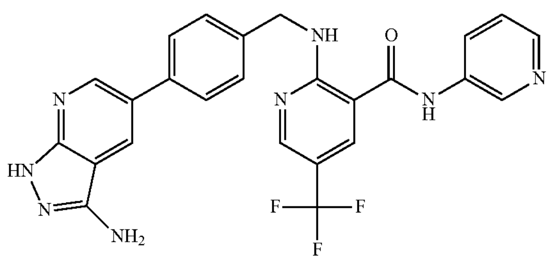 [SMILES: Nc1n[nH]c2ncc(-c3ccc(CNc4ncc(C(F)(F)F)cc4C(=O)Nc4cccnc4)cc3)cc12] | 2-(4-(3-amino-1H-pyrazolo[3,4-b]pyridin-5-yl)benzylamino)-N-(pyridin-3-yl)-5-(trifluoromethyl)nicotinamide | 505.0 | ¹H NMR (400 MHz, DMSO-d₆) δ: 10.80 (s, 1H), 8.98 (s, 1H), 8.93-8.90 (m, 1H), 8.68 (d, 1H), 8.59 (s, 1H), 8.46-8.42 (m, 3H), 8.24 (d, 1H), 7.64 (d, 2H), 7.59 (d, 1H), 7.47 (d, 2H), 4.79 (d, 2H). |

| Ex. No. | Structure | Chemical Name | ESI-MS (M + H) | ¹H NMR |
|---|---|---|---|---|
| 290 | 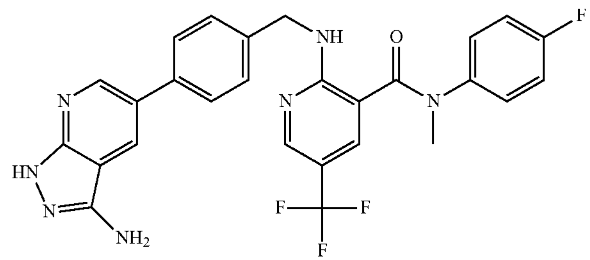 [SMILES: CN(C(=O)c1cc(C(F)(F)F)cnc1NCc1ccc(-c2cnc3[nH]nc(N)c3c2)cc1)c1ccc(F)cc1] | 2-(4-(3-amino-1H-pyrazolo[3,4-b]pyridin-5-yl)benzylamino)-N-(4-fluorophenyl)-N-methyl-5-(trifluoromethyl)nicotinamide | 536.2 | ¹H NMR (400 MHz, DMSO-d₆) δ: 8.68 (d, 1H), 8.41 (d, 1H), 8.23-8.18 (m, 1H), 7.74-7.72 (m, 1H), 7.62 (d, 2H), 7.56-7.52 (m, 1H), 7.39-7.33 (m, 4H), 7.14-7.10 (m, 2H), 4.63 (d, 2H), 3.35 (s, 3H). |
| 291 | 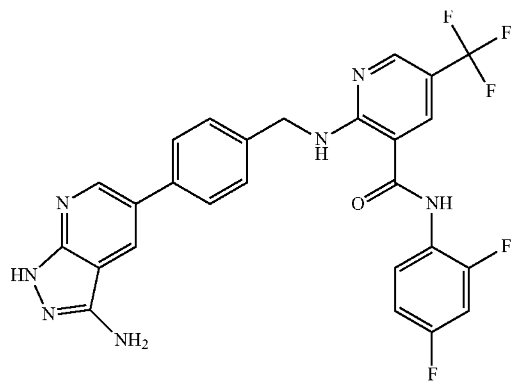 [SMILES: Nc1n[nH]c2ncc(-c3ccc(CNc4ncc(C(F)(F)F)cc4C(=O)Nc4ccc(F)cc4F)cc3)cc12] | 2-(4-(3-amino-1H-pyrazolo[3,4-b]pyridin-5-yl)benzylamino)-N-(2,4-difluorophenyl)-5-(trifluoromethyl)nicotinamide | ESI-MS (M+H⁺) 539.9 | ¹H NMR (400 MHz, CDCl₃) δ: 10.44 (s, 1H), 9.09 (t, 1H), 8.65 (d, 1H), 8.59 (s, 1H), 8.48 (d, 1H), 8.39 (d, 1H), 7.63 (d, 2H), 7.61-7.53 (m, 1H), 7.45 (d, 2H), 7.42-7.35 (m, 1H), 7.18-7.11 (m, 1H), 4.76 (d, 2H). |
| 292 | 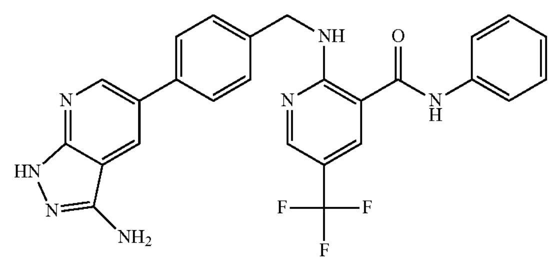 [SMILES: Nc1n[nH]c2ncc(-c3ccc(CNc4ncc(C(F)(F)F)cc4C(=O)Nc4ccccc4)cc3)cc12] | 2-(4-(3-amino-1H-pyrazolo[3,4-b]pyridin-5-yl)benzylamino)-N-phenyl-5-(trifluoromethyl)nicotinamide | 504 | ¹H NMR (400 MHz, CD₃OD) δ: 8.64 (d, 1H), 8.42 (d, 1H), 8.36 (s, 1H), 8.23 (d, 1H), 7.57-7.53 (m, 4H), 7.41 (d, 2H), 7.27-7.23 (m, 2H), 7.07-7.03 (m, 1H), 4.74 (s, 2H). |

TABLE 1-continued

| Ex. No. | Structure | Chemical Name | ESI-MS (M + H) | ¹H NMR |
|---|---|---|---|---|
| 293 | 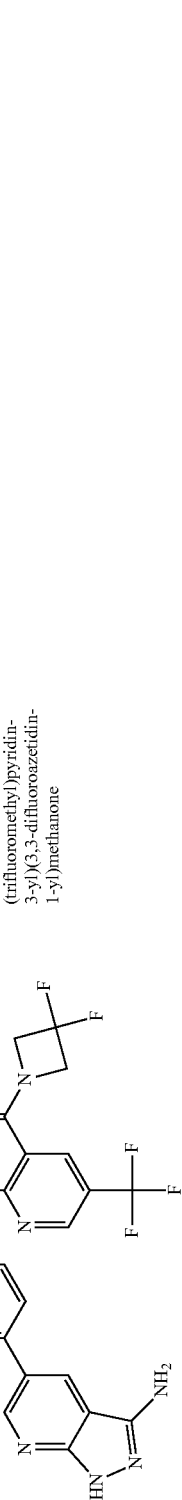 | 2-(4-(3-amino-1H-pyrazolo[3,4-b]pyridin-5-yl)benzylamino)-5-(trifluoromethyl)pyridin-3-yl)(3,3-difluoroazetidin-1-yl)methanone | 504 | ¹H NMR (400 MHz, DMSO-d6) δ: 12.00 (s, 1H), 8.65 (d, 1H), 8.50 (s, 1H), 8.38 (s, 2H), 7.95 (d, 1H), 7.63 (d, 2H), 7.45 (d, 2H), 5.61 (s, 2H), 4.74-4.65 (m, 6H). |
| 294 | 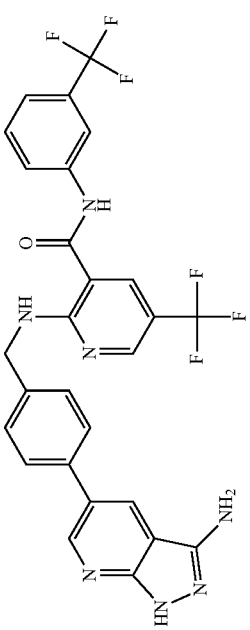 | 2-(4-(3-amino-1H-pyrazolo[3,4-b]pyridin-5-yl)benzylamino)-N-(3-(trifluoromethyl))-5-(trifluoromethyl)nicotinamide | 571.9 | ¹H NMR (400 MHz, CD3OD) δ: 8.66 (d, 1H), 8.46 (d, 1H), 8.37 (s, 1H), 8.27 (d, 1H), 8.04 (s, 1H), 7.82 (d, 1H), 7.54 (d, 2H), 7.46-7.41 (m, 3H), 7.33 (d, 1H), 4.74 (s, 2H). |
| 295 | 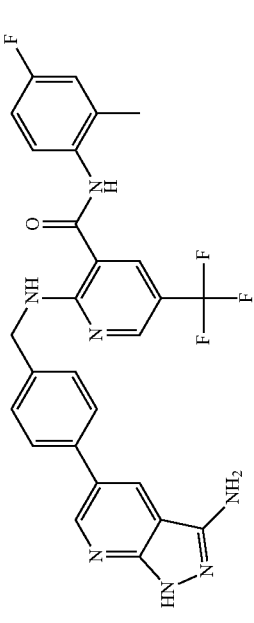 | 2-(4-(3-amino-1H-pyrazolo[3,4-b]pyridin-5-yl)benzylamino)-N-(4-fluoro-2-methylphenyl)-5-(trifluoromethyl)nicotinamide | 536.1 | ¹H NMR (400 MHz, CD3OD) δ: 8.62 (d, 1H), 8.39 (s, 2H), 8.28 (s, 1H), 8.52 (d, 2H), 7.39 (d, 2H), 7.20-7.17 (m, 1H), 6.96-6.93 (m, 1H), 6.86 (d, 1H), 4.72 (s, 2H), 2.18 (s, 3H). |

| Ex. No. | Structure | Chemical Name | ESI-MS (M + H) | ¹H NMR |
|---|---|---|---|---|
| 296 | 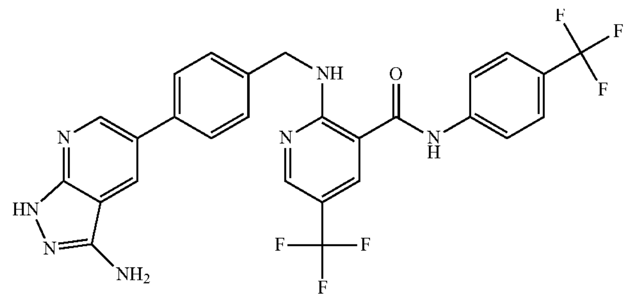 [SMILES: Nc1n[nH]c2ncc(-c3ccc(CNc4ncc(C(F)(F)F)cc4C(=O)Nc4ccc(C(F)(F)F)cc4)cc3)cc12] | 2-(4-(3-amino-1H-pyrazolo[3,4-b]pyridin-5-yl)benzylamino)-5-(trifluoromethyl)-N-(4-(trifluoromethyl)phenyl)nicotinamide | 572 | ¹H NMR (400 MHz, CD$_3$OD) δ: 8.68 (s, 1H), 8.51 (s, 1H), 8.41-8.38 (m, 2H), 7.93 (d, 1H), 7.68-7.65 (m, 4H), 7.53 (d, 2H), 4.60 (s, 2H). |
| 297 | 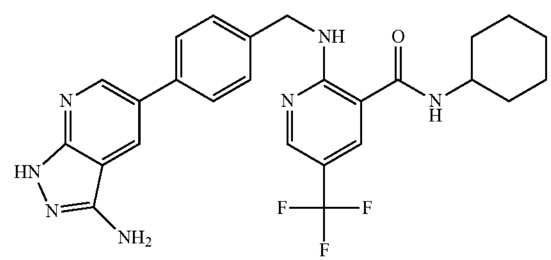 [SMILES: Nc1n[nH]c2ncc(-c3ccc(CNc4ncc(C(F)(F)F)cc4C(=O)NC4CCCCC4)cc3)cc12] | 2-(4-(3-amino-1H-pyrazolo[3,4-b]pyridin-5-yl)benzylamino)-N-cyclohexyl-5-(trifluoromethyl)nicotinamide | 510 | ¹H NMR (400 MHz, CD$_3$OD) δ: 8.65 (d, 1H), 8.43 (d, 1H), 8.30 (s, 1H), 8.03 (d, 1H), 7.54 (d, 2H), 7.40 (d, 2H), 4.70 (s, 2H), 3.75-3.70 (m, 1H), 1.84 (d, 2H), 1.73-1.70 (m, 2H), 1.59 (d, 1H), 1.30-1.17 (m, 4H), 1.13-1.10 (m, 1H). |
| 298 | 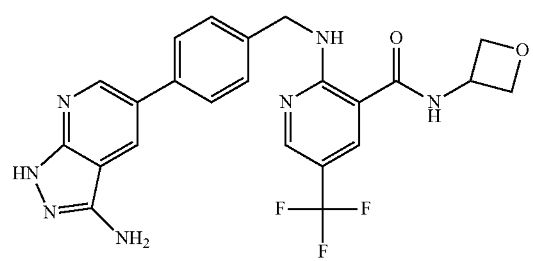 [SMILES: Nc1n[nH]c2ncc(-c3ccc(CNc4ncc(C(F)(F)F)cc4C(=O)NC4COC4)cc3)cc12] | 2-(4-(3-amino-1H-pyrazolo[3,4-b]pyridin-5-yl)benzylamino)-N-(oxetan-3-yl)-5-(trifluoromethyl)nicotinamide | 484 | ¹H NMR (400 MHz, DMSO-d$_6$) δ: 12.00 (s, 1H), 9.40 (d, 1H), 9.22 (t, 1H), 8.64 (d, 1H), 8.53 (d, 1H), 8.40-8.37 (m, 2H), 7.62 (d, 2H), 7.43 (d, 2H), 5.62 (s, 2H), 5.02-4.95 (m, 1H), 4.76-4.72 (m, 4H), 4.62-4.59 (m, 2H). |

| Ex. No. | Structure | Chemical Name | ESI-MS (M + H) | ¹H NMR |
|---|---|---|---|---|
| 299 | 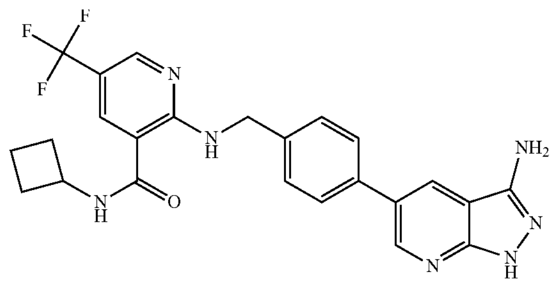 [SMILES: Nc1n[nH]c2ncc(-c3ccc(CNc4ncc(C(F)(F)F)cc4C(=O)NC4CCC4)cc3)cc12] | 2-(4-(3-amino-1H-pyrazolo[3,4-b]pyridin-5-yl)benzylamino)-N-cyclobutyl-5-(trifluoromethyl)nicotinamide | 482.0 | ¹H NMR (400 MHz, CD₃OD) δ: 8.66 (d, 1H), 8.45 (d, 1H), 8.30 (s, 1H), 8.07 (d, 1H), 7.53 (d, 2H), 7.39 (d, 2H), 4.68 (s, 2H), 4.40-4.30 (m, 1H), 2.24-2.22 (m, 2H), 2.05-1.95 (m, 2H), 1.67-1.64 (m, 2H). |
| 300 | 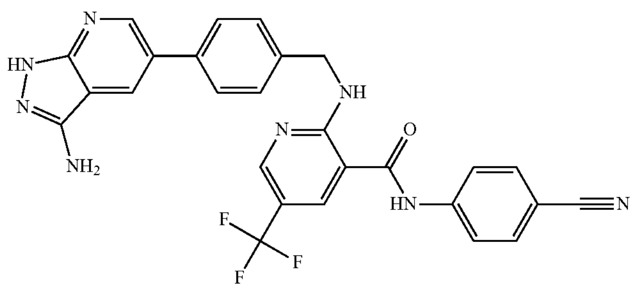 [SMILES: N#Cc1ccc(NC(=O)c2cc(C(F)(F)F)cnc2NCc2ccc(-c3cnc4[nH]nc(N)c4c3)cc2)cc1] | 2-(4-(3-amino-1H-pyrazolo[3,4-b]pyridin-5-yl)benzylamino)-N-(4-cyanophenyl)-5-(trifluoromethyl)nicotinamide | 529 | ¹H NMR (400 MHz, CD₃OD) δ: 8.68 (d, 1H), 8.49 (s, 1H), 8.42 (s, 1H), 8.37 (s, 1H), 7.89 (d, 2H), 7.69-7.61 (m, 4H), 7.52 (d, 2H), 4.84 (s, 2H). |
| 301 | 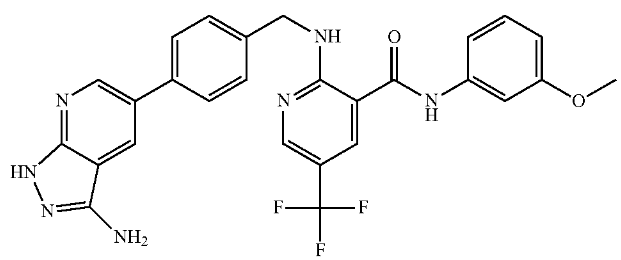 [SMILES: COc1cccc(NC(=O)c2cc(C(F)(F)F)cnc2NCc2ccc(-c3cnc4[nH]nc(N)c4c3)cc2)c1] | 2-(4-(3-amino-1H-pyrazolo[3,4-b]pyridin-5-yl)benzylamino)-N-(3-methoxyphenyl)-5-(trifluoromethyl)nicotinamide | 534 | ¹H NMR (400 MHz, CD₃OD/CDCl₃) δ: 8.64 (d, 1H), 8.46 (s, 1H), 8.35 (s, 1H), 8.32 (s, 1H), 7.73 (br, 1H), 7.61 (d, 2H), 7.50 (d, 2H), 7.32 (s, 1H), 7.25-7.21 (m, 1H), 6.73 (d, 1H), 4.82 (s, 2H), 3.81 (s, 3H). |

TABLE 1-continued

| Ex. No. | Structure | Chemical Name | ESI-MS (M + H) | ¹H NMR |
|---|---|---|---|---|
| 302 | 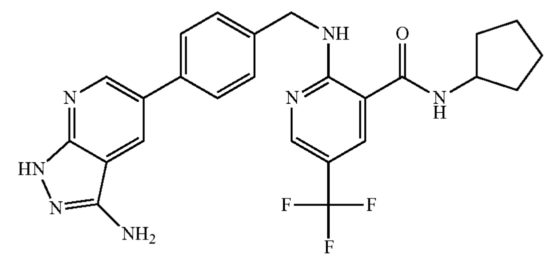 [SMILES: Nc1n[nH]c2ncc(-c3ccc(CNc4ncc(C(F)(F)F)cc4C(=O)NC4CCCC4)cc3)cc12] | 2-(4-(3-amino-1H-pyrazolo[3,4-b]pyridin-5-yl)benzylamino)-N-cyclopentyl-5-(trifluoromethyl)nicotinamide | 496 | ¹H NMR (400 MHz, CD₃OD) δ: 8.64 (d, 1H), 8.356 (d, 1H), 8.14 (d, 1H), 8.39 (d, 1H), 7.62 (d, 2H), 7.49 (d, 2H), 4.79 (s, 2H), 4.30-4.26 (m, 1H), 2.05-2.00 (m, 2H), 1.79-1.74 (m, 2H), 1.65-1.56 (m, 4H). |
| 303 | 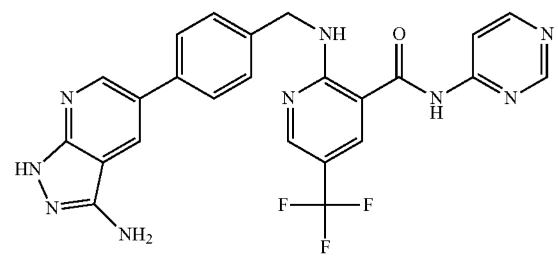 | 2-(4-(3-amino-1H-pyrazolo[3,4-b]pyridin-5-yl)benzylamino)-N-(pyrimidin-4-yl)-5-(trifluoromethyl)nicotinamide | 506 | ¹H NMR (400 MHz, CD₃OD) δ: 8.81 (s, 1H), 8.56 (d, 1H), 8.42 (d, 2H), 8.32 (d, 1H), 8.20 (d, 1H), 7.55 (d, 2H), 7.42 (d, 2H), 4.77 (s, 2H). |
| 304 | 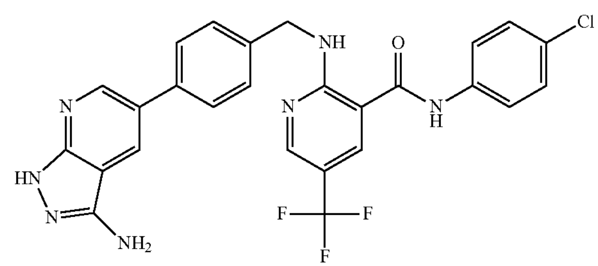 [SMILES: Nc1n[nH]c2ncc(-c3ccc(CNc4ncc(C(F)(F)F)cc4C(=O)Nc4ccc(Cl)cc4)cc3)cc12] | 2-(4-(3-amino-1H-pyrazolo[3,4-b]pyridin-5-yl)benzylamino)-N-(4-chlorophenyl)-5-(trifluoromethyl)nicotinamide | 538 | ¹H NMR (400 MHz, CD₃OD) δ: 8.56 (d, 1H), 8.37 (d, 1H), 8.28 (d, 1H), 8.23 (d, 1H), 7.60-7.58 (m, 2H), 7.53 (d, 2H), 7.40 (d, 2H), 7.26-7.24 (m, 2H), 4.72 (s, 2H). |
| 305 | 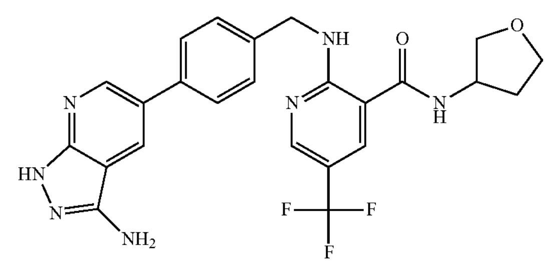 [SMILES: Nc1n[nH]c2ncc(-c3ccc(CNc4ncc(C(F)(F)F)cc4C(=O)NC4CCOC4)cc3)cc12] | 2-(4-(3-amino-1H-pyrazolo[3,4-b]pyridin-5-yl)benzylamino)-N-(tetrahydrofuran-3-yl)-5-(trifluoromethyl)nicotinamide | 498.1 | ¹H NMR (400 MHz, CD₃OD) δ: 8.75 (d, 1H), 8.53 (d, 1H), 8.42 (d, 1H), 8.21 (d, 1H), 7.64 (d, 2H), 7.50 (d, 2H), 4.80 (s, 2H), 4.57-4.54 (m, 1H), 3.99-3.93 (m, 2H), 3.86-3.82 (m, 1H), 3.75-3.72 (m, 1H), 2.33-2.24 (m, 1H), 2.05-1.97 (m, 1H). |

| Ex. No. | Structure | Chemical Name | ESI-MS (M + H) | 1H NMR |
|---|---|---|---|---|
| 306 | 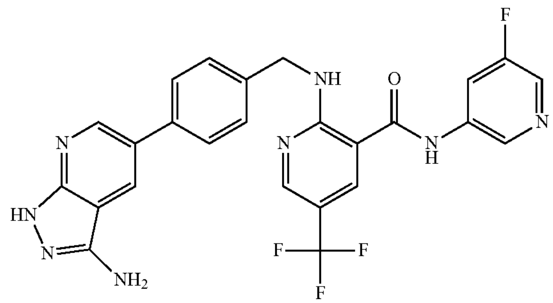 [SMILES: Nc1n[nH]c2ncc(-c3ccc(CNc4ncc(C(F)(F)F)cc4C(=O)Nc4cncc(F)c4)cc3)cc12] | 2-(4-(3-amino-1H-pyrazolo[3,4-b]pyridin-5-yl)benzylamino)-N-(5-fluoropyridin-3-yl)-5-(trifluoromethyl)nicotinamide | 522.9 | 1H NMR (400 MHz, CD3OD) δ: 8.58-8.55 (m, 2H), 8.40 (s, 1H), 8.31-8.28 (m, 2H), 8.13-8.09 (m, 2H), 7.53 (d, 2H), 7.40 (d, 2H), 4.76 (s, 2H). |
| 307 | 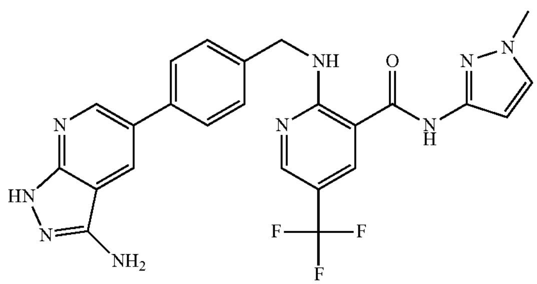 [SMILES: Cn1ccc(NC(=O)c2cc(C(F)(F)F)cnc2NCc2ccc(-c3cnc4[nH]nc(N)c4c3)cc2)n1] | 2-(4-(3-amino-1H-pyrazolo[3,4-b]pyridin-5-yl)benzylamino)-N-(1-methyl-1H-pyrazol-3-yl)-5-(trifluoromethyl)nicotinamide | 508 | 1H NMR (400 MHz, DMSO-d6) δ: 11.21 (s, 1H), 9.15 (t, 1H), 8.70 (d, 1H), 8.52 (s, 2H), 8.45 (s, 1H), 7.65-7.63 (m, 3H), 7.46 (d, 2H), 6.57 (d, 1H), 4.77 (d, 2H), 4.56 (br, 3H), 3.79 (s, 3H). |
| 308 | 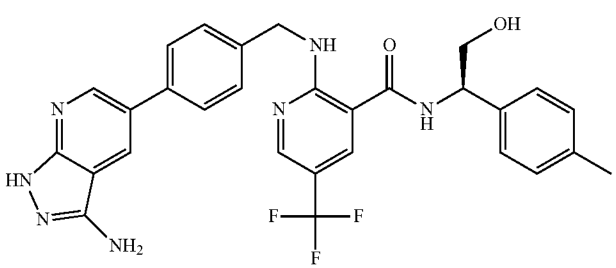 [SMILES: Cc1ccc([C@H](CO)NC(=O)c2cc(C(F)(F)F)cnc2NCc2ccc(-c3cnc4[nH]nc(N)c4c3)cc2)cc1] | (R)-2-(4-(3-amino-1H-pyrazolo[3,4-b]pyridin-5-yl)benzylamino)-N-(1-(4-fluorophenyl)-2-hydroxyethyl)-5-(trifluoromethyl)nicotinamide | 566 | 1H NMR (400 MHz, CD3OD) δ: 8.51 (d, 1H), 8.30 (s, 1H), 8.23-8.20 (m, 2H), 7.46-7.43 (m, 2H), 7.32-7.28 (m, 4H), 6.99-6.92 (m, 2H), 5.06 (t, 1H), 4.61 (s, 2H), 3.76-3.70 (m, 2H). |

TABLE 1-continued

| Ex. No. | Structure | Chemical Name | ESI-MS (M + H) | $^1$H NMR |
|---|---|---|---|---|
| 309 | 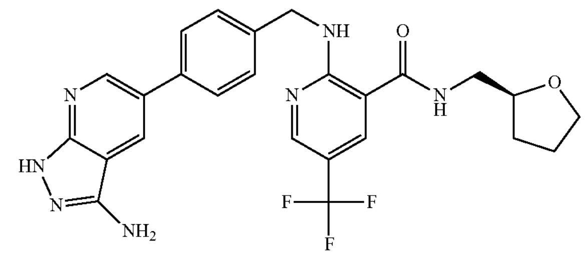 [SMILES: Nc1n[nH]c2ncc(-c3ccc(CNc4ncc(C(F)(F)F)cc4C(=O)NC[C@@H]4CCCO4)cc3)cc12] | (S)-2-(4-(3-amino-1H-pyrazolo[3,4-b]pyridin-5-yl)benzylamino)-N-((tetrahydrofuran-2-yl)methyl)-5-(trifluoromethyl)nicotinamide | 512 | $^1$H NMR (400 MHz, DMSO-d$_6$) δ: 12.03 (s, 1H), 9.30 (t, 1H), 8.96 (t, 1H), 8.65 (s, 1H), 8.51 (s, 1H), 8.38 (s, 1H), 8.31 (s, 1H), 7.63 (d, 2H), 7.43 (d, 2H), 5.65 (s, 2H), 4.73 (d, 2H), 4.01-3.96 (m, 1H), 3.80-3.75 (m, 1H), 3.66-3.61 (m, 1H), 3.32-3.30 (m, 2H), 1.95-1.80 (m, 3H), 1.59-1.54 (m, 1H). |
| 310 | 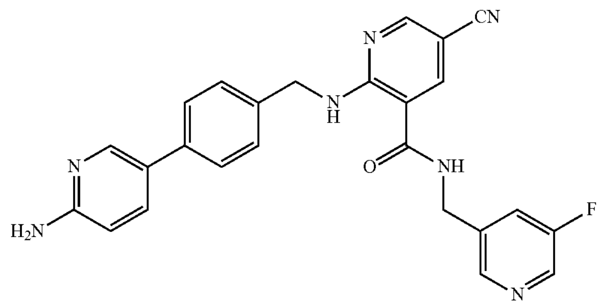 [SMILES: N#Cc1cnc(NCc2ccc(-c3ccc(N)nc3)cc2)c(C(=O)NCc2cncc(F)c2)c1] | 2-(4-(6-aminopyridin-3-yl)benzylamino)-5-cyano-N-((5-fluoropyridin-3-yl)methyl)nicotinamide | 454.0 | $^1$H NMR (400 MHz, DMSO-d$_6$) δ: 9.36 (t, 2H), 8.57 (d, 1H), 8.49-8.47 (m, 2H), 8.43 (d, 1H), 8.26-8.24 (m, 2H), 8.08 (br, 2H), 7.73 (d, 1H), 7.62 (d, 2H), 7.41 (d, 2H), 7.05 (d, 1H), 4.74 (d, 2H), 4.51 (d, 2H). |
| 311 | 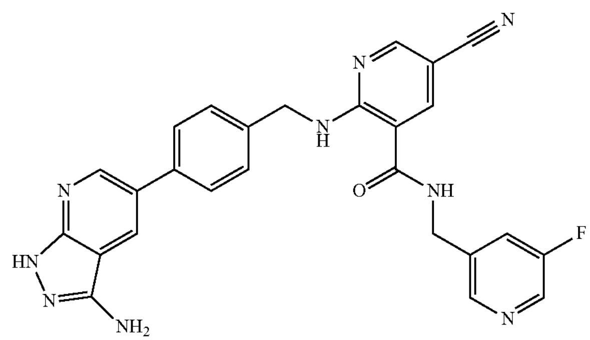 [SMILES: N#Cc1cnc(NCc2ccc(-c3cnc4[nH]nc(N)c4c3)cc2)c(C(=O)NCc2cncc(F)c2)c1] | 2-(4-(3-amino-1H-pyrazolo[3,4-b]pyridin-5-yl)benzylamino)-5-cyano-N-((5-fluoropyridin-3-yl)methyl)nicotinamide | 494.2 | $^1$H NMR (400 MHz, CD$_3$OD) δ: 9.18-9.16 (m, 1H), 8.72-8.70 (m, 1H), 8.48 (s, 2H), 8.37-8.32 (m, 1H), 7.62-7.59 (m, 4H), 7.50-7.48 (m, 2H), 4.82 (s, 2H), 4.58 (s, 2H). |

TABLE 1-continued

| Ex. No. | Structure | Chemical Name | ESI-MS (M + H) | ¹H NMR |
|---|---|---|---|---|
| 312 | 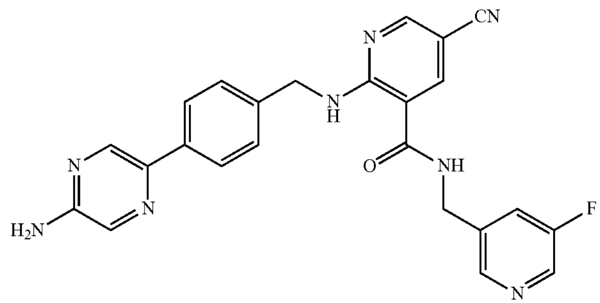 [SMILES: N#Cc1cnc(NCc2ccc(-c3cnc(N)cn3)cc2)c(C(=O)NCc2cncc(F)c2)c1] | 2-(4-(5-aminopyrazin-2-yl)benzylamino)-5-cyano-N-((5-fluoropyridin-3-yl)methyl)nicotinamide | 455.2 | ¹H NMR (400 MHz, DMSO-d₆) δ: 9.42-9.34 (m, 2H), 8.58 (d, 1H), 8.49-8.45 (m, 4H), 7.95 (s, 1H), 7.85 (d, 2H), 7.72 (d, 1H), 7.35 (d, 2H), 4.71 (d, 2H), 4.51 (d, 2H). |
| 313 | 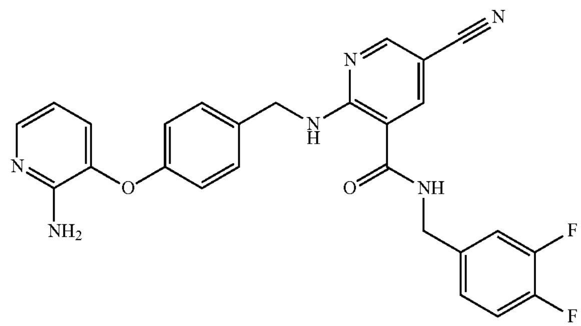 [SMILES: N#Cc1cnc(NCc2ccc(Oc3cccnc3N)cc2)c(C(=O)NCc2ccc(F)c(F)c2)c1] | 2-(4-(2-aminopyridin-3-yloxy)benzylamino)-5-cyano-N-(3,4-difluorobenzyl)nicotinamide | 487 | ¹H NMR (400 MHz, CDCl₃) δ 9.18 (t, 1H), 8.47 (d, 1H), 7.90 (d, 1H), 7.85 (dd, 1H), 7.32 (d, 2H), 7.11-7.19 (m, 2H), 7.01-7.08 (m, 2H), 6.96 (d, 2H), 6.80 (t, 1H), 6.62 (dd, 1H), 4.76 (br-s, 2H), 4.72 (d, 2H), 4.51 (d, 2H). |
| 314 | 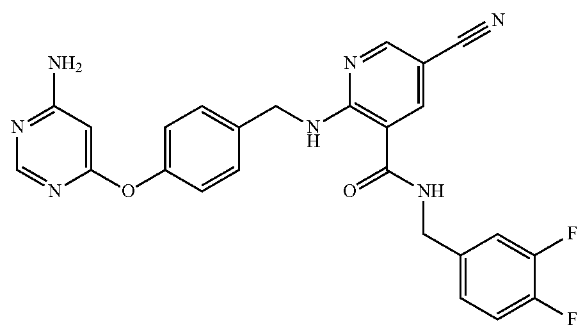 [SMILES: N#Cc1cnc(NCc2ccc(Oc3cc(N)ncn3)cc2)c(C(=O)NCc2ccc(F)c(F)c2)c1] | 2-(4-(6-aminopyrimidin-4-yloxy)benzylamino)-5-cyano-N-(3,4-difluorobenzyl)nicotinamide | 488.1 | ¹H NMR (CDCl₃, 400 MHz) δ 9.19 (t, 1H), 8.47 (d, 1H), 8.27 (s, 1H), 7.88 (d, 1H), 7.39 (s, 2H), 7.03-7.19 (m, 5H), 6.74 (t, 1H), 5.85 (s, 1H), 4.99 (s, 2H), 4.76 (d, 2H), 4.52 (d, 2H). |

TABLE 1-continued

| Ex. No. | Structure | Chemical Name | ESI-MS (M + H) | ¹H NMR |
|---|---|---|---|---|
| 315 | 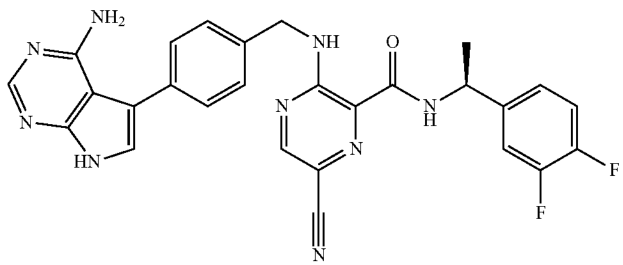 [SMILES: C[C@H](NC(=O)c1nc(C#N)cnc1NCc1ccc(-c2c[nH]c3ncnc(N)c23)cc1)c1ccc(F)c(F)c1] | (S)-3-(4-(4-amino-7H-pyrrolo[2,3-d]pyrimidin-5-yl)benzylamino)-6-cyano-N-(1-(3,4-difluorophenyl)ethyl)pyrazine-2-carboxamide | 525.9 | ¹H NMR (300 MHz, DMSO-d$_6$) δ 11.81 (br. s., 1H), 9.68 (t, J = 5.85 Hz, 1H), 9.26 (d, J = 8.31 Hz, 1H), 8.61-8.75 (m, 1H), 8.00-8.13 (m, 1H), 7.45 (ddd, J = 2.08, 7.84, 11.99 Hz, 1H), 7.24-7.38 (m, 5H), 7.13-7.23 (m, 2H), 6.03 (br. s., 1H), 5.05 (quin, J = 7.37 Hz, 1H), 4.55-4.78 (m, 2H), 1.45 (d, J = 7.18 Hz, 3H). |
| 316 | 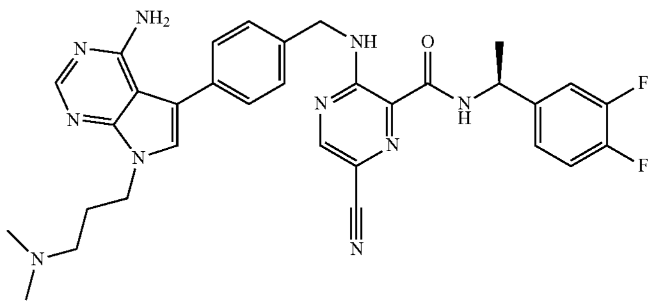 [SMILES: C[C@H](NC(=O)c1nc(C#N)cnc1NCc1ccc(-c2cn(CCCN(C)C)c3ncnc(N)c23)cc1)c1ccc(F)c(F)c1] | (S)-3-(4-(4-amino-7-(3-(dimethylamino)propyl)-7H-pyrrolo[2,3-d]pyrimidin-5-yl)benzylamino)-6-cyano-N-(1-(3,4-difluorophenyl)ethyl)pyrazine-2-carboxamide | 611.0 | ¹H NMR (300 MHz, DMSO-d$_6$) δ 9.75 (t, J = 5.85 Hz, 1H), 9.33 (d, J = 8.31 Hz, 1H), 8.73-8.79 (m, 1H), 8.12-8.18 (m, 1H), 7.31-7.58 (m, 7H), 7.27 (d, J = 4.53 Hz, 1H), 6.06 (br. s., 1H), 5.12 (quin, J = 7.37 Hz, 1H), 4.65-4.85 (m, 2H), 4.20 (t, J = 6.99 Hz, 2H), 2.56 (d, J = 6.80 Hz, 2H), 2.33-2.46 (m, 6H), 1.95-2.06 (m, 2H), 1.52 (d, J = 6.80 Hz, 3H). |
| 317 | 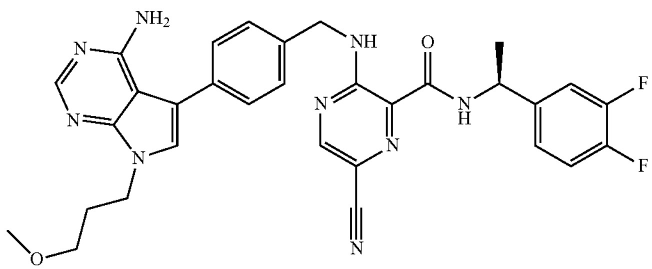 [SMILES: COCCCn1cc(-c2ccc(CNc3ncc(C#N)nc3C(=O)N[C@@H](C)c3ccc(F)c(F)c3)cc2)c2c(N)ncnc21] | (S)-3-(4-(4-amino-7-(3-methoxypropyl)-7H-pyrrolo[2,3-d]pyrimidin-5-yl)benzylamino)-6-cyano-N-(1-(3,4-difluorophenyl)ethyl)pyrazine-2-carboxamide | 597.9 | ¹H NMR (300 MHz, DMSO-d$_6$) δ 9.76 (t, J = 6.04 Hz, 1H), 9.33 (d, J = 8.31 Hz, 1H), 8.72-8.79 (m, 1H), 8.15 (s, 1H), 7.52 (ddd, J = 1.89, 7.93, 12.09 Hz, 1H), 7.30-7.46 (m, 6H), 7.22-7.30 (m, 1H), 6.10 (br. s., 1H), 5.13 (quin, J = 7.37 Hz, 1H), 4.65-4.85 (m, 2H), 4.21 (t, J = 7.18 Hz, 2H), 3.27-3.40 (m, 5H), 2.01 (quin, J = 6.70 Hz, 2H), 1.52 (d, J = 7.18 Hz, 3H). |

| Ex. No. | Structure | Chemical Name | ESI-MS (M + H) | ¹H NMR |
|---|---|---|---|---|
| 318 | 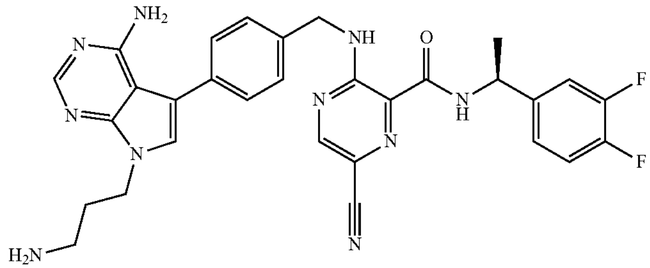 [SMILES: C[C@H](NC(=O)c1nc(C#N)cnc1NCc1ccc(-c2cn(CCCN)c3ncnc(N)c23)cc1)c1ccc(F)c(F)c1] | (S)-3-(4-(4-amino-7-(3-aminopropyl)-7H-pyrrolo[2,3-d]pyrimidin-5-yl)benzylamino)-6-cyano-N-(1-(3,4-difluorophenyl)ethyl)pyrazine-2-carboxamide | 582.9 | ¹H NMR (300 MHz, DMSO-d₆) δ 9.68 (t, J = 5.85 Hz, 1H), 9.27 (d, J = 8.31 Hz, 1H), 8.69 (s, 1H), 8.08 (s, 1H), 7.45 (ddd, J = 2.08, 7.84, 11.99 Hz, 1H), 7.24-7.39 (m, 7H), 7.21 (d, J = 4.15 Hz, 1H), 5.99 (br. s., 1H), 4.99-5.12 (m, 1H), 4.67 (dd, J = 1.89, 5.67 Hz, 2H), 4.16 (t, J = 6.80 Hz, 2H), 2.56 (t, J = 6.99 Hz, 2H), 1.88 (quin, J = 6.99 Hz, 2H), 1.45 (d, J = 7.18 Hz, 3H) |
| 319 | 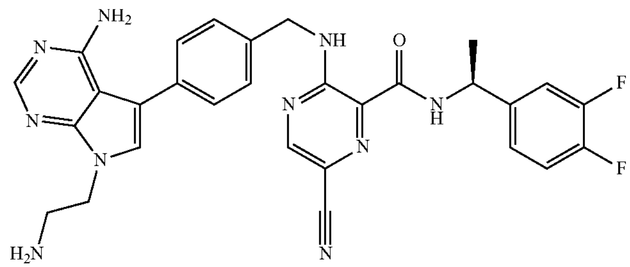 [SMILES: C[C@H](NC(=O)c1nc(C#N)cnc1NCc1ccc(-c2cn(CCN)c3ncnc(N)c23)cc1)c1ccc(F)c(F)c1] | (S)-3-(4-(4-amino-7-(2-aminoethyl)-7H-pyrrolo[2,3-d]pyrimidin-5-yl)benzylamino)-6-cyano-N-(1-(3,4-difluorophenyl)ethyl)pyrazine-2-carboxamide | 568.9 | ¹H NMR (300 MHz, DMSO-d₆) δ 9.76 (t, J = 5.85 Hz, 1H), 9.34 (d, J = 8.31 Hz, 1H), 8.76 (s, 1H), 8.15 (s, 1H), 7.52 (ddd, J = 2.08, 7.84, 11.99 Hz, 1H), 7.30-7.47 (m, 7H), 7.22-7.30 (m, 1H), 6.06 (br. s., 1H), 5.13 (quin, J = 7.37 Hz, 1H), 4.74 (dd, J = 2.45, 5.85 Hz, 2H), 4.22 (t, J = 6.42 Hz, 2H), 3.04 (t, J = 6.42 Hz, 2H), 1.49-1.57 (m, 3H) |
| 320 | 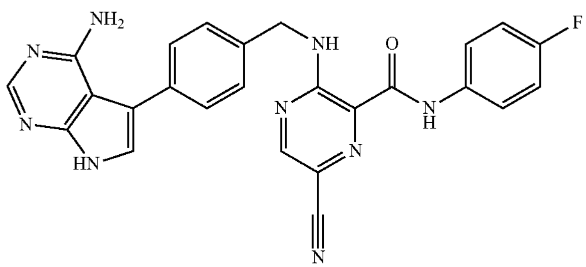 [SMILES: N#Cc1cnc(NCc2ccc(-c3c[nH]c4ncnc(N)c34)cc2)c(C(=O)Nc2ccc(F)cc2)n1] | 3-(4-(4-amino-7H-pyrrolo[2,3-d]pyrimidin-5-yl)benzylamino)-6-cyano-N-(4-fluorophenyl)pyrazine-2-carboxamide | 479.9 | ¹H NMR (300 MHz, DMSO-d₆) δ 11.78 (br. s., 1H), 10.73 (s, 1H), 9.67 (t, J = 6.04 Hz, 1H), 8.80 (s, 1H), 8.10 (s, 1H), 7.83 (dt, J = 3.40, 5.29 Hz, 2H), 7.36-7.58 (m, 4H), 7.17-7.27 (m, 3H), 5.97 (br. s., 1H), 4.80 (d, J = 6.04 Hz, 2H). |

TABLE 1-continued

| Ex. No. | Structure | Chemical Name | ESI-MS (M + H) | ¹H NMR |
|---|---|---|---|---|
| 321 | 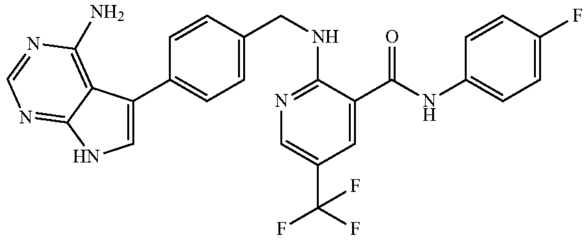 [SMILES: Nc1ncnc2[nH]cc(-c3ccc(CNc4ncc(C(F)(F)F)cc4C(=O)Nc4ccc(F)cc4)cc3)c12] | 2-(4-(4-amino-7H-pyrrolo[2,3-d]pyrimidin-5-yl)benzylamino)-N-(4-fluorophenyl)-5-(trifluoromethyl)nicotinamide | 521.9 | ¹H NMR (300 MHz, DMSO-d₆) δ 11.77 (br. s., 1H), 10.50 (s, 1H), 8.91 (t, J = 5.85 Hz, 1H), 8.56 (d, J = 1.51 Hz, 1H), 8.39 (d, J = 2.27 Hz, 1H), 8.10 (s, 1H), 7.65-7.75 (m, 2H), 7.40-7.48 (m, 4H), 7.17-7.28 (m, 3H), 5.96 (br. s., 2H), 4.77 (d, J = 6.04 Hz, 2H) |
| 322 | 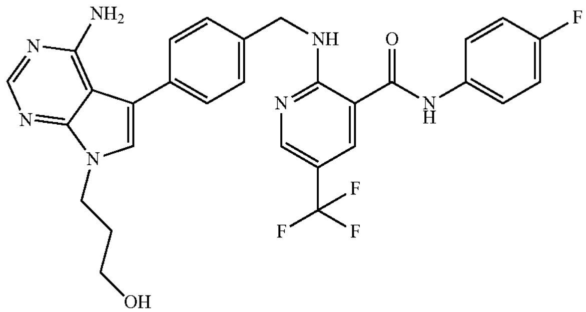 [SMILES: Nc1ncnc2c1c(-c1ccc(CNc3ncc(C(F)(F)F)cc3C(=O)Nc3ccc(F)cc3)cc1)cn2CCCO] | 2-(4-(4-amino-7-(3-hydroxypropyl)-7H-pyrrolo[2,3-d]pyrimidin-5-yl)benzylamino)-N-(4-fluorophenyl)-5-(trifluoromethyl)nicotinamide | 579.9 | ¹H NMR (300 MHz, DMSO-d₆) δ 10.51 (s, 1H), 8.92 (t, J = 5.67 Hz, 1H), 8.56 (s, 1H), 8.40 (d, J = 1.89 Hz, 1H), 8.09-8.18 (m, 1H), 7.63-7.80 (m, 2H), 7.37-7.49 (m, 4H), 7.31 (s, 1H), 7.22 (t, J = 8.88 Hz, 2H), 6.04 (br. s., 1H), 4.77 (d, J = 5.67 Hz, 2H), 4.62 (t, J = 5.10 Hz, 1H), 4.22 (t, J = 6.99 Hz, 2H), 3.36-3.48 (m, 2H), 1.84-2.01 (m, 2H) |
| 323 | 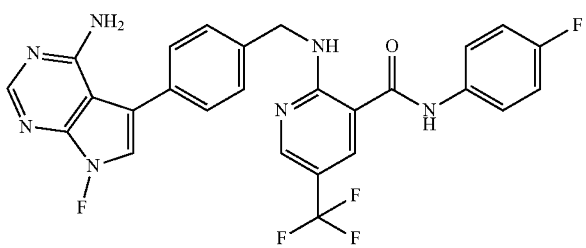 [SMILES: Nc1ncnc2c1c(-c1ccc(CNc3ncc(C(F)(F)F)cc3C(=O)Nc3ccc(F)cc3)cc1)cn2F] | 2-(4-(4-amino-7-methyl-7H-pyrrolo[2,3-d]pyrimidin-5-yl)benzylamino)-N-(4-fluorophenyl)-5-(trifluoromethyl)nicotinamide | 535.90 | ¹H NMR (400 MHz, DMSO-d₆) δ ppm 10.51 (s, 1 H) 8.92 (t, J = 5.77 Hz, 1 H) 8.56 (d, J = 0.75 Hz, 1 H) 8.40 (d, J = 2.01 Hz, 1 H) 8.16 (s, 1 H) 7.64-7.74 (m, 2 H) 7.37-7.49 (m, 4 H) 7.29 (s, 1 H) 7.21 (t, J = 8.91 Hz, 2 H) 6.09 (br. s., 2 H) 4.77 (d, J = 5.77 Hz, 2 H) 3.73 (s, 3 H) |

TABLE 1-continued

| Ex. No. | Structure | Chemical Name | ESI-MS (M + H) | ¹H NMR |
|---|---|---|---|---|
| 324 | 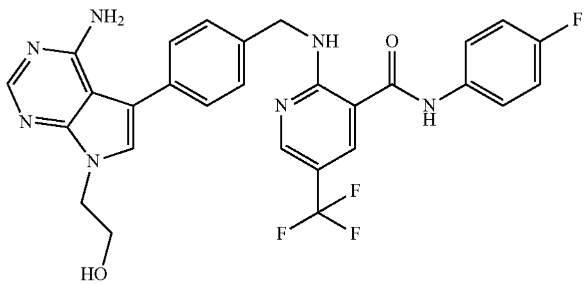 [SMILES: Nc1ncnc2c1c(-c1ccc(CNc3ncc(C(F)(F)F)cc3C(=O)Nc3ccc(F)cc3)cc1)cn2CCO] | 2-(4-(4-amino-7-(2-hydroxyethyl)-7H-pyrrolo[2,3-d]pyrimidin-5-yl)benzylamino)-5-(trifluoromethyl)nicotinamide | 565.9 | ¹H NMR (300 MHz, DMSO-d₆) δ 10.52 (s, 1H), 8.95 (t, J = 5.85 Hz, 1H), 8.56 (d, J = 1.13 Hz, 1H), 8.44 (s, 1H), 8.42 (d, J = 2.27 Hz, 1H), 7.58-7.77 (m, 4H), 7.40-7.54 (m, 4H), 7.17-7.28 (m, 2H), 4.80 (d, J = 5.67 Hz, 2H), 4.31 (t, J = 5.48 Hz, 2H), 3.78 (t, J = 5.48 Hz, 2H) |
| 325 | 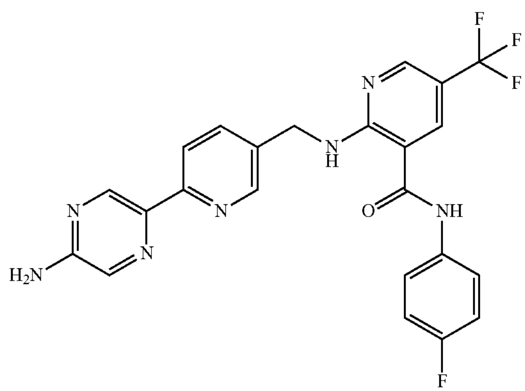 [SMILES: Nc1cnc(-c2ccc(CNc3ncc(C(F)(F)F)cc3C(=O)Nc3ccc(F)cc3)cn2)cn1] | 2-((6-(5-aminopyrazin-2-yl)pyridin-3-yl)methyl)amino)-N-(4-fluorophenyl)-5-(trifluoromethyl)nicotinamide | 483.90 | ¹H NMR (400 MHz, DMSO-d₆) δ ppm 10.51 (s, 1 H) 8.93 (t, J = 6.02 Hz, 1 H) 8.84 (s, 1 H) 8.56 (d, J = 18.57 Hz, 2 H) 8.37 (d, J = 2.01 Hz, 1 H) 8.12 (d, J = 8.28 Hz, 1 H) 7.96 (s, 2 H) 7.64-7.75 (m, 2 H) 7.22 (t, J = 8.91 Hz, 2 H) 6.77-7.03 (m, 2 H) 4.76 (d, J = 6.02 Hz, 2 H); ¹⁹F NMR (376 MHz, DMSO-d₆) δ ppm −63.32 (s, 3 F) −78.50 (TFA, s, 6 F) −122.48 (s, 1 F). |

| Ex. No. | Structure | Chemical Name | ESI-MS (M + H) | ¹H NMR |
|---|---|---|---|---|
| 326 | 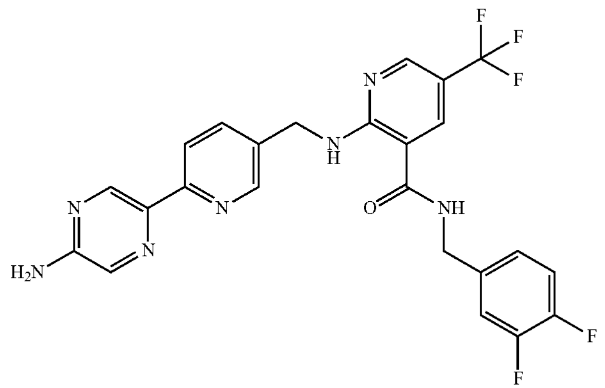 [SMILES: Nc1cnc(-c2ccc(CNc3ncc(C(F)(F)F)cc3C(=O)NCc3ccc(F)c(F)c3)cn2)cn1] | 2-((6-(5-aminopyrazin-2-yl)pyridin-3-yl)methyl)amino)-N-(3,4-difluorobenzyl)-5-(trifluoromethyl)nicotinamide | 515.90 | ¹H NMR (400 MHz, DMSO-d₆) δ ppm 9.26-9.43 (m, 2 H) 8.86 (d, J = 0.75 Hz, 1 H) 8.57 (s, 1 H) 8.50 (s, 1 H) 8.35 (d, J = 2.01 Hz, 1 H) 8.11-8.23 (m, 1 H) 7.91-8.06 (m, 2 H) 7.40 (dt, J = 10.67, 8.60 Hz, 2 H) 7.20 (br. s., 1 H) 7.02 (br. s., 2 H) 4.76 (d, J = 5.77 Hz, 2 H) 4.45 (d, J = 5.52 Hz, 2 H). ¹⁹F NMR (376 MHz, DMSO-d₆) δ ppm −63.11 (s, 3 F) −78.50 (TFA, s, 6 F) −143.06−142.80 (m, 1 F) −145.55−145.26 (m, 1 F). |
| 327 | 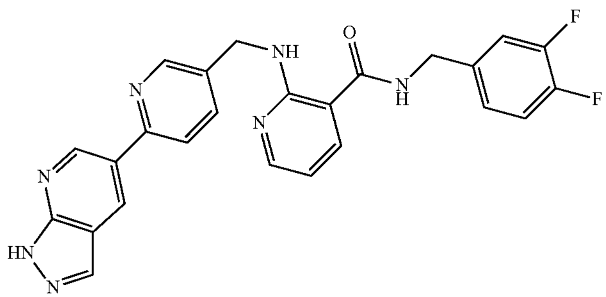 [SMILES: O=C(NCc1ccc(F)c(F)c1)c1cccnc1NCc1ccc(-c2cnc3[nH]ncc3c2)nc1] | 2-((6-(1H-pyrazolo[3,4-b]pyridin-5-yl)pyridin-3-yl)methyl)amino)-N-(3,4-difluorobenzyl)nicotinamide | 472.2 | ¹H NMR (400 MHz, DMSO-d₆) δ 9.25 (t, J = 5.77 Hz, 1H), 9.20 (d, J = 2.01 Hz, 1H), 9.02-9.15 (m, 1H), 8.84 (d, J = 2.26 Hz, 1H), 8.71 (d, J = 1.51 Hz, 1H), 8.24-8.30 (m, 1H), 8.06-8.21 (m, 3H), 7.96 (dd, J = 2.26, 8.28 Hz, 1H), 7.33-7.46 (m, 2H), 7.14-7.24 (m, 1H), 6.75 (dd, J = 5.27, 7.53 Hz, 1H), 4.75 (s, 2H), 4.45 (d, J = 5.77 Hz, 2H) |
| 328 | 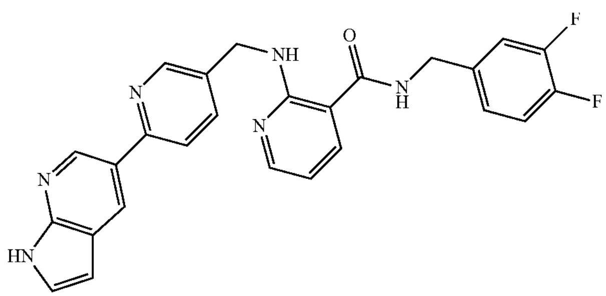 [SMILES: O=C(NCc1ccc(F)c(F)c1)c1cccnc1NCc1ccc(-c2cnc3[nH]ccc3c2)nc1] | 2-((6-(1H-pyrrolo[2,3-b]pyridin-5-yl)pyridin-3-yl)methyl)amino)-N-(3,4-difluorobenzyl)nicotinamide | 471.20 | ¹H NMR (400 MHz, DMSO-d₆) δ 11.91 (br. s., 1H), 9.20 (t, J = 5.77 Hz, 1H), 8.92-9.02 (m, 1H), 8.89 (d, J = 2.26 Hz, 1H), 8.69 (d, J = 1.76 Hz, 1H), 8.61 (d, J = 1.76 Hz, 1H), 8.18 (dd, J = 1.76, 5.02 Hz, 1H), 8.09 (d, J = 8.03 Hz, 2H), 8.02 (d, J = 1.25 Hz, 1H), 7.54-7.59 (m, 1H), 7.33-7.44 (m, 2H), 7.13-7.22 (m, 1H), 6.71 (dd, J = 5.02, 7.53 Hz, 1H), 6.58 (dd, J = 1.88, 3.39 Hz, 1H), 4.74 (br. s. 2H), 4.44 (d, 2H) |

TABLE 1-continued

| Ex. No. | Structure | Chemical Name | ESI-MS (M + H) | ¹H NMR |
|---|---|---|---|---|
| 329 | 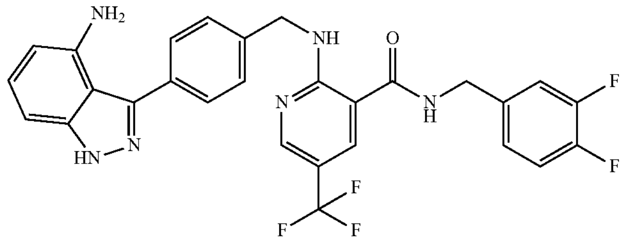 [SMILES: Nc1cccc2[nH]nc(-c3ccc(CNc4ncc(C(F)(F)F)cc4C(=O)NCc4ccc(F)c(F)c4)cc3)c12] | 2-[4-(4-Amino-1H-pyrazolo[3,4-d]pyrimidin-3-yl)-benzylamino]-N-(3,4-difluoro-benzyl)-5-trifluoromethyl-nicotinamide | 554.9 | ¹H NMR (300 MHz, DMSO-$d_6$) δ 13.56 (s, 1H), 9.36 (q, J = 5.29 Hz, 2H), 8.53 (d, J = 1.13 Hz, 1H), 8.37 (d, J = 2.27 Hz, 1H), 8.19-8.23 (m, 1H), 7.63 (d, J = 7.93 Hz, 2H), 7.34-7.53 (m, 4H), 7.16-7.24 (m, 1H), 4.79 (d, J = 5.67 Hz, 2H), 4.45 (d, J = 5.67 Hz, 2H) |
| 330 | 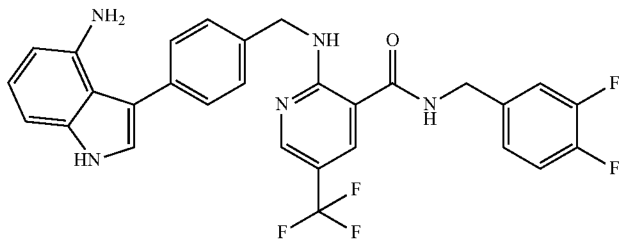 [SMILES: Nc1cccc2[nH]cc(-c3ccc(CNc4ncc(C(F)(F)F)cc4C(=O)NCc4ccc(F)c(F)c4)cc3)c12] | 2-[4-(4-Amino-7H-pyrrolo[2,3-d]pyrimidin-5-yl)-benzylamino]-N-(3,4-difluoro-benzyl)-5-trifluoromethyl-nicotinamide | 553.9 | ¹H NMR (300 MHz, DMSO-$d_6$) δ 11.80 (br. s., 1H), 9.33 (td, J = 5.76, 14.92 Hz, 2H), 8.31-8.61 (m, 2H), 8.11 (s, 1H), 7.33-7.47 (m, 6H), 7.12-7.27 (m, 2H), 6.01 (br. s., 1H), 4.75 (d, J = 6.04 Hz, 2H), 4.38-4.54 (m, 2H) |
| 331 | 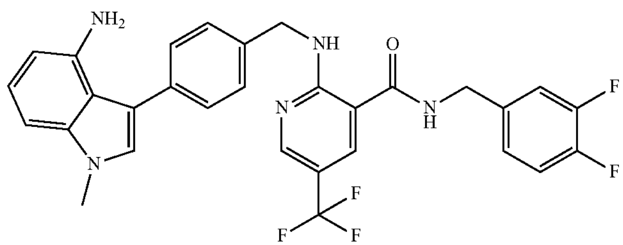 [SMILES: Cn1cc(-c2ccc(CNc3ncc(C(F)(F)F)cc3C(=O)NCc3ccc(F)c(F)c3)cc2)c2c(N)cccc21] | 2-(4-(4-amino-7-methyl-7H-pyrrolo[2,3-d]pyrimidin-5-yl)-benzylamino)-N-(3,4-(trifluoromethyl)nicotinamide | 567.9 | ¹H NMR (300 MHz, DMSO-$d_6$) δ 9.21-9.49 (m, 2H), 8.53 (d, J = 1.51 Hz, 1H), 8.36 (d, J = 1.89 Hz, 1H), 8.15 (s, 1H), 7.32-7.50 (m, 6H), 7.28 (s, 1H), 7.20 (d, J = 3.78 Hz, 1H), 4.75 (d, J = 5.67 Hz, 2H), 4.45 (d, J = 5.67 Hz, 2H), 3.67-3.81 (m, 3H) |
| 332 | 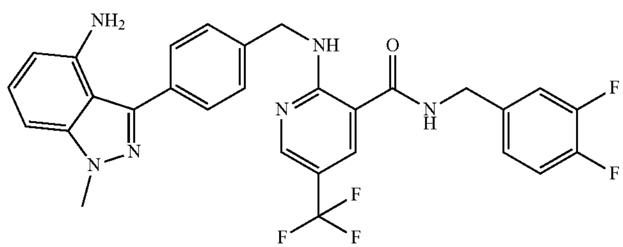 [SMILES: Cn1nc(-c2ccc(CNc3ncc(C(F)(F)F)cc3C(=O)NCc3ccc(F)c(F)c3)cc2)c2c(N)cccc21] | 2-(4-(4-amino-1-methyl-1H-pyrazolo[3,4-d]pyrimidin-3-yl)-benzylamino)-N-(3,4-difluorobenzyl)-5-(trifluoromethyl)nicotinamide | 568.9 | ¹H NMR (300 MHz, DMSO-$d_6$) δ 9.29 (d, J = 4.15 Hz, 2H), 8.24-8.54 (m, 2H), 8.12-8.24 (m, 1H), 7.93 Hz, 2H), 7.55 (d, J = 7.93 Hz, 2H), 7.22-7.47 (m, 5H), 7.02-7.19 (m, 1H), 4.63-4.82 (m, 2H), 4.38 (d, J = 5.29 Hz, 2H), 3.87 (s, 3H) |

TABLE 1-continued

| Ex. No. | Structure | Chemical Name | ESI-MS (M + H) | ¹H NMR |
|---|---|---|---|---|
| 333 | 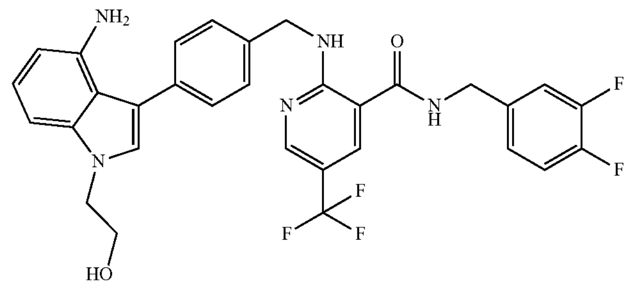 [SMILES: Nc1cccc2c1c(-c1ccc(CNc3ncc(C(F)(F)F)cc3C(=O)NCc3ccc(F)c(F)c3)cc1)cn2CCO] | 2-(4-(4-amino-7-(2-hydroxyethyl)-7H-pyrrolo[2,3-d]pyrimidin-5-yl)benzylamino)-N-(3,4-difluorobenzyl)-5-(trifluoromethyl)nicotinamide | 597.9 | ¹H NMR (300 MHz, CD₃CN) δ 9.10 (t, J = 5.48 Hz, 1H), 8.47 (d, J = 1.13 Hz, 1H), 8.18 (s, 1H), 8.08 (d, J = 2.27 Hz, 1H), 7.72 (br. s., 1H), 7.44 (s, 4H), 7.08-7.34 (m, 4H), 5.33 (br. s., 2H), 4.78 (d, J = 5.67 Hz, 2H), 4.47 (d, J = 5.67 Hz, 2H), 4.23-4.31 (m, 2H), 3.85 (t, J = 5.10 Hz, 2H), 3.57 (br. s., 1H) |
| 334 | 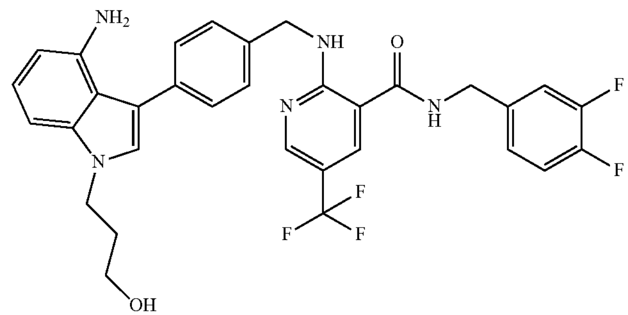 [SMILES: Nc1cccc2c1c(-c1ccc(CNc3ncc(C(F)(F)F)cc3C(=O)NCc3ccc(F)c(F)c3)cc1)cn2CCCO] | 2-(4-(4-amino-7-(3-hydroxypropyl)-7H-pyrrolo[2,3-d]pyrimidin-5-yl)benzylamino)-N-(3,4-difluorobenzyl)-5-(trifluoromethyl)nicotinamide | 611.9 | ¹H NMR (300 MHz, DMSO-d₆) δ 9.34 (td, J = 5.76, 15.30 Hz, 2H), 8.45-8.63 (m, 1H), 8.36 (s, 1H), 8.16 (s, 1H), 7.31-7.48 (m, 7H), 7.19 (ddd, J = 2.45, 4.15, 6.23 Hz, 1H), 6.16 (br. s., 1H), 4.75 (d, J = 6.04 Hz, 2H), 4.45 (d, J = 5.67 Hz, 2H), 4.23 (t, J = 6.99 Hz, 2H), 3.41 (t, J = 6.23 Hz, 2H), 1.80-2.03 (m, 2H) |
| 335 | 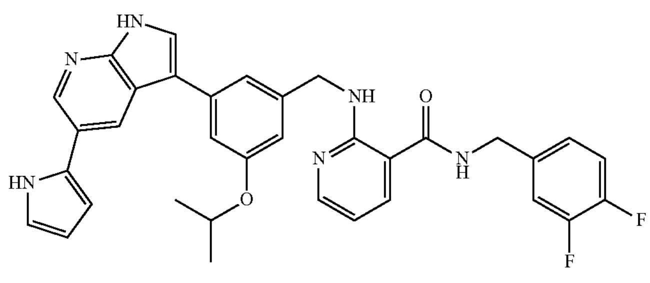 | 2-(3-(5-(1H-pyrrol-2-yl)-1H-pyrrolo[2,3-b]pyridin-3-yl)-5-isopropoxybenzylamino)-N-(3,4-difluorobenzyl)nicotinamide | 593.0 | ¹H NMR (400 MHz, DMSO-d₆) δ: 11.85 (d, 1H), 9.10 (t, 1H), 8.76 (t, 1H), 8.57 (d, 1H), 8.35 (s, 1H), 8.18 (d, 1H), 8.00 (d, 1H), 7.80 (d, 1H), 7.35-7.20 (m, 3H), 7.15-7.12 (m, 1H), 7.10 (s, 1H), 6.86 (s, 1H), 6.76 (s, 1H), 6.60 (dd, 1H), 6.48 (s, 1H), 6.13 (s, 1H), 4.68-4.67 (m, 3H), 4.39 (d, 2H), 1.29 (d, 6H). |

TABLE 1-continued

| Ex. No. | Structure | Chemical Name | ESI-MS (M + H) | ¹H NMR |
|---|---|---|---|---|
| 336 | 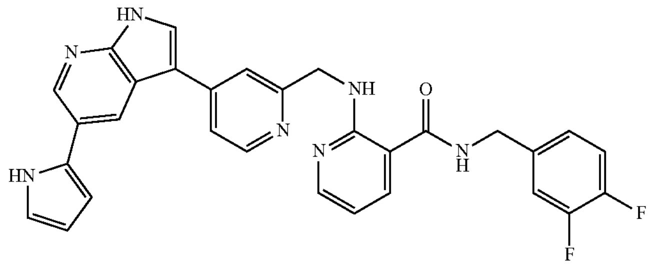 [SMILES: O=C(NCc1ccc(F)c(F)c1)c1cccnc1NCc1cc(-c2c[nH]c3ncc(-c4ccc[nH]4)cc23)ccn1] | 2-((4-(5-(1H-pyrrol-2-yl)-1H-pyrrolo[2,3-b]pyridin-2-yl)methylamino)-N-(3,4-difluorobenzyl)nicotinamide | 536.0 | ¹H NMR (400 MHz, CD₃OD/CDCl₃) δ: 8.53 (d, 1H), 8.48 (d, 1H), 8.40 (d, 1H), 8.16 (dd, 1H), 7.90 (dd, 1H), 7.82 (s, 2H), 7.59 (d, 1H), 7.18-7.15 (m, 3H), 6.88 (s, 1H), 6.64-6.60 (m, 1H), 6.45 (s, 1H), 6.24 (t, 1H), 4.88 (s, 2H), 4.47 (s, 2H). |
| 337 | 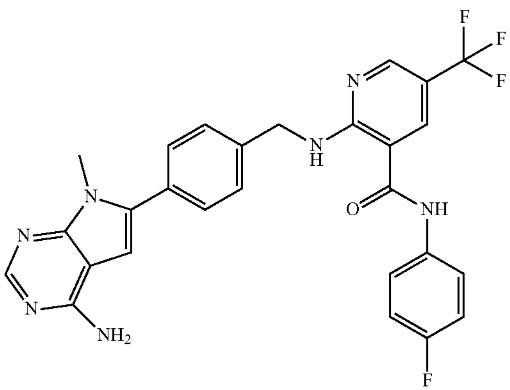 [SMILES: Cn1c(-c2ccc(CNc3ncc(C(F)(F)F)cc3C(=O)Nc3ccc(F)cc3)cc2)cc2c(N)ncnc21] | 2-(4-(4-amino-7-methyl-7H-pyrrolo[2,3-d]pyrimidin-6-yl)pyridin-2-ylamino)-benzylamino)-N-(4-fluorophenyl)-5-(trifluoromethyl)nicotinamide | 535.90 | ¹H NMR (400 MHz, DMSO-d₆) δ ppm 10.53 (s, 1 H) 8.95 (t, J = 5.90 Hz, 1 H) 8.55 (s, 1 H) 8.40 (d, J = 2.01 Hz, 1 H) 8.18 (s, 1 H) 7.63-7.77 (m, 2 H) 7.37-7.61 (m, 5 H) 7.22 (t, J = 8.91 Hz, 2 H) 6.71 (s, 1 H) 4.80 (d, J = 5.77 Hz, 2 H) 3.70 (s, 3 H); ¹⁹F NMR (376 MHz, DMSO-d₆) δ ppm –58.96 (s, 3 F) –73.45 (TFA, S, 1F), –118.16 (s, 1 F). |
| 338 | 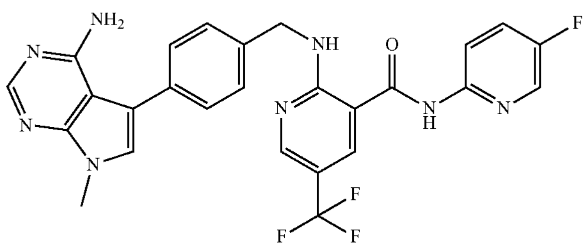 [SMILES: Cn1cc(-c2ccc(CNc3ncc(C(F)(F)F)cc3C(=O)Nc3ccc(F)cn3)cc2)c2c(N)ncnc21] | 2-(4-(4-amino-7-methyl-7H-pyrrolo[2,3-d]pyrimidin-5-yl)pyridin-2-ylamino)-benzylamino)-N-(5-fluoropyridin-2-yl)-5-(trifluoromethyl)nicotinamide | 536.90 | ¹H NMR (400 MHz, DMSO-d₆) δ ppm 11.27 (s, 1 H) 8.91 (t, J = 5.77 Hz, 1 H) 8.49-8.60 (m, 2 H) 8.41-8.47 (m, 2 H) 8.10 (dd, J = 9.16, 4.14 Hz, 1 H) 7.82 (td, J = 8.78, 3.01 Hz, 1 H) 7.61 (s, 1 H) 7.36-7.53 (m, 4 H) 4.80 (d, J = 5.77 Hz, 2 H) 3.74-3.88 (m, 3 H); ¹⁹F NMR (376 MHz, DMSO-d₆) δ ppm –63.24 (s, 3 F) –78.50 (TFA, s, 4 F) –136.53 (s, 1 F). |

| Ex. No. | Structure | Chemical Name | ESI-MS (M + H) | ¹H NMR |
|---|---|---|---|---|
| 339 | 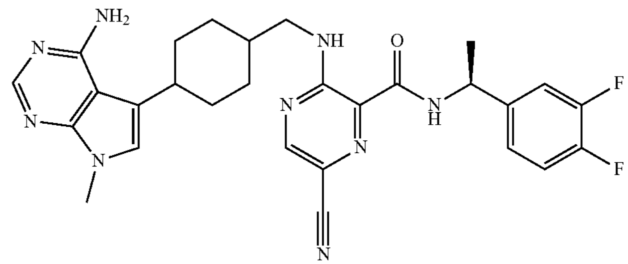 [SMILES: C[C@H](NC(=O)c1nc(C#N)cnc1NCC1CCC(c2cn(C)c3ncnc(N)c23)CC1)c1ccc(F)c(F)c1] | (S)-3-((4-(4-amino-7-methyl-7H-pyrrolo[2,3-d]pyrimidin-5-yl)cyclohexyl)methyl)amino)-6-cyano-N-(1-(3,4-difluorophenyl)ethyl)pyrazine-2-carboxamide | 546.0 | ¹H NMR (400 MHz, DMSO-d₆) δ ppm 9.37-9.53 (m, 1 H) 9.31 (d, J = 8.28 Hz, 1 H) 8.72 (s, 1 H) 8.20 (s, 1 H) 6.98-7.63 (m, 7 H) 5.04-5.21 (m, 1 H) 3.63-3.75 (m, 3 H) 3.54 (d, J = 6.78 Hz, 2 H) 1.97 (br. s., 2 H) 1.42-1.83 (m, 8 H) 1.17-1.37 (m, 2 H); |
| 340 | 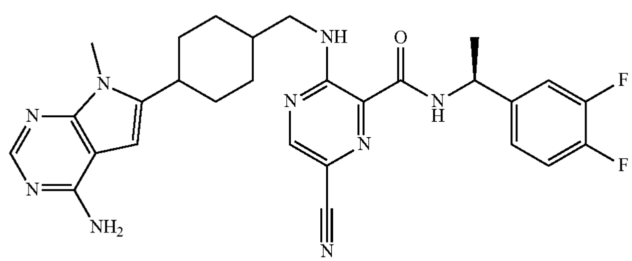 [SMILES: C[C@H](NC(=O)c1nc(C#N)cnc1NCC1CCC(c2cc3c(N)ncnc3n2C)CC1)c1ccc(F)c(F)c1] | (S)-3-((4-(4-amino-7-methyl-7H-pyrrolo[2,3-d]pyrimidin-6-yl)cyclohexyl)methyl)amino)-6-cyano-N-(1-(3,4-difluorophenyl)ethyl)pyrazine-2-carboxamide | 546.0 | ¹H NMR (400 MHz, DMSO-d₆) δ ppm 9.25-9.36 (m, 1 H) 8.65-8.78 (m, 1 H) 8.19 (s, 1 H) 7.59-8.03 (m, 2 H) 7.50 (d, J = 9.54 Hz, 1 H) 7.32-7.43 (m, 1 H) 7.27 (br. s., 1 H) 6.58 (br. s., 1 H) 5.01-5.23 (m, 1 H) 3.47-3.77 (m, 5 H) 3.37-3.46 (m, 1 H) 2.85-2.99 (m, 1 H) 1.99 (br. s., 2 H) 1.43-1.91 (m, 9 H). |
| 341 | 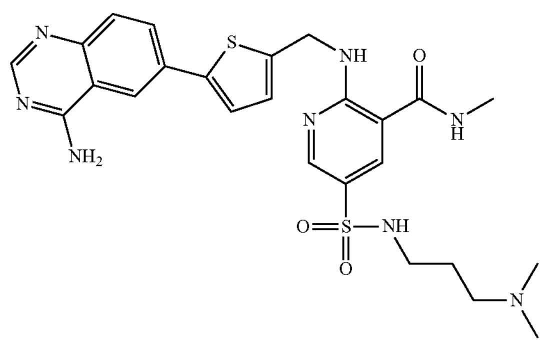 [SMILES: CNC(=O)c1cc(S(=O)(=O)NCCCN(C)C)cnc1NCc1ccc(-c2ccc3ncnc(N)c3c2)s1] | 2-((5-(4-aminoquinazolin-6-yl)thiophen-2-yl)methyl)amino)-5-(N-(3-(dimethylamino)propyl)sulfamoyl)-N-methylnicotinamide | 554.9 | ¹H NMR (400 MHz, CD₃OD) δ: 8.60 (d, 1H), 8.34 (d, 1H), 8.31 (s, 1H), 8.17 (d, 1H), 8.02 (dd, 1H), 7.67 (d, 1H), 7.38 (d, 1H), 7.06 (d, 1H), 4.92 (s, 2H), 2.91 (t, 2H), 2.86 (s, 3H), 2.48 (t, 2H), 2.29 (s, 6H), 1.62-1.58 (m, 2H) |

| Ex. No. | Structure | Chemical Name | ESI-MS (M + H) | ¹H NMR |
|---|---|---|---|---|
| 342 | 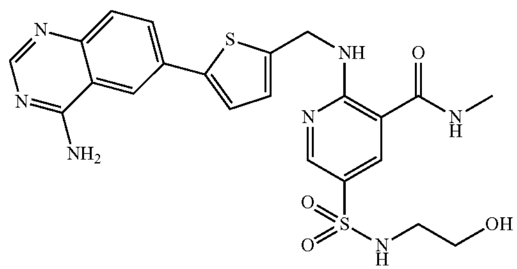 [SMILES: CNC(=O)c1cc(S(=O)(=O)NCCO)cnc1NCc1ccc(-c2ccc3ncnc(N)c3c2)s1] | 2-((5-(4-aminoquinazolin-6-yl)thiophen-2-yl)methyl)amino)-5-(N-(2-hydroxyethyl)sulfamoyl)-N-methylnicotinamide | 513.9 | ¹H NMR (400 MHz, DMSO-d₆) δ: 9.32 (t, 1H), 8.85-8.82 (m, 1H), 8.54 (d, 1H), 8.42 (d, 1H), 8.34 (d, 1H), 8.23 (d, 1H), 8.00 (br, 2H), 7.65 (d, 1H), 7.65 (d, 1H), 7.63 (d, 1H), 7.48 (t, 1H), 7.10 (d, 1H), 4.90 (d, 2H), 4.70 (t, 1H), 3.35-3.29 (m, 2H), 2.84-2.81 (m, 2H), 2.76 (d, 3H). |
| 343 | 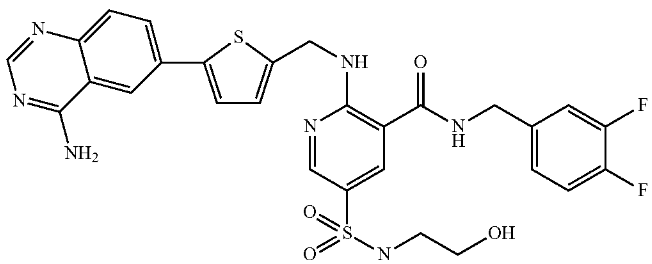 [SMILES: Nc1ncnc2ccc(-c3ccc(CNc4ncc(S(=O)(=O)NCCO)cc4C(=O)NCc4ccc(F)c(F)c4)s3)cc12] | 2-((5-(4-aminoquinazolin-6-yl)thiophen-2-yl)methyl)amino)-(N-(3,4-difluorobenzyl)-5-(N-(2-hydroxyethyl)sulfamoyl)nicotinamide | 625.9 | ¹H NMR (400 MHz, DMSO-d₆) δ: 9.46 (t, 1H), 8.59 (d, 1H), 8.42 (d, 1H), 8.34 (s, 2H), 7.99 (d, 1H), 7.89 (br, 2H), 7.64 (d, 1H), 7.45-7.35 (m, 4H), 7.18 (br, 1H), 7.11 (d, 1H), 4.90 (d, 2H), 4.72 (t, 1H), 4.43 (d, 2H), 3.41-3.37 (m, 2H), 2.84-2.79 (m, 2H). |
| 344 | 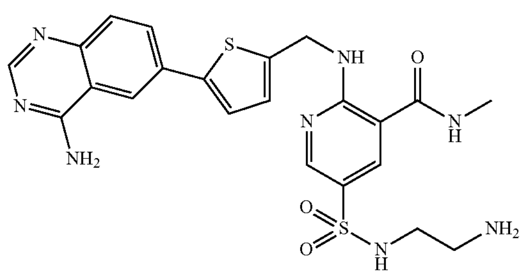 [SMILES: CNC(=O)c1cc(S(=O)(=O)NCCN)cnc1NCc1ccc(-c2ccc3ncnc(N)c3c2)s1] | 5-(N-(2-aminoethyl)sulfamoyl)-2-((5-(4-aminoquinazolin-6-yl)thiophen-2-yl)methyl)amino)-N-methylnicotinamide | 512.9 | ¹H NMR (400 MHz, DMSO-d₆) δ: 9.46-9.35 (m, 3H), 8.87 (d, 1H), 8.73 (s, 1H), 8.57 (d, 2H), 8.23 (d, 1H), 8.21 (d, 1H), 7.79-7.73 (m, 4H), 7.55 (d, 1H), 7.16 (d, 1H), 4.92 (d, 2H), 2.99-2.95 (m, 2H), 2.92-2.87 (m, 2H), 2.77 (d, 3H). |

| Ex. No. | Structure | Chemical Name | ESI-MS (M + H) | ¹H NMR |
|---|---|---|---|---|
| 345 | 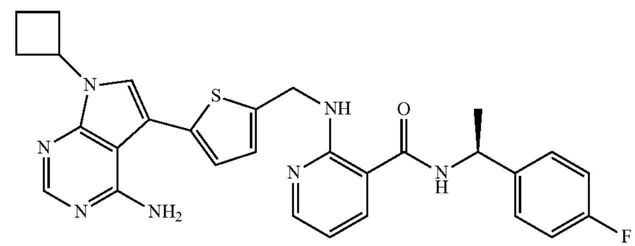 [SMILES: C[C@H](NC(=O)c1cccnc1NCc1ccc(-c2cn(C3CCC3)c3ncnc(N)c23)s1)c1ccc(F)cc1] | (S)-2-((5-(4-amino-7-cyclobutyl-7H-pyrrolo[2,3-d]pyrimidin-2-yl)methyl)thiophen-2-yl)methyl)amino)-N-(1-(4-fluorophenyl)ethyl)nicotinamide | 542.2 | ¹H NMR (400 MHz, DMSO-d₆) δ: 8.84 (d, 1H), 8.67 (t, 1H), 8.23 (d, 1H), 8.12-8.08 (m, 2H), 7.59 (s, 1H), 7.42-7.39 (m, 2H), 7.15-7.11 (m, 2H), 7.03 (d, 1H), 6.92 (d, 1H), 6.68-6.65 (m, 1H), 6.25 (br, 2H), 5.15-5.11 (m, 2H), 4.78 (d, 2H), 2.36-2.35 (m, 2H), 2.01-1.99 (m, 2H), 1.82-1.79 (m, 2H),1.46-1.44 (d, 3H). |
| 346 | 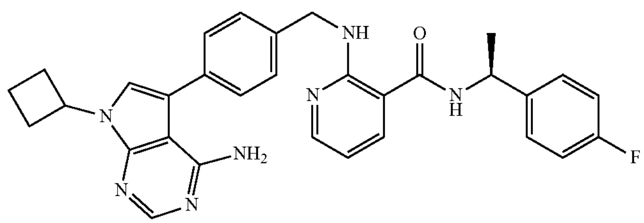 [SMILES: C[C@H](NC(=O)c1cccnc1NCc1ccc(-c2cn(C3CCC3)c3ncnc(N)c23)cc1)c1ccc(F)cc1] | (S)-2-(4-(4-amino-7-cyclobutyl-7H-pyrrolo[2,3-d]pyrimidin-5-yl)benzylamino)-N-(1-(4-fluorophenyl)ethyl)nicotinamide | 536.3 | ¹H NMR (400 MHz, CD₃OD) δ: 8.48 (d, 1H), 8.32 (s, 1H), 8.07 (d, 1H), 7.76 (s, 1H), 7.59-7.53 (m, 4H), 7.43-7.40 (m, 2H), 7.08-6.99 (m, 3H), 5.40-5.34 (m, 1H), 5.19 (q, 1H), 4.76 (s, 2H), 2.66-2.55 (m, 4H), 2.05-1.97 (m, 2H), 1.56 (d, 3H). |
| 347 | 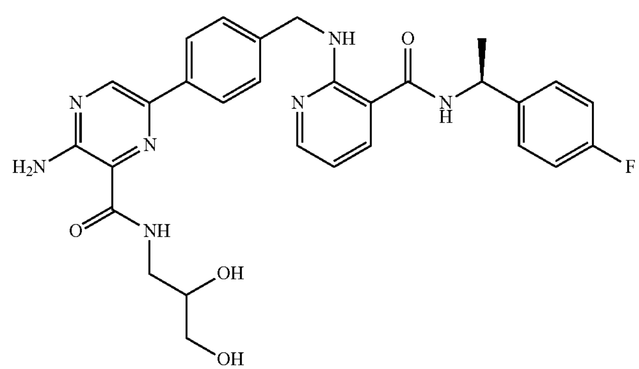 [SMILES: C[C@H](NC(=O)c1cccnc1NCc1ccc(-c2cnc(N)c(C(=O)NCC(O)CO)n2)cc1)c1ccc(F)cc1] | 3-amino-6-(4-((5-cyano-3-((S)-1-(4-fluorophenyl)ethylcarbamoyl)pyridin-2-ylamino)methyl)phenyl)-N-(2,3-dihydroxypropyl)pyrazine-2-carboxamide | 585.0 | ¹H NMR (400 MHz, DMSO-d₆) δ: 9.36 (t, 1H), 9.06 (d, 1H), 8.81 (s, 1H), 8.77 (t, 1H), 8.57 (d, 1H), 8.51 (d, 1H), 8.03 (d, 2H), 7.45-7.37 (m, 4H), 7.15 (t, 2H), 5.78 (br, 2H), 5.12-5.07 (m, 1H), 4.71 (d, 2H), 3.67-3.63 (m, 1H), 3.45-3.27 (m, 4H), 1.46 (d, 3H). |

TABLE 1-continued

| Ex. No. | Structure | Chemical Name | ESI-MS (M + H) | ¹H NMR |
|---|---|---|---|---|
| 348 | 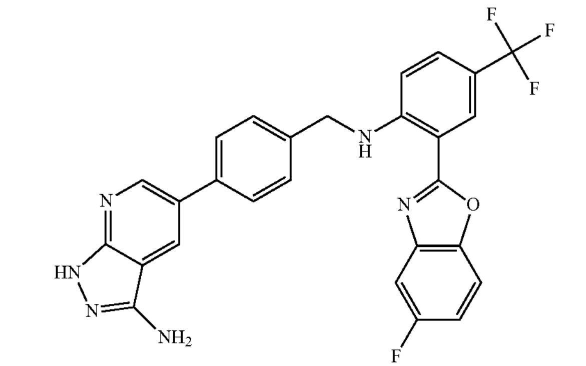 [SMILES: Nc1n[nH]c2ncc(-c3ccc(CNc4ccc(C(F)(F)F)cc4-c4nc5cc(F)ccc5o4)cc3)cc12] | 5-(4-((3-(5-fluorobenzo[d]oxazol-2-yl)-5-(trifluoromethyl)pyridin-2-ylamino)methyl)phenyl)-1H-pyrazolo[3,4-b]pyridin-3-amine | 520.0 | ¹H NMR (400 MHz, CDCl₃) δ 9.45 (br, 1H), 8.69 (d, 1H), 8.54 (s, 1H), 8.51 (s, 1H), 8.12 (d, 1H), 7.68 (dd, 1H), 7.61-7.52 (m, 4H), 7.35 (dd, 1H), 7.14 (dt, 1H), 5.02 (d, 1H), 3.42 (s, 2H). |
| 349 | 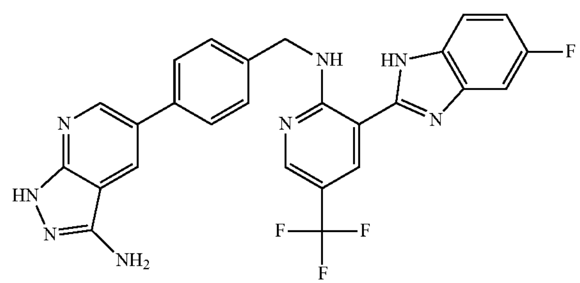 [SMILES: Nc1n[nH]c2ncc(-c3ccc(CNc4ncc(C(F)(F)F)cc4-c4nc5cc(F)ccc5[nH]4)cc3)cc12] | 5-(4-((3-(5-fluoro-1H-benzo[d]imidazol-2-yl)-5-(trifluoromethyl)pyridin-2-ylamino)methyl)phenyl)-1H-pyrazolo[3,4-b]pyridin-3-amine | 519.0 | ¹H NMR (400 MHz, CD₃OD) δ: 8.66 (d, 1H), 8.46 (d, 1H), 8.30 (s, 2H), 7.54 (d, 2H), 7.49-7.44 (m, 3H), 7.19 (dd, 1H), 6.96-6.91 (m, 1H), 4.85 (s, 2H). |
| 350 | 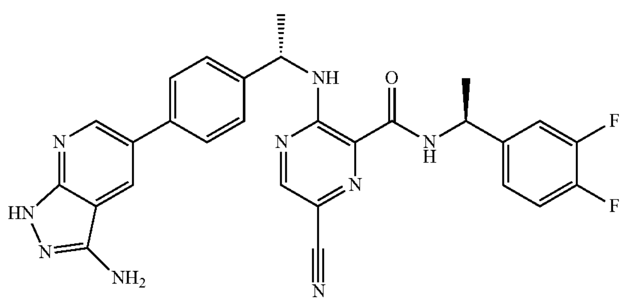 [SMILES: C[C@H](NC(=O)c1nc(C#N)cnc1N[C@@H](C)c1ccc(-c2cnc3[nH]nc(N)c3c2)cc1)c1ccc(F)c(F)c1] | 3-((R)-1-(4-(3-amino-1H-pyrazolo[3,4-b]pyridin-5-yl)phenyl)ethylamino)-6-cyano-N-((S)-1-(3,4-difluorophenyl)ethyl)pyrazine-2-carboxamide | 540.0 | ¹H NMR (400 MHz, DMSO-d₆) δ: 12.03 (s, 1H), 9.81 (d, 1H), 9.41 (d, 1H), 8.73 (s, 1H), 8.65 (d, 1H), 8.37 (s, 1H), 7.64 (d, 2H), 7.57-7.49 (m, 3H), 7.42-7.37 (m, 1H), 7.27 (br, 1H), 5.65 (s, 2H), 5.33-5.25 (m, 1H), 5.18-5.13 (m, 1H), 1.57-1.51 (m, 6H). |

TABLE 1-continued

| Ex. No. | Structure | Chemical Name | ESI-MS (M + H) | 1H NMR |
|---|---|---|---|---|
| 351 | 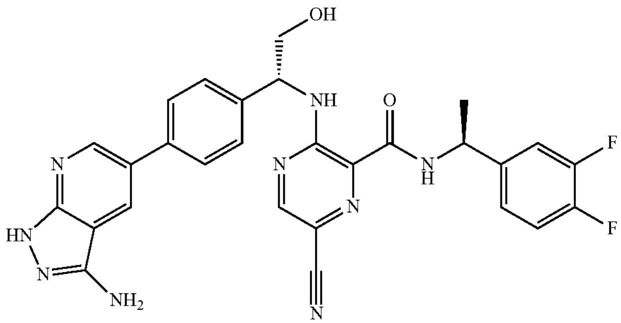 [SMILES: C[C@H](NC(=O)c1nc(C#N)cnc1N[C@@H](CO)c1ccc(-c2cnc3[nH]nc(N)c3c2)cc1)c1ccc(F)c(F)c1] | 3-((R)-1-(4-(3-amino-1H-pyrazolo[3,4-b]pyridin-5-yl)phenyl)-2-hydroxyethylamino)-6-cyano-N-((S)-1-(3,4-difluorophenyl)ethyl)pyrazine-2-carboxamide | 556.0 | 1H NMR (400 MHz, CD$_3$OD) δ: 8.64 (d, 1H), 8.50 (s, 1H), 8.36 (d, 1H), 7.63 (d, 2H), 7.49 (d, 2H), 7.41-7.36 (m, 1H), 7.26-7.22 (m, 2H), 5.38 (t, 1H), 5.23 (q, 1H), 4.00-3.96 (m, 1H), 3.92-3.88 (m, 3H). |
| 352 | 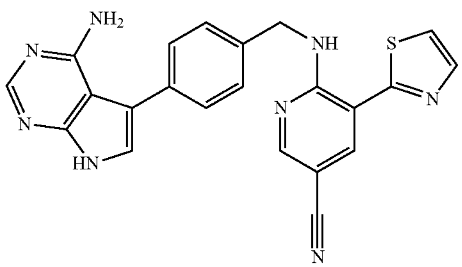 [SMILES: N#Cc1cnc(NCc2ccc(-c3c[nH]c4ncnc(N)c34)cc2)c(-c2nccs2)c1] | 6-(4-(4-amino-7H-pyrrolo[2,3-d]pyrimidin-5-yl)benzylamino)-5-(thiazol-2-yl)nicotinamide | 425.1 | 1H NMR (400 MHz, DMSO-d$_6$) δ: 12.68 (s, 1H), 10.17-10.14 (m, 1H), 8.60 (s, 1H), 8.52 (d, 1H), 8.33 (d, 1H), 8.01 (d, 1H), 7.93 (d, 1H), 7.49-7.46 (m, 7H), 4.93 (d, 2H). |
| 353 | 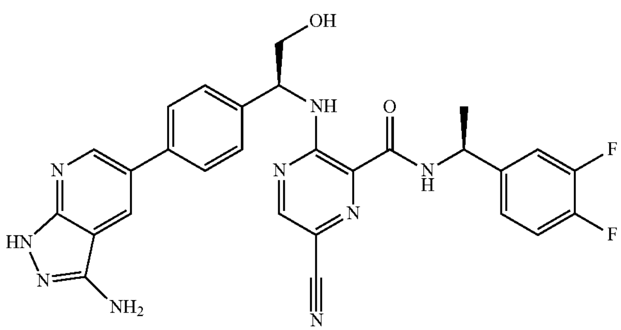 [SMILES: C[C@H](NC(=O)c1nc(C#N)cnc1N[C@H](CO)c1ccc(-c2cnc3[nH]nc(N)c3c2)cc1)c1ccc(F)c(F)c1] | 3-((S)-1-(4-(3-amino-1H-pyrazolo[3,4-b]pyridin-5-yl)phenyl)-2-hydroxyethylamino)-6-cyano-N-((S)-1-(3,4-difluorophenyl)ethyl)pyrazine-2-carboxamide | 556.1 | 1H NMR (400 MHz, CD$_3$OD) δ: 8.65 (d, 1H), 8.50 (s, 1H), 8.38 (d, 1H), 7.65 (d, 2H), 7.51 (d, 2H), 7.40-7.35 (m, 1H), 7.26-7.22 (m, 2H), 5.38 (t, 1H), 5.21 (q, 1H), 3.97-3.86 (m, 2H), 1.60 (d, 3H). |

TABLE 1-continued

| Ex. No. | Structure | Chemical Name | ESI-MS (M + H) | ¹H NMR |
|---|---|---|---|---|
| 354 | 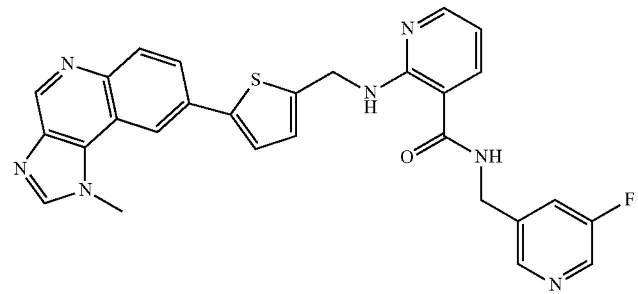 [SMILES: Cn1cnc2cnc3ccc(-c4ccc(CNc5ncccc5C(=O)NCc5cncc(F)c5)s4)cc3c21] | N-((5-fluoropyridin-3-yl)methyl)-2-((5-(1-methyl-1H-imidazo[4,5-c]quinolin-8-yl)thiophen-2-yl)methyl)amino)nicotinamide | 524.2 | ¹H NMR (300 MHz, DMSO-d₆) δ 9.16 (t, J = 6.30 Hz, 0H), 9.15 (s, 1H), 8.74 (t, J = 5.85 Hz, 1H), 8.54 (d, J = 1.89 Hz, 1H), 8.47 (d, J = 2.64 Hz, 1H), 8.44 (t, J = 1.70 Hz, 1H), 8.38 (s, 1H), 8.27 (dd, J = 1.89, 4.91 Hz, 1H), 8.15 (d, J = 8.69 Hz, 1H), 8.04 (dd, J = 1.89, 7.55 Hz, 1H), 7.93 (dd, J = 2.10, 8.60 Hz, 1H), 7.65 (ddd, J = 1.80, 2.70, 9.82 Hz, 1H), 7.59 (d, J = 3.40 Hz, 1H), 7.12 (d, J = 3.78 Hz, 1H), 6.69 (dd, J = 4.72, 7.74 Hz, 1H), 4.85 (d, J = 5.67 Hz, 2H), 4.51 (d, J = 6.04 Hz, 2H), 4.37 (s, 3H). |
| 355 | 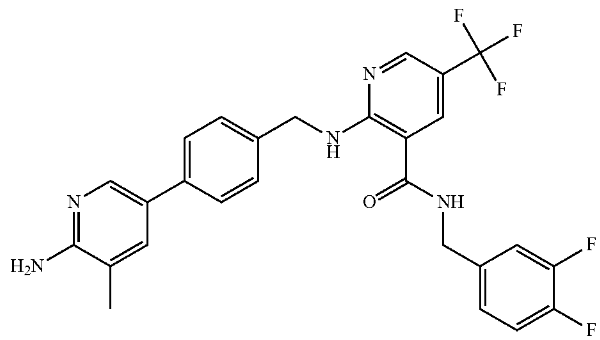 [SMILES: Cc1cc(-c2ccc(CNc3ncc(C(F)(F)F)cc3C(=O)NCc3ccc(F)c(F)c3)cc2)cnc1N] | 2-(4-(6-amino-5-methylpyridin-3-yl)benzyl)amino)-N-(3,4-difluorobenzyl)-5-(trifluoromethyl)nicotinamide | 528.2 | ¹H NMR (300 MHz, DMSO-d₆) δ 9.35 (t, J = 5.67 Hz, 1H), 9.26 (t, J = 5.67 Hz, 1H), 8.51 (d, J = 1.13 Hz, 1H), 8.34 (d, J = 2.27 Hz, 1H), 8.09 (d, J = 2.27 Hz, 1H), 7.54 (d, J = 2.27 Hz, 1H), 7.51 (d, J = 8.31 Hz, 2H), 7.30-7.45 (m, 4H), 7.14-7.24 (m, 1H), 5.80 (s, 2H), 4.70 (d, J = 5.67 Hz, 2H), 4.44 (d, J = 5.67 Hz, 2H), 2.10 (s, 3H). |
| 356 | 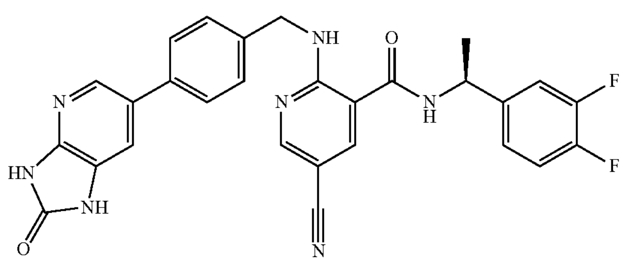 [SMILES: C[C@H](NC(=O)c1cc(C#N)cnc1NCc1ccc(-c2cnc3[nH]c(=O)[nH]c3c2)cc1)c1ccc(F)c(F)c1] | 5-cyano-N-(3,4-difluorobenzyl)-2-(4-(2-oxo-2,3-dihydro-1H-imidazo[4,5-b]pyridin-6-yl)benzylamino)nicotinamide | 512.2 | ¹H NMR (400 MHz, DMSO-d₆) δ 11.37 (br. s., 1H), 10.92 (br. s., 1H), 9.38 (t, J = 5.77 Hz, 1H), 9.26 (t, J = 5.52 Hz, 1H), 8.58 (d, J = 1.76 Hz, 1H), 8.40 (d, J = 2.01 Hz, 1H), 8.13 (d, J = 1.76 Hz, 1H), 7.58 (d, J = 8.03 Hz, 2H), 7.38 (d, J = 9.29 Hz, 2H), 7.30-7.47 (m, 3H), 7.08-7.24 (m, 1H), 4.72 (d, J = 5.77 Hz, 2H), 4.42 (d, J = 5.52 Hz, 2H). |

TABLE 1-continued

| Ex. No. | Structure | Chemical Name | ESI-MS (M + H) | ¹H NMR |
|---|---|---|---|---|
| 357 | 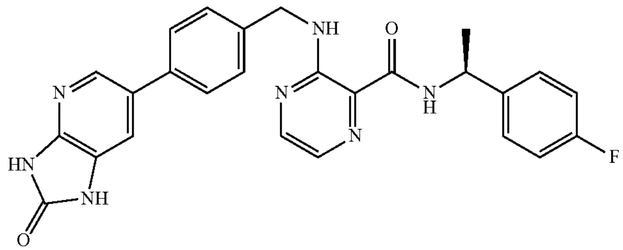 [SMILES: C[C@H](NC(=O)c1nccnc1NCc1ccc(-c2cnc3[nH]c(=O)[nH]c3c2)cc1)c1ccc(F)cc1] | (S)-N-(1-(4-fluorophenyl)ethyl)-3-(4-(2-oxo-2,3-dihydro-1H-imidazo[4,5-b]pyridin-6-yl)benzylamino)pyrazine-2-carboxamide | 484.2 | ¹H NMR (300 MHz, DMSO-d₆) δ 11.36 (br. s., 1H), 10.91 (br. s., 1H), 9.13 (d, J = 8.31 Hz, 1H), 9.07 (t, J = 5.85 Hz, 1H), 8.28 (d, J = 2.64 Hz, 1H), 8.13 (d, J = 1.89 Hz, 1H), 7.85 (d, J = 2.64 Hz, 1H), 7.58 (d, J = 7.93 Hz, 2H), 7.34-7.50 (m, 5H), 7.14 (t, J = 8.88 Hz, 2H), 5.12 (quin, J = 7.27 Hz, 1H), 4.57-4.76 (m, 2H), 1.51 (d, J = 7.18 Hz, 3H). |
| 358 | 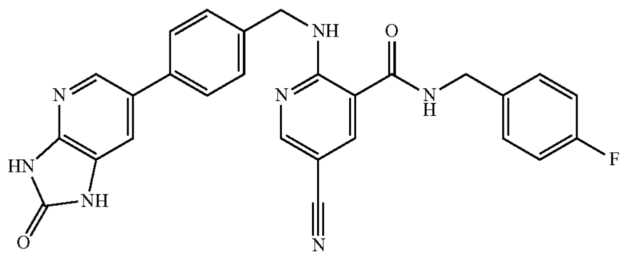 [SMILES: N#Cc1cnc(NCc2ccc(-c3cnc4[nH]c(=O)[nH]c4c3)cc2)c(C(=O)NCc2ccc(F)cc2)c1] | 5-cyano-N-(4-fluorobenzyl)-2-(4-(2-oxo-2,3-dihydro-1H-imidazo[4,5-b]pyridin-6-yl)benzylamino)nicotinamide | 494.2 | ¹H NMR (400 MHz, DMSO-d₆) δ 9.41 (br. s., 1H), 8.57 (d, J = 1.76 Hz, 1H), 8.38 (t, J = 2.01 Hz, 1H), 8.12 (d, J = 1.51 Hz, 1H), 7.58 (d, J = 7.78 Hz, 2H), 7.27-7.42 (m, 5H), 7.15 (t, J = 8.78 Hz, 2H), 4.72 (s, 2H), 4.42 (s, 2H). |
| 359 | 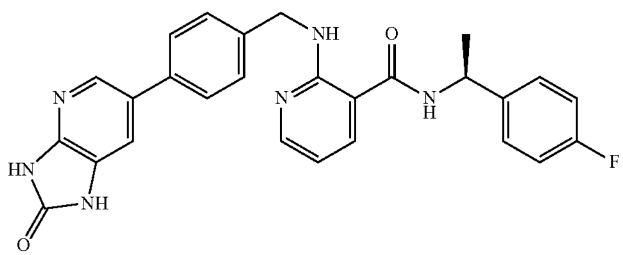 [SMILES: C[C@H](NC(=O)c1cccnc1NCc1ccc(-c2cnc3[nH]c(=O)[nH]c3c2)cc1)c1ccc(F)cc1] | (S)-N-(1-(4-fluorophenyl)ethyl)-2-(4-(2-oxo-2,3-dihydro-1H-imidazo[4,5-b]pyridin-6-yl)benzylamino)nicotinamide | 483.2 | ¹H NMR (400 MHz, DMSO-d₆) δ 11.28 (br. s., 1H), 8.82 (d, J = 7.53 Hz, 1H), 8.63 (t, J = 5.52 Hz, 1H), 8.15 (d, J = 3.51 Hz, 1H), 8.12 (d, J = 1.51 Hz, 1H), 8.07 (d, J = 6.53 Hz, 1H), 7.56 (d, J = 8.03 Hz, 2H), 7.26-7.47 (m, 5H), 7.13 (t, J = 8.78 Hz, 2H), 6.62 (dd, J = 4.89, 7.40 Hz, 1H), 5.11 (quin, J = 7.03 Hz, 1H), 4.49-4.72 (m, 2H), 1.45 (d, J = 7.03 Hz, 3H). |
| 360 | 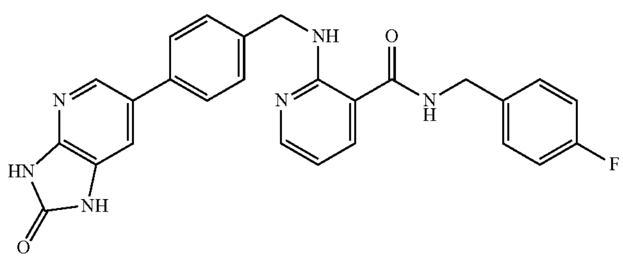 [SMILES: O=C(NCc1ccc(F)cc1)c1cccnc1NCc1ccc(-c2cnc3[nH]c(=O)[nH]c3c2)cc1] | N-(4-fluorobenzyl)-2-(4-(2-oxo-2,3-dihydro-1H-imidazo[4,5-b]pyridin-6-yl)benzylamino)nicotinamide | 469.2 | ¹H NMR (400 MHz, DMSO-d₆) δ 11.29 (br. s., 1H), 9.09 (t, J = 5.77 Hz, 1H), 8.77 (t, J = 5.65 Hz, 1H), 8.16 (dd, J = 1.38, 4.64 Hz, 1H), 8.13 (d, J = 1.76 Hz, 1H), 8.00 (dd, J = 1.51, 7.78 Hz, 1H), 7.57 (d, J = 8.03 Hz, 2H), 7.21-7.47 (m, 5H), 7.14 (t, J = 8.91 Hz, 2H), 6.61 (dd, J = 4.89, 7.65 Hz, 1H), 4.65 (d, J = 5.52 Hz, 2H), 4.42 (d, J = 5.52 Hz, 2H). |

TABLE 1-continued

| Ex. No. | Structure | Chemical Name | ESI-MS (M + H) | ¹H NMR |
|---|---|---|---|---|
| 361 | 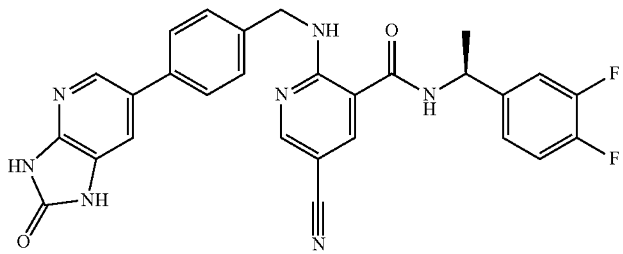 [SMILES: C[C@H](NC(=O)c1cc(C#N)cnc1NCc1ccc(-c2cnc3[nH]c(=O)[nH]c3c2)cc1)c1ccc(F)c(F)c1] | (S)-5-cyano-N-(1-(3,4-difluorophenyl)ethyl)-2-(4-(2-oxo-2,3-dihydro-1H-imidazo[4,5-b]pyridin-6-yl)benzylamino)nicotinamide | 526.2 | ¹H NMR (400 MHz, DMSO-$d_6$) δ 11.36 (br. s., 1H), 10.92 (br. s., 1H), 9.30 (t, J = 5.77 Hz, 1H), 8.98 (d, J = 7.28 Hz, 1H), 8.57 (d, J = 2.01 Hz, 1H), 8.48 (d, J = 2.01 Hz, 1H), 8.12 (d, J = 1.76 Hz, 1H), 7.57 (d, J = 8.28 Hz, 2H), 7.45 (ddd, J = 1.88, 7.97, 11.73 Hz, 1H), 7.27-7.41 (m, 4H), 7.10-7.27 (m, 1H), 5.07 (quin, J = 6.96 Hz, 1H), 4.58-4.78 (m, 2H), 1.45 (d, J = 7.03 Hz, 3H). |
| 362 | 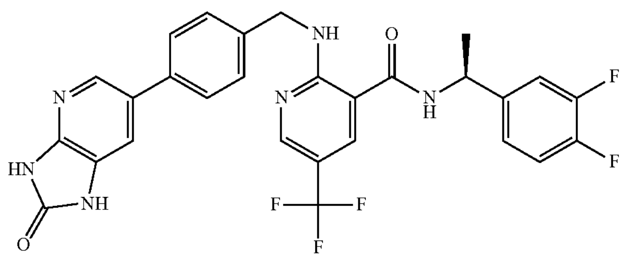 [SMILES: C[C@H](NC(=O)c1cc(C(F)(F)F)cnc1NCc1ccc(-c2cnc3[nH]c(=O)[nH]c3c2)cc1)c1ccc(F)c(F)c1] | (S)-N-(1-(3,4-difluorophenyl)ethyl)-2-(4-(2-oxo-2,3-dihydro-1H-imidazo[4,5-b]pyridin-6-yl)benzylamino)-5-(trifluoromethyl)nicotinamide | 569.2 | ¹H NMR (400 MHz, DMSO-$d_6$) δ 11.36 (br. s., 1H), 10.91 (br. s., 1H), 9.19 (t, J = 5.77 Hz, 1H), 9.08 (d, J = 7.28 Hz, 1H), 8.50 (s, 1H), 8.40 (d, J = 2.01 Hz, 1H), 8.12 (d, J = 1.76 Hz, 1H), 7.57 (d, J = 8.03 Hz, 2H), 7.30-7.50 (m, 5H), 7.17-7.27 (m, 4H), 5.10 (quin, J = 7.03 Hz, 1H), 4.61-4.78 (m, 2H), 1.47 (d, J = 7.03 Hz, 3H). |
| 363 | 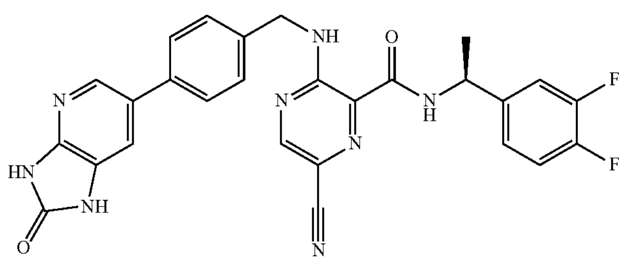 [SMILES: C[C@H](NC(=O)c1nc(C#N)cnc1NCc1ccc(-c2cnc3[nH]c(=O)[nH]c3c2)cc1)c1ccc(F)c(F)c1] | (S)-6-cyano-N-(1-(3,4-difluorophenyl)ethyl)-3-(4-(2-oxo-2,3-dihydro-1H-imidazo[4,5-b]pyridin-6-yl)benzylamino)pyrazine-2-carboxamide | 527.2 | ¹H NMR (400 MHz, DMSO-$d_6$) δ 11.37 (br. s., 1H), 10.92 (br. s., 1H), 9.74 (t, J = 5.90 Hz, 1H), 9.32 (d, J = 8.28 Hz, 1H), 8.73 (s, 1H), 8.12 (d, J = 1.76 Hz, 1H), 7.58 (d, J = 8.03 Hz, 2H), 7.51 (ddd, J = 1.76, 7.91, 11.92 Hz, 1H), 7.31-7.45 (m, 4H), 7.20-7.30 (m, 1H), 5.11 (quin, J = 7.28 Hz, 1H), 4.63-4.79 (m, 2H), 1.51 (d, J = 7.03 Hz, 3H). |
| 364 | 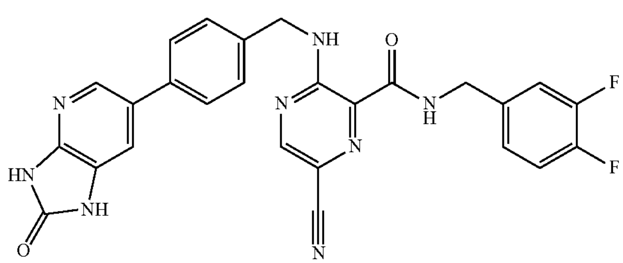 [SMILES: N#Cc1cnc(NCc2ccc(-c3cnc4[nH]c(=O)[nH]c4c3)cc2)c(C(=O)NCc2ccc(F)c(F)c2)n1] | 6-cyano-N-(3,4-difluorobenzyl)-3-(4-(2-oxo-2,3-dihydro-1H-imidazo[4,5-b]pyridin-6-yl)benzylamino)pyrazine-2-carboxamide | 513.2 | ¹H NMR (400 MHz, DMSO-$d_6$) δ 11.37 (br. s., 1H), 10.92 (br. s., 1H), 9.79 (t, J = 5.90 Hz, 1H), 9.58 (t, J = 6.27 Hz, 1H), 8.74 (s, 1H), 8.13 (d, J = 1.76 Hz, 1H), 7.59 (d, J = 8.03 Hz, 2H), 7.28-7.48 (m, 5H), 7.05-7.23 (m, 1H), 4.73 (d, J = 5.77 Hz, 2H), 4.42 (d, J = 6.02 Hz, 2H). |

TABLE 1-continued

| Ex. No. | Structure | Chemical Name | ESI-MS (M + H) | ¹H NMR |
|---|---|---|---|---|
| 365 | 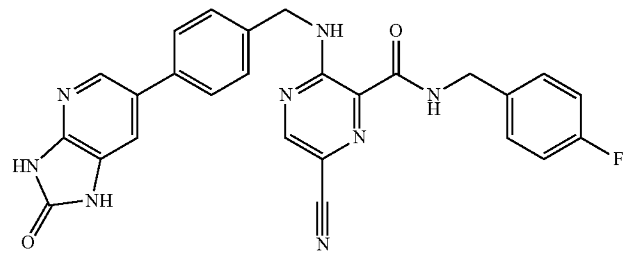 [SMILES: N#Cc1cnc(NCc2ccc(-c3cnc4[nH]c(=O)[nH]c4c3)cc2)c(C(=O)NCc2ccc(F)cc2)n1] | 6-cyano-N-(4-fluorobenzyl)-3-(4-(2-oxo-2,3-dihydro-1H-imidazo[4,5-b]pyridin-6-yl)benzylamino)pyrazine-2-carboxamide | 495.2 | ¹H NMR (400 MHz, DMSO-d₆) δ 11.37 (br. s., 1H), 10.92 (br. s., 1H), 9.83 (t, J = 5.90 Hz, 1H), 9.57 (t, J = 6.15 Hz, 1H), 8.73 (s, 1H), 8.13 (d, J = 1.76 Hz, 1H), 7.59 (d, J = 8.03 Hz, 2H), 7.28-7.49 (m, 5H), 7.13 (t, J = 8.78 Hz, 2H), 4.73 (d, J = 5.77 Hz, 2H), 4.42 (d, J = 6.02 Hz, 2H). |
| 366 | 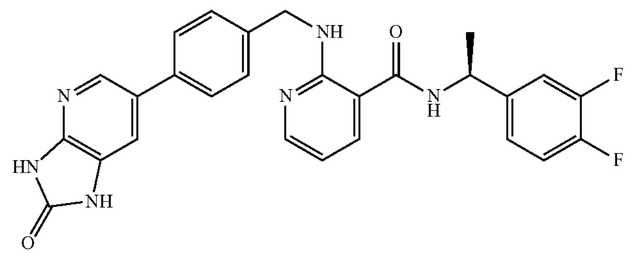 [SMILES: C[C@H](NC(=O)c1cccnc1NCc1ccc(-c2cnc3[nH]c(=O)[nH]c3c2)cc1)c1ccc(F)c(F)c1] | (S)-N-(1-(3,4-difluorophenyl)ethyl)-2-(4-(2-oxo-2,3-dihydro-1H-imidazo[4,5-b]pyridin-6-yl)benzylamino)nicotinamide | 501.2 | ¹H NMR (400 MHz, DMSO-d₆) δ 11.36 (br. s., 1H), 10.91 (br. s., 1H), 8.83 (d, J = 7.53 Hz, 1H), 8.61 (t, J = 5.77 Hz, 1H), 8.16 (dd, J = 1.51, 4.77 Hz, 1H), 8.12 (d, J = 1.76 Hz, 1H), 8.08 (dd, J = 1.63, 7.65 Hz, 1H), 7.56 (d, J = 8.03 Hz, 2H), 7.31-7.48 (m, 5H), 7.16-7.25 (m, 1H), 6.63 (dd, J = 4.77, 7.53 Hz, 1H), 5.10 (quin, J = 7.03 Hz, 1H), 4.54-4.70 (m, 2H), 1.44 (d, J = 7.03 Hz, 3H). |
| 367 | 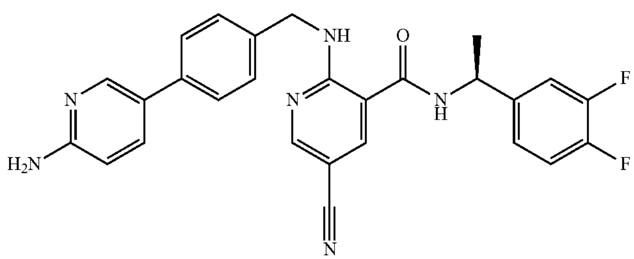 [SMILES: C[C@H](NC(=O)c1cc(C#N)cnc1NCc1ccc(-c2ccc(N)nc2)cc1)c1ccc(F)c(F)c1] | (S)-2-(4-(6-aminopyridin-3-yl)benzylamino)-5-cyano-N-(1-(3,4-difluorophenyl)ethyl)nicotinamide | 485.1 | ¹H NMR (400 MHz, DMSO-d₆) δ 9.27 (t, J = 5.77 Hz, 1H), 8.98 (d, J = 7.28 Hz, 1H), 8.57 (d, J = 2.01 Hz, 1H), 8.48 (d, J = 2.01 Hz, 1H), 8.19 (d, J = 2.26 Hz, 1H), 7.65 (dd, J = 2.51, 8.53 Hz, 1H), 7.48 (d, J = 8.28 Hz, 2H), 7.33-7.46 (m, 2H), 7.30 (d, J = 8.03 Hz, 2H), 7.17-7.26 (m, 1H), 6.50 (d, J = 8.53 Hz, 1H), 6.02 (s, 2H), 5.06 (quin, J = 7.03 Hz, 1H), 4.56-4.73 (m, 2H), 1.44 (d, J = 7.03 Hz, 3H). |

| Ex. No. | Structure | Chemical Name | ESI-MS (M + H) | ¹H NMR |
|---|---|---|---|---|
| 368 | 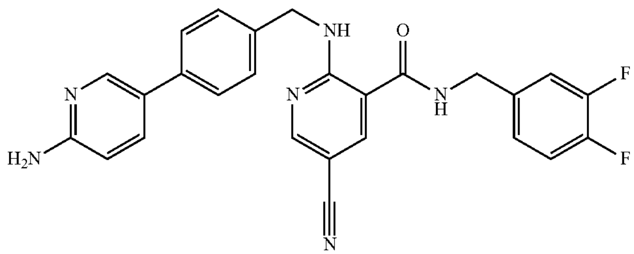 [SMILES: N#Cc1cnc(NCc2ccc(-c3ccc(N)nc3)cc2)c(C(=O)NCc2ccc(F)c(F)c2)c1] | 2-(4-(6-aminopyridin-3-yl)benzylamino)-5-cyano-N-(3,4-difluorobenzyl)nicotinamide | 471.1 | ¹H NMR (400 MHz, DMSO-d₆) δ 9.35 (t, J = 5.65 Hz, 1H), 9.25 (t, J = 5.52 Hz, 1H), 8.58 (d, J = 2.01 Hz, 1H), 8.39 (d, J = 1.76 Hz, 1H), 8.20 (d, J = 2.01 Hz, 1H), 7.65 (dd, J = 2.51, 8.53 Hz, 1H), 7.45-7.55 (m, J = 8.28 Hz, 2H), 7.35-7.44 (m, 2H), 7.27-7.35 (m, J = 8.28 Hz, 2H), 7.08-7.23 (m, 1H), 6.50 (d, J = 8.53 Hz, 1H), 6.02 (s, 2H), 4.69 (d, J = 5.77 Hz, 2H), 4.42 (d, J = 5.52 Hz, 2H). |
| 369 | 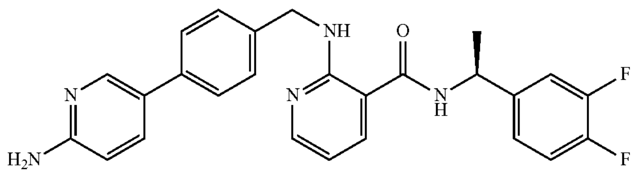 [SMILES: C[C@H](NC(=O)c1cccnc1NCc1ccc(-c2ccc(N)nc2)cc1)c1ccc(F)c(F)c1] | (S)-2-(4-(6-aminopyridin-3-yl)benzylamino)-N-(1-(3,4-difluorophenyl)ethyl)nicotinamide | 460.1 | ¹H NMR (400 MHz, DMSO-d₆) δ 8.81 (d, J = 7.53 Hz, 1H), 8.57 (t, J = 5.52 Hz, 1H), 8.19 (d, J = 2.01 Hz, 1H), 8.16 (dd, J = 1.25, 4.77 Hz, 1H), 8.07 (dd, J = 1.38, 7.66 Hz, 1H), 7.65 (dd, J = 2.26, 8.53 Hz, 1H), 7.45-7.51 (m, J = 8.03 Hz, 2H), 7.32-7.45 (m, 2H), 7.25-7.32 (m, J = 8.03 Hz, 2H), 7.16-7.25 (m, 1H), 6.62 (dd, J = 4.89, 7.66 Hz, 1H), 6.50 (d, J = 8.53 Hz, 1H), 6.00 (s, 2H), 5.09 (quin, J = 7.03 Hz, 1H), 4.51-4.66 (m, 2H), 1.44 (d, J = 7.03 Hz, 3H). |
| 370 | 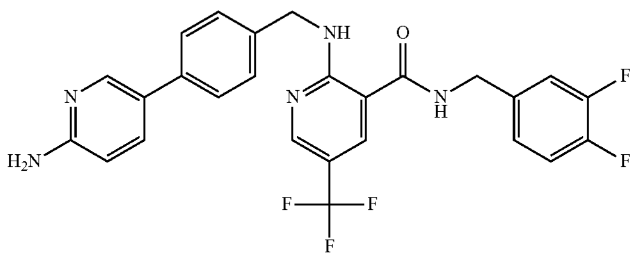 [SMILES: Nc1ccc(-c2ccc(CNc3ncc(C(F)(F)F)cc3C(=O)NCc3ccc(F)c(F)c3)cc2)cn1] | 2-(4-(6-aminopyridin-3-yl)benzylamino)-N-(3,4-difluorobenzyl)-5-(trifluoromethyl)nicotinamide | 514.0 | ¹H NMR (400 MHz, DMSO-d₆) δ 9.34 (t, J = 5.77 Hz, 1H), 9.26 (t, J = 5.77 Hz, 1H), 8.50 (s, 1H), 8.34 (d, J = 2.01 Hz, 1H), 8.20 (d, J = 2.26 Hz, 1H), 7.65 (dd, J = 2.51, 8.53 Hz, 1H), 7.49 (d, J = 8.28 Hz, 2H), 7.36-7.43 (m, 2H), 7.34 (d, J = 8.28 Hz, 2H), 7.11-7.22 (m, 1H), 6.50 (d, J = 8.78 Hz, 1H), 6.01 (s, 2H), 4.69 (d, J = 5.77 Hz, 2H), 4.43 (d, J = 5.52 Hz, 2H). |
| 371 | 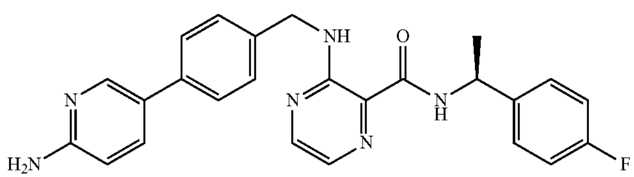 [SMILES: C[C@H](NC(=O)c1nccnc1NCc1ccc(-c2ccc(N)nc2)cc1)c1ccc(F)cc1] | (S)-3-(4-(6-aminopyridin-3-yl)benzylamino)-N-(1-(4-fluorophenyl)ethyl)pyrazine-2-carboxamide | 443.1 | ¹H NMR (400 MHz, DMSO-d₆) δ 9.12 (d, J = 8.28 Hz, 1H), 9.03 (t, J = 5.77 Hz, 1H), 8.27 (d, J = 2.26 Hz, 1H), 8.19 (d, J = 2.26 Hz, 1H), 7.83 (d, J = 2.51 Hz, 1H), 7.65 (dd, J = 2.51, 8.53 Hz, 1H), 7.49 (d, J = 8.03 Hz, 2H), 7.44 (dd, J = 5.52, 8.53 Hz, 2H), 7.33 (d, J = 8.28 Hz, 2H), 7.12 (t, J = 8.91 Hz, 2H), 6.50 (d, J = 8.53 Hz, 1H), 6.01 (s, 2H), 5.11 (quin, J = 7.28 Hz, 1H), 4.54-4.69 (m, 2H), 1.49 (d, J = 7.03 Hz, 3H). |

TABLE 1-continued

| Ex. No. | Structure | Chemical Name | ESI-MS (M + H) | ¹H NMR |
|---|---|---|---|---|
| 372 | 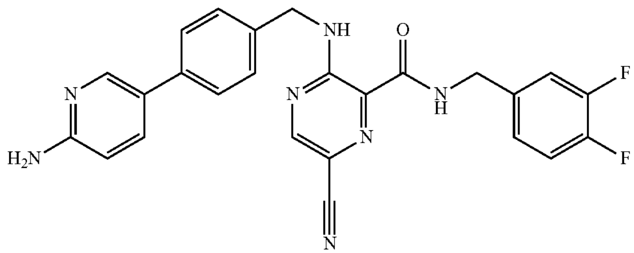 | 3-(4-(6-aminopyridin-3-yl)benzylamino)-6-cyano-N-(3,4-difluorobenzyl)pyrazine-2-carboxamide | 472.0 | ¹H NMR (400 MHz, DMSO-d₆) δ 9.76 (t, J = 5.90 Hz, 1H), 9.57 (t, J = 6.27 Hz, 1H), 8.74 (s, 1H), 8.20 (d, J = 2.26 Hz, 1H), 7.65 (dd, J = 2.51, 8.53 Hz, 1H), 7.50 (d, J = 8.28 Hz, 2H), 7.29-7.42 (m, 4H), 7.11-7.21 (m, 1H), 6.50 (d, J = 8.53 Hz, 1H), 6.02 (s, 2H), 4.70 (d, J = 5.77 Hz, 2H), 4.42 (d, J = 6.27 Hz, 2H). |
| 373 | 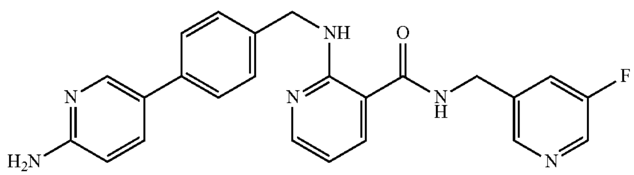 [SMILES: Nc1ccc(-c2ccc(CNc3ncccc3C(=O)NCc3cncc(F)c3)cc2)cn1] | 2-(4-(6-aminopyridin-3-yl)benzylamino)-N-((5-fluoropyridin-3-yl)methyl)nicotinamide | 429.0 | ¹H NMR (400 MHz, DMSO-d₆) δ 9.13 (t, J = 5.65 Hz, 1H), 8.67 (t, J = 5.65 Hz, 1H), 8.46 (d, J = 2.51 Hz, 1H), 8.43 (s, 1H), 8.20 (d, J = 2.26 Hz, 1H), 8.17 (dd, J = 1.51, 4.77 Hz, 1H), 8.01 (dd, J = 1.51, 7.78 Hz, 1H), 7.57-7.74 (m, 2H), 7.41-7.56 (m, J = 8.28 Hz, 2H), 7.23-7.39 (m, J = 8.03 Hz, 2H), 6.61 (dd, J = 4.77, 7.53 Hz, 1H), 6.50 (d, J = 8.53 Hz, 1H), 6.01 (s, 2H), 4.62 (d, J = 5.52 Hz, 2H), 4.49 (d, J = 5.77 Hz, 2H). |
| 374 | 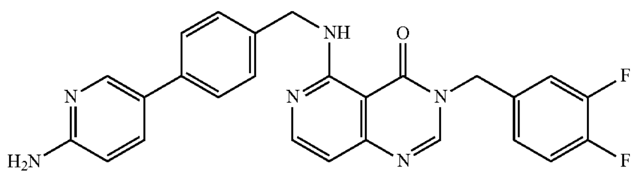 [SMILES: Nc1ccc(-c2ccc(CNc3nccc4ncn(Cc5ccc(F)c(F)c5)c(=O)c34)cc2)cn1] | 5-(4-(6-aminopyridin-3-yl)benzylamino)-3-(3,4-difluorobenzyl)pyrido[4,3-d]pyrimidin-4(3H)-one | 470.9 | ¹H NMR (400 MHz, DMSO-d₆) δ 9.06 (t, J = 5.65 Hz, 1H), 8.64 (s, 1H), 8.22 (d, J = 5.52 Hz, 1H), 8.20 (d, J = 2.26 Hz, 1H), 7.65 (dd, J = 2.38, 8.66 Hz, 1H), 7.49 (d, J = 8.28 Hz, 3H), 7.28-7.45 (m, 3H), 7.16-7.26 (m, 1H), 6.65 (d, J = 5.52 Hz, 1H), 6.50 (d, J = 8.53 Hz, 1H), 6.01 (s, 2H), 5.10 (s, 2H), 4.69 (d, J = 5.52 Hz, 2H). |
| 375 | 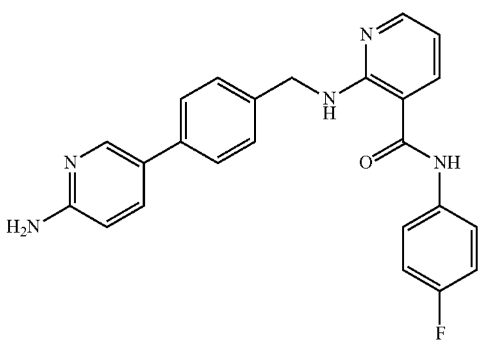 [SMILES: Nc1ccc(-c2ccc(CNc3ncccc3C(=O)Nc3ccc(F)cc3)cc2)cn1] | 2-(4-(6-aminopyridin-3-yl)benzylamino)-N-(4-fluorophenyl)nicotinamide | 414.0 | ¹H NMR (400 MHz, DMSO-d₆) δ 10.27 (s, 1H), 8.37 (t, J = 5.40 Hz, 1H), 8.21 (br. s., 0H), 8.20 (d, J = 1.51 Hz, 1H), 8.08 (d, J = 6.53 Hz, 1H), 7.59-7.76 (m, 3H), 7.42-7.55 (m, J = 8.03 Hz, 2H), 7.27-7.41 (m, J = 8.03 Hz, 2H), 7.18 (t, J = 8.91 Hz, 2H), 6.67 (dd, J = 4.89, 7.40 Hz, 1H), 6.50 (d, J = 8.53 Hz, 1H), 6.00 (s, 2H), 4.64 (d, J = 5.52 Hz, 2H). |

TABLE 1-continued

| Ex. No. | Structure | Chemical Name | ESI-MS (M + H) | ¹H NMR |
|---|---|---|---|---|
| 376 | 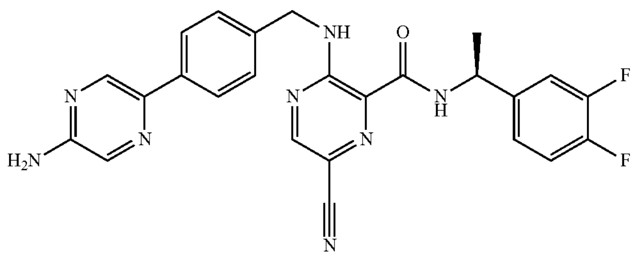 [SMILES: C[C@H](NC(=O)c1nc(C#N)cnc1NCc1ccc(-c2cnc(N)cn2)cc1)c1ccc(F)c(F)c1] | (S)-3-(4-(5-aminopyrazin-2-yl)benzylamino)-6-cyano-N-(1-(3,4-difluorophenyl)ethyl)pyrazine-2-carboxamide | 486.9 | ¹H NMR (400 MHz, DMSO-d₆) δ 9.72 (t, J = 5.90 Hz, 1H), 9.32 (d, J = 8.28 Hz, 1H), 8.73 (s, 1H), 8.45 (d, J = 1.00 Hz, 1H), 7.93 (d, J = 1.25 Hz, 1H), 7.84 (d, J = 8.28 Hz, 2H), 7.50 (ddd, J = 1.76, 7.91, 11.92 Hz, 1H), 7.30-7.44 (m, 3H), 7.20-7.28 (m, 1H), 6.52 (s, 2H), 5.11 (quin, J = 7.28 Hz, 1H), 4.59-4.78 (m, 2H), 1.50 (d, J = 7.03 Hz, 3H). |
| 377 | 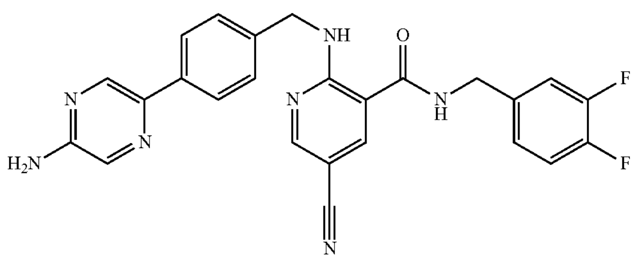 [SMILES: N#Cc1cnc(NCc2ccc(-c3cnc(N)cn3)cc2)c(C(=O)NCc2ccc(F)c(F)c2)c1] | 2-(4-(5-aminopyrazin-2-yl)benzylamino)-5-cyano-N-(3,4-difluorobenzyl)nicotinamide | 471.9 | ¹H NMR (400 MHz, DMSO-d₆) δ 9.36 (br. s., 1H), 9.26 (br. s., 1H), 8.57 (br. s., 1H), 8.45 (d, J = 1.00 Hz, 1H), 8.39 (br. s., 1H), 7.93 (d, J = 1.25 Hz, 1H), 7.84 (d, J = 8.28 Hz, 2H), 7.28-7.47 (m, 4H), 7.09-7.24 (m, 1H), 6.52 (s, 2H), 4.70 (d, J = 5.52 Hz, 2H), 4.42 (s, 2H). |
| 378 | 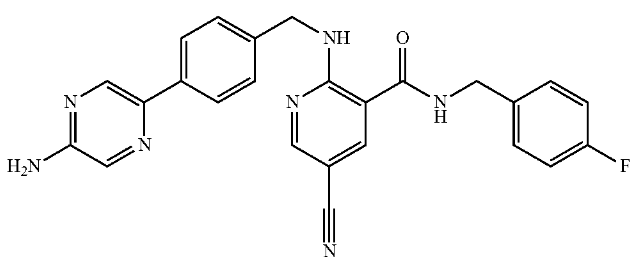 [SMILES: N#Cc1cnc(NCc2ccc(-c3cnc(N)cn3)cc2)c(C(=O)NCc2ccc(F)cc2)c1] | 2-(4-(5-aminopyrazin-2-yl)benzylamino)-5-cyano-N-(4-fluorobenzyl)nicotinamide | 453.9 | ¹H NMR (400 MHz, DMSO-d₆) δ 9.40 (t, J = 5.02 Hz, 1H), 9.24 (t, J = 5.65 Hz, 1H), 8.57 (s, 1H), 8.46 (d, J = 1.25 Hz, 1H), 8.38 (s, 1H), 7.93 (d, J = 1.25 Hz, 1H), 7.84 (d, J = 8.28 Hz, 2H), 7.26-7.44 (m, 4H), 7.15 (t, J = 8.91 Hz, 2H), 6.52 (s, 2H), 4.70 (d, J = 5.52 Hz, 2H), 4.42 (d, J = 4.52 Hz, 2H). |
| 379 | 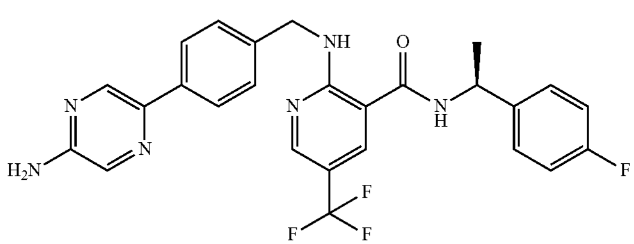 [SMILES: C[C@H](NC(=O)c1cc(C(F)(F)F)cnc1NCc1ccc(-c2cnc(N)cn2)cc1)c1ccc(F)cc1] | (S)-2-(4-(5-aminopyrazin-2-yl)benzylamino)-N-(1-(4-fluorophenyl)ethyl)-5-(trifluoromethyl)nicotinamide | 510.9 | ¹H NMR (400 MHz, DMSO-d₆) δ 9.20 (t, J = 5.77 Hz, 1H), 9.09 (d, J = 7.28 Hz, 1H), 8.49 (s, 1H), 8.45 (d, J = 1.25 Hz, 1H), 8.39 (d, J = 2.01 Hz, 1H), 7.93 (d, J = 1.25 Hz, 1H), 7.78-7.88 (m, J = 8.28 Hz, 2H), 7.41 (dd, J = 5.77, 8.53 Hz, 2H), 7.26-7.36 (m, J = 8.28 Hz, 2H), 7.15 (t, J = 8.78 Hz, 2H), 6.51 (s, 2H), 5.12 (quin, J = 7.03 Hz, 1H), 4.59-4.76 (m, 2H), 1.47 (d, J = 7.03 Hz, 3H). |

TABLE 1-continued

| Ex. No. | Structure | Chemical Name | ESI-MS (M + H) | ¹H NMR |
|---|---|---|---|---|
| 380 | (structure) | (S)-2-(4-(5-aminopyrazin-2-yl)benzylamino)-N-(1-(3,4-difluorophenyl)ethyl)nicotinamide | 460.9 | ¹H NMR (400 MHz, DMSO-$d_6$) δ 8.81 (d, J = 7.53 Hz, 1H), 8.58 (t, J = 5.65 Hz, 1H), 8.44 (d, J = 1.26 Hz, 1H), 8.16 (dd, J = 1.63, 4.64 Hz, 1H), 8.07 (dd, J = 1.63, 7.65 Hz, 1H), 7.93 (d, J = 1.51 Hz, 1H), 7.82 (d, J = 8.28 Hz, 2H), 7.34-7.47 (m, 2H), 7.32 (d, J = 8.03 Hz, 2H), 7.16-7.24 (m, 1H), 6.62 (dd, J = 4.77, 7.53 Hz, 1H), 6.50 (s, 2H), 5.10 (quin, J = 7.09 Hz, 1H), 4.52-4.69 (m, 2H), 1.44 (d, J = 7.03 Hz, 3H). |
| 381 | (structure) | 5-(4-(5-aminopyrazin-2-yl)benzylamino)-3-(3,4-difluorobenzyl)pyrido[4,3-d]pyrimidin-4(3H)-one | 471.9 | ¹H NMR (400 MHz, DMSO-$d_6$) δ 9.07 (t, J = 5.77 Hz, 1H), 8.65 (s, 1H), 8.45 (d, J = 1.25 Hz, 1H), 8.22 (d, J = 5.52 Hz, 1H), 7.93 (d, J = 1.25 Hz, 1H), 7.84 (d, J = 8.28 Hz, 2H), 7.50 (ddd, J = 2.01, 7.78, 11.29 Hz, 1H), 7.31-7.46 (m, 3H), 7.14-7.27 (m, 1H), 6.65 (d, J = 5.52 Hz, 1H), 6.51 (s, 2H), 5.11 (s, 2H), 4.71 (d, J = 5.77 Hz, 2H). |
| 382 | (structure) | (S)-2-(4-(5-aminopyrazin-2-yl)benzylamino)-N-(1-(3,4-difluorophenyl)ethyl)-5-(trifluoromethyl)nicotinamide | 528.9 | ¹H NMR (400 MHz, DMSO-$d_6$) δ 9.17 (t, J = 5.65 Hz, 1H), 9.07 (d, J = 7.28 Hz, 1H), 8.49 (s, 1H), 8.45 (d, J = 1.26 Hz, 1H), 8.39 (d, J = 2.01 Hz, 1H), 7.93 (d, J = 1.51 Hz, 1H), 7.83 (d, J = 8.28 Hz, 2H), 7.35-7.49 (m, 2H), 7.33 (d, J = 8.28 Hz, 2H), 7.13-7.27 (m, 1H), 6.51 (s, 2H), 5.10 (quin, J = 7.03 Hz, 1H), 4.55-4.79 (m, 2H), 1.46 (d, J = 7.03 Hz, 3H). |
| 383 | (structure) | 2-(4-(5-aminopyrazin-2-yl)benzylamino)-N-(4-fluorobenzyl)-5-(trifluoromethyl)nicotinamide | 496.9 | ¹H NMR (400 MHz, DMSO-$d_6$) δ 9.34 (t, J = 6.53 Hz, 1H), 9.30 (t, J = 6.02 Hz, 1H), 8.49 (s, 1H), 8.46 (d, J = 1.25 Hz, 1H), 8.33 (d, J = 2.01 Hz, 1H), 7.93 (d, J = 1.25 Hz, 1H), 7.85 (d, J = 8.28 Hz, 2H), 7.26-7.45 (m, 4H), 7.15 (t, J = 8.91 Hz, 2H), 6.51 (s, 2H), 4.70 (d, J = 5.77 Hz, 2H), 4.43 (d, J = 5.77 Hz, 2H). |
| 384 | (structure) | N-(3,4-Difluoro-benzyl)-2-{[5-(1-methyl-1H-imidazo[4,5-c]quinolin-8-yl)-thiazol-2-ylmethyl]-amino}-nicotinamide | 542.2 | ¹H NMR (300 MHz, DMSO-$d_6$) δ 9.11 (s, 1H), 8.95 (t, J = 6.04 Hz, 1H), 8.47 (d, J = 1.89 Hz, 1H), 8.31-8.33 (m, 1H), 8.26 (s, 1H), 8.16 (dd, J = 1.70, 4.72 Hz, 1H), 8.07-8.11 (m, 1H), 8.01 (dd, J = 1.70, 7.74 Hz, 1H), 7.84-7.89 (m, 1H), 7.28-7.39 (m, 1H), 7.08-7.17 (m, 1H), 6.65 (dd, J = 4.72, 7.74 Hz, 1H), 4.90 (d, J = 6.04 Hz, 2H), 4.40 (d, J = 5.67 Hz, 2H), 4.34 (d, J = 4.15 Hz, 1H), 4.29 (s, 3H). |

| Ex. No. | Structure | Chemical Name | ESI-MS (M + H) | ¹H NMR |
|---|---|---|---|---|
| 385 | 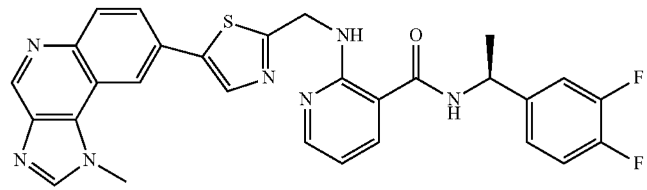 [SMILES: C[C@H](NC(=O)c1cccnc1NCc1ncc(-c2ccc3ncc4ncn(C)c4c3c2)s1)c1ccc(F)c(F)c1] | N-[(S)-1-(3,4-Difluoro-phenyl)-ethyl]-2-{[5-(1-methyl-1H-imidazo[4,5-c]quinolin-8-yl)-thiazol-2-ylmethyl]-amino}-nicotinamide | 556.2 | ¹H NMR (300 MHz, DMSO-d₆) δ 9.19 (s, 1H), 8.91 (s, 1H), 8.53 (d, J = 1.89 Hz, 1H), 8.40 (s, 1H), 8.32 (s, 1H), 8.19-8.26 (m, 1H), 8.15-8.18 (m, 1H), 8.11-8.15 (m, 1H), 7.93 (dd, J = 1.89, 8.69 Hz, 1H), 7.33-7.55 (m, 2H), 7.27 (d, J = 2.64 Hz, 1H), 6.73 (dd, J = 4.91, 6.04 Hz, 1H), 5.15 (quin, J = 7.08 Hz, 1H), 4.94 (d, J = 6.04 Hz, 2H), 4.41 (d, J = 4.53 Hz, 1H), 4.36 (s, 3H), 1.48 (d, J = 7.18 Hz, 3H) |
| 386 | 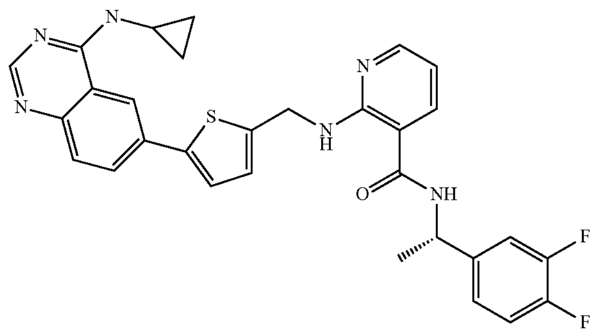 [SMILES: C[C@H](NC(=O)c1cccnc1NCc1ccc(-c2ccc3ncnc(NC4CC4)c3c2)s1)c1ccc(F)c(F)c1] | 2-{[5-(4-Cyclopropylamino-quinazolin-6-yl)-thiophen-2-ylmethyl]-amino}-N-[(S)-1-(3,4-difluoro-phenyl)-ethyl]-nicotinamide | 557.3 | ¹H NMR (300 MHz, DMSO-d₆) δ 9.94 (d, J = 4.15 Hz, 1H), 8.84 (s, 1H), 8.79 (d, J = 7.55 Hz, 1H), 8.66 (t, J = 6.04 Hz, 1H), 8.51 (d, J = 1.89 Hz, 1H), 8.14-8.22 (m, 2H), 8.06 (dd, J = 1.70, 7.74 Hz, 1H), 7.71 (d, J = 8.69 Hz, 1H), 7.46 (d, J = 3.78 Hz, 1H), 7.25-7.42 (m, 2H), 7.15 (dt, J = 2.27, 4.15 Hz, 1H), 7.04 (d, J = 3.78 Hz, 1H), 6.63 (dd, J = 4.91, 7.55 Hz, 1H), 5.03 (quin, J = 6.99 Hz, 1H), 4.77 (d, J = 5.67 Hz, 2H), 3.28 (dt, J = 3.97, 7.27 Hz, 1H), 1.39 (d, J = 6.80 Hz, 3H), 0.84-0.97 (m, 2H), 0.76-0.84 (m, 2H) |
| 387 | 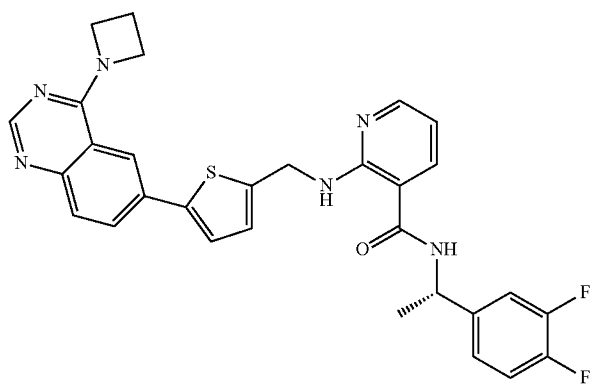 [SMILES: C[C@H](NC(=O)c1cccnc1NCc1ccc(-c2ccc3ncnc(N4CCC4)c3c2)s1)c1ccc(F)c(F)c1] | 2-{[5-(4-Azetidin-1-yl-quinazolin-6-yl)-thiophen-2-ylmethyl]-amino}-N-[(S)-1-(3,4-difluoro-phenyl)-ethyl]-nicotinamide | 557.3 | ¹H NMR (300 MHz, DMSO-d₆) δ 8.80 (d, J = 7.55 Hz, 1H), 8.69 (s, 1H), 8.63 (t, J = 5.29 Hz, 1H), 8.11-8.19 (m, 2H), 8.05 (dd, J = 1.70, 7.74 Hz, 1H), 7.95 (d, J = 1.89 Hz, 1H), 7.70 (d, J = 9.06 Hz, 1H), 7.47 (d, J = 3.78 Hz, 1H), 7.24-7.42 (m, 2H), 7.09-7.18 (m, 1H), 7.03 (d, J = 3.40 Hz, 1H), 6.63 (dd, J = 4.91, 7.93 Hz, 1H), 4.93-5.21 (m, 2H), 4.74 (d, J = 4.53 Hz, 2H), 2.44-2.54 (m, 4H), 1.23-1.46 (m, 3H) |

TABLE 1-continued

| Ex. No. | Structure | Chemical Name | ESI-MS (M + H) | ¹H NMR |
|---|---|---|---|---|
| 388 | 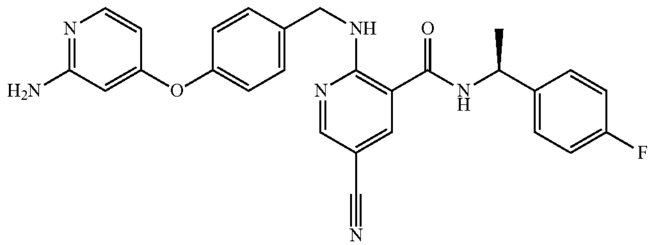 [SMILES: C[C@H](NC(=O)c1cc(C#N)cnc1NCc1ccc(Oc2ccnc(N)c2)cc1)c1ccc(F)cc1] | N-(3,4-Difluoro-benzyl)-2-((E)-3-{1-[4-(2-methoxy-ethylcarbamoyl)-3,5-dimethyl-1H-pyrrol-2-yl]-meth-(Z)-ylidene]-2-oxo-2,3-dihydro-1H-indol-6-yl}-allylamino)-nicotinamide | 483.2 | ¹H NMR (300 MHz, CD₃CN) δ 9.13 (t, J = 4.91 Hz, 1H), 8.45 (d, J = 2.27 Hz, 1H), 8.12-8.23 (m, 1H), 7.83 (d, J = 5.67 Hz, 1H), 7.29-7.54 (m, 5H), 6.97-7.14 (m, 4H), 6.18 (dd, J = 2.27, 6.04 Hz, 1H), 5.94 (d, J = 2.27 Hz, 1H), 5.11 (quin, J = 7.08 Hz, 1H), 4.88 (br. s., 2H), 4.70 (d, J = 6.04 Hz, 2H), 1.40-1.58 (m, 3H). |
| 389 | 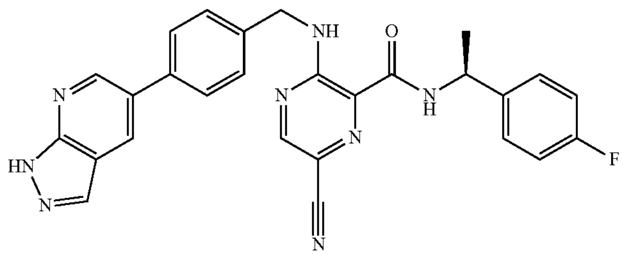 [SMILES: C[C@H](NC(=O)c1nc(C#N)cnc1NCc1ccc(-c2cnc3[nH]ncc3c2)cc1)c1ccc(F)cc1] | 6-Cyano-3-[4-(1H-pyrazolo[3,4-b]pyridin-5-yl)-benzylamino]-pyrazine-2-carboxylic acid [(S)-1-(4-fluoro-phenyl)-ethyl]-amide | 493.2 | ¹H NMR (300 MHz, DMSO-d₆) δ 13.63 (br. s., 1H), 9.73 (t, J = 6.04 Hz, 1H), 9.24 (d, J = 8.31 Hz, 1H), 8.74 (d, J = 1.89 Hz, 1H), 8.67 (s, 1H), 8.37 (d, J = 2.27 Hz, 1H), 8.12 (d, J = 1.13 Hz, 1H), 7.63 (d, J = 8.31 Hz, 2H), 7.33-7.45 (m, 4H), 7.02-7.14 (m, 2H), 4.99-5.14 (m, 1H), 4.68 (d, J = 4.53 Hz, 2H), 1.46 (d, J = 7.18 Hz, 3H) |
| 390 | 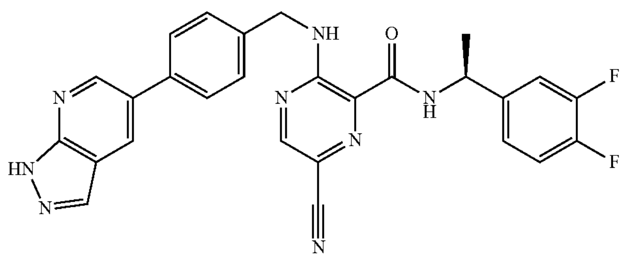 [SMILES: C[C@H](NC(=O)c1nc(C#N)cnc1NCc1ccc(-c2cnc3[nH]ncc3c2)cc1)c1ccc(F)c(F)c1] | 6-Cyano-3-[4-(1H-pyrazolo[3,4-b]pyridin-5-yl)-benzylamino]-pyrazine-2-carboxylic acid [(S)-1-(3,4-difluoro-phenyl)-ethyl]-amide | 511.2 | ¹H NMR (300 MHz, DMSO-d₆) δ 13.63 (s, 1H), 9.70 (t, J = 5.85 Hz, 1H), 9.26 (d, J = 8.31 Hz, 1H), 8.74 (d, J = 2.27 Hz, 1H), 8.68 (s, 1H), 8.37 (d, J = 1.89 Hz, 1H), 8.12 (d, J = 1.13 Hz, 1H), 7.63 (d, J = 8.31 Hz, 2H), 7.15-7.52 (m, 5H), 5.06 (quin, J = 7.27 Hz, 1H), 4.57-4.78 (m, 2H), 1.45 (d, J = 6.80 Hz, 3H) |
| 391 | 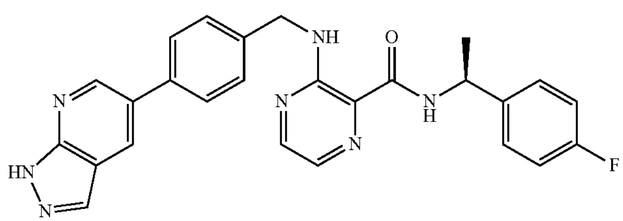 [SMILES: C[C@H](NC(=O)c1nccnc1NCc1ccc(-c2cnc3[nH]ncc3c2)cc1)c1ccc(F)cc1] | 3-[4-(1H-Pyrazolo[3,4-b]pyridin-5-yl)-benzylamino]-pyrazine-2-carboxylic acid [(S)-1-(4-fluoro-phenyl)-ethyl]-amide | 468.2 | ¹H NMR (300 MHz, DMSO-d₆) δ 13.69 (br. s., 1H), 9.01-9.23 (m, 2H), 8.81 (d, J = 1.89 Hz, 1H), 8.44 (d, J = 1.51 Hz, 1H), 8.29 (d, J = 2.27 Hz, 1H), 8.18 (s, 1H), 7.85 (d, J = 2.27 Hz, 1H), 7.69 (d, J = 8.31 Hz, 2H), 7.39-7.52 (m, 4H), 7.14 (t, J = 8.88 Hz, 2H), 5.13 (quin, J = 7.18 Hz, 1H), 4.69 (d, J = 4.15 Hz, 2H), 1.51 (d, J = 7.18 Hz, 3H) |

| Ex. No. | Structure | Chemical Name | ESI-MS (M + H) | ¹H NMR |
|---|---|---|---|---|
| 392 | 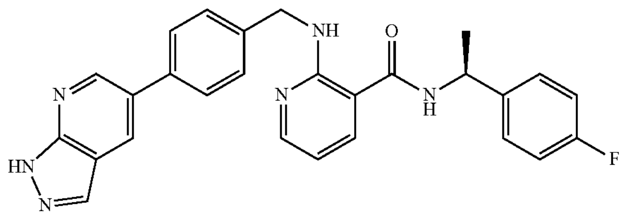 [SMILES: C[C@H](NC(=O)c1cccnc1NCc1ccc(-c2cnc3[nH]ncc3c2)cc1)c1ccc(F)cc1] | N-[(S)-1-(4-Fluoro-phenyl)-ethyl]-2-[4-(1H-pyrazolo[3,4-b]pyridin-5-yl)-benzylamino]-nicotinamide | 467.2 | ¹H NMR (300 MHz, DMSO-d₆) δ 13.62 (s, 1H), 8.71-8.80 (m, 2H), 8.59 (t, J = 5.85 Hz, 1H), 8.36 (d, J = 1.89 Hz, 1H), 8.08-8.15 (m, 2H), 8.01 (dd, J = 1.70, 7.74 Hz, 1H), 7.61 (d, J = 8.31 Hz, 2H), 7.30-7.40 (m, 4H), 7.07 (t, J = 3.02, 9.06 Hz, 2H), 6.56 (dd, J = 4.91, 7.55 Hz, 1H), 5.06 (quin, J = 7.08 Hz, 1H), 4.59 (d, J = 4.91 Hz, 2H), 1.39 (d, J = 7.18 Hz, 3H) |
| 393 | 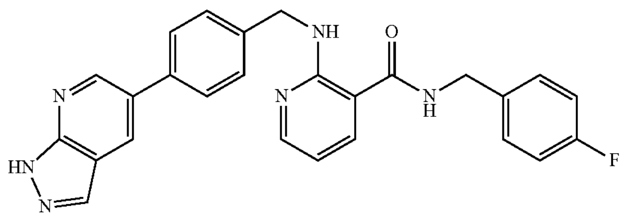 [SMILES: O=C(NCc1ccc(F)cc1)c1cccnc1NCc1ccc(-c2cnc3[nH]ncc3c2)cc1] | 2-(4-(1H-pyrazolo[3,4-b]pyridin-5-yl)benzylamino)-N-(4-fluorobenzyl)nicotinamide | 453.2 | ¹H NMR (300 MHz, DMSO-d₆) δ 13.69 (br. s., 1H), 9.10 (t, J = 6.04 Hz, 1H), 8.74-8.86 (m, 2H), 8.44 (d, J = 1.89 Hz, 1H), 8.13-8.23 (m, 2H), 8.02 (dd, J = 1.70, 7.74 Hz, 1H), 7.69 (d, J = 8.31 Hz, 2H), 7.44 (d, J = 8.31 Hz, 2H), 7.36 (dd, J = 5.67, 8.69 Hz, 2H), 7.09-7.21 (m, 2H), 6.62 (dd, J = 4.91, 7.55 Hz, 1H), 4.69 (d, J = 5.67 Hz, 2H), 4.43 (d, J = 5.67 Hz, 2H) |
| 394 | 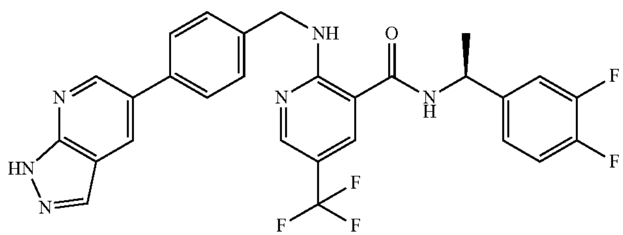 [SMILES: C[C@H](NC(=O)c1cc(C(F)(F)F)cnc1NCc1ccc(-c2cnc3[nH]ncc3c2)cc1)c1ccc(F)c(F)c1] | N-[(S)-1-(3,4-Difluoro-phenyl)-ethyl]-2-[4-(1H-pyrazolo[3,4-b]pyridin-5-yl)-benzylamino]-5-trifluoromethyl-nicotinamide | 552.9 | ¹H NMR (300 MHz, DMSO-d₆) δ 13.70 (br. s., 1H), 9.22 (t, J = 5.48 Hz, 1H), 9.09 (d, J = 7.55 Hz, 1H), 8.81 (d, J = 1.51 Hz, 1H), 8.52 (s, 1H), 8.43 (d, J = 1.89 Hz, 2H), 8.18 (s, 1H), 7.69 (d, J = 7.93 Hz, 2H), 7.29-7.56 (m, 4H), 7.24 (br. s., 1H), 5.12 (t, J = 6.99 Hz, 1H), 4.73 (d, J = 4.15 Hz, 2H), 1.48 (d, J = 6.80 Hz, 3H) |
| 395 | 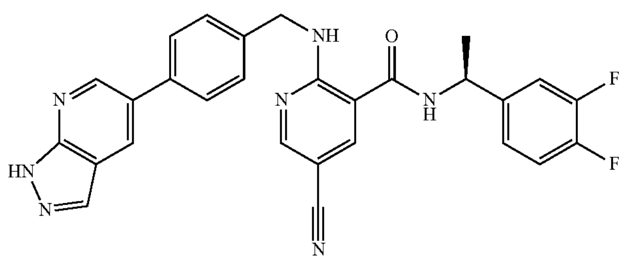 [SMILES: C[C@H](NC(=O)c1cc(C#N)cnc1NCc1ccc(-c2cnc3[nH]ncc3c2)cc1)c1ccc(F)c(F)c1] | 5-Cyano-N-[(S)-1-(3,4-difluoro-phenyl)-ethyl]-2-[4-(1H-pyrazolo[3,4-b]pyridin-5-yl)-benzylamino]-nicotinamide | 509.9 | ¹H NMR (300 MHz, DMSO-d₆) δ 13.69 (br. s., 1H), 9.33 (t, J = 5.85 Hz, 1H), 8.99 (d, J = 7.18 Hz, 1H), 8.80 (d, J = 2.27 Hz, 1H), 8.59 (d, J = 2.27 Hz, 1H), 8.50 (d, J = 2.27 Hz, 1H), 8.43 (d, J = 1.89 Hz, 1H), 8.18 (d, J = 1.13 Hz, 1H), 7.69 (d, J = 8.31 Hz, 2H), 7.30-7.53 (m, 4H), 7.18-7.28 (m, 1H), 5.09 (quin, J = 6.99 Hz, 1H), 4.73 (d, J = 6.04 Hz, 2H), 1.46 (d, J = 7.18 Hz, 3H) |

TABLE 1-continued

| Ex. No. | Structure | Chemical Name | ESI-MS (M + H) | ¹H NMR |
|---|---|---|---|---|
| 396 | 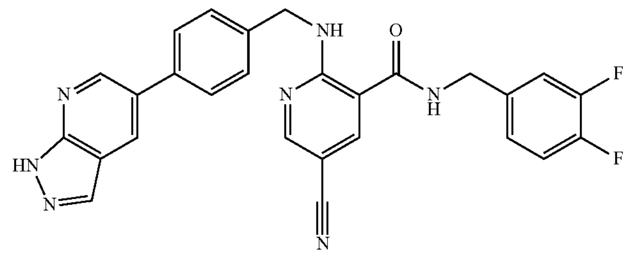 [SMILES: N#Cc1cnc(NCc2ccc(-c3cnc4[nH]ncc4c3)cc2)c(C(=O)NCc2ccc(F)c(F)c2)c1] | 5-Cyano-N-(3,4-difluorobenzyl)-2-[4-(1H-pyrazolo[3,4-b]pyridin-5-yl)-benzylamino]-nicotinamide | 496.9 | ¹H NMR (300 MHz, DMSO-d₆) δ 13.70 (br. s., 1H), 9.42 (t, J = 5.85 Hz, 1H), 9.27 (t, J = 5.67 Hz, 1H), 8.82 (d, J = 2.27 Hz, 1H), 8.60 (d, J = 1.89 Hz, 1H), 8.43 (dd, J = 1.89, 6.42 Hz, 2H), 8.19 (s, 1H), 7.70 (d, J = 8.31 Hz, 2H), 7.33-7.50 (m, 4H), 7.20 (ddd, J = 1.89, 4.25, 6.33 Hz, 1H), 4.76 (d, J = 6.04 Hz, 2H), 4.44 (d, J = 5.67 Hz, 2H) |
| 397 | 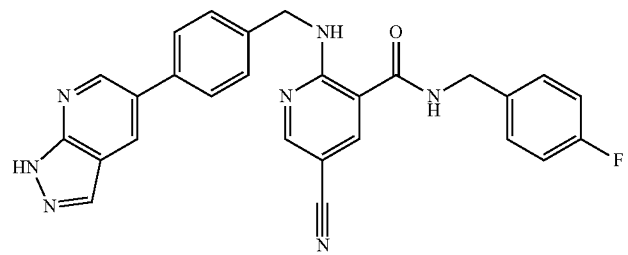 [SMILES: N#Cc1cnc(NCc2ccc(-c3cnc4[nH]ncc4c3)cc2)c(C(=O)NCc2ccc(F)cc2)c1] | 5-Cyano-N-(4-fluorobenzyl)-2-[4-(1H-pyrazolo[3,4-b]pyridin-5-yl)-benzylamino]-nicotinamide | 477.9 | ¹H NMR (300 MHz, DMSO-d₆) δ 13.63 (br. s., 1H), 9.38 (t, J = 5.85 Hz, 1H), 9.18 (t, J = 5.85 Hz, 1H), 8.69-8.79 (m, 1H), 8.52 (d, J = 1.89 Hz, 1H), 8.37 (d, J = 2.27 Hz, 1H), 8.33 (d, J = 2.27 Hz, 1H), 8.12 (s, 1H), 7.63 (d, J = 7.93 Hz, 2H), 7.27-7.41 (m, 4H), 7.03-7.14 (m, 2H), 4.69 (d, J = 6.04 Hz, 2H), 4.37 (d, J = 5.67 Hz, 2H) |
| 398 | 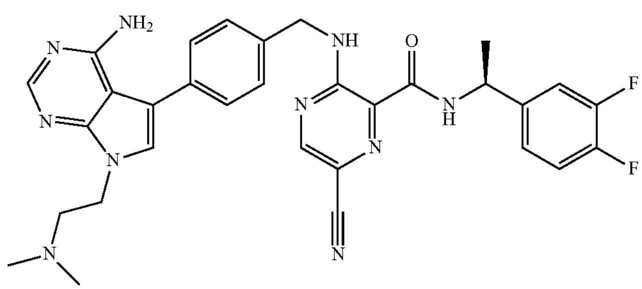 [SMILES: C[C@H](NC(=O)c1nc(C#N)cnc1NCc1ccc(-c2cn(CCN(C)C)c3ncnc(N)c23)cc1)c1ccc(F)c(F)c1] | (S)-3-(4-(4-amino-7-(2-(dimethylamino)ethyl)-7H-pyrrolo[2,3-d]pyrimidin-5-yl)benzylamino)-6-cyano-N-(1-(3,4-difluorophenyl)ethyl)pyrazine-2-carboxamide | 597.0 | ¹H NMR (300 MHz, DMSO-d₆) δ 9.75 (t, J = 5.85 Hz, 1H), 9.33 (d, J = 8.31 Hz, 1H), 8.75 (s, 1H), 8.14 (s, 1H), 7.46-7.58 (m, 1H), 7.32-7.45 (m, 5H), 7.27 (d, J = 4.15 Hz, 1H), 5.12 (quin, J = 7.46 Hz, 1H), 4.64-4.86 (m, 2H), 4.28 (t, J = 6.42 Hz, 2H), 2.75 (br. s., 1H), 2.25 (s, 6H), 1.52 (d, J = 7.18 Hz, 3H), 1.09-1.29 (m, 2H) |

| Ex. No. | Structure | Chemical Name | ESI-MS (M + H) | ¹H NMR |
|---|---|---|---|---|
| 399 | 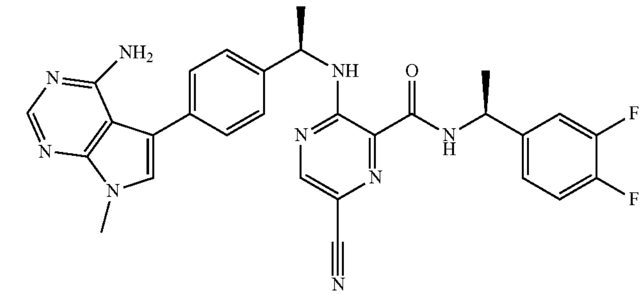 [SMILES: C[C@H](NC(=O)c1nc(C#N)cnc1N[C@H](C)c1ccc(-c2cn(C)c3ncnc(N)c23)cc1)c1ccc(F)c(F)c1] | 3-(R)-1-(4-(4-amino-7-methyl-7H-pyrrolo[2,3-d]pyrimidin-5-yl)phenyl)ethylamino)-6-cyano-N-((S)-1-(3,4-difluorophenyl)ethyl)pyrazine-2-carboxamide | 554.47 | ¹H NMR (300 MHz, DMSO-d₆) δ 9.81 (d, J = 7.78 Hz, 1H), 9.40 (d, J = 8.53 Hz, 1H), 8.74 (s, 1H), 8.43 (s, 1H), 7.59 (s, 1H), 7.49-7.57 (m, 3H), 7.43-7.47 (m, 2H), 7.38-7.42 (m, 1H), 7.37 (s, 1H), 7.28 (td, J = 2.20, 4.14 Hz, 1H), 5.33-5.41 (m, 1H), 5.14 (quin, J = 7.53 Hz, 1H), 3.83 (s, 3H), 1.54 (dd, J = 7.03, 18.32 Hz, 6H) |
| 400 | 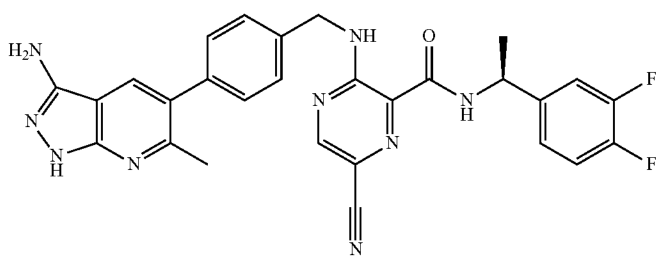 [SMILES: Cc1nc2[nH]nc(N)c2cc1-c1ccc(CNc2ncc(C#N)nc2C(=O)N[C@@H](C)c2ccc(F)c(F)c2)cc1] | (S)-3-(4-(3-amino-6-methyl-1H-pyrazolo[3,4-b]pyridin-5-yl)benzylamino)-6-cyano-N-(1-(3,4-difluorophenyl)ethyl)pyrazine-2-carboxamide | 539.9 | ¹H NMR (300 MHz, DMSO-d₆) δ 9.70 (s, 1H), 9.27 (d, J = 8.31 Hz, 1H), 8.69 (s, 1H), 7.87-7.99 (m, 1H), 7.40-7.52 (m, 1H), 7.24-7.39 (m, 5H), 7.14-7.24 (m, 1H), 5.06 (t, J = 7.37 Hz, 1H), 4.69 (br. s., 2H), 1.45 (d, J = 6.80 Hz, 6H) |
| 401 | 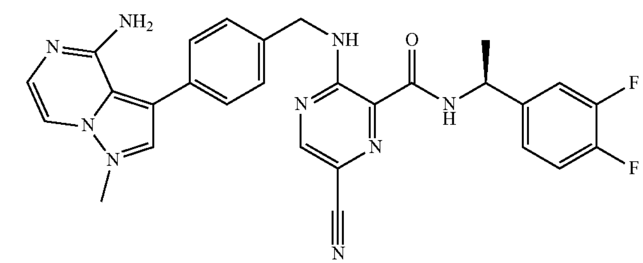 | (S)-3-(4-(8-amino-3-methylimidazo[1,5-a]pyrazin-1-yl)benzylamino)-6-cyano-N-(1-(3,4-difluorophenyl)ethyl)pyrazine-2-carboxamide | 539.9 | ¹H NMR (300 MHz, DMSO-d₆) δ 9.71 (s, 1H), 9.29 (d, J = 8.31 Hz, 1H), 8.68 (s, 1H), 7.68 (d, J = 5.67 Hz, 1H), 7.50-7.59 (m, 2H), 7.37-7.49 (m, 3H), 7.24-7.37 (m, 1H), 7.13-7.24 (m, 1H), 7.01 (d, J = 5.67 Hz, 1H), 5.05 (s, 1H), 4.72 (d, J = 5.67 Hz, 2H), 1.45 (d, J = 7.18 Hz, 6H) |

TABLE 1-continued

| Ex. No. | Structure | Chemical Name | ESI-MS (M + H) | $^1$H NMR |
|---|---|---|---|---|
| 402 | 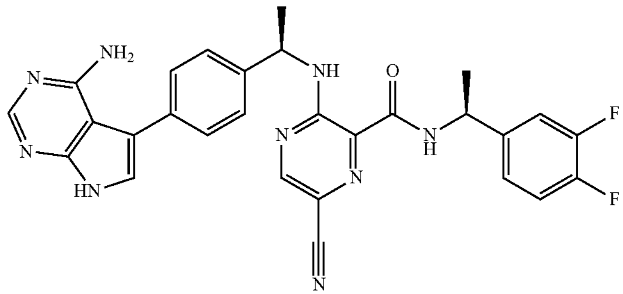 [SMILES: C[C@H](NC(=O)c1nc(C#N)cnc1N[C@H](C)c1ccc(-c2c[nH]c3ncnc(N)c23)cc1)c1ccc(F)c(F)c1] | 3-((R)-1-(4-(4-amino-7H-pyrrolo[2,3-d]pyrimidin-5-yl)phenyl)ethylamino)-6-cyano-N-((S)-1-(3,4-difluorophenyl)ethyl)pyrazine-2-carboxamide | 539.9 | $^1$H NMR (300 MHz, DMSO-d$_6$) δ 12.84 (br. s., 1H), 9.80 (d, J = 7.55 Hz, 1H), 9.39 (d, J = 8.31 Hz, 1H), 8.74 (s, 1H), 8.38 (s, 1H), 7.34-7.58 (m, 8H), 7.24-7.32 (m, 1H), 5.37 (quin, J = 7.08 Hz, 1H), 5.07-5.20 (m, 1H), 1.56 (d, J = 6.80 Hz, 3H), 1.52 (d, J = 6.80 Hz, 3H) |
| 403 | 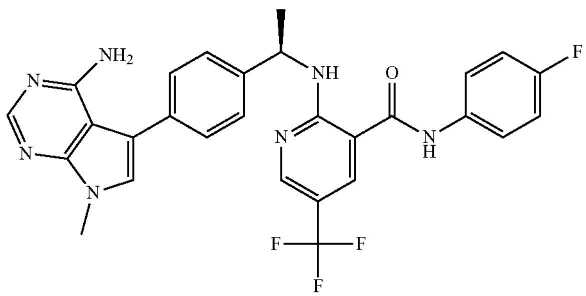 [SMILES: C[C@@H](Nc1ncc(C(F)(F)F)cc1C(=O)Nc1ccc(F)cc1)c1ccc(-c2cn(C)c3ncnc(N)c23)cc1] | (R)-2-(1-(4-(4-amino-7-methyl-7H-pyrrolo[2,3-d]pyrimidin-5-yl)phenyl)ethylamino)-N-(4-fluorophenyl)-5-(trifluoromethyl)nicotinamide | 549.9 | $^1$H NMR (300 MHz, DMSO-d$_6$) δ 10.54 (s, 1H), 9.03 (d, J = 7.55 Hz, 1H), 8.53 (d, J = 1.13 Hz, 1H), 8.48 (s, 1H), 8.46 (d, J = 2.27 Hz, 1H), 7.65-7.73 (m, 2H), 7.63 (s, 1H), 7.50-7.56 (m, 2H), 7.43-7.48 (m, 2H), 7.18-7.28 (m, 2H), 5.49 (quin, J = 6.99 Hz, 1H), 3.84 (s, 3H), 1.57 (d, J = 6.80 Hz, 3H) |
| 404 | 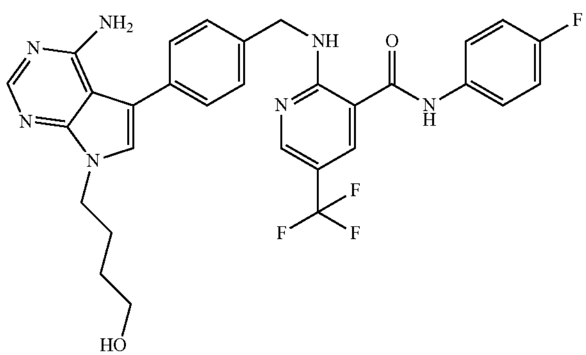 [SMILES: Nc1ncnc2c1c(-c1ccc(CNc3ncc(C(F)(F)F)cc3C(=O)Nc3ccc(F)cc3)cc1)cn2CCCCO] | 2-(4-(4-amino-7-(4-hydroxybutyl)-7H-pyrrolo[2,3-d]pyrimidin-5-yl)benzylamino)-N-(4-fluorophenyl)-5-(trifluoromethyl)nicotinamide | 594.0 | $^1$H NMR (300 MHz, DMSO-d$_6$) δ 10.46 (s, 1H), 8.87 (t, J = 5.85 Hz, 1H), 8.49 (s, 1H), 8.32-8.40 (m, 2H), 7.56-7.70 (m, 3H), 7.30-7.49 (m, 5H), 7.09-7.21 (m, 2H), 4.73 (d, J = 5.67 Hz, 2H), 4.12-4.28 (m, 2H), 3.27-3.41 (m, 2H), 1.78 (quin, J = 7.27 Hz, 2H), 1.24-1.43 (m, 2H) |

| Ex. No. | Structure | Chemical Name | ESI-MS (M + H) | ¹H NMR |
|---|---|---|---|---|
| 405 | 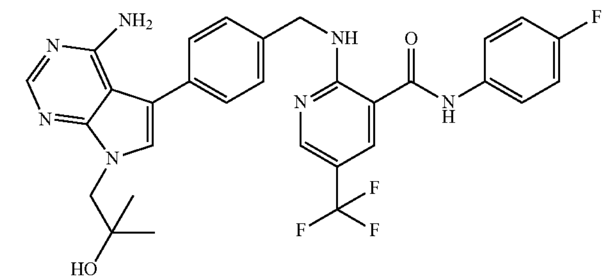 [SMILES: CC(C)(O)Cn1cc(-c2ccc(CNc3ncc(C(F)(F)F)cc3C(=O)Nc3ccc(F)cc3)cc2)c2c(N)ncnc21] | 2-(4-amino-7-(2-hydroxy-2-methylpropyl)-7H-pyrrolo[2,3-d]pyrimidin-5-yl)benzylamino)-N-(4-fluorophenyl)-5-(trifluoromethyl)nicotinamide | 593.9 | ¹H NMR (300 MHz, DMSO-$d_6$) δ 10.46 (s, 1H), 8.88 (t, J = 5.85 Hz, 1H), 8.49 (s, 1H), 8.27-8.41 (m, 2H), 7.62 (dd, J = 5.29, 9.06 Hz, 3H), 7.32-7.49 (m, 5H), 7.15 (t, J = 8.88 Hz, 2H), 4.73 (d, J = 6.04 Hz, 2H), 4.06-4.19 (m, 2H), 1.03 (s, 6H) |
| 406 | 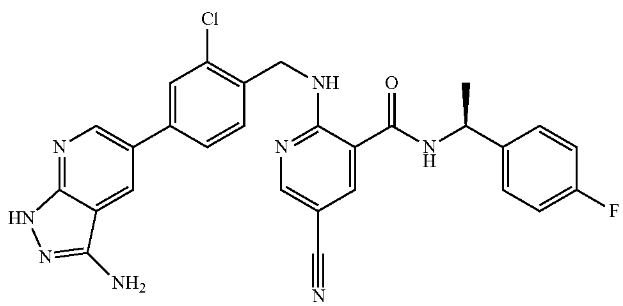 [SMILES: C[C@H](NC(=O)c1cc(C#N)cnc1NCc1ccc(-c2cnc3[nH]nc(N)c3c2)cc1Cl)c1ccc(F)cc1] | 2-[4-(3-Amino-1H-pyrazolo[3,4-b]pyridin-5-yl)-2-chloro-benzylamino]-5-cyano-N-[(S)-1-(4-fluoro-phenyl)-ethyl]-nicotinamide | 541.9 | ¹H NMR (400 MHz, CD$_3$OD) δ 8.85-8.89 (m, 1H), 8.78-8.80 (m, 1H), 8.56-8.58 (m, 1H), 8.51 (d, 1H), 8.32 (d, J = 2.26 Hz, 1H), 7.78-7.80 (m, 1H), 7.59-7.62 (m, 1H), 7.52-7.56 (m, 1H), 7.43-7.50 (m, 2H), 7.08-7.15 (m, 2H), 5.20-5.28 (m, 1H), 4.91 (br. s., 2H), 1.60 (d, J = 7.03 Hz, 3H) |
| 407 | 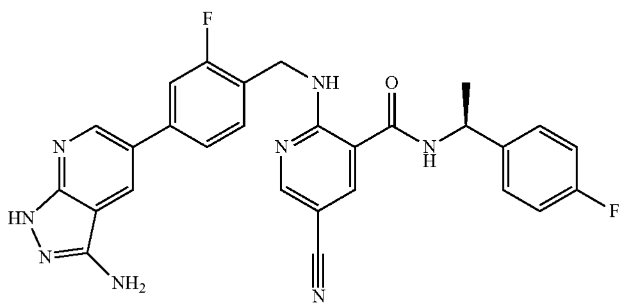 [SMILES: C[C@H](NC(=O)c1cc(C#N)cnc1NCc1ccc(-c2cnc3[nH]nc(N)c3c2)cc1F)c1ccc(F)cc1] | 2-[4-(3-Amino-1H-pyrazolo[3,4-b]pyridin-5-yl)-2-fluoro-benzylamino]-5-cyano-N-[(S)-1-(4-fluoro-phenyl)-ethyl]-nicotinamide | 525.9 | ¹H NMR (400 MHz, CD$_3$OD) δ 8.81-8.85 (m, 1H), 8.77 (d, J = 2.01 Hz, 1H), 8.54 (d, J = 2.26 Hz, 1H), 8.49 (d, J = 2.26 Hz, 1H), 8.26-8.27 (m, 1H), 7.39-7.52 (m, 5H), 7.03-7.11 (m, 2H), 5.16-5.25 (m, 1H), 1.56 (d, J = 7.28 Hz, 3H) |

TABLE 1-continued

| Ex. No. | Structure | Chemical Name | ESI-MS (M + H) | ¹H NMR |
|---|---|---|---|---|
| 408 | 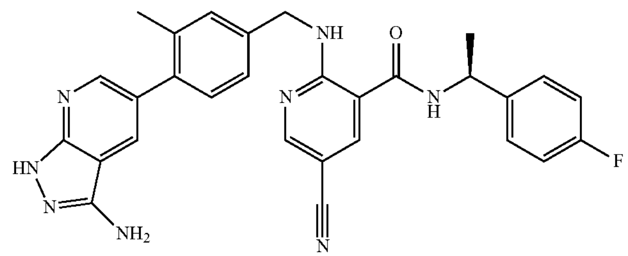 [SMILES: Cc1cc(CNc2ncc(C#N)cc2C(=O)N[C@@H](C)c2ccc(F)cc2)ccc1-c1cnc2[nH]nc(N)c2c1] | 2-[4-(3-Amino-1H-pyrazolo[3,4-b]pyridin-5-yl)-3-methyl-benzylamino]-5-cyano-N-[(S)-1-(4-fluoro-phenyl)-ethyl]-nicotinamide | 520.9 | ¹H NMR (400 MHz, CD₃OD) δ 8.49 (d, J = 2.26 Hz, 1H), 8.44 (d, J = 2.01 Hz, 1H), 8.25-8.28 (m, 2H), 7.39-7.46 (m, 3H), 7.31-7.33 (m, 1H), 7.23-7.29 (m, 2H), 7.04-7.12 (m, 3H), 5.15-5.23 (m, 1H), 4.76 (br. s., 2H), 2.29 (br. s., 3H), 1.56 (d, J = 7.03 Hz, 3H) |
| 409 | 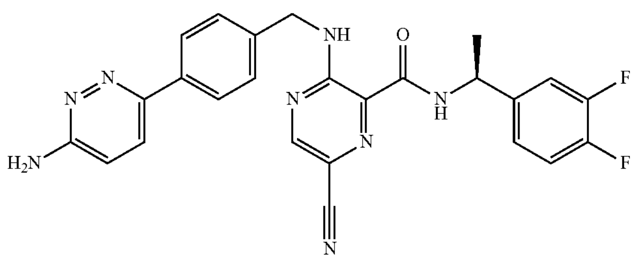 [SMILES: C[C@H](NC(=O)c1nc(C#N)cnc1NCc1ccc(-c2ccc(N)nn2)cc1)c1ccc(F)c(F)c1] | (S)-3-(4-(6-aminopyridazin-3-yl)benzylamino)-6-cyano-N-(1-(3,4-difluorophenyl)ethyl)pyrazine-2-carboxamide | 486.9 | ¹H NMR (400 MHz, DMSO-d₆) δ 9.78 (t, J = 6.02 Hz, 1H), 9.35 (d, J = 8.28 Hz, 1H), 8.72 (s, 1H), 8.51 (br. s., 2H), 8.34 (d, J = 9.54 Hz, 1H), 7.90 (d, J = 8.28 Hz, 2H), 7.43-7.58 (m, 4H), 7.38 (td, J = 8.50, 10.60 Hz, 1H), 7.27 (br. s., 1H), 5.12 (quin, J = 7.28 Hz, 1H), 4.76 (dd, J = 2.51, 5.77 Hz, 2H), 1.52 (d, J = 7.03 Hz, 3H) |
| 410 | 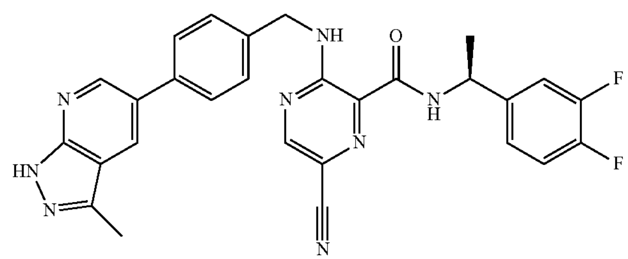 [SMILES: Cc1n[nH]c2ncc(-c3ccc(CNc4ncc(C#N)nc4C(=O)N[C@@H](C)c4ccc(F)c(F)c4)cc3)cc12] | (S)-6-cyano-N-(1-(3,4-difluorophenyl)ethyl)-3-(4-(3-methyl-1H-pyrazolo[3,4-b]pyridin-5-yl)benzylamino)pyrazine-2-carboxamide | 524.9 | ¹H NMR (400 MHz, DMSO-d₆) δ 13.26 (br. s., 1H), 9.76 (t, J = 6.02 Hz, 1H), 9.34 (d, J = 8.28 Hz, 1H), 8.68-8.83 (m, 2H), 8.43 (d, J = 2.01 Hz, 1H), 7.62-7.78 (m, 1H), 7.52 (ddd, J = 2.13, 7.91, 12.05 Hz, 1H), 7.45 (d, J = 8.53 Hz, 2H), 7.38 (td, J = 8.41, 10.79 Hz, 1H), 7.26 (ddd, J = 1.76, 4.20, 8.35 Hz, 1H), 5.12 (td, J = 7.18, 15.00 Hz, 1H), 4.65-4.83 (m, 2H), 2.53-2.54 (m, 3H), 1.52 (d, J = 7.03 Hz, 3H) |

TABLE 1-continued

| Ex. No. | Structure | Chemical Name | ESI-MS (M + H) | ¹H NMR |
|---|---|---|---|---|
| 411 | 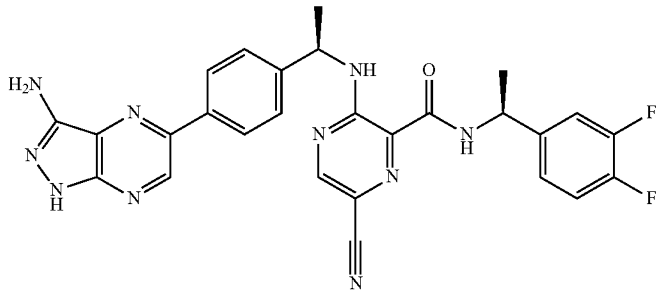 [SMILES: C[C@H](NC(=O)c1nc(C#N)cnc1N[C@H](C)c1ccc(-c2cnc3[nH]nc(N)c3n2)cc1)c1ccc(F)c(F)c1] | 3-{(R)-1-[4-(3-Amino-1H-pyrazolo[3,4-b]pyrazin-5-yl)-phenyl]-ethylamino}-6-cyano-pyrazine-2-carboxylic acid [(S)-1-(3,4-difluoro-phenyl)-ethyl]-amide | 540.9 | ¹H NMR (400 MHz, DMSO-$d_6$) δ 12.42 (s, 1H), 9.81 (d, J = 7.53 Hz, 1H), 9.39 (d, J = 8.28 Hz, 1H), 9.00 (s, 1H), 8.72 (s, 1H), 8.10 (d, J = 8.28 Hz, 2H), 7.48-7.58 (m, 3H), 7.40 (td, J = 8.53, 10.79 Hz, 1H), 7.24-7.32 (m, 1H), 5.72 (s, 2H), 5.31 (quin, J = 6.90 Hz, 1H), 5.15 (quin, J = 7.28 Hz, 1H), 1.57 (d, J = 6.78 Hz, 3H), 1.52 (d, J = 7.03 Hz, 3H) |
| 412 | 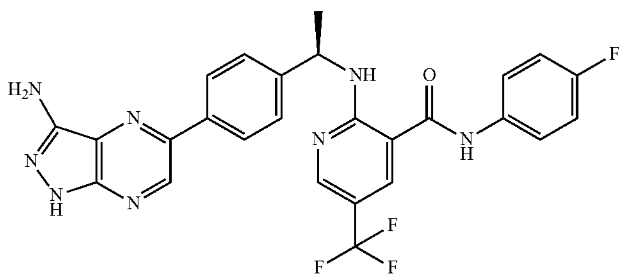 [SMILES: C[C@@H](Nc1ncc(C(F)(F)F)cc1C(=O)Nc1ccc(F)cc1)c1ccc(-c2cnc3[nH]nc(N)c3n2)cc1] | 2-{(R)-1-[4-(3-Amino-1H-pyrazolo[3,4-b]pyrazin-5-yl)-phenyl]-ethylamino}-N-(4-fluoro-phenyl)-5-trifluoromethyl-nicotinamide | 536.9 | ¹H NMR (400 MHz, DMSO-$d_6$) δ 12.40 (s, 1H), 10.52 (s, 1H), 8.94-9.03 (m, 2H), 8.51 (s, 1H), 8.44 (d, J = 2.01 Hz, 1H), 8.09 (d, J = 8.28 Hz, 2H), 7.65-7.75 (m, 2H), 7.53 (d, J = 8.28 Hz, 2H), 7.23 (t, J = 8.91 Hz, 2H), 5.71 (s, 2H), 5.42 (quin, J = 6.90 Hz, 1H), 1.57 (d, J = 6.78 Hz, 3H) |
| 413 | 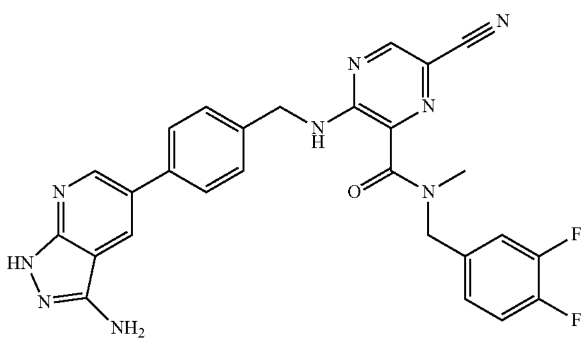 [SMILES: CN(Cc1ccc(F)c(F)c1)C(=O)c1nc(C#N)cnc1NCc1ccc(-c2cnc3[nH]nc(N)c3c2)cc1] | 3-(4-(3-amino-1H-pyrazolo[3,4-b]pyridin-5-yl)benzylamino)-6-cyano-N-(3,4-difluorobenzyl)-N-methylpyrazine-2-carboxamide | 525.9 | ¹H NMR (300 MHz, DMSO-$d_6$) (Two conformers observed) δ 12.01 (br. s., 1H), 8.62-8.69 (m, 1H), 8.61 (s, 0.48H), 8.56 (s, 0.52H), 8.47-8.55 (m, 1H), 8.37 (t, J = 2.27 Hz, 1H), 7.56-7.67 (m, 2H), 7.31-7.52 (m, 4H), 7.19-7.27 (m, 0.47H), 7.09-7.19 (m, 0.53H), 5.61 (br. s., 2H), 4.71 (d, J = 0.95H), 4.70 (s, 0.96H), 4.66 (d, 1.05H), 4.54 (s, 1.04H), 2.97 (s, 1.54H), 2.93 (s, 1.46H) |

TABLE 1-continued

| Ex. No. | Structure | Chemical Name | ESI-MS (M + H) | ¹H NMR |
|---|---|---|---|---|
| 414 | 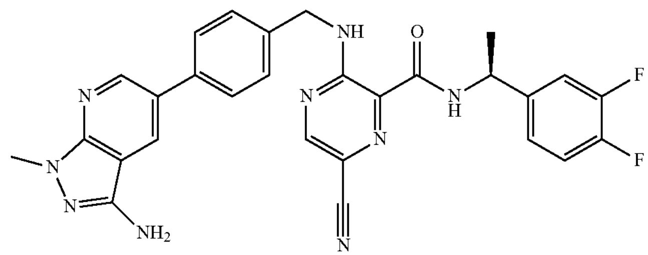 [SMILES: C[C@H](NC(=O)c1nc(C#N)cnc1NCc1ccc(-c2cnc3c(c2)c(N)nn3C)cc1)c1ccc(F)c(F)c1] | (S)-3-(4-(3-amino-1-methyl-1H-pyrazolo[3,4-b]pyridin-5-yl)benzylamino)-6-cyano-N-(1-(3,4-difluorophenyl)ethyl)pyrazine-2-carboxamide | 539.9 | ¹H NMR (400 MHz, DMSO-d₆) δ 9.76 (t, J = 5.90 Hz, 1H), 9.34 (d, J = 8.28 Hz, 1H), 8.75 (s, 1H), 8.67 (d, J = 2.26 Hz, 1H), 8.37 (d, J = 2.01 Hz, 1H), 7.56-7.65 (m, 2H), 7.52 (ddd, J = 2.01, 7.78, 12.05 Hz, 1H), 7.33-7.46 (m, 3H), 7.20-7.30 (m, 1H), 5.05-5.22 (m, 1H), 4.73 (t, J = 5.65 Hz, 2H), 3.78 (s, 3H), 1.52 (d, J = 7.28 Hz, 3H) |
| 415 | 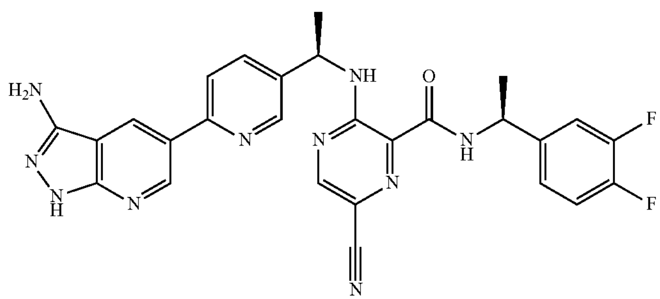 [SMILES: C[C@H](NC(=O)c1nc(C#N)cnc1N[C@H](C)c1ccc(-c2cnc3[nH]nc(N)c3c2)nc1)c1ccc(F)c(F)c1] | 3-{(R)-1-[6-(3-Amino-1H-pyrazolo[3,4-b]pyridin-5-yl)-pyridin-3-yl]-ethylamino}-6-cyano-pyrazine-2-carboxylic acid [(S)-1-(3,4-difluoro-phenyl)-ethyl]-amide | 541.9 | ¹H NMR (400 MHz, CD₃OD) δ 9.10-9.13 (m, 1H), 9.07 (d, J = 2.01 Hz, 1H), 8.85-8.87 (m, 1H), 8.74-8.76 (m, 1H), 8.52 (s, 1H), 8.11-8.15 (m, 1H), 7.98-8.02 (m, 1H), 7.34-7.41 (m, 1H), 7.22-7.27 (m, 2H), 5.40-5.48 (m, 1H), 5.17-5.26 (m, 1H), 1.71 (d, J = 6.78 Hz, 3H), 1.60 (d, J = 7.03 Hz, 3H) |
| 416 | 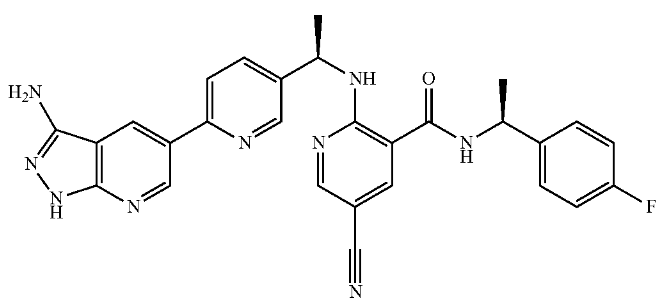 [SMILES: C[C@H](NC(=O)c1cc(C#N)cnc1N[C@H](C)c1ccc(-c2cnc3[nH]nc(N)c3c2)nc1)c1ccc(F)cc1] | 2-{(R)-1-[6-(3-Amino-1H-pyrazolo[3,4-b]pyridin-5-yl)-pyridin-3-yl]-ethylamino}-5-cyano-N-[(S)-1-(4-fluoro-phenyl)-ethyl]-nicotinamide | 522.9 | ¹H NMR (400 MHz, CD₃OD) δ 9.02-9.05 (m, 1H), 8.84-8.88 (m, 1H), 8.74-8.78 (m, 1H), 8.68-8.69 (m, 1H), 8.42 (d, J = 2.26 Hz, 1H), 8.30 (d, J = 2.01 Hz, 1H), 7.99-8.03 (m, 1H), 7.91-7.95 (m, 1H), 7.41-7.47 (m, 2H), 7.06-7.13 (m, 2H), 5.45 (q, J = 7.03 Hz, 1H), 5.18-5.27 (m, 1H), 1.64 (d, J = 7.03 Hz, 3H), 1.57 (d, J = 7.03 Hz, 3H) |

| Ex. No. | Structure | Chemical Name | ESI-MS (M + H) | $^1$H NMR |
|---|---|---|---|---|
| 417 | 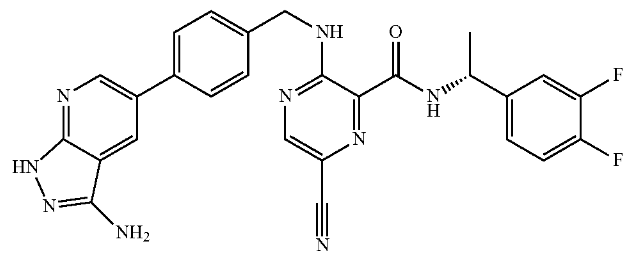 [SMILES: C[C@@H](NC(=O)c1nc(C#N)cnc1NCc1ccc(-c2cnc3[nH]nc(N)c3c2)cc1)c1ccc(F)c(F)c1] | (R)-3-(4-(3-amino-1H-pyrazolo[3,4-b]pyridin-5-yl)benzylamino)-6-cyano-N-(1-(3,4-difluorophenyl)ethyl)pyrazine-2-carboxamide | 526.0 | $^1$H NMR (400 MHz, DMSO-d$_6$) δ: 9.77 (t, 1H), 9.35 (d, 1H), 8.75 (s, 1H), 8.68 (d, 1H), 8.43 (d, 1H), 7.63 (d, 2H), 7.56-7.49 (m, 1H), 7.44 (d, 2H), 7.42-7.34 (m, 1H), 7.29-7.22 (m, 1H), 5.17-5.08 (m, 1H), 4.74 (m, 2H), 1.52 (d, 3H) |
| 418 | 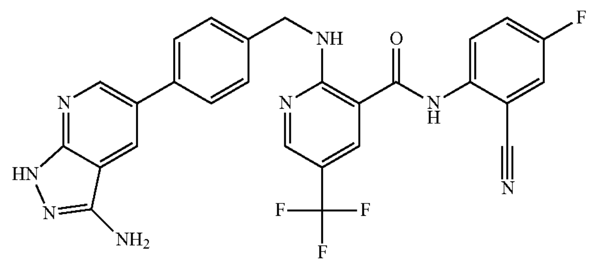 [SMILES: N#Cc1cc(F)ccc1NC(=O)c1cc(C(F)(F)F)cnc1NCc1ccc(-c2cnc3[nH]nc(N)c3c2)cc1] | 2-(4-(3-amino-1H-pyrazolo[3,4-b]pyridin-5-yl)benzylamino)-N-(2-cyano-4-fluorophenyl)-5-(trifluoromethyl)nicotinamide | 547.9 | $^1$H NMR (400 MHz, CD$_3$OD) δ: 8.66 (d, 1H), 8.49 (s, 1H), 8.43 (d, 1H), 8.37 (d, 1H), 7.73-7.69 (m, 1H), 7.63-7.58 (m, 3H), 7.51-7.49 (m, 3H), 4.84 (s, 2H) |
| 419 | 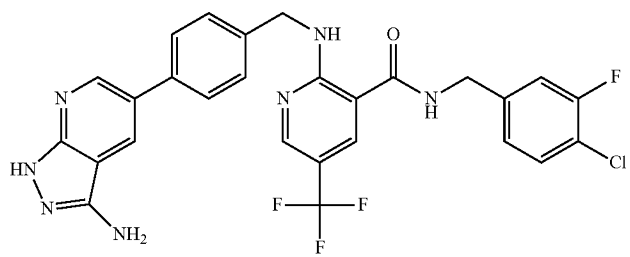 [SMILES: Nc1n[nH]c2ncc(-c3ccc(CNc4ncc(C(F)(F)F)cc4C(=O)NCc4ccc(Cl)c(F)c4)cc3)cc12] | 2-(4-(3-amino-1H-pyrazolo[3,4-b]pyridin-5-yl)benzylamino)-N-(4-chloro-3-fluorobenzyl)-5-(trifluoromethyl)nicotinamide | 570.0 | $^1$H NMR (400 MHz, CD$_3$OD) δ: 8.60 (d, 1H), 8.39 (d, 1H), 8.32 (d, 1H), 8.16 (d, 1H), 7.56 (d, 2H), 7.42-7.30 (m, 3H), 7.19 (dd, 1H), 7.12 (dd, 1H), 4.74 (s, 2H), 4.47 (s, 2H) |

TABLE 1-continued

| Ex. No. | Structure | Chemical Name | ESI-MS (M + H) | $^1$H NMR |
|---|---|---|---|---|
| 420 | 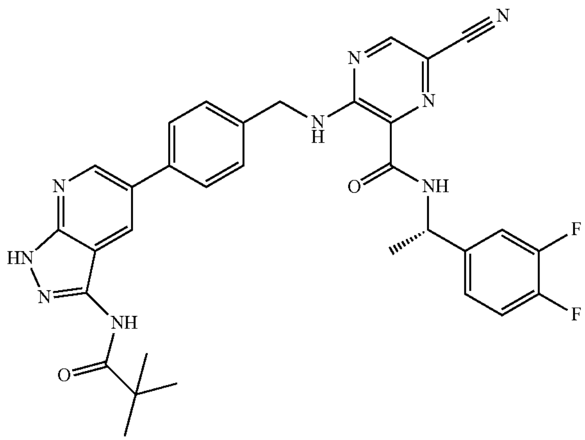 [SMILES: C[C@H](NC(=O)c1nc(C#N)cnc1NCc1ccc(-c2cnc3[nH]nc(NC(=O)C(C)(C)C)c3c2)cc1)c1ccc(F)c(F)c1] | (S)-6-cyano-N-(1-(3,4-difluorophenyl)ethyl)-3-(4-(3-pivalamido-1H-pyrazolo[3,4-b]pyridin-5-yl)benzylamino)pyrazine-2-carboxamide | 609.9 | $^1$H NMR (300 MHz, DMSO-d$_6$) δ 13.31 (br. s., 1H), 10.08 (br. s., 1H), 9.76 (br. t, J = 5.90 Hz, 1H), 9.31 (br. d, J = 8.30 Hz, 1H), 8.75 (d, J = 1.89 Hz, 1H), 8.73 (s, 1H), 8.32 (d, J = 2.27 Hz, 1H), 7.63 (d, J = 8.31 Hz, 2H), 7.45 (d, J = 8.31 Hz, 2H), 7.42-7.57 (m, 1H), 7.37 (td, J = 8.50, 10.58 Hz, 1H), 7.20-7.30 (m, 1H), 5.12 (quin, J = 7.27 Hz, 1H), 4.65-4.83 (m, 2H), 1.51 (d, J = 6.80 Hz, 3H), 1.28 (s, 9H) |
| 421 | 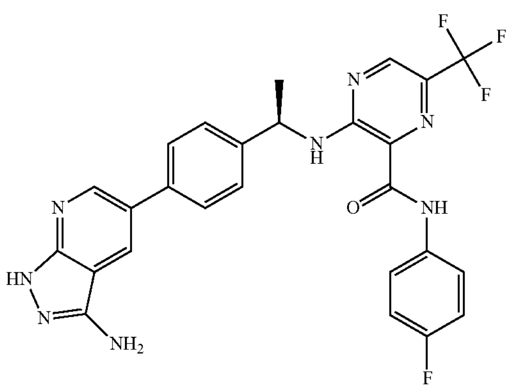 [SMILES: C[C@@H](Nc1ncc(C(F)(F)F)nc1C(=O)Nc1ccc(F)cc1)c1ccc(-c2cnc3[nH]nc(N)c3c2)cc1] | (R)-3-(1-(4-(3-amino-1H-pyrazolo[3,4-b]pyridin-5-yl)phenyl)ethylamino)-N-(4-fluorophenyl)-6-(trifluoromethyl)pyrazine-2-carboxamide | 536.9 | $^1$H NMR (300 MHz, DMSO-d$_6$) δ 10.51 (s, 1H), 9.42 (d, J = 7.55 Hz, 1H), 8.67-8.77 (m, 2H), 8.46 (d, J = 1.89 Hz, 1H), 7.73-7.84 (m, 2H), 7.66 (d, J = 8.31 Hz, 2H), 7.54 (d, J = 8.31 Hz, 2H), 7.17-7.29 (m, 2H), 5.37 (quin, J = 6.89 Hz, 1H), 1.61 (d, J = 6.80 Hz, 3H) |

TABLE 1-continued

| Ex. No. | Structure | Chemical Name | ESI-MS (M + H) | ¹H NMR |
|---|---|---|---|---|
| 422 | 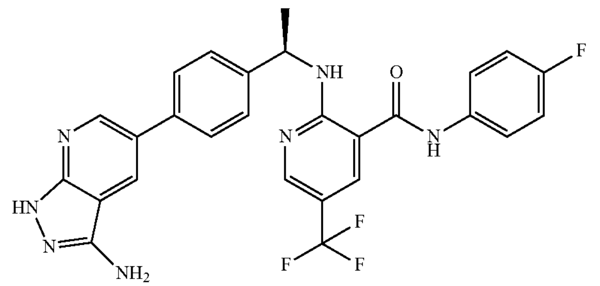 [SMILES: C[C@@H](Nc1ncc(C(F)(F)F)cc1C(=O)Nc1ccc(F)cc1)c1ccc(-c2cnc3[nH]nc(N)c3c2)cc1] | 2-[(R)-1-[4-(3-Amino-1H-pyrazolo[3,4-b]pyridin-5-yl)-phenyl]-ethylamino]-N-(4-fluoro-phenyl)-5-trifluoromethyl-nicotinamide | 536.3 | ¹H NMR (400 MHz, CD₃OD) δ 10.27 (br. s., 1H), 8.75 (d, J = 2.01 Hz, 1H), 8.51-8.54 (m, 1H), 8.41-8.43 (m, 1H), 8.33-8.36 (m, 1H), 7.63-7.72 (m, 4H), 7.55 (d, J = 8.03 Hz, 2H), 7.09-7.17 (m, 2H), 5.43-5.51 (m, 1H), 1.64 (d, J = 7.03 Hz, 3H) |
| 423 | 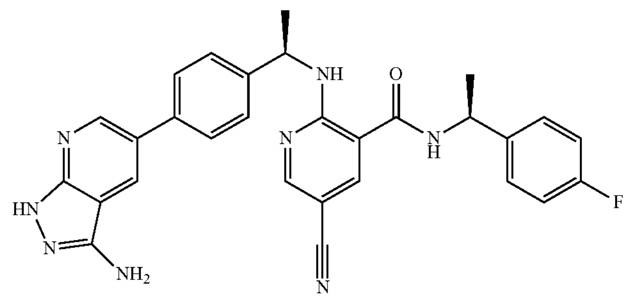 [SMILES: C[C@H](NC(=O)c1cc(C#N)cnc1N[C@H](C)c1ccc(-c2cnc3[nH]nc(N)c3c2)cc1)c1ccc(F)cc1] | 2-[(R)-1-[4-(3-Amino-1H-pyrazolo[3,4-b]pyridin-5-yl)-phenyl]-ethylamino]-5-cyano-N-[(S)-1-(4-fluoro-phenyl)-ethyl]-nicotinamide | 521.4 | ¹H NMR (400 MHz, CD₃OD) δ 8.81-8.86 (m, 1H), 8.77 (d, J = 2.26 Hz, 1H), 8.57 (d, J = 2.01 Hz, 1H), 8.42 (d, J = 2.26 Hz, 1H), 8.28 (d, J = 2.01 Hz, 1H), 7.63-7.67 (m, 2H), 7.49-7.53 (m, 2H), 7.40-7.46 (m, 2H), 7.06-7.12 (m, 2H), 5.39-5.45 (m, 1H), 5.16-5.25 (m, 1H), 1.54-1.60 (m, 6H) |
| 424 | 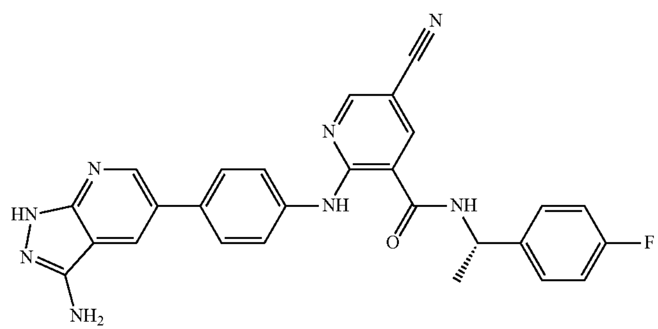 [SMILES: C[C@H](NC(=O)c1cc(C#N)cnc1Nc1ccc(-c2cnc3[nH]nc(N)c3c2)cc1)c1ccc(F)cc1] | (S)-2-(4-(3-amino-1H-pyrazolo[3,4-b]pyridin-5-yl)phenylamino)-5-cyano-N-(1-(4-fluorophenyl)ethyl)nicotinamide | 493.0 | ¹H NMR (400 MHz, DMSO-d₆) δ: 11.99 (s, 1H), 11.32 (s, 1H), 9.23 (d, 1H), 8.74 (d, 1H), 8.67 (s, 1H), 8.40 (s, 1H), 7.78-7.76 (m, 2H), 7.67-7.65 (m, 2H), 7.49-7.46 (m, 2H), 7.19-7.15 (m, 2H), 5.22-5.14 (m, 1H), 1.51 (d, 3H) |

TABLE 1-continued

| Ex. No. | Structure | Chemical Name | ESI-MS (M + H) | $^1$H NMR |
|---|---|---|---|---|
| 425 | 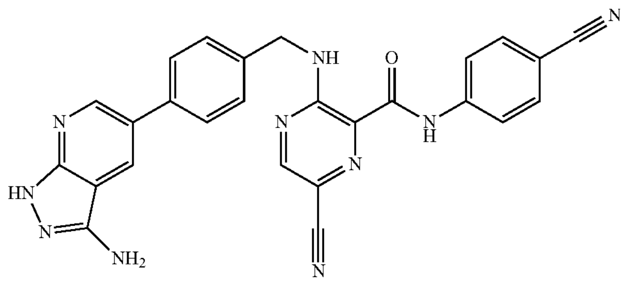 [SMILES: N#Cc1ccc(NC(=O)c2nc(C#N)cnc2NCc2ccc(-c3cnc4[nH]nc(N)c4c3)cc2)cc1] | 3-(4-(3-amino-1H-pyrazolo[3,4-b]pyridin-5-yl)benzylamino)-N-(4-cyanophenyl)pyrazine-2-carboxamide | 487.0 | $^1$H NMR (400 MHz, DMSO-d$_6$) δ: 11.02 (s, 1H), 9.61 (t, 1H), 8.82 (s, 1H), 8.68 (d, 1H), 8.43 (d, 1H), 8.07 (d, 2H), 7.85 (d, 2H), 7.65 (d, 2H), 7.49 (d, 2H), 4.81 (d, 2H) |
| 426 | 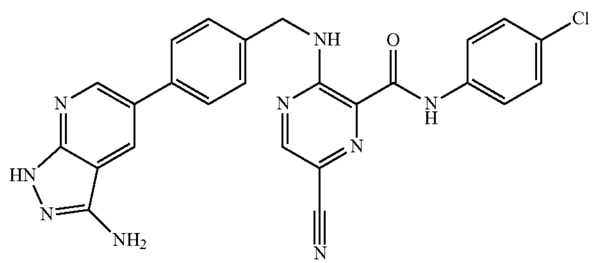 [SMILES: N#Cc1cnc(NCc2ccc(-c3cnc4[nH]nc(N)c4c3)cc2)c(C(=O)Nc2ccc(Cl)cc2)n1] | 3-(4-(3-amino-1H-pyrazolo[3,4-b]pyridin-5-yl)benzylamino)-N-(4-chlorophenyl)-6-cyanopyrazine-2-carboxamide | 495.9 | $^1$H NMR (400 MHz, CDCl$_3$/CD$_3$OD) δ: 9.75-9.63 (m, 2H), 8.57 (s, 1H), 8.49 (s, 1H), 8.11 (d, 1H), 7.58 (d, 2H), 7.51 (d, 2H), 7.41 (d, 2H), 7.29 (d, 2H), 4.77 (d, 2H) |
| 427 | 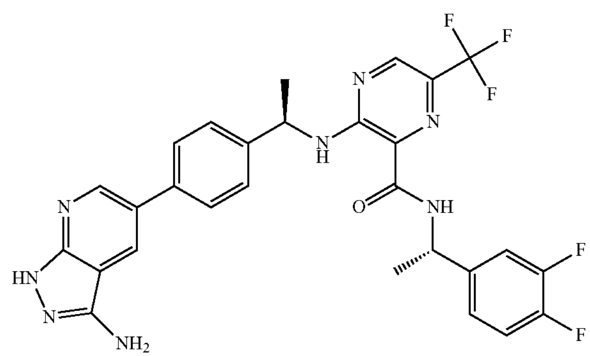 [SMILES: C[C@H](NC(=O)c1nc(C(F)(F)F)cnc1N[C@H](C)c1ccc(-c2cnc3[nH]nc(N)c3c2)cc1)c1ccc(F)c(F)c1] | 3-((R)-1-(4-(3-amino-1H-pyrazolo[3,4-b]pyridin-5-yl)phenyl)ethylamino)-N-((S)-1-(3,4-difluorophenyl)ethyl)-6-(trifluoromethyl)pyrazine-2-carboxamide | 583.9 | $^1$H NMR (400 MHz, DMSO-d$_6$) δ 12.01 (br. s, 1H), 9.58 (d, J = 7.53 Hz, 1H), 9.08 (d, J = 8.03 Hz, 1H), 8.67 (s, 1H), 8.64 (d, J = 2.26 Hz, 1H), 8.37 (d, J = 2.01 Hz, 1H), 7.64 (d, J = 8.28 Hz, 2H), 7.54 (ddd, J = 2.01, 8.03, 12.05 Hz, 1H), 7.49 (d, J = 8.28 Hz, 2H), 7.40 (td, J = 8.47, 10.67 Hz, 1H), 7.24-7.32 (m, 1H), 5.62 (br. s, 2H), 5.31 (quin, J = 6.96 Hz, 1H), 5.17 (quin, J = 7.22 Hz, 1H), 1.56 (d, J = 7.30 Hz, 3H), 1.54 (d, J = 7.30 Hz, 3H) |

| Ex. No. | Structure | Chemical Name | ESI-MS (M + H) | ¹H NMR |
|---|---|---|---|---|
| 428 | 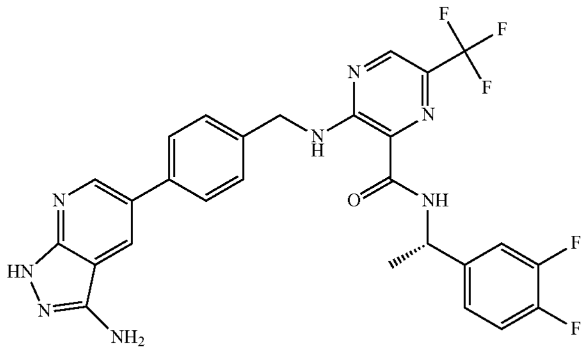 [SMILES: C[C@H](NC(=O)c1nc(C(F)(F)F)cnc1NCc1ccc(-c2cnc3[nH]nc(N)c3c2)cc1)c1ccc(F)c(F)c1] | (S)-3-(4-(3-amino-1H-pyrazolo[3,4-b]pyridin-5-yl)benzylamino)-N-(1-(3,4-difluorophenyl)ethyl)-6-(trifluoromethyl)pyrazine-2-carboxamide | 569.9 | ¹H NMR (400 MHz, DMSO-$d_6$) δ 12.01 (br. s, 1H), 9.53 (t, J = 5.90 Hz, 1H), 9.04 (d, J = 8.28 Hz, 1H), 8.70 (s, 1H), 8.63 (d, J = 2.26 Hz, 1H), 8.37 (d, J = 2.01 Hz, 1H), 7.62 (d, J = 8.03 Hz, 2H), 7.52 (ddd, J = 1.88, 7.97, 11.98 Hz, 1H), 7.44 (d, J = 8.28 Hz, 2H), 7.38 (td, J = 8.47, 10.67 Hz, 1H), 7.21-7.30 (m, 1H), 5.61 (br. s, 2H), 5.14 (quin, J = 7.28 Hz, 1H), 4.66-4.81 (m, 2H), 1.54 (d, J = 7.28 Hz, 3H) |
| 429 | 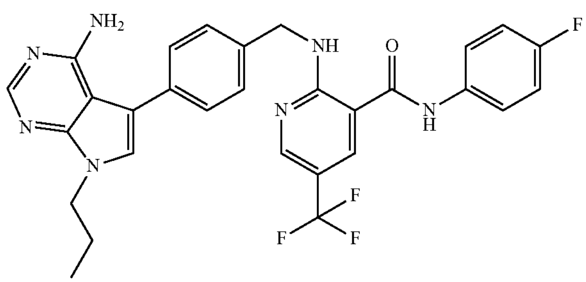 [SMILES: CCCn1cc(-c2ccc(CNc3ncc(C(F)(F)F)cc3C(=O)Nc3ccc(F)cc3)cc2)c2c(N)ncnc21] | 2-(4-(4-amino-7-propyl-7H-pyrrolo[2,3-d]pyrimidin-5-yl)benzylamino)-N-(4-fluorophenyl)-5-(trifluoromethyl)nicotinamide | 564.2 | ¹H NMR (300 MHz, DMSO-$d_6$) δ 10.43 (s, 1H), 8.85 (t, J = 5.85 Hz, 1H), 8.49 (d, J = 1.13 Hz, 1H), 8.33 (d, J = 2.27 Hz, 1H), 8.07 (s, 1H), 7.57-7.68 (m, 2H), 7.30-7.42 (m, 4H), 7.26 (s, 1H), 7.09-7.21 (m, 2H), 5.99 (br. s., 1H), 4.70 (d, J = 6.04 Hz, 2H), 4.05 (t, J = 7.18 Hz, 2H), 1.73 (sxt, J = 7.25 Hz, 2H), 0.78 (t, J = 7.37 Hz, 3H) |
| 430 | 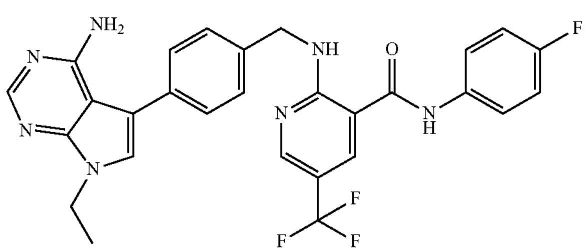 [SMILES: CCn1cc(-c2ccc(CNc3ncc(C(F)(F)F)cc3C(=O)Nc3ccc(F)cc3)cc2)c2c(N)ncnc21] | 2-(4-(4-amino-7-ethyl-7H-pyrrolo[2,3-d]pyrimidin-5-yl)benzylamino)-N-(4-fluorophenyl)-5-(trifluoromethyl)nicotinamide | 550.2 | ¹H NMR (300 MHz, DMSO-$d_6$) δ 10.50 (s, 1H), 8.91 (t, J = 5.85 Hz, 1H), 8.56 (s, 1H), 8.39 (d, J = 1.89 Hz, 1H), 8.12-8.16 (m, 1H), 7.64-7.75 (m, 2H), 7.43 (s, 4H), 7.35 (s, 1H), 7.16-7.26 (m, 2H), 6.03 (br. s., 1H), 4.77 (d, J = 5.67 Hz, 2H), 4.19 (q, J = 7.18 Hz, 2H), 1.37 (t, J = 7.18 Hz, 3H) |

TABLE 1-continued

| Ex. No. | Structure | Chemical Name | ESI-MS (M + H) | ¹H NMR |
|---|---|---|---|---|
| 431 | 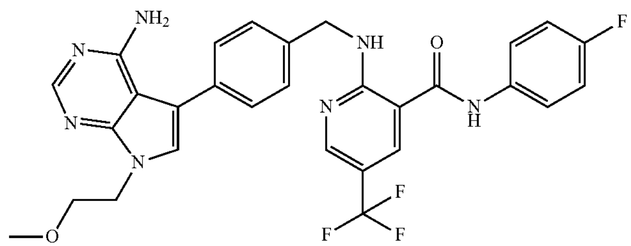 [SMILES: COCCn1cc(-c2ccc(CNc3ncc(C(F)(F)F)cc3C(=O)Nc3ccc(F)cc3)cc2)c2c(N)ncnc21] | 2-(4-(4-amino-7-(2-methoxy-ethyl-7H-pyrrolo[2,3-d]pyrimidin-5-yl)benzylamino)-N-(4-fluorophenyl)-5-(trifluoromethyl)nicotinamide | 580.2 | ¹H NMR (300 MHz, DMSO-d₆) δ 10.51 (s, 1H), 8.92 (t, J = 5.85 Hz, 1H), 8.56 (d, J = 1.51 Hz, 1H), 8.40 (d, J = 2.27 Hz, 1H), 8.10-8.17 (m, 1H), 7.65-7.76 (m, 2H), 7.38-7.51 (m, 4H), 7.28-7.35 (m, 1H), 7.15-7.27 (m, 2H), 6.12 (br. s, 1H), 4.78 (d, J = 5.67 Hz, 2H), 4.32 (t, J = 5.29 Hz, 2H), 3.70 (t, J = 5.48 Hz, 2H), 3.24 (s, 3H) |
| 432 | 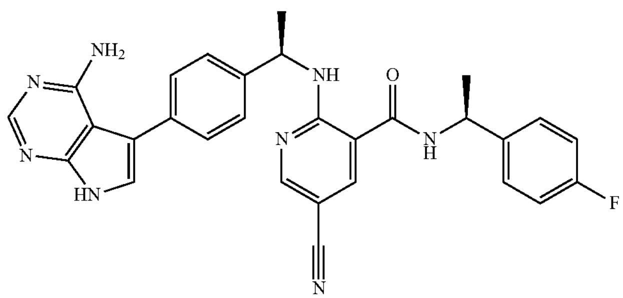 [SMILES: C[C@H](NC(=O)c1cc(C#N)cnc1N[C@H](C)c1ccc(-c2c[nH]c3ncnc(N)c23)cc1)c1ccc(F)cc1] | 2-{(R)-1-[4-(4-Amino-7H-pyrrolo[2,3-d]pyrimidin-5-yl)-phenyl]-ethylamino}-5-cyano-N-(S)(1-(4-fluoro-phenyl)-ethyl]-nicotinamide | 521.8 | ¹H NMR (400 MHz, DMSO-d₆) δ 12.85 (br. s., 1H), 9.45 (d, J = 7.78 Hz, 1H), 8.95 (d, J = 7.53 Hz, 1H), 8.49-8.51 (m, 1H), 8.47-8.49 (m, 1H), 8.33 (s, 1H), 7.50 (d, J = 2.51 Hz, 1H), 7.40 (s, 4H), 7.35-7.39 (m, 2H), 7.10 (t, J = 8.91 Hz, 2H), 5.31-5.40 (m, 1H), 5.00-5.09 (m, 1H), 1.44 (d, J = 7.03 Hz, 3H), 1.39 (d, J = 7.03 Hz, 3H) |
| 433 | 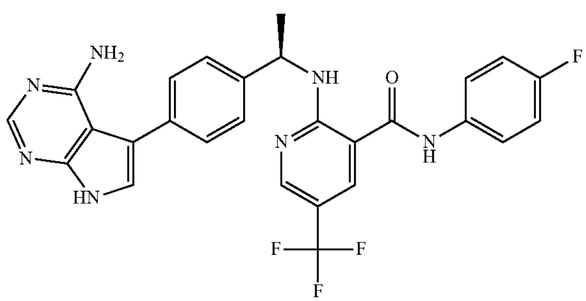 [SMILES: C[C@@H](Nc1ncc(C(F)(F)F)cc1C(=O)Nc1ccc(F)cc1)c1ccc(-c2c[nH]c3ncnc(N)c23)cc1] | 2-{(R)-1-[4-(4-Amino-7H-pyrrolo[2,3-d]pyrimidin-5-yl)-phenyl]-ethylamino}-N-(4-fluoro-phenyl)-5-trifluoromethyl-nicotinamide | 536.7 | ¹H NMR (400 MHz, DMSO-d₆) δ 12.85 (br. s., 1H), 10.47 (s, 1H), 8.95 (d, J = 7.78 Hz, 1H), 8.47 (dd, J = 0.75, 2.26 Hz, 1H), 8.38 (d, J = 2.26 Hz, 1H), 8.34 (s, 1H), 7.59-7.64 (m, 2H), 7.50 (d, J = 2.51 Hz, 1H), 7.43-7.47 (m, 2H), 7.38-7.42 (m, 2H), 7.12-7.20 (m, 2H), 5.42 (quin, J = 7.09 Hz, 1H), 1.50 (d, J = 7.03 Hz, 3H) |

TABLE 1-continued

| Ex. No. | Structure | Chemical Name | ESI-MS (M + H) | $^1$H NMR |
|---|---|---|---|---|
| 434 | 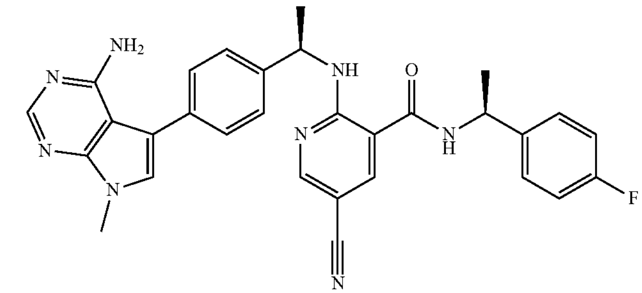 [SMILES: C[C@H](NC(=O)c1cc(C#N)cnc1N[C@H](C)c1ccc(-c2cn(C)c3ncnc(N)c23)cc1)c1ccc(F)cc1] | 2-{(R)-1-[4-(4-Amino-7-methyl-7H-pyrrolo[2,3-d]pyrimidin-5-yl)-phenyl]-ethylamino}-5-cyano-N-[(S)-1-(4-fluoro-phenyl)-ethyl]-nicotinamide | 535.8 | $^1$H NMR (400 MHz, DMSO-d$_6$) δ 9.45 (d, J = 7.78 Hz, 1H), 8.95 (d, J = 7.53 Hz, 1H), 8.47-8.51 (m, 2H), 8.34 (s, 1H), 7.49 (s, 1H), 7.34-7.43 (m, 7H), 7.06-7.14 (m, 2H), 5.31-5.39 (m, 1H), 5.01-5.09 (m, 1H), 3.75 (s, 3H), 1.44 (d, J = 7.03 Hz, 3H), 1.39 (d, J = 7.03 Hz, 3H) |
| 435 | 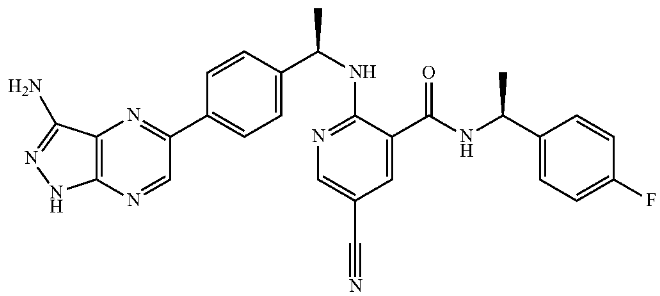 [SMILES: C[C@H](NC(=O)c1cc(C#N)cnc1N[C@H](C)c1ccc(-c2cnc3[nH]nc(N)c3n2)cc1)c1ccc(F)cc1] | 2-{(R)-1-[4-(3-Amino-1H-pyrazolo[3,4-b]pyrazin-5-yl)-phenyl]-ethylamino}-5-cyano-N-[(S)-1-(4-fluoro-phenyl)-ethyl]-nicotinamide | 522.3 | $^1$H NMR (400 MHz, DMSO-d$_6$) δ 9.51 (d, J = 7.53 Hz, 1H), 9.01 (d, J = 7.53 Hz, 1H), 8.99 (s, 1H), 8.54 (d, J = 1.76 Hz, 2H), 8.08 (d, J = 8.28 Hz, 2H), 7.48 (d, J = 8.28 Hz, 2H), 7.44 (dd, J = 5.65, 8.41 Hz, 2H), 7.17 (t, J = 8.91 Hz, 2H), 5.36 (quin, J = 6.84 Hz, 1H), 5.13 (quin, J = 7.03 Hz, 1H), 1.51 (d, J = 6.78 Hz, 3H), 1.47 (d, J = 7.03 Hz, 3H) |
| 436 | 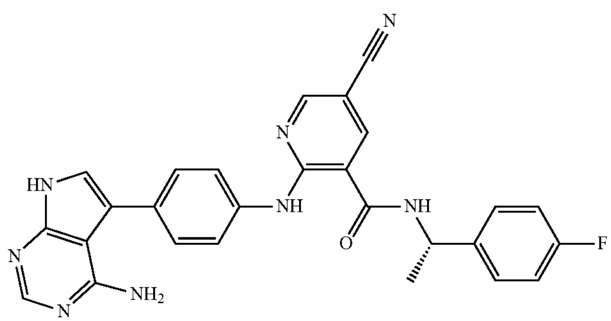 [SMILES: C[C@H](NC(=O)c1cc(C#N)cnc1Nc1ccc(-c2c[nH]c3ncnc(N)c23)cc1)c1ccc(F)cc1] | (S)-2-(4-(4-amino-7H-pyrrolo[2,3-d]pyrimidin-5-yl)phenylamino)-5-cyano-N-(1-(4-fluorophenyl)ethyl)nicotinamide | 493.0 | $^1$H NMR (400 MHz, DMSO-d$_6$) δ: 11.77 (s, 1H), 11.30 (s, 1H), 9.21 (d, 1H), 8.73 (d, 1H), 8.67 (d, 1H), 8.10 (s, 1H), 7.74 (d, 2H), 7.49-7.42 (m, 4H), 7.22-7.15 (m, 3H), 6.00 (br, 2H), 5.20-5.17 (m, 1H), 5.50 (d, 3H) |

TABLE 1-continued

| Ex. No. | Structure | Chemical Name | ESI-MS (M + H) | 1H NMR |
|---|---|---|---|---|
| 437 | 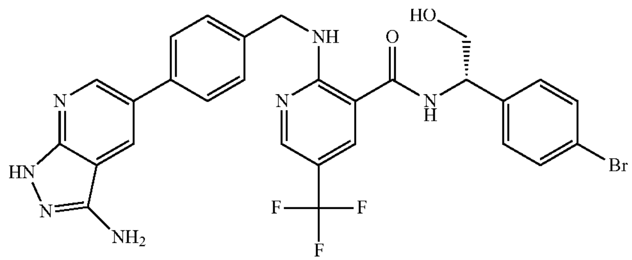 [SMILES: Nc1n[nH]c2ncc(-c3ccc(CNc4ncc(C(F)(F)F)cc4C(=O)N[C@H](CO)c4ccc(Br)cc4)cc3)cc12] | (S)-2-(4-(3-amino-1H-pyrazolo[3,4-b]pyridin-5-yl)benzylamino)-N-(1-(4-bromophenyl)-2-hydroxyethyl)-5-(trifluoromethyl)nicotinamide | 625.8 | 1H NMR (400 MHz, CD3OD) δ: 8.65 (d, 1H), 8.43 (d, 1H), 8.37 (d, 1H), 8.33 (d, 1H), 7.60 (d, 2H), 7.50 (d, 2H), 7.44 (d, 2H), 7.33 (d, 2H), 5.13 (t, 1H), 4.76 (s, 2H), 3.86-3.84 (m, 2H) |
| 438 | 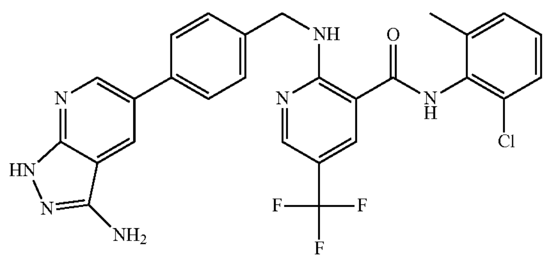 [SMILES: Cc1cccc(Cl)c1NC(=O)c1cc(C(F)(F)F)cnc1NCc1ccc(-c2cnc3[nH]nc(N)c3c2)cc1] | 2-(4-(3-amino-1H-pyrazolo[3,4-b]pyridin-5-yl)benzylamino)-N-(2-chloro-6-methylphenyl)-5-(trifluoromethyl)nicotinamide | 551.9 | 1H NMR (400 MHz, CD3OD) δ 8.65 (d, 1H), 8.52 (s, 1H), 8.47 (s, 1H), 8.37 (d, 1H), 7.62 (d, 2H), 7.47 (d, 2H), 7.38-7.36 (m, 1H), 7.29-7.21 (m, 2H), 4.82 (s, 2H), 2.32 (s, 3H) |
| 439 | 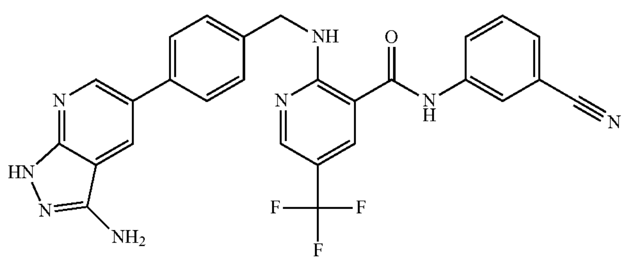 [SMILES: N#Cc1cccc(NC(=O)c2cc(C(F)(F)F)cnc2NCc2ccc(-c3cnc4[nH]nc(N)c4c3)cc2)c1] | 2-(4-(3-amino-1H-pyrazolo[3,4-b]pyridin-5-yl)benzylamino)-N-(3-cyanophenyl)-5-(trifluoromethyl)nicotinamide | 528.9 | 1H NMR (400 MHz, CD3OD) δ 8.67 (d, 1H), 8.50 (s, 1H), 8.40-8.38 (m, 2H), 8.18 (s, 1H), 7.97-7.95 (m, 1H), 7.05 (d, 2H), 7.55-7.50 (m, 4H), 4.62 (s, 2H) |
| 440 | 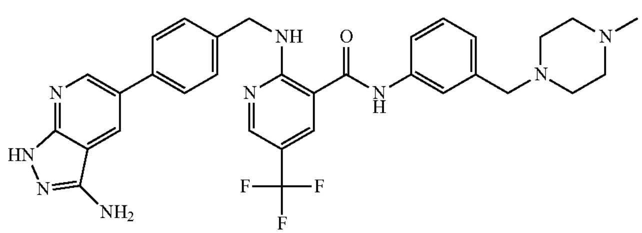 [SMILES: CN1CCN(Cc2cccc(NC(=O)c3cc(C(F)(F)F)cnc3NCc3ccc(-c4cnc5[nH]nc(N)c5c4)cc3)c2)CC1] | 2-(4-(3-amino-1H-pyrazolo[3,4-b]pyridin-5-yl)benzylamino)-N-(3-((4-methylpiperazin-1-yl)methyl)phenyl)-5-(trifluoromethyl)nicotinamide | 616.0 | 1H NMR (400 MHz, CD3OD) δ: 8.62 (d, 1H), 8.39 (d, 2H), 8.23 (d, 1H), 7.70 (s, 1H), 7.55 (d, 2H), 7.47-7.39 (m, 3H), 7.26 (t, 1H), 7.07 (d, 1H), 4.74 (s, 2H), 3.64 (s, 2H), 3.20-3.03 (m, 4H), 2.81-2.65 (m, 7H) |

TABLE 1-continued

| Ex. No. | Structure | Chemical Name | ESI-MS (M + H) | ¹H NMR |
|---|---|---|---|---|
| 441 | 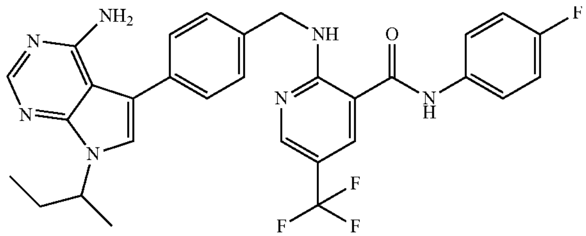 [SMILES: CCC(C)n1cc(-c2ccc(CNc3ncc(C(F)(F)F)cc3C(=O)Nc3ccc(F)cc3)cc2)c2c(N)ncnc21] | 2-(4-(4-amino-7-sec-butyl-7H-pyrrolo[2,3-d]pyrimidin-5-yl)benzylamino)-5-(4-fluorophenyl)-N-(trifluoromethyl)nicotinamide | 577.9 | ¹H NMR (300 MHz, DMSO-d₆) δ 10.43 (s, 1H), 8.85 (t, J = 5.48 Hz, 1H), 8.49 (s, 1H), 8.33 (s, 1H), 8.05 (s, 1H), 7.63 (dd, J = 5.10, 8.88 Hz, 2H), 7.24-7.49 (m, 5H), 7.14 (t, J = 8.88 Hz, 2H), 5.95 (br. s., 1H), 4.53-4.86 (m, 3H), 1.66-1.87 (m, 2H), 1.36 (d, J = 6.80 Hz, 3H), 0.65 (t, J = 7.37 Hz, 3H) |
| 442 | 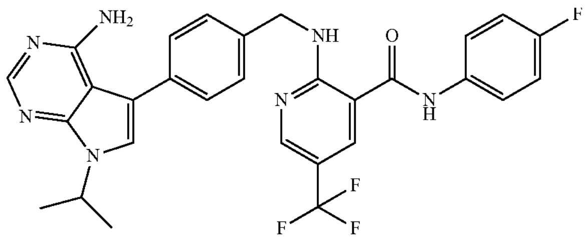 [SMILES: CC(C)n1cc(-c2ccc(CNc3ncc(C(F)(F)F)cc3C(=O)Nc3ccc(F)cc3)cc2)c2c(N)ncnc21] | 2-(4-(4-amino-7-isopropyl-7H-pyrrolo[2,3-d]pyrimidin-5-yl)benzylamino)-5-(4-fluorophenyl)-N-(trifluoromethyl)nicotinamide | 563.9 | ¹H NMR (300 MHz, DMSO-d₆) δ 10.44 (s, 1H), 8.86 (t, J = 5.48 Hz, 1H), 8.49 (s, 1H), 8.30-8.38 (m, 2H), 7.57-7.71 (m, 3H), 7.34-7.48 (m, 5H), 7.15 (t, J = 8.69 Hz, 2H), 4.95 (quin, J = 6.70 Hz, 1H), 4.72 (d, J = 5.67 Hz, 2H), 1.42 (d, J = 6.80 Hz, 6H) |
| 443 | 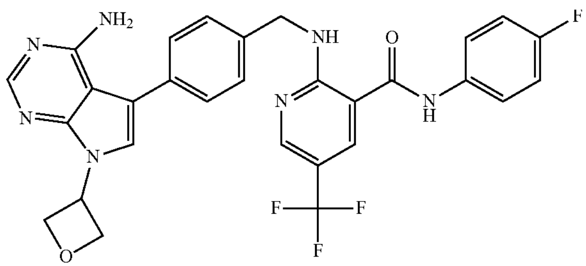 [SMILES: Nc1ncnc2c1c(-c1ccc(CNc3ncc(C(F)(F)F)cc3C(=O)Nc3ccc(F)cc3)cc1)cn2C1COC1] | 2-(4-(4-amino-7-(oxetan-3-yl)-7H-pyrrolo[2,3-d]pyrimidin-5-yl)benzylamino)-5-(4-fluorophenyl)-N-(trifluoromethyl)nicotinamide | 577.9 | ¹H NMR (300 MHz, DMSO-d₆) δ 10.51 (br. s., 1H), 8.93 (br. s., 1H), 8.57 (br. s., 1H), 8.40 (br. s., 1H), 8.15 (s, 1H), 7.71 (br. s., 3H), 7.39-7.62 (m, 5H), 7.22 (t, J = 8.50 Hz, 2H), 6.12 (br. s., 1H), 5.87 (t, J = 6.99 Hz, 1H), 4.86-5.13 (m, 4H), 4.78 (d, J = 4.91 Hz, 2H) |

Example 444

A PDK1 kinase assay was performed as follows. PDK1 (amino acids 51-359) and AKT2 (amino acids 140-467 fused to PIFtide, amino acids EEQEMFRDFDYIADW) were expressed as N-terminally tagged GST fusion proteins in insect cells and purified to homogeneity. Enzyme activity was determined in a coupled PDK1/AKT/FAM-crosstide assay and phosphorylation of FAM-crosstide was determined by standard IMAP protocol (Molecular Devices). For inhibition studies, compounds were titrated 4-fold in DMSO and diluted 40-fold into assay buffer (10 mM Tris HCl pH7.2; 10 mM $MgCl_2$; 0.01% Triton X-100; 1 mM DTT) containing PDK1, AKT2, and FAM-crosstide (final concentrations: 0.75 nM PDK1, 10 nM unphosphorylated AKT2, and 100 nM crosstide substrate). The kinase reaction was initiated by adding ATP to a final concentration of 40 μM of PDK1 and incubated at 25° C. for 30 min. To detect assay product, the kinase reaction was combined with Progressive Binding Solution (1:600 Progressive Binding Reagent, 50% Buffer A, 50% Buffer B, Molecular Devices) in a 1:3 ratio. The mixture was incubated for 2 hours at 25° C. and the plate was scanned on an Analyst AD with excitation at 485 nm and emission at 530 nm. The fluorescence polarization value "P" is defined by the equation below. The value "mP" is generated by multiplying the P value for each reaction well by a factor of 1000. The value "ΔmP" for each well is the mP value for that well minus the mP value for the average negative control.

$$P=(F\text{par}-F\text{perp})/(F\text{par}+F\text{perp}) \quad \text{Eq.:}$$

Where "par" is fluorescence intensity parallel to the excitation plane; and "perp" is fluorescence intensity perpendicular to the excitation plane. ΔmP values were plotted as a function of compound concentration and the data were analyzed with a 4-parameter fit using GraphPad Prism software.

Results of the in vitro tests are presented in Table 2.

Example 445

Determination of $EC_{50}$s for the inhibition of phospho-akt (Thr308) was accomplished by treating PC-3 cells with subject inhibitors for 2 hours in no serum then using the Meso Scale Discovery (MSD) phospho-akt 308 ELISA kit to detect p-akt (Thr308) levels.

PC-3 cells were harvested by trypsin and counted. Cells were plated in coated 96-well flat bottom plates (plate 15,000 cells/well in 100 ul growth media (10% FBS, 1× pen-strep) an place in an incubator overnight.

Subject inhibitors were stocked at 50 mM, then diluted to 30 mM (4.8 μl cpd plus 1.6 ul DMSO) in 100% DMSO. Three-fold dilutions were performed from 30 mM stock. (4 μl into 8 ul 100% DMSO). Aliquots of 1.0 μl of inhibitor solution were transferred into SF Medium (using deep well block).

Control wells were prepared as follows. For DMSO high controls, 1.0 μl of 100% DMSO was added into 1.0 ml SF. For low controls for PC-3 cells, 5 μM of Wortmannin (10 μl of 1 mM Wortmannin stock was added into 2 ml SF Medium. The supernatant media was removed and the plate was blotted. 100 μl of controls/media or compound/media were added to cells and placed in incubator for 2 hours. The supernatant media was removed and the plate was blotted. 55 μl of the MSD complete lysis buffer was added (10 mls Tris Lysis buffer, 200 ul protease inhibitor, 100 ul phosphatase inhibitor 1, and 100 ul phosphatase inhibitor II). The plate was placed on a plate shaker for 60 mins at 4 deg.

MSD plates were blocked for 1 hour by adding 150 μl of Blocking Solution (3% BSA) to each well. The MSD plates were washed 4× with TBST, and 50 μl lysates were transferred to MSD plate and place on plate shaker shake at 4 degrees O/N, light shaking (speed 3.5). The plate was washed 4× with TBST.

For detection, the following detection antibody solution was used: 1 ml Blocking Solution (3% BSA stock, 1% BSA final); 2 mls TBST; and 91 μl of stock (0.33 uM) detection antibody (final concentration 10 nM). 25 μl of Ab detection solution was added to each well. The plate was sealed and incubated 1 hr RT, light shaking (speed 3.5). The plate was washed 4 times with TBST. 150 μl of Read Buffer was added (5 mls 4×MSD Read Buffer+15 mls water). Finally the plate was read immediately on the MSD plate reader.

Materials: PC-3 (cultured in F12K media—Invitrogen cat#21127-030 plus 10% FBS and 1× pen-strep); Mesoscale Discovery phospho-akt (Thr 308) kit—cat#K151DYD-1 (includes MSD plate, Tris Wash Buffer, Blocking Solution A, Read buffer, Tris Lysis Buffer, protease inhibitor, phosphatase inhibitor I, phosphatase inhibitor II, and detection); Wortmannin-Calbiochem, cat#681675 (1 mM stock, aliquoted and stored at −20 deg); and 96 well Poly-L-Lysine coated plates—Becton Dickinson cat#35-4516 (stored at room temp).

Results are presented in Table 2.

TABLE 2

| Ex. No. | $IC_{50}$ (μM) | $EC_{50}$ (μM) |
|---|---|---|
| 1.5 | A | b |
| 1.6 | A | b |
| 1.7 | C | c |
| 1.8 | B | b |
| 1.9 | D | b |
| 1.10 | D | b |
| 1.11 | D | b |
| 1.12 | D | — |
| 1.13 | D | c |
| 1.14 | B | b |
| 1.15 | D | c |
| 1.16 | B | c |
| 1.17 | B | c |
| 1.18 | C | c |
| 1.19 | C | b |
| 1.20 | A | b |
| 2.4 | C | c |
| 2.5 | C | c |
| 2.6 | D | c |
| 2.7 | C | c |
| 2.8 | C | c |
| 2.9 | C | b |
| 2.10 | D | c |
| 2.11 | B | — |
| 2.12 | D | b |
| 2.13.1 | B | b |
| 2.13.2 | A | b |
| 2.14 | A | b |
| 2.15 | B | b |
| 2.16 | D | c |
| 2.17 | D | c |
| 2.18 | B | a |
| 2.19 | B | a |
| 2.20 | B | a |
| 2.21 | C | c |
| 2.22 | — | c |
| 2.23 | C | c |
| 2.24 | A | a |
| 2.25 | A | a |
| 2.26 | A | a |
| 2.27 | A | a |
| 2.28 | A | a |

TABLE 2-continued

| Ex. No. | IC$_{50}$ (µM) | EC$_{50}$ (µM) |
|---|---|---|
| 2.29 | A | b |
| 2.30 | A | b |
| 2.31 | B | b |
| 2.32 | A | b |
| 2.33 | D | c |
| 2.34 | D | c |
| 2.35 | A | a |
| 2.36 | A | a |
| 2.37 | A | a |
| 2.38 | A | b |
| 2.39 | A | a |
| 3.6 | B | c |
| 3.7 | A | a |
| 3.8 | A | b |
| 3.9 | A | a |
| 3.10 | B | b |
| 3.11 | A | c |
| 3.12 | D | c |
| 3.13 | B | c |
| 3.14 | D | c |
| 3.15 | B | a |
| 3.16 | A | b |
| 3.17 | B | c |
| 3.18 | B | c |
| 3.19 | B | c |
| 3.20 | D | c |
| 3.21 | A | b |
| 3.22 | B | c |
| 3.23 | A | a |
| 3.24 | B | b |
| 3.25 | C | c |
| 3.26 | D | c |
| 3.27 | B | c |
| 3.28 | C | c |
| 3.29 | B | b |
| 3.30 | D | c |
| 3.31 | D | c |
| 3.32 | D | c |
| 3.33 | B | c |
| 3.34 | D | b |
| 3.35 | D | b |
| 3.36 | D | b |
| 3.37 | B | b |
| 3.38 | C | c |
| 3.39 | A | a |
| 3.40 | B | b |
| 3.41 | A | a |
| 3.42 | B | c |
| 3.43 | B | b |
| 3.44 | B | b |
| 3.45 | B | b |
| 3.46 | B | b |
| 3.47 | B | a |
| 3.48 | B | c |
| 3.49 | B | b |
| 3.50 | D | c |
| 3.51 | C | b |
| 3.52 | D | c |
| 3.53 | D | c |
| 3.54 | C | c |
| 3.55 | B | c |
| 3.56 | B | b |
| 3.57 | C | b |
| 3.58 | B | b |
| 3.59 | A | b |
| 3.60 | B | b |
| 3.61 | B | c |
| 3.62 | A | b |
| 3.63 | A | a |
| 3.64 | D | b |
| 3.65 | A | b |
| 3.66 | B | b |
| 3.67 | C | c |
| 3.68 | A | b |
| 3.69 | A | b |
| 3.70 | A | b |
| 3.71 | A | a |
| 3.72 | D | c |
| 3.73 | A | b |
| 3.74 | B | c |
| 3.75 | A | c |
| 3.76 | A | a |
| 3.77 | A | a |
| 3.78 | B | a |
| 3.79 | B | a |
| 3.80 | B | a |
| 3.81 | A | a |
| 3.82 | A | a |
| 3.83 | A | a |
| 3.84 | B | b |
| 3.85 | C | c |
| 3.86 | C | c |
| 3.87 | C | c |
| 4.1.1 | B | c |
| 4.1.2 | D | c |
| 4.1.3 | A | a |
| 4.1.4 | A | b |
| 4.1.5 | D | c |
| 4.1.6 | D | c |
| 4.1.7 | C | b |
| 4.1.8 | D | b |
| 4.1.9 | D | b |
| 4.1.10 | D | b |
| 4.1.11 | B | b |
| 4.1.12 | C | c |
| 4.1.13 | A | b |
| 4.1.14 | A | b |
| 4.1.15 | D | b |
| 4.1.16 | B | b |
| 4.1.17 | D | c |
| 4.1.18 | A | c |
| 4.4 | A | a |
| 4.5 | A | c |
| 4.6 | A | c |
| 4.7 | B | b |
| 4.8 | A | a |
| 4.9 | A | b |
| 4.10 | A | b |
| 4.11 | A | c |
| 4.12 | A | b |
| 4.13 | A | b |
| 4.14 | A | b |
| 4.15 | A | b |
| 4.16 | A | a |
| 4.17 | A | c |
| 4.18 | C | c |
| 4.19 | B | c |
| 4.20 | B | c |
| 4.21 | D | c |
| 4.22 | B | b |
| 4.23 | C | c |
| 4.24 | A | b |
| 4.25 | D | c |
| 4.26 | D | c |
| 4.27 | C | c |
| 4.28 | B | b |
| 4.29 | D | c |
| 4.30 | B | b |
| 4.31 | D | c |
| 4.32 | B | c |
| 4.33 | A | b |
| 4.34 | A | b |
| 4.35 | A | b |
| 4.36 | A | b |
| 4.37 | B | b |
| 4.38 | A | b |
| 5.3 | B | c |
| 5.4 | C | c |
| 5.5 | A | c |
| 5.6 | A | b |
| 5.7 | A | b |
| 5.8 | A | b |
| 6.1 | A | b |
| 6.2 | A | b |
| 6.3 | A | c |
| 6.4 | D | c |

TABLE 2-continued

| Ex. No. | IC$_{50}$ (µM) | EC$_{50}$ (µM) |
|---|---|---|
| 6.5 | D | b |
| 6.6 | A | c |
| 6.7 | A | c |
| 6.8 | A | c |
| 6.9 | A | c |
| 6.10 | B | b |
| 6.11 | B | b |
| 6.12 | A | a |
| 6.13 | B | c |
| 6.14 | A | b |
| 6.15 | B | c |
| 7.1 | B | b |
| 7.2 | B | b |
| 7.3.1 | A | a |
| 7.3.2 | A | a |
| 7.4 (7.5) | B | c |
| 7.5 (7.4) | B | c |
| 7.6 | A | a |
| 7.7 | B | c |
| 7.8 | A | a |
| 7.9 | A | a |
| 7.10 | A | a |
| 7.11 | B | a |
| 7.12 | D | c |
| 7.13 | B | a |
| 7.14 | B | b |
| 7.15 | B | b |
| 7.16 | B | b |
| 7.17 | A | b |
| 7.18 | A | a |
| 7.19 | B | b |
| 7.20 | B | b |
| 7.21.1 | B | a |
| 7.21.2 | B | a |
| 7.22.1) | B | a |
| 7.22.2 | B | a |
| 7.23.1 | A | c |
| 7.23.2 | B | a |
| 7.24.1 | A | a |
| 7.24.2 | B | b |
| 7.24.3 | A | a |
| 7.24.4 | A | a |
| 7.24.5 | B | c |
| 7.24.6 | A | b |
| 7.25 | A | a |
| 8.1.1 | A | b |
| 8.1.2 | A | a |
| 8.1.3 | D | c |
| 8.2 | A | a |
| 8.3 | A | a |
| 8.4 | A | b |
| 8.5.1 | A | b |
| 8.5.2 | A | b |
| 8.5.3 | B | b |
| 8.5.4 | C | b |
| 8.5.5 | B | b |
| 8.5.6 | B | b |
| 8.5.7 | B | c |
| 8.5.8 | B | b |
| 8.6.1 | A | a |
| 8.6.2 | B | a |
| 8.6.3 | B | b |
| 8.6.4 | C | b |
| 8.6.5 | B | b |
| 8.6.6 | C | b |
| 8.6.7 | B | c |
| 8.6.8 | B | c |
| 8.6.9 | B | b |
| 8.6.10 | B | b |
| 8.6.11 | D | c |
| 8.6.12 | D | c |
| 8.6.13 | C | c |
| 8.6.14 | A | c |
| 8.6.15 | A | c |
| 8.6.16 | D | c |
| 8.6.17 | D | b |
| 8.6.18 | D | b |
| 8.6.19 | D | c |
| 8.6.20 | B | c |
| 8.7.1 | B | a |
| 8.7.2 | A | b |
| 8.7.3 | A | b |
| 8.7.4 | A | a |
| 8.7.5 | A | a |
| 8.7.6 | A | a |
| 8.7.7 | B | b |
| 8.7.8 | B | a |
| 8.7.9 | B | b |
| 8.7.10 | B | b |
| 8.7.11 | B | a |
| 8.7.12 | B | a |
| 8.7.13 | B | b |
| 8.8.1 | A | a |
| 8.8.2 | A | a |
| 8.8.3 | A | a |
| 8.8.4 | A | a |
| 8.9 | A | a |
| 8.10 | A | a |
| 8.11 | A | a |
| 8.12.1 | A | a |
| 8.12.2 | A | b |
| 8.12.3 | C | b |
| 8.12.4 | D | b |
| 8.12.5 | A | b |
| 8.12.6 | A | a |
| 8.12.7 | B | a |
| 8.12.8 | B | b |
| 8.13 | A | a |
| 8.14.1 | A | a |
| 8.14.2 | D | c |
| 8.14.3 | D | b |
| 8.14.4 | C | c |
| 8.15.1 | B | b |
| 8.15.2 | D | c |
| 9.1 | B | c |
| 9.2 | D | c |
| 10.1 | A | b |
| 10.2 | A | b |
| 10.3 | D | c |
| 10.4 | B | c |
| 10.5 | A | b |
| 10.6 | B | b |
| 10.7 | C | b |
| 10.8 | B | a |
| 10.9 | B | a |
| 10.10 | A | c |
| 11.1 | A | b |
| 11.2 | B | c |
| 11.3 | A | a |
| 11.4 | A | b |
| 11.5 | A | b |
| 12.1 | A | c |
| 13 | C | c |
| 14.1 | A | b |
| 14.2 | A | c |
| 15.1 | A | a |
| 15.2 | B | a |
| 15.3 | D | c |
| 15.4 | A | a |
| 15.5 | A | a |
| 15.6 | D | a |
| 15.7 | A | a |
| 15.8 | A | a |
| 15.9 | A | b |
| 15.10 | A | a |
| 15.11 | A | a |
| 15.12 | A | b |
| 15.13 | A | b |
| 15.14 | A | a |
| 15.15 | A | a |
| 15.16 | B | c |
| 15.17 | A | b |
| 15.18 | A | a |
| 15.19 | A | a |
| 15.20 | A | a |
| 15.21 | A | a |

TABLE 2-continued

| Ex. No. | IC$_{50}$ (μM) | EC$_{50}$ (μM) |
|---|---|---|
| 15.22 | A | a |
| 16.1 | A | a |
| 16.2 | A | b |
| 16.3 | B | b |
| 16.4 | C | b |
| 16.5 | D | b |
| 16.6 | D | c |
| 16.7 | D | c |
| 16.8 | C | c |
| 16.9 | B | a |
| 16.10 | B | a |
| 16.11 | A | a |
| 16.12 | A | a |
| 16.13 | A | b |
| 17.1 | B | c |
| 17.2 | D | c |
| 17.3 | B | c |
| 18.1 | A | b |
| 19.1 | D | c |
| 19.2 | A | a |
| 20.1 | D | c |
| 20.2 | D | d |
| 21 | A | b |
| 22 | A | a |
| 23 | A | a |
| 24 | A | b |
| 25 | A | a |
| 26 | A | a |
| 27 | A | a |
| 28 | A | a |
| 29 | A | a |
| 30 | A | a |
| 31 | A | a |
| 32 | A | a |
| 33 | A | a |
| 34 | A | a |
| 35 | A | a |
| 36 | A | a |
| 37 | A | a |
| 38 | A | a |
| 39 | A | a |
| 40 | A | a |
| 41 | A | a |
| 42 | A | a |
| 43 | C | b |
| 44 | A | b |
| 45 | B | c |
| 46 | A | c |
| 47 | A | c |
| 48 | B | b |
| 49 | A | c |
| 50 | D | c |
| 51 | D | c |
| 52 | A | a |
| 53 | A | b |
| 54 | A | a |
| 55 | A | a |
| 56 | A | a |
| 57 | A | a |
| 58 | A | a |
| 59 | A | a |
| 60 | A | a |
| 61 | C | c |
| 62 | A | a |
| 63 | A | c |
| 64 | D | c |
| 65 | A | a |
| 66 | A | a |
| 67 | A | b |
| 68 | A | b |
| 69 | B | c |
| 70 | A | a |
| 71 | A | a |
| 72 | A | b |
| 73 | A | a |
| 74 | B | b |
| 75 | A | b |
| 76 | A | a |
| 77 | A | b |
| 78 | A | b |
| 79 | A | a |
| 80 | A | b |
| 81 | A | b |
| 82 | A | a |
| 83 | A | a |
| 84 | A | a |
| 85 | A | a |
| 86 | A | a |
| 87 | A | a |
| 88 | A | a |
| 89 | A | a |
| 90 | A | a |
| 91 | A | a |
| 92 | A | b |
| 93 | A | a |
| 94 | A | a |
| 95 | A | a |
| 96 | A | b |
| 97 | A | a |
| 98 | A | b |
| 99 | A | a |
| 100 | A | b |
| 101 | D | c |
| 102 | A | b |
| 103 | A | b |
| 104 | A | a |
| 105 | A | a |
| 106 | A | a |
| 107 | D | c |
| 108 | D | c |
| 109 | D | c |
| 110 | A | a |
| 111 | D | c |
| 112 | D | c |
| 113 | A | c |
| 114 | B | c |
| 115 | A | c |
| 116 | A | a |
| 117 | D | b |
| 118 | A | b |
| 119 | A | c |
| 120 | A | a |
| 121 | B | c |
| 122 | A | a |
| 123 | A | a |
| 124 | A | a |
| 125 | A | b |
| 126 | A | a |
| 127 | A | a |
| 128 | A | b |
| 129 | B | b |
| 130 | A | b |
| 131 | A | b |
| 132 | A | a |
| 133 | A | a |
| 134 | A | a |
| 135 | A | a |
| 136 | A | b |
| 137 | A | b |
| 138 | A | a |
| 139 | A | a |
| 140 | A | a |
| 141 | A | b |
| 142 | D | b |
| 143 | D | c |
| 144 | D | c |
| 145 | D | c |
| 146 | A | a |
| 147 | A | b |
| 148 | A | c |
| 149 | A | a |
| 150 | A | a |
| 151 | A | c |
| 152 | A | b |
| 153 | A | b |
| 154 | A | a |

TABLE 2-continued

| Ex. No. | IC$_{50}$ (μM) | EC$_{50}$ (μM) |
|---|---|---|
| 155 | A | a |
| 156 | A | a |
| 157 | A | a |
| 158 | A | a |
| 159 | A | a |
| 160 | A | a |
| 161 | A | a |
| 162 | A | a |
| 163 | A | a |
| 164 | A | a |
| 165 | A | a |
| 166 | A | a |
| 167 | A | a |
| 168 | A | b |
| 169 | A | a |
| 170 | A | b |
| 171 | A | b |
| 172 | A | b |
| 173 | A | a |
| 174 | A | a |
| 175 | A | a |
| 176 | A | b |
| 177 | A | b |
| 178 | A | b |
| 179 | B | b |
| 180 | A | b |
| 181 | A | a |
| 182 | A | a |
| 183 | A | a |
| 184 | A | a |
| 185 | A | a |
| 186 | A | a |
| 187 | A | a |
| 188 | A | b |
| 189 | A | b |
| 190 | A | b |
| 191 | A | a |
| 192 | A | b |
| 193 | A | b |
| 194 | A | a |
| 195 | A | a |
| 196 | A | a |
| 197 | A | a |
| 198 | A | a |
| 199 | A | a |
| 200 | A | b |
| 201 | A | a |
| 202 | A | b |
| 203 | A | a |
| 204 | A | a |
| 205 | B | b |
| 206 | A | b |
| 207 | A | c |
| 208 | A | a |
| 209 | A | a |
| 210 | A | b |
| 211 | A | b |
| 212 | A | a |
| 213 | A | a |
| 214 | A | a |
| 215 | A | a |
| 216 | A | a |
| 217 | A | a |
| 218 | A | a |
| 219 | A | b |
| 220 | A | b |
| 221 | A | b |
| 222 | B | b |
| 223 | D | c |
| 224 | D | c |
| 225 | D | c |
| 226 | D | c |
| 227 | B | b |
| 228 | C | c |
| 229 | B | b |
| 230 | A | b |
| 231 | B | b |
| 232 | B | c |

TABLE 2-continued

| Ex. No. | IC$_{50}$ (μM) | EC$_{50}$ (μM) |
|---|---|---|
| 233 | A | a |
| 234 | A | b |
| 235 | A | b |
| 236 | A | b |
| 237 | A | a |
| 238 | A | a |
| 239 | A | b |
| 240 | A | a |
| 241 | A | a |
| 242 | A | a |
| 243 | A | a |
| 244 | A | a |
| 245 | A | a |
| 246 | A | a |
| 247 | A | c |
| 248 | A | a |
| 249 | D | c |
| 250 | A | a |
| 251 | D | b |
| 252 | B | b |
| 253 | C | c |
| 254 | B | b |
| 255 | A | a |
| 256 | A | b |
| 257 | A | a |
| 258 | A | a |
| 259 | B | c |
| 260 | B | b |
| 261 | A | b |
| 262 | A | a |
| 263 | A | a |
| 264 | A | b |
| 265 | A | b |
| 266 | B | c |
| 267 | A | a |
| 268 | B | c |
| 269 | A | b |
| 270 | C | b |
| 271 | B | b |
| 272 | B | b |
| 273 | A | b |
| 274 | A | b |
| 275 | D | c |
| 276 | A | b |
| 277 | A | a |
| 278 | A | a |
| 279 | A | a |
| 280 | B | b |
| 281 | A | a |
| 282 | A | b |
| 283 | D | b |
| 284 | D | b |
| 285 | C | c |
| 286 | A | a |
| 287 | B | c |
| 288 | A | b |
| 289 | A | a |
| 290 | D | b |
| 291 | A | a |
| 292 | A | a |
| 293 | C | c |
| 294 | A | b |
| 295 | A | a |
| 296 | A | a |
| 297 | A | a |
| 298 | C | c |
| 299 | A | b |
| 300 | A | a |
| 301 | A | b |
| 302 | A | b |
| 303 | A | b |
| 304 | A | a |
| 305 | B | b |
| 306 | A | a |
| 307 | C | b |
| 308 | A | a |
| 309 | B | b |
| 310 | A | a |

TABLE 2-continued

| Ex. No. | IC$_{50}$ (µM) | EC$_{50}$ (µM) |
|---|---|---|
| 311 | A | a |
| 312 | A | a |
| 313 | D | c |
| 314 | C | c |
| 315 | A | a |
| 316 | A | b |
| 317 | A | a |
| 318 | A | a |
| 319 | A | a |
| 320 | A | a |
| 321 | A | a |
| 322 | A | a |
| 323 | A | a |
| 324 | A | a |
| 325 | B | b |
| 326 | B | c |
| 327 | A | b |
| 328 | A | c |
| 329 | A | a |
| 330 | A | a |
| 331 | A | a |
| 332 | A | b |
| 333 | A | a |
| 334 | A | a |
| 335 | A | c |
| 336 | A | b |
| 337 | A | b |
| 338 | A | b |
| 339 | B | c |
| 340 | D | b |
| 341 | D | c |
| 342 | D | c |
| 343 | A | a |
| 344 | D | c |
| 345 | B | a |
| 346 | B | a |
| 347 | A | a |
| 348 | D | c |
| 349 | D | c |
| 350 | D | c |
| 351 | C | c |
| 352 | A | c |
| 353 | A | a |
| 354 | A | a |
| 355 | A | b |
| 356 | A | a |
| 357 | A | a |
| 358 | A | a |
| 359 | A | a |
| 360 | A | a |
| 361 | A | a |
| 362 | A | a |
| 363 | A | a |
| 364 | A | a |
| 365 | A | a |
| 366 | A | a |
| 367 | A | a |
| 368 | A | a |
| 369 | A | b |
| 370 | A | b |
| 371 | A | c |
| 372 | A | b |
| 373 | C | b |
| 374 | A | b |
| 375 | C | b |
| 376 | A | a |
| 377 | A | b |
| 378 | A | b |
| 379 | A | a |
| 380 | B | b |
| 381 | A | b |
| 382 | A | a |
| 383 | A | a |
| 384 | A | a |
| 385 | A | a |
| 386 | A | b |
| 387 | A | b |
| 388 | D | c |
| 389 | A | a |
| 390 | A | a |
| 391 | A | b |
| 392 | A | b |
| 393 | A | b |
| 394 | A | a |
| 395 | A | a |
| 396 | A | a |
| 397 | A | a |
| 398 | A | b |
| 399 | A | a |
| 400 | A | b |
| 401 | A | b |
| 402 | A | a |
| 403 | A | b |
| 404 | A | b |
| 405 | A | b |
| 406 | A | b |
| 407 | A | a |
| 408 | A | b |
| 409 | A | b |
| 410 | A | a |
| 411 | A | a |
| 412 | A | b |
| 413 | A | a |
| 414 | C | b |
| 415 | A | a |
| 416 | A | a |
| 417 | B | b |
| 418 | A | b |
| 419 | A | b |
| 420 | A | b |
| 421 | A | a |
| 422 | A | a |
| 423 | A | a |
| 424 | A | b |
| 425 | A | a |
| 426 | A | a |
| 427 | A | b |
| 428 | A | a |
| 429 | A | b |
| 430 | A | b |
| 431 | A | b |
| 432 | A | a |
| 433 | A | b |
| 434 | A | a |
| 435 | A | a |
| 436 | B | b |
| 437 | C | c |
| 438 | C | c |
| 439 | A | b |
| 440 | B | b |
| 441 | A | c |
| 442 | A | a |
| 443 | A | a |

In Table 2, IC$_{50}$ values were determined based on the inhibition of phospo-PDK1 in vitro and EC$_{50}$ values were determined based on the inhibition of P308 Akt in cells using MSD. "A" indicates an IC$_{50}$≤0.1 µM; "B" indicates an IC$_{50}$ from 0.1 µM to 1 µM; "C" indicates an IC$_{50}$ from 1 µM to 5 µM; and "D" indicates an IC$_{50}$≥5 µM. An "a" indicates an EC$_{50}$≤1 µM; "b" represents an EC$_{50}$ from 1 µM to 10 µM; and "c" represents an EC$_{50}$≥10 µM.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:
1. A method of treating cancer in a subject in need thereof, said method comprising administering to said subject a therapeutically effective amount of a compound of formula I:

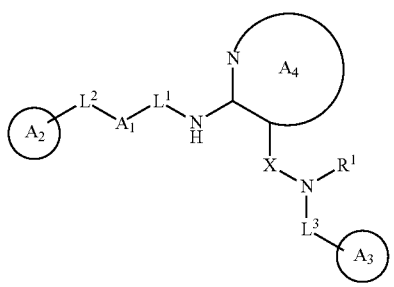

or a pharmaceutically acceptable salt thereof, wherein:
$R^1$ is hydrogen or optionally substituted $C_{1-6}$ aliphatic;
X is —C(O)— or —S(O)$_2$—,
$L^1$ is a covalent bond or a $C_{1-4}$ alkylene, optionally substituted with —(CH$_2$)$_{0-4}$R°  or —(CH$_2$)$_{0-4}$OR°, wherein R° is hydrogen;
$A_1$ is an optionally substituted bivalent ring selected from 3-7 membered saturated or partially unsaturated monocyclic carbocyclylene, 7-10 membered saturated or partially unsaturated bicyclic carbocyclylene, 4-7 membered saturated or partially unsaturated monocyclic heterocyclylene having 1-2 heteroatoms independently selected from nitrogen, oxygen, or sulfur, 7-10 membered saturated or partially unsaturated bicyclic heterocyclylene having 1-3 heteroatoms independently selected from nitrogen, oxygen, or sulfur, phenylene, 8-10 membered bicyclic arylene, 5-6 membered monocyclic heteroarylene having 1-3 heteroatoms independently selected from nitrogen, oxygen, or sulfur, or 8-10 membered bicyclic heteroarylene having 1-4 heteroatoms independently selected from nitrogen, oxygen, or sulfur;
$L^2$ is a covalent bond, or an optionally substituted alkylene chain;
Ring $A_2$ is a 3-7 membered saturated or partially unsaturated monocyclic carbocyclic ring, a 7-10 membered saturated or partially unsaturated bicyclic carbocyclic ring, a 4-7 membered saturated or partially unsaturated monocyclic heterocyclic ring having 1-2 heteroatoms independently selected from nitrogen, oxygen, or sulfur, a 7-10 membered saturated or partially unsaturated bicyclic heterocyclic ring having 1-3 heteroatoms independently selected from nitrogen, oxygen, or sulfur, a phenyl ring, an 8-10 membered bicyclic aryl ring, a 5-6 membered monocyclic heteroaryl ring having 1-3 heteroatoms independently selected from nitrogen, oxygen, or sulfur, an 8-10 membered bicyclic heteroaryl ring having 1-4 heteroatoms independently selected from nitrogen, oxygen, or sulfur, or a 10-16 membered saturated, partially unsaturated, or aromatic tricyclic ring having 0-4 heteroatoms independently selected from nitrogen, oxygen, or sulfur, wherein Ring $A_2$ is optionally substituted with 1-4 $R^x$ groups;
each $R^x$ is independently —R, optionally substituted alkylidenyl, oxo, -halo, —NO$_2$, —CN, —OR, —SR, —N(R')$_2$, —C(O)R, —CO$_2$R, —C(O)C(O)R, —C(O)CH$_2$C(O)R, —S(O)R, —S(O)$_2$R, —C(O)N(R')$_2$, —S(O)$_2$N(R')$_2$, —OC(O)R, —N(R')C(O)R, —N(R')N(R')$_2$, —N(R')OR, —N(R')C(=NR')N(R')$_2$, —C(=NR')N(R')$_2$, —C=NOR, —N(R')C(O)N(R')$_2$, —N(R')S(O)$_2$N(R')$_2$, —N(R')S(O)$_2$R, or —OC(O)N(R')$_2$;
each R is independently hydrogen or an optionally substituted group selected from $C_{1-6}$ aliphatic, a 3-7 membered saturated or partially unsaturated monocyclic carbocyclic ring, a 7-10 membered saturated or partially unsaturated bicyclic carbocyclic ring, a 4-7 membered saturated or partially unsaturated monocyclic heterocyclic ring having 1-2 heteroatoms independently selected from nitrogen, oxygen, or sulfur, a 7-10 membered saturated or partially unsaturated bicyclic heterocyclic ring having 1-3 heteroatoms independently selected from nitrogen, oxygen, or sulfur, a phenyl ring, an 8-10 membered bicyclic aryl ring, a 5-6 membered heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur;
each R' is independently —R, or two R' groups on the same nitrogen are taken together with their intervening atoms to form an optionally substituted 5-8 membered saturated, partially unsaturated, or aromatic ring having 1-4 heteroatoms independently selected from nitrogen, oxygen, or sulfur;
$L^3$ is unsubstituted methylene or methylene substituted with methyl or ethyl;
Ring $A_3$ is an optionally substituted ring selected from a 7-10 membered saturated or partially unsaturated bicyclic carbocyclic ring, a 4-7 membered saturated or partially unsaturated monocyclic heterocyclic ring having 1-2 heteroatoms independently selected from nitrogen, or sulfur, a 7-10 membered saturated or partially unsaturated bicyclic heterocyclic ring having 1-3 heteroatoms independently selected from nitrogen, oxygen, or sulfur, a phenyl ring, an 8-10 membered bicyclic aryl ring, a 5-6 membered monocyclic heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur;
Ring $A_4$ is

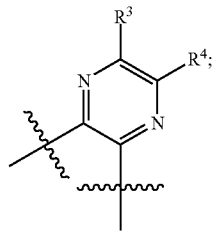

and
$R^3$ is —R, -halo, —NO$_2$, —CN, —OR, —SR, —N(R')$_2$, —C(O)R, —CO$_2$R, —C(O)C(O)R, —C(O)CH$_2$C(O)R, —S(O)R, —S(O)$_2$R, —C(O)N(R')$_2$, —S(O)$_2$N(R')$_2$, —OC(O)R, —N(R')C(O)R, —N(R')N(R')$_2$, —N(R')OR, —N(R')C(=NR')N(R')$_2$, —C(=NR')N(R')$_2$, —C=NOR, —N(R')C(O)N(R')$_2$, —N(R')S(O)$_2$N(R')$_2$, —N(R')S(O)$_2$R, or —OC(O)N(R')$_2$;

R⁴ is —R, -halo, —NO₂, —CN, —OR, —SR, —N(R')₂, —C(O)R, —CO₂R, —C(O)C(O)R, —C(O)CH₂C(O)R, —S(O)R, —S(O)₂R, —C(O)N(R')₂, —S(O)N(R')₂, —S(O)₂N(R')₂, —OC(O)R, —N(R')C(O)R, —N(R')N(R')₂, —N(R')OR, —N(R')C(=NR')N(R')₂, —C(=NR')N(R')₂, —C=NOR, —N(R')C(O)N(R')₂, —NHS(O)C₁₋₆alkyl, —N(R')S(O)₂N(R')₂, —N(R')S(O)₂R, or —OC(O)N(R')₂; or:

R³ and R⁴ are taken together with their intervening atoms to form an optionally substituted fused ring selected from a 4-7 membered partially unsaturated carbocyclic ring, phenyl, a 5-6 membered partially unsaturated heterocyclic ring having 1-3 heteroatoms independently selected from nitrogen, oxygen, or sulfur, or a 5-6 membered heteroaryl ring having 1-3 heteroatoms independently selected from nitrogen, oxygen, or sulfur, wherein the cancer is associated with dysregulated Akt activation and is selected from glioma, thyroid carcinoma, breast carcinoma, lung cancer, gastric carcinoma, gastrointestinal stromal tumors, pancreatic carcinoma, bile duct carcinoma, ovarian carcinoma, endometrial carcinoma, prostate carcinoma, renal cell carcinoma, anaplastic large-cell lymphoma, leukemia, multiple myeloma, malignant mesothelioma, malignant melanoma, and colon cancer;

wherein treating cancer does not encompass preventing cancer.

2. The method of claim 1, wherein:
R³ is hydrogen, —Cl, or —CF₃;
R⁴ is —CN, —NO₂, —NH₂, —NHC(O)C₁₋₆alkyl, —CO₂H, —CO₂C₁₋₄alkyl, —C(O)N(R')₂, —NHS(O)C₁₋₆alkyl, —NHS(O)₂C₁₋₆alkyl, —SC₁₋₆alkyl, —S(O)C₁₋₆alkyl, —S(O)₂C₁₋₆alkyl, —S(O)N(R')₂, —S(O)₂N(R')₂, —CF₃, —OCH₃, —OCH₂CH₃, or benzyloxy; and each R' is independently hydrogen or C₁₋₄ alkyl, or two R' groups on the same nitrogen are taken together with the intervening nitrogen to form an optionally substituted 5-6 membered saturated, partially unsaturated, or aromatic ring having 1-3 heteroatoms independently selected from nitrogen, oxygen, or sulfur.

3. The method of claim 1, wherein Ring A₃ is phenyl, an 8-10 membered bicyclic aryl ring, a 5-6 membered monocyclic heteroaryl ring having 1-3 heteroatoms independently selected from nitrogen, oxygen, or sulfur, or an 8-10 membered bicyclic heteroaryl ring having 1-4 heteroatoms selected from nitrogen, oxygen, or sulfur, wherein Ring A₃ is optionally substituted with one or more halo or alkyl groups.

4. The method of claim 1, wherein L¹ is optionally substituted C₁₋₃ alkylene.

5. The method of claim 1, wherein A₁ is an optionally substituted bivalent ring selected from phenylene, an 8-10 membered bicyclic arylene, a 5-6 membered monocyclic heteroarylene having 1-3 heteroatoms independently selected from nitrogen, oxygen, or sulfur, or an 8-10 membered bicyclic heteroarylene having 1-4 heteroatoms independently selected from nitrogen, oxygen, or sulfur.

6. The method of claim 1, wherein L² is a covalent bond or an optionally substituted methylene.

7. The method of claim 1, wherein Ring A₂ is optionally substituted with 1-4 R^x groups and is selected from phenyl, an 8-10 membered bicyclic aryl ring, a 5-6 membered monocyclic heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur.

8. The method of claim 1, wherein the compound is of formula III:

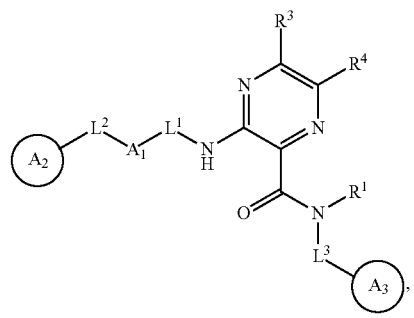

or a pharmaceutically acceptable salt thereof.

9. The method of claim 8, wherein:
R³ is hydrogen, —Cl, or —CF₃;
R⁴ is —CN, —NO₂, —SC₁₋₄alkyl, —S(O)C₁₋₄ alkyl, —S(O)₂C₁₋₄ alkyl, —S(O)N(R')₂, —S(O)₂N(R')₂, —CF₃, —OCH₃, —OCH₂CH₃, or benzyloxy; or:

R³ and R⁴ are taken together with their intervening atoms to form an optionally substituted fused ring selected from a 4-7 membered partially unsaturated carbocyclic ring, phenyl, a 5-6 membered partially unsaturated heterocyclic ring having 1-3 heteroatoms independently selected from nitrogen, oxygen, or sulfur, or a 5-6 membered heteroaryl ring having 1-3 heteroatoms independently selected from nitrogen, oxygen, or sulfur; and each R' is independently hydrogen or C₁₋₄alkyl.

10. The method of claim 1, wherein the compound is selected from the group consisting of:

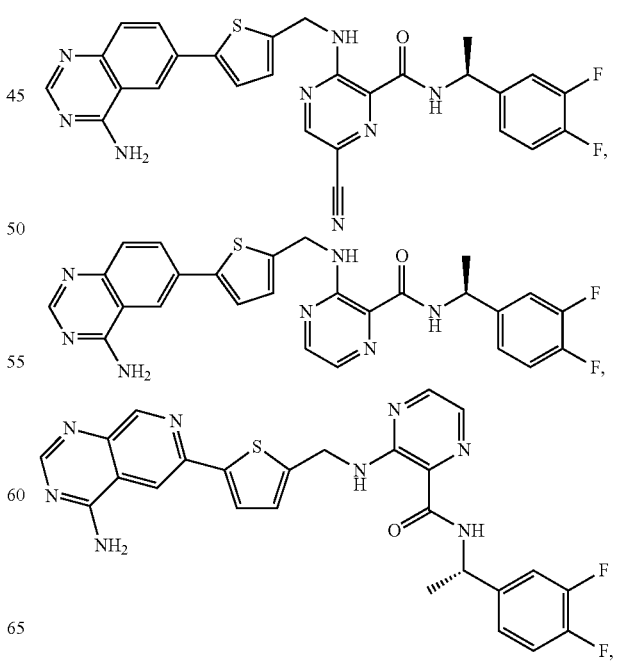

791
-continued
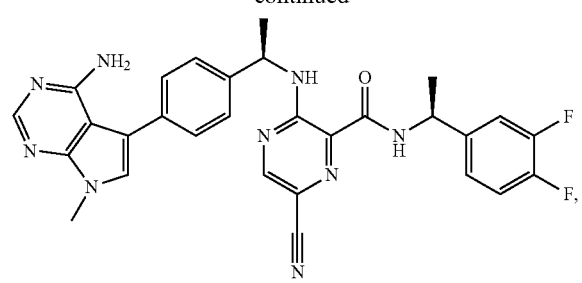
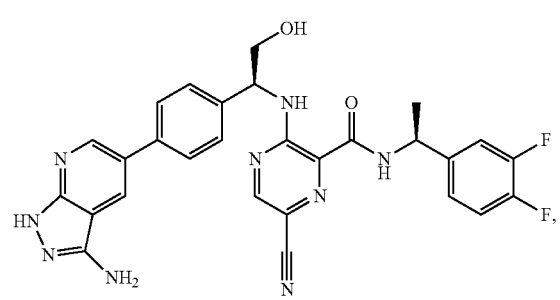
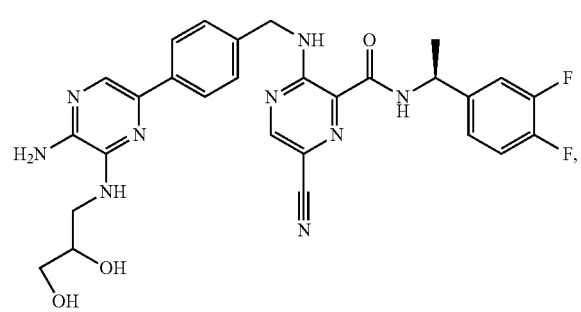
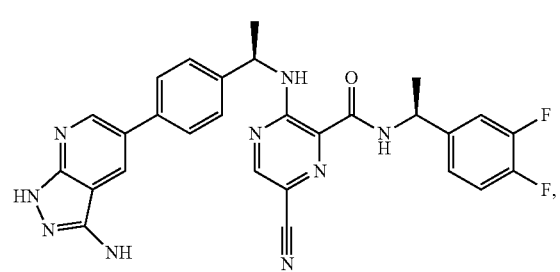
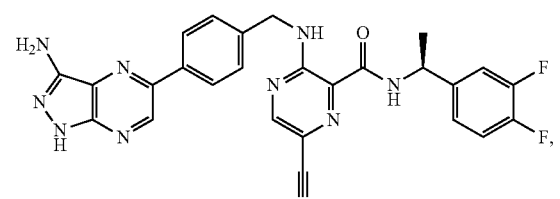
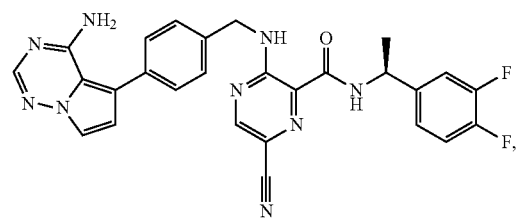
792
-continued
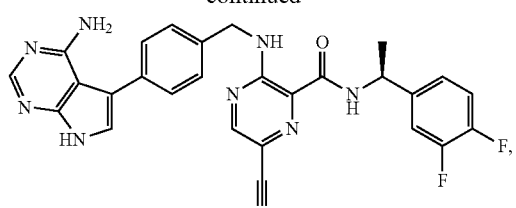
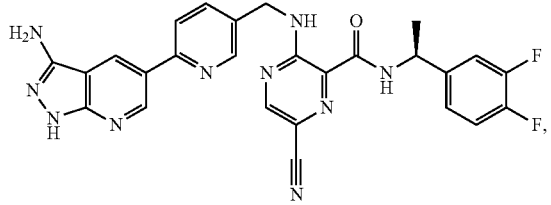
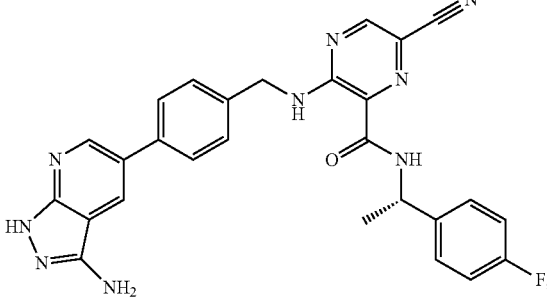
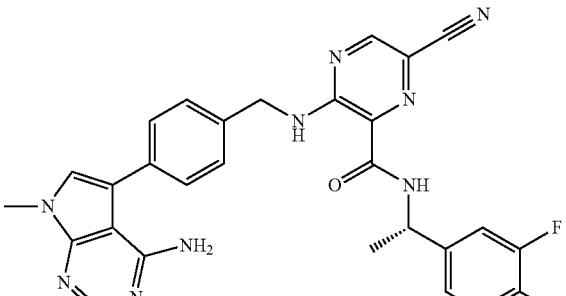
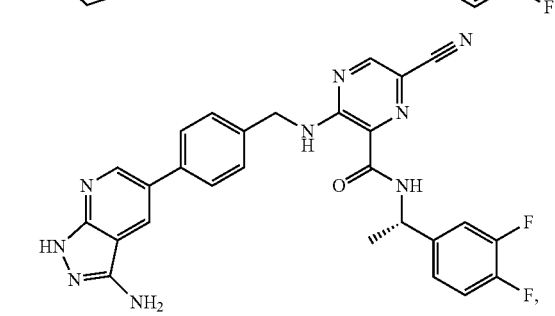
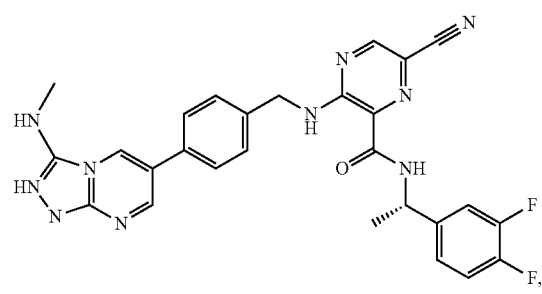
and -continued

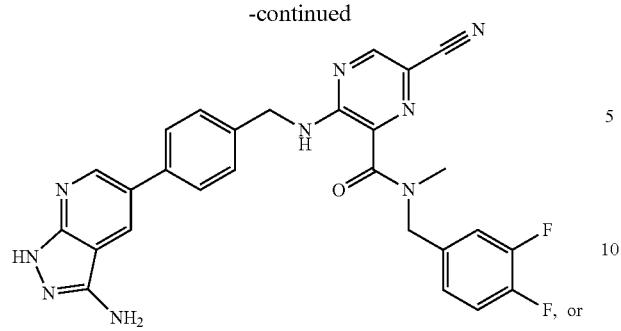

F, or a pharmaceutically acceptable salt thereof.

11. The method of claim 1, wherein the cancer is lung cancer, and the lung cancer is small-cell lung carcinoma or non-small-cell lung carcinoma.

12. The method of claim 1, wherein the cancer is leukemia and the leukemia is acute myeloid leukemia.

13. The method of claim 1, wherein the cancer is colon cancer, and the colon cancer is microsatellite instability-high colorectal cancer.

14. The method of claim 10, wherein the cancer is lung cancer, and the lung cancer is small-cell lung carcinoma or non-small-cell lung carcinoma.

15. The method of claim 10, wherein the cancer is leukemia, and the leukemia is acute myeloid leukemia.

16. The method of claim 10, wherein the cancer is colon cancer, and the colon cancer is microsatellite instability-high colorectal cancer.

* * * * *

UNITED STATES PATENT AND TRADEMARK OFFICE
CERTIFICATE OF CORRECTION

PATENT NO. : 10,030,016 B2
APPLICATION NO. : 14/966821
DATED : July 24, 2018
INVENTOR(S) : Joseph Arndt et al.

Page 1 of 2

It is certified that error appears in the above-identified patent and that said Letters Patent is hereby corrected as shown below:

In the Claims

At Column 791, Claim number 10, Line number 40, replace:

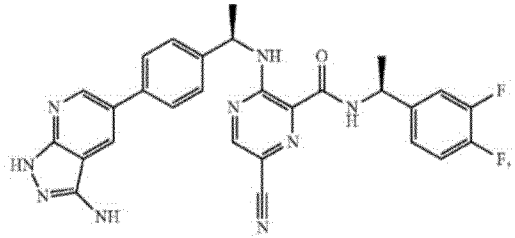

With:

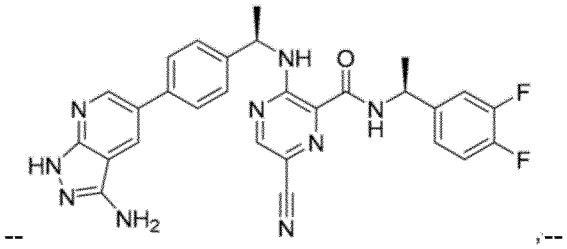

At Column 792, Claim number 10, Line number 55, replace:

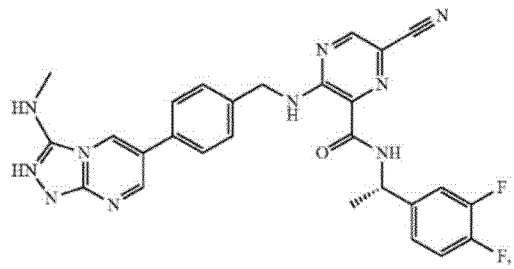

Signed and Sealed this
Eleventh Day of September, 2018

Andrei Iancu
*Director of the United States Patent and Trademark Office*

With:
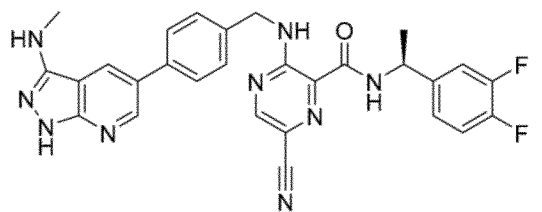
-- --